US011964945B2

(12) United States Patent
Crew et al.

(10) Patent No.: US 11,964,945 B2
(45) Date of Patent: *Apr. 23, 2024

(54) COMPOUNDS AND METHODS FOR THE TARGETED DEGRADATION OF ANDROGEN RECEPTOR

(71) Applicant: Arvinas Operations, Inc., New Haven, CT (US)

(72) Inventors: Andrew P. Crew, Chester, CT (US); Keith R. Hornberger, Southbury, CT (US); Lawrence B. Snyder, Killingworth, CT (US); Kurt Zimmermann, Durham, CT (US); Jing Wang, Milford, CT (US); Hanqing Dong, Madison, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/888,484

(22) Filed: May 29, 2020

(65) Prior Publication Data
US 2021/0171470 A1 Jun. 10, 2021

Related U.S. Application Data

(60) Continuation of application No. 16/577,901, filed on Sep. 20, 2019, now Pat. No. 10,844,021, which is a division of application No. 15/730,728, filed on Oct. 11, 2017, now Pat. No. 10,584,101.

(60) Provisional application No. 62/528,385, filed on Jul. 3, 2017, provisional application No. 62/406,888, filed on Oct. 11, 2016.

(51) Int. Cl.
| | |
|---|---|
| *C07D 401/14* | (2006.01) |
| *A61K 31/02* | (2006.01) |
| *A61K 31/166* | (2006.01) |
| *A61K 31/277* | (2006.01) |
| *A61K 31/496* | (2006.01) |
| *A61K 31/497* | (2006.01) |
| *A61K 31/501* | (2006.01) |
| *A61K 31/506* | (2006.01) |
| *A61K 45/06* | (2006.01) |
| *A61K 47/10* | (2017.01) |
| *C07D 205/04* | (2006.01) |
| *C07D 209/48* | (2006.01) |
| *C07D 211/76* | (2006.01) |
| *C07D 213/72* | (2006.01) |
| *C07D 221/20* | (2006.01) |
| *C07D 231/12* | (2006.01) |
| *C07D 233/42* | (2006.01) |
| *C07D 237/08* | (2006.01) |
| *C07D 239/24* | (2006.01) |
| *C07D 241/04* | (2006.01) |
| *C07D 401/04* | (2006.01) |

(52) U.S. Cl.
CPC ............ *C07D 233/42* (2013.01); *A61K 31/02* (2013.01); *A61K 31/166* (2013.01); *A61K 31/277* (2013.01); *A61K 31/496* (2013.01); *A61K 31/497* (2013.01); *A61K 31/501* (2013.01); *A61K 31/506* (2013.01); *A61K 45/06* (2013.01); *A61K 47/10* (2013.01); *C07D 205/04* (2013.01); *C07D 209/48* (2013.01); *C07D 211/76* (2013.01); *C07D 213/72* (2013.01); *C07D 221/20* (2013.01); *C07D 231/12* (2013.01); *C07D 237/08* (2013.01); *C07D 239/24* (2013.01); *C07D 241/04* (2013.01); *C07D 401/04* (2013.01); *C07D 401/14* (2013.01)

(58) Field of Classification Search
CPC ................................................... C07D 401/14
See application file for complete search history.

(56) References Cited

U.S. PATENT DOCUMENTS

| | | | |
|---|---|---|---|
| 6,306,663 B1 | 10/2001 | Kenten et al. | |
| 6,670,348 B1 | 12/2003 | Rosen et al. | |
| 7,030,141 B2 | 4/2006 | Bigge et al. | |
| 7,041,298 B2 | 5/2006 | Deshaies et al. | |

(Continued)

FOREIGN PATENT DOCUMENTS

| | | |
|---|---|---|
| CA | 2945975 A1 | 10/2015 |
| CN | 1844118 A | 10/2006 |

(Continued)

OTHER PUBLICATIONS

PubChem CID 118435243, National Center for Biotechnology Information. "PubChem Compound Summary for CID 118435243" PubChem, https://pubchem.ncbi.nlm.nih.gov/compound/118435243. Accessed Sep. 15, 2022, create date Feb. 23, 2016. (Year: 2016).*

U.S. Appl. No. 16/577,901, filed Oct. 11, 2027, U.S. Pat. No. 10,584,101.

Ahn, et al., "HIF-1alpha peptide derivatives with modifications at the hydroxyproline residue as activators of HIF-1alpha", Bioorg Med Chem Lett. 19(15), 2009, 4403-4405.

Allan, GF, et. al, "Therapeutic androgen receptor ligands", Nuclear Receptor Signaling, 2003, 1, e009 DOI:10.621.01009 9 1-4.

(Continued)

*Primary Examiner* — Laura L Stockton
(74) *Attorney, Agent, or Firm* — COOLEY LLP

(57) ABSTRACT

The present disclosure relates to bifunctional compounds, which find utility to degrade and (inhibit) Androgen Receptor. In particular, the present disclosure is directed to compounds, which contain on one end a cereblon ligand which binds to the E3 ubiquitin ligase and on the other end a moiety which binds Androgen Receptor, such that Androgen Receptor is placed in proximity to the ubiquitin ligase to effect degradation (and inhibition) of Androgen Receptor. The present disclosure exhibits a broad range of pharmacological activities associated with compounds according to the present disclosure, consistent with the degradation/inhibition of Androgen Receptor.

26 Claims, 336 Drawing Sheets

(56) References Cited

U.S. PATENT DOCUMENTS

| | | |
|---|---|---|
| 7,109,219 B2 | 9/2006 | Tsuruoka et al. |
| 7,153,867 B2 | 12/2006 | Shah et al. |
| 7,208,157 B2 | 4/2007 | Sakamoto et al. |
| 7,468,380 B2 | 12/2008 | Tsuruoka et al. |
| 8,012,997 B2 | 9/2011 | Robarge et al. |
| 8,481,568 B2 | 7/2013 | Muller et al. |
| 8,765,176 B2 | 7/2014 | Yamamoto et al. |
| 8,921,378 B2 | 12/2014 | Tormakangas et al. |
| 9,500,653 B2 | 11/2016 | Crews et al. |
| 9,632,089 B2 | 4/2017 | Crews et al. |
| 9,796,698 B2 | 10/2017 | Muller et al. |
| 9,801,868 B2 | 10/2017 | Muller et al. |
| 10,047,151 B2 | 8/2018 | Lopez-Girona et al. |
| 10,118,933 B2 | 11/2018 | Wohlfahrt et al. |
| 10,584,101 B2 * | 3/2020 | Crew ................. A61K 47/10 |
| 10,844,021 B2 | 11/2020 | Crew et al. |
| 11,236,051 B2 | 2/2022 | Crew et al. |
| 11,660,267 B2 | 5/2023 | Coric et al. |
| 2007/0254933 A1 | 11/2007 | Jung et al. |
| 2008/0051432 A1 | 2/2008 | Zhang |
| 2008/0214501 A1 | 9/2008 | Zhengying et al. |
| 2009/0035362 A1 | 2/2009 | Shih et al. |
| 2009/0142297 A1 | 6/2009 | Muller et al. |
| 2010/0048517 A1 | 2/2010 | Hu et al. |
| 2011/0196150 A1 | 8/2011 | Man et al. |
| 2012/0270800 A1 | 10/2012 | Verdine et al. |
| 2014/0079636 A1 | 3/2014 | Chimmanamada |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0291562 A1 | 10/2015 | Crew et al. |
| 2015/0344473 A1 | 10/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0304450 A1 | 10/2016 | Liang et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0134684 A1 | 5/2018 | Bradner et al. |
| 2018/0228907 A1 | 8/2018 | Crew et al. |
| 2020/0095205 A1 * | 3/2020 | Crew ................. A61K 31/506 |
| 2020/0155689 A1 | 5/2020 | Crew et al. |
| 2020/0155690 A1 | 5/2020 | Crew et al. |
| 2021/0009528 A1 | 1/2021 | Crew et al. |
| 2021/0040044 A1 | 2/2021 | Crew et al. |
| 2021/0087170 A1 | 3/2021 | Fan et al. |
| 2021/0113557 A1 * | 4/2021 | Crew ................. A61K 45/06 |
| 2021/0353621 A1 * | 11/2021 | Peck ................. A61K 9/20 |
| 2022/0089570 A1 | 3/2022 | Crew et al. |
| 2022/0184078 A1 * | 6/2022 | Chirnomas ......... A61K 31/501 |
| 2022/0259154 A1 * | 8/2022 | Berlin ................. A61K 31/496 |
| 2022/0313826 A1 | 10/2022 | Phillips et al. |
| 2023/0012321 A1 * | 1/2023 | Allan ................. C07D 231/16 |
| 2023/0082997 A1 * | 3/2023 | Berlin ................. A61K 45/06 |
| 2023/0084249 A1 * | 3/2023 | Berlin ................. C07D 401/14 |
| 2023/0128132 A1 | 4/2023 | Crew et al. |

FOREIGN PATENT DOCUMENTS

| | | |
|---|---|---|
| CN | 103688176 A | 3/2014 |
| EP | 2985285 | 2/2016 |
| JP | A 2004-525889 | 8/2004 |
| JP | A 2010-502627 | 1/2010 |
| JP | 2013508447 A | 3/2013 |
| JP | 2014511895 A | 5/2014 |
| JP | 7061135 B2 | 4/2022 |
| KR | 101859074 B1 | 5/2018 |
| KR | 102119465 B1 | 6/2020 |
| RU | 2298554 C2 | 5/2007 |
| RU | 2310651 C2 | 11/2007 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 1999/031061 | 6/1999 |
| WO | WO 2000/066119 | 11/2000 |
| WO | WO 2002/000617 | 1/2002 |
| WO | WO 2002/066512 | 8/2002 |
| WO | WO 2002/100845 | 12/2002 |
| WO | WO 2006/113942 | 10/2006 |
| WO | WO 2007/106670 | 9/2007 |
| WO | WO 2008/011392 | 1/2008 |
| WO | WO 2009/015254 | 1/2009 |
| WO | WO 2010/053732 A1 | 5/2010 |
| WO | WO 2010/141805 | 12/2010 |
| WO | WO 2011/008260 | 1/2011 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/106643 | 7/2013 |
| WO | WO 2013/106646 | 7/2013 |
| WO | WO 2013/170147 | 11/2013 |
| WO | WO-2014015157 A2 | 1/2014 |
| WO | WO 2014/108452 | 7/2014 |
| WO | WO 2014/123418 | 8/2014 |
| WO | WO 2015/000868 | 1/2015 |
| WO | WO 2015/038649 A1 | 3/2015 |
| WO | WO-2015114314 A1 | 8/2015 |
| WO | WO 2015/134464 A2 | 9/2015 |
| WO | WO 2015/160845 | 10/2015 |
| WO | WO 2016/105518 A1 | 6/2016 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197032 A1 | 12/2016 |
| WO | WO 2016/197114 | 12/2016 |
| WO | WO 2017/011590 | 1/2017 |
| WO | WO 2017/030814 | 2/2017 |
| WO | WO 2017/079267 | 5/2017 |
| WO | WO-2017184995 A1 | 10/2017 |
| WO | WO-2017185031 A1 | 10/2017 |
| WO | WO-2017185034 A1 | 10/2017 |
| WO | WO 2017/197051 | 11/2017 |
| WO | WO-2017197056 A1 | 11/2017 |
| WO | WO-2018098280 A1 | 5/2018 |
| WO | WO-2018177989 A1 | 10/2018 |
| WO | WO-2020047487 A1 | 3/2020 |
| WO | WO-2020211822 A1 | 10/2020 |
| WO | WO-2021081108 A1 | 4/2021 |
| WO | WO-2021231174 A1 | 11/2021 |
| WO | WO-2021231431 A1 | 11/2021 |
| WO | WO-2023205481 A1 | 10/2023 |

OTHER PUBLICATIONS

Asangani, I.A. et al., "Therapeutic Targeting of BET Bromodomain Proteins in Castration-Resistant Prostate Cancer", Nature, 2014, 510: 278-282.

Bargagna-Mohan, et al., "Use of PROTACS as molecular probes of angiogenesis", Bioorg Med Chem Lett. 15(11) 2005, 2724-2727.

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule PROTACS", National Chem Biol. 11(8) Aug. 2015, 611-617.

Bradbury, RH, et. al, "Small-molecule androgen receptor downregulators as an approach to treatment of advanced prostate cancer", Bioorganic & Medicinal Chemistry Letters, 2011, 21: 5442-5445.

(56) References Cited

OTHER PUBLICATIONS

Buckley, et al., "HaloPROTACS: use of small molecule PROTACS to induce degradation of HaloTag fusion proteins", ACS Chem Biol. 10(8), 2015, 1831-1837.
Buckley, et al., "Small-molecule inhibitors of the interaction between the E3 ligase VHL and HIF1a", Angew Chem Int Ed Engl.51(46), Oct. 12, 2012, 11463-11467.
Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.
Burslem, et al., (2017) "Small-Molecule Modulation of Protein Homeostasis." *Chem Rev* 117(17):11269-11301.
Capitosti, S., et al., "Thalidomide analogues demonstrate dual inhibition of both angiogenesis and prostate cancer", Bioorganic & Medicinal Chemistry 12, (2004) 327-336.
Carmony, KC, et al., "PROTAC-Induced Proteolytic Targeting", Methods Mol. Biol., 2012, vol. 832, pp. 627-638.
CAS 155180-53-3 published 1994.
CAS 155255-73-5 published 1995.
CAS 1818885-25-4, indexed in the Registry file on STN CAS Online Nov. 10, 2015 (Chemical Abstracts Registry Number).
CAS 186040-53-9 published 1997.
CAS 186798-71-0 published 1997.
CAS 186798-85-6 published 1997.
CAS 534612-78-7 published 2003.
CAS Registry No. 1004933-70-3, which entered STN on Feb. 21, 2008.
CAS Registry No. 1226974-40-8, indexed in the Registry file on STN CAS Online Jun. 4, 2010.
CAS Registry No. 871986-52-6 entered STN Jan. 16, 2006.
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al, "Impact of Linker Length on the Activity of PROTACs," Mol. Biosyst., 2011, vol. 7, No. 2, pp. 359-364.
Cyrus, K. et al., "Two-Headed PROTAC: An Effective New Tool for Targeted Protein Degradation," Chembiochem., 2010, vol. 11, pp. 1531-1534.
Fischer, et al., "Structure of the DDB1-DRBN E3 Ubiquitin ligase in complex with thalidomide", Nature, vol. 000, pp. 1-5 (2014).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Guo C., et. al, "Design of oxobenzimidazoles and oxindoles as novel androgen receptor antagonists", Bioorganic & Medicinal Chemistry Letters, 2012, 22:2572-2578.

Guo, C. et al "Discovery of Aryloxy Tetramethylcyclobutanes as Novel Androgen Receptor Antagonists", J. Med. Chem. 2011, 54, 7693-7704.
Gustafson, et al., "Small-Molecule-Mediated Degradation of the Androgen Receptor through Hydrophobic Tagging", Agnew Chem Int Ed., 54: 9659-9662 (2015).
Hines, J., et al., "Posttranslational protein knockdown coupled to receptor tyrosine kinase activation with phosphoPROTACs", Proc Natl Acad Sci USA 110, 8942-8947 (2013).
Hon, et al., "Structural basis for the recognition of hydroxyproline in Hlf-1 alpha by pVHL", Nature 417, Jun. 27, 2002, 975-978.
Huang, et al., (2016) "Drugging the undruggables: exploring the ubiquitin system for drug development." *Cell Res* 26(4):484-498.
Hughes, et al., (2017) "Molecular recognition of ternary complexes: a new dimension in the structure-guided design of chemical degraders." *Essays Biochem* 61(5):505-516.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Jung, M. E. et al "Structure-Activity Relationship for Thioydantoin Androgen Receptor Antagonists for Castration-Resistant Prostate Cancer (CRPC)", J. Med. Chem. 2010, 53, 2779-2796.
Knott, Edward (1955). "Compounds containing sulphur chromophores. Part I. The action of bases on heterocyclic sulphide quarternary salts", Journal of the Chemical Society (resumed). 10.1039/jr9550000916. 949-954) (USPTO summary attached).
Kronke, et al, "Lenalidomide Causes Selective Degradation of IKZF1 and IKZF3 in Multiple Myeloma Cells", Science 343, 301-305 (2014).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, B. Y., "FAK signaling in human cancer as a target for therapeutics", Pharmacol. Ther. 146, 132-149 (2015).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Lelais, G. et al., "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a novel, potent, and WT sparing covalent inhibitor of oncogenic (L858R, ex19del) and resistent (T790M) EGFR mutants for the treatment of EGFR mutant non-small-cell lung cancers", Journal of Medicinal Chemistry 2016, 59(14), 6671-6689.
Lemmon, M.A., et al., "Cell Signaling by Receptor Tyrosine Kinases", Cell 141, 1117-1134 (2010).
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012).
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).

(56) References Cited

OTHER PUBLICATIONS

Lu, NZ, et al., "International Union of Pharmacology. LXV. The pharmacology and classification of the nuclear receptor superfamily: glucocorticoid, mineralocorticoid, progesterone, and androgen receptors", Pharmacol Rev. Dec. 2006;58(4):782-797. Review. PubMed PMID: 17132855.
Maniaci C, et al. (2017) "Homo-PROTACs: bivalent small-molecule dimerizers of the VHL E3 ubiquitin ligase to induce self-degradation." *Nat Commun* 8(1):830 1-13.
Medline Plus Trusted Health Information for You, www.nlm.nih.gov/medlineplus/cancer.html pp. 1-10, (2007).
Min, Jung-hyun, et al., "Structure of an HIV-1-alpha-pVHL complex: hydroxyproline recognition in signaling", Jun. 7, 2002, 296: 1886-1889.
Mohler, M.L., et al., Androgen receptor antagonists: a patent review (2008-2011), Expert Opinion on Therapeutic Patents, vol. 22, No. 5. pp. 541-565, (2012).
Muller, G., et al., "Amino-Substituted Thalodomide Analogs: Potent Inhibitors of TNF-α Production", Bioorganic & Medicinal Chemistry Letters 9 (1999) 1625-1630.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Ohoka, N. et al. SNIPER(TACC3) induces cytoplasmic vacuolization and sensitizes cancer cells to Bortezomib. Cancer Sci. 108, 1032-1041 (2017).
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Pepe, A. et. al., "Synthesis and structure-activity relationship studies of novel dihydropyridones as androgen receptor modulators", J. Med. Chem. 2013, 56, 8280-8297.
Poutiainen, PK, et. al., "Design, synthesis, and biological evaluation of nonsteroidal cycloalkane[d]isoxazole-containing androgen receptor modulators", J. Med. Chem. 55, 6316-6327 (2012).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).

Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Ghemical Proteomics", Bioorg Med Chem Lett. 18(22), Nov. 15, 2008, 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017.
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Toure, et al., (2016) "Small-Molecule PROTACS: New Approaches to Protein Degradation." *Angew Chem Int Ed Engl* 55(6):1966-1973.
Trewartha D, Carter K. "Advances in prostate cancer treatment", Nat Rev Drug Discov. Nov. 2013;12(11):823-824. doi: 10.1038/nrd4068. PubMed PMID: 24172327.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Winter, et al., "Phthalimide Conjugation as a strategy for in vivo target protein degradation", Science, 2015 vol. 348 (6241), pp. 1376-1381 [Pub online: May 21, 2015].
Zengerle, et al., "Selective Small Molecule Induced Degradation of the BET Bromodomain Protein BRD4" ACS Chemical Biology, Jun. 2, 2015, vol. 10, pp. 1770-1777.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Fizazi, Karim, et al, Activity and Safety of ODM-201 in Patients with Progressive Metastatic Castration-Resistant Prostate Cancer (ARADES): An Open-Label Phase 1 Dose-Escalation and Randomised Phase 2 Dose Expansion Trial, Lancet Oncol, Aug. 2014, 15(9): 975-85.
CAS RN 1323488-78-3 Registry—Entered STN: Aug. 26, 2011.
CAS RN 1323488-76-1 Registry—Entered STN: Aug. 26, 2011.
CAS RN 1323403-74-2 Registry—Entered STN: Aug. 26, 2011.
U.S. Appl. No. 15/730,728, filed Oct. 11, 2027, U.S. Pat. No. 10,584,101.
U.S. Appl. No. 16/577,901, filed Sep. 20, 2019, US 2020-009505 A1.
Belikov, V.G, "Pharmaceutical Chemistry. Chapter 2.6 Relationship between the chemical structure, properties of substances and their effect on the body," MEDpress-inform, 2007, 27-29.
Caira, M. R. et al., "Crystalline Polymorphism of Organic Compounds," Topics in Current Chemistry, Jan. 1998, 198:163-208.
CAS Registry No. 1226974-40-8 indexed in the Registry file on STN CAS Online Jun. 4, 2010, 1 page.
Chevalier-Larsen, E. et al. "Castration Restores Function and Neurofilament Alterations of Aged Symptomatic Males in a Transgenic Mouse Model of Spinal and Bulbar Muscular Atrophy," The Journal of Neuroscience, May 19, 2004, 24(20):4778-4786.
Co-pending U.S. Appl. No. 17/006,193, inventor Crew, et al, filed Aug. 28, 2020.
Co-pending U.S. Appl. No. 17/075,808, inventor Crew, et al., filed Oct. 21, 2020.
Co-pending U.S. Appl. No. 17/313,679, inventors Allan; Laura E.N. et al., filed May 6, 2021.

(56) References Cited

OTHER PUBLICATIONS

Co-pending U.S. Appl. No. 17/317,235, inventor Peck, filed May 11, 2021.
Co-pending U.S. Appl. No. 17/548,161, inventor Taylor, filed Dec. 10, 2021.
Grif, M., "Guidelines for conducting preclinical studies of drugs," Part one. 2012—944 p., under the editorship of A. N. Mironov, chapter 39, pp. 640-654, p. 640 (17 pages total).
Han, X. et al., "Discovery of ARD-69 as a Highly Potent Proteolysis Targeting Chimera (PROTAC) Degrader of Androgen Receptor (AR) for the Treatment of Prostate Cancer," J. Med. Chem., Jan. 10, 2019, 62:941-964.
Smirnova, I. G. et al., "Optical Isomerism and Biological Activity of Medicines", Moscow University Gazette, Series 2, Chemistry, 2012, 53(3):147-156.
Kharkevich, D.A. "Pharmacology: Manual", 2010, $10^{th}$ edition, 72-82.
Kümmerer, K. "Pharmaceuticals in the Environment," Annu. Rev. Environ. Resour., 2010, 35:57-75.
Mashkovskiy, M.D. "Medicaments", 14th edition, vol. 1, Moscow, 2001, p. 11. (5 pages total).
Mashkovskiy, M.D. "Medicinal Drugs", Moscow, Medicine, 1993, Part I, $12^{th}$ edition, p. 8 (4 pages total).
Neklesa, T. et al., "ARV-110: An Oral Androgen Receptor PROTAC Degrader for Prostate Cancer," Journal of Clinical Oncology, Mar. 2019, 37(7):259.
Office Action and Prior Art Search Report for Russian Application No. 2020106066/04(009395), filing date of Oct. 11, 2017, dated Jul. 30, 2020, 19 pages.
Office Action issued in Russian Application No. 2020106066/04(009395), filing date of Oct. 11, 2017, dated Jun. 22, 2021, 26 pages.
Office Action for Russian Application No. 2020106066/04(009395), filing date of Oct. 11, 2017, dated Jul. 7, 2022, 20 pages.
Office Action for Russian Application No. 2019113229/04(025529), filing date of Oct. 11, 2017, dated May 25, 2022, 30 pages.
Percy and Dyson, "The Chemistry of Synthetic Drugs" USSR, Moscow: Mir Publishing House, 1964, 12-19.
Szajewska, H. "Evidence-Based Medicine and Clinical Research: Both Are Needed, Neither Is Perfect," Ann Nutr Metab, 2018, 72(suppl 3):13-23.
Wesserling and Drewa, "Will In Vitro Tests Replace Animal Models in Experimental Oncology?" J. Tissue Sci. Eng., 2011, 2(1):1-4.
Zhulenko, V.N. and Gorshkov, V.I., Russia, Moscow, "KolosS" Publishing House, edited by Zhulenko V.N., 2008, 34-35.
Co-pending U.S. Appl. No. 17/539,679, inventor Berlin, filed Dec. 1, 2021.
U.S. Appl. No. 18/085,869, filed Dec. 21, 2022, Crew et al.
Inacio, P. "FDA Clears Phase 1 Trial of ARV-110 for Advanced Prostate Cancer," Prostate Cancer News Today, Jan. 30, 2019, retrieved from internet at https://prostatecancernewstoday.com/2019/01/30/fda-clears-phase-1-trial-arv-110-advanced-prostate-cancer/, 5 pages.
Lallous, N. et al., "Functional analysis of androgen receptor mutations that confer anti-androgen resistance identified in circulating cell-free DNA from prostate cancer patients," Genome Biology, 2016, 17(10):1-15.
Li, S. et al., "IMiD immunomodulatory compounds block C/EBPβ translation through eIF4E down-regulation resulting in inhibition of MM", Blood, May 12, 2011, 117(19):5157-5165.
PubChem CID No. 134414307, "Bavdegalutamide," Created Jun. 23, 2018, modified Jan. 7, 2023, retrieved from the internet at https://pubchem.ncbi.nlm.nih.gov/compound/134414307, 15 pages.

Trial of ARV-110 in Patients with Metastatic Castration Resistant Prostate Cancer (MCRPC). ClinicalTrials.gov Identifier: NCT03888612 (first posted on Mar. 25, 2019). Retrieved from https://clinicaltrials.gov/ct2/show/NCT03888612, 10 pages.
Arvinas, Inc., "Arvinas Presents New Preclinical Data on Oral Androgen Receptor PROTAC at ASCO 2017 Genitourinary Cancers Symposium", Press Release (Feb. 17, 2017); 1 page.
[Author Unknown] "Abiraterone Mylan (abiraterone acetate)", European Medicines Agency Science Medicines Health (Aug. 1, 2021) [online] https://www.ema.europa.eu/en/documents/overview/abiraterone-mylan-epar-medicine-overview_en.pdf (Access Date: Aug. 21, 2023); 2 pages.
[Author Unknown] "VCaP" ATCC [Online] https://www.atcc.org/products/crl-2876 (May 19, 2021); 7 pages.
Berge, S. M., et al., "Pharmaceutical salts", Journal of Pharmaceutical Sciences (1977); 66(1): 1-19.
Brittain, H. G. (Ed.), "Polymorphism in Pharmaceutical Solids Second Edition", Drugs and Pharmaceutical Sciences, CRC Press (2009); vol. 192: 229 pages.
Caro-Maldonado, A., et al., "Low-dose statin treatment increases prostate cancer aggressiveness", Oncotarget (2018); 9(2): 1494-1504.
Fleisher, D., et al., "Improved oral drug delivery: solubility limitations overcome by the use of prodrugs", Advanced Drugs Delivery Reviews (May 1996); 19(2): 115-130.
Gao, X., et al., "Phase 1/2 study of ARV-110, an androgen receptor (AR) PROTAC degrader, in metastatic castration-resistant prostate cancer (mCRPC)", Journal of Clinical Oncology 2022 American Society of Clinical Oncology NId (2022); 40(6); 1 page.
Heinlein, C. A., et al., "Androgen receptor in prostate cancer", Endocrine Reviews (2004); 25(2): 276-308.
Jernberg, E., et al., "Clinical relevance of androgen receptor alterations in prostate cancer," Endocrine Connections (2017); 6: R146-R161.
Jung, J., "Human tumor xenograft models for preclinical assessment of anticancer drug development", Toxicological Research (2014); 30: 1-5.
Khadka, P., et al., "Pharmaceutical particle technologies: An approach to improve drug solubility, dissolution and bioavailability", Asian Journal of Pharmaceutical Sciences (2014); 9: 304-316.
Knuuttila, M., et al., "Castration induces up-regulation of intratumoral androgen biosynthesis and androgen receptor expression in an orthotopic VCaP human prostate cancer xenograft model", The American Journal of Pathology (2014); 184(8): 2163-2173.
Morissette, S. L., et al., "High-throughput crystallization: polymorphs, salts, cocrystals and solvates of pharmaceutical solids", Advanced Drug Delivery Reviews (2004); 56(3): 275-300.
Prabu, S. L., et al., "Impurities and its importance in pharmacy", International Journal of Pharmaceutical Sciences Review and Research (2010); 3(2): 66-71.
Robinson, R. P., et al., "Discovery of the Hemifumarate and (α-L-Alanyloxy) methyl Ether as Prodrugs of an Antirheumatic Oxindole: Prodrugs for the Enolic OH Group", Journal of Medicinal Chemistry (1996); 39(1): 10-18.
Romanel, A., et al., "Plasma AR and abiraterone-resistant prostate cancer", Science Translational Medicine (2015); 7(312): 312re10; 9 pages.
Rowe, R. C., et al. (Ed.)., "Handbook of Pharmaceutical Excipients Fifth Edition", Pharmaceutical Press [online] http://www.gmpua.corn/RD/RD/HandbookPharmaceutical%20Excipients.pdf (2006); 945 pages.
Wyatt, A. W., et al., "Genomic alterations in cell-free DNA and enzalutamide resistance in castration-resistant prostate cancer", JAMA Oncology (2016); 2(12): 1598-1606.

\* cited by examiner

FIG. 2.

Table 2. Exemplary Compounds

| Ex. No. | Compound Structure | DC50 code | Dmax code | m/z+ | 1H NMR | Prepared by General Scheme |
|---|---|---|---|---|---|---|
| 1 | 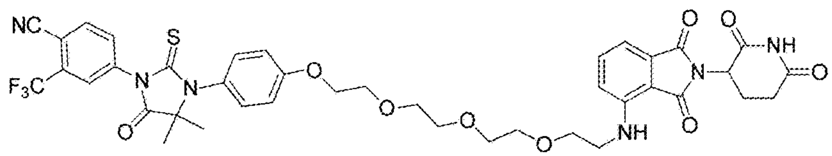 | B | B | 837.3 | ¹HNMR (400 MHz, CDCl₃): δ 1.57 (s, 6H), 2.09-2.14 (m, 1H), 2.70-2.90 (m, 3H), 3.47 (t, J = 5.2 Hz, 2H), 3.69-3.74 (m, 10H), 3.88 (t, J = 4.6 Hz, 2H), 4.17 (t, J = 4.6 Hz, 2H), 4.88-4.93 (m, 1H), 6.50 (br, 1H), 6.92 (d, J = 8.8 Hz, 1H), 7.03-7.11 (m, 3H), 7.19 (d, J = 8.8 Hz, 2H), 7.49 (t, J = 7.8 Hz, 1H), 7.83-7.86 (m, 1H), 7.97 (d, J = 8.4 Hz, 2H), 8.06 (s, 1H). | 1A |
| 2 | 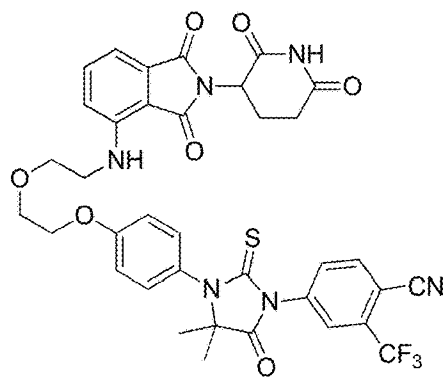 | D | B | 749.3 | ¹HNMR (400 MHz, CDCl₃): δ 1.56 (s, 6H), 2.10-2.14 (m, 1H), 2.72-2.90 (m, 3H), 3.50 (t, J = 5.4 Hz, 2H), 3.81 (t, J = 5.2 Hz, 2H), 3.90 (t, J = 4.4 Hz, 2H), 4.20 (t, J = 4.2 Hz, 2H), 4.89-4.94 (m, 1H), 6.52 (br, 1H), 6.93 (d, J = 8.4 Hz, 1H), 7.05-7.12 (m, 3H), 7.19 (d, J = 8.4 Hz, 2H), 7.49 (t, J = 7.8 Hz, 1H), 7.84 (d, J = 8.4 Hz, 1H), 7.96-7.99 (m, 2H), 8.10 (br, 1H). | 1A |

| | | | | |
|---|---|---|---|---|
| 3 |  | C | B | 925.3 | ¹HNMR (400 MHz, CDCl₃): δ 1.57 (s, 9H), 2.07-2.11 (m, 1H), 2.70-2.82 (m, 3H), 3.44-3.49 (m, 2H), 3.66-3.75 (m, 18H), 3.87-3.89 (m, 2H), 4.16-4.18 (m, 2H), 4.84-4.88 (m, 1H), 6.91 (d, $J$ = 8.4 Hz, 1H), 7.03-7.11 (m, 3H), 7.20 (t, $J$ = 7.8 Hz, 2H), 7.49 (t, $J$ = 7.8 Hz, 1H), 7.83-7.86 (m, 1H), 7.97 (d, $J$ = 8.0 Hz, 2H), 8.38 (s, 1H). | 1A |
| 4 |  | D | B | 793.3 | ¹HNMR (400 MHz, CD₃OD): δ 1.43 (s, 6H), 1.93-1.98(m, 1H), 2.57-2.73 (m, 3H), 3.40 (t, $J$ = 5.2 Hz, 2H), 3.59-3.65 (m, 6H), 3.78 (t, $J$ = 4.4 Hz, 2H), 4.06(t, $J$ = 4.4 Hz, 2H), 4.91-4.95 (m, 1H), 6.93-7.00 (m, 4H), 7.15 (d, $J$ = 8.8 Hz, 2H), 7.41-7.45 (m, 1H), 7.87-7.90 (m, 1H), 8.04-8.06(m, 2H). | 1A |

| | | | | |
|---|---|---|---|---|
| 5 |  | C | B | 807.4 | ¹HNMR (400 MHz, CDCl₃): δ 1.56 (s, 6H), 2.08-2.10 (m, 3H), 2.70-2.90 (m, 3H), 3.46 (t, J = 5.2 Hz, 2H), 3.65-3.73 (m, 8H), 4.11 (t, J = 6 Hz, 2H), 4.88-4.92 (m, 1H), 6.92 (d, J = 8.8 Hz, 1H), 7.03 (d, J = 8.8 Hz, 2H), 7.10 (d, J = 7.2 Hz, 2H), 7.18 (d, J = 8.8 Hz, 2H), 7.49 (t, J = 7.6 Hz, 1H), 7.84 (d, J = 8.0 Hz, 1H), 7.97-7.99 (m, 3H). | 1A |
| 6 |  | C | B | 865.3 | ¹HNMR (400 MHz, CD₃OD): δ 1.57 (s, 6H), 1.76-1.79 (m, 2H), 1.87-1.90 (m, 2H), 2.10-2.14 (m, 1H), 2.71-2.91 (m, 3H), 3.47-3.74 (m, 14H), 4.02 (t, J = 6.2 Hz, 2H), 4.88-4.93 (m, 1H), 6.48-6.49 (m, 1H), 6.91-7.02 (m, 3H), 7.10-7.20 (m, 3H), 7.49 (t, J = 7.8 Hz, 1H), 7.83-7.86 (m, 1H), 7.97-8.02 (m, 3H). | 1A |
| 7 |  | B | A | 851.3 | ¹HNMR (400 MHz, CD₃OD): δ 1.57 (s, 6H), 2.07-2.11 (m, 3H), 2.70-2.90 (m, 3H), 3.46-3.72 (m, 14H), 4.10 (t, J = 6.2 Hz, 2H), 4.88-4.92 (m, 2H), 6.48-6.49 (m, 1H), 6.91-7.26 (m, 6H), 7.49 (t, J = 7.8 Hz, 1H), 7.83-7.85 (m, 1H), 7.97-8.02 (m, 3H). | 1A |

| | | | | |
|---|---|---|---|---|
| 8 |  | C | B | 837.2 | 1HNMR (400 MHz, CDCl3): δ 1.57 (s, 6H), 2.09-2.14 (m, 1H), 2.70-2.90 (m, 3H), 3.47 (t, J = 5.2 Hz, 2H), 3.69-3.74 (m, 10H), 3.88 (t, J = 4.6 Hz, 2H), 4.17 (t, J = 4.6 Hz, 2H), 4.88-4.93 (m, 1H), 6.50 (br, 1H), 6.92 (d, J = 8.8 Hz, 1H), 7.03-7.11 (m, 3H), 7.19 (d, J = 8.8 Hz, 2H), 7.49 (t, J = 7.8 Hz, 1H), 7.83-7.86 (m, 1H), 7.97 (d, J = 8.4 Hz, 2H), 8.06 (s, 1H). | 1A |
| 9 |  | B | B | 837.2 | 1HNMR (400 MHz, CDCl3): δ 1.57 (s, 6H), 2.09-2.14 (m, 1H), 2.70-2.90 (m, 3H), 3.47 (t, J = 5.2 Hz, 2H), 3.69-3.74 (m, 10H), 3.88 (t, J = 4.6 Hz, 2H), 4.17 (t, J = 4.6 Hz, 2H), 4.88-4.93 (m, 1H), 6.50 (br, 1H), 6.92 (d, J = 8.8 Hz, 1H), 7.03-7.11 (m, 3H), 7.19 (d, J = 8.8 Hz, 2H), 7.49 (t, J = 7.8 Hz, 1H), 7.83-7.86 (m, 1H), 7.97 (d, J = 8.4 Hz, 2H), 8.06 (s, 1H). | 1A |

| | | | | | |
|---|---|---|---|---|---|
| 10 |  | B | B | 821.3 | ¹H NMR (400 MHz, CDCl₃): δ 1.57 (s, 6H), 1.86-1.89 (m, 2H), 2.04-2.09 (m, 3H), 2.71-2.90 (m, 3H), 3.43 (s, 2H), 3.55-3.63 (m, 8H), 4.10 (t, J = 6.0 Hz, 2H), 4.89-4.93 (m, 1H), 6.91 (d, J=8.8Hz, 1H), 7.02-7.05 (m, 2H), 7.10 (d, J=6.8Hz, 1H), 7.17-7.20 (m, 2H), 7.47-7.51 (m, 1H), 7.83-7.86 (m, 1H), 7.97-7.99(m, 2H), 8.07 (s, 1H). | 1A |
| 11 |  | D | B | 865.1 | ¹H NMR (400 MHz, CDCl₃): δ 1.42 (s, 6H), 1.85 (s, 3H), 1.92-1.96 (m, 3H), 2.44-2.49 (m, 1H), 2.56-2.64 (m, 2H), 3.34 (d, J = 5.2 Hz, 2H), 3.50-3.59 (m, 12H), 4.01 (d, J = 6.2 Hz, 2H), 6.86-6.94 (m, 4H), 7.13-7.16 (m, 2H), 7.38-7.42 (m, 1H), 7.86-7.89 (m, 1H), 8.03-8.05 (m, 2H). | 1A |
| 12 |  | B | A | | | 1A |

| | | | | |
|---|---|---|---|---|
| 15 |  | D | B | 753.7 | ¹HNMR (400 MHz, CDCl₃): δ 1.22 (s, 6H), 1.25 (s, 6H), 2.00-2.03 (m, 2H), 2.22 (t, J = 7.4 Hz, 2H), 2.67-2.88 (m, 8H), 3.35 (s, 2H), 3.72 (br, 4H), 4.04 (s, 1H), 4.13-4.22 (m, 2H), 4.32-4.36 (m, 1H), 5.34-5.39 (m, 2H), 6.09 (d, J = 8.0 Hz, 1H), 6.67 (d, J = 9.2 Hz, 1H), 6.80 (d, J = 8.4 Hz, 2H), 6.96 (d, J = 1.2 Hz, 1H), 7.29-7.30 (m, 1H), 7.38 (t, J = 7.6 Hz, 1H), 7.57 (d, J = 8.8 Hz, 1H), 7.93-7.96 (m, 1H), 8.17 (s, 1H), 8.59 (s, 1H). | 3A |
| 16 |  | B | A | 825.3 | ¹H NMR (400 MHz, CD₃OD): δ 1.24 (s, 6H), 1.31 (s, 6H), 1.96-2.12 (m, 4H), 2.71-2.81 (m, 8H), 3.48 (t, J = 6.0 Hz, 2H), 3.64-3.70 (m, 8H), 4.16 (s, 1H), 4.30 (s, 1H), 5.03-5.09 (m, 1H), 6.82 (d, J = 8.8 Hz, 1H), 6.99-7.10 (m, 3H), 7.14-7.15 (m, 1H), 7.58 (t, J = 7.8 Hz, 1H), 7.74 (d, J = 8.8 Hz, 1H), 7.95-7.98 (m, 1H), 8.60-8.61 (m, 1H). | 7A |

| | | | | |
|---|---|---|---|---|
| 19 |  | D | B | 754.3 | ¹H NMR (400 MHz, CD₃OD): δ 1.21 (s, 6H), 1.25 (s, 6H), 2.19-2.24 (m, 1H), 2.32-2.42 (m, 1H), 2.75 (br, 4H), 2.83-2.88 (m, 1H), 2.90-2.95 (m, 3H), 3.73 (br,4H), 4.04 (s, 1H), 4.14 (d, J = 8.0 Hz, 1H), 4.28-4.33 (m, 3H), 4.40, 4.44 (two singles, 1H), 5.20-5.25 (m, 1H), 6.09 (d, J = 8.0 Hz, 1H), 6.67 (d, J = 8.4 Hz, 1H), 6.80 (dd, J = 8.8, 2.4 Hz, 1H), 6.96 (d, J = 2.4 Hz, 1H), 7.06 (d, J = 8.0 Hz, 1H), 7.43-7.52 (m, 2H), 7.57 (d, J = 8.8 Hz. 1H), 7.93 (dd, J = 8.8, 2.4 Hz, 1H), 8.20 (br, 1H),8.57-8.58 (m, 1H). | 6A |
| 20 |  | D | B | 767.4 | ¹H NMR (400 MHz, CDCl₃): δ 1.22-1.25 (m, 12H), 2.01-2.02 (m, 2H), 2.59-2.69 (m, 4H), 2.75-2.91 (m, 4H), 3.39-3.40 (m, 2H), 3.73 (s, 4H), 4.04 (s, 1H), 4.14 (d, J = 8.0 Hz, 1H), 4.89-4.94 (m, 1H), 6.06 (d, J = 7.6 Hz, 1H), 6.67 (d, J = 8.8 Hz. 1H), 6.80 (d, J = 6.0 Hz, 2H), 6.89-6.97 (m, 2H), 7.12 (d, J = 7.2 Hz, 1H), 7.52-7.58 (m, 2H), 7.92-8.01 (m, 2H), 8.58 (s, 1H). | 7A |

| | | | | |
|---|---|---|---|---|
| 23 |  | B | A | 843.4 | ¹H NMR (400 MHz, CD₃OD): δ 1.18 (s, 6H), 1.24 (s, 6H), 1.50-1.66 (m, 4H), 2.08-2.14 (m, 1H), 2.39-2.75 (m, 13H), 2.81-2.86 (m, 3H), 4.11 (s, 1H), 4.23 (t, $J$ = 5.4 Hz, 2H), 4.29 (s, 1H), 4.33-4.44 (m, 2H), 5.07-5.11 (m, 1H), 7.16-7.21 (m, 2H), 7.26-7.35 (m, 4H), 7.41-7.45 (m, 1H), 7.69 (d, $J$ = 8.0 Hz, 2H), 7.86 (d, $J$ = 8.8 Hz, 1H). | 8A |
| 24 |  | B | A | 825.3 | ¹H NMR (400 MHz, CD₃OD): δ 1.24 (s, 6H), 1.31 (s, 6H), 1.93-1.98 (m, 2H), 2.06-2.12 (m, 1H), 2.67-2.86 (m, 9H), 3.37 (t, $J$ = 6.8 Hz, 2H), 3.61-3.72 (m, 8H), 4.15 (s, 1H), 4.31 (s, 1H), 4.63 (s, 1H), 5.03-5.08 (m, 1H), 6.82-6.89 (m, 2H), 6.99-7.04 (m, 2H), 7.15 (d, $J$ = 2.4 Hz, 1H), 7.56 (d, $J$ = 8.4 Hz, 1H), 7.74 (d, $J$ = 8.8 Hz, 1H), 7.96-7.99 (m, 1H), 8.62 (d, $J$ = 2.4 Hz, 1H). | 7A |

FIG. 2 Continued.

| | | | | |
|---|---|---|---|---|
| 27 | [structure] | C | A | 856.9 | 1HNMR (400 MHz, CD3OD): δ 1.24 (s, 6H), 1.30 (s, 6H), 1.87-2.12 (m, 6H), 2.57-2.85 (m, 16H), 3.41 (t, J = 8.0 Hz, 2H), 4.17 (s, 1H), 4.35 (s, 1H), 5.02-5.07 (m, 1H), 7.05 (t, J = 8.0 Hz, 2H), 7.24 (d, J = 8.0 Hz, 1H), 7.36 (s, 3H), 7.55 (t, J = 8.0 Hz, 1H), 7.76 (d, J = 4.0 Hz, 2H), 7.92 (d, J = 12.0 Hz, 1H). | 11A |
| 28 | [structure] | B | B | 921.5 | 1H NMR (400 MHz, CD3OD): δ 1.24 (s, 6H), 1.29 (s, 6H), 1.40-1.44 (m, 2H), 1.62-1.72 (m, 4H), 1.88-1.94 (m, 2H), 2.05-2.12 (m, 1H), 2.67-2.83 (m, 5H), 3.40-3.48 (m, 4H), 3.56 (t, J = 5.6 Hz, 2H), 4.15-4.17 (m, 1H), 4.29 (s, 1H), 5.01-5.05 (m, 1H), 6.95-7.02 (m, 1H), 7.01-7.10 (m, 2H), 7.14 (d, J = 2.2 Hz, 1H), 7.30 (d, J = 8.0 Hz, 2H), 7.54 (t, J = 8.0 Hz, 1H), 7.71-7.74 (m, 3H). | 12A |

| | | | | |
|---|---|---|---|---|
| 29 |  | B | A | 843.7 | $^1$H NMR (400 MHz, DMSO-d6): δ 1.12 (s, 6H), 1.21 (s, 6H), 1.79-1.82 (m, 2H), 1.99-2.05 (m, 2H), 2.33 (s, 1H), 2.55-2.67 (m, 5H), 2.82-2.91 (m, 2H), 3.48-3.61 (m, 10H), 4.05 (d, J = 9.2 Hz, 1H), 4.30 (s, 1H), 5.05-5.09 (m, 1H), 6.54-6.57 (m, 1H), 6.86 (d, J = 8.8 Hz, 1H), 6.99-7.02 (m, 1H), 7.07-7.10 (m, 1H), 7.21 (d, J = 2.0 Hz, 1H), 7.44-7.49 (m, 1H), 7.62 (d, J = 9.2 Hz, 1H), 7.90 (d, J = 8.8 Hz, 1H), 7.95-7.98 (m, 1H), 8.13 (s, 2H), 8.62 (s, 1H), 11.11 (s, 1H). | 12A |
| 30 |  | A | A | 809.8 | $^1$HNMR (400 MHz, CD$_3$OD): δ 1.13 (s, 6H), 1.18 (s, 6H), 1.52-1.65 (m, 4H), 2.01-2.09 (m, 1H), 2.18-2.54 (m, 2H), 2.61-3.03 (m, 15 H), 4.05-4.07 (m, 1H), 4.13-4.19 (m, 3H), 4.29-4.39 (m, 2H), 4.99-5.04 (m, 1H), 6.87-6.89 (m, 1H), 6.97-7.05 (m, 3H), 7.23-7.25 (m, 2H), 7.60-7.67 (m, 4H). | 13A |

| | | | | | |
|---|---|---|---|---|---|
| 31 |  | B | A | 809.8 | ¹H NMR (400 MHz, CD₃OD): δ 1.25 (s, 6H), 1.30 (s, 6H), 1.71-1.73 (m, 4H), 2.16-2.23 (m, 1H), 2.47-2.74 (m, 3H), 2.78-2.79 (m, 3H), 2.82-3.16 (m, 11H), 4.17-4.19 (m, 1H), 4.31-4.34 (m, 3H), 4.41-4.52 (m, 2H), 5.15-5.20 (m, 1H), 7.00 (dd, J = 8.8, 2.4 Hz, 1H), 7.14, 7.15 (two singles, 1H), 7.25-7.27 (m, 1H), 7.35-7.37 (m, 2H), 7.42-7.44 (m, 1H), 7.50-7.54 (m, 1H), 7.71-7.79 (m, 4H). | 13A using imide from scheme 6a |
| 32 |  | B | A | 840.3 | ¹HNMR (400 MHz, CD₃OD): δ 1.25 (s, 6H), 1.30 (s, 6H), 1.72-1.74 (m, 4H), 2.11-2.16 (m, 1H), 2.70-3.12 (m, 17H), 3.44 (t, J = 6.0 Hz, 2H), 4.17 (s, 1H), 4.31 (s. 1H), 4.61 (br. 1H), 5.06-5.11 (m, 1H), 7.00 (dd, J = 8.8 Hz, 1H), 7.12-7.15 (m, 2H), 7.33-7.38 (m, 3H), 7.73-7.79 (m, 3H). | 11a |
| 33 |  | A | A | 796.7 | ¹H NMR (400 MHz, CD₃OD): δ 1.08 (s, 6H), 1.18 (s, 6H), 1.46-1.52 (m, 2H), 1.56-1.64 (m, 2H), 1.76-1.83(m, 2H), 2.05-2.09 (m, 1H), 2.37-2.42 (m, 1H), 2.48-2.53 (m, 2H), 2.58-2.69 (m, 5H), 2.76-2.84 (m, 1H), 3.61-3.67 (m, | 6a |

| | | | | |
|---|---|---|---|---|
| 34 |  | A | A | 823.4 | 4H), 4.04-4.09 (m, 3H), 4.18 (s, 1H), 4.27-4.38 (m, 2H), 5.03-5.07 (m, 1H), 6.76 (d, J = 8.8 Hz, 1H), 6.88 (dd, J = 8.8, 2.4 Hz, 1H), 7.03 (d, J = 2.0 Hz, 1H), 7.11 (d, J = 8.0 Hz, 1H), 7.28 (d, J = 7.6 Hz, 1H), 7.62 (d, J = 8.8 Hz, 1H), 7.62-7.64 (m, 1H), 7.88 (dd, J = 9.2, 2.4 Hz, 1H), 8.51 (d, J = 2.4 Hz, 1H). ¹H NMR (400 MHz, CD₃OD): δ 1.25 (s, 6H), 1.30 (s, 6H), 1.72-1.73 (m, 4H), 2.12-2.17 (m, 1H), 2.68-3.15 (m, 17H), 4.17-4.19 (m, 1H), 4.31-4.35 (m, 3H), 5.11-5.14 (m, 1H), 7.00 (dd, J = 8.6, 2.4 Hz, 1H), 7.14-7.15 (m, 1H), 7.35-7.37 (m, 3H), 7.45-7.46 (m, 1H), 7.73-7.84 (m, 5H). 6a |
| 35 |  | A | A | 796.7 | ¹HNMR (400 MHz, CD₃OD): δ 1.12 (s, 6H), 1.22 (s, 6H), 1.45-1.62 (m, 4H), 1.75-1.82 (m, 2H), 1.95-2.03 (m, 1H), 2.33-2.45 (m, 5H), 2.57-2.61 (m, 1H), 2.88-2.95 (m, 1H), 3.59 (br, 4H), 4.05-4.10 (m, 3H), 4.24-4.31 (m, 2H), 4.37-4.41 (m, 1H), 5.05-5.10 (m, 1H), 6.87 (br, 1H), 6.99-7.06 (m, 2H), 7.17 (br, 1H), 7.20-7.21 (m, 1H). 6a |

| | | | | | |
|---|---|---|---|---|---|
| 36 |  | D | B | 797.7 | 7.61-7.63 (m, 2H), 7.89-7.91 (m, 1H), 7.96-7.98 (m, 1H), 8.63 (br, 1H), 10.96 (s, 1H).<br>¹H NMR (400 MHz, CD₃OD): δ 1.26, 1.31 (two singles, 12H), 1.73 (br, 4H), 2.14 (br, 1H), 2.65-2.76 (m, 5H), 2.79-2.86 (m, 2H),2.93 (br, 4H), 3.56 (br, 4H), 4.18 (br, 1H), 4.32 (s, 1H), 5.11-5.16 (m, 1H), 6.99-7.02 (m, 1H), 7.16 (s, 1H), 7.37-7.50 (m, 4H), 7.74-7.80 (m, 3H), 7.93 (s, 1H). | 10a |
| 37 |  | B | A | 840.7 | ¹HNMR (400 MHz, CD₃OD): δ 1.25 (s, 6H), 1.30 (s, 6H), 1.73-1.75 (m, 4H), 2.11-2.18 (m, 1H), 2.68-2.80 (m, 9H), 2.84-2.90 (m, 2H), 2.92-3.15 (m, 6H), 3.67-3.70 (m, 2H), 4.18 (s, 1H), 4.31 (s, 1H), 5.07-5.12 (m, 1H), 6.99-7.02 (m, 1H), 7.13-7.16 (m, 2H), 7.33-7.39 (m, 3H), 7.72-7.79 (m, 3H). | 11a |

| | | | | |
|---|---|---|---|---|
| 38 |  | A | A | 794.7 | 8a | ¹HNMR (400 MHz, CD₃OD): δ 1.24 (s, 6H), 1.30 (s, 6H), 1.44-1.45 (m, 4H), 1.65-1.77 (m, 4H), 2.18-2.23 (m, 1H), 2.49-2.60 (m, 1H), 2.74-2.83 (m, 5H), 2.89-3.03 (m, 5H), 3.85 (br, 4H), 4.16 (t, J = 4.4 Hz, 1H), 4.30 (s, 1H), 4.46-4.56 (m, 2H), 5.17-5.22 (m, 1H), 6.92 (d, J = 9.2 Hz, 1H), 6.98-7.01 (m, 1H), 7.14 (d, J = 2.4 Hz, 1H), 7.48-7.50 (m, 2H), 7.66-7.75 (m, 3H), 8.01-8.04 (m, 1H), 8.65 (d, J = 2.4 Hz, 1H). |
| 39 |  | A | A | 797.7 | 10a | ¹H NMR (400 MHz, CD₃OD): δ 1.14 (s, 6H), 1.23 (s, 6H), 1.43-1.54 (m, 2H), 1.60-1.65 (m, 2H), 1.97-2.06 (m, 2H), 2.33-2.45 (m, 4H), 2.57-2.61 (m, 2H), 2.66-2.69 (m, 2H), 2.84-2.93 (m, 1H), 3.16-3.30 (m, 5H), 4.07 (d, J = 8.8 Hz, 1H), 4.33 (s, 1H), 5.07-5.12 (m, 1H), 6.99-7.02 (m, 1H), 7.21-7.22 (m, 1H), 7.31-7.33 (m, 2H), 7.38 (br. 1H), 7.64-7.66 (m, 1H), 7.75-7.79 (m, 3H), 7.91 (d, J = 8.8 Hz, 1H), 11.11 (s, 1H). |

| | | | | | |
|---|---|---|---|---|---|
| 40 |  | B | A | 807.4 | 1H NMR (300 MHz, DMSO): δ 11.11 (s, 1H), 7.94–7.92 (d, J = 8.4 Hz, 1H), 7.79–7.63 (m, 4H), 7.36–7.18 (m, 6H), 7.14–6.96 (m, 1H), 5.13–4.98 (m, 1H), 4.31 (s, 1H), 4.09–4.11 (d, J = 8.4 Hz, 1H), 3.45 (s, 4H), 3.01–2.79 (m, 3H), 2.69–2.58 (m, 2H), 2.46 (s, 3H), 2.42–2.27 (m, 2H), 2.08–1.94 (m, 1H), 1.66–1.53 (m, 2H), 1.48–1.39 (m, 2H), 1.31 (s, 4H), 1.21 (s, 6H), 1.15 (s, 6H) | 10a |
| 41 |  | A | A | 810.3 | 1H NMR (400 MHz, CD3OD): δ 1.12 (s, 6H), 1.22 (s, 6H), 1.46–1.49 (m, 2H), 1.58–1.60 (m, 2H), 1.78–1.82 (m, 2H), 2.03–2.06 (m, 4H), 2.54–2.62 (m, 4H), 2.85–2.93 (m, 1H), 3.17 (d, J = 4.8 Hz, 1H), 3.58 (br, 4H), 4.05–4.07 (m, 1H), 4.20 (t, J = 6.4 Hz, 2H), 4.31 (s, 1H), 5.10–5.14 (m, 1H), 6.88–6.90 (m, 1H), 7.01 (dd, J = 8.8, 2.4 Hz, 1H), 7.21 (d, J = 2.4 Hz, 1H), 7.36 (dd, J = 8.2, 2.4 Hz, 1H), 7.43–7.44 (m, 1H), 7.62–7.64 (m, 1H), 7.84 (d, J = 8.4 Hz, 1H), 7.90 (d, J = 8.8 Hz, 1H), 7.97–7.99 (m, 1H), 8.63–8.64 (m, 1H), 11.11 (s, 1H). | 6a |

| | | | | | |
|---|---|---|---|---|---|
| 42 |  | D | B | 740.3 | H-NMR13-PH-ARV-LS-019-B-0: (300 MHz, CD3OD) δ 8.70 (s, 1H), 8.11 – 8.08 (d, J = 11.1 MHz, 1H), 7.75 -7.72 (d, J = 8.7 MHz, 1H), 7.52 -- 7.49 (m, 1H), 7.43 - 7.40 (d, J = 7.2 MHz, 1H), 7.26 - 7.23 (d, J = 7.8 MHz, 1H), 7.12 (s, 1H), 7.01 - 6.95 (m, 2H), 5.20 - 5.16 (m, 1H), 5.02 - 4.98 (m, 1H), 4.70 - 4.65 (m, 3H), 4.46 - 4.43 (d, J = 6.9 MHz, 2H), 4.24 - 4.20 (m, 2H), 3.58 - 3.81 (m, 2H), 3.25 - 3.22 (m, 6H), 3.03 - 2.75 (m, 2H), 2.74 - 2.60 (m, 4H), 2.57 - 2.34 (m, 1H), 2.29 - 2.10 (m, 1H), 1.97 - 1.87 (m, 4H), 1.67 - 1.64 (m. 2H). | 14a |
| 43 |  | D | B | 739.2 | H-NMR- PH-ARV-LS-019-C-0: (400 MHz, CD3OD) δ 7.83 - 7.81 (d, J = 8.8 MHz, 2H), 7.71 -7.69 (d, J = 8.8 MHz, 1H), 7.51 - 7.47 (m, 1H), 7.40 - 7.38 (d, J = 7.9 MHz, 1H). 7.23 - 7.21 (d, J = 8 MHz. 1H), 7.09 - 7.06 (m, 3H), 6.96 - 6.93 (d, J = 10.8 MHz, 1H), 5.18 - 5.14 (m, 1H), 5.00 - 4.99 (m, 1H), 40.65 - 4.60 (m, 1H), 4.48 - 4.37 (m, 2H), 4.21 - 4.18 (m, 2H), 4.05 - 4.02 (m, 2H), 3.69 - 3.67 (m, 2H), 3.26 - 3.14 (m, | 14a |

| | | | | | |
|---|---|---|---|---|---|
| 44 |  | A | A | 793.5 | 1H NMR (300 MHz, Methanol-d4) δ 7.78- 7.63 (m, 4H), 7.43 (d, J = 2.2 Hz, 1H), 7.36-7.25 (m, 3H), 7.10 (d, J = 2.4 Hz, 1H), 6.95 (dd, J = 8.8, 2.5 Hz, 1H), 5.06 (dd, J = 12.4, 5.4 Hz, 1H), 4.26 (s, 1H), 4.14 (d, J = 5.1 Hz, 1H), 3.65 (s, 4H), 3.23 (d, J = 5.3 Hz, 4H), 2.99 (t, J = 8.2 Hz, 2H), 2.89-2.62 (m, 5H), 2.15- 2.02 (m, 1H), 1.74 (h, J = 7.8 Hz, 4H), 1.43 (q, J = 7.6 Hz, 2H), 1.23 (d, J = 16.2 Hz, 6H), 1.15 (d, J = 16.2 Hz, 6H) | 10a |
| 45 |  | A | A | 779.5 | 1H NMR (300 MHz, Chloroform-d) δ 8.05 (s, 1H), 7.69 (dd, J = 8.2, 5.8 Hz, 3H), 7.55 (d, J = 8.7 Hz, 1H), 7.27 (d, J = 2.8 Hz, 2H), 7.05 (d, J = 8.4 Hz, 1H), 6.90 (m, 1H), 6.75(m, 1H), 6.14 (d, J = 2.4 Hz, 1H), 4.79 (dd, J = 8.9, 2.4 Hz, 1H), 4.19 (d, J = 8.1 Hz, 1H), 3.92 (s, 51H), 3.88- 3.39 (m, 4H), 3.00-2.49 (m, 9H), 2.14-2.12 (m, 1H), 1.94-1.68 (m, 6H), 1.32- 6H), 2.91 - 2.74 (m, 2H), 2.66 - 2.59 (m, 4H), 2.47 - 2.41 (m, 1H), 2.21 - 2.11 (m, 1H), 1.95 - 1.85 (m, 4H), 1.65 - 1.61 (m, 2H) | 10a |

FIG. 2 Continued.

| | | | | | |
|---|---|---|---|---|---|
| 46 | [Structure: glutarimide-phthalimide-F-piperazine-(CH2)5-phenyl-C(O)NH-tetramethylcyclobutyl-O-phenyl-Cl-CN] | A | A | 825.4 | 1.30 (m, 1H), 1.23 (s, 6H), 1.19 (s, 6H).<br>1H NMR (400 MHz, DMSO): δ 11.11 (s, 1H), 7.90 (d, J = 8.8 Hz, 1H), 7.78-7.71 (m, 4H), 7.44 (d, J = 7.2 Hz, 1H), 7.30 (d, J = 8.0 Hz, 2H), 7.21 (s, 1H), 7.01 (d, J = 8.8 Hz, 1H), 5.13-5.08 (m, 1H), 4.32 (s, 1H), 4.06 (d, J = 9.2 Hz, 1H), 3.40-3.26 (m, 5H), 3.25-3.22 (m, 4H), 2.91-2.84 (m, 1H), 2.69-2.59 (m, 3H), 2.34-2.27 (m, 2H), 2.10-2.02 (m, 1H), 1.65-1.58 (m, 2H), 1.48-1.40 (m, 2H), 1.38-1.30 (m, 4H), 1.22 (s, 6H), 1.13 (s, 6H) | 10a |
| 47 | [Structure: glutarimide-isoindolinone-O-(CH2)4-phenyl-C(O)NH-tetramethylcyclobutyl-O-phenyl-Cl-CN] | D | B | 697.3 | 1H NMR (400 MHz, DMSO-d6): δ 1.14 (s, 6H), 1.23 (s, 6H), 1.77 (br, 4H), 1.98-2.00 (m, 1H), 2.43-2.48 (m, 3H), 2.56-2.61 (m, 1H), 2.69-2.73 (m, 2H), 2.87-2.96 (m, 1H), 4.06-4.15 (m, 3H), 4.20-4.25 (m, 1H), 4.33-4.39 (m, 2H), 5.09-5.13 (m, 1H), 7.00-7.02 (m, 1H), 7.21-7.25 (m, 2H), 7.30-7.35 (m, 3H), 7.48 (t, J = 7.6 Hz, 1H), 7.75-7.79 (m, 3H), 7.91 (d, J = 8.8 Hz, 1H), 10.98 (s, 1H). | 15A |

| | | | | | |
|---|---|---|---|---|---|
| 48 |  | D | B | 711.3 | ¹HNMR (400 MHz, CD₃OD): δ 1.25 (s, 6H), 1.30 (s, 6H), 1.53-1.60 (m, 2H), 1.73-1.80 (m, 2H), 1.84-1.91 (m, 2H), 2.15-2.21 (m, 1H), 2.45-2.56 (m, 1H), 2.75 (t, J = 7.6 Hz, 2H), 2.81-2.83 (m, 1H), 2.89-2.93 (m, 1H), 4.13-4.18 (m, 3H), 4.30 (s, 1H), 4.35-4.44 (m, 2H), 5.15 (d, J = 13.6 Hz, 1H), 7.00 (d, J = 8.8 Hz, 1H), 7.14 (d, J = 2.4 Hz, 1H), 7.20 (d, J = 8.4 Hz, 1H), 7.33 (d, J = 8.0 Hz, 2H), 7.39 (d, J = 7.6 Hz, 1H), 7.49 (t, J = 8.0 Hz, 1H), 7.73-7.76 (m, 3H). | 15a |
| 49 |  | D | B | 727.3 | ¹HNMR (400 MHz, CD₃OD): δ 1.25 (s, 6H), 1.30 (s, 6H), 1.90-1.96 (m, 2H), 2.12-2.19 (m, 1H), 2.38-2.49 (m, 1H), 2.74-2.80 (m, 3H), 2.86-2.95 (m, 1H), 3.55-3.58 (m, 2H), 3.85-3.86 (m, 2H), 4.16-4.18 (m, 1H), 4.30-4.33 (m, 3H), 4.44-4.50 (m, 2H), 5.13-5.17 (m, 1H), 6.99-7.02 (m, 1H), 7.14-7.15 (m, 1H), 7.26-7.32 (m, 3H), 7.42-7.44 (m, 1H), 7.50-7.54 (m, 1H), 7.71-7.75 (m, 3H). | 15a |

| | | | | | |
|---|---|---|---|---|---|
| 50 |  | D | B | 741.3 | ¹H NMR (400 MHz, CD₃OD): δ 1.14 (s, 6H), 1.23 (s, 6H), 1.49-1.56 (m, 2H), 1.59-1.66 (m, 2H), 1.95-1.99 (m, 1H), 2.35-2.45 (m, 1H), 2.55-2.60 (m, 1H), 2.64 (t, J = 7.2 Hz, 2H), 2.86-2.95 (m, 1H), 3.49 (t, J = 6.4 Hz, 2H), 3.72-3.74 (m, 2H), 4.07 (d, J = 9.2 Hz, 1H), 4.21-4.27 (m, 3H), 4.33-4.38 (m, 2H), 5.08-5.12 (m, 1H), 7.01 (dd, J = 8.8, 2.4 Hz, 1H), 7.22 (d, J = 2.4 Hz, 1H), 7.26-7.28 (m, 3H), 7.31-7.33 (m, 1H), 7.48 (t, J = 7.6 Hz, 1H), 7.73-7.76 (m, 3H), 7.91 (d, J = 8.8 Hz, 1H), 10.97 (s, 1H). | 15a |
| 51 |  | D | B | 755.3 | ¹HNMR (400 MHz, CD₃OD): δ 1.25 (s, 6H), 1.30 (s, 6H), 1.38-1.46 (m, 2H), 1.60-1.71 (m, 4H), 2.11-2.23 (m, 1H), 2.41-2.52 (m, 1H), 2.68 (t, J = 7.2 Hz, 2H), 2.73-2.79 (m, 1H), 2.86-2.95 (m, 1H), 3.56 (t, J = 6.0 Hz, 2H), 3.82 (t, J = 4.4 Hz, 2H), 4.15-4.18 (m, 1H), 4.28-4.30 (m, 2H), 4.39-4.49 (m, 2H), 4.59 (s, 1H), 5.14 (d, J = 13.2 Hz, 1H), 7.00 (d, J = 8.8 Hz, 1H), 7.14 (d, J = 2.4 Hz, 1H), 7.23-7.29 (m, 3H), 7.40-7.42 (m, 1H), 7.50 (t, J | 15a |

| | | | | | |
|---|---|---|---|---|---|
| 52 |  | D | B | 769.3 | 15a<br><br>$^1$HNMR (400 MHz, CD$_3$OD): δ 1.25 (s, 6H), 1.31 (s, 6H), 1.36-1.46 (m, 4H), 1.56-1.67 (m, 4H), 2.11-2.17 (m, 1H), 2.41-2.52 (m, 1H), 2.65-2.68 (m, 2H), 2.71-2.78 (m, 1H), 2.83-2.90 (m, 1H), 3.53-3.56 (m, 2H), 3.81-3.83 (m, 2H), 4.16-4.18 (m, 1H), 4.28-4.30 (m, 3H), 4.40-4.50 (m, 2H), 5.11-5.16 (m, 1H), 6.99-7.01 (m, 1H), 7.14-7.15 (m, 1H), 7.24-7.30 (m, 3H), 7.40-7.41 (m, 1H), 7.48-7.52 (m, 1H), 7.73-7.75 (m, 3H). = 7.6 Hz, 1H), 7.70-7.75 (m, 3H). |
| 53 |  | D | B | 780.6 | 16a<br><br>$^1$H NMR (400 MHz, CD$_3$OD): δ 1.26-1.28 (m, 3H), 1.61-1.64 (m, 2H), 1.70-1.71 (m, 4H), 2.03-2.07 (m, 3H), 2.09-2.14 (m, 1H), 2.19-2.23 (t, $J$ = 7.6 Hz, 2H), 2.55-2.64 (m, 4H), 2.70-2.76 (m, 2H), 3.36-3.43 (m, 2H), 3.67 (s, 2H), 4.32-4.37 (m, 1H), 4.40-4.45 (m, 1H), 4.55-4.60 (m, 1H), 5.04-5.09 (m, 1H), 5.35-5.38 (m, 1H), 6.64 (br, 1H), 6.78 (d, $J$ = 2.4 Hz, 1H), 7.04-7.09 (m, 2H), 7.52-7.56 (m, 1H), 7.73 (d, $J$ = 2.4 Hz, 1H), 7.79-7.81 |

FIG. 2 Continued.

| # | Structure | | | ID |
|---|---|---|---|---|
| 54 | (structure: glutarimide-isoindolinone-hexyl-piperazine-phenyl-amide-tetramethylcyclobutyl-O-chlorobenzonitrile) | D | B | 807.8 | 8a |
| 55 | (structure: glutarimide-isoindolinone-O-propyl-phenyl-amide-tetramethylcyclobutyl-O-chlorobenzonitrile) | D | B | 683.3 | 15a |
| 56 | (structure: glutarimide-isoindolinone-piperazine-propyl-O-pyrazole-amide-methyl-pyrrole-chlorobenzonitrile) | B | A | 767.7 | 17a |

NMR data:

8a: H-NMR (300 MHz, DMSO) δ11.14 (s, 1H), 7.91-7.73 (m, 6H), 7.51-7.47 (m, 1H), 7.19 (s, 1H), 7.01-6.91 (m, 3H), 5.17-5.11 (m, 1H), 4.32 (s, 1H), 4.07-4.04 (d, J=9.3 Hz, 7H), 3.33-3.31 (m, 1H), 3.24-3.18 (m, 4H), 2.89-2.73 (m, 3H), 2.61-2.51 (m, 5H), 2.30-2.21 (m, 2H), 2.10-2.00 (m, 1H), 1.67-1.59 (m, 2H), 1.43-1.35 (m, 2H), 1.39-1.25 (m, 4H), 1.19 (s, 6H), 1.09 (m, 6H);

15a: ¹HNMR (400 MHz, CD₃OD): δ 1.24 (s, 6H), 1.29 (s, 6H), 2.18-2.21 (m, 3H), 2.46-2.60 (m, 1H), 2.73-2.95 (m, 4H), 4.16 (s, 3H), 4.30 (s, 1H), 4.42-4.43 (m, 2H), 5.13-5.18 (m, 1H), 6.99-7.01 (m, 1H), 7.14-7.18 (m, 2H), 7.37-7.50 (m, 4H), 7.72-7.78 (m, 4H).

17a: ¹HNMR (400 MHz, DMSO-d6): δ 1.12 (br, 3H), 1.72 (br, 2H), 1.99-2.03 (m, 1H), 2.33-2.40 (m, 3H), 2.57-2.67 (m, 2H), 2.84-2.92 (m, 1H), 3.17 (s, 1H), 3.34 (m, 6H), 4.07-4.11 (m, 1H), 4.26-4.49 (m, 5H), 5.06-5.08 (m, 1H), 6.54 (s, 1H), 6.93 (s, 1H), 7.21-7.25 (m,

FIG. 2 Continued.

| | Structure | | | NMR | ID |
|---|---|---|---|---|---|
| 57 | (structure with glutarimide-isoindolinone-O-propyl-triazole-phenyl-amide-cyclobutyl-O-phenyl-Cl-CN) | D | B | 694.2 | 1H, 7.33 (s, 1H), 7.66-7.68 (m, 1H), 7.82 (s, 1H), 7.98 (s, 1H), 8.07 (s, 1H), 8.26-8.27 (m, 1H), 11.08 (s, 1H), 13.29 (s, 1H). <br> ¹H NMR (300 MHz, DMSO-d6) 8.63-8.54 (m, 1H), 8.19-7.95 (m, 4H), 7.86-7.83 (m, 1H), 7.52-7.49 (m, 1H), 7.36-7.34 (m, 1H), 7.26-7.20 (m, 2H), 7.04-7.01 (m, 1H), 5.05-4.96 (m, 2H), 4.58-4.49 (m, 1H), 4.41-4.10 (m, 4H), 2.96-2.56 (m, 8H), 2.32-1.89 (m, 4H); | 18a |
| 58 | (structure with glutarimide-phthalimide-F-NH-hexyl-piperazine-pyridine-amide-dimethylcyclobutyl-O-phenyl-Cl-CN) | B | A | 841.3 | ¹H NMR (400 MHz, DMSO-d₆) δ1.12 (6H, s), 1.23 (6H, s), 1.31-1.41 (6H, m), 1.48-1.60 (5H, m), 2.30-2.34 (2H, m), 2.45-2.46 (2H, m), 2.54-2.60 (1H, m), 3.24-3.28 (4H, m), 3.57-3.60 (4H, m), 4.04-4.07 (1H, m), 4.30 (1H, s), 5.04-5.07 (1H, m), 6.88 (1H, d, J = 8.8 Hz), 6.94 (1H, brs), 7.00 (1H, dd, J = 8.4, 2.4 Hz), 7.10 (1H, d, J = 7.2 Hz), 7.21 (1H, d, J = 2.4 Hz), 7.57 (1H, d, J = 10.4 Hz), 7.62-7.68 (1H, m), 7.91 (1H, d, J = 8.8 Hz), 7.99 (1H, dd, J = 8.8, 2.4 Hz), 8.64 (1 H, d, J = 2.4 Hz), 11.09 (1H, s). | 19a |

| | | | | | |
|---|---|---|---|---|---|
| 59 |  | D | B | 810.3 | 20a<br>¹HNMR (400 MHz, CD₃OD): δ 1.27 (t, J = 6.8 Hz, 3H), 1.89-1.93 (m, 2H), 2.11-2.13 (m, 1H), 2.70-2.74 (m, 7H), 2.77-2.78 (d, 8H), 3.43 (t, J = 6.4 Hz, 2H), 3.59 (t, J = 6.0 Hz, 2H), 4.31-4.37 (m, 1H), 4.40-4.44 (m, 1H), 4.55-4.60 (m, 3H), 5.05-5.08 (m, 1H), 6.69 (br, 1H), 6.77 (d, J = 2.4 Hz, 1H), 7.05-7.09 (m, 2H), 7.56-7.60 (m, 1H), 7.72 (d, J = 2.4 Hz, 1H), 7.78-7.80 (m, 1H), 7.89-7.91 (m, 1H), 8.02-8.03 (m, 1H). |
| 60 |  | D | B | 722.2 | 18a<br>¹H NMR (300 MHz, DMSO) 8.57 (s, 1H), 8.05-7.94 (m, 4H), 7.87-7.84 (m, 1H), 7.53-7.48 (m, 1H), 7.35-7.32 (m, 1H), 7.26-7.20 (m, 2H), 7.04-7.01 (m, 1H), 5.05-4.81 (m, 2H), 4.57-4.50 (m, 1H), 4.41-4.22 (m, 2H), 4.14-4.07 (m, 3H), 2.92-2.77 (m, 4H), 2.65-2.55 (m, 4H), 2.05-1.90 (m, 1H), 1.81-1.69 (m, 4H), 1.53-1.40 (m, 2H) |

| | | | | | |
|---|---|---|---|---|---|
| 61 |  | D | B | 736.3 | 1H NMR (300 MHz, DMSO) 8.501 (s, 1H), 8.01-7.97 (m, 2H), 7.97-7.91 (m, 2H), 7.81-7.78 (m, 1H), 7.47-7.41 (m, 1H), 7.29-7.26 (m, 1H), 7.19-7.14 (m, 2H), 6.98-6.95 (m, 1H), 5.00-4.90 (m, 2H), 4.54-4.45 (m, 1H), 4.37-4.32 (m, 1H), 4.23-4.17 (m, 1H), 4.06-3.92 (m, 2H), 2.81-2.75 (m, 1H), 2.70-2.68 (m, 2H), 2.66-2.56 (m, 3H), 2.49-2.35 (m, 3H), 2.01-1.90 (m, 1H), 1.70-1.50 (m, 4H), 1.49-1.37 (m, 4H); | 18a |
| 62 |  | A | A | 824.3 | 1H NMR (400 MHz, CD3OD): δ 8.64-8.63 (d, J=2.0Hz, 1H), 8.18-8.15 (m, 1H), 7.81-7.68 (m, 4H), 7.13-7.11 (m, 2H), 6.99-6.96 (m, 1H), 5.14-5.09 (m, 1H), 4.60-4.51 (m, 2H), 4.29 (s, 1H), 4.15 (s, 1H), 3.83-3.81 (m, 2H), 3.72-3.65 (m, 2H), 3.59-3.56 (m, 2H), 3.46-3.44 (m, 4H), 3.31-3.29 (m, 2H), 2.88-2.82 (m, 3H), 2.77-2.70 (m, 2H), 2.14-2.11 (m, 1H), 1.82-1.65 (m, 4H), 1.29 (s, 6H), 1.21 (s, 6H); | 8a |

| | | | | | |
|---|---|---|---|---|---|
| 65 |  | D | B | 838.4 | H-NMR (300 MHz, CD₃OD ) δ 8.61 - 8.60 (d, J = 2.4 Hz, 1H), 7.98 - 7.95 (m, 1H), 7.81 - 7.67 (m, 4H), 7.14 - 7.13 (d, J = 2.4Hz, 1H), 7.01 - 6.97 (m, 1H), 6.86 - 6.83 (d, J = 8.7 Hz, 1H), 5.14 - 5.08 (m, 1H), 4.29 (s, 1H), 4.14 (s, 1H), 3.69 - 3.61 (m, 6H), 3.55 - 3.46 (m, 2H), 2.88 - 2.82 (m, 3H), 2.77 - 2.69 (m, 8H), 2.13 - 2.11 (m, 1H), 1.77 - 1.70 (m, 2H), 1.67 - 1.60 (m, 2H), 1.49 - 1.43 (m, 2H), 1.29 (s, 6H), 1.23 (s, 6H). | 8a |
| 66 |  | A | A | 837.4 | H-NMR (300 MHz, CD₃OD, ppm ) δ 7.80 - 7.66 (m, 6H), 7.14 (s, 1H), 7.00 - 6.98 (m, 3H), 5.14 - 5.08 (m, 1H), 4.29 (s, 1H), 4.14 (s, 1H), 3.64 - 3.60 (m, 2H), 3.50 - 3.46 (m, 2H), 3.39 - 3.32 (m, 4H), 2.92 - 2.80 (m, 3H), 2.77 - 2.65 (m, 8H), 2.14 - 2.08 (m, 1H), 1.80 - 1.62 (m, 4H), 1.52 - 1.39 (m, 2H), 1.29 (s, 6H), 1.23 (s, 6H). | 8a |

| | | | | | |
|---|---|---|---|---|---|
| 67 |  | D | B | 837.4 | H-NMR (300 MHz, CD₃OD, ppm) δ 7.80 - 7.66 (m, 6H), 7.14 (s, 1H), 7.01 - 6.97 (m, 3H), 5.14 - 5.08 (m, 1H), 4.29 (s, 1H), 4.14 (s, 1H), 3.64 - 3.61 (m, 2H), 3.55 - 3.46 (m, 2H), 3.39 - 3.33 (m, 4H), 2.92 - 2.64 (m, 11H), 2.14 - 2.08 (m, 1H), 1.80 - 1.65 (m, 4H), 1.53 - 1.38 (m, 2H), 1.30 (s, 6H), 1.22 (s, 6H). | 8a |
| 68 |  | D | B | 793.4 | H-NMR (300 MHz, CD₃OD ) δ 7.81-7.79 (d, J = 6.6 Hz, 2H), 7.73-7.71 (d, J = 6.6 Hz, 2H), 7.43-7.37 (t, J = 18.9 Hz, 2H), 7.13-7.07 (q, J = 16.8 Hz, 3H), 6.99-6.96 (q, J = 8.4 Hz, 1H), 5.17-5.12 (q, J = 13.8 Hz, 1H), 4.47-4.45 (d, J = 5.7 Hz, 2H), 4.28 (s, 1H), 4.14 (s, 1H), 4.05-4.02 (d, J = 8.1 Hz, 2H), 3.68-3.66 (d, J = 5.7 Hz, 2H), 3.18-3.12 (m, 6H), 2.91-2.86 (t, J = 13.5 Hz, 1H), 2.81-2.77 (t, J = 11.1 Hz, 3H), 2.49-2.47 (d, J = 6.3Hz, 1H), 2.19 (s, 1H), 1.76-1.72 (t, J = 10.8 Hz, 4H), 1.45 (s, 4H) , 1.28 (s, 6H) , 1.22 (s, 6H); | 8a |

| | | | | |
|---|---|---|---|---|
| 69 |  | A | A | 765.3 | H-NMR (400 MHz, CD₃OD) δ 7.77–7.66 (m, 4H), 7.37–7.35 (d, J=8.4 Hz, 3H), 7.23–7.21 (d, J=7.6 Hz, 1H), 7.13–7.12 (d, J=2.4 Hz, 1H), 6.99–6.96 (m, 1H), 5.09–5.04 (m, 1H), 4.58 (s, 1H), 4.29 (s, 1H), 4.15 (s, 1H), 3.48–3.46 (m, 4H), 2.87–2.62 (m, 9H), 2.48–2.44 (m, 2H), 2.12–2.09 (m, 2H), 1.31 (s, 6H), 1.26 (s, 6H) | 10A |
| 70 |  | A | A | 827.4 | ¹H NMR (300 MHz, CD₃OD): δ 7.94–7.87 (d, J=7.8Hz, 1H), 7.75–7.68 (d, J=7.8Hz 2H), 7.67–7.48 (m,1H), 7.41–7.12 (m, 4H), 7.11–6.95 (m, 2H), 5.18–4.99 (m, 1H), 4.58–3.99 (m 4H),3.76–3.51 (m, 1H), 3.35 (s, 4H), 2.97–2.51(m, 8H), 2.50–2.26(m, 3H), 2.19–2.04 (m, 1H), 1.76–1.44 (m, 4H), 1.43–1.31 (m, 4H),1.28–1.17(m,12H) | 21A |

| | | | | |
|---|---|---|---|---|
| 71 |  | B | A | 827.4 | ¹H NMR (300 MHz, CD₃OD): δ7.94–7.87 (d, J=7.8Hz, 1H), 7.75–7.68 (d, J=7.8Hz 2H),7.67–7.48 (m,1H), 7.41–7.12 (m, 4H), 7.11–6.95(m, 2H), 5.18–4.99 (m, 1H), 4.58–3.99 (m, 4H),3.76–3.51 (m, 1H), 3.35 (s, 4H), 2.97–2.51 (m, 8H), 2.50–2.26(m, 3H), 2.19–2.04 (m, 1H), 1.76–1.44 (m, 4H), 1.43–1.31 (m, 4H),1.28–1.17(m,12H) | 21A |
| 72 |  | A | A | 828.3 | ¹H NMR (400 MHz, DMSO-d₆) δ 1.12 (6H, s), 1.22 (6H, s) 1.23-1.26 (2H, m), 1.33-1.40 (2H, m), 1.33-1.49 (4H, m), 1.68-1.73 (2H, m), 1.97-2.01 (1H, m), 2.30-2.47 (6H, m), 2.57-2.61 (1H, m), 2.87-2.93 (1H, m), 3.57 (3H, s), 4.06 (1H, d, J = 8.8 Hz), 4.21 (2H, t, J = 6.0 Hz), 4.30 (1H, s), 4.39 (1H, d, J = 17.2 Hz), 4.56 (1H, d, J = 17.6 Hz), 5.11 (1H, dd, J = 13.2, 4.2 Hz), 6.86 (1H, d, J = 8.8 Hz), 7.00 (1H, dd, J = 8.8, 1.8 Hz), 7.21 (1H, d, J = 2.4 Hz), 7.39-7.44 (2H, m), 7.63 (1H, d, J = 9.2 Hz), 7.91 (1H, d, J = 8.8 Hz), 7.96 (1H, d, J = 8.4 Hz), 8.63 (1H, s), 11.02 (1H, s). | 22A |

FIG. 2 Continued.

| | | | | |
|---|---|---|---|---|
| 73 | (structure) | B | A | 842.3 | ¹H NMR (400 MHz, DMSO-d₆) δ1.12 (6H, s), 1.22 (6H, s), 1.23-1.26 (3H, m),1.30-1.53 (8H, m), 1.78-1.81 (2H, m), 1.99-2.06 (2H, m), 2.18-2.24 (1H, m), 2.54-2.62 (2H, m), 2.87-2.89 (1H, m), 3.51-3.58 (3H, m), 4.06 (1H, d, $J$ = 9.2 Hz), 4.27-4.31 (3H, m), 5.13 (1H, dd, $J$ = 13.2, 5.6 Hz), 6.88 (1H, d, $J$ = 8.8 Hz), 7.00 (1H, dd, $J$ = 8.8, 2.4 Hz), 7.21 (1H, d, $J$ = 2.4 Hz), 7.63 (1H, d, $J$ = 8.8 Hz), 7.72 (1H, d, $J$ = 6.8 Hz), 7.87 (1H, d, $J$ = 9.6 Hz), 7.91 (1H, d, $J$ = 8.4 Hz), 7.97 (1H, d, $J$ = 9.2 Hz), 8.63 (1H, d, $J$ = 2.0 Hz), 11.13 (1H, s). | 19A |
| 74 | (structure) | B | A | 827.4 | ¹H NMR (300 MHz, CD₃OD):δ7.94–7.87 (m, 1H), 7.76–7.68 (m, 2H),7.47–7.19 (m,7H), 5.17–5.05 (m, 1H), 4.53–4.06(m, 4H), 3.71 (s, 1H), 3.25(s., 4H),2.94–2.56 (m, 8H), 2.51–2.28 (m, 3H), 2.26–2.07(m, 1H), 1.72–1.48(m, 4H), 1.42(s, 4H), 1.25-1.22 (m, 8H), 1.21–1.18(m,6H). | 21A |

FIG. 2 Continued.

| | | | | |
|---|---|---|---|---|
| 75 | (structure) | A | A | 827.4 | ¹H NMR (300 MHz, CD₃OD): δ7.94–7.88 (m, 1H), 7.73–7.67 (m, 2H),7.45–7.17(m,7H), 5.16–4.88 (m, 1H), 4.59–4.09(m, 4H), 3.71–3.52 (m, 1H), 3.04–2.62(m, 7H),2.56–2.01 (m, 5H), 1.76–1.45 (m, 4H), 1.41–1.31(m, 4H), 1.25(s, 7H), 1.21(s, 6H). | 21A |

Table 3. Exemplary Compounds

| Ex. No. | Compound Structure | DC50 Code | M/Z+ | 1H NMR | Synthetic Scheme |
|---|---|---|---|---|---|
| 76 | 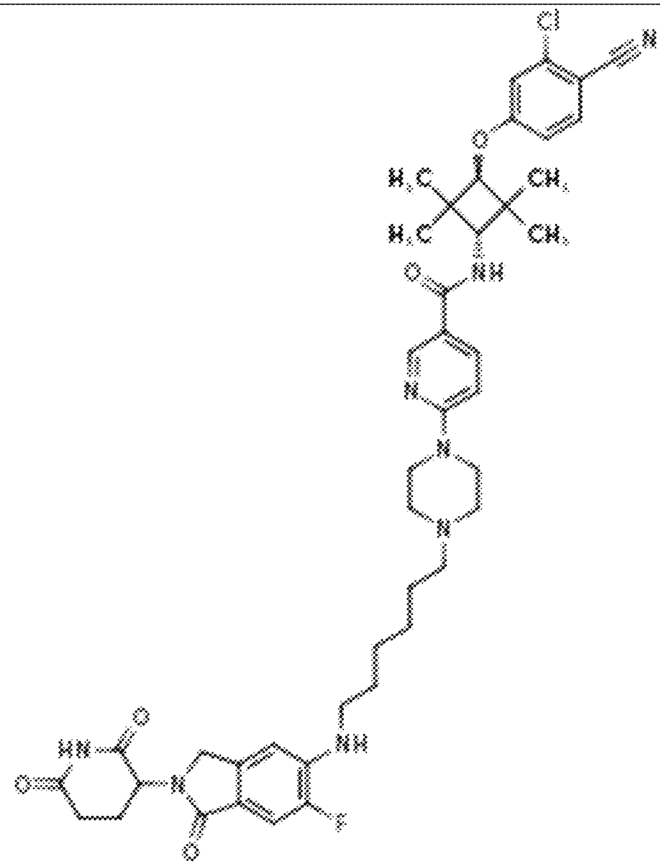 | A | 827.3 | $^1$H NMR (400 MHz, CDCl$_3$) δ 1.21 (6H, s), 1.25 (6H, s), 1.37-1.49 (4H, m), 1.50-1.57 (2H, m), 1.62-1.74 (2H, m), 2.18-2.30 (2H, m), 2.32-2.41 (2H, m), 2.53-2.55 (4H, m), 2.81-2.93 (2H, m), 3.18-3.23 (2H, m), 3.64-3.68 (4H, m), 4.04 (1H, s), 4.13-4.24 (2H, m), 4.34-4.38 (2H, m), 5.15-5.20 (1H, m), 6.07 (1H, d, $J$ = 8.4Hz), 6.64 (2H, m), 6.79-6.82 (1H, m), 6.96-6.97 (1H, d, $J$ = 2.4 Hz), 7.42 (1H, d, $J$ = 8.8 Hz), 7.57 (1H, d, $J$ = 8.8 Hz), 7.91-7.94 (1H, m), 8.04 (1H, brs), 8.74 (1H, d, $J$ = 2.0 Hz). | 57 |

FIG. 3 Continued.

| 77 | [structure] | A | 836.4 | 1H NMR (400 MHz, δ6-DMSO): δ 1.12 (s, 6H), 1.22 (s, 6H), 1.99-2.05 (m, 1H), 2.54-2.73 (m, 12H), 2.84-2.92 (m, 1H), 3.41-3.70 (m, 10H), 4.06 (d, J = 9.2 Hz, 1H), 4.30 (s, 1H), 5.05-5.10 (m, 1H), 6.89 (d, J = 9.2 Hz, 1H), 6.99-7.02 (m, 1H), 7.21 (d, J = 2.4 Hz, 1H), 7.25-7.30 (m, 1H), 7.37 (br, 1H), 7.63 (d, J = 9.2 Hz, 1H), 7.69 (d, J = 8.4 Hz, 1H), 7.90 (d, J = 8.4 Hz, 1H), 7.96-7.99 (m, 1H), 8.63 (d, J = 2.0 Hz, 1H), 11.08 (s, 1H). | 38 |

| 78 |  | A | 835.4 | ¹H NMR (400 MHz, CD₃OD): δ 1.22 (s, 6H), 1.28 (s, 6H), 1.61-1.72 (m, 3H), 1.87-1.90 (m, 2H), 2.04-2.20 (m, 2H), 2.69-2.76 (m, 2H), 2.82-2.87 (m, 1H), 2.93-3.07 (m, 8H), 3.87 (br, 4H), 4.04-4.07 (m, 2H), 4.14-4.16 (m, 1H), 4.28 (s, 1H), 5.04-5.09 (m, 1H), 6.89 (d, $J$ = 9.2 Hz, 1H), 6.99-7.02 (m, 1H), 7.04-7.06 (m, 1H), 7.13 (d, $J$ = 2.4 Hz, 1H), 7.20-7.23 (m, 1H), 7.34-7.35 (m, 1H), 7.37-7.39 (m, 1H), 7.51-7.53 (m, 1H), 7.66 (d, $J$ = 8.4 Hz, 1H), 7.72 (d, $J$ = 8.8 Hz, 1H), 7.87 (d, $J$ = 7.8 Hz, 1H), 8.00-8.03 (m, 1H), 8.63 (d, $J$ = 2.0 Hz, 1H). | 58 |
| --- | --- | --- | --- | --- | --- |
| 79 |  | A | 824.6 | H-NMR (300 MHz, CD₃OD) δ: (300 MHz, CD₃OD) δ 8.62 - 8.61 (d, $J$ = 2.4 Hz, 1H), 8.00 - 7.96 (d, $J$ = 11.4 Hz, 1H), 7.74 - 7.71 (d, $J$ = 9 Hz, 1H), 7.65 - 7.62 (m, 1H), 7.48 - 7.46 (m, 2H), 7.14 - 7.13 (d, $J$ = 2.4 Hz, 1H), 7.00 - 6.97 (d, $J$ = 11.1 Hz, 1H), 6.86 - 6.83 (d, $J$ = 9Hz, 1H), 5.20 - 5.14 (m, 1H), 4.51 - 4.49 (d, $J$ = 5.4 Hz, 2H), 4.28 (s, 1H), 4.15 (s, 1H), 3.70 - 3.62 (m, 6H), 3.51 - 3.46 | 30 |

| 80 |  A | 823.4 | H-NMR: (300 MHz, CD₃OD) δ 7.77 – 7.71 (m, 3H), 7.65 – 7.62 (m, 1H), 7.50 – 7.46 (m, 2H), 7.14 – 7.13 (d, J = 2.4 Hz, 1H), 7.00 – 6.97 (d, J = 9 Hz, 3H), 5.19 – 5.13 (m, 1H), 4.50 – 4.49 (d, J = 4.8 Hz, 2H), 4.29 (s, 1H), 4.14 (s, 1H), 3.64 – 3.61 (m, 2H), 3.50 – 3.46 (m, 2H), 3.32 – 3.31 (m, 3H), 2.90 – 2.71 (m, 11H), 2.55 – 2.49 (m, 1H), 2.20 – 2.19 (m, 1H), 1.76 – 1.62 (m, 4H), 1.51 – 1.44 (m, 2H), 1.29 (s, 6H), 1.23 (s, 6H); (m, 2H), 2.99 – 2.88 (m, 1H), 2.86 – 2.65 (m, 9H), 2.62 – 2.46 (m, 1H), 2.25 – 2.11 (m, 1H), 1.76 – 1.62 (m, 4H), 1.48 – 1.44 (m, 2H), 1.29 (s, 6H), 1.22 (s, 6H) | 30 |

| | | | |
|---|---|---|---|
| 81 |  | A | 804.6 | ¹H NMR (300 MHz, CD₃OD): δ 8.10-7.90 (m, 3H), 7.76-7.71 (m, 4H), 7.34-7.31 (m, 2H), 7.13 (s, 1H), 7.00-6.96 (m, 1H), 6.41(m, 1H), 5.19-5.13 (m, 1H), 4.29 (s, 1H), 4.17-4.14 (m, 2H), 3.90-3.60 (m, 3H), 3.26-3.23 (m, 2H), 2.96-2.70 (m, 7H), 2.20-2.10 (m, 1H), 1.81-1.72 (m, 4H), 1.47-1.38 (m, 3H), 1.28-1.23 (d, *J*=16.5Hz, 12H) | 42 |

| 82 | | A | 790.4 | ¹H NMR (300 MHz, CD₃OD): δ 7.75-7.60 (m, 6H), 7.33-7.30 (m, 2H), 7.13-7.12 (s, 1H), 7.00-6.96 (m, 1H), 6.31 (s, 1H), 5.18-5.12 (m, 1H), 4.49-4.48 (s, 2H), 4.29 (s, 1H), 4.10 (s, 1H), 3.23-3.22 (s, 2H), 2.91-2.46 (m, 11H), 2.19-2.10 (m, 1H), 1.69-1.60 (m, 4H), 1.40-1.30 (s, 4H), 1.28-1.23 (d, $J=16.5$ Hz, 12H); | 27 |

| 83 |  | A | 822.7 | ¹H NMR (400 MHz, DMSO-d₆): δ 1.12 (s, 6H), 1.22 (s, 6H), 1.44 (s, 4H), 1.72-1.80 (m, 3H), 1.88-1.90 (m, 1H), 2.03-2.07 (m, 1H), 2.54-2.65 (m, 2H), 2.85-2.95 (m, 2H), 3.32-3.35 (m, 2H), 3.49-3.51 (m, 2H), 3.66 (s, 2H), 4.05 (d, $J$ = 9.2 Hz, 1H), 4.16 (t, $J$ = 6.4 Hz, 2H), 4.30 (s, 1H), 4.69-4.75 (m, 1H), 5.09-5.14 (m, 1H), 6.51-6.54 (m, 1H), 7.00-7.02 (m, 1H), 7.20-7.21 (m, 1H), 7.32-7.34 (m, 1H), 7.41 (s, 1H), 7.55 (d, $J$ = 9.2 Hz, 1H), 7.82 (d, $J$ = 8.4 Hz, 1H), 7.89-7.93 (m, 2H), 8.16 (s, 1H), 8.59 (s, 1H), 11.11 (s, 1H). | 45 |

| 84 | <br><br> | A | 795.4 | H-NMR: (300 MHz, DMSO-$d6$, ppm) δ 7.89 - 7.86 (d, $J$ = 9 Hz, 1 H), 7.75 7.72 (d, $J$ = 9 Hz, 2 H), 7.62 - 7.59 (d, $J$ = 9 Hz,1 H), 7.52 - 7.49 (d, $J$ = 9 Hz, 1 H), 7.19 - 7.14 (m, 2 H), 7.04 - 6.94 (m, 4 H), 5.07 - 5.01 (m, 1 H), 4.40 - 4.21 (m, 3 H), 4.08 - 4.02 (m, 3 H), 3.36 - 3.27 (m, 4 H), 2.88 - 2.79 (m, 1 H), 2.71 - 2.55 (m, 4 H), 2.38 - 2.27 (m, 2 H), 1.99 - 1.94 (m, 1 H), 1.79 - 1.74 (m, 2 H), 1.56 - 1.44 (m, 4 H), 1.21 - 1.19 (m, 7 H), 1.10 (s, 6 H); | 31 |

| | | | | |
|---|---|---|---|---|
| 85 |  | A | 806.35 | H-NMR01-PH-ARV-LS-024-J-0: (300 MHz, DMSO-*d6*, ppm) δ 8.12 (br, 1 H), 7.89 - 7.79 (m, 5 H), 7.54 -7.51 (d, *J* = 9 Hz, 2 H), 7.47 - 7.41 (m, 1 H), 7.35 - 7.32 (m, 1 H), 7.22 - 7.18 (m, 1 H), 7.10 - 6.97 (m, 1 H), 6.28 (s, 1 H), 5.13 - 5.06 (m, 1 H), 4.31 (s, 1 H), 4.20 - 4.16 (m, 2 H), 4.07 - 4.04 (d, *J* = 9 Hz, 1 H), 3.29 - 3.24 (m, 2 H), 2.93 - 2.83 (m, 3 H), 2.60 - 2.56 (m, 5 H), 2.04 - 1.98 (m, 1 H), 1.81 - 1.76 (m, 2 H), 1.61 - 1.59 (m, 2 H), 1.48 - 1.45 (m, 2 H), 1.46 (s, 6 H), 1.21 (s, 6 H). | 45, 50 |
| 86 |  | A | 779.75 | ¹H NMR (400 MHz, CDCl₃): δ 7.71-7.61(m, 4H), 7.58-7.56 (m, 1H), 6.99-6.91 (m, 2H), 6.83-9.79 (m, 2H), 6.22-6.19 (m, 1H), 5.30-5.28 (m, 1H), 4.76-4.74 (m, 1H), 4.17-4.15 (m, 1H), 4.06 (s, 1H), 3.86-3.20 (m, 4H), 2.98-2.89 (m, 2H), 2.72-2.40 (m, 6H), 2.23-2.17 (m, 2H), 1.70-1.62 (m, | 42 |

FIG. 3 Continued.

| 87 | [structure] | A | 779.75 | 1H NMR (400 MHz, CDCl₃): δ 7.71-7.61(m, 4H), 7.58-7.56 (m, 1H), 6.99-6.91 (m, 2H), 6.83-9.79 (m, 2H), 6.22-6.19 (m, 1H), 5.30-5.28 (m, 1H), 4.76-4.74 (m, 1H), 4.17-4.15 (m, 1H), 4.06 (s, 1H), 3.75-3.20 (m, 4H), 2.98-2.89 (m, 2H), 2.80-2.50 (m, 6H), 2.23-2.17 (m, 2H), 1.70-1.62 (m, 3H), 1.44-1.39 (m, 3H), 1.27 (s, 7H), 1.23 (s, 6H); | 42 |

| 88 | <br>(structure) | A | 811.45 | $^1$H NMR (400 MHz, CDCl$_3$): δ 7.71-7.61(m, 4H), 7.58-7.56 (m, 1H), 6.99-6.91 (m, 2H), 6.83-9.79 (m, 2H), 6.22-6.19 (m, 1H), 5.30-5.28 (m, 1H), 4.76-4.74 (m, 1H), 4.17-4.15 (m, 1H), 4.06 (s, 1H), 3.75-3.20 (m, 4H), 2.98-2.89 (m, 2H), 2.80-2.50 (m, 6H), 2.23-2.17 (m, 2H), 1.70-1.62 (m, 3H), 1.44-1.39 (m, 3H),1.27 (s, 7H), 1.23 (s, 6H); | 59 |

FIG. 3 Continued.

| 89 | | A | 811.45 | ¹H NMR (300 MHz, CD₃OD): δ7.81–7.69 (m, 3H), 7.53–7.46 (m, 1H), 7.42–7.28(m,3H), 7.15 (s, 1H), 7.01–6.88(m,1H), 5.17–5.06(m, 1H), 4.52–4.41 (m, 2H), 4.27(s, 1H), 4.16 (s, 1H), 3.75–3.57(m,4H),3.36(s,2H),3.33–3.12(m,4H),2.95–2.69(m,4H),2.59–2.35(m,1H),2.232.01(m,1H),1.89–1.65(m,4H),1.52–1.38(m,4H),1.33–1.16(m,12) | 59 |

FIG. 3 Continued.

| 90 | [structure] | A | 828.3 | ¹H NMR (400 MHz, DMSO-d₆) δ 1.20 (6H, s), 1.22 (6H, s), 1.37-1.49 (6H, m), 1.79 (2H, t, J = 7.2 Hz), 1.98 (1H, t, J = 6.0 Hz), 2.29-2.43 (7H, m), 2.56-2.61 (1H, m), 2.87-2.91 (1H, m), 3.59 (4H, s), 4.05 (1H, d, J = 9.2 Hz), 4.14 (2H, t, J = 6.0 Hz), 4.24-4.40 (3H, m), 5.08 (1H, dd, J = 13.2, 4.8 Hz), 6.85 (1H, d, J = 8.8 Hz), 7.00 (1H, dd, J = 8.8, 2.0 Hz), 7.21 (1H, d, J = 2.0 Hz), 7.43 (1H, d, J = 6.8 Hz), 7.52 (1H, d, J = 10.0 Hz), 7.62 (1H, d, J = 9.2 Hz), 7.89-7.97 (2H, m), 8.62 (1H, d, J = 2.0 Hz), 11.00 (1H, s). | 54, 45 |

| | | | |
|---|---|---|---|
| 91 |  | A | 781.25 | ¹H NMR (300 MHz, DMSO-$d_6$) δ 11.08 (s, 1H), 8.52 -8.20 (brs, 1H), 7.85-7.81 (m, 4H), 7.55-7.46 (m, 3H), 7.40-7.30 (m, 1H), 7.09-6.92 (m, 3H), 5.10 (dd, $J$ = 12.9, 5.4 Hz, 1H), 4.38 (d, $J$ = 7.2 Hz, 1H), 4.28-4.14 (m, 2H), 4.06 (s, 1H), 3.16 (m, 3H), 3.04 (m, 3H), 2.87-2.42 (m, 4H), 2.10-1.90 (m, 3H), 1.19-1.00 (m, 14H); | 45 |
| 92 |  | A | 795.75 | ¹H NMR (300 MHz, DMSO-$d_6$) δ 11.08 (s, 1H), 7.92 – 7.66 (m, 4H), 7.56 – 7.28 (m, 3H), 7.17 (d, $J$ = 2.4 Hz, 1H), 7.02 – 6.88 (m, 3H), 5.08 (dd, $J$ = 12.9, 5.4 Hz, 1H), 4.28 - 4.19 (t, $J$ = 6.4 Hz, 3H), 4.02 (d, $J$ = 9.1 Hz, 1H), 3.21 (t, $J$ = 5.0 Hz, 4H), 2.90 – 2.76 (m, 1H), 2.62 – 2.46 (m, 6H), 2.37 (t, $J$ | 45 |

FIG. 3 Continued.

| 93 | [structure] | A | 792.8 | 1H NMR (300 MHz, CD3OD): δ 7.76-7.71 (m, 4H), 7.49-7.31 (m, 4H), 7.13-7.12 (s, 1H), 7.00-6.96 (m, 1H), 6.31 (s, 1H), 5.18-5.11 (m, 1H), 4.48-4.47 (m, 2H), 4.29 (s, 1H), 4.15 (s, 1H), 3.32-3.31 (m, 2H), 2.90-2.36 (m, 10H), 2.20-2.10 (m, 1H), 2.03-1.88 (m, 4H), 1.70-1.65 (m, 4H), 1.40-1.30 (s, 4H), 1.28-1.23 (d, J=16.5Hz, 12H) | 42 |
| --- | --- | --- | --- | --- | --- |

(continuation of prior entry): = 7.2 Hz, 2H), 2.01 (dd, J = 11.3, 5.6 Hz, 1H), 1.76 (q, J = 9.6, 8.3 Hz, 2H), 1.60 (t, J = 7.4 Hz, 2H), 1.18 (s, 6H), 1.09 (s, 6H).

FIG. 3 Continued.

| 94 | | | | 27 |
|---|---|---|---|---|
| (structure) | A | 793.4 | ¹H NMR (300 MHz, CD₃OD): δ7.81–7.69 (m, 3H), 7.53–7.46 (m, 1H),7.42–7.28(m,3H), 7.15 (s, 1H),7.01–6.88(m,1H), 5.17–5.06(m, 1H), 4.52–4.41 (m, 2H), 4.27(s , 1H),4.16 (s, 1H), 3.75–3.57(m,4H),3.36(s,2H),3.33–3.12(m,4H),2.95–2.69(m,4H),2.59–2.35(m,1H),2.232.01(m,1H),1.89–1.65(m,4H),1.52–1.38(m,4H),1.33–1.16(m,12) | |

FIG. 3 Continued.

| 95 | [structure] | A | 790.8 | $^1$H NMR (400 MHz, DMSO-d$_6$): δ 1.14 (m, 6H), 1.23 (s, 6H), 1.34-1.35 (m, 2H), 1.62-1.66 (m, 4H), 2.05-2.09 (m, 1H), 2.65-2.69 (m, 6H), 2.86-2.956 (m, 2H), 3.17 (d, $J$ = 4.4 Hz, 1H), 4.07 (d, $J$ = 8.8 Hz, 1H), 4.33 (s, 1H), 5.14-5.19 (m, 1H), 6.53 (s, 1H), 6.99-7.02 (m, 1H), 7.21 (d, $J$ = 2.4 Hz, 1H), 7.32 (d, $J$ = 8.4 Hz, 2H), 7.76-7.79 (m, 3H), 7.90-7.97 (m, 4H), 11.14 (s, 1H). | 1 |

| 96 |  | A | 796.4 | 1H NMR (400 MHz, CDCl3): δ 1.21 (s, 6H), 1.25 (s, 6H), 1.50-1.57 (m, 2H), 1.66-1.75 (m, 2H), 1.82-1.89 (m, 2H), 2.31-2.42 (m, 2H), 2.57-2.62 (m, 2H), 2.68-2.97 (m, 6H), 3.79 (s, 4H), 4.02-4.15 (m, 4H), 4.27, 4.31 (two singles, 1H), 4.40, 4.44 (two singles, 1H), 5.18-5.23 (m, 1H), 6.07 (d, J = 8.4 Hz, 1H), 6.67 (d, J = 9.2 Hz, 1H), 6.79-6.82 (m, 1H), 6.93-7.03 (m, 1H), 7.11-7.19 (m, 1H), 7.31-7.43 (m, 2H), 7.57 (d, J = 8.8 Hz, 1H), 7.89-8.00 (m, 1H), 8.01-8.12 (m, 1H), 8.52-8.66 (m, 1H). | 31 |

| 97 |  | A | 776.4 | ¹H NMR (400 MHz, CD₃OD):δ 1.25 (s, 6H), 1.31 (s, 6H), 1.66-1.77 (m, 4H), 2.13-2.18 (m, 1H), 2.61-2.65 (m, 2H), 2.71-2.81 (m, 6H), 2.85-2.91 (m, 3H), 3.28-3.31 (m, 2H), 4.18 (s, 1H), 4.31 (s, 1H), 5.14-5.18 (m, 1H), 6.44-6.46 (m, 1H), 7.00 (dd, J = 8.8, 2.4 Hz, 1H), 7.15-7.16 (m. 1H), 7.36-7.38 (m, 2H), 7.73-7.79 (m, 3H), 7.86-7.88 (m, 1H), 7.91-7.93 (m, 1H), 7.97 (br, 1H). | |
|---|---|---|---|---|---|
| 98 |  | A | 776.4 | ¹H NMR (400 MHz, CD₃OD): δ 1.25 (s, 6H), 1.31 (s, 6H), 1.39, 1.40 (d, J =6.4 Hz, 1H), 1.46-1.52 (m, 2H), 1.74-1.83 (m, 4H), 2.17-2.24 (m, 1H), 2.46-2.57 (m, 1H), 2.75-2.79 (t, J =7.6 Hz, 2H), 2.78-2.96 (m, 4H), 3.01-3.09 (m, 2H), 3.78 (s, 2H), 4.16-4.19 (m, 2H), 4.30 (s, 1H), 4.45-4.60 (m, 2H), 5.16-5.19 (m, 1H), 6.32 (s, 1H), 6.99-7.01 (m, 1H), | 27 |

| 99 |  | A | 808.35 | H-NMR01-PH-ARV-LS-024-H-0: (300 MHz, DMSO-d6, ppm) δ 8.14 (br, 1 H). 7.89 - 7.74 (m, 5 H), 7.47 7.32 (m, 4 H), 7.18 - 6.96 (m, 2 H), 5.13 - 5.06 (m, 1 H), 4.30 (s, 1 H). 4.20 - 4.16 (m, 2 H), 4.05 - 4.02 (d, J = 9 Hz, 1 H), 3.27 - 3.24 (m, 2 H), 2.91 - 2.81 (m, 1 H), 2.77 - 2.64 (m, 3 H), 2.60 - 2.54 (m, 3 H), 2.04 - 1.97 (m, 1 H), 1.87 - 1.74 (m, 6 H), 1.70 - 1.62 (m, 2 H), 1.47 - 1.45 (m, 2 H), 1.20 (s, 6 H), 1.11 (s, 6 H), 7.15 (d, J =2.4 Hz, 1H), 7.36 (d, J =8.4 Hz, 2H), 7.66-7.83 (m, 6H). | 45 |

| | A | 778.25 | 1H NMR (300 MHz, DMSO) 8.53 (s, 1H), 8.02-7.89 (m, 5H), 7.89-7.75 (m, 1H), 7.59-7.57 (m, 1H), 7.16-7.10 (m, 2H), 7.01-6.96 (m, 2H), 5.00-4.90 (m, 1H), 4.32-4.15 (m, 3H), 4.15-3.77 (m, 3H), 2.89-2.48 (m, 4H), 2.38-2.20 (m, 1H), 1.99-1.90 (m, 1H), 1.77-1.68 (m, 4H), 1.48-1.39 (m, 2H), 1.19-1.10 (m, 6H), 1.10-1.01 (m, 6H) | 25 |

FIG. 3 Continued.

| 102 | A | 779.35 | ¹H NMR (300MHz, DMSO-d6): δ 8.97 (s, 1H), 8.69 (s, 1H), 8.51-8.47 (m, 1H), 8.25-8.16 (m, 2H), 7.94-7.88 (m, 1H), 7.63-7.57 (m, 1H), 7.26-6.85 (m , 4H), 5.13-4.97 (m, 1H), 4.51-3.99 (m, 6H), 2.98-2.22 (m, 5H), 2.07-1.89 (m, 1H), 1.87-1.73 (m, 4H), 1.58-1.43 (m, 2H), 1.31-1.08 (m, 13H) | 48 |

FIG. 3 Continued.

| 103 | [structure] | A | 807.4 | ¹H NMR (400 MHz, CD₃OD): δ 1.25 (s, 6H), 1.32 (s, 6H), 1.49-1.51 (m, 4H), 1.78-1.84 (m, 4H), 2.00-2.09 (m, 2H), 2.13-2.23 (m, 2H), 2.73-2.95 (m, 6H), 3.10-3.18 (m, 4H), 3.63-3.71 (m, 2H), 4.20 (s, 1H), 4.31 (s, 1H), 5.16-5.18 (m, 1H), 6.99-7.01 (m, 1H), 7.15 (d, $J$ =2.4 Hz, 1H), 7.46 (d, $J$ =8.0 Hz, 1H), 7.74 (d, $J$ =8.8 Hz, 1H), 7.79 (d, $J$ =8.4 Hz, 1H), 7.86 (s, 1H), 7.89 (d, $J$ =8.0 Hz, 1H), 8.16-8.18 (m, 1H), 8.89 (d, $J$ =2.0 Hz, 1H). | 11 |

| 105 | | | |
|---|---|---|---|
| | A | 833.4 | H-NMR-PH-ARV-LS-026-D-0: (300 MHz, CD₃OD, ppm) δ 8.47 (s, 1H), 8.06 - 7.98 (m, 4H), 7.75 -7.71 (m, 2H), 7.18 - 7.11 (m, 3H), 7.02 - 6.98 (m, 1H), 5.15 - 5.09 (m, 1H), 4.70 - 4.57 (m, 3H), 4.45 - 4.44 (m, 1H), 4.31 (s, 1H), 4.20 (s, 1H), 3.11 - 3.08 (m, 2H), 2.92 - 2.75 (m, 7H), 2.51 - 2.45 (m, 1H), 2.20 - 2.01 (m, 7H), 1.32 (s, 6H), 1.25 (s, 6H). | 10 |

| 106 | A | 806.32 | ¹H NMR (400 MHz, DMSO) 8.610 (s, 1H), 8.10-8.02 (m, 5H), 7.99-7.90 (m, 1H), 7.21-7.19 (m, 1H), 7.07-6.90 (m, 3H), 5.05-5.00 (m, 1H), 4.95-4.85 (m, 1H), 4.45-4.25 (m, 3H), 4.15-4.05 (m, 1H), 3.09-3.00 (m, 2H), 2.90-2.80 (m, 1H), 2.79-2.70 (m, 2H), 2.65-2.60 (m, 4H), 2.05-1.95 (m, 1H), 1.75-1.65 (m, 2H), 1.25-1.12 (m, 14H); | 12, 13 |

| | A | 819 | H-NMR (400 MHz, CD$_3$OD) δ 8.69-8.64 (m, 2H), 8.63-8.40 (m, 2H), 8.13-8.11 (d, J= 8.0 Hz, 1H), 8.01-7.98 (m, 1H), 7.75-7.73 (d, J=8.4Hz, 1H), 7.15-7.15 (m, 1H), 7.01-6.99 (m, 1H), 6.90-6.88 (d, J=9.6, 1H), 5.24-5.20 (m, 1H), 4.30 (s, 1H), 4.17-4.16 (d, J=4.4z, 1H), 3.79-3.32 (m, 4H), 3.16-3.12 (m, 2H), 2.97-2.93 (m, 2H), 2.89-2.87 (d, J=6 Hz, 1H), 2.81-2.77 (m, 6H), 2.21-2.19 (m, 1H), 1.30 (s, 6H), 1.24 (s, 6H) | 4 |

107

| 108 |  | 833.35 | H-NMR (400 MHz, CD₃OD) δ 8.62-8.60 (m, 2H), 8.41-8.35 (m, 2H), 8.13-8.11 (m, 1H), 8.02-7.99 (m, 1H), 7.71-7.71 (m, 1H), 7.14 (s, 1H), 7.01-6.94 (m, 1H), 6.85-6.83 (m, 1H), 5.25-5.15 (m, 1H), 4.29 (s, 1H), 4.12 (s, 1H), 3.80-3.75 (m, 4H), 2.94-2.72 (m, 11H), 2.20-2.02 (m, 3H), 1.28 (s, 6H), 1.22 (s, 6H); | 7 |

| 109 | A | 808.85 | ¹HNMR (300 MHz, CD₃OD): δ 8.86 (s, 1H), 8.16-8.09 (m, 1H), 7.72-7.64 (m, 2H), 7.47-7.33 (m, 2H), 7.24-7.17 (m, 1H), 7.12 (s, 1H), 6.98-6.89 (m, 1H), 5.09-5.02 (m, 1H), 4.26 (s, 1H), 4.15(s, 1H), 3.48-3.42 (m, 4H), 2.92-2.49 (m, 9H), 2.46-2.35 (m, 2H), 2.16-2.01 (m, 1H), 1.81-1.71 (m, 2H),1.59-1.47 (m, 2H), 1.42-1.36 (m, 4H), 1.27-1.18 (m, 12H); | 11 |

| 111 | A | 782.28 | 1H NMR (400 MHz, DMSO-d6): δ 1.12 (s, 6H), 1.22 (s, 6H), 1.99-2.03 (m, 3H), 2.54-2.62 (m, 6H), 2.85-2.94 (m, 1H), 3.63 (br, 4H), 4.06 (d, J = 5.2 Hz, 1H), 4.24-4.31 (m, 3H), 5.10-5.15 (m, 1H), 6.88 (d, J = 9.2 Hz, 1H), 6.99-7.02 (m, 1H), 7.21 (d, J = 2.0 Hz, 1H), 7.36-7.38 (m, 1H), 7.45 (d, J = 1.6 Hz, 1H), 7.64 (d, J = 9.2 Hz, 1H), 7.85 (d, J = 8.4 Hz, 1H), 7.91 (d, J = 8.4 Hz, 1H), 7.98 (d, J = 2.4 Hz, 1H), 8.64 (d, J = 1.6 Hz, 1H), 11.13 (s, 1H). | 45 |

FIG. 3 Continued.

| 112 | A | 809.4 | ¹HNMR (400 MHz, CD₃OD): δ 1.13 (s, 6H), 1.19 (s, 6H), 1.46-1.55 (m, 2H), 1.63-1.73 (m, 2H), 1.78-1.86 (m, 2H), 1.88-2.07 (m, 5H), 2.59-2.84 (m, 7H), 2.90-2.95 (m, 1H), 3.31-3.41 (m, 2H), 4.08-4.12 (m, 2H), 4.19 (s, 1H), 4.52 (br. 1H), 4.99-5.03 (m, 1H), 6.89 (d, J = 8.8 Hz, 1H), 7.03 (d, J = 2.4 Hz, 1H), 7.22 (d, J = 8.4 Hz, 1H), 7.31 (d, J = 2.0 Hz, 1H), 7.37 (d, J = 8.0 Hz, 1H), 7.63 (d, J = 8.8 Hz, 1H), 7.71 (d, J = 8.4 Hz, 1H), 8.06 (d, J = 8.0 Hz, 1H), 8.80-8.81 (m, 1H). | 45 |

| 113 |  | A | 781.4 | $^1$H NMR (400 MHz, CD$_3$OD): δ 1.13(s, 6H), 1.19 (s, 6H), 1.86-1.89 (m, 4H), 2.01-2.05(m, 3H), 2.20-2.26 (m, 2H), 2.60-2.68 (m, 4H), 2.76-2.82 (m, 2H), 3.12 (d, J = 11.9 Hz, 2H), 4.07-4.18 (m, 4H), 4.99-5.03 (m,1H), 6.88 (d, J = 8.8 Hz, 1H), 7.03 (d, J = 2.4 Hz ,1H), 7.23 (d, J = 8.4 Hz, 1H), 7.32-7.37 (m, 2H), 7.62 (d, J = 8.8 Hz, 1H), 7.71 (d, J = 8.0 Hz ,1H), 8.05 (d, J = 8.0 Hz ,1H), 8.78 (d, J = 2.0 Hz ,1H). | 45 |

| | | | |
|---|---|---|---|
| 13.5 |  | A | 796.4 | ¹H NMR (400 MHz, CD₃OD): δ 0.88-0.93 (m, 2H), 1.24 (s, 6H), 1.30 (s, 6H), 1.78-1.96 (m, 4H), 2.02-2.18 (m, 2H), 2.63 (t, J = 7.2 Hz, 2H), 2.68-2.75 (m, 4H), 2.78-2.82 (m, 1H), 2.83-2.92 (m, 1H), 3.26-3.30 (m, 1H), 3.72-3.77 (m, 4H), 4.16 (s, 1H), 4.24 (t, J = 6.4 Hz, 2H), 4.30 (s, 1H), 5.10-5.16 (m, 1H), 6.87 (d, J = 8.8 Hz, 1H), 6.98-7.02 (m, 1H), 7.15 (d, J = 2.4 Hz, 1H), 7.32-7.36 (m, 1H), 7.44 (d, J = 8.8 Hz, 1H), 7.83 (d, J = 8.8 Hz, 1H), 7.97-8.01 (m, 1H), 8.63 (d, J = 2.4 Hz, 1H). | 47 |

| 117 | A | 806.25 | 1H NMR (400 MHz, CDCl3): δ8.93 – 8.81 (m, 1H), 8.40 (s, 1H),8.26 (s,2H), 8.18–8.12 (m, 1H), 7.82–7.69(m, 1H), 7.61–7.48 (m, 1H), 6.98 (s , 1H),6.89–6.78 (m,3H), 6.36–6.25 (m, 1H), 5.24–5.15(m, 1H), 4.96–4.82(m, 1H), 4.49–4.18(m, 3H),4.12–3.96(m,3H),3.31(s,1H),2.97–2.77(m,5H),2.43–2.15(m,2H),2.07–1.68(m,4H),1.31(s,6H),1.25(s,6 H) | 2 |

FIG. 3 Continued.

| | | | | |
|---|---|---|---|---|
| 118 | [structure] | A | 842.85 | 11 | ¹H NMR (300 MHz, CD₃OD): δ 8.85 (s, 1H), 8.17-8.08 (m, 1H), 7.93-7.88 (m, 1H), 7.71-7.66 (m, 1H), 7.43-7.29 (m, 3H), 7.26-7.17 (m, 2H), 5.11-5.02 (m, 1H), 4.32 (s, 1H), 4.15 (s, 1H), 3.49-3.43 (m, 4H), 2.92-2.58 (m, 9H), 2.46-2.37 (m, 2H), 2.13-2.02 (m, 1H), 1.81-1.72 (m, 2H), 1.58-1.49 (m, 2H), 1.41-1.33 (m, 4H), 1.27-1.18 (m, 12H); |
| 119 | [structure] | A | 752.3 | 28 | ¹H NMR (300 MHz, CD₃OD): δ 8.89 (s, 1H), 8.15 (dd, J = 8.1, 2.3 Hz, 1H), 7.85 (d, J = 8.8 Hz, 1H), 7.70 (d, J = 8.7 Hz, 1H), 7.46 (d, J = 8.1 Hz, 1H), 7.23-7.15 (m, 1H), 7.15-7.05 (m, 2H), 6.95 (dd, J = 8.8, 2.4 Hz, 1H), 5.48 (s, 2H), 4.91 - 4.81 (m, 1H), 4.26 (d, J |

| 120 |  | A | 766.25 | = 0.9 Hz, 1H), 4.16 (d, J = 0.9 Hz, 1H), 3.60 (t, J = 4.9 Hz, 4H), 3.21 (t, J = 5.0 Hz, 4H), 3.01 (dt, J = 17.9, 7.4 Hz, 4H), 2.80-2.69 (m, 2H), 2.29-2.03 (m, 5.8 Hz, 4H), 1.30 (s, 6H). 1.21 (s, 6H). | |
|---|---|---|---|---|---|
| | | | | $^1$H NMR (300 MHz, CD$_3$OD): δ 8.92 (m, 1H), 8.14 (dd, J = 8.1, 2.3 Hz, 1H), 7.70 (dd, J = 8.6, 1.9 Hz, 2H), 7.50-7.45 (m, 1H), 7.40 (s, 1H),7.27 (dd, J = 8.6, 2.3 Hz, 1H), 7.10 (d, J = 2.4 Hz, 1H), 6.95 (dd, J = 8.8, 2.4 Hz, 1H), 5.05 (dd, J = 12.3, 5.4 Hz, 1H), 4.26 (s, 1H), 4.15 (s, 1H), 3.59 (t, J = 5.2 Hz, 4H), 3.12- 3.00 (m, 4H), 3.00-2.82 (m, 4H), 2.82-2.62 (m, 3H), 2.21-2.02 (m, 3H), 1.24 (m, 6H) , 1.20 (s, 6H); | 1 |

| 121 |  | A | 765.8 | ¹HNMR (400 MHz, CD₃OD): δ 1.25 (s, 6H), 1.32 (s, 6H), 1.86-1.88 (m, 4H), 2.01-2.08 (m, 2H), 2.06-2.21 (m, 3H), 2.46-2.57 (m, 1H), 2.77-2.83 (m, 1H), 2.89-3.00 (m, 3H), 3.05-3.24 (m, 5H), 3.67-3.70 (m, 2H), 4.20 (s, 1H), 4.31 (s, 1H), 4.46-4.57 (m, 2H), 5.15-5.17 (m, 1H), 6.99-7.01 (m, 1H), 7.15 (d, J = 2.4 Hz, 1H), 7.46-7.54 (m, 3H), 7.75 (d, J = 8.8 Hz, 1H), 7.79 (d, J = 8.0 Hz, 1H), 8.17-8.19 (m, 1H), 8.92 (d, J = 1.6 Hz, 1H). | 27 |
| 122 |  | A | 768.4 | ¹H NMR (400 MHz, CD₃OD): δ 1.12 (s, 6H), 1.18 (s, 6H), 1.91-2.05 (m, 2H), 2.61-2.68 (m, 5H), 2.72-2.78 (m, 1H), 2.84 (s, 2H), 3.60-3.64 (m, 3H), 4.04 (s, 1H), 4.18 (s, 1H), 4.26 (s, 2H), 4.47-4.51 (m, 1H), 4.99-5.04 (m, 1H), 6.72-6.78 (m, 1H), 6.86-6.91 (m, 1H), 7.03 (d, J = 2.4 Hz, 1H), | 47 |

| 123 |  | A | 779.35 | (400 MHz, CDCl3) δ 8.94-8.94 (d, J=2.0 Hz, 1H), 8.07-8.04 (m, 1H), 7.86-7.78 (m, 3H), 7.68-7.66 (d, J=7.6 Hz, 1H), 7.61-7.59 (d, J=8.8 Hz, 1H), 7.31-7.29 (d, J=10.4 Hz, 1H), 7.00-6.99 (d, J=2.0 Hz, 1H), 6.85-6.82 (m, 1H), 6.36-6.34 (d, J=8.4 Hz, 1H), 5.02-4.98 (m, 1H), 4.20-4.18 (d, J=8.0 Hz, 1H), 4.10 (s, 1H), 3.41-3.38 (d, J=10.8 Hz, 2H), 2.96-2.74 (m, 8H), 2.43-2.40 (d, J=11.2 Hz, 2H), 2.20-2.15 (m, 3H), 1.98-1.95 (d, J=12.8 Hz, 2H), 1.88-1.77 (m, 4H), 1.31 (s, 6H), 1.26 (s, 6H) | 1 |
| | 7.25-7.30 (m, 1H), 7.37 (d, J = 2.0 Hz, 1H), 7.61 (s, 1H), 7.70-7.75 (m, 1H), 7.84-7.89 (m, 1H), 8.48-8.54 (m, 1H). | | | | |

| 124 | | A | 780.4 | H-NMR (400 MHz, CD3OD) δ 8.91-8.90 (d, J=2.0 Hz, 1H), 8.19-8.16 (m, 3H), 7.76-7.73 (m, 2H), 7.49-7.43 (m, 2H), 7.31-7.29 (m, 1H), 7.16-7.15 (d, J=2.4 Hz, 1H), 7.02-6.99 (m, 1H), 5.12-5.08 (m, 1H), 4.31 (s, 1H), 4.21 (s, 1H), 3.61-3.58 (m, 4H), 2.98-2.72 (m, 11H), 2.14-2.13 (d, J=5.2 Hz, 1H), 1.88-1.84 (m, 2H), 1.75-1.72 (m, 2H), 1.32 (s, 6H), 1.26 (s, 2H); | 1 |

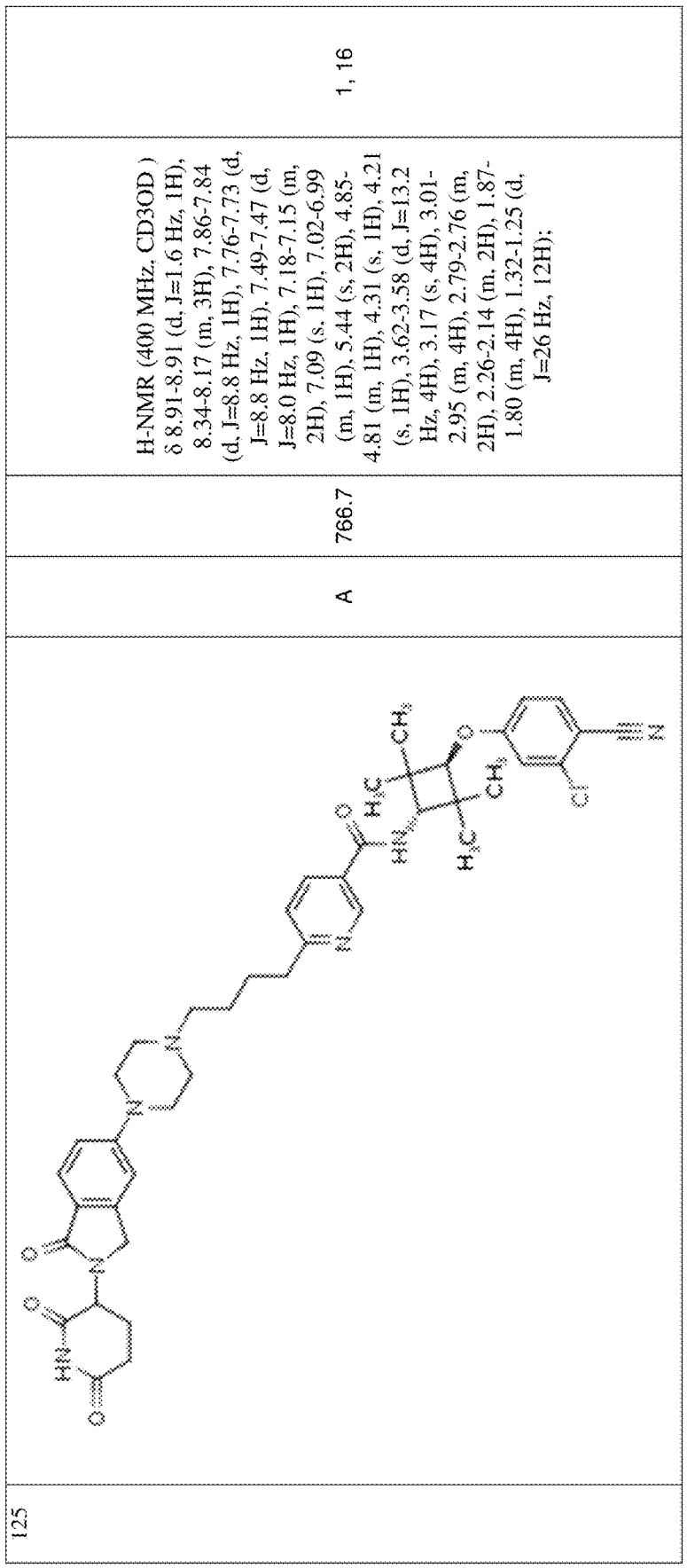

| 128 | | | | |
|---|---|---|---|---|
|  | A | 781.4 | $^1$HNMR (400 MHz, CD$_3$OD): δ 1.12 (s, 6H), 1.22 (s, 6H), 1.27-1.43 (m, 5H), 1.65-1.71 (m, 2H), 2.01-2.07 (m, 1H), 2.53-2.60 (m, 4H), 2.75-2.79 (m, 3H), 2.83-2.94 (m, 2H), 4.05-4.07 (m, 2H), 4.30 (s, 1H), 5.08-5.16 (m, 2H), 6.98-7.01 (m, 1H), 7.19-7.22 (m, 1H), 7.28-7.37 (m, 3H), 7.84-7.90 (m, 2H), 7.99-8.08 (m, 2H), 8.88 (s, 1H), 11.11 (s, 1H). | 83 |

FIG. 3 Continued.

| # | Structure | | | NMR |
|---|---|---|---|---|
| 129 | (structure) | A | 821.5 | ¹H NMR (400 MHz, DMSO-d6): δ 1.04-1.06 (m, 1H), 1.10 (s, 6H), 1.20 (s, 6H), 1.75-1.85 (m, 3H), 1.98-2.02 (m, 1H), 2.18 (d, $J$ = 6.4 Hz, 2H), 2.51-2.60 (m, 2H), 2.82-2.92 (m, 4H), 3.30-3.32 (m, 4H), 3.42-3.44 (m, 4H), 4.03 (d, $J$ = 9.2 Hz, 1H), 4.29 (s, 1H), 4.37-4.43 (m, 2H), 5.03-5.08 (m, 1H), 6.82 (s, 1H), 6.97-7.00 (m, 1H), 7.19 (d, $J$ = 2.0 Hz, 1H), 7.22-7.26 (m, 1H), 7.33 (s, 1H), 7.57 (d, $J$ = 9.2 Hz, 1H), 7.66 (d, $J$ = 8.4 Hz, 1H), 7.87-7.93 (m, 2H), 8.60 (d, $J$ = 2.4 Hz, 1H), 11.07 (s, 1H). | 49 |
| 130 | (structure) | A | 795.5 | ¹H NMR (400 MHz, CD₃OD): δ 1.23 (s, 6H), 1.30 (s, 6H), 1.38-1.38 (m, 1H), 1.64-1.69 (m, 2H), 1.77-1.84 (m, 2H), 1.93-1.95 (m, 2H), 2.11-2.15 (m, 3H), 2.68-2.77 (m, 5H), 2.83-2.98 (m, 5H), 4.18 (s, 1H), 4.29 (s, 1H), 4.74 (s, 1H), 5.09, 5.12 (d, $J$ = 5.6 Hz, 1H), 6.97-6.99 (m, 1H), 7.13-7.14 (m, 1H), 7.33-7.35 (m, 1H), 7.43-7.47 (m, 2H), 7.71-7.74 (m, 1H), 7.81 (d, $J$ = 8.0 Hz, 1H), 8.14-8.16 (m, 1H), 8.87 (d, $J$ = 2.0 Hz, 1H). | 83 |

| 131 | | A | 835.5 | ¹H NMR (400 MHz, DMSO-d6): δ 1.12 (s, 6H), 1.22 (s, 6H), 1.43-1.44 (m, 2H), 1.62-1.63 (m, 1H), 1.75-1.78 (m, 2H), 2.01-2.03 (m, 1H), 2.35-2.43 (m, 3H), 2.59-2.64 (m, 2H), 2.85-2.89 (m, 4H), 3.17-3.45 (m, 8H), 4.05-4.07 (m, 1H), 4.31 (s, 1H), 4.39-4.42 (m, 2H), 5.06-5.10 (m, 1H), 6.85 (d, J = 8.8 Hz, 1H), 7.00 (d, J = 8.4 Hz, 1H), 7.21-7.27 (m, 2H), 7.35 (s, 1H), 7.59-7.70 (m, 2H), 7.90-7.95 (m, 2H), 8.62 (s, 1H), 11.09 (s, 1H). | 23 |

| 132 | A | 811.4 | ¹H-NMR (300 MHz, CD3OD) δ8.78 (s, 2H), 7.85- 7.79(m, 1H), 7.74-7.68(m, 1H), 7.42-7.39(m, 1H), 7.35 - 7.28(m, 1H), 7.14 - 7.10 (m, 1H), 7.01 - 6.96 (m, 1H), 5.15- 5.06(m, 1H), 4.29- 4.03(m, 8H), 2.95 - 2.69(m, 9H), 2.17 - 2.12 (m, 1H), 1.96 - 1.87 (m, 2H), 1.81 - 1.72 (m, 2H), 1.64 - 1.54 (m, 2H), 1.28 - 1.21 (d, *J = 20.4Hz*, 12H). | 9 |

| 133 | | A | 845.3 | ¹H NMR (400 MHz, CDCl₃): δ 1.23 (s, 6H), 1.27 (s, 6H), 1.52-1.69 (m, 2H), 1.70-1.86 (m, 2H), 2.12-2.14 (m, 1H), 2.30-2.51 (m, 2H), 2.52-2.66 (m, 3H), 2.72-2.85 (m, 2H), 2.87-2.92 (m, 1H), 3.00 (t, J = 6.8 Hz, 2H), 3.31-3.46 (m, 3H), 3.51 (t, J = 6.0 Hz, 2H), 3.65 (t, J = 6.4 Hz, 2H), 4.07 (s, 1H), 4.13 (d, J = 8.0 Hz, 1H), 4.92-4.96 (m, 1H), 6.01-6.21 (m, 1H), 6.80 (dd, J = 2.4, 8.8 Hz, 1H), 6.96 (d, J = 2.0 Hz, 1H), 7.06 (dd, J = 2.0, 8.4 Hz, 1H), 7.28-7.33 (m, 2H), 7.57 (d, J = 8.4 Hz, 1H), 7.70 (d, J = 8.4 Hz, 1H), 8.02 (s, 1H). | 84 |

| | | | | |
|---|---|---|---|---|
| 134 |  | A | 837.3 | 21 | ¹H NMR (300 MHz, CD₃OD): δ 11.08 (s, 1H), 7.84 (dd, J = 21.4, 8.5 Hz, 2H), 7.71 (d, J = 8.6 Hz, 2H), 7.50-7.39 (m, 2H), 7.33 (dd, J = 8.3, 2.3 Hz, 1H), 7.18 (d, J = 2.4 Hz, 1H), 7.03-6.88 (m, 3H), 5.09 (dd, J = 12.9, 5.4 Hz, 1H), 4.30 (s, 1H), 4.16 (t, J = 6.5 Hz, 2H), 4.02 (d, J = 9.1 Hz, 1H), 3.67 (d, J = 11.5 Hz, 2H), 2.92-2.78 (m, 1H), 2.72-2.50 (m, 5H), 2.42 (s, 1H), 2.34 (d, J = 27.9 Hz, 2H), 2.03 (dq, J = 13.5, 5.6, 4.6 Hz, 1H), 1.76 (dd, J = 8.1, 5.2 Hz, 2H), 1.39 (d, J = 12.5 Hz, 4H), 1.19 (s, 6H), 1.14-0.95 (m, 12H); |
| 135 |  | A | 819.5 | 55 | ¹H NMR (400 MHz, DMSO-d6): δ 1.13 (s, 6H), 1.23 (s, 6H), 1.73-1.80 (m, 2H), 1.93-2.00 (m, 2H), 2.00-2.07 (m, 1H), 2.53-2.67 (m, 2H), 2.85-2.93 (m, 1H), 4.06-4.08 (m, 2H), 4.17-4.22 (m, 4H), 4.31 (s, 1H), 4.51 (br, 2H), 4.73 (s, 2H), 5.09-5.14 (m, 1H), 6.60-6.62 (m, 1H), 7.00-7.03 (m, 1H), 7.21-7.22 (m, 1H), 7.33-7.35 (m, 1H), 7.42-7.43 (m, 1H), 7.65-7.67 (m, 1H), 7.81-7.83 (m, 2H), 7.90-7.92 (m, 1H), 8.03-8.05 (m, 1H), 8.65-8.66 (m, 1H), 11.12 (s, 1H). |

| | | | |
|---|---|---|---|
| 136 | (structure) | A | 819.53 | 85 | ¹H NMR (400 MHz, DMSO-d6): δ 1.13 (s, 6H), 1.23 (s, 6H), 1.73-1.80 (m, 2H), 1.93-2.00 (m, 2H), 2.00-2.07 (m, 1H), 2.53-2.67 (m, 2H), 2.85-2.93 (m, 1H), 4.06-4.08 (m, 2H), 4.17-4.22 (m, 4H), 4.31 (s, 1H), 4.51 (br, 2H), 4.73 (s, 2H), 5.09-5.14 (m, 1H), 6.60-6.62 (m, 1H), 7.00-7.03 (m, 1H), 7.21-7.22 (m, 1H), 7.33-7.35 (m, 1H), 7.42-7.43 (m, 1H), 7.65-7.67 (m, 1H), 7.81-7.83 (m, 2H), 7.90-7.92 (m, 1H), 8.03-8.05 (m, 1H), 8.65-8.66 (m, 1H), 11.12 (s, 1H). |
| 137 | (structure) | A | 819.27 | 86 | ¹HNMR (400 MHz, CD₃OD): δ 1.14 (s, 6H), 1.21 (s, 6H), 1.72-2.04 (m, 6H), 2.60-2.75 (m, 4H), 2.88 (t, J = 7 Hz, 2H), 3.82 (s, 2H), 4.09-4.27 (m, 6H), 4.98-5.03 (m, 1H), 6.89 (d, J = 6.8 Hz, 1H), 7.04 (s, 1H), 7.25 (d, J = 8.8 Hz, 1H), 7.33 (s, 1H), 7.45 (s, 1H), 7.62 (d, J = 4 Hz, 1H), 7.70 (d, J = 8 Hz, 1H), 7.88 (d, J = 8.4 Hz, 1H), 8.21 (d, J = 8.8 Hz, 1H), 8.74 (s, 1H). |

| 138 | A | 794.45 | ¹H NMR (300 MHz, DMSO-d6): δ 11.04 (s, 1H), 8.86 (d, J = 2.2 Hz, 1H), 8.10-8.00 (m, 2H), 8.00-7.80 (m, 1H), 7.64 (d, J = 8.4 Hz, 1H), 7.39-7.14 (m, 4H), 6.97 (dd, J = 8.7, 2.4 Hz, 1H), 5.03 (dd, J = 12.8, 5.3 Hz, 1H), 4.28 (s, 1H), 4.04 (d, J = 9.1 Hz, 1H), 3.38 (t, J = 5.0 Hz, 4H), 3.00-2.73 (m, 3H), 2.73-2.51 (m, 2H), 2.51-2.39 (m, 4H), 2.27 (t, J = 7.3 Hz, 2H), 2.02-1.93 (m, 1H), 1.69-1.63 (m, 2H), 1.47 (p, J = 7.4 Hz, 2H), 1.30 (q, J = 8.0 Hz, 2H), 1.20 (s, 6H), 1.09 (s, 6H) | 8 |

FIG. 3 Continued.

| | | | | |
|---|---|---|---|---|
| 141 | [structure] | A | 821.35 | ¹H NMR (400 MHz, CD₃OD): δ 7.77-7.50 (m, 5H), 7.38-7.34 (m, 3H), 7.23-7.13 (m, 2H), 7.00-6.96 (m, 1H), 5.10-5.00 (m, 1H), 4.29 (s, 1H), 4.17-4.14 (m, 1H), 3.76-3.67 (m, 4H), 3.36-3.32 (m, 2H), 2.87-2.42 (m, 11H), 2.10-2.00 (m, 3H), 1.70-1.60 (m, 2H), 1.28-1.23 (m, 12H) | 39 |
| 142 | [structure] | A | 797.4 | 1H NMR (300 MHz, DMSO-d6) δ 11.08 (s, 1H), 8.73 (s, 2H), 7.83 (dd, J = 18.2, 8.5 Hz, 2H), 7.69 (d, J = 9.2 Hz, 1H), 7.41 (d, J = 2.2 Hz, 1H), 7.33 (dd, J = 8.3, 2.3 Hz, 1H), 7.18 (d, J = 2.4 Hz, 1H), 6.97 (dd, J = 8.8, 2.5 Hz, 1H), 5.08 (dd, J = 12.8, 5.4 Hz, 1H), 4.29 – 4.13 (m, 3H), 4.00 (d, J = 9.1 Hz, 1H), 3.79 (t, J = 4.7 Hz, 4H), 2.95 – 2.76 (m, 1H), 2.56 (d, J = 16.4 Hz, 2H), 2.45 – 2.30 (m, 6H), 2.00 (dd, J = 12.3, 6.2 Hz, 1H), 1.69 (dq, J = 46.8, 7.0 Hz, 4H), 1.18 (s, 6H), 1.08 (s, 6H). | 9 |

| 143 | <br>(structure) | A | 783.55 | 1H NMR (300 MHz, DMSO-d6) δ 11.08 (s, 1H), 8.75 (s, 2H), 8.21-7.63 (m, 3H), 7.60-7.16 (m, 2H), 7.18 (d, J = 2.4 Hz, 1H), 6.97 (dd, J = 8.8, 2.5 Hz, 1H), 5.09 (dd, J = 12.8, 5.3 Hz, 1H), 4.25 (d, J = 7.4 Hz, 3H), 4.01 (d, J = 9.1 Hz, 1H), 3.28 (s, 4H), 2.89-2.76 (m, 1H), 2.56 (d, J = 19.0 Hz, 2H), 2.24 (s, 6H), 1.99 (s, 3H), 1.13 (d, J = 30.8 Hz, 12H) | 9 |

FIG. 3 Continued.

| | | | | |
|---|---|---|---|---|
| 144 | [structure] | A | 769.3 | 1H NMR (300 MHz, DMSO-d6) δ 11.09 (s, 1H), 10.18 (s, 1H), 8.83 (s, 2H), 7.93-7.74 (m, 3H), 7.54 (d, J = 2.2 Hz, 1H), 7.42 (dd, J = 8.3, 2.3 Hz, 1H), 7.27-7.14 (m, 1H), 7.03-6.86 (m, 1H), 5.10 (dd, J = 12.8, 5.4 Hz, 1H), 4.88-4.47 (m, 4H), 4.27 (s, 1H), 4.02 (d, J = 9.1 Hz, 1H), 3.92- 3.62 (s, 4H), 3.30 (d, J = 54.5 Hz, 4H), 2.92-2.77 (m, 1H), 2.57 (d, J = 19.1 Hz, 2H), 2.08-1.97 (m, 1H), 1.18 (s, 6H), 1.08 (s, 6H). | 9 |
| 145 | [structure] | A | 822.57 | 1H NMR (300 MHz, CD3OD): δ 8.70 (s, 2H), 7.71-7.66 (m, 2H), 7.36 (m, 1H), 7.24-7.21 (m, 1H), 7.10-7.09 (m, 1H), 6.97-6.93 (m, 1H), 5.08-5.02 (m, 1H), 4.90-4.87 (m, 2H), 4.80 (s, 1H), 4.28-4.24 (m, 2H), 4.10 (s, 1H), 3.51 (m, 4H), 3.03-2.95 (m, 2H), 2.78-2.67 (m, 6H), 2.44-2.42 (m, 2H), 2.15-1.80 (m, 4H), 1.75-1.55 (m, 1H), 1.25-1.18 (m, 12H); | 49 |
| 146 | [structure] | A | 800.21 | 1H NMR (400 MHz, CDCl3): δ 1.25 (s, 6H), 1.30 (s, 6H), 1.98-2.07 (m, 2H), 2.11-2.16 (m, 1H), 2.46-2.51(m, 2H), 2.57-2.66 (m, 3H), 2.70-2.87 (m, 3H), 2.88-2.96 (m, 3H), 3.40-3.49 (m, 4H), 4.11 (s, 1H), 4.18 | 1 |

| 147 |  A | 781.51 | (d, J = 8.0 Hz, 1H), 4.92-4.97 (m, 1H), 6.20 (d, J = 8.0 Hz, 1H), 7.03-7.08 (m, 2H),7.24 (d, J = 2.4 Hz, 1H), 7.28-7.32 (m, 2H), 7.70 (d, J = 8.4 Hz, 1H), 7.76 (d, J = 8.4 Hz, 1H), 7.98-8.11 (m, 2H), 8.92 (d, J = 2.0 Hz, 1H). <br><br> $^1$H NMR (400 MHz, DMSO-$d_6$): δ 1.42-1.58 (m, 4H), 1.98-2.04 (m,1H), 2.26-2.34 (m, 2H), 2.40-2.48 (m, 6H), 2.62-2.70 (m, 3H), 2.82-2.94 (m, 1H), 3.36-3.52 (m, 7H), 4.24-4.50 (m, 5H), 5.02-5.10 (m, 1H), 5.76 (s, 1H), 6.53 (s, 1H), 6.93 (s, 1H), 7.23 (d, J = 8.4 Hz, 1H), 7.31 (s, 1H), 7.67 (d, J = 8.8 Hz, 1H), 7.98 (s, 2H), 8.07 (s, 1H), 8.26-8.34 (m, 1H), 11.08 (s, 1H). 13.28 (s, 1H). | 17a |

| | | | | |
|---|---|---|---|---|
| 148 |  | A | 835.8 | 39 |
| | | | | ¹H NMR (300 MHz, CD3OD) 7.76-7.64 (m, 4H), 7.35-7.32 (m, 3H), 7.23-7.20 (m, 1H), 7.13-7.12 (m, 1H), 7.00-6.96(m, 1H), 5.09-5.03 (m, 1H), 4.28-4.25 (m, 1H), 4.15-4.11 (m, 1H), 3.77-3.68 (m, 4H), 3.38-3.32 (m, 2H), 2.86-2.69 (m, 5H), 2.41-2.29 (m, 6H), 2.11-2.03 (m, 3H), 1.86-1.64 (m, 4H), 1.28-1.23 (m, 12H); |
| 149 |  | A | 801.5 | 37 |
| | | | | ¹H NMR (400 MHz, DMSO-$d_6$) δ 11.07 (s, 1H), 7.91 (d, $J$ = 8.8 Hz, 1H), 7.71 (dd, $J$ = 19.0, 8.4 Hz, 3H), 7.46 (d, $J$ = 9.2 Hz, 1H), 7.35 (d, $J$ = 2.4 Hz, 1H), 7.27 (dd, $J$ = 8.7, 2.3 Hz, 1H), 7.22 (d, $J$ = 2.4 Hz, 1H), 7.01 (dd, $J$ = 8.8, 2.4 Hz, 1H), 6.44 (d, $J$ = 8.4 Hz, 2H), 5.08 (dd, $J$ = 12.9, 5.4 Hz, 1H), 4.32 (s, 1H), 4.06 (d, $J$ = 9.1 Hz, 1H), 3.91 (t, $J$ = 7.3 Hz, 2H), |

| | | | |
|---|---|---|---|
| 150 |  | A | 836.6 | ¹H-NMR (300 MHz, CDCl3) δ8.69 (s, 2H), 8.01(m, 1H), 7.75- 7.69(m, 1H), 7.62- 7.53(m, 1H), 7.29(m, 1H), 7.10 - 7.04(m, 1H), 6.98 - 6.91 (m, 1H), 6.84 - 6.78 (m, 1H), 5.95- 5.88(m, 1H), 4.98- 4.81(m, 3H), 4.15- 4.01(m, 2H), 3.54(m, 4H), 3.11 - 2.60(m, 1H), 2.17 -2.09 (m, 1H), 1.87 - 1.61(m, 5H), 1.24 - 1.21 (m, 14H) | 32 |

(row above cell shows: 3.64 (ddd, J = 24.3, 9.7, 5.1 Hz, 3H), 3.43 (dt, J = 18.6, 4.7 Hz, 6H), 3.03 – 2.82 (m, 4H), 2.64 – 2.51 (m, 2H), 2.40 (t, J = 4.8 Hz, 4H), 2.02 (dt, J = 15.2, 5.6 Hz, 1H), 1.22 (s, 6H), 1.13 (s, 6H).)

| | | | | |
|---|---|---|---|---|
| 154 |  | A | 824.21 | 1HNMR (400 MHz, DMSO-d6): δ 1.12 (s, 6H), 1.22 (s, 6H), 1.39-1.44 (m, 2H), 1.55-1.61 (m, 2H), 1.75-1.81 (m, 2H), 2.02-2.06 (m, 1H), 2.54-2.69 (m, 2H), 2.85-2.94 (m, 1H), 3.39 (t, $J$ = 7.2 Hz, 2H), 3.46 (t, $J$ = 5.0 Hz, 2H), 3.88 (t, $J$ = 5.2 Hz, 2H), 4.06 (d, $J$ = 9.2 Hz, 1H), 4.16-4.19 (m, 4H), 4.31 (s, 1H), 5.10-5.14 (m, 1H), 6.87 (d, $J$ = 9.2 Hz, 1H), 6.99-7.02 (m, 1H), 7.21 (d, $J$ = 2.0 Hz, 1H), 7.32-7.35 (m, 1H), 7.43 (s, 1H), 7.66-7.68 (m, 1H), 7.82 (d, $J$ = 8.4 Hz, 1H), 7.90 (d, $J$ = 8.8 Hz, 1H), 8.01-8.03 (m, 1H), 8.66 (d, $J$ = 2.0 Hz, 1H), 11.12 (m, 1H). | 87 |
| 155 |  | A | 852.25 | 1H NMR (400 MHz, CD3OD): δ 1.17 (s, 6H), 1.24 (s, 6H), 1.43-1.46 (m, 2H), 1.56-1.59 (m, 2H), 2.07-2.10 (m, 1H), 2.42 (t, $J$ = 7.2 Hz, 2H), 2.54 (t, $J$ = 4.0 Hz, 4H), 2.62-2.73 (m, 4H), 2.79-2.84 (m, 1H), 3.32-3.35 (m, 2H), 3.86-3.91 (m, 6H), 4.10 (s, 1H), 4.23 (s, 1H), 5.01 (t, $J$ = 5.2 Hz, 1H), 5.05- | 73 |

FIG. 3 Continued.

| 156 | [structure] | A | 838.23 | ¹H NMR (400 MHz, DMSO-d6): δ 1.11 (s, 6H), 1.21 (s, 6H), 1.49-1.60 (m, 2H), 2.01-2.08 (m, 1H), 2.29-2.49 (m, 7H), 2.53-2.64 (m, 3H), 2.85-2.94 (m, 1H), 3.08-3.26 (m, 2H), 3.85 (s, 6H), 4.04 (d, J = 9.2 Hz, 1H), 4.29 (s, 1H), 5.06-5.16 (m, 2H), 6.99-7.02 (m, 1H), 7.22 (d, J = 2.4 Hz, 1H), 7.26-7.32 (m, 2H), 7.75 (d, J = 9.2 Hz, 1H), 7.86 (d, J = 8.8 Hz, 1H), 7.90 (d, J = 8.8 Hz, 1H), 8.77 (s, 2H), 11.14 (s, 1H). | 73 |

(previous row continued): 5.10 (m, 1H), 6.93-6.95 (m, 1H), 7.09 (d, J = 20.0 Hz, 1H), 7.20-7.25 (m, 2H), 7.68 (d, J = 8.8 Hz, 1H), 7.78 (d, J = 8.4 Hz, 1H), 8.71 (s, 2H).

| | | | | |
|---|---|---|---|---|
| 157 |  | A | 784.1 | H-NMR-PH-ARV-LS-031-M-0: (300 MHz, DMSO-*d6*, ppm) δ 11.10 (br, 1H), 8.20 -8.17 (d, *J* = 9Hz, 1H), 8.02 (s, 1H), 7.74 - 7.66 (m, 2H), 7.53 - 7.47 (m, 1H), 7.34 - 7.15 (m, 4H), 5.11 - 5.05 (m, 1H), 3.42 - 3.35 (m, 4H), 2.91 - 2.83 (m, 1H), 2.71 - 2.60 (m, 4H), 2.56 - 2.49 (m, 4H), 2.35 - 2.30 (m, 2H), 2.08 - 2.00 (m, 1H), 1.67 - 1.65 (m, 2H), 1.62 (s, 8H), 1.60 - 1.37 (m, 2H). | 43 |
| 158 |  | A | 820.35 | ¹H NMR (300 MHz, CDCl₃) δ 7.95 (s, 1H), 7.70-7.55 (m, 4H), 7.30 (s, 1H), 7.26-6.97 (m, 1H), 6.96-6.79 (m, 4H), 6.12-6.09 (m, 1H), 4.96-4.94 (m, 1H), 4.16-4.04 (m, 2H), 3.89-3.39 (m, 5H), 3.20-2.50 (m, 8H), 2.49-1.60 (m, 6H), 1.26-1.20 (m, 15H); | 49 |

| 159 |  | A | 796.65 | H-NMR06-PH-ARV-LS-031-A-0: (300 MHz, CD3OD, ppm) δ 7.96 - 7.93 (d, *J* = 9 Hz, 1 H), 7.83 (s, 1 H), 7.69 - 7.61 (m, 2 H), 7.51 - 7.48 (m, 1 H), 7.35 (s, 1 H), 7.24 - 7.15 (m, 3 H), 5.09 - 5.05 (m, 1 H), 3.48 - 3.45 (m, 4H), 2.82 - 2.42 (m, 15 H), 2.12 - 2.09 (m, 2 H), 1.76 - 1.73 (m, 2 H), 1.66 - 1.61 (m, 3 H), 1.48 - 1.46 (m, 2 H). | 43 |

| 160 | | A | 821.35 | ¹H NMR (300 MHz, DMSO-d₆) δ 10.70 (s, 1H), 8.62 (d, J = 2.4 Hz, 1H), 7.92 (dd, J = 10.0, 6.5 Hz, 2H), 7.56 (dd, J = 17.5, 8.9 Hz, 2H), 7.22 (d, J = 2.4 Hz, 1H), 7.03 (ddd, J = 14.6, 8.6, 2.1 Hz, 3H), 6.86 (d, J = 9.1 Hz, 1H), 5.31 (s, 2H), 4.57 (dd, J = 9.1, 5.2 Hz, 1H), 4.41 (d, J = 13.3 Hz, 2H), 4.31 (s, 1H), 4.06 (d, J = 9.2 Hz, 1H), 3.29 (t, J = 4.9 Hz, 4H), 2.96 – 2.81 (m, 2H), 2.61 (t, J = 5.6 Hz, 2H), 2.54 – 2.50 (m, 4H), 2.38 (t, J = 7.4 Hz, 2H), 2.00 (qd, J = 8.2, 3.9 Hz, 2H), 1.77 (d, J = 12.7 Hz, 2H), 1.63 (s, 1H), 1.43 (q, J = 7.2 Hz, 2H), 1.22 (s, 6H), 1.12 (s, 8H). | 41 |

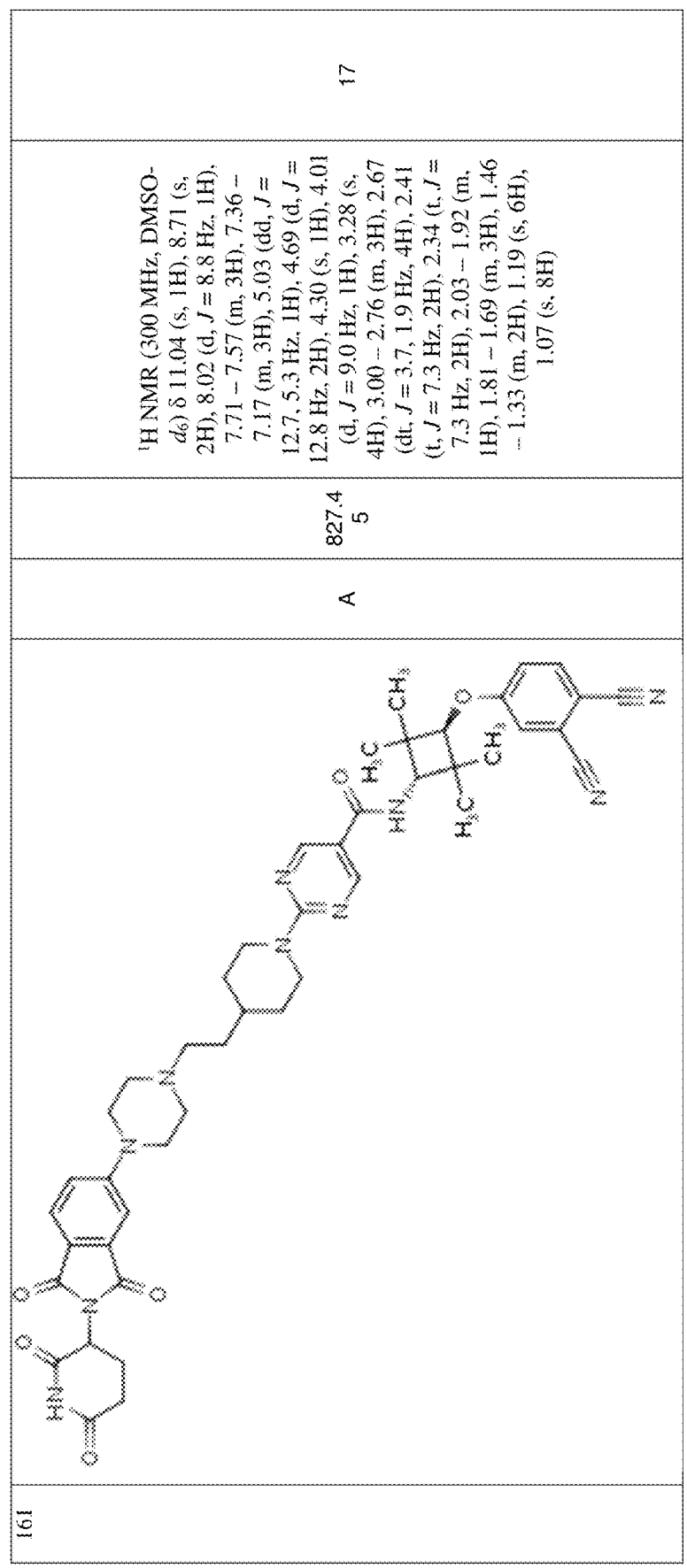
FIG. 3 Continued.
| 161 | 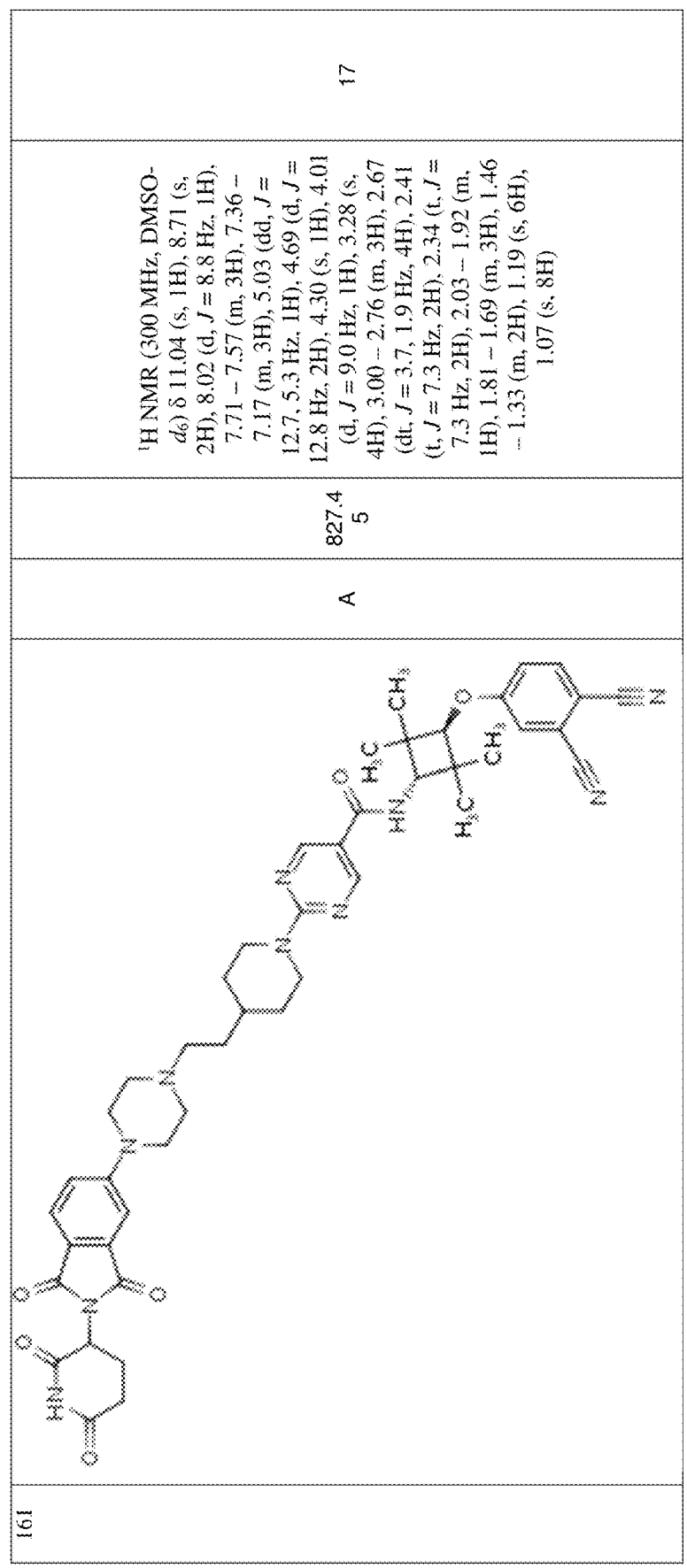 | A | 827.45 | ¹H NMR (300 MHz, DMSO-d₆) δ 11.04 (s, 1H), 8.71 (s, 2H), 8.02 (d, J = 8.8 Hz, 1H), 7.71 – 7.57 (m, 3H), 7.36 – 7.17 (m, 3H), 5.03 (dd, J = 12.7, 5.3 Hz, 1H), 4.69 (d, J = 12.8 Hz, 2H), 4.30 (s, 1H), 4.01 (d, J = 9.0 Hz, 1H), 3.28 (s, 4H), 3.00 – 2.76 (m, 3H), 2.67 (dt, J = 3.7, 1.9 Hz, 4H), 2.41 (t, J = 7.3 Hz, 2H), 2.34 (t, J = 7.3 Hz, 2H), 2.03 – 1.92 (m, 1H), 1.81 – 1.69 (m, 3H), 1.46 – 1.33 (m, 2H), 1.19 (s, 6H), 1.07 (s, 8H) | 17 |

| 162 | | A | 764.3 | H-NMR (300 MHz, DMSO) δ 11.05 (s, 1H), 8.64-8.63 (d, J=2.4 Hz, 1H), 7.98-7.89 (m, 2H), 7.67-7.60 (m, 2H), 7.22-7.21 (d, J=2.4 Hz, 1H), 7.03-6.92 (m, 2H), 6.80-6.79 (d, J=1.8Hz, 1H), 6.69-6.65 (m, 1H), 5.09-5.03 (m, 1H), 4.31 (s, 1H), 4.08-4.05 (d, J=9 Hz, 1H), 3.85 (s, 4H), 3.67 (s, 4H), 2.73-2.72 (m, 1H), 2.60 (s, 2H), 2.01-1.99(d, J=5.1 Hz, 1H), 1.82 (s, 4H), 1.22 (s, 6H), 1.12(s, 6H); | 44 |

| | | | | |
|---|---|---|---|---|
| 163 |  | A | 764.35 | H-NMR (300 MHz, DMSO) δ 11.04 (s, 1H), 8.58 (s, 1H), 7.95-7.86 (m, 2H), 7.66-7.63 (d, J=8.4Hz, 1H), 7.57-7.54 (d, J=9.3Hz, 1H), 7.35-7.18 (m, 3H), 7.00-6.96 (m, 1H), 6.39-6.36 (d, J=9Hz, 1H), 5.08-5.02 (m, 1H), 4.28 (s, 1H), 4.05-4.02 (d, J=9.3Hz, 1H), 3.80 (s, 4H), 3.51 (s, 4H), 2.92-2.81 (m, 1H), 2.70-2.59 (m, 2H), 2.05-1.98 (m, 4H), 1.19 (s, 6H), 1.10 (s, 6H); | 19 |
| 164 |  | A | 833.54 | ¹H NMR (400 MHz, DMSO-d6): δ 1.13 (s, 6H), 1.24 (s, 6H), 1.38-1.47 (m, 2H), 1.74-1.90 (m, 4H), 1.96-2.10 (m, 2H), 2.54-2.65 (m, 2H), 2.85-2.94 (m, 1H), 3.33 (s, 1H), 4.04-4.11 (m, 1H), 4.14-4.19 (m, 3H), 4.32 (s, 1H), 4.55 (s, 3H), 5.07-5.18 (m, 1H), 6.62 (d, J = 8.8 Hz, 1H), 6.96-7.08 (m, 1H), 7.23 (d, J = 2.4 Hz, | 85 |

| | | | |
|---|---|---|---|
| | | | 1H), 7.31-7.38 (m, 1H), 7.43 (d, J = 1.6 Hz, 1H), 7.66 (s, 2H), 7.79-7.86 (m, 1H), 7.89-7.95 (m, 1H), 7.98-8.05 (m, 1H), 8.69 (s, 1H), 11.08-11.19 (m, 1H). |
| 165 |  | A | 740.46 | 1H NMR (400 MHz, DMSO-d6): δ 1.11 (s, 6H), 1.21 (s, 6H), 2.03-2.15 (m, 2H), 2.58 (m, 2H), 3.86-3.89 (m, 2H), 4.04 (d, J = 8.8 Hz, 1H), 4.23-4.29 (m, 5H), 5.10-5.15 (m, 1H), 6.99-7.02 (m, 1H), 7.21 (d, J = 2.0 Hz, 1H), 7.35-7.38 (m, 1H), 7.45 (d, J = 2.0 Hz, 1H), 7.74 (d, J = 8.8 Hz, 1H), 7.84-7.91 (m, 2H), 8.74 (s, 2H), 11.12 (s, 1H). | 88 |

| 166 | | | |
|---|---|---|---|
| | | 831.53 | 89 |
| | A | | ¹H NMR (400 MHz, DMSO-d6): δ 1.10 (s, 6H), 1.17 (s, 6H), 1.61-1.64 (m, 2H), 1.76-1.82 (m, 2H), 2.01-2.07 (m, 1H), 2.38 (s, 2H), 2.44-2.49 (m, 4H), 2.57 (s, 1H), 2.85-2.94 (m, 1H), 3.24 (s, 4H), 3.32 (s, 1H), 4.00 (d, J = 9.2 Hz, 1H), 4.20-4.26 (m, 3H), 5.10-5.15 (m, 1H), 6.66 (d, J = 11.6 Hz, 2H), 7.00 (dd, J = 8.8, 2.4 Hz, 1H), 7.22 (d, J = 2.4 Hz, 1H), 7.36 (dd, J = 8.4, 2.4 Hz, 1H), 7.44 (d, J = 2.4 Hz, 1H), 7.84 (d, J = 8.4 Hz, 1H), 7.90 (d, J = 8.8 Hz, 1H), 8.19 (d, J = 9.2 Hz, 1H), 11.13 (s, 1H). |

| 167 | | A | 836.5 | 1HNMR (400 MHz, DMSO-d6) : δ 1.11 (s, 6H), 1.22 (s, 6H), 1.73-1.83 (m, 5H), 1.99-2.02 (m, 1H), 2.29 (s, 2H), 2.57 (s, 6H), 2.74 (s, 2H), 2.91-2.97 (m, 3H), 3.82-3.86 (m, 4H), 4.01-4.03 (m, 3H), 4.29 (s, 1H), 5.06-5.09 (m, 1H), 7.01 (d, J = 8.0 Hz, 1H), 7.22-7.30 (m, 3H), 7.64 (d, J = 7.6 Hz, 1H), 7.75 (d, J = 8.4 Hz, 1H), 7.90 (d, J = 8.4 Hz, 1H), 8.77 (s, 2H), 11.10 (s, 1H). | 49 |

| 168 | <br><br> | A | 837.75 | H-NMR-PH-ARV-LS-032-D-0: (300 MHz, DMSO-d6, ppm) δ 11.11 (s, 1H), 7.86 (dd, J = 22.3, 8.5 Hz, 2H), 7.72 (d, J = 8.6 Hz, 2H), 7.52 – 7.43 (m, 2H), 7.36 (dd, J = 8.3, 2.3 Hz, 1H), 7.20 (d, J = 2.4 Hz, 1H), 7.05 – 6.90 (m, 3H), 5.11 (dd, J = 13.0, 5.2 Hz, 1H), 4.31 (s, 3H), 4.04 (d, J = 9.1 Hz, 1H), 3.65 (s, 2H), 3.10 (d, J = 11.5 Hz, 2H), 2.89 (s, 1H), 2.69 (s, 5H), 2.37 (s, 3H), 2.04 (d, J = 11.3 Hz, 1H), 1.85 (s, 2H), 1.58 (s, 2H), 1.21 (s, 6H), 1.12 (s, 6H). | 47 |

| 169 | | A | 851.25 | H-NMR-PH-ARV-LS-032-F-0: (300 MHz, DMSO-d6,ppm) (300 MHz, DMSO-$d_6$) δ 11.08 (s, 1H), 7.84 (dd, $J$ = 19.4, 8.5 Hz, 2H), 7.69 (d, $J$ = 8.6 Hz, 2H), 7.49 – 7.26 (m, 3H), 7.17 (d, $J$ = 2.3 Hz, 1H), 7.02 – 6.87 (m, 3H), 5.09 (dd, $J$ = 12.8, 5.3 Hz, 1H), 4.31 – 4.14 (m, 3H), 4.01 (d, $J$ = 9.1 Hz, 1H), 3.62 (t, $J$ = 4.6 Hz, 2H), 3.44 (d, $J$ = 12.6 Hz, 2H), 3.07 (t, $J$ = 11.3 Hz, 2H), 2.91 – 2.76 (m, 1H), 2.47 (m, 2H), 2.42 – 2.30 (m,4H), 2.23 (s, 2H), 2.01-1.88 (m, 5H), 1.55 (dd, $J$ = 12.6, 8.4 Hz, 2H), 1.18 (s, 6H), 1.09 (s, 6H). | 47 |

| | | | |
|---|---|---|---|
| 170 | | A | 769.3 | 1H NMR (300 MHz, CDCl₃) 8.12 (s, 1H), 7.73-7.71 (m, 2H), 7.60-7.25 (m, 5H), 6.97-6.96 (m, 1H), 6.82-6.79 (m, 1H), 6.21-6.18 (m, 1H), 4.96-4.90 (m, 1H), 4.17-4.14 (m, 1H), 4.05-4.00 (m, 1H), 3.48-3.35 (m, 4H), 2.93-2.68 (m, 10H), 2.16-2.12 (m, 1H), 1.37-1.23 (m, 13H); | 1 |

FIG. 3 Continued.

| | | | | |
|---|---|---|---|---|
| 171 | [structure] | A | 763.6 | ¹H NMR (300 MHz, CD₃OD) δ 7.770-7.66 (m, 3H), 7.60 (d, J = 8.5 Hz, 1H), 7.31 (d, J = 8.1 Hz, 2H), 7.10 (d, J = 2.4 Hz, 1H), 7.04-6.89 (m, 2H), 6.84 (dd, J = 8.6, 2.2 Hz, 1H), 5.02 (dd, J = 12.3, 5.4 Hz, 1H), 4.54 (s, 1H), 4.25 (s, 1H), 4.11 (s, 1H), 3.75 (s, 1H), 3.46 (d, J = 2.5 Hz, 2H), 3.07-2.96 (m, 1H), 2.88-2.61 (m, 8H), 2.13-1.87 (m, 3H), 1.24 (s, 6H), 1.19 (s, 6H); | 1 |
| 172 | [structure] | A | 834.56 | | |

| 173 |  | A | 856.56 | 1HNMR (400 MHz, DMSO-d6): δ 1.11 (s, 6H), 1.21-1.22 (m, 6H), 1.52-1.57 (m, 1H), 1.60-1.69 (m, 2H), 1.98-2.07 (m, 2H), 2.12-2.23 (m, 1H), 2.35-2.43 (m, 2H), 2.55-2.68 (m, 4H), 2.83-2.93 (m, 1H), 3.28-3.34 (m, 3H), 3.40 (s, 4H), 3.52-3.57 (m, 1H), 3.65-3.69 (m, 2H), 4.05-4.08 (m, 1H), 4.31 (s, 1H), 5.06-5.10 (m, 1H), 6.99-7.02 (m, 1H), 7.21-7.28 (m, 2H), 7.36 (s, 1H), 7.51-7.54 (m, 2H), 7.63-7.70 (m, 2H), 7.90-7.92 (m, 1H), 11.09 (s, 1H). | 49 |

| | | | |
|---|---|---|---|
| 174 |  | A | 834.55 | 1H NMR (300 MHz, DMSO-d6) δ 11.04 (s, 1H), 7.87 (d, J = 8.7 Hz, 1H), 7.67 (dd, J = 15.3, 8.5 Hz, 3H), 7.44 (d, J = 9.2 Hz, 1H), 7.30 (d, J = 2.4 Hz, 1H), 7.27-7.13 (m, 2H), 7.02-6.87 (m, 3H), 5.03 (dd, J = 12.7, 5.3 Hz, 1H), 4.28 (s, 1H), 4.01 (d, J = 9.1 Hz, 1H), 3.81 (d, J = 12.4 Hz, 2H), 3.28 (s, 5H), 2.93-2.69 (m, 4H), 3.0-2.6 (m, 4H), 2.54 (d, J = 16.1 Hz, 5H), 2.35 (t, J = 7.2 Hz, 2H), 2.03-1.93 (m, 1H), 1.73 (d, J = 12.8 Hz, 2H), 1.40 (d, J = 7.3 Hz, 3H), 1.18 (s, 8H), 1.09 (s, 6H). | 23 |
| 175 |  | A | 832.3 | 1H NMR (400 MHz, CD3OD) δ 7.74 (dd, J = 8.8, 2.7 Hz, 3H), 7.66 (d, J = 8.4 Hz, 1H), 7.15 (d, J = 2.4 Hz, 1H), 7.07-7.04 (m, 1H), 7.00 (td, J = 6.3, 3.1 Hz, 3H), 6.93-6.85 (m, 1H), 5.07 (dd, J = 12.6, 5.5 Hz, 1H), 4.57 (d, J = 2.3 Hz, 1H), 4.30 (s, 1H), 4.15 (s, 1H), 3.90 (d, J = 12.2 Hz, 2H), 3.72 (s, 1H), 3.51 (s, 2H), 3.08 (d, J = 9.6 Hz, 1H), 2.94-2.70 (m, 5H), | 35 |

FIG. 3 Continued.

| | | | | |
|---|---|---|---|---|
| 176 | [structure] | A | 832.3 | 35 | 2.66 (d, J = 10.0 Hz, 1H), 2.51 (d, J = 6.9 Hz, 2H), 2.17-2.03 (m, 2H), 1.99-1.83 (m, 3H), 1.66 (s, 1H), 1.29 (s, 8H), 1.24 (s, 6H) |
| | | | | | ¹H NMR (400 MHz, CD₃OD) δ 7.73 (dd, J = 8.9, 2.8 Hz, 3H), 7.66 (d, J = 8.5 Hz, 1H), 7.15 (d, J = 2.4 Hz, 1H), 7.05 (s, 1H), 6.99 (td, J = 6.3, 3.1 Hz, 3H), 6.89 (d, J = 8.5 Hz, 1H), 5.07 (dd, J = 12.5, 5.4 Hz, 1H), 4.57 (s, 1H), 4.30 (s, 1H), 4.15 (s, 1H), 3.90 (d, J = 12.3 Hz, 2H), 3.71 (s, 1H), 3.51 (s, 2H), 3.07 (d, J = 9.7 Hz, 1H), 2.90-2.70 (m, 5H), 2.66 (d, J = 10.0 Hz, 1H), 2.50 (d, J = 6.9 Hz, 2H), 2.17-2.03 (m, 2H), 1.99-1.83 (m, 3H), 1.66 (s, 1H), 1.29 (s, 8H), 1.24 (s, 6H) |
| 177 | [structure] | A | 838.57 | 49 | ¹H NMR (400 MHz, DMSO-d6): δ 1.12 (s, 6H), 1.22 (s, 6H), 1.62-1.67 (m, 2H), 1.82-1.88 (m, 2H), 2.00-2.07 (m, 1H), 2.11-2.15 (m, 1H), 2.24-2.28 (m, 1H), 2.56-2.58 (m, 1H), 2.61-2.62 (m, 1H), 2.85-2.93 (m, 2H), 3.14-3.20 (m, 2H), 3.22-3.28 (m, 4H), 3.62-3.65 (m, 4H), 4.06 (d, J = 8.8 Hz, 1H), 4.24-4.27 (m, 2H), 4.32 (s, 1H), 5.08-5.13 (m, |

| | | | | |
|---|---|---|---|---|
| 178 |  | A | 835.2 | 1H NMR (400 MHz, CD3OD): δ7.80-7.78 (d, J=8.4Hz, 1H), 7.73-7.70 (m, 3H), 7.25-7.19 (m, 2H), 7.13-7.12 (d, J=2.4Hz, 1H), 6.99-6.96 (m, 3H), 5.12-5.07 (m, 1H), 4.91-4.89 (m, 1H), 4.28 (s, 1H), 4.13 (s, 1H), 3.92-3.88 (m, 2H), 3.13-3.12 (m, 1H), 2.87-2.65 (m, 6H), 2.47-2.44 (m, 2H), 2.34-2.29 (m, 2H), 2.18-2.13 (m, 6H), 1.92-1.89 (m, 2H), 1.80-1.70 (m, 1H), 1.32-1.31 (m, 1H), 1.28 (s, 6H), 1.21 (s, 6H); | 51 |
| | | | | 1H), 6.72 (t, J=8.8 Hz, 1H), 7.21 (d, J=2.4Hz, 1H), 7.36-7.39 (m, 1H), 7.51-7.55 (m, 2H), 7.60-7.67 (m, 2H), 7.77 (d, J=8.8 Hz, 1H), 7.91 (d, J=8.80 Hz, 1H), 9.65 (br, 1H), 11.11 (s, 1H). | |
| 179 |  | A | 839.57 | | 49 |

FIG. 3 Continued.

| | | | | |
|---|---|---|---|---|
| 180 | [structure] | A | 838.57 | | 49 |
| 181 | [structure] | A | 856.56 | | 49 |
| 182 | [structure] | A | 824.45 | 1H-NMR (300 MHz, DMSO-d6) δ11.10 (s, 1H), 7.93- 7.86 (m, 1H), 7.77- 7.69 (m, 3H), 7.50- 7.34 (m, 2H), 7.22- 7.18 (m, 1H), 7.04- 6.96 (m, 1H), 6.58- 6.51 (m, 2H), 5.16 - 5.06 (m, 1H), 4.32(s, 1H), 4.09- 4.02 (m, 1H), 3.55- 3.20 (m, 6H), 3.09- 2.73 (m, 2H), 2.70- 2.38 (m, 10H), 2.20- 2.01 (m, 2H), 1.86- 1.67 (m, 1H), 1.24 - 1.13 (d, $J$=33 Hz, 12H). | 46 |

FIG. 3 Continued.

| | | | | |
|---|---|---|---|---|
| 183 | [structure] | A | 819.58 | ¹H NMR (400 MHz, DMSO-d⁶) δ 0.97-1.07 (2H, m), 1.13 (6H, s), 1.23 (6H, s), 1.49-1.69 (5H, m), 1.80-2.02 (4H, m), 2.19-2.20 (1H, m), 2.33-2.43(1H, m), 2.50-2.60(2H, m), 2.81-2.91(1H, m), 3.30-3.35 (4H, m), 3.40-3.45 (4H, m), 4.06 (1H, d, *J* = 9.2 Hz), 4.32 (1H, s), 5.03-5.07 (1H, m), 6.99-7.02 (1H, m), 7.21 (1H, d, *J* = 2.4 Hz), 7.27 (1H, d, *J* = 8.8 Hz), 7.33-7.39 (3H, m), 7.68 (1H, d, *J* = 8.4 Hz),7.73-7.77 (3H, m), 7.91 (1H, d, *J* = 8.8 Hz), 11.09 (1H, s). | 90 |
| 184 | [structure] | A | 799.63 | ¹H NMR (400 MHz, DMSO-d⁶) δ 0.97-1.07 (2H, m), 1.13 (6H, s), 1.23 (6H, s), 1.46-1.69 (5H, m), 1.81-2.02 (4H, m), 2.19-2.20 (1H, m), 2.39-2.41(1H, m), 2.45 (3H, m), 2.53-2.59(2H, m), 2.81-2.89(1H, m), 3.30-3.35 (4H, m), 3.42-3.48 (4H, m), 4.05 (1H, d, *J* = 9.2 Hz), 4.23 (1H, s), 5.02-5.07 (1H, m), 6.80-6.83 (1H, m), 7.25-7.40 (4H, m), 7.67-7.78 (5H, m), 11.10 (1H, s). | 90 |

| | | | | |
|---|---|---|---|---|
| 185 | [structure] | A | 824.35 | ¹H NMR (300 MHz, CDCl₃) 7.83-7.80 (m, 1H), 7.63-7.39 (m, 4H), 7.19-7.05 (m, 1H), 6.90-6.71 (m, 4H), 6.04-6.01 (m, 1H), 5.14-5.08 (m, 1H), 4.38-4.07 (m, 3H), 3.97-3.95 (m, 1H), 3.81-3.30 (m, 4H), 3.19-2.98 (m, 3H), 2.89-2.55 (m, 6H), 2.31-2.18 (m, 4H), 1.82-1.61 (m, 2H), 1.19-1.15 (m, 15H); | 20, 33 |
| 186 | [structure] | A | 824.35 | ¹H NMR (300 MHz, CDCl₃) 7.81-7.80 (m, 1H), 7.62-7.60 (m, 2H), 7.53-7.48 (m, 2H), 6.90-6.71 (m, 5H), 6.04-6.01 (m, 1H), 5.13-5.07 (m, 1H), 4.37-4.06 (m, 3H), 3.97-3.41 (m, 5H), 3.12-3.06 (m, 3H), 2.88-2.42 (m, 7H), 2.30-2.15 (m, 4H), 1.82-1.75 (m, 1H), 1.19-1.05 (m, 15H); | 41 |

| 187 | [structure] | A | 838.38 | ¹H NMR (300 MHz, DMSO) 10.96 (s, 1H), 7.91-7.88 (m, 1H), 7.74-7.71 (m, 2H), 7.48-7.41 (m, 2H), 7.24-7.20 (m, 2H), 7.01-6.93 (m, 3H), 5.09-5.03 (m, 1H), 4.39-4.21 (m, 3H), 4.06-4.03 (m, 1H), 3.86-3.82 (m, 2H), 3.30-3.28 (m, 1H), 3.11-3.05 (m, 4H), 2.90-2.72 (m, 3H), 2.61-2.50 (m, 4H), 2.42-2.35 (m, 3H), 2.07-1.95 (m, 1H), 1.78-1.75 (m, 2H), 1.51-1.42 (m, 3H), 1.30-1.05 (m, 14H); | 33 |

FIG. 3 Continued.

| | | | |
|---|---|---|---|
| 188 | [structure] | A | 838.4 | ¹H NMR (300 MHz, DMSO-d6) 10.96 (s, 1H), 7.91-7.88 (m, 1H), 7.74-7.70 (m, 2H), 7.48-7.20 (m, 4H), 7.02-6.93 (m, 3H), 5.09-5.05 (m, 1H), 4.39-4.21 (m, 3H), 4.06-4.03 (m, 1H), 3.96-3.82 (m, 2H), 3.30-3.28 (m, 1H), 3.11-3.05 (m, 4H), 2.90-2.72 (m, 3H), 2.70-2.62 (m, 4H), 2.39-2.26 (m, 3H), 2.07-1.79 (m, 1H), 1.75-1.70 (m, 2H), 1.52-1.46 (m, 3H), 1.31-1.05 (m, 14H); | 33 |

| | | | | |
|---|---|---|---|---|
| 189 |  | A | 806.4 | 34 | ¹H NMR (300 MHz, DMSO-d₆): δ11.04 (s, 1H), 7.87 (d, J = 8.7 Hz, 1H), 7.67 (dd, J = 13.3, 8.3 Hz, 3H), 7.44-7.13 (m, 4H), 7.02-6.91 (m, 1H), 6.38 (d, J = 8.3 Hz, 2H), 5.04 (dd, J = 12.4, 5.2 Hz, 1H), 4.28 (s, 1H), 3.99 (q, J = 8.1, 7.6 Hz, 3H), 3.50 (t, J = 6.5 Hz, 2H), 3.41 (d, J = 6.4 Hz, 4H), 2.96-2.47 (m, 4H), 2.47 (d, J = 3.4 Hz, 2H), 2.30 (d, J = 7.4 Hz, 2H), 2.09-1.90 (m, 1H), 1.85- 1.71 (m, 2H), 1.18 (s, 6H), 1.09 (s, 6H). |
| 190 |  | A | 821.35 | 23 | ¹H NMR (300 MHz, DMSO): δ 11.11 (s, 1H), 7.91-7.81 (m, 2H), 7.73 (d, J = 9.0 Hz, 2H), 7.48 (d, J = 9.1 Hz, 1H), 7.30-7.27 (m, 2H), 7.20 (m, 1H), 7.02-6.90 (m, 3H), 5.18-5.00 (m, 2H), 4.32 (s, 1H), 4.05 (d, J = 9.0 Hz, 1H), 3.89-3.70 (m, 4H), 3.05-2.98 (m, 2H), 2.98-2.81 (m, 1H), 2.80-2.69 (m, 2H), 2.64-2.56 (m, 2H), 2.49- |

| 191 |  | A | 836.5 | 1H NMR (400 MHz, DMSO-d6): δ 1.11 (s, 6H), 1.22 (s, 6H), 1.58-1.70 (m, 2H), 1.81-2.05 (m, 6H), 2.10-2.18 (m, 2H), 2.80-2.92 (m, 1H), 3.34-3.76 (m, 7H), 3.53-3.67 (m, 3H), 3.72-3.89 (m, 3H), 3.98-4.08 (m, 2H), 4.27-4.33 (m, 1H), 5.05-5.14 (m, 1H), 7.01 (s, 1H), 7.23-7.33 (m, 3H), 7.67-7.78 (m, 2H), 7.91 (m, 1H), 8.76-8.77 (m, 2H), 11.09 (s, 1H). 2.40 (m, 2H), 2.10-1.93 (m, 1H), 1.80-1.79 (m, 2H), 1.60-1.44 (m, 1H), 1.32-1.14 (m, 10H), 1.12 (s, 6H) | 49 |

| 192 |  | A | 805.56 | ¹H NMR (400 MHz, CDCl₃) δ 1.13 (6H, s), 1.22 (6H, s), 1.37-1.57 (4H, m), 1.86-2.03 (5H, m), 2.32-2.42 (2H, m), 2.54-2.63 (2H, m), 2.67 (4H, brs), 2.84-2.91 (1H, m), 3.44 (4H, brs), 4.05 (1H, d, $J$ = 9.2 Hz), 4.31 (1H, s), 5.07 (1H, dd, $J$ = 5.6, 9.2 Hz), 7.00 (1H, dd, $J$ = 2.0, 8.8 Hz), 7.21 (1H, d, $J$ = 2.4 Hz), 7.25-7.27 (1H, m), 7.33-7.35 (3H, m), 7.67-7.69 (1H, m), 7.70-7.75 (3H, m), 7.89-7.92 (1H, m), 11.10 (1H, s). | 91 |

FIG. 3 Continued.

| | | | | |
|---|---|---|---|---|
| 193 | ![structure] | A | 810.35 | 3 | ¹H NMR (300 MHz, CD₃OD): δ 8.60 (s, 1H), 7.99-7.95 (m, 1H), 7.83-7.70 (m, 2H), 7.42-7.31 (m, 2H), 7.13-7.12(s, 1H), 7.00-6.86 (m, 2H), 5.09-5.08 (m, 1H), 4.37-4.14 (m, 6H), 3.19-3.13 (m, 2H), 2.89-2.73 (m, 7H), 2.20-2.03 (m, 3H), 1.29-1.22 (m, 18H); |
| 194 | ![structure] | A | 809.2 | 21 | ¹H NMR (300 MHz, Methanol-d₄): δ 7.82 (d, $J$ = 8.3 Hz, 1H), 7.79-7.70 (m, 3H), 7.42 (d, $J$ = 2.2 Hz, 1H), 7.33 (dd, $J$ = 8.3, 2.3 Hz, 1H), 7.14 (d, $J$ = 2.4 Hz, 1H), 7.05-6.95 (m, 3H), 5.12 (dd, $J$ = 12.3, 5.4 Hz, 1H), 4.29 (d, $J$ = 0.9 Hz, 1H), 4.21 (t, $J$ = 5.8 Hz, 2H), 4.14 (d, $J$ = 0.8 Hz, 1H), 3.77 (s, 1H), 3.73 (s, 1H), 3.15-3.05 (m, 2H), 2.96-2.69 (m, 5H), 2.60 (t, $J$ = 11.3 Hz, 2H), 2.19-2.08 (m, 1H), 2.03 (d, $J$ = 8.6 Hz, 2H), 1.29 (s, 6H), 1.26 (s, 3H), 1.23 (d, $J$ = 2.1 Hz, 9H). |

| | | | |
|---|---|---|---|
| 195 |  | A | 811.3 | ¹H NMR (400 MHz, DMSO): δ 11.11 (s, 1H), 8.76 (s, 2H), 7.90 (d, J = 8.7 Hz, 1H), 7.84 (d, J = 8.3 Hz, 1H), 7.72 (d, J = 9.2 Hz, 1H), 7.43 (d, J = 2.3 Hz, 1H), 7.36-7.33 (m, 1H), 7.22 (m, 1H), 7.02-6.99 (m, 1H), 5.14-5.09 (m, 1H), 4.53 (d, J = 11.9 Hz, 2H), 4.29 (s, 1H), 4.20 (m, 2H), 4.03 (d, J = 9.1 Hz, 1H), 2.97-2.83 (m, 3H), 2.74 (m, 2H), 2.65-2.52 (m, 3H), 2.49 (m, 1H), 2.11-2.01 (m, 1H), 1.83 (m, 2H), 1.22 (s, 6H), 1.11 (m, 12H) | 3 |

197    A    769.5

| | | | | |
|---|---|---|---|---|
| 202 |  | A | 779.35 | 22 | ¹H NMR (300 MHz, CD3OD) 7.78-7.68 (m, 4H), 7.37-7.34 (m, 3H), 7.26-7.23 (m, 1H), 7.13-7.11 (m, 1H), 7.00-6.96(m, 1H), 5.08-5.04 (m, 1H), 4.29-4.27 (m, 1H), 4.16-4.14 (m, 1H), 3.92-3.89 (m, 2H), 3.11-2.71 (m, 11H), 2.13-2.11 (m, 1H), 1.31-1.28 (m, 18H); |
| 203 |  | A | 833.25 | 36 | ¹H NMR (400 MHz, DMSO-d₆) δ 11.07 (s, 1H), 7.91 (d, J = 8.8 Hz, 1H), 7.71 (dd, J = 19.0, 8.4 Hz, 3H), 7.46 (d, J = 9.2 Hz, 1H), 7.35 (d, J = 2.4 Hz, 1H), 7.27 (dd, J = 8.7, 2.3 Hz, 1H), 7.22 (d, J = 2.4 Hz, 1H), 7.01 (dd, J = 8.8, 2.4 Hz, 1H), 6.44 (d, J = 8.4 Hz, 2H), 5.08 (dd, J = 12.9, 5.4 Hz, 1H), 4.32 (s, 1H), 4.06 (d, J = 9.1 Hz, 1H), 3.91 (t, J = 7.3 Hz, 2H), 3.64 (ddd, J = 24.3, 9.7, 5.1 Hz, 3H), 3.43 (dt, J = 18.6, 4.7 Hz, 6H), 3.03 – 2.82 (m, 4H), 2.64 – 2.51 (m, 2H), 2.40 (t, J = 4.8 Hz, 4H), 2.02 (dt, J = 15.2, 5.6 Hz, 1H), 1.22 (s, 6H), 1.13 (s, 6H). |

| | | |
|---|---|---|
| 204 | A | 850.25 | 51 |

$^1$H NMR (400 MHz, CD$_3$OD): δ7.78-7.70 (m, 4H), 7.26-7.20 (m, 2H), 7.13-7.12 (d, J=2.0Hz, 1H), 6.99-6.96 (m, 3H), 5.12-5.07 (m, 1H), 4.93-4.89 (m, 1H), 4.28 (s, 1H), 4.13 (s, 1H), 3.32-3.30 (m, 4H), 3.28-3.26 (m, 1H), 2.87-2.67 (m, 7H), 2.58-2.46 (m, 6H), 2.39-2.34 (m, 2H), 2.25 (s, 3H), 2.14-2.11 (m, 1H), 1.28 (s, 6H), 1.21 (s, 6H);

| 205 |  | A | $^1$H NMR (300 MHz, DMSO-*d6*) 11.12 (s, 1H), 7.92-7.73 (m, 4H), 7.22-7.19 (m, 3H), 7.20-6.95 (m, 3H), 5.20-5.11 (m, 1H), 4.32 (s, 1H), 4.20-4.16 (m, 2H), 4.07-4.04 (m, 1H), 3.47-3.41 (m, 2H), 3.32-3.25 (m, 4H), 2.96-2.94 (m, 6H), 2.61-2.50 (m, 7H), 2.10-2.01 (m, 1H), 1.21 (s, 6H), 1.23 (s, 6H); | 93 |
| --- | --- | --- | --- | --- |
| 206 |  | A | 806.5 6 | |

| # | Structure | | MS | NMR | |
|---|---|---|---|---|---|
| 207 | 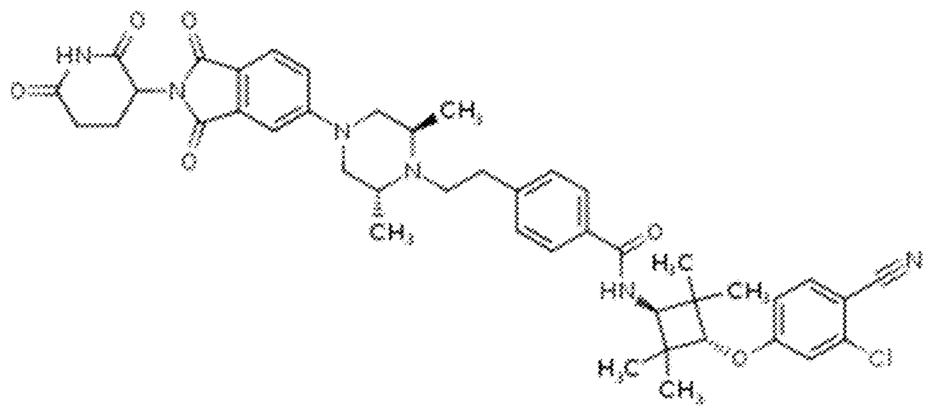 | A | 779.25 | ¹H NMR (300 MHz, CD₃OD) 7.78-7.64 (m, 4H), 7.39-7.32 (m, 3H), 7.21-7.18 (m, 2H), 7.12-6.95 (m, 1H), 5.09-5.03(m, 1H), 4.28-4.27 (m, 1H), 4.15-4.13 (m, 1H), 3.52-3.47 (m, 2H), 3.29-3.22 (m, 4H), 3.18-2.63 (m, 7H), 2.13-2.05 (m, 1H), 1.28-1.11 (m, 18H); | 22 |
| 208 | 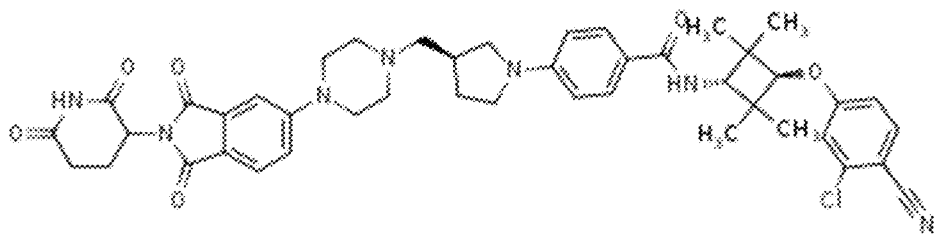 | A | 806.55 | | 49 |
| 209 | 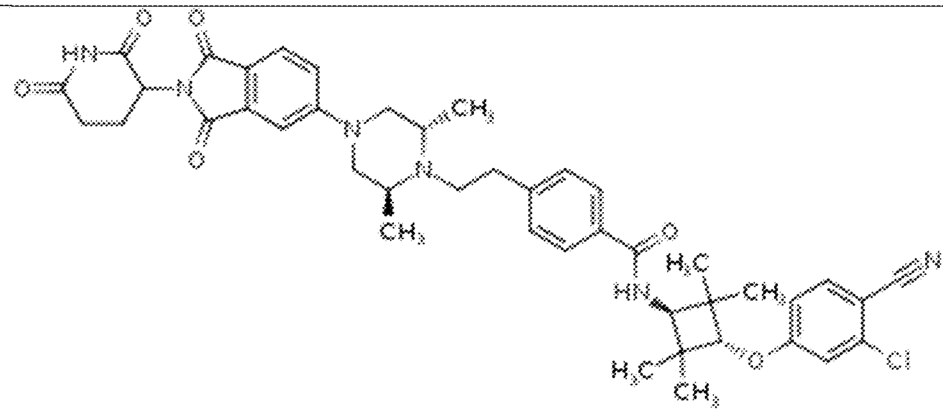 | A | 779.1 | 1H NMR (300 MHz, DMSO-d6) δ 11.03 (s, 1H), 7.87 (d, J = 8.8 Hz, 1H), 7.73 (dd, J = 8.6, 6.7 Hz, 3H), 7.61 (d, J = 8.5 Hz, 1H), 7.38-7.26 (m, 3H), 7.25-7.14 (m, 2H), 6.97 (dd, J = 8.8, 2.4 Hz, 1H), 5.03 (dd, J = 12.6, 5.3 Hz, 1H), 4.29 (s, 1H), 4.03 (d, J = 9.1 Hz, 1H), 3.45 (dd, J = 12.6, 3.3 Hz, 2H), 3.19 (dd, J = 12.5, 6.5 Hz, 2H), 3.00 (td, J = 6.4, 3.4 Hz, 2H), | 22 |

| | | | |
|---|---|---|---|
| 210 |  | A | 792.4 | ¹H NMR (300 MHz, DMSO-*d6*) δ 11.08 (s, 1H), 7.92-7.89 (d, *J* = 9 Hz, 1H), 7.75-7.67 (m, 3H), 7.45-7.42 (d, *J* = 9.0 Hz, 1H), 7.35 (s, 1H), 7.28-7.25 (d, *J* = 9Hz, 1H), 7.21 (s, 1H), 7.02-6.98 (m, 1H), 6.45-6.42 (d, *J* = 9Hz,2H),5.10-5.05 (m, 1H), 4.32 (s, 1H),4.07-3.99 (m, 3H), 3.59-3.55 (m, 2H), 3.47-3.45 (m,4H), 3.00-2.89 (m, 2H), 2.66-2.50(m, 8H), 2.04-2.00 (m, 1H), 1.21 (s, 6H),1.12 (s, 6H); 2.91-2.62 (m, 4H), 2.60-2.47 (m, 2H), 1.98 (dd, *J* = 10.9, 5.6 Hz, 1H), 1.19 (s, 6H), 1.10 (s, 6H), 0.98 (d, *J* = 6.2 Hz, 6H). | 40 |
| 211 |  | A | 820.58 | | |

FIG. 3 Continued.

| | | | | |
|---|---|---|---|---|
| 212 | [structure] | A | 836.55 | ¹H-NMR (300 MHz, DMSO-$d_6$) δ11.08 (s, 1H), 8.61 (s, 1H), 7.90- 7.84 (m, 1H), 7.74- 7.67 (m, 2H), 7.49- 7.41 (m, 1H), 7.20- 7.16 (m, 1H), 7.02- 6.89 (m, 3H), 5.17 - 5.07 (m, 1H), 4.29 (s, 1H), 4.06- 3.99 (m, 1H), 3.91- 3.68 (m, 6H), 2.92- 2.50 (m, 7H), 2.42- 2.34 (m, 4H), 2.06- 1.98 (m, 1H), 1.78- 1.60 (m, 2H), 1.54- 1.38 (m, 3H), 1.26 - 1.10 (m, 14H) | 5 |
| 213 | [structure] | A | 838.56 | | 49 |

FIG. 3 Continued.

| | | | | |
|---|---|---|---|---|
| 214 | (structure) | A | 824.59 | |
| 215 | (structure) | A | | 94 |

Row 215 NMR:
¹H NMR (300 MHz, DMSO-$d_6$): δ 11.07 (s, 1H), 8.60 (s, 1H), 7.95-7.85 (m, 2H), 7.69 (d, J = 8.6 Hz, 1H), 7.57 (d, J = 9.2 Hz, 1H), 7.34 (s, 1H), 7.31(m, 1H) 7.17 (m, 1H), 7.00 (dd, J = 8.8, 2.5 Hz, 1H), 6.85 (d, J = 9.0 Hz, 1H), 5.07 (dd, J = 12.7, 5.6 Hz, 1H), 4.47 (s, 1H), 4.33 (d, J = 19.6 Hz, 2H), 4.05 (d, J = 9.1 Hz, 1H), 3.47 (s, 4H), 2.86 (d, J = 14.6 Hz, 2H), 2.55 (s, 5H), 2.24 (s, 1H),2.02 (m, 3H) 1.67 (m, 2H), 1.58 (m, 3H), 1.20 (m, 7H). 1.16 (m, 10H

| 216 | | | 51 |
|---|---|---|---|
| | A | 821.4 | 1H NMR (400 MHz, DMSO-$d_6$) δ 11.12 (s, 1H), 7.91 (d, J = 8.8 Hz, 1H), 7.88-7.82 (m, 1H), 7.74 (d, J = 8.4 Hz, 2H), 7.43 (d, J = 9.2 Hz, 1H), 7.32-7.24 (m, 2H), 7.21 (d, J = 2.3 Hz, 1H), 7.01 (dd, J = 8.8, 2.4 Hz, 1H), 6.43 (d, J = 8.4 Hz, 2H), 5.13 (dd, J = 12.9, 5.3 Hz, 1H), 4.97 (td, J = 6.5, 3.2 Hz, 1H), 4.33 (s, 1H), 4.04-4.02 (m, 3H), 3.54 (t, J = 6.6 Hz, 2H), 3.12-3.10 (m, 1H), 2.93-2.90 (m, 13.9, 5.4 Hz, 1H), 2.79-2.77 (m, 1H), 2.71- 2.52 (m, 2H), 2.40 (dt, J = 12.7, 6.6 Hz, 2H), 2.22 (q, J = 7.4 Hz, 4H), 2.12 - 2.00 (m, 4H), 1.76 (q, J = 7.2 Hz, 2H), 1.22 (s, 6H), 1.13 (s, 6H); |

FIG. 3 Continued.

| | | | |
|---|---|---|---|
| 217 | [structure] | A | 799.52 |
| 218 | [structure] | A | 791.3 | ¹H NMR (400 MHz, DMSO-d6) δ 1.13 (6H, s), 1.22 (6H, s), 1.73-1.78 (2H, m), 1.99-2.02 (1H, m), 2.42-2.49 (5H, m), 2.53-2.60 (6H, m), 2.83-2.89 (1H, m), 3.43 (5H, s), 4.06 (1H, d, J = 8.8 Hz), 4.32 (1H, s), 5.07 (1H, dd, J = 5.2, 12.8 Hz), 7.00 (1H, dd, J = 2.4, 8.8 Hz), 7.20-7.26 (2H, m), 7.31-7.33 (3H, m), 7.67 (1H, d, J = 8.8 Hz), 7.73-7.79 (3H, m), 7.90 | 56 |

| | | | |
|---|---|---|---|
| 219 |  | A | (1H, d, $J$ = 8.8 Hz), 11.0 (1H, s). |
| | | | $^1$H NMR (400 MHz, DMSO-$d_6$) δ 1.13 (6H, s), 1.23 (6H, s), 1.98-2.02 (1H, m), 2.15-2.49 (5H, m), 2.52-2.67 (8H, m), 2.83-2.92 (1H, m), 3.44 (4H, s), 3.64-3.68 (1H, m), 4.06 (1H, d, $J$ = 9.2 Hz), 4.32 (1H, s), 5.07 (1H, dd, $J$ = 5.6, 12.8 Hz), 7.00 (1H, dd, $J$ = 2.4, 8.8 Hz), 7.21 (1H, d, $J$ = 2.4 Hz), 7.25 (1H, d, $J$ = 8.8 Hz), 7.34-7.39 (3H, m), 7.68 (1H, d, $J$ = 8.4 Hz),7.74-7.80 (3H, m), 7.90 (1H, d, $J$ = 8.4 Hz), 11.0 (1H, s). | 56 |

| | A | 94 | ¹H NMR (300 MHz, DMSO-$d_6$): δ 11.06 (s, 1H), 8.57 (d, J = 2.4 Hz, 1H), 7.95-7.83 (m, 2H), 7.66 (d, J = 8.5 Hz, 1H), 7.55 (d, J = 9.2 Hz, 1H), 7.34-7.17 (m, 3H), 7.00 (dd, J = 8.8, 2.4 Hz, 1H), 6.83 (d, J = 9.1 Hz, 1H), 5.06 (dd, J = 12.6, 5.3 Hz, 1H), 4.53 (d, J = 13.1 Hz, 1H), 4.31 (d, J = 10.7 Hz, 2H), 4.04 (d, J = 9.2 Hz, 1H), 3.39 (m, 4H), 3.06 (d, J = 12.5 Hz, 1H), 2.86 (d, J = 11.6 Hz, 2H), 2.59 (m, 6H), 2.03 (s, 2H), 1.72 (t, J = 13.2 Hz, 4H), 1.60-1.32 (m, 5H), 1.21 (d, J = 2.0 Hz, 7H), 1.11 (s, 6H); |

| 221 | A | $^1$H NMR (300 MHz, DMSO-$d_6$): δ 11.07 (s, 1H), 8.61 (d, J = 2.4 Hz, 1H), 7.96-7.85 (m, 2H), 7.68 (d, J = 8.5 Hz, 1H), 7.56 (d, J = 9.1 Hz, 1H), 7.34-7.17 (m, 3H), 7.00 (dd, J = 8.7, 2.4 Hz, 1H), 6.85 (d, J = 9.0 Hz, 1H), 5.07 (dd, J = 12.7, 5.4 Hz, 1H), 4.30 (s, 1H), 4.20 (d, J = 13.0 Hz, 1H), 4.05 (d, J = 9.2 Hz, 2H), 3.43 (s, 4H), 3.08 (dd, J = 23.5, 12.0 Hz, 2H), 2.88 (t, J = 13.6 Hz, 1H), 2.68 (s, 5H), 2.38 (s, 2H), 2.07-1.96 (m, 1H), 1.87-1.49 (m, 9H), 1.41-1.28 (m, 1H), 1.21 (s, 6H), 1.11 (s, 6H) | 94 |

| 222 |  | A | 808.3 | ¹H NMR (300 MHz, DMSO-$d_6$): δ 11.08 (s, 1H), 8.24 (d, $J$ = 9.2 Hz, 1H), 7.90 (d, $J$ = 8.8 Hz, 1H), 7.83 (d, $J$ = 9.5 Hz, 1H), 7.67 (d, $J$ = 8.5 Hz, 1H), 7.40 (d, $J$ = 9.6 Hz, 1H), 7.33 (d, $J$ = 2.1 Hz, 1H), 7.25 (q, $J$ = 4.0, 3.0 Hz, 2H), 7.03 (dd, $J$ = 8.8, 2.5 Hz, 1H), 5.06 (dd, $J$ = 12.7, 5.3 Hz, 1H), 4.53 (d, $J$ = 13.2 Hz, 2H), 4.46 (s, 1H), 4.00 (d, $J$ = 9.1 Hz, 1H), 3.43 (brs, 4H), 3.05 (t, $J$ = 12.5 Hz, 2H), 2.89 (s, 1H), 2.60 (d, $J$ = 31.4 Hz, 7H), 2.01 (m, 1H), 1.91 (m, 2H), 1.46 (m, 2H), 1.22 (s, 6H), 1.14 (s, 6H). | 52 |
| --- | --- | --- | --- | --- | --- |
| 223 |  | A | 792.3 | ¹H NMR (300 MHz, DMSO-$d_6$) δ 11.06 (s, 1H), 7.87 (d, $J$ = 8.8 Hz, 1H), 7.69 (dd, $J$ = 16.6, 8.5 Hz, 3H), 7.43 – 7.30 (m, 2H), 7.30 (m, 1H), 7.14 (m, 1H), 6.97 (dd, $J$ = 8.8, 2.5 Hz, 1H), 6.56 (d, $J$ = 8.7 Hz, 2H), 5.05 (dd, $J$ = 12.7, 5.4 Hz, 1H), 4.29 (s, 1H), 4.02 (d, $J$ = 9.3 Hz, 1H), 3.56 (t, $J$ = 8.4 Hz, 1H), 3.39 (s, 5H), 3.13 (t, $J$ = 8.7 Hz, 1H), 2.97 (d, $J$ = 8.7 Hz, 2H), 2.83-2.56 (m, 5H), | 26 |

FIG. 3 Continued.

| 224 | | A | 778.5 | H-NMR-PH-ARV-LS-049-Q-0 (300 MHz, DMSO-$d_6$, ppm) :δ 11.08 (s, 1H), 7.91 (d, $J$ = 8.7 Hz, 1H), 7.77 (d, $J$ = 8.6 Hz, 2H), 7.67 (d, $J$ = 8.3 Hz, 1H), 7.52 (d, $J$ = 9.2 Hz, 1H), 7.21 (d, $J$ = 2.4 Hz, 1H), 7.06- 6.95 (m, 3H), 6.82 (d, $J$ = 2.0 Hz, 1H), 6.68 (dd, $J$ = 8.4, 2.1 Hz, 1H), 5.07 (dd, $J$ = 12.6, 5.4 Hz, 1H), 4.33 (s, 1H), 4.21-4.12(m, 2H), 4.11-4.01 (m, 1H), 3.93 (dd, $J$ = 8.8, 4.8 Hz, 2H), 3.41 (p, $J$ = 5.7 Hz, 1H), 3.29 (s, 3H), 2.94-2.80 (m, 1H), 2.64-2.51 (m, 4H), 2.50-2.40 (m, 3H), 2.11-1.97 (m, 1H), 1.22 (s, 6H), 1.13 (s, 6H), 2.52-2.04 (m, 2H), 1.88 (m, 3H), 1.18 (d, $J$ = 27.9 Hz, 6H), 1.04 (d, $J$ = 27.9 Hz, 6H). | 19 |

| | A | 820.3 | H NMR (400 MHz, DMSO-*d6*) δ11.05 (s, 1H), 7.88 (d, J = 8.7 Hz, 1H), 7.71 (t, J = 8.4 Hz, 3H), 7.37 (d, J = 8.9 Hz, 2H), 7.31- 7.15 (m, 2H), 6.98 (dd, J = 8.7, 2.4 Hz, 1H), 6.56 (d, J = 8.6 Hz, 2H), 5.06 (m, 1H), 4.30 (s, 1H), 4.04 (d, J = 9.1 Hz, 1H), 3.75 (m, 2H), 3.70-3.51 (m, 5H), 3.51- 3.32 (m, 5H), 2.85 (m, 1H), 2.57 (m, 2H), 2.37-1.81 (m, 4H), 1.15 (d, 12H) | 18 |

| 227 |  | A | 824.3 | 1H NMR (300 MHz, DMSO-d6): δ 11.07 (s, 1H), 7.87 (d, J = 8.7 Hz, 1H), 7.70 (m, 3H), 7.38 (dd, J = 27.2, 8.3 Hz, 2H), 7.17 (d, J = 2.4 Hz, 1H), 6.97 (dd, J = 8.8, 2.4 Hz, 1H), 6.51 (d, J = 8.7 Hz, 2H), 5.07 (dd, J = 12.9, 5.3 Hz, 1H), 4.28 (s, 1H), 4.02 (d, J = 9.1 Hz, 1H), 3.49-3.30 (m, 2H), 3.24-3.17 (m, 4H), 3.09-2.98 (m, 1H), 2.91-2.78 (m, 1H), 2.65-2.48 (m, 6H), 2.47-2.42 (m, 2H), 2.41-2.39 (m, 2H), 2.15-1.98 (m, 2H), 1.80-1.60 (m, 1H), 1.18 (s, 6H), 1.09 (s, 6H).; | 49 |

| | | | | |
|---|---|---|---|---|
| 228 |  | A | 824.2 | 1H NMR (300 MHz, DMSO-d6) δ 11.04 (s, 1H), 7.87 (d, J = 8.7 Hz, 1H), 7.72 (d, J = 8.6 Hz, 2H), 7.52 (m, 2H), 7.17 (d, J = 2.4 Hz, 1H), 7.06 – 6.89 (m, 4H), 5.03 (dd, J = 12.8, 5.4 Hz, 1H), 4.28 (s, 1H), 4.02 (d, J = 9.1 Hz, 1H), 3.78-3.58 (m, 3H), 3.44 -3.21(m, 4H), 2.94-2.75 (m, 1H), 2.64-2.55 (m, 5H), 2.42 (m, 3H), 2.37 (d, J = 7.4 Hz, 2H), 2.12 – 1.92 (m, 2H), 1.68 (m, 1H), 1.18 (s, 6H), 1.09 (s, 6H) | 53 |
| 229 |  | A | 779.3 | ¹H NMR (300 MHz, d6-DMSO) δ 1.13 (s, 6H), 1.22 (s, 6H), 2.07 (s, 1H), 2.52-2.64 (m, 2H), 2.82-2.90 (m, 3H), 3.37-3.44 (m, 4H), 3.96 (s, 4H), 4.04-4.07 (m, 1H), 4.18 (s, 2H), 4.32 (s, 1H), 5.16 (s, 1H), 6.42-6.45 (m, 2H), 7.00-7.03 (m, 1H), 7.21 (s, 1H), 7.35-7.44 (m, 3H), 7.72-7.74 (m, 2H), 7.84-7.93 (m, 2H), 11.13 (s, 1H). | 24 |

| | | | | |
|---|---|---|---|---|
| 230 |  | A | 848.4 | 1H NMR (400 MHz, DMSO-d6): δ 11.06 (s, 1H), 7.90 (m, 1H), 7.75 (m, 2H), 7.65 (m, 1H), 7.55 (m, 1H), 7.20 (m, 1H), 7.02 (m, 3H), 6.97 (m, 1H), 6.85 (m, 1H), 5.04 (m, 1H), 4.50 (m, 1H), 4.30 (m, 1H), 4.12 (m, 1H), 4.05 (m, 1H), 3.95 (m, 2H), 3.70 (m, 1H), 3.50 (m, 3H), 3.30 (m, 1H), 3.00 -2.88 (m, 4H), 2.62-2.52 (m, 4H), 2.41-2.02 (m, 3H), 2.01-1.4 (m, 3H), 1.30-1.10 (d, 12H | 6 |
| 231 |  | A | 854.45 | 1H NMR (300 MHz, CDCl3): δ 8.12 (d, J = 9.1 Hz, 1H), 8.03 (s, 1H), 7.94 (d, J = 9.5 Hz, 1H), 7.54 (d, J = 8.7 Hz, 1H), 7.45 (d, J = 11.0 Hz, 1H), 7.37 (d, J = 7.3 Hz, 1H), 7.01 – 6.91 (m, 2H), 6.78 (dd, J = 8.7, 2.4 Hz, 1H), 4.91 (dd, J = 12.2, 5.3 Hz, 1H), 4.50 (d, J = 13.3 Hz, 2H), 4.17 (d, J = 9.1 Hz, 1H), 4.04 (s, 1H), 3.28 (s, 4H), 3.03 (t, J = 12.3 Hz, 2H), 2.94 – 2.66 (m, 3H), 2.62 (s, 4H), 2.46 (s, 2H), 2.17 – 2.06 (m, 1H), 1.98 (s, 0H), 1.86 (d, J = 12.9 Hz, 2H), 1.69 (s, 1H), 1.26 (s, 9H), 1.19 (s, 6H), | 29 |

FIG. 3 Continued.

| 232 | [structure] | A | 850.5 | ¹H NMR (400 MHz, DMSO-d6): δ 1.11 (s, 6H), 1.17-1.32 (m, 16H), 1.77-1.82 (m, 1H), 1.95-2.07 (m, 2H), 2.17-2.33 (m, 4H), 2.54-2.61 (m, 4H), 2.83-2.94 (m, 1H), 3.47 (s, 4H), 4.04 (d, J = 9.2 Hz, 1H), 4.29 (s, 1H), 4.95-5.01 (m, 1H), 5.04-5.11 (m, 1H), 6.98-7.04 (m, 1H), 7.20-7.37 (m, 3H), 7.66-7.73 (m, 2H), 7.90 (d, J = 8.8 Hz, 1H), 8.74-8.85 (m, 2H), 11.08 (s, 1H). | 95 |
| --- | --- | --- | --- | --- | --- |
| 233 | [structure] | A | 850.5 | ¹H NMR (400 MHz, DMSO-d6): δ 1.11 (s, 6H), 1.22-1.32 (m, 14H), 1.80 (d, J = 12.4 Hz, 2H), 1.99-2.03 (m, 1H), 2.24-2.33 (m, 3H), 2.55-2.61 (m, 6H), 2.84-2.93 (m, 1H), 3.47 (m, 4H), 4.04 (d, J = 9.2 Hz, 1H), 4.29 (s, 1 H), 4.96-5.01 (m, 2H), 5.07 (dd, J = 5.2, 12.8Hz, 1H), 5.07 (dd, J = 2.4, 8.8Hz, 1H), 7.21 (d, J = 2.0 Hz, 1H), 7.28 (d, J = 8.8 Hz, 1H), 7.36 (s, 1H), 7.68-7.74 (m, 2H), 7.90 (d, J = 8.8 Hz, 1H), 8.79 (s, 2H), 11.08 (s, 1H). | 95 |

FIG. 3 Continued.

| 234 | [structure] | A | 850.6 | $^1$H NMR (400 MHz, DMSO-d6): δ 1.12 (s, 6H), 1.22 (d, $J$ = 7.2 Hz, 6H), 1.26-1.30 (m, 6H), 1.68 (d, $J$ = 13.0 Hz, 1H), 1.78-1.88 (m, 2H), 2.00-2.04 (m, 1H), 2.16-2.38 (m, 5H), 2.54-2.68 (m, 5H), 2.84-2.94 (m, 1H), 3.47 (s, 4H), 4.04 (d, $J$ = 8.8 Hz, 1H), 4.29 (s, 1H), 4.48-4.56 (m, 2H), 5.08(d, $J$ = 12.8 Hz,1H), 7.01 (d, $J$ = 8.8 Hz, 1H), 7.21 (d, $J$ = 2.4 Hz, 1H), 7.27 (d, $J$ = 8.4 Hz, 1H), 7.36 (s, 1H), 7.68-7.71 (m, 2H), 7.90 (d, $J$ = 8.8 Hz, 1H), 8.78 (s, 2H), 11.09 (s, 1H). | 95 |

FIG. 3 Continued.

| 236 | | A | 875.65 | H-NMR-PH-ARV-LS-035-H-O: (300 MHz, CD₃OD, ppm) δ 8.60-8.59 (d, *J*=2.4Hz, 1H), 7.97-7.94 (m, 1H), 7.87-7.70 (m, 4H), 7.13-7.12 (d, *J*=2.4Hz, 1H), 6.99-6.96 (m, 1H), 6.86-6.83 (m, 1H), 5.17-5.11 (m, 1H), 4.40-4.35 (m, 2H), 4.28 (s, 1H), 4.14 (s, 1H), 3.07-2.77 (m, 10H), 2.28-2.13 (m, 6H), 2.00-1.78 (m, 8H), 1.61-1.58 (m, 1H), 1.42-1.33 (m, 1H), 1.28 (s, 6H), 1.21 (s, 6H), 1.13-1.00 (m, 1H). | 96 |
| --- | --- | --- | --- | --- | --- |
| 237 | | A | 835.4 | ¹H NMR (300 MHz, CD₃OD): δ 7.77-7.70 (m, 4H), 7.25-7.19 (m, 2H), 7.13-7.12 (d, *J*=2.4Hz, 1H), 7.01-6.95 (m, 3H), 5.12-5.06 (m, 1H), 4.96-4.90 (m, 1H), 4.28 (s, 1H), 4.13 (s, 1H), 4.01-3.97 (m, 2H), 2.88-2.68 (m, 9H), 2.36-2.31 (m, 7H), 2.10-2.00 (m, 1H), 1.95-1.85 (m, 2H), 1.67-1.60 (m, 2H), 1.24 (s, 6H), 1.18 (s, 6H); | 23 |

| 238 |  | 820.35 | ¹H NMR (300 MHz, CDCl₃) 7.92 (s, 1H), 7.63-7.47 (m, 4H), 7.22-7.19 (m, 1H), 7.01-6.98 (m, 1H), 6.97-6.89 (m, 1H), 6.88-6.71 (m, 1H), 6.53-6.50 (m, 2H), 6.00 (m, 1H), 4.88-4.84 (m, 1H), 4.08-4.05 (m, 1H), 3.96-3.92 (m, 3H), 3.30 (s, 1H), 2.97-2.80 (m, 5H), 2.65-2.64 (m, 2H), 2.77-2.64 (m, 1H), 2.33 (s, 1H), 2.06-2.03 (m, 3H), 1.93 (m,2H), 1.51-1.35 (m, 5H), 1.18 (m, 6H), 1.14(m, 6H), 0.81-0.76 (m, 1H); | 36 |

| | | | | |
|---|---|---|---|---|
| 239 |  | A | 835.1 | ¹H-NMR (400 MHz, DMSO-d6) δ 11.05 (s, 1H), 7.88-7.85 (d, J=9.0 Hz, 1H), 7.73-7.63 (m, 3H), 7.50-7.47 (d, J=9.0 Hz, 1H), 7.30-7.17 (m, 3H), 6.99-6.92 (m, 3H), 5.06-5.00 (m, 1H), 4.28 (s, 1H), 4.03-4.00 (m, 1H), 3.40-3.22 (m, 8H), 2.86-2.79 (m, 1H), 2.53-2.46 (m, 14H), 2.03-1.98 (m, 1H), 1.18-1.08 (m, 12H); | 38 |
| 240 |  | A | 863.4 | ¹H-NMR (300 MHz, DMSO-d6) δ 11.09 (s, 1H), 7.90-7.87 (d, J = 9Hz, 1H), 7.82-7.80 (d, J = 6 Hz, 1H), 7.72-7.69 (d, J = 9 Hz, 2H), 7.47-7.44 (d, J = 9 Hz, 1H), 7.26-7.18 (m, 3H), 7.00-6.92 (m, 3H), 5.12-5.06 (m, 1H), 4.88 (s, 1H), 4.30 (s, 1H), 4.04-4.01 (d, J = 9 Hz, 1H), 3.88-3.84 (d, J = 12 Hz, 2H), 3.67-3.30 (m, 1H), 2.91- | 23 |

| | | | |
|---|---|---|---|
| 241 |  | A | 834.5 | 1H NMR (400 MHz, DMSO): δ 11.08 (s, 1H), 8.77-8.68 (m, 2H), 7.91 (d, J = 8.8 Hz, 1H), 7.68 (d, J = 8.7 Hz, 2H), 7.33 (d, J = 2.3 Hz, 1H), 7.29-7.19 (m, 2H), 7.02-6.99 (m, 1H), 5.09-5.05 (m, 1H), 4.64 (s, 1H), 4.29 (s, 1H), 4.04 (d, J = 9.1 Hz, 1H), 3.55 (m, 1H), 3.44-3.42 (m, 4H), 3.35-3.32 (m, 1H), 2.92-2.81 (m, 1H), 2.68-2.53 (m, 5H), 2.48-2.36 (m, 3H), 2.35-2.18 (m, 2H), 2.08-1.91 (m, 2H), 1.81 (m, 1H), 1.69 (m, 1H), 1.22 (s, 6H), 1.12 (s, 6H), 1.06 (m, 1H) 2.70 (m, 4H), 2.60-2.37 (m, 4H), 2.24-2.13 (m, 4H), 2.05-2.00 (m, 1H), 1.82-1.78 (d, J = 12 Hz, 2H), 1.54 (s, 1H), 1.19 (s, 6H), 1.10 (s, 8H), 0.91-0.89 (d, J=6 Hz, 6H) | 97 |

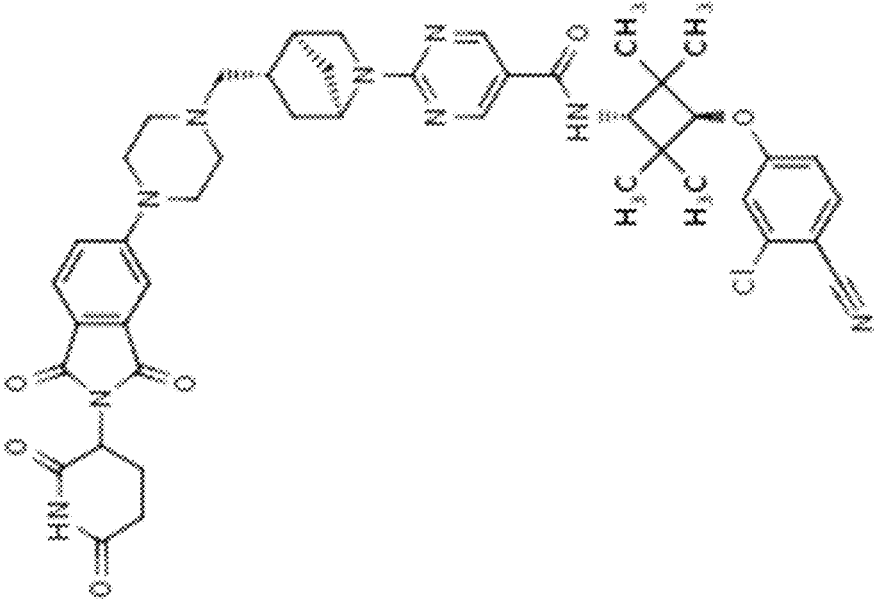
FIG. 3 Continued.
| 242 | 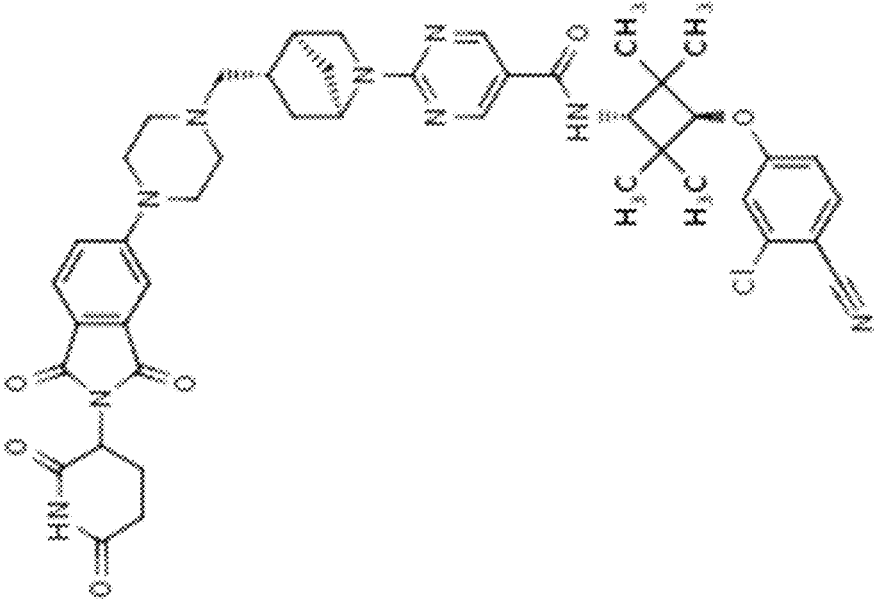 | A | 834.1 | 1H NMR (400 MHz, DMSO): δ 11.08 (s, 1H), 8.73 (d, J = 2.7 Hz, 2H), 7.91 (d, J = 8.8 Hz, 1H), 7.67 (m, 2H), 7.34 (d, J = 2.1 Hz, 1H), 7.29-7.24 (m, 1H), 7.22 (d, J = 2.4 Hz, 1H), 7.01 (m, 1H), 5.07 (m, 1H), 4.68 (s, 1H), 4.30 (s, 1H), 4.04 (d, J = 9.2 Hz, 1H), 3.51-3.39 (m, 5H), 3.34 (m, 1H), 3.26 (m, 1H), 2.96-2.82 (m, 1H), 2.56 (m, 5H), 2.44-2.34 (m, 1H), 2.17 (m, 1H), 2.04-1.96 (m, 2H), 1.80-1.54 (m, 3H), 1.37 (d, J = 11.8 Hz, 1H), 1.22 (m, 7H), 1.12 (s, 6H) | 97 |

| 243 |  | A | 840.35 | H-NMR (400 MHz, DMSO-d6) δ11.12 (s, 1H), 8.76 (s, 2H), 7.92-7.90 (d, J = 8.8Hz, 2H), 7.76-7.70 (m, 2H), 7.48-7.46 (d, J=7.2Hz, 1H), 7.23-7.22 (d, J=2.4Hz, 1H), 7.03-7.01 (m, 1H), 5.14-5.1 (m, 1H), 4.78-4.74 (d, J=12.8Hz, 2H), 4.30 (s, 1H), 4.06-4.04 (d, J=9.2Hz, 1H), 3.27 (s, 3H), 3.03-2.97 (m, 3H), 2.63-2.52 (m, 6H), 2.24-2.23 (m, 2H), 2.05-2.04 (m, 1H), 1.86-1.83 (m, 3H), 1.23 (s, 6H), 1.12 (s, 6H), 1.09-1.06 (m, 2H) | 49 |

| 244 |  | A | 781.3 | ¹H NMR (300 MHz, DMSO-$d_6$): δ 11.12 (s, 1H), 7.91 (d, $J$ = 8.8 Hz, 1H), 7.84 (d, $J$ = 8.3 Hz, 1H), 7.75 (d, $J$ = 8.6 Hz, 2H), 7.48 (d, $J$ = 2.3 Hz, 1H), 7.45-7.32 (m, 2H), 7.21 (d, $J$ = 2.4 Hz, 1H), 7.01 (dd, $J$ = 8.8, 2.5 Hz, 1H), 6.57 (d, $J$ = 8.8 Hz, 2H), 5.13 (dd, $J$ = 12.8, 5.2 Hz, 1H), 4.33 (s, 3H), 4.06 (d, $J$ = 9.1 Hz, 1H), 3.55 (t, $J$ = 8.3 Hz, 1H), 3.45 (t, $J$ = 8.7 Hz, 1H), 3.29 (d, $J$ = 8.9 Hz, 2H), 3.20-3.07 (m, 1H), 2.88 (d, $J$ = 12.3 Hz, 3H), 2.60 (d, $J$ = 18.2 Hz, 2H), 2.36 (s, 3H), 2.22 (s, 1H), 2.06 (d, $J$ = 10.6 Hz, 1H), 1.96-1.83 (m, 1H), 1.22 (s, 6H), 1.13 (s, 6H). | 93 |

| | | | |
|---|---|---|---|
| 245 |  | A | 779.15 | 1H NMR (300 MHz, DMSO-$d_6$) δ 11.08 (s, 1H), 7.84 (dd, $J$ = 18.3, 8.7 Hz, 2H), 7.71 (d, $J$ = 8.2 Hz, 2H), 7.35-7.26 (d, $J$ = 6.5 Hz, 4H), 7.17 (s, 1H), 6.49 (d, $J$ = 8.5 Hz, 2H), 5.15 – 5.02 (m, 2H), 4.29 (s, 1H), 4.02 (d, $J$ = 9.2 Hz, 1H), 3.76 (d, $J$ = 6.9 Hz, 3H), 3.09 (dd, $J$ = 25.1, 8.6 Hz, 4H), 2.98 (s, 2H), 2.54 (s, 2H), 1.97(s,4H),1.18 (s, 6H), 1.09 (s, 6H). | 23 |
| 246 |  | A | 793.25 | 1H NMR (300 MHz, CDCL3) δ 11.07 (s, 1H), 7.76 (t, $J$ = 8.0 Hz, 3H), 7.58 (d, $J$ = 8.6 Hz, 1H), 7.33 (d, $J$ = 18.6 Hz, 2H), 7.19 (d, $J$ = 8.2 Hz, 1H), 6.99 (d, $J$ = 2.3 Hz, 1H), 6.84 (dd, $J$ = 8.8, 2.4 Hz, 1H), 6.53 (d, $J$ = 8.4 Hz, 2H), 4.22 (d, $J$ = 8.3 Hz, 3H), 4.10 (s, 1H), 3.45 (s, 4H), 3.19 (s, 2H), 3.08 (s, 4H), 2.67 (d, $J$ = 17.7 Hz, 4H), 2.57 (d, $J$ = 13.7 Hz, 1H), 2.28 (s, 1H), 1.77 (s, 1H), 1.37 (s, 3H), 1.28 (d, $J$ = 4.9 Hz, 9H).; | 55 |

FIG. 3 Continued.

| 247 | [structure] | A | 802.5 | ¹H NMR (400 MHz, d-DMSO):δ11.086(s,1H),8.754(s,2H),7.708-7.674(m,3H),7.348(s,1H),7.275-7.253(d,J=8.8Hz,1H),6.938-6.933(d,J=2Hz,1H),6.830-6.803(m,1H),5.098-5.052(m,1H),4.764-4.732(d,J=12.8Hz,2H),4.193(s,1H),4.036-4.013(d,J=9.2Hz,1H),3.450(s,4H),3.020-2.961(m,2H),2.932-2.840(m,1H),2.608-2.537(m,6H),2.507-2.498(m,3H),2.216-2.199(d,J=6.8Hz,2H),2.076-2.018(m,1H),2.005-1.914(m,1H),1.851-1.819(d,J=12.8Hz,2H),1.215(s,6H),1.110(s,6H),1.073-1.018(m,2H) | 49 |

| 248 | B | 765.7 | 21A |

¹H NMR (400 MHz, d-DMSO): δ 10.69 (s,1H), 7.91-7.89 (d, J=8.8Hz, 1H), 7.78-7.74 (m, 3H), 7.53-7.51 (d, J=8.4Hz, 1H), 7.32-7.30 (d, J=8.0Hz, 2H), 7.21-7.20 (d, J=2.4Hz, 1H), 7.05-6.98 (m, 3H), 5.30 (s, 2H), 4.58-4.54 (m, 1H), 4.32 (s,1H), 4.07-4.05 (d, J=9.2Hz, 1H), 3.29-3.26 (m, 4H), 2.69-2.58 (m, 4H), 2.50-2.49 (m, 4H), 2.33-2.32 (s, 2H), 2.07-1.95 (m, 2H), 1.64-1.50 (m, 4H), 1.20 (s, 6H), 1.10 (s, 6H);

| 249 | B | 765.7 | ¹H NMR (400 MHz, d-DMSO): δ10.69 (s, 1H), 7.91-7.89 (d, J=8.8Hz, 1H), 7.78-7.74 (m, 3H), 7.53-7.51 (d, J=8.4Hz, 1H), 7.32-7.30 (d, J=8.0Hz, 2H), 7.21-7.20 (d, J=2.4Hz, 1H), 7.05-6.98 (m, 3H), 5.29 (s, 2H), 4.58-4.54 (m, 1H), 4.32 (s,1H), 4.07-4.05 (d, J=9.2Hz, 1H), 3.29-3.27 (m, 4H), 2.69-2.58 (m, 4H), 2.50-2.49 (m, 4H), 2.34-2.32 (s, 2H), 2.01-1.92 (m, 2H), 1.66-1.48 (m, 4H), 1.23 (s, 6H), 1.18 (s, 6H); | 21A |

| 252 |  | B | 843.4 | ¹H NMR (300 MHz, DMSO-$d_6$) δ 11.11 -11.04 (m, 1 H), 8.07 (d, J = 8.7 Hz, 1 H), 7.96 (dd, J = 24.7, 8.4 Hz, 1 H), 7.78 (dd, J = 24.7, 8.4 Hz, 2 H), 7.50 (d, J = 9.2 Hz, 1 H), 7.44- 7.21 (m, 4 H), 6.93 (d, J = 8.7 Hz, 2 H), 5.08 (dd, J = 12.8, 5.3 Hz, 1 H), 4.36 (s, 1 H), 4.16 (t, J = 6.3 Hz, 2 H), 4.04 (d, J = 9.3 Hz, 1 H), 3.21 (t, J = 4.8 Hz, 3 H), 2.83 (dd, J = 13.5, 5.3 Hz, 1 H), 2.56 (m, 7 H), 2.31 (t, J = 6.7 Hz, 2 H), 2.00 (s, 1H), 1.96 (t, J = 7.0 Hz, 2 H), 1.47 (s, 4 H), 1.20 (s, 6 H), 1.11 (s, 6 H); | 9 |

FIG. 3 Continued.

| | | | |
|---|---|---|---|
| 253 | B | 868.4 | 98 |
| | | | ¹H NMR (300 MHz, CD3OD) 7.93-7.90 (m, 1H), 7.77-7.70 (m, 2H), 7.68-7.65 (m, 1H), 7.36-7.29 (m, 4H), 7.29-7.19 (m, 2H), 5.09-5.03 (m, 1H), 4.34-4.31 (m, 1H), 4.17-4.10 (m, 1H), 3.87-3.80 (m, 2H), 2.84-2.67 (m, 10H), 2.11-2.08 (m, 1H), 1.67-1.50 (m, 2H), 1.50-1.08 (m, 25H); |
| 254 | B | 804.3 | 99 |
| | | | ¹H NMR (300 MHz, CD₃OD): δ 7.84-7.64 (m, 6H), 7.60-7.35 (m, 2H), 7.13-7.12 (s, 1H), 7.00-6.96 (m, 1H), 6.30 (s, 1H), 5.18-5.12 (m, 1H), 4.70-4.43 (m, 6H), 4.29 (s, 1H), 4.16 (s, 1H), 3.31-3.07 (m, 6H), 2.96-2.48 (m, 8H), 2.21-2.17 (m, 1H), 1.97-1.92 (m, 1H), 1.28-1.15 (s, 12H); |

FIG. 3 Continued.

| 258 | [structure] | B | 805.4 | $^1$H NMR (300 MHz, Methanol-d4) δ 7.84-7.64 (m, 4H), 7.44 (d, J = 2.2 Hz, 1H), 7.34 (dd, J = 8.3, 2.3 Hz, 1H), 7.10 (d, J = 2.4 Hz, 1H), 7.03-6.90 (m, 3H), 5.09-5.07 (m, 1H), 4.39- 4.22 (m, 3H), 4.14-4.12 (m, 1H), 3.38-3.32 (m, 4H), 2.89-2.87 (m, 2H), 2.86-2.63 (m, 7H), 2.17 - 2.02 (m, 1H), 1.22 (d, J = 17.9 Hz, 12H) ; | 21A |

FIG. 3 Continued.

| 259 | B | 805.4 | 21A |
|---|---|---|---|

¹H NMR (400 MHz, CDCl₃) 7.85 (s, 1H), 7.62-7.60 (m, 3H), 7.50-7.48 (m, 1H), 7.19-7.16 (m, 1H), 6.89-6.85 (m, 1H), 6.75-6.72 (m, 1H), 6.52-6.50 (m, 1H), 6.32-6.30 (m, 1H), 6.13-6.11 (m, 1H), 5.22-5.13 (m, 2H), 4.67-4.64 (m, 1H), 4.21-4.15 (m, 1H), 4.10-4.07 (m, 1H), 4.07-3.98 (m, 1H), 3.57-3.50 (m, 1H), 3.32-3.21 (m, 2H), 2.97-2.84 (m, 2H), 2.58-2.40 (m, 6H), 2.12-2.08 (m, 2H), 1.96-1.83 (m, 2H), 1.54-1.40 (m, 2H), 1.40-1.04 (m, 18H);

FIG. 3 Continued.

| | | | | |
|---|---|---|---|---|
| 260 | [structure] | B | 807.4 | ¹H NMR (300 MHz, CDCl₃): δ 7.85-7.71 (m, 4H), 7.58-7.56 (m, 1H), 7.26-7.22 (m, 2H), 6.99-6.97 (m, 2H), 6.83-6.79 (m, 2H), 6.25-6.22 (m, 1H), 5.31-5.30 (m, 2H), 4.76-4.65 (m, 3H), 4.45-4.43 (m, 2H), 4.18-4.06 (m, 2H), 3.49-3.30 (s, 4H), 3.07-2.59 (m, 9H), 2.25-2.20 (m, 2H), 2.01-1.94 (m, 2H), 1.28-1.23 (d, J=15.0Hz, 13H); | 100 |
| 261 | [structure] | B | 767.4 | ¹H NMR (400 MHz, CD₃OD): δ 1.24 (s, 6H), 1.30 (s, 6H), 1.96-2.01 (m, 4H), 2.11-2.17 (m, 1H), 2.44-2.50 (m, 2H), 2.71-2.78 (m, 2H), 2.83-2.92 (m, 2H), 3.03 (t, J = 5.2 Hz, 2H), 3.27 (s, 2H), 4.18 (s, 1H), 4.29 (s, 1H), 4.38 (t, J = 5.2 Hz, 2H), 5.10-5.13 (m, 1H), 6.97-6.99 (m, 1H), 7.13-7.14 (m, 1H), 7.37-7.39 (m, 1H), 7.45-7.48 (m, 2H), 7.72-7.74 (m, 1H), 7.82-7.85 (m, 1H), 8.14-8.16 (m, 1H), 8.88 (d, J = 2.0 Hz, 1H). | 9, 101 |

FIG. 3 Continued.

| 262 | B | 795.4 | ¹H NMR (400 MHz, CD₃OD): δ 1.13 (s, 6H), 1.19 (s, 6H), 1.70-2.05 (m, 10H), 2.35-2.48 (m, 2H), 2.58-2.90 (m, 7H), 4.08 (s, 1H), 4.12 (t, J = 5.6 Hz, 2H), 4.19 (s, 1H), 4.98-5.04 (m, 1H), 6.87-6.91 (m, 1H), 7.03 (d, J = 2.4 Hz, 1H), 7.22-7.26 (m, 1H), 7.32 (d, J = 2.0 Hz, 1H), 7.35 (d, J = 8.4 Hz, 1H), 7.63 (d, J = 8.8 Hz, 1H), 7.72 (d, J = 8.4 Hz, 1H), 8.04-8.08 (m, 1H), 8.79 (d, J = 2.0 Hz, 1H). | 9, 101 |

| 264 | | B | 811.3 | ¹H-NMR (300 MHz,d-DMSO) δ11.12(s, 1H), 8.65 (s, 1H), 8.38(m, 1H), 7.92- 7.81(m, 3H), 7.50- 7.33(m, 2H), 7.25-7.24(m, 1H), 7.14- 7.01(m, 1H), 5.17- 5.07(m, 1H), 4.44(s, 1H), 4.24- 4.17(m, 2H), 3.99-3.36(m, 5H), 2.91- 2.83(m, 2H), 2.64 - 2.54(m, 3H), 2.45-2.41(m, 2H), 2.28(s, 1H), 2.09-2.02(m, 1H), 1.85- 1.47(m, 7H), 1.19 - 1.13 (d, *J = 18Hz*, 12H). | 9 |

| | | | |
|---|---|---|---|
| 265 |  | B 811.7 | H-NMR (300 MHz, CD3OD) δ 7.94 (s, 1H), 7.79-7.68 (m, 2H), 7.38-7.27 (m, 3H), 7.13-7.12 (d, J=2.4 Hz, 1H), 6.99-6.96 (m, 1H), 5.11-5.05 (m, 1H), 4.31 (s, 1H), 4.19-4.15 (m, 2H), 4.08 (s, 1H), 3.91 (s, 1H), 3.02-2.99 (m, 4H), 2.85-2.71 (m, 5H), 1.92-1.87 (m, 2H),1.76-1.74 (d, J=4.8 Hz, 2H), 1.60-1.58 (d, J=7.2 Hz, 2H), 1.28 (s, 6H), 1.20 (s, 6H); | 9 |

| 266 | | B | 810.29 | H-NMR (400MHz,CD3OD, *ppm*): δ 8.37 (d, J = 2.8 Hz, 1H), 7.97 (d, J = 8.8 Hz, 1H), 7.83 (d, J = 8.3 Hz, 1H), 7.74 (d, J = 8.7 Hz, 1H), 7.51 – 7.40 (m, 2H), 7.34 (dd, J = 8.4, 2.3 Hz, 1H), 7.17 (d, J = 2.4 Hz, 1H), 7.01 (dd, J = 8.8, 2.4 Hz, 1H), 5.13 (dd, J = 12.6, 5.5 Hz, 1H), 4.34 (s, 1H), 4.22 (t, J = 6.2 Hz, 2H), 4.09 (s, 1H), 3.54 (t, J = 4.9 Hz, 4H), 2.98 (t, J = 4.8 Hz, 5H), 2.95 – 2.67 (m, 4), 2.15 (m, 1H), 2.00 – 1.88 (m, 2H), 1.84 – 1.71 (m, 2H), 1.63 (q, J = 7.9 Hz, 2H), 1.31 (s, 6H), 1.23 (s, 6H). | 9 |

FIG. 3 Continued.

| 267 | | | |
|---|---|---|---|
| | B | 798.4 | ¹H NMR (300 MHz, CD₃OD): δ 11.11 (s, 1H), 8.36 (s, 1H), 8.16-7.81 (m, 3H), 7.44 (m, 1H), 7.37-7.22 (m, 2H), 7.21 (m, 1H), 7.03-6.99 (m, 1H), 5.15-5.09 (m, 5.3 Hz, 1H), 4.29 (s, 1H), 4.22-4.10 (m, 3H), 4.05 (d, J = 9.3 Hz, 1H), 3.00-2.80 (m, 3H), 2.64-2.52 (m, 2H), 2.40-2.25 (m, 2H), 2.11-1.70 (m, 9H), 1.70-1.39 (m, 4H), 1.20 (s, 6H), 1.09 (s, 6H); | 9, 102 |

| 268 |  | B | 798.3 | H-NMR (300 MHz, CDCl$_3$) δ 8.43 (s, 1H), 7.79-7.77 (d, J=8.4 Hz, 2H), 7.59-7.52 (m, 2H)7.33-7.32 (d, J=2.1 Hz, 1H), 7.21-7.17 (m, 1H), 6.97-6.96 (d, J=2.4 Hz, 2H), 6.82-6.78 (m, 1H), 6.54-6.53 (d, J=2.1 Hz, 1H), 6.11-6.08 (d, J=8.4 Hz. 1H), 5.34 (s, 1H), 4.99-4.93 (m, 1H), 4.12-4.05 (m, 4H), 3.49-3.44 (m, 2H), 2.94-2.72 (m, 7H), 2.48-2.45 (d, J=9.9 Hz, 2H), 2.32 (s, 2H), 2.18-2.13 (m, 1H), 1.91-1.85 (m, 4H), 1.60-1.53 (m, 2H), 1.26-1.21 (d, J=10.5 Hz. 12H); | 9, 103 |

| 269 |  | B | 770.7 | H-NMR-PH-ARV-LS-029-E-0(400MHz,CD3OD, *ppm*): δ 8.30 (d, J = 0.8 Hz, 1H), 8.00 (s, 1H), 7.76 (dd, J = 24.6, 8.5 Hz, 2H), 7.40 (d, J = 2.2 Hz, 1H), 7.32 (dd, J = 8.3, 2.3 Hz, 1H), 7.12 (d, J = 2.4 Hz, 1H), 6.97 (dd, J = 8.8, 2.4 Hz, 1H), 5.10 (dt, J = 9.7, 5.2 Hz, 2H), 4.29-4.10 (m, 4H), 3.24 (d, J = 5.7 Hz, 3H), 2.97-2.55 (m, 6H), 2.30 (m, 1H), 2.27 (s, 1H), 2.20-2.05 (m, 1H), 1.88 (dq, J = 27.1, 7.5 Hz, 4H), 1.23 (d, J = 21.8 Hz, 12H). | 9, 104 |

| 270 |  | B | 751.5 1 | 1H NMR (300 MHz, DMSO-$d_6$): δ 11.04 (s, 1H), 7.87 (d, $J$ = 8.8 Hz, 1H), 7.79-7.60 (m, 3H), 7.51(m, 1H), 7.38-7.35 (m, 3H), 7.34-7.32 (m, 1H), 7.14 (m, 1H), 6.97 (dd, $J$ = 8.8, 2.4 Hz, 1H), 5.04 (dd, $J$ = 12.7, 5.4 Hz, 1H), 4.29 (s, 1H), 4.03 (d, $J$ = 9.1 Hz, 1H), 3.59 (s, 4H), 3.29 (s, 1H), 2.88-2.76 (m, 3H), 2.58-2.52 (m, 7H), 2.07-1.92 (m, 1H), 1.19 (d, $J$ = 28.2 Hz, 12H); | 1 |

| 271 | | B | 811.4 | ¹H NMR (300 MHz, DMSO-$d_6$): δ 11.04 (s, 1H), 7.87 (d, $J$ = 8.8 Hz, 1H), 7.79-7.60 (m, 3H), 7.51(m, 1H), 7.38-7.35 (m, 3H), 7.34-7.32 (m, 1H), 7.14 (m, 1H), 6.97 (dd, $J$ = 8.8, 2.4 Hz, 1H), 5.04 (dd, $J$ = 12.7, 5.4 Hz, 1H), 4.29 (s, 1H), 4.03 (d, $J$ = 9.1 Hz, 1H), 3.59 (s, 4H), 3.29 (s, 1H), 2.88-2.76 (m, 3H), 2.58-2.52 (m, 7H), 2.07-1.92 (m, 1H), 1.19 (d, $J$ = 28.2 Hz, 12H); | 20 |

| | | | | |
|---|---|---|---|---|
| 272 |  | B | 812.4 | ¹H NMR (300 MHz, Chloroform-*d*) δ 8.92 (d, *J* = 2.3 Hz, 1H), 8.22 (s, 1H), 8.04 (dd, *J* = 8.1, 2.4 Hz, 1H), 7.62 – 7.45 (m, 2H),7.02 – 6.93 (m, 2H), 6.81 (dd, *J* = 8.8, 2.4 Hz, 1H), 6.24 (d, *J* = 8.2 Hz, 1H), 5.18 (dd, *J* = 13.1, 5.2 Hz, 1H), 4.41- 4.07 (m, 4H), 3.28 (s, 4H), 2.99 – 2.74 (m, 8H), 2.53 (s, 2H), 2.33-2.02 (d, *J* = 6.7 Hz, 3H), 1.78 (s, 3H), 1.40 (s, 4H), 1.26 (d, *J* = 13.8 Hz, 12H), 0.86 (s, 1H). | 20 |
| 273 |  | B | 799.3 | ¹H NMR (400 MHz, DMSO-d6): δ 1.15 (s, 6H), 1.24 (s, 6H), 1.78 (t, *J* = 7.6 Hz, 2H), 1.99-2.03 (m, 1H), 2.33-2.35 (m, 2H), 2.54-2.60 (m, 2H), 2.69 (t, *J* = 6.8 Hz, 2H), 2.85-2.83 (m. 1H), 3.33 (s, 4H), 3.45 (s, 4H), 4.09 (d, *J* = 8.8 Hz, 1H), 4.10 (s, 1H), 55.05-5.09 (m, 1H), 7.25-7.23 (m, 5H), | 1 |

| 274 |  | B | 777.27 | ¹H NMR (400 MHz, CD₃OD): δ 1.19 (s, 6H), 1.26 (s, 6H), 1.69-1.85 (m, 4H), 2.07-2.13 (m, 1H), 2.65-2.75 (m, 4H), 2.80-2.86 (m, 3H), 2.91 (t, *J* =7.2 Hz, 2H), 3.09 (t, *J* = 5.2 Hz, 2H), 3.52 (s, 2H), 4.14 (s, 1H), 4.25 (s, 1H), 5.09-5.13 (m, 1H), 6.39 (s, 1H), 6.93-6.96 (m, 1H), 7.09 (d, *J* = 2.4 Hz, 1H), 7.43 (d, *J* = 8.0 Hz, 1H), 7.68 (d, *J* = 8.8 Hz, 1H), 7.83 (d, *J* = 8.0 Hz, 1H), 7.87-7.90 (m, 1H), 7.93 (s, 1H), 8.11-8.13 (m, 1H), 8.89 (d, *J* = 2.0 Hz, 1H). 7.41 (d, *J* = 2.0 Hz, 1H), 7.68 (d, *J* = 8.4 Hz, 1H), 7.78 (d, *J* = 7.6 Hz, 3H), 8.10 (d, *J* =12.8 Hz, 1H), 11.09 (s. 1H). | 1,105 |

| 275 |  | B | 807.2 | 1HNMR (400 MHz, CD3OD): δ 1.25 (s, 6H), 1.32 (s, 6H), 1.61-1.64 (m, 2H), 1.78-1.82 (m, 2H), 1.91-1.98 (m, 2H), 2.13-2.16 (m, 1H), 2.76-2.88 (m, 7H), 3.09 (t, J = 5.4 Hz, 2H), 3.53 (s, 2H), 4.10-4.12 (m, 1H), 4.22 (t, J = 6.2 Hz, 2H), 4.36 (s, 1H), 5.11-5.15 (m, 1H), 6.43 (s, 1H), 7.00-7.03 (m, 1H), 7.17 (d, J = 2.4 Hz, 1H), 7.33-7.35 (m, 1H), 7.42 (d, J = 2.0 Hz, 1H), 7.74 (d, J = 8.8 Hz, 1H), 7.82 (d, J = 8.4 Hz, 1H), 8.05-8.11 (m, 2H), 8.78 (s, 1H). | 9, 101 |
|---|---|---|---|---|---|
| 276 |  | B | 833.28 | 1HNMR (400 MHz, CD3OD): δ 1.20 (s, 6H), 1.27 (s, 6H), 1.57-1.65 (m, 2H), 1.74-1.79 (m, 2H), 1.87-1.94 (m, 2H), 2.07-2.11 (m, 1H), 2.67-2.73 (m, 2H), 2.79-2.85 (m, 1H), 3.13 (t, J = 7.8 Hz, 2H), 4.13 (s, 2H), 4.17 (t, J = 7.0 Hz, 3H), 4.26 (s, 1H), 4.59 (s, 2H), 5.05-5.09 (m, 1H), 6.94-6.97 (m, 1H), | 86 |

FIG. 3 Continued.

| # | Structure | | NMR | |
|---|---|---|---|---|
| 277 | (structure) | B | 781.51 | 7.10 (d, J = 2.4 Hz, 1H), 7.27-7.30 (m, 1H), 7.37 (d, J = 2.4 Hz, 1H), 7.57 (s, 1H), 7.69 (d, J = 8.8 Hz, 1H), 7.76 (d, J = 8.4 Hz, 1H), 7.97 (d, J = 8.8 Hz, 1H), 8.28-8.31 (m, 1H), 8.34 (br, 1H), 8.80 (d, J = 2 Hz, 1H). | 17A |
| | | | | ¹HNMR (400 MHz, CD₃OD): δ 1.20 (s, 6H), 1.27 (s, 6H), 1.57-1.65 (m, 2H), 1.74-1.79 (m, 2H), 1.87-1.94 (m, 2H), 2.07-2.11 (m, 1H), 2.67-2.73 (m, 2H), 2.79-2.85 (m, 1H), 3.13 (t, J = 7.8 Hz, 2H), 4.13 (s, 2H), 4.17 (t, J = 7.0 Hz, 3H), 4.26 (s, 1H), 4.59 (s, 2H), 5.05-5.09 (m, 1H), 6.94-6.97 (m, 1H), 7.10 (d, J = 2.4 Hz, 1H), 7.27-7.30 (m, 1H), 7.37 (d, J = 2.4 Hz, 1H), 7.57 (s, 1H), 7.69 (d, J = 8.8 Hz, 1H), 7.76 (d, J = 8.4 Hz, 1H), 7.97 (d, J = 8.8 Hz, 1H), 8.28-8.31 (m, 1H), 8.34 (br, 1H), 8.80 (d, J = 2 Hz, 1H). | |
| 278 | (structure) | B | 781.25 | ¹H NMR (400 MHz, DMSO-d6): δ 1.11 (d, J = 5.6 Hz, 3H), 1.23 (s, 1H), 1.57 (s, 1H), 1.70-1.80 (m, 2H), 1.98-2.08 (m, 2H), 2.22-2.40 (m, 8H), 2.52-2.68 (m, 2H), 2.84-2.94 (m, 1H), 3.30 (s, 1H), 3.51 (s, 2H), | 106 |

| | | | |
|---|---|---|---|
| 279 |  | B | 840.3 | 4.18 (t, J = 6.4 Hz, 2H), 4.42-4.48 (m, 3H), 5.08-5.15 (m, 1H), 6.43 (s, 1H), 6.94 (d, J = 2.4 Hz, 1H), 7.32-7.6 (m, 1H), 7.42 (d, J = 2.0 Hz, 1H), 7.80-7.85 (m, 2H), 7.99 (s, 2H), 8.08 (s, 1H), 8.23 (d, J = 8.0 Hz, 1H), 11.1 (s, 1H), 13.1 (s, 1H). | 14 |
| | | | ¹H NMR (400 MHz, DMSO-d6): δ 1.12 (s, 6H), 1.22 (s, 6H), 1.46-1.55 (m, 4H), 1.79-1.82 (m, 2H), 1.91-1.97 (m, 2H), 2.03-2.07 (m, 1H), 2.30 (br, 2H), 2.58-2.69 (m, 2H), 2.84-3.03 (m, 3H), 3.14-3.18 (m, 1H), 3.30 (s, 1H), 3.42 (br, 1H), 3.72-3.76 (m, 1H), 4.05 (d, J = 9.2 Hz, 1H), 4.18-4.21 (m, 2H), 4.30-4.34 (m, 2H), 4.72 (br, 1H), 5.10-5.14 (m, 1H), 6.80-6.82 (m, 1H), 7.00-7.02 (m, 1H), 7.21 (d, J = 2.0Hz, 1H), 7.35-7.37 (m, 1H), 7.44 (d, J = 2.0 Hz, 1H), 7.59 (d, J = 8.8 Hz, 1H), 7.83 (d, J = 8.4 Hz, 1H), 7.90 (d, J = 8.8 Hz, 1H), 7.94 (br, 1H), 8.61 (s, 1H), 11.12 (s, 1H). | |

FIG. 3 Continued.

| 280 | | | |
|---|---|---|---|
| (structure) | B | 807.28 | ¹H NMR (400 MHz, DMSO-d6): δ 1.14 (s, 6H), 1.24 (s, 6H), 1.45-1.49 (m, 2H), 1.56-1.60 (m, 2H), 1.78-1.82 (m, 2H), 1.99-2.05 (m, 2H), 2.45-2.47 (m, 3H), 2.58-2.67 (m, 5H), 2.84-2.94 (m, 1H), 3.16 (s, 1H), 4.08 (d, $J$ = 9.2 Hz, 1H), 4.20 (t, $J$ = 6.4 Hz, 2H), 4.32 (s, 1H), 5.10-5.14 (m, 1H), 6.83 (s, 1H), 7.00-7.03 (m, 1H), 7.22 (d, $J$ = 2.4 Hz ,1H), 7.34-7.36 (m ,1H), 7.44 (d, $J$ = 2.0 Hz ,1H), 7.64 (d, $J$ = 8.0 Hz ,1H), 7.83 (d, $J$ = 8.4 Hz, 1H), 7.90 (d, $J$ = 8.8 Hz, 1H), 8.03 (d, $J$ = 9.2 Hz, 1H), 8.13-8.15 (m, 1H), 8.94 (s, 1H), 11.12 (s, 1H). | 9,101 |

| | | | | |
|---|---|---|---|---|
| 281 |  | B | 824.27 | ¹H NMR (400 MHz, DMSO-d6): δ 1.13 (s, 6H), 1.24 (s, 6H), 1.42-1.64 (m, 4H), 1.72-1.87 (m, 2H), 1.99-2.10 (m, 1H), 2.56-2.70 (m, 3H), 2.77-2.95 (m, 3H), 3.22-3.29 (m, 2H), 3.84-4.00 (m, 2H), 4.05-4.13 (m, 1H), 4.15-4.26 (m, 2H), 4.29-4.37 (m, 1H), 5.07-5.17 (m, 1H), 6.96-7.09 (m, 1H), 7.16-7.29 (m, 1H), 7.33-7.50 (m, 2H), 7.76-7.97 (m, 2H), 8.01-8.22 (m, 3H), 8.81-8.91 (m, 1H), 11.07-11.19 (m, 1H). | 87 |
| 282 |  | B | 794.29 | ¹H NMR (400 MHz, DMSO-d6): δ 1.13 (s, 6H), 1.24 (s, 6H), 1.42-1.64 (m, 4H), 1.72-1.87 (m, 2H), 1.99-2.10 (m, 1H), 2.56-2.70 (m, 3H), 2.77-2.95 (m, 3H), 3.22-3.29 (m, 2H), 3.84-4.00 (m, 2H), 4.05-4.13 (m, 1H), 4.15-4.26 (m, 2H), 4.29-4.37 (m, 1H), 5.07-5.17 (m, 1H), 6.96-7.09 (m, | 9,105 |

| 283 |  | B | 780.27 | 1H NMR (400 MHz, DMSO-d6): δ 1.14 (s, 6H), 1.23 (s, 6H), 1.75-2.07 (m, 8H), 2.54-2.68 (m, 5H), 2.85-3.17 (m, 4H), 4.06 (d, J = 9.2 Hz, 1H), 4.27 (br, 2H), 4.32 (s, 1H), 5.11-5.15 (m, 1H), 7.00-7.02 (m, 1H), 7.21 (d, J = 2.4 Hz, 1H), 7.35-7.39 (m, 3H), 7.46 (d, J = 1.6 Hz, 1H), 7.78 (d, J = 8.8 Hz, 3H), 7.86 (d, J = 8.0 Hz, 1H), 7.91 (d, J = 8.8 Hz, 1H), 11.13 (s, 1H). | 9,105 |

FIG. 3 Continued.

| 284 | (structure) | B | 778.3 | H-NMR (300 MHz, CD$_3$OD, ppm) δ 7.78 - 7.68 (m, 4 H), 7.41 - 7.34 (m, 3 H), 7.22 - 7.18 (m, 1 H), 7.13 (s, 1 H), 6.99 - 6.96 (d, J = 9 Hz, 1 H), 5.10 - 5.04 (m, 1 H), 4.27 (s, 1 H), 4.13 (s, 1 H), 3.76 - 3.65 (m, 4 H), 3.46 - 3.43 (m, 2 H), 3.32 - 3.31 (m, 2 H), 3.07 - 3.02 (m, 2 H), 2.87 - 2.68 (m, 5 H), 2.13 - 2.08 (m, 1 H), 1.25 (s, 6 H), 1.21 (s, 6 H). | 107 |

FIG. 3 Continued.

| # | Structure | Class | MS (m/z) | ¹H NMR | Ex. |
|---|---|---|---|---|---|
| 285 | 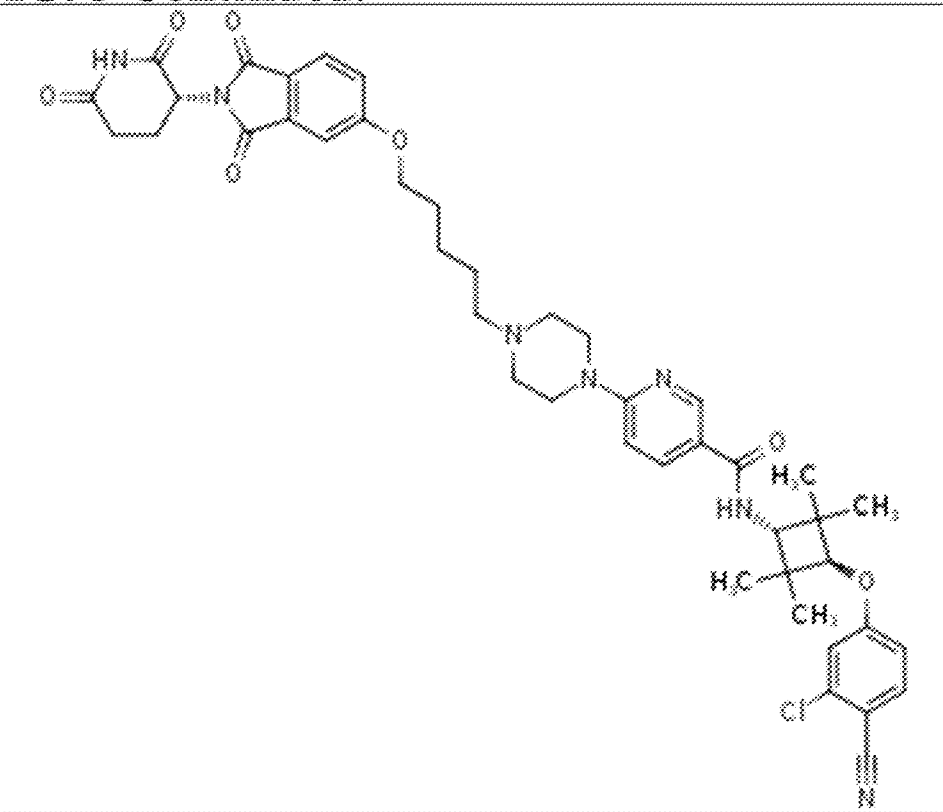 | B | 810.23 | | 9 |
| 286 | 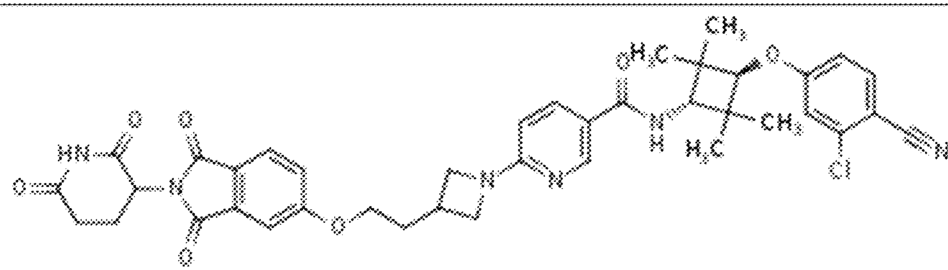 | B | 739.16 | ¹H NMR (400 MHz, DMSO-d6): δ 1.12 (s, 6H), 1.21 (s, 6H), 2.04-2.16 (m, 3H), 2.56-2.69 (m, 2H), 2.85-2.97 (m, 2H), 3.76-3.79 (m ,2H), 4.05 (d, J = 9.2 Hz 1H), 4.16 (t, J = 8.4 Hz ,2H), 4.25 (t, J = 6.0 Hz ,2H), 4.30 (s, 1H), 5.13 (dd, J = | 9 |

| | | | |
|---|---|---|---|
| 287 | <br>B | 767.19 | 12.8 Hz ,1H), 6.37 (d, J = 8.8 Hz,1H), 7.00 (dd, J = 8.8 Hz,1H), 7.20 (d, J = 2.4 Hz ,1H), 7.37 (dd, J = 8.0 Hz,1H), 7.45 (s, 1H), 7.60 (d, J = 9.2 Hz, 1H), 7.84-7.95 (m, 3H), 8.58 (d, J = 1.6 Hz ,1H), 11.12 (s, 1H).<br>$^1$H NMR (400 MHz, DMSO-d$_6$): δ 1.12 (s, 6H), 1.21 (s, 6H), 1.42-1.46 (m, 2H), 1.66-1.81 (m, 4H), 2.03-2.07 (m, 1H), 2.50-2.62 (m, 2H), 2.73-2.78 (m, 1H), 2.85-2.87 (m, 1H), 3.64 (dd, J = 5.6 Hz, 8.0Hz, 2H), 4.05 (d, J = 9.2 Hz, 1H), 4.12 (t, J = 8.0 Hz, 2H), 4.20 (t, J = 6.4 Hz, 2H), 4.30 (s, 1H), 5.12 (dd, J = 5.2 Hz, 12.8Hz, 1H), 6.36 (d, J = 8.8 Hz, 1H), 7.00 (dd, J = 2.4 Hz, 8.8Hz, 1H), 7.21 (d, J = 2.4 Hz, 1H), 7.36 (dd, J = 2.0 Hz, 8.4Hz, 1H), 7.44 (d, J = 2.0 Hz, 1H), 7.59 (d, J = 9.2 Hz, 1H), 7.83 (d, J = 8.0 Hz, 1H), 7.89-7.95 (m, 2H), 8.57 (d, J = 2.0 Hz, 1H), 11.12 (s, 1H). |

| 288 |  | B | 818.3 | $^1$H NMR (400 MHz, DMSO-d$_6$): δ 1.12 (s, 6H), 1.21 (s, 6H). 1.42-1.46 (m, 2H), 1.66-1.81 (m, 4H), 2.03-2.07 (m, 1H), 2.50-2.62 (m, 2H), 2.73-2.78 (m, 1H), 2.85-2.87 (m, 1H), 3.64 (dd, J = 5.6 Hz, 8.0Hz, 2H), 4.05 (d, J = 9.2 Hz, 1H), 4.12 (t, J = 8.0 Hz, 2H), 4.20 (t, J = 6.4 Hz, 2H), 4.30 (s, 1H), 5.12 (dd, J = 5.2 Hz, 12.8Hz, 1H), 6.36 (d, J = 8.8 Hz. 1H), 7.00 (dd, J = 2.4 Hz, 8.8Hz, 1H), 7.21 (d, J = 2.4 Hz, 1H), 7.36 (dd, J = 2.0 Hz, 8.4Hz, 1H), 7.44 (d, J = 2.0 Hz, 1H), 7.59 (d, J = 9.2 Hz, 1H), 7.83 (d, J = 8.0 Hz, 1H), 7.89-7.95 (m, 2H), 8.57 (d, J = 2.0 Hz, 1H), 11.12 (s, 1H). | 43 |

| 289 | [structure] | B | 836.35 | 1H NMR (300 MHz, DMSO): δ 11.10 (s, 1H), 8.25 (d, J = 9.2 Hz, 1H), 7.92 (d, J = 8.8 Hz, 1H), 7.82 (d, J = 9.6 Hz, 1H), 7.69 (d, J = 8.5 Hz, 1H), 7.43-7.32 (m, 2H), 7.28-7.25 (m, 2H), 7.05-7.02 (m, 1H), 5.10-5.04 (m, 1H), 4.53-4.44 (m, 3H), 4.01 (d, J = 9.2 Hz, 1H), 3.45 (m, 4H), 3.14-2.79 (m, 3H), 2.64-2.51 (m, 2H), 2.45 (m, 3H), 2.41-2.34 (m, 2H), 2.08-1.97 (m, 1H), 1.88-1.62 (m, 3H), 1.47-1.43 (m, 2H), 1.22-1.08 (m, 15H); | 17 |

FIG. 3 Continued.

| 290 | | | |
|---|---|---|---|
| | | B | 836.4 | ¹H NMR (300 MHz, DMSO-$d_6$) δ 11.08 (s, 1H), 8.59 (d, $J$ = 1.2 Hz, 1H), 8.32 (d, $J$ = 1.4 Hz, 1H), 7.90 (d, $J$ = 8.7 Hz, 1H), 7.80 (d, $J$ = 8.9 Hz, 1H), 7.67 (d, $J$ = 8.5 Hz, 1H), 7.34 (s, 1H), 7.30 – 7.20 (m, 2H), 7.02 (dd, $J$ = 8.8, 2.4 Hz, 1H), 5.07 (dd, $J$ = 12.9, 5.4 Hz, 1H), 4.52 – 4.39 (m, 3H), 3.95 (d, $J$ = 9.0 Hz, 1H), 3.43 (s, 4H), 3.06 – 2.79 (m, 5H), 2.36 (d, $J$ = 7.6 Hz, 2H), 2.07 (s, 2H), 1.80 (d, $J$ = 13.0 Hz, 2H), 1.48 – 1.36 (m, 4H), 1.15 (d, $J$ = 18.7 Hz, 16H) | 17 |

| 291 |  | B | 781.51 | ¹H NMR (400 MHz, DMSO-d6): δ 1.41-1.42 (m, 3H), 1.63-1.65 (m, 2H), 1.99-2.03 (m, 1H), 2.30-2.32 (m, 2H), 2.44 (br, 4H), 2.53-2.71 (m, 2H), 2.84-2.92 (m, 1H), 3.10-3.14 (m, 1H), 3.16-3.17 (m, 1H), 3.34-3.38 (m, 4H), 3.57-3.62 (m, 1H), 4.10-4.29 (m, 2H), 4.33-4.47 (m, 2H), 4.56-4.58 (m, 1H), 5.02-5.10 (m, 1H), 6.51 (br, 1H), 6.93-6.94 (m, 1H), 7.22-7.34 (m, 2H), 7.65-7.67 (m, 1H), 7.83 (s, 1H), 7.98 (s, 2H), 8.08 (s, 1H), 8.24-8.26 (m, 1H), 8.75 (br, 1H), 11.10 (s, 1H), 13.30 (br, 1H). | 17A, 108 |

| | | | | |
|---|---|---|---|---|
| 292 |  | B | 840.58 | ¹H NMR (400 MHz, CD₃OD): δ 1.23 (s, 6H), 1.31 (s, 6H), 1.53-1.73 (m, 4H), 1.88-1.95 (m, 2H), 2.11-2.17 (m, 1H), 2.55-2.80 (m, 5H), 2.84-2.94 (m, 2H), 2.05-2.09 (m, 1H), 3.12-3.22 (m, 2H), 3.63-3.85 (m, 4H), 4.08 (s, 1H), 4.20 (t, $J$ = 6.2 Hz, 2H), 4.34 (s, 1H), 5.10-5.15 (m, 1H), 7.00-7.03 (m, 1H), 7.17 (d, $J$ = 2.4 Hz, 1H), 7.32-7.34 (m, 1H), 7.40-7.43 (m, 2H), 7.74 (d, $J$ = 8.4 Hz, 1H), 7.81 (d, $J$ = 8.4 Hz, 1H), 7.94 (d, $J$ = 8.8 Hz, 1H), 8.34 (d, $J$ = 2.4 Hz, 1H). | 14 |
| 293 |  | B | 822.35 | ¹H NMR (400 MHz, DMSO): δ 11.07 (s, 1H), 8.23 (d, $J$ = 9.2 Hz, 1H), 7.89 (d, $J$ = 8.7 Hz, 1H), 7.80 (d, $J$ = 9.6 Hz, 1H), 7.67 (d, $J$ = 8.5 Hz, 1H), 7.39-7.30 (m, 2H), 7.24 (m, 2H), 7.01 (m, 1H), 5.06 (m, 1H), 4.53-4.42 (m, 3H), 3.99 (m, | 49 |

FIG. 3 Continued.

| 294 | [structure] | B | 792.4 | ¹H-NMR (300 MHz, DMSO) δ11.07(s, 1H), 8.64- 8.60(m, 1H), 7.98- 7.87(m, 2H), 7.69- 7.55(m, 2H), 7.35- 7.20(m, 3H), 7.04- 6.96(m, 1H), 6.90- 6.83(m, 1H), 5.11 - 5.01 (m, 1H), 4.30(s, 1H), 4.09- 4.02(m, 1H), 3.70- 3.61(m, 4H), 3.58- 3.49(m, 4H), 2.97- 2.79(m, 1H), 2.65- 2.53(m, 2H), 2.05 - 1.97(m, 1H), 1.61- 1.55(m, 8H), 1.21 - 1.12 (d, *J=29.4 Hz*, 12H). | 19 |

(previous row continued: 1H), 3.43 (m, 4H), 3.08-2.96 (m, 2H), 2.87 (m, 1H), 2.61- 2.49 (m, 2H), 2.51 (m, 4H), 2.19 (m, 2H), 2.04-1.87 (m, 2H), 1.83 (m, 2H), 1.16 (m, 14H);

FIG. 3 Continued.

| 295 | [structure] | B | 793.35 | ¹H-NMR (300 MHz, DMSO) δ11.07(s, 1H), 8.64- 8.60(m, 1H), 7.98- 7.87(m, 2H), 7.69- 7.55(m, 2H), 7.35- 7.20(m, 3H), 7.04- 6.96(m, 1H), 6.90- 6.83(m , 1H), 5.11 - 5.01 (m, 1H), 4.30(s, 1H), 4.09- 4.02(m, 1H), 3.70- 3.61(m, 4H), 3.58- 3.49(m, 4H), 2.97- 2.79(m, 1H), 2.65- 2.53(m, 2H), 2.05 - 1.97(m, 1H), 1.61- 1.55(m, 8H), 1.21 - 1.12 (d, $J=29.4$ Hz, 12H). | 19 |

| | | | | |
|---|---|---|---|---|
| 296 |  | B | 781.3 | ¹H NMR (300 MHz, CD₃OD) 7.75-7.70 (m, 1H), 7.48-7.44 (m, 1H), 7.36-7.33 (m, 2H), 7.16-7.12 (m, 2H), 6.99-6.96 (m, 1H), 5.08-5.02 (m, 1H), 4.63-4.61 (m, 1H), 4.28-4.26 (m, 1H), 4.14-4.11 (m, 1H), 3.73-3.55 (m, 3H), 3.07-3.02 (m, 1H), 2.86-2.64 (m, 8H), 2.11-1.92 (m, 3H), 1.27-1.22 (m, 12H); | 1, 16 |
| 297 |  | B | 817.51 | ¹H NMR (400 MHz, DMSO-d6): δ 1.10 (s, 6H), 1.17 (s, 6H), 1.92-2.09 (m, 3H), 2.50 (s, 4H), 2.51-2.73 (m, 4H), 2.84-2.93 (m, 1H), 3.28 (br, 4H), 4.00 (d, J = 9.6 Hz, 1H), 4.23-4.26 (m, 3H), 5.10-5.15 (m, 1H), 6.67 (d, J = 12.0 Hz, 2H), 6.98-7.01 (m, 1H), 7.22 (d, J = 2.33 Hz, 1H), 7.35-7.38 (m, 1H), 7.45 (d, J = 2.0 Hz, 1H), 7.84 (d, J = 8.4 Hz, 1H). | 9 |

FIG. 3 Continued.

| 298 | [structure] | B | 845.55 | ¹H NMR (400 MHz, DMSO-d6): δ 1.10 (s, 6H), 1.17 (s, 6H), 1.41-1.58 (m, 4H), 1.77-1.81 (m, 2H), 2.01-2.07 (m, 1H), 2.28-2.39 (m, 2H), 2.42-2.49 (m, 4H), 2.54-2.62 (m, 2H), 2.84-2.91 (m, 1H), 3.23 (br, 4H), 4.00 (d, $J$ = 9.2 Hz, 1H), 4.19 (t, $J$ = 6.4 Hz, 2H), 4.25 (s, 1H), 5.09-5.14 (m, 1H), 6.67 (d, $J$ = 11.2 Hz, 2H), 7.00 (dd, $J$ = 8.8, 2.4 Hz, 1H), 7.21 (d, $J$ = 2.4 Hz, 1H), 7.34-7.36 (m, 1H), 7.43 (d, $J$ = 2.0 Hz, 1H), 7.84 (d, $J$ = 8.4 Hz, 1H), 7.89 (d, $J$ = 9.2 Hz, 1H), 8.18 (d, $J$ = 9.2 Hz, 1H), 11.12 (s, 1H). | 9 |
| --- | --- | --- | --- | --- | --- |
| 299 | [structure] | B | 813.53 | ¹H NMR (400 MHz, DMSO-d6): δ 1.10 (s, 6H), 1.17 (s, 6H), 1.41-1.58 (m, 4H), 1.77-1.81 (m, 2H), 2.01-2.07 (m, 1H), 2.28-2.39 (m, 2H), 2.42-2.49 (m, 4H), 2.54-2.62 (m, 2H), 2.84-2.91 (m, 1H), 3.23 (br, 4H), 4.00 (d, $J$ = 9.2 Hz, 1H), 4.19 (t, $J$ = 6.4 Hz, 2H), 4.25 (s, 1H), 5.09-5.14 (m, 1H), 6.67 (d, $J$ = 11.2 Hz, 2H), 7.00 (dd, $J$ = 8.8, 2.4 Hz, 1H), | 9 |

| 300 |  | B | 890.57 | 7.21 (d, J = 2.4 Hz, 1H), 7.34-7.36 (m, 1H), 7.43 (d, J = 2.0 Hz, 1H), 7.84 (d, J = 8.4 Hz, 1H), 7.89 (d, J = 8.8 Hz, 1H), 8.18 (d, J = 9.2 Hz, 1H), 11.12 (s, 1H). ¹H NMR (400 MHz, DMSO-d6): δ 1.00-1.07 (m, 2H), 1.09 (s, 6H), 1.18 (s, 6H), 1.82-1.88 (m, 2H), 1.96-2.05 (m, 2H), 2.17-2.25 (m, 2H), 2.53-2.64 (m, 2H), 2.84-2.92 (m, 1H), 2.98-3.06 (m, 2H), 3.30-3.33 (m, 4H), 3.40-3.50 (m, 4H), 3.99 (d, J = 9.2 Hz, 1H), 4.26 (s, 1H), 4.63-4.72 (m, 2H), 5.05-5.10 (m, 1H), 6.99-7.02 (m, 1H), 7.22-7.28 (m, 2H), 7.33-7.37 (m, 1H), 7.68 (d, J = 8.8 Hz, 1H), 7.89 (d, J = 9.2 Hz, 1H), 8.24 (d, J = 8.4 Hz, 1H), 8.60 (s, 1H), 11.09 (s, 1H). | 49 starting with ethyl 2-chloro-4-(trifluoromethyl)pyrimidine-5-carboxylate |

| | | | |
|---|---|---|---|
| 301 | [structure] | B | 813.54 | |
| 302 | [structure] | B | 888.58 | $^1$H NMR (400 MHz, DMSO-d6): δ 1.00-1.07 (m, 2H), 1.09 (s, 6H), 1.18 (s, 6H), 1.82-1.88 (m, 2H), 1.96-2.05 (m, 2H), 2.17-2.25 (m, 2H), 2.53-2.64 (m, 2H), 2.84-2.92 (m, 1H), 2.98-3.06 (m, 2H), 3.30-3.33 (m, 4H), 3.40-3.50 (m, 4H), 3.99 (d, J = 9.2 Hz, 1H), 4.26 (s, 1H), 4.63-4.72 (m, 2H), 5.05-5.10 (m, 1H), 6.99-7.02 (m, 1H), 7.22-7.28 (m, 2H), 7.33-7.37 (m, 1H), 7.68 (d, J = 8.4 Hz, 1H), 7.89 (d, J = 8.8 Hz, 1H), 8.24 (d, J = 9.2 Hz, | 49 starting with 4-fluoro-3-(trifluoromethyl)benzoic acid |

| 303 | | B | 827.56 | 1H), 8.60 (s, 1H), 11.09 (s, 1H). |

FIG. 3 Continued.

| | | | | |
|---|---|---|---|---|
| 304 | [structure] | B | 862.64 | |
| 305 | [structure] | B | 822.4 | H-NMR (300 MHz, DMSO) δ 11.04 (s, 1H), 8.55 (s, 2H), 8.10-8.07 (d, J=9 Hz, 1H), 7.89-7.86 (d, J=9 Hz, 1H), 7.67-7.65 (d, J=8.4 Hz, 1H), 7.32 (s, 1H), 7.26-7.22 (m, 2H), 7.03-6.99 (m, 1H), 5.08-5.02 (m, 1H), 4.40 (s, 1H), 4.01-3.92 (m, 3H), 3.43 (s, 4H), 2.95-2.80 (m, 3H), 2.59 (s, 6H), 2.21-2.19 (d, J=6.3 Hz, 2H), 2.05-1.98 (m, 1H), 1.83-1.79 (d, J=11.1 Hz, 3H), 1.18 (s, 6H), 1.11 (s, 6H); 49 starting with 5-fluoropyrimidine-2-carbonitrile |

| | | | | | |
|---|---|---|---|---|---|
| 306 |  | B | 836.5 | H-NMR (300 MHz, DMSO) δ 11.04 (s, 1H), 8.55 (s, 2H), 8.09-8.06 (d, J=9 Hz, 1H), 7.89-7.86 (d, J=9 Hz, 1H), 7.67-7.64 (d, J=8.4 Hz, 1H), 7.32 (s, 1H), 7.25-7.22 (m, 2H), 7.03-6.99 (m, 1H), 5.08-5.02 (m, 1H), 4.40 (s, 1H), 4.00-3.92 (m, 3H), 3.42 (s, 4H), 2.91-2.83 (m, 3H), 2.59-2.54 (m, 6H), 2.39-2.25 (m, 2H), 2.05-1.98 (m, 1H), 1.80-1.76 (d, J=12 Hz, 2H), 1.58 (s,1H), 1.46-1.39 (m,2H),1.28-1.24 (d, J=11.1 Hz, 8H), 1.18 (s, 6H); | 17 starting with 5-fluoropyrimidine-2-carbonitrile |
| 307 |  | B | 838.2 | ¹H NMR (300 MHz, DMSO-$d_6$) δ 11.06 (s, 1H), 7.87 (d, J = 8.8 Hz, 1H), 7.69 (dd, J = 15.0, 10.0 Hz, 3H), 7.44 (dd, J = 18.6, 8.3 Hz, 2H), 7.17 (d, J = 2.4 Hz, 1H), 7.02 – 6.89 (m, 3H), 5.07 (dd, J = 12.9, 5.3 Hz, 1H), 4.28 (s, 1H), 4.07 – 3.95 (m, 1H), 3.77 (m, 2H),3.31 – 3.18 (m, 4H), 2.95 – 2.76 (m, 3H), 2.62 – 2.46 (m, 6H), 2.21 (d, J = 6.8 Hz, 2H), 1.99 (d, J = 19.3 Hz, 1H), 1.82 (d, J = 13.2 Hz, 3H), | 49 |

FIG. 3 Continued.

| | | | |
|---|---|---|---|
| 308 | [structure] | B | 778.3 | HNMR (300 MHz, DMSO-d6, ppm) δ 11.08 (s, 1 H), 7.92-7.89 (d, J= 8.7Hz, 1H), 7.76-7.68 (m, 3H), 7.44 - 7.213 (m, 4H), 7.02 - 7.01 (d, J= 2.4Hz, 1H), 6.47-6.44 (d, J= 8.7 Hz, 2H), 5.08-5.04 (m, 1H), 4.32(s, 1H), 4.07-4.02 (m, 3H), 3.77-3.73 (m, 2H), 3.49-3.46 (m, 4H), 3.32-3.31 (m, 1H), 2.96-2.82 (m, 1H), 2.60-2.55 (m, 6H), 2.09-1.95 (m, 1H), 1.22 (s, 6H), 1.12 (s, 6H); 1.34 (d, J = 27.3 Hz, 8H) . 1.11 (d, J = 27.3 Hz, 6H). | 19 |
| 309 | [structure] | B | 822.4 | ¹H NMR (400 MHz, CD₃OD): δ7.82-7.80 (d, J=8.0Hz, 1H), 7.75-7.70 (m, 3H), 7.28-7.22 (m, 2H), 7.13-7.12 (d, J=2.4Hz, 1H), 6.99-6.96 (m, 3H), 5.12-5.02 (m, 2H), 4.28 (s, 1H), 4.13 (s, 1H), 3.94-3.90 (m, 2H), 3.38-3.30(m, 6H), 2.82-2.70 (m. 5H), 2.67-2.64(m, 4H), 2.50-2.47 (m, | 23 |

FIG. 3 Continued.

| | | | | |
|---|---|---|---|---|
| 310 | [structure] | B | 836.59 | ¹H NMR (400 MHz, CD₃OD): δ 7.82-7.80 (d, J=8.0Hz, 1H), 7.75-7.70 (m, 3H), 7.28-7.22 (m, 2H), 7.13-7.12 (d, J=2.4Hz, 1H), 6.99-6.96 (m, 3H), 5.12-5.02 (m, 2H), 4.28 (s, 1H), 4.13 (s, 1H), 3.94-3.90 (m, 2H), 3.38-3.30(m, 6H), 2.82-2.70 (m, 5H), 2.67-2.64(m, 4H), 2.50-2.47 (m, 2H), 2.13-2.11 (m, 1H), 1.27 (s, 6H), 1.21 (s, 6H); | 49 starting with ethyl 2-chloro-4-methylpyrimidine-5-carboxylate |
| 311 | [structure] | B | 850.6 | ¹HNMR (400 MHz, DMSO-d6): δ 1.10 (s, 6H), 1.18 (s, 6H), 1.25 (d, J = 6.4 Hz, 2H), 1.80 (d, J = 13.2 Hz, 2H), 1.91 (s, 1H), 2.01-2.04 (m, 1H), 2.18-2.22 (m, 8H), 2.55-2.61 (m, 3H), 2.83-2.89 (m, 3H), 3.34 (s, 2H), 3.45 (br, 4H), 4.08 (d, J = 9.6 Hz, 1H), 4.26 (s, 1H), 4.72 (d, J = 12.4 Hz, 2H), 5.06-5.10 (m, 1H), 6.99-7.02 (m, 1H), 7.22-7.27 (m, 2H), 7.35 (s, 1H), 7.69 (d, J = 8.4 Hz, 1H), 7.90 (d, J = 8.8 Hz, 1H), 8.23 (d, J = 9.2 Hz, 1H), 11.10 (s, 1H). | 49 starting with ethyl 2-chloro-4-methylpyrimidine-5-carboxylate |

| | | | |
|---|---|---|---|
| 312 |  | 795.5 / 5 | |
| 313 |  | 843.5 / 5 | |

FIG. 3 Continued.

| | B | 823.6 | 1H NMR (300 MHz, DMSO-d6) δ 11.07 (s, 1H), 7.83 (dd, J = 20.2, 8.5 Hz, 2H), 7.69 (d, J = 8.6 Hz, 2H), 7.54-7.36 (m, 2H), 7.32 (dd, J = 8.3, 2.3 Hz, 1H), 7.17 (d, J = 2.3 Hz, 1H), 7.02-6.86 (m, 3H), 5.08 (dd, J = 12.8, 5.3 Hz, 1H), 4.28 (s, 1H), 4.16 (t, J = 6.3 Hz, 2H), 4.01 (d, J = 9.1 Hz, 1H), 3.66 (d, J = 11.5 Hz, 2H), 2.94 – 2.83 (m, 1H), 2.65 (dt, J = 29.5, 6.6 Hz, 5H), 2.53 (d, J = 3.1 Hz, 3H), 2.07-1.94 (m, 1H), 1.74-1.63 (m, 2H), 1.48 (p, J = 8.0 Hz, 2H), 1.18 (s, 6H), 1.14-0.98 (m, 12H).. | 9 |

FIG. 3 Continued.

| | | | | |
|---|---|---|---|---|
| 315 | [structure] | B | 792.54 | H-NMR (300 MHz, DMSO) δ 11.06 (s, 1H), 7.98-7.89 (d, J=9 Hz, 1H), 7.77-7.74 (d, J=8.7 Hz, 2H), 7.65-7.62 (d, J=8.4 Hz, 1H), 7.52-7.49 (d, J=9.3 Hz, 1H), 7.21-7.20 (d, J=2.4 Hz, 1H), 7.02-76.96 (m, 3H), 6.79 (s, 1H), 6.67-6.64 (d, J=8.1 Hz, 1H), 5.08-5.02 (m, 1H), 4.32 (s, 1H), 4.18-4.04 (m, 3H), 3.74-3.70 (m, 2H), 3.30-3.26 (d, J=12 Hz, 1H), 3.05 (s, 1H), 2.94-2.82 (m, 3H), 2.73-2.27 (m, 11H), 2.03-1.99 (m,1H), 1.22 (s, 6H), 1.13 (s, 6H); | 65 |
| 316 | [structure] | B | 820.57 | $^1$H NMR (300 MHz, DMSO-$d_6$) δ 11.03 (s, 1H), 7.87 (d, J = 8.7 Hz, 1H), 7.72 (d, J = 8.7 Hz, 2H), 7.62 (d, J = 8.5 Hz, 1H), 7.47 (d, J = 9.2 Hz, 1H), 7.31 (m, 1H), 7.20 – 7.13 (m, 2H), 7.02 – 6.89 (m, 3H), 5.23 (dd, J = 12.6, 5.4 Hz, 1H), 4.93 (dd, J = 12.6, 5.4 Hz, 3H), 3.31 – 3.17 (m, 3H), 3.02 – 2.76 (m, 3H), 2.62 – 2.49 (m, 6H), 2.17 (d, J = 6.7 Hz, 2H), 1.98 (dt, J = 10.9, 5.3 Hz, 1H), 1.90 – 1.74 (m, 3H), 1.14 (d, J = 27.4 Hz, 14H). | 49, 70 |

FIG. 3 Continued.

| | | | | |
|---|---|---|---|---|
| 317 | [structure] | B | 840.57 | ¹H NMR (300 MHz, DMSO-d6): δ 11.03 (s, 1H), 7.87 (d, J = 8.7 Hz, 1H), 7.72 (d, J = 8.7 Hz, 2H), 7.62 (d, J = 8.5 Hz, 1H), 7.47 (d, J = 9.2 Hz, 1H), 7.31 (m, 1H), 7.20 – 7.13 (m, 2H), 7.02 – 6.89 (m, 3H), 5.23 (dd, J = 12.6, 5.4 Hz, 1H), 4.93 (dd, J = 12.6, 5.4 Hz, 3H), 3.31 – 3.17 (m, 3H), 3.02 – 2.76 (m, 3H), 2.62 – 2.49 (m, 6H), 2.17 (d, J = 6.7 Hz, 2H), 1.98 (dt, J = 10.9, 5.3 Hz, 1H), 1.90 – 1.74 (m, 3H), 1.14 (d, J = 27.4 Hz, 14H). | 14 |
| 318 | [structure] | B | 814.53 | ¹H NMR (400 MHz, DMSO-d6): δ 1.12 (s, 6H), 1.19 (s, 6H), 1.62-1.67 (m, 2H), 1.77-1.84 (m, 2H), 2.00-2.07 (m, 1H), 2.24-2.44 (m, 6H), 2.54-2.62 (m, 2H), 2.86-2.90 (m, 1H), 3.60 (br, 4H), 3.96 (d, J = 9.6 Hz, 1H), 4.20-4.24 (m, 2H), 4.32 (s, 1H), 5.08-5.13 (m, 1H), 6.74-6.77 (m, 1H), 6.99- | 109 |

FIG. 3 Continued.

| 319 | [structure] | B | 787.49 | ¹H NMR (400 MHz, DMSO-*d6*): δ 1.11 (s, 6H), 1.18 (s, 6H), 1.98-2.07 (m, 1H), 2.51-2.64 (m, 6H), 2.83-2.94 (m, 3H), 3.45 (s, 4H), 4.05 (d, *J* = 9.2 Hz, 1H), 4.27 (s, 1H), 5.02-5.13 (m, 1H), 6.97-7.05 (m, 1H), 7.12 (d, *J* = 8.8 Hz, 2H), 7.23-7.29 (m, 2H), 7.36 (s, 1H), 7.69 (d, *J* = 8.4 Hz, 1H), 7.90 (d, *J* = 8.4 Hz, 1H), 8.50 (d, *J* = 9.2 Hz, 1H), 11.10 (s, 1H). | 110 |

(continued row): 7.02 (m, 1H), 7.21 (d, *J* = 2.4 Hz, 1H), 7.36-7.39 (m, 1H), 7.44-7.45 (m, 1H), 7.51-7.55 (m, 1H), 7.84 (d, *J* = 8.4 Hz, 1H), 7.91 (d, *J* = 8.8 Hz, 1H), 8.39 (d, *J* = 10.4 Hz, 1H), 11.11 (s, 1H).

| B | 752.49 | 1HNMR (400 MHz, CD3OD): δ 1.12 (s, 6H), 1.18 (s, 6H), 1.78-1.79 (m, 4H), 1.92-2.11 (m, 2H), 2.61-2.67 (m, 2H), 2.71-2.77 (m, 2H), 3.50 (t, J = 6.0 Hz, 2H), 3.97-4.04 (m, 3H), 4.09 (br, 2H), 4.18 (s, 1H), 4.92-5.03 (m, 1H), 6.35 (d, J = 8.4 Hz, 2H), 6.86-6.89 (m, 1H), 7.02 (d, J = 2.4 Hz, 1H), 7.21-7.23 (m, 1H), 7.29-7.31 (m, 2H), 7.59-7.63 (m, 3H), 7.70 (d, J = 8.0 Hz, 1H). | 111 |

FIG. 3 Continued.

| | | |
|---|---|---|
| B (structure shown) | 821.56 | ¹H NMR (400 MHz, DMSO-d6): δ 1.12 (s, 6H), 1.21 (s, 6H), 1.73-1.77 (m, 2H), 1.99-2.02 (m, 1H), 2.06-2.10 (m, 2H), 2.54-2.60 (m, 2H), 2.83-2.98 (m, 3H), 3.27-3.34 (m, 5H), 3.45-3.47 (m, 4H), 4.03-4.07 (m, 3H), 4.19 (s, 1H), 4.32 (s, 1H), 5.04-5.08 (m, 1H), 6.55 (d, J =8.8 Hz, 2H), 6.99-7.02 (m, 1H), 7.20-7.23 (m, 2H), 7.29 (d, J =1.6 Hz, 1H), 7.40 (d, J = 9.2 Hz, 1H), 7.64 (d, J = 8.4 Hz, 1H), 7.74 (d, J = 8.8 Hz, 2H), 7.90 (d, J = 8.8 Hz, 1H), 11.08 (s, 1H). | 112 |

FIG. 3 Continued.

| | B | 806.56 | ¹H NMR (400 MHz, DMSO-d6): δ 1.13 (s, 6H), 1.22 (s, 6H), 1.72-2.17 (m, 4H), 2.34-2.42 (m, 3H), 2.58-2.71 (m, 2H), 2.84-2.93 (m, 1H), 3.14-3.20 (m, 2H), 3.28-3.33 (m, 6H), 3.43-3.60 (m, 3H), 4.05-4.07 (m, 1H), 4.32 (s, 1H), 5.04-5.08 (m, 1H), 6.81-7.01 (m, 5H), 7.21 (s, 1H), 7.53 (d, $J$ = 11.6 Hz, 1H), 7.64 (d, $J$ = 7.2 Hz, 1H), 7.76 (d, $J$ = 6.8 Hz, 2H), 7.90 (d, $J$ = 7.2 Hz, 1H), 11.08 (s, 1H). | 53 |

| | | | |
|---|---|---|---|
| 323 |  | B | 806.5 6 | 53 |
| 324 |  | B | 779.5 5 | |

| | | | |
|---|---|---|---|
| 325 |  | B | 821.56 | ¹H NMR (400 MHz, DMSO-d6): δ 1.12 (s, 6H), 1.21 (s, 9H), 1.73-1.74 (m, 2H), 1.80-1.84 (m, 1H), 1.99-2.02 (m, 1H), 2.06-2.08 (m, 2H), 2.33-2.39 (m, 3H), 2.54-2.60 (m, 2H), 2.83-2.98 (m, 3H), 3.27-3.27 (m, 2H), 3.33-3.34 (m, 2H), 3.46-3.50 (m, 1H), 4.03-4.07 (m, 3H), 4.19 (s, 1H), 4.32 (s, 1H), 5.04-5.08 (m, 1H), 6.55 (d, $J$ = 8.8 Hz, 2H), 6.99-7.02 (m, 1H), 7.20-7.23 (m, 2H), 7.30 (s, 1H), 7.40 (d, $J$ = 8.8 Hz, 1H), 7.64 (d, $J$ = 8.8 Hz, 1H), 7.75 (d, $J$ = 8.8 Hz, 2H), 7.90 (d, $J$ = 8.4 Hz, 1H), 11.12 (s, 1H). | 113 |

FIG. 3 Continued.

| | Structure | | | NMR |
|---|---|---|---|---|
| 326 | (structure) | B | 811.4 | ¹H-NMR (300 MHz, CD3OD) δ 8.71(s, 2H), 7.75- 7.67(m, 2H), 7.21- 7.17(m, 1H), 7.16- 7.08(m, 2H), 7.01- 6.93(m, 1H), 5.16- 5.06 (m, 1H), 4.26(s, 1H), 4.12(s, 1H), 4.02- 3.66(m, 6H), 3.11- 3.3.03(m, 2H), 2.94- 2.777(m, 3H), 2.75- 2.58(m. 1H), 2.48- 2.29(m. 1H), 2.16 - 2.04(m, 1H), 1.82- 1.65(m, 2H), 1.27 - 1.20 (d, J=20.7 Hz, 12H), 1.06- 0.09(m, 6H) |
| 327 | (structure) | B | 806.55 | ¹HNMR (400 MHz, DMSO-$d_6$): δ 1.13 (s, 6H), 1.22 (s, 6H), 1.78-1.84 (m, 1H), 2.02-2.05 (m, 1H), 2.25-2.27 (m, 1H), 2.55-2.62 (m, 2H), 2.85-2.93 (m, 2H), 3.08-3.21 (m, 3H), 3.32-3.47 (m, 6H), 3.60-3.73 (m, 3H), 4.07-4.08 (m, 1H), 4.25-4.28 (m, 2H), 4.33 (s, 2H), 5.09-5.13 (m, 1H), 6.57 (d, J = 8.8 Hz, 2H), 7.00-7.02 (m, 1H), 7.20-7.21 (m, 1H), 7.38-7.45 (m, 2H), 7.52 (s, 1H), 7.78 (d, J = 8.4 Hz, 3H), 7.91 (d, J = 8.4 Hz, 1H), 9.97 (br, 1H), 11.12 (s, 1H). |

| 328 |  | B | 824.55 | ¹H NMR (400 MHz, DMSO-d₆): δ 1.12 (s, 6H), 1.21 (s, 6H), 1.71-1.79 (m, 1H), 2.00-2.05 (m, 1H), 2.12-2.15 (m, 1H), 2.42 (d, J = 6.4 Hz, 2H), 2.57-2.61 (m, 6H), 2.84-2.93 (m, 1H), 3.05 (t, J = 7.2 Hz, 1H), 3.26-3.31 (m, 6H), 3.38-3.40 (m, 1H), 3.46 (t, J = 8.4 Hz, 1H), 4.05 (d, J = 8.8 Hz, 1H), 4.32 (s, 1H), 5.09-5.13 (m, 1H), 6.54 (d, J = 8.8 Hz, 2H), 6.99-7.01 (m, 1H), 7.20 (d, J = 2.0 Hz, 1H), 7.39 (d, J = 9.2 Hz, 1H), 7.46 (d, J = 3.6 Hz, 1H), 7.72-7.75 (m, 3H), 7.90 (d, J = 8.4 Hz, 1H), 11.12 (s, 1H). | 53 |

| | | | |
|---|---|---|---|
| 329 | 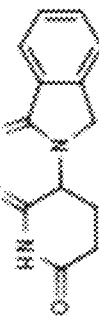 | B | 765.56 | ¹H NMR (400 MHz, DMSO-d⁶) δ 1.12 (6H, s), 1.22 (6H, s), 1.50-1.53 (2H, m), 1.63-1.66 (2H, m), 1.99-2.02 (1H, m), 2.34-2.47 (7H, m), 2.55-2.59 (1H, m), 2.66-2.70 (2H, m), 2.88-2.97 (1H, m), 3.25-3.31 (4H, m), 4.05 (1H, d, J = 9.2 Hz), 4.30-4.34 (2H, m), 4.46-4.50 (1H, m), 5.14 (1H, dd, J = 13.2, 4.8 Hz), 6.95-7.02 (3H, m), 7.21 (1H, d, J = 2.4 Hz), 7.46-7.48 (2H, m), 7.51-7.57 (2H, m), 7.74 (2H, d, J = 8.8 Hz), 7.91 (1H, d, J = 8.8 Hz), 11.02 (1H, s). | 8A |
| 330 | 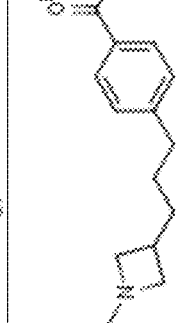 | B | 736.5 | ¹H NMR (400 MHz, DMSO-d⁶) δ 1.12 (6H, s), 1.22 (6H, s), 1.50-1.53 (2H, m), 1.63-1.66 (2H, m), 1.99-2.02 (1H, m), 2.34-2.47 (7H, m), 2.55-2.59 (1H, m), 2.66-2.70 (2H, m), 2.88-2.97 (1H, m), 3.25-3.31 | 113 |
FIG. 3 Continued.
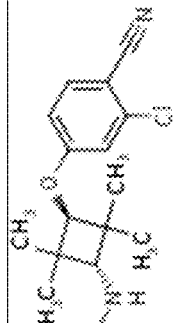

| | | | |
|---|---|---|---|
| | B | | 8A |
| 331 |  | 779.54 | ¹H NMR (400 MHz, CDCl₃) δ 1.13 (6H, s), 1.22 (6H, s), 1.50-1.55 (2H, m), 1.62-1.67 (2H, m), 2.04-2.08 (1H, m), 2.33-2.36 (2H, m), 2.47-2.50 (4H, m), 2.55-2.62 (2H, m), 2.86-2.90 (1H, m), 3.07 (2H, t, J = 7.2 Hz), 3.23 (4H, s), 4.05 (1H, d, J = 9.2 Hz), 4.32 (1H, s), 5.14 (1H, dd, J = 12.8, 5.6 Hz), 6.95-7.02 (3H, m), 7.21 (1H, d, J = 2.4 Hz), 7.52 (1H, d, J = 9.2 Hz), 7.71-7.81 (5H, m), 7.91 (1H, d, J = 8.8 Hz), 11.13 (1H, s). |
| | | | (4H, m), 4.05 (1H, d, J = 9.2 Hz), 4.30-4.34 (2H, m), 4.46-4.50 (1H, m), 5.14 (1H, dd, J = 13.2, 4.8 Hz), 6.95-7.02 (3H, m), 7.21 (1H, d, J = 2.4 Hz), 7.46-7.48 (2H, m), 7.51-7.57 (2H, m), 7.74 (2H, d, J = 8.8 Hz), 7.91 (1H, d, J = 8.8 Hz), 11.02 (1H, s). |

FIG. 3 Continued.

| | | | | |
|---|---|---|---|---|
| 332 | [structure] | B | 798.2 | ¹H NMR (400 MHz, CD₃OD): δ 8.51 (s, 1H), 7.71-7.66 (m, 2H), 7.35-7.34 (d, J=1.6Hz, 1H), 7.23-7.21 (d, J=8.4Hz, 1H), 7.10-7.09 (d, J=2.0Hz, 1H), 6.96-6.93 (m, 1H), 5.09-5.04 (m, 1H), 4.19 (s, 1H), 3.98 (s, 1H), 3.52-3.31 (m, 7H), 3.06-3.02 (m, 1H), 2.87-2.81 (m, 1H), 2.76-2.51 (m, 10H), 2.42-2.31 (m, 4H), 2.11-2.10 (m, 3H), 1.90 (m, 1H), 1.45-1.35 (m, 2H), 1.20 (s, 6H), 1.10 (s, 6H); | 114 |
| 333 | [structure] | B | 822.03 | ¹H NMR (400 MHz, CD₃OD): δ 8.51 (s, 1H), 7.71-7.66 (m, 2H), 7.35-7.34 (d, J=1.6Hz, 1H), 7.23-7.21 (d, J=8.4Hz, 1H), 7.10-7.09 (d, J=2.0Hz, 1H), 6.96-6.93 (m, 1H), 5.09-5.04 (m, 1H), 4.19 (s, 1H), 3.98 (s, 1H), 3.52-3.31 (m, 7H), 3.06-3.02 (m, 1H), 2.87-2.81 (m, 1H), 2.76-2.51 (m, 10H), 2.42-2.31 (m, 4H), 2.11-2.10 (m, 3H), 1.90 (m, 1H), 1.45-1.35 (m, 2H), 1.20 (s, 6H), 1.10 (s, 6H); | 49 |

| | | | | |
|---|---|---|---|---|
| 334 |  | B | 821.55 | ¹H-NMR (300 MHz, CD₃OD) δ 7.82-7.68 (m, 4H), 7.28-7.10 (m, 3H), 7.02-6.94 (m, 1H), 6.64-6.57 (m, 2H), 5.14-5.05 (m, 1H), 4.94-4.90 (m, 1H), 4.28 (s, 1H), 4.13 (s, 1H), 3.69-3.35 (m, 3H), 3.22-3.06 (m, 2H), 2.96-2.57 (m, 4H), 2.56-2.24 (m, 6H), 2.24-2.03 (m, 5H), 1.92-1.74 (m, 1H), 1.28-1.22 (d, *J=18 Hz*, 12H); | 73 |
| 335 |  | B | 821.56 | ¹H-NMR (300 MHz, CD₃OD) δ 7.82-7.68 (m, 4H), 7.28-7.10 (m, 3H), 7.02-6.94 (m, 1H), 6.64-6.57 (m, 2H), 5.14-5.05 (m, 1H), 4.94-4.90 (m, 1H), 4.28 (s, 1H), 4.13 (s, 1H), 3.69-3.35 (m, 3H), 3.22-3.06 (m, 2H), 2.96-2.57 (m, 4H), 2.56-2.24 (m, 6H), 2.24-2.03 (m, 5H), 1.92-1.74 (m, 1H), 1.28-1.22 (d, *J=18 Hz*, 12H); | 113 |

| | | | | |
|---|---|---|---|---|
| 336 |  | B | 821.56 | ¹H NMR (400 MHz, DMSO-d6): δ 1.12 (s, 6H), 1.22 (s, 6H), 1.52-1.54 (m, 2H), 1.81-1.83 (m, 1H), 1.86-1.94 (m, 3H), 1.98-2.03 (m, 1H), 2.16-2.20 (m, 1H), 2.55-2.60 (m, 2H), 2.70 (s, 2H), 2.84-2.93 (m, 1H), 3.03-3.08 (m, 1H), 3.18-3.22 (m, 1H), 3.29-3.32 (m, 2H), 3.48-3.55 (m, 3H), 3.57-3.63 (m, 2H), 4.05 (d, J = 9.2 Hz, 1H), 4.32 (s, 1H), 5.05 (d, J = 12.8 Hz, 1H), 6.81 (d, J = 8.4 Hz, 1H), 6.90 (d, J = 1.6 Hz, 1H), 6.96-7.02 (m, 3H), 7.21 (d, J = 2.4 Hz, 1H), 7.50 (d, J = 9.2 Hz, 1H), 7.63(d, J = 8.8 Hz, 1H), 7.73(d, J = 8.8 Hz, 2H), 7.90 (d, J = 8.8 Hz, 1H), 11.09 (s, 1H). | 113 |
| 337 |  | B | 807.54 | ¹H NMR (400 MHz, d6-DMSO): δ11.11 (s, 1H), 7.91-7.73 (m, 4H), 7.44-7.01 (m, 5H), 6.43 (s, 2H), 5.12-4.96 (m, 2H), 4.31 (s, 1H), 4.04-3.98 (m, 3H), 3.53-3.33 (m, 3H), 3.08 (m, 1H), 3.01-2.92 (m, 2H), 2.61-2.30 (m, 5H), 2.23-2.08 (m, 6H), 1.21 (s, 6H), 1.12 (s, 6H); | 73 |

| | | | | |
|---|---|---|---|---|
| 338 |  | B | 821.45 | ¹H-NMR (300 MHz, CD₃OD) δ 7.82- 7.68 (m, 4H), 7.28- 7.10 (m, 3H), 7.02- 6.94 (m, 1H), 6.64- 6.57 (m, 2H), 5.14 - 5.05 (m, 1H), 5.01- 4.90 (m, 1H), 4.28 (s, 1H), 4.15- 4.10 (m, 1H), 3.60- 3.33 (m, 3H), 3.21- 3.09 (m, 2H), 2.92- 2.30 (m, 10H), 2.28- 2.05 (m, 5H), 1.90- 1.73 (m, 1H), 1.28- 1.22 (d, $J=18\ Hz$, 12H). | 73 |
| 339 |  | B | 839.56 | ¹H NMR (400 MHz, DMSO-d6): δ 1.00-1.08 (m, 2H), 1.12 (s, 6H), 1.19 (s, 6H), 1.73-1.94 (m, 3H), 1.99-2.06 (m, 1H), 2.19 (d, $J = 6.8$ Hz, 2H), 2.46-2.49 (m, 4H), 2.54-2.67 (m, 2H), 2.84-2.96 (m, 3H), 3.38-3.49 (m, 4H), 3.95 (d, $J = 8.8$ Hz, 1H), 4.31-4.40 (m, 3H), 5.05-5.10 (m, 1H), 6.71, 6.75 (two singles, 1H), 7.00-7.02 (m, 1H), 7.22-7.27 (m, 2H), 7.35 (s, 1H), 7.46-7.49 (m, 1H), 7.68 (d, $J = 8.4$ Hz, 1H), 7.89 (d, $J = 8.8$ Hz, 1H), 8.39 (d, $J = 11.2$ Hz, 1H), 11.10 (s, 1H). | 49, 109 |

| 340 | B | 852.59 | $^1$H NMR (400 MHz, DMSO-d6): δ 1.12 (s, 6H), 1.21 (s, 6H), 1.47-1.51 (m, 3H), 1.67-1.78 (m, 3H), 1.99-2.03 (m, 2H), 2.23 (s, 3H), 2.43-2.45 (m, 2H), 2.53-2.60 (m, 3H), 2.73-2.92 (m, 3H), 3.32 (s, 1H), 3.55-3.65 (m, 3H), 3.89-3.92 (m, 2H), 4.05 (d, J = 9.2 Hz, 1H), 4.31 (s, 1H), 5.04-5.09 (m, 1H), 6.94-7.04 (m, 4H), 7.21 (d, J = 2.4 Hz, 1H), 7.41 (d, J = 9.2 Hz, 1H), 7.60 (d, J = 12.4 Hz, 1H), 7.73 (d, J = 8.8 Hz, 2H), 7.90 (d, J = 8.8 Hz, 1H), 11.10 (s, 1H). | 115 |

| | | 852.59 | 1H NMR (400 MHz, DMSO-d6): δ 1.12 (s, 6H), 1.21 (s, 6H), 1.48-1.49 (m, 3H), 1.67-1.78 (m, 3H), 1.99-2.06 (m, 2H), 2.23 (s, 3H), 2.43-2.45 (m, 2H), 2.53-2.60 (m, 3H), 2.73-2.92 (m, 3H), 3.32 (s, 1H), 3.55-3.65 (m, 3H), 3.89-3.92 (m, 2H), 4.05 (d, $J$ = 9.2 Hz, 1H), 4.31 (s, 1H), 5.04-5.09 (m, 1H), 6.94-7.04 (m, 4H), 7.21 (d, $J$ = 2.0 Hz, 1H), 7.51 (d, $J$ = 9.2 Hz, 1H), 7.60 (d, $J$ = 12.8 Hz, 1H), 7.73 (d, $J$ = 8.8 Hz, 2H), 7.90 (d, $J$ = 8.8 Hz, 1H), 11.10 (s, 1H). | 115 |

| | | | | |
|---|---|---|---|---|
| 342 |  | B | 861.7 | ¹H NMR (300 MHz, DMSO-$d_6$): δ 11.08 (s, 1H), 8.61 (d, J = 2.3 Hz, 1H), 7.91 (dd, J = 11.7, 8.8 Hz, 1H), 7.70 (d, J = 8.4 Hz, 2H), 7.60 (d, J = 9.3 Hz, 1H), 7.38 (s, 1H), 7.28 (d, J = 8.8 Hz, 1H), 7.20 (d, J = 2.4 Hz, 1H), 7.00 (dd, J = 8.8, 2.5 Hz, 1H), 6.87 (d, J = 9.1 Hz, 1H), 5.07 (dd, J = 12.8, 5.3 Hz, 1H), 4.43 (dd, J = 25.1, 12.8 Hz, 2H), 4.30 (s, 1H), 4.04 (d, J = 9.1 Hz, 1H), 2.98 - 2.82 (m, 7H), 2.62 (m, 2H), 2.51 (m, 1H), 2.01-1.75 (m, 5H), 1.64 (d, J = 11.7 Hz, 1H), 1.50-1.11 (m, 21H). | 94 |
| 343 |  | B | 856.56 | H-NMR-PH-ARV-LS-049-E-0: (300 MHz, DMSO-$d_6$, ppm) δ 11.11 (br, 1H), 7.92-7.89 (d, J=8.7Hz, 1H), 7.75-7.61 (m, 4H), 7.47-7.45 (d, J=7.5Hz, 1H), 7.22-7.21 (d, J=2.4Hz, 1H), 7.12-7.06 (m, 1H), 7.03-6.99 (m, 1H), 5.14-5.08 (m, 1H), 4.32 (s, 1H), 4.08-4.05 (d, J=9.3Hz, 1H), 3.51-3.47 (m, | 49 |

FIG. 3 Continued.

| | | | |
|---|---|---|---|
| 344 | [structure] | B | 806.55 | 52 | H-NMR (300 MHz, DMSO-d6, ppm) δ 11.11 (br, 1H), 7.92-7.89 (d, J=8.7Hz, 1H), 7.75-7.61 (m, 4H), 7.47-7.45 (d, J =7.5Hz, 1H),7.22-7.21 (d, J =2.4Hz, 1H), 7.12-7.06 (m, 1H), 7.03-6.99 (m, 1H), 5.14-5.08 (m, 1H), 4.32 (s, 1H), 4.08-4.05 (d, J =9.3Hz, 1H), 3.51-3.47 (m, 2H), 3.26-3.24 (m, 4H), 2.89-2.82 (m, 1H), 2.78-2.71 (m, 2H), 2.62-2.55 (m, 6H), 2.27-2.25 (m, 2H), 2.08-2.04 (m, 1H), 1.86-1.73 (m, 3H), 1.31-1.28 (m, 2H), 1.22 (s, 6H), 1.13 (s, 6H); |

| | | | |
|---|---|---|---|
| 345 |  | B | 824.4 | 1H NMR (300 MHz, DMSO-d6) δ 11.04 (s, 1H), 7.87 (d, J = 8.7 Hz, 1H), 7.72 (d, J = 8.6 Hz, 2H), 7.52 (m, 2H), 7.17 (d, J = 2.4 Hz, 1H), 7.06 – 6.89 (m, 4H), 5.03 (dd, J = 12.8, 5.4 Hz, 1H), 4.28 (s, 1H), 4.02 (d, J = 9.1 Hz, 1H), 3.78-3.56 (m, 3H), 3.35-3.26 (m, 4H), 2.94 – 2.75 (m, 1H), 2.60 – 2.48 (m, 5H), 2.45-2.37 (m, 3H), 2.32 – 2.28 (m, 2H), 2.19-1.98 (m, 2H), 1.88-1.75 (m, 1H), 1.18 (s, 6H), 1.09 (s, 6H). | 53 |
| 346 |  | B | 840.55 | 1H NMR (300 MHz, DMSO-d6) δ 11.04 (s, 1H), 7.87 (d, J = 8.7 Hz, 1H), 7.72 (d, J = 8.6 Hz, 2H), 7.52 (m, 2H), 7.17 (d, J = 2.4 Hz, 1H), 7.06 – 6.89 (m, 4H), 5.03 (dd, J = 12.8, 5.4 Hz, 1H), 4.28 (s, 1H), 4.02 (d, J = 9.1 Hz, 1H), 3.78-3.56 (m, 3H), 3.35-3.26 (m, 4H), 2.94 – 2.75 (m, 1H), 2.60 – 2.48 (m, 5H), 2.45-2.37 (m, 3H), 2.32 – 2.28 (m, 2H), 2.19-1.98 (m, 2H), 1.88-1.75 (m, 1H), 1.18 (s, 6H), 1.09 (s, 6H). | 49 |

FIG. 3 Continued.

| 347 | [structure] | B | 938.66 | $^1$H NMR (400 MHz, DMSO-d$_6$) δ 1.13 (6H, s), 1.22 (6H, s), 1.29-1.34 (2H, m), 1.68-1.73 (1H, m), 1.80-1.83 (2H, m), 1.99-2.03 (1H, m), 2.24 (2H, d, J = 6.8 Hz), 2.51-2.61 (8H, m), 2.84-2.92 (1H, m), 3.25 (3H, s), 3.46-3.48 (6H, m), 3.55-3.57 (2H, m), 3.60-3.64 (2H, m), 3.78-3.80 (2H, m), 4.05 (1H, d, J = 9.6 Hz), 4.14-4.16 (2H, m), 4.32 (1H, s), 5.05-5.10 (1H, m), 6.93 (1H, d, J = 8.4 Hz), 6.99-7.02 (1H, m), 7.21 (1H, d, J = 2.4 Hz), 7.25-7.28 (1H, m), 7.32-7.35 (2H, m), 7.44 (1H, d, J = 8.4 Hz), 7.60 (1H, d, J = 9.2 Hz), 7.69 (1H, d, J = 8.4 Hz), 7.90 (1H, d, J = 8.8 Hz), 11.09 (1H, s). | 52, 116 |

| 348 | B | 777.56 | ¹H NMR (400 MHz, DMSO-d₆) δ 1.13 (6H, s), 1.22 (6H, s), 1.29-1.34 (2H, m), 1.68-1.73 (1H, m), 1.80-1.83 (2H, m), 1.99-2.03 (1H, m), 2.24 (2H, d, $J$ = 6.8 Hz), 2.51-2.61 (8H, m), 2.84-2.92 (1H, m), 3.25 (3H, s), 3.46-3.48 (6H, m), 3.55-3.57 (2H, m), 3.60-3.64 (2H, m), 3.78-3.80 (2H, m), 4.05 (1H, d, $J$ = 9.6 Hz), 4.14-4.16 (2H, m), 4.32 (1H, s), 5.05-5.10 (1H, m), 6.93 (1H, d, $J$ = 8.4 Hz), 6.99-7.02 (1H, m), 7.21 (1H, d, $J$ = 2.4 Hz), 7.25-7.28 (1H, m), 7.32-7.35 (2H, m), 7.44 (1H, d, $J$ = 8.4 Hz), 7.60 (1H, d, $J$ = 9.2 Hz), 7.69 (1H, d, $J$ = 8.4 Hz), 7.90 (1H, d, $J$ = 8.8 Hz), 11.09 (1H, s). | 117 |

| | | | | |
|---|---|---|---|---|
| 349 |  | B | 821.56 | ¹H NMR (400 MHz, CDCl₃) δ 1.12 (6H, s), 1.26 (6H, s), 1.49-1.54 (4H, m), 1.89-1.91 (4H, m), 1.99-2.02 (1H, m), 2.54-2.67 (1H, m), 2.85-2.89 (1H, m), 3.04 (2H, t, $J$ = 10.0 Hz), 3.23-3.26 (3H, m), 3.64-3.83 (6H, m), 4.04 (1H, d, $J$ = 9.2 Hz), 4.32 (1H, s), 5.04 (1H, dd, $J$ = 5.2, 12.8 Hz), 6.96-7.02 (3H, d, m), 7.20 (1H, d, $J$ = 2.4 Hz), 7.24 (1H, d, $J$ = 10.4 Hz), 7.33 (1H, s), 7.49 (1H, d, $J$ = 8.8 Hz), 7.65 (1H, d, $J$ = 8.8 Hz), 7.72 (2H, d, $J$ = 8.8 Hz), 7.89 (1H, d, $J$ = 8.8 Hz), 11.08 (1H, s). | 52, 118 |
| 350 |  | B | 839.35 | ¹H-NMR (400 MHz, CD₃OD) δ 8.54 (s, 1H), 7.77-7.64 (m, 2H), 7.36 (s, 1H), 7.26-7.12 (m, 2H), 7.02-6.96 (m, 1H), 6.65-6.57 (m, 1H), 5.12-5.04 (m, 1H), 4.28 (s, 1H), 4.12-4.04 (m, 3H), 3.71 (m, 4H), 3.08-2.98 (m, 2H), 2.90-2.55 (m, 7H), 2.37-2.31 (m, 2H), 2.15-1.93 (m, 4H), 1.37-1.30 (m, |

FIG. 3 Continued.

| | | | | |
|---|---|---|---|---|
| 351 | (structure) | B | 763.5 | 2H), 1.28 - 1.23 (d, J=21 Hz, 12H). | |
| 352 | (structure) | B | 818.55 | ¹H NMR (400 MHz, DMSO-d6): δ 1.13 (s, 6H), 1.23 (s, 6H), 1.88-1.92 (m, 1H), 1.99-2.03 (m, 1H), 2.18 (t, J = 8 Hz. 1H), 2.25 (br, 2H), 2.46 (br, 3H), 2.55-2.60 (m, 1H), 2.70 (s, 1H), 2.84-2.89 (m, 1H), 2.96 (s, 2H), 3.46-3.47 (m, 5H), 3.79 (s, 2H), 4.06 (d, J = 9.2 Hz, 1H), 4.35 (s, 1H), 5.05-5.11 (m, 1H), 5.76 (s, 1H), 6.96 (d, J = 8.8 Hz, 2H), 6.99-7.02 (m, 1H), 7.21 (d, J = 2.4 Hz, 1H), 7.26 (d, J = 8.4 Hz, 1H), 7.34 (s, 1H), 7.53 (d, J = 8.4 Hz, 1H), 7.68 (d, J = 8.4 Hz, 1H), 7.78 (d, J = 8.8 Hz, 2H), 7.90 (d, J = 8.8 Hz, 1H), 11.08 (s, 1H). | 119 |

FIG. 3 Continued.

| | | | | |
|---|---|---|---|---|
| 353 | [structure] | B | 821.2 | ¹H NMR (300 MHz, CDCl₃): 7.74-7.67 (m, 3H), 7.58-7.55(m, 1H), 7.29-7.26 (m, 1H), 7.04-7.08 (m, 1H), 6.97-6.93 (m, 3H), 6.83-6.81 (m, 1H), 6.14-6.11 (m, 1H), 4.97-4.91 (m, 1H), 4.42 (s, 1H), 4.16-4.13 (m, 1H), 4.05-3.99 (m, 3H), 3.04-2.92 (m, 4H), 2.88-2.51 (m, 3H) , 2.16-2.10 (m, 3H), 1.96-1.88 (m, 3H), 1.84-1.73(m, 2H) ,1.67-1.65 (m, 4H), 1.46 (m, 6H), 1.27-1.22 (m, 6H); | 120 |
| 354 | [structure] | B | 868.3 | ¹H NMR (400 MHz, CDCl₃): δ 8.04 (s, 1H), 7.55 (d, J = 8.7 Hz, 1H), 7.41 (dd, J = 25.5, 9.1 Hz, 2H), 6.93 (d, J = 2.4 Hz, 1H), 6.77 (dd, J = 8.7, 2.4 Hz, 1H), 5.66 (d, J = 8.5 Hz, 1H), 4.97-4.78 (m, 3H), 4.14 (d, J = 8.5 Hz, 1H), 3.99 (s, 1H), 3.27 (s, 4H), 2.96-2.63 (m, 6H), 2.59 (s, 4H), 2.33 (s, 6H), 2.13 (dd, J = 14.4, 6.4 Hz, 1H), 1.83 (d, J = 13.2 Hz, 3H), 1.20 (s, 12H), 1.11 (s, 2H). | 63 |
| 355 | [structure] | B | 786.2 | ¹H NMR (400 MHz, CDCl₃): δ 8.04 (s, 1H), 7.55 (d, J = 8.7 Hz, 1H), 7.41 (dd, J = 25.5, 9.1 Hz, 2H), 6.93 (d, J = 2.4 Hz, 1H), 6.77 (dd, J = 8.7, 2.4 Hz, 1H), 5.66 (d, J = 8.5 Hz, 1H), | 49 |

FIG. 3 Continued.

| | | | | |
|---|---|---|---|---|
| 356 | [structure] | B | | 4.97-4.78 (m, 3H), 4.14 (d, J = 8.5 Hz, 1H), 3.99 (s, 1H), 3.27 (s, 4H), 2.96-2.63 (m, 6H), 2.59 (s, 4H), 2.33 (s, 6H), 2.13 (dd, J = 14.4, 6.4 Hz, 1H), 1.83 (d, J = 13.2 Hz, 3H), 1.20 (s, 12H), 1.11 (s, 2H). |
| 357 | [structure] | B | 854.2 | $^1$H NMR (300 MHz, DMSO-$d_6$) δ 11.09 (s, 1H), 8.11 (d, J = 8.6 Hz, 1H), 7.72 (dd, J = 17.8, 8.5 Hz, 3H), 7.52 (d, J = 9.2 Hz, 1H), 7.44-7.22 (m, 4H), 6.96 (d, J = 8.6 Hz, 2H), 5.08 (dd, J = 12.7, 5.4 Hz, 1H), 4.40 (s, 1H), 4.08 (d, J = 9.1 Hz, 1H), 3.95-3.75 (m, 2H), 3.60-3.40 (m, 4H), 3.38-3.20 (m, 4H), 2.95-2.70 (m, 3H), 2.68-2.59 (m, 2H), 2.32 (brs, 2H), 2.04-2.02 (m, 1H), 1.82-1.70 (m, 3H), 1.19 (d, J = 26.9 Hz, 14H). | 49 |
| | | | 778.5 | $^1$H NMR (300 MHz, d6-DMSO) δ 1.13 (s, 6H), 1.22 (s, 6H), 1.89-2.08 (m, 5H), 2.31-2.40 (m, 3H), 2.51-2.64 (m, 2H), 2.82-2.98 (m, 1H), 3.80 (s, 2H), 3.92 (s, 2H), 4.04-4.07 (m, 1H), 4.14 (s, 2H), 4.32 (s, 1H), 5.10-5.16 (m, 1H), 6.40-6.42 (m, 2H), 6.99-7.02 (m, 1H), 7.20 (s, 1H), 7.34-7.36 (m, 1H), 7.43-7.46 (m, 2H). | 121 |

FIG. 3 Continued.

| 358 | [structure] | B | 811.32 | 1H NMR (300 MHz, CDCL3) δ 8.29 (s, 1H), 7.81 (d, J = 8.3 Hz, 1H), 7.60 (d, J = 8.6 Hz, 1H), 7.36 (d, J = 2.2 Hz, 1H), 7.22 (dd, J = 8.3, 2.3 Hz, 1H), 6.99 (d, J = 2.4 Hz, 1H), 6.83 (dd, J = 8.8, 2.4 Hz, 1H), 5.96 (d, J = 8.6 Hz, 1H), 4.99 (dd, J = 11.9, 5.5 Hz, 1H), 4.24 (dt, J = 11.9, 7.0 Hz, 1H), 4.08 (s, 1H), 3.09 (s, 9H), 2.98 – 2.77 (m, 5H), 2.40(s, 2H), 2.21-2.14 (m, 1H), 1.27 (d, J = 3.9 Hz, 12H); 7.72-7.74 (m, 2H), 7.83-7.92 (m. 2H), 11.1 (s, 1H); | 9, 63 |

FIG. 3 Continued.

| 359 | [structure] | B | 783.1 | ¹H NMR (300 MHz, DMSO-d₆) δ 11.13 (s, 1H), 8.65 (s, 1H), 8.38 (s, 1H), 8.15 (s, 1H), 7.96-7.81 (m, 3H), 7.47 (d, $J$ = 2.2 Hz, 1H), 7.38 (dd, $J$ = 8.4, 2.3 Hz, 1H), 7.26 (d, $J$ = 2.4 Hz, 1H), 7.04 (dd, $J$ = 8.8, 2.4 Hz, 1H), 5.14 (dd, $J$ = 12.9, 5.4 Hz, 1H), 4.45 (s, 1H), 4.28 (t, $J$ = 6.1 Hz, 2H), 3.98 (d, $J$ = 9.0 Hz, 1H), 3.74 (s, 3H), 2.89 (d, $J$ = 12.5 Hz, 1H), 2.60 (d, $J$ = 15.9 Hz, 4H), 2.04 (s, 4H), 1.17 (d, $J$ = 18.4 Hz, 12H), 1.05 (s, 4H); | 9, 63 |

FIG. 3 Continued.

| | | | | |
|---|---|---|---|---|
| 360 | (structure) | B | 783.1 | ¹H NMR (300 MHz, DMSO-$d_6$) δ 11.09 (s, 1H), 8.27 – 8.12 (m, 1H), 7.92 – 7.76 (m, 3H), 7.46 – 7.29 (m, 3H), 7.22 (d, $J$ = 2.4 Hz, 1H), 7.00 (dd, $J$ = 8.8, 2.4 Hz, 1H), 5.09 (dd, $J$ = 12.9, 5.3 Hz, 1H), 4.43 (s, 1H), 4.23 (t, $J$ = 6.3 Hz, 2H), 3.97 (d, $J$ = 9.1 Hz, 1H), 3.70 (t, $J$ = 4.9 Hz, 4H), 2.95 – 2.76 (m, 1H), 2.59-2.50 (s, 6H), 2.45(s,2H), 2.07 – 1.89 (m, 3H), 1.19 (s, 6H), 1.11 (s, 6H). | 9, 63 |
| 361 | (structure) | B | 854.3 | ¹H NMR (300 MHz, DMSO-$d_6$) δ 11.09 (s, 1H), 8.27 – 8.12 (m, 1H), 7.92 – 7.76 (m, 3H), 7.46 – 7.29 (m, 3H), 7.22 (d, $J$ = 2.4 Hz, 1H), 7.00 (dd, $J$ = 8.8, 2.4 Hz, 1H), 5.09 (dd, $J$ = 12.9, 5.3 Hz, 1H), 4.43 (s, 1H), 4.23 (t, $J$ = 6.3 Hz, 2H), 3.97 (d, $J$ = 9.1 Hz, 1H), 3.70 (t, $J$ = 4.9 Hz, 4H), 2.95 – 2.76 (m, | 49 |

FIG. 3 Continued.

| | | | |
|---|---|---|---|
| 362 | [structure] | B | 872.7 | H-NMR (400 MHz, DMSO-*d6*) 11.12 (s, 1H), 7.91-7.86 (m, 2H), 7.75-7.72 (d, *J* = 11.6Hz, 1H), 7.47-7.45 (d, *J*=7.6Hz, 1H), 7.34-7.32 (d, *J* = 8Hz, 1H), 7.22-7.21 (d, *J* = 4Hz, 1H), 7.01-6.91 (m, 3H), 5.14 - 5.09 (m, 1H), 4.27 (s, 1H), 4.01- 3.98 (d, *J* = 9.2Hz, 1H), 3.84-3.81 (d, *J* = 12.8Hz, 2H), 3.26 (s, 4H), 2.94-2.85 (m, 1H), 2.81-2.755 (m, 2H), 2.54-2.48 (m, 6H), 2.22-2.21 (d, *J* = 6Hz, 2H), 2.08-2.03 (m, 1H), 1.81-1.78 (m, 3H), 1.28 (s, 6H), 1.21-1.12 (m, 2H), 1.05 (s, 6H), 2.59-2.50 (s, 6H), 2.45(s,2H), 2.07 – 1.89 (m, 3H), 1.19 (s, 6H), 1.11 (s, 6H). | 49 |

| | | | |
|---|---|---|---|
| 363 |  | C 811.4 | ¹H NMR (300 MHz, CD$_3$OD): δ 7.79-7.68 (m, 2H), 7.37 (s, 1H), 7.31-7.28 (m, 1H), 7.13-7.11 (m, 1H), 6.99-6.94 (m, 1H), 5.10-5.04 (m, 1H), 4.29 (s, 1H), 4.18-4.14 (m, 2H), 4.06 (s, 1H), 3.51-3.45 (m, 4H), 2.80-2.60 (m, 7H), 2.57-2.48 (m, 2H), 2.13-2.02 (m, 1H), 1.92-1.80 (m, 2H), 1.75-1.46 (m, 4H), 1.26 (s, 6H), 1.19 (s, 6H); 9 |

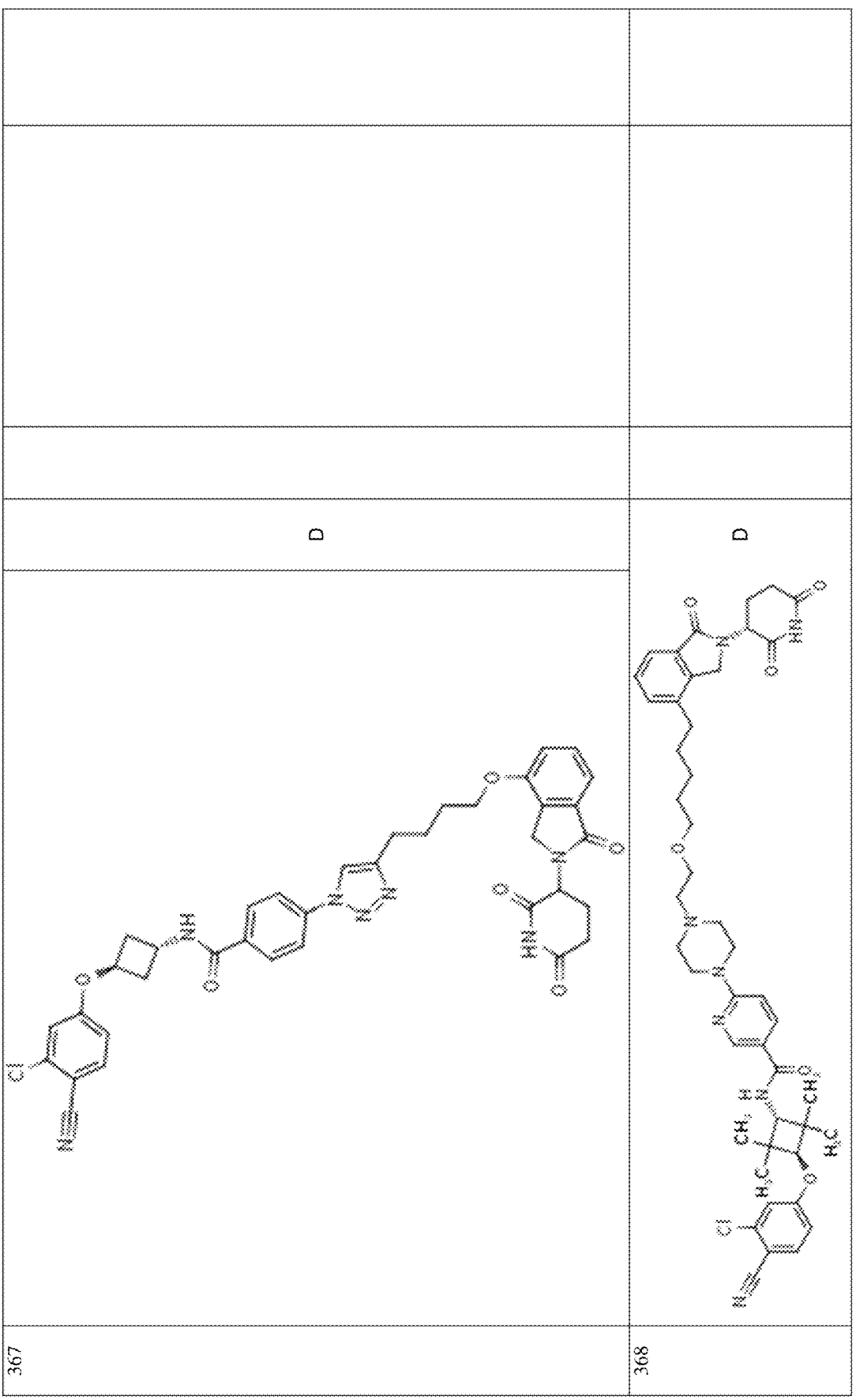

FIG. 3 Continued.

| | | | |
|---|---|---|---|
| 376 | (structure) | D | 816.2 |
| 377 | (structure) | D | 782.2 |

| | | | | |
|---|---|---|---|---|
| 379 |  | D | 729.18 | |
| 380 |  | D | 766.27 | |
| 381 |  | D | 800.3 | |
| 382 |  | D | 817.2 | |

| 383 |  | D | 848.2 | H-NMR (300 MHz, CDCl3) δ 8.04-7.95 (m, 3H), 7.84-7.77 (m, 2H), 7.60-7.55 (m, 1H), 7.34-7.33 (d, J=1.8 Hz, 1H), 7.21-7.09 (m, 3H), 4.98-4.93 (m, 1H), 4.14-4.10 (m, 2H), 3.91 (s, 2H), 3.49 (s, 2H), 2.94-2.72 (m, 3H), 2.67-2.56 (m, 5H), 2.25-2.13 (m, 2H), 1.92-1.88 (m, 2H), 1.76 (s, 2H), 1.68 (s, 6H); | 122 |

FIG. 3 Continued.

| | | | |
|---|---|---|---|
| 390 | (structure) | D | 722.4 |
| 391 | (structure) | D | 856.5 7 |

| | | | |
|---|---|---|---|
| 393 | [structure] | D | 855.5 |
| 394 | [structure] | D | 736.49 |

FIG. 4
Table 4. Exemplary Compounds

| | Compound Structure | MW | Vcap DC50 (μM) | Dmax (%) | Chemical Name | Prepared by General Scheme |
|---|---|---|---|---|---|---|
| 399 | 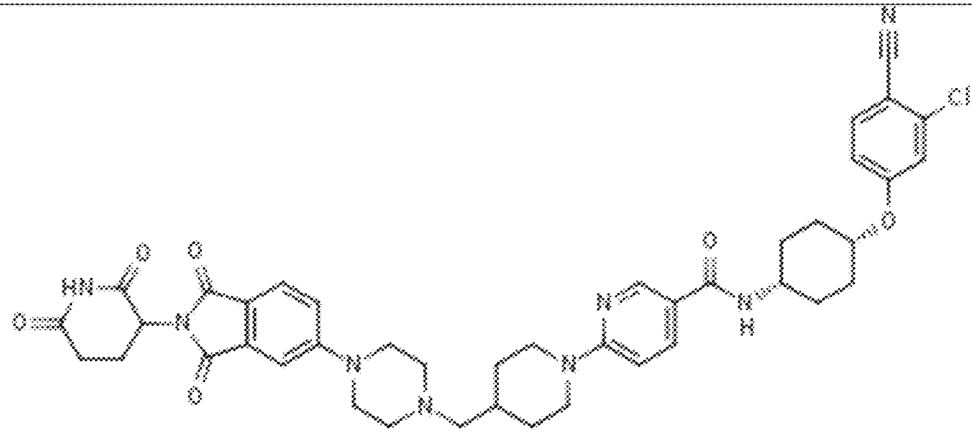 | 793.32 | 0.00235 | 60.15 | N-((1s,4s)-4-(3-chloro-4-cyanophenoxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide | 1B |
| 400 | 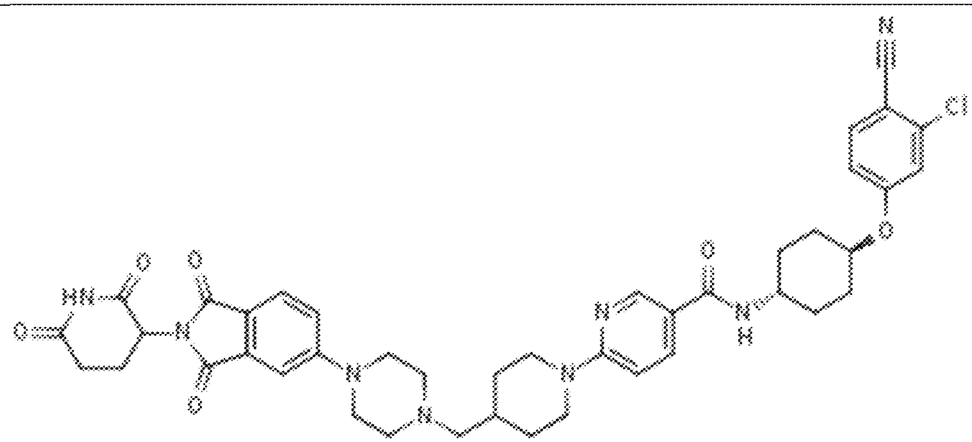 | 793.32 | 0.00066 | 78.6 | N-((1r,4r)-4-(3-chloro-4-cyanophenoxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide | 1B |

| | | | | | |
|---|---|---|---|---|---|
| 401 |  | 792.33 | 0.000625 | 81.8 | N-((1r,4r)-4-(3-chloro-4-cyanophenoxy)cyclohexyl)-4-(4-((4-(2-(2,6-dioxopiperidin-3-yl)-1,3-dioxoisoindolin-5-yl)piperazin-1-yl)methyl)piperidin-1-yl)benzamide | 2B |
| 402 |  | 792.33 | 0.0019 | 58.7 | N-((1s,4s)-4-(3-chloro-4-cyanophenoxy)cyclohexyl)-4-(4-((4-(2-(2,6-dioxopiperidin-3-yl)-1,3-dioxoisoindolin-5-yl)piperazin-1-yl)methyl)piperidin-1-yl)benzamide | 2B (using cis aminocyclobutanol) |

FIG. 4 Continued.

| | | | | | |
|---|---|---|---|---|---|
| 403 | [structure] | 794.31 | 0.00075 | 81.15 | N-((1r,4r)-4-(3-chloro-4-cyanophenoxy)cyclohexyl)-2-(4-((4-(2-(2,6-dioxopiperidin-3-yl)-1,3-dioxoisoindolin-5-yl)piperazin-1-yl)methyl)piperidin-1-yl)pyrimidine-5-carboxamide | 1B |
| 404 | [structure] | 794.31 | 0.00041 | 84.65 | N-((1r,4r)-4-(3-chloro-4-cyanophenoxy)cyclohexyl)-5-(4-((4-(2-(2,6-dioxopiperidin-3-yl)-1,3-dioxoisoindolin-5-yl)piperazin-1-yl)methyl)piperidin-1-yl)pyrazine-2-carboxamide | 1B |

FIG. 4 Continued.

| | | | | | |
|---|---|---|---|---|---|
| 405 | [structure] | 794.31 | 0.000165 | 85.3 | N-((1r,4r)-4-(3-chloro-4-cyanophenoxy)cyclohexyl)-6-(4-((4-(2-(2,6-dioxopiperidin-3-yl)-1,3-dioxoisoindolin-5-yl)piperazin-1-yl)methyl)piperidin-1-yl)pyridazine-3-carboxamide | 1B |
| 406 | [structure] | 812.3 | 0.000242 | 82.4 | N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide | 22B |

FIG. 4 Continued.

| | | | | | |
|---|---|---|---|---|---|
| 407 | [structure] | 812.3 | 0.00062 | 82.05 | N-((1r,4r)-4-(3-chloro-4-cyanophenoxy)cyclohexyl)-2-(4-((4-(2-(2,6-dioxopiperidin-3-yl)-6-fluoro-1,3-dioxoisoindolin-5-yl)piperazin-1-yl)methyl)piperidin-1-yl)pyrimidine-5-carboxamide | 1B |
| 408 | [structure] | 812.3 | 0.000285 | 84.05 | N-((1r,4r)-4-(3-chloro-4-cyanophenoxy)cyclohexyl)-5-(4-((4-(2-(2,6-dioxopiperidin-3-yl)-6-fluoro-1,3-dioxoisoindolin-5-yl)piperazin-1-yl)methyl)piperidin-1-yl)pyrazine-2-carboxamide | 22B |

FIG. 4 Continued.

| | | | | | |
|---|---|---|---|---|---|
| 409 | | 778.31 | 0.00035 | 78.35 | N-((1r,4r)-4-(3-chloro-4-cyanophenoxy)cyclohexyl)-4-(4-(2-(2,6-dioxopiperidin-3-yl)-1,3-dioxoisoindolin-5-yl)piperazin-1-yl)piperidin-1-yl)benzamide | 5B |
| 410 | | 778.31 | 0.00097 | 68.4 | N-((1r,4r)-4-(3-chloro-4-cyanophenoxy)cyclohexyl)-4-(4-(1-(2-(2,6-dioxopiperidin-3-yl)-1,3-dioxoisoindolin-5-yl)piperidin-4-yl)piperazin-1-yl)benzamide | 8B |

FIG. 4 Continued.

| | | | | | |
|---|---|---|---|---|---|
| 411 | (structure) | 780.28 | 0.000195 | 78.25 | N-((1r,4r)-4-(3-chloro-4-cyanophenoxy)cyclohexyl)-6-(4-(1-(2-(2,6-dioxopiperidin-3-yl)-1,3-dioxoisoindolin-5-yl)piperidin-4-yl)piperazin-1-yl)pyridazine-3-carboxamide | 7B |
| 412 | (structure) | 780.28 | 0.000355 | 71.05 | N-((1r,4r)-4-(3-chloro-4-cyanophenoxy)cyclohexyl)-2-(4-(1-(2-(2,6-dioxopiperidin-3-yl)-1,3-dioxoisoindolin-5-yl)piperidin-4-yl)piperazin-1-yl)pyrimidine-5-carboxamide | 6B |

| 413 |  | 780.28 | 0.000335 | 62.85 | N-((1r,4r)-4-(3-chloro-4-cyanophenoxy)cyclohexyl)-6-(4-(2-(2,6-dioxopiperidin-3-yl)-1,3-dioxoisoindolin-5-yl)piperazin-1-yl)piperidin-1-yl)pyridazine-3-carboxamide | 5B |
| 414 |  | 780.28 | 0.00074 | 59.85 | N-((1r,4S)-4-(3-chloro-4-cyanophenoxy)cyclohexyl)-2-((3S)-3-((4-(2-(2,6-dioxopiperidin-3-yl)-1,3-dioxoisoindolin-5-yl)piperazin-1-yl)methyl)pyrrolidin-1-yl)pyrimidine-5-carboxamide | 4B |

FIG. 4 Continued.

| | | | | | |
|---|---|---|---|---|---|
| 415 | 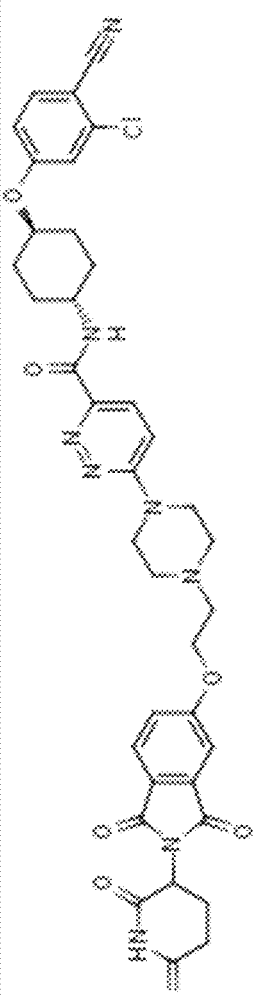 | 741.2 | 0.0004 | 62.1 | N-((1r,4r)-4-(3-chloro-4-cyanophenoxy)cyclohexyl)-6-(4-(2-((2-(2,6-dioxopiperidin-3-yl)-1,3-dioxoisoindolin-5-yl)oxy)ethyl)piperazin-1-yl)pyridazine-3-carboxamide | 3B |
| 416 | 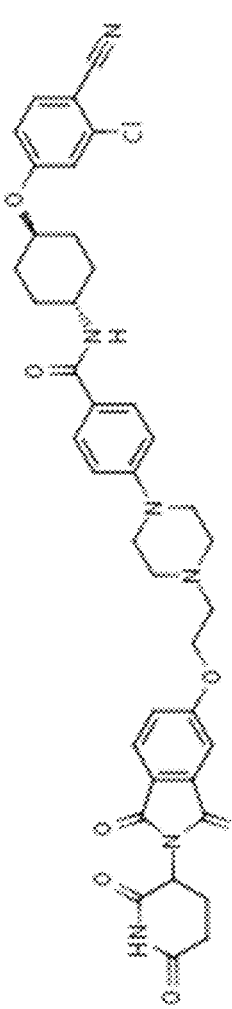 | 739.23 | 0.000305 | 44.35 | N-((1r,4r)-4-(3-chloro-4-cyanophenoxy)cyclohexyl)-4-(2-((2-(2,6-dioxopiperidin-3-yl)-1,3-dioxoisoindolin-5-yl)oxy)ethyl)piperazin-1-yl)benzamide | 3B |
| 417 | 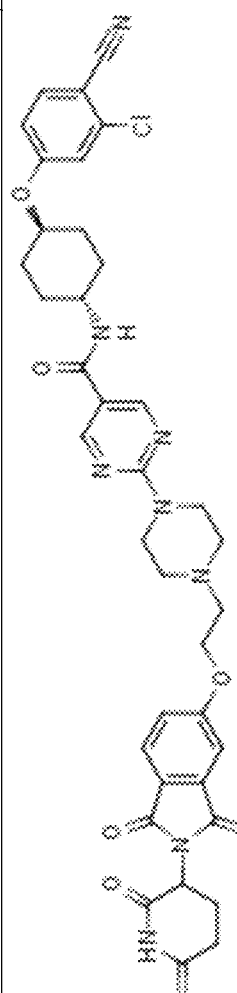 | 741.2 | 0.00062 | 55.62 | N-((1r,4r)-4-(3-chloro-4-cyanophenoxy)cyclohexyl)-2-(4-(2-((2-(2,6-dioxopiperidin-3-yl)-1,3-dioxoisoindolin-5-yl)oxy)ethyl)piperazin-1-yl)pyrimidine-5-carboxamide | 3B |

| 418 | 755.23 | 0.00025 | 68.4 | N-((1r,4r)-4-(3-chloro-4-cyanophenoxy)cyclohexyl)-2-(4-(3-((2-(2,6-dioxopiperidin-3-yl)-1,3-dioxoisoindolin-5-yl)oxy)propyl)piperazin-1-yl)pyrimidine-5-carboxamide | 3B |

FIG. 4 Continued.

| | | | | | |
|---|---|---|---|---|---|
| 419 | | 806.36 | 0.0025 | 38.6 | N-((1r,4r)-4-(3-chloro-4-cyanophenoxy)-4-methylcyclohexyl)-4-(4-((4-(2-(2,6-dioxopiperidin-3-yl)-1,3-dioxoisoindolin-5-yl)piperazin-1-yl)methyl)piperidin-1-yl)benzamide | 1B, 24B |
| 420 | | 741.2 | 0.00017 | 75.4 | N-((1r,4r)-4-(3-chloro-4-cyanophenoxy)cyclohexyl)-5-(4-(2-((2-(2,6-dioxopiperidin-3-yl)-1,3-dioxoisoindolin-5-yl)oxy)ethyl)piperazin-1-yl)picolinamide | 14B |

| # | Structure | MW | IC50 | Name | Class |
|---|---|---|---|---|---|
| 421 |  | 793.32 | 0.000575 | yl)pyrazine-2-carboxamide | |
| | | | | N-((1r,4r)-4-(3-chloro-4-cyanophenoxy)cyclohexyl)-5-(4-((4-(2-(2,6-dioxopiperidin-3-yl)-1,3-dioxoisoindolin-5-yl)piperazin-1-yl)methyl)piperidin-1-yl)picolinamide | 1B |
| 422 |  | 776.19 | | N-((1r,4r)-4-(3-chloro-4-cyanophenoxy)cyclohexyl)-6-(4-(2-((2-(2,6-dioxopiperidin-3-yl)-6-fluoro-1,3-dioxoisoindolin-5-yl)oxy)ethyl)piperazin-1-yl)-5-fluoronicotinamide | 23B |

FIG. 4 Continued.

| | | | | |
|---|---|---|---|---|
| 423 | | 773.22 | N-((1r,4r)-4-(3-chloro-4-cyanophenoxy)cyclohexyl)-5-(4-(3-((2-(2,6-dioxopiperidin-3-yl)-6-fluoro-1,3-dioxoisoindolin-5-yl)oxy)propyl)piperazin-1-yl)pyrazine-2-carboxamide | 3B |
| 424 | | 808.34 | N-((1r,4r)-4-(3-chloro-4-cyanophenoxy)cyclohexyl)-2-(4-(2-(4-(2-(2,6-dioxopiperidin-3-yl)-1,3-dioxoisoindolin-5-yl)piperazin-1-yl)ethyl)piperidin-1-yl)pyrimidine-5-carboxamide | 21B |

| 425 |  | 806.36 | | N-((1r,4r)-4-(3-chloro-4-cyanophenoxy)cyclohexyl)-4-(4-(2-(4-(2-(2,6-dioxopiperidin-3-yl)-1,3-dioxoisoindolin-5-yl)piperazin-1-yl)ethyl)piperidin-1-yl)benzamide | 21B |

FIG. 4 Continued.

| 426 | [structure] | 755.23 | 0.000295 | 79.6 | N-((1r,4r)-4-(3-chloro-4-cyanophenoxy)cyclohexyl)-5-(4-(3-((2-(2,6-dioxopiperidin-3-yl)-1,3-dioxoisoindolin-5-yl)oxy)propyl)piperazin-1-yl)pyrazine-2-carboxamide | 3B |

FIG. 4 Continued.

| 427 | [structure] | 808.34 | 0.00014 | 81.1 | N-((1r,4r)-4-(3-chloro-4-cyanophenoxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)pyridazine-3-carboxamide | 21B |

Table 5. Exemplary Compounds

| Ex. No. | Compound Structure | MW | Vcap DC50 (μM) | Dmax (%) | |
|---|---|---|---|---|---|
| 428 | 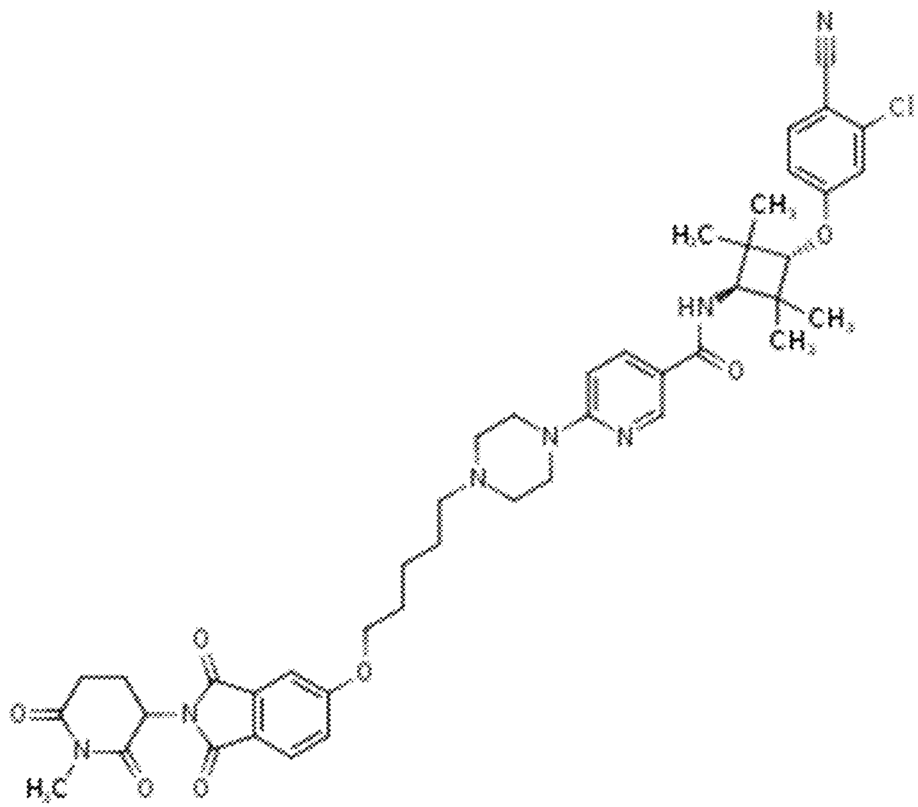 | 824.38 | >1 | 2.1 | N-((1r,3r)-3-(3-chloro-4-cyanophenoxy)-2,2,4,4-tetramethylcyclobutyl)-6-(4-(5-((2-(1-methyl-2,6-dioxopiperidin-3-yl)-1,3-dioxoisoindolin-5-yl)oxy)pentyl)piperazin-1-yl)nicotinamide |

| 429 |  | 812.37 | >1 | 1.3 | N-((1r,3r)-3-(3-chloro-4-cyanophenoxy)-2,2,4,4-tetramethylcyclobutyl)-1-(1-(5-((2-(1-methyl-2,6-dioxopiperidin-3-yl)-1,3-dioxoisoindolin-5-yl)oxy)pentyl)piperidin-4-yl)-1H-pyrazole-4-carboxamide |

| 430 |  | 812.37 | >1 | 8.5 | N-((1r,3r)-3-(3-chloro-4-cyanophenoxy)-2,2,4,4-tetramethylcyclobutyl)-1-(1-(5-((2-(1-methyl-2,6-dioxopiperidin-3-yl)-1,3-dioxoisoindolin-5-yl)oxy)pentyl)piperidin-4-yl)-1H-pyrazole-3-carboxamide |

| 431 |  | 784.31 | >1 | 12.5 | N-((1r,3r)-3-(3-chloro-4-cyanophenoxy)-2,2,4,4-tetramethylcyclobutyl)-1-(1-(4-((2-(1-methyl-2,6-dioxopiperidin-3-yl)-1,3-dioxoisoindolin-5-yl)oxy)butyl)pyrrolidin-3-yl)-1H-pyrazole-4-carboxamide |

| | | | | |
|---|---|---|---|---|
| 432 |  | 798.34 | >1 | 10.1 | N-((1r,3r)-3-(3-chloro-4-cyanophenoxy)-2,2,4,4-tetramethylcyclobutyl)-1-(5-((2-(1-methyl-2,6-dioxopiperidin-3-yl)-1,3-dioxoisoindolin-5-yl)oxy)pentyl)pyrrolidin-3-yl)-1H-pyrazole-4-carboxamide |
| 433 |  | 813.35 | >1 | 15.5 | N-((1r,3r)-3-(3-chloro-4-cyanophenoxy)-2,2,4,4-tetramethylcyclobutyl)-1-(2-(3-(4-(2-(1-methyl-2,6-dioxopiperidin-3-yl)-1,3-dioxoisoindolin-5-yl)piperazin-1-yl)propoxy)ethyl)-1H-pyrazole-4-carboxamide |

| 434 | | 824.38 | >1 | -1 | N-((1r,3r)-3-(3-chloro-4-cyanophenoxy)-2,2,4,4-tetramethylcyclobutyl)-5-(4-(5-((2-(1-methyl-2,6-dioxopiperidin-3-yl)-1,3-dioxoisoindolin-5-yl)oxy)pentyl)piperazin-1-yl)picolinamide |

| 435 | 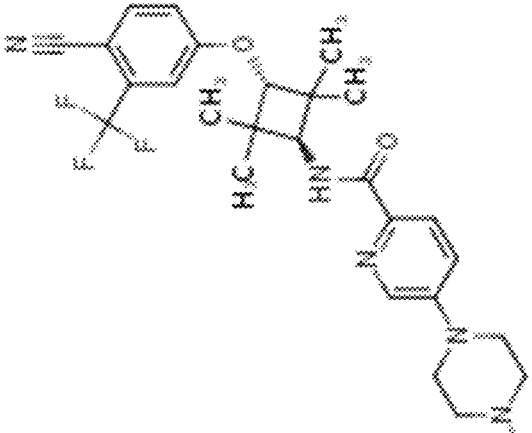 | 857.93 | >1 | 0 | N-((1r,3r)-3-(4-cyano-3-(trifluoromethyl)phenoxy)-2,2,4,4-tetramethylcyclobutyl)-5-(4-(5-((2-(1-methyl-2,6-dioxopiperidin-3-yl)-1,3-dioxoisoindolin-5-yl)oxy)pentyl)piperazin-1-yl)picolinamide |
|---|---|---|---|---|---|
| 436 | 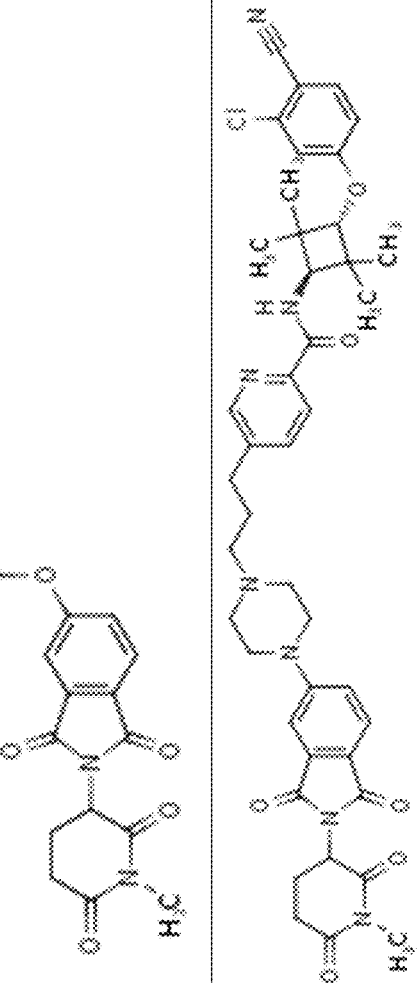 | 780.32 | >1 | 15.9 | N-((1r,3r)-3-(3-chloro-4-cyanophenoxy)-2,2,4,4-tetramethylcyclobutyl)-5-(3-(4-(2-(1-methyl-2,6-dioxopiperidin-3-yl)-1,3-dioxoisoindolin-5-yl)piperazin-1-yl)propyl)picolinamide |

FIG. 5 Continued.

| # | Structure | MW | Activity | Name |
|---|---|---|---|---|
| 437 | | 619.72 | >1 | 6-(4-(4-((2-(1-butyl-2,6-dioxopiperidin-3-yl)-1,3-dioxoisoindolin-5-yl)oxy)butyl)piperazin-1-yl)-N,N-dimethylpyridazine-3-carboxamide |
| 438 | | 811.34 | >1 | N-((1r,3r)-3-(3-chloro-4-cyanophenoxy)-2,2,4,4-tetramethylcyclobutyl)-2-(4-(4-((2-(1-methyl-2,6-dioxopiperidin-3-yl)-1,3-dioxoisoindolin-5-yl)oxy)butyl)piperazin-1-yl)pyrimidine-5-carboxamide |
| 439 | | 834.42 | 0.508 ++ | N-((1r,3r)-3-(3-chloro-4-cyanophenoxy)-2,2,4,4-tetramethylcyclobutyl)-4-(4-((4-(2-(1-methyl-2,6-dioxopiperidin-3-yl)-1,3-dioxoisoindolin-5-yl)piperazin-1-yl)methyl)piperidin-1-yl)benzamide |

FIG. 5 Continued.

| # | Structure | MW | Value | IC50 |  Name |
|---|---|---|---|---|---|
| 440 | 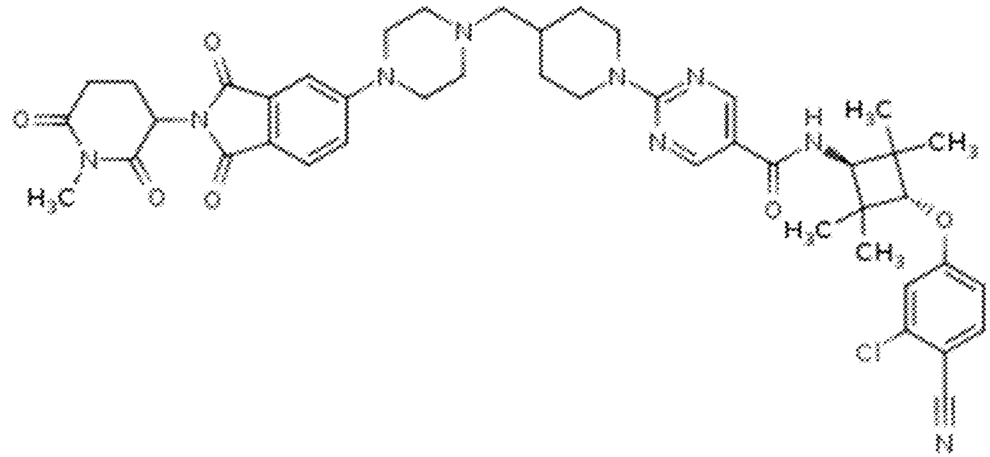 | 836.39 | 0.667 ++ | 31.67 | N-((1r,3r)-3-(3-chloro-4-cyanophenoxy)-2,2,4,4-tetramethylcyclobutyl)-2-(4-((4-(2-(1-methyl-2,6-dioxopiperidin-3-yl)-1,3-dioxoisoindolin-5-yl)piperazin-1-yl)methyl)piperidin-1-yl)pyrimidine-5-carboxamide |
| 441 | 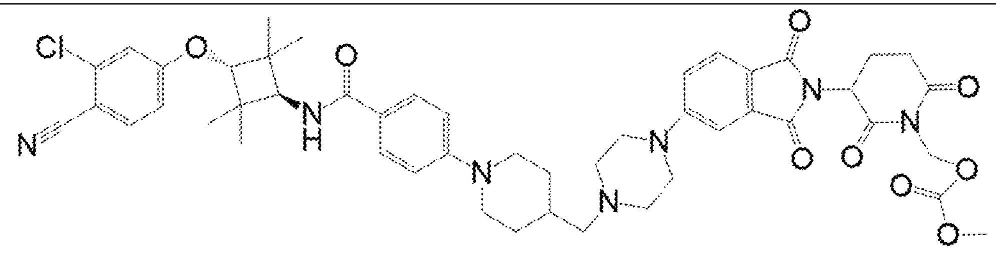 | 908.45 | 0.000575 | 78.8 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl methyl carbonate |
| 442 | 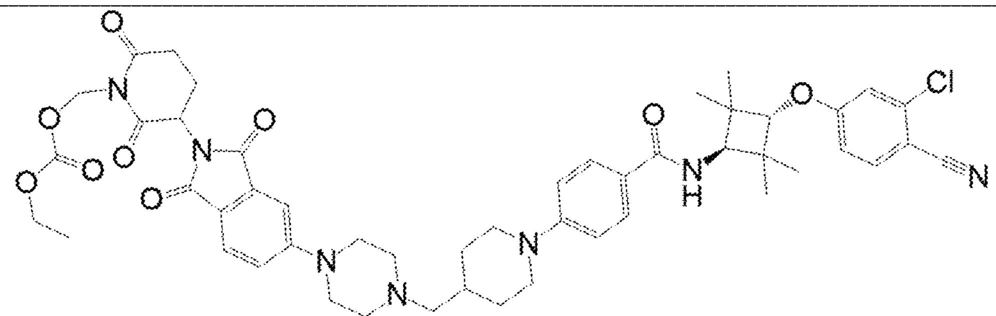 | 922.48 | 0.00081 | 77.6 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl ethyl carbonate |

| | | | | |
|---|---|---|---|---|
| 443 |  | 936.5 | 0.000755 | 71.5 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl isopropyl carbonate |
| 444 |  | 978.54 | 0.000635 | 79.5 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (tetrahydro-2H-pyran-4-yl) carbonate |

FIG. 5 Continued.

| | | | | |
|---|---|---|---|---|
| 445 | 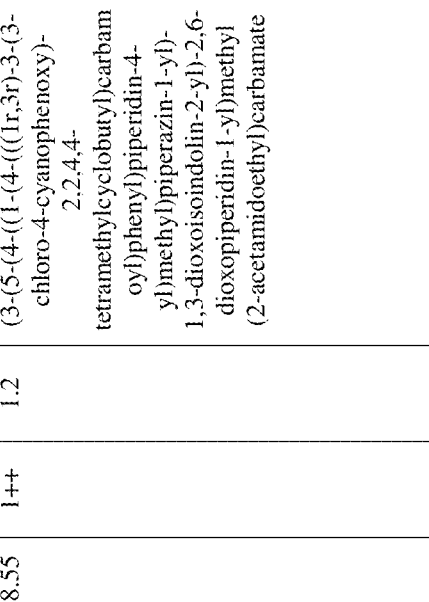 | 978.55 | 1++ | 1.2 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-acetamidoethyl)carbamate |
| 446 | 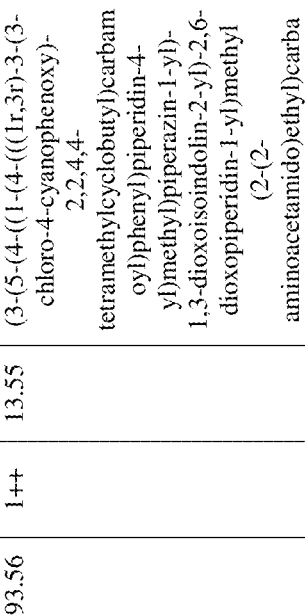 | 993.56 | 1++ | 13.55 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-(2-aminoacetamido)ethyl)carbamate |

| 447 | 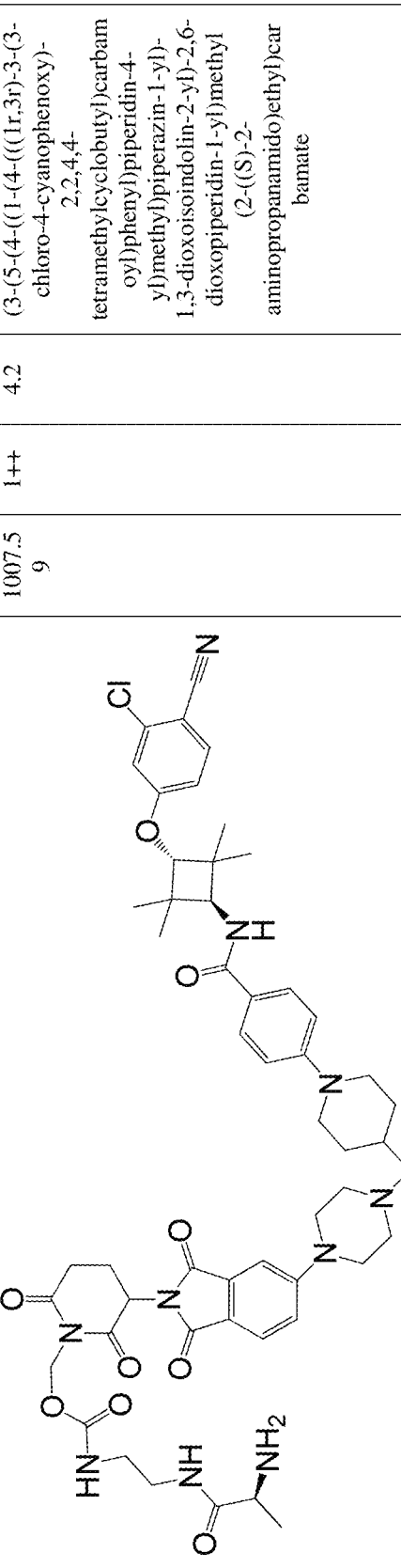 | 1007.59 | 1++ | 4.2 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-((S)-2-aminopropanamido)ethyl)carbamate |
| 448 | 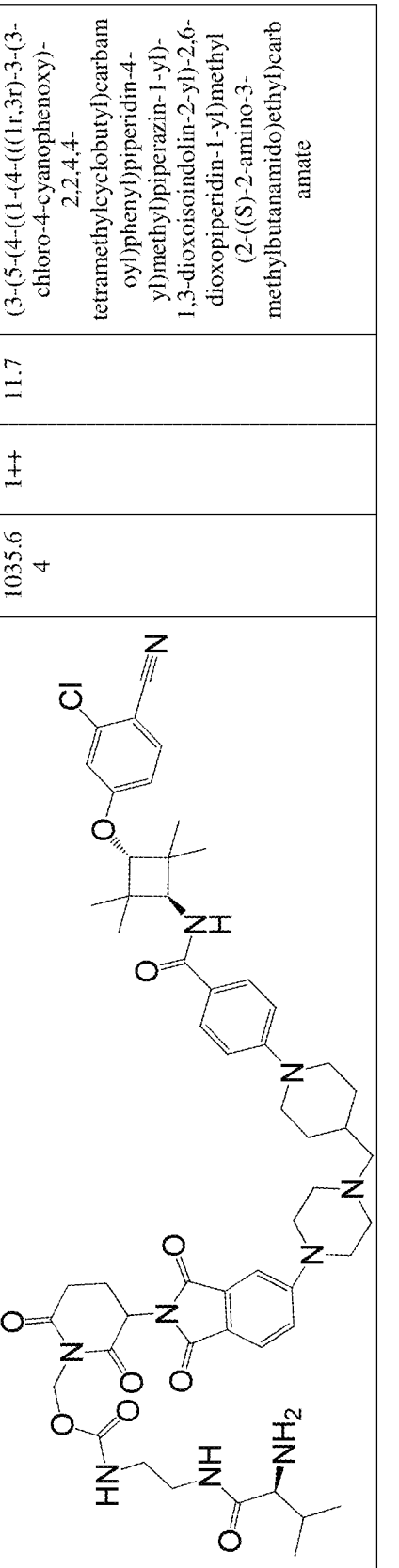 | 1035.64 | 1++ | 11.7 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-((S)-2-amino-3-methylbutanamido)ethyl)carbamate |

| | | | | |
|---|---|---|---|---|
| 449 | [structure] | 1134.77 | 0.017 | 21.7 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-((S)-2-((S)-2-amino-3-methylbutanamido)-3-methylbutanamido)ethyl)carbamate |
| 450 | [structure] | 1084.66 | 0.00034 | 77.4 | (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2,5,8,11-tetraoxatridecan-13-yl) carbonate |
| 451 | [structure] | 798.33 | 1++ | 13.4 | 2-chloro-4-(3-(3-fluoro-4-(5-(4-(2-(1-methyl-2,6-dioxopiperidin-3-yl)-1,3-dioxoisoindolin-5-yl)piperazin-1-yl)pentyl)phenyl)-4,4-dimethyl-5-oxo-2-thioxoimidazolidin-1-yl)benzonitrile |

| 452 | 810.34 | 1++ | 17.1 | 2-chloro-4-(5-(3-fluoro-4-(5-(4-(2-(1-methyl-2,6-dioxopiperidin-3-yl)-1,3-dioxoisoindolin-5-yl)piperazin-1-yl)pentyl)phenyl)-8-oxo-6-thioxo-5,7-diazaspiro[3.4]octan-7-yl)benzonitrile |

Table 6. Exemplary Compounds

| Ex. No. | Compound Structure | Vcap DC50 | Dmax | m/z+ | 1H NMR |
|---|---|---|---|---|---|
| 528 | 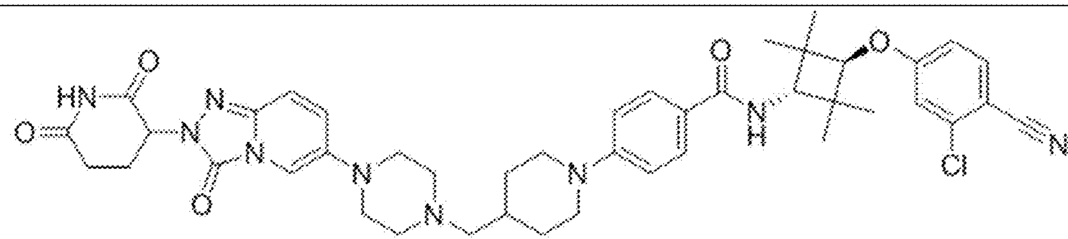 | A | A | | |

FIG. 7
Table 7. Exemplary Compounds

| Ex. # | Chemical Structure | m/z observed | DC50 category | 1H NMR | General Scheme |
|---|---|---|---|---|---|
| 529 | 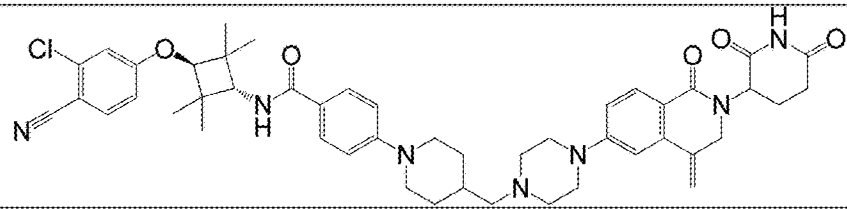 | 832.610 | A | | |
| 530 | 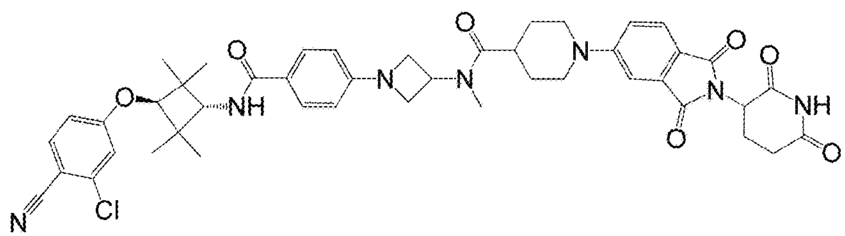 | 834.2 | A | ¹H NMR (300 MHz, d6-DMSO) δ 1.13 (s, 6H), 1.22 (s, 6H), 1.59-1.74 (m, 4H), 1.90-2.10 (m, 1H), 2.61-2.69 (m, 2H), 2.89-2.94 (m, 2H), 3.08-3.15 (m, 5H), 3.87-3.90 (m, 1H), 4.04-4.12 (m, 5H), 4.15-4.21 (m, 1H), 4.32 (s, 1H), 5.06-5.10 (m, 1H), 5.15-5.30 (m, 1H), 6.47-6.49 (m, 2H), 6.99-7.02 (m, 1H), 7.20-7.21 (m, 1H), 7.33 (s, 1H), 7.45-7.48 (m, 1H), 7.65-7.68 (m, 1H), 7.74-7.77 (m, 2H), 7.89-7.92 (m, 1H), 11.07 (s, 1H) | 18 |
| 531 | 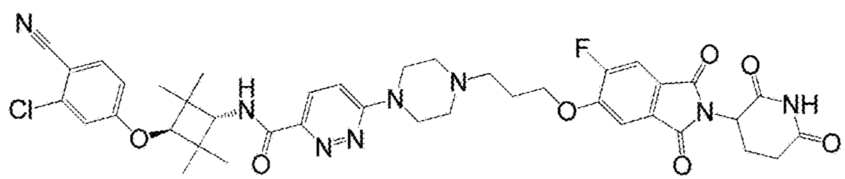 | 801.500 | B | ¹H NMR (300 MHz, DMSO-d₆) δ 11.15 (s, 1H), 8.29 (d, J = 9.4 Hz, 1H), 7.92 (dd, J = 9.0, 4.3 Hz, 3H), 7.77 (d, J = 7.1 Hz, 1H), 7.49 (s, 1H), 7.26 (d, J = 2.4 Hz, 1H), 7.05 (dd, J = 8.6, 2.5 Hz, 1H), 5.15 (dd, J = 12.9, 5.4 Hz, 1H), 4.48 -4.41 (s, 3H), 4.03 (d, J = 9.2 Hz, 1H), 3.35 (s, 9H), | 9 |

FIG. 7 Continued.

| | | | | |
|---|---|---|---|---|
| 532 | [structure] | 801.500 | B | ¹H NMR (300 MHz, DMSO-$d_6$) δ 11.14 (s, 1H), 8.64 (d, $J$ = 1.2 Hz, 1H), 8.36 (s, 1H), 7.96 – 7.80 (m, 3H), 7.76 (d, $J$ = 7.1 Hz, 1H), 7.70 – 7.51 (m, 1H), 7.26 (d, $J$ = 2.4 Hz, 1H), 7.04 (dd, $J$ = 8.8, 2.5 Hz, 1H), 5.14 (dd, $J$ = 12.9, 5.3 Hz, 1H), 4.48 – 4.33 (m, 4H), 3.97 (d, $J$ = 9.0 Hz, 1H), 3.74 (s, 4H), 2.98 – 2.81 (m, 1H), 2.68 – 2.52 (m, 6H), 2.13 – 2.01 (m, 1H), 2.03 (s, 3H), 1.17 (d, $J$ = 18.6 Hz, 12H). 2.94 – 2.53 (m, 4H), 2.35-2.08 (s, 3H), 1.24 (s, 6H), 1.16 (s, 6H). | 9 |
| 533 | [structure] | 773.470 | A | ¹H NMR (400 MHz, DMSO-$d_6$): δ 11.12 (s, 1H), 8.76 (s, 2H), 8.15 (d, $J$ = 7.2 Hz, 1H), 7.86 (d, $J$ = 8.8 Hz, 2H), 7.74 (d, $J$ = 7.2 Hz, 1H), 7.37 (d, $J$ = 2 Hz, 1H), 7.14-7.12 (m, 1H), 5.12 (m, 1H), 4.55 (s, 1H), 4.37-4.34 (m, 2H), 3.82 (s, 6H), 2.94-2.85 (m, 1H), 2.64-2.61(m, 2H), 2.56-2.44 (m, 5H), 2.11-1.91 (m, 7H), 1.57-1.44 (m, 4H) | 3 B |
| 534 | [structure] | 826.540 | A | ¹H NMR (300 MHz, DMSO-$d_6$) 11.12 (s, 1H), 8.74 (s, 2H), 8.12-8.10 (d, $J$ = 7.5Hz, 1H), 7.88-7.85 (d, $J$ = 8.7Hz, 1H), 7.75-7.71 (d, $J$ = 11.4Hz, 1H), 7.47-7.39 (m, 2H), 7.16-7.13 (m, 1H), 5.08-5.04 (m, 1H), 4.74-4.55 (m, 3H), 3.86-3.80 (m, 1H), 3.55-3.51 (m, 6H), 2.96-2.92 (m, 2H), 2.59-2.46 (m, 7H), 2.05-1.80 (m, 5H), 1.79-1.61 (m, 4H), 1.56-1.42 (m, 5H), 1.21-1.14 (m, 2H); | 9 B |

| | | | | |
|---|---|---|---|---|
| 535 |  | 957.650 | C | ¹H-NMR (300 MHz, CD₃OD) δ 8.6 (s, 1H), 8.08- 8.01 (m, 1H), 7.76-7.69 (m, 1H), 7.59- 7.36 (m, 2H), 7.14 (s, 1H), 7.03- 6.96 (m, 1H), 6.35 (s, 1H), 5.12 - 5.04 (m, 1H), 4.60 (s, 1H), 4.50- 4.39 (m, 4H), 4.30- 4.27 (m, 1H), 4.18- 4.10 (m, 1H), 3.96-3.90 (m, 2H), 3.73- 3.52 (m, 4H), 3.09- 2.66 (m. 10H), 2.37- 2.31(m, 2H), 2.15- 1.88 (m, 5H), 1.29 - 1.20 (m. 18H) |
| 536 |  | 751.500 | A | 1H NMR (300 MHz, DMSO-d6) 11.05 (s, 1H), 8.21-8.18 (m, 1H), 7.85-7.82 (m, 1H), 7.76-7.73 (m, 2H), 7.63-7.60 (m, 1H), 7.37-7.30 (m, 4H), 7.22-7.10 (m, 2H), 5.07-5.01 (m, 1H), 4.52-4.45 (m, 1H), 3.80-3.70 (m, 1H), 3.47-3.43 (m, 2H), 3.22-3.16 (m, 2H), 3.00-2.90 (m, 2H), 2.85-2.52 (m, 7H), 2.25-1.87 (m, 5H), 1.54-1.45 (m, 4H), 1.21-0.97 (m, 6H). |
| 537 |  | 811.600 | A | ¹H NMR (300 MHz, DMSO-$d_6$): δ 11.05 (s, 1H), 8.03 (d, J = 8.8 Hz, 1H), 7.87-7.59 (m, 4H), 7.45 (d, J = 9.1 Hz, 1H), 7.36-7.16 (m, 3H), 6.92 (d, J = 8.9 Hz, 2H), 5.06-5.03 (m, 1H), 4.33 (s, 1H), 4.03 (d, J = 9.1 Hz, 1H), 3.83 (d, J = 12.6 Hz, 2H), 3.41 (s, 4H), 2.76 (s, 3H), 2.90-2.72 (m, 3H), 2.70-2.65 (m, 2H), 2.28-2.20 (s, 2H), 2.10-1.90 (m, 1H), 1.86-1.70 (m, 3H), 1.19 (s, 9H), 1.08 (s, 6H |

FIG. 7 Continued.

| | | | | |
|---|---|---|---|---|
| 538 | (structure) | 800.620 | A | ¹H NMR (300 MHz, DMSO-d₆): δ 11.06 (s, 1H), 7.75-7.57 (m, 5H), 7.46 (d, J = 9.2 Hz, 1H), 7.36-7.15 (m, 2H), 6.93 (d, J = 8.6 Hz, 2H), 6.80 (d, J = 8.8 Hz, 1H), 5.04 (dd, J = 12.7, 5.3 Hz, 1H), 4.22 (s, 1H), 4.04 (d, J = 9.1 Hz, 1H), 3.83 (d, J = 12.5 Hz, 2H), 3.41 (s, 4H), 2.81 (dt, J = 23.9, 12.5 Hz, 3H), 2.55 (d, J = 17.4 Hz, 2H), 2.47 (p, J = 1.8 Hz, 6H), 2.22 (s, 5H), 1.98 (d, J = 11.9 Hz, 1H), 1.78 (d, J = 12.0 Hz, 3H), 1.20 (s, 6H), 1.10 (s, 6H). | 49 |
| 539 | (structure) | 811.600 | D | ¹H NMR (300 MHz, DMSO-d₆): δ 11.08 (s, 1H), 8.43 (d, J = 2.1 Hz, 1H), 8.13 (dd, J = 8.9, 2.2 Hz, 1H), 7.75 (d, J = 8.6 Hz, 3H), 7.70 (d, J = 8.5 Hz, 1H), 7.52 (d, J = 9.0 Hz, 1H), 7.36 (s, 1H), 7.28 (d, J = 7.9 Hz, 1H), 7.17 (d, J = 9.0 Hz, 1H), 6.98 (d, J = 8.7 Hz, 2H), 5.09 (dd, J = 12.6, 5.4 Hz, 1H), 4.45 (s, 1H), 4.11 (d, J = 9.0 Hz, 1H), 3.88 (d, J = 12.3 Hz, 2H), 3.46 (brs, 4H), 2.95-2.75 (m, 3H), 2.66-2.46 (m, 8H), 2.23 (d, J = 6.4 Hz, 2H), 2.02 (brs, 1H), 1.83 (d, J = 12.1 Hz, 3H), 1.26 (s, 6H), 1.17 (s, 6H). | 49 |
| 540 | (structure) | 814.640 | D | ¹H NMR (400 MHz, DMSO-d₆): δ 11.10 (s, 1H), 7.71 (dd, J = 11.8, 8.6 Hz, 3H), 7.6-7.52 (m, 3H), 7.35 (d, J = 2.1 Hz, 1H), 7.27 (d, J = 8.9 Hz, 1H), 6.96 (d, J = 8.6 Hz, 2H), 5.09 (dd, J = 12.9, 5.4 Hz, 1H), 4.33 (s, 1H), 3.99 (d, J = 9.9 Hz, 1H), 3.86 (d, J = 12.6 Hz, 2H), 3.44 (d, J = 5.8 Hz, 4H), 2.95-2.75 (m, 3H), 2.67- | 49 |

FIG. 7 Continued.

| | | | | |
|---|---|---|---|---|
| 541 | [structure] | 816.620 | A | 2.53 (m, 1H), 2.50 (s, 5H), 2.32 (s, 6H), 2.20 (d, J = 6.6 Hz, 2H), 2.10-2.00 (m, 1H), 1.81 (d, J = 12.3 Hz, 3H), 1.35 (s, 6H), 1.20 (q, J = 12.3, 10.9 Hz, 2H), 1.06 (s, 6H) | 49 |
| | | | | $^1$H NMR (300 MHz, DMSO-$d_6$): δ 11.07 (s, 1H), 7.77-7.58 (m, 4H), 7.48 (d, J = 9.1 Hz, 1H), 7.33 (s, 1H), 7.24 (d, J = 8.7 Hz, 1H), 6.94 (d, J = 8.7 Hz, 2H), 6.62 (d, J = 2.1 Hz, 1H), 6.52 (d, J = 8.7 Hz, 1H), 5.05 (dd, J = 12.6, 5.3 Hz, 1H), 4.25 (s, 1H), 4.03 (d, J = 9.2 Hz, 1H), 3.89 (s, 5H), 3.43 (s, 4H), 2.77 (q, J = 13.8, 11.8 Hz, 3H), 2.53 (s, 5H), 2.19 (d, J = 6.4 Hz, 2H), 2.01 (s, 1H), 1.79 (d, J = 12.2 Hz, 3H), 1.16 (d, J = 23.6 Hz, 15H) | |
| 542 | [structure] | 817.620 | A | $^1$H NMR (300 MHz, DMSO-$d_6$): δ 11.13 (s, 1H), 8.60 (d, J = 1.2 Hz, 1H), 8.27 (s, 1H), 8.09 (d, J = 8.4 Hz, 1H), 7.85 (d, J = 8.0 Hz, 1H), 7.67 (d, J = 8.6 Hz, 1H), 7.27 (d, J = 8.3 Hz, 2H), 7.05 (d, J = 2.3 Hz, 1H), 7.00-6.90 (m, 1H), 5.13 (dd, J = 12.9, 5.4 Hz, 1H), 4.91-4.85 (m, 1H), 4.57-4.40 (m, 3H), 3.84-3.73 (m, 1H), 3.68 (t, J = 8.1 Hz, 1H), 3.00-2.94 (m, 4H), 2.70-2.61 (m, 1H), 2.60-2.30 (m, 5H), 2.29-2.10 (m, 4H), 2.08-2.01 (m, 3H), 2.00-1.81 (m, 12.9 Hz, | 72 |

| | | | | |
|---|---|---|---|---|
| 543 |  | 755.440 | B | 4H), 1.76-1.45 (m, 6H), 1.07 (d, J = 12.4 Hz, 2H), 0.94 (d, J = 6.5 Hz, 6H) |
| | | | | 11 B |
| | | | | H-NMR (300 MHz, DMSO-d6) δ 11.11 (s, 1H), 7.97 (d, J=7.5 Hz, 1H), 7.85-7.70 (m, 6H), 7.37 (d, J=2.4 Hz, 1H), 7.14-7.10 (m, 1H), 6.92 (d, J=8.7 Hz, 2H), 5.15-5.09 (m, 1H), 4.51 (s, 1H), 3.78 (s, 1H), 3.38-3.36 (m, 2H), 3.22 (s, 4H), 2.87-2.57 (m, 9H), 2.10-2.00 (m, 3H), 1.88-1.86 (m, 2H), 1.53-1.45 (m, 4H) |
| 544 |  | 829.540 | B | 62 |
| | | | | 1H NMR (300 MHz, CDCL3) δ 8.09 (s, 1H), 7.65 – 7.48 (m, 3H), 6.99 (d, J = 2.4 Hz, 1H), 6.83 (dd, J = 8.7, 2.4 Hz, 1H), 5.71 (d, J = 8.5 Hz, 1H), 4.98 (dd, J = 12.2, 5.3 Hz, 1H), 4.31 (t, J = 6.3 Hz, 2H), 4.20 (d, J = 8.5 Hz, 1H), 4.05 (s, 1H), 3.92 (s, 4H), 3.01 – 2.69 (m, 3H), 2.63 (s, 2H), 2.55 (s, 4H), 2.39 (s, 6H), 2.19 (d, J = 14.7 Hz, 4H), 1.26 (s, 12H) |
| 545 |  | 886.590 | B | 63 |
| | | | | 1H NMR (300 MHz, CDCL3): δ 8.05 (s, 1H), 7.60 (d, J = 8.7 Hz, 1H), 7.23 (d, J = 6.0 Hz, 1H), 6.99 (d, J = 2.4 Hz, 1H), 6.83 (dd, J = 8.7, 2.4 Hz, 1H), 5.71 (d, J = 8.6 Hz, 1H), 5.02 – 4.84 (m, 3H), 4.20 (d, J = 8.4 Hz, 1H), 4.05 (s, 1H), 3.39 (s, 3H), 3.00 – 2.73 (m, 5H), 2.64 (s, 4H), 2.38 (s, 5H), 2.31 (s, 2H), 2.23 – 2.12 (m, 1H), 1.89 (d, J = 13.3 Hz, 3H), 1.26 (s, 15H), 1.05 - 0.87 (m, 1H); |

| | | | | |
|---|---|---|---|---|
| 546 |  | 789.530 | B | ¹H NMR (300 MHz, DMSO-d6): δ 11.86 (d, J = 15.5 Hz, 1H), 11.09 (s, 1H), 7.89 (d, J = 8.8 Hz, 1H), 7.70 (d, J = 8.5 Hz, 1H), 7.41-6.80 (m, 7H), 5.09 (dd, J = 12.7, 5.4 Hz, 1H), 4.64 (brs, 1H), 3.58-3.46 (m, 6H), 2.94-2.82 (m, 2H), 2.68-2.55 (m, 4H), 2.55-2.47 (m, 4H), 2.26-1.99 (m, 7H), 1.87-1.51 (m, 7H), 1.31 (q, J = 12.4, 11.6 Hz, 2H). | 12 B |
| 547 |  | 807.550 | A | ¹HNMR (300 MHz, DMSO-d6) 11.07(s, 1H), 8.56 (s, 1H), 8.00-7.98 (m, 1H), 7.98-7.88(m, 2H). 7.85-7.67(m, 1H), 7.37-7.36 (m, 3H), 7.24-7.13 (m, 1H), 6.81-6.78 (m, 1H), 5.08-5.02 (m. 1H), 4.52-4.39 (m, 1H), 4.37-4.31 (m, 2H), 3.80 (s. 1H), 3.77-3.41 (m, 4H), 2.86-2.82 (m, 3H), 2.79(m. 2H), 2.58-2.56 (m, 4H), 2.52-2.47 (m, 2H), 2.32-2.08 (m, 3H), 2.00-1.97 (m, 2H), 1.86-1.74 (m, 2H), 1.71-1.48 (m, 7H), 1.37-1.09 (m, 2H) | 9 B |
| 548 |  | 826.540 | A | 1H NMR (300 MHz, DMSO-d6) δ 11.09 (s, 1H), 8.55 (d, J = 8.2 Hz, 1H), 7.74 (d, J = 13.7, 11.7, 7.4 Hz, 3H), 7.42 (d, J = 7.4 Hz, 1H), 7.26 (dd, J = 23.7, 9.3 Hz, 2H), 5.07 (dd, J = 12.8, 5.3 Hz, 1H), 4.45 (d, J = 13.5 Hz, 3H), 3.86 (s, 1H), 3.22 (s, 5H), 3.03-2.95 (m, 2H), 2.87-2.79 (m, 1H), 2.59-2.48 (m, 4H), 2.20-2.18 (m, 5H), 2.10 – 1.95 (m, 3H), 1.90-1.78 (m, 5H), 1.58 (td, J = 21.0, 18.4, 11.8 Hz, 4H), 1.20 (s, 1H), 1.09 (q, J = 11.7 Hz, 2H). | 1 B |

| | | | | |
|---|---|---|---|---|
| 549 |  | 792.570 | A | ¹H NMR (400 MHz, DMSO-*d6*): δ 11.11 (s, 1H), 8.58 (d, *J* = 8.2 Hz, 1H), 7.81 (d, *J* = 9.5 Hz, 1H), 7.73 (d, *J* = 11.4 Hz, 1H), 7.66 (d, *J* = 8.6 Hz, 1H), 7.46 (d, *J* = 7.4 Hz, 1H), 7.34 (d, *J* = 9.6 Hz, 1H), 7.06 (d, *J* = 2.5 Hz, 1H), 6.95 (dd, *J* = 8.8, 2.5 Hz, 1H), 5.11 (dd, *J* = 12.8, 5.4 Hz, 1H), 4.47 (t, *J* = 13.0 Hz, 3H), 3.87 (d, *J* = 10.3 Hz, 1H), 3.26 (d, *J* = 5.6 Hz, 4H), 3.03 (t, *J* = 12.5 Hz, 2H), 2.96 – 2.84 (m, 1H), 2.60 (d, *J* = 18.0 Hz, 2H), 2.55 (s, 4H), 2.44 (s, 3H), 2.23 (d, *J* = 7.0 Hz, 2H), 2.15 – 2.00 (m, 3H), 1.95 – 1.84 (m, 4H), 1.83 (s, 1H), 1.57 (dq, *J* = 52.6, 12.2, 11.7 Hz, 4H), 1.14 (q, *J* = 11.5 Hz, 2H); 1 B |
| 550 |  | 800.620 | A | 49 |
| 551 |  | 801.620 | B | ¹H NMR (400 MHz, DMSO-*d6*): δ 11.09 (s, 1H), 8.07-8.05 (d, *J* = 8.8Hz, 1H), 7.77-7.74 (m, 3H), 7.70-7.68 (d, *J* = 8.4Hz, 1H), 7.56-7.53 (d, *J* = 9.2Hz, 1H), 7.35 (s, 1H), 7.28-7.25 (d, *J* = 8.8Hz, 1H), 6.97 -6.95 (d, *J* = 8.8Hz, 2H), 6.87-6.85 (d, *J* = 8.8Hz, 1H), 5.10-5.05 (m, 1H), 4.75 (s, 1H), 4.04-4.02 (d, *J* = 9.2Hz, 1H), 3.88-3.85 (m, 2H), 3.45 (s, 4H), 2.93-2.76 (m, 3H), 2.61-2.51 (m, 4H), 2.50 (m, 6H), 2.22-2.21(d, *J* = 6.4Hz, 49 |

| # | Structure | Mass | Activity | NMR | Ex |
|---|---|---|---|---|---|
| 552 | 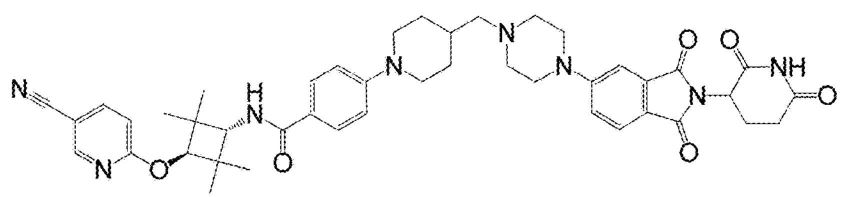 | 787.600 | D | 2H), 2.08-1.98 (m, 1H), 1.88-1.68 (m, 3H), 1.21 (s, 6H), 1.12 (s, 6H) | 49 |
| 553 | 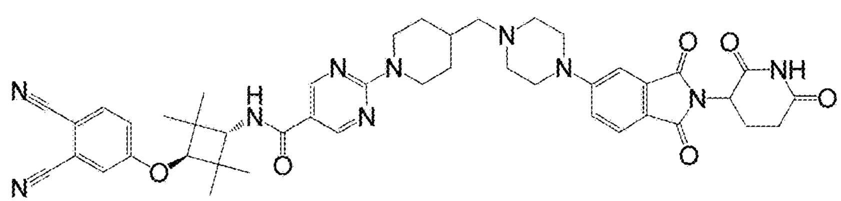 | 813.600 | A | $^1$H NMR (300 MHz, DMSO-$d_6$): δ 11.06 (s, 1H), 8.64 (s, 1H), 8.13 (d, $J$ = 8.4 Hz, 1H), 7.73-7.65 (m, 3H), 7.55-7.45 (m, 1H), 7.40 (s, 1H), 7.25-7.15 (m, 1H), 7.10-7.00 (m, 1H), 6.95-6.91 (m, 2H), 5.07-5.01 (m, 1H), 4.76 (s, 1H), 4.02 (d, $J$ = 9 Hz, 1H), 3.85 (d, $J$ = 11.7 Hz, 2H), 3.41 (s, 4H), 2.90-2.72 (m, 3H), 2.58-2.47 (m, 4H), 2.19-2.01(m, 2H), 2.00-1.90 (m, 1H), 1.89-1.76 (m, 3H), 1.36-0.98(m, 15H); | 49 |
| 554 | 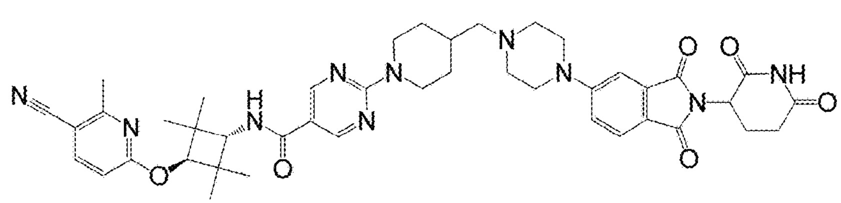 | 803.610 | A | $^1$H NMR (400 MHz, $d_6$-DMSO): δ 11.09 (s, 1H), 8.75 (s, 2H), 8.07-8.05 (d, $J$=8.8Hz, 1H), 7.72-7.65 (m, 3H), 7.36-7.34 (m, 2H), 7.28-7.25 (d, $J$=9.2Hz, 1 H), 5.09-5.05 (m, 1H), 4.77-4.73 (m, 2H), 4.34 (s, 1H), 4.06-4.04 (m, 1H), 3.45 (m, 4H), 3.02-2.85 (m, 3H), 2.61-2.54 (m, 2H), 2.51 (m, 4H), 2.22-2.20 (m, 2H), 2.03-2.01 (m, 1H), 1.92 (s, 1H), 1.85-1.82 (m, 2H), 1.23 (s, 6H), 1.10-1.07 (m, 8H); | 49 |
| | | | | $^1$H NMR (400 MHz, d-DMSO):δ11.051(s,1H),8.740(s,2H),8.055-8.027(d,J=11.2Hz,2H),7.731-7.647(m,2H),7.327(s,1H),7.255-7.226(d,J=11.6Hz,1H),6.854-6.825(d,J=11.6Hz,1H),5.082-5.064(m,1H),4.747-4.692(m,3H),4.002-3.971(d,J=12.4Hz,1H),3.427(s,4H),3.305-2.806(m,3H),2.589-2.545(m,9H),2.247- | 49 |

FIG. 7 Continued.

| # | Structure | Mass | Class | NMR | |
|---|---|---|---|---|---|
| 555 | 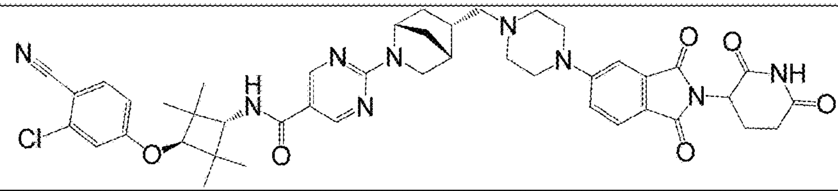 | 834.560 | A | 2.173(m,2H),2.052-1.792(m,4H),1.178(s,6H),1.087-1.17(m,8H) | |
| 556 | 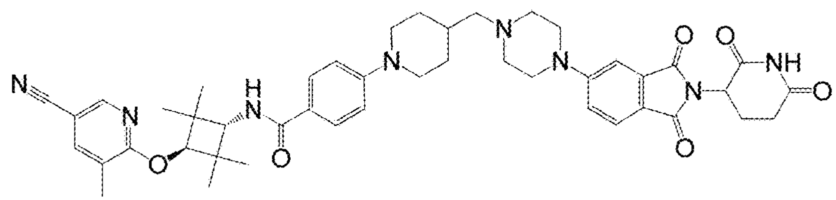 | 801.620 | C | 1H NMR (300 MHz, DMSO-d6,ppm) ¹H NMR (300 MHz, DMSO-d₆) δ 8.48 (d, J = 2.3 Hz, 1H), 8.01 (dd, J = 2.3, 1.1 Hz, 1H), 7.71 (dd, J = 17.4, 8.5 Hz, 1H), 7.51 (d, J = 9.3 Hz, 1H), 7.38(m, 1H) 7.21 (m, 1H), 6.95 (d, J = 9.0 Hz, 2H), 5.07 (dd, J = 12.8, 5.4 Hz, 1H), 4.82 (s, 1H), 4.05 (d, J = 9.1 Hz, 1H), 3.86 (d, J = 12.5 Hz, 2H),3.35(m, 8H) ,2.98-2.72 (m, 3H), 2.59 (m, 3H), 2.25 (m, 5H), 2.08-1.97 (m, 1H). 1.81 (d, J = 11.8 Hz. 3H), 1.16 (d, J = 23.5 Hz. 14H) | 49 |
| 557 | 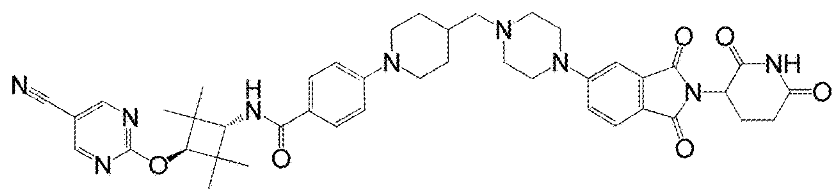 | 788.595 | D | ¹H NMR (400 MHz, DMSO-d₆): δ 11.09 (s, 1H), 9.11 (s, 2H), 7.76 (d, J = 8.7 Hz, 2H), 7.70 (d, J = 8.5 Hz, 1H), 7.57 (d, J = 9.2 Hz, 1H), 7.35 (d, J = 2.1 Hz, 1H), 7.31-7.24 (m, 1H), 6.97 (d, J = 8.8 Hz, 2H), 5.09 (dd, J = 12.9, 5.4 Hz, 1H), 4.79 (s, 1H), 4.07 (d, J = 9.1 Hz, 1H), 3.87 (d, J = 12.4 Hz, 2H), 3.46 (s, 4H), 3.32 (s, 3H), 2.85 (dt, J = 37.2, 12.7 Hz, 3H), 2.64-2.53 (m, 1H), 2.22 (d, J = 6.6 Hz, 2H), 2.03 (d, J = 11.4 Hz, 1H), 1.82 (d, J = 12.3 Hz, 3H), 1.18 (d, J = 26.1 Hz, 16H). | 49 |

FIG. 7 Continued.

| | | | |
|---|---|---|---|
| 558 | [structure] | 814.643 | A | ¹H NMR (300 MHz, DMSO-$d_6$) δ 11.10 (s, 1H), 7.73 (dd, J = 16.0, 8.6 Hz, 3H), 7.49 (d, J = 9.2 Hz, 1H), 7.45 – 7.33 (m, 1H), 7.28 (d, J = 8.7 Hz, 1H), 6.97 (d, J = 8.7 Hz, 2H), 6.75 (s, 2H), 5.09 (dd, J = 12.6, 5.4 Hz, 1H), 4.24 (s, 1H), 4.05 (d, J = 9.1 Hz, 1H), 3.87 (d, J = 12.8 Hz, 2H), 3.47 (s, 6H), 2.83 (q, J = 14.0, 12.0 Hz, 3H), 2.60 (d, J = 16.4 Hz, 2H), 2.44 (s, 8H), 2.24 (s, 2H), 2.03 (d, J = 11.2 Hz, 1H), 1.83 (d, J = 12.0 Hz, 3H), 1.23 (s, 8H), 1.13 (s, 6H). | 49 |
| 559 | [structure] | 780.510 | A | ¹H NMR (400 MHz, DMSO) 11.08 (s, 1H), 8.59 (s, 1H), 8.28 (s, 1H), 8.10 (m, 1H), 7.87-7.85 (m, 1H), 7.68-7.66 (m, 1H), 7.38-7.33 (m, 2H), 7.28-7.22 (m, 1H), 7.14-7.11 (m, 1H), 5.09-5.01 (m, 1H), 4.51-4.45 (m, 3H), 3.90-3.80 (m, 1H), 3.42-3.40 (m, 4H), 3.05-2.80 (m, 3H), 2.64-2.49 (m, 7H), 2.10-1.88 (m, 7H), 1.62-1.38 (m, 6H). | 5 B |
| 560 | [structure] | 780.510 | A | ¹H NMR (300 MHz, DMSO-$d_6$) 11.09 (s, 1H), 8.78-8.72 (m, 2H), 8.29-8.22 (m, 1H), 7.89-7.86 (m, 1H), 7.73-7.70 (m, 1H), 7.40-7.14 (m, 4H), 5.12-5.06 (m, 1H), 4.80-4.56 (m, 3H), 3.81-3.70 (m, 1H), 3.03-2.63 (m, 11H), 2.30-1.92 (m, 8H), 1.55-1.24 (m, 8H); | 5 B |
| 561 | [structure] | 834.560 | A | | |

| | | | | |
|---|---|---|---|---|
| 562 |  | 781.520 | A | ¹H NMR (300 MHz, DMSO-$d_6$): δ 11.11 (s, 1H), 7.88 (dd, J=20.8, 8.5 Hz, 2H), 7.75 (d, J=8.6 Hz, 2H), 7.48 (d, J=2.3 Hz, 1H), 7.45 – 7.32 (m, 2H), 7.21 (d, J = 2.4 Hz, 1H), 7.01 (dd, J = 8.8, 2.5 Hz, 1H), 6.57 (d, J = 8.7 Hz, 2H), 5.13 (dd, J = 12.8, 5.4 Hz, 1H), 4.31 (d, J = 7.5 Hz, 3H), 4.06 (d, J = 9.1 Hz, 1H), 3.50 (dt, J = 30.2, 8.2 Hz, 2H), 3.27 (m, 2H), 3.20 -3.07 (m, 1H), 2.91 (m, 3H), 2.60 (d, J = 19.3 Hz, 2H), 2.36 (s, 3H), 2.21 (s, 1H), 2.04 (s, 1H), 1.96 -1.83 (m, 1H), 1.22 (s, 6H), 1.13 (s, 6H) |
| 563 |  | 807.540 | A | ¹H NMR (300 MHz, DMSO-$d_6$): δ 11.12 (s, 1H), 7.85-7.82 (m, 1H), 7.78-7.75 (m, 1H), 7.75 (d, J = 8.6 Hz, 2H), 7.51 (d, J = 9.2 Hz, 1H), 7.42-7.28 (m, 2H), 7.21 (d, J = 2.4 Hz, 1H), 7.06-6.91 (m, 3H), 5.18-75.03 (m, 2H), 4.32 (s, 1H), 4.05 (d, J = 9.1 Hz, 1H), 3.25-3.43 (m, 4H), 2.99 -2.80 (m, 1H), 2.68-2.62 (m, 2H), 2.56 (s, 6H), 2.11-1.95 (m, 4H), 1.70-1.51 (m, 2H), 1.22 (s, 6H), 1.13 (s, 6H) |
| 564 |  | 801.620 | B | ¹H NMR (300 MHz, DMSO-$d_6$) δ 11.10 (s, 1H), 8.25 (d, J = 2.7 Hz, 1H), 7.73 (dd, J = 17.0, 8.5 Hz, 3H), 7.50 (d, J = 9.1 Hz, 1H), 7.40 – 7.23 (m, 3H), 6.97 (d, J = 8.7 Hz, 2H), 5.09 (dd, J = 12.6, 5.4 Hz, 1H), 4.35 (s, 1H), 4.08 (d, J = 9.0 Hz, 1H), 3.88 (d, J = 12.5 Hz, 2H), 3.00 – 2.73 (m, 5H), 2.66 – 2.54 (m, 6H), 2.50 (s, 4H), 2.23 (d, J = 6.6 Hz, 2H), 2.03 (d, J = 11.5 Hz, 1H), 1.83 (d, J = |

FIG. 7 Continued.

| | | | | |
|---|---|---|---|---|
| 565 | [structure] | 855.600 | B | 1H NMR (300 MHz, DMSO-$d_6$): δ 11.09 (s, 1H), 8.70 (d, $J$ = 2.6 Hz, 1H), 7.86-7.65 (m, 4H), 7.52 (d, $J$ = 9.3 Hz, 1H), 7.36-7.28 (m, 2H), 6.98 (d, $J$ = 8.8 Hz, 2H), 5.12-5.08 (m, 1H), 4.60 (s, 1H), 4.11 (d, $J$ = 9.1 Hz, 1H), 3.88 (d, $J$ = 12.4 Hz, 2H), 3.47-3.43 (m, 4H), 2.93-2.70 (m, 3H), 2.63-2.56(m, 5H), 2.55-2.47 (m, 3H), 2.23 (d, $J$ = 6.5 Hz, 2H), 2.11-1.96 (m, 1H), 1.83 (d, $J$ = 12.2 Hz, 3H), 1.25 (s, 6H), 1.17 (s, 6H), 12.0 Hz, 3H), 1.20 (d, $J$ = 31.9 Hz, 15H). | 49 |
| 566 | [structure] | 794.520 | B | 1H NMR (400 MHz, CDCl3): δ 8.85 (d, $J$ = 1.3 Hz, 1H), 8.06 (s, 1H), 7.76 (m, 8.7 Hz, 2H), 7.67-7.62 (m, 1H), 7.58 (d, $J$ = 8.7 Hz, 1H), 7.32 (d, $J$ = 2.3 Hz, 1H), 7.10 (d, $J$ = 8.5 Hz, 1H), 6.99 (d, $J$ = 2.4 Hz, 1H), 6.83 (m, 1H), 4.96 (m, 1H), 4.36 (s, 2H), 4.15 (d, $J$ = 8.8 Hz, 1H), 4.08 (s, 1H), 3.95 (s, 2H), 3.50 (s, 4H), 3.15 (s, 1H), 2.96-2.56 (m, 9H), 2.20-2.12 (m, 1H), 1.28 (s, 6H), 1.23 (s, 6H); | 65 |
| 567 | [structure] | 766.490 | A | 1H NMR (400 MHz,CDCl3): δ 8.85 (d, $J$ = 1.4 Hz, 1H), 8.03 (s, 1H), 7.72 (d, $J$ = 8.5 Hz, 1H), 7.63-7.54 (m, 2H), 7.40 (d, $J$ = 8.2 Hz, 1H), 7.31 (d, $J$ = 2.3 Hz, 1H), 7.08 (m, 1H), 7.01 (d, $J$ = 2.4 Hz, 1H), 6.86 (m, 1H), 4.96 (m, 1H), 4.33 (m, 3H), 4.11-3.99 (m, 1H), 3.91 (m, 2H), 3.45 (s, 4H), 3.11 (s, 1H), 2.96-2.78 (m, 2H), 2.82-2.68 (m, 3H), 2.64 (m, 4H), 2.25-2.10 (m, 5H), 1.78-1.63 (m, 2H), 1.55-1.40 (m, 2H); | 7, 16 B |

FIG. 7 Continued.

| | | | |
|---|---|---|---|
| 568 | [structure] | 806.590 | A | 13 B | ¹H NMR (300 MHz, DMSO): δ10.68(s, 1H), 7.91-7.87 (m, 1H), 7.72-7.69 (m, 2H), 7.49-7.46(m, 2H), 7.19-7.18 (m, 1H), 7.05-6.89 (m, 5H), 5.28(s, 2H), 4.57-4.52(m, 1H), 4.29 (s, 1H), 4.04-4.01 (m, 1H), 3.86-3.82 (m, 2H), 3.31-3.26(m, 10H), 2.80-2.72 (m, 2H), 2.61-2.57 (m, 2H), 2.19-2.17(m, 2H), 2.10-1.87 (m, 2H), 1.82-1.67 (m, 3H), 1.19 (s, 6H), 1.10 (s, 6H); |
| 569 | [structure] | 776.450 | A | 14 B | H-NMR (300 MHz, DMSO) δ 8.37-8.33 (d, J=10.8Hz, 1H), 7.92-7.80 (m, 3H), 7.34 (s, 1H), 7.10-7.08 (d, J=8.1Hz, 1H), 6.89-6.84 (d, J=14.1Hz, 1H), 5.14-5.08 (m, 1H), 4.67-4.30 (m, 4H), 3.83-3.67 (m, 3H), 3.37-2.93 (m, 6H), 2.91-2.56 (m, 2H), 2.38 (s, 2H), 2.11-1.73 (m, 5H), 1.17 (s, 4H); |
| 570 | [structure] | 812.520 | A | 15 B | ¹H NMR (300 MHz, DMSO-d6) δ 11.10 (s, 1H), 8.60 (d, J = 8.4 Hz, 1H), 7.84 (m, 2H), 7.40-7.35 (m, 2H), 7.25 (s, 1H), 7.15 – 6.99 (m, 3H), 5.10 (m, 1H), 4.74 – 4.50 (m, 3H), 3.95 – 3.75 (m, 1H), 3.60 (s, 4H), 3.10 – 2.80 (m, 3H), 2.53 – 2.50 (m, 5H), 2.21 – 2.15 (m, 2H), 2.14 – 1.75 (m, 8H), 1.74 – 1.50 (m, 4H), 1.25 – 1.00 (m, 2H) |
| 571 | [structure] | 840.560 | A | 66 and 49 | ¹H NMR (300 MHz, DMSO-d6) δ 11.10 (s, 1H), 8.75 (s, 2H), 7.90 (d, J = 8.7 Hz, 1H), 7.71 (d, J = 9.0 Hz, 1H), 7.24–7.21 (m, 2H), 7.07 – 6.99 (m, 2H), 5.10 (m, 1H), 4.74 (d, J = 13.2 Hz, 2H), 4.29 (s, 1H), 4.04 (d, J = 9.0 Hz, 1H), 3.50 (s, 4H), 3.00 – |

| | | | | |
|---|---|---|---|---|
| 572 |  | 848.650 | B | 2.95 (m, 3H), 2.53 – 2.50 (m, 5H), 2.21 – 2.19 (m, 2H), 2.08 – 1.81 (m, 5H), 1.21 – 1.04 (m, 14H) | 63 |
| | | | | ¹H NMR (300 MHz, DMSO-d6):δ 11.12 (s, 1H), 8.22 (d, J = 9.6 Hz, 1H), 7.80 – 7.65 (m, 2H), 7.47 (d, J = 7.4 Hz, 1H), 6.95 (d, J = 2.4 Hz, 1H), 6.83 (dd, J = 8.6, 2.5 Hz, 1H), 5.12 (dd, J = 12.9, 5.4 Hz, 1H), 4.74 (d, J = 12.6 Hz, 2H), 4.17 (s, 1H), 4.08 (d, J = 9.5 Hz, 1H),3.26 – 3.18    (m, 4H), 2.89 (q, J = 11.2 Hz, 3H), 2.56 (s, 5H), 2.46 (s, 3H), 2.24 (s, 8H), 2.10 – 1.99 (m, 1H), 1.81 (d, J = 13.2 Hz, 3H), 1.26 -1.17 (m, 7H), 1.12 (s, 6H), 1.06 - 0.94 (m,2H); | |
| 573 |  | 794.520 | B | ¹H NMR (300 MHz, DMSO-d6) δ 11.08 (s, 1H), 8.23 (d, J=9.0 Hz, 1H), 7.92-7.83 (m, 2H), 7.69 (d, J=8.7 Hz, 1H), 7.35 (m, 1H), 7.29-7.25 (m, 2H), 7.05-7.01 (m, 1H), 6.89 (d, J=9.3 Hz, 1H), 5.10-5.05 (m, 1H), 4.46 (s, 1H), 4.26 (t, J=8.3 Hz, 2H), 4.00 (d, J=9.0 Hz, 1H), 3.86-3.81 (m, 2H), 3.46 (s, 4H), 3.10 (m, 1H), 2.95-2.83 (m, 2H), 2.69 (d, J=7.2 Hz, 2H), 2.62-2.56 (m, 6H), 2.08-2.00 (m, 1H), 1.22-1.14 (m, 12H); | 65 |
| 574 |  | 766.490 | A | ¹H NMR (300 MHz, DMSO-d6): δ 11.11 (s, 1H), 8.75 (s, 2H), 8.17 (d, J = 7.3 Hz, 1H), 7.88 (d, J = 8.8 Hz, 1H), 7.70 (d, J = 8.4 Hz, 1H), 7.38-7.36 (m, 2H), 7.28 (d, J = 8.6 Hz, 1H), 7.18-7.16 (m, 1H), 5.12-5.09 (m, 1H), 4.56 (s, 1H), 4.22 (t, J = 8.6 Hz, 2H), 3.82-3.70 (m, 3H), 3.48-3.46 (m, 4H), 3.09-2.75 (m, 2H), | 7, 16 B |

FIG. 7 Continued.

| # | Structure | Mass | | NMR | |
|---|---|---|---|---|---|
| 575 | 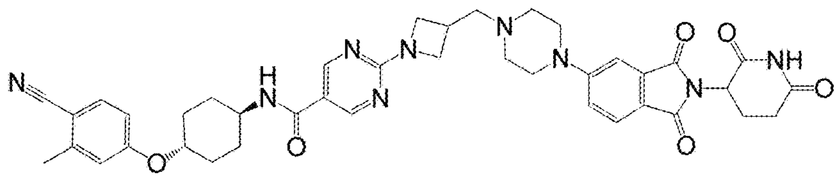 | 746.540 | A | 1H NMR (300 MHz, DMSO-d6): δ 2.67 (d, J = 7.4 Hz, 3H), 2.56 (s, 3H), 2.54-2.52 (m, 2H), 2.20-1.68 (m, 5H), 1.51 (s, 4H); | 7, 16 B |
| 576 | 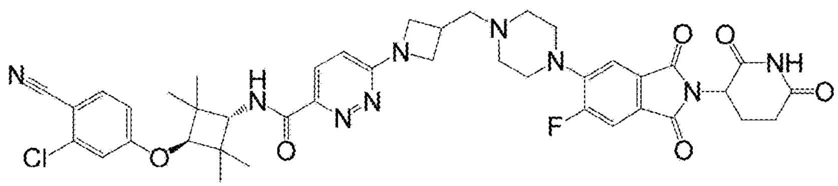 | 812.520 | B | 1H NMR (300 MHz, DMSO-d6): δ 11.11 (s, 1H), 8.75 (d, J = 3.1 Hz, 2H), 8.16 (d, J = 7.4 Hz, 1H), 7.70-7.60 (m, 2H), 7.46-7.19 (m, 2H), 7.16-6.89 (m, 2H), 5.11-5.01 (m, 1H), 4.47 (brs, 1H), 4.22 (t, J = 8.6 Hz, 2H), 3.80-3.71 (m, 3H), 3.50-3.42 (m, 4H), 3.10-2.80 (m, 2H), 2.72-2.63 (m, 3H), 2.55-2.52 (m, 5H), 2.45-2.43 (m, 3H), 2.24-1.84 (m, 5H), 1.53-1.48 (m, 4H). | 65 |
| 577 | 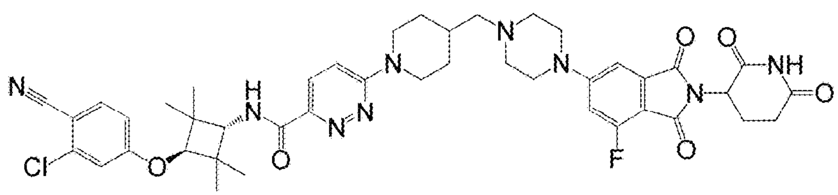 | 840.560 | B | 1H NMR (300 MHz, DMSO) δ 11.11 (s, 1H), 8.23 (d, J=9.0 Hz, 1H), 7.92-7.83 (m, 2H), 7.74 (d, J=11.4 Hz, 1H), 7.47 (d, J=7.2 Hz, 1H), 7.25 (d, J=2.4 Hz, 1H), 7.05-7.01 (m, 1H), 6.89 (d, J=9.3 Hz, 1H), 5.14-5.08 (m, 1H), 4.46 (s, 1H), 4.26 (t, J=8.3 Hz, 2H), 4.00 (d, J=9.0 Hz, 1H), 3.86-3.81 (m, 2H), 3.27 (s, 4H), 3.11 (m, 1H), 2.96-2.83 (m, 1H), 2.71 (d, J=7.2 Hz, 2H), 2.60 (m, 6H), 2.06-2.02 (m, 1H), 1.22 (s, 6H), 1.14 (s, 6H); | 49, 66 |
| | | | | 1H NMR (400 MHz, DMSO-d6) δ 11.09 (s, 1H), 8.24 (d, J = 9.2 Hz, 1H), 7.90 (d, J = 8.7 Hz, 1H), 7.82 (d, J = 9.6 Hz, 1H), 7.37 (d, J = 9.7 Hz, 1H), 7.25 (d, J = 2.4 Hz, 2H), 7.10-7.00 (m, 2H), 5.07 (dd, J = 12.7, 5.4 Hz, 1H), 4.54-4.44 (m, 3H), 4.01 (d, J = 9.1 Hz, 1H), 3.51 (s, 4H), 3.05 (t, J = 12.2 Hz, 2H), 2.88 (ddd, J = 16.6, 13.6, 5.3 Hz, 1H), 2.63-2.51 | |

FIG. 7 Continued.

| | | | | |
|---|---|---|---|---|
| 578 | [structure] | 808.580 | A | (m, 3H), 2.24 (s, 2H), 2.20-2.10 (m, 2H), 2.10-2.00(m, 1H), 1.95-1.85(m, 1H). 1.85-1.76(m, 2H), 1.18 (d, $J$ = 31.8 Hz, 15H). | 49, 67 |
| 579 | [structure] | 837.568 | A | 1H NMR (300 MHz, DMSO-$d6$) δ 10.78(s, 1H), 8.77 (s, 2 H), 7.92 (d, $J$ = 8.8 Hz, 1H), 7.75 (d, $J$ = 9.6 Hz, 2H), 7.34 – 6.92 (m, 4H), 5.43 (s, 2H), 4.77 (d, $J$ = 13.2 Hz, 3H), 4.32 (s, 1H), 4.06 (d, $J$ = 9.1 Hz, 2H), 3.65 (s, 1H), 3.05 – 3.09 (m, 5H), 2.82 – 2.62 (m, 2H), 1.91 – 2.29 (m, 8H), 1.18 (d, $J$ = 31.3 Hz. 16H); | 25B |
| 580 | [structure] | 837.567 | A | H-NMR (300 MHz, DMSO-$d6$) δ 11.09 (s, 1H), 8.57 (s, 1H), 8.24-8.04 (m, 2H), 7.86-7.80 (m, 2H), 7.36-7.09 (m, 4H), 5.13-5.07 (m, 1H), 4.88 (s, 1H), 4.50-4.46 (d, $J$ = 12 Hz. 3H), 3.82-3.65 (m, 2H), 2.99-2.82 (m, 4H), 2.60 (s, 1H), 2.41-2.40 (d, $J$ = 4.8 Hz, 2H), 2.22-2.06 (m, 7H), 1.85 (s, 4H), 1.64-1.51 (m, 5H), 1.46-1.32 (m, 9H); | 25B |
| | | | | H-NMR-PH-ARV-LS-059-H-0: (300 MHz, DMSO-$d6$, ppm) δ 11.09 (s, 1H), 8.72 (s, 2H), 8.08 (d, $J$ = 7.5 Hz, 1H), 7.86-7.82 (m, 2H), 7.37 (s, 1H), 7.26-7.14 (m, 2H), 7.14-7.11 (m, 1H), 5.15-5.09 (m, 1H), 4.91-4.88 (m, 1H), 4.78-4.72 (m, 2H), 4.56-4.53 (m, 1H), 3.77-3.61 (m, 2H), 2.94-2.90 (m, 4H), 2.54-2.51 (m, 1H), 2.48-2.47 (m, 2H), 2.24-2.14 (m, 7H), 1.91-1.80 (m, 4H), 1.71-1.50 (m, 5H), 0.96-0.90 (m, 9H); | |

| | | | | |
|---|---|---|---|---|
| 581 |  | 886.590 | A | ¹H NMR (300 MHz, DMSO): δ 11.15 (s, 1H), 8.23 (d, J = 9.6 Hz, 1H), 7.91 (d, J = 8.8 Hz, 1H), 7.70 (d, J = 9.8 Hz, 1H), 7.24 (d, J = 2.4 Hz, 1H), 7.02 (dd, J = 8.8, 2.4 Hz, 1H), 5.13 (dd, J = 12.8, 5.4 Hz, 1H), 4.74 (d, J = 12.6 Hz, 2H), 4.27 (s, 1H), 4.09 (d, J = 9.5 Hz, 1H), 3.31 - 3.22 (m, 6H), 2.89 (q, J = 14.1, 11.4 Hz, 3H), 2.61 (d, J = 18.0 Hz, 2H), 2.46 – 2.43(m, 2H), 2.24 (s, 8H), 2.04 (d, J = 12.2 Hz, 1H), 1.81 (d, J = 12.5 Hz, 3H), 1.19 (s, 6H), 1.12 (s, 6H), 1.01 (d, J = 12.8 Hz, 2H); | 63 |
| 582 |  | 872.570 | A | ¹H NMR (300 MHz, DMSO-d₆) δ 11.14 (s, 1H), 8.30 – 8.14 (m, 1H), 7.92 (d, J = 8.7 Hz, 1H), 7.83 (d, J = 9.5 Hz, 1H), 7.69 (d, J = 9.8 Hz, 1H), 7.38 (d, J = 9.7 Hz, 1H), 7.26 (d, J = 2.4 Hz, 1H), 7.05 (dd, J = 8.8, 2.4 Hz, 1H), 5.13 (dd, J = 12.8, 5.3 Hz, 1H), 4.52-4.46 (m, 3H), 4.02-3.99 (d, J = 9.1 Hz, 1H), 3.44-3.29 (m, 3H), 3.05-2.93 (m, 4H), 2.62-2.56 (m, 4H), 2.47 – 2.35 (m, 4H), 2.10 – 1.99 (m, 1H), 1.82-1.80 (m, 2H), 1.70-1.69 (m, 1H), 1.54-1.44 (m, 2H), 1.22-1.20 (m, 14H) | 49 |

| | | | | |
|---|---|---|---|---|
| 583 |  | 968.670 | C | ¹H NMR (300 MHz, DMSO-d₆) δ11.11 (s, 1H), 8.55 (s, 1H), 7.89 (d, J = 9.0 Hz, 1H), 7.75-7.65 (m, 2H), 7.46 (d, J = 9.0 Hz, 1H), 7.23 (m, 1H), 7.04-7.00 (m, 1H), 6.38 (s, 1H), 5.13-5.07 (m, 1H), 4.47-4.42 (m, 2H), 4.36 (m, 2H), 4.29 (s, 1H), 4.04 (d, J = 9.0 Hz, 1H), 3.60 (m, 4H), 3.31 (m, 1H), 3.26 (m, 4H), 2.94-2.85 (m, 3H), 2.80-2.76 (m, 2H), 2.63 (m, 1H), 2.54 (m, 4H), 2.47 (m, 4H), 2.23 (m, 2H), 2.08 (m, 1H), 1.80 (m, 3H), 1.22 (s, 6H), 1.19 (m, 1H), 1.10 (s, 6H), 1.05 (m, 1H); | 60 |
| 584 |  | 837.570 | A | | 72 |
| 585 |  | 815.640 | D | ¹H NMR (400 MHz, DMSO-d₆): δ 11.07 (s, 1H), 8.07 (d, J = 8.6 Hz, 1H), 7.75 (d, J = 8.6 Hz, 2H), 7.68 (d, J = 8.5 Hz, 1H), 7.52 (d, J = 9.4 Hz, 1H), 7.35 (d, J = 2.3 Hz, 1H), 7.26 (dd, J = 8.6, 2.1 Hz, 1H), 6.96 (d, J = 8.6 Hz, 2H), 6.87 (d, J = 8.6 Hz, 1H), 5.07 (dd, J = 12.9, 5.4 Hz, 1H), 4.79 (s, 1H), 4.04 (d, J = 9.2 Hz, 1H), 3.86 (d, J = 12.4 Hz, 2H), 3.44 (d, J = 5.2 Hz, 4H), 2.96 -2.74 (m, 5H), 2.63-2.53 (m, 2H), 2.52 (s, 1H), 2.50(s, 3H), 2.22 (d, J = 6.6 Hz, 2H), 2.02 (d, J = 12.7 Hz, 1H), 1.81 (d, J = 12.2 Hz, 3H), 1.32-1.24 (m, 3H),1.22 (s, 8H), 1.12 (s, 6H); | 49 |

FIG. 7 Continued.

| # | Structure | Mass | Activity | NMR | Value |
|---|---|---|---|---|---|
| 586 | 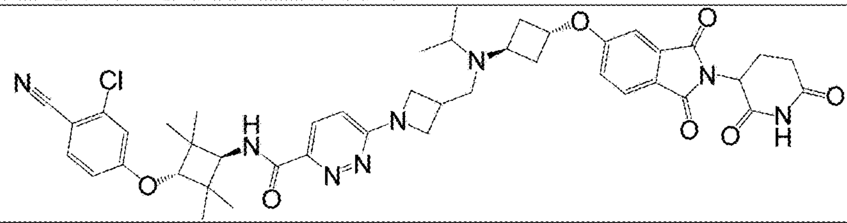 | 837.570 | B | | 72 |
| 587 | 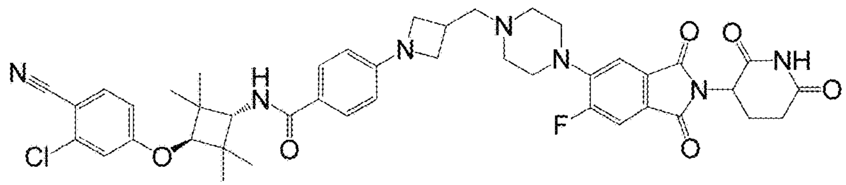 | 810.530 | A | ¹H NMR (400 MHz, d6-DMSO) δ11.13 (s, 1H), 7.93-7.90 (d, J = 8.8Hz, 1H), 7.76-7.73 (m, 3H), 7.48-7.44 (m, 2H), 7.22-7.21 (d, J = 2.4Hz, 1H), 7.02-7.00 (m, 1H), 6.45-6.43 (d, J = 8.8Hz, 2H), 5.14-5.10 (m, 1H), 4.32 (s, 1H), 4.07-4.00 (m, 3H), 3.59-3.56 (m, 2H), 3.26 (s, 4H), 3.00-2.80 (m, 2H), 2.69-2.62 (m, 2H), 2.59-2.51 (m, 6H), 2.08-2.03 (m, 1H), 1.22 (s, 6H), 1.13 (m, 6H) | 65 |
| 588 | 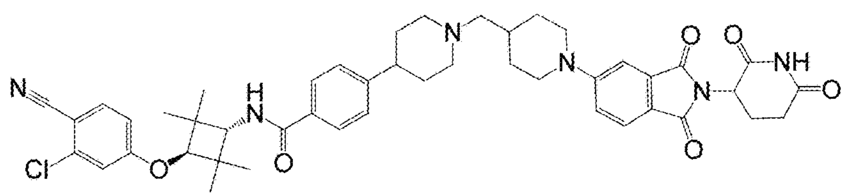 | 819.575 | A | ¹H NMR (400 MHz, DMSO-d6) δ 11.07 (s, 1H), 7.90 (d, J = 8.7 Hz, 1H), 7.77 (dd, J = 8.6, 5.8 Hz, 3H), 7.66 (d, J = 8.6 Hz, 1H), 7.40 – 7.29 (m, 3H), 7.27 – 7.18 (m, 2H), 7.01 (dd, J = 8.8, 2.5 Hz, 1H), 5.07 (dd, J = 12.9, 5.4 Hz, 1H), 4.32 (s, 1H), 4.06 (dd, J = 10.3, 5.2 Hz, 3H), 3.02 – 2.82 (m, 5H), 2.68 – 2.51 (m, 3H), 2.18 (d, J = 6.7 Hz, 2H), 2.05 – 1.94 (m, 3H), 1.82 (d, J = 12.2 Hz, 3H), 1.79 – 1.61 (m, 4H), 1.18 (d, J = 35.8 Hz, 14H). | 69 |

FIG. 7 Continued.

| | Structure | Mass | Activity | NMR | Value |
|---|---|---|---|---|---|
| 589 | 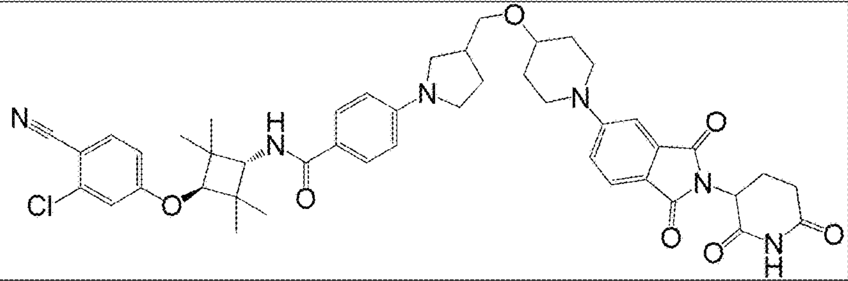 | 821.560 | A | | |
| 590 | 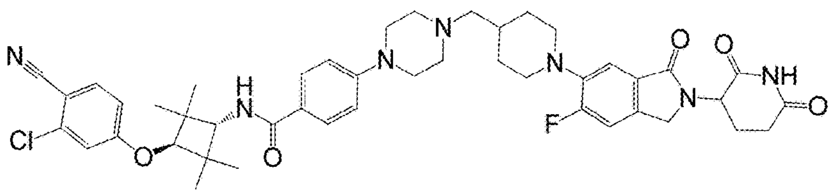 | 824.580 | A | ¹H NMR (300 MHz, DMSO-d6): δ10.96 (s, 1H), 7.90-7.87 (m, 1H), 7.76-7.70 (m, 2H), 7.54-7.48(m, 1H), 7.42-7.38(m, 1H), 7.29-7.27(m, 1H), 7.19-7.18(m, 1H), 7.00-6.94 (m, 3H), 5.09-5.03(m, 1H), 4.37-4.18 (m, 3H), 4.05-4.02 (m, 1H), 3.63-3.45(m, 2H), 3.28-3.16(m, 5H), 2.93-2.59 (m, 5H), 2.48-2.18 (m, 4H), 1.98-1.70(m, 4H), 1.35-0.96 (m, 15H) | 70 |
| 591 | 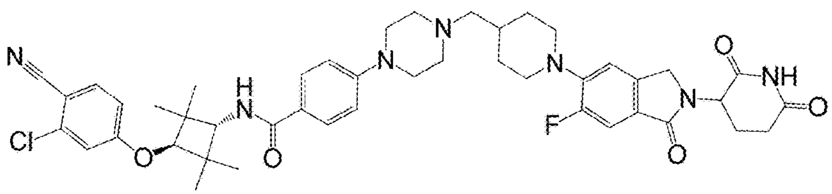 | 824.580 | A | ¹H NMR (300 MHz, DMSO-d6): δ 10.95 (s, 1H), 7.91-7.86 (m, 1H), 7.76-7.69 (m, 2H), 7.56-7.46(m, 1H), 7.42-7.34 (m, 1H), 7.30-7.16 (m, 2H), 7.05-6.89 (m, 3H), 5.08-5.00 (m, 1H), 4.38-4.13 (m, 3H), 4.06-4.01 (m, 1H), 3.49-3.42 (m, 2H), 3.24-3.13 (m, 4H), 2.94-2.58 (m, 5H), 2.36-2.14 (m, 4H), 2.07-1.71 (m, 5H), 1.43-0.96 (m, 15H); | 70 |
| 592 | 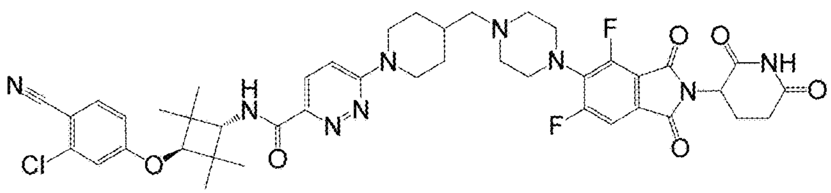 | 858.550 | A | 1H NMR (400 MHz, DMSO-d6) δ 11.12 (s, 1H), 8.24 (d, J = 9.3 Hz, 1H), 7.90 (d, J = 8.8 Hz, 1H), 7.82 (d, J = 9.6 Hz, 1H), 7.68 (d, J = 9.8 Hz, 1H), 7.37 (d, J = 9.7 Hz, 1H), 7.25 (d, J = 2.4 Hz, 1H), 7.04 (dd, J = 8.7, 2.4 Hz, 1H), 5.11 (dd, J = 12.9, 5.5 Hz, 1H), 4.55 – 4.44 (m, 3H). | 49 |

FIG. 7 Continued.

| | | | | |
|---|---|---|---|---|
| 593 | [Structure with biphenyl-pyrazole linker, methylpiperidine-cyclohexyl-O-phenyl(Cl)(CN), glutarimide-phthalimide] | | C | 4.01 (d, J = 9.1 Hz, 1H), 3.36-3.29 (m, 4H), 3.04 (t, J = 12.5 Hz, 2H), 2.91 – 2.81 (m, 1H), 2.60-2.51 (m, 3H), 2.48-2.40 (m, 3H)2.23 (d, J = 7.1 Hz, 2H), 2.10 – 1.99 (m, 1H), 1.93 (s, 1H), 1.85 (d, J = 13.5 Hz, 2H), 1.22 (s, 6H), 1.14 (s, 8H); | 19 B |
| 594 | [Structure with difluorophthalimide-glutarimide, piperazine-pyridine-amide-cyclohexyl-O-phenyl(Cl)(CN)] | 804.480 | A | ¹H NMR (300 MHz, DMSO-d₆) δ11.16 (s, 1H), 8.33-8.29 (m, 2H), 8.06 (d, J = 7.8 Hz, 1H), 7.96-7.68 (m, 10H), 7.54 (s, 1H), 7.45 (d, J = 2.4 Hz, 1H), 7.19-7.15 (m, 1H), 5.25-5.19 (m, 1H), 4.69 (m, 1H), 3.94 (s, 3H), 3.65 (s, 3H), 2.86 (m, 2H), 2.65-2.54 (m, 2H), 2.20-2.16 (m, 3H), 1.96-1.84 (m, 4H), 1.59-1.55 (m, 2H); | 5 B |
| 595 | [Structure with difluorophthalimide-glutarimide, piperazine-pyridine-amide-dimethylcyclobutyl-O-phenyl(Cl)(CN)] | 830.510 | A | ¹H NMR (400 MHz, DMSO-d₆): δ 11.12 (s, 1H), 8.58 (d, J = 8.3 Hz, 1H), 7.83 (dd, J = 20.9, 9.2 Hz, 2H), 7.69 (d, J = 9.8 Hz, 1H), 7.39 (d, J = 2.4 Hz, 1H), 7.34 (d, J = 9.7 Hz, 1H), 7.14 (dd, J = 8.7, 2.4 Hz, 1H), 5.13-5.11 (m, 1H), 4.51 (t, J = 13.8 Hz, 3H), 3.87 (s, 1H), 3.21 (s, 1H),3.02 (t, J = 12.4 Hz, 2H), 2.94-2.81 (m, 1H), 2.59 (d, J = 18.6 Hz, 5H), 2.46 (m, 3H), 2.24-2.11(m, 2H), 2.07-1.87 (m, 9H), 1.66-1.62 (m, 2H), 1.55-1.52 (m, 2H), 1.14-1.05 (m, 2H); | 49 |
| | | 858.550 | A | ¹H NMR (300 MHz, Methanol-d4) δ 8.75 (s, 2H), 7.75 (d, J = 8.7 Hz, 1H), 7.49 (d, J = 9.8 Hz, 1H), 7.15 (d, J = 2.4 Hz, 1H), 7.00 (dd, J = 8.8, 2.5 Hz, 1H), 5.12 (dd, J = 12.5, 5.5 Hz, 1H), 4.91 (s, 2H), 4.29 (s, 1H), 4.15 (s, 1H), 3.43 (s, 4H), 3.10-2.70 | |

| | | | | |
|---|---|---|---|---|
| 596 |  | 764.500 | A | (m,5H), 2.66 (m, 4H), 2.36 (d, J = 6.7 Hz, 2H), 2.14 (s, 1H), 1.94 (d, J = 13.4 Hz, 3H), 1.30 (s, 6H), 1.23 (s, 8H) |
| 597 |  | 865.600 | A | ¹H NMR (400 MHz, d6-DMSO) δ 11.09 (s, 1H), 7.93-7.91 (d, J = 7.6Hz, 1H), 7.87-7.84 (d, J = 8.8Hz, 1H), 7.72-7.67 (m, 3H), 7.39-7.35 (m, 2H), 7.28-7.25 (m, 1H), 7.15-7.12 (m, 1H), 6.41-6.39 (d, J = 8.4Hz, 2H), 5.09-5.05 (m, 1H), 4.54-4.53 (m, 1H), 4.01-3.97 (m, 2H), 3.80(s, 1H), 3.56-3.53 (m, 2H), 3.44 (s, 4H), 2.99-2.80 (m, 2H), 2.65-2.53 (m, 8H), 2.11-2.00 (m, 3H), 1.89-1.87 (m, 2H), 1.53-1.46 (m, 4H); 5, 16 B |
| | | | | ¹H NMR (300 MHz, DMSO-d6) 11.09 (s, 1H), 8.59 (s, 1H), 8.31(s, 1H), 7.91-7.73 (m, 3H), 7.25-7.22 (m, 3H), 7.02-6.99 (m, 1H), 5.16-5.03 (m, 1H), 4.88-4.79 (s, 1H), 4.51-4.47 (m, 3H), 3.96-3.90 (m, 1H), 3.72-3.61 (s, 1H), 2.96-2.81 (m, 4H), 2.71-2.69 (m, 1H), 2.68-2.48 (m, 2H), 2.34-2.16 (m, 4H), 2.12-2.00 (s, 1H), 1.91-1.82 (m, 2H), 1.80-1.78 (s, 1H), 1.31-1.06 (m, 15H), 0.96-0.80 (m, 6H); 71 |
| 598 |  | 821.570 | A | ¹H NMR (400 MHz, DMSO-d6) 11.09 (s, 1H), 9.06 (s,2H), 8.24 (m, 1H), 7.92 (m, 1H), 7.67 (m, 1H), 7.31 (s, 1H), 7.24 (m, 2H), 7.03 (m, 1H), 5.21-5.02 (m, 1H), 4.31 (m, 1H), 4.21-4.15 (m, 3H), 3.00-2.81 (m, 6H), 2.71-2.56 (m, 2H), 2.31-2.20 (s, 2H), 2.10-2.02 (m, 3H), 2.00-1.91 (m, 2H), 2.96-2.81 (m, 5H), 70 |

FIG. 7 Continued.

| | | | | |
|---|---|---|---|---|
| 599 | [structure] | 826.540 | A | 1.30-1.28 (m, 6H), 1.21-1.06 (m, 8H); <br> ¹H NMR (300 MHz, *d6*-DMSO) δ11.09 (s, 1H), 8.26-8.23 (d, *J* = 9.0Hz, 1H), 7.92-7.89 (d, *J* = 8.7Hz, 1H), 7.85-7.82 (d, *J* = 9.3Hz, 1H), 7.42-7.40 (d, *J* = 9.9Hz, 1H), 7.25-7.23 (m, 2H), 7.07-7.01 (m, 2H), 5.09-5.05 (m, 1H), 4.56-4.51 (m, 2H), 4.46 (s, 1H), 4.02-3.99 (d, *J* = 9.0Hz, 1H), 3.47 (m, 4H), 3.08-3.04 (m, 2H), 3.00-2.80 (m, 1H), 2.63-2.56 (m, 6H), 2.50-2.49 (m, 1H), 2.01-1.89 (m, 3H), 1.47-1.43 (m, 2H), 1.22 (s, 6H), 1.14 (s, 6H); | 49, 66 |
| 600 | [structure] | 865.600 | A | H-NMR (300 MHz, DMSO-*d6* ) δ 11.09 (s, 1H), 8.23-8.20 (d, *J* = 9.3 Hz, 1H), 7.90-7.78 (m, 3H), 7.36-7.33 (d, *J* = 9.9 Hz, 1H), 7.26-7.23 (m, 3H), 7.03-7.00 (m, 1H), 5.12-5.06 (m, 1H), 4.88 (s, 1H), 4.53-4.44 (m, 3H), 4.00-3.97 (d, *J* = 9.0 Hz, 1H), 3.33-2.87 (m, 4H), 2.81-2.38 (m, 3H), 2.25-2.14 (m, 4H), 2.04-2.00 (m, 1H), 1.86-1.69 (m, 3H), 1.20-1.00 (m, 15H), 0.92-0.89 (d, *J* = 9.9 Hz, 6H); | 72 |
| 601 | [structure] | 836.570 | A | ¹H NMR (300 MHz, DMSO-d₆) δ 8.26 (s, 1H), 7.84 (dd, *J* = 8.6, 4.9 Hz, 3H), 7.43 (d, *J* = 8.7 Hz, 1H), 7.38 – 7.26 (m, 3H), 7.10 (d, *J* = 8.9 Hz, 1H), 5.16 – 5.03 (m, 2H), 4.51 (s, 1H), 4.17 (d, *J* = 9.2 Hz, 1H), 3.93 (s, 2H), 3.79 (s, 1H), 3.05 (s, 1H), 3.05 (s, 3H), 2.86 (s, 4H), 2.60 (s, 3H), 2.06 (dd, *J* = 11.1, 12.5 Hz, 8H), 1.57 | 72 |

| | | | | |
|---|---|---|---|---|
| 602 |  | 812.590 | A | (dd, J = 25.4, 12.6 Hz, 4H), 1.32 – 1.12 (m, 9H); | 20 |
| 603 |  | 787.520 | D | $^1$H NMR (300 MHz, DMSO-$d_6$): δ 10.96 (s, 1H), 8.88 (s, 1H), 8.15-7.94 (m, 2H), 7.88 (d, J = 8.8 Hz, 1H), 7.45-7.30 (m, 2H), 7.25-7.16 (m, 2H), 7.02-6.99 (m, 1H), 5.10-5.02 (m, 1H), 4.41-4.26 (m, 3H), 4.22 (d, J = 17.1 Hz, 1H), 3.08-2.67 (m, 3H), 2.98-2.60 (m, 6H), 2.53-2.50 (m, 2H), 2.42-2.24 (m, 3H), 2.09-1.90 (m, 1H) 1.72-1.68 (m, 2H), 1.50-1.37 (m, 2H), 1.35-1.30 (m, 4H),1.21 (s, 6H), 1.11 (s, 7H). | 20 B |
| 604 |  | 809.570 | B | $^1$H NMR (300 MHz, Me$_2$SO-$d_6$): δ 11.08 (s, 1H), 7.86 (d, J = 8.8 Hz, 1H), 7.71-7.67 (m, 3H), 7.39-7.25 (m, 3H), 7.13 (dd, J = 8.8, 2.3 Hz, 1H), 6.74 (s, 1H), 6.45 (d, J = 8.4 Hz, 2H), 5.07 (dd, J = 12.7, 5.5 Hz, 1H), 4.60 (brs, 1H), 3.98 (t, J = 7.6 Hz, 2H), 3.54-3.30 (m, 7H), 3.29-3.120 (m, 5H), 3.11-2.79 (m, 3H), 2.67-2.55 (m, 3H), 2.18-2.01 (m, 5H), 1.75-1.35 (m, 4H); | |

| | | | |
|---|---|---|---|
| 605 |  | 687.420 | D | ¹H NMR (300 MHz, DMSO-d6) δ 11.13 (s, 1H), 7.97 – 7.82 (m, 3H), 7.45 (d, J = 2.2 Hz, 1H), 7.36 (dd, J = 8.3, 2.3 Hz, 1H), 7.27 – 7.17 (m, 2H), 7.01 (dd, J = 8.8, 2.4 Hz, 1H), 6.67 (d, J = 2.3 Hz, 1H), 5.14 (dd, J = 12.8, 5.3 Hz, 1H), 4.47 – 4.30 (m, 3H), 4.19 (t, J = 5.8 Hz, 2H), 3.92 (d, J = 8.9 Hz, 1H), 2.93 – 2.81 (m, 1H), 2.60 (d, J = 19.9 Hz, 2H), 2.31 (d, J = 7.4 Hz, 2H), 2.06 (s, 1H), 1.14 – 1.06 (m, 12H); | 73 |
| 606 |  | 781.530 | A | | |
| 607 |  | 823.470 | A | ¹H NMR (400 MHz, DMSO-d6) δ 11.08 (s, 1H), 8.89 (s, 1H), 8.53 (s, 1H), 7.69 – 7.56 (m, 2H), 7.35 – 7.21 (m, 4H), 5.10-5.00 (m, 1H), 4.06 (d, J = 13.0 Hz, 2H), 3.0-2.90 (m, 4H), 2.88-2.86 (m, 2H), 2.61- 2.59 (m, 4H), 2.50-2.40 (m, 2H), 2.20-2.18 (m, 2H), 2.03-1.90 (m, 4H), 1.90-1.80 (m, 7H), 1.60-1.50 (m, 1H), 1.26 – 1.13 (m, 2H). | 74 |

| | | | | |
|---|---|---|---|---|
| 608 |  | 806.470 | A | ¹H NMR (300 MHz, DMSO-$d_6$) δ 11.07 (s, 1H), 8.88 (d, $J$ = 1.9 Hz, 1H), 8.52 (d, $J$ = 1.9 Hz, 1H), 7.67 (d, $J$ = 8.5 Hz, 1H), 7.33 (d, $J$ = 1.9 Hz. 1H), 7.30 – 7.12 (m, 3H), 7.07 (d, $J$ = 9.0 Hz, 2H), 5.06 (dd, $J$ = 12.6, 5.3 Hz, 1H), 3.81 (d, $J$ = 12.1 Hz, 2H), 3.44 (s, 4H), 2.87 (t, $J$ = 13.4 Hz,4H), 2.76 (t, $J$ = 12.6 Hz, 5H), 2.56 (d, $J$ = 15.3 Hz, 3H), 2.41 (s, 2H), 1.97 -1.75 (s, 6H), 1.55 (s, 1H), 1.23 (d, $J$ = 10.9 Hz, 2H). | 75 |
| 609 |  | 820.610 | A | H-NMR-PH-ARV-LS-046-E-0: (300 MHz, DMSO, ppm) δ 10.90-10.88 (br, 1H), 7.92-7.89 (d, $J$ = 9Hz, 1H), 7.75-7.72 (d, $J$ = 9Hz, 2H), 7.51-7.44 (m, 2H), 7.21 (br, 1H), 7.10-6.94 (m, 5H), 4.65-4.64 (m, 1H), 4.54-4.52 (m, 1H), 4.32 (s, 1H), 4.06-4.03 (d, $J$ = 9Hz, 1H), 3.88-3.84 (m, 2H), 3.31-3.28 (m, 4H), 2.83-2.75 (m, 3H), 2.63-2.58 (m, 6H), 2.22-2.20 (m, 2H), 1.96-1.94 (m, 1H), 1.83-1.79 (m, 3H), 1.43-1.38 (m, 3H), 1.21 (s, 6H), 1.18-1.17 (m, 2H), 1.12 (s, 6H); | 49, 76 |
| 610 |  | 820.610 | A | | 49, 76 |

| | | | | |
|---|---|---|---|---|
| 611 |  | 840.560 | B | ¹H NMR (400 MHz, DMSO-*d*₆): δ 11.12 (s, 1H), 8.25 (d, J = 9.2 Hz, 1H), 7.92 (d, J = 8.7 Hz, 1H), 7.82 (d, J = 9.5 Hz, 1H), 7.65 (d, J = 8.1 Hz, 1H), 7.38 (t, J = 8.2 Hz, 2H), 7.25 (d, J = 2.4 Hz, 1H), 7.03 (dd, J = 8.8, 2.5 Hz, 1H), 5.10 (dd, J = 12.7, 5.4 Hz, 1H), 4.55-4.44 (m, 3H), 4.01 (d, J = 9.2 Hz, 1H), 3.25-3.22 (m, 4H), 3.04 (t, J = 12.4 Hz, 2H), 2.95-2.81 (m, 1H), 2.60-2.56 (m, 5H), 2.23 (d, J = 7.1 Hz, 2H), 2.10-1.99 (m, 1H), 1.94 (s, 1H), 1.84 (d, J = 12.7 Hz, 2H), 1.22 (s, 6H), 1.14 (s, 9H). | 49.77 |
| 612 |  | 824.470 | A | ¹H NMR (300 MHz, DMSO-*d*₆) δ 11.06 (s, 1H), 8.87 (d, J = 2.0 Hz, 1H), 8.51 (d, J = 2.0 Hz, 1H), 7.67 (d, J = 8.5 Hz, 1H), 7.34 – 7.09 (m, 5H), 5.06 (dd, J = 12.7, 5.3 Hz, 1H), 3.47 (d, J = 14.2 Hz, 6H), 3.47 (s, 1H), 2.76 (t, J = 12.5 Hz, 3H), 2.56 (d, J = 14.7 Hz, 6H), 2.25 (d, J = 6.4 Hz, 3H), 2.00 - 1.56 (d, J = 12.1 Hz, 7H), 1.36 – 1.19 (m, 3H). | 75 |

| | | | | |
|---|---|---|---|---|
| 613 |  | 805.480 | B | 74 |
| 614 |  | 666.520 | D | 78 |
| 615 |  | 865.600 | A | 72 1H NMR (300 MHz, DMSO-*d6*) δ 11.10 (s, 1H), 8.75 (s, 2H), 7.90 (d, *J* = 6.6 Hz, 1H), 7.83 (d, *J* = 6.3 Hz, 1H), 7.71–7.69 (m, 1H), 7.28 – 7.21 (m, 3H), 7.02 – 7.00 (m, 1H), 5.13 – 5.09 (m, 1H), 4.90 – 4.85 (m, 1H), 4.79 – 4.75 (m, 2H), 4.29 (s, 1H), 4.05 (d, *J* = 6.9 Hz, 1H), 3.70 – 3.60 (m, 1H), 2.94 – 2.89 (m, 4H), 2.57 – 2.50 (m, 1H), 2.49 – 2.40 (m, 2H), 2.25 – 2.19 (m, 4H), 2.08 – 2.00 (m, 1H), 1.90 – 1.80 (m, 2H), 1.75 – 1.65 (s, 1H), 1.20 (s, 7H), 1.10 (s, 6H), 1.00 – 0.91 (m, 8H); |

Row 614 NMR: 1H NMR (300 MHz, Methanol-*d4*) δ 7.69 (d, *J* = 8.5 Hz, 1H), 7.53 (d, *J* = 8.8 Hz, 2H), 7.36 (d, *J* = 2.3 Hz, 1H), 7.29 – 7.15 (m, 2H), 7.14 – 7.05 (m, 2H), 5.07 (dd, *J* = 12.3, 5.4 Hz, 1H), 4.39 (t, *J* = 4.9 Hz, 2H), 4.23 (t, *J* = 7.0 Hz, 2H), 3.62-3.47 (m, 9H), 3.07–2.69 (m, 14H), 2.35 (d, *J* = 7.1 Hz, 2H), 2.13-2.09 (m, 3H), 1.94-1.90 (m, 1H), 1.51-1.47 (m, 2H)

| | | | | |
|---|---|---|---|---|
| 616 |  | 861.570 | A | 1H NMR (300 MHz, DMSO-*d6*): δ 11.06 (s ,1H), 7.92 (d, *J* = 8.7 Hz, 1H), 7.75-7.71 (m, 3H), 7.42 (d, *J* = 9.3 Hz, 1H), 7.34 (s, 1H), 7.29 – 7.18 (m, 2H), 7.01 (dd, *J* = 8.8, 2.5 Hz, 1H), 6.58 (d, *J* = 8.7 Hz, 2H), 5.08 (dd, *J* = 12.7, 5.3 Hz, 1H), 4.33 (s, 1H), 4.07 (d, *J* = 9.1 Hz, 1H), 3.73 - 3.63 (m, 2H), 3.51 - 3.48 (m, 4H), 3.32 – 3.16 (m, 3H), 3.31 - 3.19 (m, 4H), 3.17 - 2.81 (m, 3H), 2.06 (d, *J* = 14.9 Hz, 1H), 1.22 (s, 6H), 1.13 (s, 6H); | 49, 79 |
| 617 |  | 823.590 | D | ¹H NMR (400 MHz, DMSO-*d6*) 11.08 (s, 1H), 7.91-7.89 (m, 2H), 7.66-7.64 (m, 1H), 7.32-7.23 (m, 4H), 7.04-7.01 (m, 1H), 6.67-6.66 (m, 1H), 5.08-5.04 (m, 1H), 4.36-4.30 (m, 2H), 4.12-4.09 (m, 2H), 3.95-3.92 (m, 1H), 3.02-2.88 (m, 4H), 2.67-2.49 (m, 3H), 2.18-1.84 (m, 10H), 1.71-1.46 (m, 6H), 1.20-1.09 (m, 12H). | 49, 80 |
| 618 |  | 622.480 | D | ¹H NMR (300 MHz, DMSO-*d6*) δ 8.27 (s, 1H), 7.66 (d, *J* = 8.5 Hz, 1H), 7.41 – 7.28 (m, 3H), 7.24 (dd, *J* = 8.7, 2.3 Hz, 1H), 7.04 – 6.89 (m, 3H), 5.05 (dd, *J* = 12.8, 5.4 Hz, 1H), 4.09 (t, *J* = 7.0 Hz, 2H), 3.70-3.60 (m, 2H), 2.95 – 2.76 (m, 1H), 2.73 – 2.49 (m, 5H), 2.20 (d, *J* = 6.9 Hz, 2H), 1.99 (d, *J* = 12.3 Hz, 1H), 1.79 (d, *J* = 13.1 Hz, 2H), 1.70-1.65 (m, 1H), 1.29-1.10 (m, 3H) | 81 |

| 619 | | 837.570 | B | 72 |

| | | | | |
|---|---|---|---|---|
| 620 |  | 852.605 | B | |
| 621 |  | 861.650 | A | ¹H-NMR (400 MHz, CDCl₃) δ 8.70 (s, 2H), 8.05 (s, 1H), 7.77 (d, $J$ = 8.0 Hz, 1H), 7.45 (d, $J$ = 8.0 Hz, 1H), 7.18 (s, 1H), 7.17-7.0 (m, 1H), 6.45-6.37 (m, 2H), 5.94-5.92 (d, $J$ = 8.0 Hz, 1H), 4.97-4.87 (m, 3H), 4.74 (m, 1H), 4.13-4.11 (d, $J$ = 8.0 Hz, 1H), 4.03 (s, 1H), 3.91 (s, 3H), 3.82-3.72 (m, 1H), 2.96-2.74 (m, 6H), 2.40-2.14 (m, 7H), 1.94-1.91 (m, 2H), 1.32-1.24 (m, 14H), 1.22-1.06 (m, 1H), 0.98-0.97 (m, 6H). | 72 |

| | | | | |
|---|---|---|---|---|
| 622 |  | 845.650 | A | 1H-NMR (400 MHz, CDCl₃) δ 8.70 (s, 2H), 7.98 (s, 1H), 7.78-7.76 (d, J = 8.0 Hz, 1H), 7.52-7.50(d, J = 8.0 Hz, 1H), 7.18 (s, 1H), 7.13-7.11 (d, J = 8.0 Hz, 1H), 6.77 (s, 1H), 6.69-6.67 (d, J = 8.0 Hz, 1H), 5.94-5.92 (d, J = 8.0 Hz, 1H), 4.97-4.87 (m, 3H), 4.74 (m, 1H), 4.12-4.10 (d, J = 8.0 Hz, 1H), 4.03 (s, 1H), 3.74-3.70 (m, 1H), 2.96-2.74 (m, 6H), 2.51 (s, 3H), 2.38-2.13 (m, 7H), 1.94-1.91 (m, 2H), 1.67-1.30 (m, 2H), 1.24 (s, 12H), 1.22-0.96 (m, 7H). | 72 |
| 623 | | 859.670 | A | | 72 |
| 624 |  | 806.595 | A | 1H NMR (300 MHz, DMSO): δ10.68(s, 1H), 7.91-7.87 (m, 1H), 7.72-7.69 (m, 2H), 7.49-7.46(m, 2H), 7.19-7.18 (m, 1H), 7.05-6.89 (m, 5H), 5.28(s, 2H), 4.57-4.52(m, 1H), 4.29 (s, 1H), 4.04-4.01 (m, 1H), 3.86-3.82 (m, 2H), 3.31- | 13B |

FIG. 7 Continued.

| | | |
|---|---|---|
| 625 | 823.590 | A<br>3.26(m, 10H), 2.80-2.72 (m, 2H), 2.61-2.57 (m, 2H), 2.19-2.17(m, 2H), 2.10-1.87 (m, 2H), 1.82-1.67 (m, 3H), 1.19 (s, 6H), 1.10 (s, 6H)<br>$^1$H NMR (300 MHz, DMSO-d6) δ 10.96 (s, 1H), 8.72 (s, 2H), 8.09 (d, J = 7.4 Hz, 1H), 7.84 (d, J = 8.8 Hz, 1H), 7.60 (d, J = 8.4 Hz, 1H), 7.37 (d, J = 2.4 Hz, 1H), 7.14-7.12 (m, 1H), 7.04 – 7.01 (m, 1H),6.98-6.88(m,1H), 5.13-5.05 (m, 1H), 4.74 (d, J = 11.8 Hz,3H), 4.53 (s, 1H), 4.42-4.36 (m, 1H), 4.28-4.22 (m, 1H), 3.77 (s, 1H), 3.62 (t, J = 8.0 Hz, 1H), 2.89 (t, J = 12.9 Hz, 4H),2.62- 2.57 (m ,1H), 2.43-2.35 (m, 3H), 2.28- 2.12 (m, 6H), 2.08-1.79 (m, 5H), 1.77-1.38 (m, 5H), 0.90 (d, J = 6.5 Hz, 8H). |

COMPOUNDS AND METHODS FOR THE TARGETED DEGRADATION OF ANDROGEN RECEPTOR

CROSS-REFERENCE TO RELATED APPLICATIONS

This application is a continuation of U.S. patent application Ser. No. 16/577,901, filed 20 Sep. 2019, now U.S. Pat. No. 10,844,021, which is a divisional of U.S. patent application Ser. No. 15/730,728, filed 11 Oct. 2017, now U.S. Pat. No. 10,584,101, which claims priority to, and the benefit of, U.S. Provisional Application No. 62/528,385, filed 3 Jul. 2017, and U.S. Provisional Application No. 62/406,888, filed 11 Oct. 2016, each of which is incorporated by reference herein in its entirety for all purposes.

STATEMENT REGARDING FEDERALLY FUNDED RESEARCH

This invention was made with government support under grant number 1R44CA203199-01 awarded by the National Institutes of Health. The government has certain rights in the invention.

INCORPORATION BY REFERENCE

U.S. patent application Ser. No. 14/686,640, filed on Apr. 14, 2015, published as U.S. Patent Application Publication No. 2016/0058872; U.S. patent application Ser. No. 14/792,414, filed on Jul. 6, 2015, published as U.S. Patent Application Publication No. 2015/0291562; U.S. patent application Ser. No. 14/371,956, filed on Jul. 11, 2014, published as U.S. Patent Application Publication No. 2014/0356322; U.S. patent application Ser. No. 15/074,820, filed on Mar. 18, 2016, published as U.S. Patent Application Publication No. 2016/0272639, are incorporated herein in their entireties. Furthermore, all references cited herein are incorporated by reference herein in their entirety.

FIELD OF THE INVENTION

The present description provides imide-based compounds, including bifunctional compounds comprising the same, and associated methods of use. The bifunctional compounds are useful as modulators of targeted ubiquitination, especially with respect to a variety of polypeptides and other proteins, which are degraded and/or otherwise inhibited by bifunctional compounds according to the present disclosure. In certain aspects, the bifunctional compounds comprise a Cereblon E3 Ubiquitin Ligase (CRBN) binding moiety, which binds to the cereblon E3 ubiquitin ligase, a target protein binding moiety, which binds to the target protein (e.g., androgen receptor), and optionally a linker moiety which links the cereblon binding moiety and target protein binding moiety. These compounds work in such a way that the target protein/polypeptide is placed in proximity to the ubiquitin ligase to effect degradation (and inhibition) of that protein (e.g., androgen receptor).

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are know in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases, but the field remains underdeveloped.

One E3 ligase with therapeutic potential is Cereblon, a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Thalidomide, which has been approved for the treatment of a number of immunological indications, has also been approved for the treatment of certain neoplastic diseases, including multiple myeloma. In addition to multiple myeloma, thalidomide and several of its analogs are also currently under investigation for use in treating a variety of other types of cancer. While the precise mechanism of thalidomide's anti-tumor activity is still emerging, it is known to inhibit angiogenesis. Recent literature discussing the biology of the imides includes Lu et al. *Science* 343, 305 (2014) and Krönke et al. *Science* 343, 301 (2014).

Significantly, thalidomide and its analogs e.g. pomolinamiode and lenalinomide, are known to bind cereblon. These agents bind to cereblon, altering the specificity of the complex to induce the ubiquitination and degradation of Ikaros (IKZF1) and Aiolos (IKZF3), transcription factors essential for multiple myeloma growth. Indeed, higher expression of cereblon has been linked to an increase in efficacy of imide drugs in the treatment of multiple myeloma.

Androgen Receptor (AR) belongs to a nuclear hormone receptor family that is activated by androgens, such as testosterone and dihydrotestosterone (*Pharmacol. Rev.* 2006, 58(4), 782-97; *Vitam. Horm.* 1999, 55:309-52). In the absence of androgens, AR is bound by Heat Shock Protein 90 (Hsp90) in the cytosol. When an androgen binds AR, its conformation changes to release AR from Hsp90 and to expose the Nuclear Localization Signal (NLS). The latter enables AR to translocate into the nucleus where AR acts as a transcription factor to promote gene expression responsible for male sexual characteristics (*Endocr. Rev.* 1987, 8(1):1-28; *Mol. Endocrinol.* 2002, 16(10), 2181-7). AR deficiency leads to Androgen Insensitivity Syndrome, formerly termed testicular feminization.

While AR is responsible for development of male sexual characteristics, it is also a well-documented oncogene in certain forms cancers including prostate cancers (*Endocr. Rev.* 2004, 25(2), 276-308). A commonly measured target gene of AR activity is the secreted Prostate Specific Antigen (PSA) protein. The current treatment regimen for prostate cancer involves inhibiting the androgen-AR axis by two methods. The first approach relies on reduction of androgens, while the second strategy aims to inhibit AR function (*Nat. Rev. Drug Discovery,* 2013, 12, 823-824). Despite the development of effective targeted therapies, most patients develop resistance and the disease progresses. An alternative approach for the treatment of prostate cancer involves eliminating the AR protein. Because AR is a critical driver of tumorigenesis in many forms of prostate cancers, its elimination should lead to therapeutically beneficial response.

There exists an ongoing need in the art for effective treatments for diseases, especially cancer, prostate cancer, and Kennedy's Disease. However, non-specific effects, and the inability to target and modulate certain classes of proteins altogether, such as transcription factors, remain as obstacles to the development of effective anti-cancer agents. As such, small molecule therapeutic agents that leverage or potentiate cereblon's substrate specificity and, at the same time, are "tunable" such that a wide range of protein classes can be targeted and modulated with specificity would be very useful as a therapeutic.

BRIEF SUMMARY OF THE INVENTION

The present disclosure describes bi-functional compounds, which function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins (such as androgen receptor), which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition including cancer, e.g., prostate cancer, and Kennedy's Disease.

Thus, in one aspect, the disclosure provides novel imide-based compounds as described herein.

In an additional aspect, the disclosure provides bifunctional or PROTAC compounds, which comprise an E3 Ubiqutin Ligase binding moiety (i.e. a ligand for an E3 Ubiquitin Ligase or "ULM" group), and a moiety that binds a target protein (i.e. a protein/polypeptide targeting ligand or "PTM" group) such that the target protein/polypeptide is placed in proximity to the ubiquitin ligase to effect degradation (and inhibition) of that protein. In a proffered embodiment the ULM is a cereblon E3 Ubiquitin Ligase binding moiety (i.e. a "CLM"). For example, the structure of the bifunctional compound can be depicted as:

PTM-CLM.

The respective positions of the PTM and CLM moieties as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments the bifunctional compound may further comprise a chemical linker ("L"). In this example, the structure of the bifunctional compunds can be depicted as:

PTM-L-CLM, wherein the PTM is a protein/polypeptide targeting moiety, the L is a chemical linker moiety or bond that links the PTM and the CLM, and the CLM is a cereblon E3 ubiquitin ligase binding moiety.

In certain preferred embodiments, the E3 Ubiquitin Ligase is cereblon. As such, in certain additional embodiments, the CLM of the bifunctional compound comprises chemistries such as imide, amide, thioamide, thioimide derived moieties. In additional embodiments, the CLM comprises a phthalimido group or an analog or derivative thereof. In still additional embodiments, the CLM comprises a phthalimido-glutarimide group or an analog or derivative thereof. In still other embodiments, the CLM comprises a member of the group consisting of thalidomide, lenalidomide, pomalidomide, and analogs or derivatives thereof.

In certain embodiments, the compounds as described herein comprise multiple CLMs, multiple PTMs, multiple chemical linkers or a combination thereof.

It will be understood that the general structures are exemplary and the respective moieties can be arranged spatially in any desired order or configuration, e.g., CLM-L-PTM, and PTM-L-CLM respectively.

In certain embodiments, the PTM is an AR binding moieties (ABM). In particular embodiments, the ABM is selected from following structures:

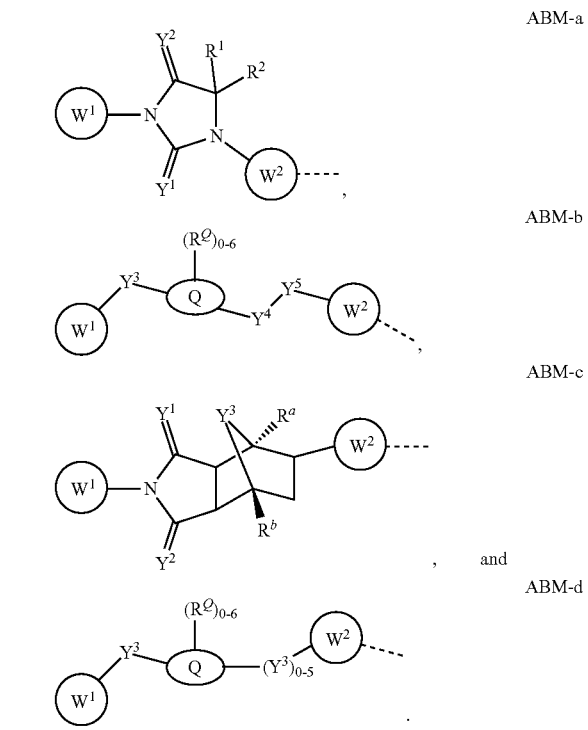

wherein:
W$^1$ is aryl, heteroaryl, bicyclic, or biheterocyclic, each independently substituted by 1 or more H, halo, hydroxyl, nitro, CN, C≡CH, C$_{1-6}$ alkyl (linear, branched, optionally substituted; for example, optionally substituted by 1 or more halo, $C_{1-6}$ alkoxyl), $C_{1-6}$ alkoxyl (linear, branched, optionally substituted; for example, optionally substituted by by 1 or more halo), $C_{2-6}$ alkenyl, $C_{2-6}$ alkynyl, or $CF_3$;

$Y^1$, $Y^2$ are each independently $NR^{Y1}$, O, S;

$Y^3$, $Y^4$, $Y^5$ are each independently a bond, O, $NR^{Y2}$, $CR^{Y1}R^{Y2}$, C=O, C=S, SO, $SO_2$, heteroaryl, or aryl;

Q is a 3-6 membered alicyclic or aromatic ring with 0-4 heteroatoms, optionally substituted with 0-6 $R^Q$, each $R^Q$, is independently H, $C_{1-6}$ alkyl (linear, branched, optionally substituted; for example, optionally substituted by 1 or more halo, $C_{1-6}$ alkoxyl), halogen, $C_{1-6}$ alkoxy, or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted; for example, optionally substituted by 1 or more halo, $C_{1-6}$ alkoxyl), halogen, $C_{1-6}$ alkoxy, cyclic, heterocyclic, or $R^1$, $R^2$ together with the atom they are attached to, form a 3-8 membered ring system containing 0-2 heteroatoms);

$W^2$ is a bond, $C_{1-6}$ alkyl, $C_{1-6}$ heteroalkyl, O, $C_{1-6}$ alicyclic, heterocyclic, aryl, heteroaryl, biheterocyclic, biaryl, or biheteroaryl, each optionally substituted by 1-10 $R^{W2}$;

each $R^{W2}$ is independently H, halo, $C_{1-6}$ alkyl (linear, branched, optionally substituted; for example, optionally substituted by 1 or more F), $C_{1-6}$ heteroalkyl (linear, branched, optionally substituted), $-OR^{W2A}$, $C_{3-6}$ cycloalkyl, $C_{4-6}$ cycloheteroalkyl, $OC_{1-3}$alkyl (optionally substituted; for example, optionally substituted by 1 or more —F), $C_{1-6}$ alicyclic (optionally substituted), heterocyclic (optionally substituted), aryl (optionally substituted), or heteroaryl (optionally substituted), bicyclic heretoaryl or aryl, OH, $NH_2$, $NR^{Y1}R^{Y2}$, CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation and/or inhibition of proteins of interest for the treatment or amelioration of a disease, e.g., cancer. In yet another aspect, the present disclosure provides a method of ubiquitinating/ degrading a target protein in a cell. In certain embodiments, the method comprises administering a bifunctional compound as described herein comprising an CLM and a PTM, preferably linked through a linker moiety, as otherwise described herein, wherein the CLM is coupled to the PTM and wherein the CLM recognizes a ubiquitin pathway protein (e.g., a ubiquitin ligase, preferably an E3 ubiquitin ligase such as cereblon) and the PTM recognizes the target protein such that degradation of the target protein will occur when the target protein is placed in proximity to the ubiquitin ligase, thus resulting in degradation/inhibition of the effects of the target protein and the control of protein levels.

The control of protein levels afforded by the present disclosure provides treatment of a disease state or condition, which is modulated through the target protein by lowering the level of that protein in the cells of a patient.

In an additional aspect, the description provides a method for assessing (i.e., determining and/or measuring) a CLM's binding affinity. In certain embodiments, the method comprises providing a test agent or compound of interest, for example, an agent or compound having an imide moiety, e.g., a phthalimido group, phthalimido-glutarimide group, derivatized thalidomide, derivatized lenalidomide or derivatized pomalidomide, and comparing the cereblon binding affinity and/or inhibitory activity of the test agent or compound as compared to an agent or compound known to bind and/or inhibit the activity of cereblon.

In still another aspect, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present disclosure. The publications and other materials used herein to illuminate the background of the invention, and in particular cases, to provide additional details respecting the practice, are incorporated by reference.

Where applicable or not specifically disclaimed, any one of the embodiments described herein are contemplated to be able to combine with any other one or more embodiments, even though the embodiments are described under different aspects of the disclosure. As such, the preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional advantages objects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the present disclosure. The drawings are only for the purpose of illustrating an embodiment of the disclosure and are not to be construed as limiting the invention. Further objects, features and advantages of the invention will become apparent from the following detailed description taken in conjunction with the accompanying figures showing illustrative embodiments of the disclosure, in which:

FIG. 1A: Exemplary PROTACs comprise an androgen receptor targeting moiety (ABM; darkly shaded rectangle), a E3 ubiquitin Ligase binding moiety, such as a cereblon E3 ubiquitin ligase binding moiety (CLM; lightly shaded triangle), and a linker moiety (L; black line) coupling or tethering the ABM to the CLM (as described herein, L can be absent or a bond or a chemical linker moiety). FIG. 1B Illustrates the functional use of the PROTACs as described herein. Briefly, the CLM recognizes and binds to cereblon E3 ubiquitin ligase, and the ABM binds and recruits androgen receptor and brings it into close proximity to the cereblon E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
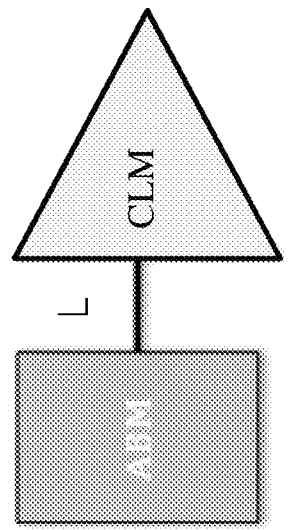
FIG. 1A and FIG. 1B. Illustration of general principle for PROTAC function.
Figure 1B:
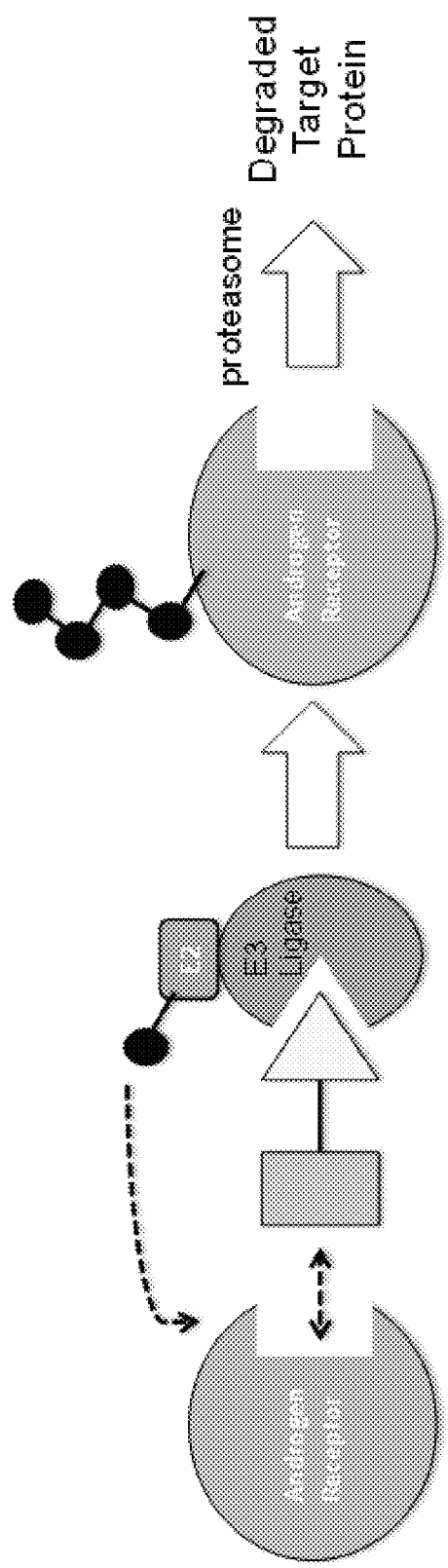
Figure 2:
FIG. 2. Table 2 that include Exemplary Compounds 1-75, as well as the General Scheme that may be used to produce each of the Exemplary Compounds. Table 2 also includes the DC50, Dmax, M/Z+, and 1H NMR data for each of the Exemplary Compounds. DC50 (µM) categories (degradation of AR ELISA in LNCaP and/or VCaP cells): A<1 nM; B: 1-10 nM; C: 10-100 nM; D: >100 nM. Dmax categories (degradation of AR-maximum inhibition (%) AR ELISA in LNCaP and/or VCaP cells): A>50%; B<50%.
Figure 2:
Figure 2:

Figure 2:

Figure 2:

Figure 2:

Figure 2:

Figure 2:

Figure 2:
Figure 2:
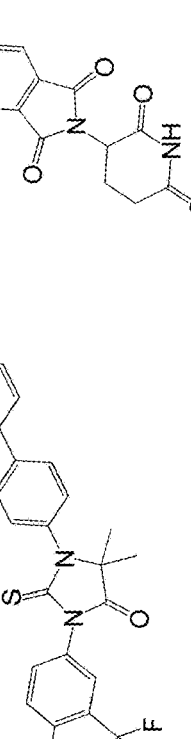
Figure 2:
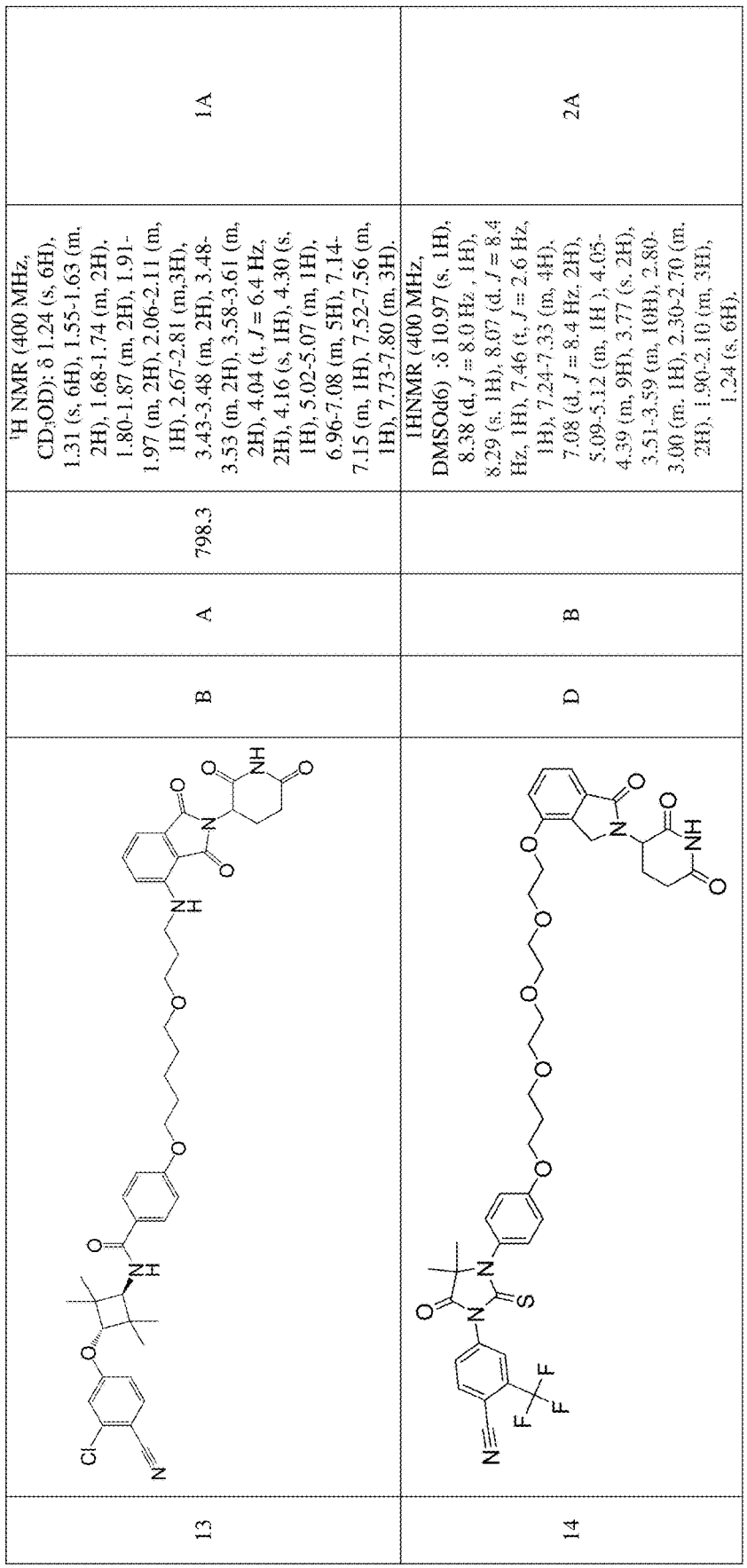
Figure 2:
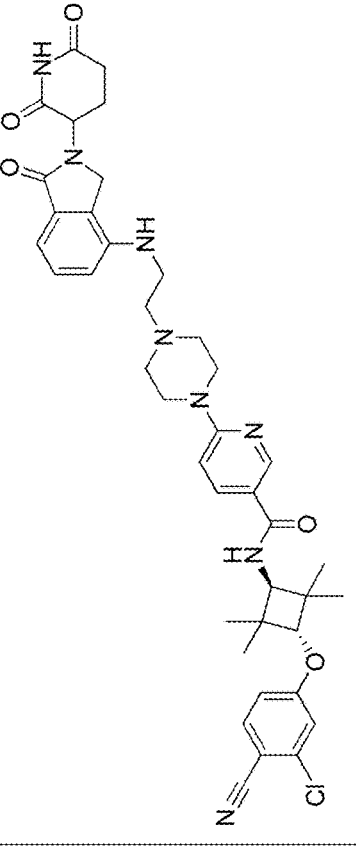
Figure 2:
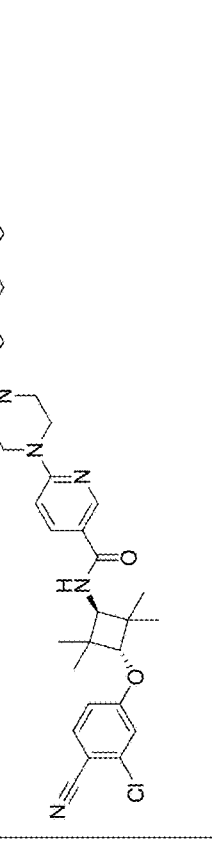
Figure 2:
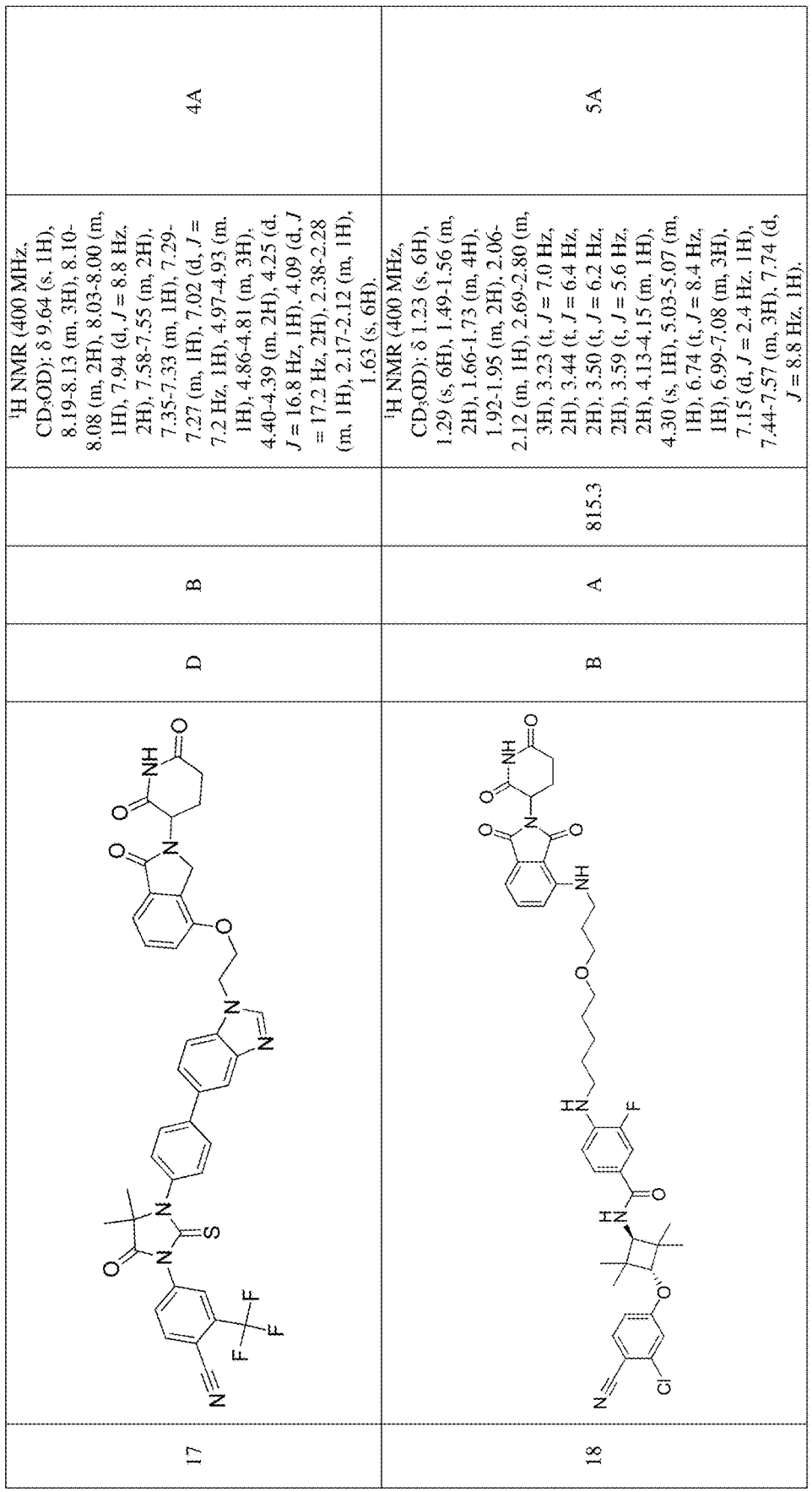
Figure 2:
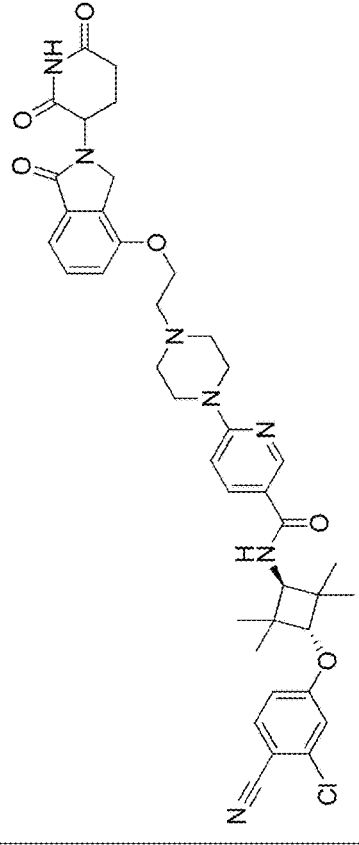
Figure 2:
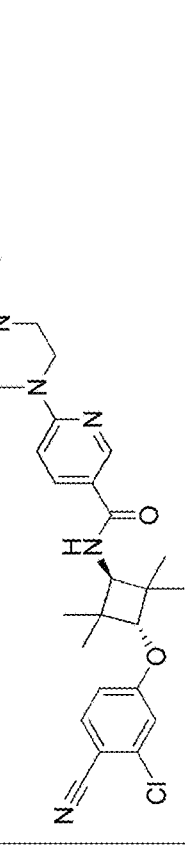
Figure 2:
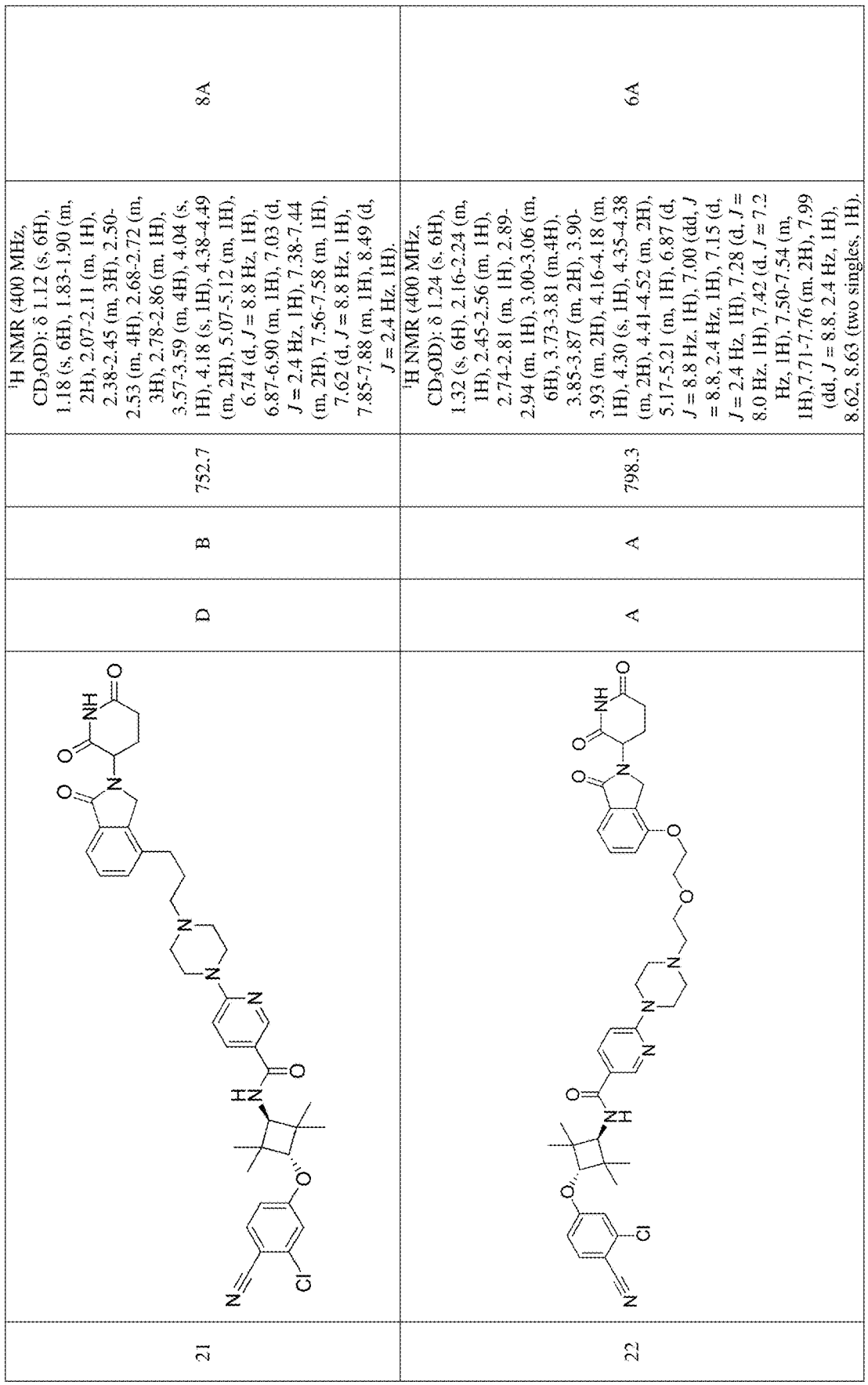
Figure 2:
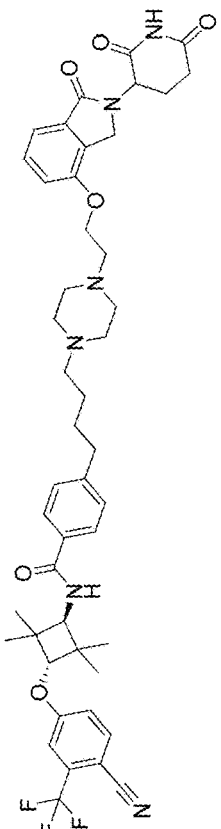
Figure 2:
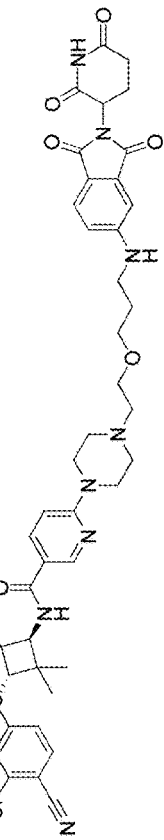
Figure 2:
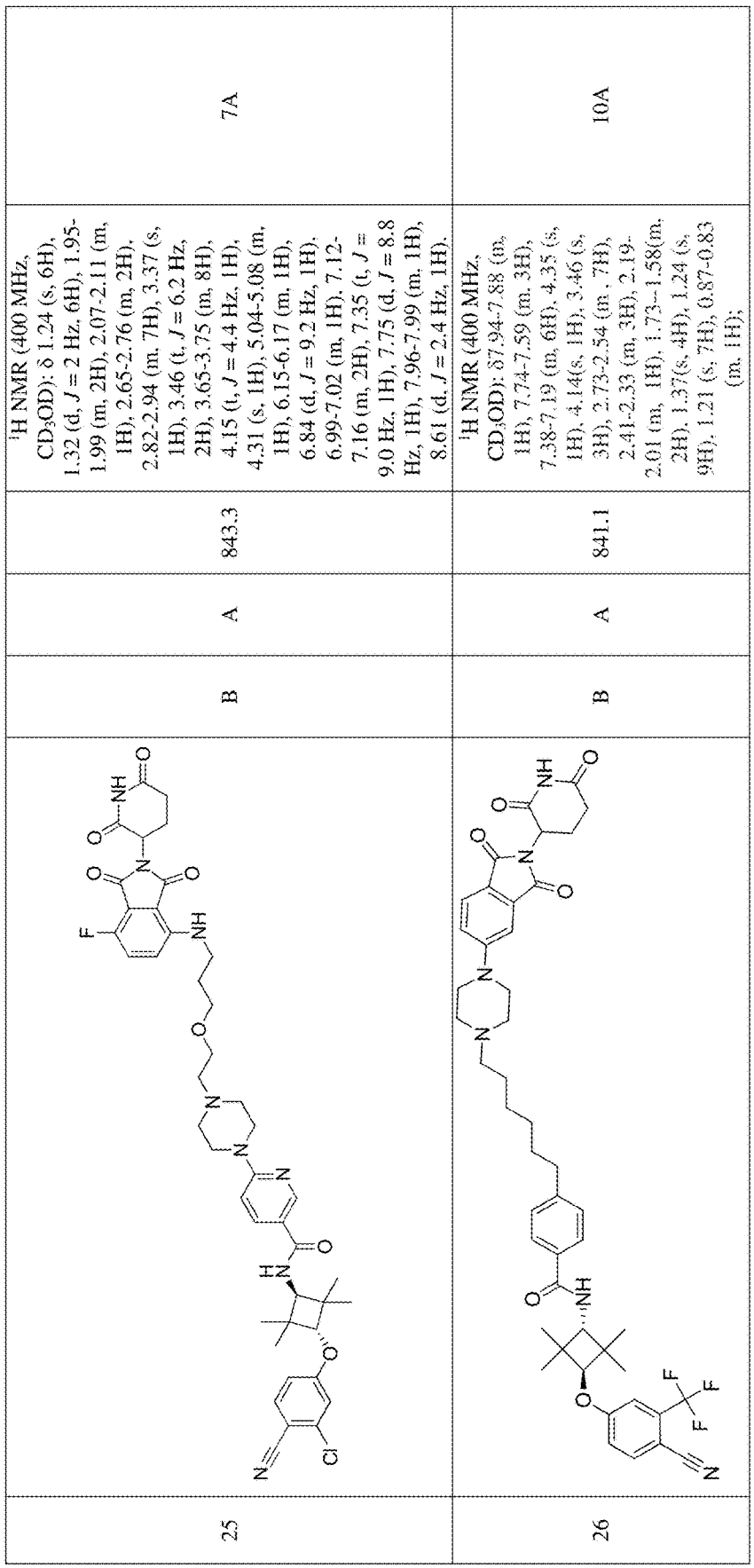
Figure 2:
Figure 2:
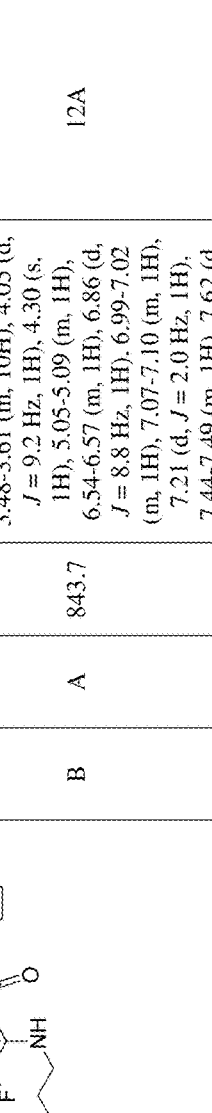
Figure 2:
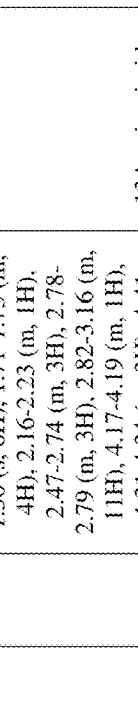
Figure 2:
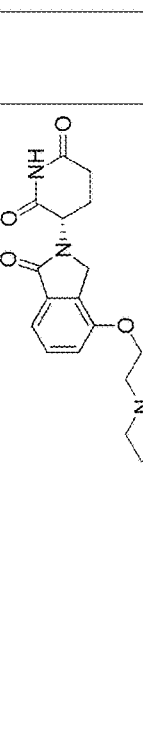
Figure 2:
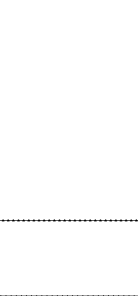
Figure 2:
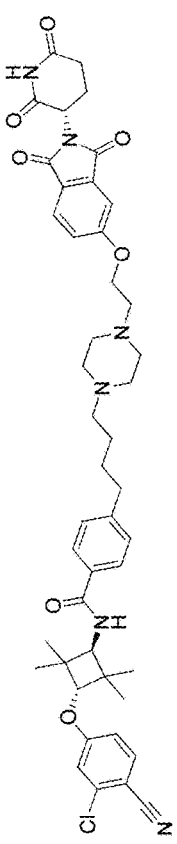
Figure 2:
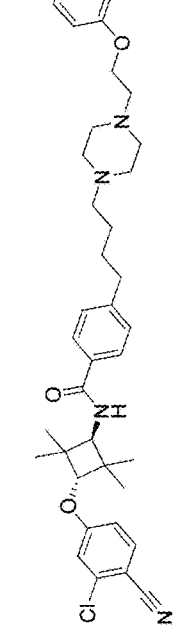
Figure 2:
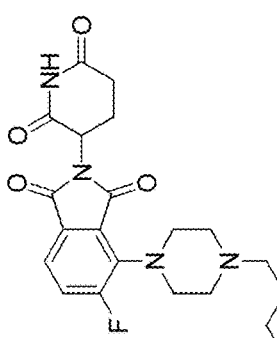
Figure 2:
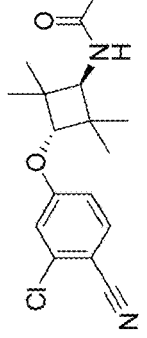
Figure 2:
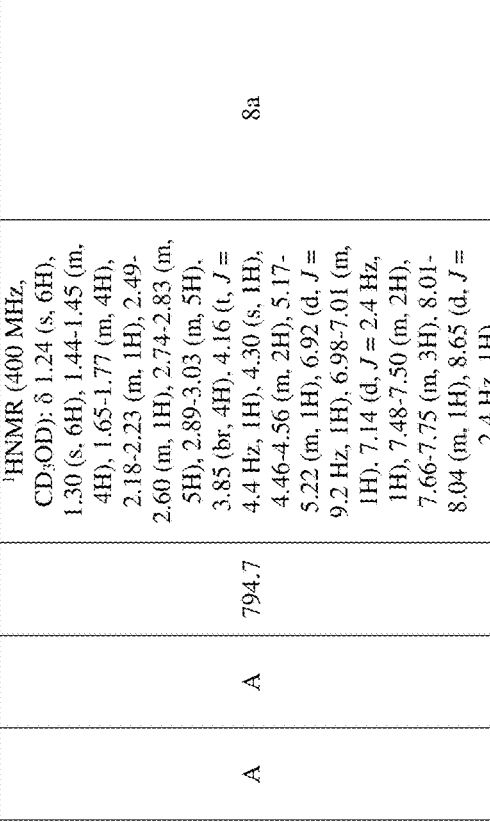
Figure 2:
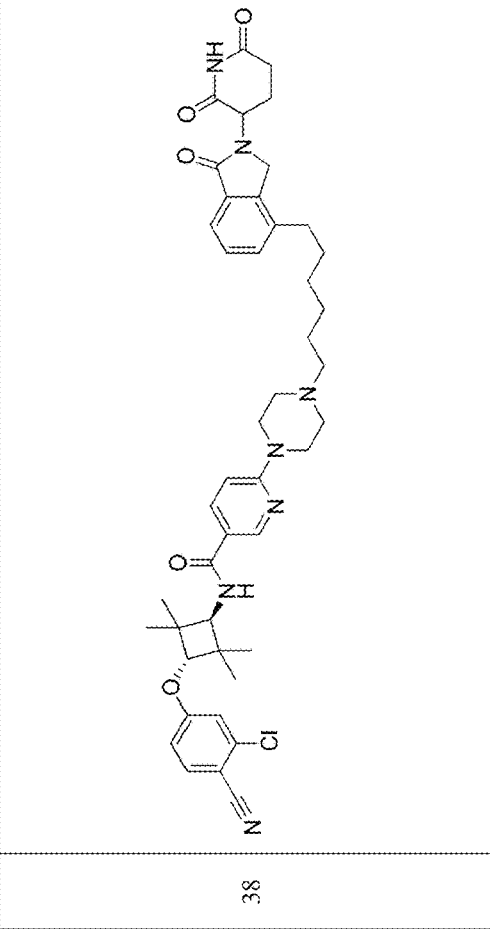
Figure 2:

Figure 2:

Figure 2:
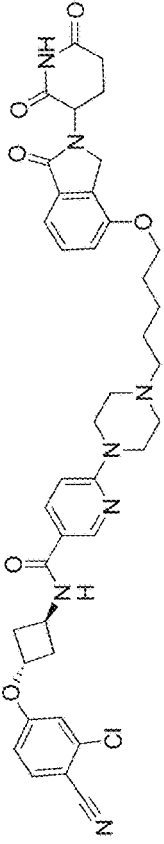
Figure 2:
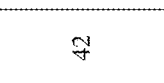
Figure 2:
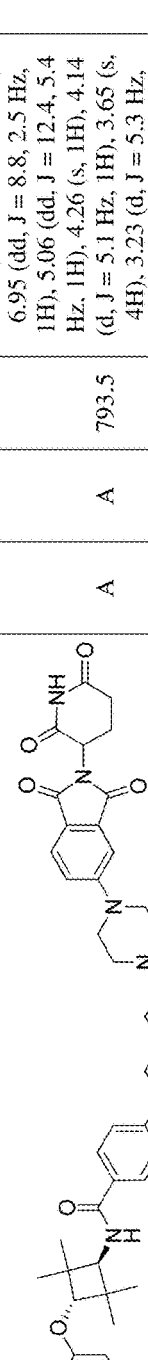
Figure 2:
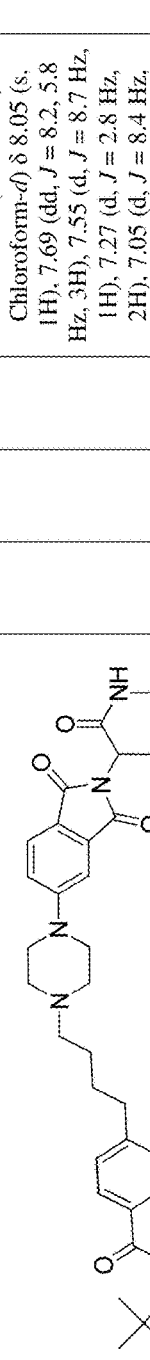
Figure 2:
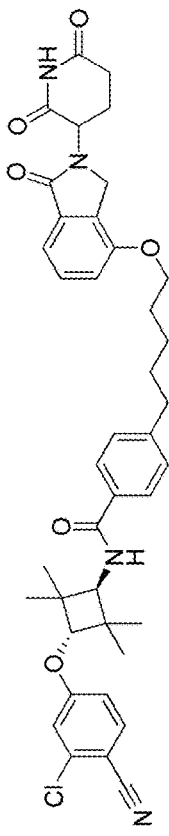
Figure 2:
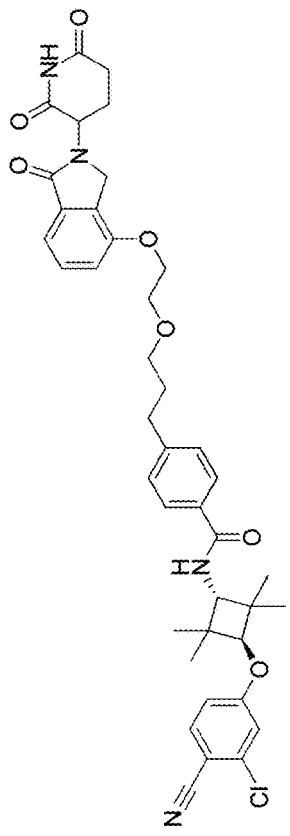
Figure 2:
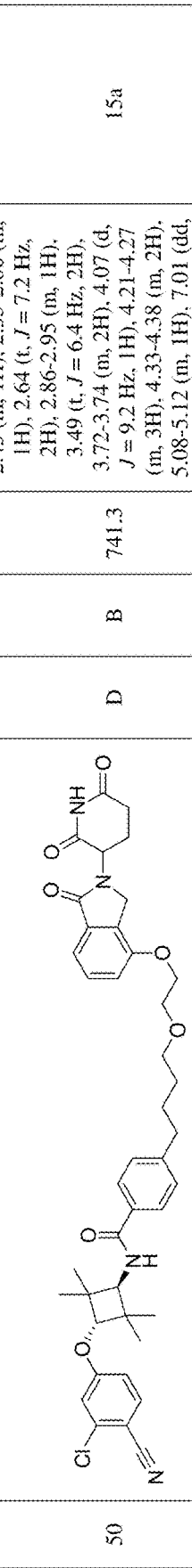
Figure 2:
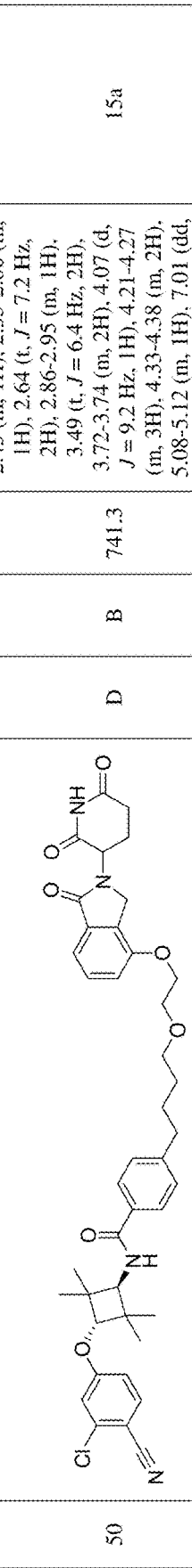
Figure 2:

Figure 2:

Figure 2:

Figure 2:

Figure 2:
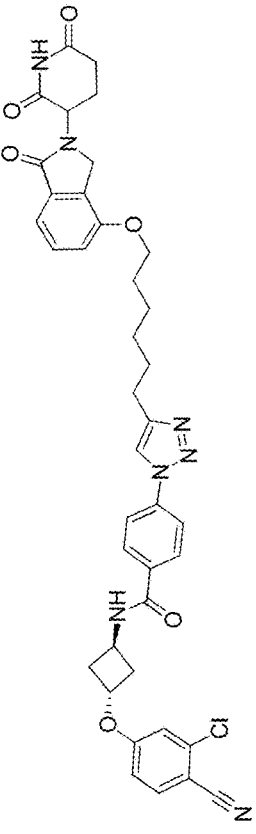
Figure 2:
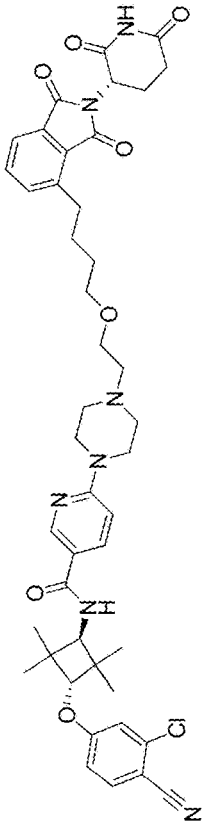
Figure 2:
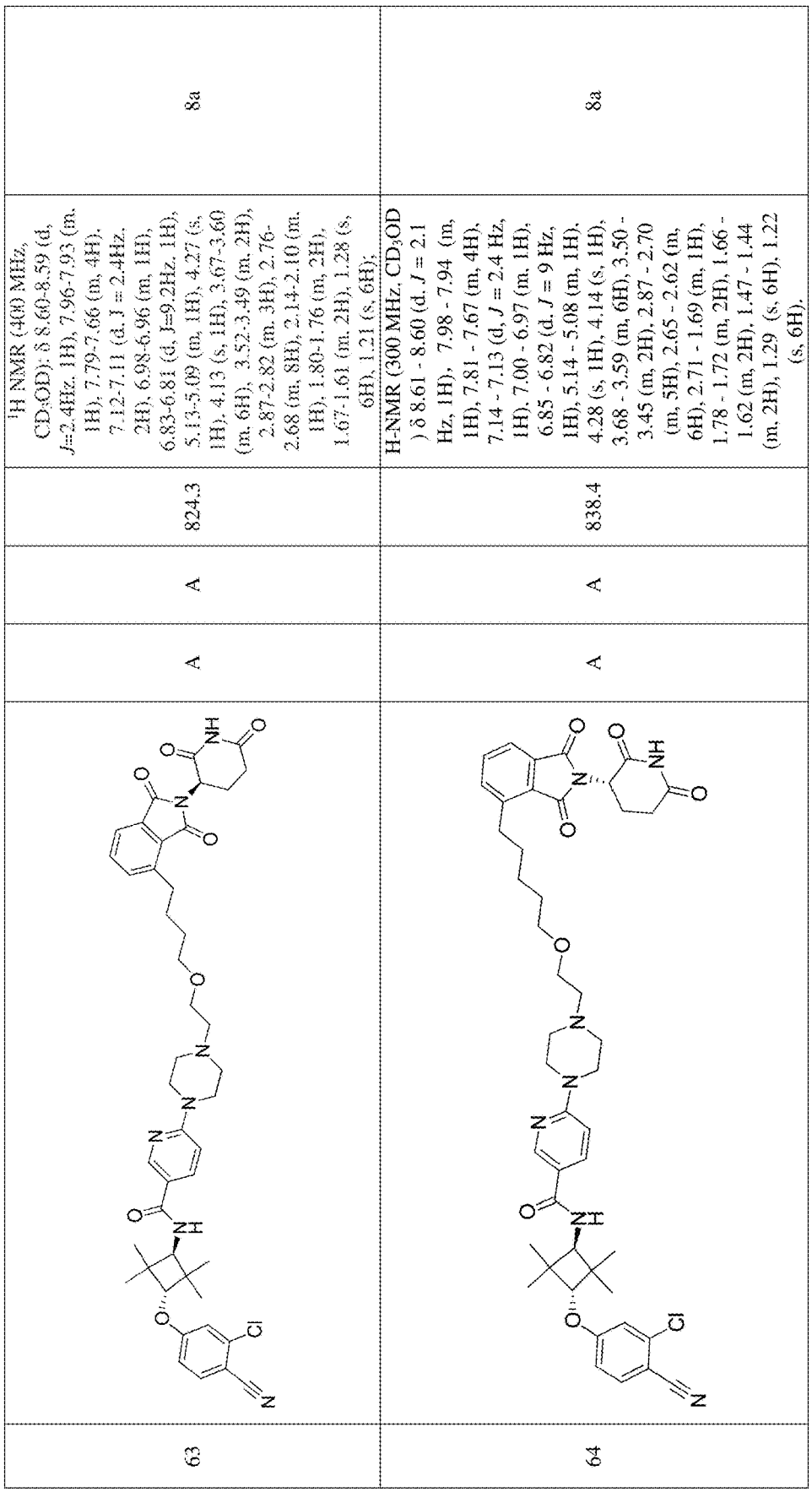
Figure 2:

Figure 2:

Figure 2:
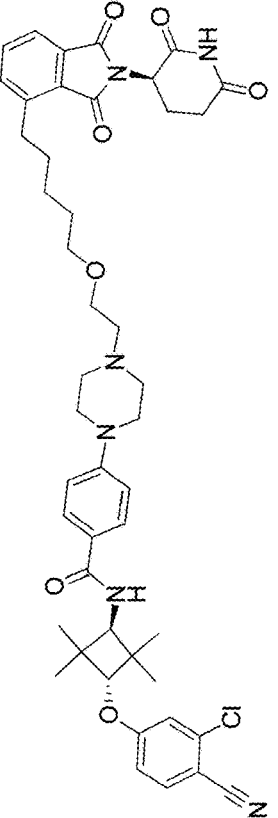
Figure 2:

Figure 2:
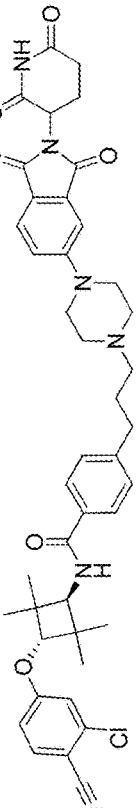
Figure 2:
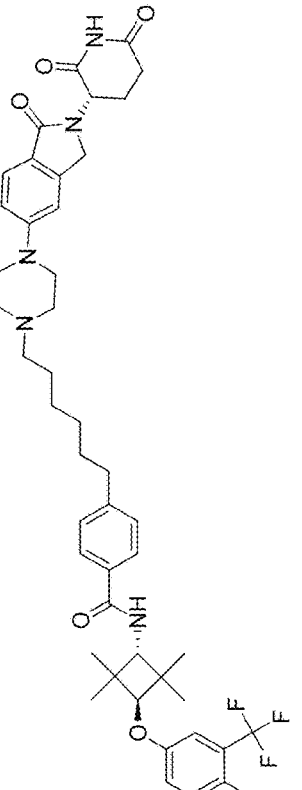
Figure 2:
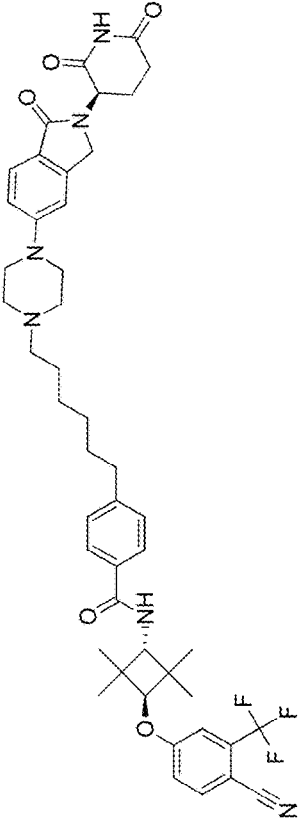
Figure 2:
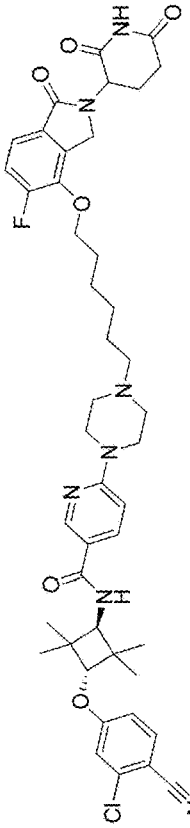
Figure 3:
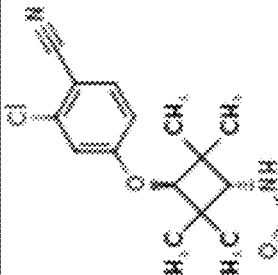
FIG. 3. Table 3 that include Exemplary Compounds 76-398, as well as the General Scheme that may be used to produce each of the Exemplary Compounds. Table 3 also includes the DC50, M/Z+, and 1H NMR data for each of the Exemplary Compounds. DC50 (µM) categories (degradation of AR ELISA in LNCaP and/or VCaP cells): A<1 nM; B: 1-10 nM; C: 10-100 nM; D: >100 nM.
Figure 3:
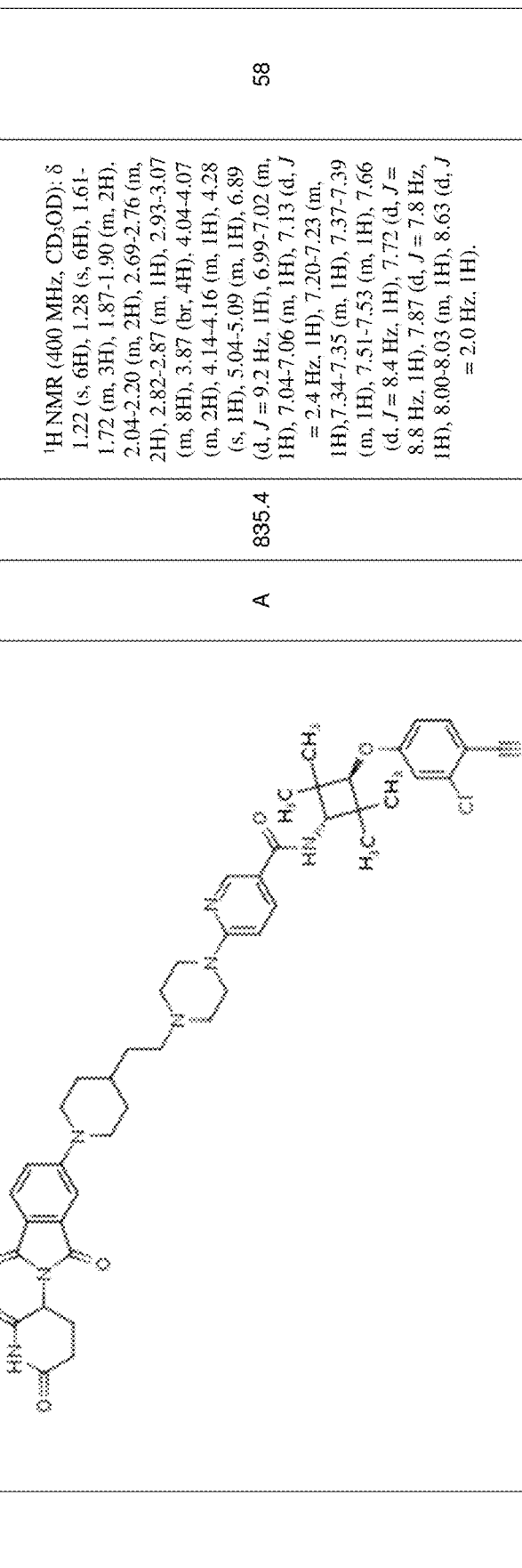
Figure 3:
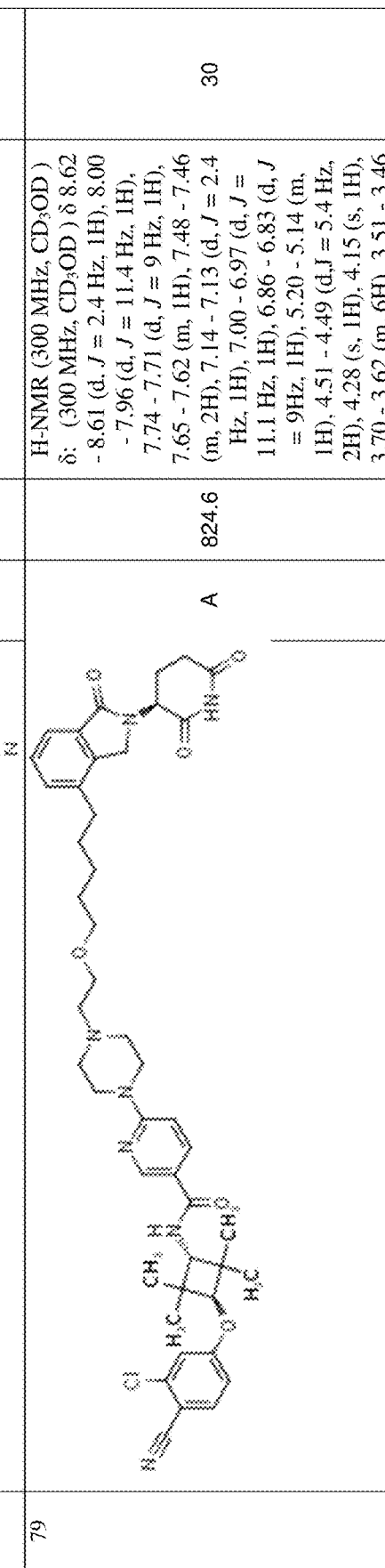
Figure 3:
Figure 3:
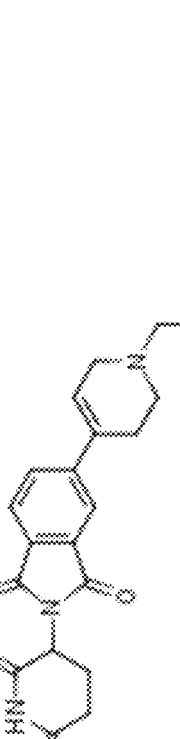
Figure 3:
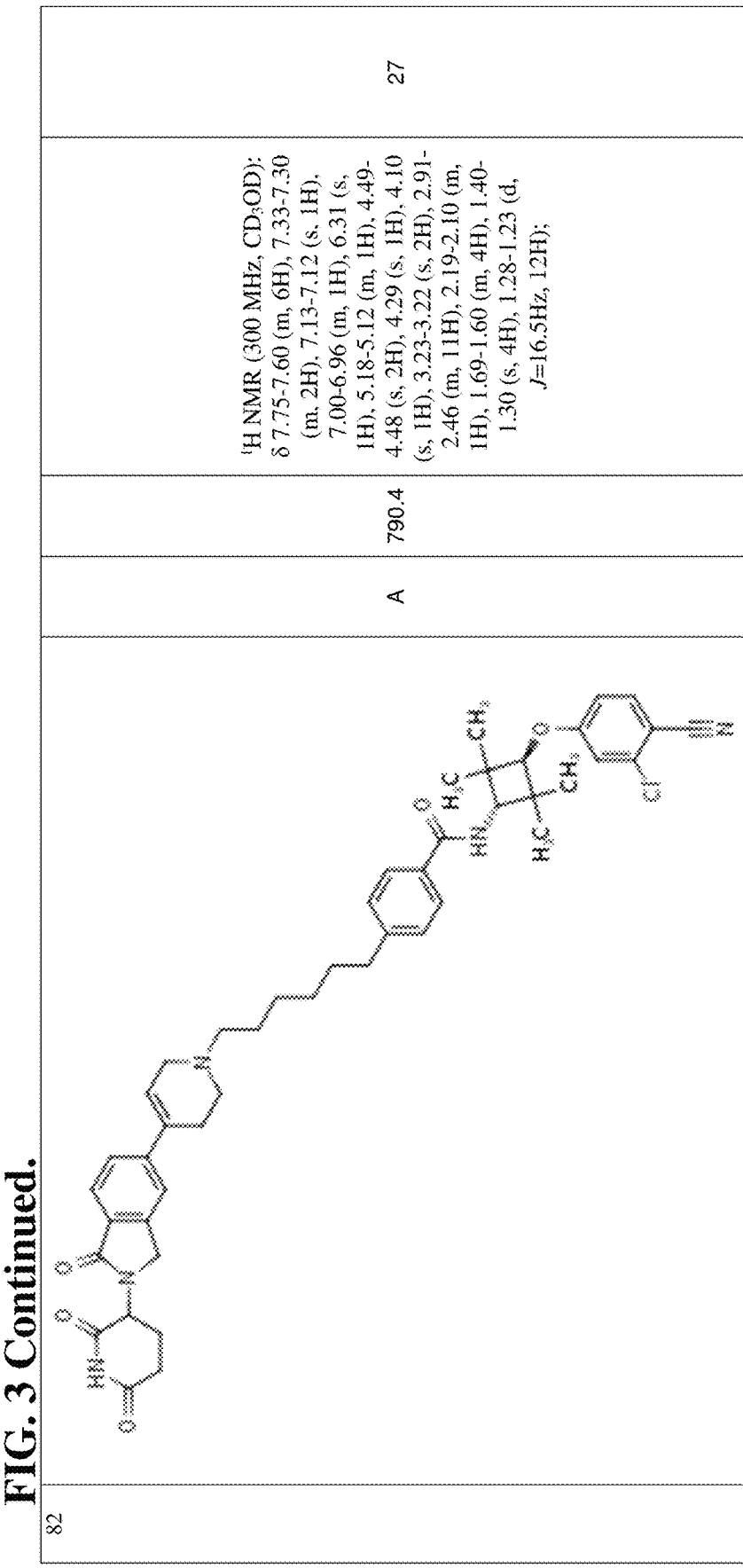
Figure 3:
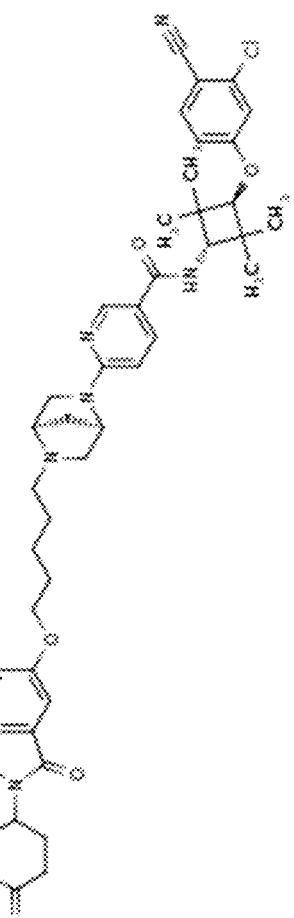
Figure 3:
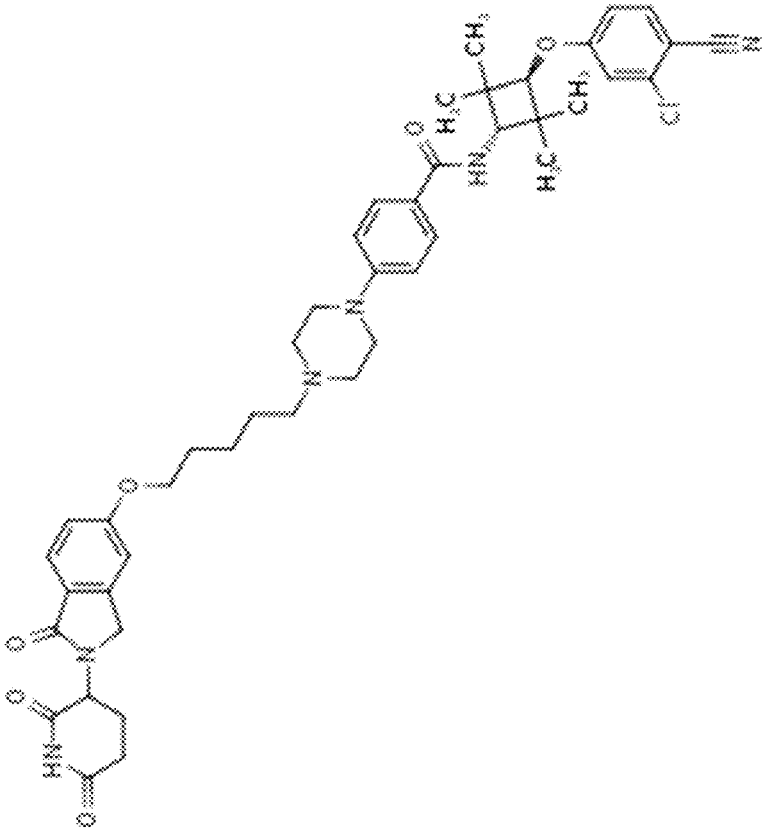
Figure 3:
Figure 3:
Figure 3:
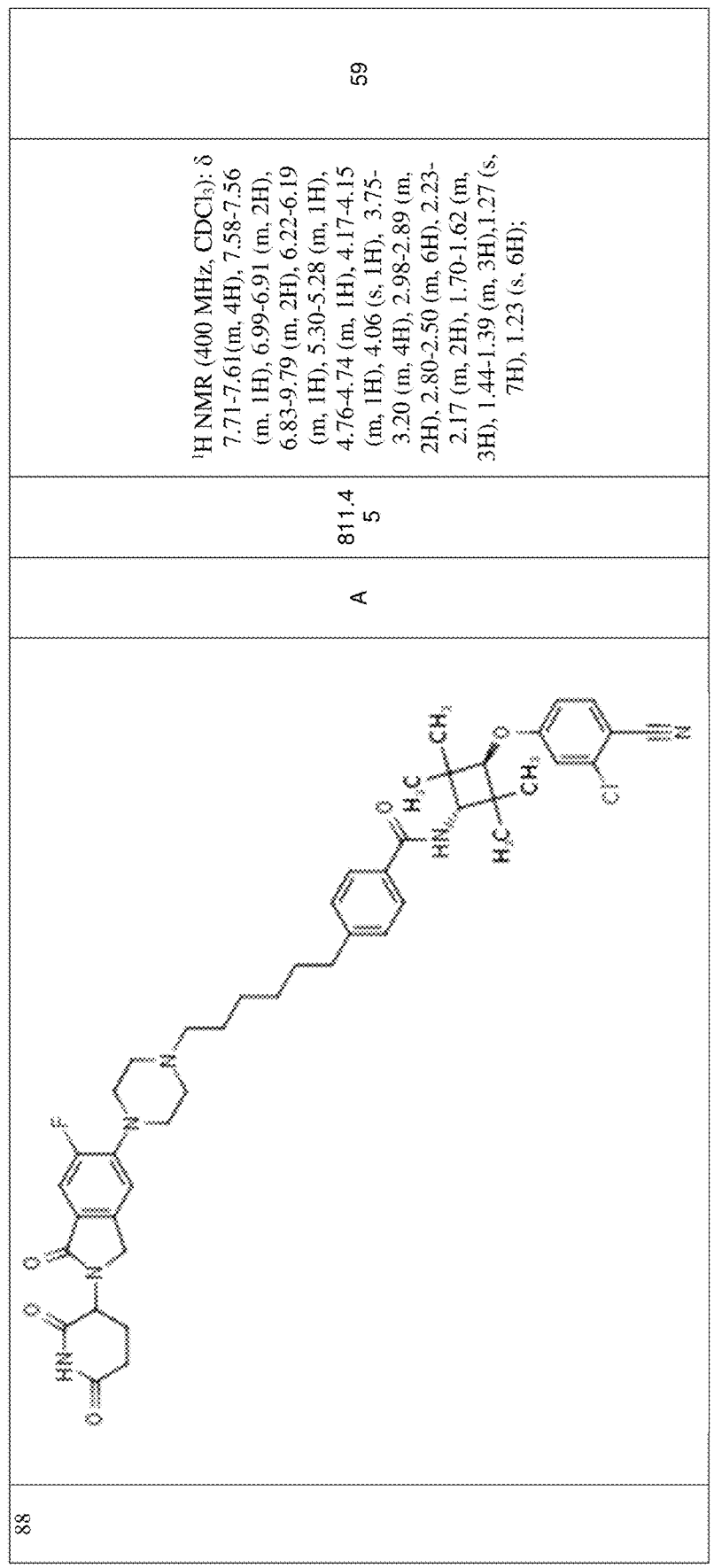
Figure 3:
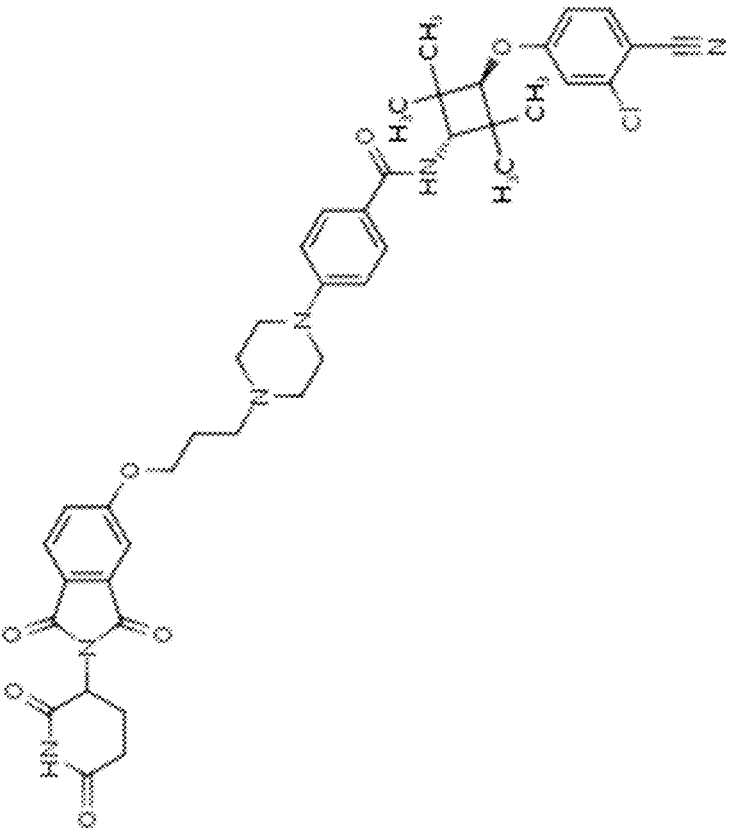
Figure 3:
Figure 3:
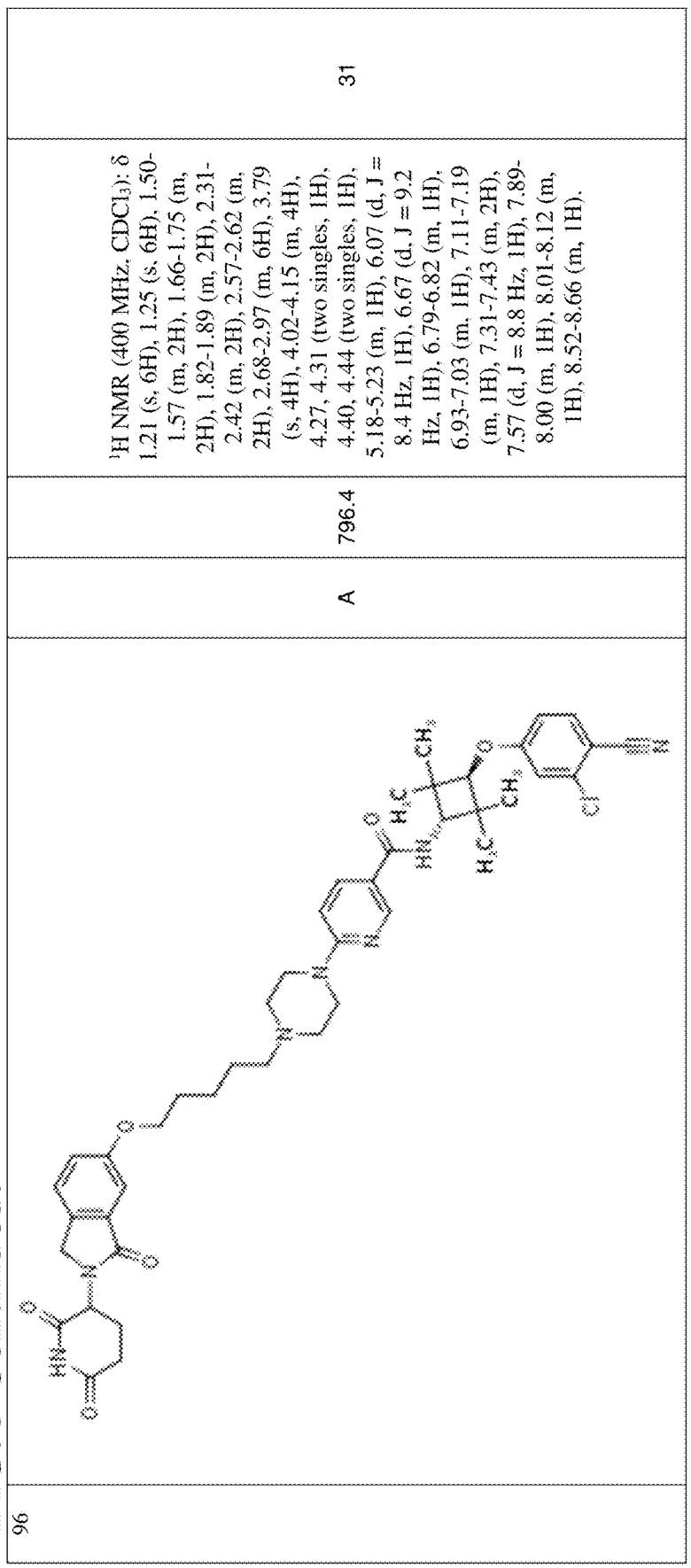
Figure 3:
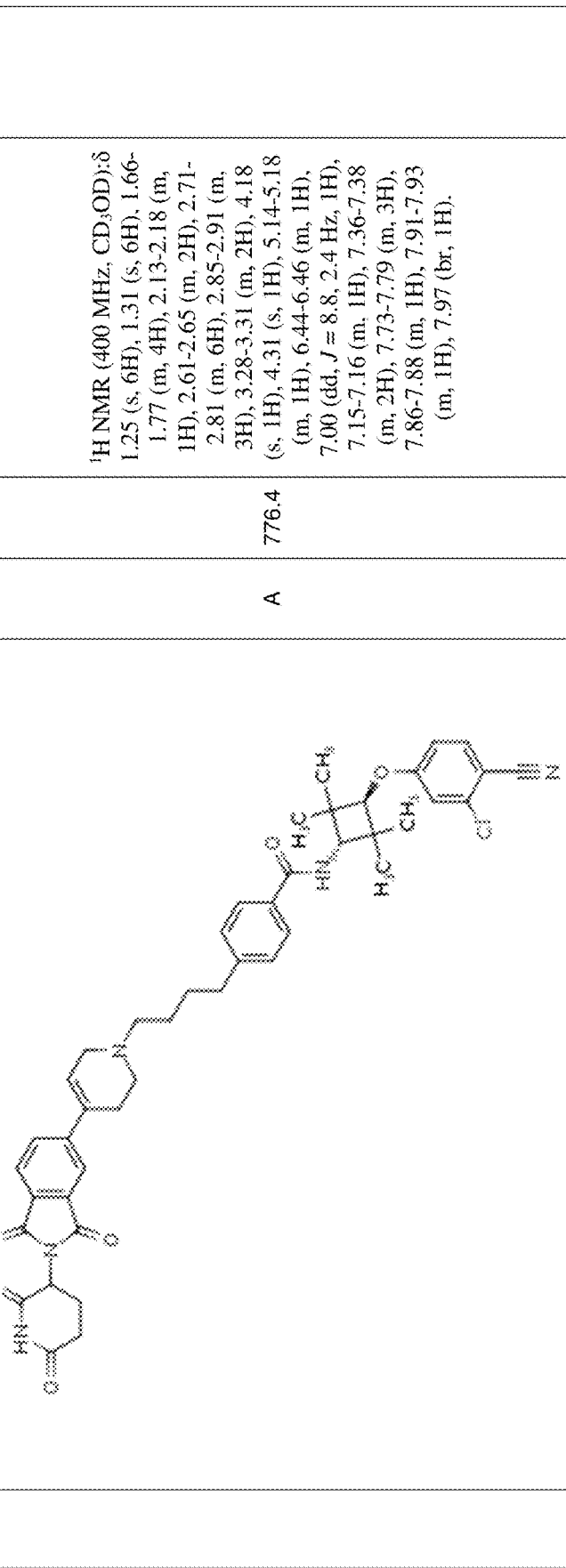
Figure 3:
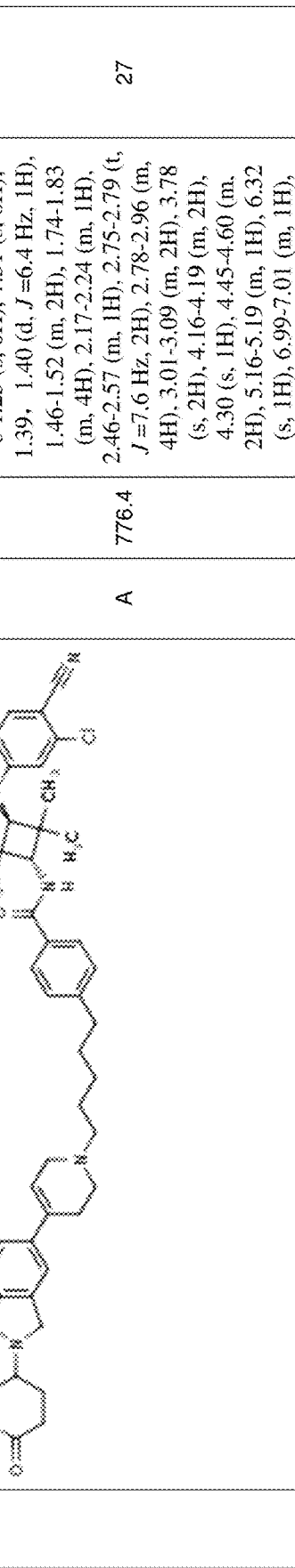
Figure 3:
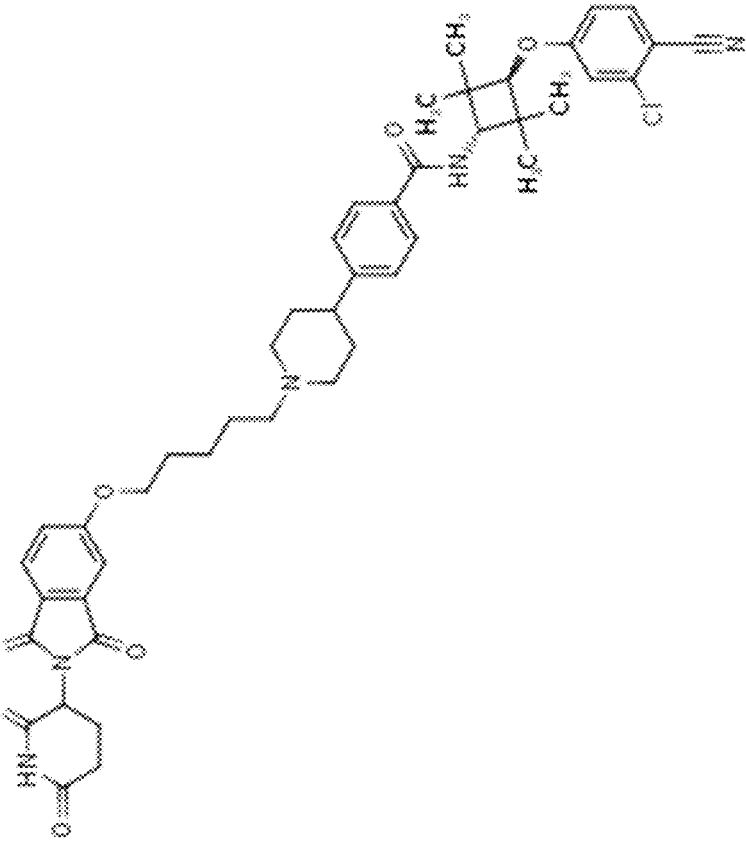
Figure 3:
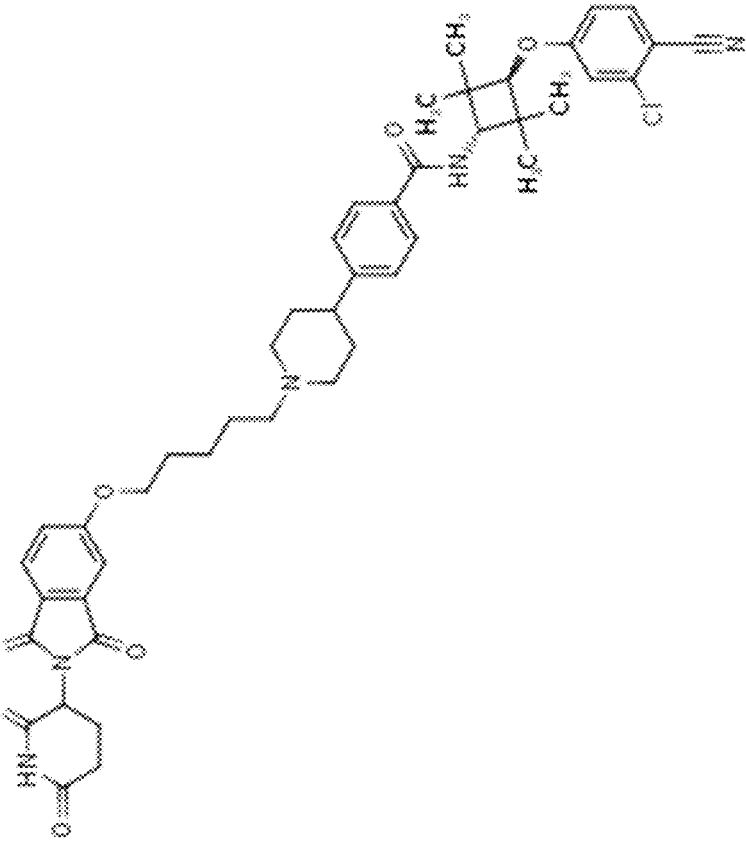
Figure 3:
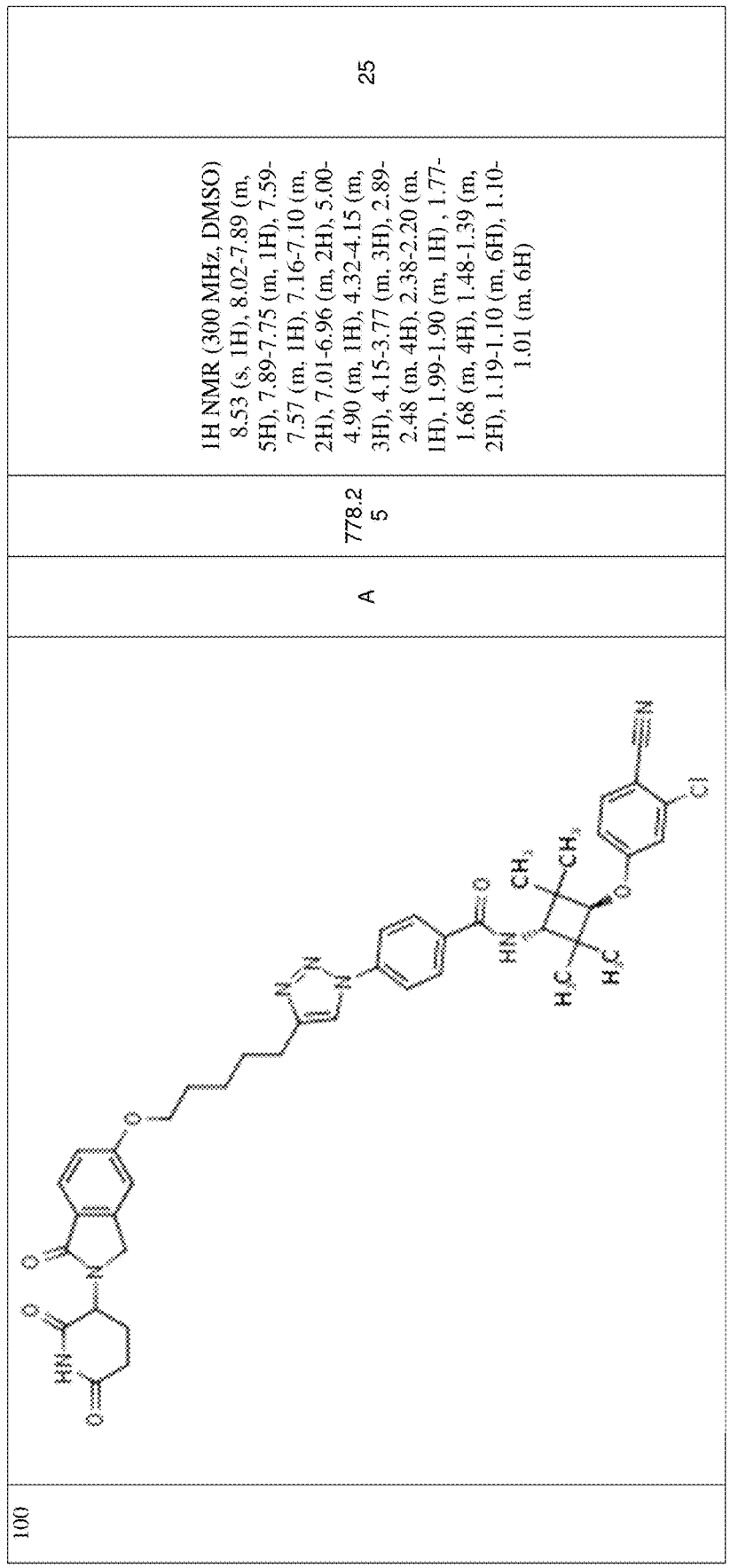
Figure 3:
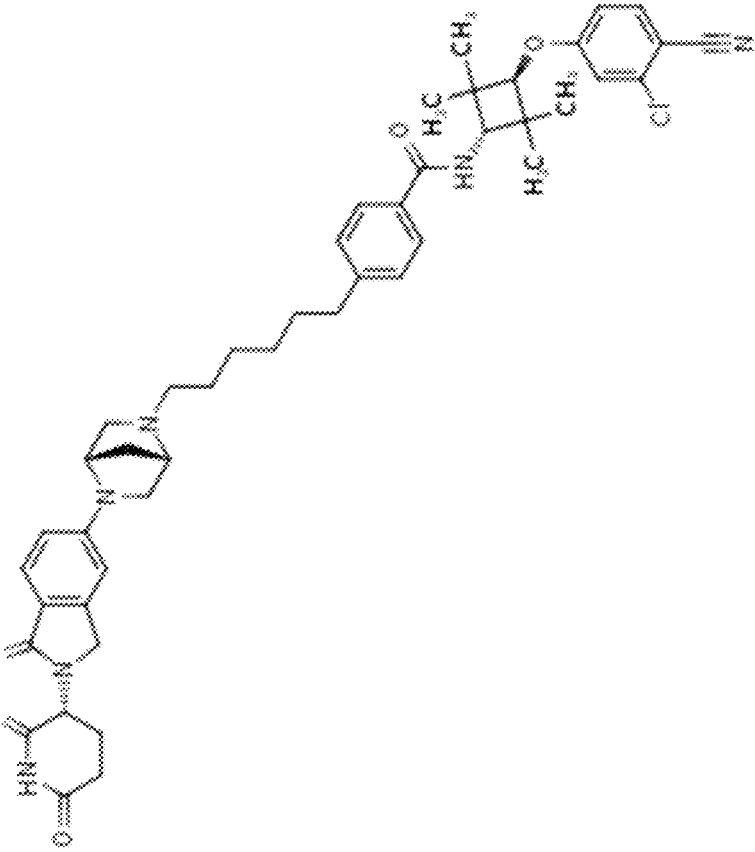
Figure 3:
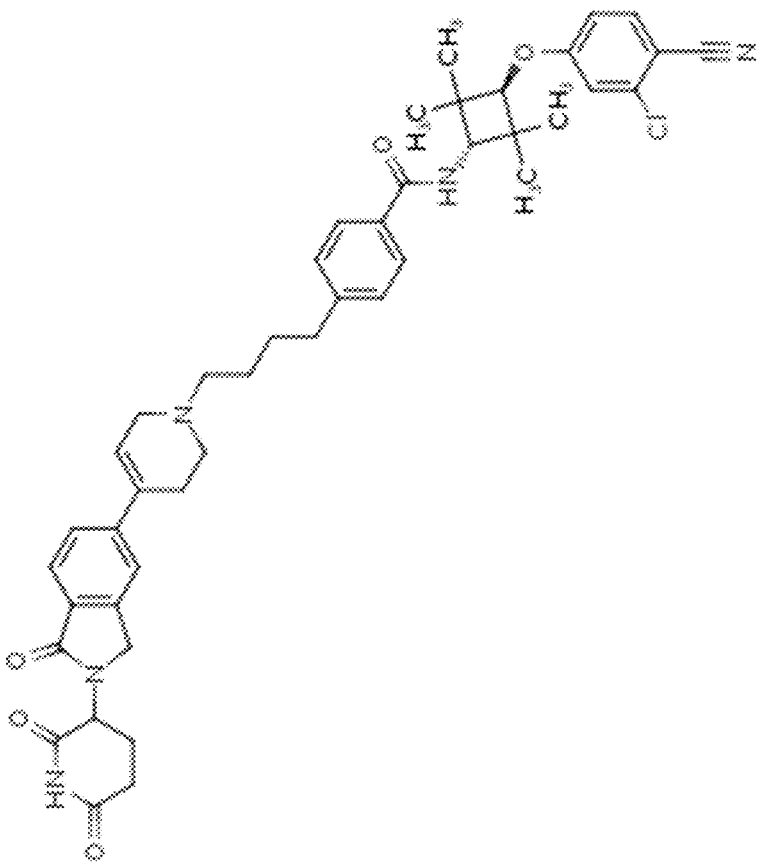
Figure 3:
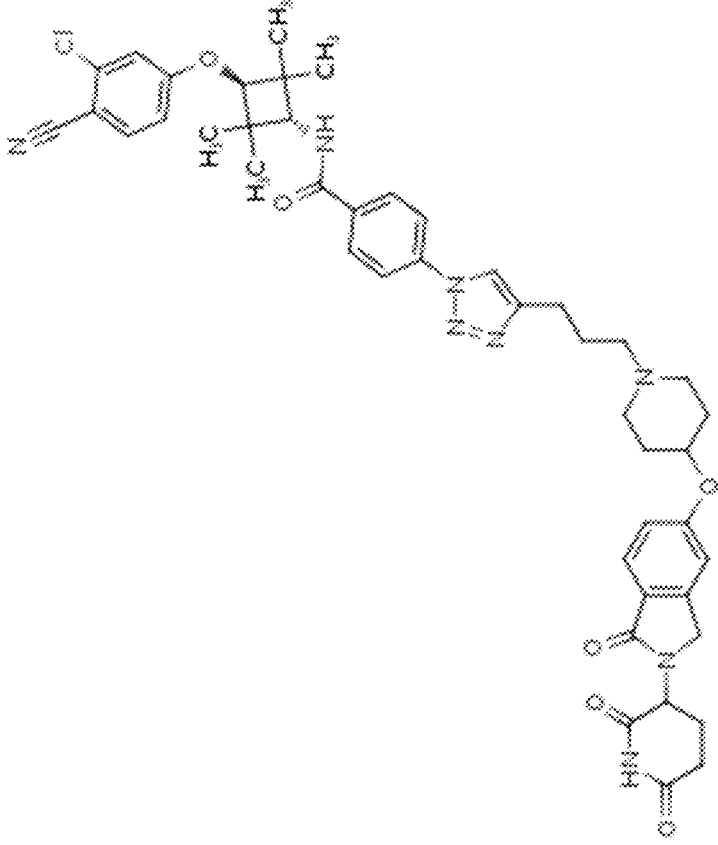
Figure 3:
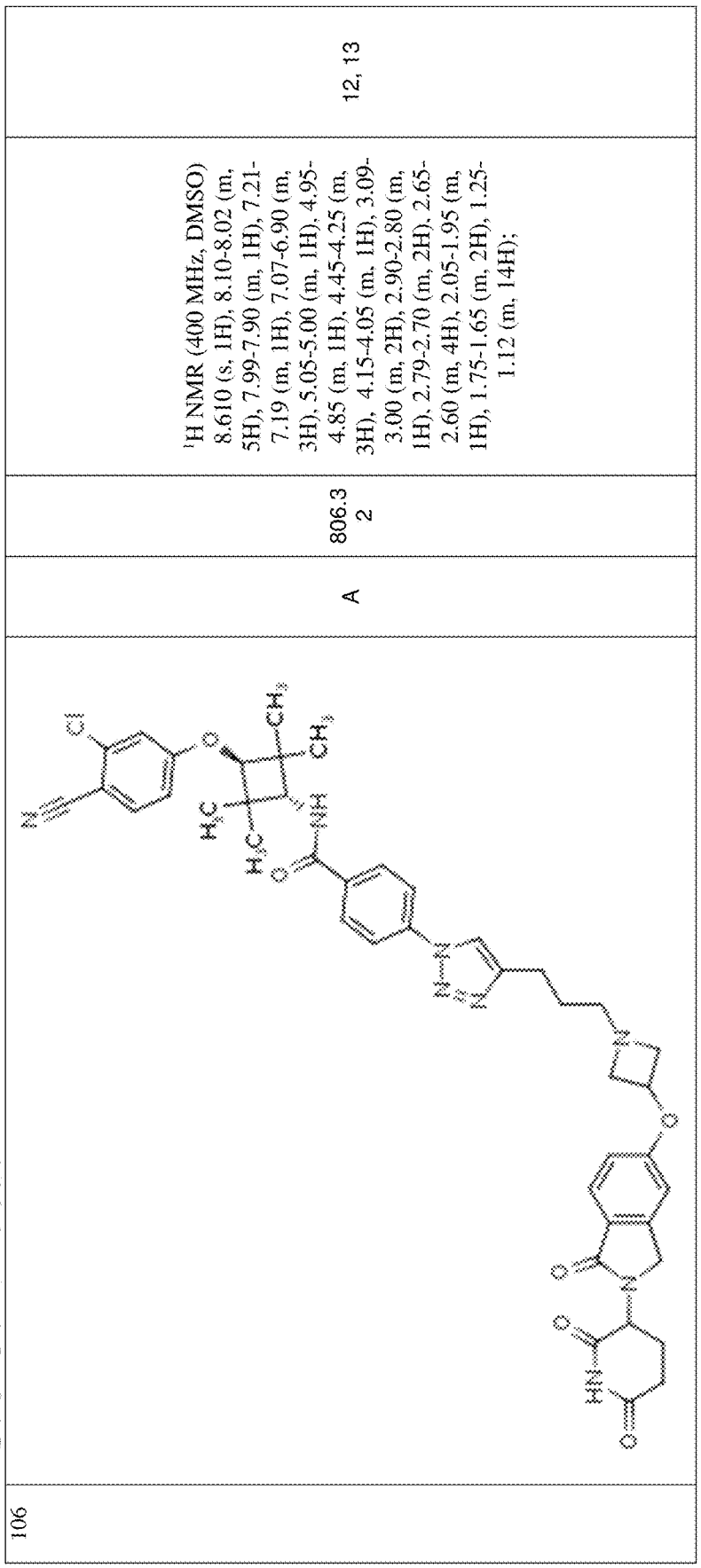
Figure 3:
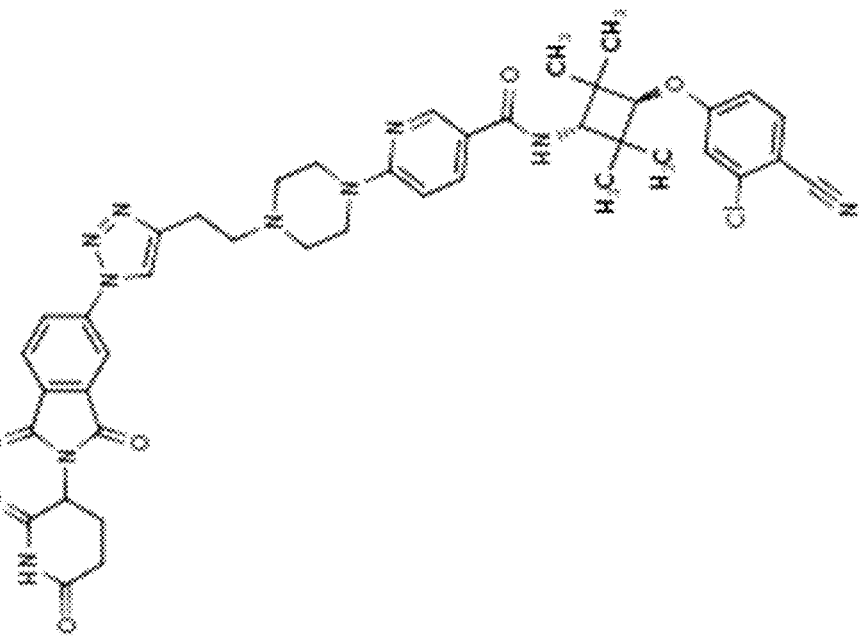
Figure 3:
Figure 3:
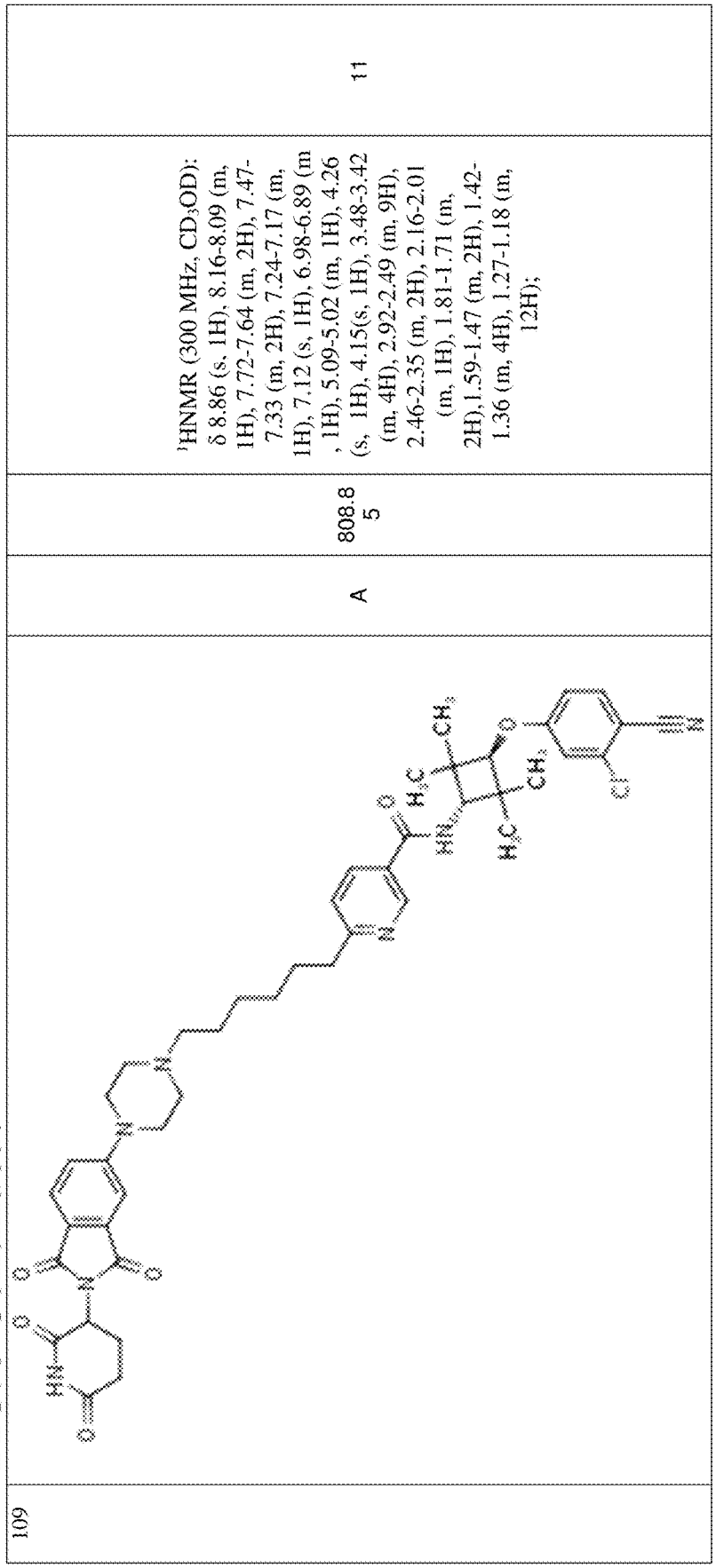
Figure 3:
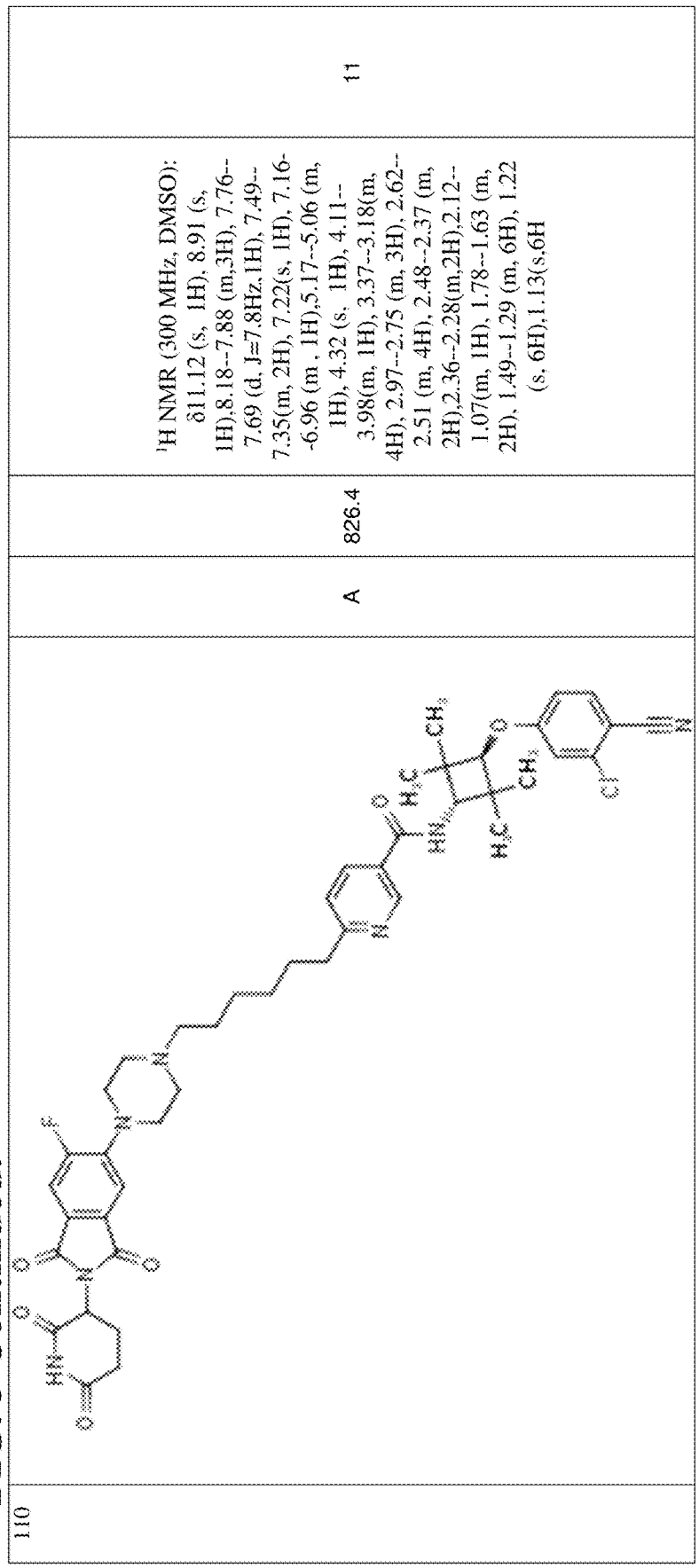
Figure 3:
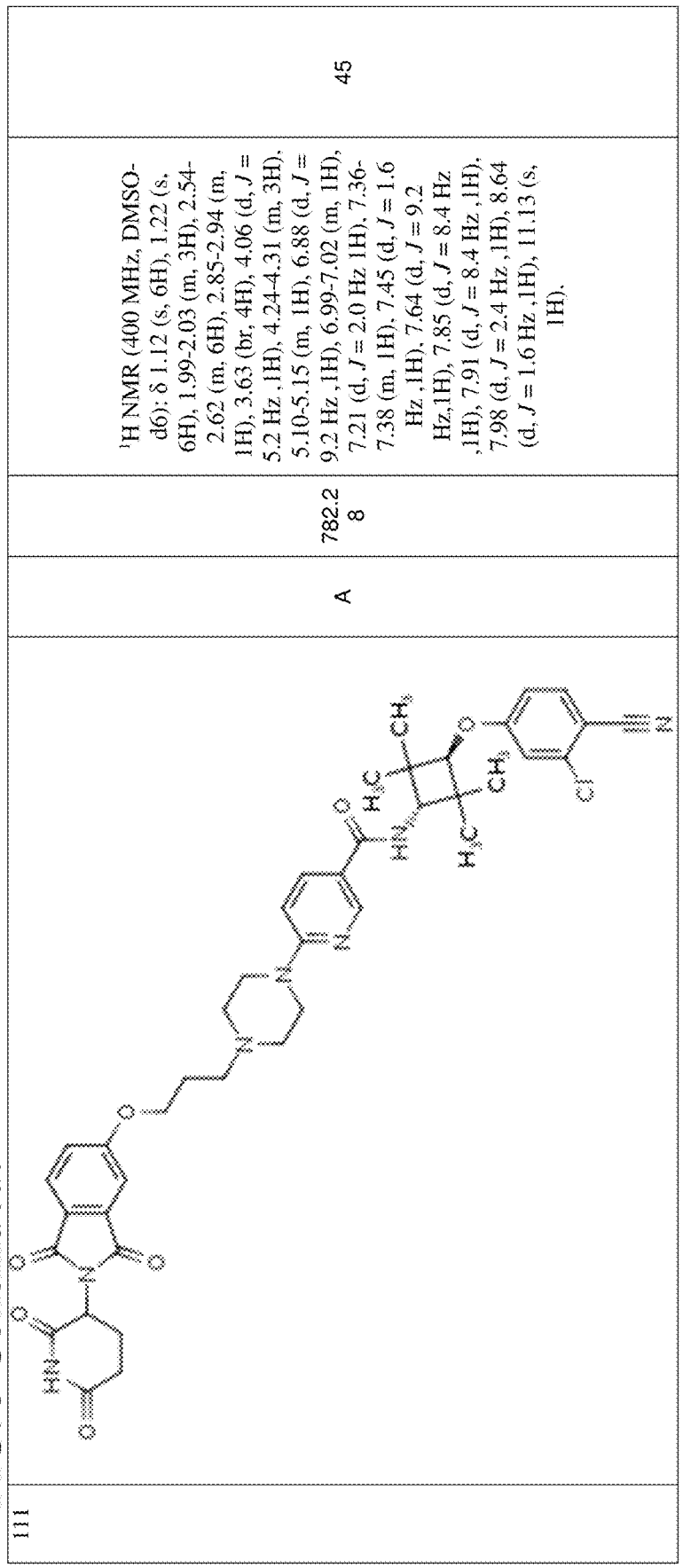
Figure 3:
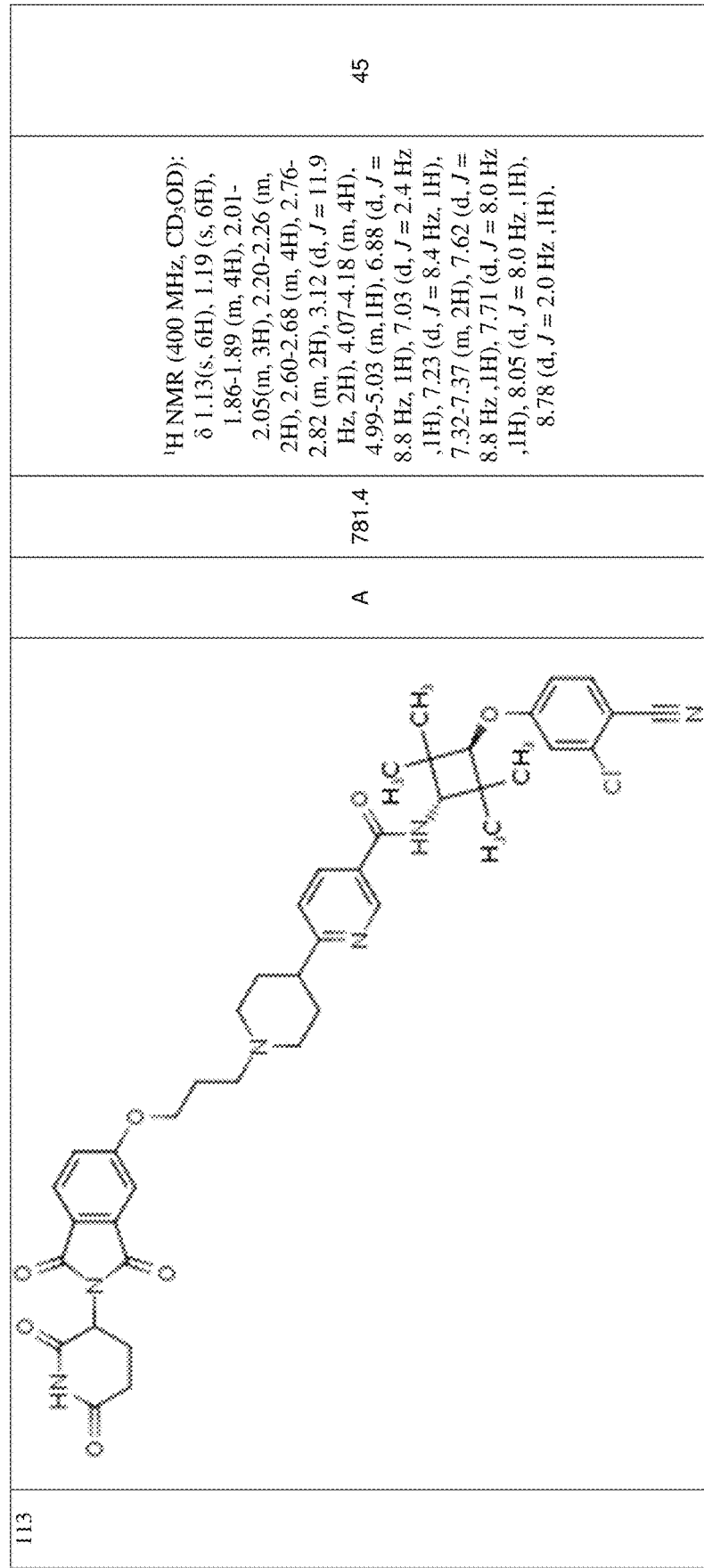
Figure 3:
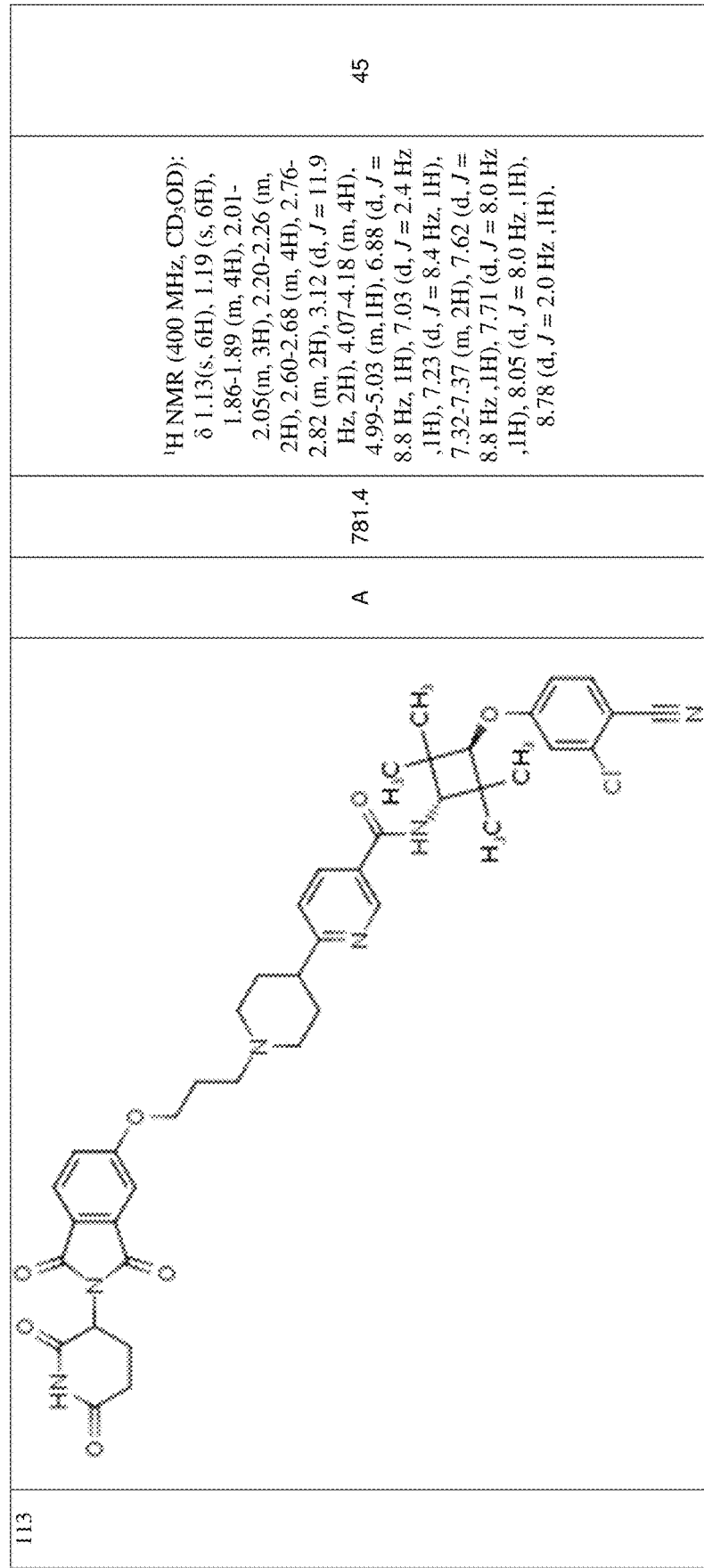
Figure 3:
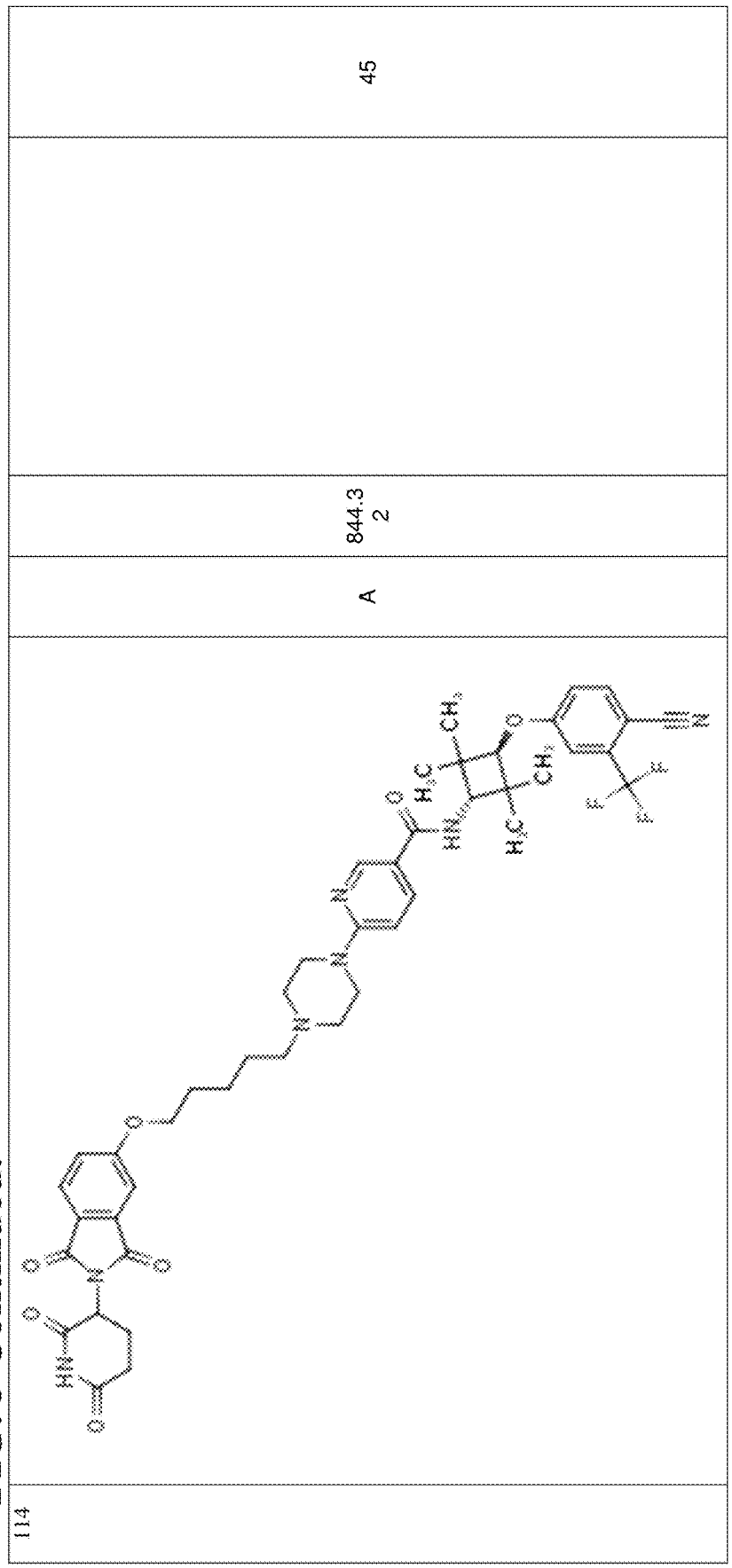
Figure 3:
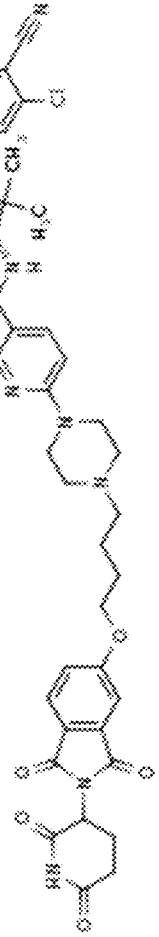
Figure 3:
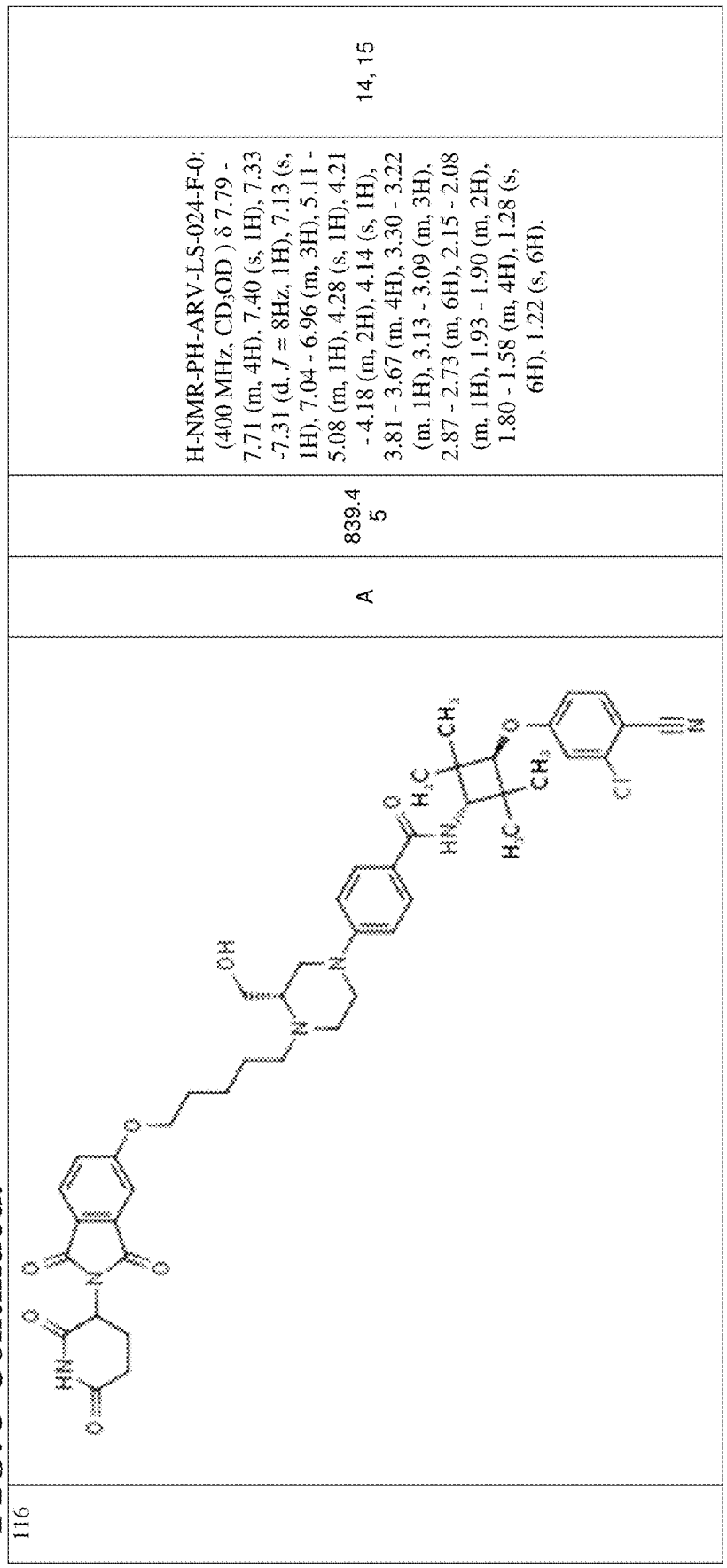
Figure 3:
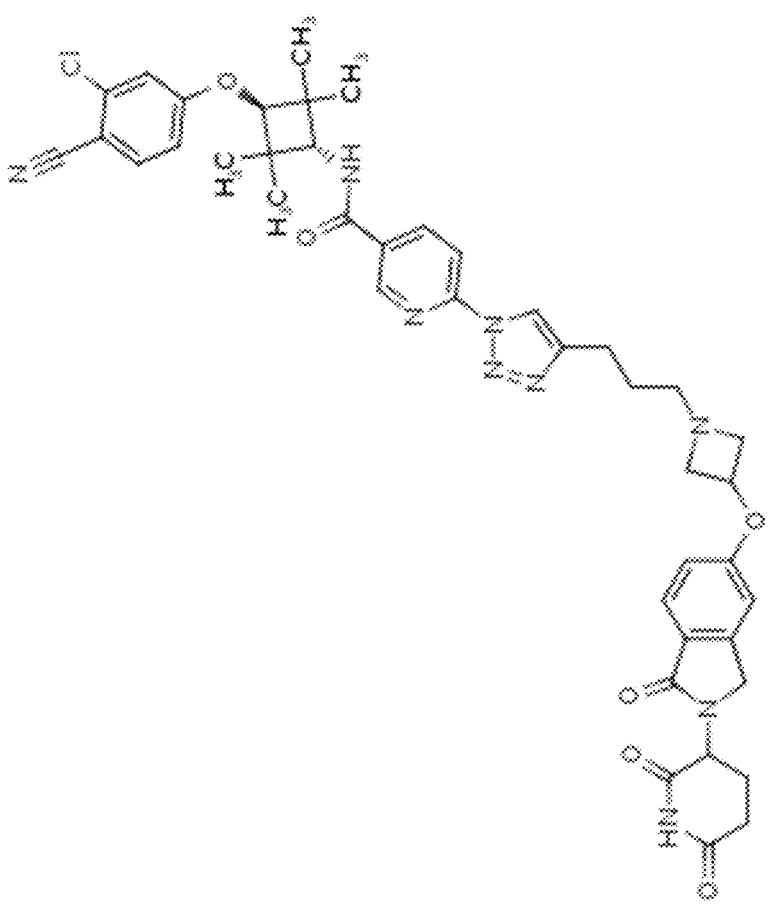
Figure 3:
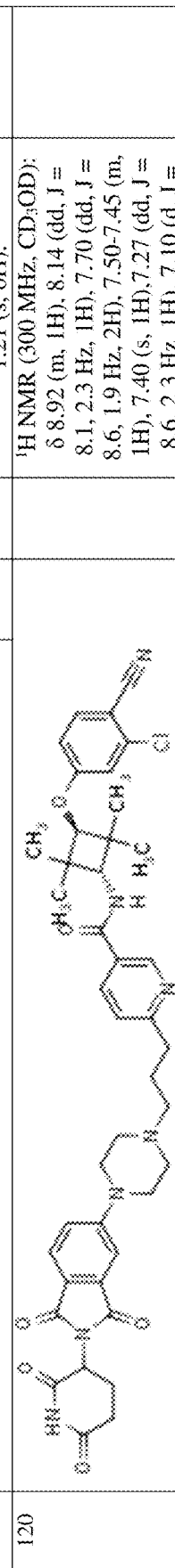
Figure 3:
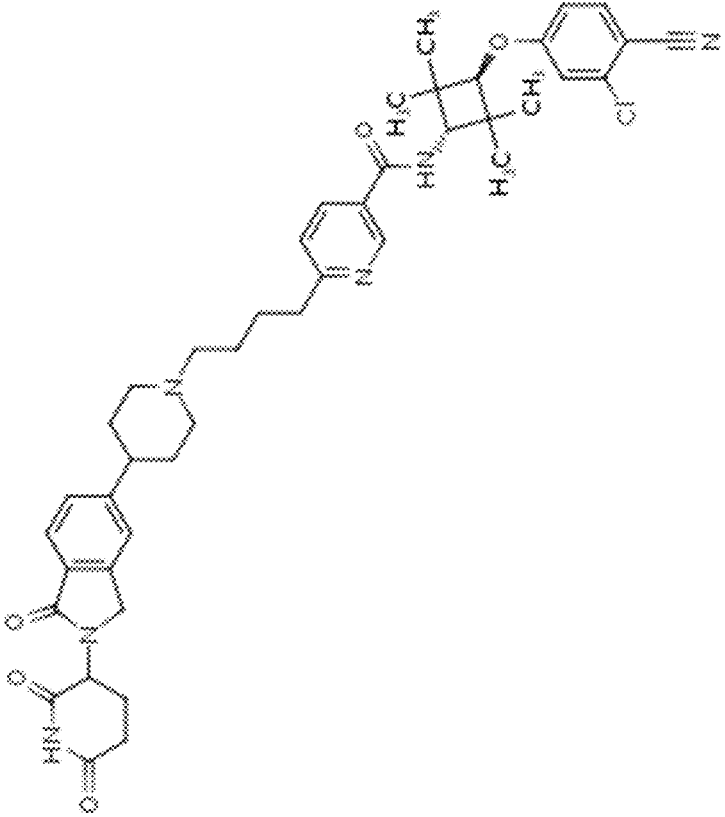
Figure 3:

Figure 3:
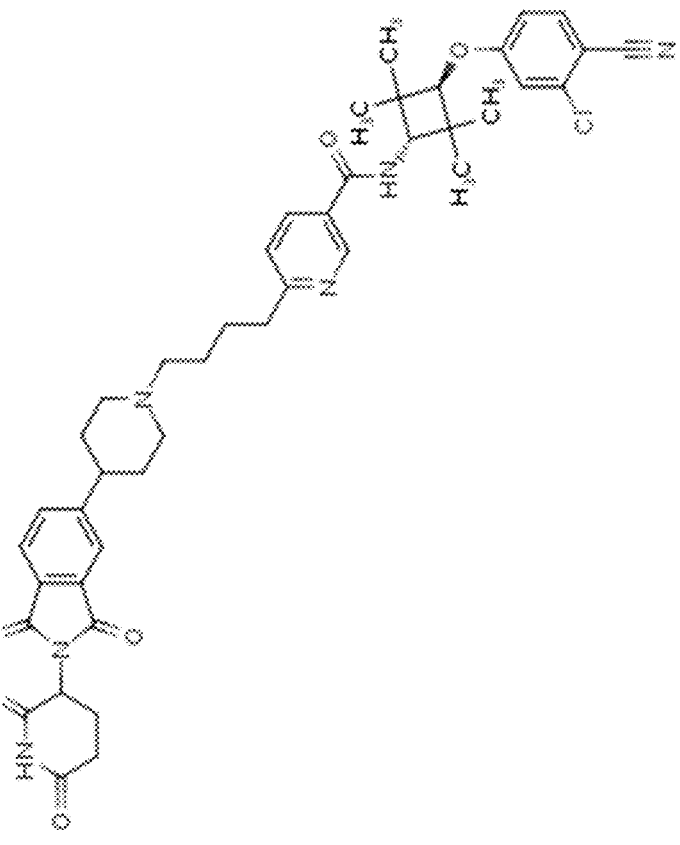
Figure 3:

Figure 3:
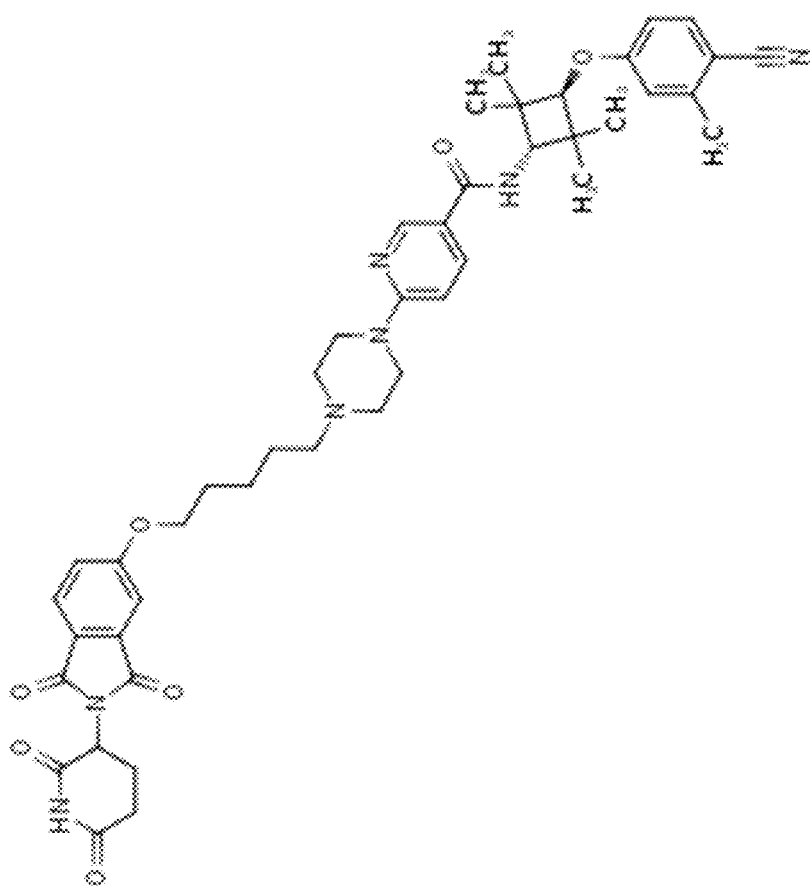
Figure 3:
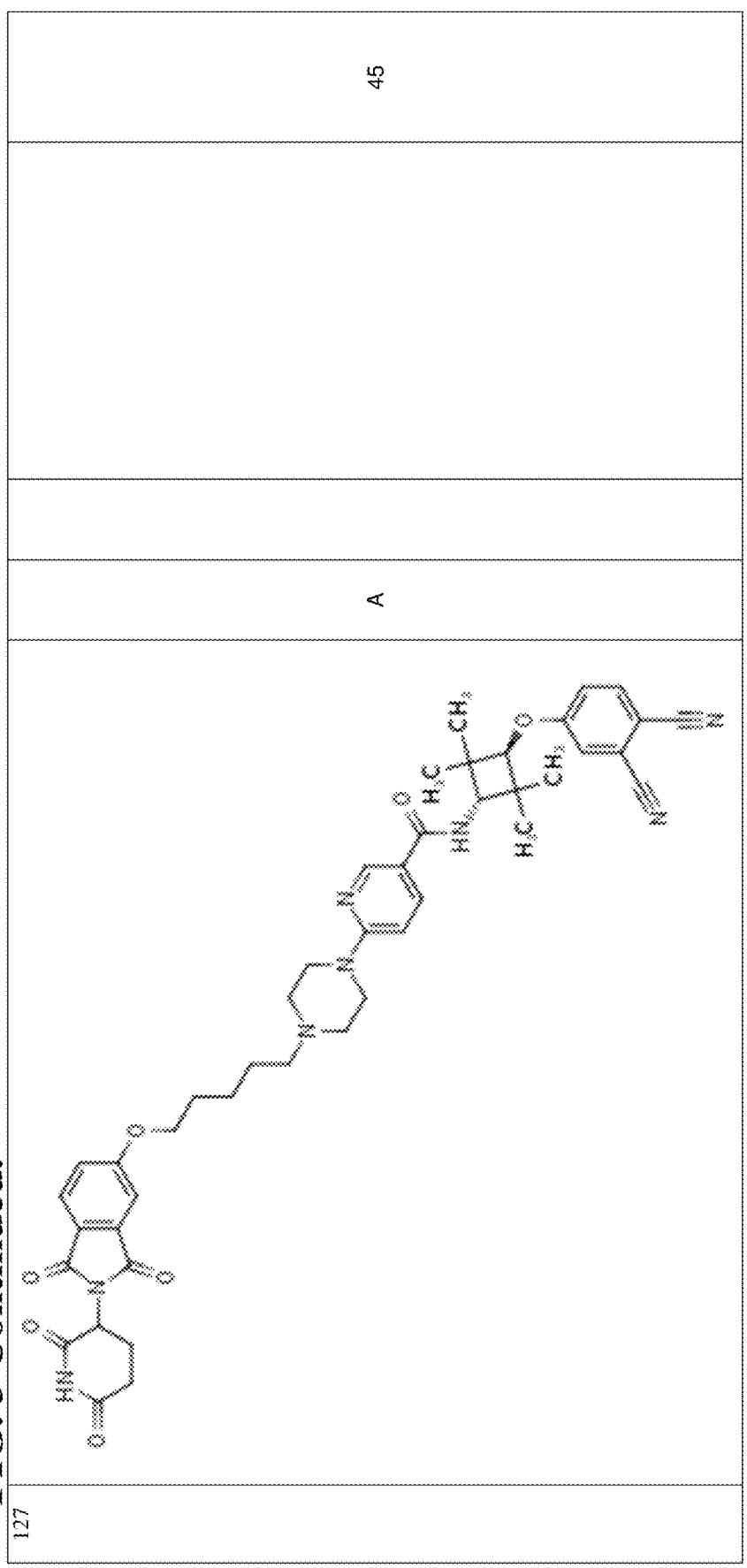
Figure 3:
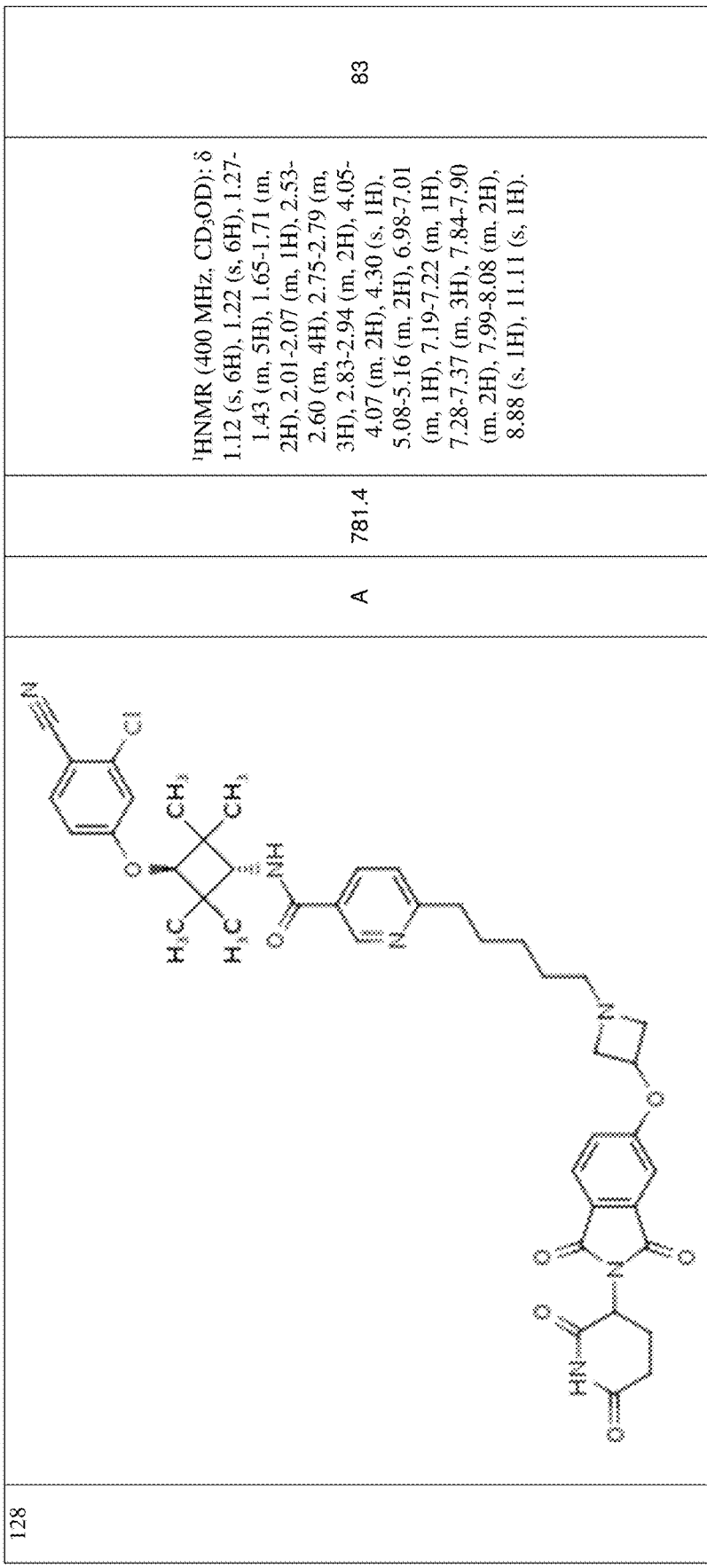
Figure 3:
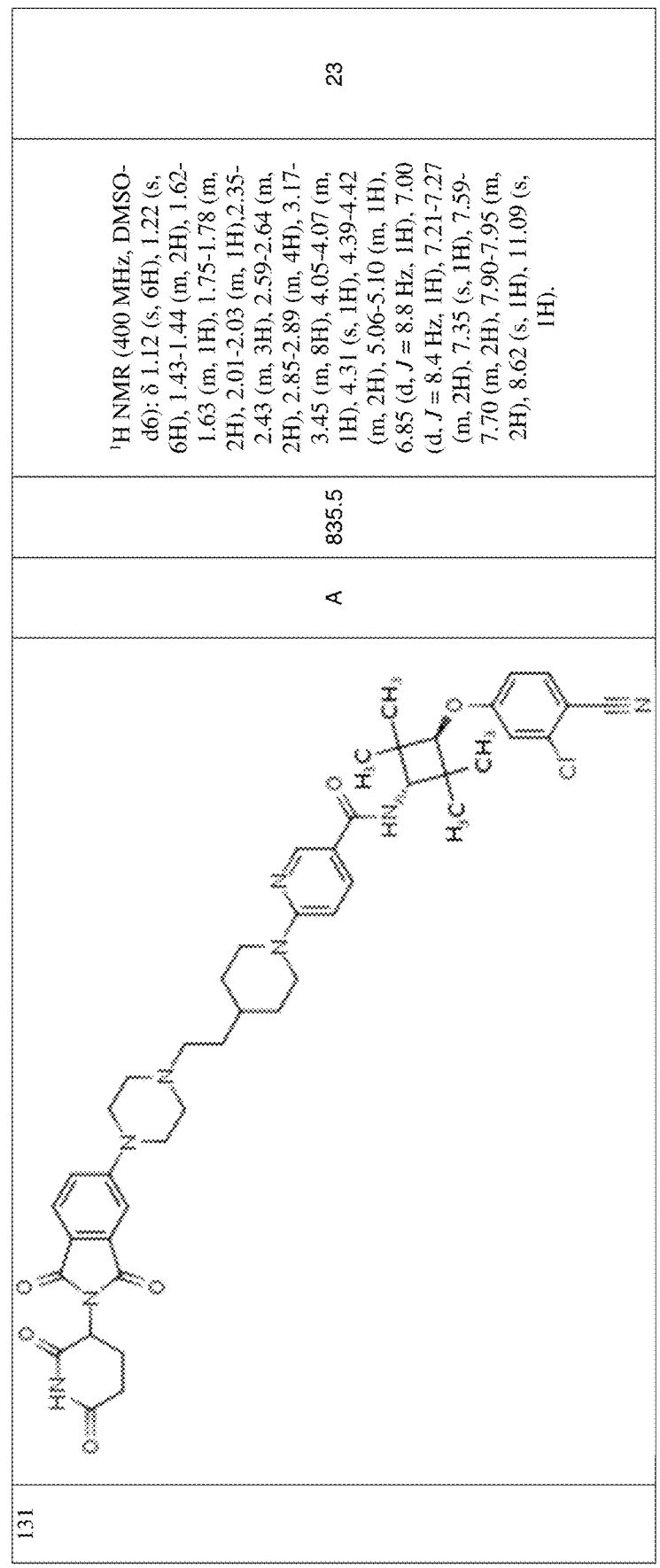
Figure 3:
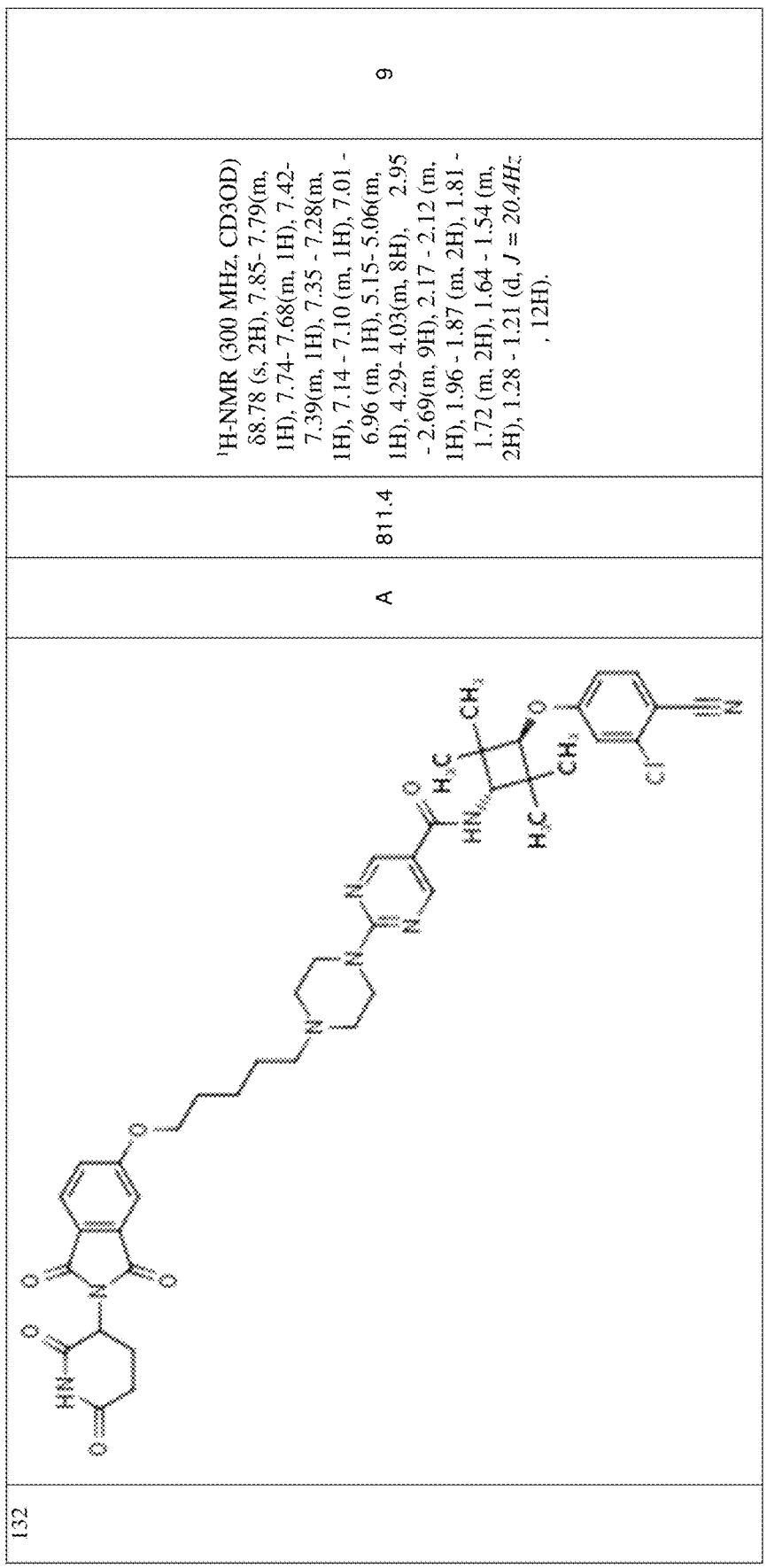
Figure 3:
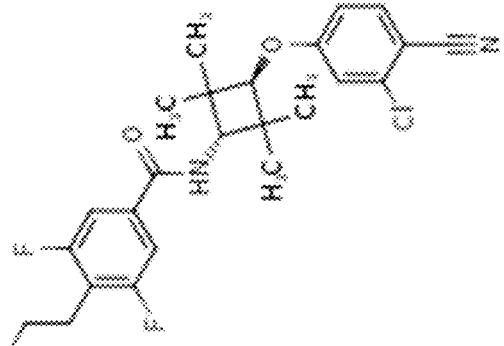
Figure 3:

Figure 3:

Figure 3:
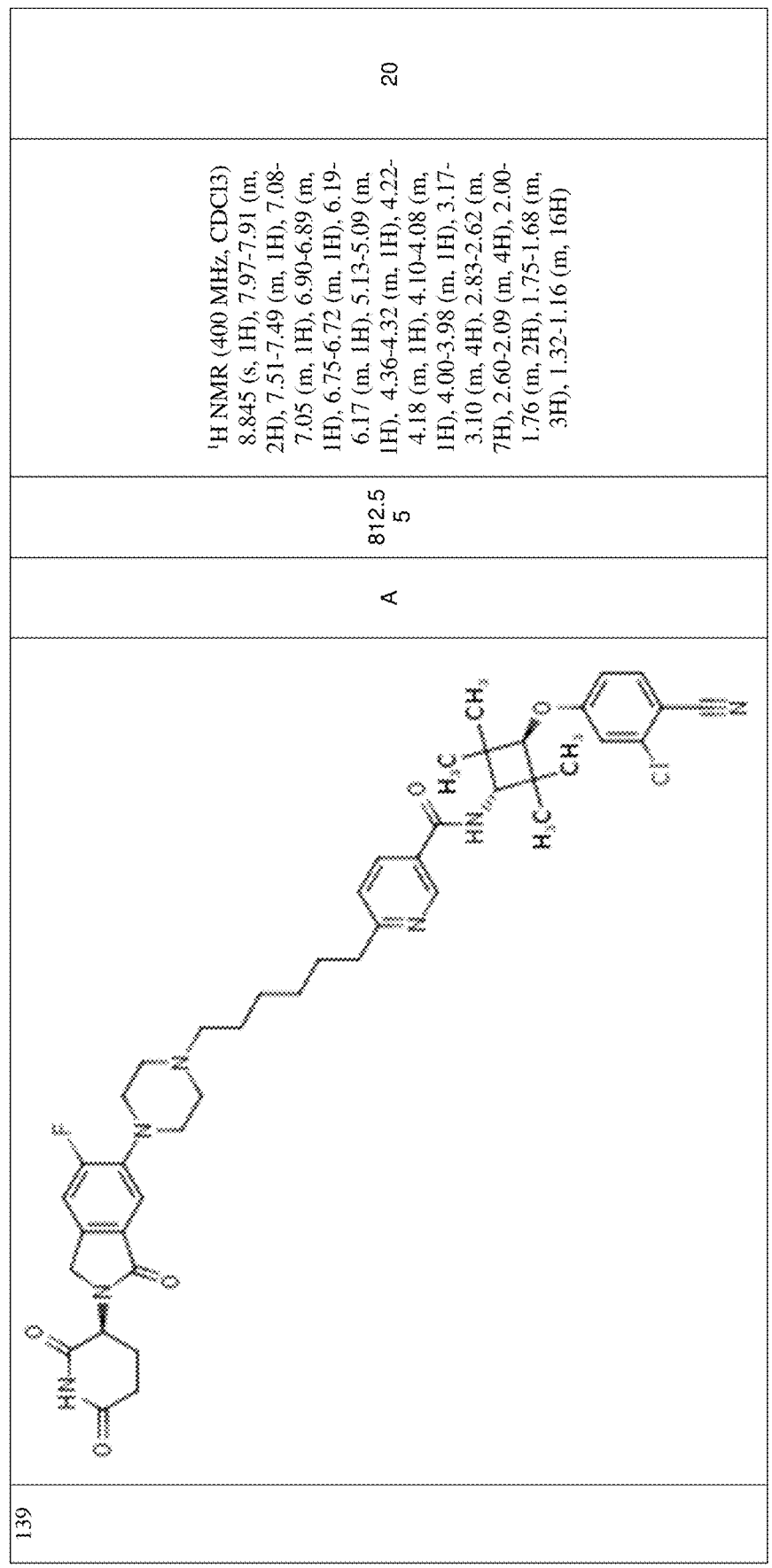
Figure 3:
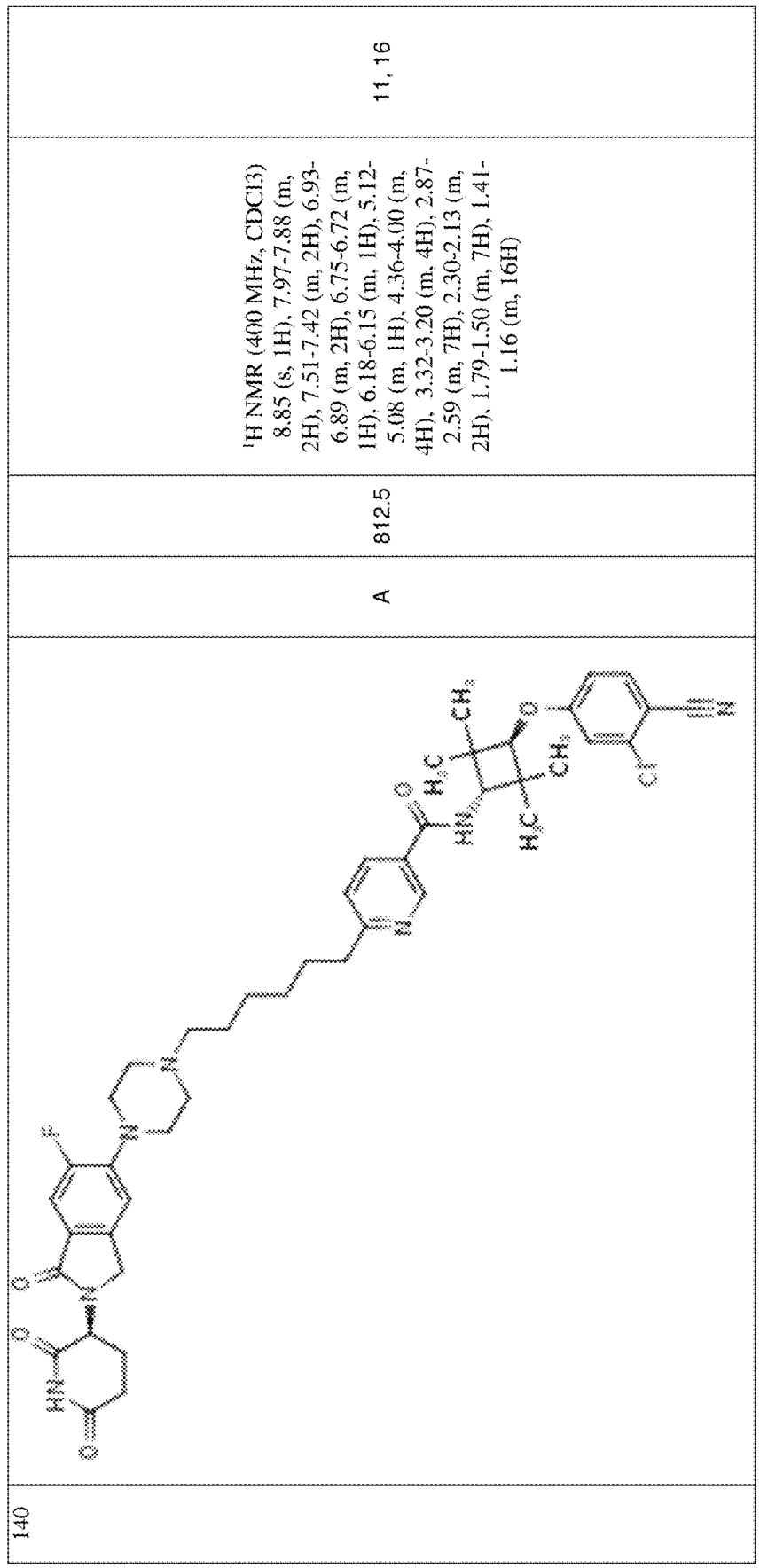
Figure 3:
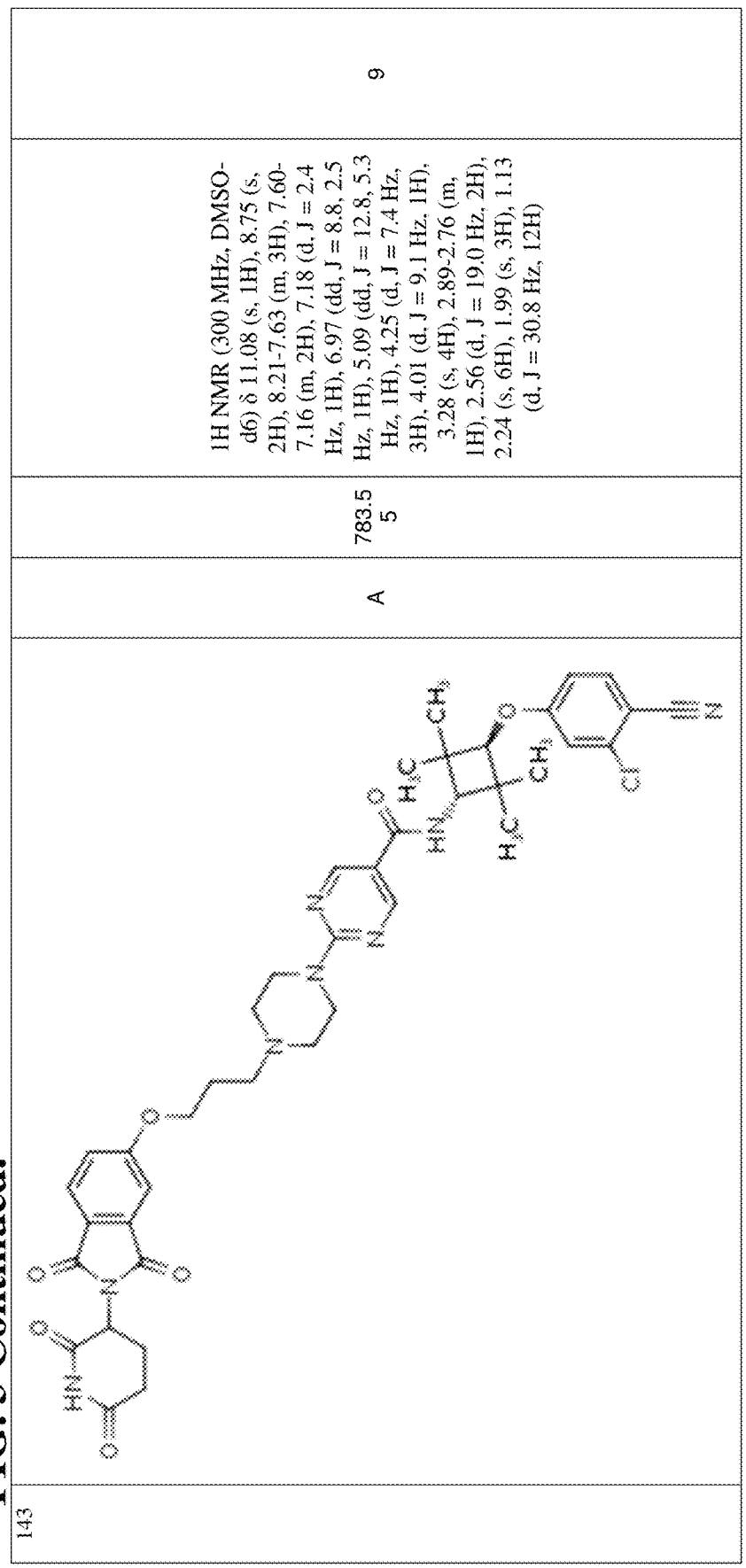
Figure 3:
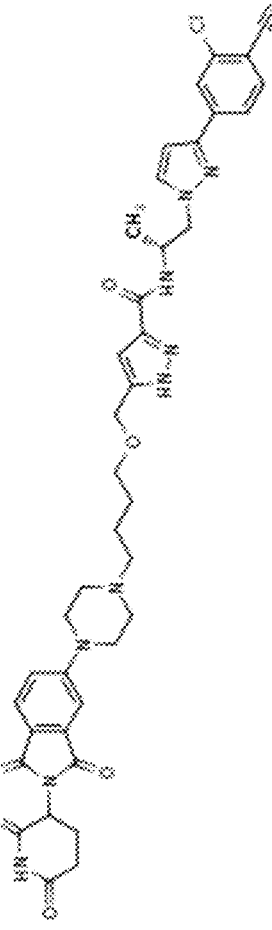
Figure 3:
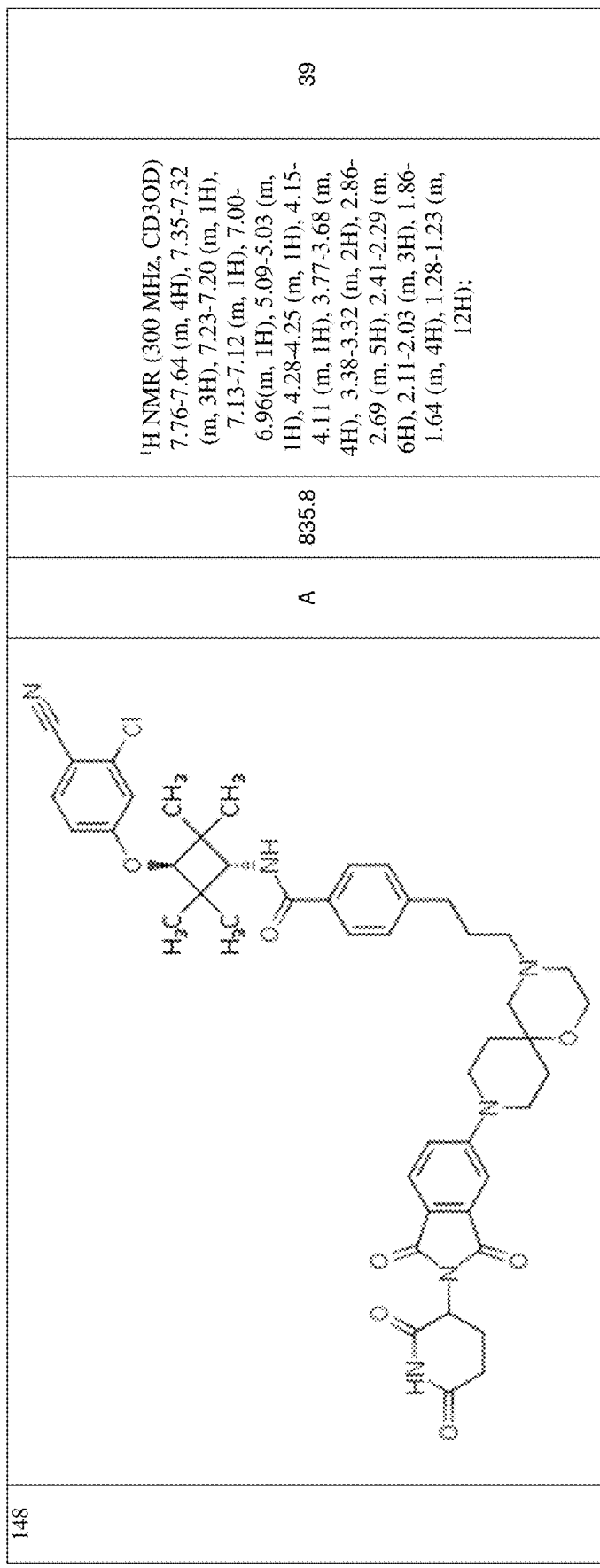
Figure 3:
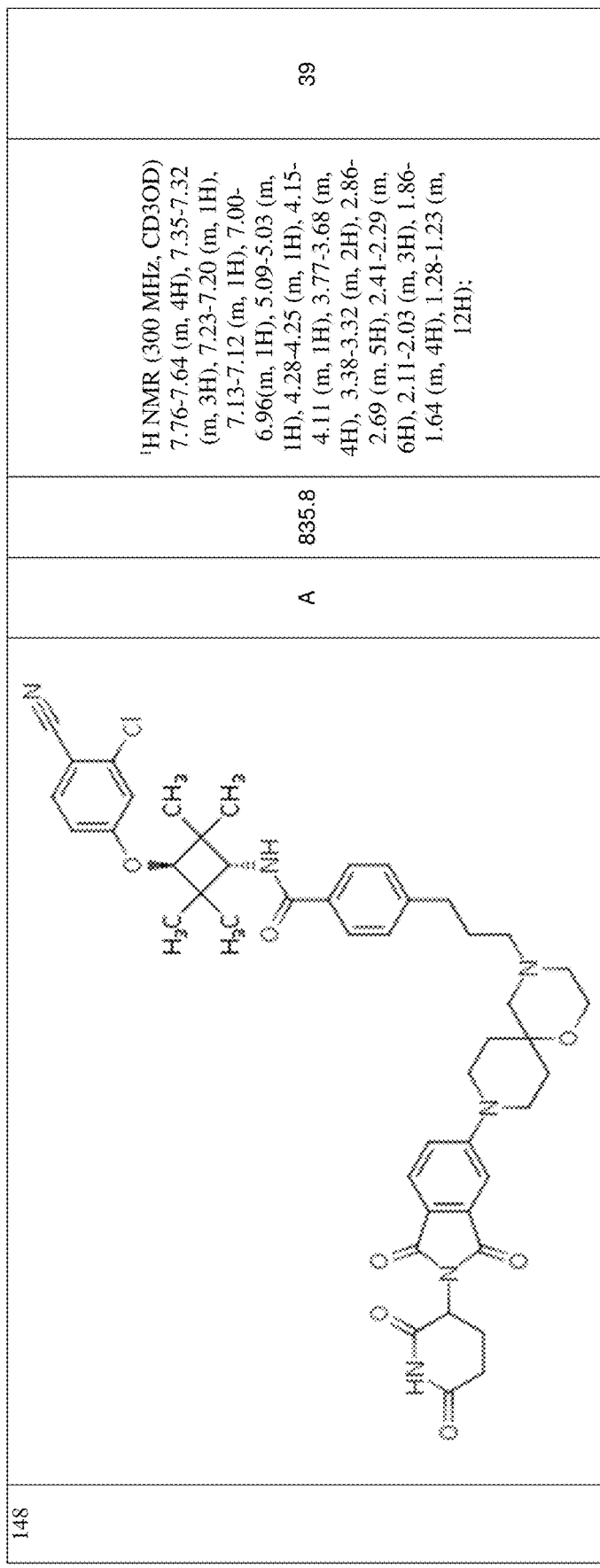
Figure 3:
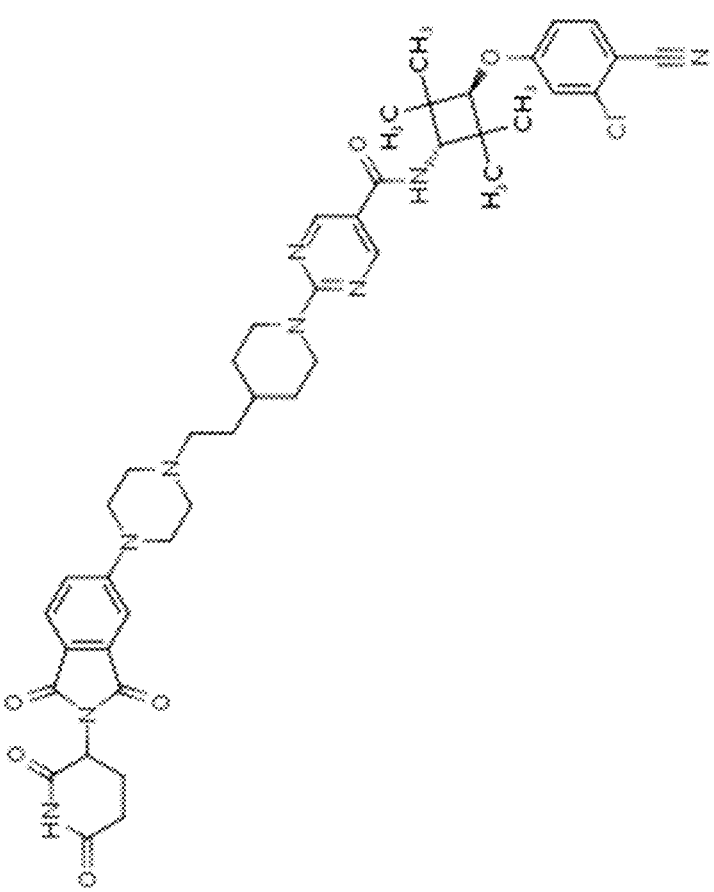
Figure 3:
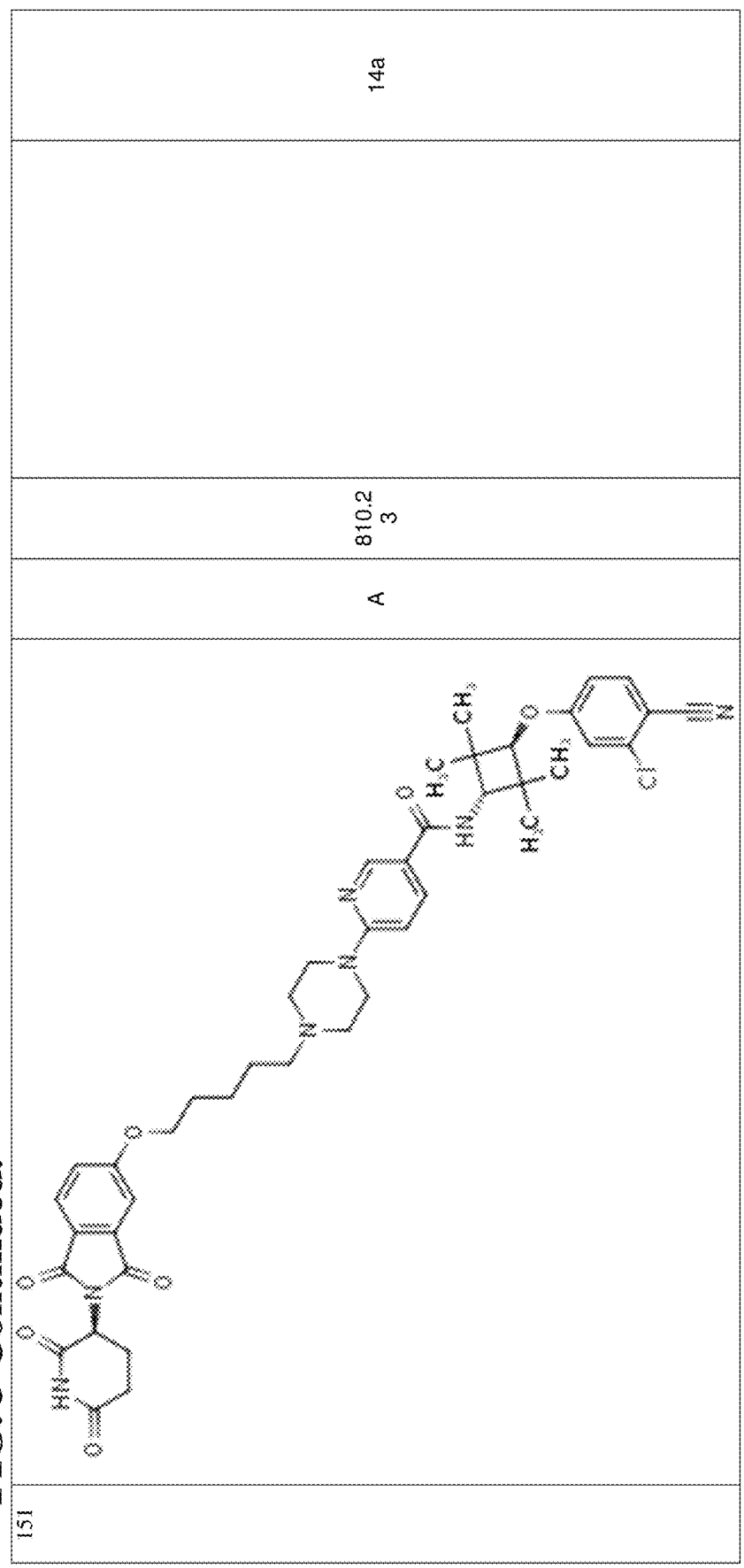
Figure 3:
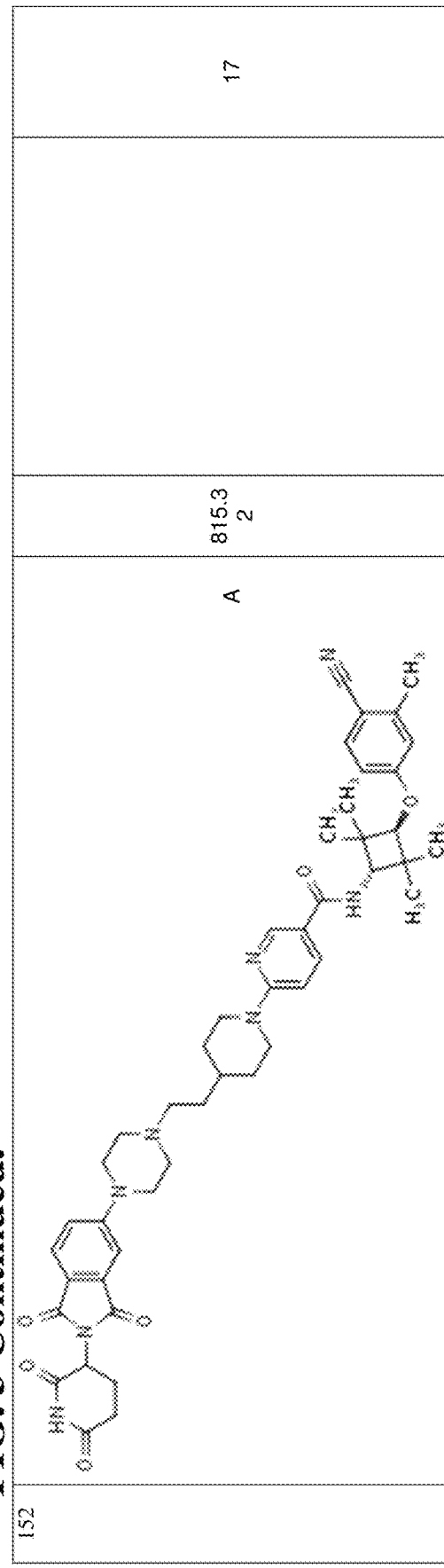
Figure 3:
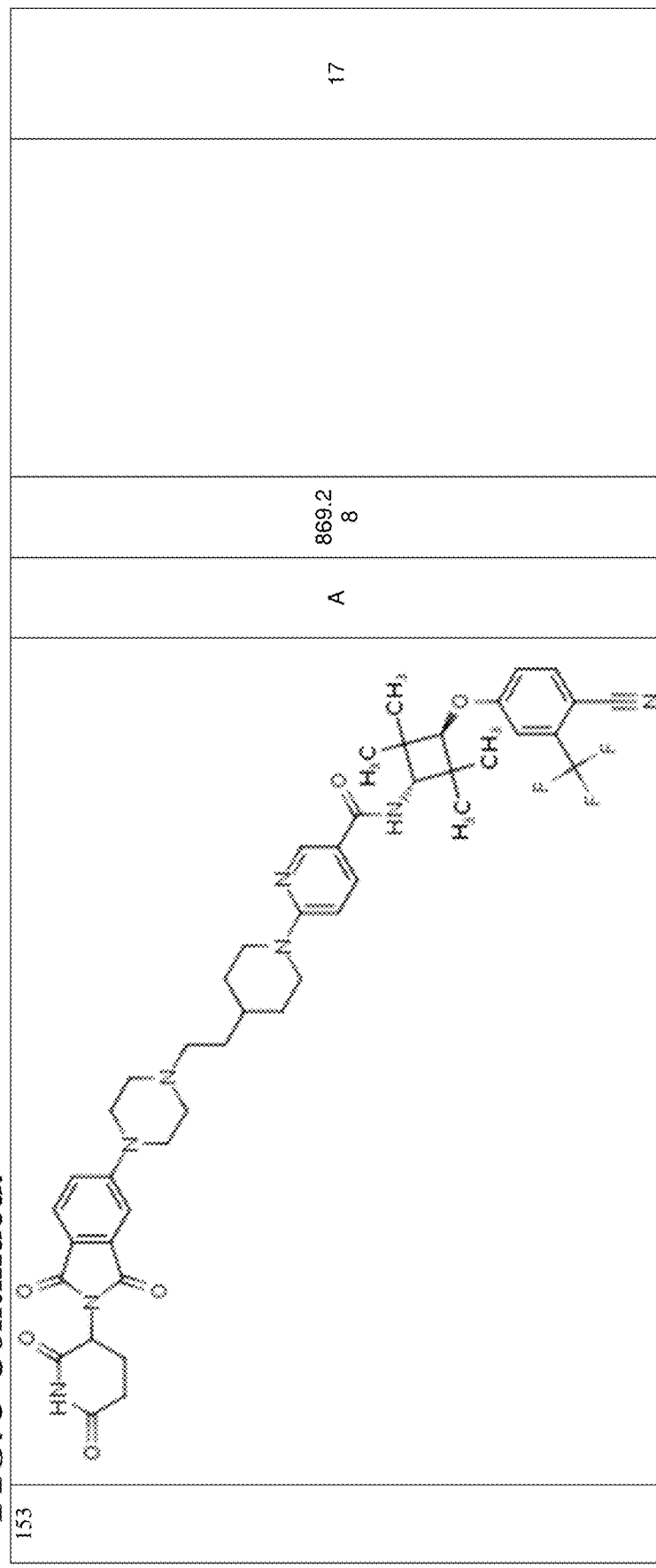
Figure 3:
Figure 3:
Figure 3:
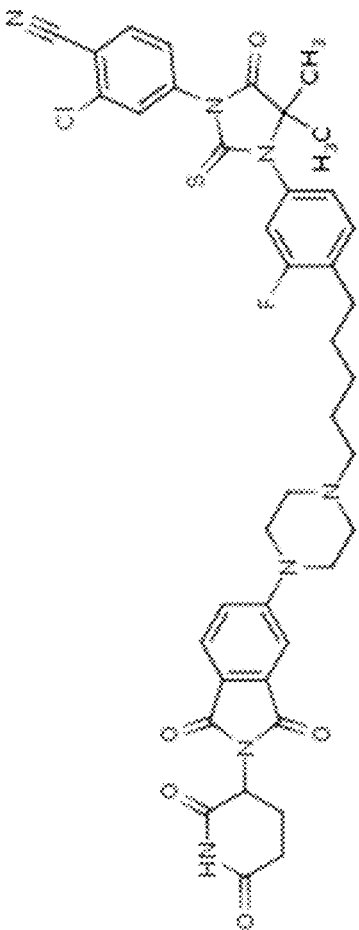
Figure 3:
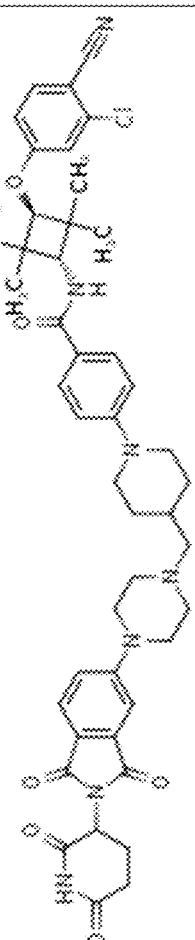
Figure 3:
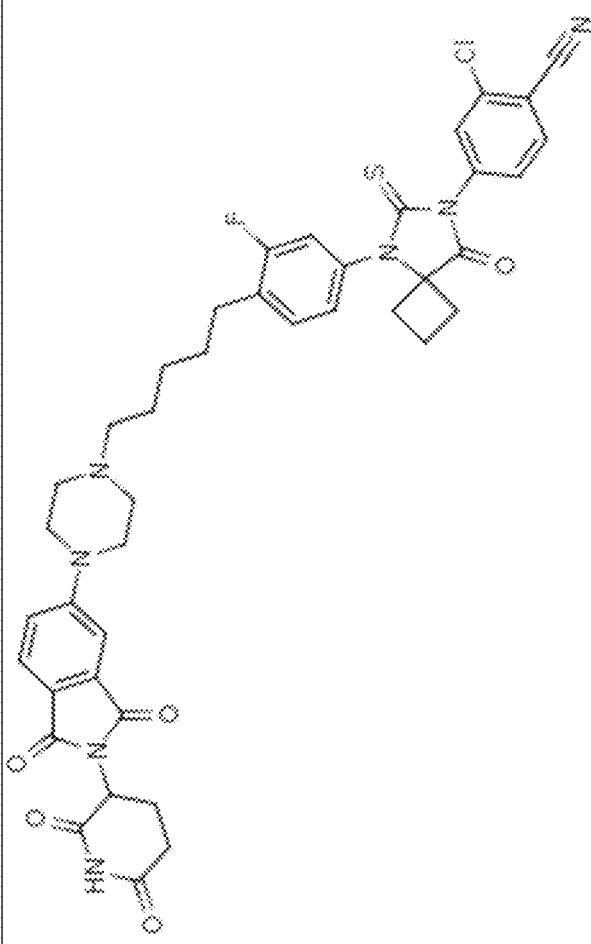
Figure 3:
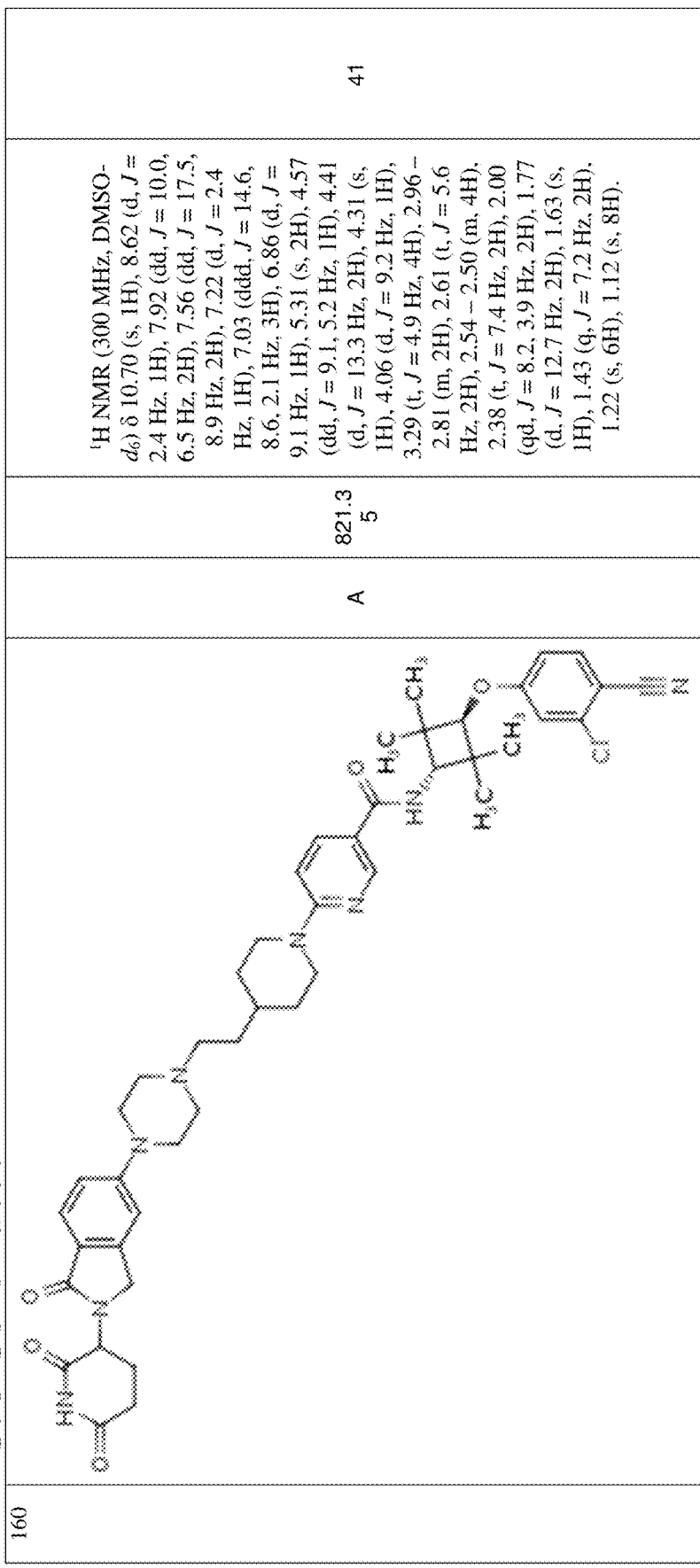
Figure 3:
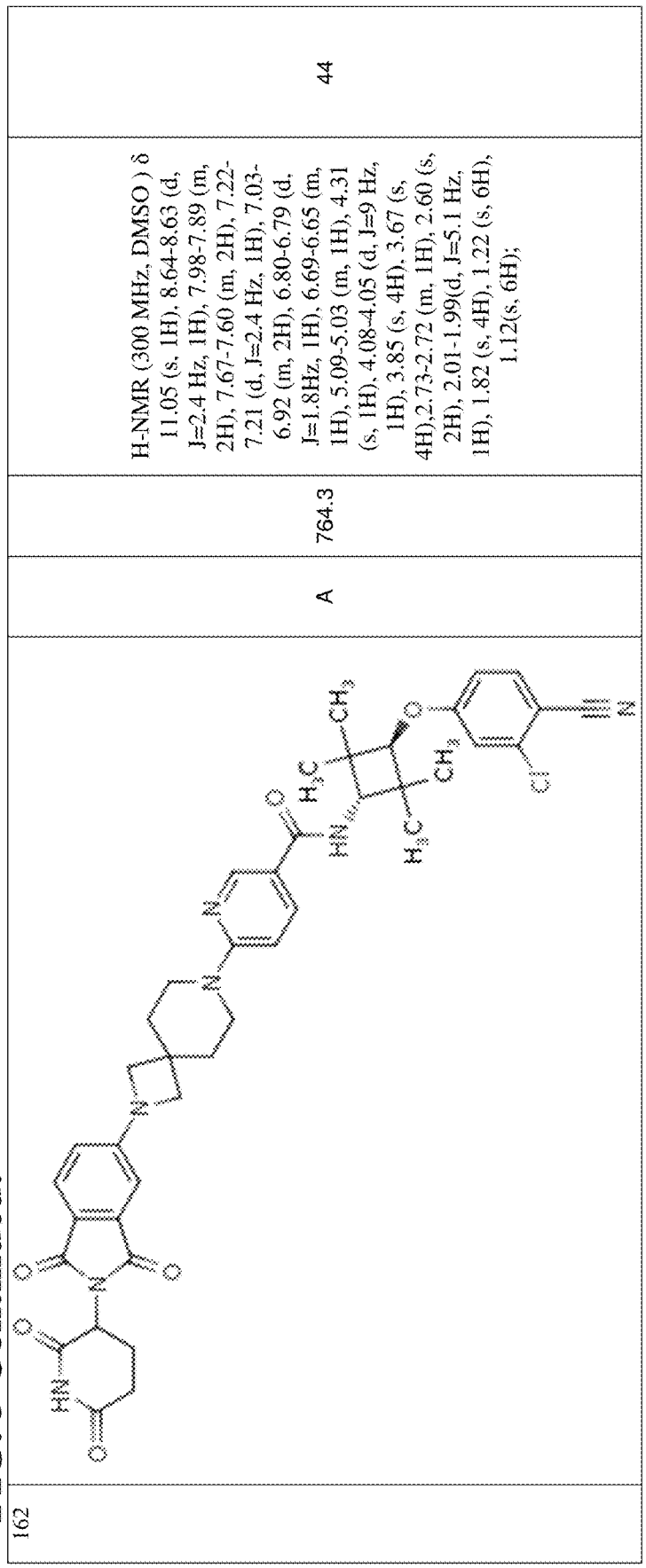
Figure 3:
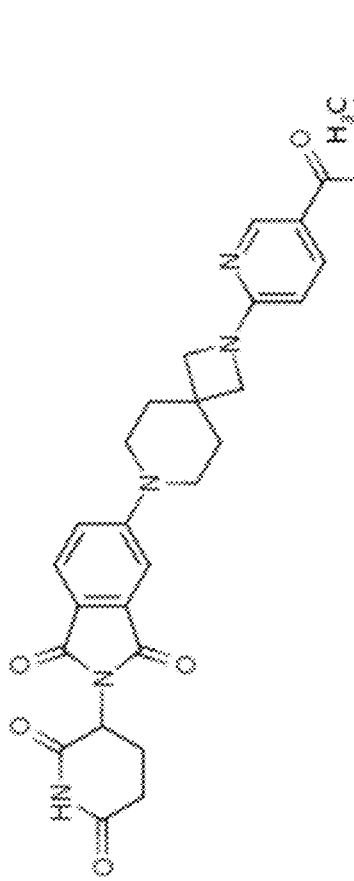
Figure 3:
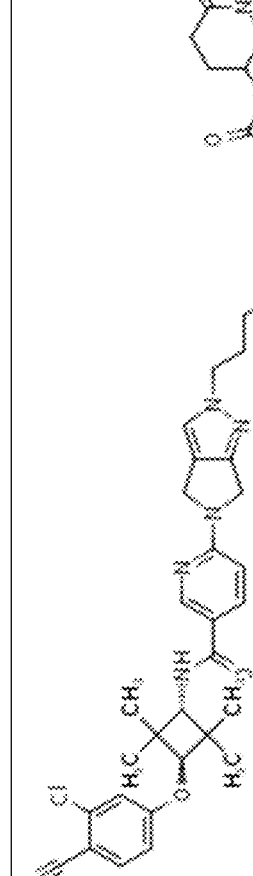
Figure 3:
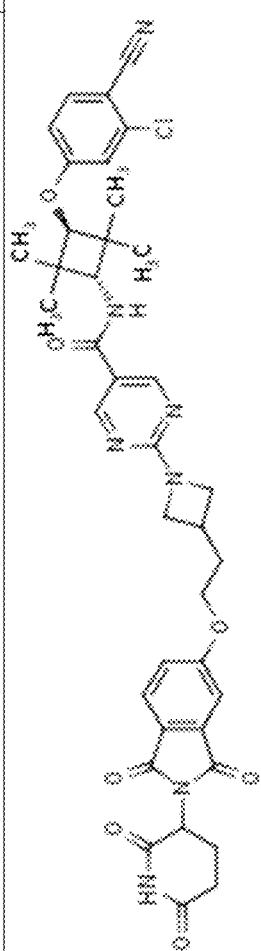
Figure 3:
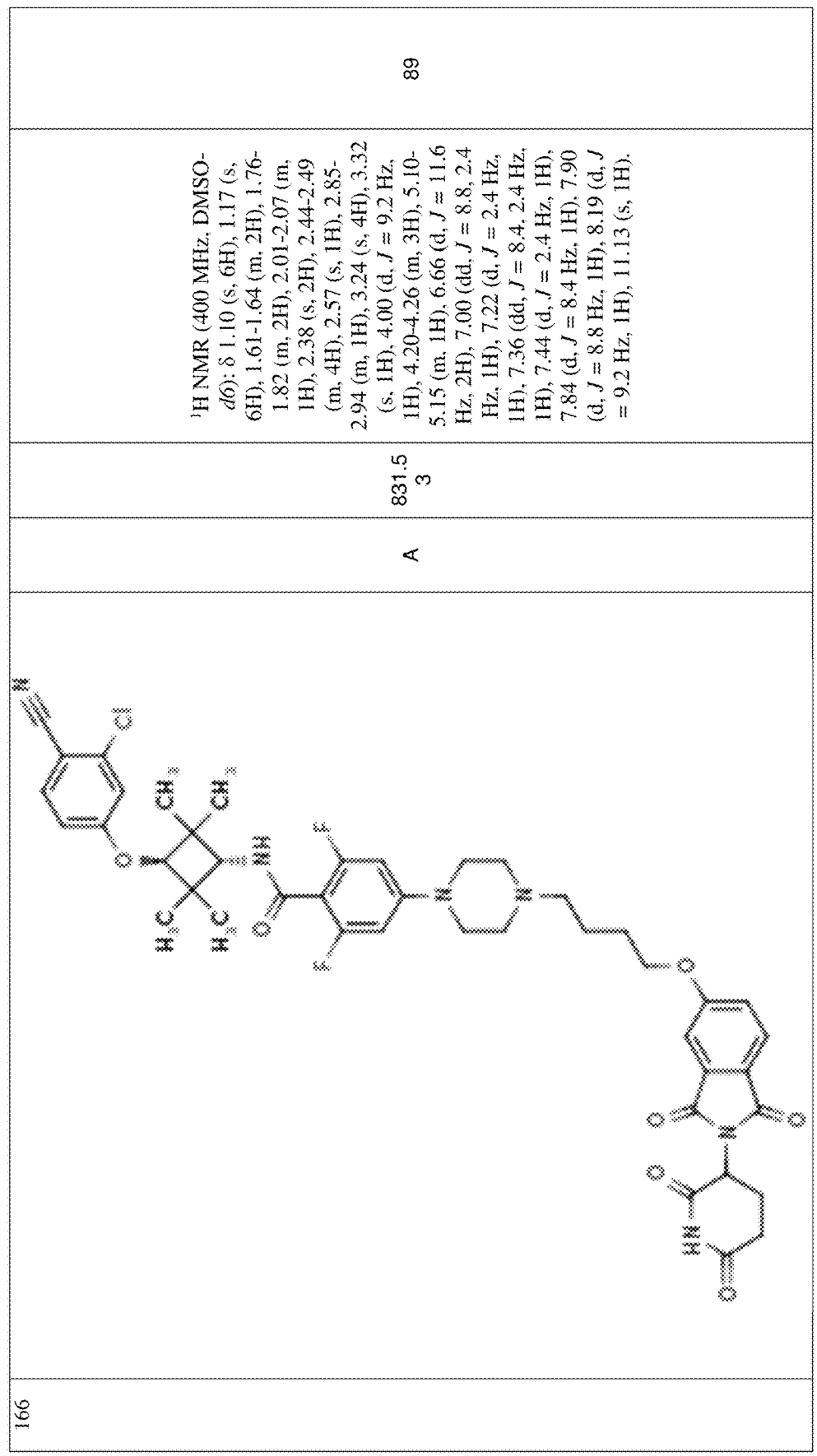
Figure 3:
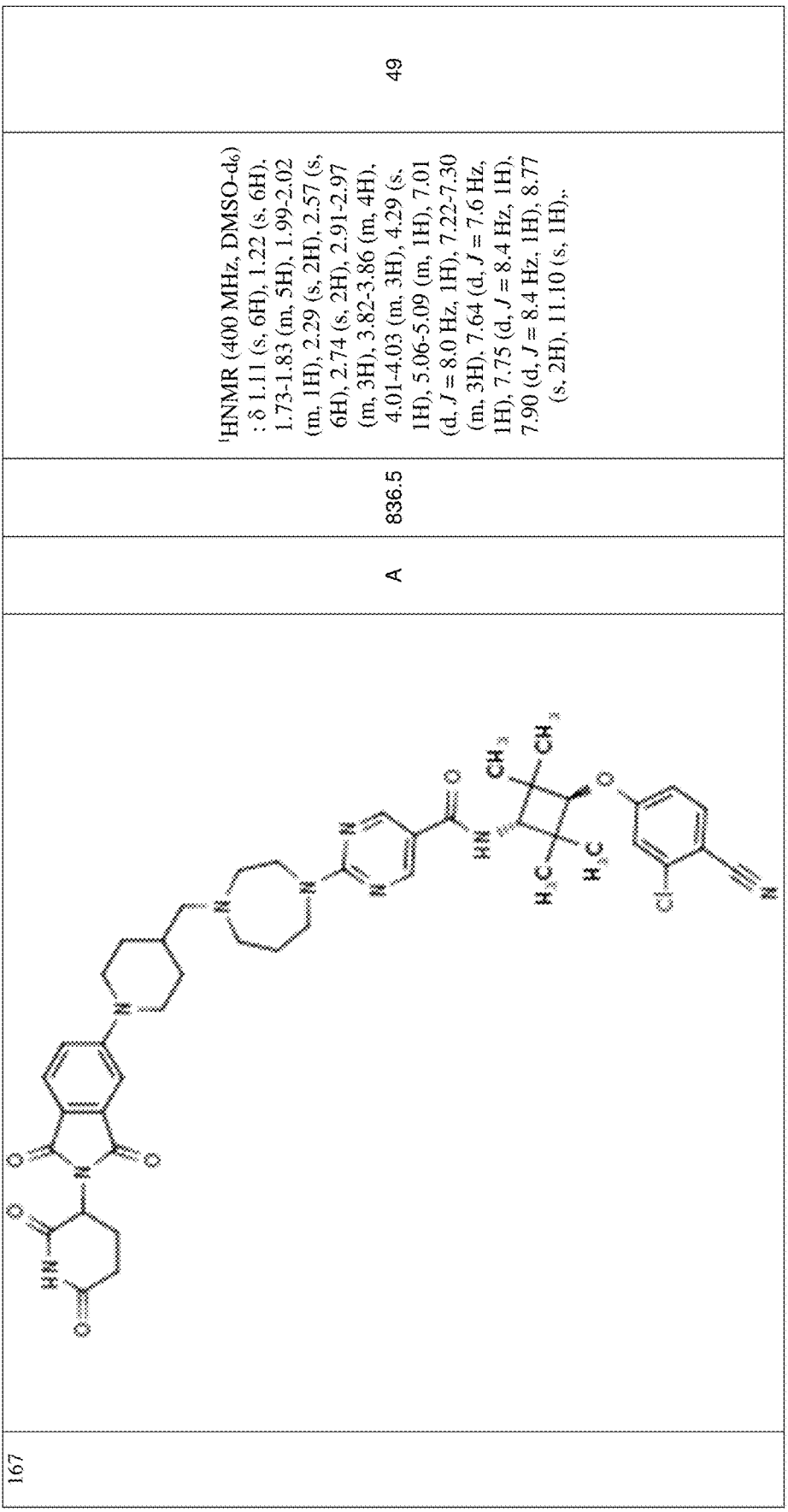
Figure 3:
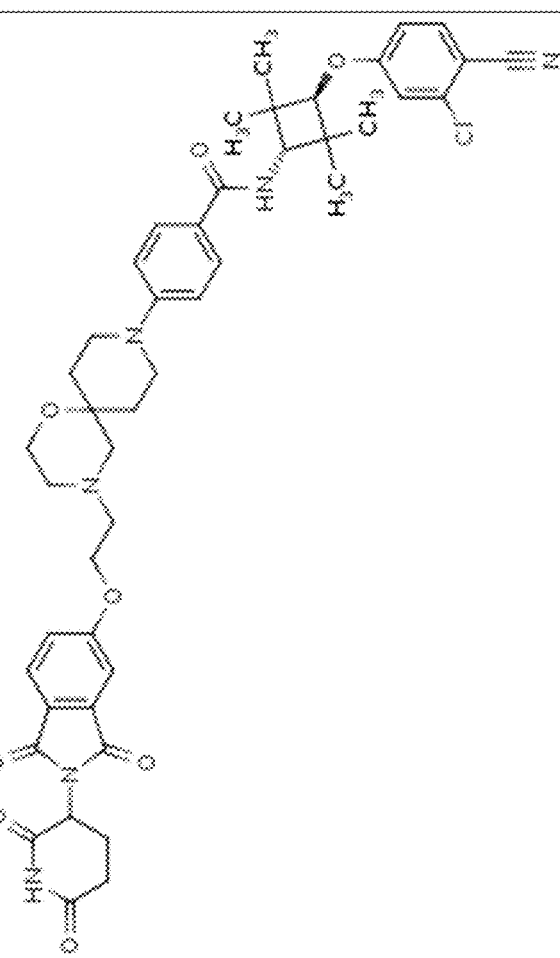
Figure 3:
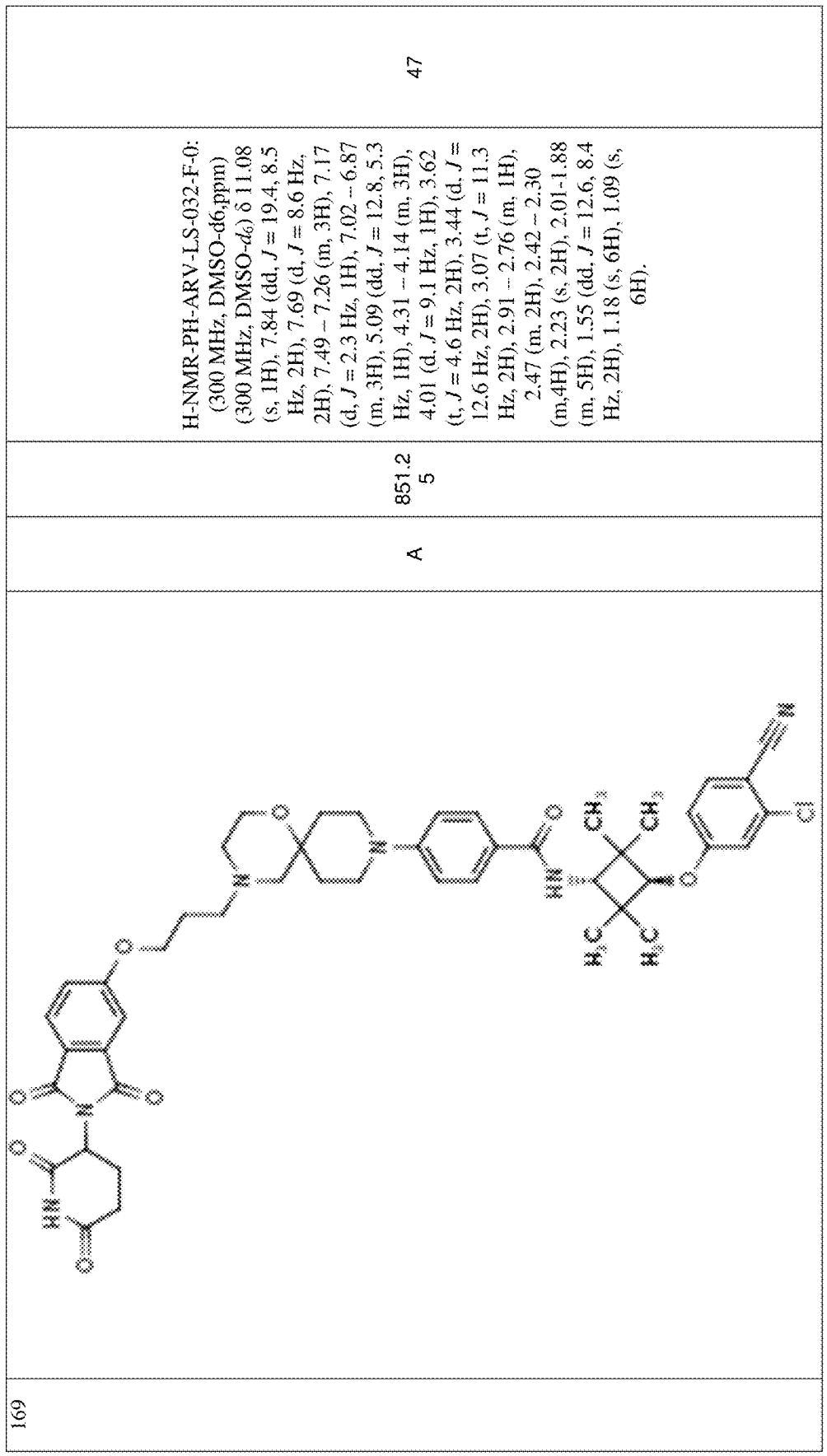
Figure 3:
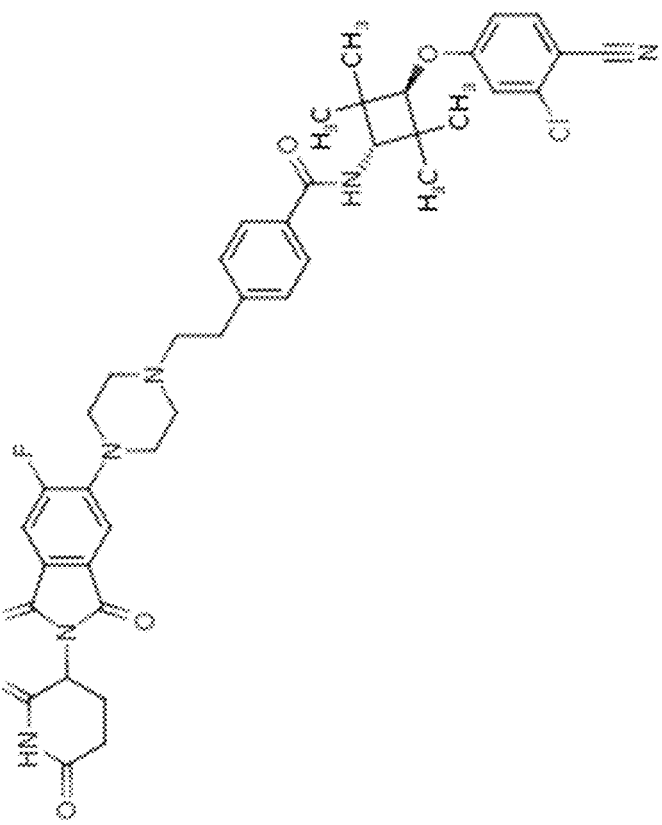
Figure 3:
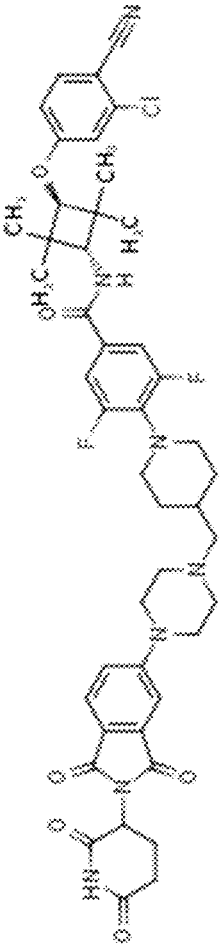
Figure 3:
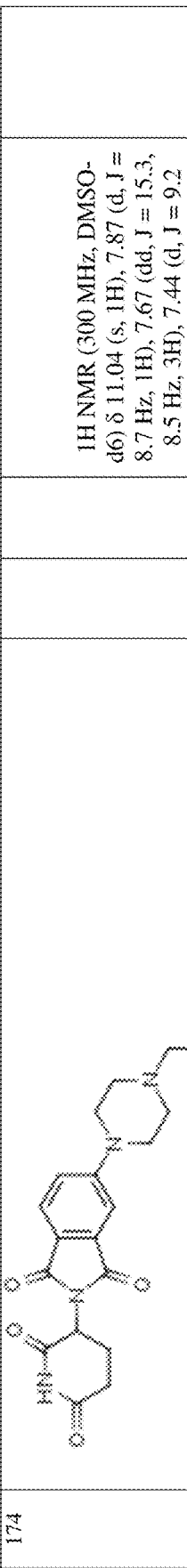
Figure 3:
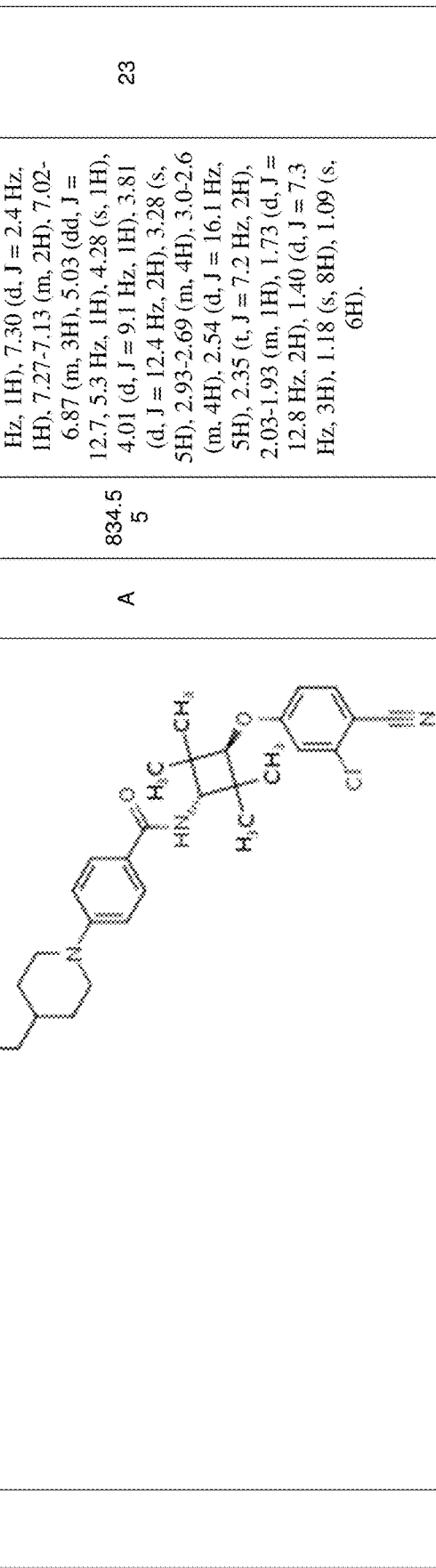
Figure 3:
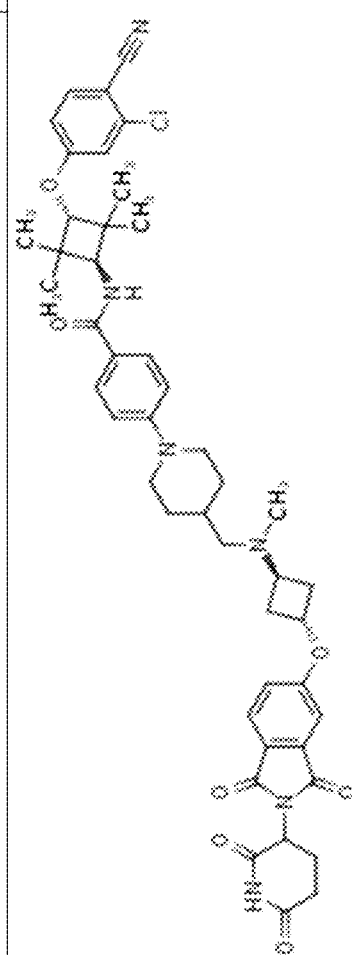
Figure 3:
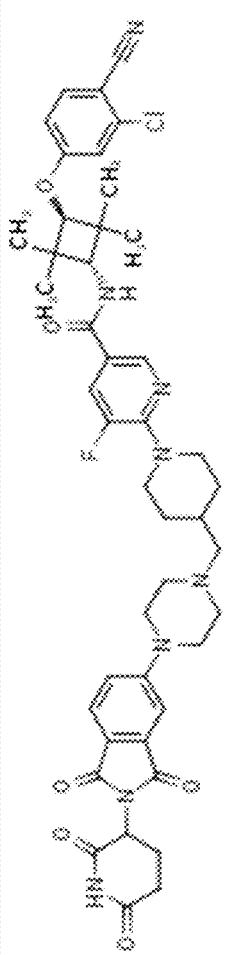
Figure 3:
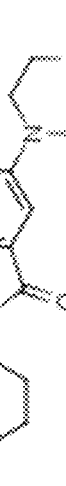
Figure 3:
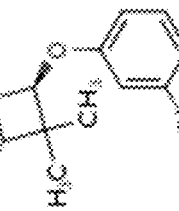
Figure 3:
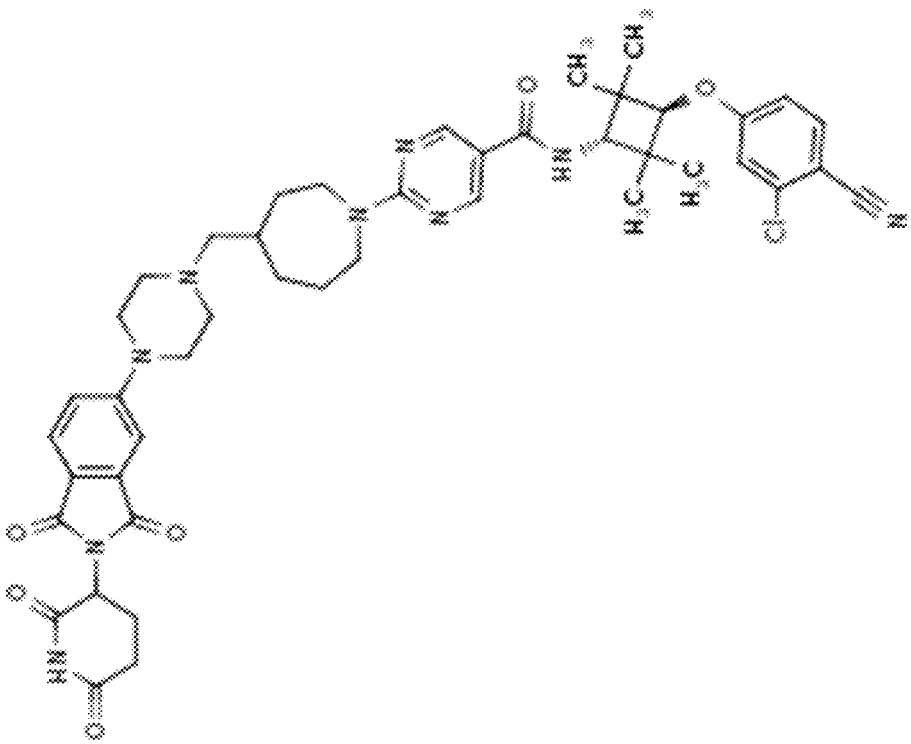
Figure 3:
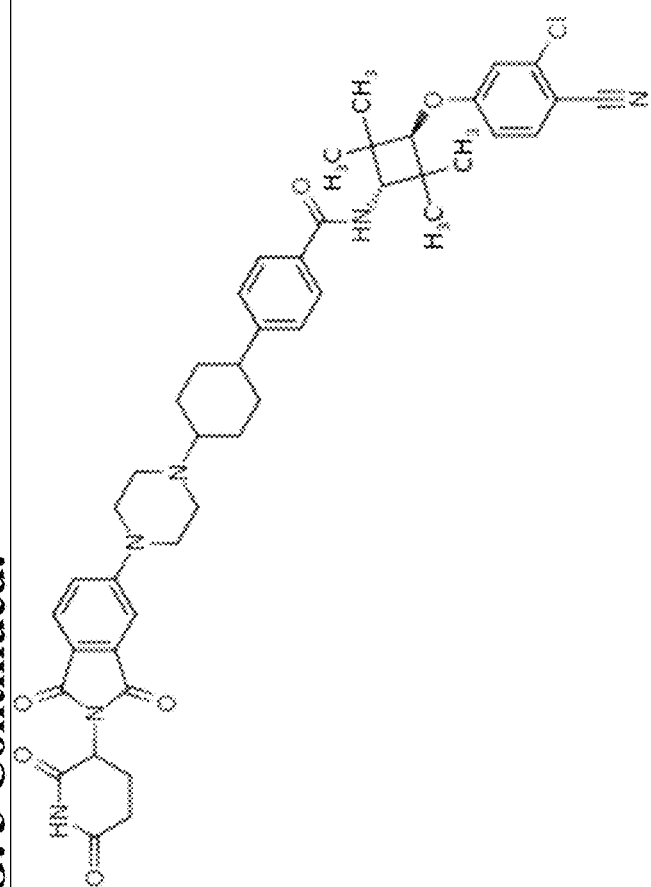
Figure 3:

Figure 3:
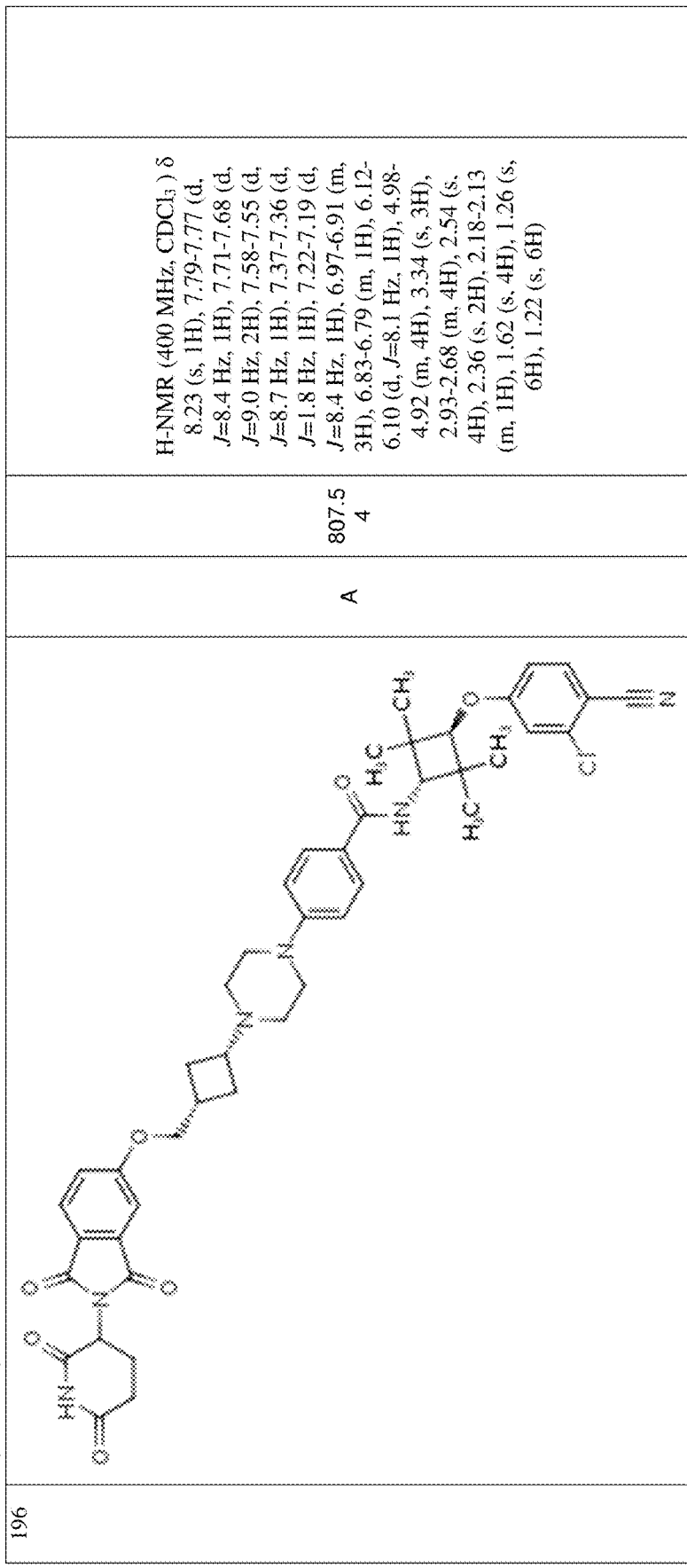
Figure 3:
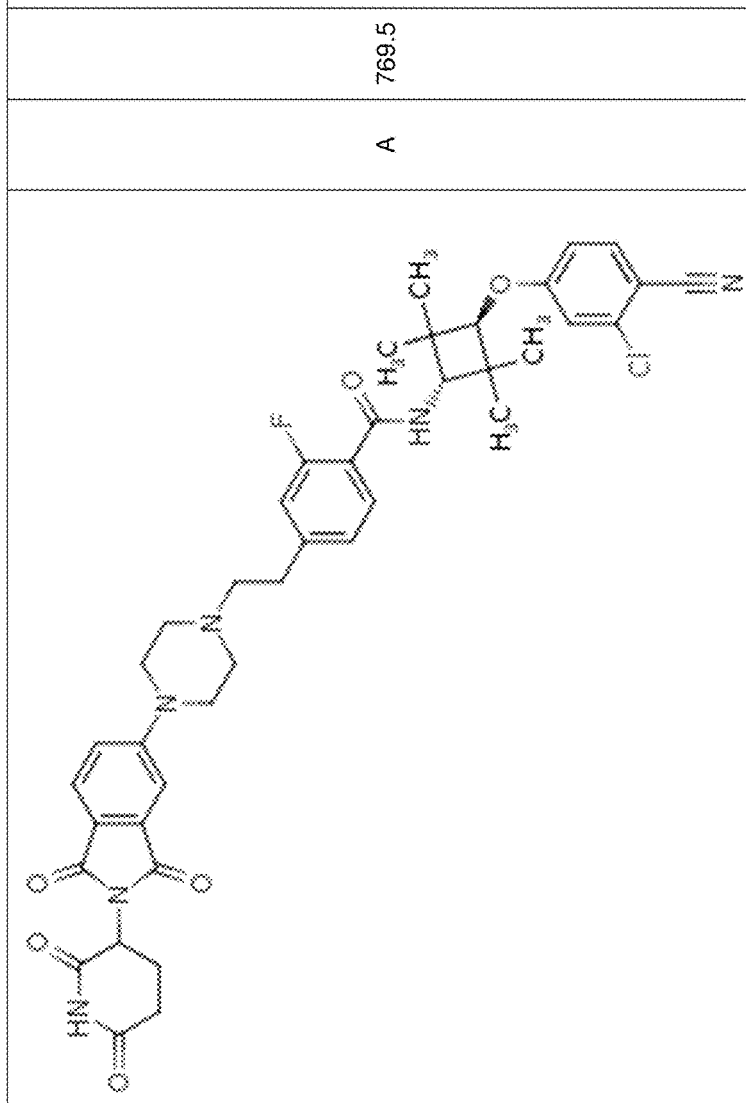
Figure 3:
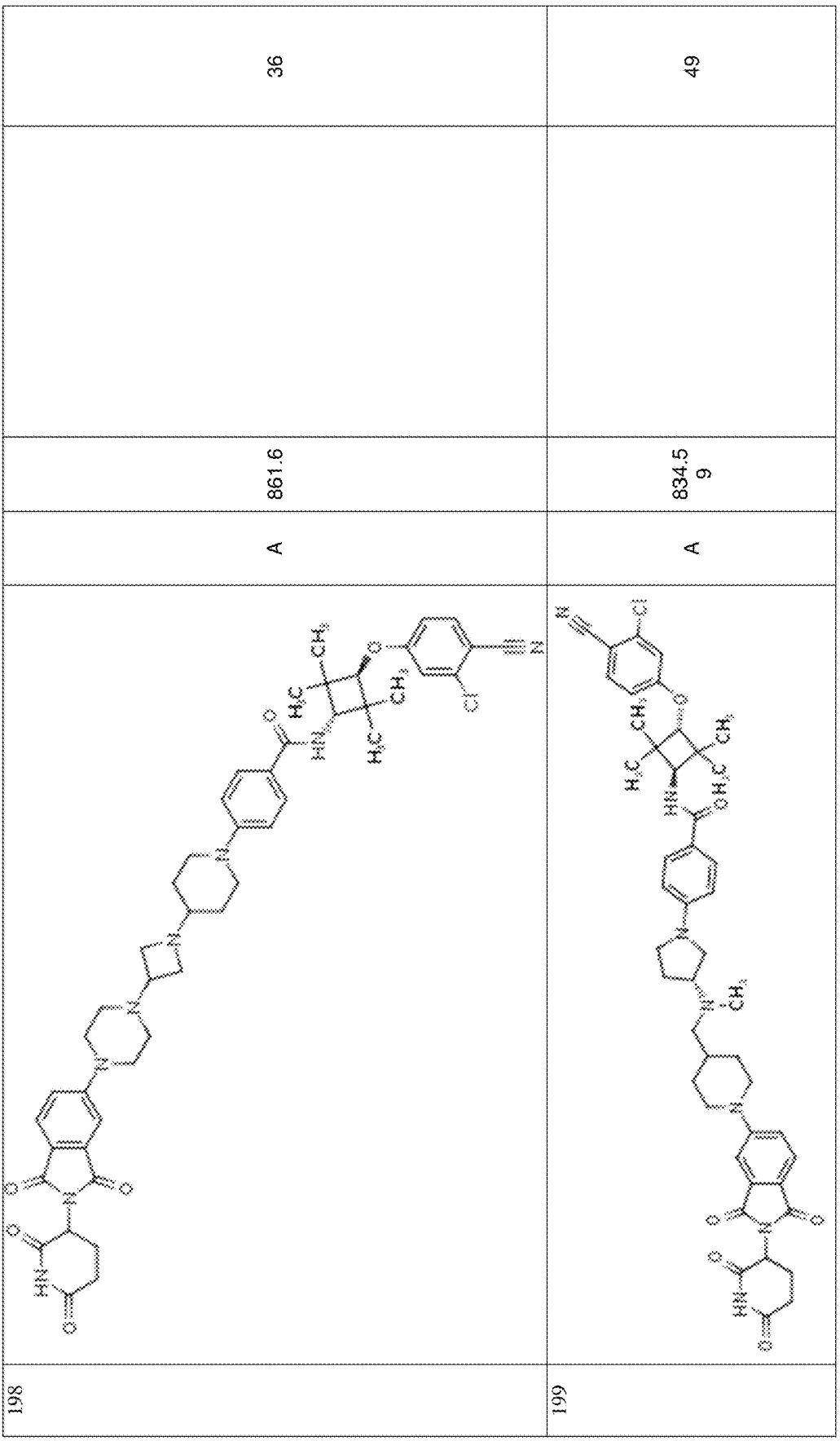
Figure 3:
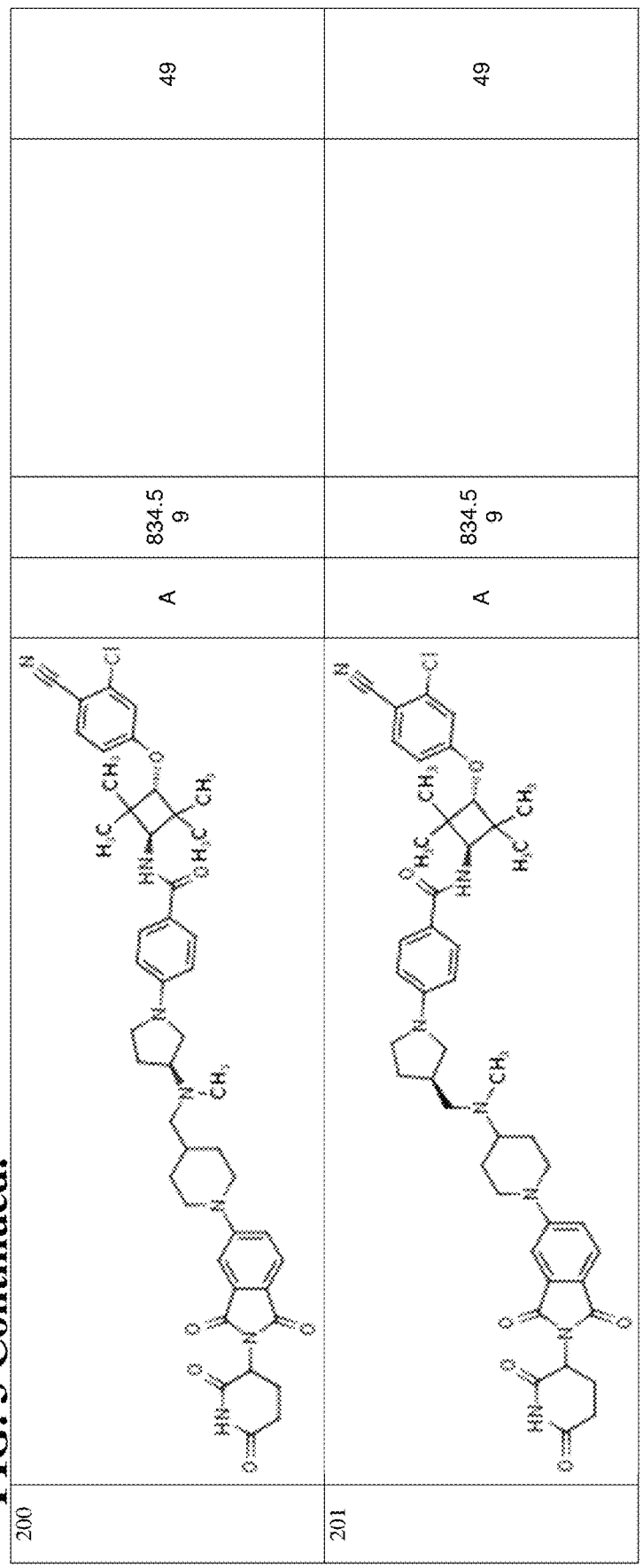
Figure 3:
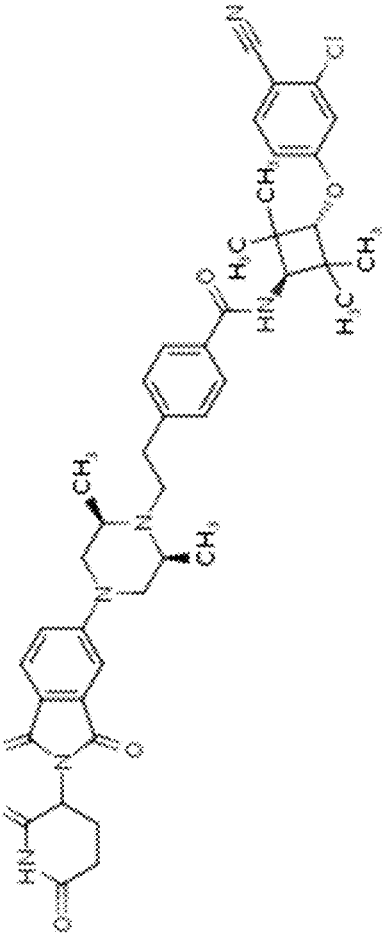
Figure 3:
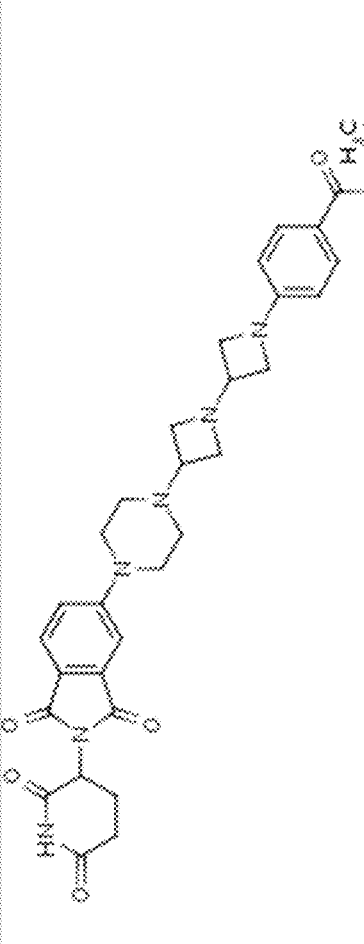
Figure 3:
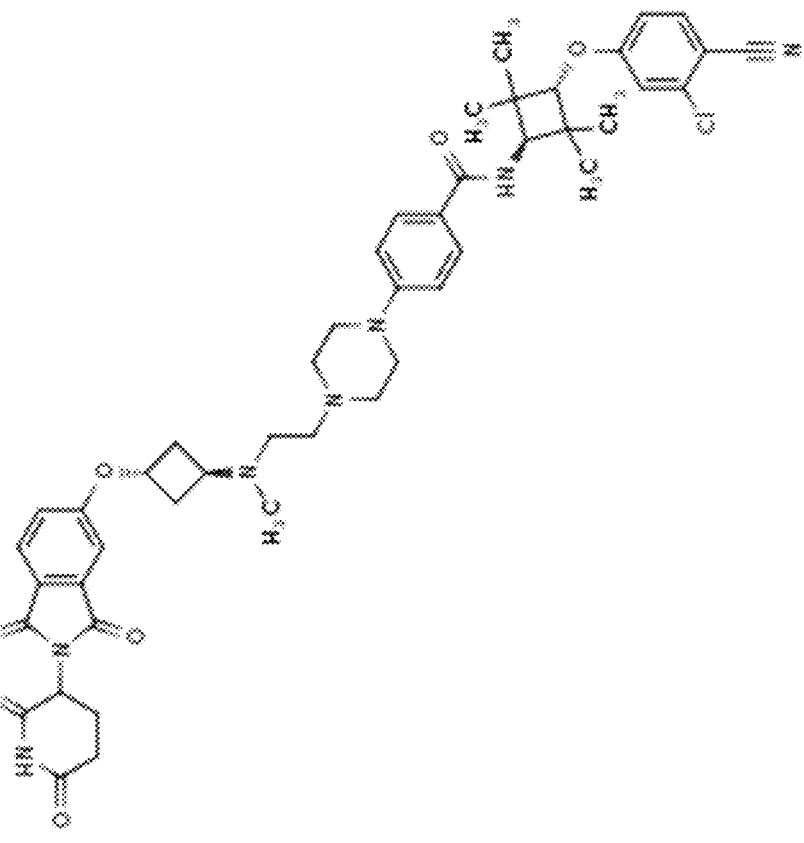
Figure 3:
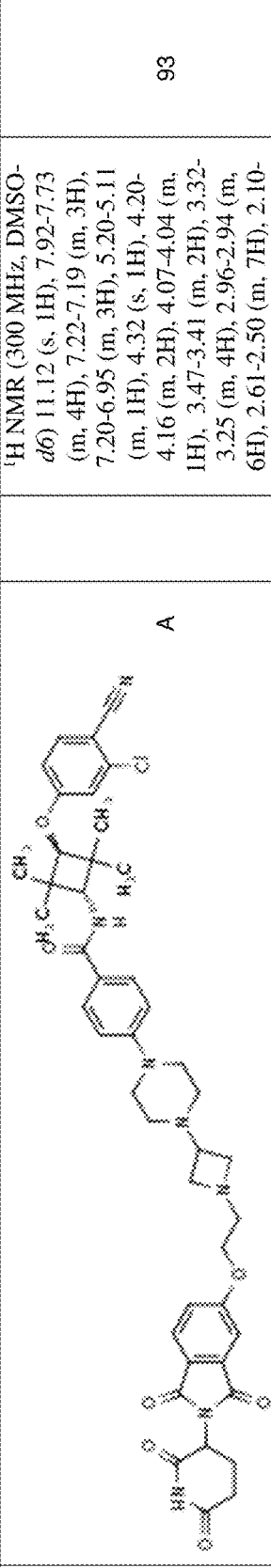
Figure 3:
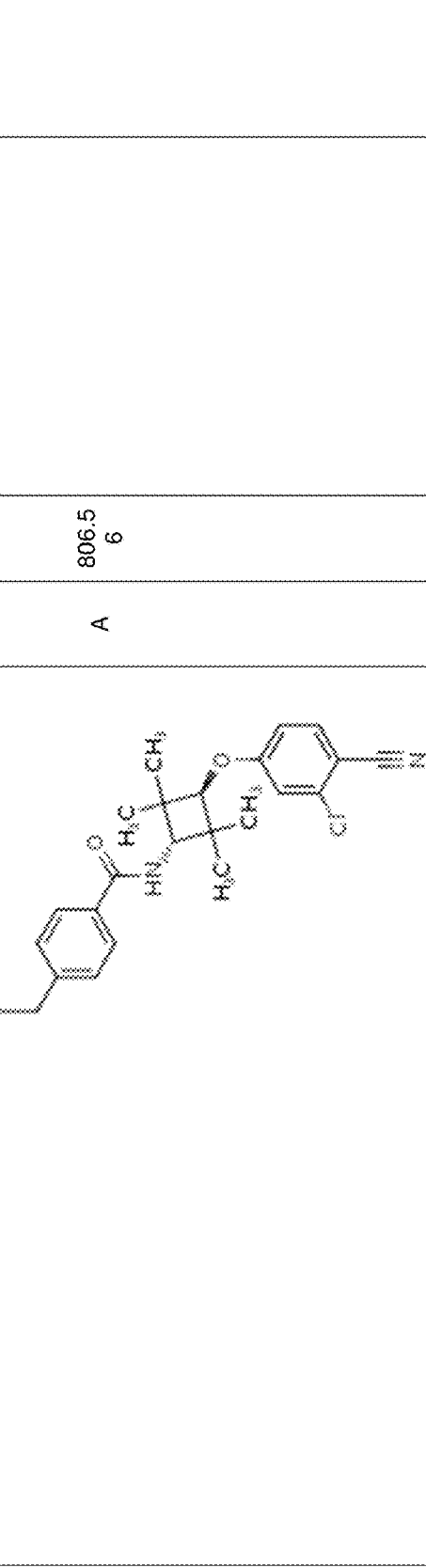
Figure 3:
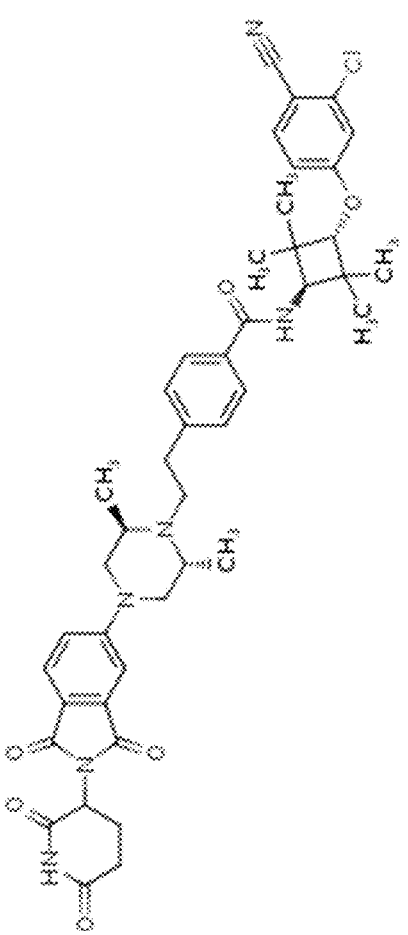
Figure 3:
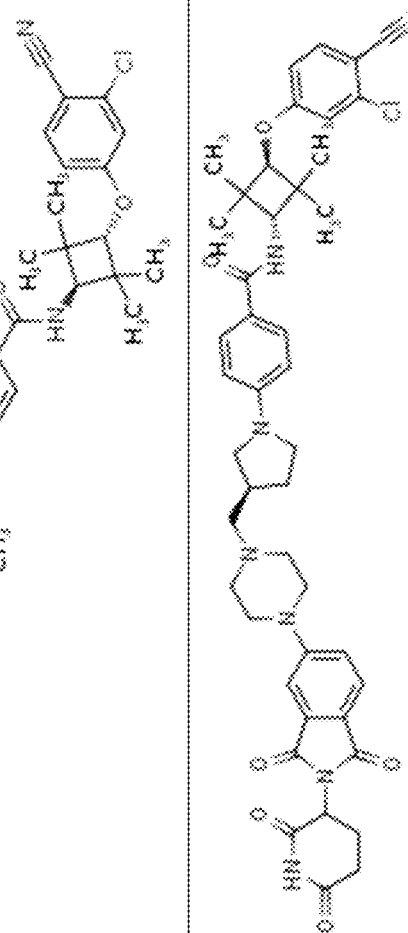
Figure 3:
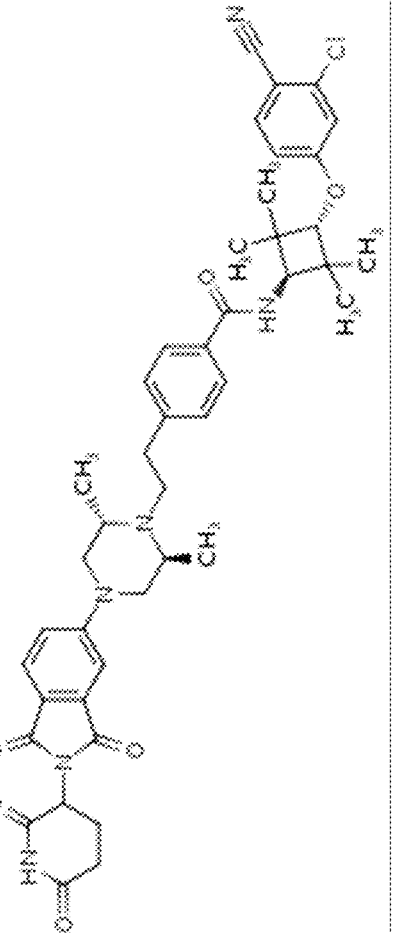
Figure 3:
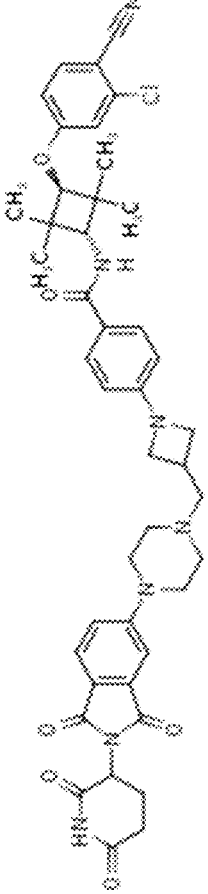
Figure 3:
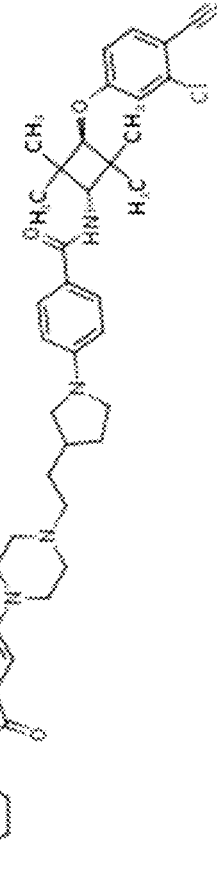
Figure 3:
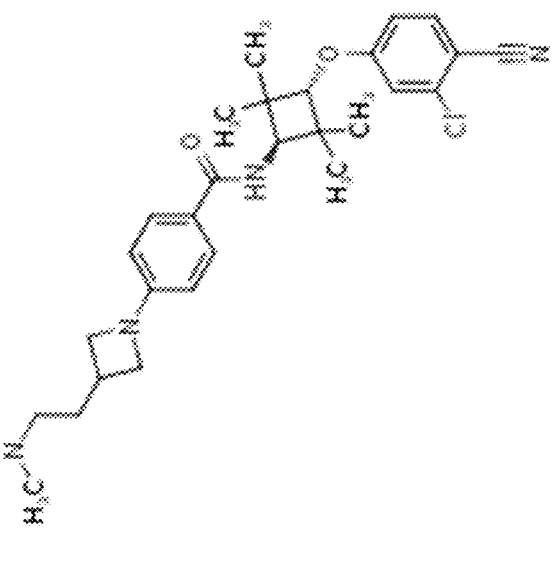
Figure 3:
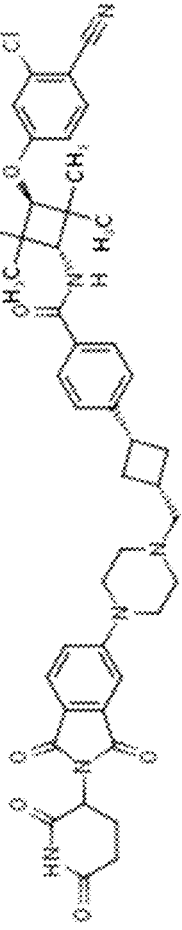
Figure 3:
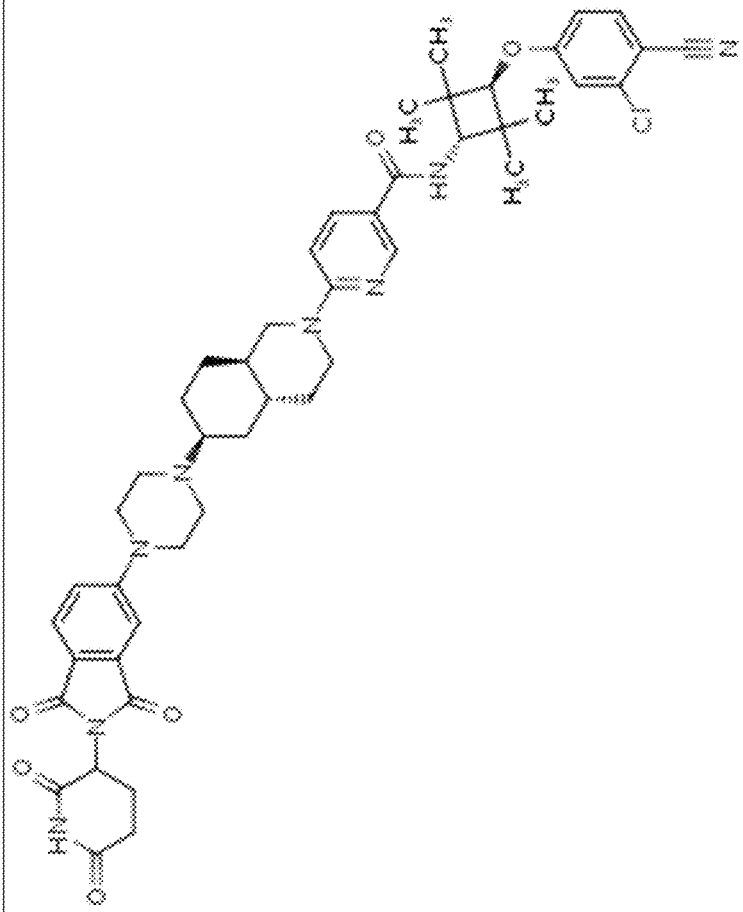
Figure 3:
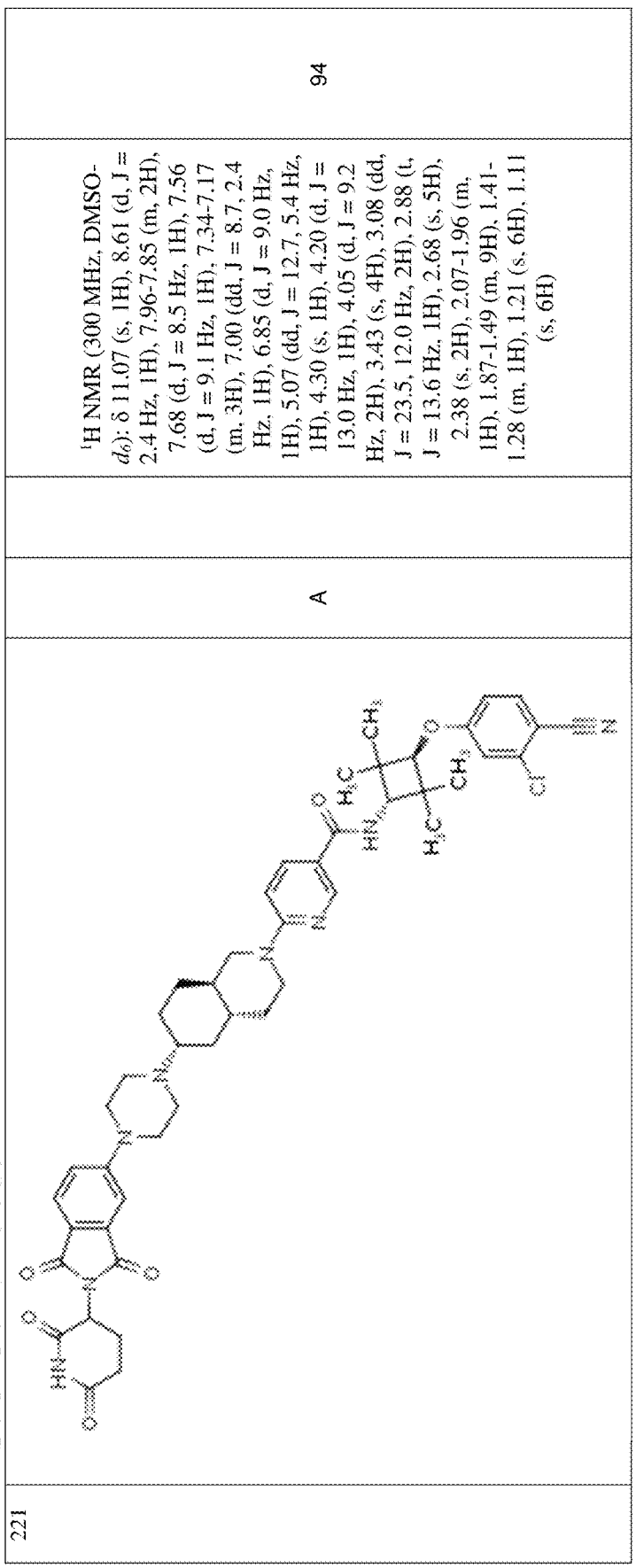
Figure 3:
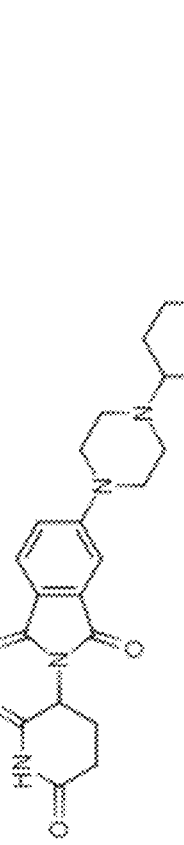
Figure 3:
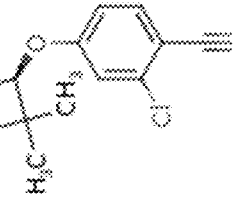
Figure 3:
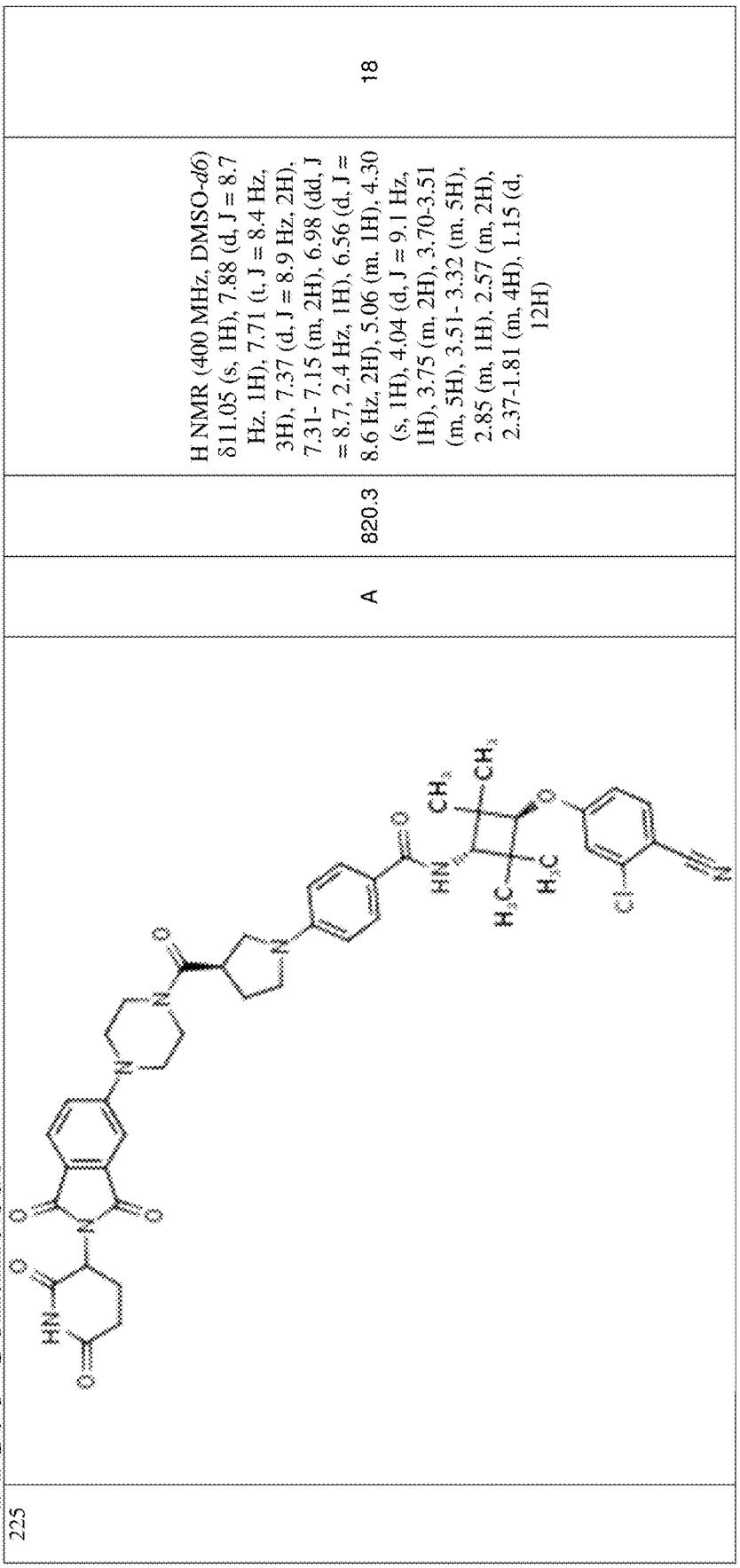
Figure 3:
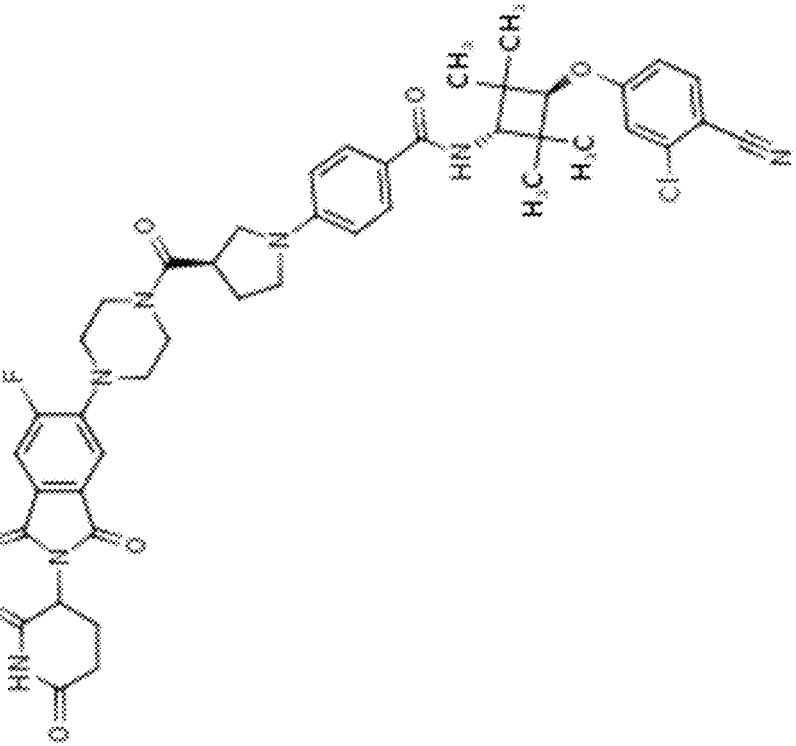
Figure 3:
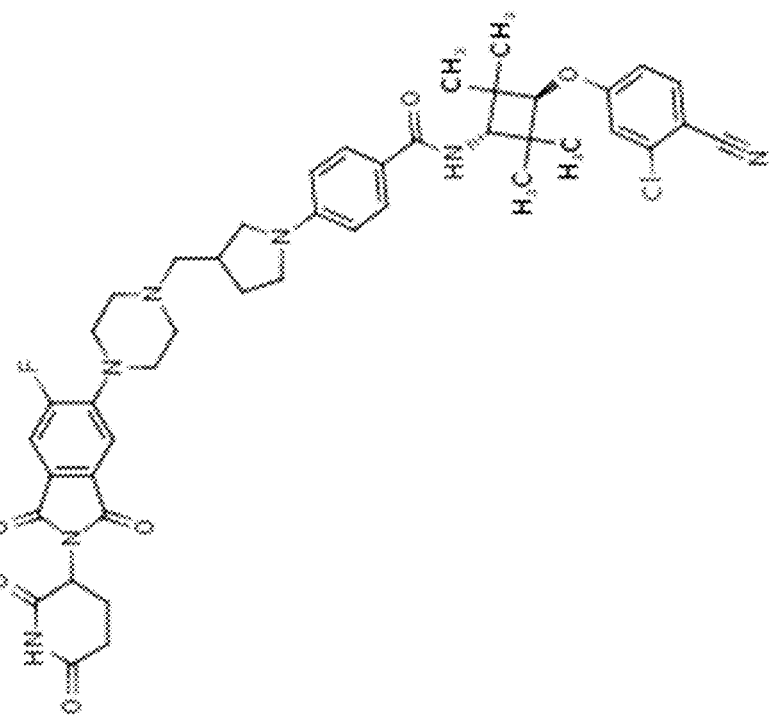
Figure 3:
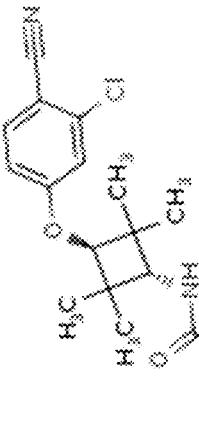
Figure 3:
Figure 3:
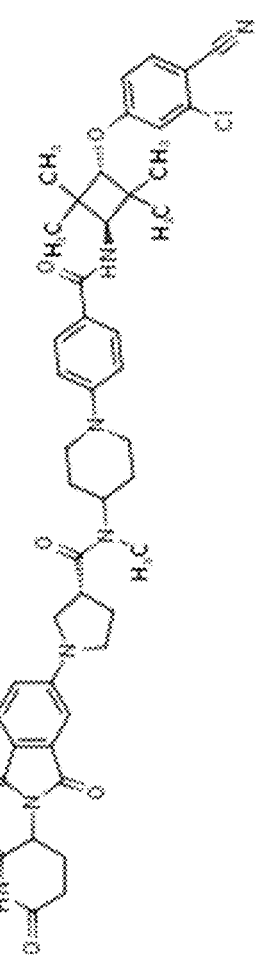
Figure 3:
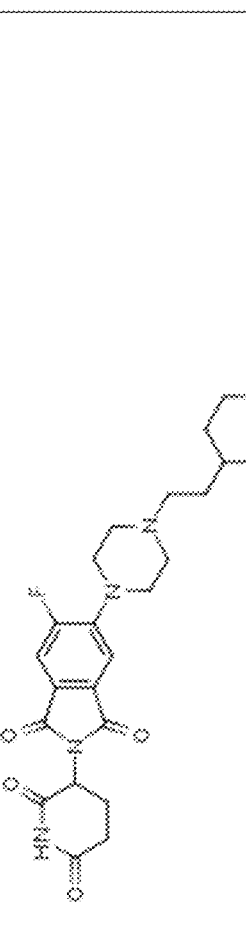
Figure 3:
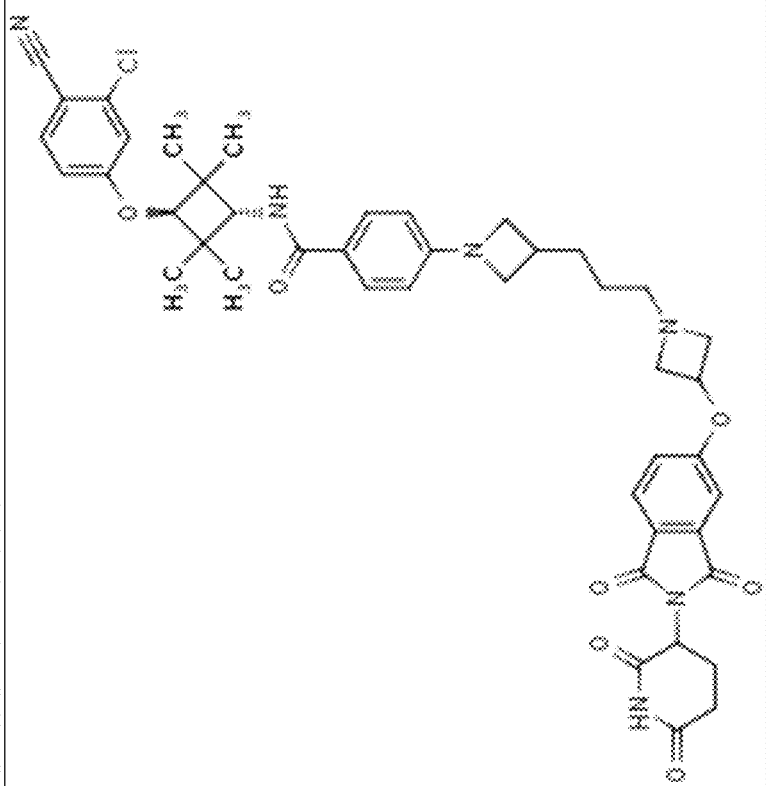
Figure 3:
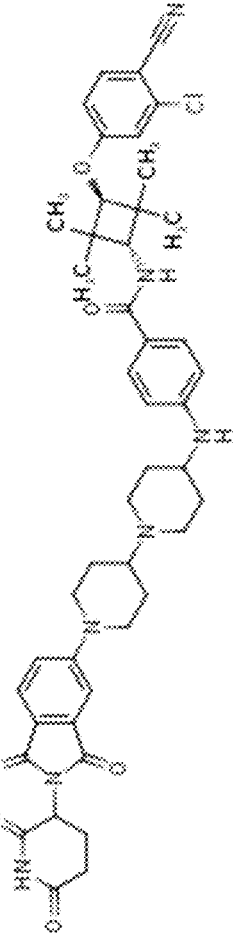
Figure 3:
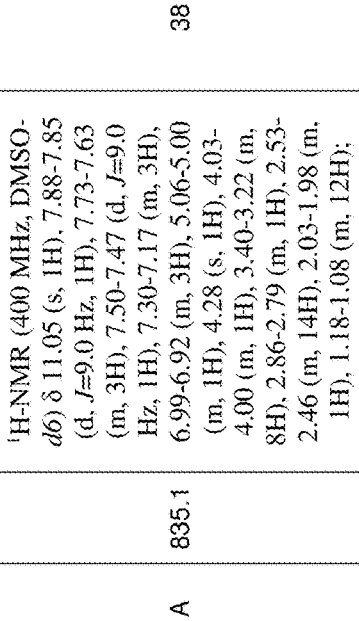
Figure 3:
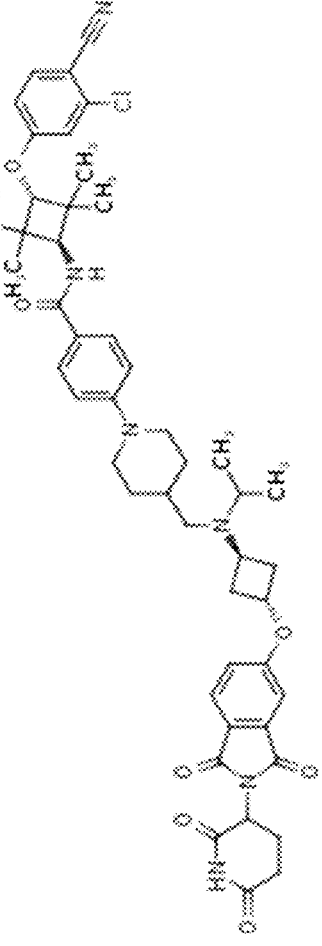
Figure 3:
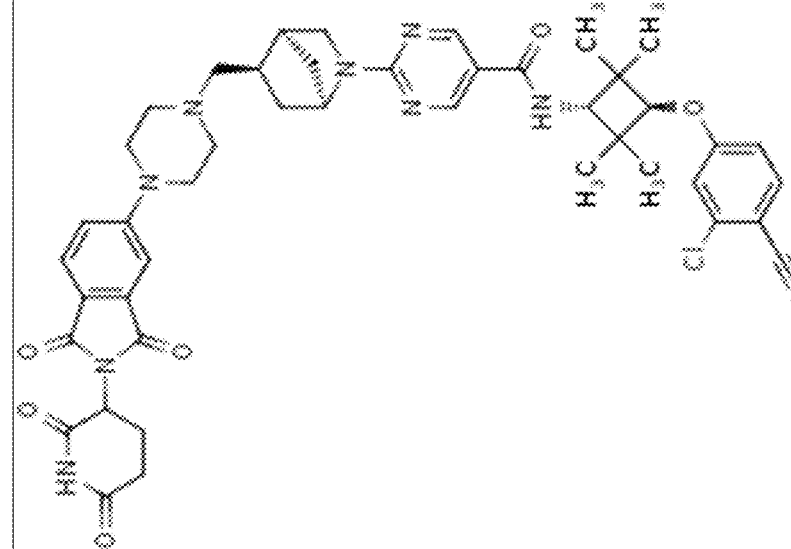
Figure 3:
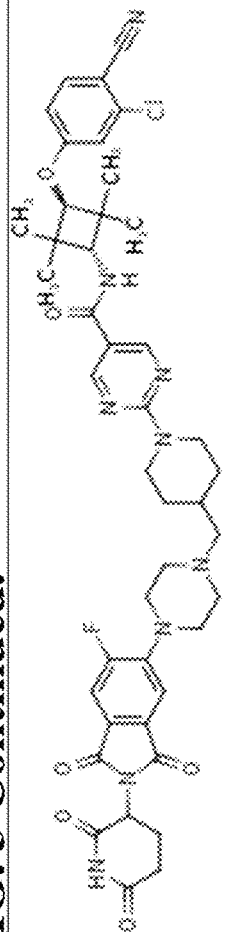
Figure 3:
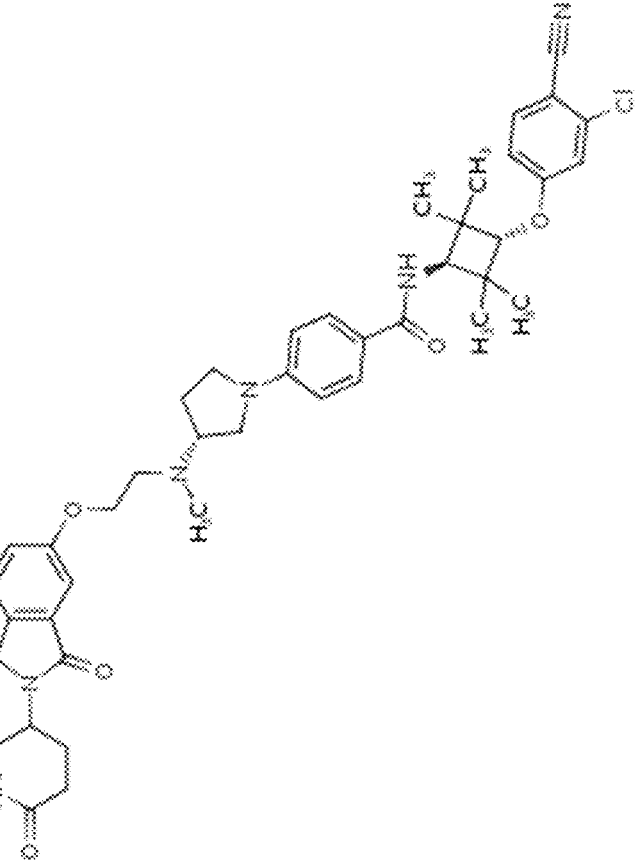
Figure 3:
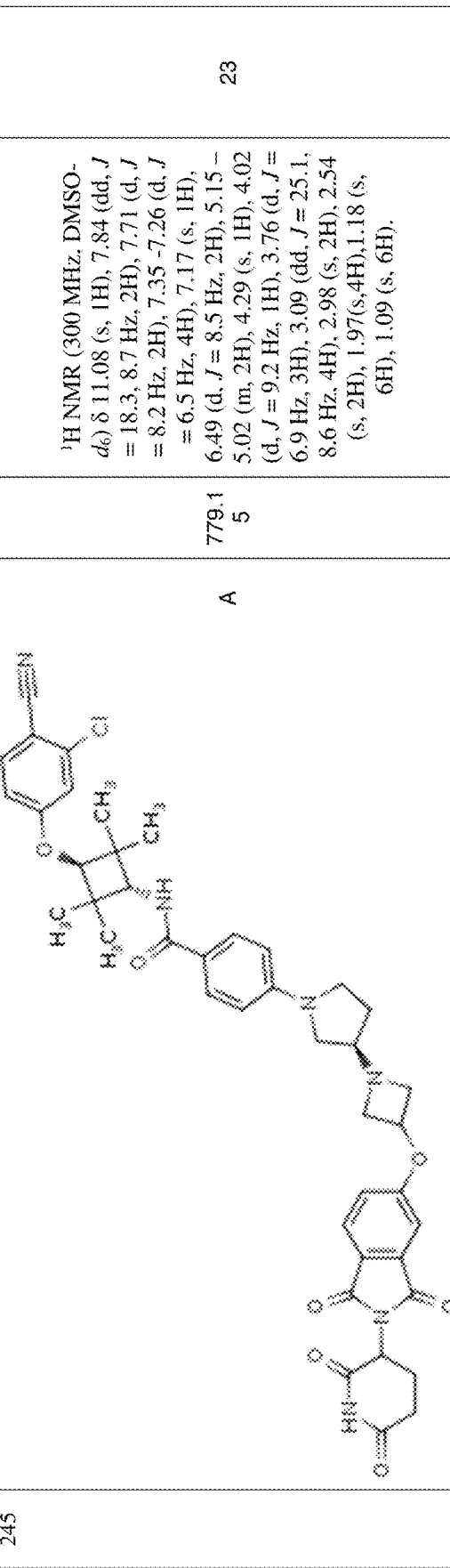
Figure 3:
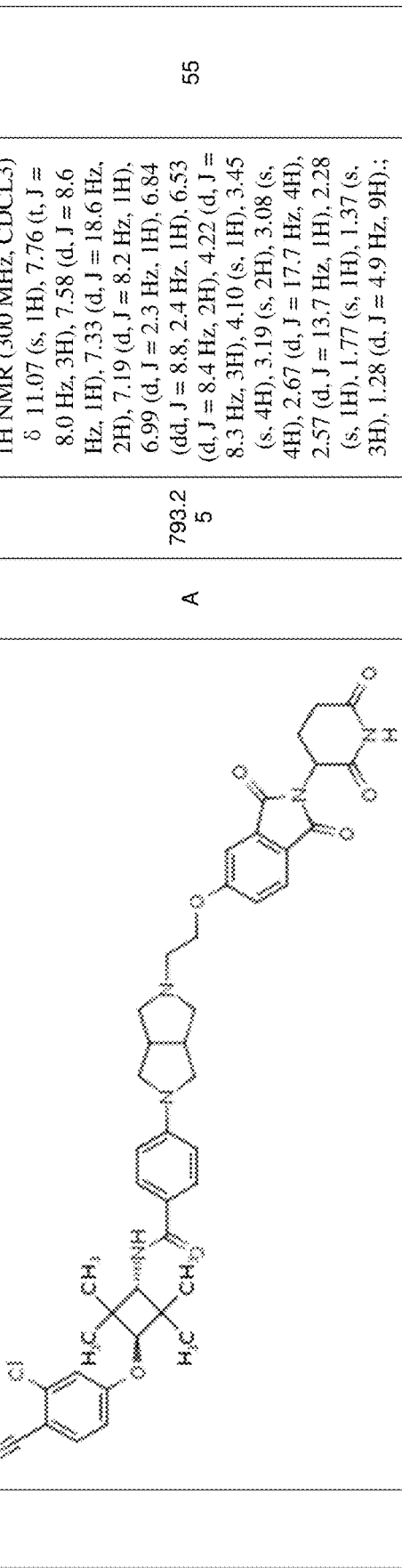
Figure 3:
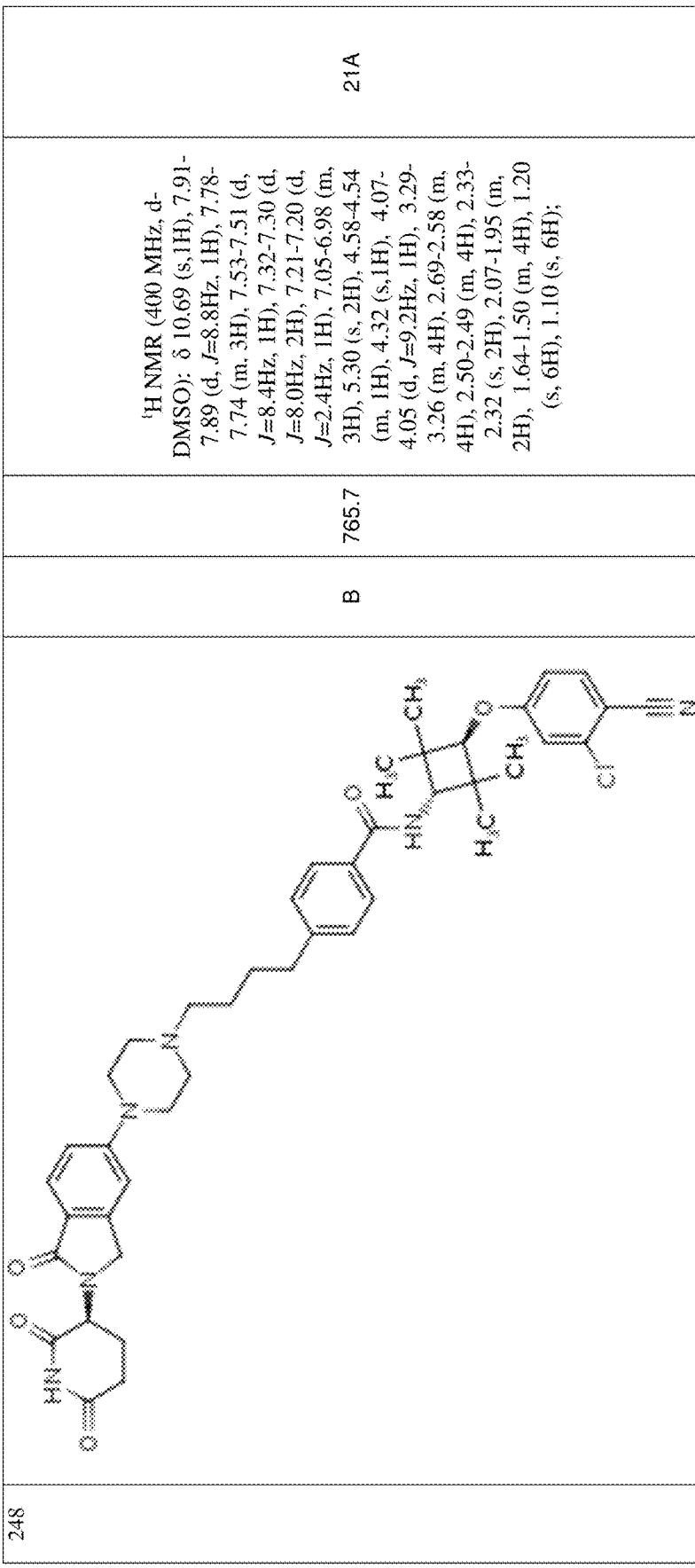
Figure 3:
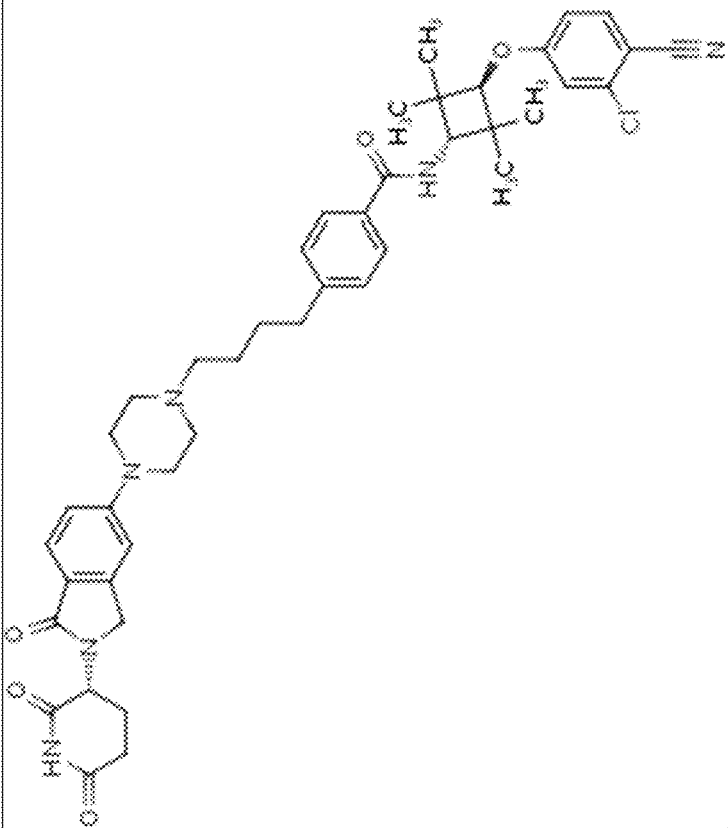
Figure 3:
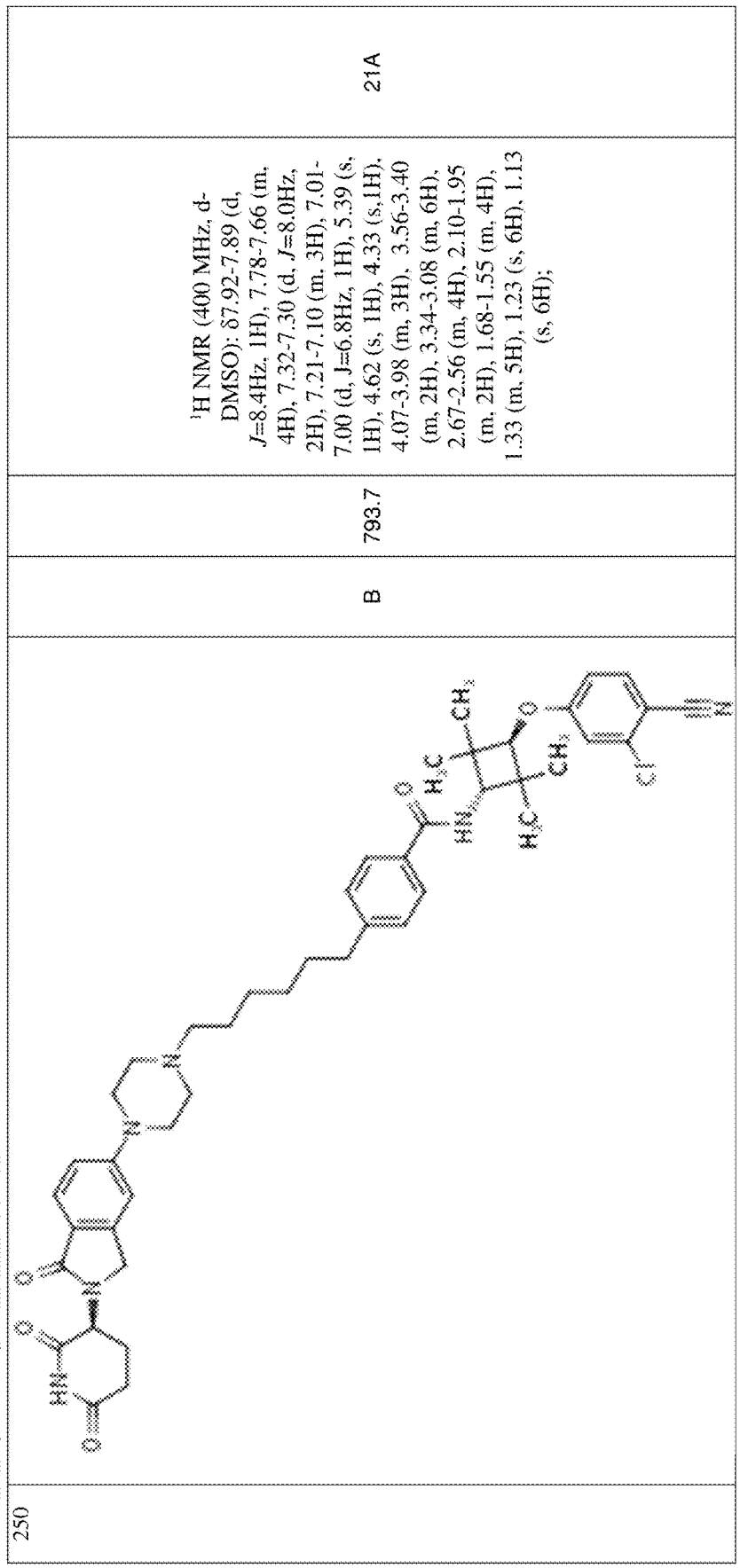
Figure 3:
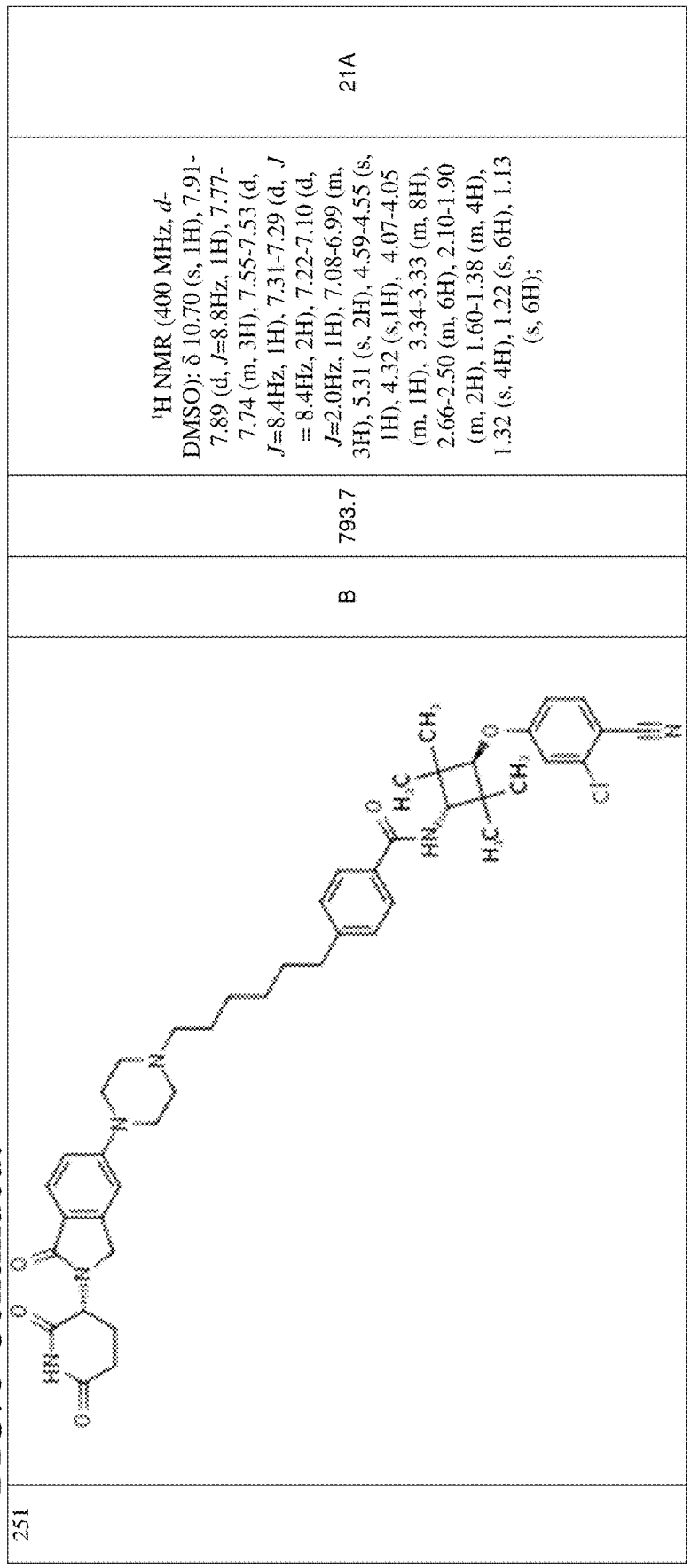
Figure 3:
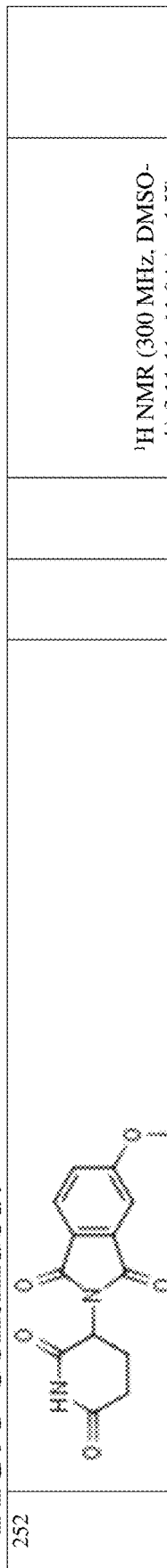
Figure 3:
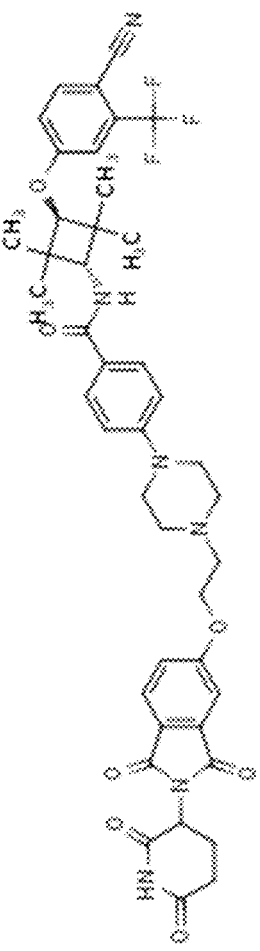
Figure 3:
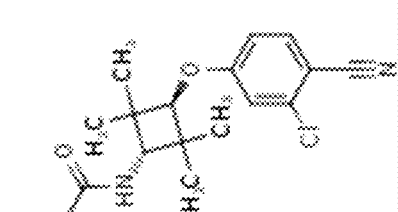
Figure 3:
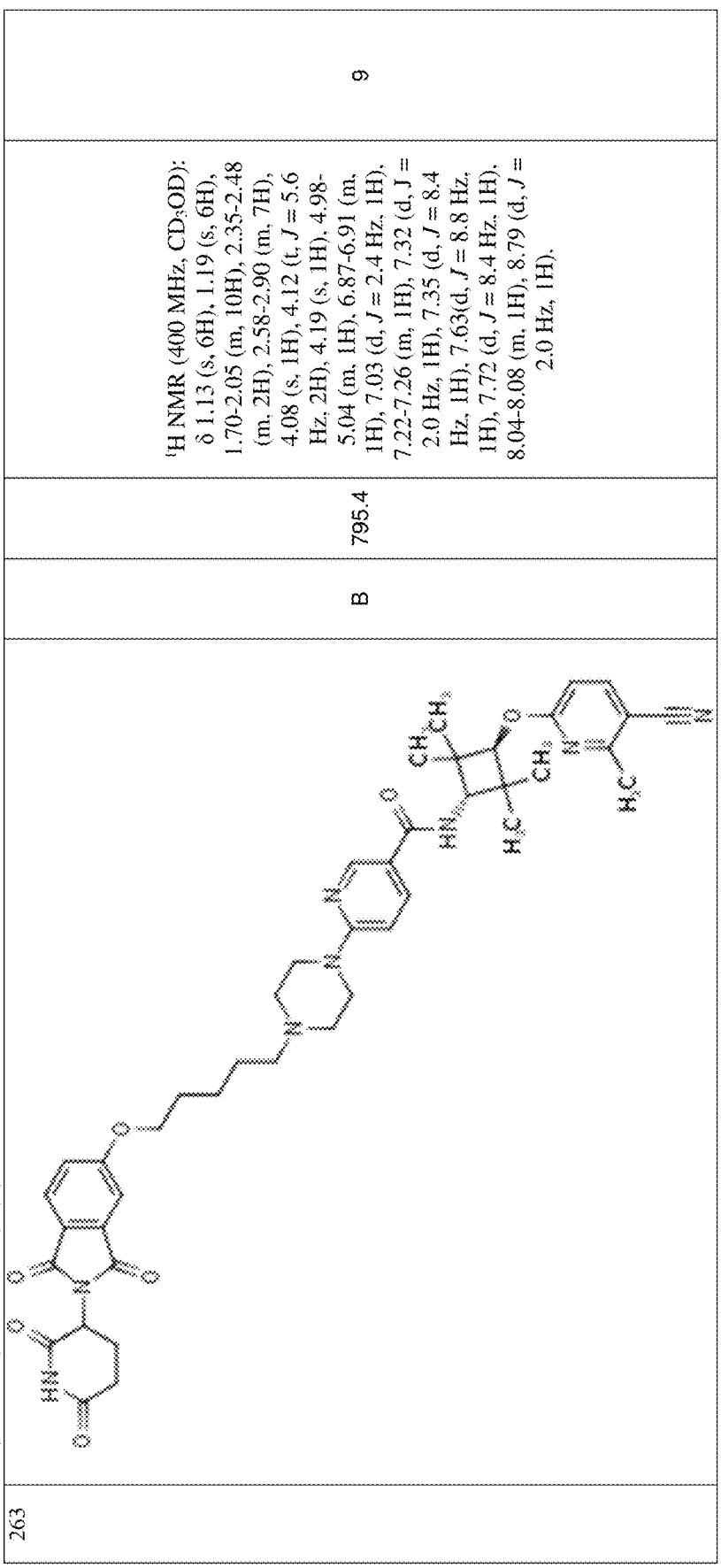
Figure 3:
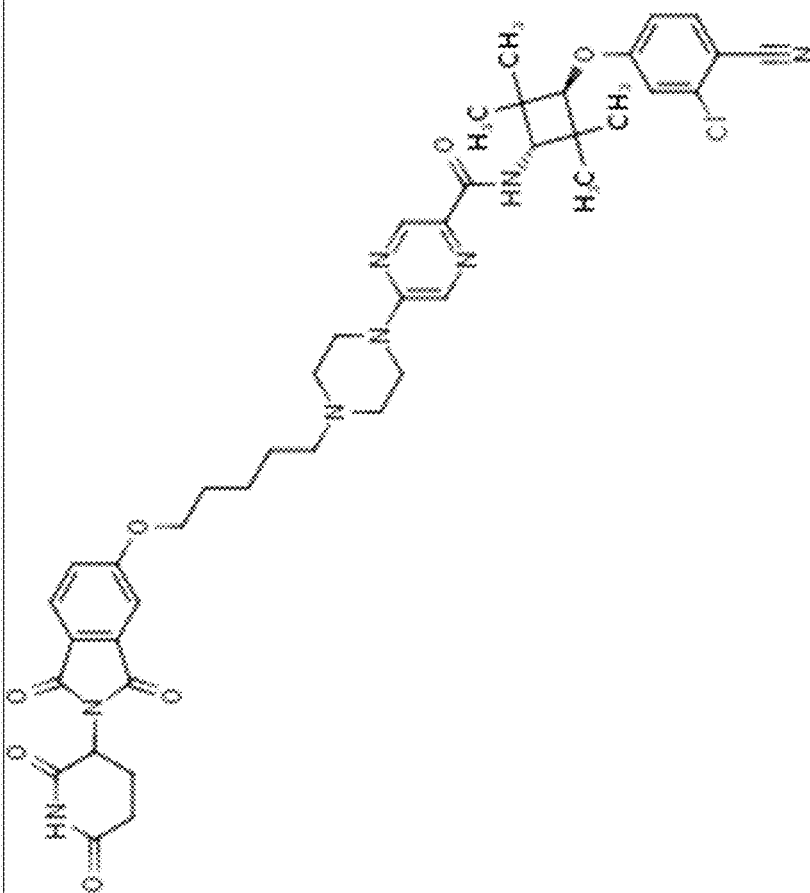
Figure 3:
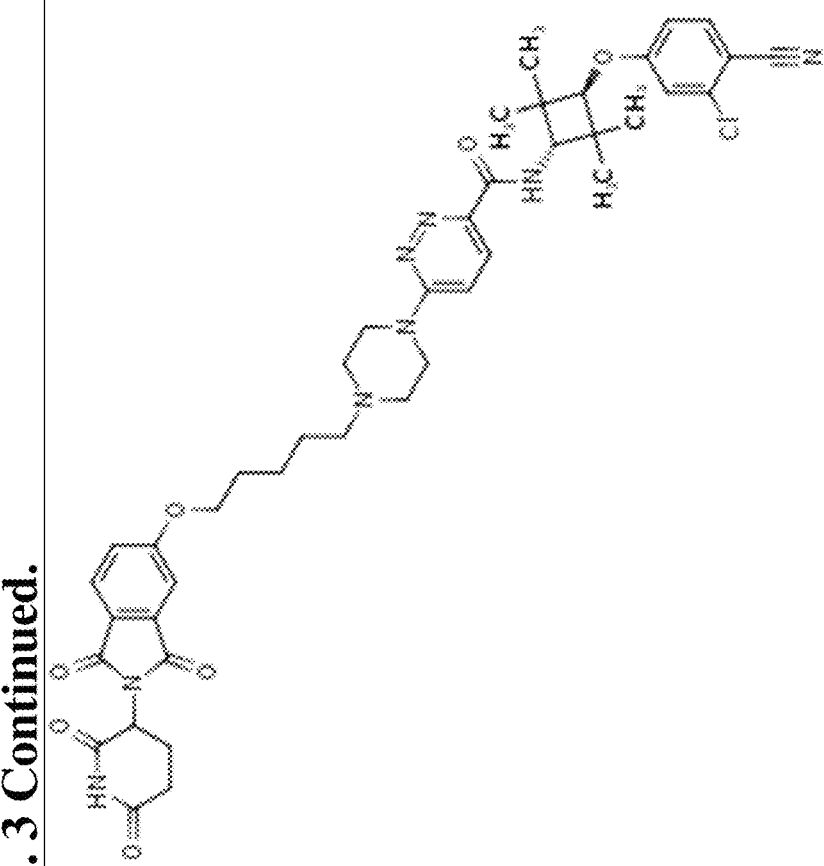
Figure 3:
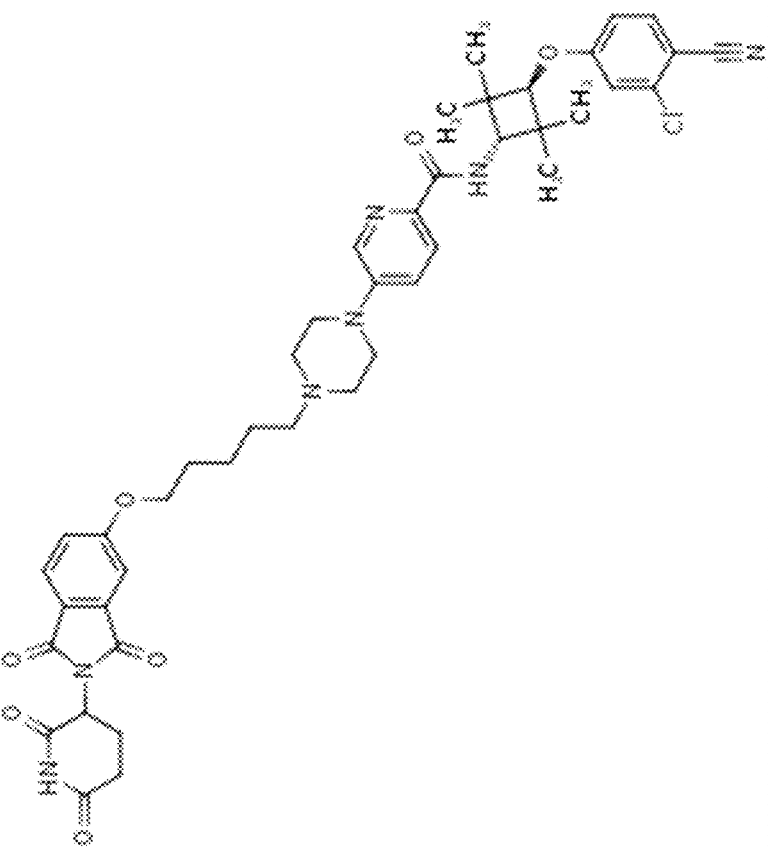
Figure 3:
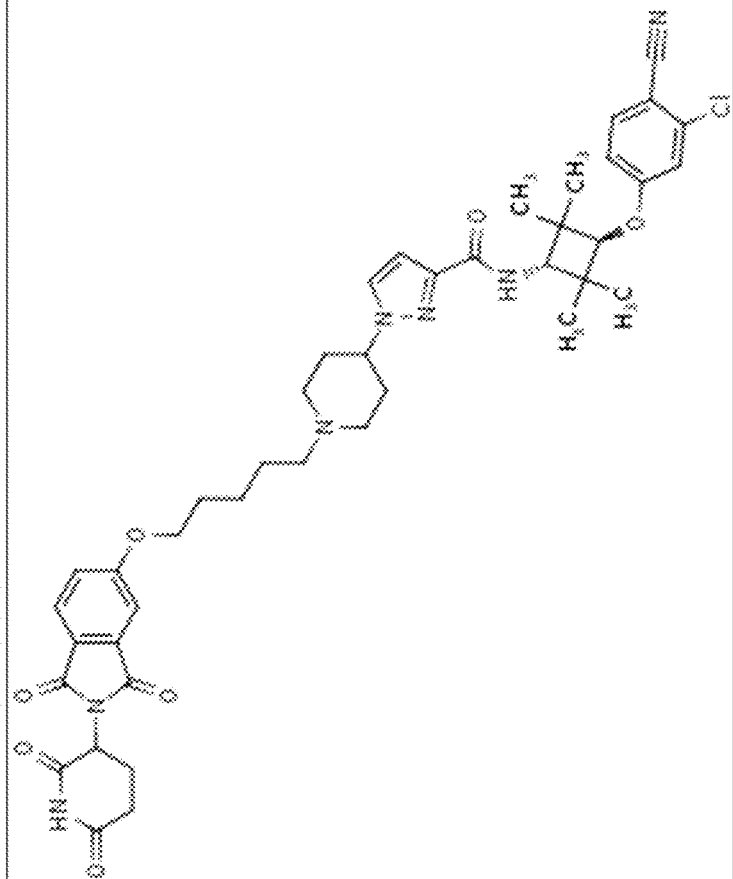
Figure 3:
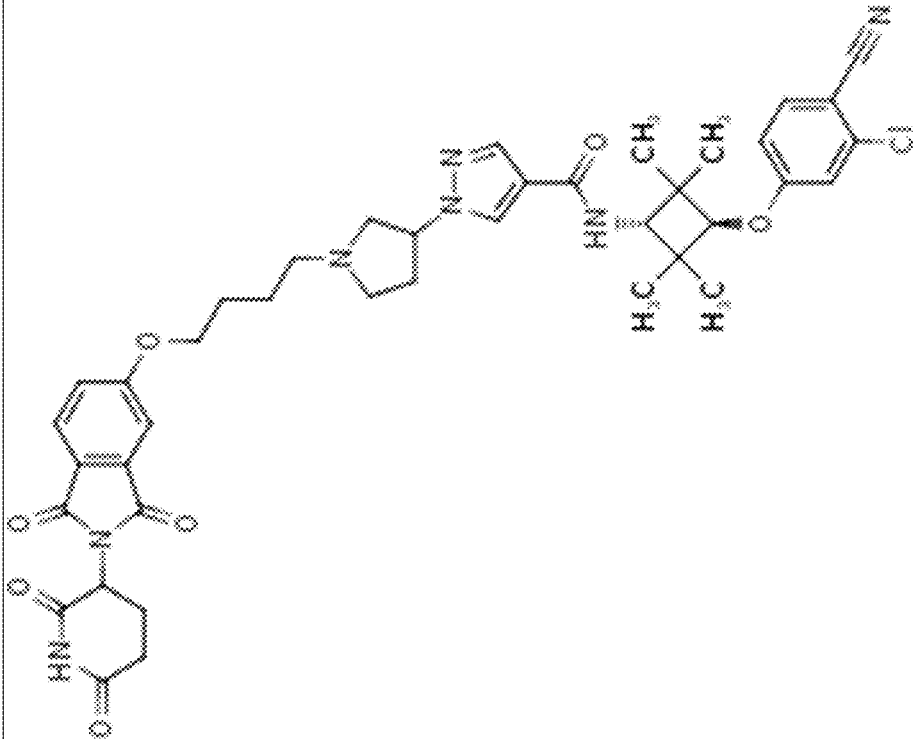
Figure 3:
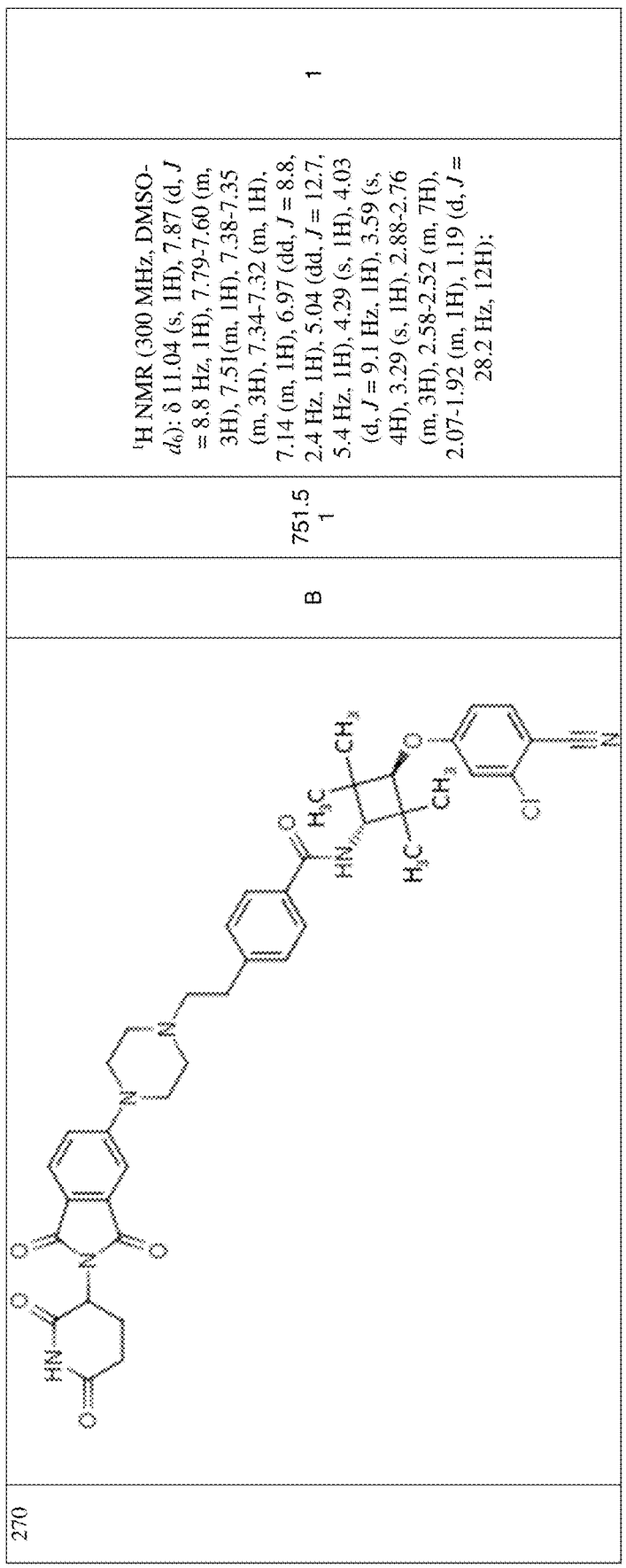
Figure 3:
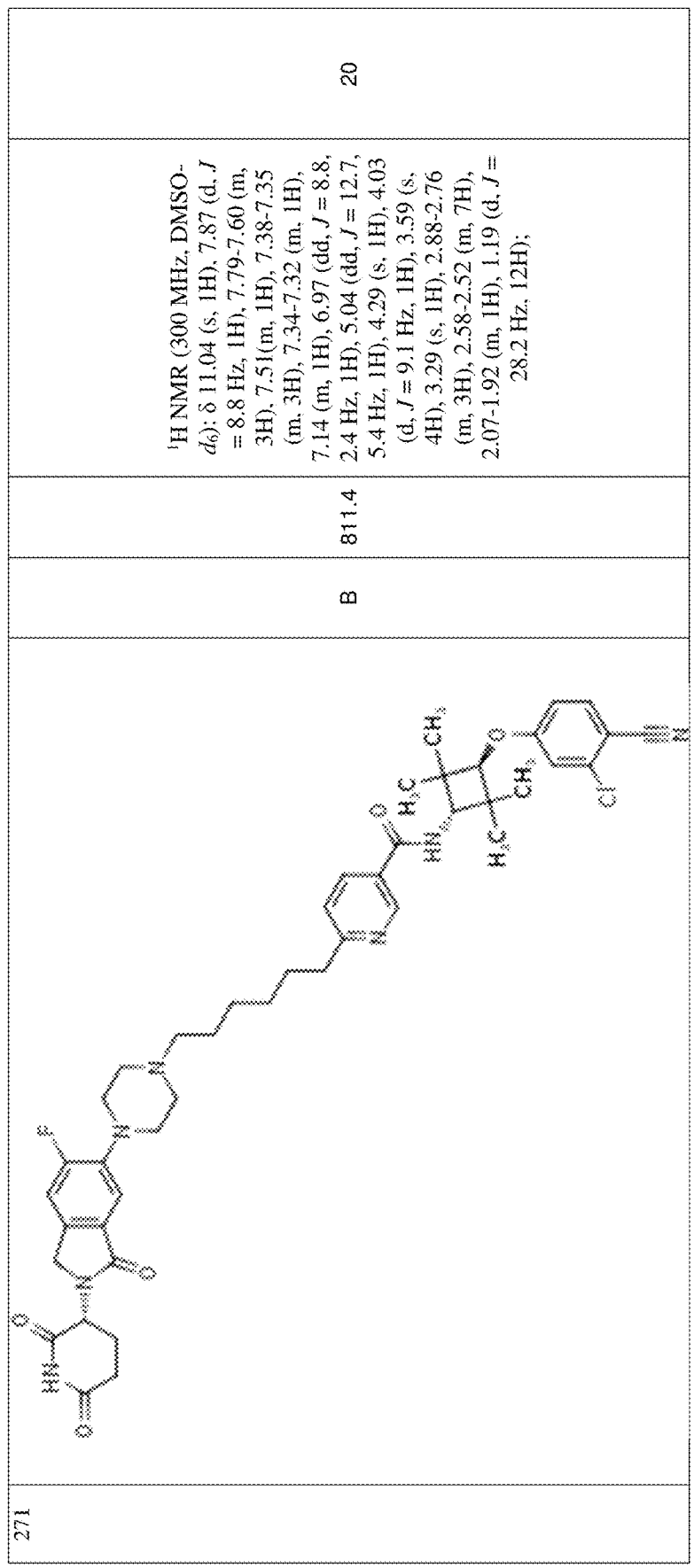
Figure 3:
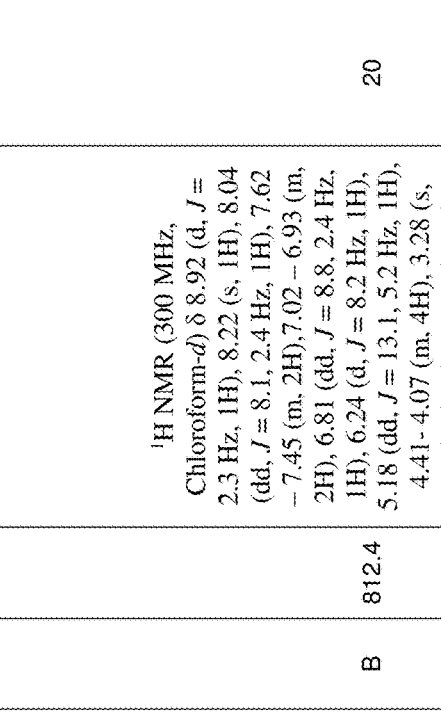
Figure 3:
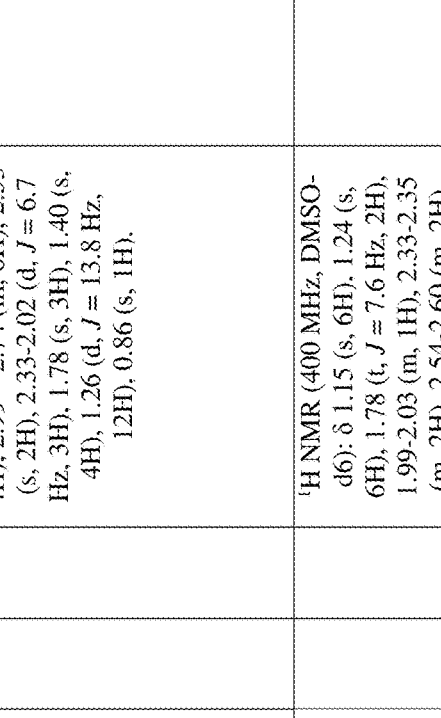
Figure 3:
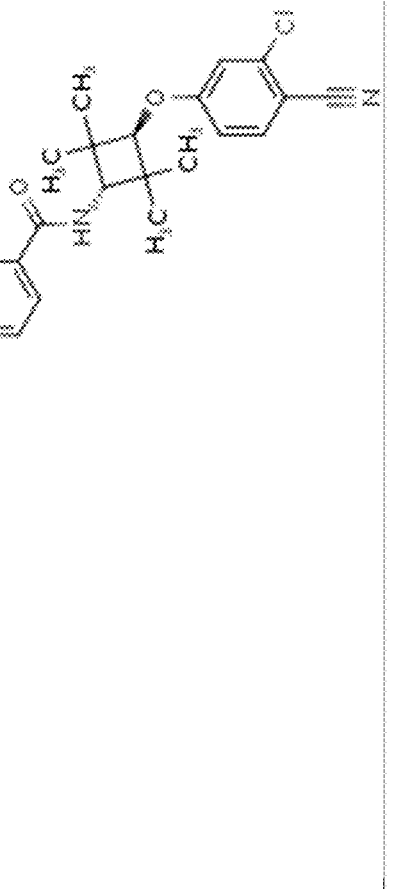
Figure 3:
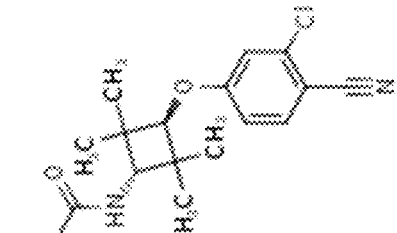
Figure 3:
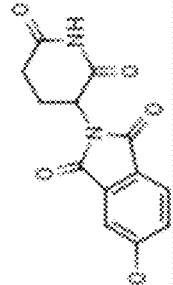
Figure 3:
Figure 3:
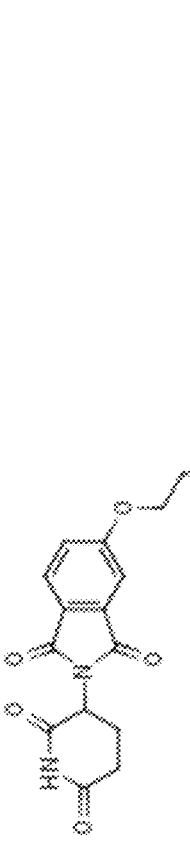
Figure 3:
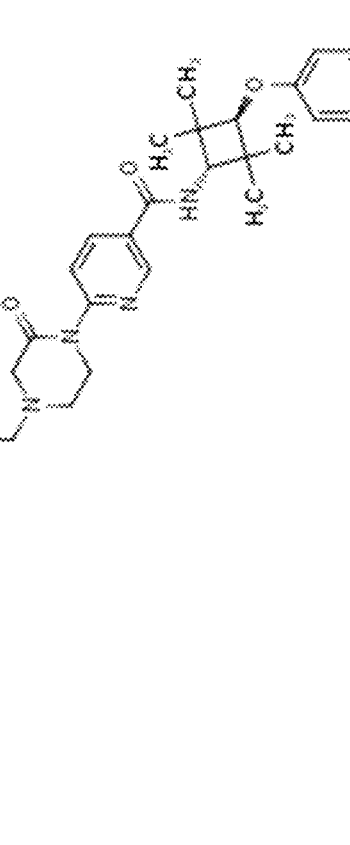
Figure 3:
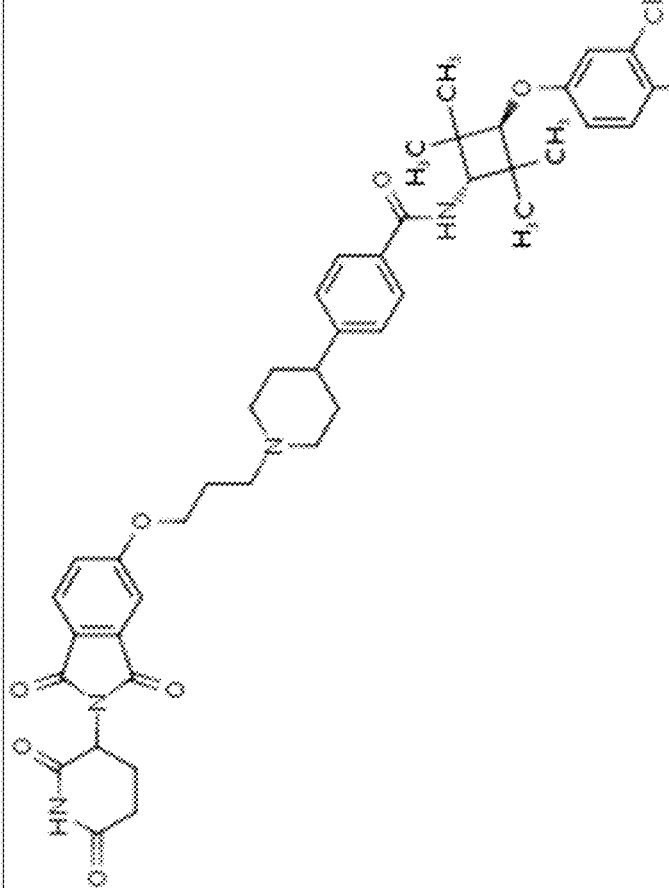
Figure 3:
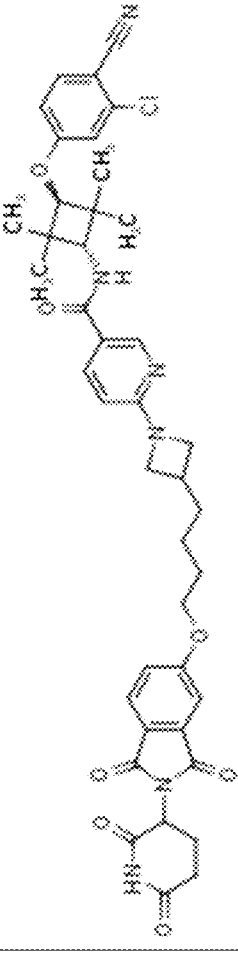
Figure 3:
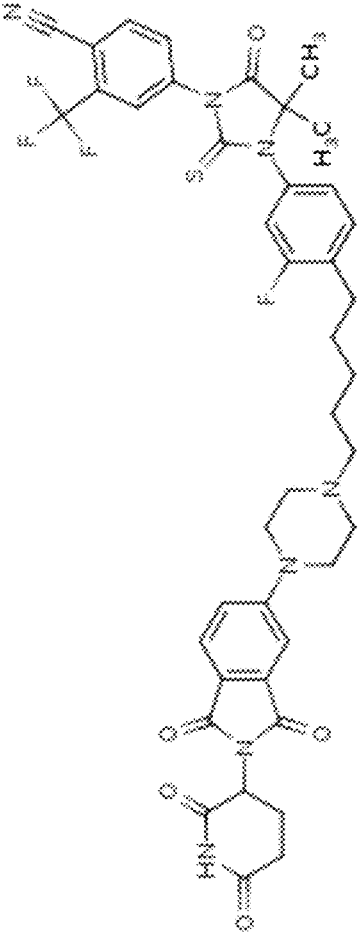
Figure 3:
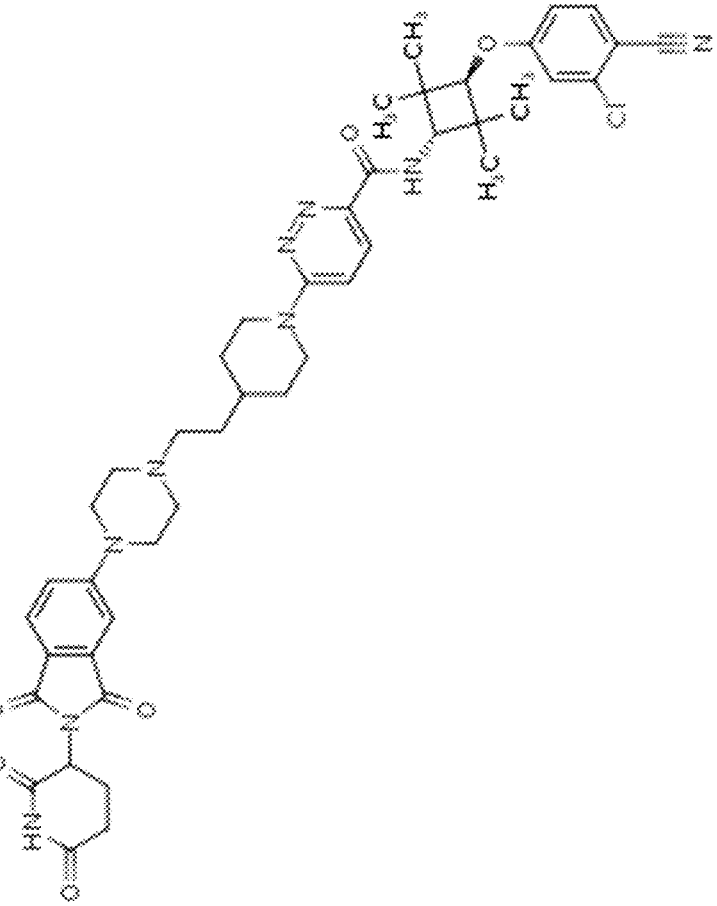
Figure 3:
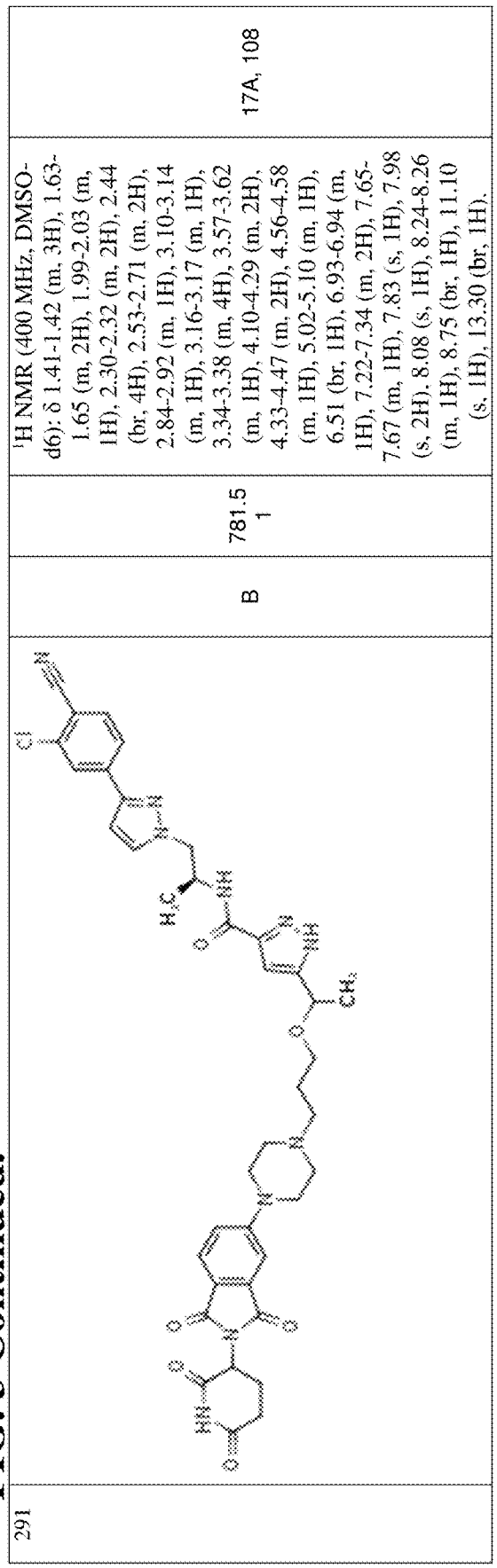
Figure 3:
Figure 3:
Figure 3:
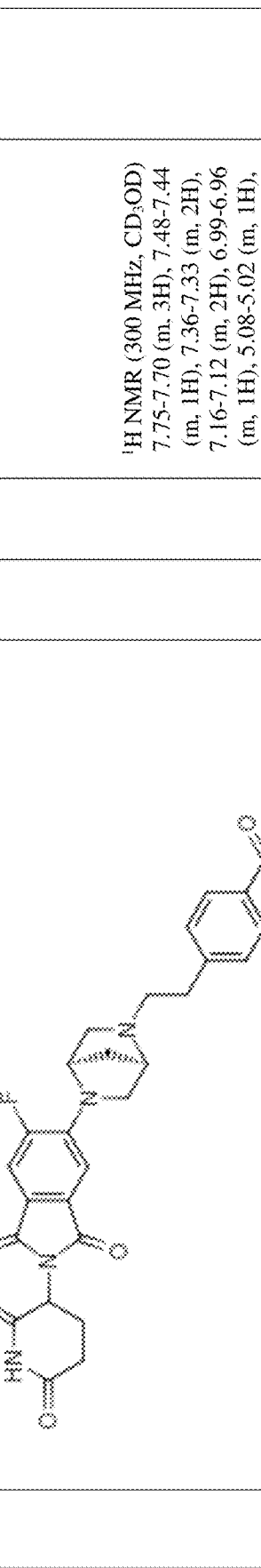
Figure 3:
Figure 3:
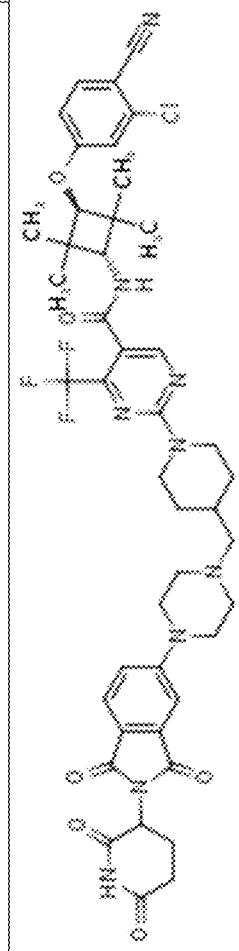
Figure 3:
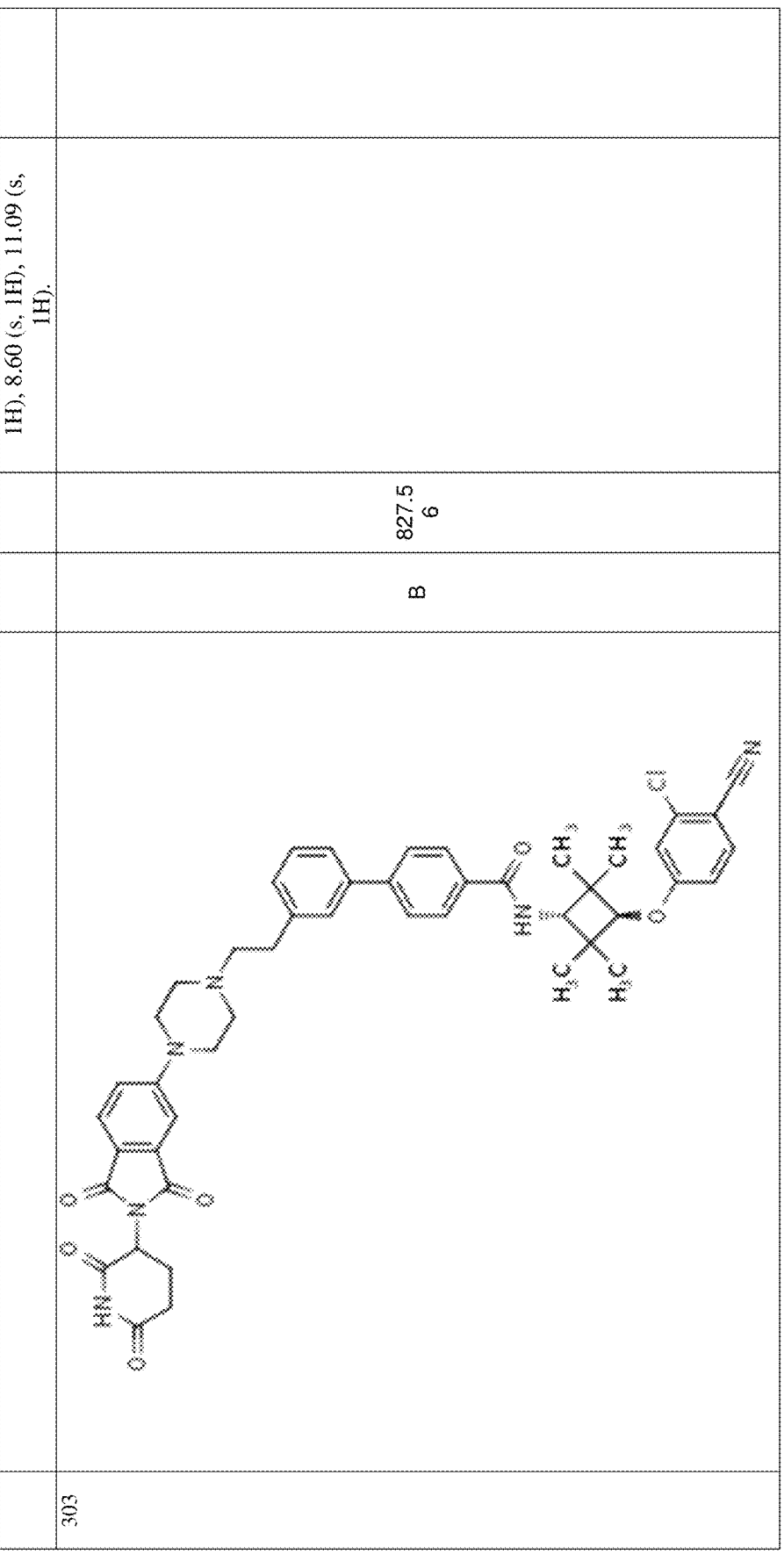
Figure 3:
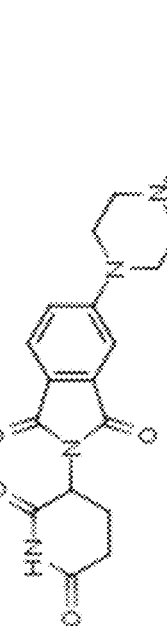
Figure 3:
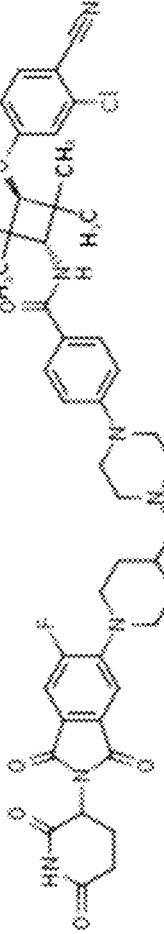
Figure 3:
Figure 3:
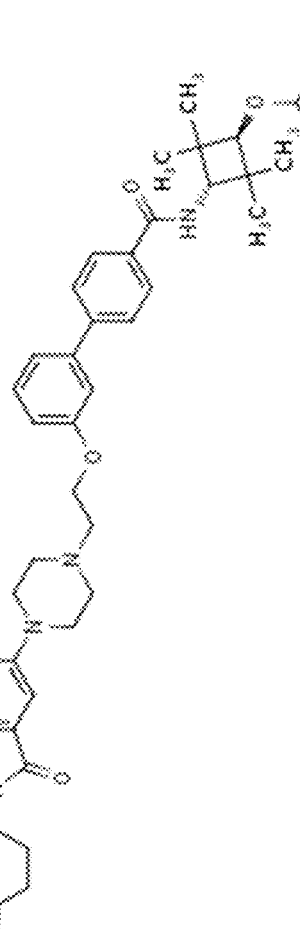
Figure 3:
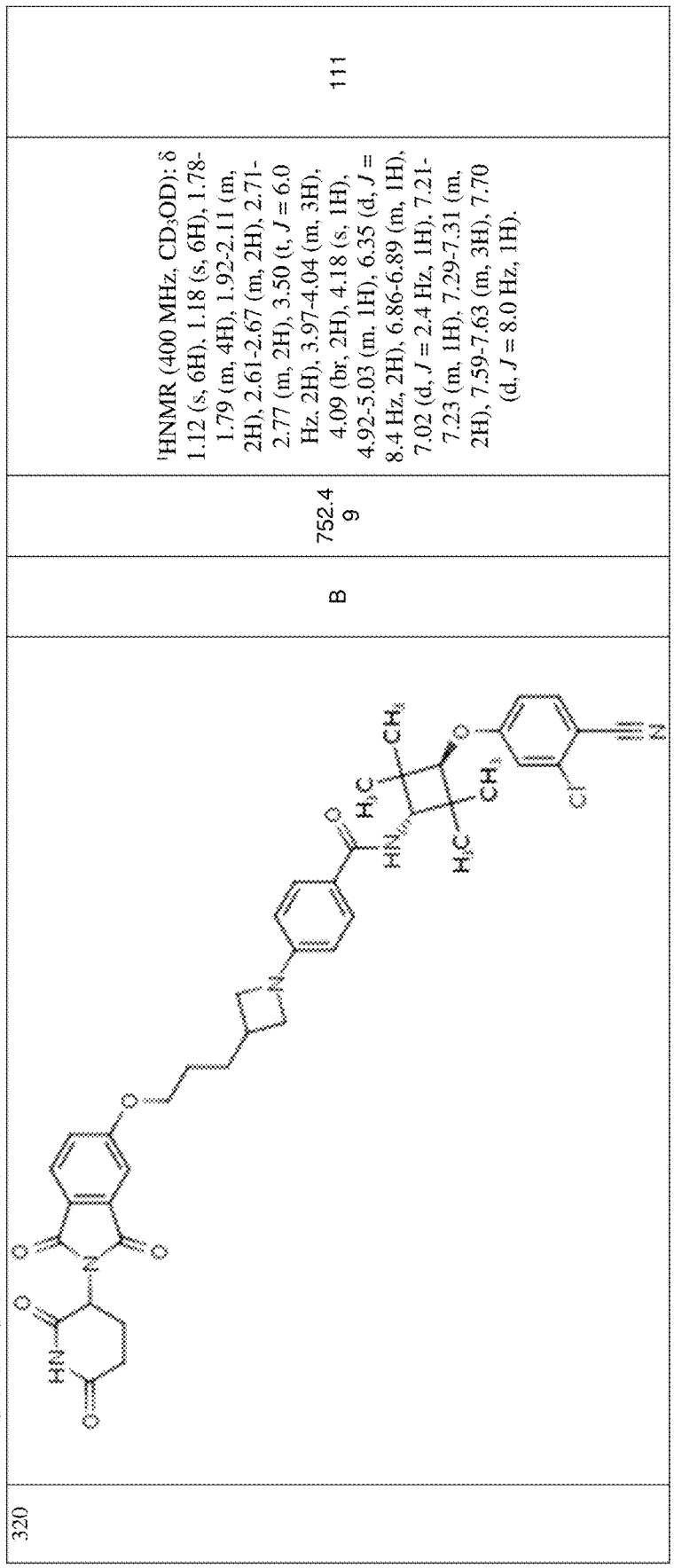
Figure 3:
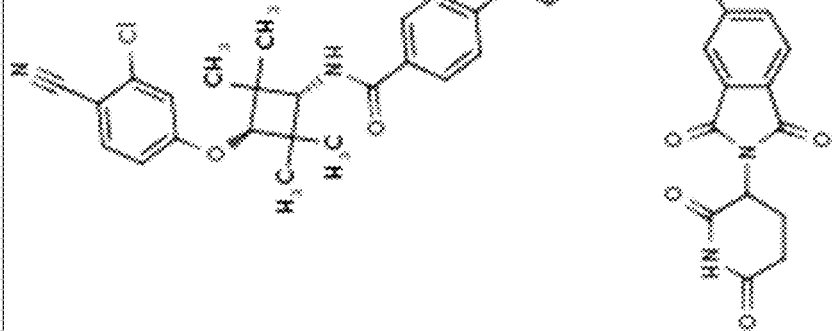
Figure 3:
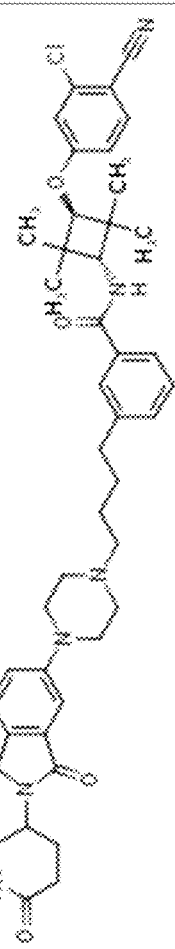
Figure 3:

Figure 3:

Figure 3:
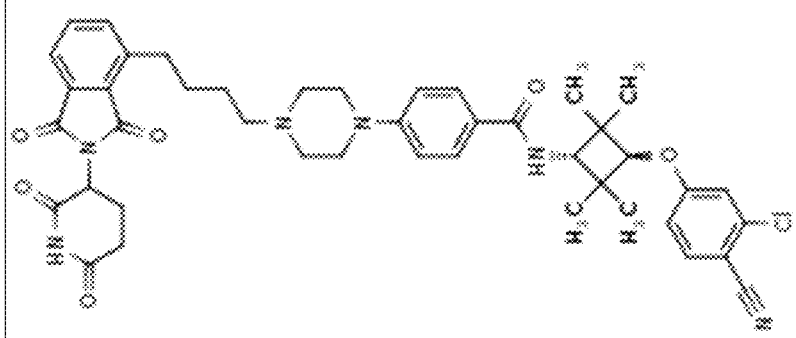
Figure 3:

Figure 3:

Figure 3:

Figure 3:

Figure 3:
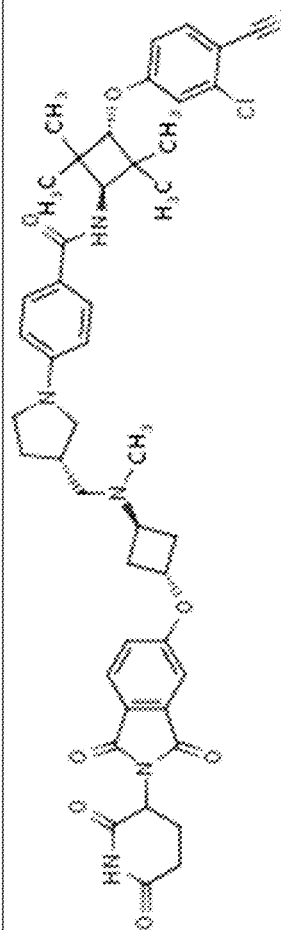
Figure 3:
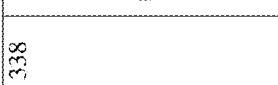
Figure 3:
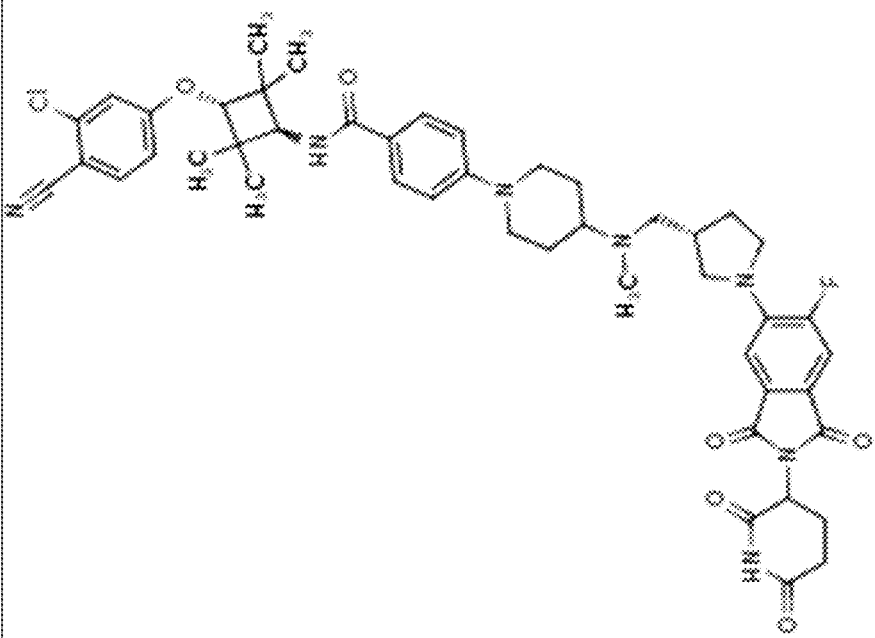
Figure 3:
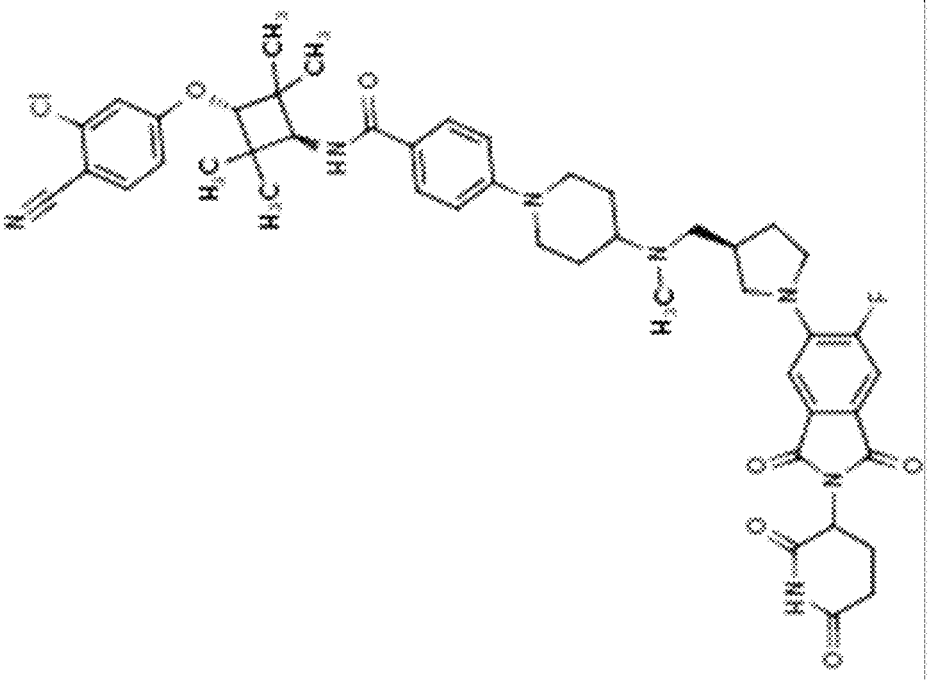
Figure 3:
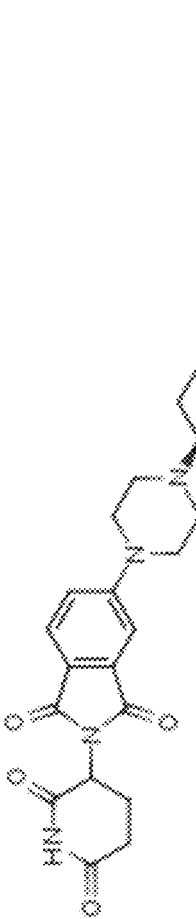
Figure 3:
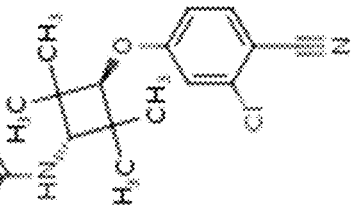
Figure 3:
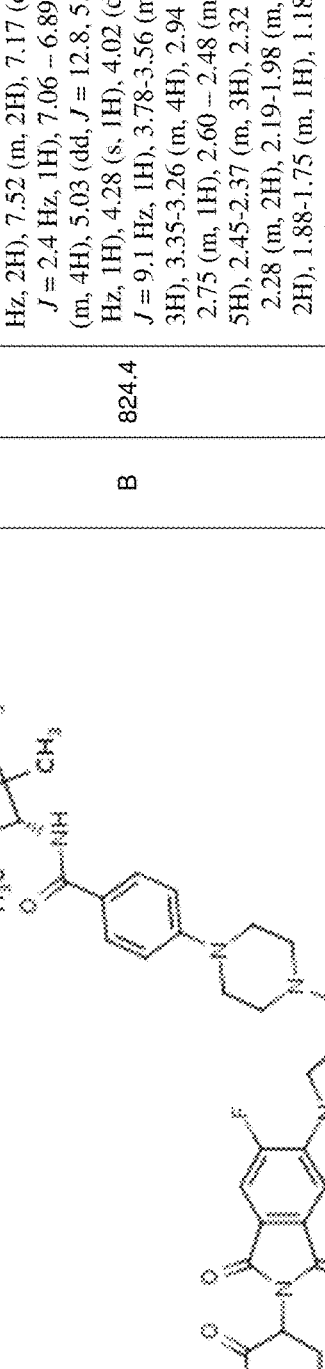
Figure 3:
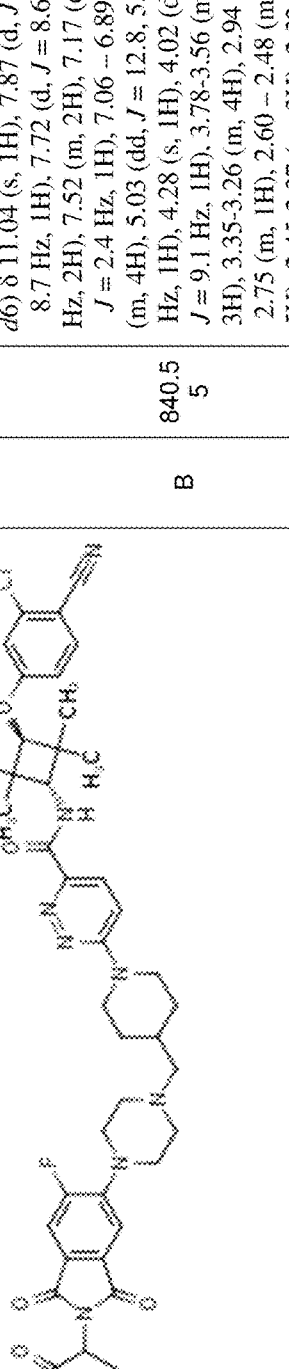
Figure 3:
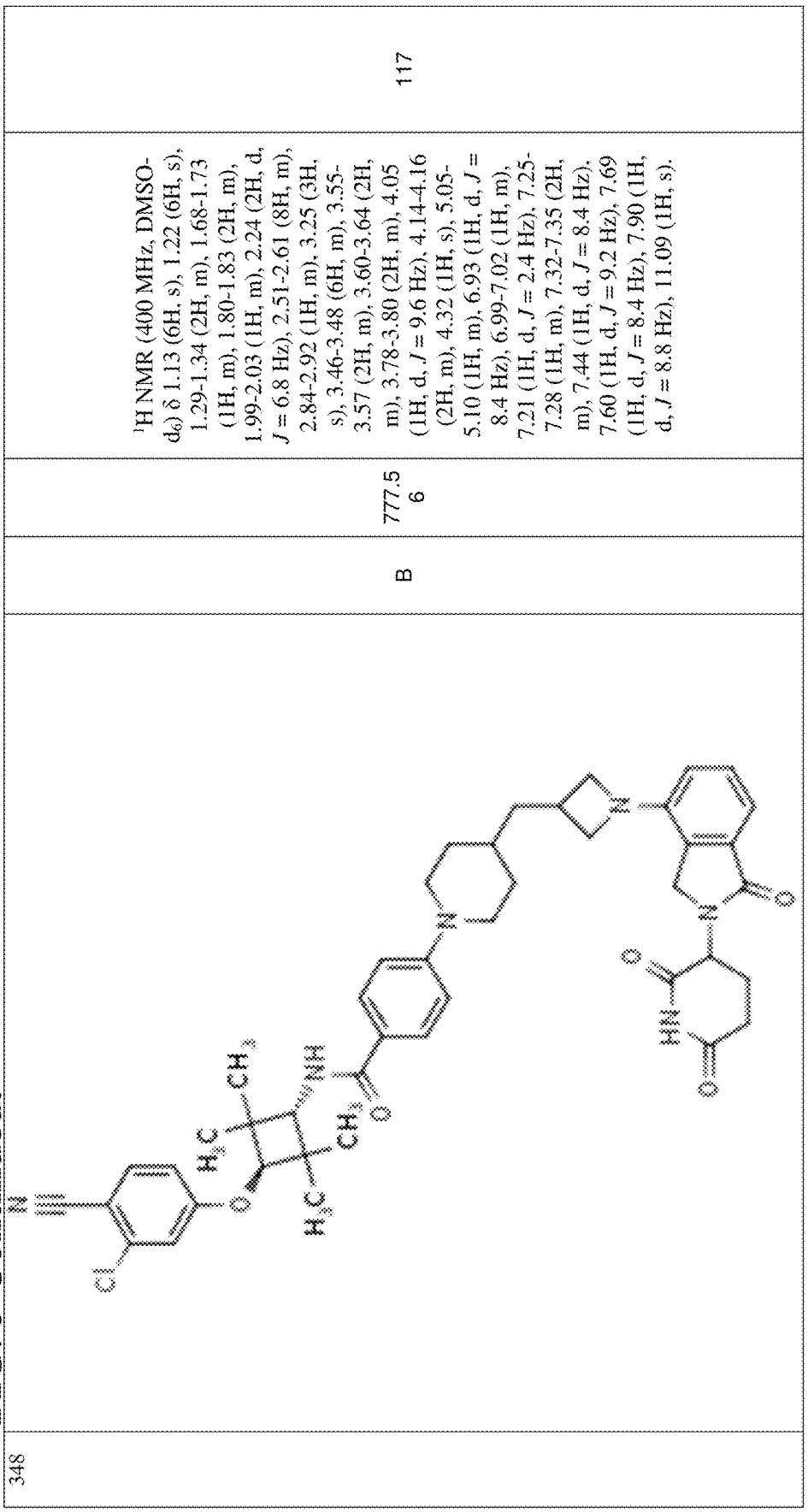
Figure 3:
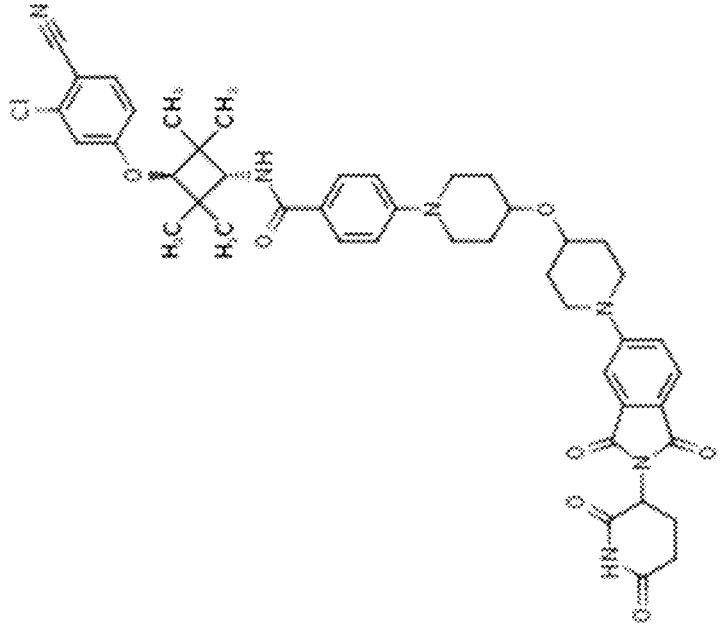
Figure 3:
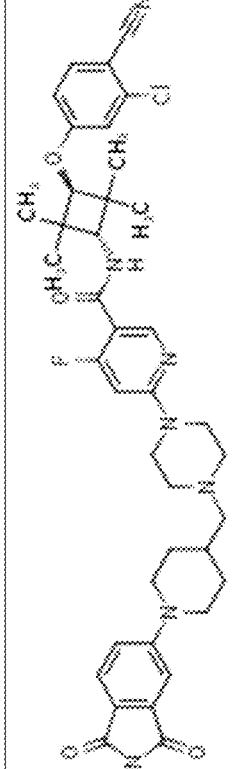
Figure 3:
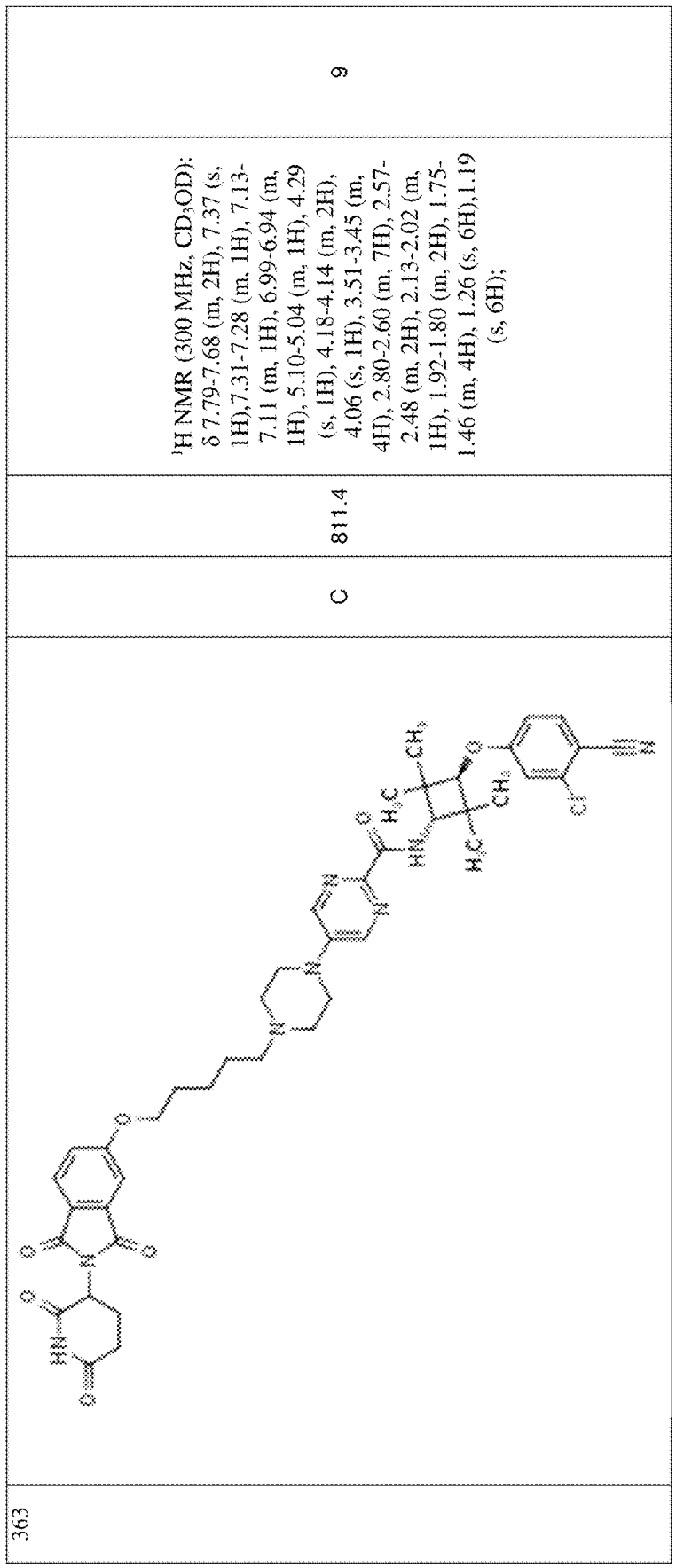
Figure 3:
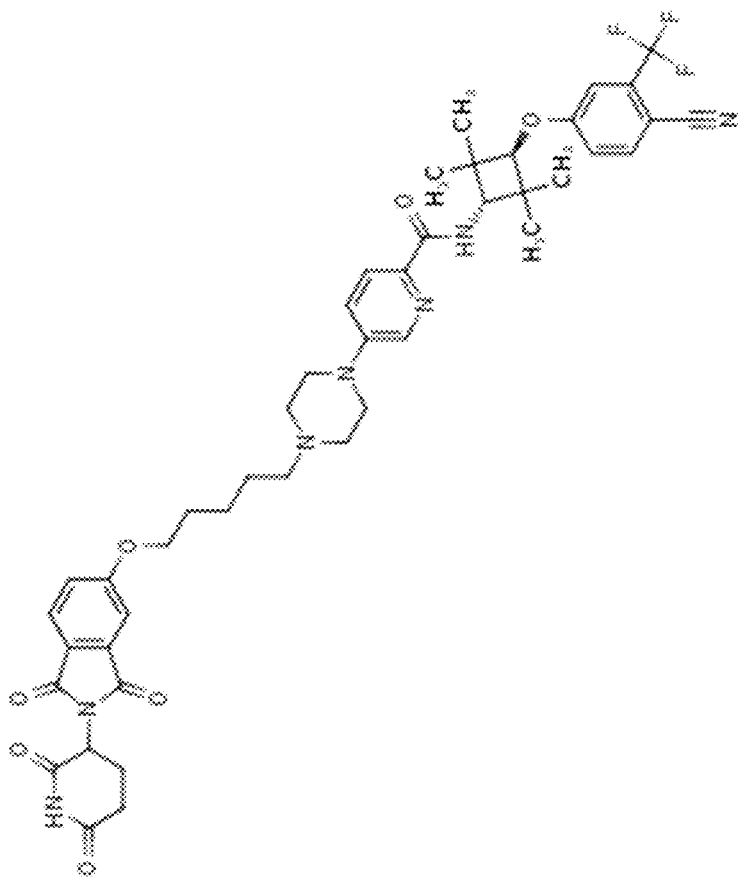
Figure 3:
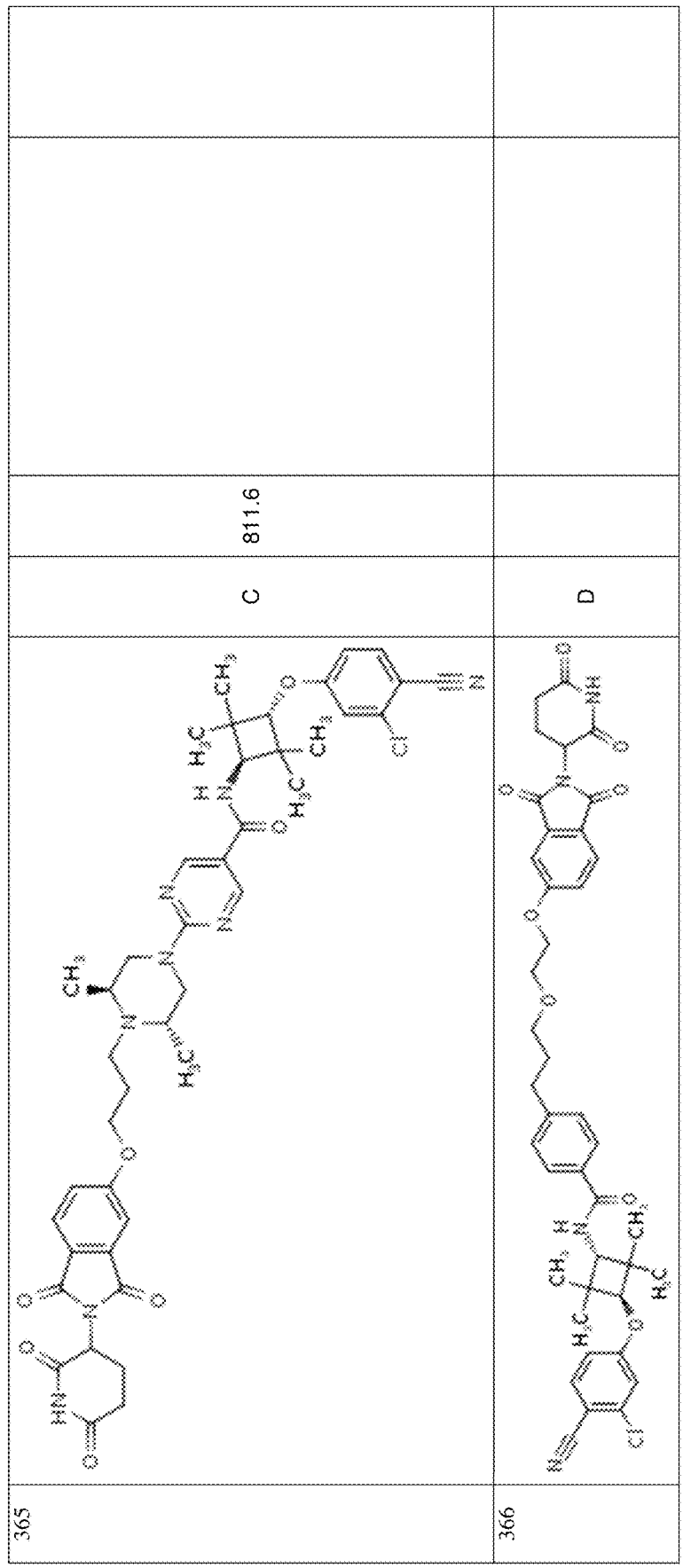
Figure 3:
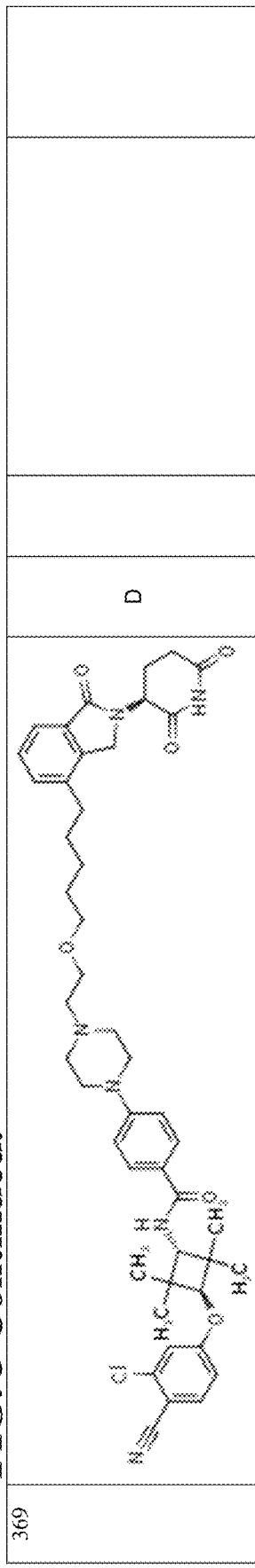
Figure 3:
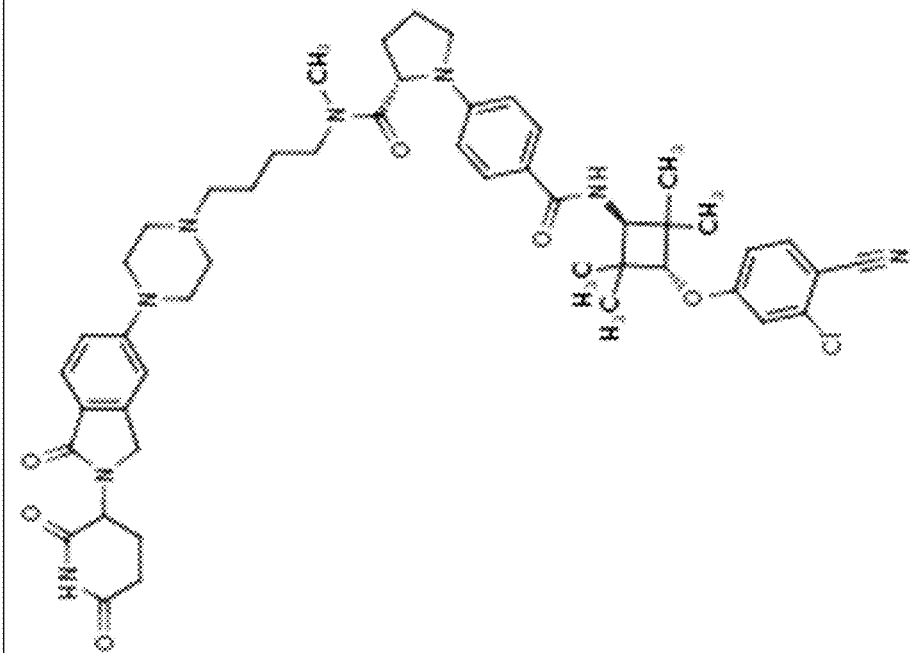
Figure 3:
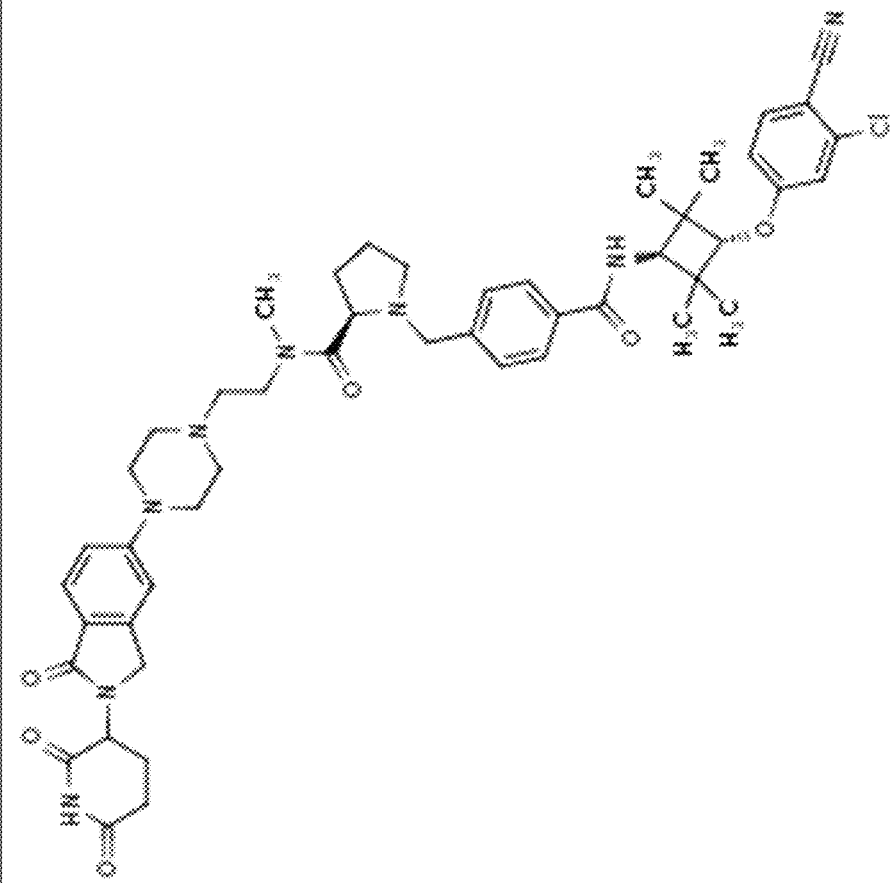
Figure 3:
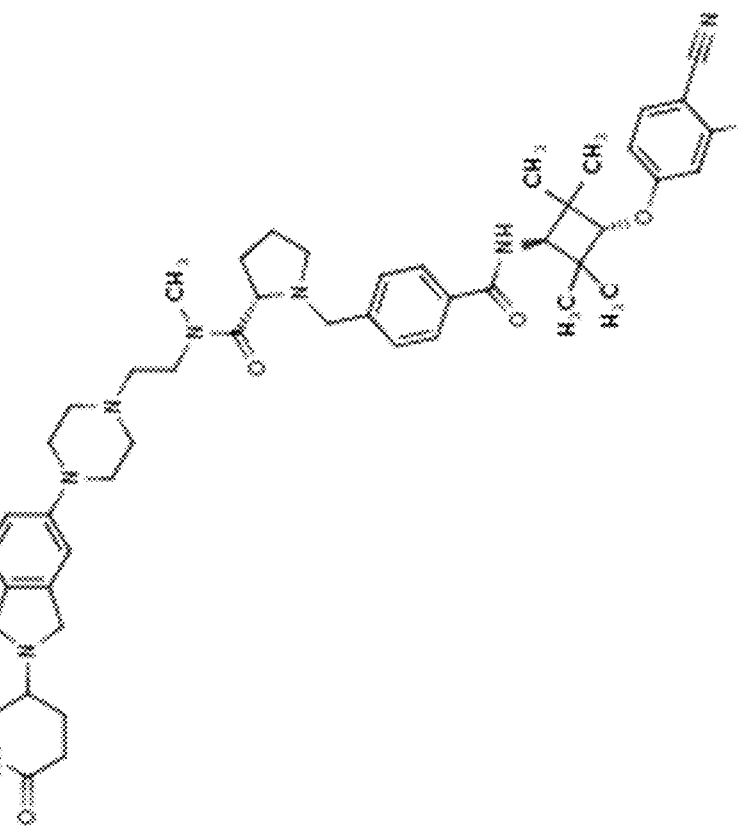
Figure 3:
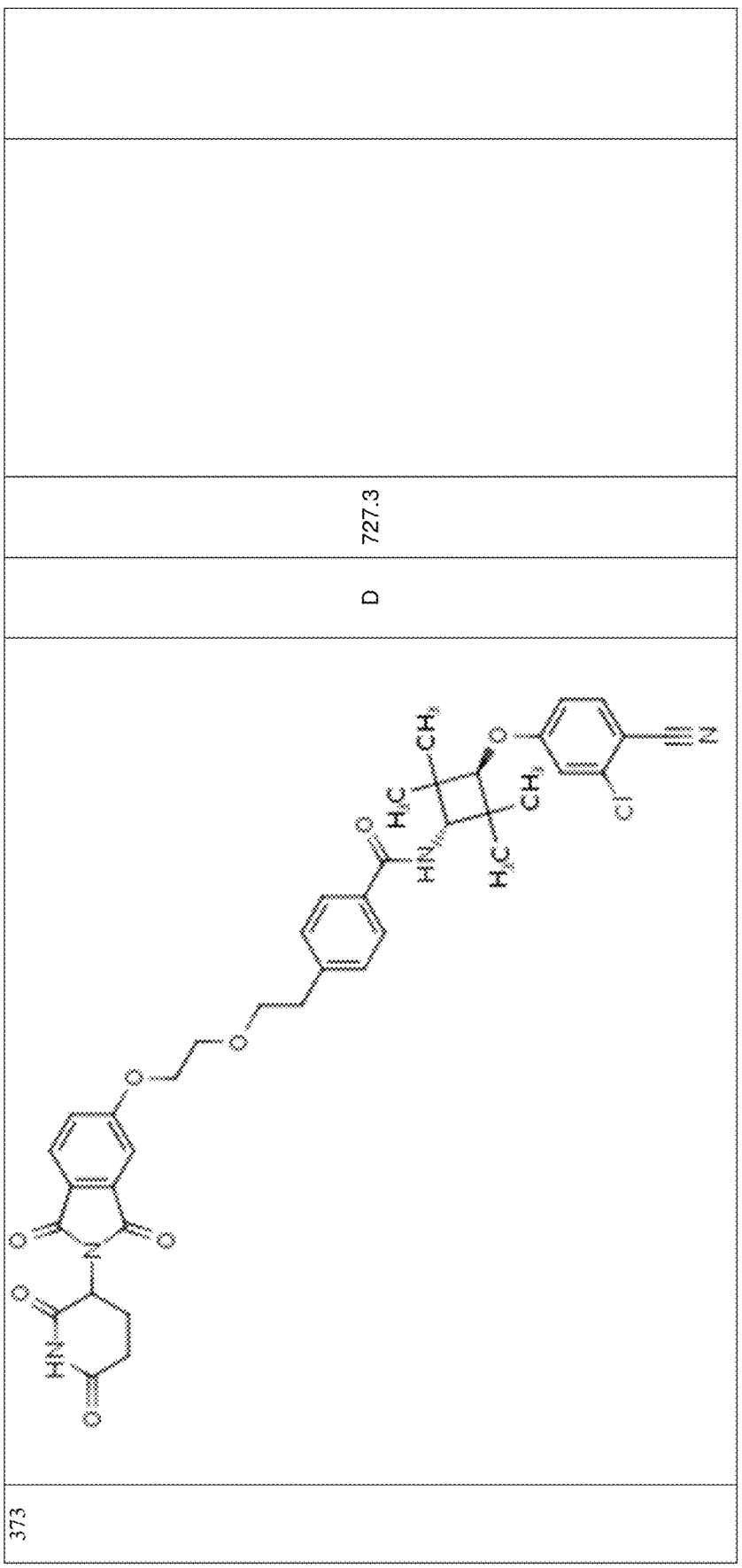
Figure 3:
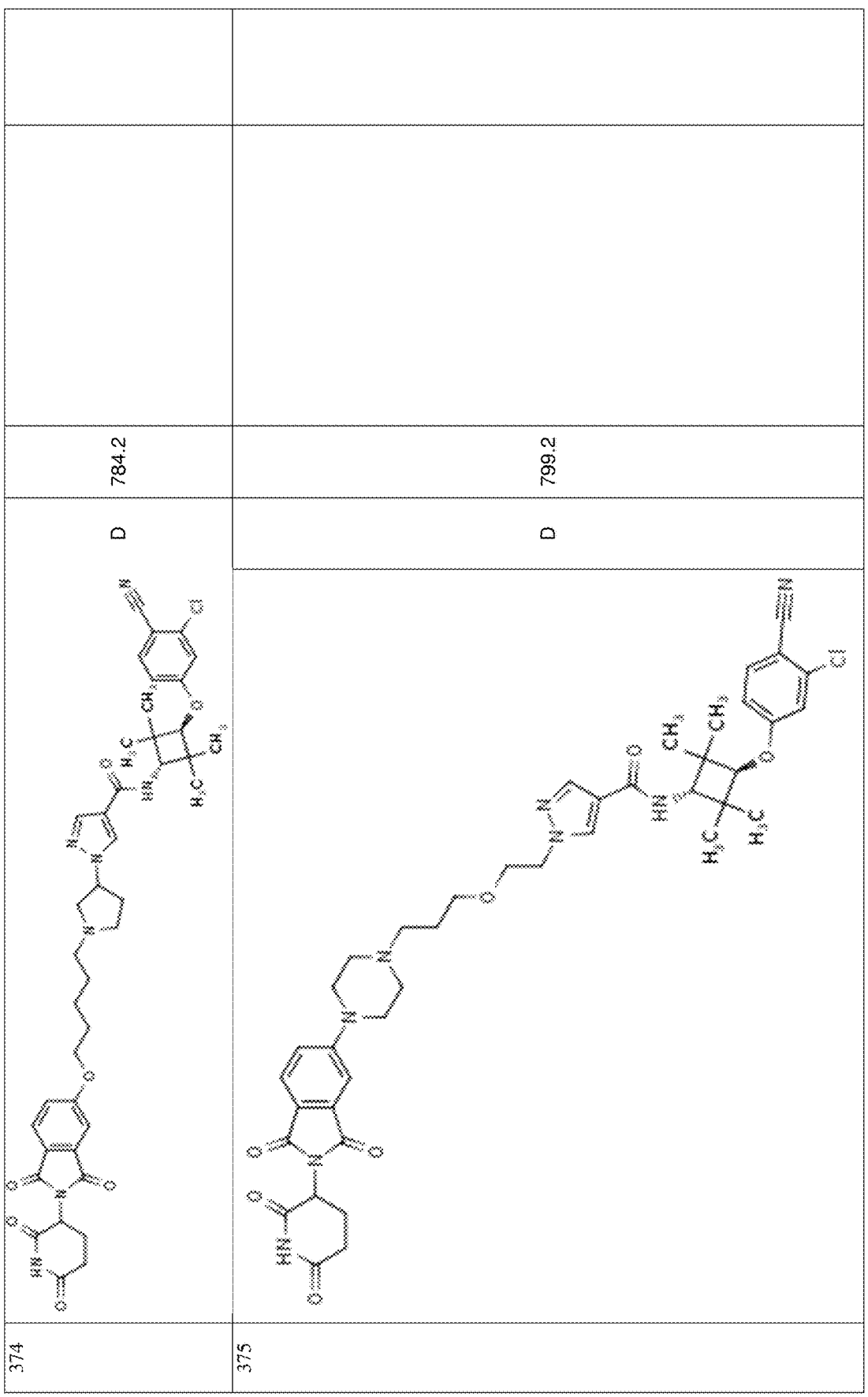
Figure 3:
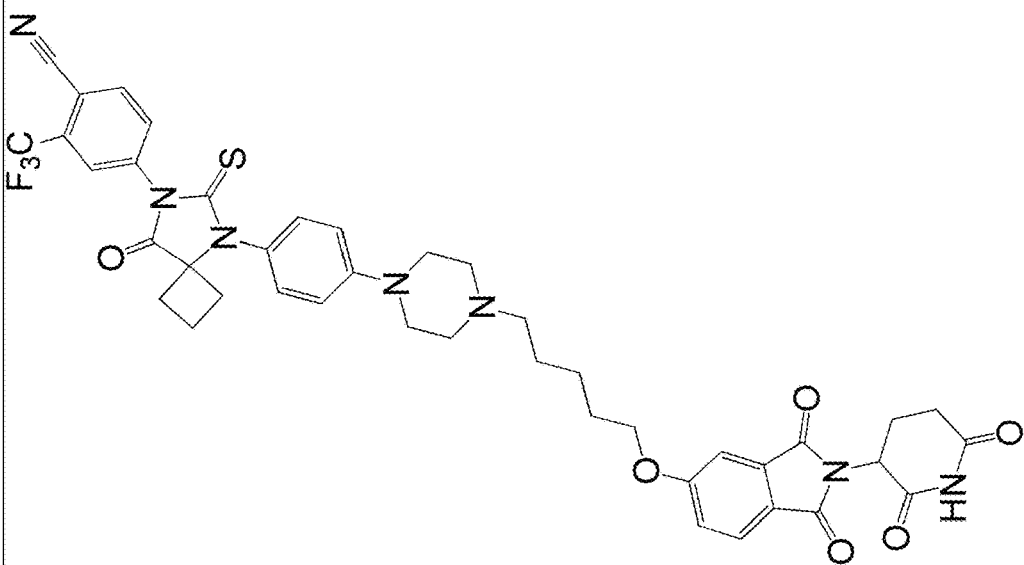
Figure 3:
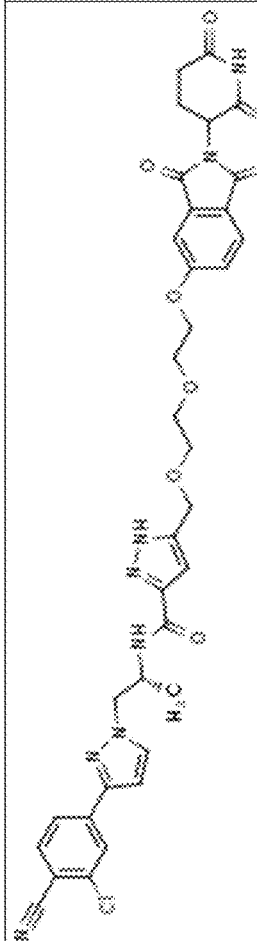
Figure 3:
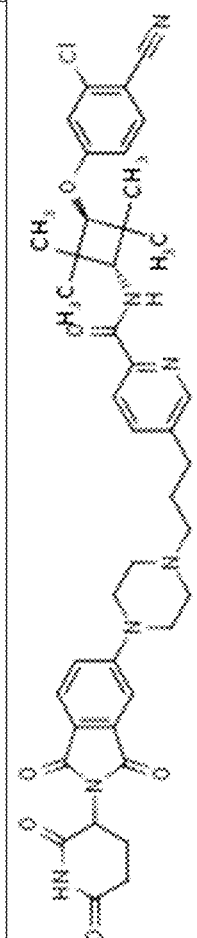
Figure 3:
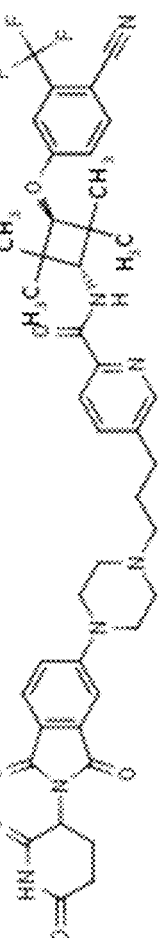
Figure 3:
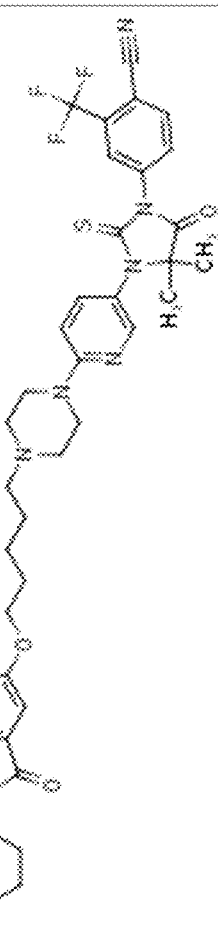
Figure 3:
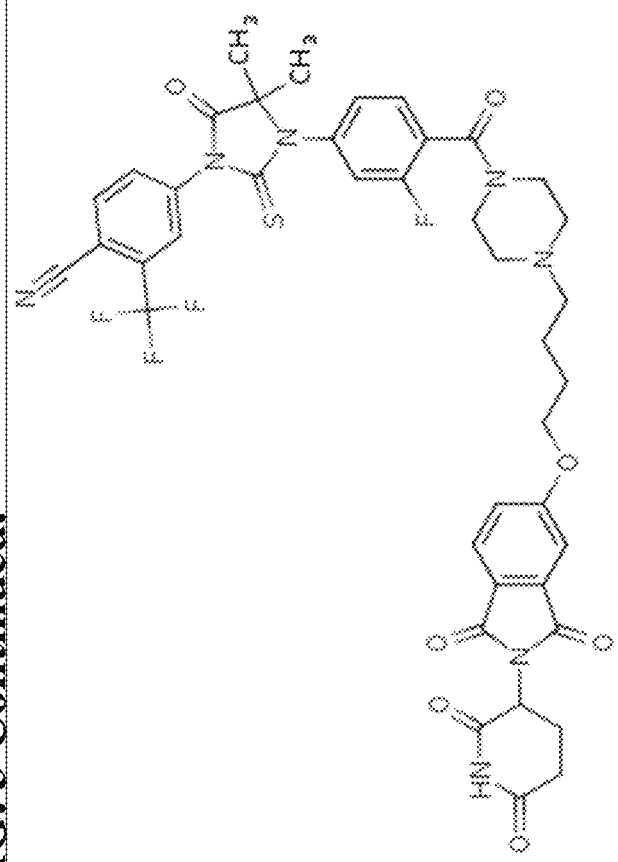
Figure 3:
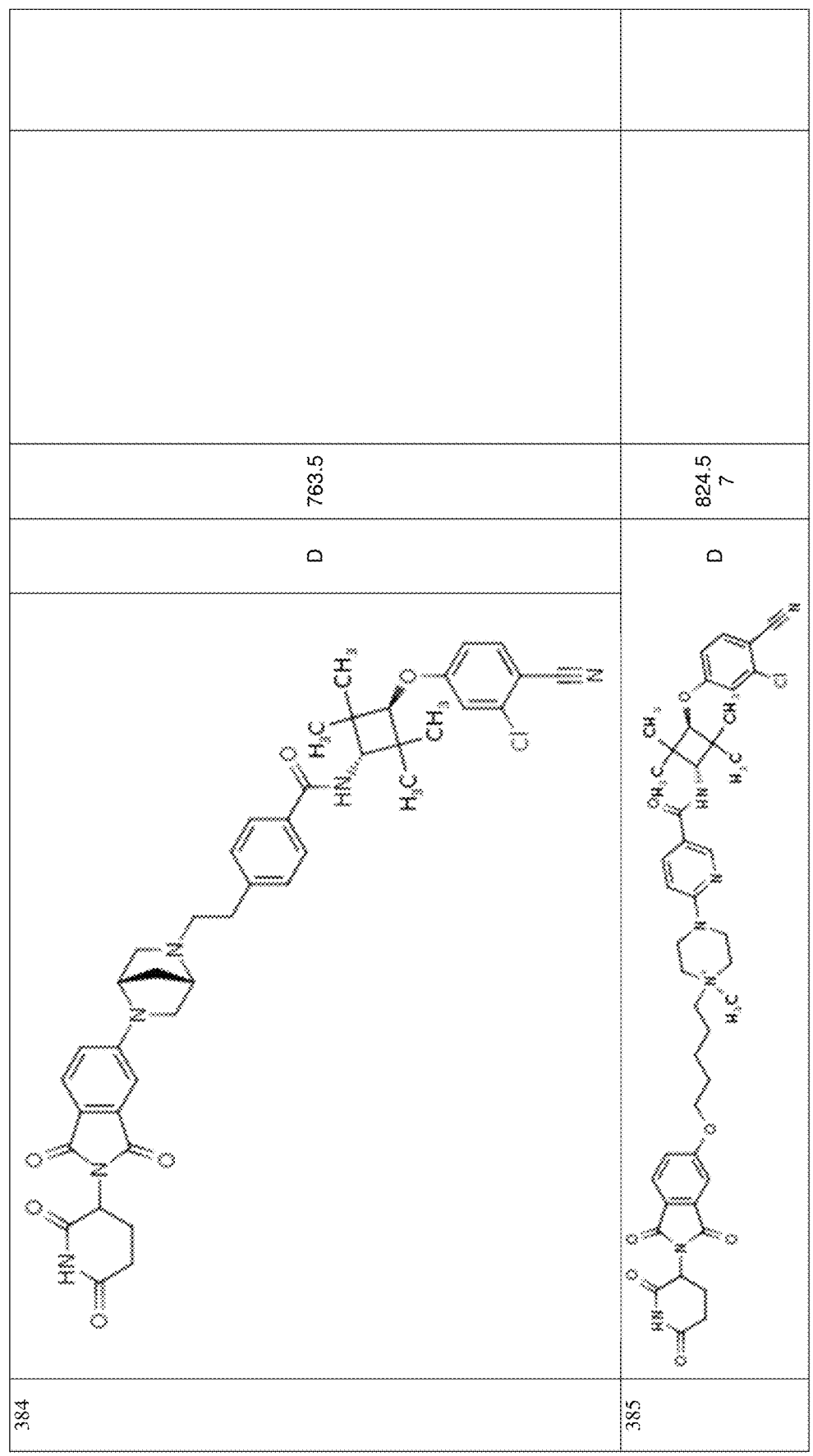
Figure 3:
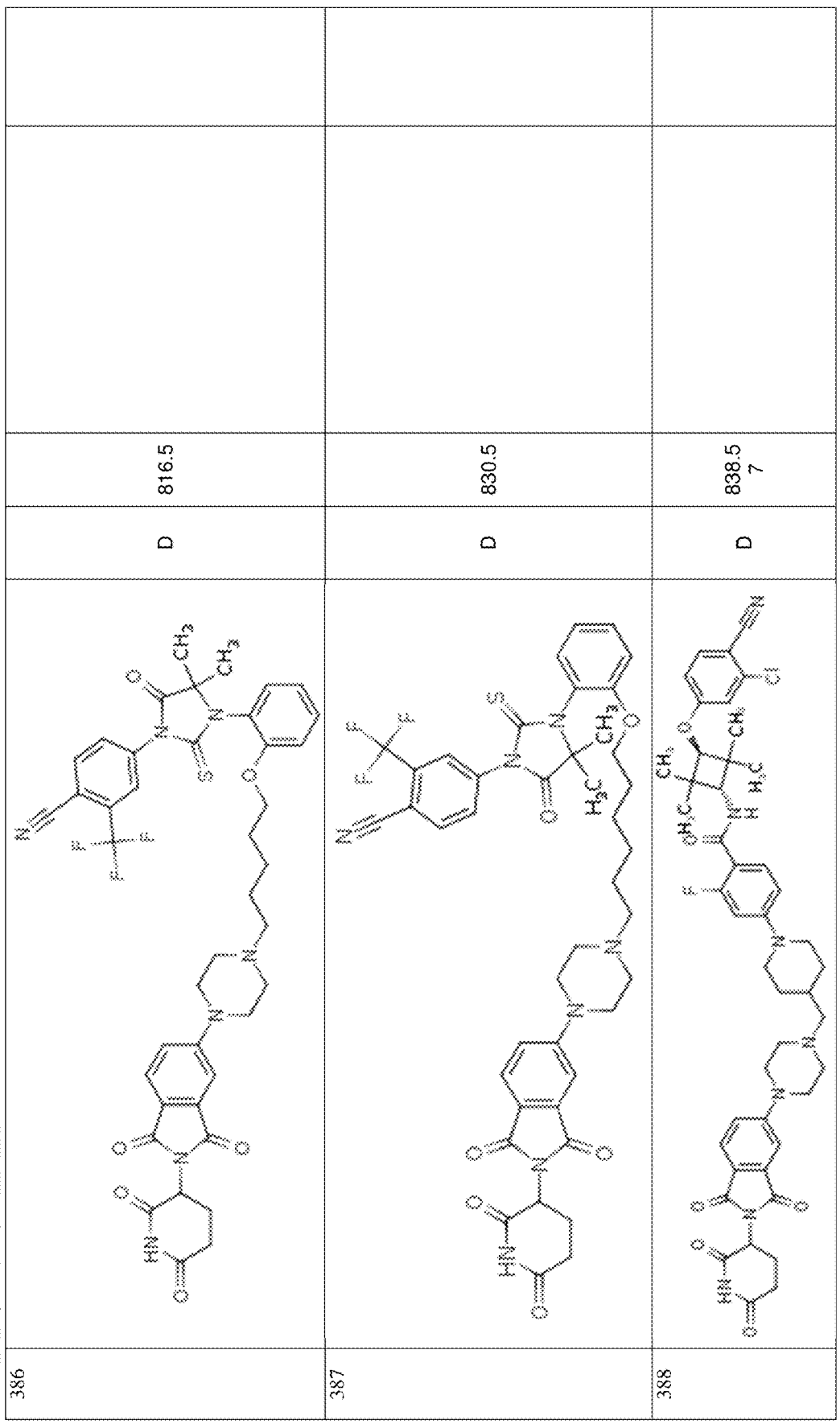
Figure 3:
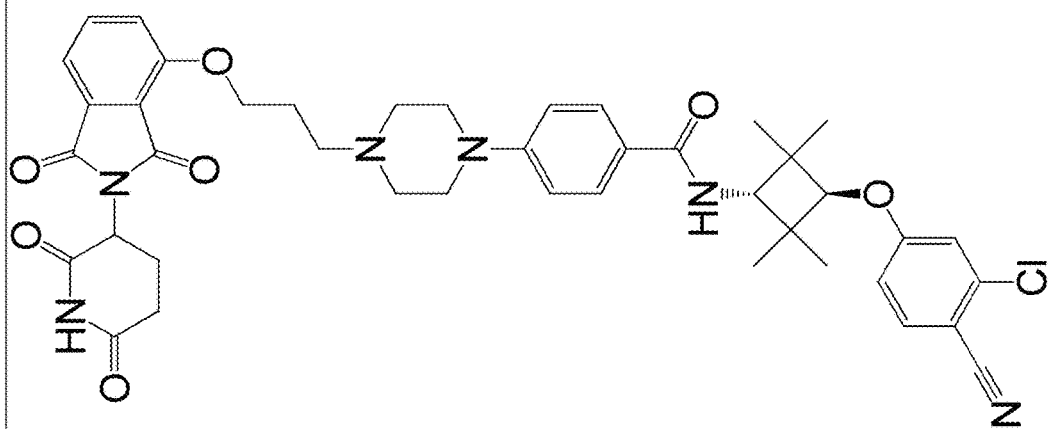
Figure 3:
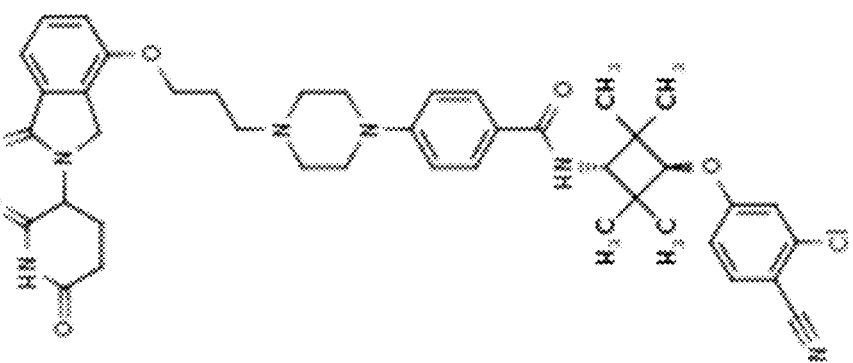
Figure 3:
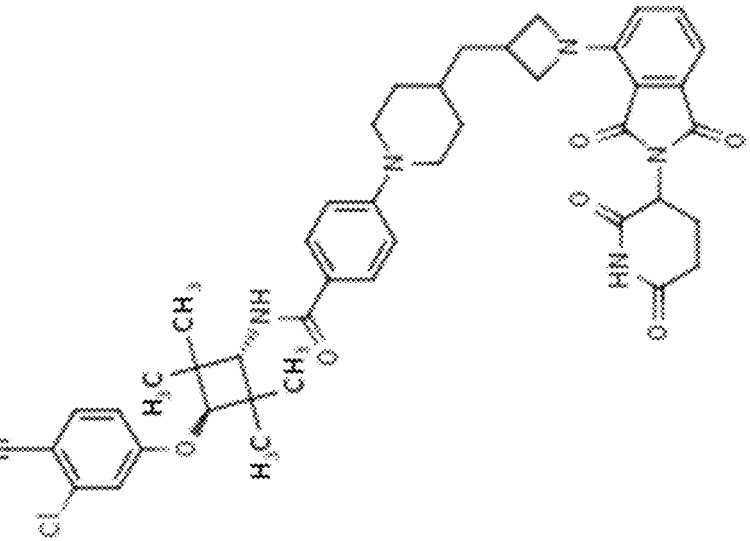
Figure 3:
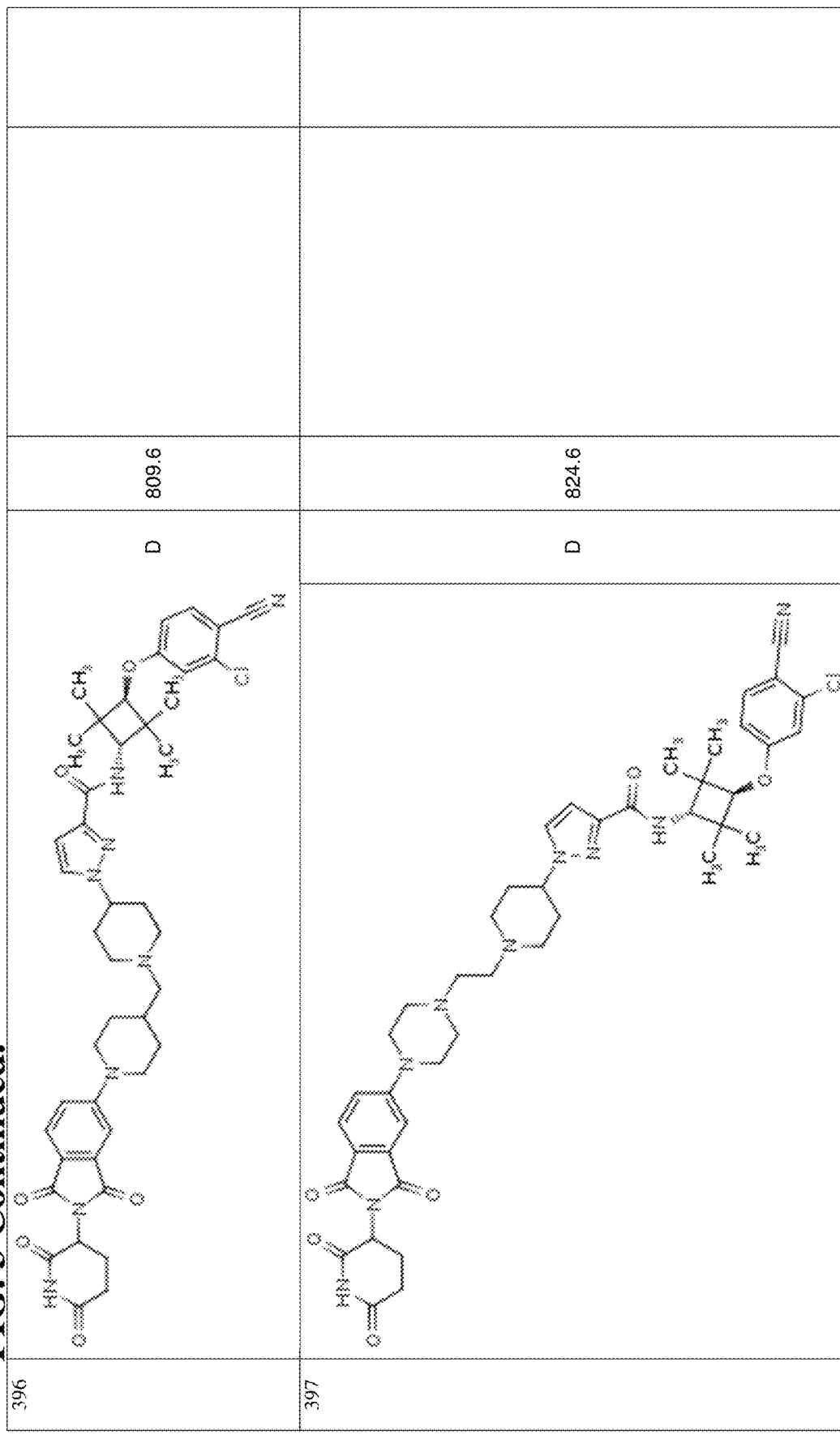
Figure 3:
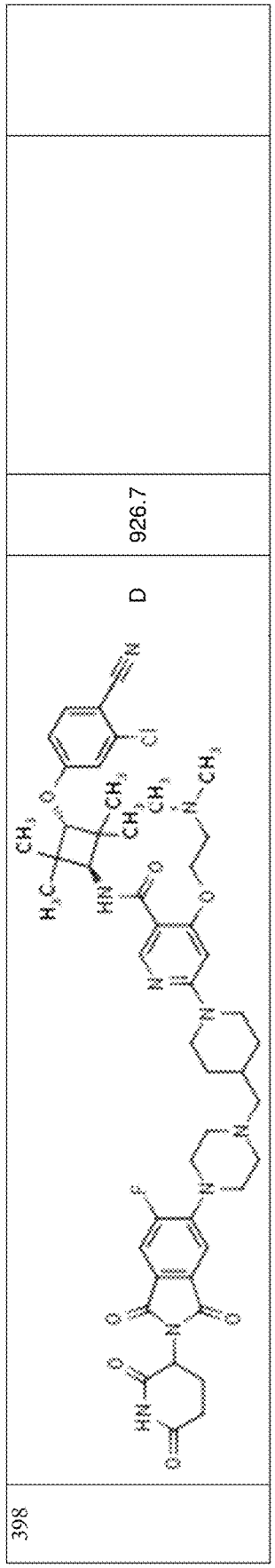
Figure 4:
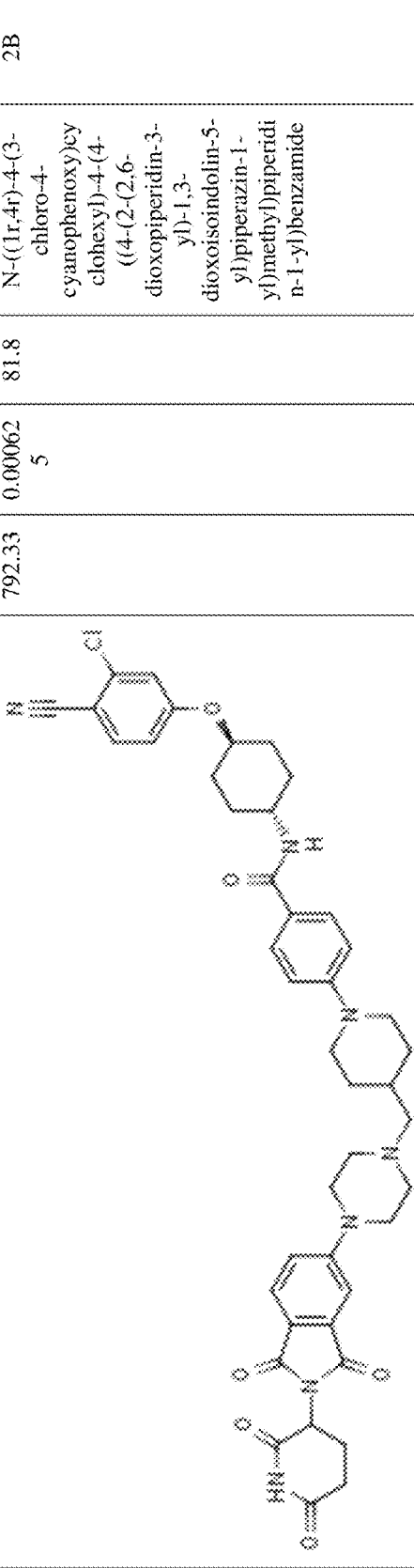
FIG. 4. Table 4 that include Exemplary Compounds 399-427, as well as the General Scheme that may be used to produce each of the Exemplary Compounds. Table 4 also includes the DC50, Dmax (%), M/Z+, and 1H NMR data for each of the Exemplary Compounds. DC50 (µM) categories (degradation of AR ELISA in LNCaP and/or VCaP cells): A<1 nM; B: 1-10 nM; C: 10-100 nM; D: >100 nM.
Figure 4:
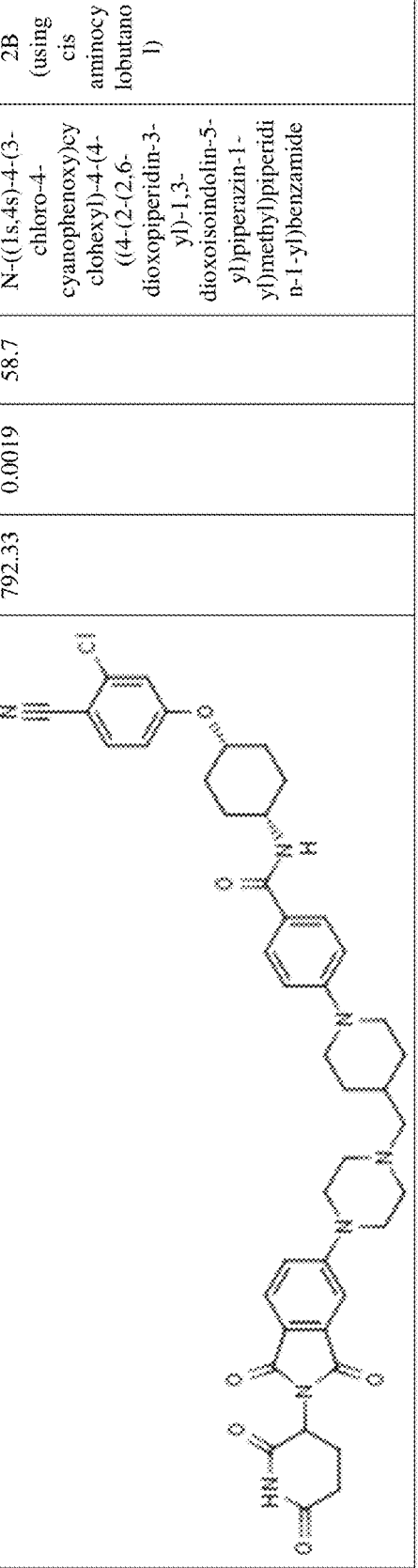
Figure 4:
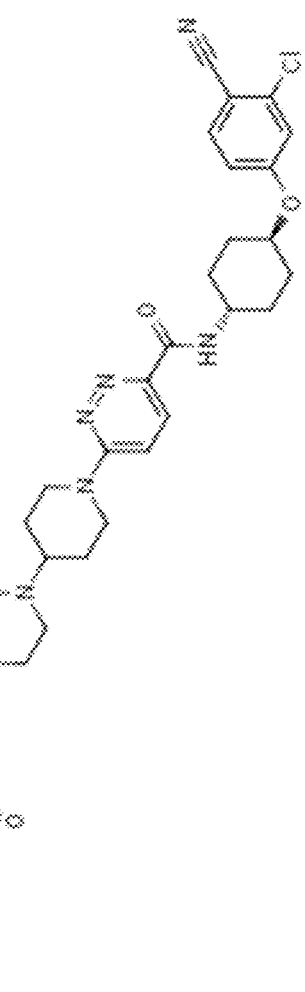
Figure 4:
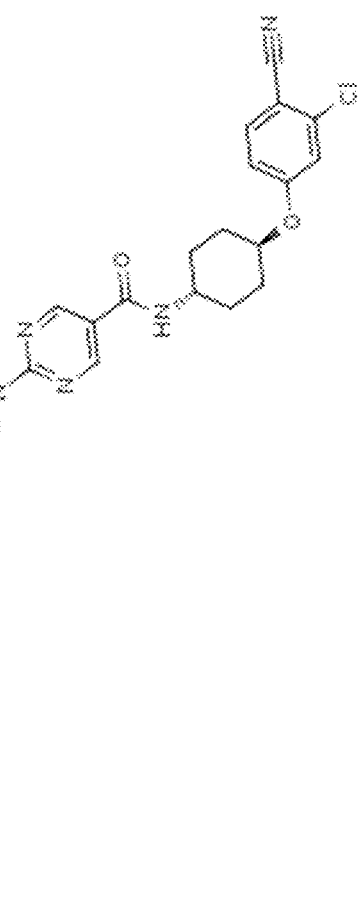
Figure 4:
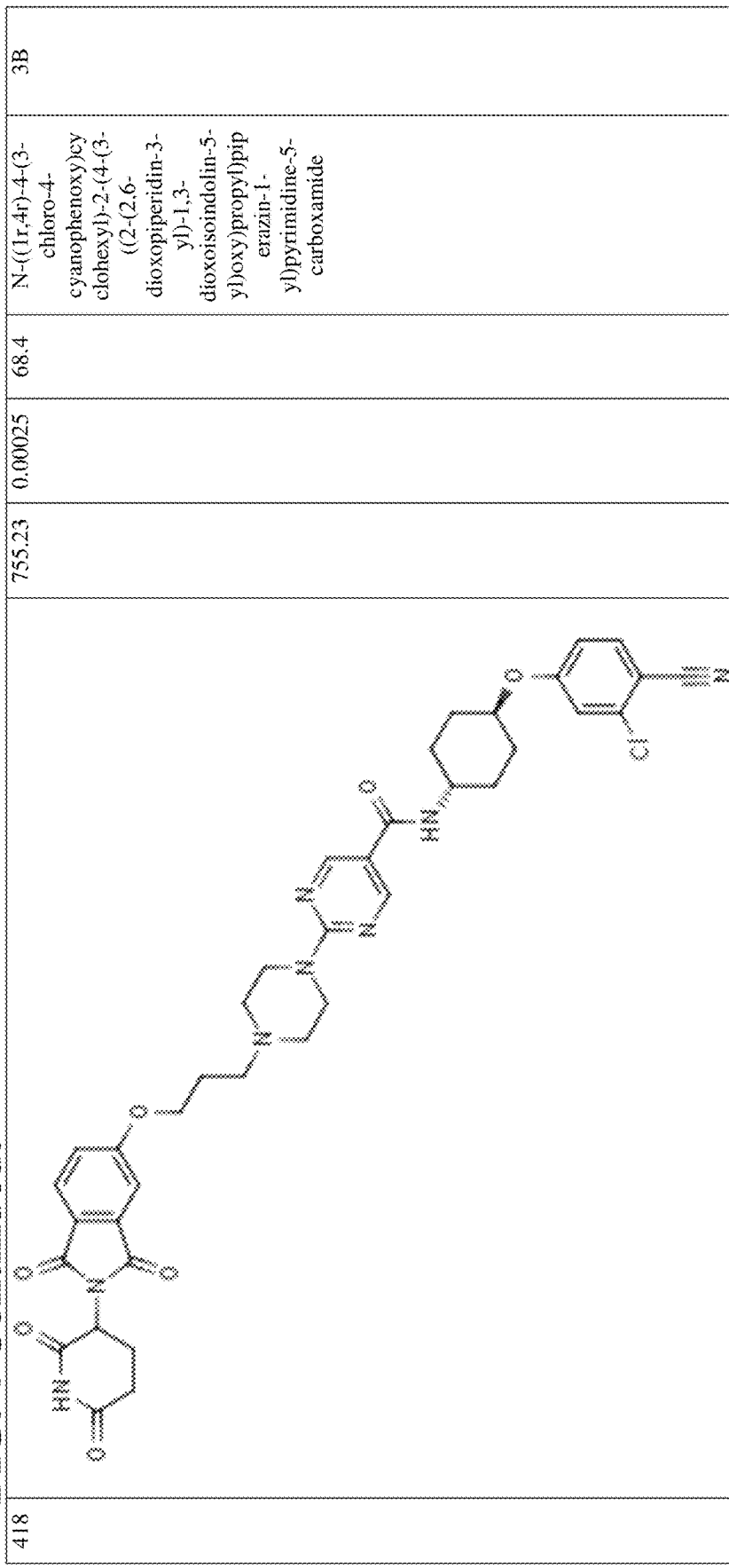
Figure 4:
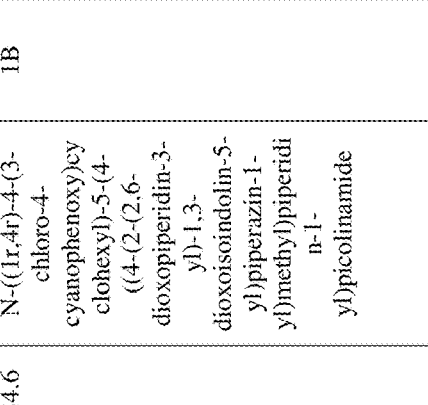
Figure 4:
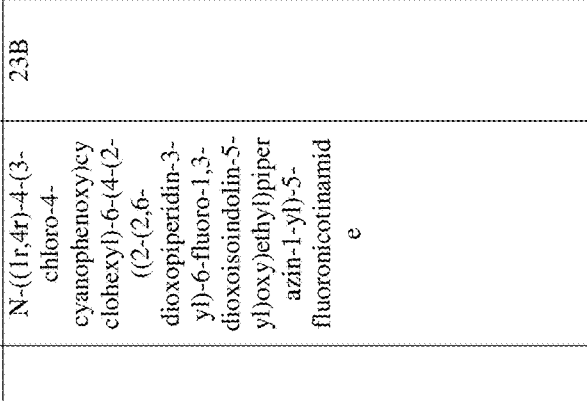
Figure 4:
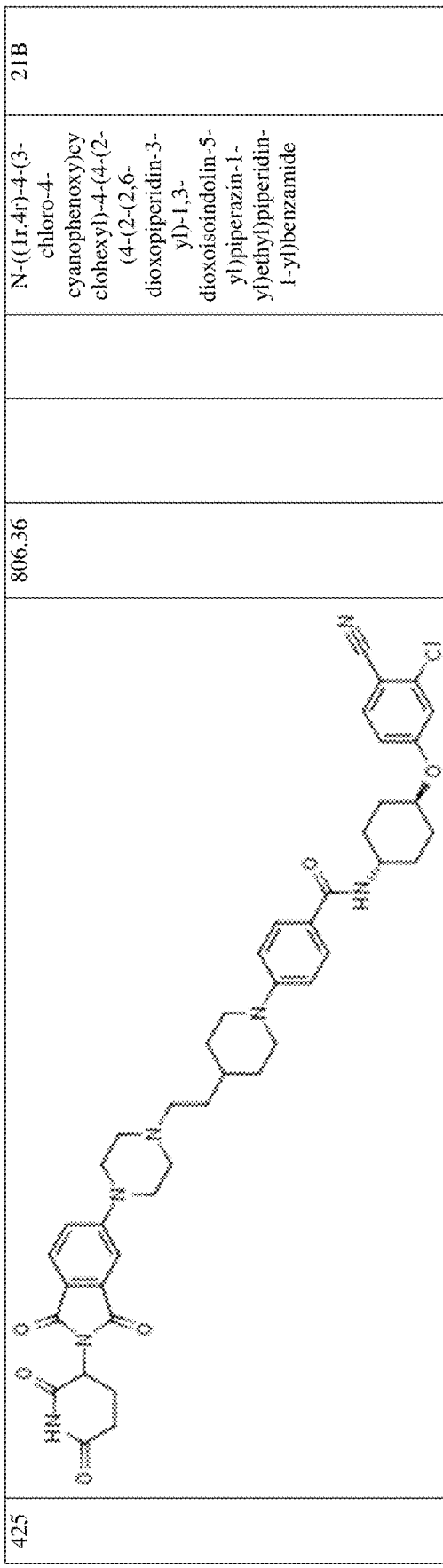
Figure 5:
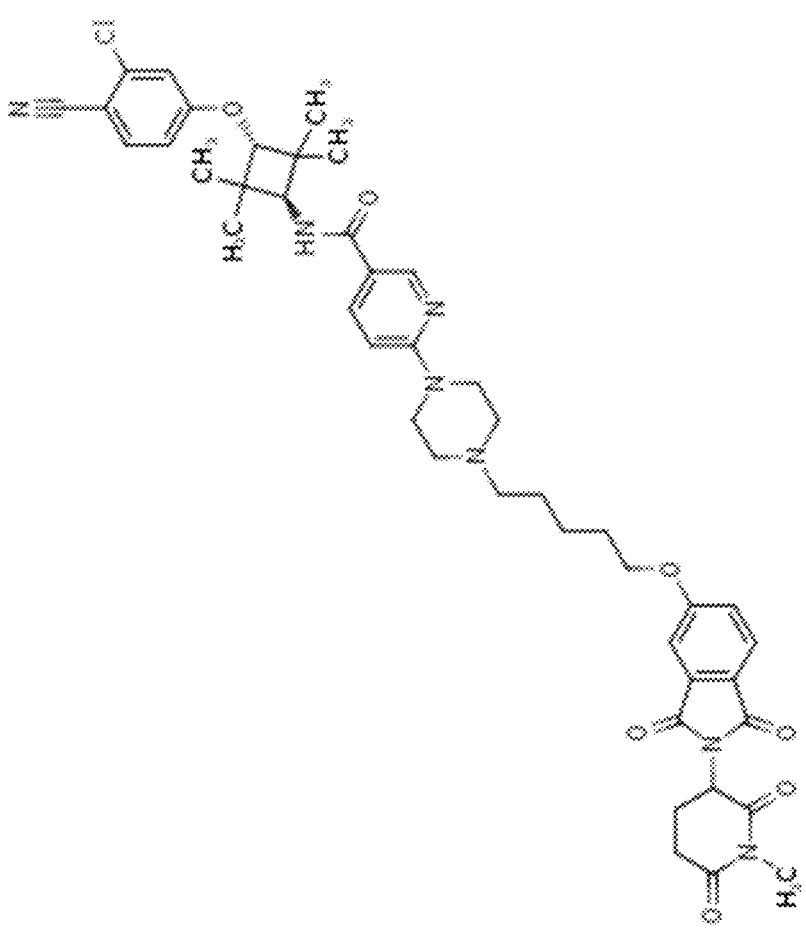
FIG. 5. Table 5 that include Exemplary Compounds 428-452. Table 5 also includes the DC50, Dmax (%), M/Z+, and 1H NMR data for each of the Exemplary Compounds. DC50 (µM) categories (degradation of AR ELISA in LNCaP and/or VCaP cells): A<1 nM; B: 1-10 nM; C: 10-100 nM; D: >100 nM.
Figure 5:
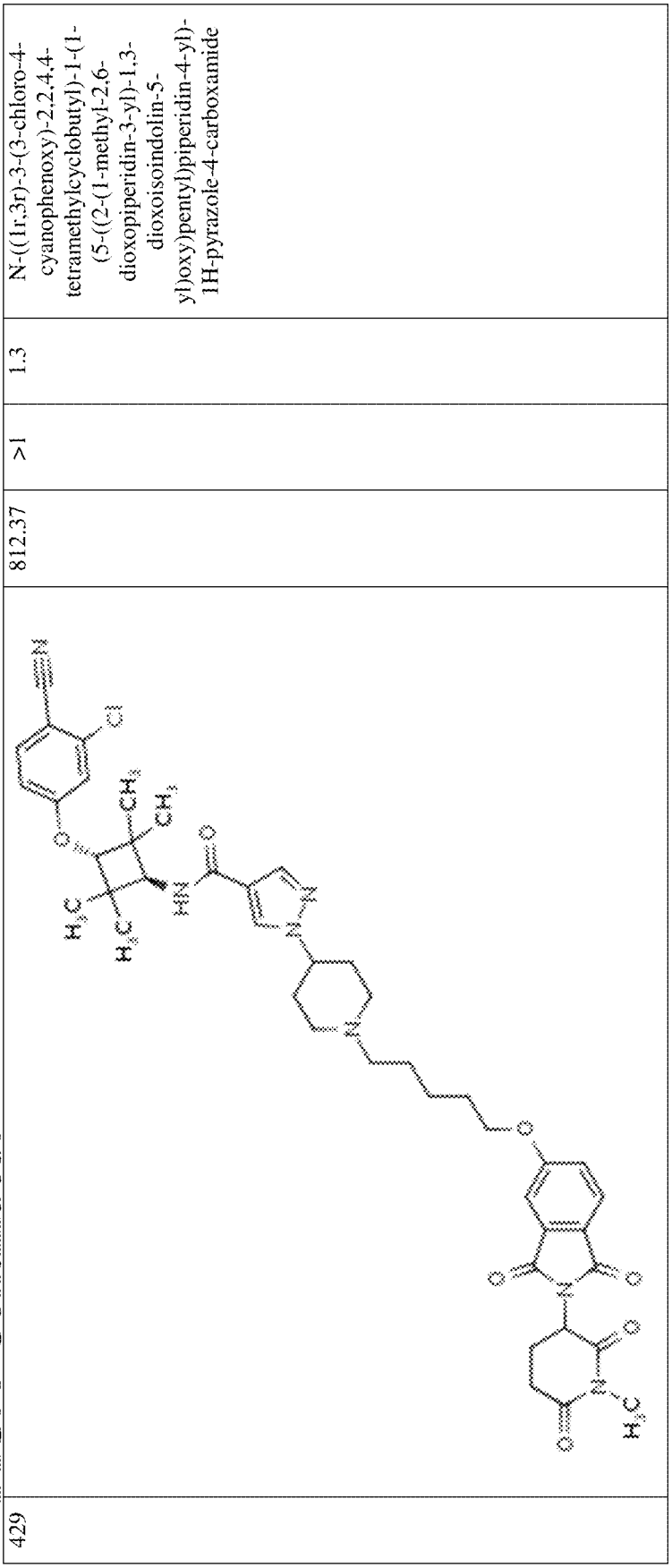
Figure 5:
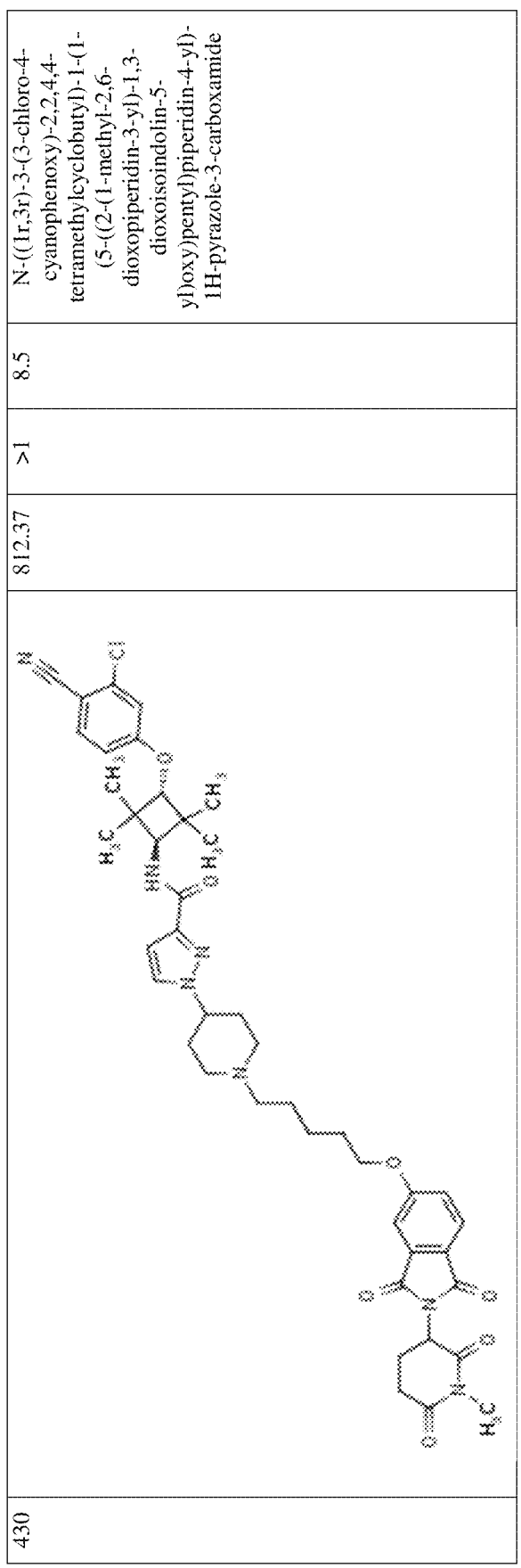
Figure 5:
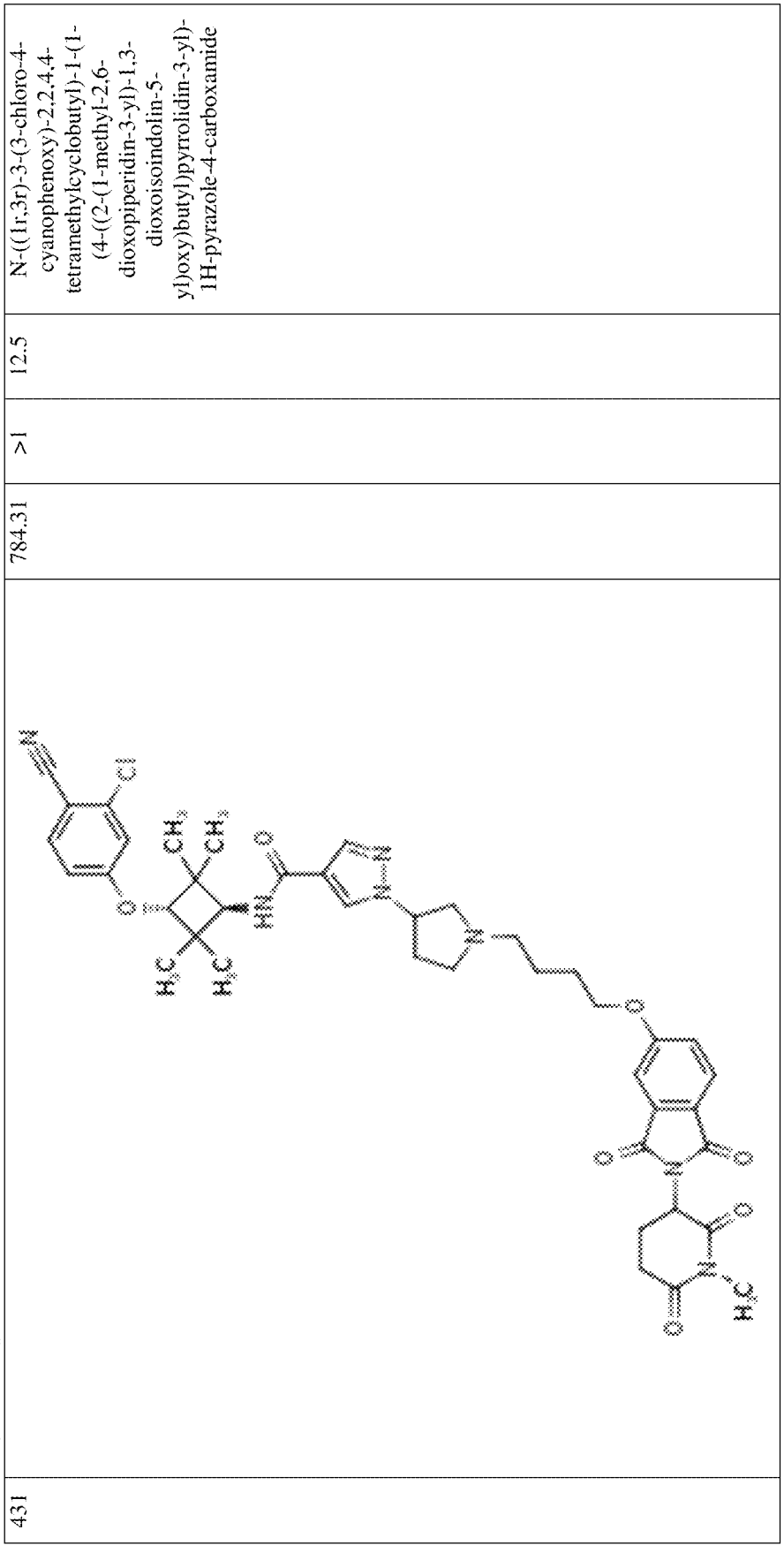
Figure 5:
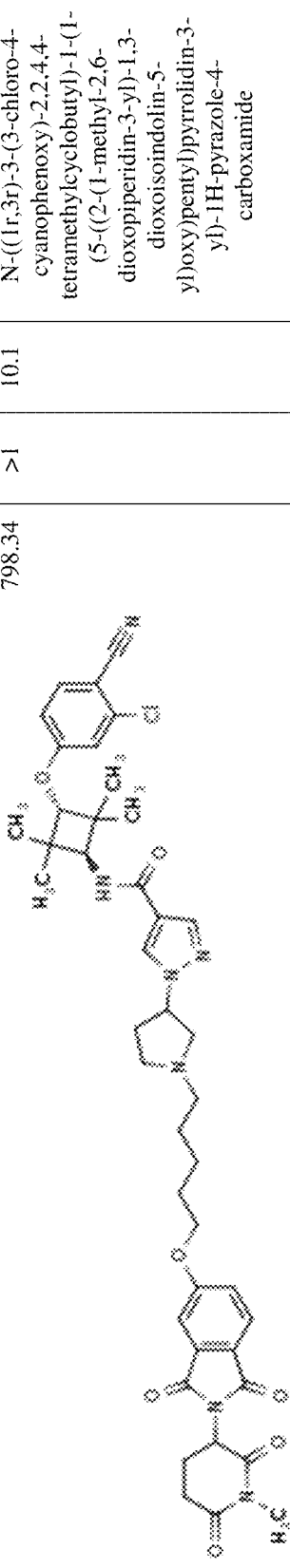
Figure 5:
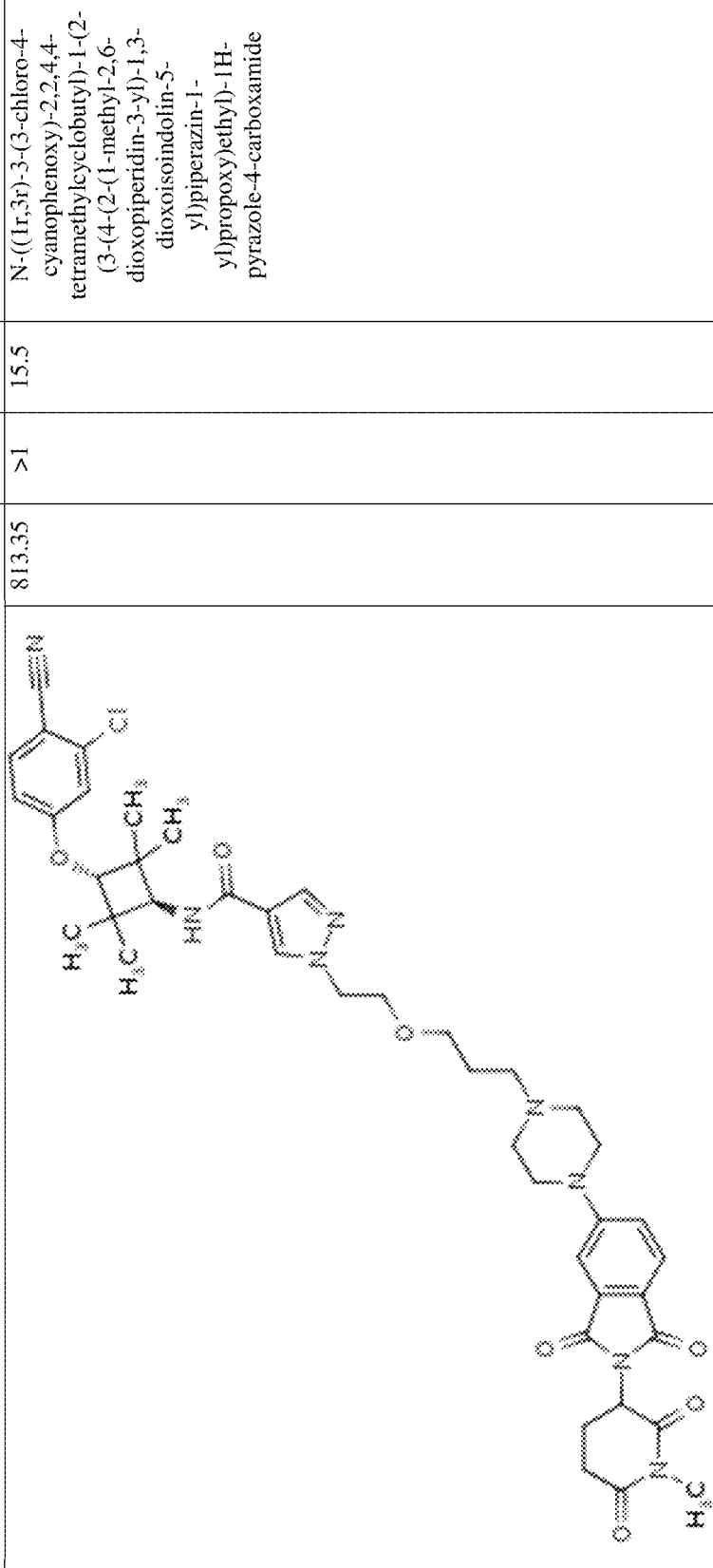
Figure 5:
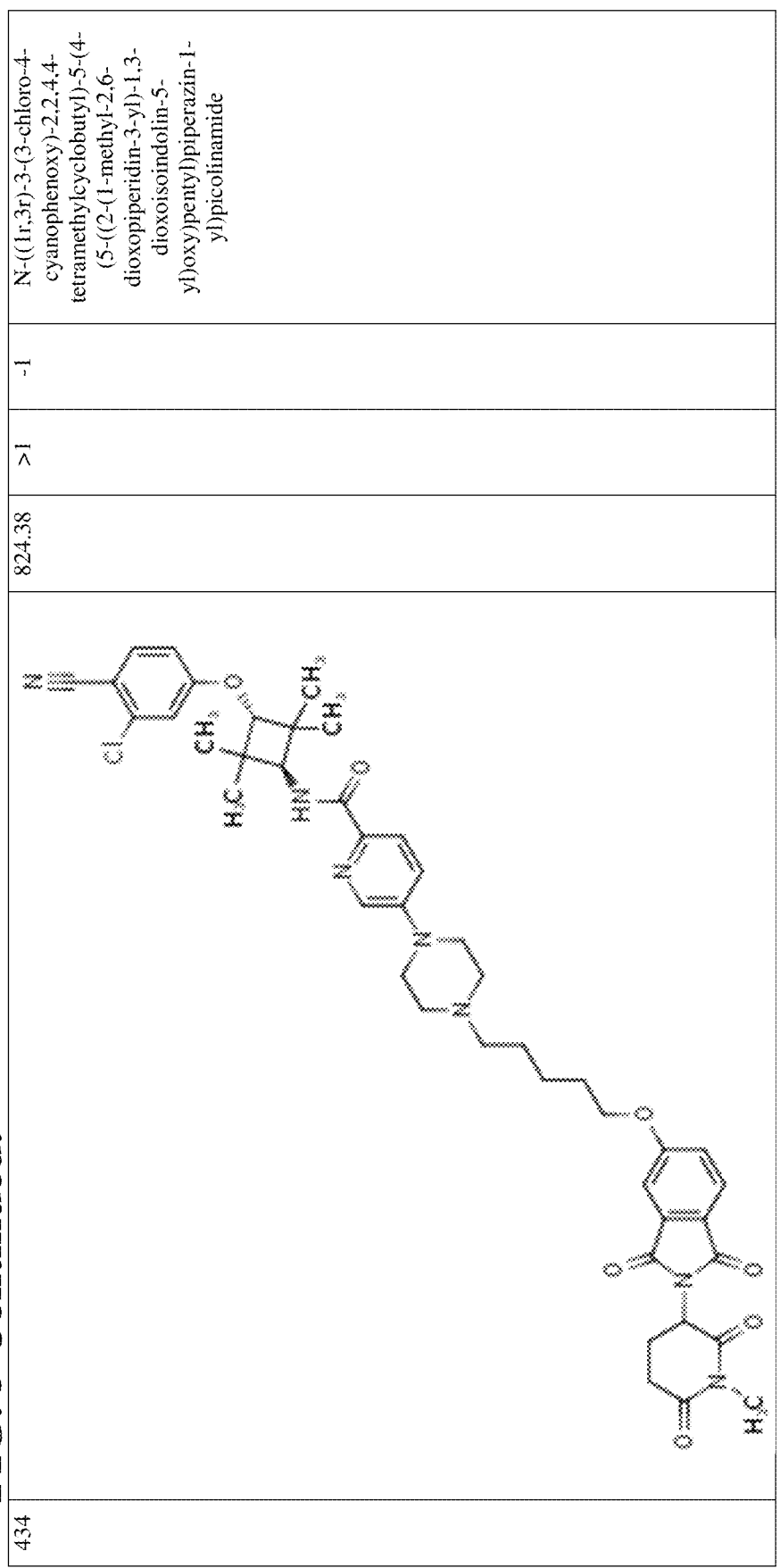
Figure 5:
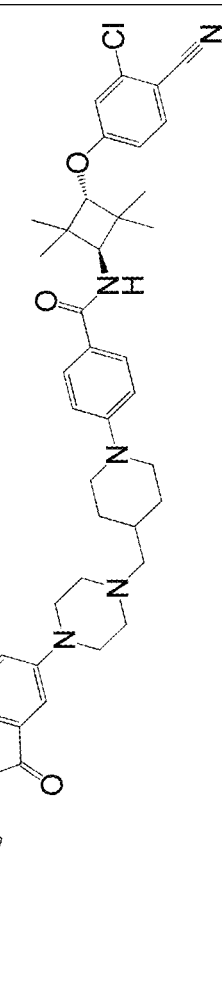
Figure 5:
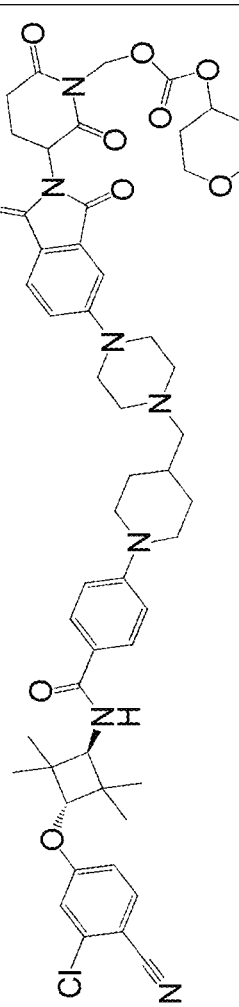
Figure 5:
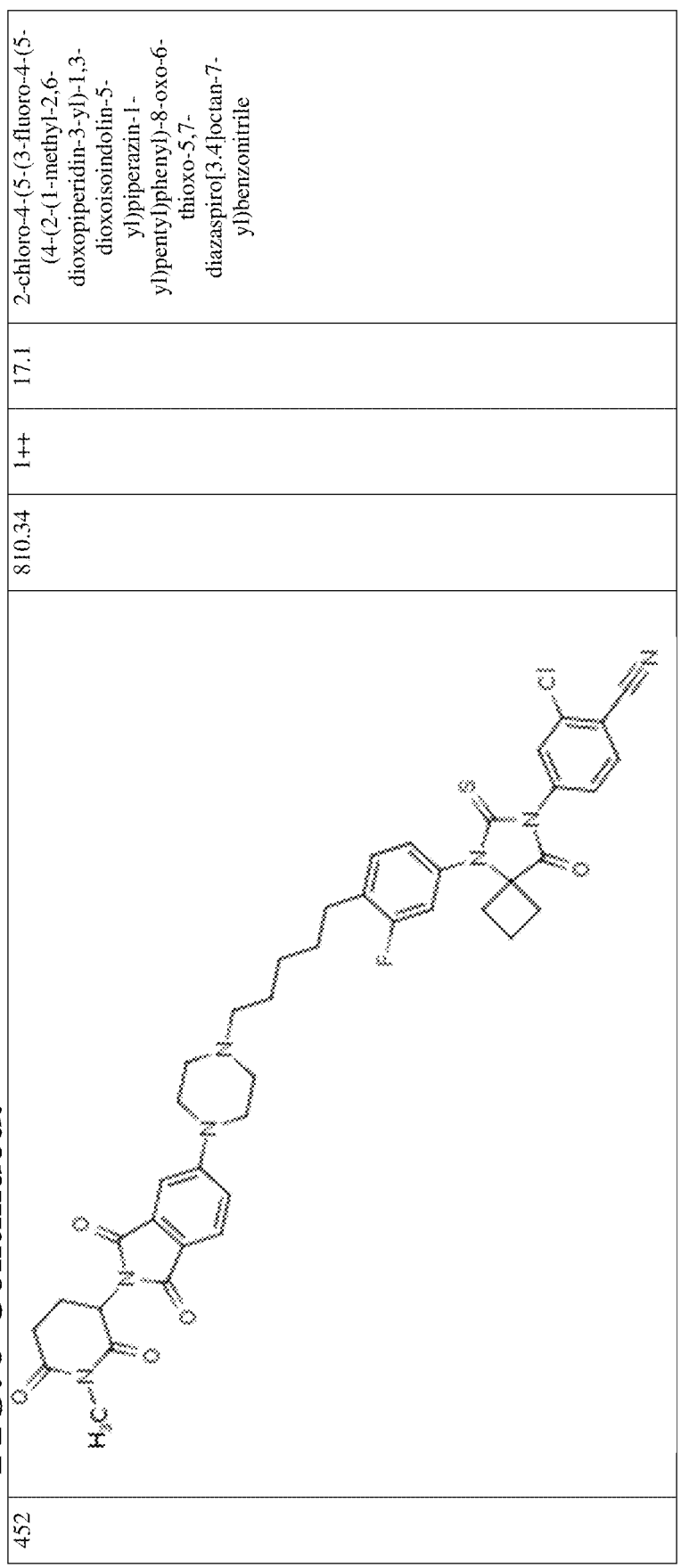
Figure 6:
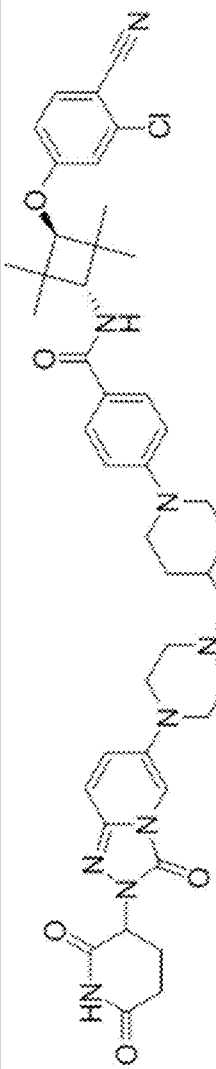
FIG. 6. Table 6 that include Exemplary Compound 528. Table 6 also includes the DC50, Dmax, M/Z+, and 1H NMR data for each of the Exemplary Compounds. DC50 (µM) categories (degradation of AR ELISA in LNCaP and/or VCaP cells): A<1 nM; B: 1-10 nM; C: 10-100 nM; D: >100 nM. Dmax categories (degradation of AR-maximum inhibition (%) AR ELISA in LNCaP and/or VCaP cells): A>50%; B<50%.
Figure 7:
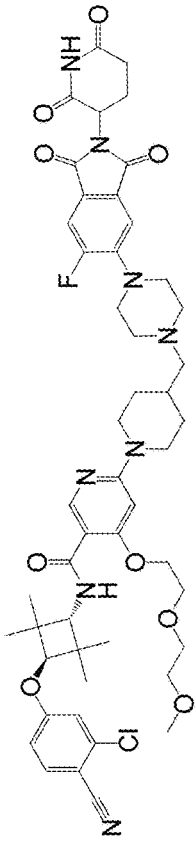
FIG. 7. Table 7 that include Exemplary Compounds 529-625. Table 7 also includes the DC50, M/Z+, and 1H NMR data for each of the Exemplary Compounds. DC50 (µM) categories (degradation of AR ELISA in LNCaP and/or VCaP cells): A<1 nM; B: 1-10 nM; C: 10-100 nM; D: >100 nM.
Figure 7:
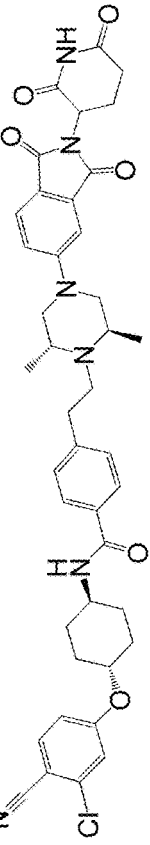
Figure 7:
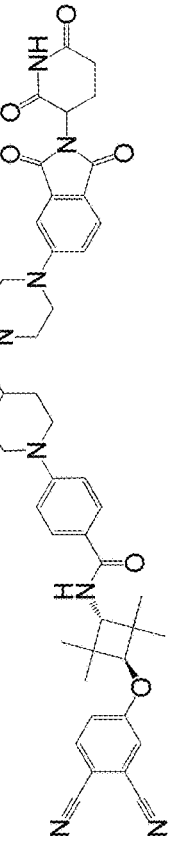
Figure 7:
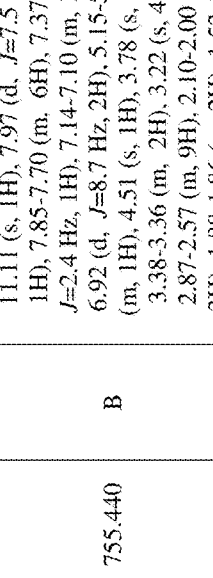
Figure 7:
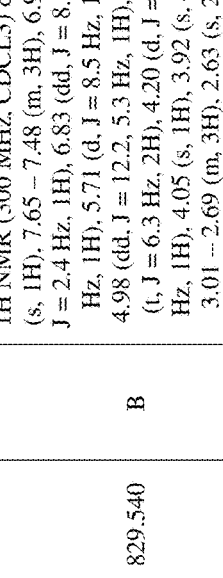
Figure 7:
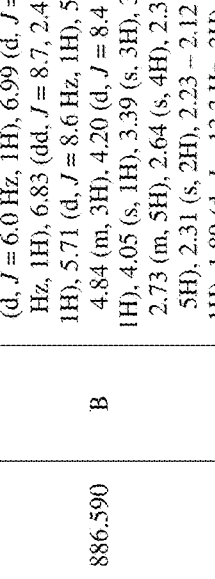
Figure 7:
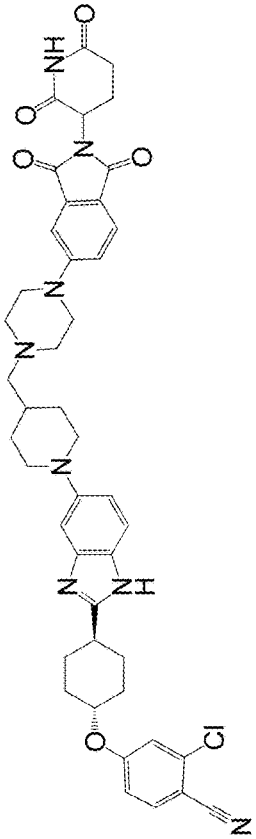
Figure 7:
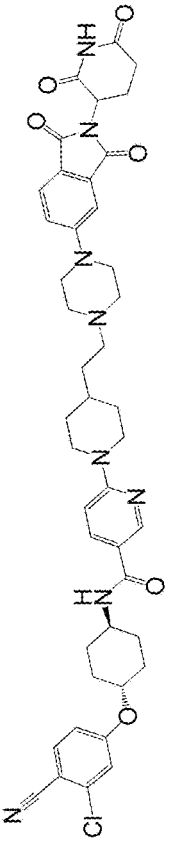
Figure 7:
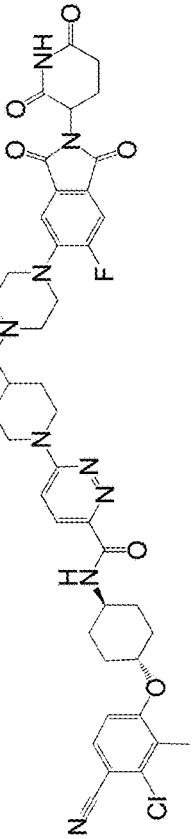
Figure 7:
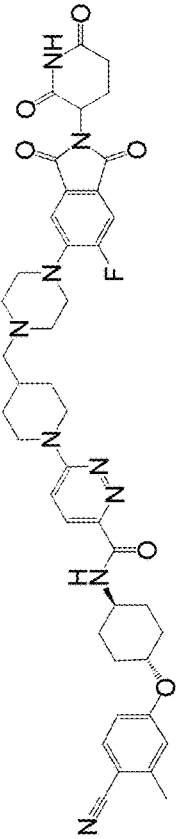
Figure 7:
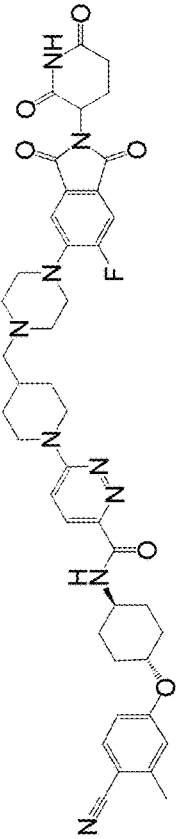
Figure 7:
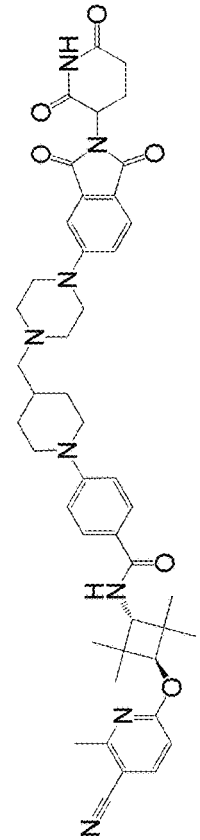
Figure 7:
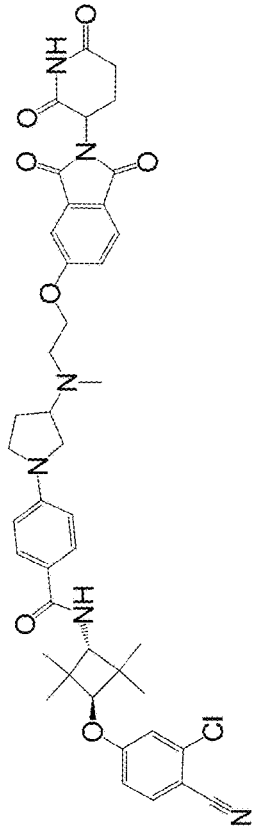
Figure 7:
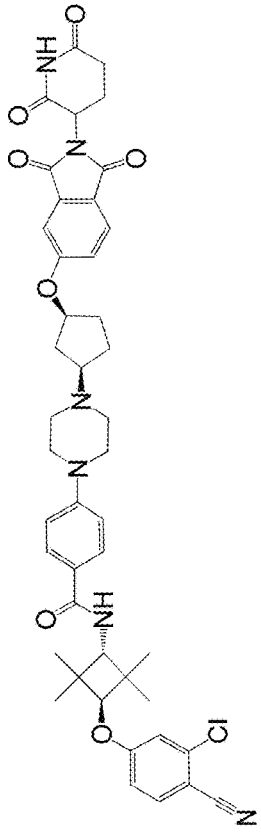
Figure 7:
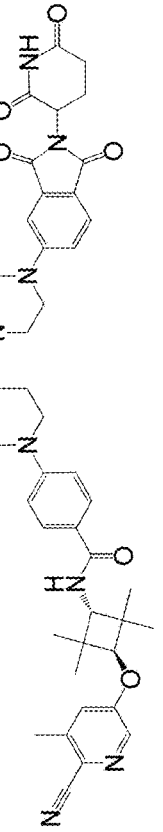
Figure 7:
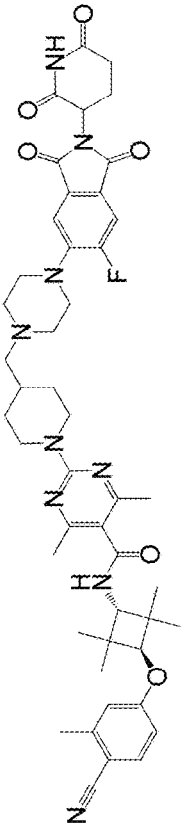
Figure 7:
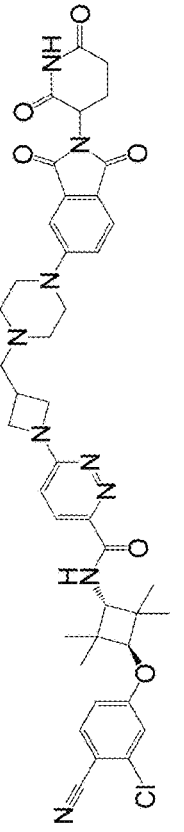
Figure 7:
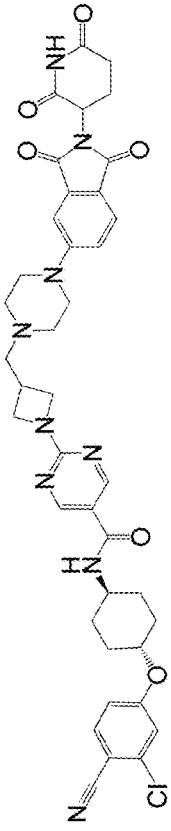
Figure 7:
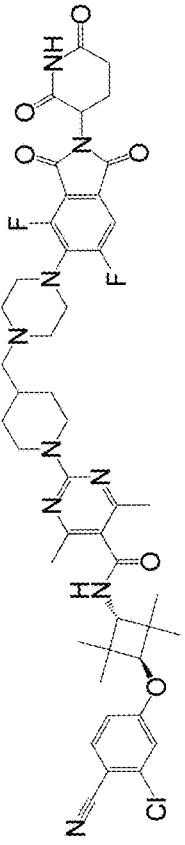
Figure 7:
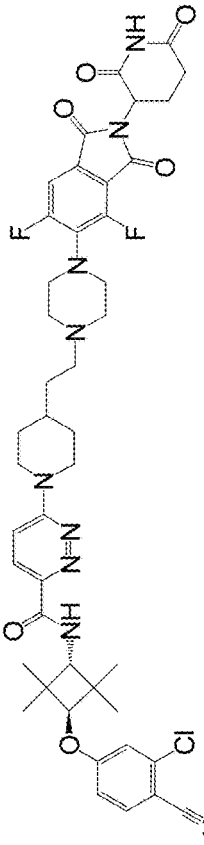
Figure 7:
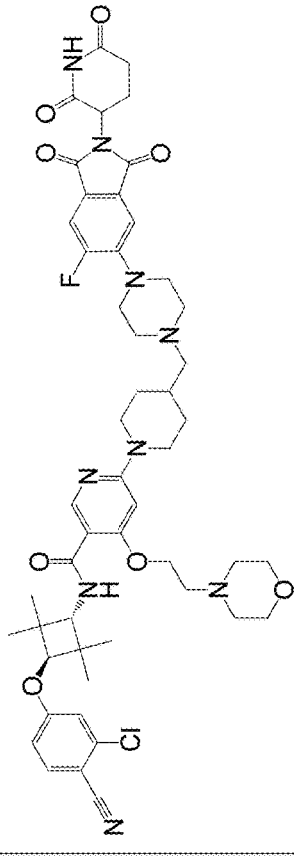
Figure 7:
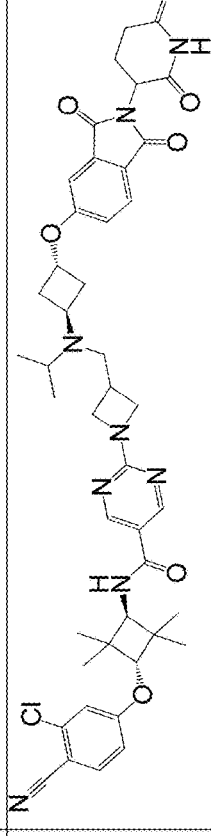
Figure 7:
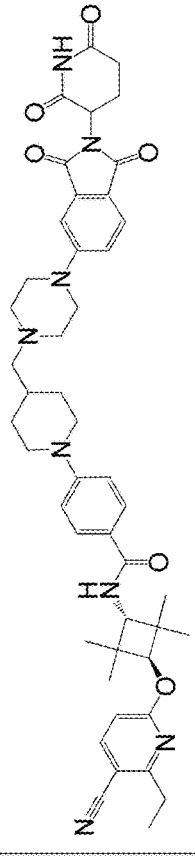
Figure 7:
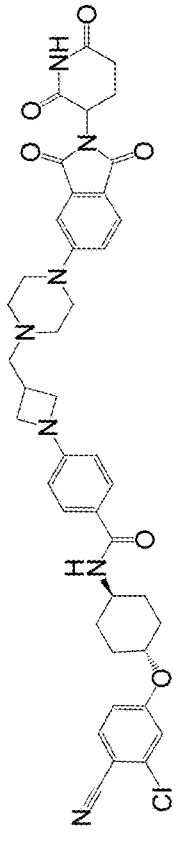
Figure 7:
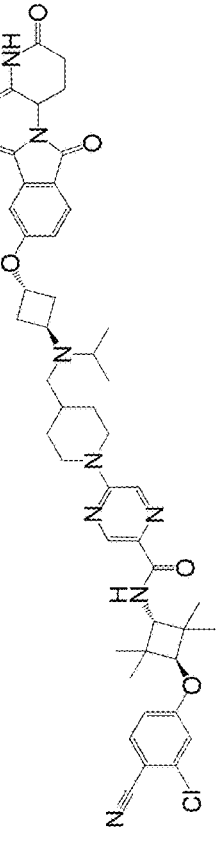
Figure 7:
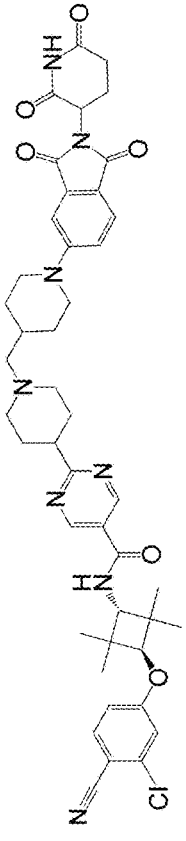
Figure 7:
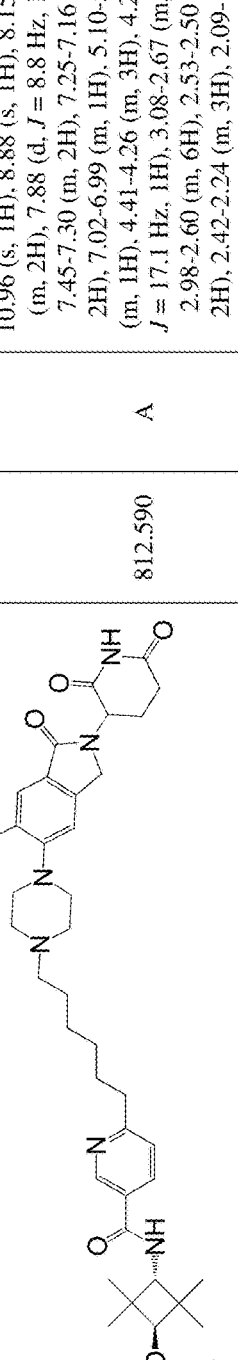
Figure 7:
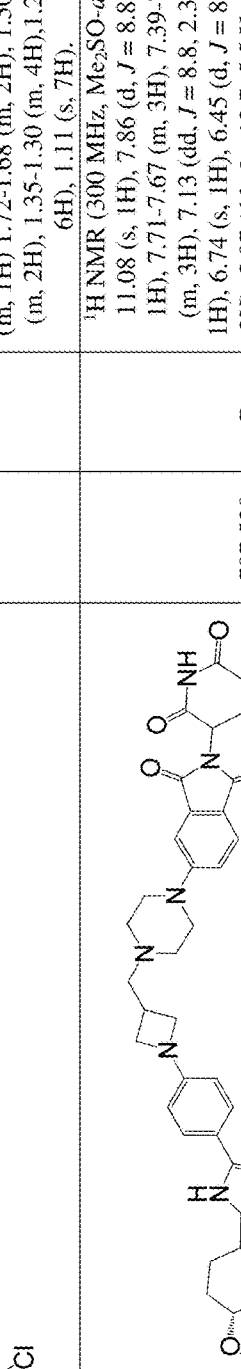
Figure 7:
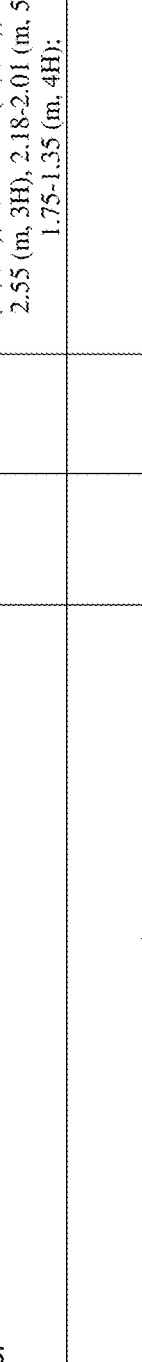
Figure 7:
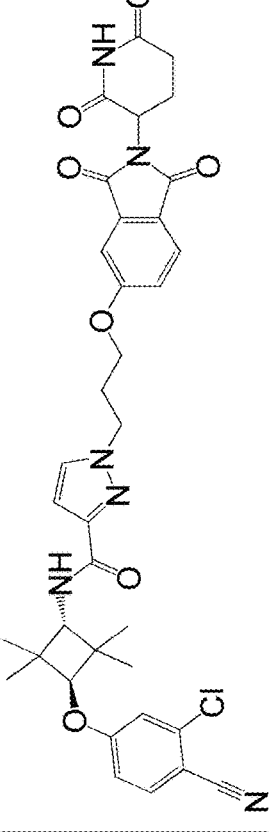
Figure 7:
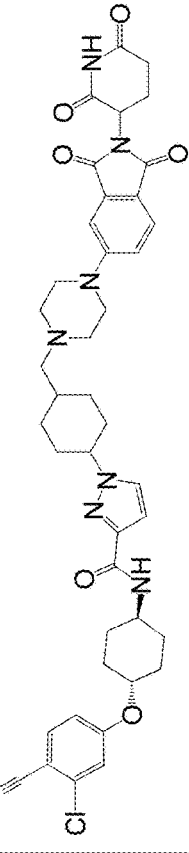
Figure 7:
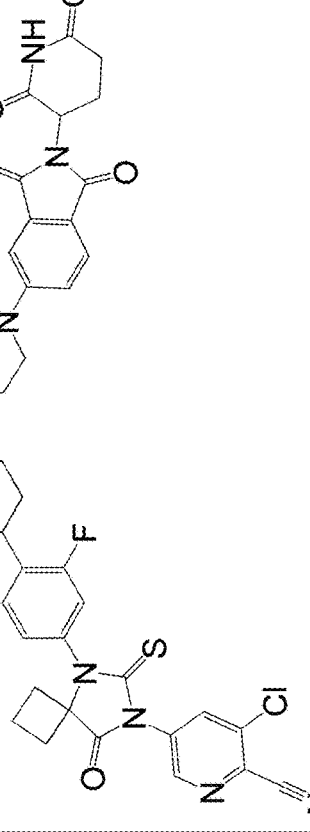
Figure 7:
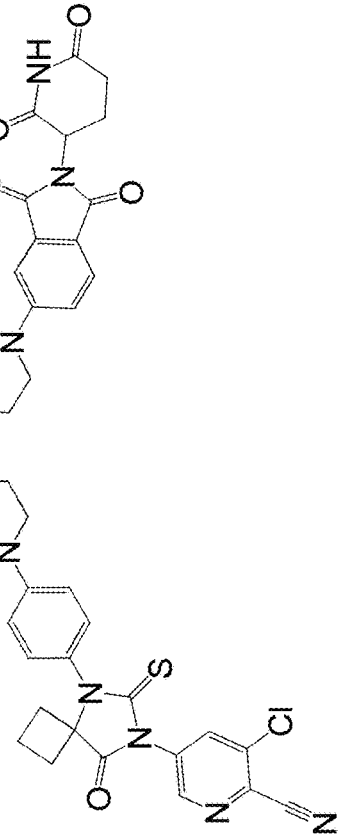
Figure 7:
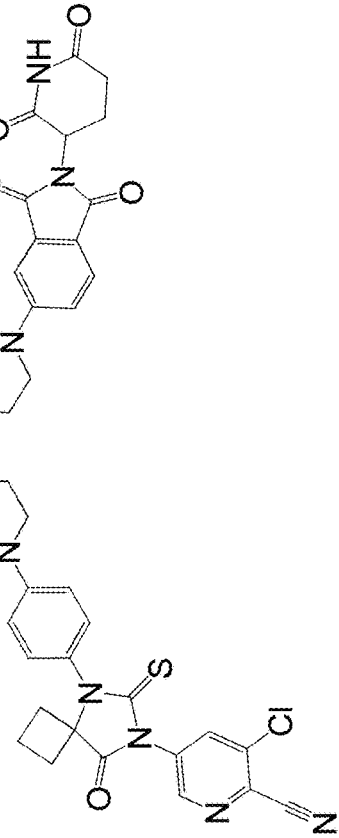
Figure 7:
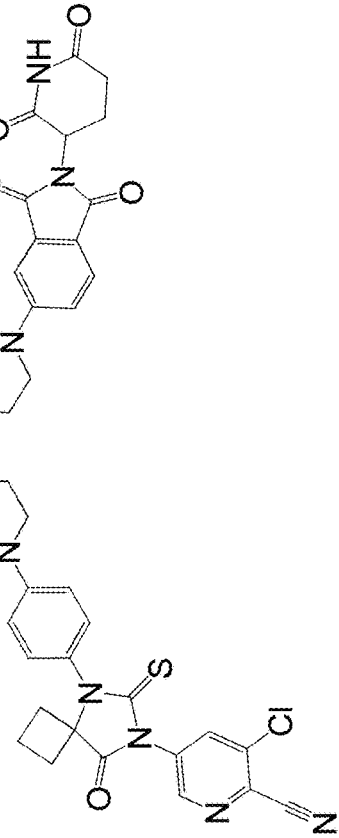
Figure 7:
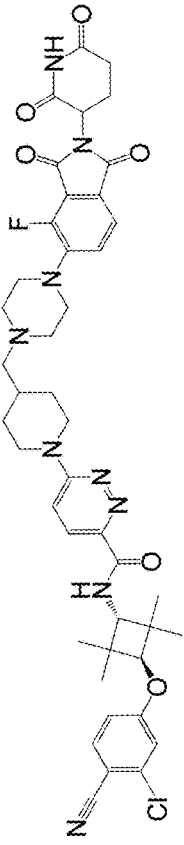
Figure 7:
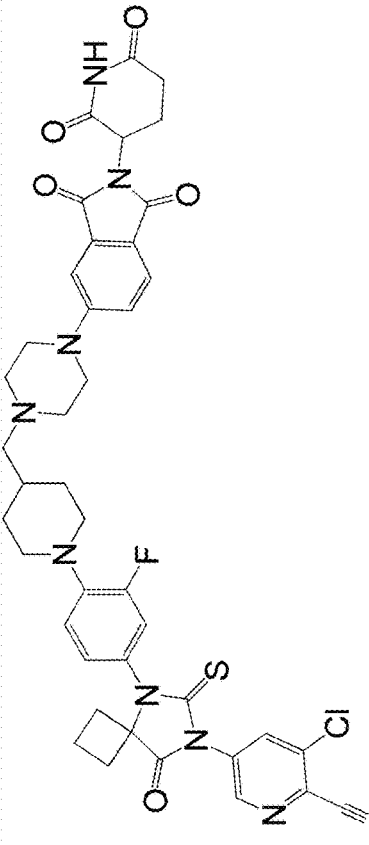
Figure 7:
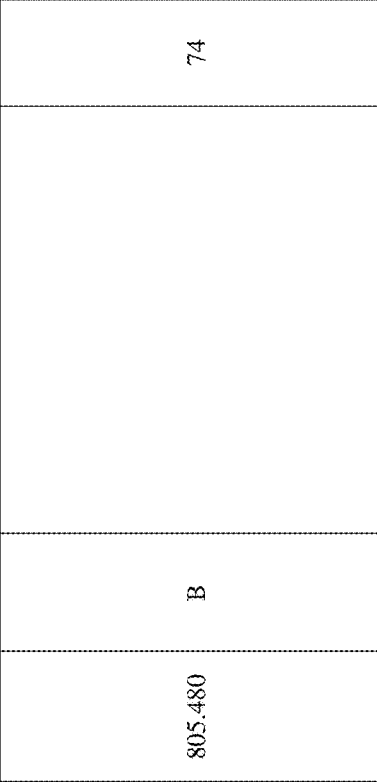
Figure 7:
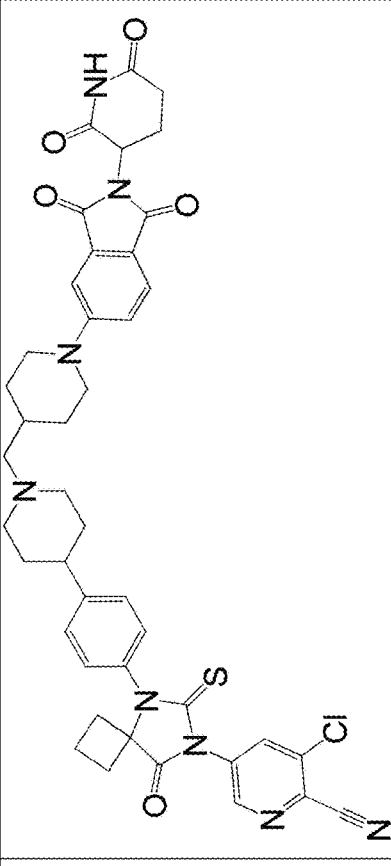
Figure 7:
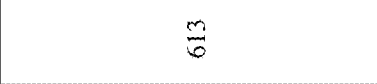
Figure 7:
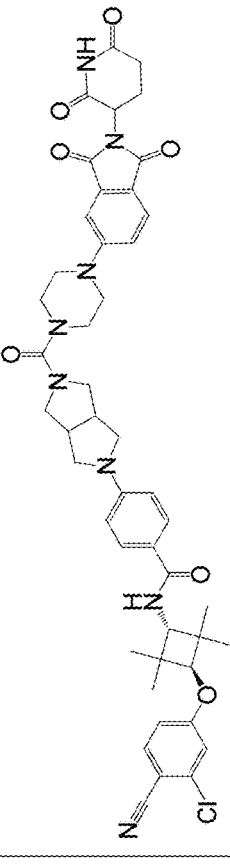
Figure 7:
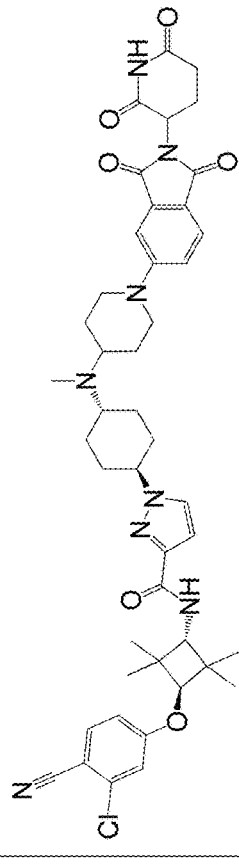
Figure 7:
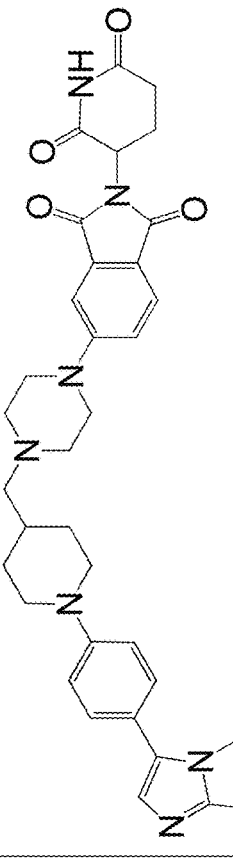
Figure 7:
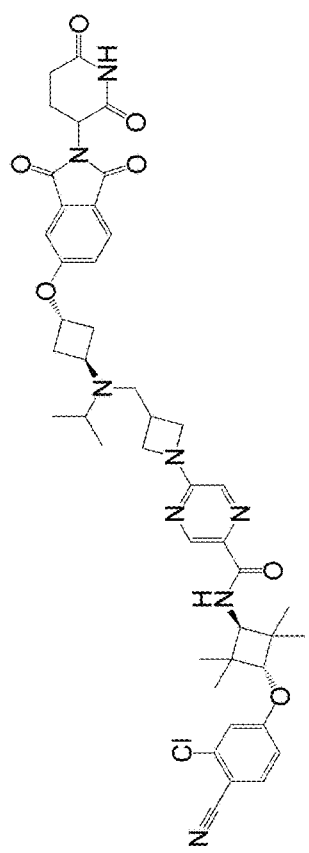
Figure 7:
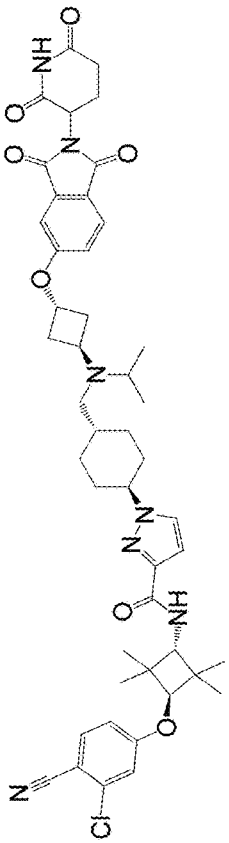
Figure 7:
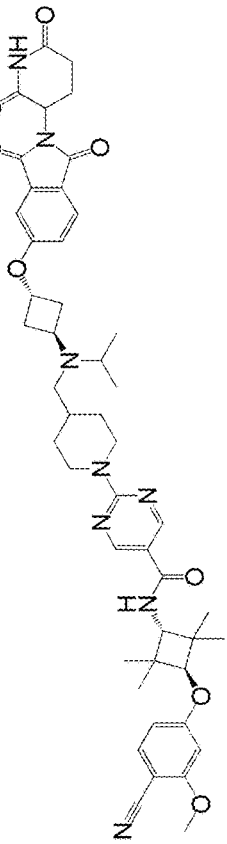
Figure 7:
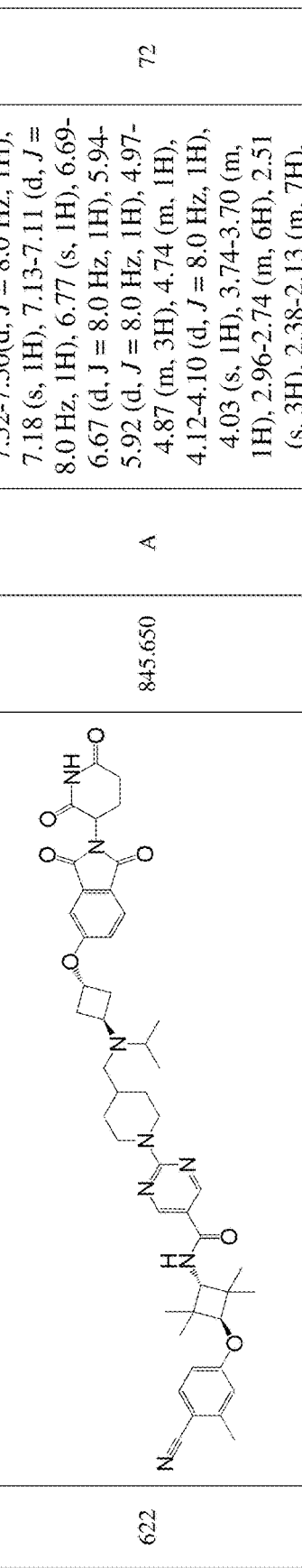
Figure 7:
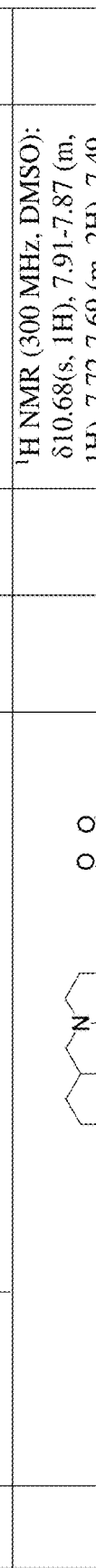

The present description relates to the surprising and unexpected discovery that an E3 ubiquitin ligase protein can ubiquitinate a target protein, in particular androgen receptor, once the E3 ubiquitin ligase protein and the target protein are brought into proximity by a chimeric construct (e.g., PROTAC) as described herein, in which a moiety that binds the E3 ubiquitin ligase protein is coupled, e.g., covalently, to a moiety that bind the androgen receptor target protein. Accordingly, the present description provides compounds, compositions comprising the same, and associated methods of use for ubiquitination and degradation of a chosen target protein, e.g., androgen receptor (See FIG. 1A and FIG. 1B).

The present description is related in certain aspects to U.S. Patent Publications 2014/0356322A1, 2015/0291562A1, and 2016/0214972A1, all of which are incorporated herein by reference in its entirety for all purposes.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present disclosure. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "about" and the like, as used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about" is normally used to encompass values within the standard deviation or standard error.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" can refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "effective" can mean, but is in no way limited to, that amount/dose of the active pharmaceutical ingredient, which, when used in the context of its intended use, effectuates or is sufficient to prevent, inhibit the occurrence, ameliorate, delay or treat (alleviate a symptom to some extent, preferably all) the symptoms of a condition, disorder or disease state in a subject in need of such treatment or receiving such treatment. The term effective subsumes all other effective amount or effective concentration terms, e.g., "effective amount/dose," "pharmaceutically effective amount/dose" or "therapeutically effective amount/dose," which are otherwise described or used in the present application.

The effective amount depends on the type and severity of disease, the composition used, the route of administration, the type of mammal being treated, the physical characteristics of the specific mammal under consideration, concurrent medication, and other factors which those skilled in the medical arts will recognize. The exact amount can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "pharmacological composition," "therapeutic composition," "therapeutic formulation" or "pharmaceutically acceptable formulation" can mean, but is in no way limited to, a composition or formulation that allows for the effective distribution of an agent provided by the present disclosure, which is in a form suitable for administration to the physical location most suitable for their desired activity, e.g., systemic administration.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant disclosure can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "local administration" refers to a route of administration in which the agent is delivered to a site that is apposite or proximal, e.g., within about 10 cm, to the site of the lesion or disease.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described.

It is understood by those of ordinary skill that molecules which are described herein are stable compounds as generally described hereunder. When the bond  is shown, both a double bond and single bond are represented or understood within the context of the compound shown and well-known rules for valence interactions.

As used herein, "derivatives" can mean compositions formed from the native compounds either directly, by modification, or by partial substitution. As used herein, "analogs" can mean compositions that have a structure similar to, but not identical to, the native compound.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe a cell, tissue, or animal, preferably a mammal, e.g., a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

Compounds and Compositions

In one aspect, the present disclosure provides compounds useful for regulating protein activity. The composition comprises a ubiquitin pathway protein binding moiety (preferably for an E3 ubiquitin ligase, alone or in complex with an E2 ubiquitin conjugating enzyme which is responsible for the transfer of ubiquitin to targeted proteins) according to a defined chemical structure and a protein targeting moiety which are linked or coupled together, preferably through a linker, wherein the ubiquitin pathway protein binding moiety recognizes a ubiquitin pathway protein and the targeting moiety recognizes a target protein (e.g., androgen receptor). Such compounds may be referred to herein as PROTAC compounds or PROTACs.

In one aspect, the description provides compounds comprising an E3 Ubiquitin Ligase binding moiety ("ULM") that is a cereblon E3 Ubiquitin Ligase binding moiety ("CLM"). In one embodiment, the CLM is coupled to a chemical linker group (L) according to the structure:

L-CLM  (I)

wherein L is a chemical linker group and CLM is a cereblon E3 Ubiquitin Ligase binding moiety. The number and/or relative positions of the moieties in the compounds illustrated herein is provided by way of example only. As would be understood by the skilled artisan, compounds as described herein can be synthesized with any desired number and/or relative position of the respective functional moieties.

The terms ULM and CLM are used in their inclusive sense unless the context indicates otherwise. For example, the term ULM is inclusive of all ULMs, including those that bind cereblon (i.e., CLMs). Further, the term CLM is inclusive of all possible cereblon E3 Ubiquitin Ligase binding moieties.

In another embodiment, the description provides a compound which comprises a plurality of CLMs coupled directly or via a chemical linker moiety (L). For example, a compound having two CLMs can be depicted as:

CLM-CLM  (II) or

CLM-L-CLM  (III).

In certain embodiments, where the compound comprises multiple CLMs, the CLMs are identical. In additional embodiments, the compound comprising a plurality of CLMs further comprises at least one PTM coupled to a CLM directly or via a chemical linker (L) or both. In certain additional embodiments, the compound comprising a plurality of CLMs further comprises multiple PTMs. In still additional embodiments, the PTMs are the same or, optionally, different. In still further embodiments, wherein the PTMs are different the respective PTMs may bind the same protein target or bind specifically to a different protein target.

In additional embodiments, the description provides a compound comprising at least two different CLMs coupled directly or via a chemical linker (L) or both. For example, such a compound having two different CLMs can be depicted as:

CLM-CLM'  (IV) or

CLM-L-CLM'  (V)

wherein CLM' indicates a cereblon E3 Ubiquitin Ligase binding moiety that is structurally different from CLM. In certain embodiments, the compound may comprise a plurality of CLMs and/or a plurality of CLM's. In further embodiments, the compound comprising at least two different CLMs, a plurality of CLMs, and/or a plurality of CLM's further comprises at least one PTM coupled to a CLM or a CLM' directly or via a chemical linker or both. In any of the embodiments described herein, a compound comprising at least two different CLMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM or CLM (or ULM' or CLM')

In another aspect, the description provides bifunctional or PROTAC compounds, which comprise an E3 Ubiqutin Ligase binding moiety ("ULM") that is a cereblon E3 Ubiquitin Ligase binding moiety ("CLM"), and a moiety that binds a target protein (i.e. a protein/polypeptide targeting ligand or "PTM" group) that is an AR binding moiety ("ABM"). In one embodiment the structure of the bifunctional compound can be depicted as:

ABM-CLM  (VI),

The respective positions of the ABM and CLM moieties as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the compounds having the following general structure: ABM-L, wherein ABM is an AR binding moiety as described herein, and L is a chemical linker moiety, e.g., a linker as described herein, or optionally a bond.

In certain embodiments the bifunctional compound further comprises a chemical linker ("L"). In this example, the structure of the bifunctional compunds can be depicted as:

ABM-L-CLM  (VII)

where ABM is an AR binding moiety as described herein, CLM is a cereblon E3 ligase binding moiety as described herein, and L is a chemical linker moiety, e.g., a linker as described herein, or optionally a bond, that links the ABM and CLM.

Further, CLM is inclusive of all possible cereblon E3 Ubiquitin Ligase binding moieties. The CLM group and ABM group may be covalently linked to the linker group through any covalent bond which is appropriate and stable to the chemistry of the linker.

In certain embodiments, the CLM comprises a moiety that is a ligand of the cereblon E3 Ubiquitin Ligase (CRBN). In certain embodiments, the CLM comprises a chemotype from the "imide" class of molecules. In certain additional embodiments, the CLM comprises a phthalimido group or an analog or derivative thereof. In still additional embodiments, the CLM comprises a phthalimido-glutarimide group or an analog or derivative thereof. In still other embodiments, the CLM comprises a member of the group consisting of thalidomide, lenalidomide, pomalidomide, and analogs or derivatives thereof.

It will be understood that the general structures are exemplary and the respective moieties can be arranged in any desired order or configuration, e.g., CLM-L-ABM, and CLM-L-ABM respectively. In certain additional embodiments, the compounds comprise a plurality of E3 ligase binding moieties and/or a plurality of ABMs.

In certain embodiments, the compounds as described herein comprise multiple ABMs (targeting the same or different locations of the AR), multiple CLMs, one or more ULMs (i.e., moieties that bind specifically to another E3 Ubiquitin Ligase, e.g., VHL) or a combination thereof. In any of the aspects of embodiments described herein, the ABMs, CLMs, and ULMs can be coupled directly or via one or more chemical linkers or a combination thereof. In additional embodiments, where a compound has multiple ULMs, the ULMs can be for the same E3 Ubiquitin Ligase or each respective ULM can bind specifically to a different E3 Ubiquitin Ligase. In still further embodiments, where a compound has multiple ABMs, the ABMs are the same or, optionally, different.

In certain embodiments, where the compound comprises multiple CLMs, the CLMs are identical or, optionally, different. In additional embodiments, the compound comprising a plurality of CLMs further comprises at least one ABM coupled to a CLM directly or via a chemical linker (L) or both. In certain additional embodiments, the compound comprising a plurality of CLMs further comprises multiple ABMs. In still additional embodiments, the ABMs are the same or, optionally, different.

In certain embodiments, ABM alone, without forming ABM-L-CLM, provides desired properties in regulating protein activity.

In any of the aspects or embodiments of compounds described herein, unless indicated otherwise, the compounds are intended to encompass pharmaceutically acceptable salts, enantiomers, stereoisomers, solvates or polymorphs thereof.

In certain embodiments, the compounds as described herein comprise multiple PTMs (targeting the same or different protein targets), multiple ABMs, multiple CLMs, one or more ULMs (i.e., moieties that bind specifically to another E3 Ubiquitin Ligase, e.g., cereblon) or a combination thereof. In any of the aspects of embodiments described herein, the PTMs, ABMs, CLMs, and ULMs can be coupled directly or via one or more chemical linkers or a combination thereof. In additional embodiments, where a compound has multiple ULMs, the ULMs can be for the same E3 Ubiquintin Ligase or each respective ULM can bind specifically to a different E3 Ubiquitin Ligase. In still further embodiments, where a compound has multiple PTMs, the PTMs can bind the same target protein or each respective PTM can bind specifically to a different target protein.

Exemplary CLMs

Neo-Imide Compounds

In one aspect the description provides compounds useful for binding and/or inhibiting cereblon. In certain embodiments, the compound or CLM is selected from the group consisting of chemical structures:

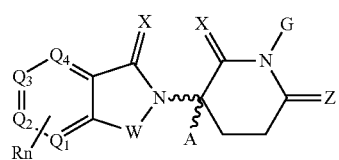 (a)

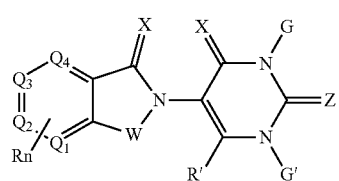 (b)

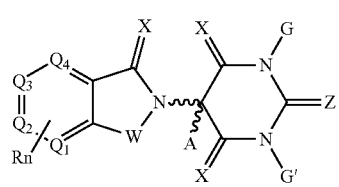 (c)

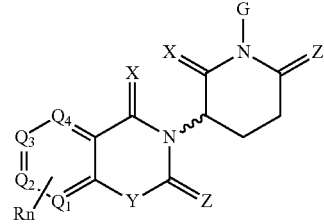 (d)

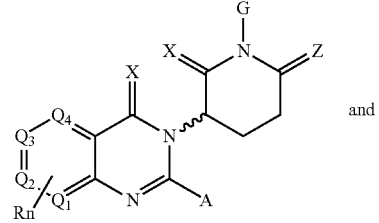 (e)

and

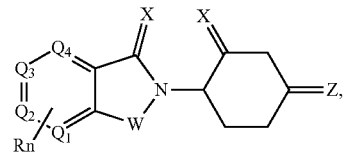 (f)

wherein:
W is independently selected from the group consisting of $CH_2$, CHR, C=O, $SO_2$, NH, and N-alkyl (linear, branched, optionally substituted);
Y is independently selected from the group consisting of $CH_2$, —C=CR', NH, N-alkyl, N-aryl, N-hetaryl, N-cycloalkyl, N-heterocyclyl, O, and S;
X and Z are each independently O, S, or $H_2$, except that both X and Z cannot be $H_2$;
G and G' are independently selected from the group consisting of H, alkyl (linear, branched, optionally substituted with R'), OH, R'OCOOR, R'OCONRR", $CH_2$-heterocyclyl optionally substituted with R', and benzyl optionally substituted with R';
Q1-Q4 are each independently C optionally substituted with R', N, or N-oxide;
A is independently selected from the group consisting of alkyl (linear, branched, optionally substituted), cycloalkyl (optionally substituted), $C_1$, H and F;
R comprises, but is not limited to: —CONR'R", —OR', —NR'R", —SR', —$SO_2$R', —$SO_2$NR'R", —CR'R"—, —CR'NR'R"—, -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$, —R'NR'R", (—R'O)$_n$R", or —$OCF_3$
R' and R" are each independently a bond, H, alkyl (linear, branched), cycloalkyl, aryl, hetaryl, heterocyclyl, or —C(=O)R, each of which is optionally substituted;
n is an integer from 1-10 (e.g., 1-4, 1, 2, 3, 4, 5, 6, 7, 8, 9, or 10);

∽ represents a bond that may be stereospecific ((R) or (S)) or non-stereospecific; and $R_n$ comprises 1-4 independent functional groups or atoms, and optionally, one of which is modified to be covalently joined to an ABM, a chemical linker group (L), a ULM, a CLM (CLM'), or combination thereof.

Exemplary CLMs

In any of the compounds described herein, the CLM comprises a chemical structure selected from the group:

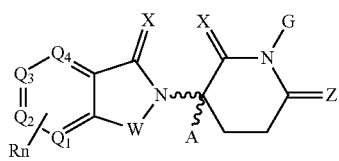

(a)

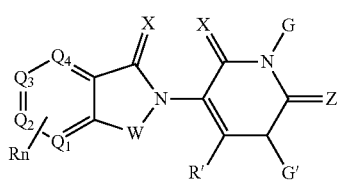

(b)

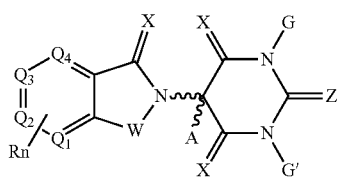

(c)

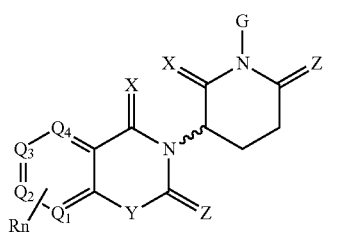

(d)

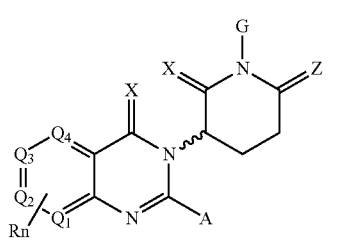

(e)

and

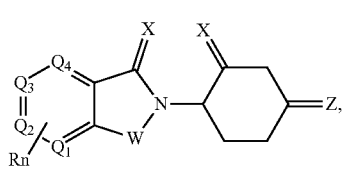

(f)

wherein:
- W is $CH_2$, CHR, C=O, $SO_2$, NH, or N-alkyl (linear, branched, optionally substituted);
- X and Z are each independently O, S or $H_2$, except that both X and Z cannot be $H_2$;
- Y is independently selected from the group $CH_2$, —C=CR', NH, N-alkyl, N-aryl, N-hetaryl, N-cycloalkyl, N-heterocyclyl, O, and S;
- G is H, alkyl (linear, branched), OH, R'OCOOR, R'OCONRR", $CH_2$-heterocyclyl, heterocyclic, aryl, or benzyl, each optionally substituted with R';
- Q1-Q4 are each independently C is optionally substituted with R', N, or N-oxide;
- A is $C_1$-$C_6$ alkyl (linear, branched, optionally substituted), cycloalkyl (optionally substituted), H, Cl or F;
- R is —CONR'R", —OR', —NR'R", —SR', —$SO_2$R', —$SO_2$NR'R", —CR'R"—, —CR'NR'R"—, (—CR'O)$_n$R", -aryl, -heteroaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", alicyclic, heterocyclic, —$SF_5$, or —$OCF_3$;
- R' and R" are each independently a bond, H, N, N-oxide, alkyl (linear, branched), cycloalkyl, aryl, heteroaryl, heterocyclic, —C(=O)R, or, heterocyclyl, each of which is optionally substituted;
- n is an integer from 1-10;
- ∽ represents a bond that may be stereospecific ((R) or (S)) or non-stereospecific; and
- $R_n$ comprises 1-4 independent functional groups or atoms, and optionally, one of which is modified to be covalently joined to an ABM, a chemical linker group (L), a ULM, a CLM (CLM'), or combination thereof.

In certain embodiments described herein, the CLM or ULM comprises a chemical structure selected from the group:

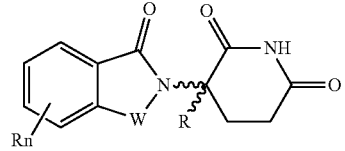

wherein:
- W is independently selected from the group consisting of $CH_2$, C=O, NH, and N-alkyl;
- R is a H, methyl, or $C_1$-$C_6$ alkyl (linear, branched, optionally substituted);
- ∽ represents a bond that may be stereospecific ((R) or (S)) or non-stereospecific; and
- Rn comprises 1-4 independently selected functional groups or atoms, and optionally, one of which is modified to be covalently joined to an ABM, a chemical linker group (L), a ULM, CLM (or CLM') or combination thereof.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure, which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C≡C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substituents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or $C_1$), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$ (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$—O—$(C_1$-$C_6$ alkyl), —$(CH_2)_n$C(O)—$(C_1$-$C_6$ alkyl), —$(CH_2)_n$OC(O)—$(C_1$-$C_6$ alkyl), —$(CH_2)_n$C(O)O—$(C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—$(C_1$-$C_6$ alkyl), —$(CH_2O)_n$C(O)—$(C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or $C_1$), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—$(C_1$-$C_6$)alkyl, —$(CH_2)_n$—O—$(CH_2)_n$—$(C_1$-$C_6$)alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, $C_1$) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a ABM group, including a ULM group), and/or at least one of F, $C_1$, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—C(O)—O—C$_1$-C$_6$ alkyl group), an optionally substituted pyridine (2-, 3, or 4-pyridine) or a group according to the chemical structure:

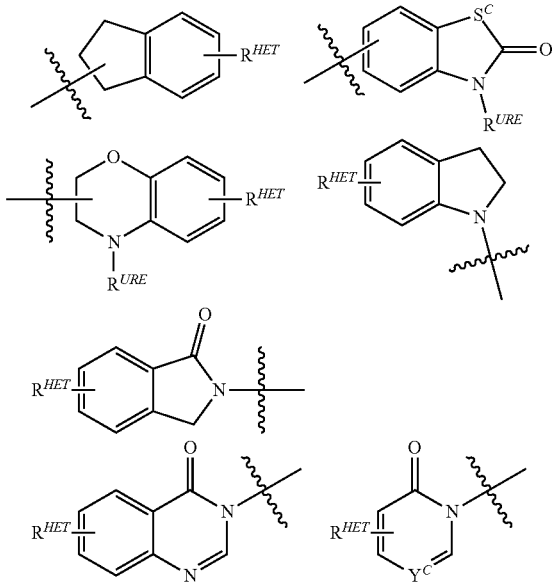

wherein

S$^c$ is CHR$^{SS}$, NR$^{URE}$, or O;

R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$^a$ where R$^a$ is H or a C$_1$-C$_6$ alkyl group (preferably C$_1$-C$_3$ alkyl);

R$^{SS}$ is H, CN, NO$_2$, halo (preferably F or C$_1$), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and Y$^C$ is N or C—R$^{Y}$c, where R$^{Y}$c is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolan, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (═O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

In any of the embodiments described herein, the W, X, Y, Z, G, G', R, R', R", Q1-Q4, A, and Rn can independently be covalently coupled to a linker and/or a linker to which is attached one or more ABM, ULM, CLM or CLM' groups.

More specifically, non-limiting examples of CLMs include those shown below as well as those 'hybrid' molecules that arise from the combination of 1 or more of the different features shown in the molecules below, wherein Rn comprises 1-4 independently selected functional groups or atoms, and optionally, one of which is modified to be covalently joined to a ABM, a chemical linker group (L), a ULM, CLM (or CLM') or combination thereof.

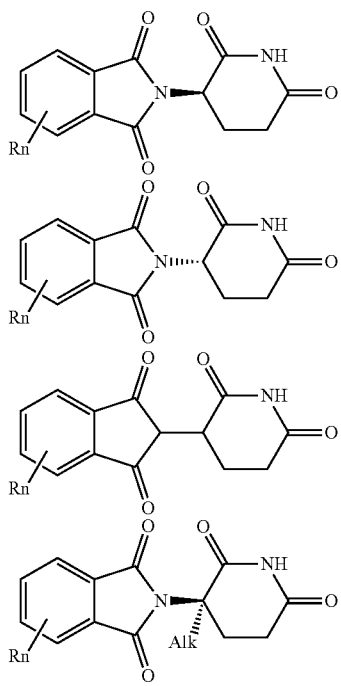

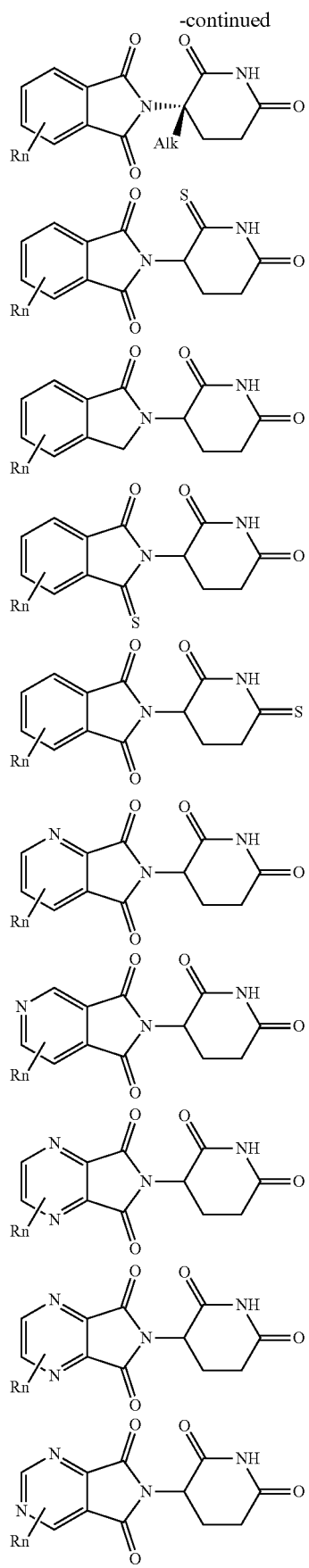

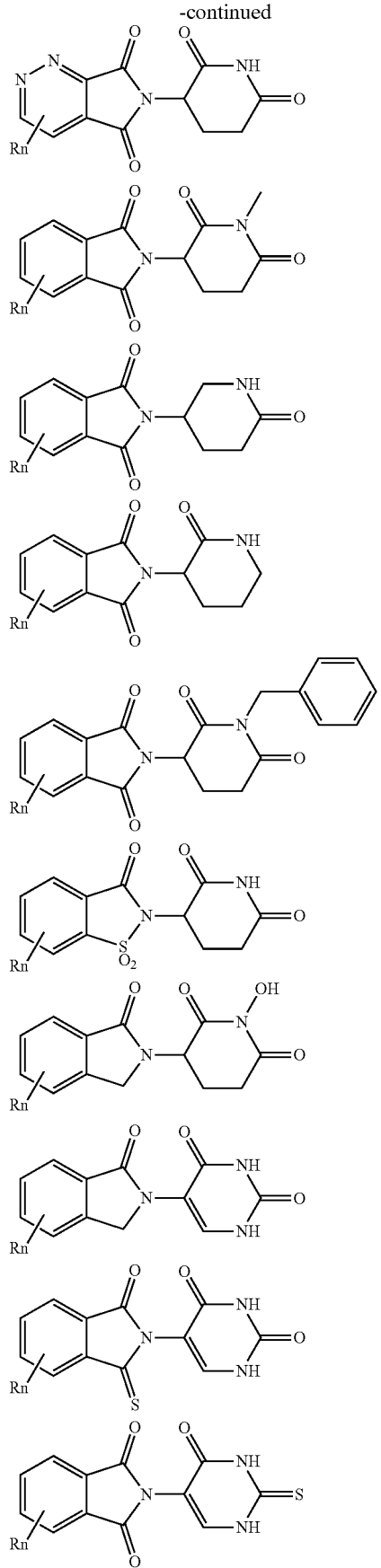
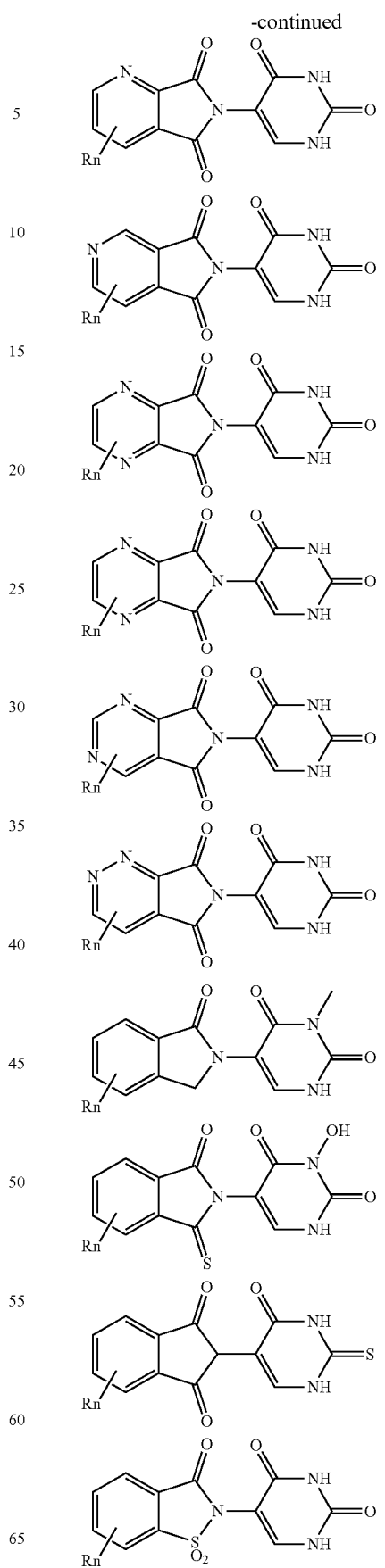

-continued
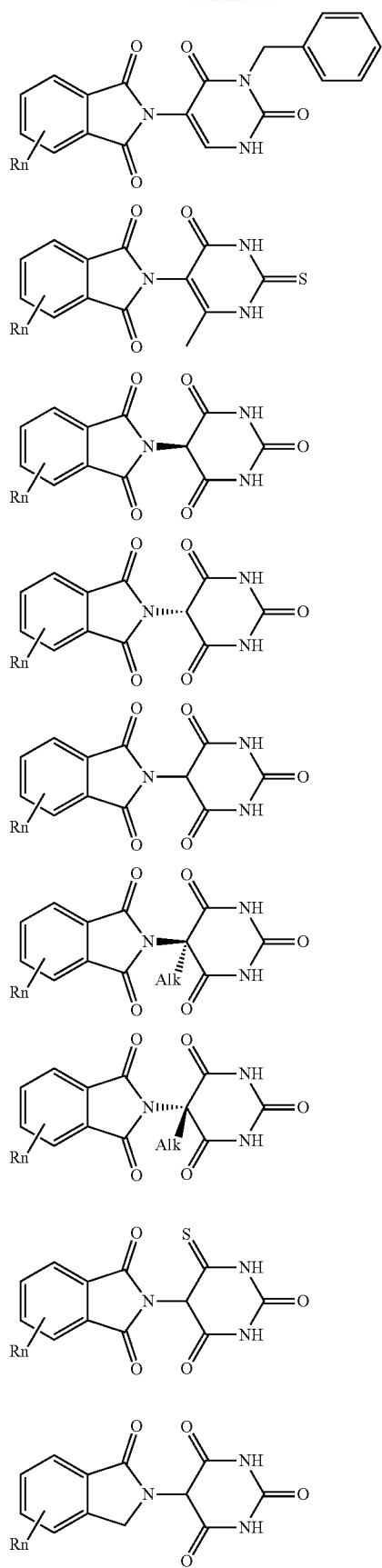
-continued
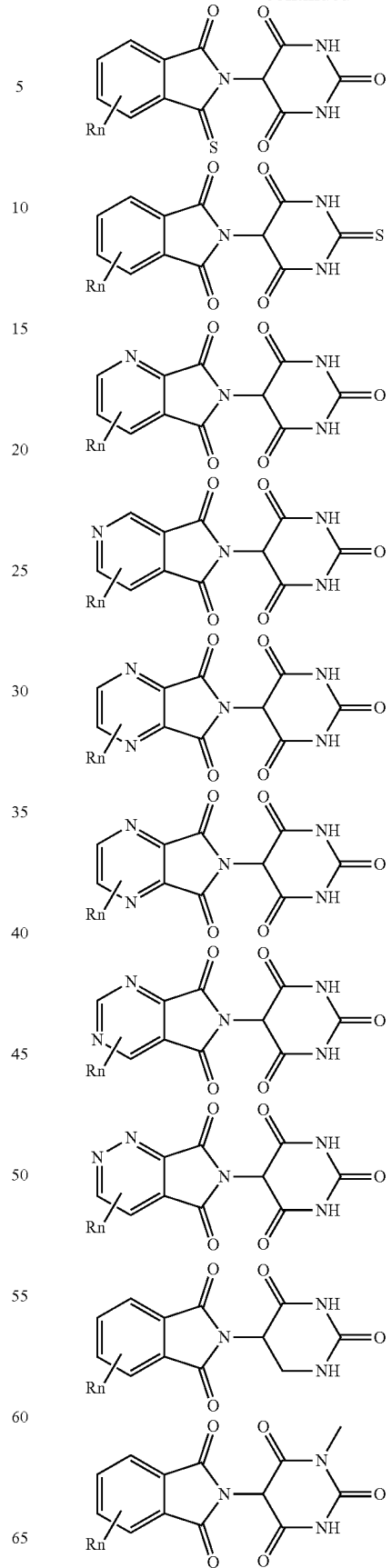

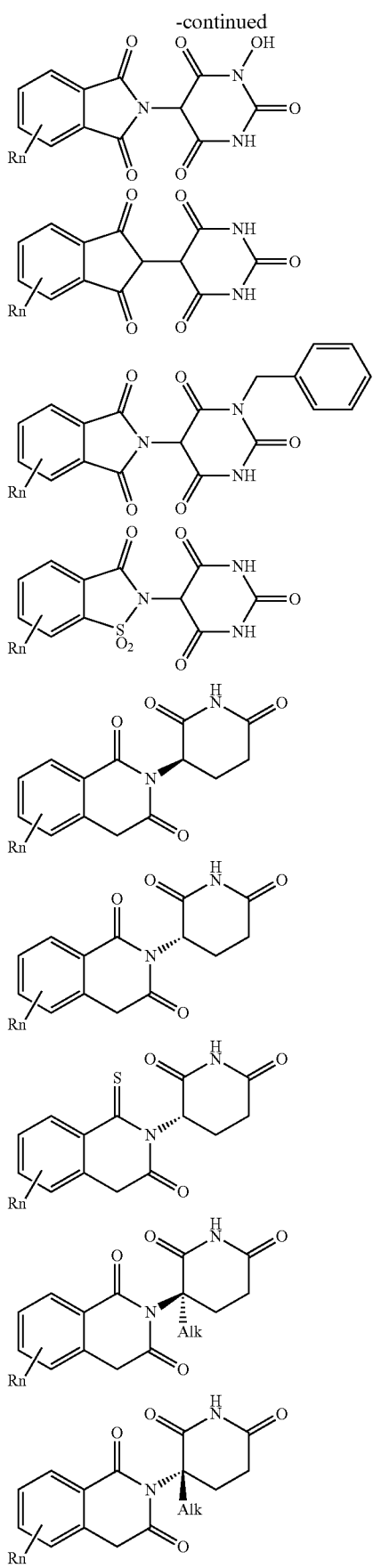
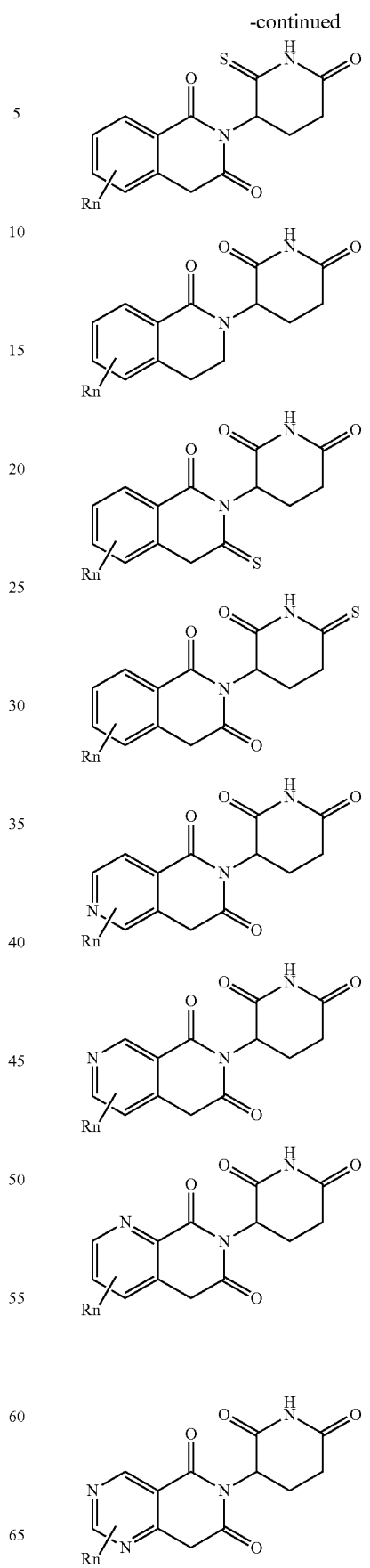

-continued

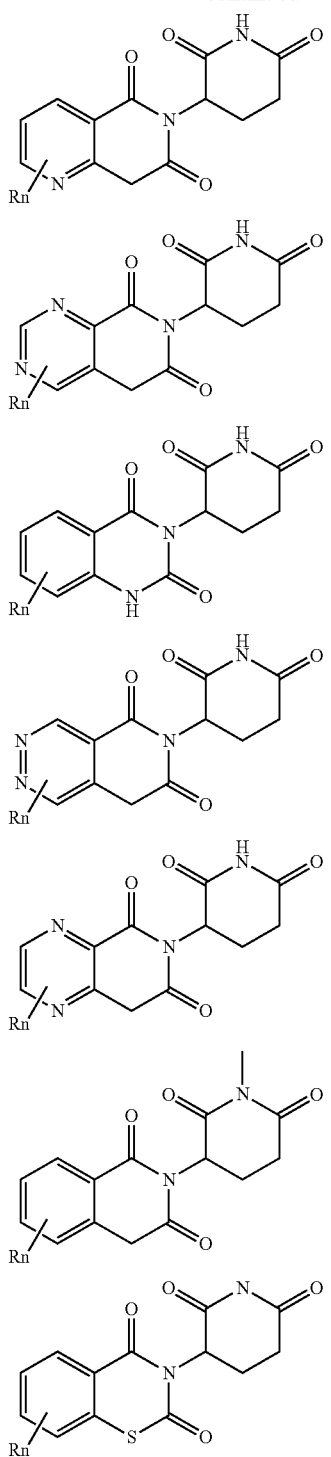

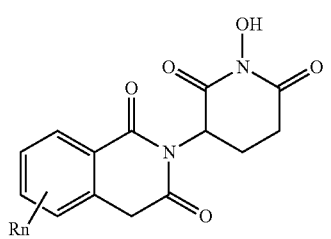

-continued

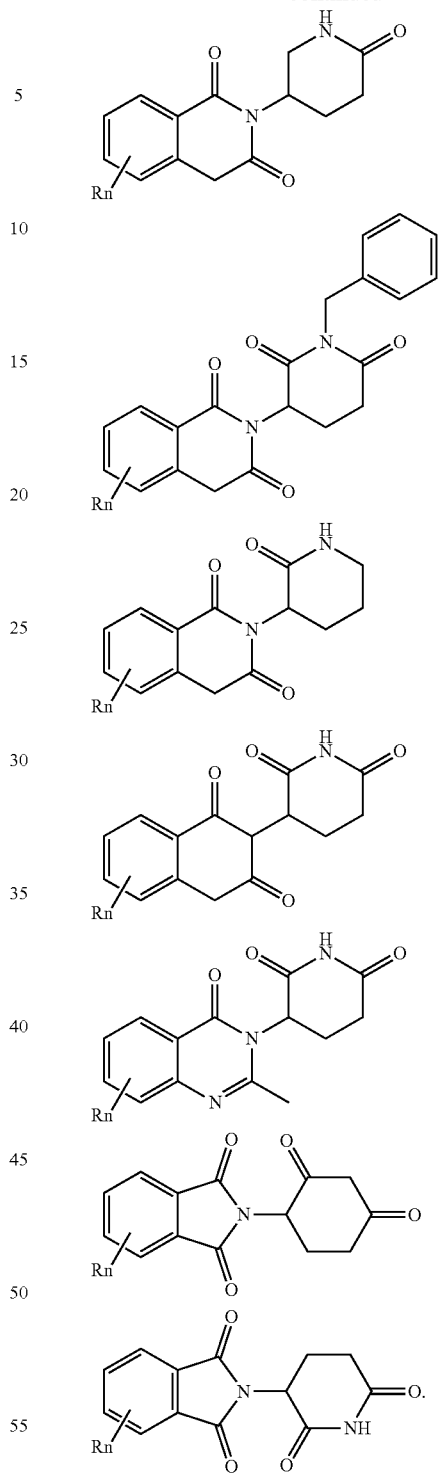

Exemplary Linkers

In certain embodiments, the compounds as described herein include one or more ABM chemically linked or coupled to one or more ULMs or CLMs via a chemical linker (L). In certain embodiments, the linker group L is a group comprising one or more covalently connected structural units (e.g., -$A_1$ . . . $A_q$- or -$A_q$-), wherein $A_1$ is a group coupled to ABM, and $A_q$ is a group coupled to ULM.

In certain embodiments, the linker group L is selected from $A_q$-;
  $A_q$ is a group which is connected to a ULM or ABM moiety; and
  q is an integer greater than or equal to 1,
  wherein $A_q$ is selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups;
  $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl$)(C_{1-8}$alkyl$)$, OH, $NH_2$, SH, $SO_2C_{1-8}$alkyl, $P(O)(OC_{1-8}$alkyl$)(C_{1-8}$alkyl$)$, $P(O)(OC_{1-8}$alkyl$)_2$, $CC-C_{1-8}$alkyl, CCH, $CH=CH(C_{1-8}$alkyl$)$, $C(C_{1-8}$alkyl$)=CH(C_{1-8}$alkyl$)$, $C(C_{1-8}$alkyl$)=C(C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl$)CONH(C_{1-8}$alkyl$)$, $N(C_{1-8}$alkyl$)CON(C_{1-8}$alkyl$)_2$, $NHCONH(C_{1-8}$alkyl$)$, $NHCON(C_{1-8}$alkyl$)_2$, $NHCONH_2$, $N(C_{1-8}$alkyl$)SO_2NH(C_{1-8}$alkyl$)$, $N(C_{1-8}$alkyl$)SO_2N(C_{1-8}$alkyl$)_2$, $NH\ SO_2NH(C_{1-8}$alkyl$)$, $NH\ SO_2N(C_{1-8}$alkyl$)_2$, $NH\ SO_2NH_2$.

In certain embodiments, q is an integer greater than or equal to 0. In certain embodiments, q is an integer greater than or equal to 1.

In certain embodiments, e.g., where q is greater than 2, $A_q$ is a group which is connected to ULM, and $A_1$ and $A_q$ are connected via structural units of the linker (L).

In certain embodiments, e.g., where q is 2, $A_q$ is a group which is connected to $A_1$ and to a ULM.

In certain embodiments, e.g., where q is 1, the structure of the linker group L is -$A_1$-, and $A_1$ is a group which is connected to a ULM moiety and a ABM moiety.

In certain embodiments, the linker (L) comprises a group represented by a general structure selected from the group consisting of:
  —NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(hetero cycloalkyl)-, —NR(CH$_2$CH$_2$O)$_n$-(lower alkyl)-O—CH$_2$—, —NR(CH$_2$CH$_2$O)$_n$-(hetero cycloalkyl)-O—CH$_2$—, —NR(CH$_2$CH$_2$O)$_n$-Aryl-O—CH$_2$—, —NR(CH$_2$CH$_2$O)$_n$-(hetero aryl)-O—CH$_2$—, —NR(CH$_2$CH$_2$O)$_n$-(cyclo alkyl)-O-(hetero aryl)-O—CH$_2$—, —NR(CH$_2$CH$_2$O)$_n$-(cyclo alkyl)-O-Aryl-O—CH$_2$—, —NR(CH$_2$CH$_2$O)$_n$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(hetero aryl)l-, —NR(CH2CH2)n-(cycloalkyl)-O-(heterocycle)-CH2, —NR(CH2CH2)n-(heterocycle)-(heterocycle)-CH2, —N(R1R2)-(heterocycle)-CH$_2$; where n can be 0 to 10;

R can be H, lower alkyl;

R1 and R2 can form a ring with the connecting N.

In certain embodiments, the linker (L) comprises a group represented by a general structure selected from the group consisting of:

—N(R)—(CH2)$_m$-O(CH2)$_n$-O(CH2)$_o$-O(CH2)$_p$-O(CH2)$_q$-O(CH2)$_r$-OCH2-, —O—(CH2)$_m$-O(CH2)$_n$-O(CH2)$_o$-O(CH2)$_p$-O(CH2)$_q$-O(CH2)$_r$-OCH2-, —O—(CH2)$_m$-O(CH2)$_n$-O(CH2)$_o$-O(CH2)$_p$-O(CH2)$_q$-O(CH2)$_r$-O—; —N(R)—(CH2)$_m$-O(CH2)$_n$-O(CH2)$_o$-O(CH2)$_p$-O(CH2)$_q$-O(CH2)$_r$-O—; —(CH2)$_m$-O(CH2)$_n$-O(CH2)$_o$-O(CH2)$_p$-O(CH2)$_q$-O(CH2)$_r$-O—; —(CH2)$_m$-O(CH2)$_n$-O(CH2)$_o$-O(CH2)$_p$-O(CH2)$_q$-O(CH2)$_r$-OCH2-;

-continued

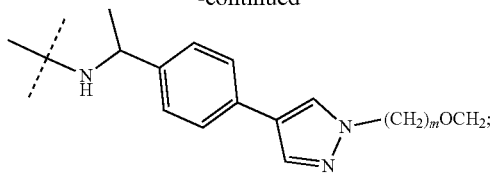

wherein
m, n, o, p, q, and r are each independently 0, 1, 2, 3, 4, 5, 6;
when the number is zero, there is no N—O or O—O bond
R is H, methyl or ethyl; and
X is H or F.

In certain embodiments, the linker (L) comprises a group represented by a general structure:

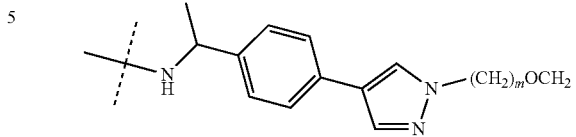

wherein m can be 2, 3, 4, 5.

In certain embodiments, the linker (L) comprises a group represented by a general structure selected from the group consisting of:

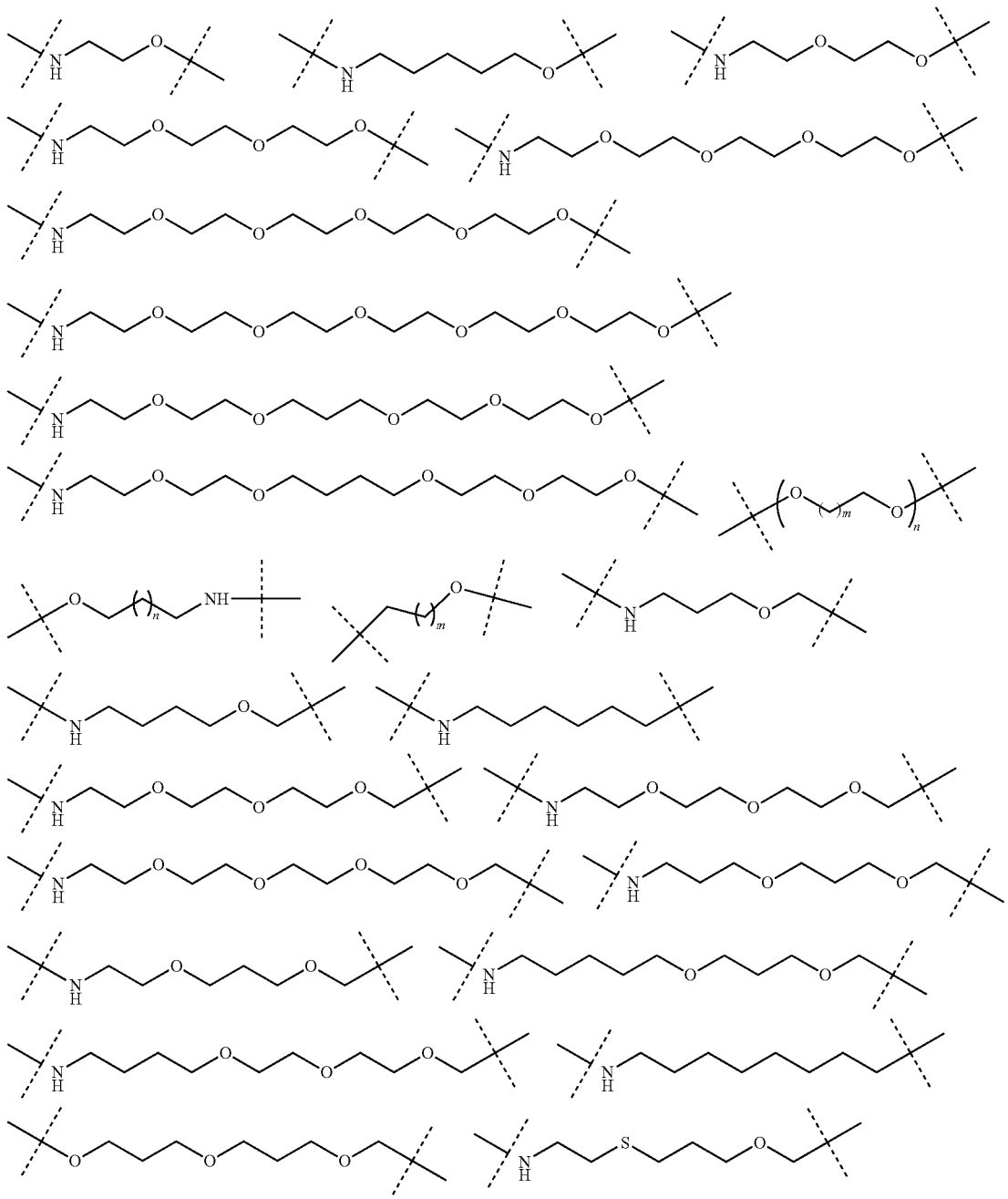

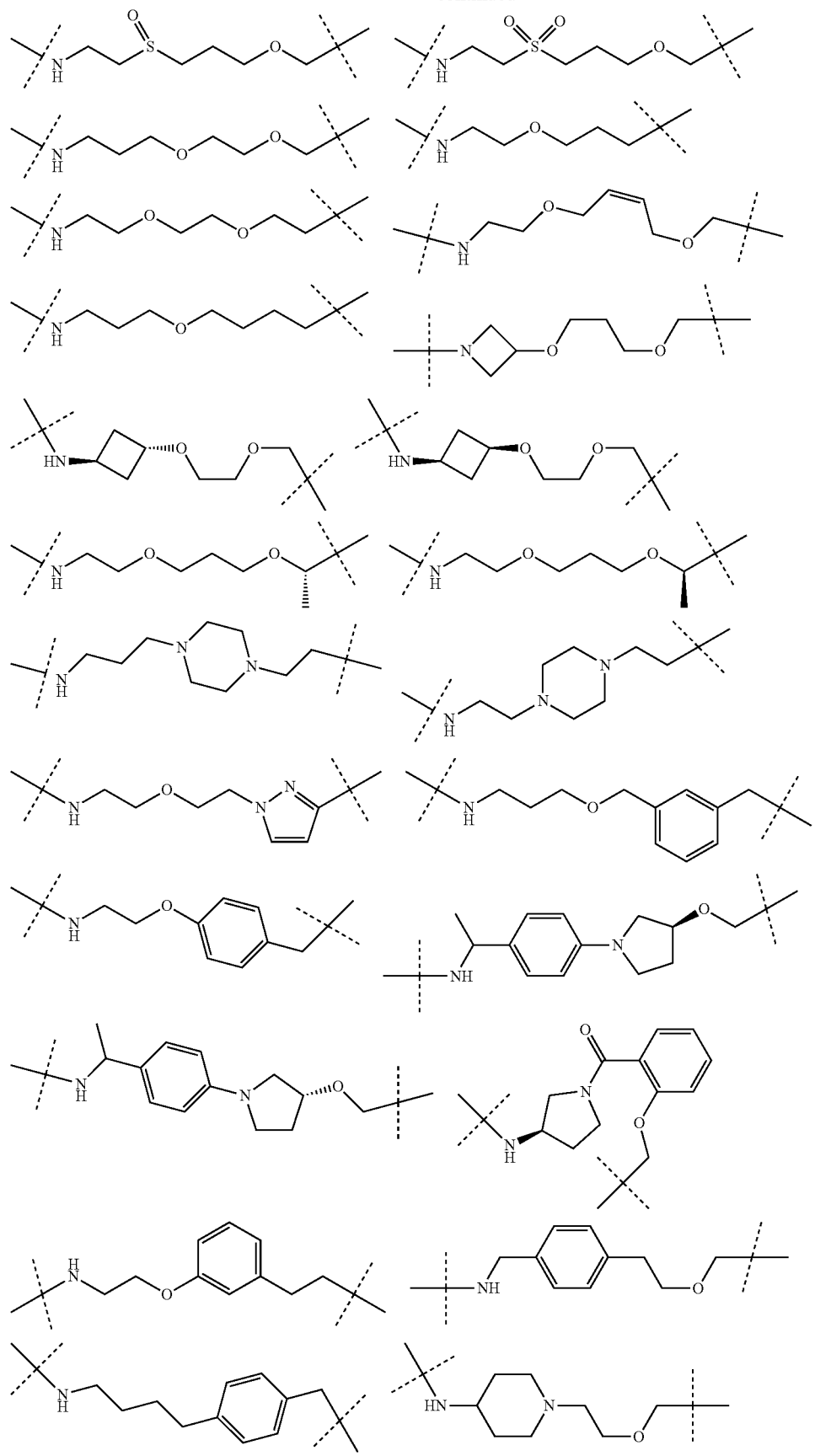

-continued
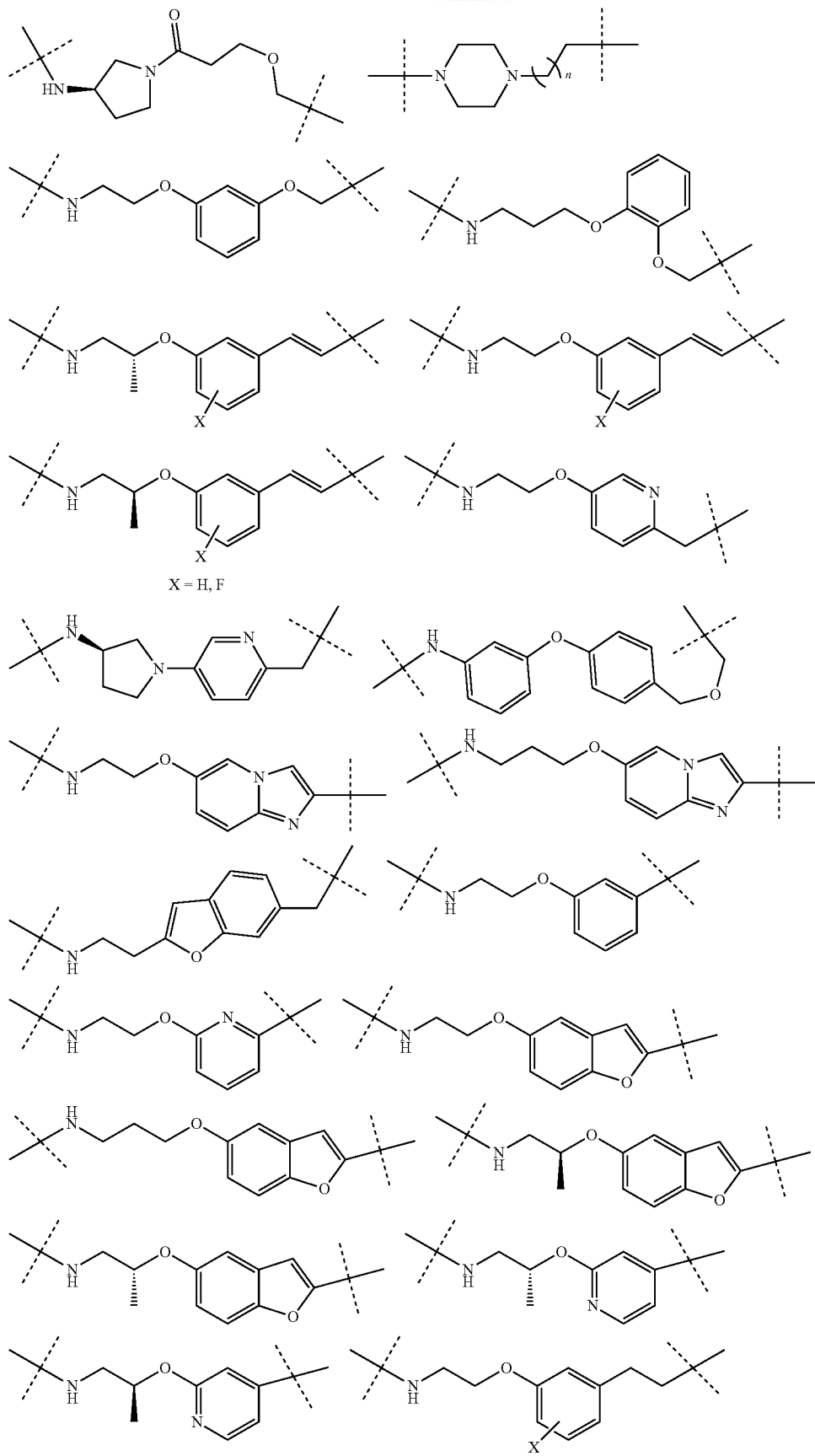

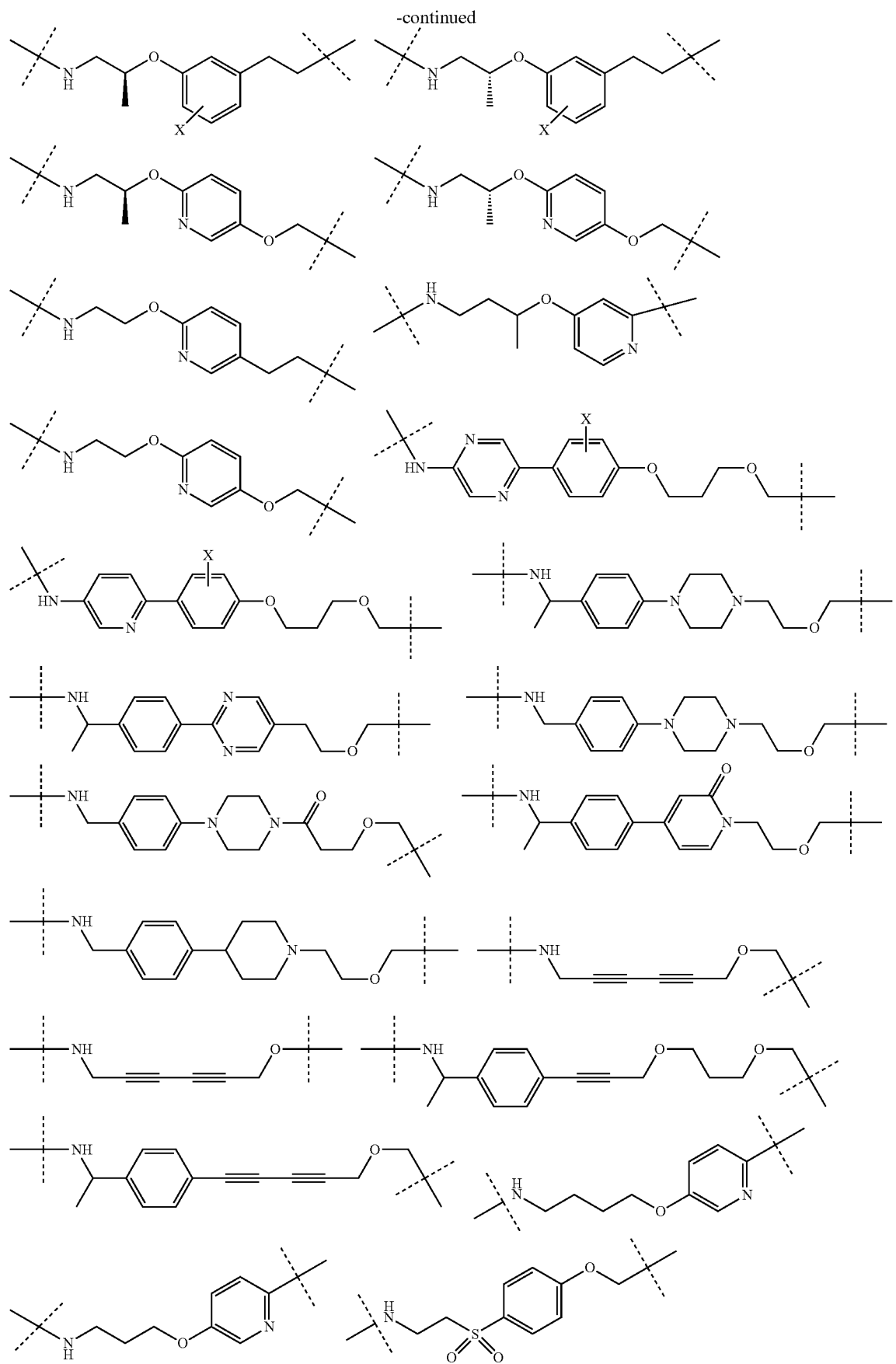

-continued
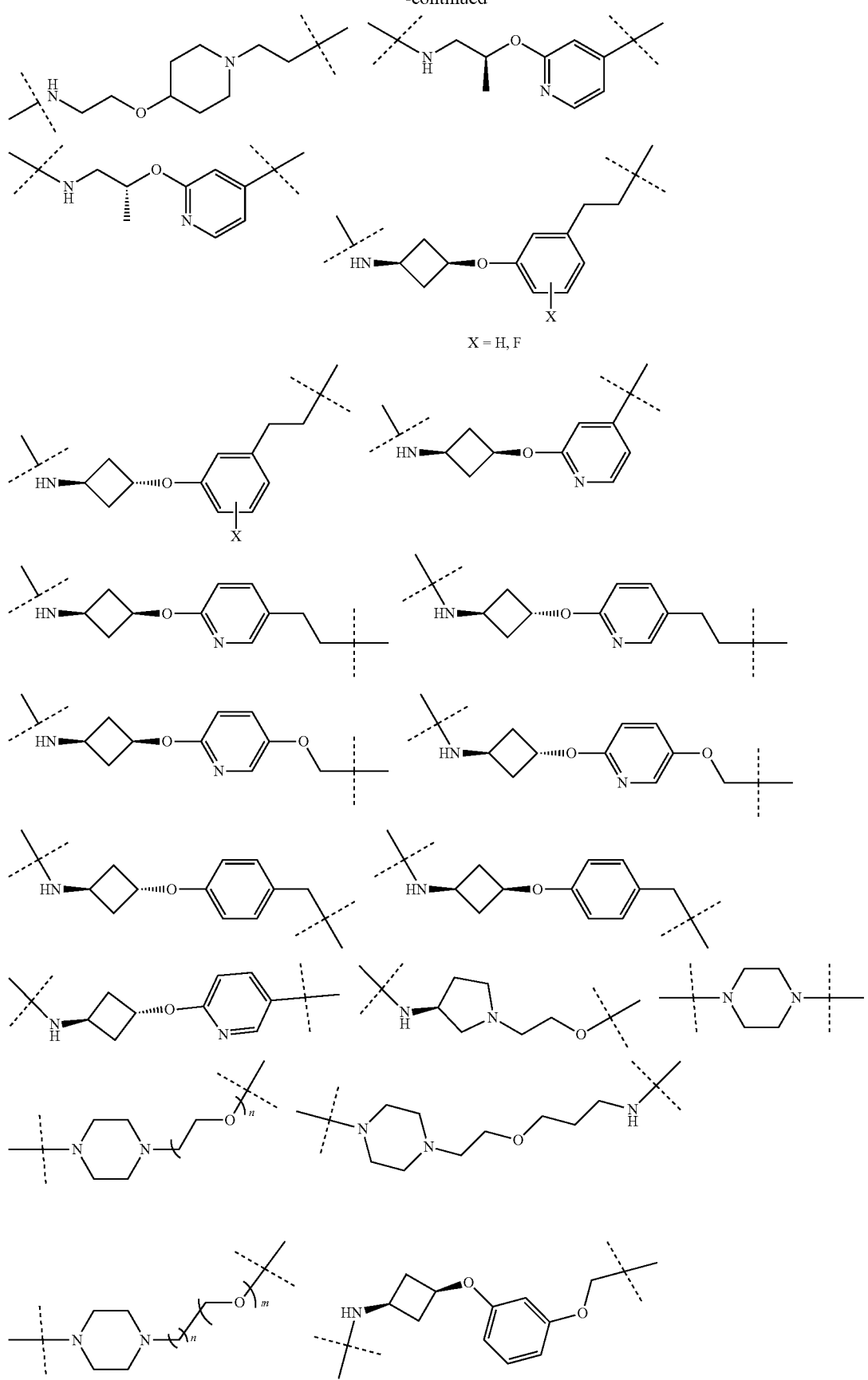

-continued
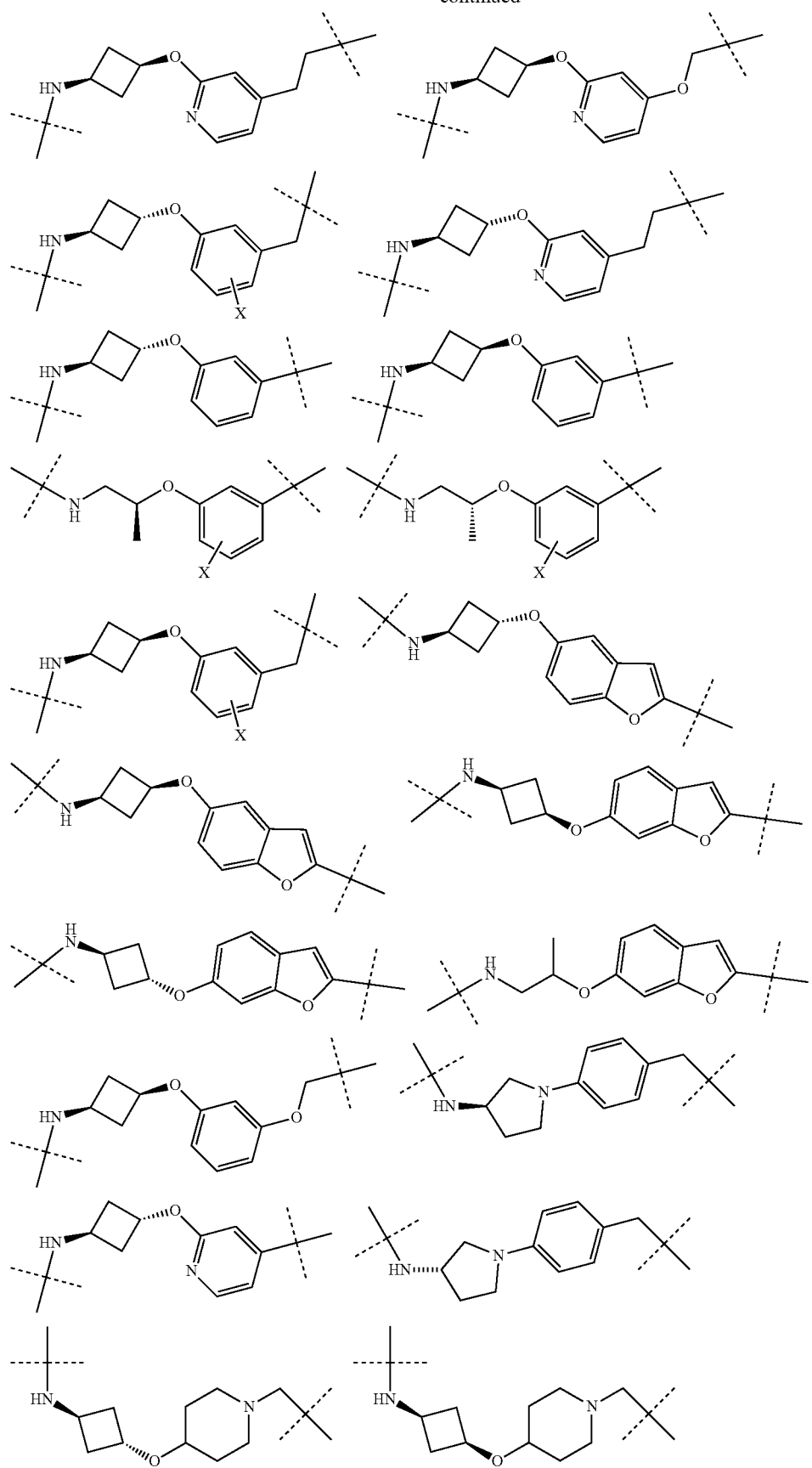

-continued
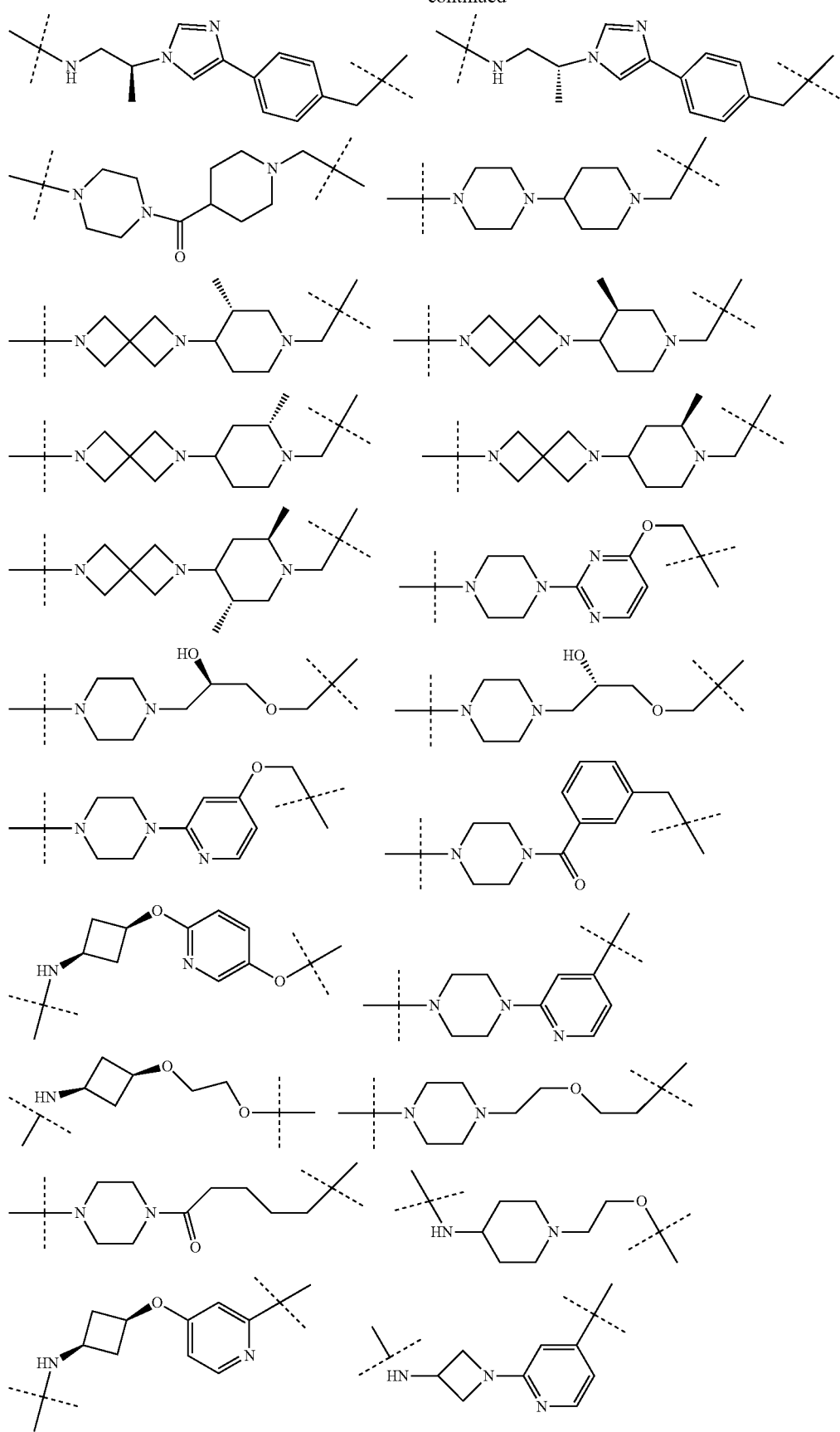

-continued
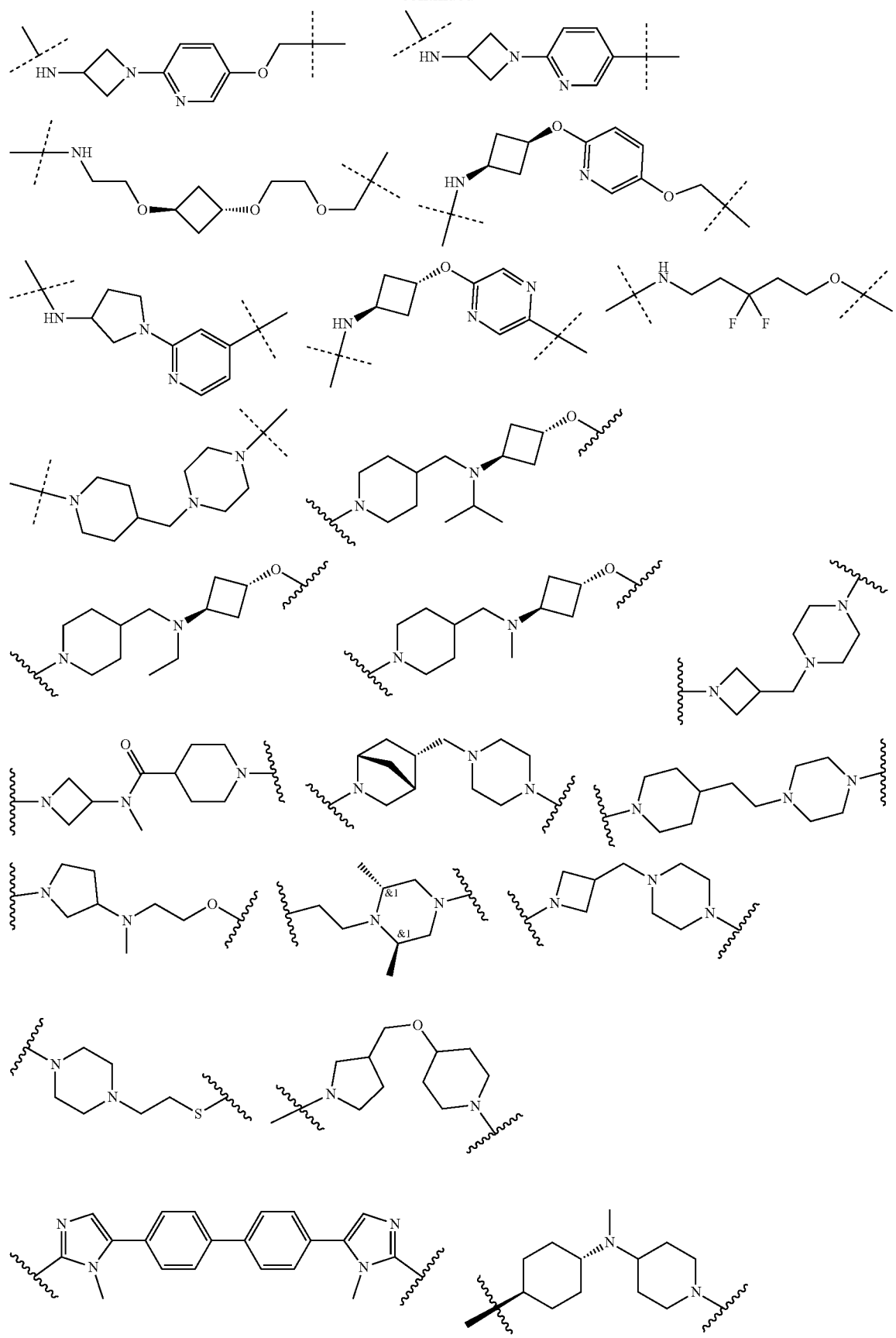

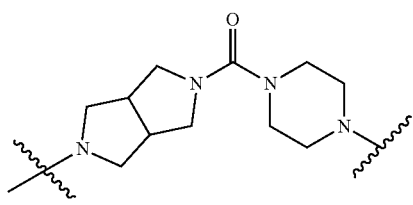
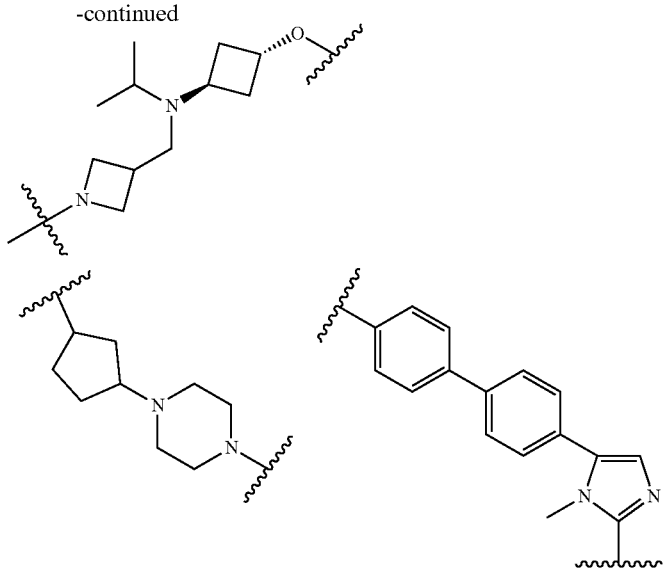

wherein n and m are each independently 0, 1, 2, 3, 4, 5, 6; and X is H, or F.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a ABM group as described above which binds to a target protein (e.g., Androgen Receptor) or polypeptide, which is ubiquitinated by an ubiquitin ligase and is chemically linked directly to the ULM group or through a linker moiety L, or ABM is alternatively a ULM' group which is also an ubiquitin ligase binding moiety, which may be the same or different than the ULM group as described above and is linked directly to the ULM group directly or through the linker moiety; and L is a linker moiety as described above which may be present or absent and which chemically (covalently) links ULM to ABM, or a pharmaceutically acceptable salt, enantiomer, stereoisomer, solvate or polymorph thereof.

In certain embodiments, the ULM shows activity or binds to an E3 ubiquitin ligase with an $IC_{50}$ of less than about 200 µM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM.

Although the ULM group and ABM group may be covalently linked to the linker group through any group which is appropriate and stable to the chemistry of the linker, in preferred aspects of the present disclosure, the linker is independently covalently bonded to the ULM group and the ABM group preferably through an amide, ester, thioester, keto group, carbamate (urethane), carbon or ether, each of which groups may be inserted anywhere on the ULM group and ABM group to provide maximum binding of the ULM group on the ubiquitin ligase and the ABM group on the target protein to be degraded. In certain preferred aspects, the linker may be linked to an optionally substituted alkyl, alkylene, alkene or alkyne group, an aryl group or a heterocyclic group on the ULM and/or ABM groups.

Exemplary Androgen Binding Moieties (ABMs)

In another aspect, the description provides AR binding moieties (ABM), which in certain aspects and embodiments are coupled to a linker and/or a ULM as described herein.

In any of the compounds described herein, the ABM comprises a chemical moiety that binds to the androgen receptor (AR). Various androgen receptor binding compounds have been described in literature, including various androgen derivatives such as testosterone, dihydrotestosterone, and metribolone (also known as methyltrienolone or R1881), and non-steroidal compounds such as bicalutamide, enzalutamide. Those of ordinary skill in the art would appreciate that these androgen receptor binding compounds could be potentially used as an ABM moiety in a PROTAC compound. Such literature includes, but not limited to, G. F. Allan et. al, *Nuclear Receptor Signaling*, 2003, 1, e009; R. H. Bradbury et. al, *Bioorganic & Medicinal Chemistry Letters*, 2011 5442-5445; C. Guo et. al, *Bioorganic & Medicinal Chemistry Letters*, 2012 2572-2578; P. K. Poutiainen et. al, *J. Med. Chem.* 2012, 55, 6316-6327 A. Pepe et. al, *J. Med. Chem.* 2013, 56, 8280-8297; M. E. Jung et al, *J. Med. Chem.* 2010, 53, 2779-2796, which are incorporated by reference herein In certain embodiments, the ABM comprises a structure selected from, but not limited to, the structures shown below, where a dashed line indicates the attachment point of a linker moiety or a ULM:

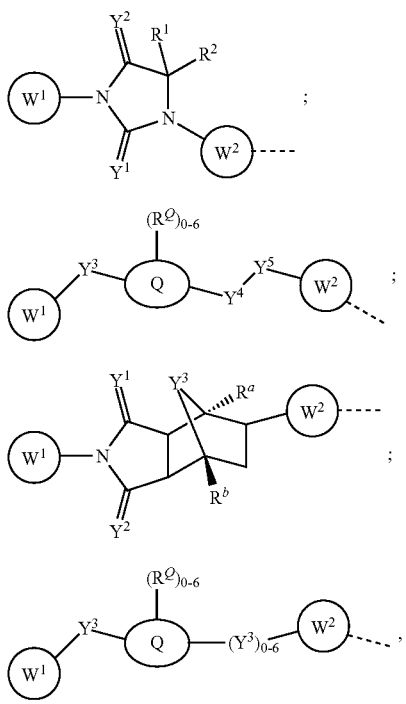

ABM-a

ABM-b

ABM-c

ABM-d wherein:
W$^1$ is aryl, heteroaryl, bicyclic, or biheterocyclic, each independently substituted by 1 or more H, halo, hydroxyl, nitro, CN, C≡CH, C$_{1-6}$ alkyl (linear, branched, optionally substituted; for example, optionally substituted by 1 or more halo, C$_{1-6}$ alkoxyl), C$_{1-6}$ alkoxyl (linear, branched, optionally substituted; for example, optionally substituted by 1 or more halo), C$_{2-6}$ alkenyl, C$_{2-6}$ alkynyl, or CF$_3$;

Y$^1$, Y$^2$ are each independently NR$^{Y1}$, O, S;

Y$^3$, Y$^4$, Y$^5$ are each independently a bond, O, NR$^{Y2}$, CR$^{Y1}$R$^{Y2}$, C=O, C=S, SO, SO$_2$, heteroaryl, or aryl;

Q is a 3-6 membered ring with 0-4 heteroatoms, optionally substituted with 0-6 R$^Q$, each R$^Q$, is independently H, C$_{1-6}$ alkyl (linear, branched, optionally substituted; for example, optionally substituted by 1 or more halo, C$_{1-6}$ alkoxyl), halogen, C$_{1-6}$ alkoxy, or 2 R$^Q$ groups taken together with the atom they are attached to, form a 3-8 membered ring system containing 0-2 heteroatoms);

R$^1$, R$^2$, R$^a$, R$^b$, R$^{Y1}$, R$^{Y2}$ are each independently H, C$_{1-6}$ alkyl (linear, branched, optionally substituted; for example, optionally substituted by 1 or more halo, C$_{1-6}$ alkoxyl), halogen, C$_{1-6}$ alkoxy, cyclic, heterocyclic, or R$^1$, R$^2$ together with the atom they are attached to, form a 3-8 membered ring system containing 0-2 heteroatoms);

W$^2$ is a bond, C$_{1-6}$ alkyl, C$_{1-6}$ heteroalkyl, O, aryl, heteroaryl, alicyclic, heterocyclic, biheterocyclic, biaryl, or biheteroaryl, each optionally substituted by 1-10 R$^{W2}$;

each R$^{W2}$ is independently H, halo, C$_{1-6}$ alkyl (linear, branched, optionally substituted; for example, optionally substituted by 1 or more F), —OR$^{W2A}$, C$_{3-6}$ cycloalkyl, C$_{4-6}$ cycloheteroalkyl, C$_{1-6}$ alicyclic (optionally substituted), heterocyclic (optionally substituted), aryl (optionally substituted), or heteroaryl (optionally substituted), bicyclic heretoaryl or aryl, OC$_{1-3}$alkyl (optionally substituted), OH, NH$_2$, NR$^{Y1}$R$^{Y2}$, CN; and R$^{W2A}$ is H, C$_{1-6}$ alkyl (linear, branched), or C$_{1-6}$ heteroalkyl (linear, branched), each optionally substituted by a cycloalkyl, cycloheteroalkyl, aryl, heterocyclic, heteroaryl, halo, or OC$_{1-3}$alkyl.

In any of the embodiments described herein, the W$^2$ is covalently coupled to one or more ULM or CLM groups, or a linker to which is attached one or more ULM or CLM groups as described herein.

In certain embodiments, W$^1$ is

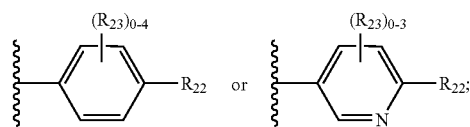

wherein each R$_{22}$ is independently halo, H, optionally substituted alkyl, haloalkyl, cyano, or nitro; and each R$_{23}$ is independently H, halo, CF$_3$, optionally substituted alkyl, alkoxy, haloalkyl, cyano, or nitro.

In certain additional embodiments, W$^1$ is selected from the group consisting of:

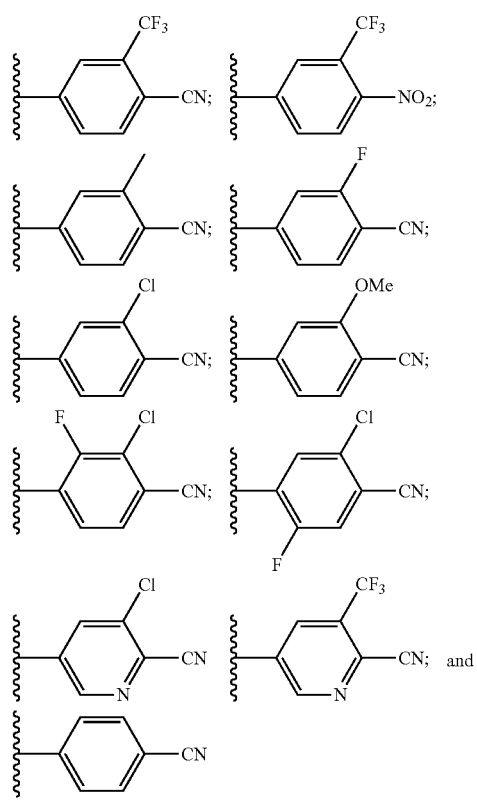

In particular embodiments, the ABM comprises a structure selected from the following structures shown below, where a ⌇ indicates the attachment point of a linker or a ULM:

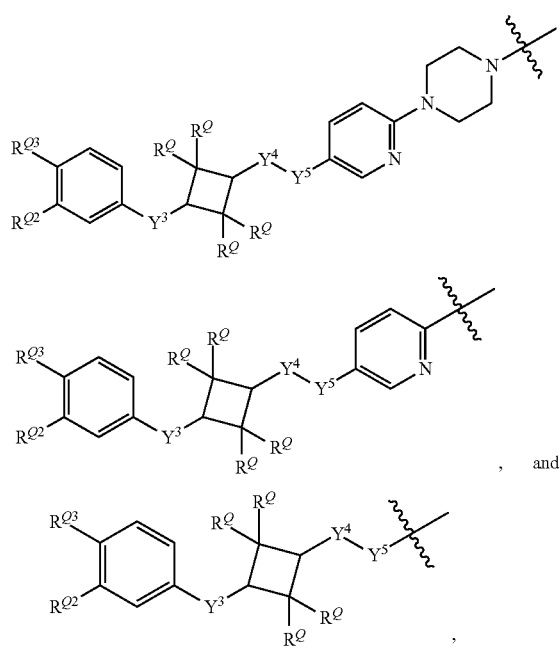

, wherein:
- $R^{Q2}$ is a H, halogen, $CH_3$ or $CF_3$;
- $R^{Q3}$ is H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;
- $Y^3$, $Y^4$, $Y^5$ are each independently a bond, O, $NR^{Y2}$, $CR^{Y1}R^{Y2}$, C=O, heteroaryl, or aryl;
- $R^{Y1}$, $R^{Y2}$ are each independently H, or $C_{1-6}$ alkyl (linear, branched, optionally substituted by 1 or more halo, $C_{1-6}$ alkoxyl, cyclic, or heterocyclic); and
- $R^Q$ each independently is H, $C_1$-$C_6$ alkyl (linear, branched, optionally substituted by 1 or more halo, or $C_{1-6}$ alkoxyl), or two $R^Q$ together with the atom they are attached to, form a 3-8 membered ring system containing 0-2 heteroatoms.

In a particular embodiment, each $R^Q$ is independently H or $CH_3$. In another embodiment $R^{Q3}$ is CN.

In particular embodiments, the ABM comprises a structure selected from the following structures shown below, where  a indicates the attachment point of a linker or a ULM:

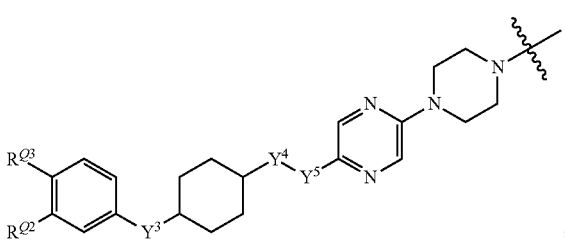

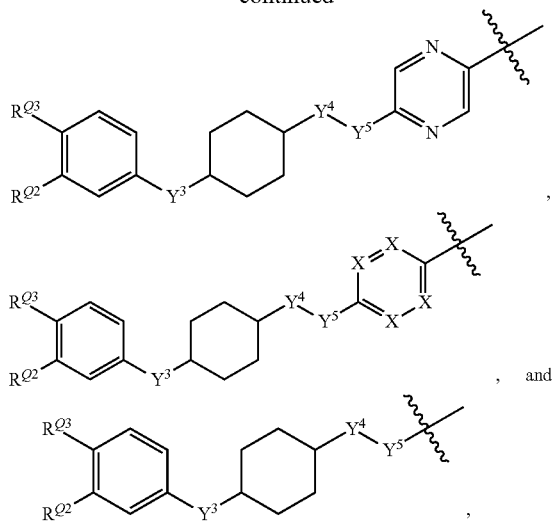

wherein:
- $R^{Q2}$ is a H, halogen, $CH_3$ or $CF_3$; and
- $R^{Q3}$ is H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;
- $Y^3$, $Y^4$, $Y^5$ are each independently a bond, O, $NR^{Y2}$, $CR^{Y1}R^{Y2}$, C=O, heteroaryl, or aryl; and
- $R^{Y1}$, $R^{Y2}$ are each independently H or $C_{1-6}$ alkyl (linear, branched, optionally substituted by 1 or more halo, $C_{1-6}$ alkoxyl, cyclic, or heterocyclic); and
- X is N or C.

In a particular embodiment $R^{Q3}$ is a CN.

In certain additional embodiments, the ABM comprises a structure shown below, where a dashed line indicates the attachment point of a linker moiety or a ULM or a CLM:

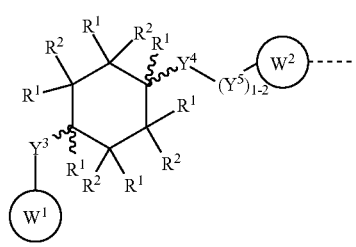

wherein:

$W^1$ is

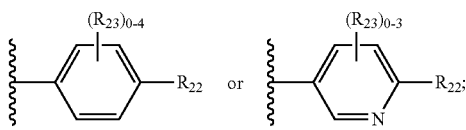

each $R_{22}$ is independently H or —CN;
each $R_{23}$ is independently H, halo, $C_1$-$C_6$ alkyl (linear, branched, optionally substituted), $C_1$-$C_6$alkoxy, or —$CF_3$;

Y³ is a bond or O;

Y⁴ is a bond or NH;

Y⁵ is a bond, C=O, $C_1$-$C_6$ heteroaryl, or $C_1$-$C_6$ aryl;

R¹, R², are each independently H, or $C_1$-$C_6$ alkyl (linear or branched, optionally substituted; for example, optionally substituted by 1 or more halo, or $C_{1-6}$ alkoxyl);

W² is a bond, $C_{1-6}$ aryl, $C_{1-6}$ heteroaryl, $C_{1-6}$ alicyclic, or $C_{1-6}$ heterocyclic, biheterocyclic, biaryl, or biheteroaryl, each optionally substituted by 1-10 $R^{W2}$; and each $R^{W2}$ is independently H, or halo; and ∿∿ represents a bond that may be stereospecific ((R) or (S)) or non-stereospecific.

In any of the embodiments described herein, the W² is covalently coupled to one or more ULM or CLM groups, or a linker to which is attached one or more ULM or CLM groups as described herein.

In certain additional embodiments, W¹ is selected from the group consisting of:

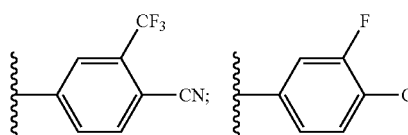

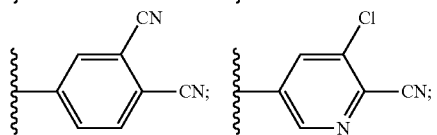

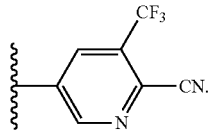

In any aspect or embodiment described herein, W² is selected from the group consisting of:

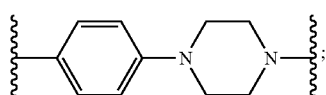

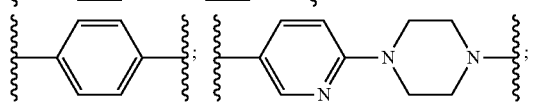

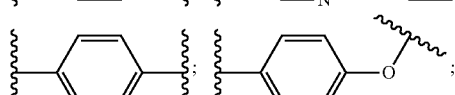

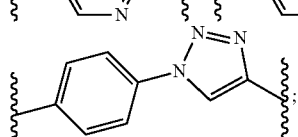

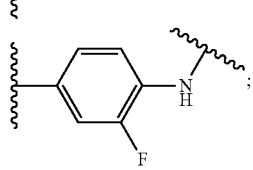

-continued

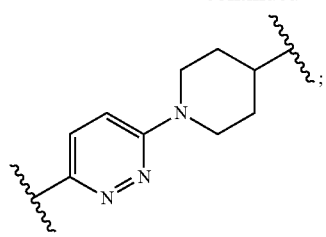

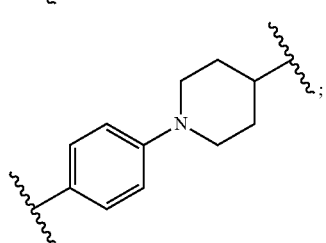

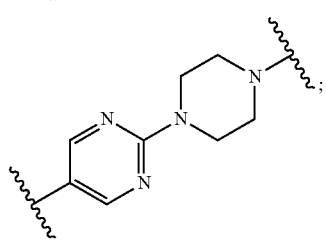

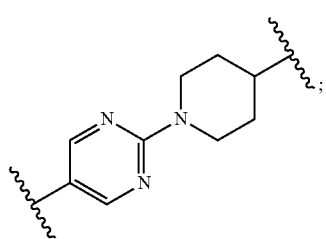

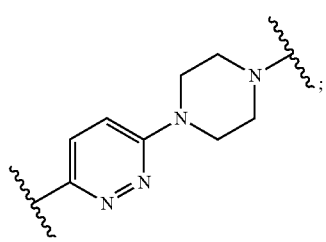

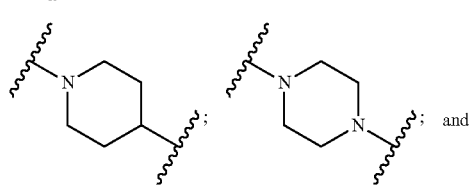

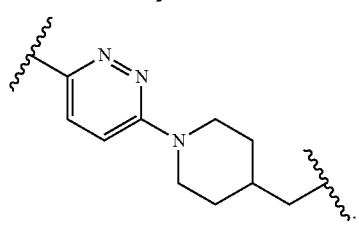

In certain embodiments, the ABM comprises a structure selected from, but not limited to the structures shown below, where a dashed line indicates the attachment point of a linker moiety or a ULM:

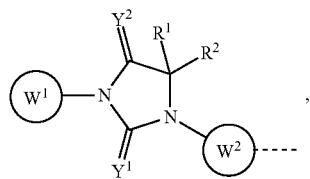

ABM-a wherein W¹ is

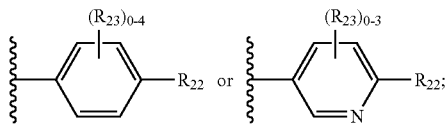

each $R_{22}$ is independently H or —CN;
each $R_{23}$ is independently H, halo, or —CF$_3$;
$Y^1$, $Y^2$ are each independently O or S;
$R^1$, $R^2$, are each independently H or a methyl group;
$W^2$ is a bond, $C_{1-6}$ aryl, or heteroaryl, each optionally substituted by 1, 2 or 3 $R^{W2}$; and
each $R^{W2}$ is independently H, halo, $C_{1-6}$ alkyl (optionally substituted by 1 or more F), $OC_{1-3}$alkyl (optionally substituted by 1 or more —F).

In any of the embodiments described herein, the $W^2$ is covalently coupled to one or more ULM or CLM groups, or a linker to which is attached one or more ULM or CLM groups as described herein.

In certain additional embodiments, W¹ is selected from the group consisting of:

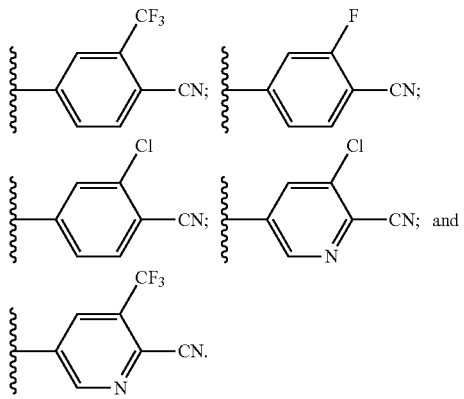

In certain additional embodiments, W2 is selected from the group consisting of:

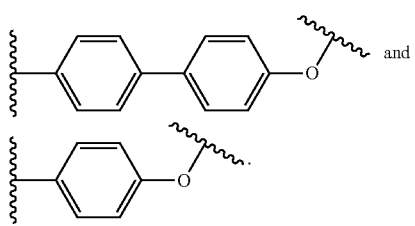

In certain embodiments, ABM is selected from the group consisting of:

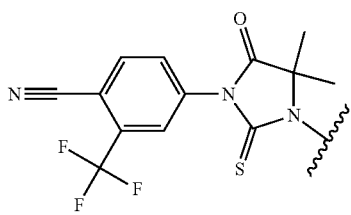

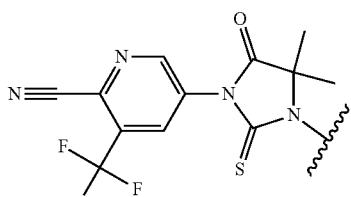

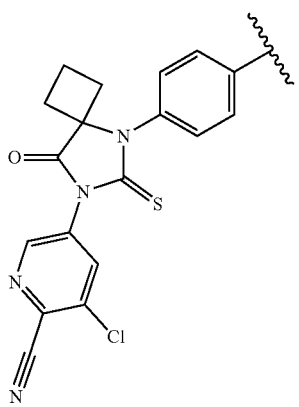

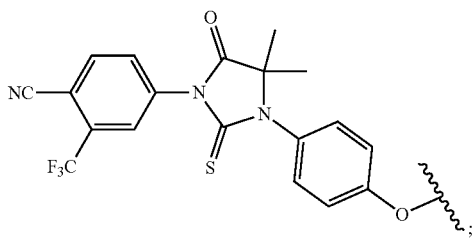

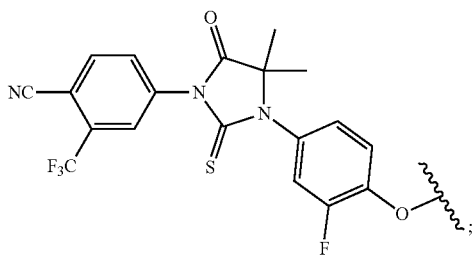

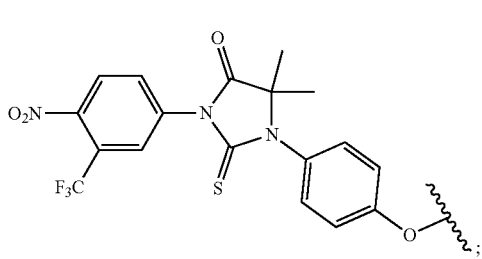

63
-continued
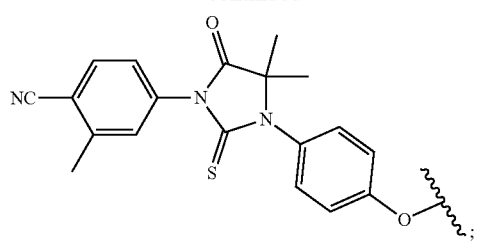
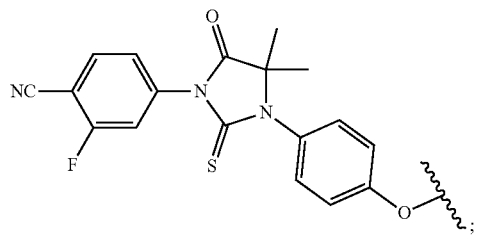
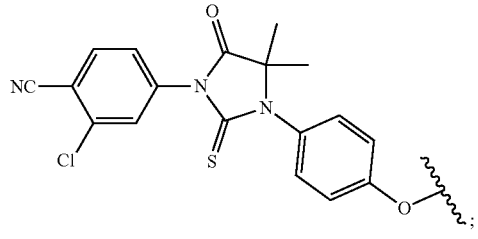
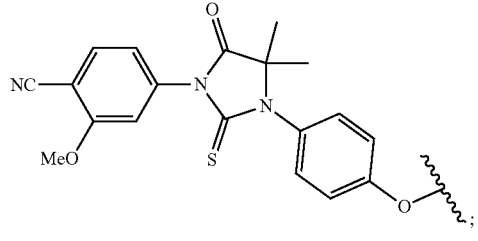
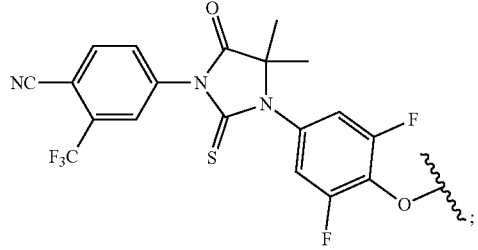
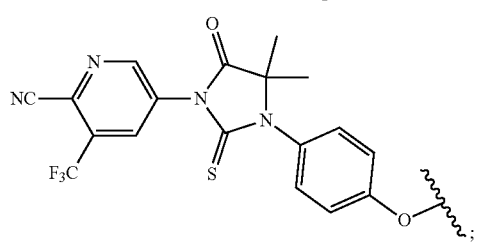
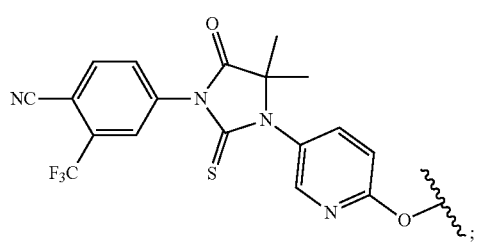
64
-continued
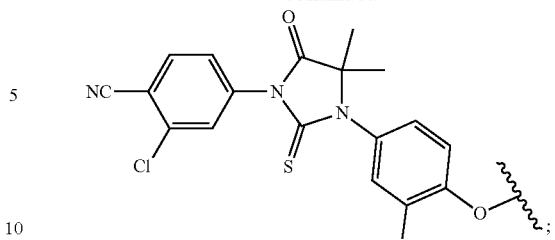
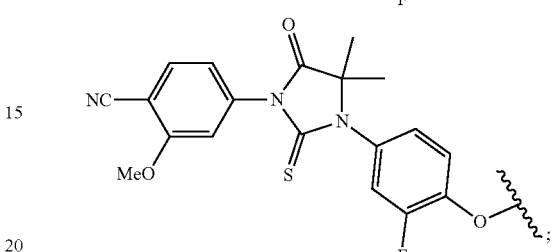
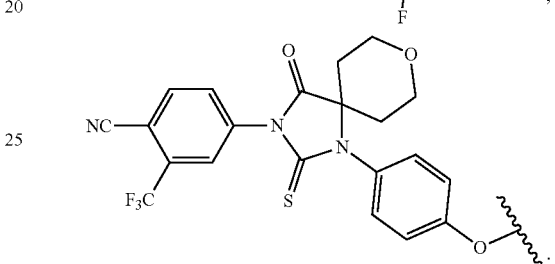
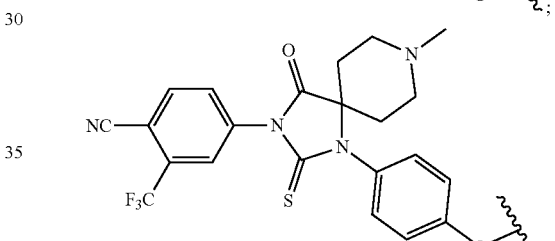
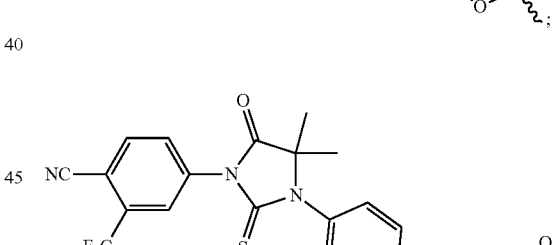
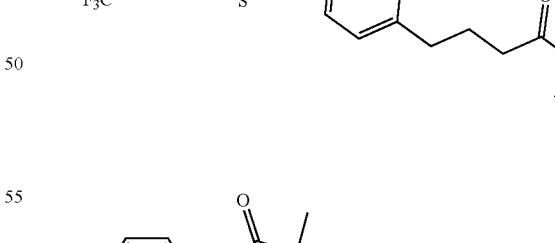
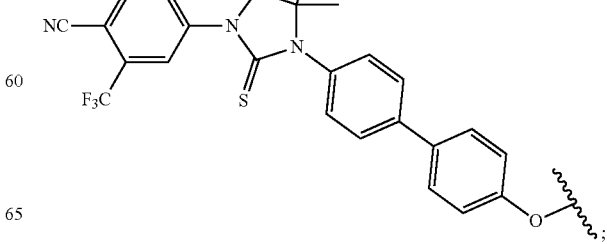

65
-continued
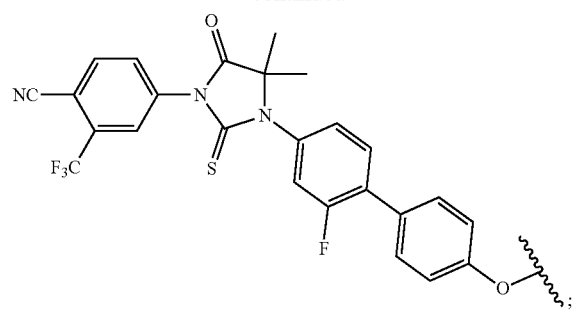
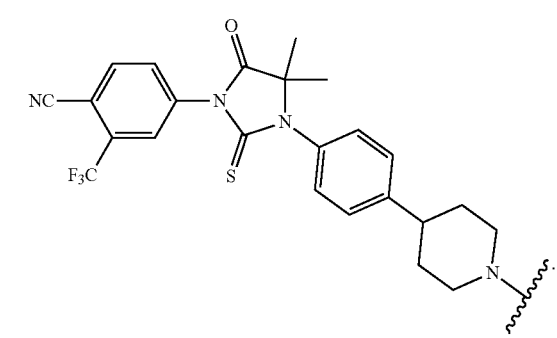
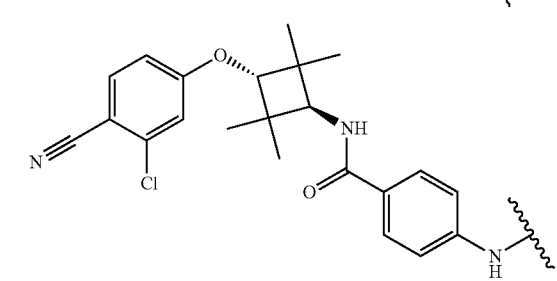
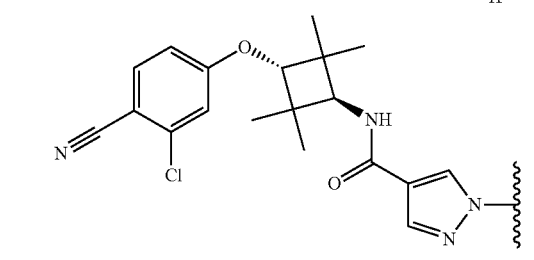
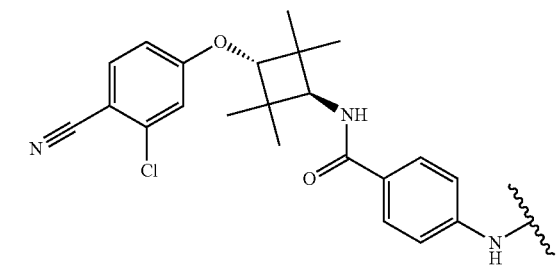
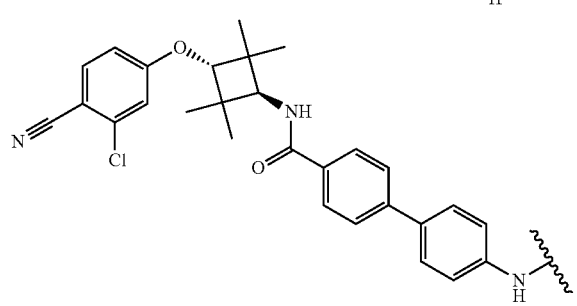
66
-continued
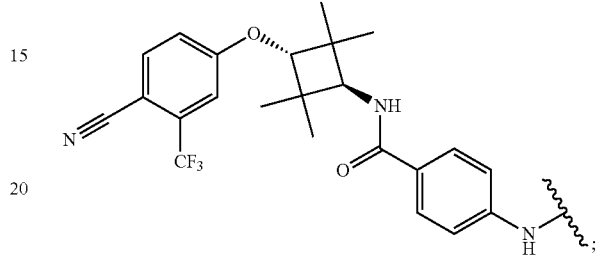
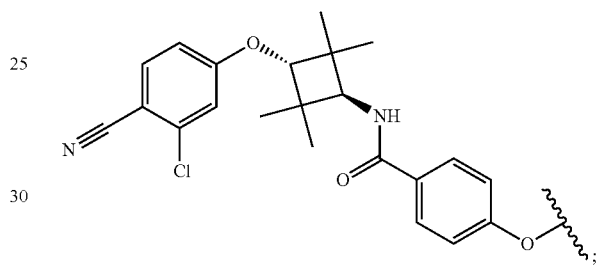
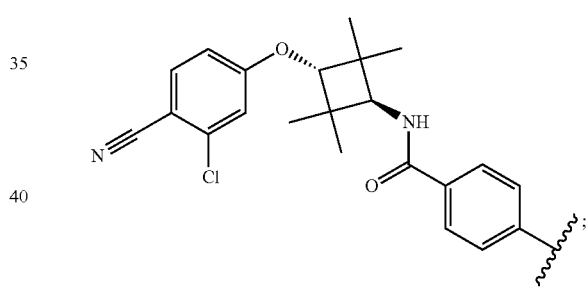
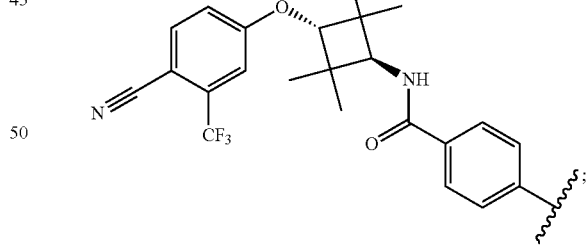
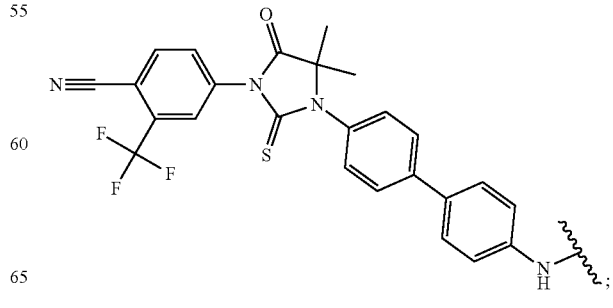

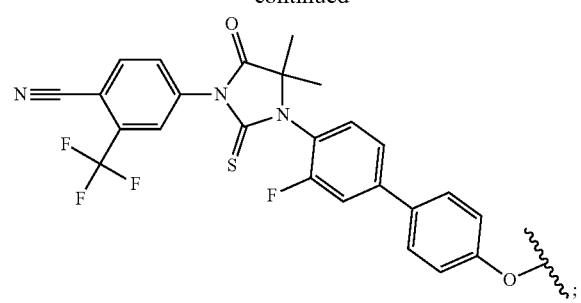
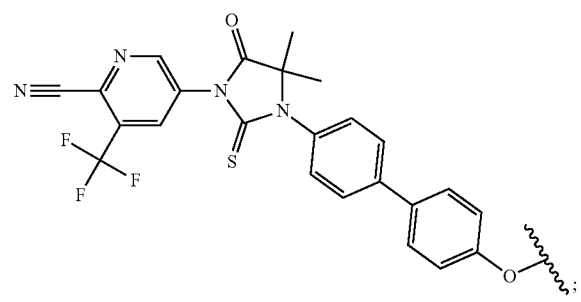
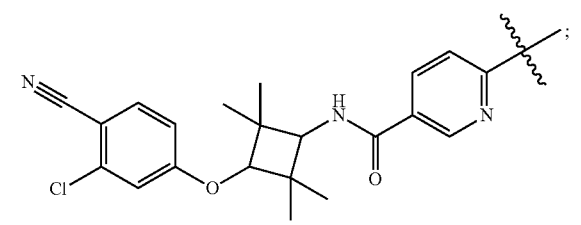
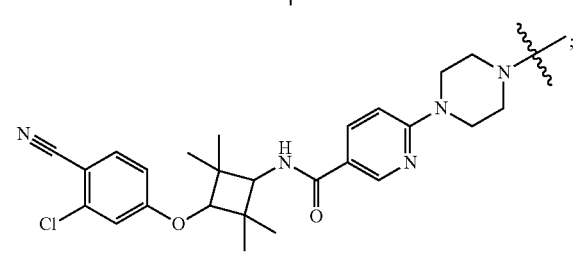
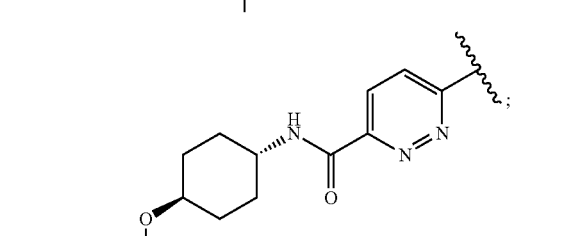
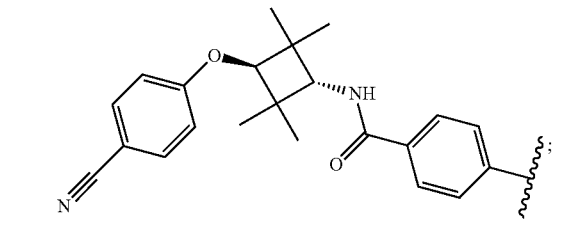
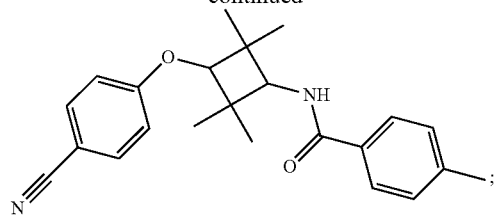
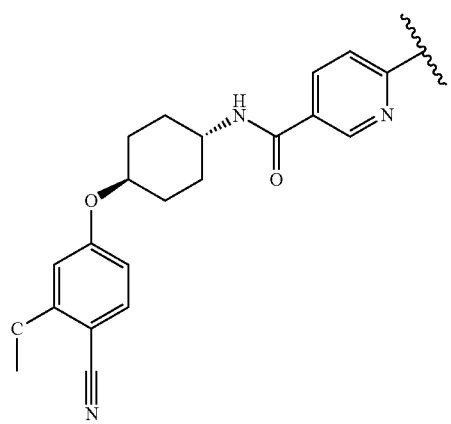
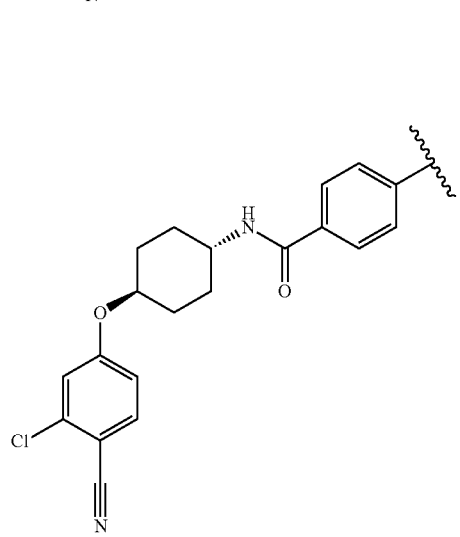
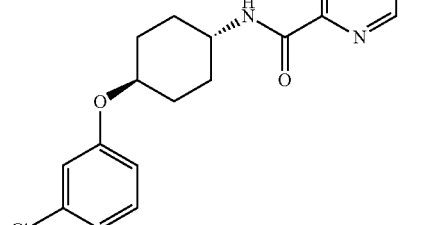

69
-continued
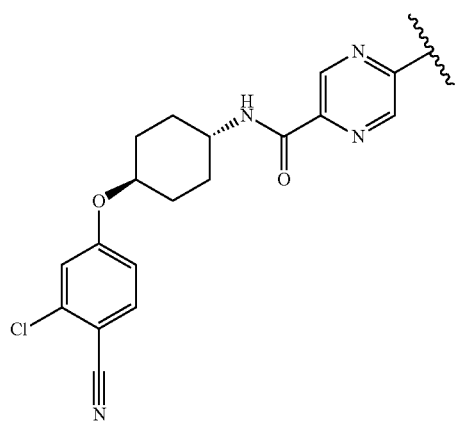
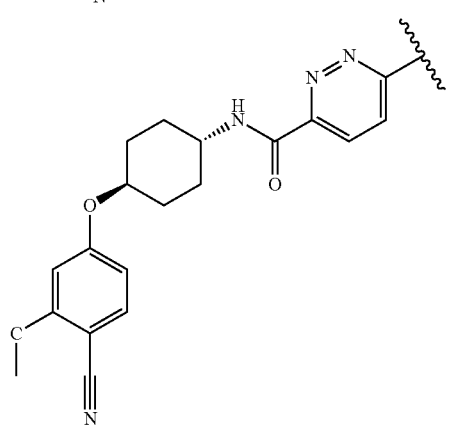
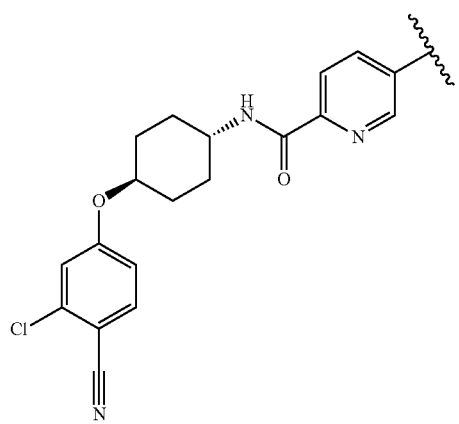
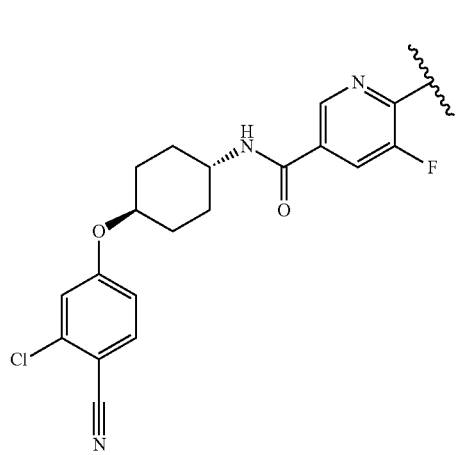
70
-continued
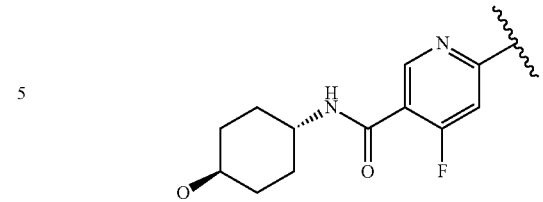
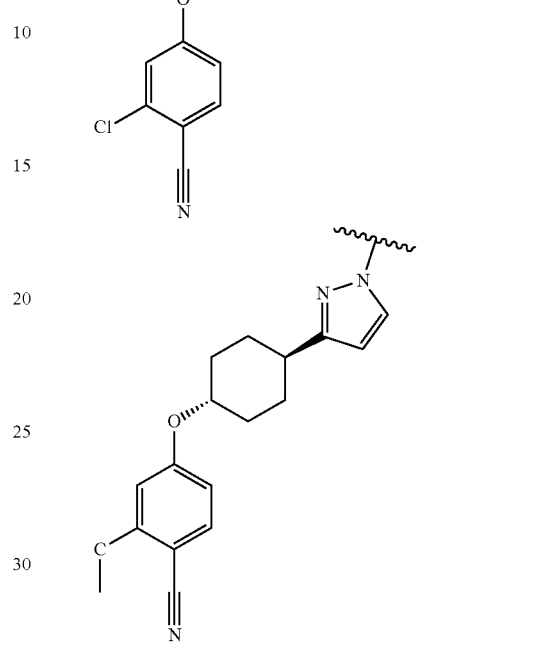
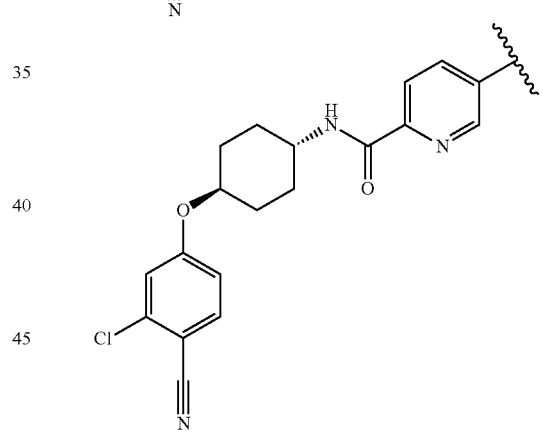
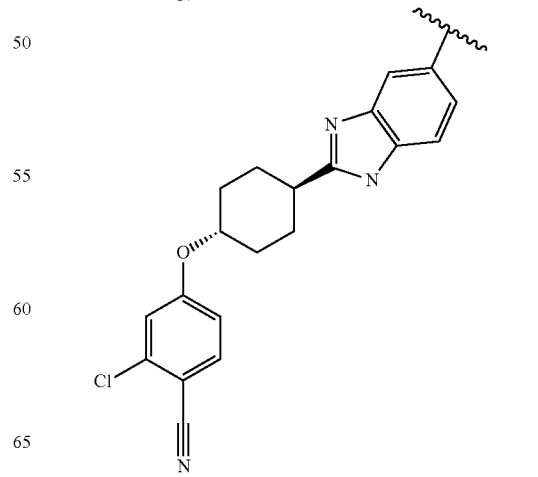

71
-continued
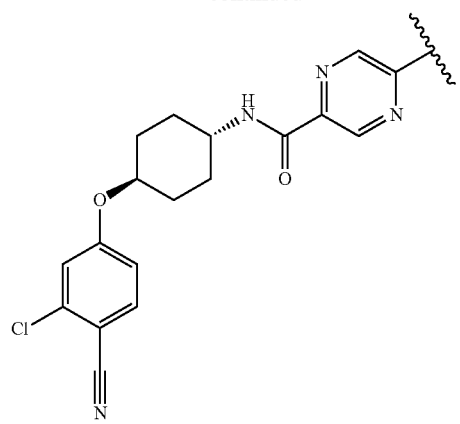
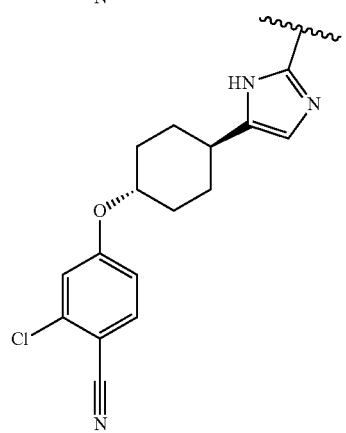
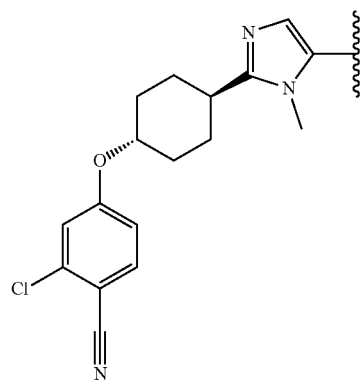
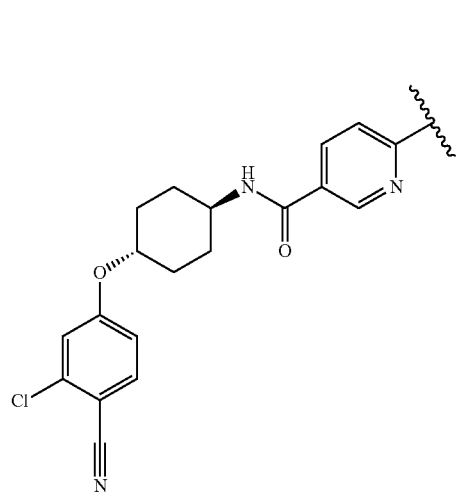
72
-continued
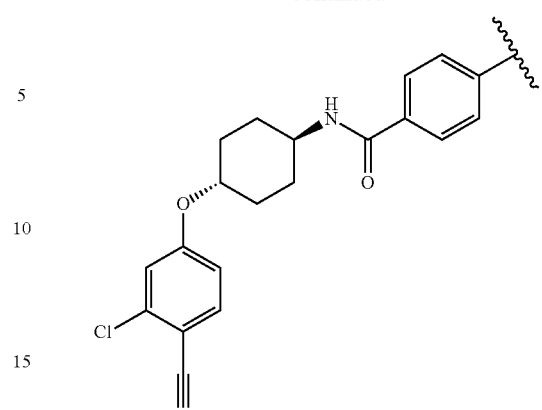
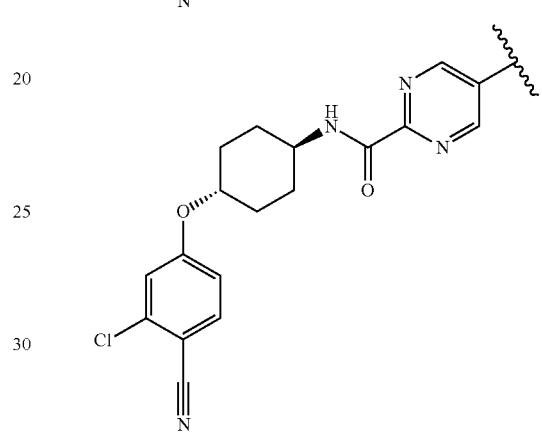
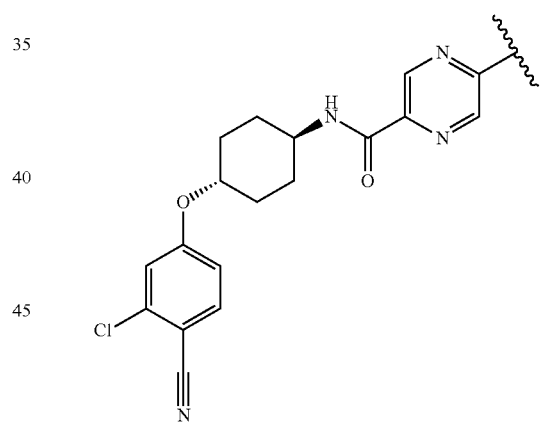
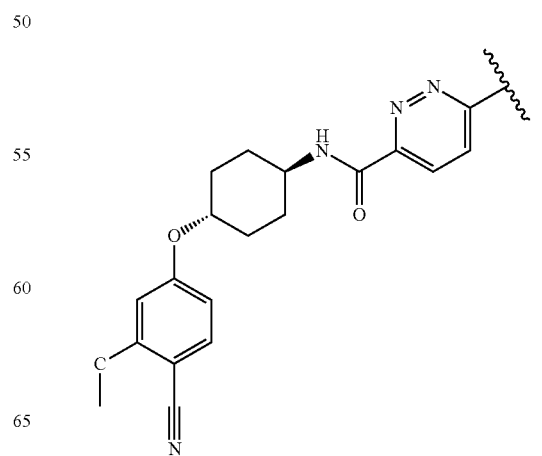

73
-continued
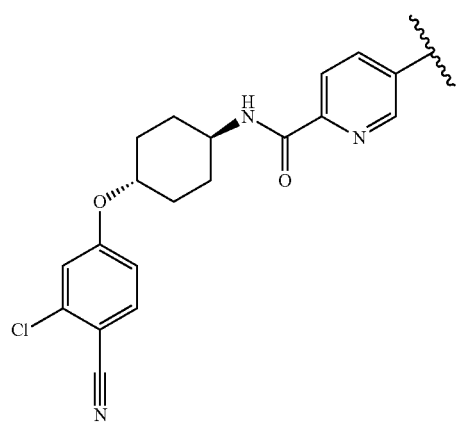
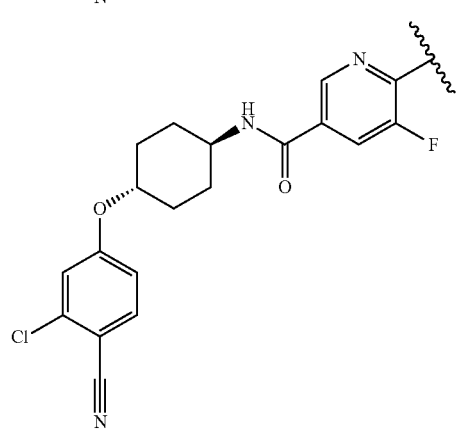
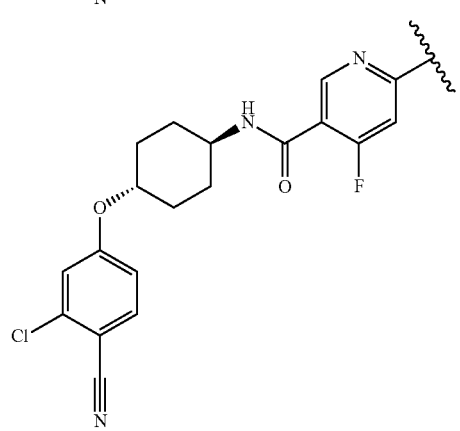
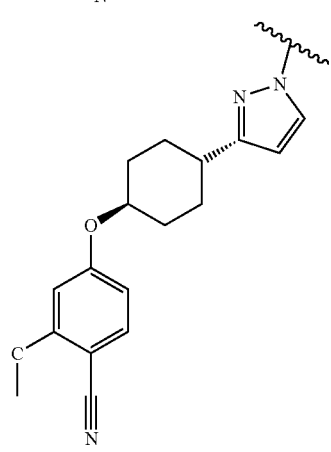
74
-continued
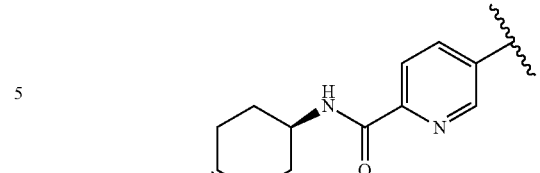
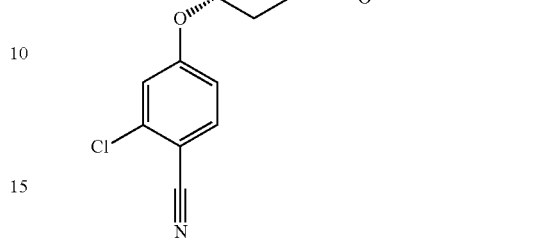
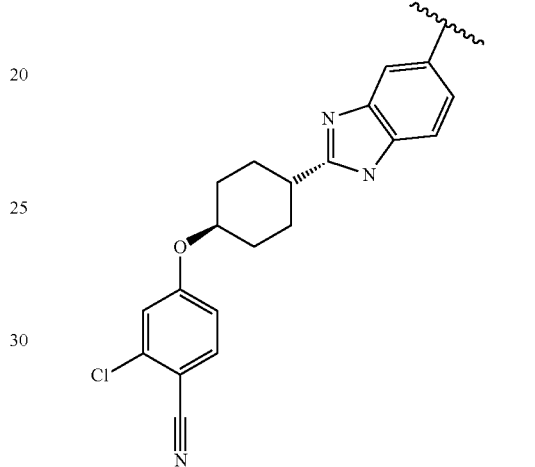
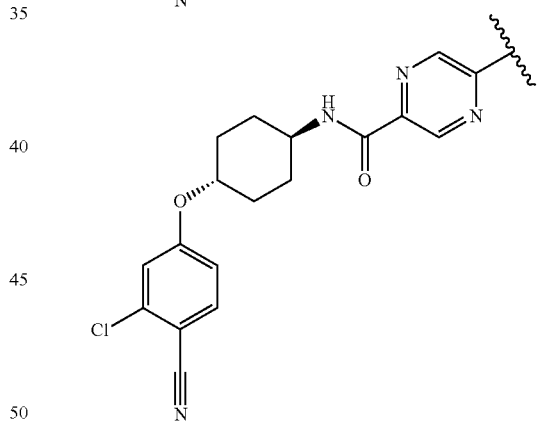
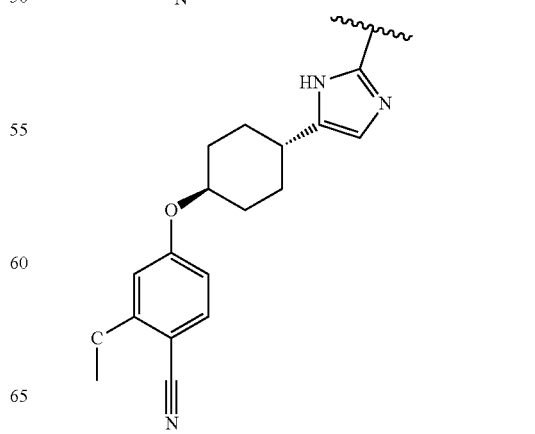

-continued

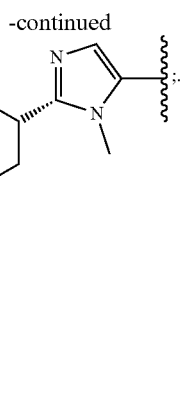

In certain embodiments, the ABM comprises the structure:

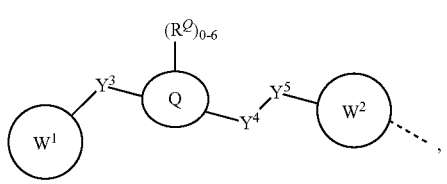

ABM-b wherein $W^1$ is aryl, or heteroaryl, each independently substituted by 1 or more H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;

$Y^3$, $Y^4$, $Y^5$ are each independently a bond, O, $NR^{Y2}$, $CR^{Y1}R^{Y2}$, C=O, C=S, SO, $SO_2$, heteroaryl, or aryl;

Q is a 4 membered alicyclic ring with 0-2 heteroatoms, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{Y1}$, $R^{Y2}$ are each independently H, $C_{1-6}$ alkyl (linear, branched, optionally substituted by 1 or more halo, $C_{1-6}$ alkoxyl);

$W^2$ is a bond, $C_{1-6}$ alkyl, $C_{1-6}$ heteroalkyl, O, $C_{1-6}$ alicyclic, heterocyclic, aryl, biheterocyclic, biaryl, or biheteroaryl, or heteroaryl, each optionally substituted by 1, 2 or 3 $R^{W2}$; and each $R^{W2}$ is independently H, halo, $C_{1-6}$ alkyl (linear, branched, optionally substituted by 1 or more F), $C_{1-6}$ heteroalkyl (linear, branched, optionally substituted), —$OR^{W2A}$ $OC_{1-3}$alkyl (optionally substituted by 1 or more —F), $C_{3-6}$ cycloalkyl, $C_{4-6}$ cycloheteroalkyl (optionally substituted), $C_{1-6}$ alkyl (optionally substituted), $C_{1-6}$ alicyclic (optionally substituted), heterocyclic (optionally substituted), aryl (optionally substituted), heteroaryl (optionally substituted), bicyclic heteroaryl (optionally substituted), bicyclic aryl, OH, $NH_2$, $NR^{Y1}R^{Y2}$, or CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In an additional aspect, the description provides an androgen receptor binding compound comprising a structure of:

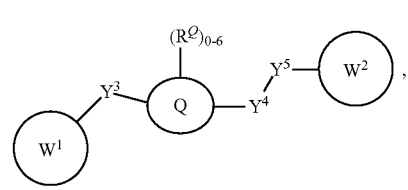

ABM-e wherein $W^1$ is aryl, heteroaryl, bicyclic, or biheterocyclic, each independently substituted by 1 or more H, halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl, or $CF_3$;

$Y^1$, $Y^2$ are each independently $NR^{Y1}$, O, or S;

$Y^3$, $Y^4$, $Y^5$ are each independently a bond, O, $NR^{Y2}$, $CR^{Y1}R^{Y2}$, C=O, C=S, SO, $SO_2$, heteroaryl, or aryl;

Q is a 3-6 membered alicyclic or aromatic ring with 0-4 heteroatoms, optionally substituted with 0-6 $R^Q$, each $R^Q$, is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

$W^2$ is a bond, $C_{1-6}$ alkyl, $C_{1-6}$ heteroalkyl, O, $C_{1-6}$ alicyclic, heterocyclic, aryl, biheterocyclic, biaryl, or biheteroaryl, or heteroaryl, each optionally substituted by 1, 2 or 3 $R^{W2}$;

each $R^{W2}$ is independently H, halo, $C_{1-6}$ alkyl (linear, branched, optionally substituted by 1 or more F), $C_{1-6}$ heteroalkyl (linear, branched, optionally substituted), —$OR^{W2A}$, $OC_{1-3}$alkyl (optionally substituted by 1 or more —F), $C_{3-6}$ cycloalkyl, $C_{4-6}$ cycloheteroalkyl, $C_{1-6}$ alkyl (optionally substituted), $C_{1-6}$ alicyclic (optionally substituted), heterocyclic (optionally substituted), aryl (optionally substituted), or heteroaryl (optionally substituted), bicyclic heteroaryl or aryl, OH, $NH_2$, $NR^{Y1}R^{Y2}$, CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In certain embodiments, an androgen receptor binding moiety has a structure of:

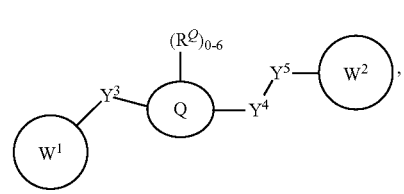

ABM-e wherein W¹ is

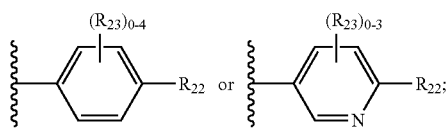

each R₂₂ is independently H or —CN;
each R₂₃ is independently H, halo, or —CF₃;
Y³ is a bond or O;
Q is a 4 member ring, optionally substituted with 0-4 R$^Q$, each R$^Q$ is independently H or methyl;
Y4 is a bond or NH;
Y5 is a bond, a C=O, or a C=S;
each W² is independently a bond, $C_{1-6}$ aryl or heteroaryl, each optionally substituted by 1, 2 or 3 R$^{W2}$, each R$^{W2}$ is independently H, halo, a 6 member alicyclic ring with 1 or 2 heteroatoms or a 5 member aromatic ring with 1 or 2 or 3 heteroatoms.

In certain additional embodiments, W² is selected from the group consisting of:

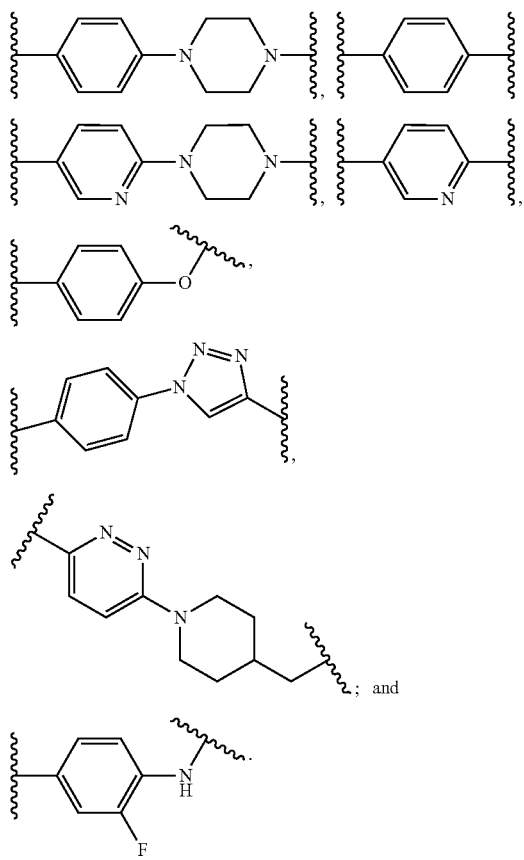

In any of the embodiments described herein, the W² is covalently coupled to one or more ULM or CLM groups, or a linker to which is attached one or more ULM or CLM groups as described herein.

In certain additional embodiments, W¹ is selected from the group consisting of:

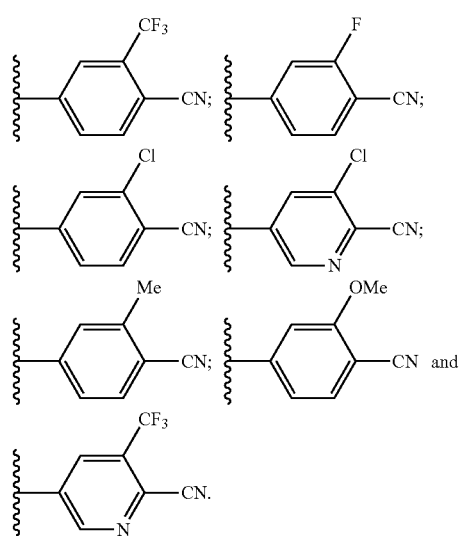

In certain embodiments, an androgen binding moiety has a structure of:

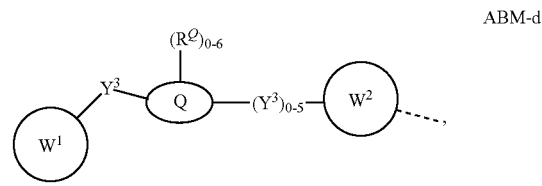

ABM-d wherein W¹ is aryl, independently substituted by 1 or more halo, CN;
Y³ are each independently a bond, NR$^{Y2}$, CR$^{Y1}$R$^{Y2}$, C=O;
Q is a 5 membered aromatic ring with 1 or 2 heteroatoms;
R$^{Y1}$, R$^{Y2}$ are each independently H, $C_{1-6}$ alkyl (linear, branched);
W² is a bond, aryl, or heteroaryl, each optionally substituted by 1, 2 or 3 R$^{W2}$; and
each R$^{W2}$ is independently H, halo, $C_{1-6}$ alkyl (optionally substituted by 1 or more F), $OC_{1-3}$alkyl (optionally substituted by 1 or more —F).

In any of the embodiments described herein, the W² is covalently coupled to one or more ULM or CLM groups, or a linker to which is attached one or more ULM or CLM groups as described herein.

In certain embodiments, W¹ is

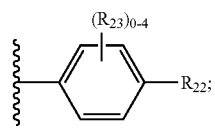

wherein each R₂₂ is independently halo or CN; and
each R₂₃ is independently H or halo.

In certain additional embodiments, $W^1$ is selected from the group consisting of:

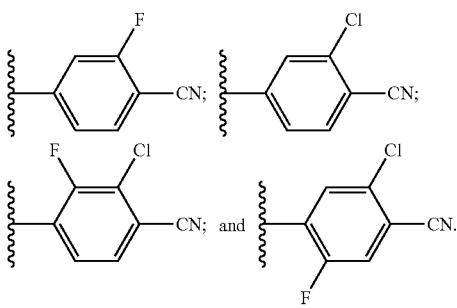

In certain additional embodiments, Q is

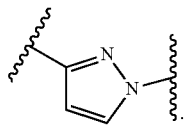 [SMILES: *c1ccn(*)n1]

In certain additional embodiments, $W^2$ is

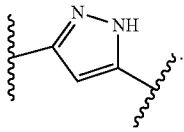 [SMILES: *c1cc(*)[nH]n1]

In certain additional embodiments, $(Y^3)_{0-5}$ is

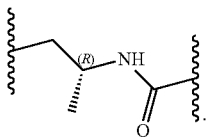

In certain embodiments, the ABM comprises a structure selected from, but not limited to, the structures shown below, where a dashed line indicates the attachment point of a linker moiety or a ULM:

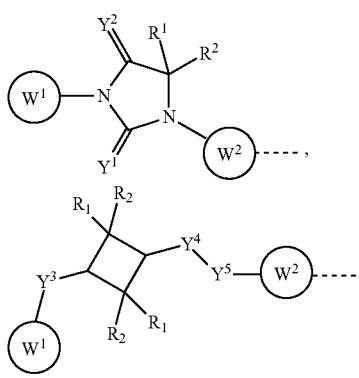

ABM-a

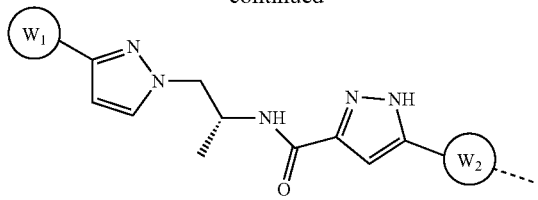

wherein:
W is

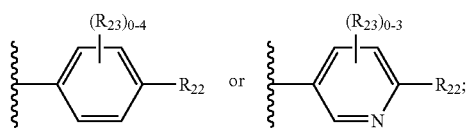

each $R_{22}$ is independently H or —CN;
each $R_{23}$ is independently H, halo, or —CF$_3$;
$Y^1$, $Y^2$ are each independently O or S;
$Y^3$, $Y^4$, $Y^5$ are each independently a bond, O, NR$^{Y2}$, CR$^{Y1}$R$^{Y2}$, C=O, C=S, SO, or SO$_2$;
$R^1$, $R^2$, are each independently H or a methyl group;
$W^2$ is a bond, $C_{1-6}$ aryl, or heteroaryl, each optionally substituted by 1, 2 or 3 R$^{W2}$; and
each R$^{W2}$ is independently H, halo, $C_{1-6}$ alkyl (optionally substituted by 1 or more F), $C_{3-6}$ cycloalkyl, $C_{4-6}$ cycloheteroalkyl, OC$_{1-3}$alkyl (optionally substituted by 1 or more —F).

In any of the embodiments described herein, the $W^2$ is covalently coupled to one or more ULM or CLM groups, or a linker to which is attached one or more ULM or CLM groups as described herein.

In certain additional embodiments, $W^1$ is selected from the group consisting of:

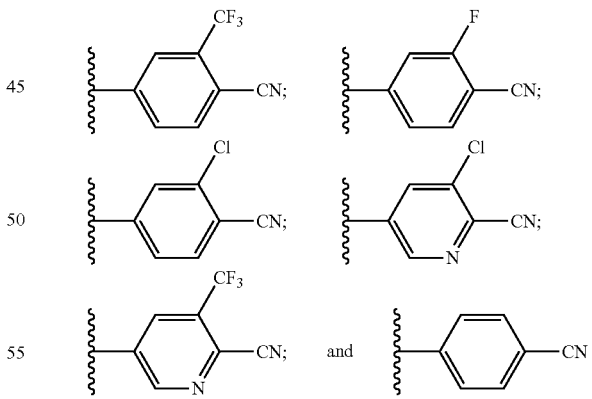

In certain additional embodiments, W2 is selected from the group consisting of:

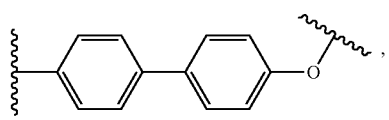

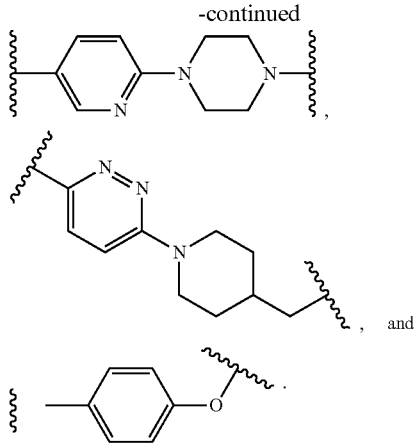

In certain embodiments, the ABM comprises a structure shown below, where a dashed line indicates the attachment point of a linker moiety or a ULM or a CLM:

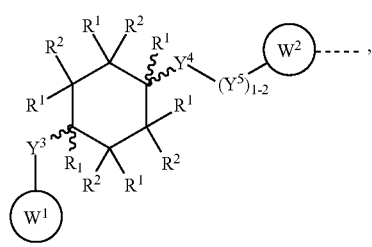

wherein:
W¹ is

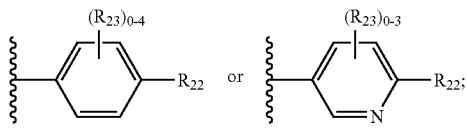

each $R_{22}$ is independently H or —CN;
each $R_{23}$ is independently H, halo, or —CF$_3$;
$Y^3$ is a bond or O;
$Y^4$ is a bond or NH;
$Y^5$ is a bond, C=O, $C_1$-$C_6$ heteroaryl, or $C_1$-$C_6$ aryl;
$R^1$, $R^2$, are each independently H, or $C_1$-$C_6$ alkyl (linear or branched, optionally
substituted by 1 or more halo, or $C_{1-6}$ alkoxyl);
$W^2$ is a bond, $C_{1-6}$ aryl, $C_{1-6}$ heteroaryl, $C_{1-6}$ alicyclic, or $C_{1-6}$ heterocyclic, each optionally substituted by 1-10 $R^{W2}$; and
each $R^{W2}$ is independently H, or halo; and
⁓ represents a bond that may be stereospecific ((R) or (S)) or non-stereospecific.

In any of the embodiments described herein, the W² is covalently coupled to one or more ULM or CLM groups, or a linker to which is attached one or more ULM or CLM groups as described herein.

In certain additional embodiments, W¹ is selected from the group consisting of:

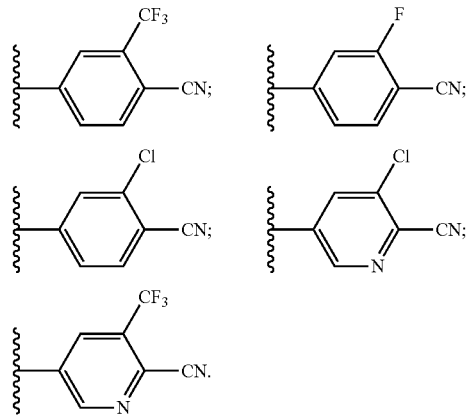

In certain additional embodiments, W² is selected from the group consisting of:

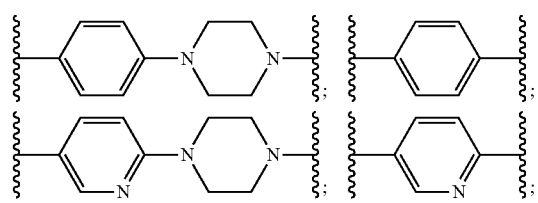

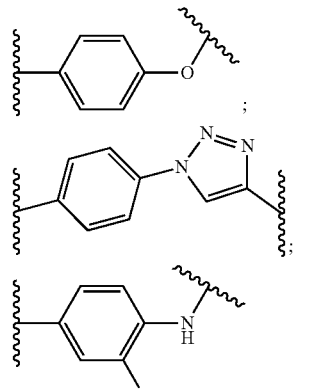

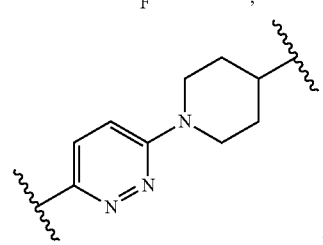

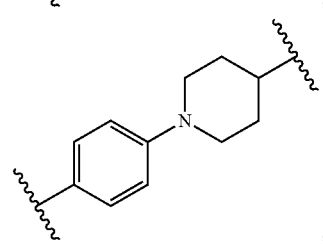

In certain embodiments, the androgen receptor binding compound of ABM is selected from the group consisting of:

trans-2-Chloro-4-[3-amino-2,2,4,4-tetramethylcyclobutoxy]benzonitrile;

cis-2-Chloro-4-[3-amino-2,2,4,4-tetramethylcyclobutoxy]benzonitrile;

trans 6-Amino-N-[3-(3-chloro-4-cyanophenoxy)-2,2,4,4-tetramethylcyclobutyl]pyridazine-3-carboxamide;

trans tert-Butyl N-[3-(3-chloro-4-cyanophenoxy)-2,2,4,4-tetramethylcyclobutyl]carbamate;

trans 4-Amino-N-[3-(3-chloro-4-cyanophenoxy)-2,2,4,4-tetramethylcyclobutyl]benzamide;

trans 5-Amino-N-[3-(3-chloro-4-cyanophenoxy)-2,2,4,4-tetramethylcyclobutyl]pyrazine-2-carboxamide;

trans 2-Amino-N-[3-(3-chloro-4-cyanophenoxy)-2,2,4,4-tetramethylcyclobutyl]pyrimidine-5-carboxamide;

4-Methoxy-N-[(1r,3r)-3-(3-chloro-4-cyanophenoxy)-2,2,4,4-tetramethylcyclobutyl]benzamide;

trans 1-(2-Hydroxyethyl)-N-[3-(3-chloro-4-cyanophenoxy)-2,2,4,4-tetramethylcyclobutyl]-1H-pyrazole-4-carboxamide;

trans 6-Amino-N-[3-(3-chloro-4-cyanophenoxy)-2,2,4,4-tetramethylcyclobutyl]pyridine-3-carboxamide;

trans 4-[(5-Hydroxypentyl)amino]-N-[3-(3-chloro-4-cyanophenoxy)-2,2,4,4-tetramethylcyclobutyl]benzamide; and trans tert-Butyl 2-({5-[(4-{[3-(3-chloro-4-cyanophenoxy)-2,2,4,4-tetramethylcyclobutyl]carbamoyl}phenyl)aminopentyl}oxy)acetate; and N-((1r,3r)-3-(4-cyanophenoxy)-2,2,4,4-tetramethylcyclobutyl)-4-methylbenzamide.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon. The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or $C_1$), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$ or —$(CH_2)_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties that are substituted, are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —$N(R_1)$—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_nC(O)$—$NR_1R_2$, —$S(O)_2$—$R_S$, —S(O)—$R_S$ ($R_S$ is $C_1$-$C_6$ alkyl or a —$(CH_2)_m$—$NR_1R_2$ group), $NO_2$, CN or halogen (F, Cl, Br, I, preferably F or $C_1$), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

Exemplary AR-PROTAC Compounds

As described above, in certain aspects, the description provides bifunctional PROTAC compounds comprising at least one ABM group, a linker, and at least one ULM (or CLM) group as described herein.

In certain embodiments, the compound is selected from the group consisting of compounds 1-625 (i.e., the chemical structures described in Table 2, Table 3, Table 4, Table 5, Table 6, and Table 7 of FIGS. 2, 3, 4, 5, 6, and 7, respectively), and salts and polymorphs thereof.

In additional embodiments, the compound is selected from the group consisting of: 4-{3-[4-({1-[2-(2,6-dioxopiperidin-3-yl)-1,3-dioxo-2,3-dihydro-1H-isoindol-4-yl]-4,7,10-trioxa-1-azadodecan-12-yl}oxy)phenyl]-4,4-dimethyl-5-oxo-2-sulfanylideneimidazolidin-1-yl}-2-(trifluoromethyl)benzonitrile (1); 4-(3-{4-[2-(2-{[2-(2,6-dioxopiperidin-3-yl)-1,3-dioxo-2,3-dihydro-1H-isoindol-4-yl]amino}ethoxy)ethoxy]phenyl}-4,4-dimethyl-5-oxo-2-sulfanylideneimidazolidin-1-yl)-2-(trifluoromethyl)benzonitrile (2); 4-{3-[4-({1-[2-(2,6-dioxopiperidin-3-yl)-1,3-dioxo-2,3-dihydro-1H-isoindol-4-yl]-4,7,10,13,16-pentaoxa-1-azaoctadecan-18-yl}oxy)phenyl]-4,4-dimethyl-5-oxo-2-sulfanylideneimidazolidin-1-yl}-2-(trifluoromethyl)benzonitrile (3); 4-[3-(4-{2-[2-(2-{[2-(2,6-dioxopiperidin-3-yl)-1,3-dioxo-2,3-dihydro-1H-isoindol-4-yl]amino}ethoxy)ethoxy]ethoxy}phenyl)-4,4-dimethyl-5-oxo-2-sulfanylideneimidazolidin-1-yl]-2-(trifluoromethyl)benzonitrile (4); 4-[3-(4-{3-[2-(2-{[2-(2,6-dioxopiperidin-3-yl)-1,3-dioxo-2,3-dihydro-1H-isoindol-4-yl]amino}ethoxy)ethoxy]propoxy}phenyl)-4,4-dimethyl-5-oxo-2-sulfanylideneimidazolidin-1-yl]-2-(trifluoromethyl)benzonitrile (5); 4-{3-[4-({1-[2-(2,6-dioxopiperidin-3-yl)-1,3-dioxo-2,3-dihydro-1H-isoindol-4-yl]-4,7,10-trioxa-1-azatetradecan-14-yl}oxy)phenyl]-4,4-dimethyl-5-oxo-2-sulfanylideneimidazolidin-1-yl}-2-(trifluoromethyl)benzonitrile (6); 4-{3-[4-({1-[2-(2,6-dioxopiperidin-3-yl)-1,3-dioxo-2,3-dihydro-1H-isoindol-4-yl]-4,7,10-trioxa-1-azatridecan-13-yl}oxy)phenyl]-4,4-dimethyl-5-oxo-2-sulfanylideneimidazolidin-1-yl}-2-(trifluoromethyl)benzonitrile (7); 4-(3-{4-[(1-{2-[(3R)-2,6-dioxopiperidin-3-yl]-1,3-dioxo-2,3-dihydro-1H-isoindol-4-yl}-4,7,10-trioxa-1-azadodecan-12-yl)oxy]phenyl}-4,4-dimethyl-5-oxo-2-sulfanylideneimidazolidin-1-yl)-2-(trifluoromethyl)benzonitrile (8); 4-(3-{4-[(1-{2-[(3S)-2,6-dioxopiperidin-3-yl]-1,3-dioxo-2,3-dihydro-1H-isoindol-4-yl}-4,7,10-trioxa-1-azadodecan-12-yl)oxy]phenyl}-4,4-dimethyl-5-oxo-2-sulfanylideneimidazolidin-1-yl)-2-(trifluoromethyl)benzonitrile (9); 4-[3-(4-{3-[3-(2-{[2-(2,6-dioxopiperidin-3-yl)-1,3-dioxo-2,3-dihydro-1H-isoindol-4-yl]amino}ethoxy)propoxy]propoxy}phenyl)-4,4-dimethyl-5-oxo-2-sulfanylideneimidazolidin-1-yl]-2-(trifluoromethyl)benzonitrile (10); 4-{4,4-dimethyl-3-[4-({1-[2-(3-methyl-2,6-dioxopiperidin-3-yl)-1,3-dioxo-2,3-dihydro-1H-isoindol-4-yl]-4,7,10-trioxa-1-azatridecan-13-yl}oxy)phenyl]-5-oxo-2-sulfanylideneimidazolidin-1-yl}-2-(trifluoromethyl)benzonitrile (11); 4-[3-(4-{4-[(5-{[2-(2,6-dioxopiperidin-3-yl)-1,3-dioxo-2,3-dihydro-1H-isoindol-4-yl]amino}pentyl)oxy]phenyl}phenyl)-4,4-dimethyl-5-oxo-2-sulfanylideneimidazolidin-1-yl]-2-(trifluoromethyl)benzonitrile (12); 4-{[5-(3-{[2-(2,6-dioxopiperidin-3-yl)-1,3-dioxo-2,3-dihydro-1H-isoindol-4-yl]amino}propoxy)pentyl]oxy}-N-[(1r,3r)-3-(3-chloro-4-cyanophenoxy)-2,2,4,4-tetramethylcyclobutyl]benzamide (13); 4-{3-[4-({1-[2-(2, 6-dioxopiperidin-3-yl)-1-oxo-2,3-dihydro-1H-isoindol-4-yl]-1,4,7,10-tetraoxatridecan-13-yl}oxy)phenyl]-4,4-dimethyl-5-oxo-2-sulfanylideneimidazolidin-1-yl}-2-(trifluoromethyl)benzonitrile (14); 6-[4-(2-{[2-(2,6-dioxopiperidin-3-yl)-1-oxo-2,3-dihydro-1H-isoindol-4-yl]amino}ethyl)piperazin-1-yl]-N-[(1r,3r)-3-(3-chloro-4-cyanophenoxy)-2,2,4,4-tetramethylcyclobutyl]pyridine-3-carboxamide (15); 6-{4-[2-(3-{[2-(2,6-dioxopiperidin-3-yl)-1,3-dioxo-2,3-dihydro-1H-isoindol-4-yl]amino}propoxy)ethyl]piperazin-1-yl}-N-[(1r,3r)-3-(3-chloro-4-cyanophenoxy)-2,2,4,4-tetramethylcyclobutyl]pyridine-3-carboxamide (16); 4-(3-{4-[1-(2-{[2-(2,6-dioxopiperidin-3-yl)-1-oxo-2,3-dihydro-1H-isoindol-4-yl]oxy}ethyl)-1H-1,3-benzodiazol-5-yl]phenyl}-4,4-dimethyl-5-oxo-2-sulfanylideneimidazolidin-1-yl)-2-(trifluoromethyl)benzonitrile (17); 4-{[5-(3-{[2-(2,6-dioxopiperidin-3-yl)-1,3-dioxo-2,3-dihydro-1H-isoindol-4-yl]amino}propoxy)pentyl]amino}-3-fluoro-N-[(1r,3r)-3-(3-chloro-4-cyanophenoxy)-2,2,4,4-tetramethylcyclobutyl]benzamide (18); 6-[4-(2-{[2-(2,6-dioxopiperidin-3-yl)-1-oxo-2,3-dihydro-1H-isoindol-4-yl]oxy}ethyl)piperazin-1-yl]-N-[(1r,3r)-3-(3-chloro-4-cyanophenoxy)-2,2,4,4-tetramethylcyclobutyl]pyridine-3-carboxamide (19); 6-[4-(2-{[2-(2,6-dioxopiperidin-3-yl)-1,3-dioxo-2,3-dihydro-1H-isoindol-4-yl]amino}ethyl)piperazin-1-yl]-N-[(1r,3r)-3-(3-chloro-4-cyanophenoxy)-2,2,4,4-tetramethylcyclobutyl]pyridine-3-carboxamide (20); 6-(4-{3-[2-(2,6-dioxopiperidin-3-yl)-1-oxo-2,3-dihydro-1H-isoindol-4-yl]propyl}piperazin-1-yl)-N-[(1r,3r)-3-(3-chloro-4-cyanophenoxy)-2,2,4,4-tetramethylcyclobutyl]pyridine-3-carboxamide (21); 6-{4-[2-(2-{[2-(2,6-dioxopiperidin-3-yl)-1-oxo-2,3-dihydro-1H-isoindol-4-yl]oxy}ethoxy)ethyl]piperazin-1-yl}-N-[(1r,3r)-3-(3-chloro-4-cyanophenoxy)-2,2,4,4-tetramethylcyclobutyl]pyridine-3-carboxamide (22); 4-{4-[4-(2-{[2-(2,6-dioxopiperidin-3-yl)-1-oxo-2,3-dihydro-1H-isoindol-4-yl]oxy}ethyl)piperazin-1-yl]butyl}-N-[(1r,3r)-3-[4-cyano-3-(trifluoromethyl)phenoxy]-2,2,4,4-tetramethylcyclobutyl]benzamide (23); 6-{4-[2-(3-{[2-(2,6-dioxopiperidin-3-yl)-1,3-dioxo-2,3-dihydro-1H-isoindol-5-yl]amino}propoxy)ethyl]piperazin-1-yl}-N-[(1r,3r)-3-(3-chloro-4-cyanophenoxy)-2,2,4,4-tetramethylcyclobutyl]pyridine-3-carboxamide (24); 6-{4-[2-(3-{[2-(2,6-dioxopiperidin-3-yl)-7-fluoro-1,3-dioxo-2,3-dihydro-1H-isoindol-4-yl]amino}propoxy)ethyl]piperazin-1-yl}-N-[(1r,3r)-3-(3-chloro-4-cyanophenoxy)-2,2,4,4-tetramethylcyclobutyl]pyridine-3-carboxamide (25); 4-(6-{4-[2-(2,6-dioxopiperidin-3-yl)-1,3-dioxo-2,3-dihydro-1H-isoindol-5-yl]piperazin-1-yl}hexyl)-N-[(1r,3r)-3-[4-cyano-3-(trifluoromethyl)phenoxy]-2,2,4,4-tetramethylcyclobutyl]benzamide (26); 4-{3-[4-(3-{[2-(2,6-dioxopiperidin-3-yl)-1,3-dioxo-2,3-dihydro-1H-isoindol-4-yl]amino}propyl)piperazin-1-yl]propyl}-N-[(1r,3r)-3-[4-cyano-3-(trifluoromethyl)phenoxy]-2,2,4,4-tetramethylcyclobutyl]benzamide (27); 4-[5-(3-{[2-(2,6-dioxopiperidin-3-yl)-1,3-dioxo-2,3-dihydro-1H-isoindol-4-yl]amino}propoxy)pentyl]-N-[(1r,3r)-3-(3-chloro-4-cyanophenoxy)-2,2,4,4-tetramethylcyclobutyl]benzamide (28); 6-{4-[2-(3-{[2-(2,6-dioxopiperidin-3-yl)-5-fluoro-1,3-dioxo-2,3-dihydro-1H-isoindol-4-yl]amino}propoxy)ethyl]piperazin-1-yl}-N-[(1r,3r)-3-(3-chloro-4-cyanophenoxy)-2,2,4,4-tetramethylcyclobutyl]pyridine-3-carboxamide (29); 4-(4-{4-[2-({2-[(3S)-2,6-dioxopiperidin-3-yl]-1-oxo-2,3-dihydro-1H-isoindol-5-yl}oxy)ethyl]piperazin-1-yl}butyl)-N-[(1r,3r)-3-(3-chloro-4-cyanophenoxy)-2,2,4,4-tetramethylcyclobutyl]benzamide (30); 4-(4-{4-[2-({2-[(3S)-2,6-dioxopiperidin-3-yl]-1-oxo-2,3-dihydro-1H-isoindol-4-yl}oxy)ethyl]piperazin-1-yl}butyl)-N-[(1r,3r)-3-(3-chloro-4-cyanophenoxy)-2,2,4,4-tetramethylcyclobutyl]benzamide (31); 4-{4-[4-(2-{[2-(2,6-dioxopiperidin-3-yl)-7-fluoro-1,3-dioxo-2,3-dihydro-1H-isoindol-4-yl]amino}ethyl)piperazin-1-yl]butyl}-N-[(1r,3r)-3-(3-chloro-4-cyanophenoxy)-2,2,4,4-tetramethylcyclobutyl]benzamide (32); 6-{4-[5-({2-[(3S)-2,6-dioxopiperidin-3-yl]-1-oxo-2,3-dihydro-1H-isoindol-4-yl}oxy)pentyl]piperazin-1-yl}-N-[(1r,3r)-3-(3-chloro-4-cyanophenoxy)-2,2,4,4-tetramethylcyclobutyl]pyridine-3-carboxamide (33); 4-(4-{4-[2-({2-[(3S)-2,6-dioxopiperidin-3-yl]-1,3-dioxo-2,3-dihydro-1H-isoindol-5-yl}oxy)ethyl]piperazin-1-yl}butyl)-N-[(1r,3r)-3-(3-chloro-4-cyanophenoxy)-2,2,4,4-tetramethylcyclobutyl]benzamide (34); 6-{4-[5-({2-[(3S)-2,6-dioxopiperidin-3-yl]-1-oxo-2,3-dihydro-1H-isoindol-5-yl}oxy)pentyl]piperazin-1-yl}-N-[(1r,3r)-3-(3-chloro-4-cyanophenoxy)-2,2,4,4-tetramethylcyclobutyl]pyridine-3-carboxamide (35); 4-(4-{4-[2-(2,6-dioxopiperidin-3-yl)-5-fluoro-1,3-dioxo-2,3-dihydro-1H-isoindol-4-yl]piperazin-1-yl}butyl)-N-[(1r,3r)-3-(3-chloro-4-cyanophenoxy)-2,2,4,4-tetramethylcyclobutyl]benzamide (36); 4-{4-[4-(2-{[2-(2,6-dioxopiperidin-3-yl)-5-fluoro-1,3-dioxo-2,3-dihydro-1H-isoindol-4-yl]amino}ethyl)piperazin-1-yl]butyl}-N-[(1r,3r)-3-(3-chloro-4-cyanophenoxy)-2,2,4,4-tetramethylcyclobutyl]benzamide (37); 6-(4-{6-[2-(2,6-dioxopiperidin-3-yl)-1-oxo-2,3-dihydro-1H-isoindol-4-yl]hexyl}piperazin-1-yl)-N-[(1r,3r)-3-(3-chloro-4-cyanophenoxy)-2,2,4,4-tetramethylcyclobutyl]pyridine-3-carboxamide (38); 4-(4-{4-[2-(2,6-dioxopiperidin-3-yl)-4-fluoro-1,3-dioxo-2,3-dihydro-1H-isoindol-5-yl]piperazin-1-yl}butyl)-N-[(1r,3r)-3-(3-chloro-4-cyanophenoxy)-2,2,4,4-tetramethylcyclobutyl]benzamide (39); 4-(6-{4-[2-(2,6-dioxopiperidin-3-yl)-1,3-dioxo-2,3-dihydro-1H-isoindol-5-yl]piperazin-1-yl}hexyl)-N-[(1r,3r)-3-(3-chloro-4-cyanophenoxy)-2,2,4,4-tetramethylcyclobutyl]benzamide (40); 6-{4-[5-({2-[(3S)-2,6-dioxopiperidin-3-yl]-1,3-dioxo-2,3-dihydro-1H-isoindol-5-yl}oxy)pentyl]piperazin-1-yl}-N-[(1r,3r)-3-(3-chloro-4-cyanophenoxy)-2,2,4,4-tetramethylcyclobutyl]pyridine-3-carboxamide (41); 6-[4-(5-{[2-(2,6-dioxopiperidin-3-yl)-1-oxo-2,3-dihydro-1H-isoindol-4-yl]oxy}pentyl)piperazin-1-yl]-N-[(1r,3r)-3-(3-chloro-4-cyanophenoxy)cyclobutyl]pyridine-3-carboxamide (42); 4-[4-(5-{[2-(2,6-dioxopiperidin-3-yl)-1-oxo-2,3-dihydro-1H-isoindol-4-yl]oxy}pentyl)piperazin-1-yl]-N-[(1r,3r)-3-(3-chloro-4-cyanophenoxy)cyclobutyl]benzamide (43); 4-(5-{4-[2-(2,6-dioxopiperidin-3-yl)-1,3-dioxo-2,3-dihydro-1H-isoindol-5-yl]piperazin-1-yl}pentyl)-N-[(1r,3r)-3-(3-chloro-4-cyanophenoxy)-2,2,4,4-tetramethylcyclobutyl]benzamide (44); 4-(4-{4-[2-(2,6-dioxopiperidin-3-yl)-1,3-dioxo-2,3-dihydro-1H-isoindol-5-yl]piperazin-1-yl}butyl)-N-[(1r,3r)-3-(3-chloro-4-cyanophenoxy)-2,2,4,4-tetramethylcyclobutyl]benzamide (45); 4-(6-{4-[2-(2,6-dioxopiperidin-3-yl)-6-fluoro-1,3-dioxo-2,3-dihydro-1H-isoindol-5-yl]piperazin-1-yl}hexyl)-N-[(1r,3r)-3-(3-chloro-4-cyanophenoxy)-2,2,4,4-tetramethylcyclobutyl]benzamide (46); 4-(4-{[2-(2,6-dioxopiperidin-3-yl)-1-oxo-2,3-dihydro-1H-isoindol-4-yl]oxy}butyl)-N-[(1r,3r)-3-(3-chloro-4-cyanophenoxy)-2,2,4,4-tetramethylcyclobutyl]benzamide (47); 4-(5-{[2-(2,6-dioxopiperidin-3-yl)-1-oxo-2,3-dihydro-1H-isoindol-4-yl]oxy}pentyl)-N-[(1r,3r)-3-(3-chloro-4-cyanophenoxy)-2,2,4,4-tetramethylcyclobutyl]benzamide (48); 4-{3-(2-{[2-(2,6-dioxopiperidin-3-yl)-1-oxo-2,3-dihydro-1H-isoindol-4-yl]oxy}ethoxy)propyl]-N-[(1r,3r)-3-(3-chloro-4-cyanophenoxy)-2,2,4,4-tetramethylcyclobutyl]benzamide (49); 4-[4-(2-{[2-(2,6-dioxopiperidin-3-yl)-1-oxo-2,3-dihydro-1H-isoindol-4-yl]oxy}ethoxy)butyl]-N-[(1r,3r)-3-(3-chloro-4-cyanophenoxy)-2,2,4,4-tetramethylcyclobutyl]benzamide (50); 4-[5-(2-{[2-(2,6- dioxopiperidin-3-yl)-1-oxo-2,3-dihydro-1H-isoindol-4-yl]oxy}ethoxy)pentyl]-N-[(1r,3r)-3-(3-chloro-4-cyanophenoxy)-2,2,4,4-tetramethylcyclobutyl]benzamide (51); 4-[6-(2-{[2-(2,6-dioxopiperidin-3-yl)-1-oxo-2,3-dihydro-1H-isoindol-4-yl]oxy}ethoxy)hexyl]-N-[(1r,3r)-3-(3-chloro-4-cyanophenoxy)-2,2,4,4-tetramethylcyclobutyl]benzamide (52); N-[(2R)-1-[3-(3-chloro-4-cyanophenyl)-1H-pyrazol-1-yl]propan-2-yl]-5-{[4-(4-{[2-(2,6-dioxopiperidin-3-yl)-1,3-dioxo-2,3-dihydro-1H-isoindol-4-yl]amino}butyl)piperazin-1-yl]methyl}-1H-pyrazole-3-carboxamide (53); 4-(4-{6-[2-(2,6-dioxopiperidin-3-yl)-1,3-dioxo-2,3-dihydro-1H-isoindol-5-yl]hexyl}piperazin-1-yl)-N-[(1r,3r)-3-(3-chloro-4-cyanophenoxy)-2,2,4,4-tetramethylcyclobutyl]benzamide (54); 4-(3-{[2-(2,6-dioxopiperidin-3-yl)-1-oxo-2,3-dihydro-1H-isoindol-4-yl]oxy}propyl)-N-[(1r,3r)-3-(3-chloro-4-cyanophenoxy)-2,2,4,4-tetramethylcyclobutyl]benzamide (55); N-[(2R)-1-[3-(3-chloro-4-cyanophenyl)-1H-pyrazol-1-yl]propan-2-yl]-5-[(3-{4-[2-(2,6-dioxopiperidin-3-yl)-1,3-dioxo-2,3-dihydro-1H-isoindol-5-yl]piperazin-1-yl}propoxy)methyl]-1H-pyrazole-3-carboxamide (56); 4-[4-(3-{[2-(2,6-dioxopiperidin-3-yl)-1-oxo-2,3-dihydro-1H-isoindol-4-yl]oxy}propyl)-1H-1,2,3-triazol-1-yl]-N-[(1r,3r)-3-(3-chloro-4-cyanophenoxy)cyclobutyl]benzamide (57); 6-[4-(6-{[2-(2,6-dioxopiperidin-3-yl)-6-fluoro-1,3-dioxo-2,3-dihydro-1H-isoindol-5-yl]amino}hexyl)piperazin-1-yl]-N-[(1r,3r)-3-(3-chloro-4-cyanophenoxy)-2,2,4,4-tetramethylcyclobutyl]pyridine-3-carboxamide (58); N-[(2R)-1-[3-(3-chloro-4-cyanophenyl)-1H-pyrazol-1-yl]propan-2-yl]-5-({3-[4-(2-{[2-(2,6-dioxopiperidin-3-yl)-1,3-dioxo-2,3-dihydro-1H-isoindol-4-yl]amino}ethyl)piperazin-1-yl]propoxy}methyl)-1H-pyrazole-3-carboxamide (59); (60); 4-[4-(5-{[2-(2,6-dioxopiperidin-3-yl)-1-oxo-2,3-dihydro-1H-isoindol-4-yl]oxy}pentyl)-1H-1,2,3-triazol-1-yl]-N-[(1r,3r)-3-(3-chloro-4-cyanophenoxy)cyclobutyl]benzamide (61); 6-{4-[2-(4-{2-[(3S)-2,6-dioxopiperidin-3-yl]-1,3-dioxo-2,3-dihydro-1H-isoindol-4-yl}butoxy)ethyl]piperazin-1-yl}-N-[(1r,3r)-3-(3-chloro-4-cyanophenoxy)-2,2,4,4-tetramethylcyclobutyl]pyridine-3-carboxamide (62); 6-{4-[2-(4-{2-[(3R)-2,6-dioxopiperidin-3-yl]-1,3-dioxo-2,3-dihydro-1H-isoindol-4-yl}butoxy)ethyl]piperazin-1-yl}-N-[(1r,3r)-3-(3-chloro-4-cyanophenoxy)-2,2,4,4-tetramethylcyclobutyl]pyridine-3-carboxamide (63); 6-(4-{2-[(5-{2-[(3S)-2,6-dioxopiperidin-3-yl]-1,3-dioxo-2,3-dihydro-1H-isoindol-4-yl}pentyl)oxy]ethyl}piperazin-1-yl)-N-[(1r,3r)-3-(3-chloro-4-cyanophenoxy)-2,2,4,4-tetramethylcyclobutyl]pyridine-3-carboxamide (64); 6-(4-{2-[(5-{2-[(3R)-2,6-dioxopiperidin-3-yl]-1,3-dioxo-2,3-dihydro-1H-isoindol-4-yl}pentyl)oxy]ethyl}piperazin-1-yl)-N-[(1r,3r)-3-(3-chloro-4-cyanophenoxy)-2,2,4,4-tetramethylcyclobutyl]pyridine-3-carboxamide (65); 4-(4-{2-[(5-{2-[(3S)-2,6-dioxopiperidin-3-yl]-1,3-dioxo-2,3-dihydro-1H-isoindol-4-yl}pentyl)oxy]ethyl}piperazin-1-yl)-N-[(1r,3r)-3-(3-chloro-4-cyanophenoxy)-2,2,4,4-tetramethylcyclobutyl]benzamide (66); 4-(4-{2-[(5-{2-[(3R)-2,6-dioxopiperidin-3-yl]-1,3-dioxo-2,3-dihydro-1H-isoindol-4-yl}pentyl)oxy]ethyl}piperazin-1-yl)-N-[(1r,3r)-3-(3-chloro-4-cyanophenoxy)-2,2,4,4-tetramethylcyclobutyl]benzamide (67); 4-(4-{6-[2-(2,6-dioxopiperidin-3-yl)-1-oxo-2,3-dihydro-1H-isoindol-5-yl]hexyl}piperazin-1-yl)-N-[(1r,3r)-3-(3-chloro-4-cyanophenoxy)-2,2,4,4-tetramethylcyclobutyl]benzamide (68); 4-(3-{4-[2-(2,6-dioxopiperidin-3-yl)-1,3-dioxo-2,3-dihydro-1H-isoindol-5-yl]piperazin-1-yl}propyl)-N-[(1r,3r)-3-(3-chloro-4-cyanophenoxy)-2,2,4,4-tetramethylcyclobutyl]benzamide (69); 4-[6-(4-{2-[(3S)-2,6-dioxopiperidin-3-yl]-1-oxo-2,3-dihydro-1H-isoindol-5-yl}piperazin-1-yl)hexyl]-N-[(1r,3r)-3-[4-cyano-3-(trifluoromethyl)phenoxy]-2,2,4,4-tetramethylcyclobutyl]benzamide (70); 4-[6-(4-{2-[(3R)-2,6-dioxopiperidin-3-yl]-1-oxo-2,3-dihydro-1H-isoindol-5-yl}piperazin-1-yl)hexyl]-N-[(1r,3r)-3-[4-cyano-3-(trifluoromethyl)phenoxy]-2,2,4,4-tetramethylcyclobutyl]benzamide (71); 6-[4-(6-{[2-(2,6-dioxopiperidin-3-yl)-5-fluoro-1-oxo-2,3-dihydro-1H-isoindol-4-yl]oxy}hexyl)piperazin-1-yl]-N-[(1r,3r)-3-(3-chloro-4-cyanophenoxy)-2,2,4,4-tetramethylcyclobutyl]pyridine-3-carboxamide (72); 6-[4-(6-{[2-(2,6-dioxopiperidin-3-yl)-6-fluoro-1,3-dioxo-2,3-dihydro-1H-isoindol-5-yl]oxy}hexyl)piperazin-1-yl]-N-[(1r,3r)-3-(3-chloro-4-cyanophenoxy)-2,2,4,4-tetramethylcyclobutyl]pyridine-3-carboxamide (73); 4-[6-(4-{2-[(3S)-2,6-dioxopiperidin-3-yl]-3-oxo-2,3-dihydro-1H-isoindol-5-yl}piperazin-1-yl)hexyl]-N-[(1r,3r)-3-[4-cyano-3-(trifluoromethyl)phenoxy]-2,2,4,4-tetramethylcyclobutyl]benzamide (74); and 4-[6-(4-{2-[(3R)-2,6-dioxopiperidin-3-yl]-3-oxo-2,3-dihydro-1H-isoindol-5-yl}piperazin-1-yl)hexyl]-N-[(1r,3r)-3-[4-cyano-3-(trifluoromethyl)phenoxy]-2,2,4,4-tetramethylcyclobutyl]benzamide (75); N-((1r,3r)-3-(3-chloro-4-cyanophenoxy)-2,2,4,4-tetramethylcyclobutyl)-6-(4-(6-((2-(2,6-dioxopiperidin-3-yl)-6-fluoro-1-oxoisoindolin-5-yl)amino)hexyl)piperazin-1-yl)nicotinamide (76); N-((1r,3r)-3-(3-chloro-4-cyanophenoxy)-2,2,4,4-tetramethylcyclobutyl)-6-(4-(2-(4-(2-(2,6-dioxopiperidin-3-yl)-1,3-dioxoisoindolin-5-yl)piperazin-1-yl)ethyl)piperazin-1-yl)nicotinamide (77); N-((1r,3r)-3-(3-chloro-4-cyanophenoxy)-2,2,4,4-tetramethylcyclobutyl)-6-(4-(2-(1-(2-(2,6-dioxopiperidin-3-yl)-1,3-dioxoisoindolin-5-yl)piperidin-4-yl)ethyl)piperazin-1-yl)nicotinamide (78); N-((1r,3r)-3-(3-chloro-4-cyanophenoxy)-2,2,4,4-tetramethylcyclobutyl)-6-(4-(2-((5-(2-((S)-2,6-dioxopiperidin-3-yl)-1-oxoisoindolin-4-yl)pentyl)oxy)ethyl)piperazin-1-yl)nicotinamide (79); N-((1r,3r)-3-(3-chloro-4-cyanophenoxy)-2,2,4,4-tetramethylcyclobutyl)-4-(4-(2-((5-(2-((R)-2,6-dioxopiperidin-3-yl)-1-oxoisoindolin-4-yl)pentyl)oxy)ethyl)piperazin-1-yl)benzamide (80); N-((1r,3r)-3-(3-chloro-4-cyanophenoxy)-2,2,4,4-tetramethylcyclobutyl)-4-(6-(4-(2-(2,6-dioxopiperidin-3-yl)-1,3-dioxoisoindolin-5-yl)-3,6-dihydropyridin-1(2H)-yl)hexyl)benzamide (81); N-((1r,3r)-3-(3-chloro-4-cyanophenoxy)-2,2,4,4-tetramethylcyclobutyl)-4-(6-(4-(2-(2,6-dioxopiperidin-3-yl)-1-oxoisoindolin-5-yl)-3,6-dihydropyridin-1(2H)-yl)hexyl)benzamide (82); N-((1r,3R)-3-(3-chloro-4-cyanophenoxy)-2,2,4,4-tetramethylcyclobutyl)-6-((1R,4R)-5-(5-((2-(2,6-dioxopiperidin-3-yl)-1,3-dioxoisoindolin-5-yl)oxy)pentyl)-2,5-diazabicyclo[2.2.1]heptan-2-yl)nicotinamide (83); N-((1r,3r)-3-(3-chloro-4-cyanophenoxy)-2,2,4,4-tetramethylcyclobutyl)-4-(4-(5-((2-(2,6-dioxopiperidin-3-yl)-1-oxoisoindolin-5-yl)oxy)pentyl)piperazin-1-yl)benzamide (84); N-((1r,3r)-3-(3-chloro-4-cyanophenoxy)-2,2,4,4-tetramethylcyclobutyl)-4-(1-(5-((2-(2,6-dioxopiperidin-3-yl)-1,3-dioxoisoindolin-5-yl)oxy)pentyl)-1,2,3,6-tetrahydropyridin-4-yl)benzamide (85); N-((1r,3r)-3-(3-chloro-4-cyanophenoxy)-2,2,4,4-tetramethylcyclobutyl)-4-(5-(4-(2-((S)-2,6-dioxopiperidin-3-yl)-1-oxoisoindolin-5-yl)piperazin-1-yl)pentyl)benzamide (86); N-((1r,3r)-3-(3-chloro-4-cyanophenoxy)-2,2,4,4-tetramethylcyclobutyl)-4-(5-(4-(2-((R)-2,6-dioxopiperidin-3-yl)-1-oxoisoindolin-5-yl)piperazin-1-yl)pentyl)benzamide (87); N-((1r,3r)-3-(3-chloro-4-cyanophenoxy)-2,2,4,4-tetramethylcyclobutyl)-4-(6-(4-(2-(2,6-dioxopiperidin-3-yl)-6-fluoro-1-oxoisoindolin-5-yl)piperazin-1-yl)hexyl)benzamide (88); N-((1r,3r)-3-(3-chloro-4-cyanophenoxy)-2,2,4,4-tetramethylcyclobutyl)-4-(6-(4-(2-(2,6-dioxopiperidin-3-yl)-6- fluoro-3-oxoisoindolin-5-yl)piperazin-1-yl)hexyl)benzamide (89); N-((1r,3r)-3-(3-chloro-4-cyanophenoxy)-2,2,4,4-tetramethylcyclobutyl)-6-(4-(6-((2-(2,6-dioxopiperidin-3-yl)-6-fluoro-1-oxoisoindolin-5-yl)oxy)hexyl)piperazin-1-yl)nicotinamide (90); N-((1r,3r)-3-(3-chloro-4-cyanophenoxy)-2,2,4,4-tetramethylcyclobutyl)-4-(4-(3-((2-(2,6-dioxopiperidin-3-yl)-1,3-dioxoisoindolin-5-yl)oxy)propyl)piperazin-1-yl)benzamide (91); N-((1r,3r)-3-(3-chloro-4-cyanophenoxy)-2,2,4,4-tetramethylcyclobutyl)-4-(4-(4-((2-(2,6-dioxopiperidin-3-yl)-1,3-dioxoisoindolin-5-yl)oxy)butyl)piperazin-1-yl)benzamide (92); N-((1r,3r)-3-(3-chloro-4-cyanophenoxy)-2,2,4,4-tetramethylcyclobutyl)-4-(6-(4-(2-(2,6-dioxopiperidin-3-yl)-1-oxoisoindolin-5-yl)piperidin-1-yl)hexyl)benzamide (93); N-((1r,3r)-3-(3-chloro-4-cyanophenoxy)-2,2,4,4-tetramethylcyclobutyl)-6-(6-(4-(2-(2,6-dioxopiperidin-3-yl)-1-oxoisoindolin-5-yl)piperidin-1-yl)hexyl)nicotinamide (94); N-((1r,3r)-3-(3-chloro-4-cyanophenoxy)-2,2,4,4-tetramethylcyclobutyl)-4-(5-(4-(2-(2,6-dioxopiperidin-3-yl)-1,3-dioxoisoindolin-5-yl)-3,6-dihydropyridin-1(2H)-yl)pentyl)benzamide (95); N-((1r,3r)-3-(3-chloro-4-cyanophenoxy)-2,2,4,4-tetramethylcyclobutyl)-6-(4-(5-((2-(2,6-dioxopiperidin-3-yl)-3-oxoisoindolin-5-yl)oxy)pentyl)piperazin-1-yl)nicotinamide (96); N-((1r,3r)-3-(3-chloro-4-cyanophenoxy)-2,2,4,4-tetramethylcyclobutyl)-4-(4-(4-(2-(2,6-dioxopiperidin-3-yl)-1,3-dioxoisoindolin-5-yl)-3,6-dihydropyridin-1(2H)-yl)butyl)benzamide (97); N-((1r,3r)-3-(3-chloro-4-cyanophenoxy)-2,2,4,4-tetramethylcyclobutyl)-4-(5-(4-(2-(2,6-dioxopiperidin-3-yl)-1-oxoisoindolin-5-yl)-3,6-dihydropyridin-1(2H)-yl)pentyl)benzamide (98); N-((1r,3r)-3-(3-chloro-4-cyanophenoxy)-2,2,4,4-tetramethylcyclobutyl)-4-(1-(5-((2-(2,6-dioxopiperidin-3-yl)-1,3-dioxoisoindolin-5-yl)oxy)pentyl)piperidin-4-yl)benzamide (99); N-((1r,3r)-3-(3-chloro-4-cyanophenoxy)-2,2,4,4-tetramethylcyclobutyl)-4-(4-(5-((2-(2,6-dioxopiperidin-3-yl)-1-oxoisoindolin-5-yl)oxy)pentyl)-1H-1,2,3-triazol-1-yl)benzamide (100); N-((1r,3r)-3-(3-chloro-4-cyanophenoxy)-2,2,4,4-tetramethylcyclobutyl)-4-(6-((1S,4S)-5-(2-((R)-2,6-dioxopiperidin-3-yl)-1-oxoisoindolin-5-yl)-2,5-diazabicyclo[2.2.1]heptan-2-yl)hexyl)benzamide (101); N-((1r,3r)-3-(3-chloro-4-cyanophenoxy)-2,2,4,4-tetramethylcyclobutyl)-6-(4-(5-((2-(2,6-dioxopiperidin-3-yl)-1-oxoisoindolin-5-yl)oxy)pentyl)-1H-1,2,3-triazol-1-yl)nicotinamide (102); N-((1r,3r)-3-(3-chloro-4-cyanophenoxy)-2,2,4,4-tetramethylcyclobutyl)-6-(6-(4-(2-(2,6-dioxopiperidin-3-yl)-1,3-dioxoisoindolin-5-yl)piperidin-1-yl)hexyl)nicotinamide (103); N-((1r,3r)-3-(3-chloro-4-cyanophenoxy)-2,2,4,4-tetramethylcyclobutyl)-4-(4-(4-(2-(2,6-dioxopiperidin-3-yl)-1-oxoisoindolin-5-yl)-3,6-dihydropyridin-1(2H)-yl)butyl)benzamide (104); N-((1r,3r)-3-(3-chloro-4-cyanophenoxy)-2,2,4,4-tetramethylcyclobutyl)-4-(4-(3-(4-((2-(2,6-dioxopiperidin-3-yl)-1-oxoisoindolin-5-yl)oxy)piperidin-1-yl)propyl)-1H-1,2,3-triazol-1-yl)benzamide (105); N-((1r,3r)-3-(3-chloro-4-cyanophenoxy)-2,2,4,4-tetramethylcyclobutyl)-4-(4-(3-(3-((2-(2,6-dioxopiperidin-3-yl)-1-oxoisoindolin-5-yl)oxy)azetidin-1-yl)propyl)-1H-1,2,3-triazol-1-yl)benzamide (106); N-((1r,3r)-3-(3-chloro-4-cyanophenoxy)-2,2,4,4-tetramethylcyclobutyl)-6-(4-(2-(1-(2-(2,6-dioxopiperidin-3-yl)-1,3-dioxoisoindolin-5-yl)-1H-1,2,3-triazol-4-yl)ethyl)piperazin-1-yl)nicotinamide (107); N-((1r,3r)-3-(3-chloro-4-cyanophenoxy)-2,2,4,4-tetramethylcyclobutyl)-6-(4-(3-(1-(2-(2,6-dioxopiperidin-3-yl)-1,3-dioxoisoindolin-5-yl)-1H-1,2,3-triazol-4-yl)propyl)piperazin-1-yl)nicotinamide (108); N-((1r,3r)-3-(3-chloro-4-cyanophenoxy)-2,2,4,4-tetramethylcyclobutyl)-6-(6-(4-(2-(2,6-dioxopiperidin-3-yl)-1,3-dioxoisoindolin-5-yl)piperazin-1-yl)hexyl)nicotinamide (109); N-((1r,3r)-3-(3-chloro-4-cyanophenoxy)-2,2,4,4-tetramethylcyclobutyl)-6-(6-(4-(2-(2,6-dioxopiperidin-3-yl)-6-fluoro-1,3-dioxoisoindolin-5-yl)piperazin-1-yl)hexyl)nicotinamide (110); N-((1r,3r)-3-(3-chloro-4-cyanophenoxy)-2,2,4,4-tetramethylcyclobutyl)-6-(4-(3-((2-(2,6-dioxopiperidin-3-yl)-1,3-dioxoisoindolin-5-yl)oxy)propyl)piperazin-1-yl)nicotinamide (111); N-((1r,3r)-3-(3-chloro-4-cyanophenoxy)-2,2,4,4-tetramethylcyclobutyl)-6-(1-(5-((2-(2,6-dioxopiperidin-3-yl)-1,3-dioxoisoindolin-5-yl)oxy)pentyl)piperidin-4-yl)nicotinamide (112); N-((1r,3r)-3-(3-chloro-4-cyanophenoxy)-2,2,4,4-tetramethylcyclobutyl)-6-(1-(3-((2-(2,6-dioxopiperidin-3-yl)-1,3-dioxoisoindolin-5-yl)oxy)propyl)piperidin-4-yl)nicotinamide (113); N-((1r,3r)-3-(4-cyano-3-(trifluoromethyl)phenoxy)-2,2,4,4-tetramethylcyclobutyl)-6-(4-(5-((2-(2,6-dioxopiperidin-3-yl)-1,3-dioxoisoindolin-5-yl)oxy)pentyl)piperazin-1-yl)nicotinamide (114); N-((1r,3r)-3-(3-chloro-4-cyanophenoxy)-2,2,4,4-tetramethylcyclobutyl)-6-(4-(4-((2-(2,6-dioxopiperidin-3-yl)-1,3-dioxoisoindolin-5-yl)oxy)butyl)piperazin-1-yl)nicotinamide (115); N-((1r,3S)-3-(3-chloro-4-cyanophenoxy)-2,2,4,4-tetramethylcyclobutyl)-4-((3S)-4-(5-((2-(2,6-dioxopiperidin-3-yl)-1,3-dioxoisoindolin-5-yl)oxy)pentyl)-3-(hydroxymethyl)piperazin-1-yl)benzamide (116); N-((1r,3r)-3-(3-chloro-4-cyanophenoxy)-2,2,4,4-tetramethylcyclobutyl)-6-(4-(3-(3-((2-(2,6-dioxopiperidin-3-yl)-1-oxoisoindolin-5-yl)oxy)azetidin-1-yl)propyl)-1H-1,2,3-triazol-1-yl)nicotinamide (117); N-((1r,3r)-3-(4-cyano-3-(trifluoromethyl)phenoxy)-2,2,4,4-tetramethylcyclobutyl)-6-(6-(4-(2-(2,6-dioxopiperidin-3-yl)-1,3-dioxoisoindolin-5-yl)piperazin-1-yl)hexyl)nicotinamide (118); N-((1r,3r)-3-(3-chloro-4-cyanophenoxy)-2,2,4,4-tetramethylcyclobutyl)-6-(3-(4-(2-(2,6-dioxopiperidin-3-yl)-1-oxoisoindolin-5-yl)piperazin-1-yl)propyl)nicotinamide (119); N-((1r,3r)-3-(3-chloro-4-cyanophenoxy)-2,2,4,4-tetramethylcyclobutyl)-6-(3-(4-(2-(2,6-dioxopiperidin-3-yl)-1,3-dioxoisoindolin-5-yl)piperazin-1-yl)propyl)nicotinamide (120); N-((1r,3r)-3-(3-chloro-4-cyanophenoxy)-2,2,4,4-tetramethylcyclobutyl)-6-(4-(4-(2-(2,6-dioxopiperidin-3-yl)-1-oxoisoindolin-5-yl)piperidin-1-yl)butyl)nicotinamide (121); N-((1r,3r)-3-(3-chloro-4-cyanophenoxy)-2,2,4,4-tetramethylcyclobutyl)-6-(4-(2-((2-(2,6-dioxopiperidin-3-yl)-1,3-dioxoisoindolin-5-yl)oxy)ethyl)piperazin-1-yl)nicotinamide (122); N-((1r,3r)-3-(3-chloro-4-cyanophenoxy)-2,2,4,4-tetramethylcyclobutyl)-6-(4-(4-(2-(2,6-dioxopiperidin-3-yl)-1,3-dioxoisoindolin-5-yl)piperidin-1-yl)butyl)nicotinamide (123); N-((1r,3r)-3-(3-chloro-4-cyanophenoxy)-2,2,4,4-tetramethylcyclobutyl)-6-(4-(4-(2-(2,6-dioxopiperidin-3-yl)-1,3-dioxoisoindolin-5-yl)piperazin-1-yl)butyl)nicotinamide (124); N-((1r,3r)-3-(3-chloro-4-cyanophenoxy)-2,2,4,4-tetramethylcyclobutyl)-6-(4-(4-(2-(2,6-dioxopiperidin-3-yl)-1-oxoisoindolin-5-yl)piperazin-1-yl)butyl)nicotinamide (125); N-((1r,3r)-3-(4-cyano-3-methylphenoxy)-2,2,4,4-tetramethylcyclobutyl)-6-(4-(5-((2-(2,6-dioxopiperidin-3-yl)-1,3-dioxoisoindolin-5-yl)oxy)pentyl)piperazin-1-yl)nicotinamide (126); N-((1r,3r)-3-(3,4-dicyanophenoxy)-2,2,4,4-tetramethylcyclobutyl)-6-(4-(5-((2-(2,6-dioxopiperidin-3-yl)-1,3-dioxoisoindolin-5-yl)oxy)pentyl)piperazin-1-yl)nicotinamide (127); N-((1r,3r)-3-(3-chloro-4-cyanophenoxy)-2,2,4,4-tetramethylcyclobutyl)-6-(5-(3-((2-(2,6-dioxopiperidin-3-yl)-1,3-dioxoisoindolin-5-yl)oxy)azetidin-1-yl)pentyl)nicotinamide (128); N-((1r,3r)-3-(3-chloro-4-cyanophenoxy)-2,2,4,4-tetramethylcyclobutyl)-6-(4-((4-(2-(2,6-dioxopiperidin-3-yl)-1,3-dioxoisoindolin-5-yl)piperazin-1-yl)methyl)piperidin-1-yl)nicotinamide (129); N-((1r,3r)-3-(3-chloro-4-cyanophenoxy)-2,2,4,4-tetramethylcyclobutyl)-6-(4-(4-((2-(2,6-dioxopiperidin-3-yl)-1,3-dioxoisoindolin-5-yl)oxy)piperidin-1-yl)butyl)nicotinamide (130); N-((1r,3r)-3-(3-chloro-4-cyanophenoxy)-2,2,4,4-tetramethylcyclobutyl)-6-(4-(2-(4-(2-(2,6-dioxopiperidin-3-yl)-1,3-dioxoisoindolin-5-yl)piperazin-1-yl)ethyl)piperidin-1-yl)nicotinamide (131); N-((1r,3r)-3-(3-chloro-4-cyanophenoxy)-2,2,4,4-tetramethylcyclobutyl)-2-(4-(5-((2-(2,6-dioxopiperidin-3-yl)-1,3-dioxoisoindolin-5-yl)oxy)pentyl)piperazin-1-yl)pyrimidine-5-carboxamide (132); N-((1r,3r)-3-(3-chloro-4-cyanophenoxy)-2,2,4,4-tetramethylcyclobutyl)-4-(2-(3-(4-(2-(2,6-dioxopiperidin-3-yl)-1,3-dioxoisoindolin-5-yl)piperazin-1-yl)propoxy)ethyl)-3,5-difluorobenzamide (133); N-((1r,3R)-3-(3-chloro-4-cyanophenoxy)-2,2,4,4-tetramethylcyclobutyl)-4-((3S,5R)-4-(5-((2-(2,6-dioxopiperidin-3-yl)-1,3-dioxoisoindolin-5-yl)oxy)pentyl)-3,5-dimethylpiperazin-1-yl)benzamide (134); N-((1r,3r)-3-(3-chloro-4-cyanophenoxy)-2,2,4,4-tetramethylcyclobutyl)-6-(2-(4-((2-(2,6-dioxopiperidin-3-yl)-1,3-dioxoisoindolin-5-yl)oxy)butyl)-2,6-dihydropyrrolo[3,4-c]pyrazol-5(4H)-yl)nicotinamide (135); N-((1r,3r)-3-(3-chloro-4-cyanophenoxy)-2,2,4,4-tetramethylcyclobutyl)-6-(1-(4-((2-(2,6-dioxopiperidin-3-yl)-1,3-dioxoisoindolin-5-yl)oxy)butyl)-4,6-dihydropyrrolo[3,4-c]pyrazol-5(1H)-yl)nicotinamide (136); N-((1r,3r)-3-(3-chloro-4-cyanophenoxy)-2,2,4,4-tetramethylcyclobutyl)-6-(5-(4-((2-(2,6-dioxopiperidin-3-yl)-1,3-dioxoisoindolin-5-yl)oxy)butyl)-5,6-dihydropyrrolo[3,4-c]pyrazol-2(4H)-yl)nicotinamide (137); N-((1r,3r)-3-(3-chloro-4-cyanophenoxy)-2,2,4,4-tetramethylcyclobutyl)-6-(5-(4-(2-(2,6-dioxopiperidin-3-yl)-1,3-dioxoisoindolin-5-yl)piperazin-1-yl)pentyl)nicotinamide (138); N-((1r,3r)-3-(3-chloro-4-cyanophenoxy)-2,2,4,4-tetramethylcyclobutyl)-6-(6-(4-(2-((S)-2,6-dioxopiperidin-3-yl)-6-fluoro-3-oxoisoindolin-5-yl)piperazin-1-yl)hexyl)nicotinamide (139); N-((1r,3r)-3-(3-chloro-4-cyanophenoxy)-2,2,4,4-tetramethylcyclobutyl)-6-(6-(4-(2-((S)-2,6-dioxopiperidin-3-yl)-6-fluoro-1-oxoisoindolin-5-yl)piperazin-1-yl)hexyl)nicotinamide (140); N-((1r,3r)-3-(3-chloro-4-cyanophenoxy)-2,2,4,4-tetramethylcyclobutyl)-4-(2-(9-(2-(2,6-dioxopiperidin-3-yl)-1,3-dioxoisoindolin-5-yl)-1-oxa-4,9-diazaspiro[5.5]undecan-4-yl)ethyl)benzamide (141); N-((1r,3r)-3-(3-chloro-4-cyanophenoxy)-2,2,4,4-tetramethylcyclobutyl)-2-(4-(4-((2-(2,6-dioxopiperidin-3-yl)-1,3-dioxoisoindolin-5-yl)oxy)butyl)piperazin-1-yl)pyrimidine-5-carboxamide (142); N-((1r,3r)-3-(3-chloro-4-cyanophenoxy)-2,2,4,4-tetramethylcyclobutyl)-2-(4-(3-((2-(2,6-dioxopiperidin-3-yl)-1,3-dioxoisoindolin-5-yl)oxy)propyl)piperazin-1-yl)pyrimidine-5-carboxamide (143); N-((1r,3r)-3-(3-chloro-4-cyanophenoxy)-2,2,4,4-tetramethylcyclobutyl)-2-(4-(2-((2-(2,6-dioxopiperidin-3-yl)-1,3-dioxoisoindolin-5-yl)oxy)ethyl)piperazin-1-yl)pyrimidine-5-carboxamide (144); N-((1r,3r)-3-(3-chloro-4-cyanophenoxy)-2,2,4,4-tetramethylcyclobutyl)-2-(4-((4-(2-(2,6-dioxopiperidin-3-yl)-1,3-dioxoisoindolin-5-yl)piperazin-1-yl)methyl)piperidin-1-yl)pyrimidine-5-carboxamide (145); N-((1r,3r)-3-(4-cyano-3-(trifluoromethyl)phenoxy)-2,2,4,4-tetramethylcyclobutyl)-6-(3-(4-(2-(2,6-dioxopiperidin-3-yl)-1,3-dioxoisoindolin-5-yl)piperazin-1-yl)propyl)nicotinamide (146); N—(R)-1-(3-(3-chloro-4-cyanophenyl)-1H-pyrazol-1-yl)propan-2-yl)-5-((4-(4-(2-(2,6-dioxopiperidin-3-yl)-1,3-dioxoisoindolin-5-yl)piperazin-1-yl)butoxy)methyl)-1H-pyrazole-3-carboxamide (147); N-((1r,3r)-3-(3-chloro-4-cyanophenoxy)-2,2,4,4-tetramethylcyclobutyl)-4-(3-(9-(2-(2,6-dioxopiperidin-3-yl)-1,3-dioxoisoindolin-5-yl)-1-oxa-4,9-diazaspiro[5.5]undecan-4-yl)propyl)benzamide (148); N-((1r,3r)-3-(4-cyano-3-methylphenoxy)-2,2,4,4-tetrameth-ylcyclobutyl)-6-(4-((4-(2-(2,6-dioxopiperidin-3-yl)-1,3-dioxoisoindolin-5-yl)piperazin-1-yl)methyl)piperidin-1-yl) nicotinamide (149); N-((1r,3r)-3-(3-chloro-4-cyanophenoxy)-2,2,4,4-tetramethylcyclobutyl)-2-(4-(2-(4-(2-(2,6-dioxopiperidin-3-yl)-1,3-dioxoisoindolin-5-yl)piperazin-1-yl)ethyl)piperidin-1-yl)pyrimidine-5-carboxamide (150); N-((1r,3r)-3-(3-chloro-4-cyanophenoxy)-2,2,4,4-tetramethylcyclobutyl)-6-(4-(5-((2-((S)-2,6-dioxopiperidin-3-yl)-1,3-dioxoisoindolin-5-yl)oxy)pentyl)piperazin-1-yl)nicotinamide (151); N-((1r,3r)-3-(4-cyano-3-methylphenoxy)-2,2,4,4-tetramethylcyclobutyl)-6-(4-(2-(4-(2-(2,6-dioxopiperidin-3-yl)-1,3-dioxoisoindolin-5-yl)piperazin-1-yl)ethyl)piperidin-1-yl)nicotinamide (152); N-((1r,3r)-3-(4-cyano-3-(trifluoromethyl)phenoxy)-2,2,4,4-tetramethylcyclobutyl)-6-(4-(2-(4-(2-(2,6-dioxopiperidin-3-yl)-1,3-dioxoisoindolin-5-yl)piperazin-1-yl)ethyl)piperidin-1-yl)nicotinamide (153); N-((1r,3r)-3-(3-chloro-4-cyanophenoxy)-2,2,4,4-tetramethylcyclobutyl)-6-(4-(5-((2-(2,6-dioxopiperidin-3-yl)-1,3-dioxoisoindolin-5-yl)oxy)pentyl)-3-oxopiperazin-1-yl)nicotinamide (154); N-((1r,3r)-3-(3-chloro-4-cyanophenoxy)-2,2,4,4-tetramethylcyclobutyl)-2-(4-(4-(3-((2-(2,6-dioxopiperidin-3-yl)-1,3-dioxoisoindolin-5-yl)oxy)azetidin-1-yl)butyl)piperazin-1-yl)pyrimidine-5-carboxamide (155); N-((1r,3r)-3-(3-chloro-4-cyanophenoxy)-2,2,4,4-tetramethylcyclobutyl)-2-(4-(3-(3-((2-(2,6-dioxopiperidin-3-yl)-1,3-dioxoisoindolin-5-yl)oxy)azetidin-1-yl)propyl)piperazin-1-yl)pyrimidine-5-carboxamide (156); 2-chloro-4-(3-(4-(5-(4-(2-(2,6-dioxopiperidin-3-yl)-1,3-dioxoisoindolin-5-yl)piperazin-1-yl)pentyl)-3-fluorophenyl)-4,4-dimethyl-5-oxo-2-thioxoimidazolidin-1-yl)benzonitrile (157); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (158); 2-chloro-4-(5-(4-(5-(4-(2-(2,6-dioxopiperidin-3-yl)-1,3-dioxoisoindolin-5-yl)piperazin-1-yl)pentyl)-3-fluorophenyl)-8-oxo-6-thioxo-5,7-diazaspiro[3.4]octan-7-yl)benzonitrile (159); N-((1r,3r)-3-(3-chloro-4-cyanophenoxy)-2,2,4,4-tetramethylcyclobutyl)-6-(4-(2-(4-(2-(2,6-dioxopiperidin-3-yl)-1-oxoisoindolin-5-yl)piperazin-1-yl)ethyl)piperidin-1-yl)nicotinamide (160); N-((1r,3r)-3-(3,4-dicyanophenoxy)-2,2,4,4-tetramethylcyclobutyl)-2-(4-(2-(4-(2-(2,6-dioxopiperidin-3-yl)-1,3-dioxoisoindolin-5-yl)piperazin-1-yl)ethyl)piperidin-1-yl)pyrimidine-5-carboxamide (161); N-((1r,3r)-3-(3-chloro-4-cyanophenoxy)-2,2,4,4-tetramethylcyclobutyl)-6-(2-(2-(2,6-dioxopiperidin-3-yl)-1,3-dioxoisoindolin-5-yl)-2,7-diazaspiro[3.5]nonan-7-yl)nicotinamide (162); N-((1r,3r)-3-(3-chloro-4-cyanophenoxy)-2,2,4,4-tetramethylcyclobutyl)-6-(7-(2-(2,6-dioxopiperidin-3-yl)-1,3-dioxoisoindolin-5-yl)-2,7-diazaspiro[3.5]nonan-2-yl)nicotinamide (163); N-((1r,3r)-3-(3-chloro-4-cyanophenoxy)-2,2,4,4-tetramethylcyclobutyl)-6-(2-(5-((2-(2,6-dioxopiperidin-3-yl)-1,3-dioxoisoindolin-5-yl)oxy)pentyl)-2,6-dihydropyrrolo[3,4-c]pyrazol-5(4H)-yl)nicotinamide (164); N-((1r,3r)-3-(3-chloro-4-cyanophenoxy)-2,2,4,4-tetramethylcyclobutyl)-2-(3-(2-((2-(2,6-dioxopiperidin-3-yl)-1,3-dioxoisoindolin-5-yl)oxy)ethyl)azetidin-1-yl)pyrimidine-5-carboxamide (165); N-((1r,3r)-3-(3-chloro-4-cyanophenoxy)-2,2,4,4-tetramethylcyclobutyl)-4-(4-((2-(2,6-dioxopiperidin-3-yl)-1,3-dioxoisoindolin-5-yl)oxy)butyl)piperazin-1-yl)-2,6-difluorobenzamide (166); N-((1r,3r)-3-(3-chloro-4-cyanophenoxy)-2,2,4,4-tetramethylcyclobutyl)-2-(4-((1-(2-(2,6-dioxopiperidin-3-yl)-1,3-dioxoisoindolin-5-yl)piperidin-4-yl)methyl)-1,4-diazepan-1-yl)pyrimidine-5-carboxamide (167); N-((1r,3r)-3-(3-chloro-4-cyanophenoxy)-2,2,4,4- tetramethylcyclobutyl)-4-(4-(2-((2-(2,6-dioxopiperidin-3-yl)-1,3-dioxoisoindolin-5-yl)oxy)ethyl)-1-oxa-4,9-diazaspiro[5.5]undecan-9-yl)benzamide (168); N-((1r,3r)-3-(3-chloro-4-cyanophenoxy)-2,2,4,4-tetramethylcyclobutyl)-4-(4-(3-((2-(2,6-dioxopiperidin-3-yl)-1,3-dioxoisoindolin-5-yl)oxy)propyl)-1-oxa-4,9-diazaspiro[5.5]undecan-9-yl)benzamide (169); N-((1r,3r)-3-(3-chloro-4-cyanophenoxy)-2,2,4,4-tetramethylcyclobutyl)-4-(2-(4-(2-(2,6-dioxopiperidin-3-yl)-6-fluoro-1,3-dioxoisoindolin-5-yl)piperazin-1-yl)ethyl)benzamide (170); N-((1r,3R)-3-(3-chloro-4-cyanophenoxy)-2,2,4,4-tetramethylcyclobutyl)-4-(2-((1R,4R)-5-(2-(2,6-dioxopiperidin-3-yl)-1,3-dioxoisoindolin-5-yl)-2,5-diazabicyclo[2.2.1]heptan-2-yl)ethyl)benzamide (171); N-((1r,3r)-3-(3-chloro-4-cyanophenoxy)-2,2,4,4-tetramethylcyclobutyl)-4-(4-(4-(2-(2,6-dioxopiperidin-3-yl)-1,3-dioxoisoindolin-5-yl)piperazine-1-carbonyl)piperidin-1-yl)benzamide (172); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)-3,5-difluorobenzamide (173); N-((1r,3r)-3-(3-chloro-4-cyanophenoxy)-2,2,4,4-tetramethylcyclobutyl)-4-(4-(2-(4-(2-(2,6-dioxopiperidin-3-yl)-1,3-dioxoisoindolin-5-yl)piperazin-1-yl)ethyl)piperidin-1-yl)benzamide (174); N-((1r,3R)-3-(3-chloro-4-cyanophenoxy)-2,2,4,4-tetramethylcyclobutyl)-4-(4-(((1R,4R)-5-(2-(2,6-dioxopiperidin-3-yl)-1,3-dioxoisoindolin-5-yl)-2,5-diazabicyclo[2.2.1]heptan-2-yl)methyl)piperidin-1-yl)benzamide (175); N-((1r,3S)-3-(3-chloro-4-cyanophenoxy)-2,2,4,4-tetramethylcyclobutyl)-4-(4-(((1S,4S)-5-(2-(2,6-dioxopiperidin-3-yl)-1,3-dioxoisoindolin-5-yl)-2,5-diazabicyclo[2.2.1]heptan-2-yl)methyl)piperidin-1-yl)benzamide (176); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)-3-fluorobenzamide (177); N-((1r,3r)-3-(3-chloro-4-cyanophenoxy)-2,2,4,4-tetramethylcyclobutyl)-4-(4-((((1r,3r)-3-((2-(2,6-dioxopiperidin-3-yl)-1,3-dioxoisoindolin-5-yl)oxy)cyclobutyl)(methyl)amino)methyl)piperidin-1-yl)benzamide (178); N-((1r,3r)-3-(3-chloro-4-cyanophenoxy)-2,2,4,4-tetramethylcyclobutyl)-6-(4-((4-(2-(2,6-dioxopiperidin-3-yl)-1,3-dioxoisoindolin-5-yl)piperazin-1-yl)methyl)piperidin-1-yl)-5-fluoronicotinamide (179); N-((1r,3r)-3-(3-chloro-4-cyanophenoxy)-2,2,4,4-tetramethylcyclobutyl)-4-(4-((4-(2-(2,6-dioxopiperidin-3-yl)-4-fluoro-1,3-dioxoisoindolin-5-yl)piperazin-1-yl)methyl)piperidin-1-yl)benzamide (180); N-((1r,3r)-3-(3-chloro-4-cyanophenoxy)-2,2,4,4-tetramethylcyclobutyl)-4-((4-(2-(2,6-dioxopiperidin-3-yl)-4,6-difluoro-1,3-dioxoisoindolin-5-yl)piperazin-1-yl)methyl)piperidin-1-yl)benzamide (181); N-((1r,3R)-3-(3-chloro-4-cyanophenoxy)-2,2,4,4-tetramethylcyclobutyl)-4-((3R)-3-((4-(2-(2,6-dioxopiperidin-3-yl)-6-fluoro-1,3-dioxoisoindolin-5-yl)piperazin-1-yl)methyl)pyrrolidin-1-yl)benzamide (182); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)cyclohexyl)benzamide (183); N-((1r,3r)-3-(4-cyano-3-methylphenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)cyclohexyl)benzamide (184); N-((1r,3r)-3-(3-chloro-4-cyanophenoxy)-2,2,4,4-tetramethylcyclobutyl)-4-(4-((4-(2-(2,6-dioxopiperidin-3-yl)-6-fluoro-1-oxoisoindolin-5-yl)piperazin-1-yl)methyl)piperidin-1-yl)benzamide (185); N-((1r,3r)-3-(3-chloro-4-cyanophenoxy)-2,2,4,4-tetramethylcyclobutyl)-4-(4-((4-(2-(2,6-dioxopiperidin-3-yl)-6-fluoro-1-oxoisoindolin-5-yl)piperazin-1-yl)methyl)piperidin-1-yl)benzamide (186); N-((1r,3r)-3-(3-chloro-4-cyanophenoxy)-2,2,4,4-tetramethylcyclobutyl)-4-(4-(2-(4-(2-(2,6-dioxopiperidin-3-yl)-6-fluoro-1-oxoisoindolin-5-yl)piperazin-1-yl)ethyl)piperidin-1-yl)benzamide (187); N-((1r,3r)-3-(3-chloro-4-cyanophenoxy)-2,2,4,4-tetramethylcyclobutyl)-4-(4-(2-(4-(2-(2,6-dioxopiperidin-3-yl)-6-fluoro-3-oxoisoindolin-5-yl)piperazin-1-yl)ethyl)piperidin-1-yl)benzamide (188); N-((1r,3r)-3-(3-chloro-4-cyanophenoxy)-2,2,4,4-tetramethylcyclobutyl)-4-(3-(2-(4-(2-(2,6-dioxopiperidin-3-yl)-1,3-dioxoisoindolin-5-yl)piperazin-1-yl)ethyl)azetidin-1-yl)benzamide (189); N-((1r,3r)-3-(3-chloro-4-cyanophenoxy)-2,2,4,4-tetramethylcyclobutyl)-4-(4-(2-(3-((2-(2,6-dioxopiperidin-3-yl)-1,3-dioxoisoindolin-5-yl)oxy)azetidin-1-yl)ethyl)piperidin-1-yl)benzamide (190); N-((1r,3r)-3-(3-chloro-4-cyanophenoxy)-2,2,4,4-tetramethylcyclobutyl)-2-(4-((4-(2-(2,6-dioxopiperidin-3-yl)-1,3-dioxoisoindolin-5-yl)piperazin-1-yl)methyl)azepan-1-yl)pyrimidine-5-carboxamide (191); N-((1r,3r)-3-(3-chloro-4-cyanophenoxy)-2,2,4,4-tetramethylcyclobutyl)-4-(4-(4-(2-(2,6-dioxopiperidin-3-yl)-1,3-dioxoisoindolin-5-yl)piperazin-1-yl)cyclohexyl)benzamide (192); N-((1r,3R)-3-(3-chloro-4-cyanophenoxy)-2,2,4,4-tetramethylcyclobutyl)-6-((3S,5R)-4-(3-((2-(2,6-dioxopiperidin-3-yl)-1,3-dioxoisoindolin-5-yl)oxy)propyl)-3,5-dimethylpiperazin-1-yl)nicotinamide (193); N-((1r,3R)-3-(3-chloro-4-cyanophenoxy)-2,2,4,4-tetramethylcyclobutyl)-4-((3S,5R)-4-(3-((2-(2,6-dioxopiperidin-3-yl)-1,3-dioxoisoindolin-5-yl)oxy)propyl)-3,5-dimethylpiperazin-1-yl)benzamide (194); N-((1r,3R)-3-(3-chloro-4-cyanophenoxy)-2,2,4,4-tetramethylcyclobutyl)-2-((3S,5R)-4-(3-((2-(2,6-dioxopiperidin-3-yl)-1,3-dioxoisoindolin-5-yl)oxy)propyl)-3,5-dimethylpiperazin-1-yl)pyrimidine-5-carboxamide (195); N-((1r,3r)-3-(3-chloro-4-cyanophenoxy)-2,2,4,4-tetramethylcyclobutyl)-4-(4-((1s,3S)-3-(((2-(2,6-dioxopiperidin-3-yl)-1,3-dioxoisoindolin-5-yl)oxy)methyl)cyclobutyl)piperazin-1-yl)benzamide (196); N-((1r,3r)-3-(3-chloro-4-cyanophenoxy)-2,2,4,4-tetramethylcyclobutyl)-4-(2-(4-2-(2,6-dioxopiperidin-3-yl)-1,3-dioxoisoindolin-5-yl)piperazin-1-yl)ethyl)-2-fluorobenzamide (197); N-((1r,3r)-3-(3-chloro-4-cyanophenoxy)-2,2,4,4-tetramethylcyclobutyl)-4-(3-(4-(2-(2,6-dioxopiperidin-3-yl)-1,3-dioxoisoindolin-5-yl)piperazin-1-yl)azetidin-1-yl)piperidin-1-yl)benzamide (198); N-((1r,3R)-3-(3-chloro-4-cyanophenoxy)-2,2,4,4-tetramethylcyclobutyl)-4-((3R)-3-(((1-(2-(2,6-dioxopiperidin-3-yl)-1,3-dioxoisoindolin-5-yl)piperidin-4-yl)methyl)(methyl)amino)pyrrolidin-1-yl)benzamide (199); N-((1r,3S)-3-(3-chloro-4-cyanophenoxy)-2,2,4,4-tetramethylcyclobutyl)-4-((3S)-3-(((1-(2-(2,6-dioxopiperidin-3-yl)-1,3-dioxoisoindolin-5-yl)piperidin-4-yl)methyl)(methyl)amino)pyrrolidin-1-yl)benzamide (200); N-((1r,3R)-3-(3-chloro-4-cyanophenoxy)-2,2,4,4-tetramethylcyclobutyl)-4-((3R)-3-(((1-(2-(2,6-dioxopiperidin-3-yl)-1,3-dioxoisoindolin-5-yl)piperidin-4-yl)(methyl)amino)methyl)pyrrolidin-1-yl)benzamide (201); N-((1r,3R)-3-(3-chloro-4-cyanophenoxy)-2,2,4,4-tetramethylcyclobutyl)-4-(2-((2S,6R)-4-(2-(2,6-dioxopiperidin-3-yl)-1,3-dioxoisoindolin-5-yl)-2,6-dimethylpiperazin-1-yl)ethyl)benzamide (202); N-((1r,3r)-3-(3-chloro-4-cyanophenoxy)-2,2,4,4-tetramethylcyclobutyl)-4-(3-(4-(2-(2,6-dioxopiperidin-3-yl)-1,3-dioxoisoindolin-5-yl)piperazin-1-yl)-[1,3'-biazetidin]-1'-yl)benzamide (203); N-((1r,3r)-3-(3-chloro-4-cyanophenoxy)-2,2,4,4-tetramethylcyclobutyl)-4-(4-(2-(((1r,3r)-3-((2-(2,6-dioxopiperidin-3-yl)-1,3-dioxoisoindolin-5-yl)oxy)cyclobutyl)(methyl)amino)ethyl)piperazin-1-yl)benzamide (204); N-((1r,3r)-3-(3-chloro-4-cyanophenoxy)-2,2,4,4-tetramethylcyclobutyl)-4-(4-(1-(2-

((2-(2,6-dioxopiperidin-3-yl)-1,3-dioxoisoindolin-5-yl)oxy)ethyl)azetidin-3-yl)piperazin-1-yl)benzamide (205); N-((1r,3r)-3-(3-chloro-4-cyanophenoxy)-2,2,4,4-tetramethylcyclobutyl)-4-(2-(4-(1-(2-(2,6-dioxopiperidin-3-yl)-1,3-dioxoisoindolin-5-yl)azetidin-3-yl)piperazin-1-yl)ethyl)benzamide (206); N-((1r,3R)-3-(3-chloro-4-cyanophenoxy)-2,2,4,4-tetramethylcyclobutyl)-4-(2-((2R,6R)-4-(2-(2,6-dioxopiperidin-3-yl)-1,3-dioxoisoindolin-5-yl)-2,6-dimethylpiperazin-1-yl)ethyl)benzamide (207); N-((1r,3S)-3-(3-chloro-4-cyanophenoxy)-2,2,4,4-tetramethylcyclobutyl)-4-((3S)-3-((4-(2-(2,6-dioxopiperidin-3-yl)-1,3-dioxoisoindolin-5-yl)piperazin-1-yl)methyl)pyrrolidin-1-yl)benzamide (208); N-((1r,3S)-3-(3-chloro-4-cyanophenoxy)-2,2,4,4-tetramethylcyclobutyl)-4-(2-((2S,6S)-4-(2-(2,6-dioxopiperidin-3-yl)-1,3-dioxoisoindolin-5-yl)-2,6-dimethylpiperazin-1-yl)ethyl)benzamide (209); N-((1r,3r)-3-(3-chloro-4-cyanophenoxy)-2,2,4,4-tetramethylcyclobutyl)-4-(3-((4-(2-(2,6-dioxopiperidin-3-yl)-1,3-dioxoisoindolin-5-yl)piperazin-1-yl)methyl)azetidin-1-yl)benzamide (210); N-((1r,3r)-3-(3-chloro-4-cyanophenoxy)-2,2,4,4-tetramethylcyclobutyl)-4-(3-(2-(4-(2-(2,6-dioxopiperidin-3-yl)-1,3-dioxoisoindolin-5-yl)piperazin-1-yl)ethyl)pyrrolidin-1-yl)benzamide (211); N-((1r,3r)-3-(3-chloro-4-cyanophenoxy)-2,2,4,4-tetramethylcyclobutyl)-4-(4-(2-(4-(6-(2,6-dioxopiperidin-3-yl)-5,7-dioxo-6,7-dihydro-5H-pyrrolo[3,4-b]pyrazin-2-yl)piperazin-1-yl)ethyl)piperidin-1-yl)benzamide (212); N-((1r,3r)-3-(3-chloro-4-cyanophenoxy)-2,2,4,4-tetramethylcyclobutyl)-4-(4-((4-(2-(2,6-dioxopiperidin-3-yl)-7-fluoro-1,3-dioxoisoindolin-5-yl)piperazin-1-yl)methyl)piperidin-1-yl)benzamide (213); N-((1r,3r)-3-(3-chloro-4-cyanophenoxy)-2,2,4,4-tetramethylcyclobutyl)-4-(4-((4-(2-(2,6-dioxopiperidin-3-yl)-4-fluoro-1-oxoisoindolin-5-yl)piperazin-1-yl)methyl)piperidin-1-yl)benzamide (214); N-((1r,3S)-3-(3-chloro-4-cyanophenoxy)-2,2,4,4-tetramethylcyclobutyl)-6-((4aR,6R,8aS)-6-(4-(2-(2,6-dioxopiperidin-3-yl)-1,3-dioxoisoindolin-5-yl)piperazin-1-yl)octahydroisoquinolin-2(1H)-yl)nicotinamide (215); N-((1r,3r)-3-(3-chloro-4-cyanophenoxy)-2,2,4,4-tetramethylcyclobutyl)-4-(3-(2-(((1r,3r)-3-((2-(2,6-dioxopiperidin-3-yl)-1,3-dioxoisoindolin-5-yl)oxy)cyclobutyl)(methyl)amino)ethyl)azetidin-1-yl)benzamide (216); N-((1r,3r)-3-(3-chloro-4-cyanophenoxy)-2,2,4,4-tetramethylcyclobutyl)-4-(4-(3-((2-(2,6-dioxopiperidin-3-yl)-4-fluoro-1,3-dioxoisoindolin-5-yl)oxy)propyl)piperazin-1-yl)benzamide (217); N-((1r,3R)-3-(3-chloro-4-cyanophenoxy)-2,2,4,4-tetramethylcyclobutyl)-4-((1r,3R)-3-((4-(2-(2,6-dioxopiperidin-3-yl)-1,3-dioxoisoindolin-5-yl)piperazin-1-yl)methyl)cyclobutyl)benzamide (218); N-((1r,3R)-3-(3-chloro-4-cyanophenoxy)-2,2,4,4-tetramethylcyclobutyl)-4-((1s,3S)-3-((4-(2-(2,6-dioxopiperidin-3-yl)-1,3-dioxoisoindolin-5-yl)piperazin-1-yl)methyl)cyclobutyl)benzamide (219); N-((1r,3R)-3-(3-chloro-4-cyanophenoxy)-2,2,4,4-tetramethylcyclobutyl)-6-((4aR,6S,8aR)-6-(4-(2-(2,6-dioxopiperidin-3-yl)-1,3-dioxoisoindolin-5-yl)piperazin-1-yl)octahydroisoquinolin-2(1H)-yl)nicotinamide (220); N-((1r,3R)-3-(3-chloro-4-cyanophenoxy)-2,2,4,4-tetramethylcyclobutyl)-6-((4aR,6R,8aR)-6-(4-(2-(2,6-dioxopiperidin-3-yl)-1,3-dioxoisoindolin-5-yl)piperazin-1-yl)octahydroisoquinolin-2(1H)-yl)nicotinamide (221); N-((1r,3r)-3-(3-chloro-4-cyanophenoxy)-2,2,4,4-tetramethylcyclobutyl)-6-(4-(4-(2-(2,6-dioxopiperidin-3-yl)-1,3-dioxoisoindolin-5-yl)piperazin-1-yl)piperidin-1-yl)pyridazine-3-carboxamide (222); N-((1r,3r)-3-(3-chloro-4-cyanophenoxy)-2,2,4,4-tetramethylcyclobutyl)-4-((3R)-3-(4-(2-(2,6-dioxopiperidin-3-yl)-1,3-dioxoisoindolin-5-yl)piperazin-1-yl)pyrrolidin-1-yl)benzamide (223); N-((1r,3r)-3-(3-chloro-4-cyanophenoxy)-2,2,4,4-tetramethylcyclobutyl)-4-(4-(1-(2-(2,6-dioxopiperidin-3-yl)-1,3-dioxoisoindolin-5-yl)azetidin-3-yl)piperazin-1-yl)benzamide (224); N-((1r,3R)-3-(3-chloro-4-cyanophenoxy)-2,2,4,4-tetramethylcyclobutyl)-4-((3R)-3-(4-(2-(2,6-dioxopiperidin-3-yl)-1,3-dioxoisoindolin-5-yl)piperazine-1-carbonyl)pyrrolidin-1-yl)benzamide (225); N-((1r,3R)-3-(3-chloro-4-cyanophenoxy)-2,2,4,4-tetramethylcyclobutyl)-4-((3R)-3-(4-(2-(2,6-dioxopiperidin-3-yl)-6-fluoro-1,3-dioxoisoindolin-5-yl)piperazine-1-carbonyl)pyrrolidin-1-yl)benzamide (226); N-((1r,3r)-3-(3-chloro-4-cyanophenoxy)-2,2,4,4-tetramethylcyclobutyl)-4-(3-((4-(2-(2,6-dioxopiperidin-3-yl)-6-fluoro-1,3-dioxoisoindolin-5-yl)piperazin-1-yl)methyl)pyrrolidin-1-yl)benzamide (227); N-((1r,3R)-3-(3-chloro-4-cyanophenoxy)-2,2,4,4-tetramethylcyclobutyl)-4-(4-(((3R)-1-(2-(2,6-dioxopiperidin-3-yl)-6-fluoro-1,3-dioxoisoindolin-5-yl)pyrrolidin-3-yl)methyl)piperazin-1-yl)benzamide (228); N-((1r,3r)-3-(3-chloro-4-cyanophenoxy)-2,2,4,4-tetramethylcyclobutyl)-4-(6-(2-((2-(2,6-dioxopiperidin-3-yl)-1,3-dioxoisoindolin-5-yl)oxy)ethyl)-2,6-diazaspiro[3.3]heptan-2-yl)benzamide (229); (3R)—N-(1-(4-(((1r,3R)-3-(3-chloro-4-cyanophenoxy)-2,2,4,4-tetramethylcyclobutyl)carbamoyl)phenyl)piperidin-4-yl)-1-(2-(2,6-dioxopiperidin-3-yl)-1,3-dioxoisoindolin-5-yl)-N-methylpyrrolidine-3-carboxamide (230); N-((1r,3r)-3-(3-chloro-4-cyanophenoxy)-2,2,4,4-tetramethylcyclobutyl)-6-(4-(2-(4-(2-(2,6-dioxopiperidin-3-yl)-6-fluoro-1,3-dioxoisoindolin-5-yl)piperazin-1-yl)ethyl)piperidin-1-yl)pyridazine-3-carboxamide (231); N-((1r,3R)-3-(3-chloro-4-cyanophenoxy)-2,2,4,4-tetramethylcyclobutyl)-2-((2S,4R,6R)-4-((4-(2-(2,6-dioxopiperidin-3-yl)-1,3-dioxoisoindolin-5-yl)piperazin-1-yl)methyl)-2,6-dimethylpiperidin-1-yl)pyrimidine-5-carboxamide (232); N-((1r,3R)-3-(3-chloro-4-cyanophenoxy)-2,2,4,4-tetramethylcyclobutyl)-2-((2S,4S,6R)-4-((4-(2-(2,6-dioxopiperidin-3-yl)-1,3-dioxoisoindolin-5-yl)piperazin-1-yl)methyl)-2,6-dimethylpiperidin-1-yl)pyrimidine-5-carboxamide (233); N-((1r,3S)-3-(3-chloro-4-cyanophenoxy)-2,2,4,4-tetramethylcyclobutyl)-2-((2S,6S)-4-((4-(2-(2,6-dioxopiperidin-3-yl)-1,3-dioxoisoindolin-5-yl)piperazin-1-yl)methyl)-2,6-dimethylpiperidin-1-yl)pyrimidine-5-carboxamide (234); N-((1r,3r)-3-(3-chloro-4-cyanophenoxy)-2,2,4,4-tetramethylcyclobutyl)-4-(3-(3-((2-(2,6-dioxopiperidin-3-yl)-1,3-dioxoisoindolin-5-yl)oxy)azetidin-1-yl)propyl)azetidin-1-yl)benzamide (235); N-((1r,3r)-3-(3-chloro-4-cyanophenoxy)-2,2,4,4-tetramethylcyclobutyl)-6-(7-((3-(2-(2,6-dioxopiperidin-3-yl)-1,3-dioxoisoindolin-5-yl)piperidin-1-yl)methyl)octahydro-2H-pyrido[1,2-a]pyrazin-2-yl)nicotinamide (236); N-((1r,3r)-3-(3-chloro-4-cyanophenoxy)-2,2,4,4-tetramethylcyclobutyl)-4-(4-((((1r,3r)-3-((2-(2,6-dioxopiperidin-3-yl)-1,3-dioxoisoindolin-5-yl)oxy)cyclobutyl)methyl)(methyl)amino)piperidin-1-yl)benzamide (237); N-((1r,3r)-3-(3-chloro-4-cyanophenoxy)-2,2,4,4-tetramethylcyclobutyl)-4-((1'-(2-(2,6-dioxopiperidin-3-yl)-1,3-dioxoisoindolin-5-yl)-[1,4'-bipiperidin]-4-yl)amino)benzamide (238); N-((1r,3r)-3-(3-chloro-4-cyanophenoxy)-2,2,4,4-tetramethylcyclobutyl)-4-(4-(2-(4-(2-(2,6-dioxopiperidin-3-yl)-1,3-dioxoisoindolin-5-yl)piperazin-1-yl)ethyl)piperazin-1-yl)benzamide (239); N-((1r,3r)-3-(3-chloro-4-cyanophenoxy)-2,2,4,4-tetramethylcyclobutyl)-4-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)benzamide (240); N-((1r,3S)-3-(3-chloro-4-cyanophenoxy)-2,2,4,4-tetramethylcyclobutyl)-2-((1S,4S,5R)-5-((4-(2-(2,6-dioxopiperidin-3-yl)-1,3-dioxoisoindolin-5-yl)piperazin-1-yl)methyl)-2-azabicyclo[2.2.1]heptan-2-yl)pyrimidine-5- carboxamide (241); N-((1r,3S)-3-(3-chloro-4-cyanophenoxy)-2,2,4,4-tetramethylcyclobutyl)-2-((1S,4S,5S)-5-((4-(2-(2,6-dioxopiperidin-3-yl)-1,3-dioxoisoindolin-5-yl)piperazin-1-yl)methyl)-2-azabicyclo[2.2.1]heptan-2-yl)pyrimidine-5-carboxamide (242); N-((1r,3r)-3-(3-chloro-4-cyanophenoxy)-2,2,4,4-tetramethylcyclobutyl)-2-(4-((4-(2-(2,6-dioxopiperidin-3-yl)-6-fluoro-1,3-dioxoisoindolin-5-yl)piperazin-1-yl)methyl)piperidin-1-yl)pyrimidine-5-carboxamide (243); N-((1r,3R)-3-(3-chloro-4-cyanophenoxy)-2,2,4,4-tetramethylcyclobutyl)-4-((3R)-3-((2-((2-(2,6-dioxopiperidin-3-yl)-1,3-dioxoisoindolin-5-yl)oxy)ethyl)(methyl)amino)pyrrolidin-1-yl)benzamide (244); N-((1r,3R)-3-(3-chloro-4-cyanophenoxy)-2,2,4,4-tetramethylcyclobutyl)-4-((3R)-3-(3-((2-(2,6-dioxopiperidin-3-yl)-1,3-dioxoisoindolin-5-yl)oxy)azetidin-1-yl)pyrrolidin-1-yl)benzamide (245); N-((1r,3r)-3-(3-chloro-4-cyanophenoxy)-2,2,4,4-tetramethylcyclobutyl)-4-(5-(2-((2-(2,6-dioxopiperidin-3-yl)-1,3-dioxoisoindolin-5-yl)oxy)ethyl)hexahydropyrrolo[3,4-c]pyrrol-2(1H)-yl)benzamide (246); N-((1r,3r)-3-(4-cyano-3-methylphenoxy)-2,2,4,4-tetramethylcyclobutyl)-2-(4-((4-(2-(2,6-dioxopiperidin-3-yl)-1,3-dioxoisoindolin-5-yl)piperazin-1-yl)methyl)piperidin-1-yl)pyrimidine-5-carboxamide (247); N-((1r,3r)-3-(3-chloro-4-cyanophenoxy)-2,2,4,4-tetramethylcyclobutyl)-4-(4-(4-(2-((S)-2,6-dioxopiperidin-3-yl)-1-oxoisoindolin-5-yl)piperazin-1-yl)butyl)benzamide (248); N-((1r,3r)-3-(3-chloro-4-cyanophenoxy)-2,2,4,4-tetramethylcyclobutyl)-4-(4-(4-(2-((R)-2,6-dioxopiperidin-3-yl)-1-oxoisoindolin-5-yl)piperazin-1-yl)butyl)benzamide (249); N-((1r,3r)-3-(3-chloro-4-cyanophenoxy)-2,2,4,4-tetramethylcyclobutyl)-4-(6-(4-(2-((S)-2,6-dioxopiperidin-3-yl)-1-oxoisoindolin-5-yl)piperazin-1-yl)hexyl)benzamide (250); N-((1r,3r)-3-(3-chloro-4-cyanophenoxy)-2,2,4,4-tetramethylcyclobutyl)-4-(6-(4-(2-((R)-2,6-dioxopiperidin-3-yl)-1-oxoisoindolin-5-yl)piperazin-1-yl)hexyl)benzamide (251); N-((1r,3r)-3-(4-cyano-3-(trifluoromethyl)phenoxy)-2,2,4,4-tetramethylcyclobutyl)-4-(4-(5-((2-(2,6-dioxopiperidin-3-yl)-1,3-dioxoisoindolin-5-yl)oxy)pentyl)piperazin-1-yl)benzamide (252); N-((1r,3r)-3-(4-cyano-3-(trifluoromethyl)phenoxy)-2,2,4,4-tetramethylcyclobutyl)-4-(6-((2S,6R)-4-(2-(2,6-dioxopiperidin-3-yl)-1,3-dioxoisoindolin-5-yl)-2,6-dimethylpiperazin-1-yl)hexyl)benzamide (253); N-((1r,3r)-3-(3-chloro-4-cyanophenoxy)-2,2,4,4-tetramethylcyclobutyl)-4-((3-(2-(4-(2-(2,6-dioxopiperidin-3-yl)-1-oxoisoindolin-5-yl)-3,6-dihydropyridin-1(2H)-yl)ethyl)oxetan-3-yl)methyl)benzamide (254); N-((1r,3r)-3-(4-cyano-3-(trifluoromethyl)phenoxy)-2,2,4,4-tetramethylcyclobutyl)-4-(4-(2-((2-(2,6-dioxopiperidin-3-yl)-1,3-dioxoisoindolin-5-yl)oxy)ethyl)piperazin-1-yl)benzamide (255); N-((1r,3r)-3-(3-chloro-4-cyanophenoxy)-2,2,4,4-tetramethylcyclobutyl)-4-(6-((1S,4S)-5-(2-((S)-2,6-dioxopiperidin-3-yl)-1-oxoisoindolin-5-yl)-2,5-diazabicyclo[2.2.1]heptan-2-yl)hexyl)benzamide (256); N-((1r,3r)-3-(3-chloro-4-cyanophenoxy)-2,2,4,4-tetramethylcyclobutyl)-4-(4-(2-((2-(2,6-dioxopiperidin-3-yl)-1,3-dioxoisoindolin-5-yl)oxy)ethyl)piperazin-1-yl)benzamide (257); N-((1r,3r)-3-(3-chloro-4-cyanophenoxy)-2,2,4,4-tetramethylcyclobutyl)-4-(6-((1R,4R)-5-(2-((S)-2,6-dioxopiperidin-3-yl)-1-oxoisoindolin-5-yl)-2,5-diazabicyclo[2.2.1]heptan-2-yl)hexyl)benzamide (258); N-((1r,3r)-3-(3-chloro-4-cyanophenoxy)-2,2,4,4-tetramethylcyclobutyl)-4-(6-((1R,4R)-5-((R)-2,6-dioxopiperidin-3-yl)-1-oxoisoindolin-5-yl)-2,5-diazabicyclo[2.2.1]heptan-2-yl)hexyl)benzamide (259); N-((1r,3r)-3-(3-chloro-4-cyanophenoxy)-2,2,4,4-tetramethylcyclobutyl)-4-((3-(2-(4-(2-(2,6-dioxopiperidin-3-yl)-1-oxoisoindolin-5-yl)piperazin-1-yl)ethyl)oxetan-3-yl)methyl)benzamide (260); N-((1r,3r)-3-(3-chloro-4-cyanophenoxy)-2,2,4,4-tetramethylcyclobutyl)-6-(1-(2-((2-(2,6-dioxopiperidin-3-yl)-1,3-dioxoisoindolin-5-yl)oxy)ethyl)piperidin-4-yl)nicotinamide (261); N-((1r,3r)-3-(3-chloro-4-cyanophenoxy)-2,2,4,4-tetramethylcyclobutyl)-6-(1-(4-((2-(2,6-dioxopiperidin-3-yl)-1,3-dioxoisoindolin-5-yl)oxy)butyl)piperidin-4-yl)nicotinamide (262); N-((1r,3r)-3-((5-cyano-6-methylpyridin-2-yl)oxy)-2,2,4,4-tetramethylcyclobutyl)-6-(4-(5-((2-(2,6-dioxopiperidin-3-yl)-1,3-dioxoisoindolin-5-yl)oxy)pentyl)piperazin-1-yl)nicotinamide (263); N-((1r,3r)-3-(3-chloro-4-cyanophenoxy)-2,2,4,4-tetramethylcyclobutyl)-5-(4-(5-((2-(2,6-dioxopiperidin-3-yl)-1,3-dioxoisoindolin-5-yl)oxy)pentyl)piperazin-1-yl)pyrazine-2-carboxamide (264); N-((1r,3r)-3-(3-chloro-4-cyanophenoxy)-2,2,4,4-tetramethylcyclobutyl)-6-(4-(5-((2-(2,6-dioxopiperidin-3-yl)-1,3-dioxoisoindolin-5-yl)oxy)pentyl)piperazin-1-yl)pyridazine-3-carboxamide (265); N-((1r,3r)-3-(3-chloro-4-cyanophenoxy)-2,2,4,4-tetramethylcyclobutyl)-5-(4-(5-((2-(2,6-dioxopiperidin-3-yl)-1,3-dioxoisoindolin-5-yl)oxy)pentyl)piperazin-1-yl)picolinamide (266); N-((1r,3r)-3-(3-chloro-4-cyanophenoxy)-2,2,4,4-tetramethylcyclobutyl)-1-(1-(5-((2-(2,6-dioxopiperidin-3-yl)-1,3-dioxoisoindolin-5-yl)oxy)pentyl)piperidin-4-yl)-1H-pyrazole-4-carboxamide (267); N-((1r,3r)-3-(3-chloro-4-cyanophenoxy)-2,2,4,4-tetramethylcyclobutyl)-1-(1-(5-((2-(2,6-dioxopiperidin-3-yl)-1,3-dioxoisoindolin-5-yl)oxy)pentyl)piperidin-4-yl)-1H-pyrazole-3-carboxamide (268); N-((1r,3r)-3-(3-chloro-4-cyanophenoxy)-2,2,4,4-tetramethylcyclobutyl)-1-(1-(4-((2-(2,6-dioxopiperidin-3-yl)-1,3-dioxoisoindolin-5-yl)oxy)butyl)pyrrolidin-3-yl)-1H-pyrazole-4-carboxamide (269); N-((1r,3r)-3-(3-chloro-4-cyanophenoxy)-2,2,4,4-tetramethylcyclobutyl)-4-(2-(4-(2-(2,6-dioxopiperidin-3-yl)-1,3-dioxoisoindolin-5-yl)piperazin-1-yl)ethyl)benzamide (270); N-((1r,3r)-3-(3-chloro-4-cyanophenoxy)-2,2,4,4-tetramethylcyclobutyl)-6-(6-(4-(2-((R)-2,6-dioxopiperidin-3-yl)-6-fluoro-3-oxoisoindolin-5-yl)piperazin-1-yl)hexyl)nicotinamide (271); N-((1r,3r)-3-(3-chloro-4-cyanophenoxy)-2,2,4,4-tetramethylcyclobutyl)-6-(6-(4-(2-((R)-2,6-dioxopiperidin-3-yl)-6-fluoro-1-oxoisoindolin-5-yl)piperazin-1-yl)hexyl)nicotinamide (272); N-((1r,3r)-3-(4-cyano-3-(trifluoromethyl)phenoxy)-2,2,4,4-tetramethylcyclobutyl)-4-(3-(4-(2-(2,6-dioxopiperidin-3-yl)-1,3-dioxoisoindolin-5-yl)piperazin-1-yl)propyl)benzamide (273); N-((1r,3r)-3-(3-chloro-4-cyanophenoxy)-2,2,4,4-tetramethylcyclobutyl)-6-(4-(2-(2,6-dioxopiperidin-3-yl)-1,3-dioxoisoindolin-5-yl)-3,6-dihydropyridin-1(2H)-yl)butyl)nicotinamide (274); N-((1r,3r)-3-(3-chloro-4-cyanophenoxy)-2,2,4,4-tetramethylcyclobutyl)-1'-(5-((2-(2,6-dioxopiperidin-3-yl)-1,3-dioxoisoindolin-5-yl)oxy)pentyl)-1',2',3',6'-tetrahydro-[3,4'-bipyridine]-6-carboxamide (275); N-((1r,3r)-3-(3-chloro-4-cyanophenoxy)-2,2,4,4-tetramethylcyclobutyl)-6-(5-(5-((2-(2,6-dioxopiperidin-3-yl)-1,3-dioxoisoindolin-5-yl)oxy)pentyl)-5,6-dihydropyrrolo[3,4-c]pyrazol-2(4H)-yl)nicotinamide (276); N—(S)-1-(3-(3-chloro-4-cyanophenyl)-1H-pyrazol-1-yl)propan-2-yl)-5-((3-(4-(2-(2,6-dioxopiperidin-3-yl)-1,3-dioxoisoindolin-5-yl)piperazin-1-yl)propoxy)methyl)-1H-pyrazole-3-carboxamide (277); N—((R)-1-(3-(3-chloro-4-cyanophenyl)-1H-pyrazol-1-yl)propan-2-yl)-5-((4-(4-((2-(2,6-dioxopiperidin-3-yl)-1,3-dioxoisoindolin-5-yl)oxy)butyl)piperazin-1-yl)methyl)-1H-pyrazole-3-carboxamide (278); N-((1r,3R)-3-(3-chloro-4-cyanophenoxy)-2,2,4,4-tetramethylcyclobutyl)-6-((2R)-4-(5-((2-(2,6-dioxopiperidin-3-yl)-1,3-dioxoisoindolin-5-yl)oxy)pentyl)-2-(hydroxymethyl)piperazin-1-yl)nicotinamide (279); N-((1r,3r)-3-(3-chloro-4-cyanophenoxy)-2,2,4,4-tetramethylcyclobutyl)-1'-(5-((2-(2,6-dioxopiperidin-3-yl)-1, 3-dioxoisoindolin-5-yl)oxy)pentyl)-1',2',3',6'-tetrahydro-[2,4'-bipyridine]-5-carboxamide (280); N-((1r,3r)-3-(3-chloro-4-cyanophenoxy)-2,2,4,4-tetramethylcyclobutyl)-6-(4-(5-((2-(2,6-dioxopiperidin-3-yl)-1,3-dioxoisoindolin-5-yl)oxy)pentyl)-2-oxopiperazin-1-yl)nicotinamide (281); N-((1r,3r)-3-(3-chloro-4-cyanophenoxy)-2,2,4,4-tetramethylcyclobutyl)-4-(1-(4-((2-(2,6-dioxopiperidin-3-yl)-1,3-dioxoisoindolin-5-yl)oxy)butyl)piperidin-4-yl)benzamide (282); N-((1r,3r)-3-(3-chloro-4-cyanophenoxy)-2,2,4,4-tetramethylcyclobutyl)-4-(1-(3-((2-(2,6-dioxopiperidin-3-yl)-1,3-dioxoisoindolin-5-yl)oxy)propyl)piperidin-4-yl)benzamide (283); N-((1r,3r)-3-(3-chloro-4-cyanophenoxy)-2,2,4,4-tetramethylcyclobutyl)-4-(3-(4-(2-(2,6-dioxopiperidin-3-yl)-1,3-dioxoisoindolin-5-yl)piperazin-1-yl)-3-oxopropyl)benzamide (284); N-((1r,3r)-3-(3-chloro-4-cyanophenoxy)-2,2,4,4-tetramethylcyclobutyl)-6-(4-(5-((2-((R)-2,6-dioxopiperidin-3-yl)-1,3-dioxoisoindolin-5-yl)oxy)pentyl)piperazin-1-yl)nicotinamide (285); N-((1r,3r)-3-(3-chloro-4-cyanophenoxy)-2,2,4,4-tetramethylcyclobutyl)-6-(3-(2-((2-(2,6-dioxopiperidin-3-yl)-1,3-dioxoisoindolin-5-yl)oxy)ethyl)azetidin-1-yl)nicotinamide (286); N-((1r,3r)-3-(3-chloro-4-cyanophenoxy)-2,2,4,4-tetramethylcyclobutyl)-6-(3-(4-((2-(2,6-dioxopiperidin-3-yl)-1,3-dioxoisoindolin-5-yl)oxy)butyl)azetidin-1-yl)nicotinamide (287); 4-(3-(4-(5-(4-(2-(2,6-dioxopiperidin-3-yl)-1,3-dioxoisoindolin-5-yl)piperazin-1-yl)pentyl)-3-fluorophenyl)-4,4-dimethyl-5-oxo-2-thioxoimidazolidin-1-yl)-2-(trifluoromethyl)benzonitrile (288); N-((1r,3r)-3-(3-chloro-4-cyanophenoxy)-2,2,4,4-tetramethylcyclobutyl)-6-(4-(2-(4-(2-(2,6-dioxopiperidin-3-yl)-1,3-dioxoisoindolin-5-yl)piperazin-1-yl)ethyl)piperidin-1-yl)pyridazine-3-carboxamide (289); N-((1r,3r)-3-(3-chloro-4-cyanophenoxy)-2,2,4,4-tetramethylcyclobutyl)-5-(4-(2-(4-(2-(2,6-dioxopiperidin-3-yl)-1,3-dioxoisoindolin-5-yl)piperazin-1-yl)ethyl)piperidin-1-yl)pyrazine-2-carboxamide (290); N—((S)-1-(3-(3-chloro-4-cyanophenyl)-1H-pyrazol-1-yl)propan-2-yl)-5-(1-(3-(4-(2-(2,6-dioxopiperidin-3-yl)-1,3-dioxoisoindolin-5-yl)piperazin-1-yl)propoxy)ethyl)-1H-pyrazole-3-carboxamide (291); N-((1r,3S)-3-(3-chloro-4-cyanophenoxy)-2,2,4,4-tetramethylcyclobutyl)-5-((3S)-4-(5-((2-(2,6-dioxopiperidin-3-yl)-1,3-dioxoisoindolin-5-yl)oxy)pentyl)-3-(hydroxymethyl)piperazin-1-yl)picolinamide (292); N-((1r,3r)-3-(3-chloro-4-cyanophenoxy)-2,2,4,4-tetramethylcyclobutyl)-6-(4-((4-(2-(2,6-dioxopiperidin-3-yl)-1,3-dioxoisoindolin-5-yl)piperazin-1-yl)methyl)piperidin-1-yl)pyridazine-3-carboxamide (293); N-((1r,3r)-3-(3-chloro-4-cyanophenoxy)-2,2,4,4-tetramethylcyclobutyl)-6-(9-(2-(2,6-dioxopiperidin-3-yl)-1,3-dioxoisoindolin-5-yl)-3,9-diazaspiro[5.5]undecan-3-yl)nicotinamide (294); N-((1r,3r)-3-(3-chloro-4-cyanophenoxy)-2,2,4,4-tetramethylcyclobutyl)-2-(9-(2-(2,6-dioxopiperidin-3-yl)-1,3-dioxoisoindolin-5-yl)-3,9-diazaspiro[5.5]undecan-3-yl)pyrimidine-5-carboxamide (295); N-((1r,3R)-3-(3-chloro-4-cyanophenoxy)-2,2,4,4-tetramethylcyclobutyl)-4-(2-((1R,4R)-5-(2-(2,6-dioxopiperidin-3-yl)-6-fluoro-1,3-dioxoisoindolin-5-yl)-2,5-diazabicyclo[2.2.1]heptan-2-yl)ethyl)benzamide (296); N-((1r,3r)-3-(3-chloro-4-cyanophenoxy)-2,2,4,4-tetramethylcyclobutyl)-4-(4-(3-((2-(2,6-dioxopiperidin-3-yl)-1,3-dioxoisoindolin-5-yl)oxy)propyl)piperazin-1-yl)-2,6-difluorobenzamide (297); N-((1r,3r)-3-(3-chloro-4-cyanophenoxy)-2,2,4,4-tetramethylcyclobutyl)-4-(4-(5-((2-(2,6-dioxopiperidin-3-yl)-1,3-dioxoisoindolin-5-yl)oxy)pentyl)piperazin-1-yl)-2,6-difluorobenzamide (298); N-((1r,3r)-3-(3-chloro-4-cyanophenoxy)-2,2,4,4-tetramethylcyclobutyl)-4-(4-((2-(2,6-dioxopiperidin-3-yl)-1,3-dioxoisoindolin-5-yl)oxy)butyl)piperazin-1-yl)-2-fluorobenzamide (299); N-((1r,3r)-3-(3-chloro-4-cyanophenoxy)-2,2,4,4-tetramethylcyclobutyl)-2-(4-((4-(2-(2,6-dioxopiperidin-3-yl)-1,3-dioxoisoindolin-5-yl)piperazin-1-yl)methyl)piperidin-1-yl)-4-(trifluoromethyl)pyrimidine-5-carboxamide (300); N-((1r,3r)-3-(3-chloro-4-cyanophenoxy)-2,2,4,4-tetramethylcyclobutyl)-3'-((4-(2-(2,6-dioxopiperidin-3-yl)-1,3-dioxoisoindolin-5-yl)piperazin-1-yl)methyl)-[1,1'-biphenyl]-4-carboxamide (301); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)-3-(trifluoromethyl)benzamide (302); N-((1r,3r)-3-(3-chloro-4-cyanophenoxy)-2,2,4,4-tetramethylcyclobutyl)-3'-(2-(4-(2-(2,6-dioxopiperidin-3-yl)-1,3-dioxoisoindolin-5-yl)piperazin-1-yl)ethyl)-[1,1'-biphenyl]-4-carboxamide (303); N-((1r,3R)-3-(3-chloro-4-cyanophenoxy)-2,2,4,4-tetramethylcyclobutyl)-4-((3S,5R)-4-(2-(1-(2-(2,6-dioxopiperidin-3-yl)-1,3-dioxoisoindolin-5-yl)piperidin-4-yl)ethyl)-3,5-dimethylpiperazin-1-yl)benzamide (304); N-((1r,3r)-3-(3-chloro-4-cyanophenoxy)-2,2,4,4-tetramethylcyclobutyl)-5-(4-((4-(2-(2,6-dioxopiperidin-3-yl)-1,3-dioxoisoindolin-5-yl)piperazin-1-yl)methyl)piperidin-1-yl)pyrimidine-2-carboxamide (305); N-((1r,3r)-3-(3-chloro-4-cyanophenoxy)-2,2,4,4-tetramethylcyclobutyl)-5-(4-(2-(4-(2-(2,6-dioxopiperidin-3-yl)-1,3-dioxoisoindolin-5-yl)piperazin-1-yl)ethyl)piperidin-1-yl)pyrimidine-2-carboxamide (306); N-((1r,3r)-3-(3-chloro-4-cyanophenoxy)-2,2,4,4-tetramethylcyclobutyl)-4-(4-((1-(2-(2,6-dioxopiperidin-3-yl)-6-fluoro-1,3-dioxoisoindolin-5-yl)piperidin-4-yl)methyl)piperazin-1-yl)benzamide (307); N-((1r,3r)-3-(3-chloro-4-cyanophenoxy)-2,2,4,4-tetramethylcyclobutyl)-4-(3-(4-(2-(2,6-dioxopiperidin-3-yl)-1,3-dioxoisoindolin-5-yl)piperazin-1-yl)azetidin-1-yl)benzamide (308); N-((1r,3r)-3-(3-chloro-4-cyanophenoxy)-2,2,4,4-tetramethylcyclobutyl)-4-(4-(2-(3-((2-(2,6-dioxopiperidin-3-yl)-1,3-dioxoisoindolin-5-yl)oxy)azetidin-1-yl)ethyl)piperazin-1-yl)benzamide (309); N-((1r,3r)-3-(3-chloro-4-cyanophenoxy)-2,2,4,4-tetramethylcyclobutyl)-2-(4-((4-(2-(2,6-dioxopiperidin-3-yl)-1,3-dioxoisoindolin-5-yl)piperazin-1-yl)methyl)piperidin-1-yl)-4-methylpyrimidine-5-carboxamide (310); N-((1r,3r)-3-(3-chloro-4-cyanophenoxy)-2,2,4,4-tetramethylcyclobutyl)-2-(4-((4-(2-(2,6-dioxopiperidin-3-yl)-1,3-dioxoisoindolin-5-yl)piperazin-1-yl)methyl)piperidin-1-yl)-4,6-dimethylpyrimidine-5-carboxamide (311); N-((1r,3r)-3-(3-chloro-4-cyanophenoxy)-2,2,4,4-tetramethylcyclobutyl)-4-(2-(4-(2-((2-(2,6-dioxopiperidin-3-yl)-1,3-dioxoisoindolin-5-yl)oxy)ethyl)piperazin-1-yl)ethyl)benzamide (312); N-((1r,3r)-3-(3-chloro-4-cyanophenoxy)-2,2,4,4-tetramethylcyclobutyl)-3'-(2-(4-(2-(2,6-dioxopiperidin-3-yl)-1,3-dioxoisoindolin-5-yl)piperazin-1-yl)ethoxy)-[1,1'-biphenyl]-4-carboxamide (313); N-((1r,3R)-3-(3-chloro-4-cyanophenoxy)-2,2,4,4-tetramethylcyclobutyl)-4-((3S,5R)-4-(4-((2-(2,6-dioxopiperidin-3-yl)-1,3-dioxoisoindolin-5-yl)oxy)butyl)-3,5-dimethylpiperazin-1-yl)benzamide (314); N-((1r,3r)-3-(3-chloro-4-cyanophenoxy)-2,2,4,4-tetramethylcyclobutyl)-4-(4-((1-(2-(2,6-dioxopiperidin-3-yl)-1,3-dioxoisoindolin-5-yl)azetidin-3-yl)methyl)piperazin-1-yl)benzamide (315); N-((1r,3r)-3-(3-chloro-4-cyanophenoxy)-2,2,4,4-tetramethylcyclobutyl)-4-(4-((1-(2-(2,6-dioxopiperidin-3-yl)-1,3-dioxoisoindolin-5-yl)piperidin-4-yl)methyl)piperazin-1-yl)benzamide (316); N-((1r,3S)-3-(3-chloro-4-cyanophenoxy)-2,2,4,4-tetramethylcyclobutyl)-6-((3S)-4-(5-((2-(2,6-dioxopiperidin-3-yl)-1,3-dioxoisoindolin-5-yl)oxy)pentyl)-3-(hydroxymethyl)piperazin-1-yl)nicotinamide (317); N-((1r,3r)-3-(3-chloro- 4-cyanophenoxy)-2,2,4,4-tetramethylcyclobutyl)-6-(4-(4-((2-(2,6-dioxopiperidin-3-yl)-1,3-dioxoisoindolin-5-yl)oxy)butyl)piperazin-1-yl)-4-fluoronicotinamide (318); N-((1r,3r)-3-(3-chloro-4-cyanophenoxy)-2,2,4,4-tetramethylcyclobutyl)-4-(2-(4-(2-(2,6-dioxopiperidin-3-yl)-1,3-dioxoisoindolin-5-yl)piperazin-1-yl)ethyl)-2,6-difluorobenzamide (319); N-((1r,3r)-3-(3-chloro-4-cyanophenoxy)-2,2,4,4-tetramethylcyclobutyl)-4-(3-(3-((2-(2,6-dioxopiperidin-3-yl)-1,3-dioxoisoindolin-5-yl)oxy)propyl)azetidin-1-yl)benzamide (320); N-((1r,3S)-3-(3-chloro-4-cyanophenoxy)-2,2,4,4-tetramethylcyclobutyl)-4-((3S)-3-((1-(2-(2,6-dioxopiperidin-3-yl)-1,3-dioxoisoindolin-5-yl)piperidin-4-yl)methoxy)pyrrolidin-1-yl)benzamide (321); N-((1r,3S)-3-(3-chloro-4-cyanophenoxy)-2,2,4,4-tetramethylcyclobutyl)-4-(4-(((3S)-1-(2-(2,6-dioxopiperidin-3-yl)-1,3-dioxoisoindolin-5-yl)pyrrolidin-3-yl)methyl)piperazin-1-yl)benzamide (322); N-((1r,3R)-3-(3-chloro-4-cyanophenoxy)-2,2,4,4-tetramethylcyclobutyl)-4-(4-(((3R)-1-(2-(2,6-dioxopiperidin-3-yl)-1,3-dioxoisoindolin-5-yl)pyrrolidin-3-yl)methyl)piperazin-1-yl)benzamide (323); N-((1r,3r)-3-(3-chloro-4-cyanophenoxy)-2,2,4,4-tetramethylcyclobutyl)-3-(4-(4-(2-(2,6-dioxopiperidin-3-yl)-1,3-dioxoisoindolin-5-yl)piperazin-1-yl)butyl)benzamide (324); N-((1r,3R)-3-(3-chloro-4-cyanophenoxy)-2,2,4,4-tetramethylcyclobutyl)-4-((3R)-3-((1-(2-(2,6-dioxopiperidin-3-yl)-1,3-dioxoisoindolin-5-yl)piperidin-4-yl)methoxy)pyrrolidin-1-yl)benzamide (325); N-((1r,3R)-3-(3-chloro-4-cyanophenoxy)-2,2,4,4-tetramethylcyclobutyl)-2-((3R,5R)-4-(3-((2-(2,6-dioxopiperidin-3-yl)-1,3-dioxoisoindolin-5-yl)oxy)propyl)-3,5-dimethylpiperazin-1-yl)pyrimidine-5-carboxamide (326); N-((1r,3R)-3-(3-chloro-4-cyanophenoxy)-2,2,4,4-tetramethylcyclobutyl)-4-((3R)-3-((4-(2-(2,6-dioxopiperidin-3-yl)-1,3-dioxoisoindolin-5-yl)piperazin-1-yl)methyl)pyrrolidin-1-yl)benzamide (327); N-((1r,3S)-3-(3-chloro-4-cyanophenoxy)-2,2,4,4-tetramethylcyclobutyl)-4-((3S)-3-((4-(2-(2,6-dioxopiperidin-3-yl)-6-fluoro-1,3-dioxoisoindolin-5-yl)piperazin-1-yl)methyl)pyrrolidin-1-yl)benzamide (328); N-((1r,3r)-3-(3-chloro-4-cyanophenoxy)-2,2,4,4-tetramethylcyclobutyl)-4-(4-(4-(2-(2,6-dioxopiperidin-3-yl)-1-oxoisoindolin-4-yl)butyl)piperazin-1-yl)benzamide (329); N-((1r,3r)-3-(3-chloro-4-cyanophenoxy)-2,2,4,4-tetramethylcyclobutyl)-4-(3-(1-(2-(2,6-dioxopiperidin-3-yl)-1,3-dioxoisoindolin-5-yl)azetidin-3-yl)propyl)benzamide (330); N-((1r,3r)-3-(3-chloro-4-cyanophenoxy)-2,2,4,4-tetramethylcyclobutyl)-4-(4-(4-(2-(2,6-dioxopiperidin-3-yl)-1,3-dioxoisoindolin-4-yl)butyl)piperazin-1-yl)benzamide (331); N-((1r,3r)-3-(3-chloro-4-cyanophenoxy)-2,2,4,4-tetramethylcyclobutyl)-3-(4-((4-(2-(2,6-dioxopiperidin-3-yl)-1,3-dioxoisoindolin-5-yl)piperazin-1-yl)methyl)piperidin-1-yl)cyclobutane-1-carboxamide (332); N-((1r,3r)-3-(3-chloro-4-cyanophenoxy)-2,2,4,4-tetramethylcyclobutyl)-5-(4-((4-(2-(2,6-dioxopiperidin-3-yl)-1,3-dioxoisoindolin-5-yl)piperazin-1-yl)methyl)piperidin-1-yl)pyrazine-2-carboxamide (333); N-((1r,3R)-3-(3-chloro-4-cyanophenoxy)-2,2,4,4-tetramethylcyclobutyl)-4-((3R)-3-(((((1r,3R)-3-((2-(2,6-dioxopiperidin-3-yl)-1,3-dioxoisoindolin-5-yl)oxy)cyclobutyl)(methyl)amino)methyl)pyrrolidin-1-yl)benzamide (334); N-((1r,3R)-3-(3-chloro-4-cyanophenoxy)-2,2,4,4-tetramethylcyclobutyl)-4-(4-(((3R)-1-(2-(2,6-dioxopiperidin-3-yl)-1,3-dioxoisoindolin-5-yl)pyrrolidin-3-yl)methoxy)piperidin-1-yl)benzamide (335); N-((1r,3S)-3-(3-chloro-4-cyanophenoxy)-2,2,4,4-tetramethylcyclobutyl)-4-(4-(((3S)-1-(2-(2,6-dioxopiperidin-3-yl)-1,3-dioxoisoindolin-5-yl)pyrrolidin-3-yl)methoxy)piperidin-1-yl)benzamide (336); N-((1r,3r)-3-(3-chloro-4-cyanophenoxy)-2,2,4,4-tetramethylcyclobutyl)-4-(3-(((((1r,3r)-3-((2-(2,6-dioxopiperidin-3-yl)-1,3-dioxoisoindolin-5-yl)oxy)cyclobutyl)(methyl)amino)methyl)azetidin-1-yl)benzamide (337); N-((1r,3S)-3-(3-chloro-4-cyanophenoxy)-2,2,4,4-tetramethylcyclobutyl)-4-((3S)-3-(((((1r,3S)-3-((2-(2,6-dioxopiperidin-3-yl)-1,3-dioxoisoindolin-5-yl)oxy)cyclobutyl)(methyl)amino)methyl)pyrrolidin-1-yl)benzamide (338); N-((1r,3r)-3-(3-chloro-4-cyanophenoxy)-2,2,4,4-tetramethylcyclobutyl)-6-(4-((4-(2-(2,6-dioxopiperidin-3-yl)-1,3-dioxoisoindolin-5-yl)piperazin-1-yl)methyl)piperidin-1-yl)-4-fluoronicotinamide (339); N-((1r,3S)-3-(3-chloro-4-cyanophenoxy)-2,2,4,4-tetramethylcyclobutyl)-4-(4-((((3S)-1-(2-(2,6-dioxopiperidin-3-yl)-6-fluoro-1,3-dioxoisoindolin-5-yl)pyrrolidin-3-yl)methyl)(methyl)amino)piperidin-1-yl)benzamide (340); N-((1r,3R)-3-(3-chloro-4-cyanophenoxy)-2,2,4,4-tetramethylcyclobutyl)-4-(4-((((3R)-1-(2-(2,6-dioxopiperidin-3-yl)-6-fluoro-1,3-dioxoisoindolin-5-yl)pyrrolidin-3-yl)methyl)(methyl)amino)piperidin-1-yl)benzamide (341); N-((1r,3S)-3-(3-chloro-4-cyanophenoxy)-2,2,4,4-tetramethylcyclobutyl)-6-((4aR,6S,8aS)-6-(4-(2-(2,6-dioxopiperidin-3-yl)-1,3-dioxoisoindolin-5-yl)piperazin-1-yl)octahydroisoquinolin-2(1H)-yl)nicotinamide (342); N-((1r,3r)-3-(3-chloro-4-cyanophenoxy)-2,2,4,4-tetramethylcyclobutyl)-4-(4-((4-(2-(2,6-dioxopiperidin-3-yl)-6-fluoro-1,3-dioxoisoindolin-5-yl)piperazin-1-yl)methyl)piperidin-1-yl)-3-fluorobenzamide (343); N-((1r,3r)-3-(3-chloro-4-cyanophenoxy)-2,2,4,4-tetramethylcyclobutyl)-4-(4-(4-(2-(2,6-dioxopiperidin-3-yl)-1,3-dioxoisoindolin-5-yl)piperazin-1-yl)piperidin-1-yl)benzamide (344); N-((1r,3S)-3-(3-chloro-4-cyanophenoxy)-2,2,4,4-tetramethylcyclobutyl)-4-(4-(((3S)-1-(2-(2,6-dioxopiperidin-3-yl)-6-fluoro-1,3-dioxoisoindolin-5-yl)pyrrolidin-3-yl)methyl)piperazin-1-yl)benzamide (345); N-((1r,3r)-3-(3-chloro-4-cyanophenoxy)-2,2,4,4-tetramethylcyclobutyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide (346); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)-3-(2-(2-methoxyethoxy)ethoxy)benzamide (347); N-((1r,3r)-3-(3-chloro-4-cyanophenoxy)-2,2,4,4-tetramethylcyclobutyl)-4-(4-((1-(2-(2,6-dioxopiperidin-3-yl)-1-oxoisoindolin-4-yl)azetidin-3-yl)methyl)piperidin-1-yl)benzamide (348); N-((1r,3r)-3-(3-chloro-4-cyanophenoxy)-2,2,4,4-tetramethylcyclobutyl)-4-(4-((1-(2-(2,6-dioxopiperidin-3-yl)-1,3-dioxoisoindolin-5-yl)piperidin-4-yl)oxy)piperidin-1-yl)benzamide (349); N-((1r,3r)-3-(3-chloro-4-cyanophenoxy)-2,2,4,4-tetramethylcyclobutyl)-6-(4-((1-(2-(2,6-dioxopiperidin-3-yl)-1,3-dioxoisoindolin-5-yl)piperidin-4-yl)methyl)piperazin-1-yl)-4-fluoronicotinamide (350); N-((1r,3r)-3-(3-chloro-4-cyanophenoxy)-2,2,4,4-tetramethylcyclobutyl)-4-(3-((1-(2-(2,6-dioxopiperidin-3-yl)-1,3-dioxoisoindolin-5-yl)azetidin-3-yl)methyl)azetidin-1-yl)benzamide (351); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)-3,6-dihydropyridin-1(2H)-yl)benzamide (352); N-((1r,3r)-3-(3-chloro-4-cyanophenoxy)-2,2,4,4-tetramethylcyclobutyl)-4-((1'-(2-(2,6-dioxopiperidin-3-yl)-1,3-dioxoisoindolin-5-yl)-[1,4'-bipiperidin]-4-yl)oxy)benzamide (353); N-((1r,3r)-3-(3-chloro-4-cyanophenoxy)-2,2,4,4-tetramethylcyclobutyl)-2-(4-((4-(2-(2,6-dioxopiperidin-3-yl)-6-fluoro-1,3-dioxoisoindolin-5-yl)piperazin-1-yl)methyl)piperidin-1-yl)-4,6-dimethylpyrimidine-5-carboxamide (354); N-((1r,3r)-3-(4-cyanophenoxy)-2,2,4,4-tetramethylcyclobutyl)-4-(4-((4-

(2-(2,6-dioxopiperidin-3-yl)-1,3-dioxoisoindolin-5-yl)piperazin-1-yl)methyl)piperidin-1-yl)benzamide (355); N-((1r,3r)-3-(4-cyano-3-(trifluoromethyl)phenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (356); N-((1r,3r)-3-(3-chloro-4-cyanophenoxy)-2,2,4,4-tetramethylcyclobutyl)-4-(6-(2-((2-(2,6-dioxopiperidin-3-yl)-1,3-dioxoisoindolin-5-yl)oxy)ethyl)-2-azaspiro[3.3]heptan-2-yl)benzamide (357); N-((1r,3r)-3-(3-chloro-4-cyanophenoxy)-2,2,4,4-tetramethylcyclobutyl)-2-(4-(3-((2-(2,6-dioxopiperidin-3-yl)-1,3-dioxoisoindolin-5-yl)oxy)propyl)piperazin-1-yl)-4,6-dimethylpyrimidine-5-carboxamide (358); N-((1r,3r)-3-(3-chloro-4-cyanophenoxy)-2,2,4,4-tetramethylcyclobutyl)-5-(4-(3-((2-(2,6-dioxopiperidin-3-yl)-1,3-dioxoisoindolin-5-yl)oxy)propyl)piperazin-1-yl)pyrazine-2-carboxamide (359); N-((1r,3r)-3-(3-chloro-4-cyanophenoxy)-2,2,4,4-tetramethylcyclobutyl)-6-(4-(3-((2-(2,6-dioxopiperidin-3-yl)-1,3-dioxoisoindolin-5-yl)oxy)propyl)piperazin-1-yl)pyridazine-3-carboxamide (360); 2-chloro-N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (361); 2-chloro-N-((1r,3r)-3-(3-chloro-4-cyanophenoxy)-2,2,4,4-tetramethylcyclobutyl)-4-(4-((4-(2-(2,6-dioxopiperidin-3-yl)-6-fluoro-1,3-dioxoisoindolin-5-yl)piperazin-1-yl)methyl)piperidin-1-yl)benzamide (362); N-((1r,3r)-3-(3-chloro-4-cyanophenoxy)-2,2,4,4-tetramethylcyclobutyl)-5-(4-(5-((2-(2,6-dioxopiperidin-3-yl)-1,3-dioxoisoindolin-5-yl)oxy)pentyl)piperazin-1-yl)pyrimidine-2-carboxamide (363); N-((1r,3r)-3-(4-cyano-3-(trifluoromethyl)phenoxy)-2,2,4,4-tetramethylcyclobutyl)-5-(4-(5-((2-(2,6-dioxopiperidin-3-yl)-1,3-dioxoisoindolin-5-yl)oxy)pentyl)piperazin-1-yl)picolinamide (364); N-((1r,3S)-3-(3-chloro-4-cyanophenoxy)-2,2,4,4-tetramethylcyclobutyl)-2-((3S,5S)-4-(3-((2-(2,6-dioxopiperidin-3-yl)-1,3-dioxoisoindolin-5-yl)oxy)propyl)-3,5-dimethylpiperazin-1-yl)pyrimidine-5-carboxamide (365); N-((1r,3r)-3-(3-chloro-4-cyanophenoxy)-2,2,4,4-tetramethylcyclobutyl)-4-(3-(2-((2-(2,6-dioxopiperidin-3-yl)-1,3-dioxoisoindolin-5-yl)oxy)ethoxy)propyl)benzamide (366); N-((1r,3r)-3-(3-chloro-4-cyanophenoxy)cyclobutyl)-4-(4-(4-((2-(2,6-dioxopiperidin-3-yl)-1-oxoisoindolin-4-yl)oxy)butyl)-1H-1,2,3-triazol-1-yl)benzamide (367); N-((1r,3r)-3-(3-chloro-4-cyanophenoxy)-2,2,4,4-tetramethylcyclobutyl)-6-(4-(2-((5-(2-((R)-2,6-dioxopiperidin-3-yl)-1-oxoisoindolin-4-yl)pentyl)oxy)ethyl)piperazin-1-yl)nicotinamide (368); N-((1r,3r)-3-(3-chloro-4-cyanophenoxy)-2,2,4,4-tetramethylcyclobutyl)-4-(4-(2-((5-(2-((S)-2,6-dioxopiperidin-3-yl)-1-oxoisoindolin-4-yl)pentyl)oxy)ethyl)piperazin-1-yl)benzamide (369); (2S)-1-(4-(((1r,3S)-3-(3-chloro-4-cyanophenoxy)-2,2,4,4-tetramethylcyclobutyl)carbamoyl)phenyl)-N-(4-(4-(2-(2,6-dioxopiperidin-3-yl)-1-oxoisoindolin-5-yl)piperazin-1-yl)butyl)-N-methylpyrrolidine-2-carboxamide (370); (2R)-1-(4-(((1r,3R)-3-(3-chloro-4-cyanophenoxy)-2,2,4,4-tetramethylcyclobutyl)carbamoyl)benzyl)-N-(2-(4-(2-(2,6-dioxopiperidin-3-yl)-1-oxoisoindolin-5-yl)piperazin-1-yl)ethyl)-N-methylpyrrolidine-2-carboxamide (371); (2S)-1-(4-(((1r,3S)-3-(3-chloro-4-cyanophenoxy)-2,2,4,4-tetramethylcyclobutyl)carbamoyl)benzyl)-N-(2-(4-(2-(2,6-dioxopiperidin-3-yl)-1-oxoisoindolin-5-yl)piperazin-1-yl)ethyl)-N-methylpyrrolidine-2-carboxamide (372); N-((1r,3r)-3-(3-chloro-4-cyanophenoxy)-2,2,4,4-tetramethylcyclobutyl)-4-(2-(2-((2-(2,6-dioxopiperidin-3-yl)-1,3-dioxoisoindolin-5-yl)oxy)ethoxy)ethyl)benzamide (373); N-((1r,3r)-3-(3-chloro-4-cyanophenoxy)-2,2,4,4-tetramethylcyclobutyl)-1-(1-(5-((2-(2,6-dioxopiperidin-3-yl)-1,3-dioxoisoindolin-5-yl)oxy)pentyl)pyrrolidin-3-yl)-1H-pyrazole-4-carboxamide (374); N-((1r,3r)-3-(3-chloro-4-cyanophenoxy)-2,2,4,4-tetramethylcyclobutyl)-1-(2-(3-(4-(2-(2,6-dioxopiperidin-3-yl)-1,3-dioxoisoindolin-5-yl)piperazin-1-yl)propoxy)ethyl)-1H-pyrazole-4-carboxamide (375); 4-(3-(4-(4-(5-((2-(2,6-dioxopiperidin-3-yl)-1,3-dioxoisoindolin-5-yl)oxy)pentyl)piperazin-1-yl)phenyl)-4,4-dimethyl-5-oxo-2-thioxoimidazolidin-1-yl)-2-(trifluoromethyl)benzonitrile (376); 2-chloro-4-(3-(4-(4-(5-((2-(2,6-dioxopiperidin-3-yl)-1,3-dioxoisoindolin-5-yl)oxy)pentyl)piperazin-1-yl)phenyl)-4,4-dimethyl-5-oxo-2-thioxoimidazolidin-1-yl)benzonitrile (377); 4-(5-(4-(4-(5-((2-(2,6-dioxopiperidin-3-yl)-1,3-dioxoisoindolin-5-yl)oxy)pentyl)piperazin-1-yl)phenyl)-8-oxo-6-thioxo-5,7-diazaspiro[3.4]octan-7-yl)-2-(trifluoromethyl)benzonitrile (378); N—(R)-1-(3-(3-chloro-4-cyanophenyl)-1H-pyrazol-1-yl)propan-2-yl)-5-((2-(2-((2-(2,6-dioxopiperidin-3-yl)-1,3-dioxoisoindolin-5-yl)oxy)ethoxy)ethoxy)methyl)-1H-pyrazole-3-carboxamide (379); N-((1r,3r)-3-(3-chloro-4-cyanophenoxy)-2,2,4,4-tetramethylcyclobutyl)-5-(3-(4-(2-(2,6-dioxopiperidin-3-yl)-1,3-dioxoisoindolin-5-yl)piperazin-1-yl)propyl)picolinamide (380); N-((1r,3r)-3-(4-cyano-3-(trifluoromethyl)phenoxy)-2,2,4,4-tetramethylcyclobutyl)-5-(3-(4-(2-(2,6-dioxopiperidin-3-yl)-1,3-dioxoisoindolin-5-yl)piperazin-1-yl)propyl)picolinamide (381); 4-(3-(6-(4-(5-((2-(2,6-dioxopiperidin-3-yl)-1,3-dioxoisoindolin-5-yl)oxy)pentyl)piperazin-1-yl)pyridin-3-yl)-4,4-dimethyl-5-oxo-2-thioxoimidazolidin-1-yl)-2-(trifluoromethyl)benzonitrile (382); 4-(3-(4-(4-(4-((2-(2,6-dioxopiperidin-3-yl)-1,3-dioxoisoindolin-5-yl)oxy)butyl)piperazine-1-carbonyl)-3-fluorophenyl)-4,4-dimethyl-5-oxo-2-thioxoimidazolidin-1-yl)-2-(trifluoromethyl)benzonitrile (383); N-((1r,3S)-3-(3-chloro-4-cyanophenoxy)-2,2,4,4-tetramethylcyclobutyl)-4-(2-((1S,4S)-5-(2-(2,6-dioxopiperidin-3-yl)-1,3-dioxoisoindolin-5-yl)-2,5-diazabicyclo[2.2.1]heptan-2-yl)ethyl)benzamide (384); 4-(5-(((1r,3r)-3-(3-chloro-4-cyanophenoxy)-2,2,4,4-tetramethylcyclobutyl)carbamoyl)pyridin-2-yl)-1-(5-((2-(2,6-dioxopiperidin-3-yl)-1,3-dioxoisoindolin-5-yl)oxy)pentyl)-1-methylpiperazin-1-ium (385); 4-(3-(2-((5-(4-(2-(2,6-dioxopiperidin-3-yl)-1,3-dioxoisoindolin-5-yl)piperazin-1-yl)pentyl)oxy)phenyl)-4,4-dimethyl-5-oxo-2-thioxoimidazolidin-1-yl)-2-(trifluoromethyl)benzonitrile (386); 4-(3-(2-((6-(4-(2-(2,6-dioxopiperidin-3-yl)-1,3-dioxoisoindolin-5-yl)piperazin-1-yl)hexyl)oxy)phenyl)-4,4-dimethyl-5-oxo-2-thioxoimidazolidin-1-yl)-2-(trifluoromethyl)benzonitrile (387); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)-2-fluorobenzamide (388); N-((1r,3r)-3-(3-chloro-4-cyanophenoxy)-2,2,4,4-tetramethylcyclobutyl)-4-(4-(3-((2-(2,6-dioxopiperidin-3-yl)-1,3-dioxoisoindolin-4-yl)oxy)propyl)piperazin-1-yl)benzamide (389); N-((1r,3r)-3-(3-chloro-4-cyanophenoxy)-2,2,4,4-tetramethylcyclobutyl)-4-(2-(1-(2-(2,6-dioxopiperidin-3-yl)-1,3-dioxoisoindolin-5-yl)azetidin-3-yl)ethyl)benzamide (390); N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)-2,6-difluorobenzamide (391); N-((1r,3r)-3-(3-chloro-4-cyanophenoxy)-2,2,4,4-tetramethylcyclobutyl)-4-(4-(3-((2-(2,6-dioxopiperidin-3-yl)-1-oxoisoindolin-4-yl)oxy)propyl)piperazin-1-yl)benzamide (392); 4-(3-(2-(4-((1-(2-(2,6-dioxopiperidin-3-yl)-1,3-dioxoisoindolin-5-yl)piperidin-4-yl)methyl)piperazin-1-yl)ethyl)phenyl)-4,4-dimethyl-5-oxo-2-thioxoimidazolidin-1-yl)-2-

(trifluoromethyl)benzonitrile (393); N-((1r,3r)-3-(3-chloro-4-cyanophenoxy)-2,2,4,4-tetramethylcyclobutyl)-4-(3-(1-(2-(2,6-dioxopiperidin-3-yl)-1,3-dioxoisoindolin-4-yl)azetidin-3-yl)propyl)benzamide (394); N-((1r,3r)-3-(3-chloro-4-cyanophenoxy)-2,2,4,4-tetramethylcyclobutyl)-4-(4-((1-(2-(2,6-dioxopiperidin-3-yl)-1,3-dioxoisoindolin-4-yl)azetidin-3-yl)methyl)piperidin-1-yl)benzamide (395); N-((1r,3r)-3-(3-chloro-4-cyanophenoxy)-2,2,4,4-tetramethylcyclobutyl)-1-(1-((1-(2-(2,6-dioxopiperidin-3-yl)-1,3-dioxoisoindolin-5-yl)piperidin-4-yl)methyl)piperidin-4-yl)-1H-pyrazole-3-carboxamide (396); N-((1r,3r)-3-(3-chloro-4-cyanophenoxy)-2,2,4,4-tetramethylcyclobutyl)-1-(1-(2-(4-(2-(2,6-dioxopiperidin-3-yl)-1,3-dioxoisoindolin-5-yl)piperazin-1-yl)ethyl)piperidin-4-yl)-1H-pyrazole-3-carboxamide (397); N-((1r,3r)-3-(3-chloro-4-cyanophenoxy)-2,2,4,4-tetramethylcyclobutyl)-4-(2-(dimethylamino)ethoxy)-6-(4-((4-(2-(2,6-dioxopiperidin-3-yl)-6-fluoro-1,3-dioxoisoindolin-5-yl)piperazin-1-yl)methyl)piperidin-1-yl)nicotinamide (398); N-((1s,4s)-4-(3-chloro-4-cyanophenoxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide (399); N-((1r,4r)-4-(3-chloro-4-cyanophenoxy)cyclohexyl)-6-(4-((4-(2-(2,6-dioxopiperidin-3-yl)-1,3-dioxoisoindolin-5-yl)piperazin-1-yl)methyl)piperidin-1-yl)nicotinamide (400); N-((1r,4r)-4-(3-chloro-4-cyanophenoxy)cyclohexyl)-4-(4-((4-(2-(2,6-dioxopiperidin-3-yl)-1,3-dioxoisoindolin-5-yl)piperazin-1-yl)methyl)piperidin-1-yl)benzamide (401); N-((1s,4s)-4-(3-chloro-4-cyanophenoxy)cyclohexyl)-4-(4-((4-(2-(2,6-dioxopiperidin-3-yl)-1,3-dioxoisoindolin-5-yl)piperazin-1-yl)methyl)piperidin-1-yl)benzamide (402); N-((1r,4r)-4-(3-chloro-4-cyanophenoxy)cyclohexyl)-2-(4-((4-(2-(2,6-dioxopiperidin-3-yl)-1,3-dioxoisoindolin-5-yl)piperazin-1-yl)methyl)piperidin-1-yl)pyrimidine-5-carboxamide (403); N-((1r,4r)-4-(3-chloro-4-cyanophenoxy)cyclohexyl)-5-(4-((4-(2-(2,6-dioxopiperidin-3-yl)-1,3-dioxoisoindolin-5-yl)piperazin-1-yl)methyl)piperidin-1-yl)pyrazine-2-carboxamide (404); N-((1r,4r)-4-(3-chloro-4-cyanophenoxy)cyclohexyl)-6-(4-((4-(2-(2,6-dioxopiperidin-3-yl)-1,3-dioxoisoindolin-5-yl)piperazin-1-yl)methyl)piperidin-1-yl)pyridazine-3-carboxamide (405); N-((1r,4r)-4-(3-chloro-4-cyanophenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide (406); N-((1r,4r)-4-(3-chloro-4-cyanophenoxy)cyclohexyl)-2-(4-((4-(2-(2,6-dioxopiperidin-3-yl)-6-fluoro-1,3-dioxoisoindolin-5-yl)piperazin-1-yl)methyl)piperidin-1-yl)pyrimidine-5-carboxamide (407); N-((1r,4r)-4-(3-chloro-4-cyanophenoxy)cyclohexyl)-5-(4-((4-(2-(2,6-dioxopiperidin-3-yl)-6-fluoro-1,3-dioxoisoindolin-5-yl)piperazin-1-yl)methyl)piperidin-1-yl)pyrazine-2-carboxamide (408); N-((1r,4r)-4-(3-chloro-4-cyanophenoxy)cyclohexyl)-4-(4-(4-(2-(2,6-dioxopiperidin-3-yl)-1,3-dioxoisoindolin-5-yl)piperazin-1-yl)piperidin-1-yl)benzamide (409); N-((1r,4r)-4-(3-chloro-4-cyanophenoxy)cyclohexyl)-4-(4-(1-(2-(2,6-dioxopiperidin-3-yl)-1,3-dioxoisoindolin-5-yl)piperidin-4-yl)piperazin-1-yl)benzamide (410); N-((1r,4r)-4-(3-chloro-4-cyanophenoxy)cyclohexyl)-6-(4-(1-(2-(2,6-dioxopiperidin-3-yl)-1,3-dioxoisoindolin-5-yl)piperidin-4-yl)piperazin-1-yl)pyridazine-3-carboxamide (411); N-((1r,4r)-4-(3-chloro-4-cyanophenoxy)cyclohexyl)-2-(4-(1-(2-(2,6-dioxopiperidin-3-yl)-1,3-dioxoisoindolin-5-yl)piperidin-4-yl)piperazin-1-yl)pyrimidine-5-carboxamide (412); N-((1r,4r)-4-(3-chloro-4-cyanophenoxy)cyclohexyl)-6-(4-(4-(2-(2,6-dioxopiperidin-3-yl)-1,3-dioxoisoindolin-5-yl)piperazin-1-yl)piperidin-1-yl)pyridazine-3-carboxamide (413); N-((1r,4S)-4-(3-chloro-4-cyanophenoxy)cyclohexyl)-2-((3S)-3-((4-(2-(2,6-dioxopiperidin-3-yl)-1,3-dioxoisoindolin-5-yl)piperazin-1-yl)methyl)pyrrolidin-1-yl)pyrimidine-5-carboxamide (414); N-((1r,4r)-4-(3-chloro-4-cyanophenoxy)cyclohexyl)-6-(4-(2-((2-(2,6-dioxopiperidin-3-yl)-1,3-dioxoisoindolin-5-yl)oxy)ethyl)piperazin-1-yl)pyridazine-3-carboxamide (415); N-((1r,4r)-4-(3-chloro-4-cyanophenoxy)cyclohexyl)-4-(4-(2-((2-(2,6-dioxopiperidin-3-yl)-1,3-dioxoisoindolin-5-yl)oxy)ethyl)piperazin-1-yl)benzamide (416); N-((1r,4r)-4-(3-chloro-4-cyanophenoxy)cyclohexyl)-2-(4-(2-((2-(2,6-dioxopiperidin-3-yl)-1,3-dioxoisoindolin-5-yl)oxy)ethyl)piperazin-1-yl)pyrimidine-5-carboxamide (417); N-((1r,4r)-4-(3-chloro-4-cyanophenoxy)cyclohexyl)-2-(4-(3-((2-(2,6-dioxopiperidin-3-yl)-1,3-dioxoisoindolin-5-yl)oxy)propyl)piperazin-1-yl)pyrimidine-5-carboxamide (418); N-((1r,4r)-4-(3-chloro-4-cyanophenoxy)-4-methylcyclohexyl)-4-(4-((4-(2-(2,6-dioxopiperidin-3-yl)-1,3-dioxoisoindolin-5-yl)piperazin-1-yl)methyl)piperidin-1-yl)benzamide (419); N-((1r,4r)-4-(3-chloro-4-cyanophenoxy)cyclohexyl)-5-(4-(2-((2-(2,6-dioxopiperidin-3-yl)-1,3-dioxoisoindolin-5-yl)oxy)ethyl)piperazin-1-yl)pyrazine-2-carboxamide (420); N-((1r,4r)-4-(3-chloro-4-cyanophenoxy)cyclohexyl)-5-(4-((4-(2-(2,6-dioxopiperidin-3-yl)-1,3-dioxoisoindolin-5-yl)piperazin-1-yl)methyl)piperidin-1-yl)picolinamide (421); N-((1r,4r)-4-(3-chloro-4-cyanophenoxy)cyclohexyl)-6-(4-(2-((2-(2,6-dioxopiperidin-3-yl)-6-fluoro-1,3-dioxoisoindolin-5-yl)oxy)ethyl)piperazin-1-yl)-5-fluoronicotinamide (422); N-((1r,4r)-4-(3-chloro-4-cyanophenoxy)cyclohexyl)-5-(4-(3-((2-(2,6-dioxopiperidin-3-yl)-6-fluoro-1,3-dioxoisoindolin-5-yl)oxy)propyl)piperazin-1-yl)pyrazine-2-carboxamide (423); N-((1r,4r)-4-(3-chloro-4-cyanophenoxy)cyclohexyl)-2-(4-(2-(4-(2-(2,6-dioxopiperidin-3-yl)-1,3-dioxoisoindolin-5-yl)piperazin-1-yl)ethyl)piperidin-1-yl)pyrimidine-5-carboxamide (424); N-((1r,4r)-4-(3-chloro-4-cyanophenoxy)cyclohexyl)-4-(4-(2-(4-(2-(2,6-dioxopiperidin-3-yl)-1,3-dioxoisoindolin-5-yl)piperazin-1-yl)ethyl)piperidin-1-yl)benzamide (425); N-((1r,4r)-4-(3-chloro-4-cyanophenoxy)cyclohexyl)-5-(4-(3-((2-(2,6-dioxopiperidin-3-yl)-1,3-dioxoisoindolin-5-yl)oxy)propyl)piperazin-1-yl)pyrazine-2-carboxamide (426); N-((1r,4r)-4-(3-chloro-4-cyanophenoxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)pyridazine-3-carboxamide (427); N-((1r,3r)-3-(3-chloro-4-cyanophenoxy)-2,2,4,4-tetramethylcyclobutyl)-6-(4-(5-((2-(1-methyl-2,6-dioxopiperidin-3-yl)-1,3-dioxoisoindolin-5-yl)oxy)pentyl)piperazin-1-yl)nicotinamide (428); N-((1r,3r)-3-(3-chloro-4-cyanophenoxy)-2,2,4,4-tetramethylcyclobutyl)-1-(1-(5-((2-(1-methyl-2,6-dioxopiperidin-3-yl)-1,3-dioxoisoindolin-5-yl)oxy)pentyl)piperidin-4-yl)-1H-pyrazole-4-carboxamide (429); N-((1r,3r)-3-(3-chloro-4-cyanophenoxy)-2,2,4,4-tetramethylcyclobutyl)-1-(1-(5-((2-(1-methyl-2,6-dioxopiperidin-3-yl)-1,3-dioxoisoindolin-5-yl)oxy)pentyl)piperidin-4-yl)-1H-pyrazole-3-carboxamide (430); N-((1r,3r)-3-(3-chloro-4-cyanophenoxy)-2,2,4,4-tetramethylcyclobutyl)-1-(1-(4-((2-(1-methyl-2,6-dioxopiperidin-3-yl)-1,3-dioxoisoindolin-5-yl)oxy)butyl)pyrrolidin-3-yl)-1H-pyrazole-4-carboxamide (431); N-((1r,3r)-3-(3-chloro-4-cyanophenoxy)-2,2,4,4-tetramethylcyclobutyl)-1-(1-(5-((2-(1-methyl-2,6-dioxopiperidin-3-yl)-1,3-dioxoisoindolin-5-yl)oxy)pentyl)pyrrolidin-3-yl)-1H-pyrazole-4-carboxamide (432); N-((1r,3r)-3-(3-chloro-4-cyanophenoxy)-2,2,4,4-tetramethylcyclobutyl)-1-(2-(3-(4-(2-(1-methyl-2,6-dioxopiperidin-3-yl)-1,3-dioxoisoindolin-5-yl)piperazin-1-yl)propoxy)ethyl)-1H-pyrazole-4-carboxamide (433); N-((1r, 3r)-3-(3-chloro-4-cyanophenoxy)-2,2,4,4-tetramethylcyclobutyl)-5-(4-(5-((2-(1-methyl-2,6-dioxopiperidin-3-yl)-1,3-dioxoisoindolin-5-yl)oxy)pentyl)piperazin-1-yl)picolinamide (434); N-((1r,3r)-3-(4-cyano-3-(trifluoromethyl)phenoxy)-2,2,4,4-tetramethylcyclobutyl)-5-(4-(5-((2-(1-methyl-2,6-dioxopiperidin-3-yl)-1,3-dioxoisoindolin-5-yl)oxy)pentyl)piperazin-1-yl) picolinamide (435); N-((1r,3r)-3-(3-chloro-4-cyanophenoxy)-2,2,4,4-tetramethylcyclobutyl)-5-(3-(4-(2-(1-methyl-2,6-dioxopiperidin-3-yl)-1,3-dioxoisoindolin-5-yl)piperazin-1-yl)propyl)picolinamide (436); 6-(4-(4-((2-(1-butyl-2,6-dioxopiperidin-3-yl)-1,3-dioxoisoindolin-5-yl)oxy)butyl)piperazin-1-yl)-N,N-dimethylpyridazine-3-carboxamide (437); N-((1r,3r)-3-(3-chloro-4-cyanophenoxy)-2,2,4,4-tetramethylcyclobutyl)-2-(4-(4-((2-(1-methyl-2,6-dioxopiperidin-3-yl)-1,3-dioxoisoindolin-5-yl)oxy)butyl)piperazin-1-yl)pyrimidine-5-carboxamide (438); N-((1r,3r)-3-(3-chloro-4-cyanophenoxy)-2,2,4,4-tetramethylcyclobutyl)-4-(4-((4-(2-(1-methyl-2,6-dioxopiperidin-3-yl)-1,3-dioxoisoindolin-5-yl)piperazin-1-yl)methyl)piperidin-1-yl)benzamide (439); N-((1r,3r)-3-(3-chloro-4-cyanophenoxy)-2,2,4,4-tetramethylcyclobutyl)-2-(4-((4-(2-(1-methyl-2,6-dioxopiperidin-3-yl)-1,3-dioxoisoindolin-5-yl)piperazin-1-yl)methyl)piperidin-1-yl) pyrimidine-5-carboxamide (440); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl methyl carbonate (441); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl ethyl carbonate (442); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl isopropyl carbonate (443); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (tetrahydro-2H-pyran-4-yl) carbonate (444); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-acetamidoethyl)carbamate (445); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-(2-aminoacetamido)ethyl)carbamate (446); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-((S)-2-aminopropanamido)ethyl)carbamate (447); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-((S)-2-amino-3-methylbutanamido)ethyl)carbamate (448); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-((S)-2-((S)-2-amino-3-methylbutanamido)-3-methylbutanamido)ethyl)carbamate (449); (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2,5,8,11-tetraoxatridecan-13-yl) carbonate (450); 2-chloro-4-(3-(3-fluoro-4-(5-(4-(2-(1-methyl-2,6-dioxopiperidin-3-yl)-1,3-dioxoisoindolin-5-yl)piperazin-1-yl)pentyl)phenyl)-4,4-dimethyl-5-oxo-2-thioxoimidazolidin-1-yl)benzonitrile (451); 2-chloro-4-(5-(3-fluoro-4-(5-(4-(2-(1-methyl-2,6-dioxopiperidin-3-yl)-1,3-dioxoisoindolin-5-yl)piperazin-1-yl)pentyl)phenyl)-8-oxo-6-thioxo-5,7-diazaspiro[3.4]octan-7-yl)benzonitrile (452); N-((1r,3r)-3-(3-chloro-4-cyanophenoxy)-2,2,4,4-tetramethylcyclobutyl)-4-(4-((4-(2-(2,6-dioxopiperidin-3-yl)-3-oxo-2,3-dihydro-[1,2,4]triazolo[4,3-a]pyridin-6-yl)piperazin-1-yl)methyl)piperidin-1-yl)benzamide (528); rac-N-((1r,3r)-3-(3-chloro-4-cyanophenoxy)-2,2,4,4-tetramethylcyclobutyl)-4-(4-((4-(2-(2,6-dioxopiperidin-3-yl)-4-methylene-1-oxo-1,2,3,4-tetrahydroisoquinolin-6-yl)piperazin-1-yl)methyl)piperidin-1-yl)benzamide (529); rac-N-(1-(4-(((1r,3r)-3-(3-chloro-4-cyanophenoxy)-2,2,4,4-tetramethylcyclobutyl)carbamoyl)phenyl)azetidin-3-yl)-1-(2-(2,6-dioxopiperidin-3-yl)-1,3-dioxoisoindolin-5-yl)-N-methylpiperidine-4-carboxamide (530); rac-N-((1r,3r)-3-(3-chloro-4-cyanophenoxy)-2,2,4,4-tetramethylcyclobutyl)-6-(4-(3-((2-(2,6-dioxopiperidin-3-yl)-6-fluoro-1,3-dioxoisoindolin-5-yl)oxy)propyl)piperazin-1-yl)pyridazine-3-carboxamide (531); rac-N-((1r,3r)-3-(3-chloro-4-cyanophenoxy)-2,2,4,4-tetramethylcyclobutyl)-5-(4-(3-((2-(2,6-dioxopiperidin-3-yl)-6-fluoro-1,3-dioxoisoindolin-5-yl)oxy)propyl)piperazin-1-yl)pyrazine-2-carboxamide (532); rac-N-((1r,4r)-4-(3-chloro-4-cyanophenoxy)cyclohexyl)-2-(4-(3-((2-(2,6-dioxopiperidin-3-yl)-6-fluoro-1,3-dioxoisoindolin-5-yl)oxy)propyl)piperazin-1-yl)pyrimidine-5-carboxamide (533); rac-N-((1r,4r)-4-(3-chloro-4-cyanophenoxy)cyclohexyl)-2-(4-(2-(4-(2-(2,6-dioxopiperidin-3-yl)-6-fluoro-1,3-dioxoisoindolin-5-yl)piperazin-1-yl)ethyl)piperidin-1-yl) pyrimidine-5-carboxamide (534); rac-N-((1r,3r)-3-(3-chloro-4-cyanophenoxy)-2,2,4,4-tetramethylcyclobutyl)-6-(4-((4-(2-(2,6-dioxopiperidin-3-yl)-6-fluoro-1,3-dioxoisoindolin-5-yl)piperazin-1-yl)methyl)piperidin-1-yl)-4-(2-(2-methoxyethoxy)ethoxy)nicotinamide (535); rac-N-((1r,4R)-4-(3-chloro-4-cyanophenoxy)cyclohexyl)-4-(2-((2R,6R)-4-(2-(2-(2,6-dioxopiperidin-3-yl)-1,3-dioxoisoindolin-5-yl)-2,6-dimethylpiperazin-1-yl)ethyl) benzamide (536); rac-N-((1r,3r)-3-(3,4-dicyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (537); rac-N-((1r,3r)-3-(4-cyano-2-methylphenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl) piperidin-1-yl)benzamide (538); rac-N-((1r,3r)-3-(2,4-dicyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (539); rac-N-((1r,3r)-3-(4-cyano-2,6-dimethylphenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl) piperidin-1-yl)benzamide (540); rac-N-((1r,3r)-3-(4-cyano-3-methoxyphenoxy)-2,2,4,4-tetramethylcyclobutyl)-4-(4-((4-(2-(2,6-dioxopiperidin-3-yl)-1,3-dioxoisoindolin-5-yl) piperazin-1-yl)methyl)piperidin-1-yl)benzamide (541); N-((1r,4r)-4-(4-cyano-3-methylphenoxy)cyclohexyl)-5-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide (542); rac-N-((1r,4r)-4-(3-chloro-4-cyanophenoxy)cyclohexyl)-4-(4-(2-((2-(2,6-dioxopiperidin-3-yl)-1,3-dioxoisoindolin-5-yl)thio)ethyl) piperazin-1-yl)benzamide (543); rac-N-((1r,3r)-3-(3-chloro- 4-cyanophenoxy)-2,2,4,4-tetramethylcyclobutyl)-2-(4-(3-((2-(2,6-dioxopiperidin-3-yl)-6-fluoro-1,3-dioxoisoindolin-5-yl)oxy)propyl)piperazin-1-yl)-4,6-dimethylpyrimidine-5-carboxamide (544); rac-N-((1r,3r)-3-(3-chloro-4-cyanophenoxy)-2,2,4,4-tetramethylcyclobutyl)-2-(4-((4-(2-(2-(2,6-dioxopiperidin-3-yl)-6,7-difluoro-1,3-dioxoisoindolin-5-yl)piperazin-1-yl)methyl)piperidin-1-yl)-4,6-dimethylpyrimidine-5-carboxamide (545); rac-2-chloro-4-(((1r,4r)-4-(5-(4-((4-(2-(2,6-dioxopiperidin-3-yl)-1,3-dioxoisoindolin-5-yl)piperazin-1-yl)methyl)piperidin-1-yl)-1H-benzo[d]imidazol-2-yl)cyclohexyl)oxy)benzonitrile (546); rac-N-((1r,4r)-4-(3-chloro-4-cyanophenoxy)cyclohexyl)-6-(4-(2-(4-(2-(2,6-dioxopiperidin-3-yl)-1,3-dioxoisoindolin-5-yl)piperazin-1-yl)ethyl)piperidin-1-yl)nicotinamide (547); rac-N-((1r,4r)-4-(3-chloro-4-cyano-2-methylphenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide (548); rac-N-((1r,4r)-4-(4-cyano-3-methylphenoxy)cyclohexyl)-6-(4-((4-(2-(2,6-dioxopiperidin-3-yl)-6-fluoro-1,3-dioxoisoindolin-5-yl)piperazin-1-yl)methyl)piperidin-1-yl)pyridazine-3-carboxamide (549); rac-N-((1r,3r)-3-(4-cyano-3-methylphenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (550); rac-N-((1r,3r)-3-((5-cyano-6-methylpyridin-2-yl)oxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (551); rac-N-((1r,3r)-3-((5-cyanopyridin-2-yl)oxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (552); rac-N-((1r,3r)-3-(3,4-dicyanophenoxy)-2,2,4,4-tetramethylcyclobutyl)-2-(4-((4-(2-(2,6-dioxopiperidin-3-yl)-1,3-dioxoisoindolin-5-yl)piperazin-1-yl)methyl)piperidin-1-yl)pyrimidine-5-carboxamide (553); rac-N-((1r,3r)-3-((5-cyano-6-methylpyridin-2-yl)oxy)-2,2,4,4-tetramethylcyclobutyl)-2-(4-((4-(2-(2,6-dioxopiperidin-3-yl)-1,3-dioxoisoindolin-5-yl)piperazin-1-yl)methyl)piperidin-1-yl)pyrimidine-5-carboxamide (554); rac-N-((1r,3R)-3-(3-chloro-4-cyanophenoxy)-2,2,4,4-tetramethylcyclobutyl)-2-((1R,4R,5S)-5-((4-(2-(2,6-dioxopiperidin-3-yl)-1,3-dioxoisoindolin-5-yl)piperazin-1-yl)methyl)-2-azabicyclo[2.2.1]heptan-2-yl)pyrimidine-5-carboxamide (555); rac-N-((1r,3r)-3-((5-cyano-3-methylpyridin-2-yl)oxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (556); rac-N-((1r,3r)-3-((5-cyanopyrimidin-2-yl)oxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (557); rac-N-((1r,3r)-3-(4-cyano-3,5-dimethylphenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (558); rac-N-((1r,4r)-4-(3-chloro-4-cyanophenoxy)cyclohexyl)-5-(4-(4-(2-(2,6-dioxopiperidin-3-yl)-1,3-dioxoisoindolin-5-yl)piperazin-1-yl)piperidin-1-yl)pyrazine-2-carboxamide (559); rac-N-((1r,4r)-4-(3-chloro-4-cyanophenoxy)cyclohexyl)-2-(4-(4-(2-(2,6-dioxopiperidin-3-yl)-1,3-dioxoisoindolin-5-yl)piperazin-1-yl)piperidin-1-yl)pyrimidine-5-carboxamide (560); rac-N-((1r,3R)-3-(3-chloro-4-cyanophenoxy)-2,2,4,4-tetramethylcyclobutyl)-2-((1R,4R,5R)-5-((4-(2-(2,6-dioxopiperidin-3-yl)-1,3-dioxoisoindolin-5-yl)piperazin-1-yl)methyl)-2-azabicyclo[2.2.1]heptan-2-yl)pyrimidine-5-carboxamide (561); rac-N-((1r,3r)-3-(3-chloro-4-cyanophenoxy)-2,2,4,4-tetramethylcyclobutyl)-4-(3-((2-((2-(2,6-dioxopiperidin-3-yl)-1,3-dioxoisoindolin-5-yl)oxy)ethyl)(methyl)amino)pyrrolidin-1-yl)benzamide (562); rac-N-((1r,3R)-3-(3-chloro-4-cyanophenoxy)-2,2,4,4-tetramethylcyclobutyl)-4-(4-((1R,3S)-3-((2-(2,6-dioxopiperidin-3-yl)-1,3-dioxoisoindolin-5-yl)oxy)cyclopentyl)piperazin-1-yl)benzamide (563); rac-N-((1r,3r)-3-((6-cyano-5-methylpyridin-3-yl)oxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (564); rac-N-((1r,3r)-3-((6-cyano-5-(trifluoromethyl)pyridin-3-yl)oxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (565); rac-N-((1r,3r)-3-(3-chloro-4-cyanophenoxy)-2,2,4,4-tetramethylcyclobutyl)-5-(3-((4-(2-(2,6-dioxopiperidin-3-yl)-1,3-dioxoisoindolin-5-yl)piperazin-1-yl)methyl)azetidin-1-yl)pyrazine-2-carboxamide (566); rac-N-((1r,4r)-4-(3-chloro-4-cyanophenoxy)cyclohexyl)-5-(3-((4-(2-(2,6-dioxopiperidin-3-yl)-1,3-dioxoisoindolin-5-yl)piperazin-1-yl)methyl)azetidin-1-yl)pyrazine-2-carboxamide (567); rac-N-((1r,3r)-3-(3-chloro-4-cyanophenoxy)-2,2,4,4-tetramethylcyclobutyl)-4-(4-((4-(2-(2,6-dioxopiperidin-3-yl)-1-oxoisoindolin-5-yl)piperazin-1-yl)methyl)piperidin-1-yl)benzamide (568); rac-N-((1r,4r)-4-(3-chloro-4-cyanophenoxy)cyclohexyl)-6-(4-(2-((2-(2,6-dioxopiperidin-3-yl)-6-fluoro-1,3-dioxoisoindolin-5-yl)oxy)ethyl)piperazin-1-yl)-4-fluoronicotinamide (569); rac-N-((1r,4r)-4-(3-chloro-4-cyanophenoxy)cyclohexyl)-6-(4-((4-(2-(2,6-dioxopiperidin-3-yl)-7-fluoro-1,3-dioxoisoindolin-5-yl)piperazin-1-yl)methyl)piperidin-1-yl)pyridazine-3-carboxamide (570); rac-N-((1r,3r)-3-(3-chloro-4-cyanophenoxy)-2,2,4,4-tetramethylcyclobutyl)-2-(4-((4-(2-(2,6-dioxopiperidin-3-yl)-7-fluoro-1,3-dioxoisoindolin-5-yl)piperazin-1-yl)methyl)piperidin-1-yl)pyrimidine-5-carboxamide (571); rac-N-((1r,3r)-3-(4-cyano-3-methylphenoxy)-2,2,4,4-tetramethylcyclobutyl)-2-(4-((4-(2-(2,6-dioxopiperidin-3-yl)-6-fluoro-1,3-dioxoisoindolin-5-yl)piperazin-1-yl)methyl)piperidin-1-yl)-4,6-dimethylpyrimidine-5-carboxamide (572); rac-N-((1r,3r)-3-(3-chloro-4-cyanophenoxy)-2,2,4,4-tetramethylcyclobutyl)-6-(3-((4-(2-(2,6-dioxopiperidin-3-yl)-1,3-dioxoisoindolin-5-yl)piperazin-1-yl)methyl)azetidin-1-yl)pyridazine-3-carboxamide (573); rac-N-((1r,4r)-4-(3-chloro-4-cyanophenoxy)cyclohexyl)-2-(3-((4-(2-(2,6-dioxopiperidin-3-yl)-1,3-dioxoisoindolin-5-yl)piperazin-1-yl)methyl)azetidin-1-yl)pyrimidine-5-carboxamide (574); rac-N-((1r,4r)-4-(4-cyano-3-methylphenoxy)cyclohexyl)-2-(3-((4-(2-(2,6-dioxopiperidin-3-yl)-1,3-dioxoisoindolin-5-yl)piperazin-1-yl)methyl)azetidin-1-yl)pyrimidine-5-carboxamide (575); rac-N-((1r,3r)-3-(3-chloro-4-cyanophenoxy)-2,2,4,4-tetramethylcyclobutyl)-6-(3-((4-(2-(2,6-dioxopiperidin-3-yl)-6-fluoro-1,3-dioxoisoindolin-5-yl)piperazin-1-yl)methyl)azetidin-1-yl)pyridazine-3-carboxamide (576); rac-N-((1r,3r)-3-(3-chloro-4-cyanophenoxy)-2,2,4,4-tetramethylcyclobutyl)-6-(4-((4-(2-(2,6-dioxopiperidin-3-yl)-7-fluoro-1,3-dioxoisoindolin-5-yl)piperazin-1-yl)methyl)piperidin-1-yl)pyridazine-3-carboxamide (577); rac-N-((1r,3r)-3-(3-chloro-4-cyanophenoxy)-2,2,4,4-tetramethylcyclobutyl)-2-(4-((4-(2-(2,6-dioxopiperidin-3-yl)-1-oxoisoindolin-5-yl)piperazin-1-yl)methyl)piperidin-1-yl)pyrimidine-5-carboxamide (578); rac-N-((1r,4r)-4-(3-chloro-4-cyanophenoxy)cyclohexyl)-5-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)

pyrazine-2-carboxamide (579); rac-N-((1r,4r)-4-(3-chloro-4-cyanophenoxy)cyclohexyl)-2-(4-(((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrimidine-5-carboxamide (580); rac-N-((1r,3r)-3-(3-chloro-4-cyanophenoxy)-2,2,4,4-tetramethylcyclobutyl)-2-(4-((4-(2-(2,6-dioxopiperidin-3-yl)-4,6-difluoro-1,3-dioxoisoindolin-5-yl)piperazin-1-yl)methyl)piperidin-1-yl)-4,6-dimethylpyrimidine-5-carboxamide (581); rac-N-((1r,3r)-3-(3-chloro-4-cyanophenoxy)-2,2,4,4-tetramethylcyclobutyl)-6-(4-(2-(4-(2-(2,6-dioxopiperidin-3-yl)-4,6-difluoro-1,3-dioxoisoindolin-5-yl)piperazin-1-yl)ethyl)piperidin-1-yl)pyridazine-3-carboxamide (582); rac-N-((1r,3r)-3-(3-chloro-4-cyanophenoxy)-2,2,4,4-tetramethylcyclobutyl)-6-(4-((4-(2-(2,6-dioxopiperidin-3-yl)-6-fluoro-1,3-dioxoisoindolin-5-yl)piperazin-1-yl)methyl)piperidin-1-yl)-4-(2-morpholinoethoxy)nicotinamide (583); N-((1r,3r)-3-(3-chloro-4-cyanophenoxy)-2,2,4,4-tetramethylcyclobutyl)-2-(3-(((((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrimidine-5-carboxamide (584); rac-N-((1r,3r)-3-((5-cyano-6-ethylpyridin-2-yl)oxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (585); N-((1r,3r)-3-(3-chloro-4-cyanophenoxy)-2,2,4,4-tetramethylcyclobutyl)-6-(3-(((((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyridazine-3-carboxamide (586); rac-N-((1r,3r)-3-(3-chloro-4-cyanophenoxy)-2,2,4,4-tetramethylcyclobutyl)-4-(3-((4-(2-(2,6-dioxopiperidin-3-yl)-6-fluoro-1,3-dioxoisoindolin-5-yl)piperazin-1-yl)methyl)azetidin-1-yl)benzamide (587); rac-N-((1r,3r)-3-(3-chloro-4-cyanophenoxy)-2,2,4,4-tetramethylcyclobutyl)-4-(1-((1-(2-(2,6-dioxopiperidin-3-yl)-1,3-dioxoisoindolin-5-yl)piperidin-4-yl)methyl)piperidin-4-yl)benzamide (588); rac-N-((1r,3r)-3-(3-chloro-4-cyanophenoxy)-2,2,4,4-tetramethylcyclobutyl)-4-(3-(((1-(2-(2,6-dioxopiperidin-3-yl)-1,3-dioxoisoindolin-5-yl)piperidin-4-yl)oxy)methyl)pyrrolidin-1-yl)benzamide (589); rac-N-((1r,3r)-3-(3-chloro-4-cyanophenoxy)-2,2,4,4-tetramethylcyclobutyl)-4-(4-((1-(2-(2,6-dioxopiperidin-3-yl)-6-fluoro-3-oxoisoindolin-5-yl)piperidin-4-yl)methyl)piperazin-1-yl)benzamide (590); rac-N-((1r,3r)-3-(3-chloro-4-cyanophenoxy)-2,2,4,4-tetramethylcyclobutyl)-4-(4-((1-(2-(2,6-dioxopiperidin-3-yl)-6-fluoro-1-oxoisoindolin-5-yl)piperidin-4-yl)methyl)piperazin-1-yl)benzamide (591); rac-N-((1r,3r)-3-(3-chloro-4-cyanophenoxy)-2,2,4,4-tetramethylcyclobutyl)-6-(4-((4-(2-(2,6-dioxopiperidin-3-yl)-4,6-difluoro-1,3-dioxoisoindolin-5-yl)piperazin-1-yl)methyl)piperidin-1-yl)pyridazine-3-carboxamide (592); rac-2-chloro-4-(((1r,4r)-4-(5-(4'-(2-(2-(2,6-dioxopiperidin-3-yl)-1,3-dioxoisoindolin-5-yl)-1-methyl-1H-imidazol-5-yl)-[1,1'-biphenyl]-4-yl)-1-methyl-1H-imidazol-2-yl)cyclohexyl)oxy)benzonitrile (593); rac-N-((1r,4r)-4-(3-chloro-4-cyanophenoxy)cyclohexyl)-6-(4-((4-(2-(2,6-dioxopiperidin-3-yl)-4,6-difluoro-1,3-dioxoisoindolin-5-yl)piperazin-1-yl)methyl)piperidin-1-yl)pyridazine-3-carboxamide (594); rac-N-((1r,3r)-3-(3-chloro-4-cyanophenoxy)-2,2,4,4-tetramethylcyclobutyl)-2-(4-((4-(2-(2,6-dioxopiperidin-3-yl)-4,6-difluoro-1,3-dioxoisoindolin-5-yl)piperazin-1-yl)methyl)piperidin-1-yl)pyrimidine-5-carboxamide (595); rac-N-((1r,4r)-4-(3-chloro-4-cyanophenoxy)cyclohexyl)-4-(3-((4-(2-(2,6-dioxopiperidin-3-yl)-1,3-dioxoisoindolin-5-yl)piperazin-1-yl)methyl)azetidin-1-yl)benzamide (596); rac-N-((1r,3r)-3-(3-chloro-4-cyanophenoxy)-2,2,4,4-tetramethylcyclobutyl)-5-(4-(((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrazine-2-carboxamide (597); rac-N-((1r,3r)-3-(3-chloro-4-cyanophenoxy)-2,2,4,4-tetramethylcyclobutyl)-2-(1-((1-(2-(2,6-dioxopiperidin-3-yl)-1,3-dioxoisoindolin-5-yl)piperidin-4-yl)methyl)piperidin-4-yl)pyrimidine-5-carboxamide (598); rac-N-((1r,3r)-3-(3-chloro-4-cyanophenoxy)-2,2,4,4-tetramethylcyclobutyl)-6-(4-(4-(2-(2,6-dioxopiperidin-3-yl)-7-fluoro-1,3-dioxoisoindolin-5-yl)piperazin-1-yl)piperidin-1-yl)pyridazine-3-carboxamide (599); rac-N-((1r,3r)-3-(3-chloro-4-cyanophenoxy)-2,2,4,4-tetramethylcyclobutyl)-6-(4-(((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyridazine-3-carboxamide (600); rac-N-((1r,4r)-4-(3-chloro-4-cyanophenoxy)cyclohexyl)-5-(4-(((((1r,3r)-3-((2-(2,6-dioxopiperidin-3-yl)-1,3-dioxoisoindolin-5-yl)oxy)cyclobutyl)(isopropyl)amino)methyl)piperidin-1-yl)picolinamide (601); rac-N-((1r,3r)-3-(3-chloro-4-cyanophenoxy)-2,2,4,4-tetramethylcyclobutyl)-6-(6-(4-(2-(2,6-dioxopiperidin-3-yl)-6-fluoro-1-oxoisoindolin-5-yl)piperazin-1-yl)hexyl)nicotinamide (602); rac-2-chloro-4-(((1r,4r)-4-(2-(4-(3-((4-(2-(2,6-dioxopiperidin-3-yl)-1,3-dioxoisoindolin-5-yl)piperazin-1-yl)methyl)azetidin-1-yl)phenyl)-1H-imidazol-5-yl)cyclohexyl)oxy)benzonitrile (603); rac-N-((1r,3r)-3-(3-chloro-4-cyanophenoxy)-2,2,4,4-tetramethylcyclobutyl)-1-(4-((4-(2-(2,6-dioxopiperidin-3-yl)-1,3-dioxoisoindolin-5-yl)piperazin-1-yl)methyl)cyclohexyl)-1H-pyrazole-3-carboxamide (604); rac-N-((1r,3r)-3-(3-chloro-4-cyanophenoxy)-2,2,4,4-tetramethylcyclobutyl)-1-(3-((2-(2,6-dioxopiperidin-3-yl)-1,3-dioxoisoindolin-5-yl)oxy)propyl)-1H-pyrazole-3-carboxamide (605); rac-N-((1r,4r)-4-(3-chloro-4-cyanophenoxy)cyclohexyl)-1-(4-((4-(2-(2,6-dioxopiperidin-3-yl)-1,3-dioxoisoindolin-5-yl)piperazin-1-yl)methyl)cyclohexyl)-1H-pyrazole-3-carboxamide (606); 3-chloro-5-(5-(4-(1-((1-(2-(2,6-dioxopiperidin-3-yl)-1,3-dioxoisoindolin-5-yl)piperidin-4-yl)methyl)piperidin-4-yl)-3-fluorophenyl)-8-oxo-6-thioxo-5,7-diazaspiro[3.4]octan-7-yl)picolinonitrile (607); 3-chloro-5-(5-(4-(4-((4-(2-(2,6-dioxopiperidin-3-yl)-1,3-dioxoisoindolin-5-yl)piperazin-1-yl)methyl)piperidin-1-yl)phenyl)-8-oxo-6-thioxo-5,7-diazaspiro[3.4]octan-7-yl)picolinonitrile (608); rac-N-((1r,3r)-3-(3-chloro-4-cyanophenoxy)-2,2,4,4-tetramethylcyclobutyl)-4-(4-((4-(2-(2,6-dioxopiperidin-3-yl)-3-methyl-1-oxoisoindolin-5-yl)piperazin-1-yl)methyl)piperidin-1-yl)benzamide (609); rac-N-((1r,3r)-3-(3-chloro-4-cyanophenoxy)-2,2,4,4-tetramethylcyclobutyl)-4-(4-((4-(2-(2,6-dioxopiperidin-3-yl)-1-methyl-3-oxoisoindolin-5-yl)piperazin-1-yl)methyl)piperidin-1-yl)benzamide (610); rac-N-((1r,3r)-3-(3-chloro-4-cyanophenoxy)-2,2,4,4-tetramethylcyclobutyl)-6-(4-((4-(2-(2,6-dioxopiperidin-3-yl)-4-fluoro-1,3-dioxoisoindolin-5-yl)piperazin-1-yl)methyl)piperidin-1-yl)pyridazine-3-carboxamide (611); 3-chloro-5-(5-(4-(4-((4-(2-(2,6-dioxopiperidin-3-yl)-1,3-dioxoisoindolin-5-yl)piperazin-1-yl)methyl)piperidin-1-yl)-3-fluorophenyl)-8-oxo-6-thioxo-5,7-diazaspiro[3.4]octan-7-yl)picolinonitrile (612); 3-chloro-5-(5-(4-(1-((1-(2-(2,6-dioxopiperidin-3-yl)-1,3-dioxoisoindolin-5-yl)piperidin-4-yl)methyl)piperidin-4-yl)phenyl)-8-oxo-6-thioxo-5,7-diazaspiro[3.4]octan-7-yl)picolinonitrile (613); 5-(4-((1-(2-(4-(6,7-dihydro-5H-pyrrolo[1,2-a]imidazol-3-yl)phenoxy)ethyl)piperidin-4-yl)methyl)piperazin-1-yl)-2-(2,6-dioxopiperidin-3-yl)isoindoline-1,3-dione (614); rac-N-((1r,3r)-3-(3-chloro-4-cyanophenoxy)-2,2,4,4-tetramethylcyclobutyl)-2-(4-(((((1r,3r)-3-((2-(2,6- dioxopiperidin-3-yl)-1,3-dioxoisoindolin-5-yl)oxy)cyclobutyl)(isopropyl)amino)methyl)piperidin-1-yl)pyrimidine-5-carboxamide (615); rac-N-((1r,3r)-3-(3-chloro-4-cyanophenoxy)-2,2,4,4-tetramethylcyclobutyl)-4-(5-(4-(2-(2,6-dioxopiperidin-3-yl)-1,3-dioxoisoindolin-5-yl)piperazine-1-carbonyl)hexahydropyrrolo[3,4-c]pyrrol-2(1H)-yl)benzamide (616); rac-N-((1r,3R)-3-(3-chloro-4-cyanophenoxy)-2,2,4,4-tetramethylcyclobutyl)-1-((1r,4R)-4-((1-(2-(2,6-dioxopiperidin-3-yl)-1,3-dioxoisoindolin-5-yl)piperidin-4-yl)(methyl)amino)cyclohexyl)-1H-pyrazole-3-carboxamide (617); 5-(4-((1-(4-(6,7-dihydro-5H-pyrrolo[1,2-a]imidazol-3-yl)phenyl)piperidin-4-yl)methyl)piperazin-1-yl)-2-(2,6-dioxopiperidin-3-yl)isoindoline-1,3-dione (618); rac-N-((1r,3r)-3-(3-chloro-4-cyanophenoxy)-2,2,4,4-tetramethylcyclobutyl)-5-(3-((((1r,3r)-3-((2-(2,6-dioxopiperidin-3-yl)-1,3-dioxoisoindolin-5-yl)oxy)cyclobutyl)(isopropyl)amino)methyl)azetidin-1-yl)pyrazine-2-carboxamide (619); N-((1r,3R)-3-(3-chloro-4-cyanophenoxy)-2,2,4,4-tetramethylcyclobutyl)-1-((1R,4R)-4-(((((1r,3R)-3-((2-(2,6-dioxopiperidin-3-yl)-1,3-dioxoisoindolin-5-yl)oxy)cyclobutyl)(isopropyl)amino)methyl)cyclohexyl)-1H-pyrazole-3-carboxamide (620); N-((1r,3r)-3-(4-cyano-3-methoxyphenoxy)-2,2,4,4-tetramethylcyclobutyl)-2-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrimidine-5-carboxamide (621); N-((1r,3r)-3-(4-cyano-3-methylphenoxy)-2,2,4,4-tetramethylcyclobutyl)-2-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrimidine-5-carboxamide (622); N-((1r,3r)-3-(4-cyano-3,5-dimethylphenoxy)-2,2,4,4-tetramethylcyclobutyl)-2-(4-((((1r,3r)-3-((2-(2,6-dioxopiperidin-3-yl)-1,3-dioxoisoindolin-5-yl)oxy)cyclobutyl)(isopropyl)amino)methyl)piperidin-1-yl)pyrimidine-5-carboxamide (623); N-((1r,3r)-3-(3-chloro-4-cyanophenoxy)-2,2,4,4-tetramethylcyclobutyl)-4-(4-((4-(2-(2,6-dioxopiperidin-3-yl)-3-oxoisoindolin-5-yl)piperazin-1-yl)methyl)piperidin-1-yl)benzamide (624); and N-((1r,4r)-4-(3-chloro-4-cyanophenoxy)cyclohexyl)-2-(4-((((1r,3r)-3-((2-(2,6-dioxopiperidin-3-yl)-1-oxoisoindolin-5-yl)oxy)cyclobutyl)(isopropyl)amino)methyl)piperidin-1-yl)pyrimidine-5-carboxamide (625).

In another embodiment, the present disclosure provides a library of compounds. The library comprises more than one compound wherein each compound has a formula of ABM-L-ULM, wherein ULM is a ubiquitin pathway protein binding moiety (preferably, an E3 ubiquitin ligase moiety as otherwise disclosed herein), e.g., a CLM, and ABM is an AR protein binding moiety, wherein ABM is coupled (preferably, through a linker moiety) to ULM, and wherein the ubiquitin pathway protein binding moiety recognizes an ubiquitin pathway protein, in particular, an E3 ubiquitin ligase.

The present description includes, where applicable, the compositions comprising the pharmaceutically acceptable salts, in particular, acid or base addition salts of compounds of the present disclosure.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The acids which are used to prepare the pharmaceutically acceptable acid addition salts of the aforementioned base compounds useful in this disclosure are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

Compositions

In another aspect, the description provides compositions comprising compounds as described herein, including salts thereof, and a pharmaceutically acceptable carrier. In certain embodiments, the compositions are therapeutic or pharmaceutical compositions comprising an effective amount of a compound as described herein and a pharmaceutically acceptable carrier.

The amount of compound in a pharmaceutical composition of the instant disclosure that may be combined with the carrier materials to produce a single dosage form will vary depending upon the host and disease treated, the particular mode of administration. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The compositions of the present disclosure may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Modes of Administration

In any of the aspects or embodiments described herein, the therapeutic compositions comprising compounds described herein can be in any suitable dosage form configured to be delivered by any suitable route. For example, the compounds can be administered by any appropriate route, for example, orally, parenterally, intravenously, intradermally, subcutaneously, or topically, including transdermally, in liquid, cream, gel, or solid form, rectally, nasally, buccally, vaginally or via an implanted reservoir or by aerosol form.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The compounds as described herein may be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient.

Administration of compounds as sprays, mists, or aerosols for intra-nasal, intra-tracheal or pulmonary administration may also be used. Compounds as described herein may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials are included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions of the disclosure may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used. For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds as described herein can be treated by administering to the patient (subject) an effective amount of the compound including pharmaceutically acceptable salts, solvates or polymorphs, thereof optionally in a pharmaceutically acceptable carrier or diluent, either alone, or in combination with other known agents.

Co-Administration

Disease states of conditions which may be treated using compounds or compositions according to the present description include, but not limited to, for example, cancer (e.g., prostate cancer), and Kennedy's disease. In certain embodiments, the therapeutic or pharmaceutical compositions comprise an effective amount of an additional biologically or bioactive active agent, e.g., an agent effective for the treatment of cancer, that is co-administered.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present disclosure may be co-administered to a patient at the same time, the term embraces both administration of two or more agents at the same time or at different times, provided that effective concentrations of all coadministered compounds or compositions are found in the subject at a given time. In certain preferred aspects of the present disclosure, one or more of the present compounds described above, are coadministered in combination with at least one additional bioactive agent, especially including an anticancer agent. In particularly preferred aspects of the disclosure, the co-administration of compounds results in synergistic therapeutic, including anticancer therapy.

In another aspect, the description provides a composition comprising an effective amount of two or more of the PROTAC compounds as described herein, and a pharmaceutically acceptable carrier. In certain embodiments, the composition further comprises an effective or synergistic amount of another bioactive agent that is not a PROTAC compound.

Pharmaceutical compositions comprising combinations of an effective amount of at least one bifunctional compound according to the present disclosure, and one or more of the compounds otherwise described herein, all in effective amounts, in combination with a pharmaceutically effective amount of a carrier, additive or excipient, represents a further aspect of the present disclosure.

The term "bioactive agent" is used to describe an agent, other than the PROTAC compounds described herein, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents.

The term "additional anti-cancer agent" is used to describe an anti-cancer agent, which may be combined with PROTAC compounds according to the present description to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, an androgen receptor inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH 2 acetate [$C_{59}H_{84}N_{18}Oi_4$-$(C_2H_4O_2)_X$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

Methods of Treatment

In another aspect, the disclosure provides methods of modulating protein ubiquitination and degradation in a subject, e.g., a cell, a tissue, mammal, or human patient, the method comprising administering an effective amount of a PROTAC compound as described herein or a composition comprising an effective amount of the same to a subject, wherein the compound or composition comprising the same is effective in modulating protein ubiquitination and degradation of the protein in the subject. In certain embodiments, the protein is androgen receptor (AR).

In certain embodiments, the description provides a method for regulating protein activity of the androgen receptor in a patient in need comprising administering to said patient an amount of a compound as described herein to a patient.

In still additional embodiments, the description provides a method of treating a disease state or condition in a patient wherein dysregulated protein activity is responsible for said disease state or condition, said method comprising administering to said patient an effective amount of a compound as described herein to said patient in order to regulate said protein activity in said patient. In certain embodiments, the protein is AR.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

In another aspect, the disclosure provides methods of modulating AR protein ubiquitination and degradation in a subject, e.g., a cell, a tissue, mammal, or human patient, the method comprising administering an effective amount of a compound as described herein or a composition comprising an effective amount of a compound as described herein to a subject, wherein the compound or composition comprising the same is effective in modulating AR protein ubiquitination and degradation of the protein in the subject.

In another aspect, the disclosure provides methods of treating or ameliorating a symptom of a disease related to AR activity in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to AR activity in the subject.

In certain embodiments, the disease or disorder is asthma, multiple sclerosis, cancer, prostate cancer, Kenney's disease, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome. The method according to claim 48 wherein said cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas. In certain embodiments, the disease to be treated is cancer, e.g., prostate cancer, or Kennedy's Disease. In a preferred embodiment, the subject is a human.

In another aspect, the disclosure provides methods of treating or ameliorating a symptom of a disease related to AR activity in a subject, e.g., a cell, a tissue, mammal, or human patient, the method comprising administering an effective amount of a compound as described herein or a composition comprising an effective amount of the same and an effective or synergistic amount of another bioactive agent to a subject in need thereof, wherein the composition comprising the same is effective in treating or ameliorating a symptom of a disease related to AR activity in the subject. In certain embodiments, the disease to be treated is cancer, e.g., prostate cancer, or Kennedy's Disease. In a preferred embodiment, the subject is a human. In certain additional embodiments, the additional bioactive agent is an anti-cancer agent.

In alternative aspects, the present disclosure relates to a method for treating a disease state by degrading a protein or polypeptide through which a disease state or condition is modulated comprising administering to said patient or subject an effective amount of at least one compound as described hereinabove, optionally in combination with an additional bioactive agent. The method according to the present disclosure may be used to treat a large number of disease states or conditions including cancer, by virtue of the administration of effective amounts of at least one compound described herein.

In another aspect, the disclosure provides methods for identifying the effects of the degradation of proteins of interest in a biological system using compounds according to the present disclosure.

Kits

In another aspect, the description provides kits comprising compounds or compositions as described herein. The kit may be promoted, distributed, or sold as a unit for performing the methods of the present disclosure. In addition, the kits of the present disclosure may preferably contain instructions, which describe a suitable use. Such kits can be conveniently used, e.g., in clinical settings, to treat patients exhibiting symptoms of, e.g., cancer, prostate cancer or Kennedy's Disease.

EXAMPLES

General Chemistry—Analysis and Synthesis

Unless otherwise noted, all materials/reagents were obtained from commercial suppliers and used without further purification. Reactions were monitored by LC-MS and/or thin layer chromatography (TLC) on silica gel 60 $F_{25}4$ (0.2 mm) pre-coated aluminum foil or glass-backed and visualized using UV light. Flash chromatography (alternatively called "ISCO chromatography") was performed using an ISCO CombiFiash RF 75 PSI or equivalent with RediSep normal-phase silica gel cartridges. Preparative TLC was performed on Whatman LK6F Silica Gel 60A size 20×20 cm plates with a thickness of 1000 μm or equivalent.

$^1$HNMR (300 or 400 MHz) and $^{13}$CNMR (100.6 MHz) spectra were recorded on Bruker spectrometers at room temperature with TMS or the residual solvent peak as the internal standard. The line positions or multiples are given in (δ) and the coupling constants (J) are given as absolute values in Hertz (Hz). The multiplicities in $^1$HNMR spectra are abbreviated as follows: s (singlet), d (doublet), t (triplet), q (quartet), m (multiplet), br or broad (broadened).

Preparative HPLC purifications were performed on a Waters® UV-Directed Purification System equipped with 2545 Binary Gradient Module, 2767 Sample Manager and 2489 UV/Visible Detector, controlled by MassLynx V4.1 software. All purification work was completed using the following columns: Atlantis Prep T3 OBD Column, SunFire Prep C18 OBD Column and XBridge Prep Phenyl OBD Column. The mobile phases were water (with 0.1% TFA or 0.01% $NH_4HCO_3$) and acetonitrile; all reagents used were of HPLC grade. The flow rate was 30 ml/min. After the columns, a 1:1000 LC packings flow splitter allowed transfer of a small portion of the eluent into the UV detector. The electrospray source was set at 3.0 kV capillary voltage, 30 V cone voltage, 110° C. source temperature, 350° C. desolvation temperature, 600 L/h desolvation gas flow, and 60 L/h cone gas flow. For the analyzer, the multiplier was set at 550 for preparative tune method.

Analytical LC-MS data was collected on a Shimadzu LCMS-2020 with a mobile phase of 0.05% TFA in Acetonitrile (A) and 0.05% TFA in HPLC grade water (B); 0.1% FA in Acetonitrile (A) and 0.1% FA in HPLC grade water (B); Acetonitrile (A) and 5 mM ammonium bicarbonate in HPLC grade water (B).

Shimadzu LCMS-2020 equipped with LC-20AD or 30AD pumps, SPD-M20A PDA and Alltech 3300 ELSD. The system uses the following conditions for 2.0 min, 2.6 min, 3 min, 3.6 min, 5 min or 5.6 min run time.

2.0 minute run: Kinetex XB-C 18 100A column, 2.6 μm, 3.0×50 mm. The flow rate is 1.5 mL/min, the run time is 2.0 min, and the gradient profiles are 0.01 min 10% A, 1.10 min 100% A, 1.60 min 100% A, 1.70 min 10% A, 2.00 min 10% A.

2.6 minute run: Shim-pack VP-ODS column, 2.2 μm, 3.0×50 mm. The flow rate is 1.5 mL/min, the run time is 2.6 min, and the gradient profiles are 0.01 min 5% A, 1.20 min 100% A, 2.20 min 100% A, 2.30 min 5% A, 2.60 min 5% A.

3.0 minute run: ACE UltraCore Super C18 column, 2.5 μm, 3.0×50 mm. The flow rate is 1.5 mL/min, the run time is 3.0 min, and the gradient profiles are 0.01 min 10% A, 2.00 min 95% A, 2.60 min 95% A, 2.70 min 10% A, 3.00 min 10% A.

3.6 minute run: Shim-pack VP-ODS column, 2.2 μm, 3.0×50 mm. The flow rate is 1.5 mL/min, the run time is 3.6 min, and the gradient profiles are 0.01 min 5% A, 2.20 min 100% A, 3.20 min 100% A, 3.30 min 5% A, 3.60 min 5% A.

5.0 minute run: ACE UltraCore Super C18 column, 2.5 μm, 3.0×50 mm. The flow rate is 1.5 mL/min, the run time is 5.0 min, and the gradient profiles are 0.01 min 10% A, 4.00 min 60% A, 4.70 min 60% A, 4.80 min 10% A, 5.00 min 10% A.

5.6 minute run: Shim-pack VP-ODS column, 2.2 μm, 3.0×50 mm. The flow rate is 1.5 mL/min, the run time is 5.6 min, and the gradient profiles are 0.01 min 5% A, 3.00 min 50% A, 5.00 min 50% A, 5.20 min 5% A, 5.60 min 5% A Alternatively, analytical LC-MS data was collected on Agilent infinity 1260 LC, Agilent 6230 TOF mass spectrometer. The analysis is conducted on a Poroshell 120 EC C18 column (50 mm×3.0 mm internal diameter 2.7 μm packing diameter) at 45° C.

The solvents employed are:

A=0.1% v/v solution of formic acid in water.

B=0.1% v/v solution of formic acid in acetonitrile.

The gradient employed are as follows:

TABLE 1

Exemplary Column Gradients.

| Time (minutes) | Flow Rate (mL/min) | % A | % B |
|---|---|---|---|
| 0 | 1 | 95 | 5 |
| 0.5 | 1 | 95 | 5 |
| 3.0 | 1 | 1 | 99 |
| 4.0 | 1 | 1 | 99 |
| 4.1 | 1 | 95 | 5 |
| 4.5 | 1 | 95 | 5 |

The UV detection is an averaged signal from wavelength of 210 nm to 350 nm and mass spectra are recorded on a mass spectrometer using positive mode electrospray ionization.

Unless otherwise noted, all compounds were prepared with LC-MS purity>95%.

Chemical Synthesis

Figure 8A:
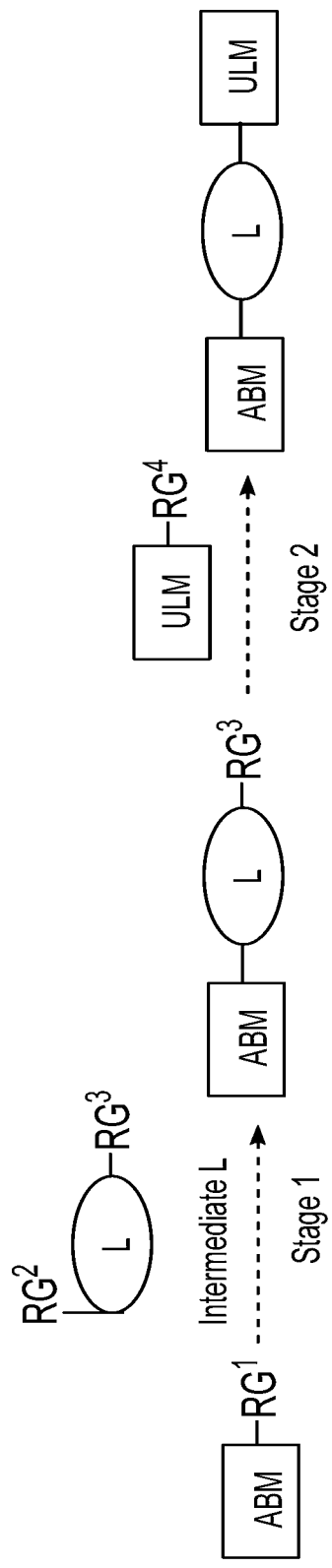
FIG. 8A and FIG. 8B illustrate general approaches for preparing compounds of the application.
Figure 8B:
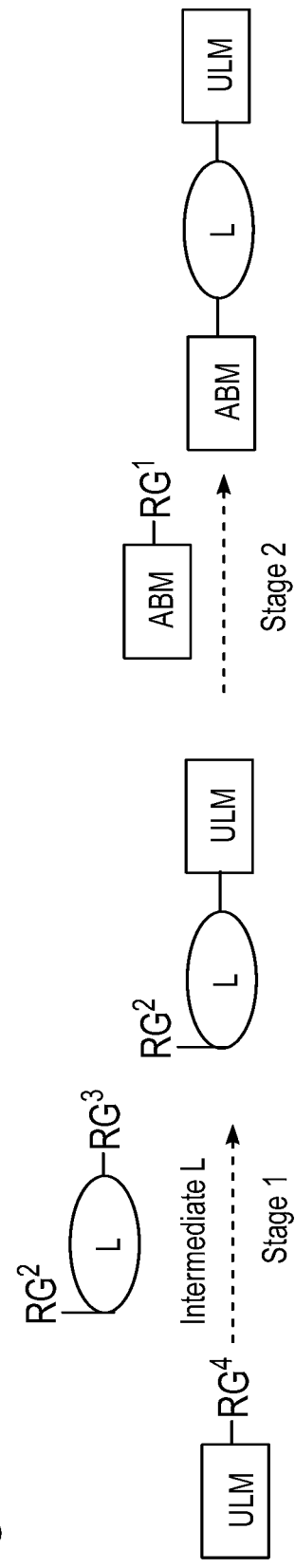

A PROTAC of ABM-L-ULM, or their pharmaceutically acceptable salts, polymorphic forms, prodrugs, solvate forms and isotope containing derivatives thereof, may be prepared by the general approaches described in FIGS. 8a and 8b and below in General Schemes 1-122, 1A-22A, and 1B-25B, together with synthetic methods known in the art of organic chemistry, or modifications and derivatizations that are familiar to those of ordinary skill in the art.

General Scheme 1
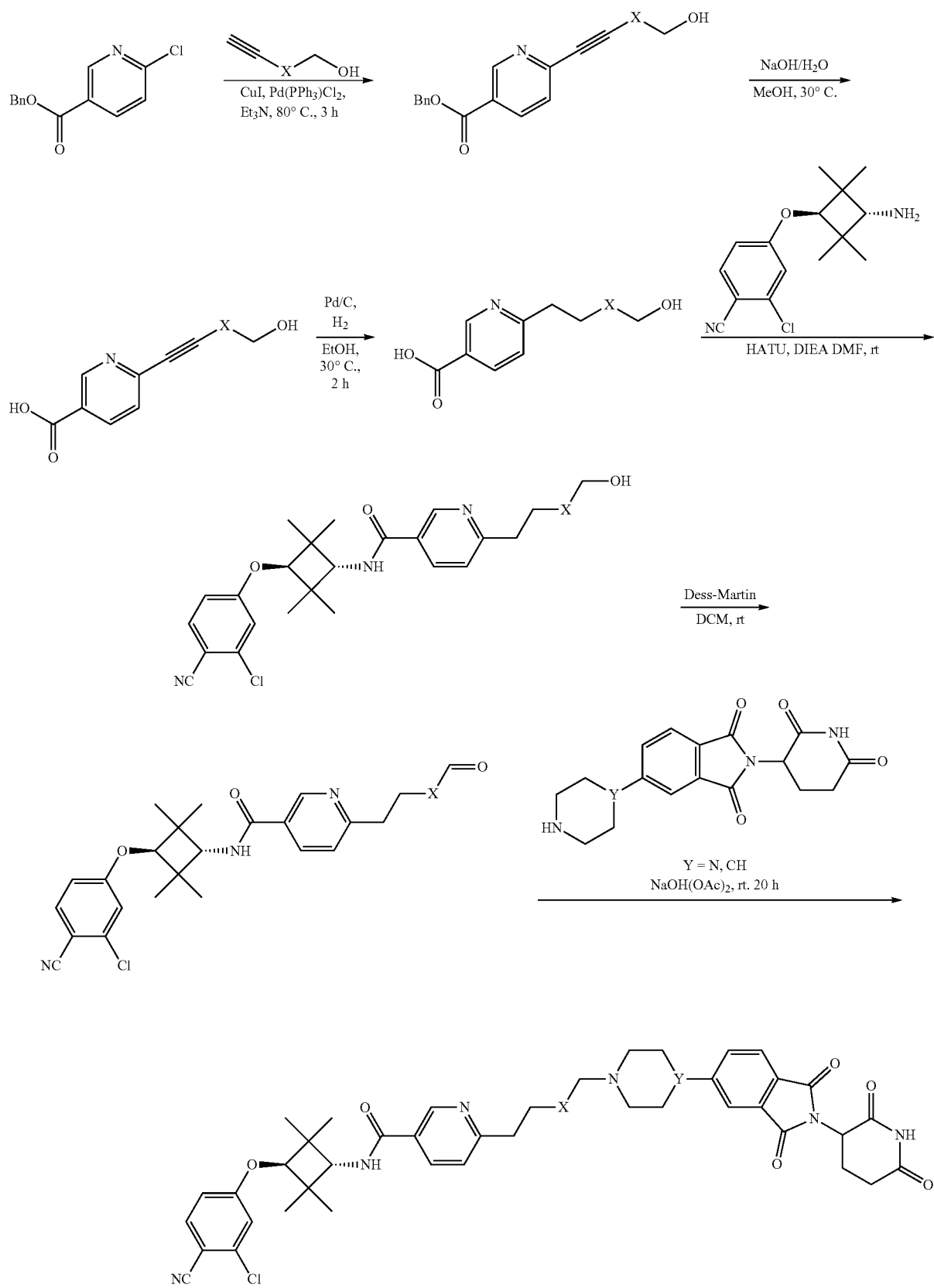

General Scheme 2
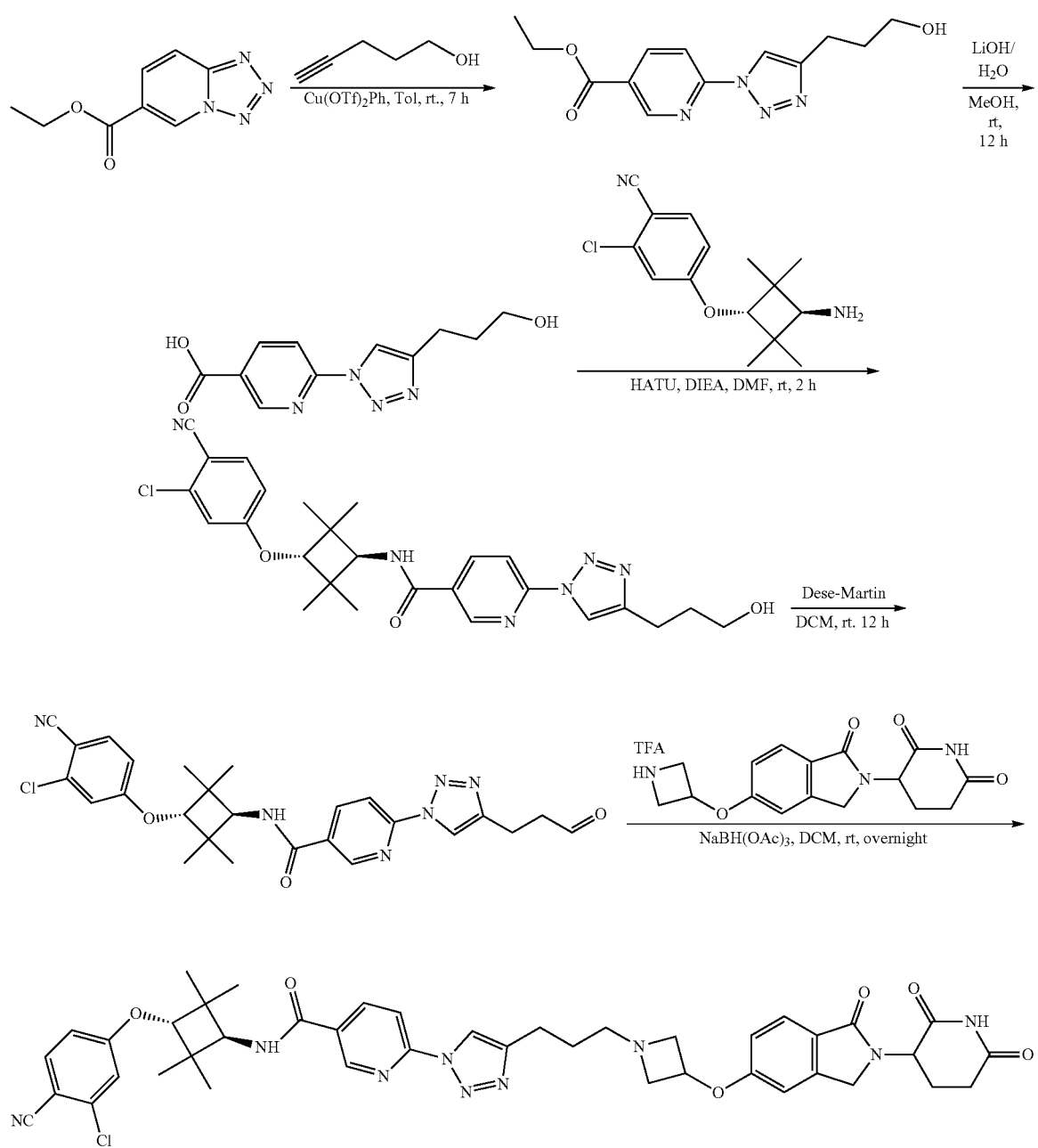
General Scheme 3
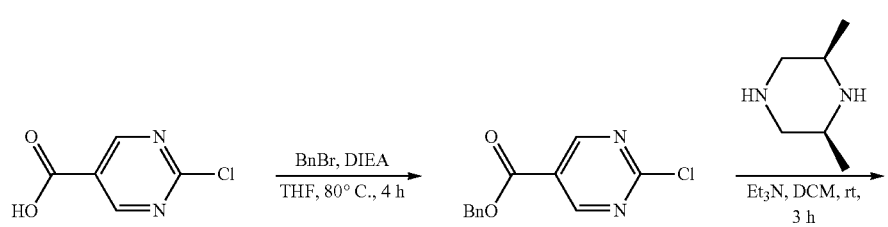

131    132
-continued
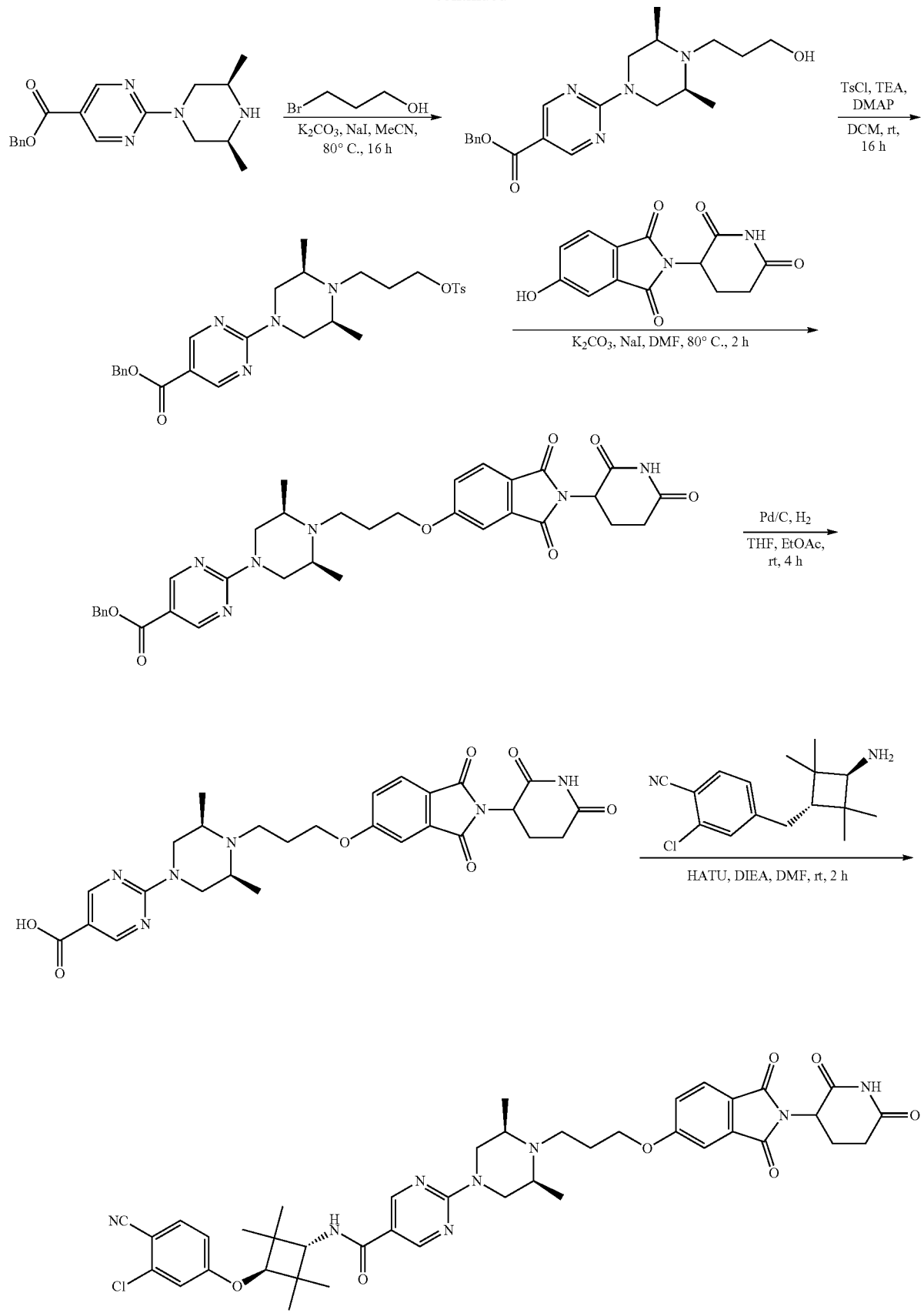

General Scheme 4
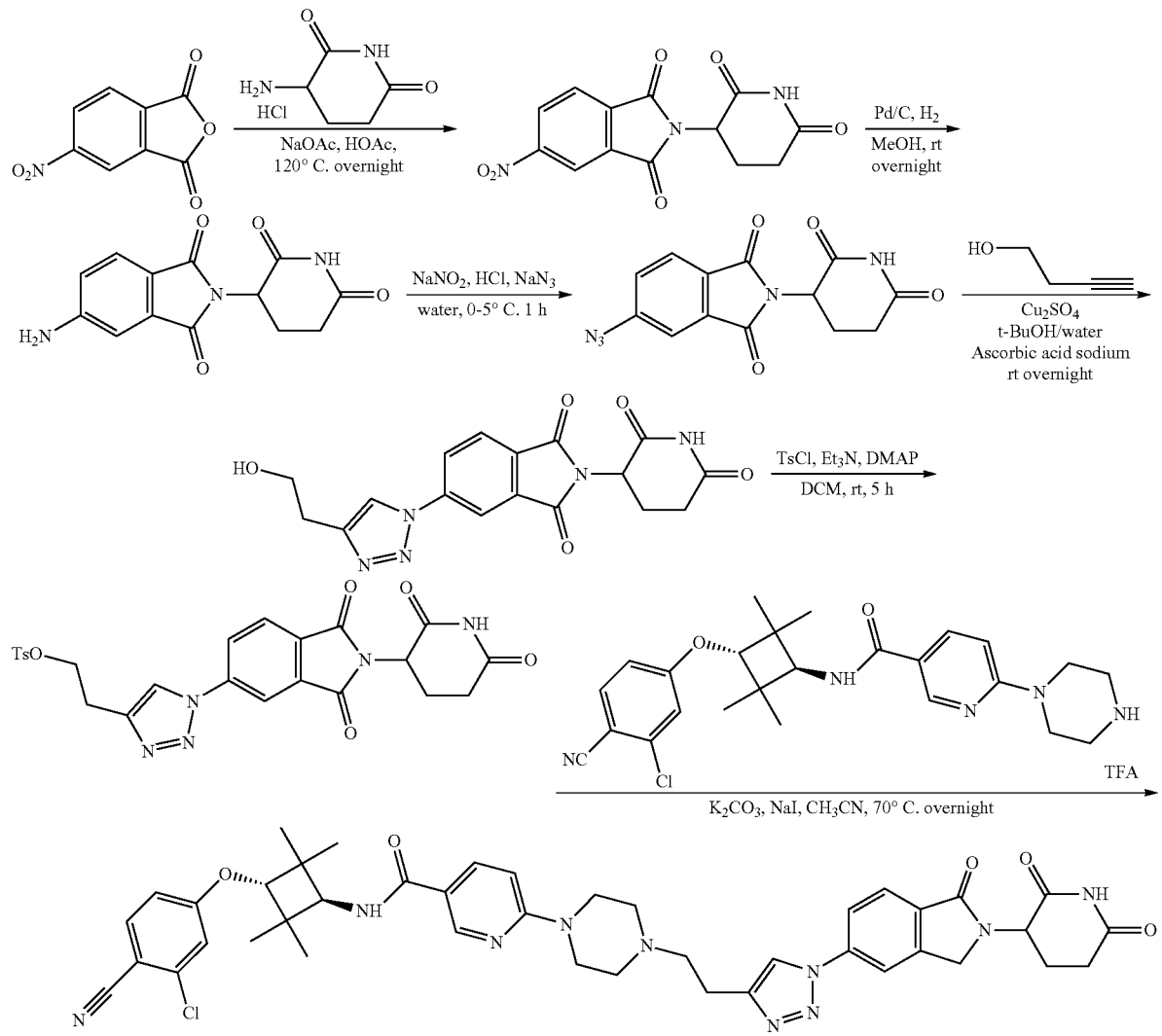
General Scheme 5
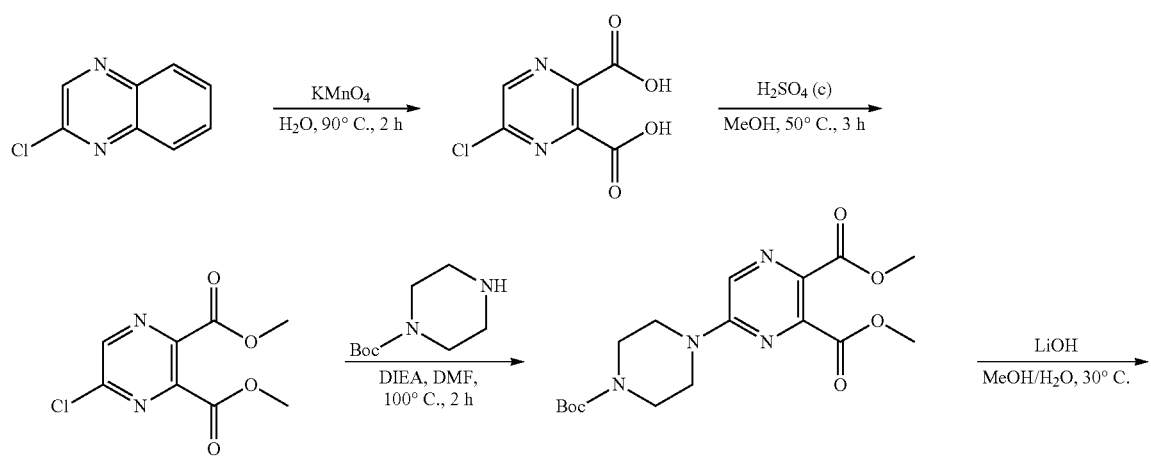

135 136
-continued
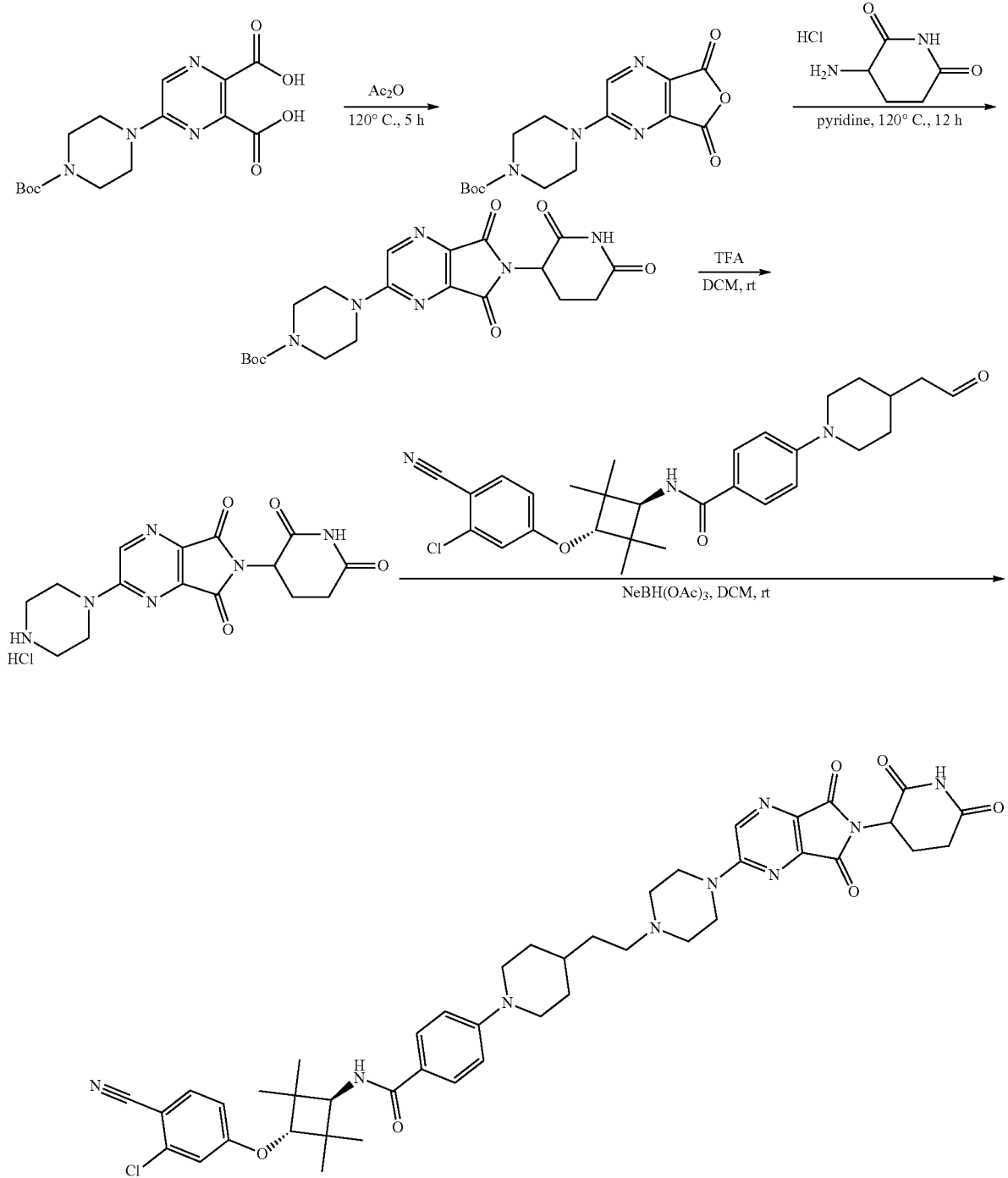
General Scheme 6
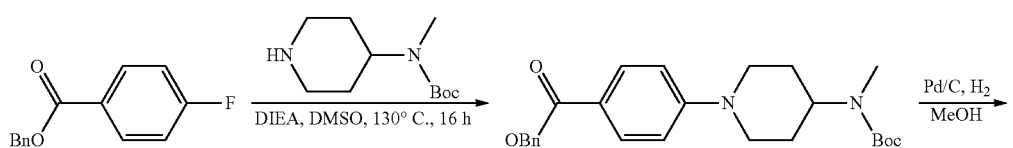

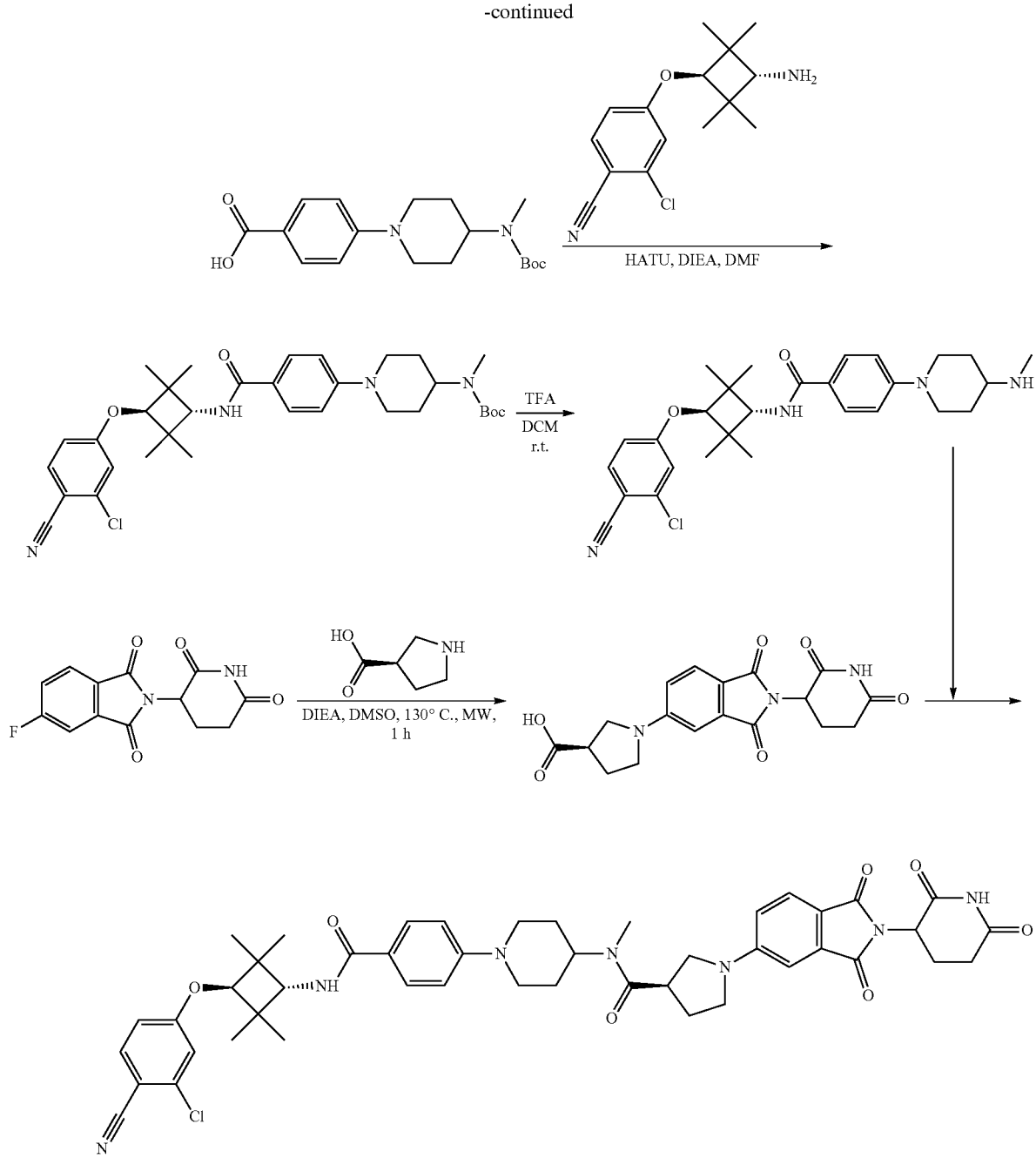
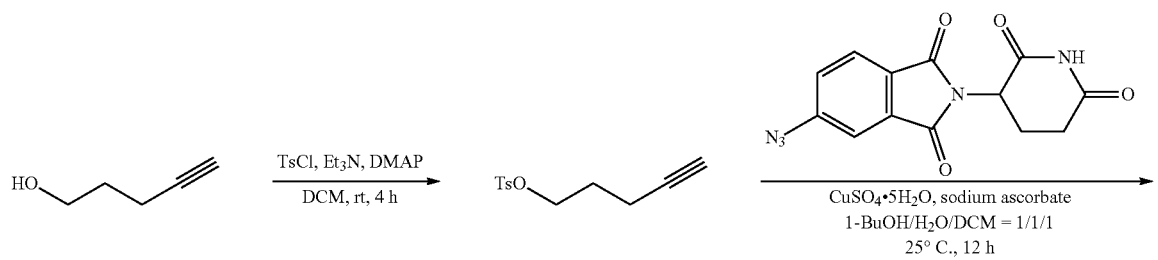
General Scheme 7

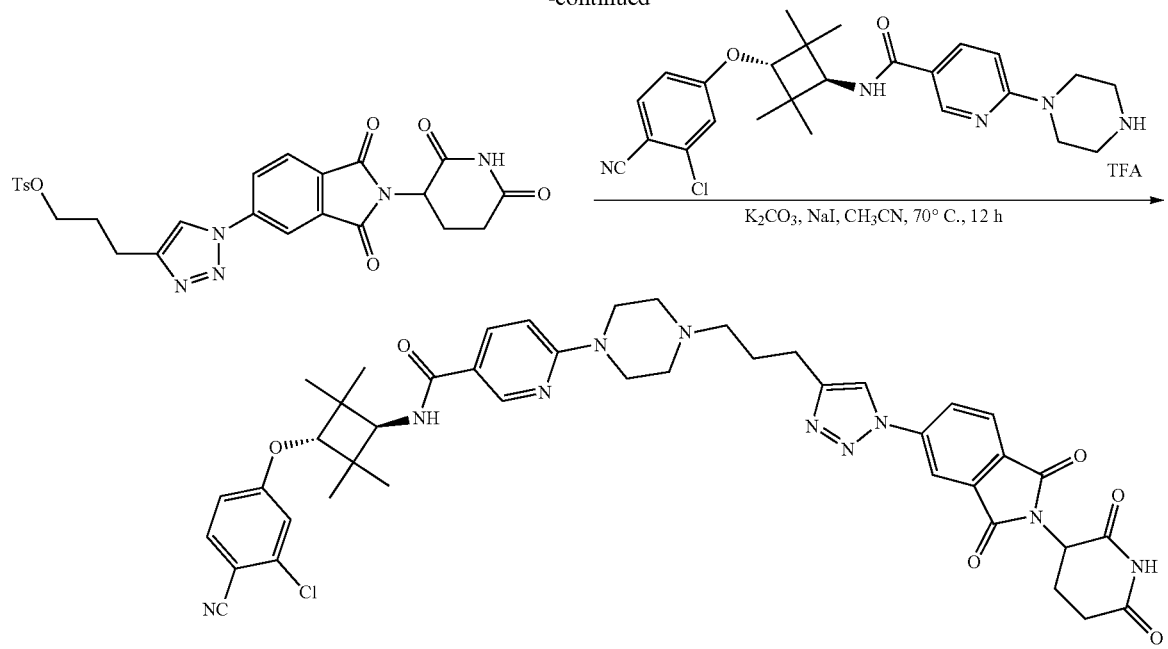
General Scheme 8
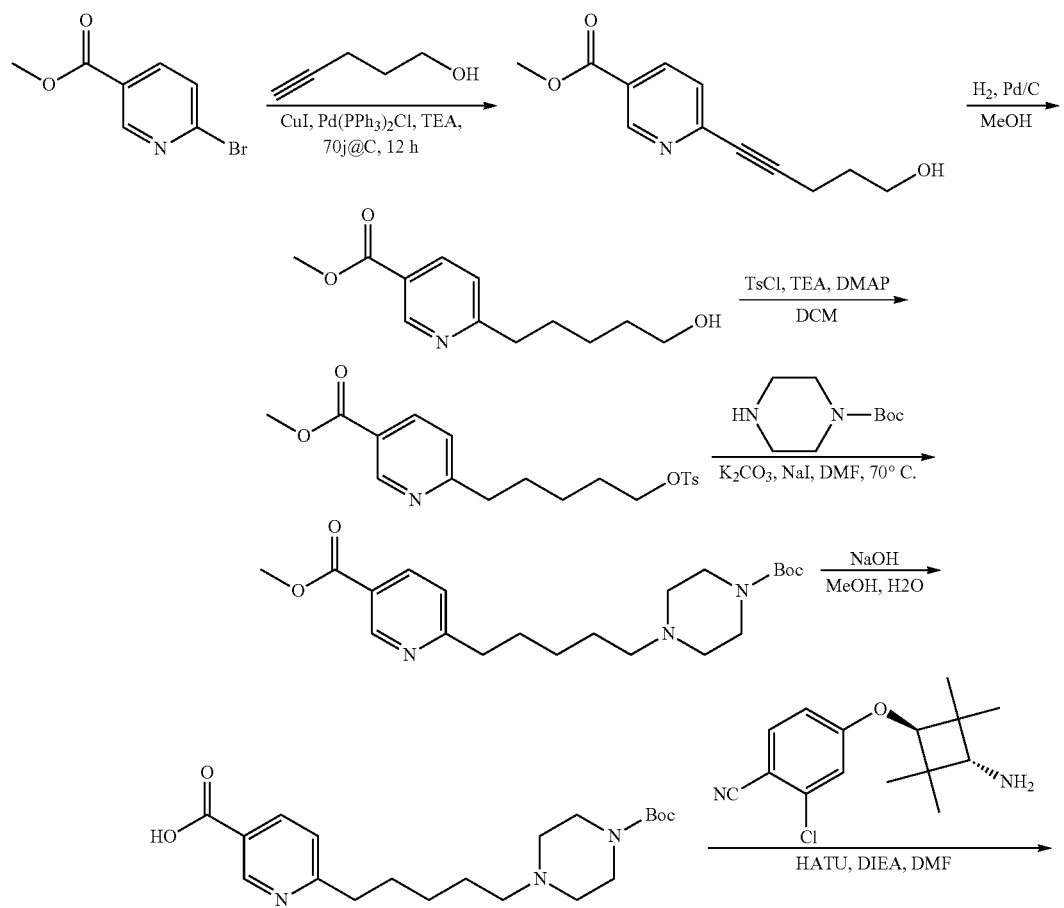

-continued
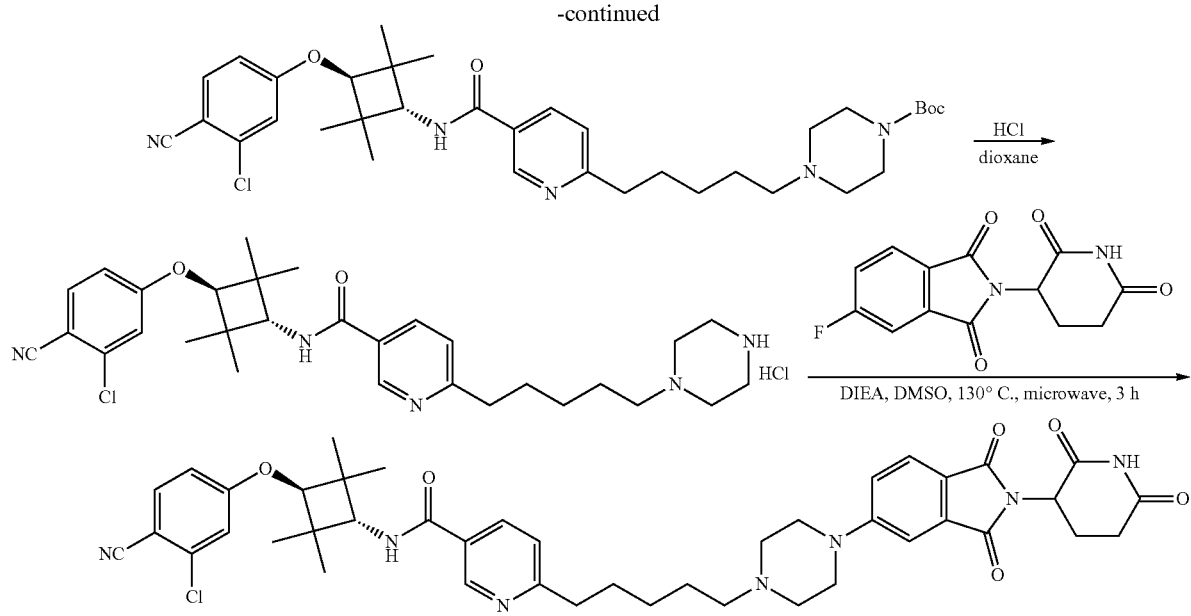
General Scheme 9
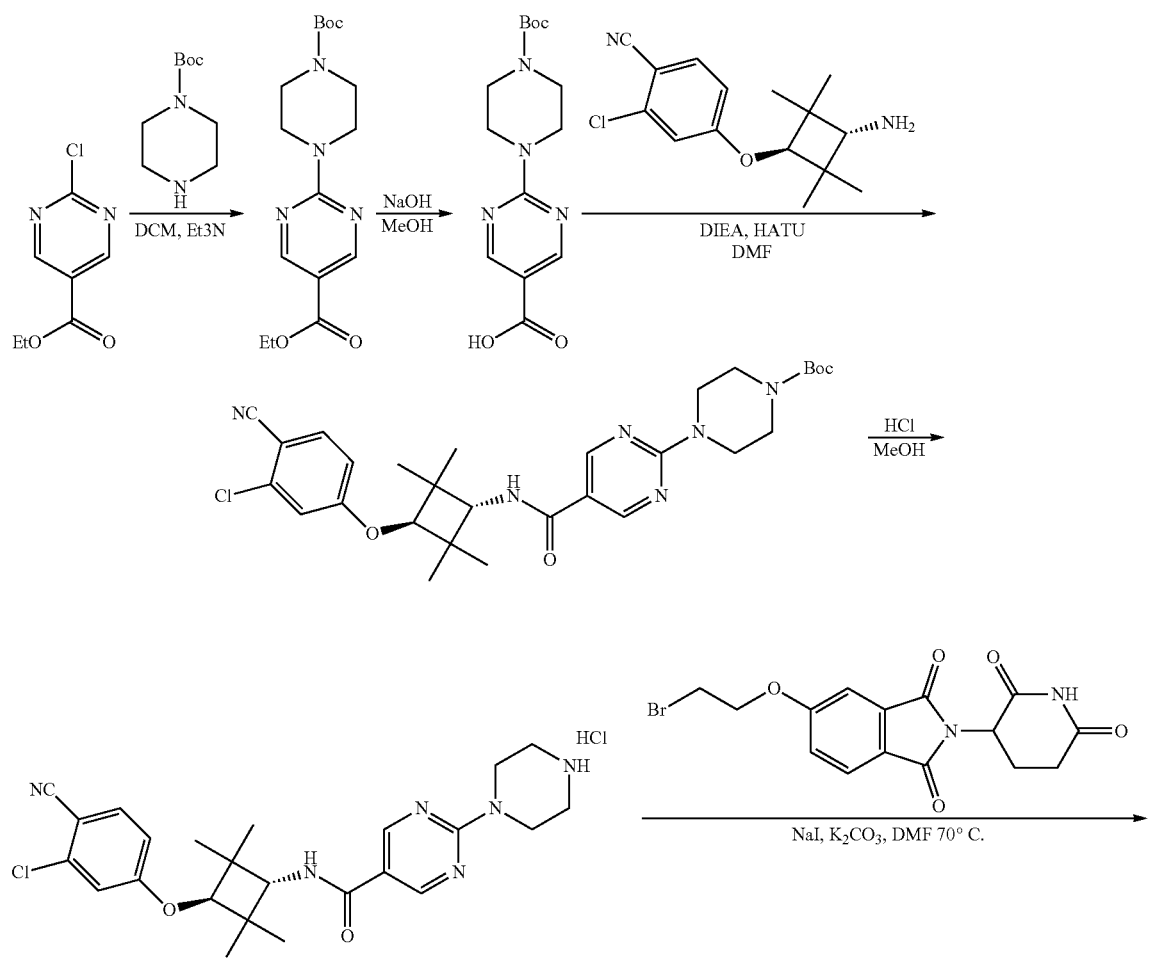

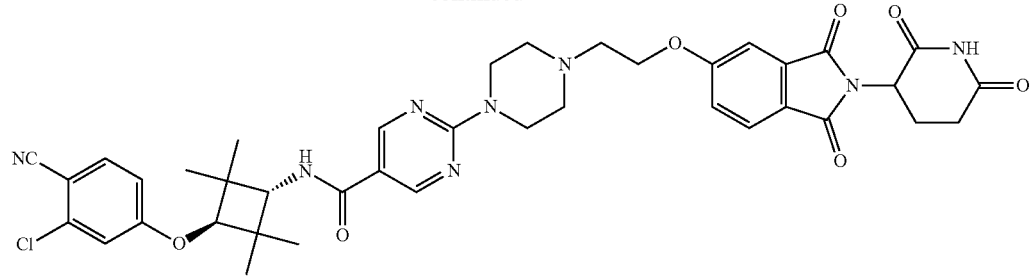

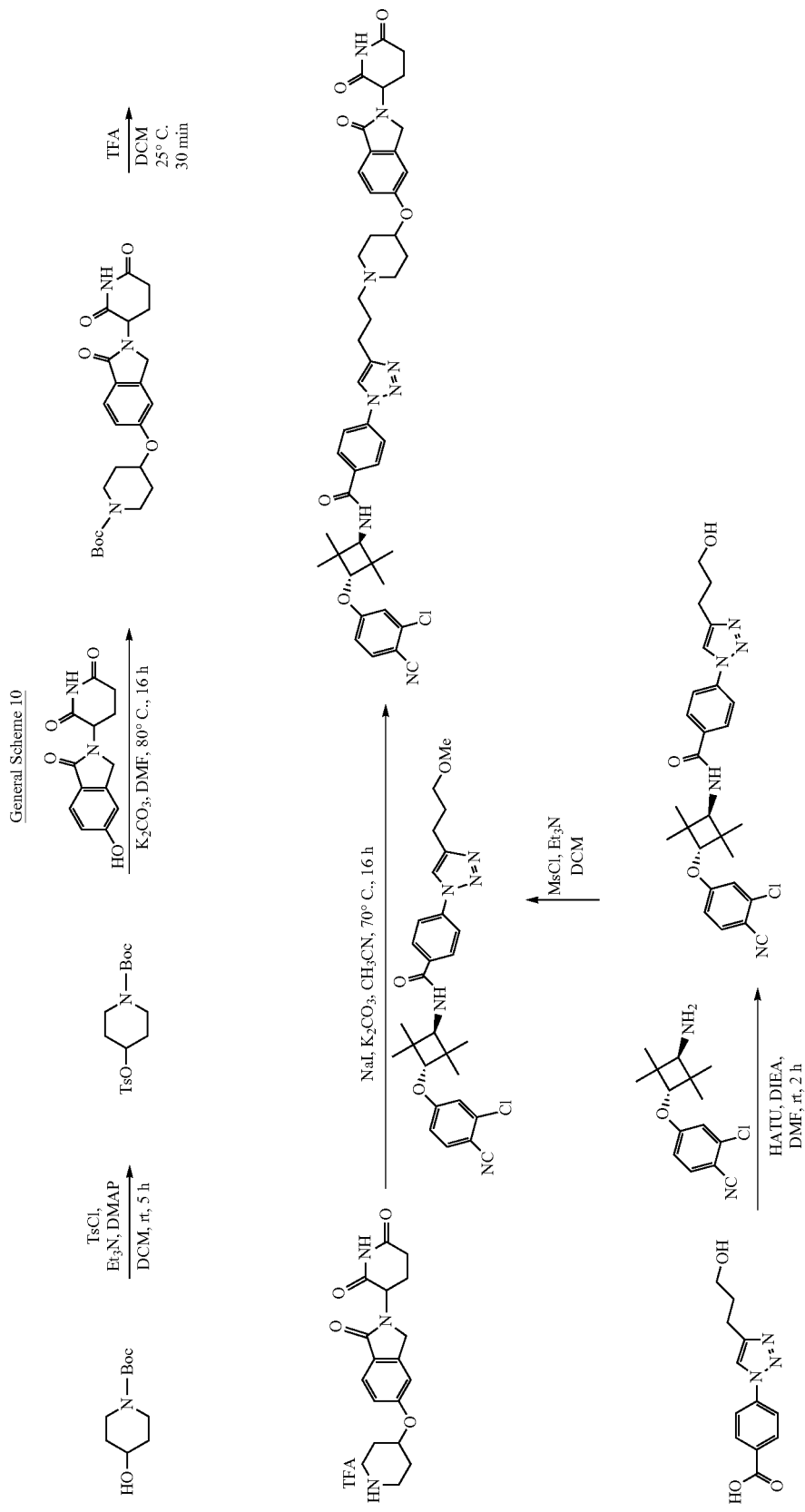
General Scheme 10

General Scheme 11
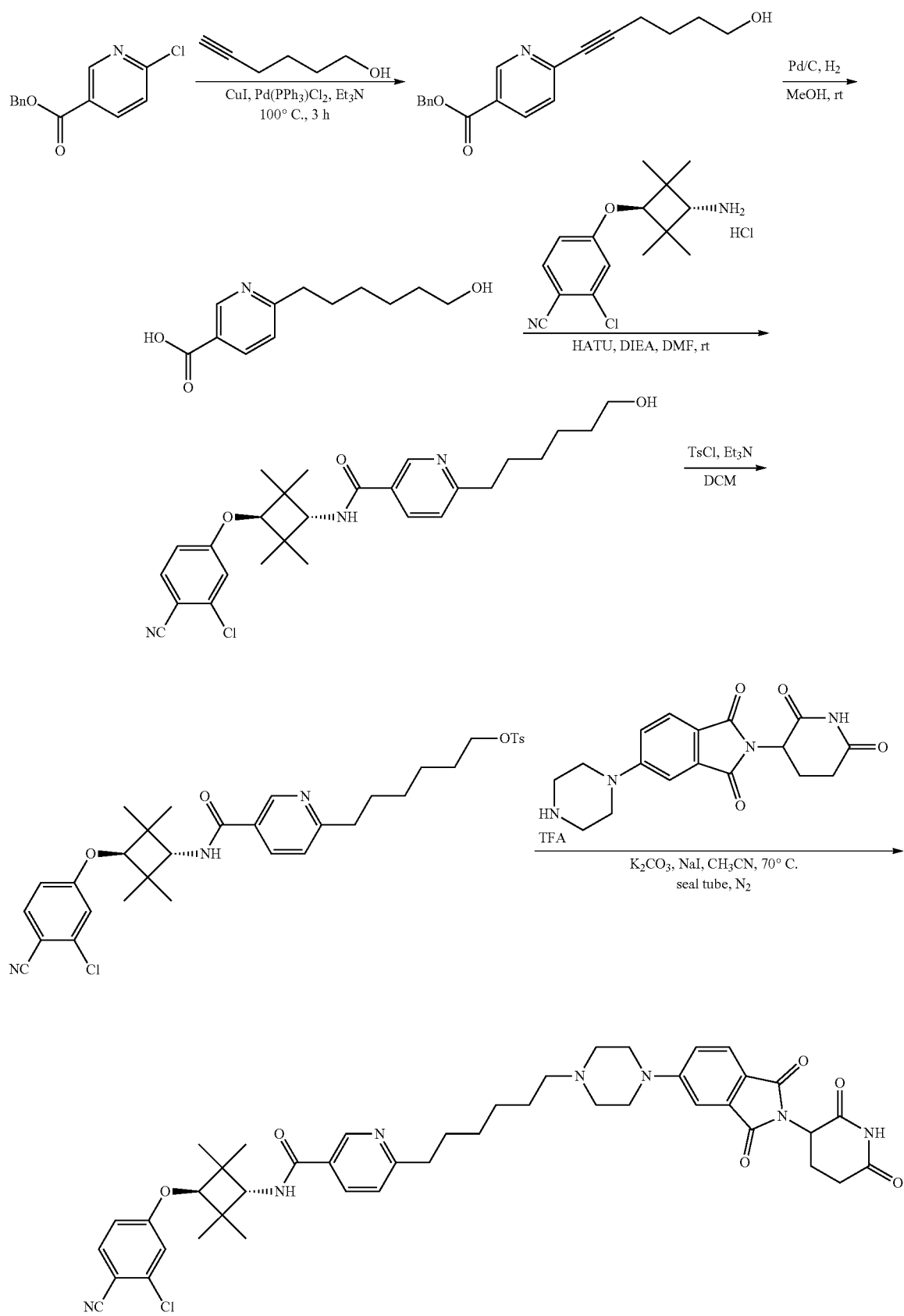

General Scheme 12
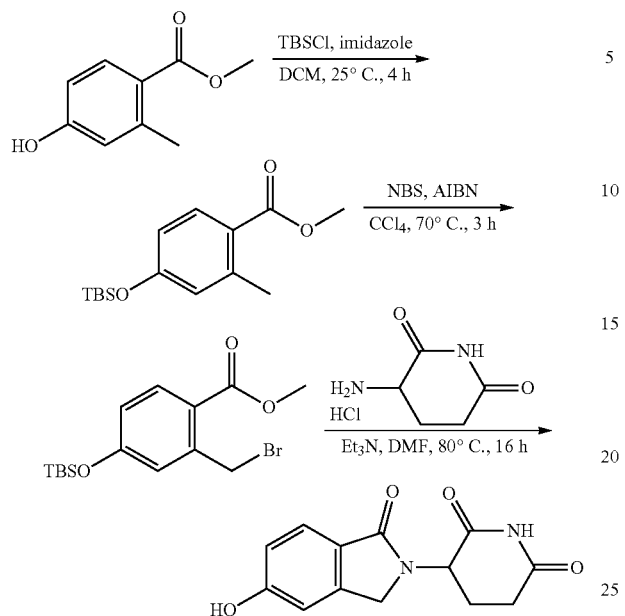

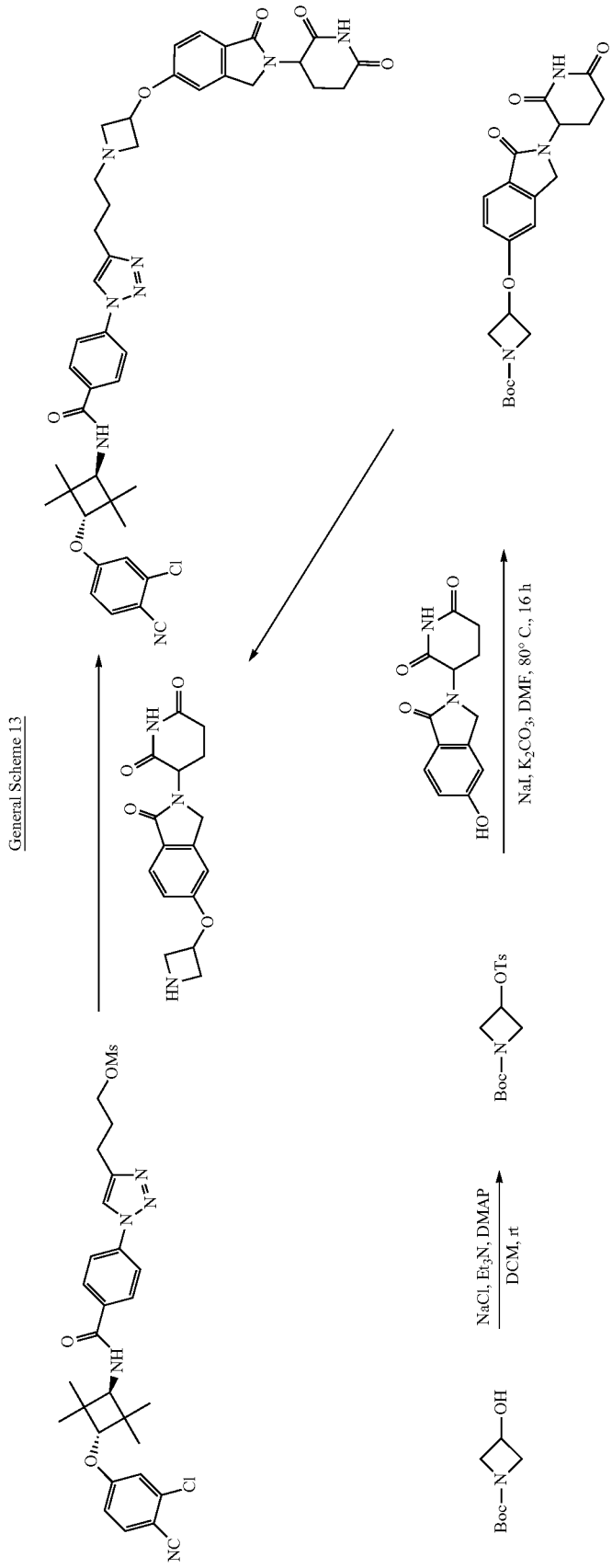

General Scheme 14
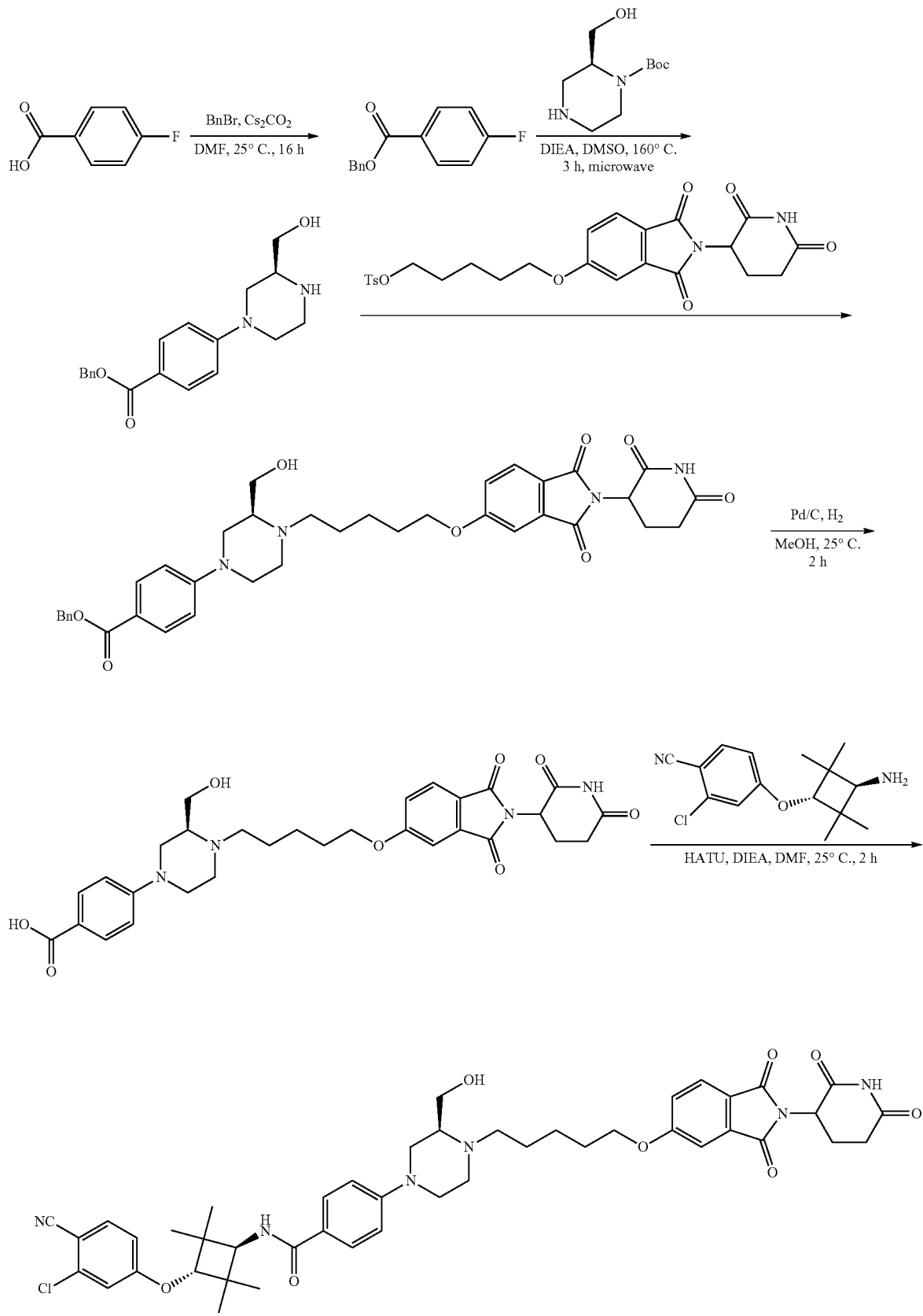

General Scheme 15
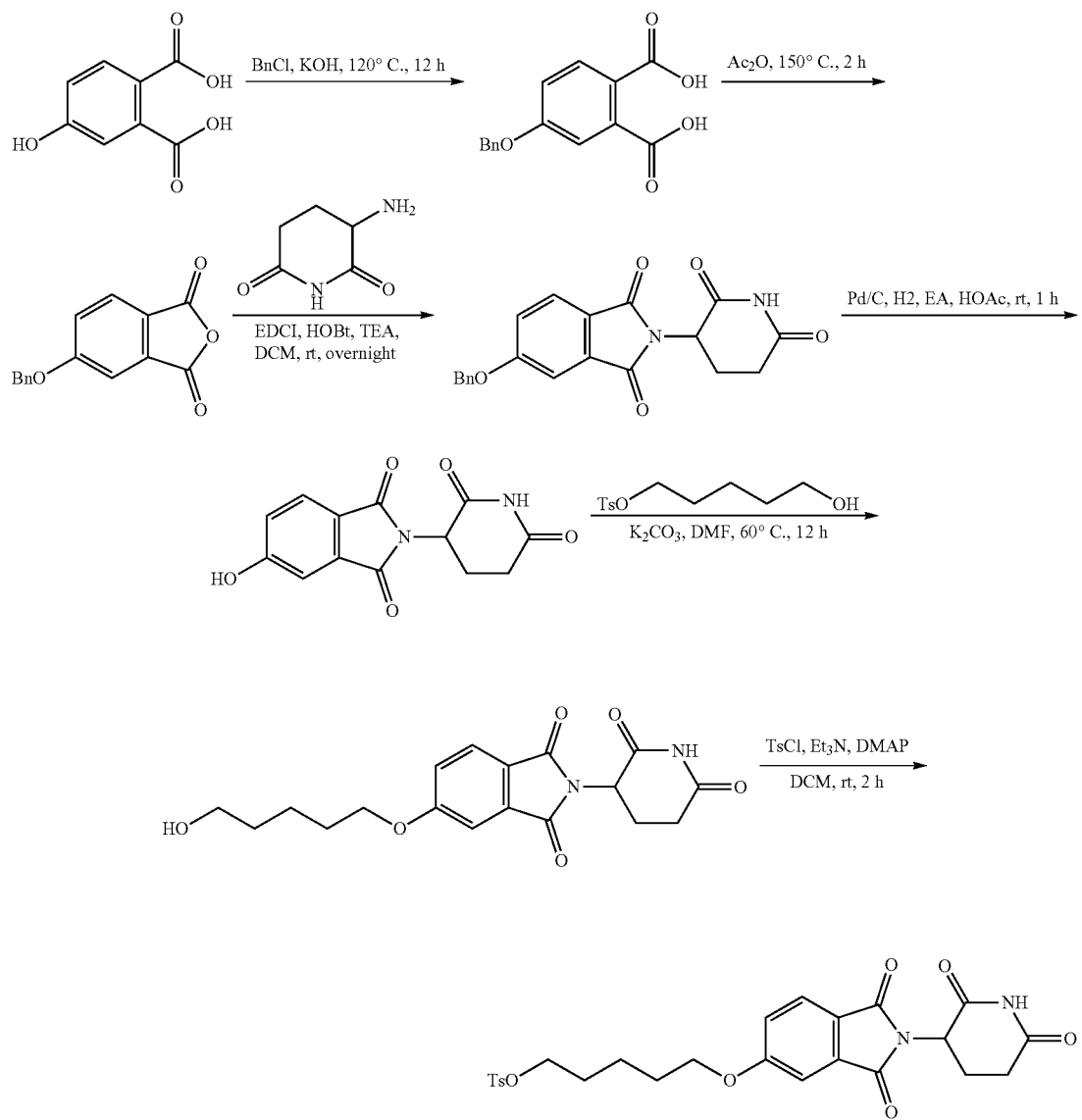
General Scheme 16
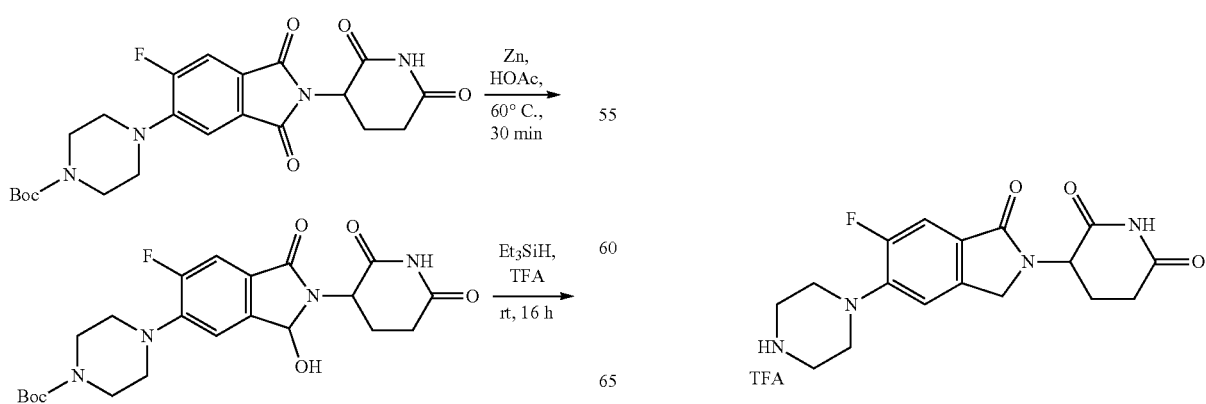

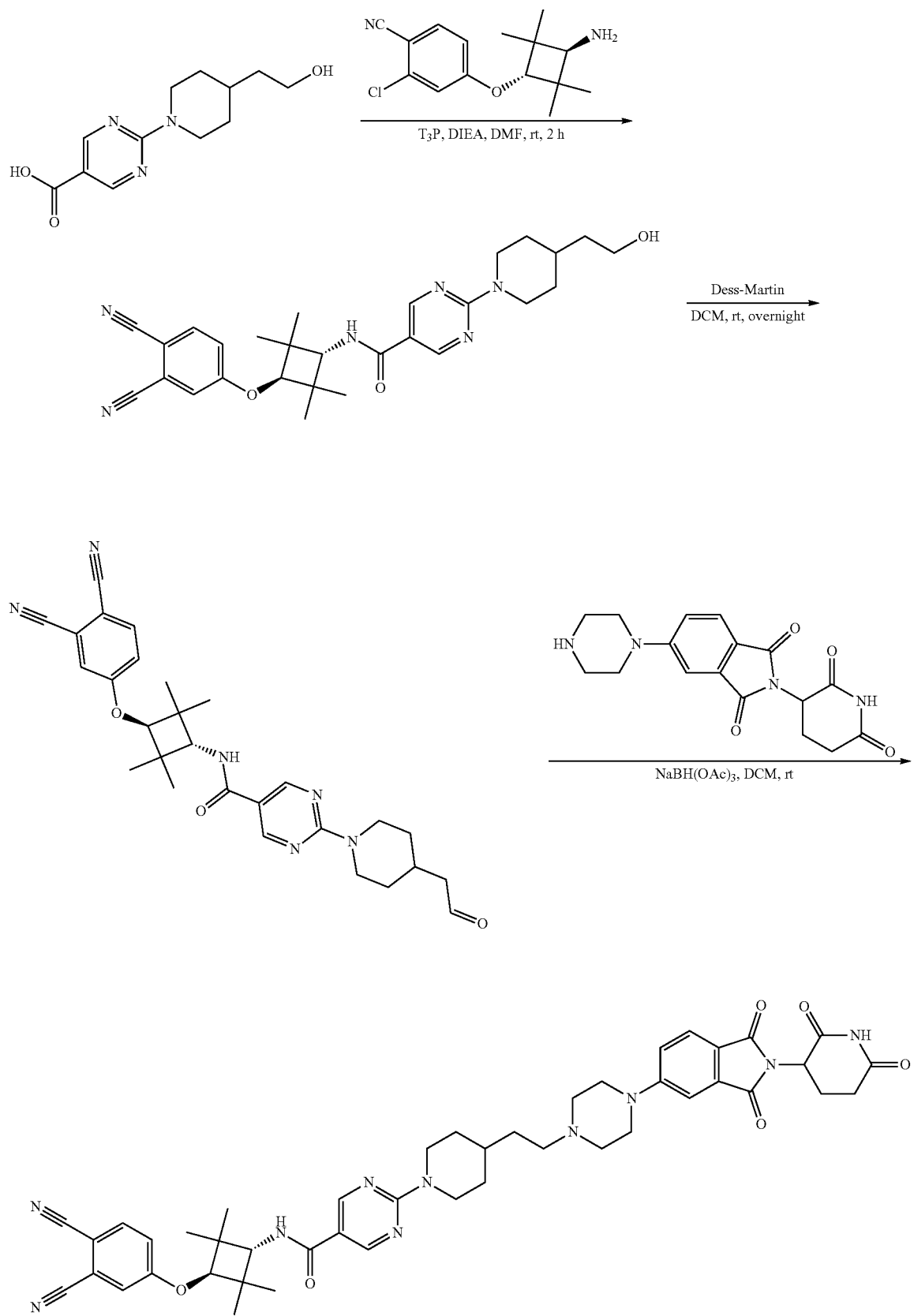

General Scheme 18
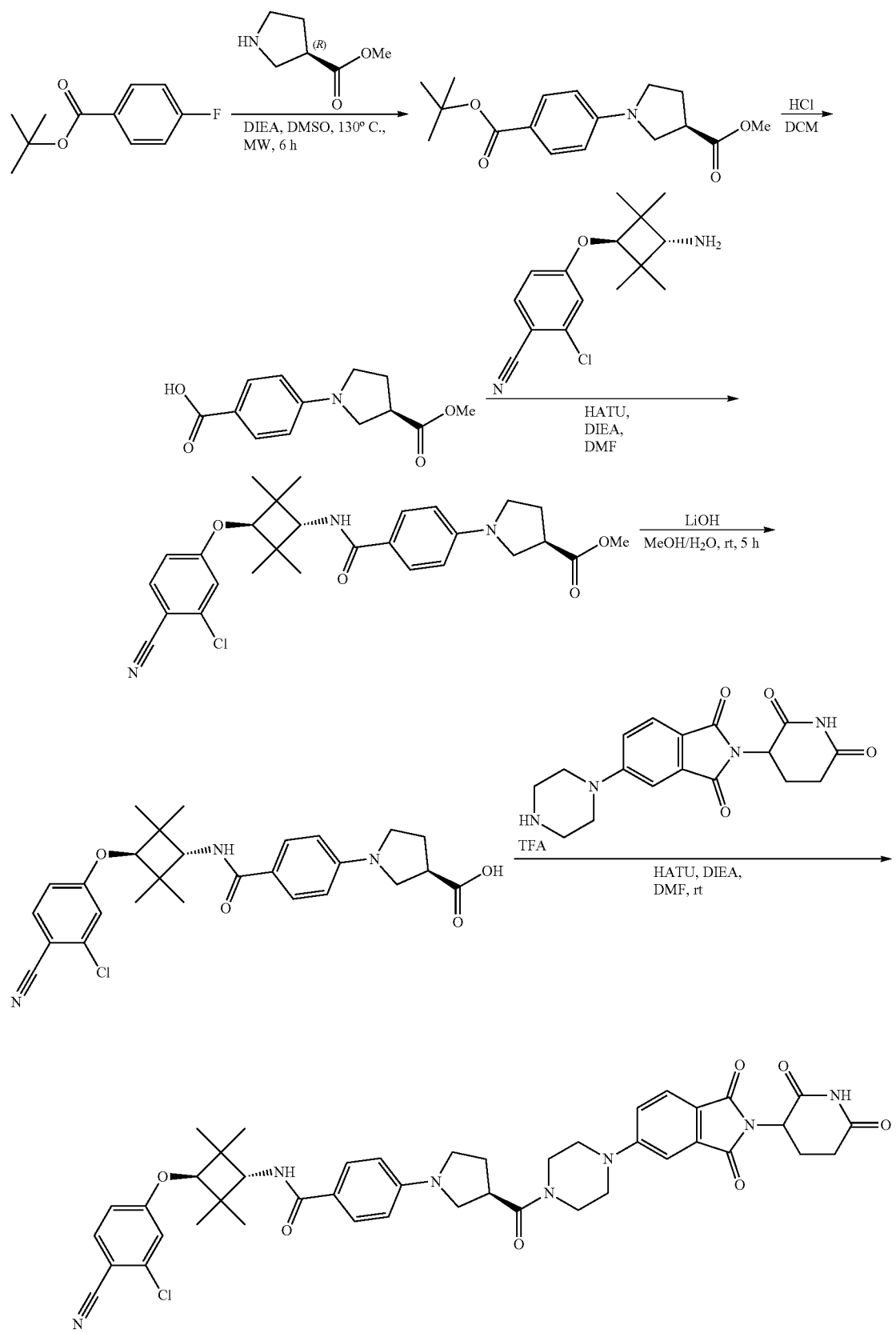

General Scheme 19
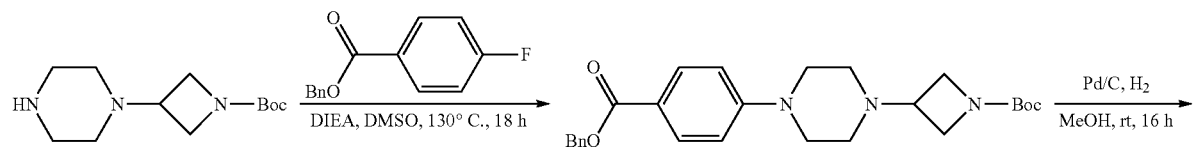
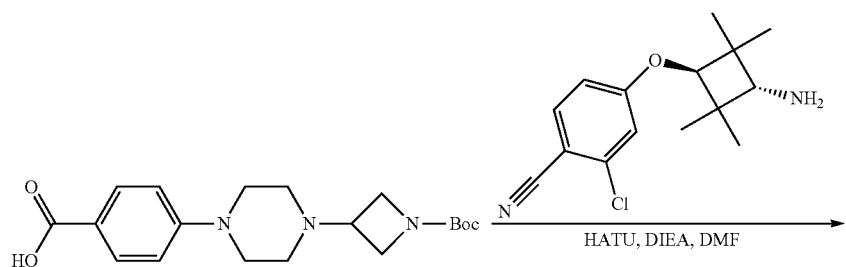
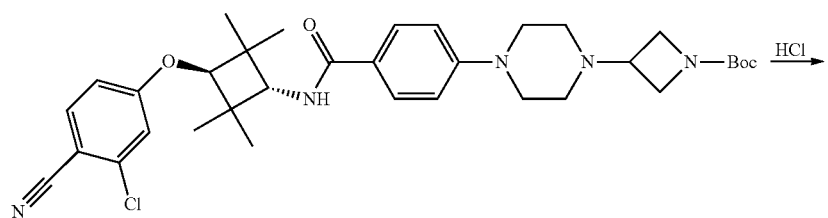
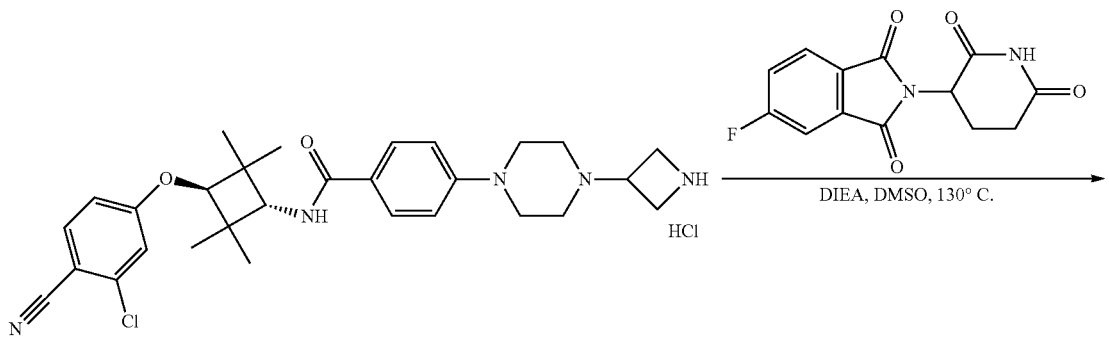
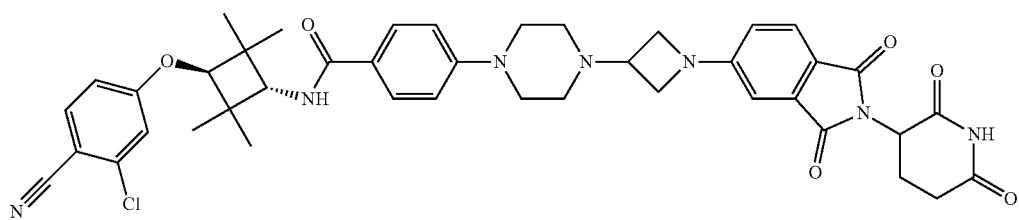

General Scheme 20
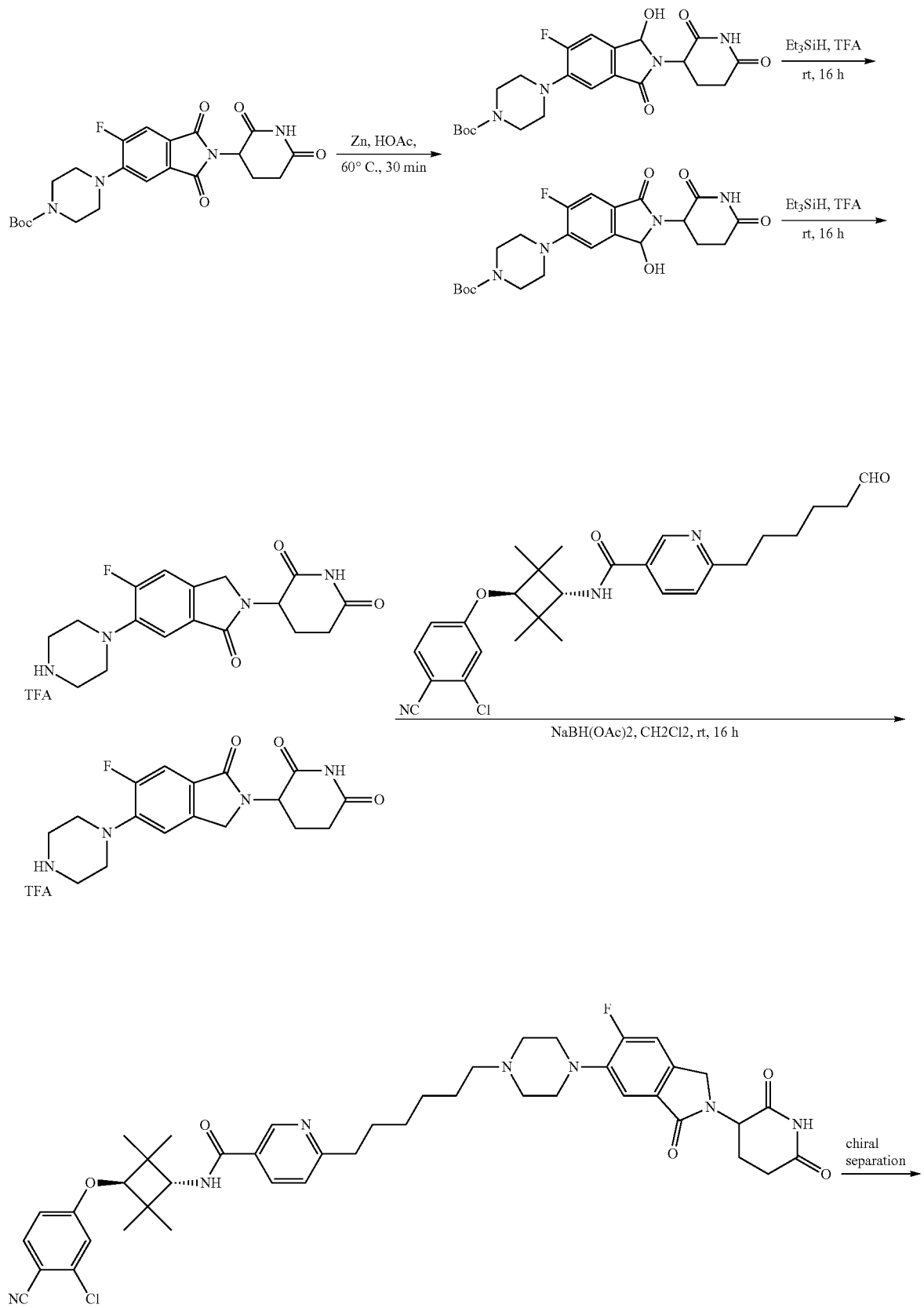

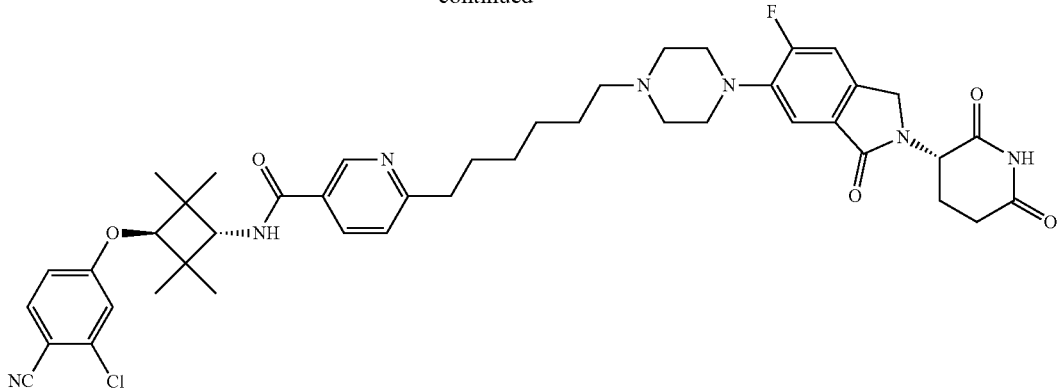
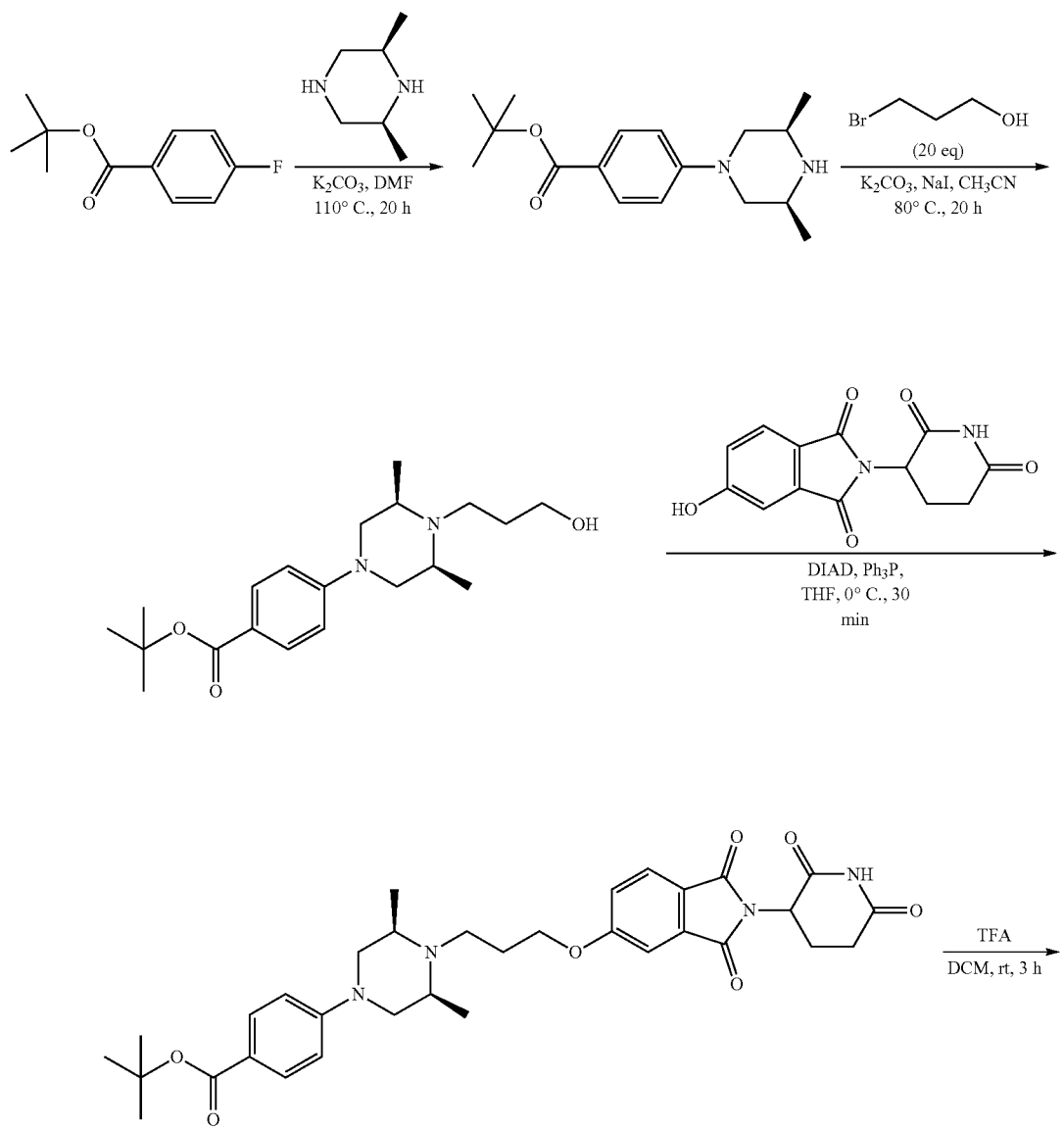
General Scheme 21

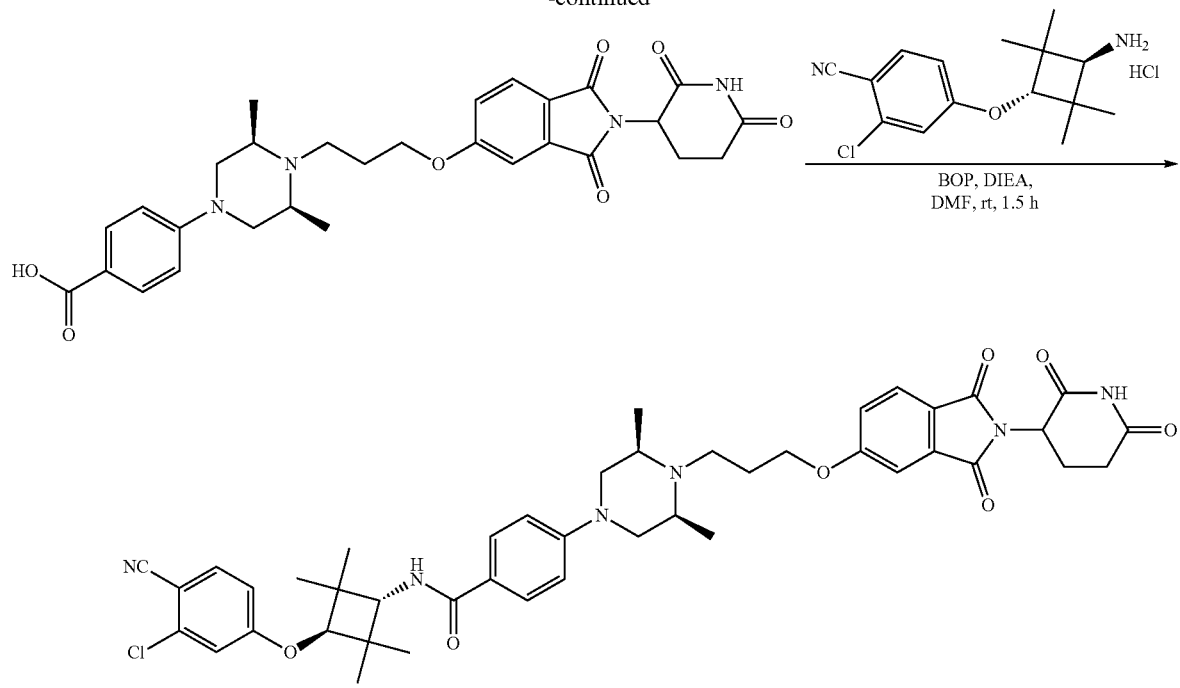
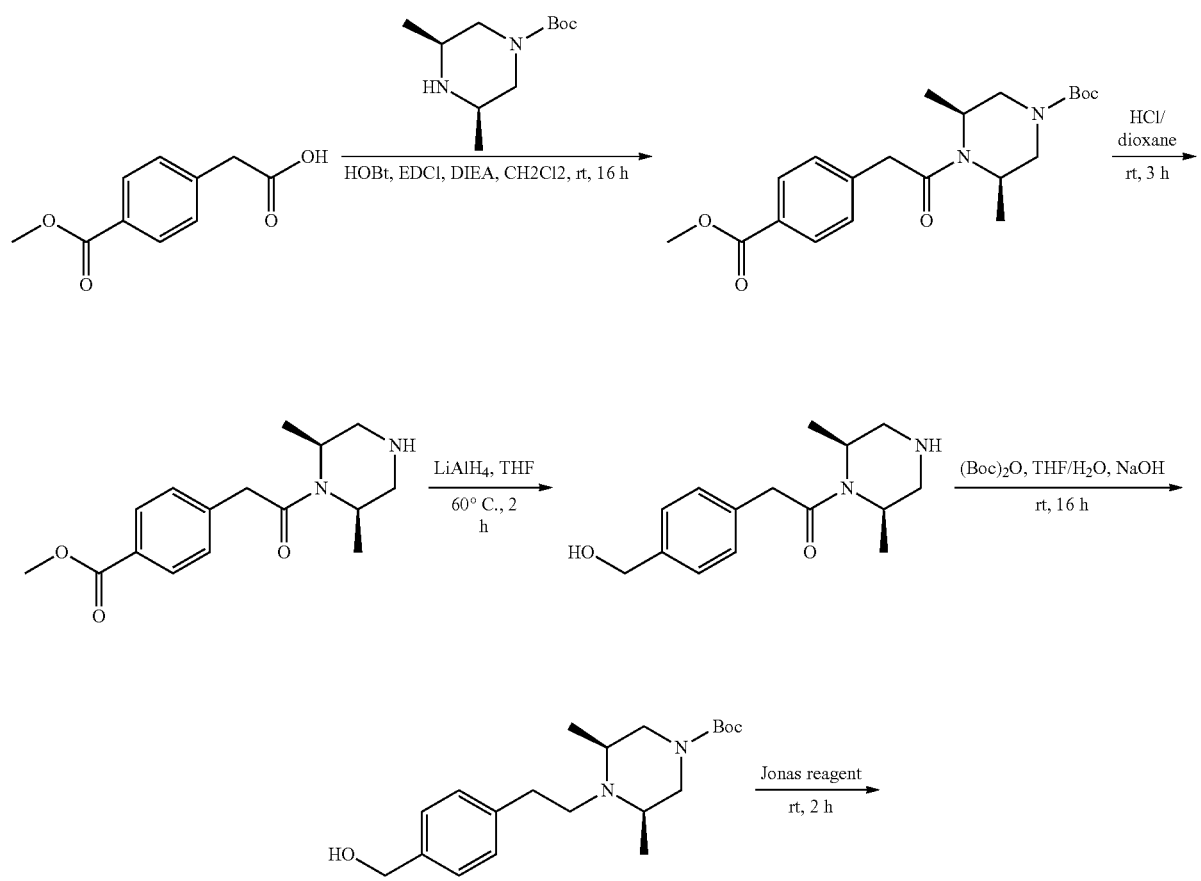
General Scheme 22

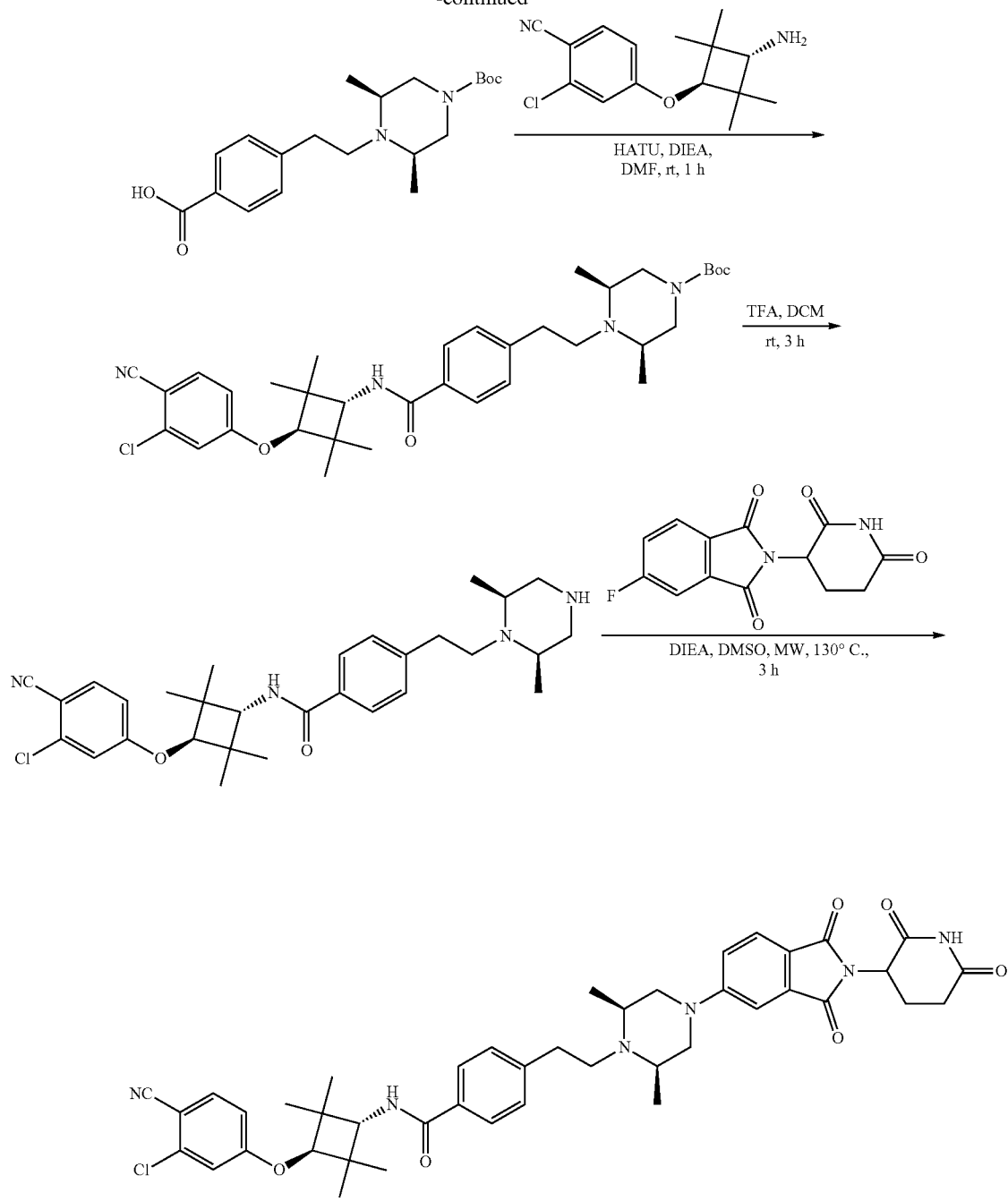
General Scheme 23
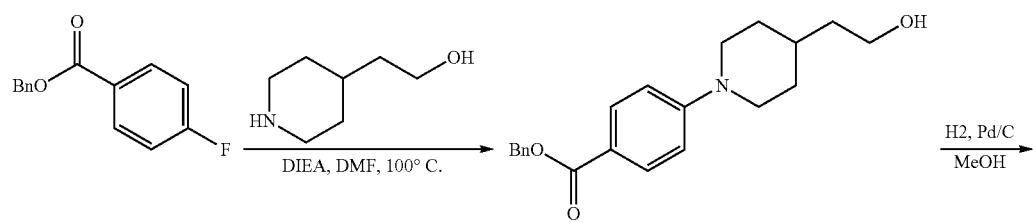

171 172
-continued
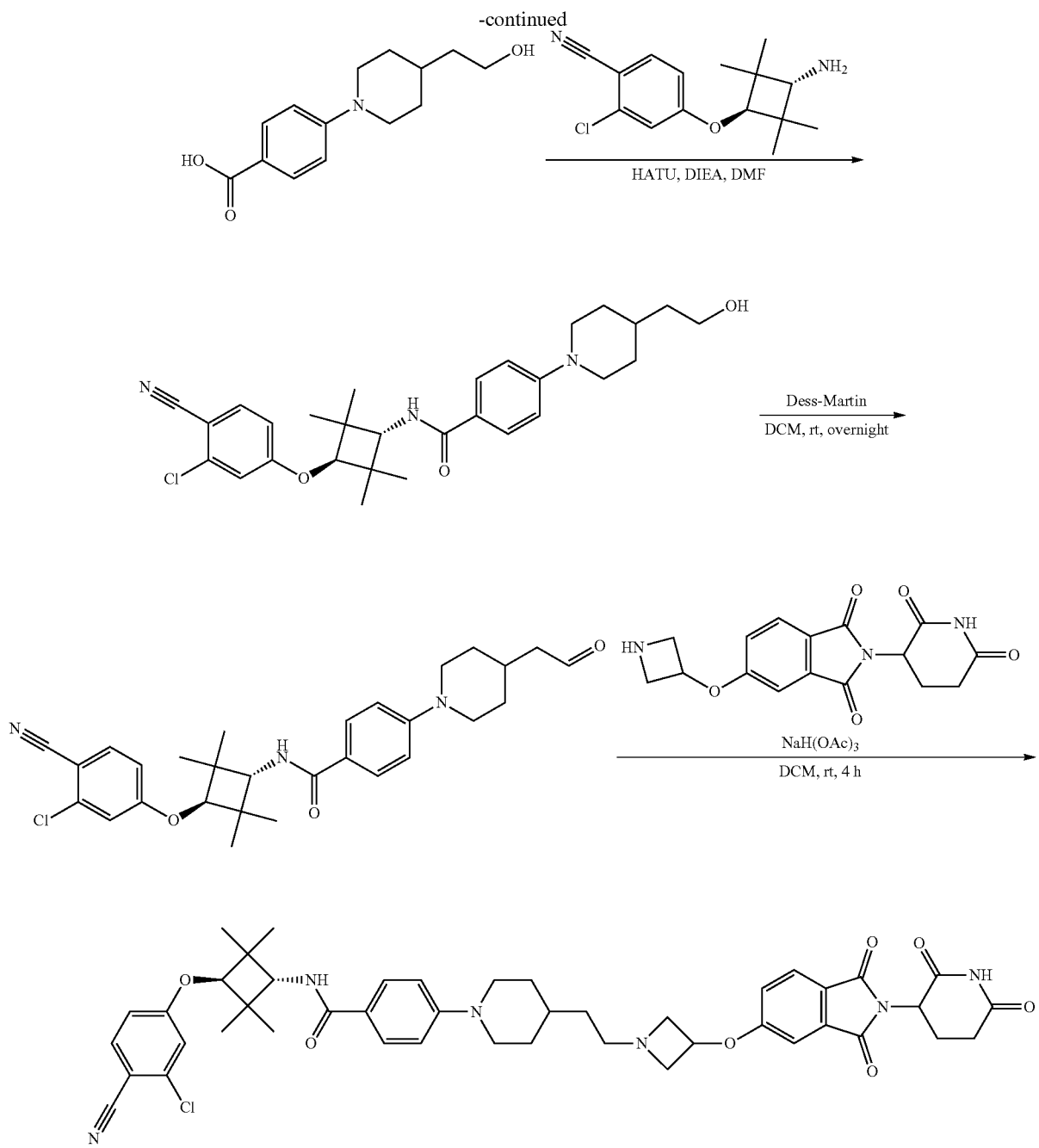
General Scheme 24
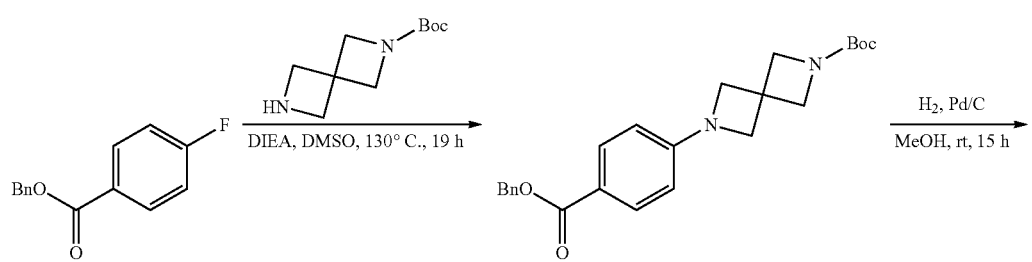

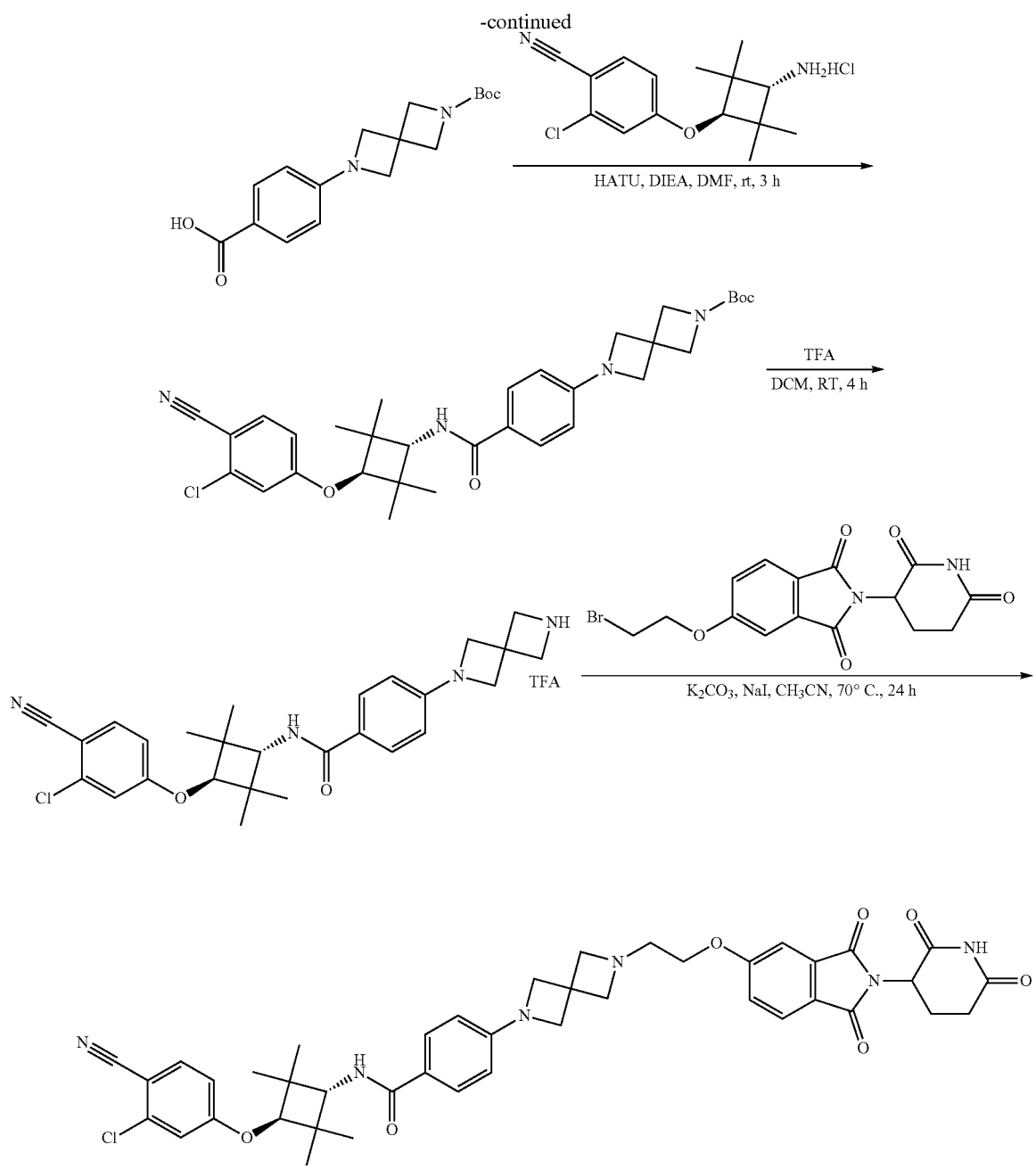
General Scheme 25
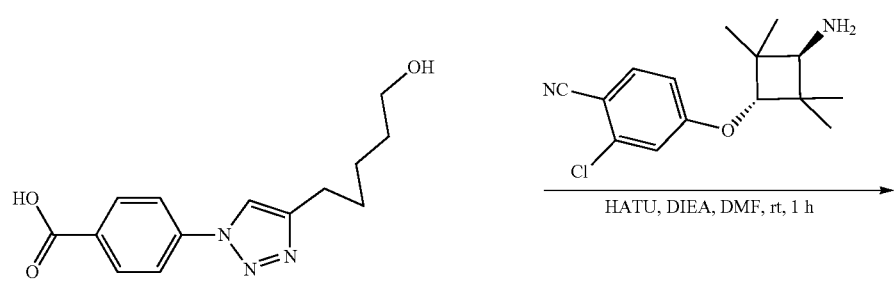

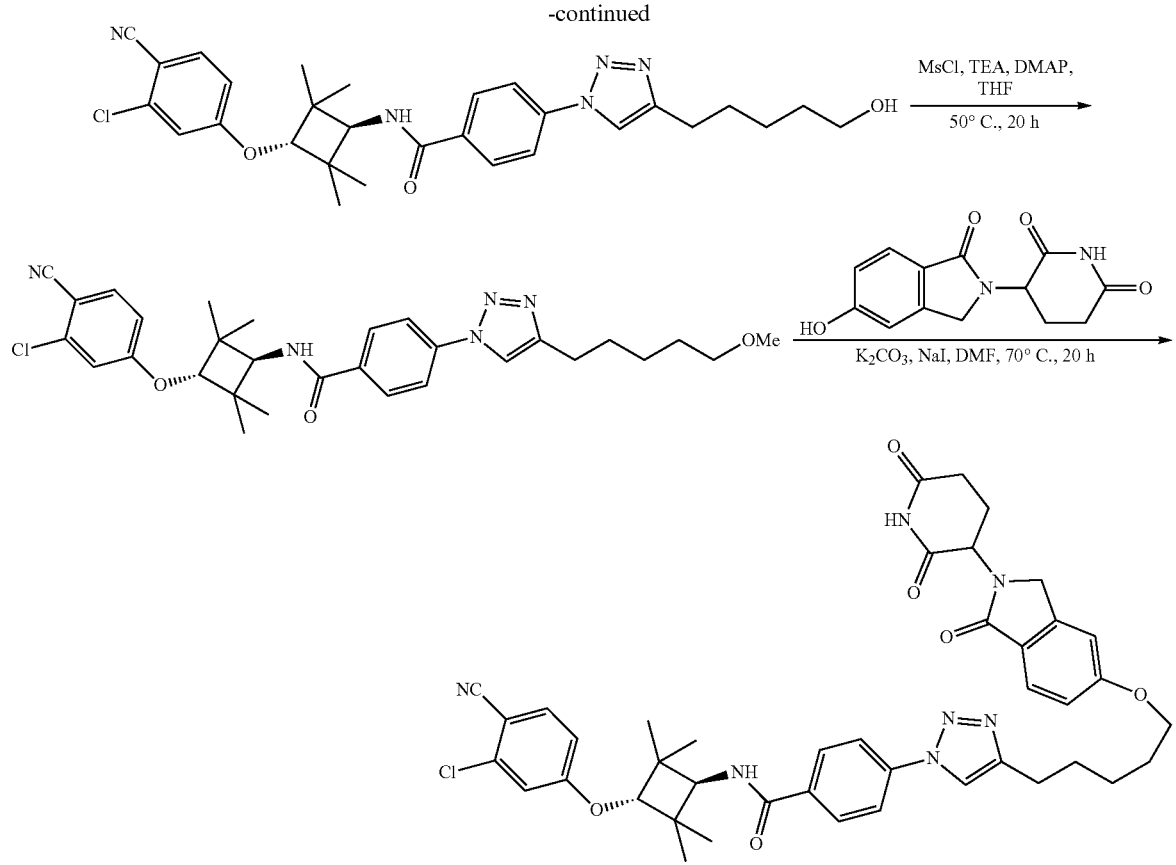
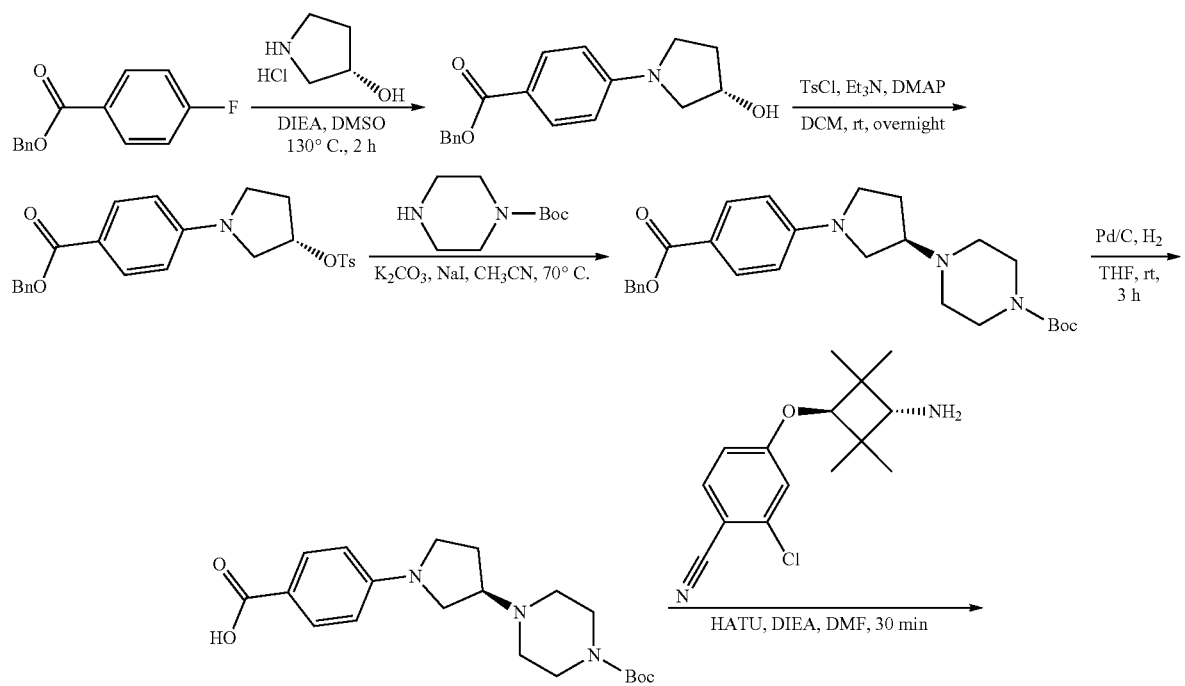
General Scheme 26

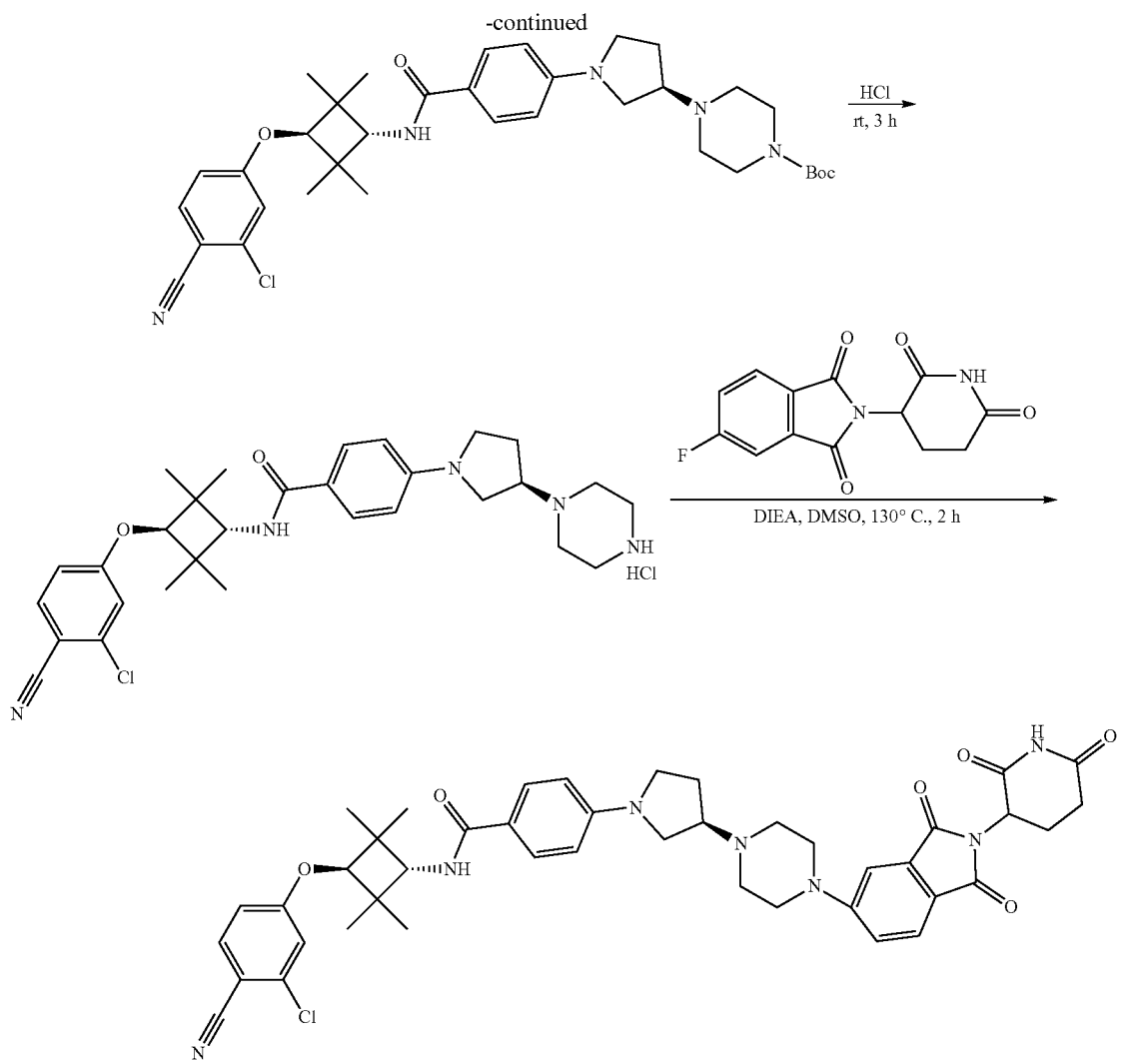
General Scheme 27
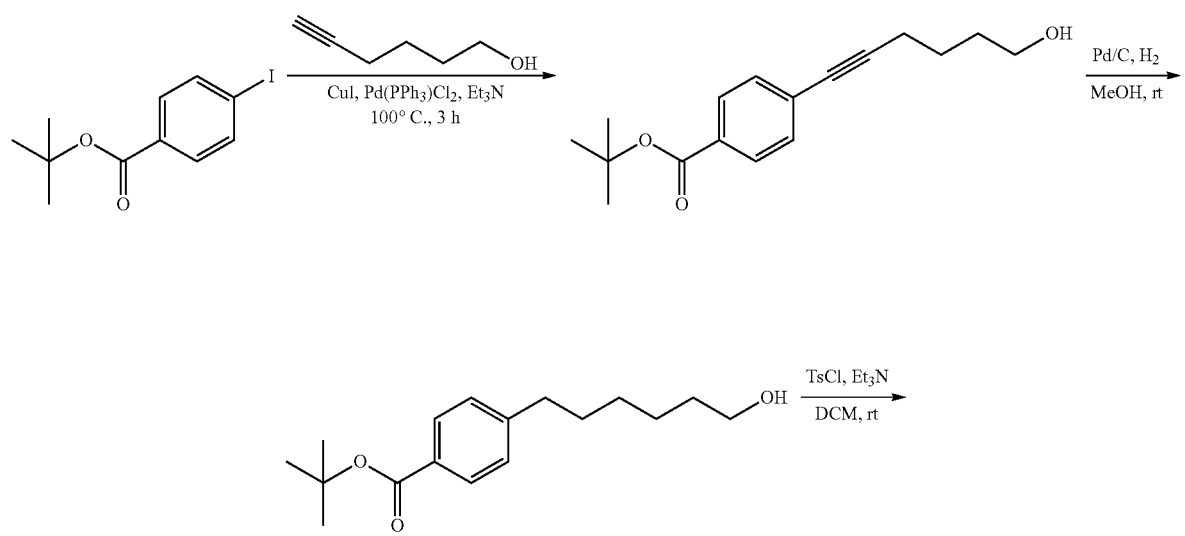

-continued
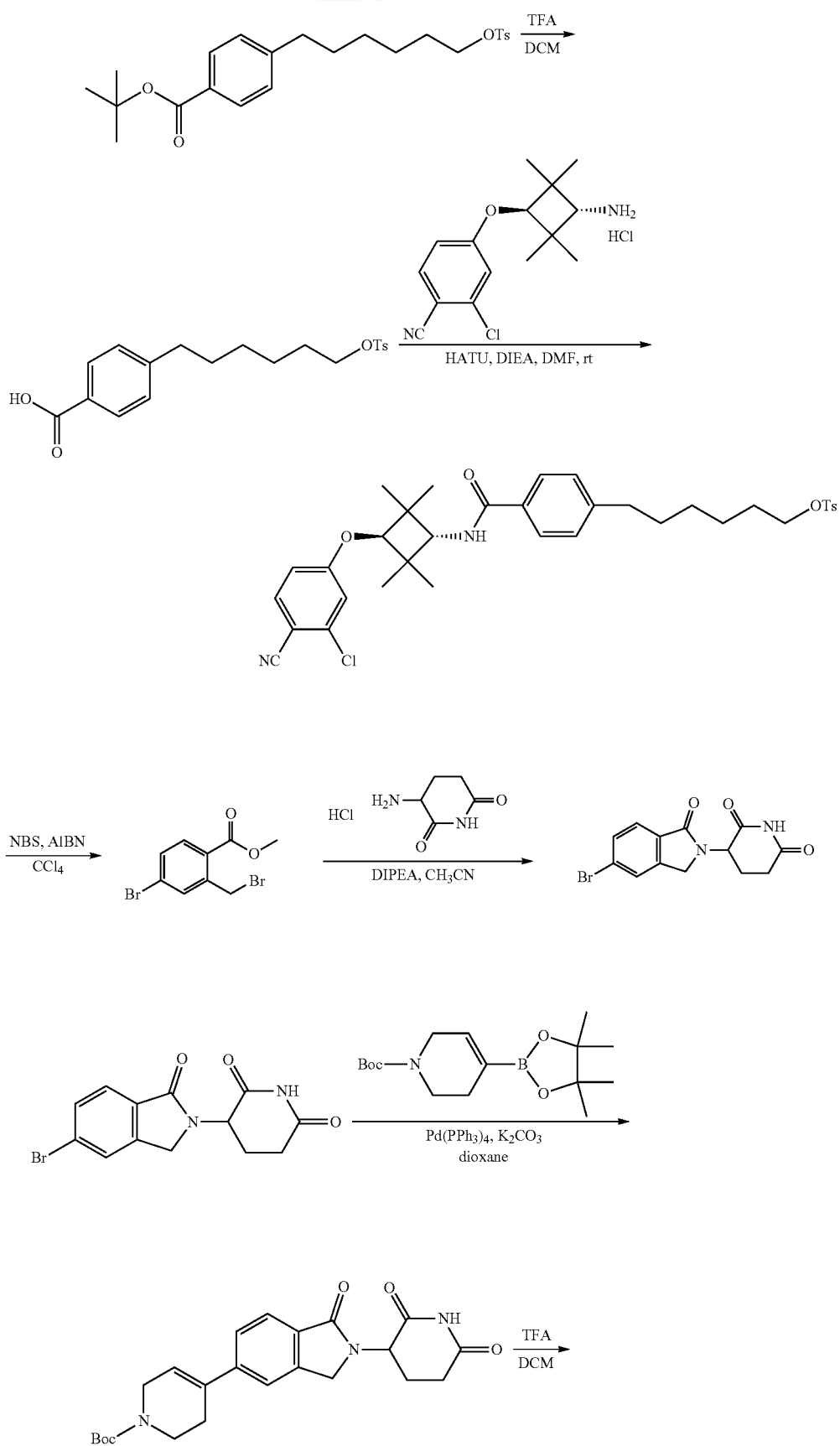

181
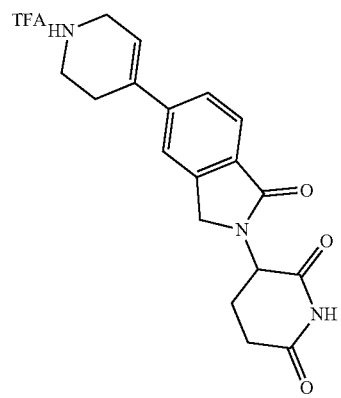
182
-continued
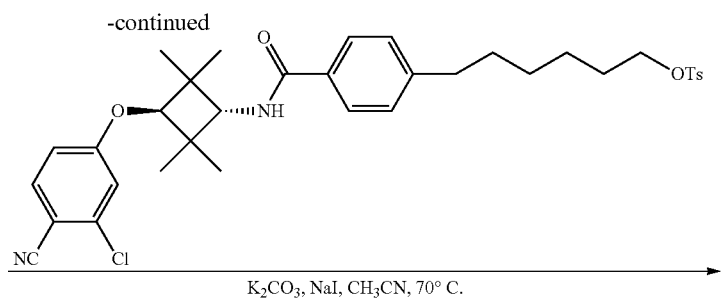
K₂CO₃, NaI, CH₃CN, 70° C.
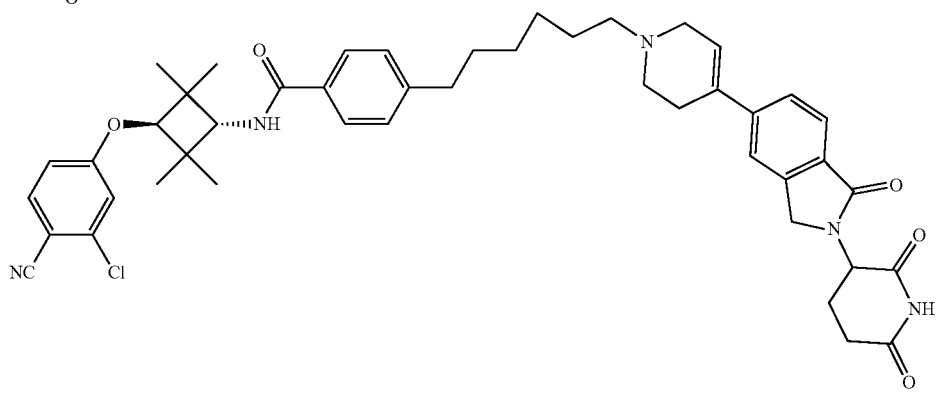
General Scheme 28
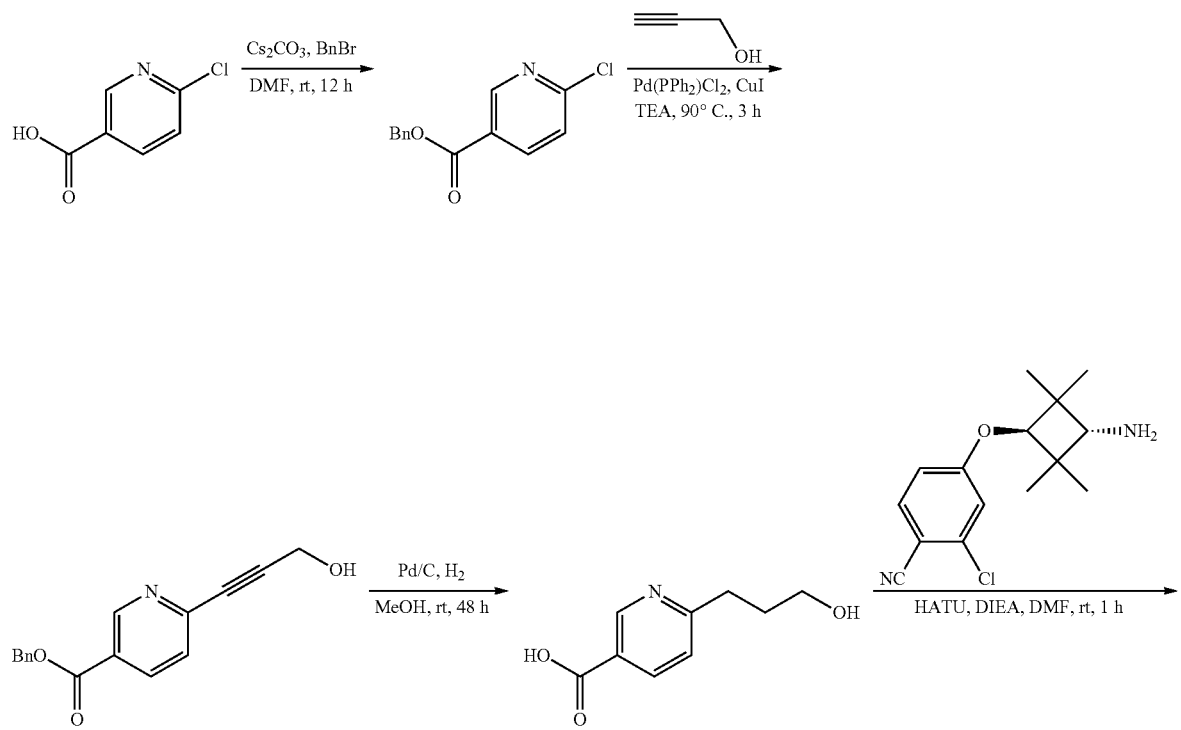

-continued
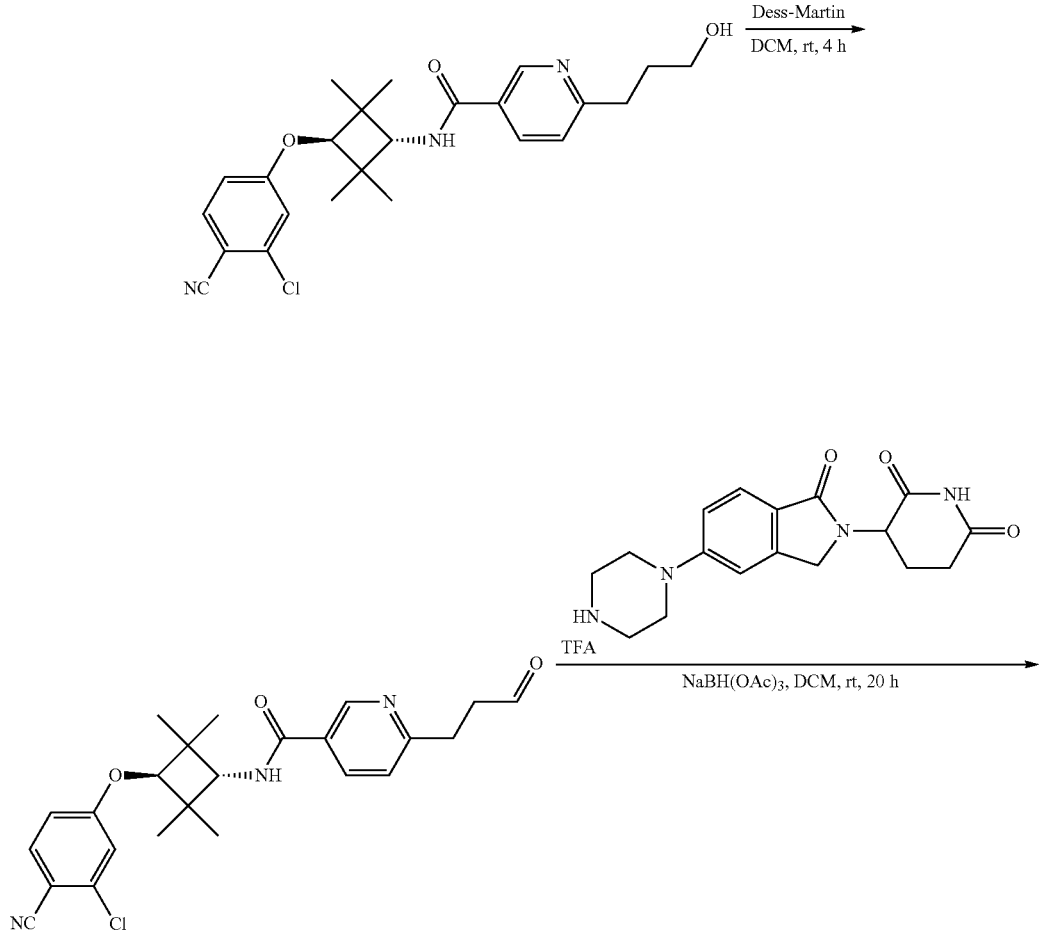
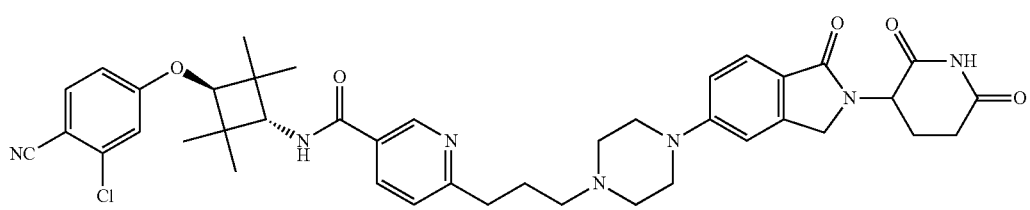
50
General Scheme 29
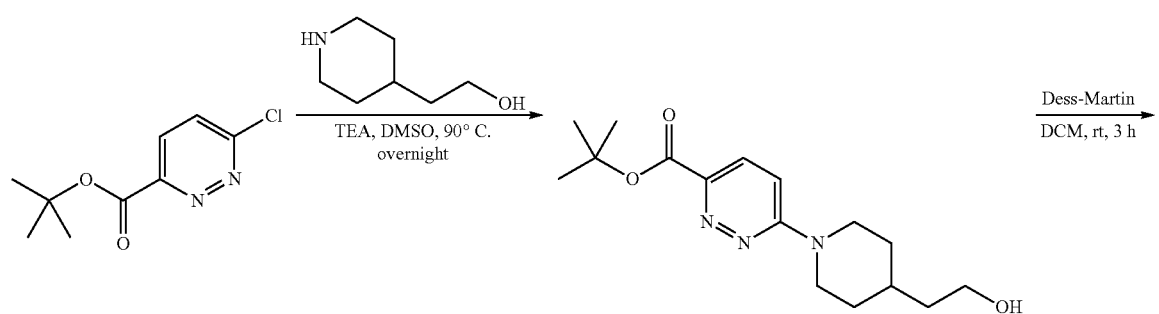

-continued
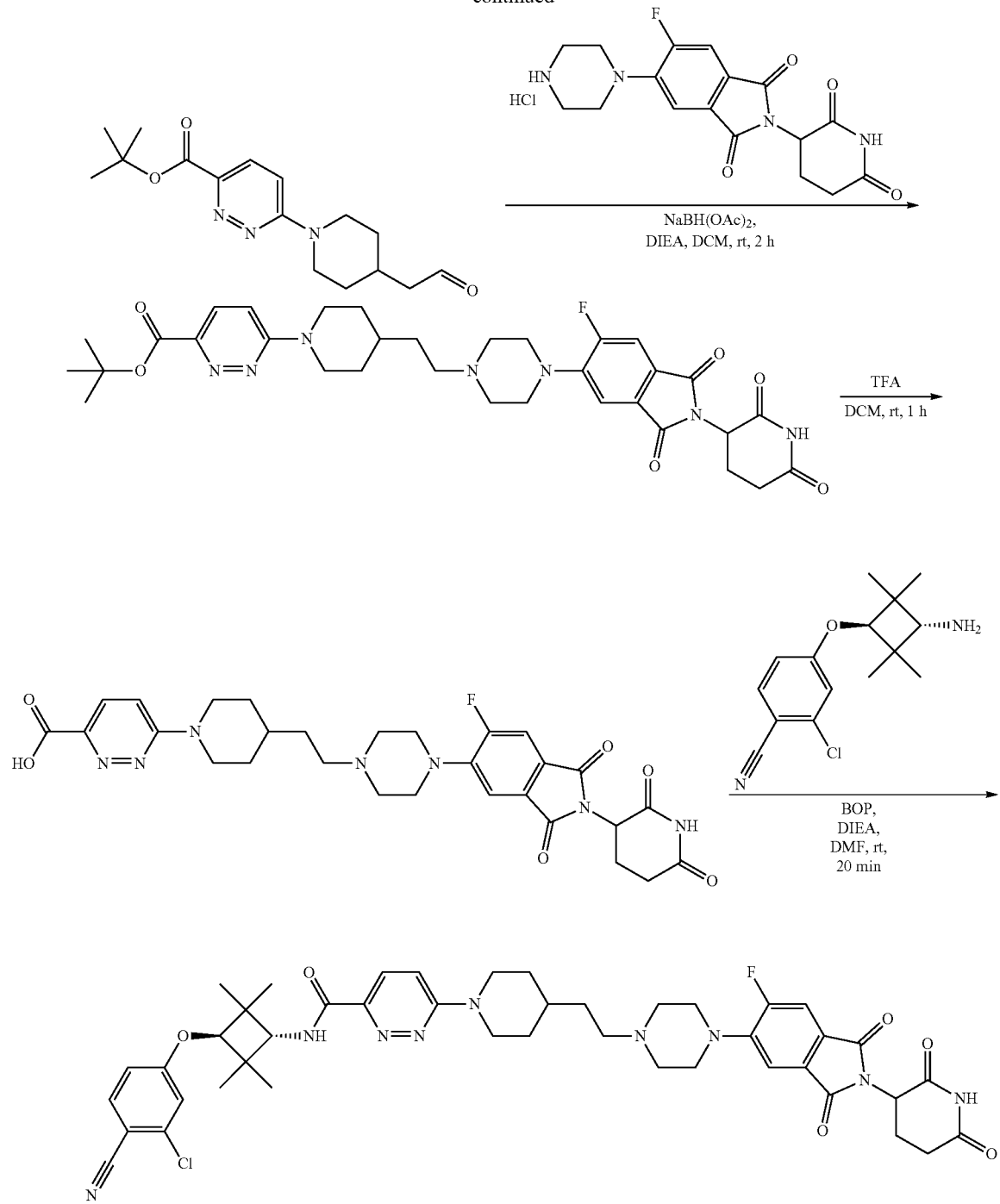
General Scheme 30
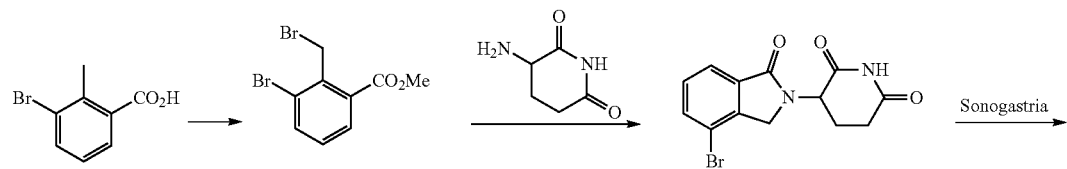

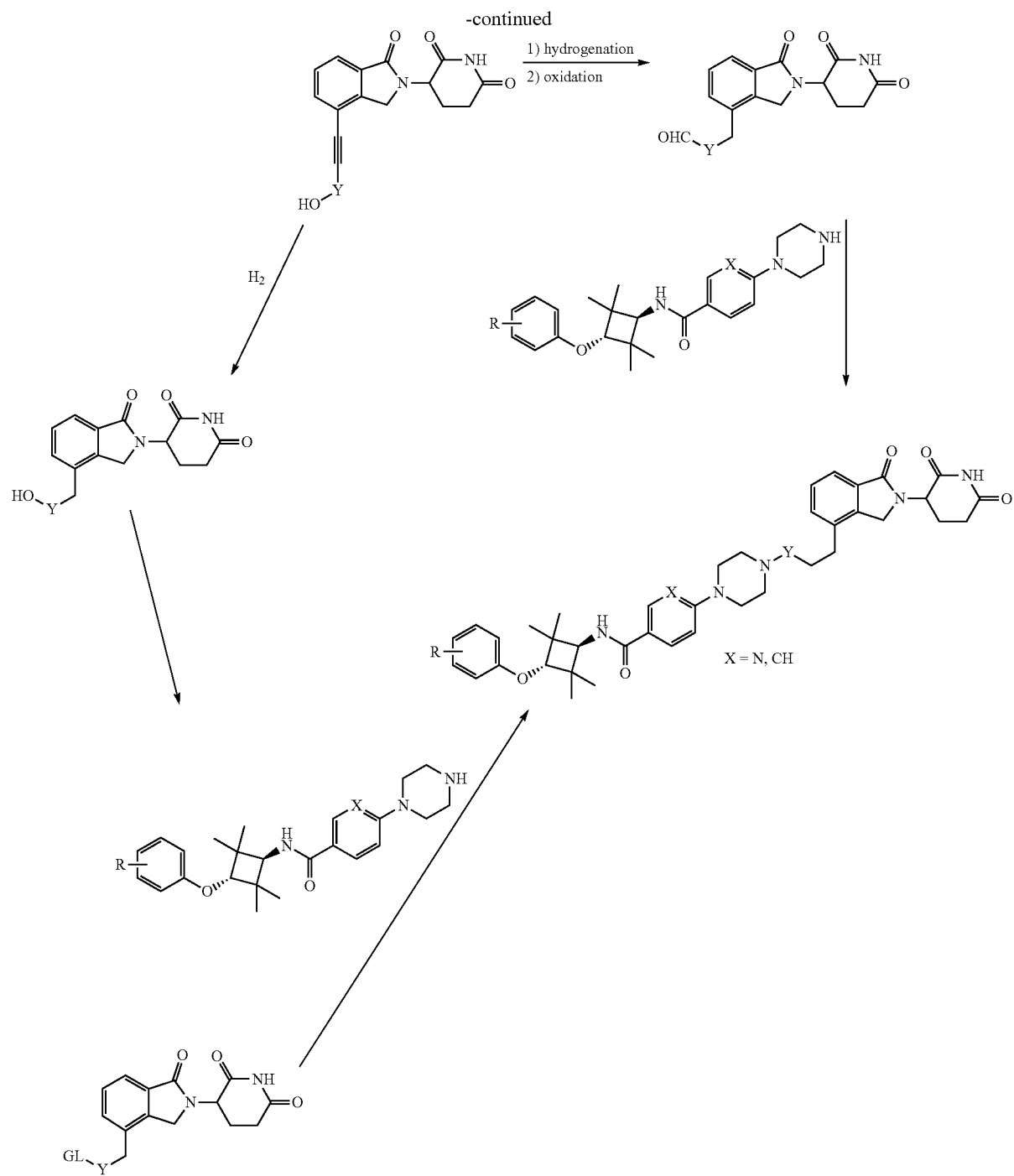
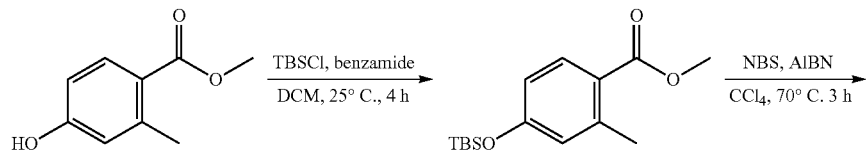
General Scheme 31

189 190
-continued
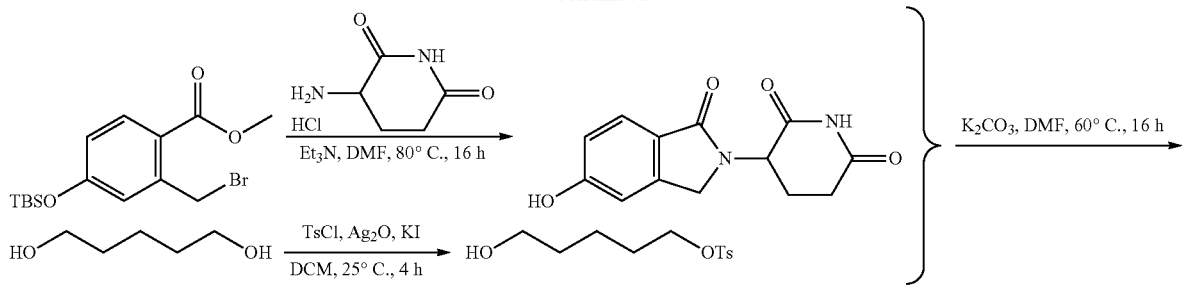
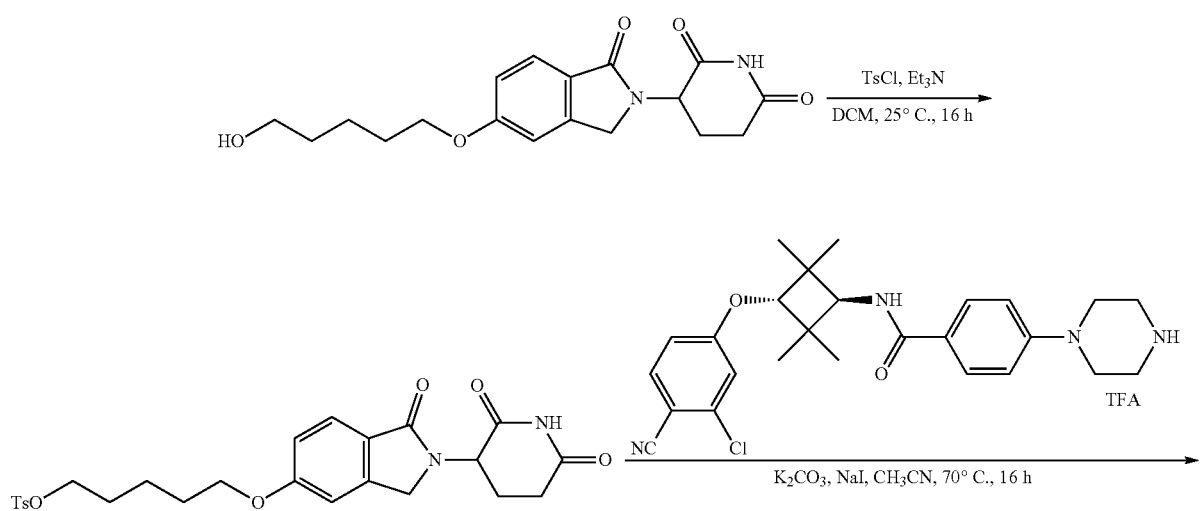
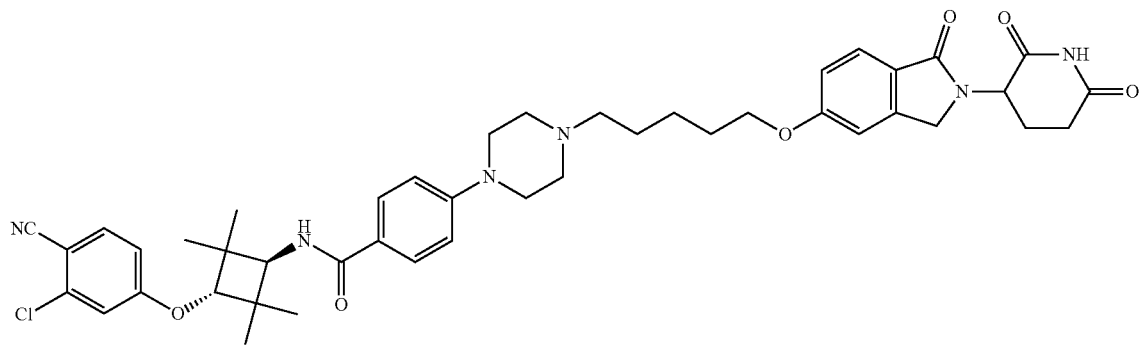
General Scheme 32
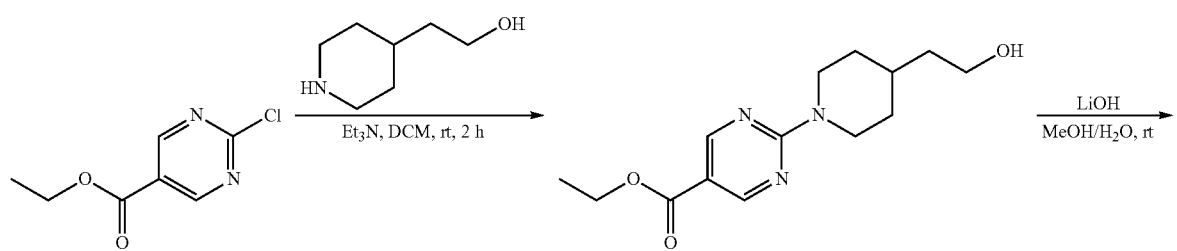

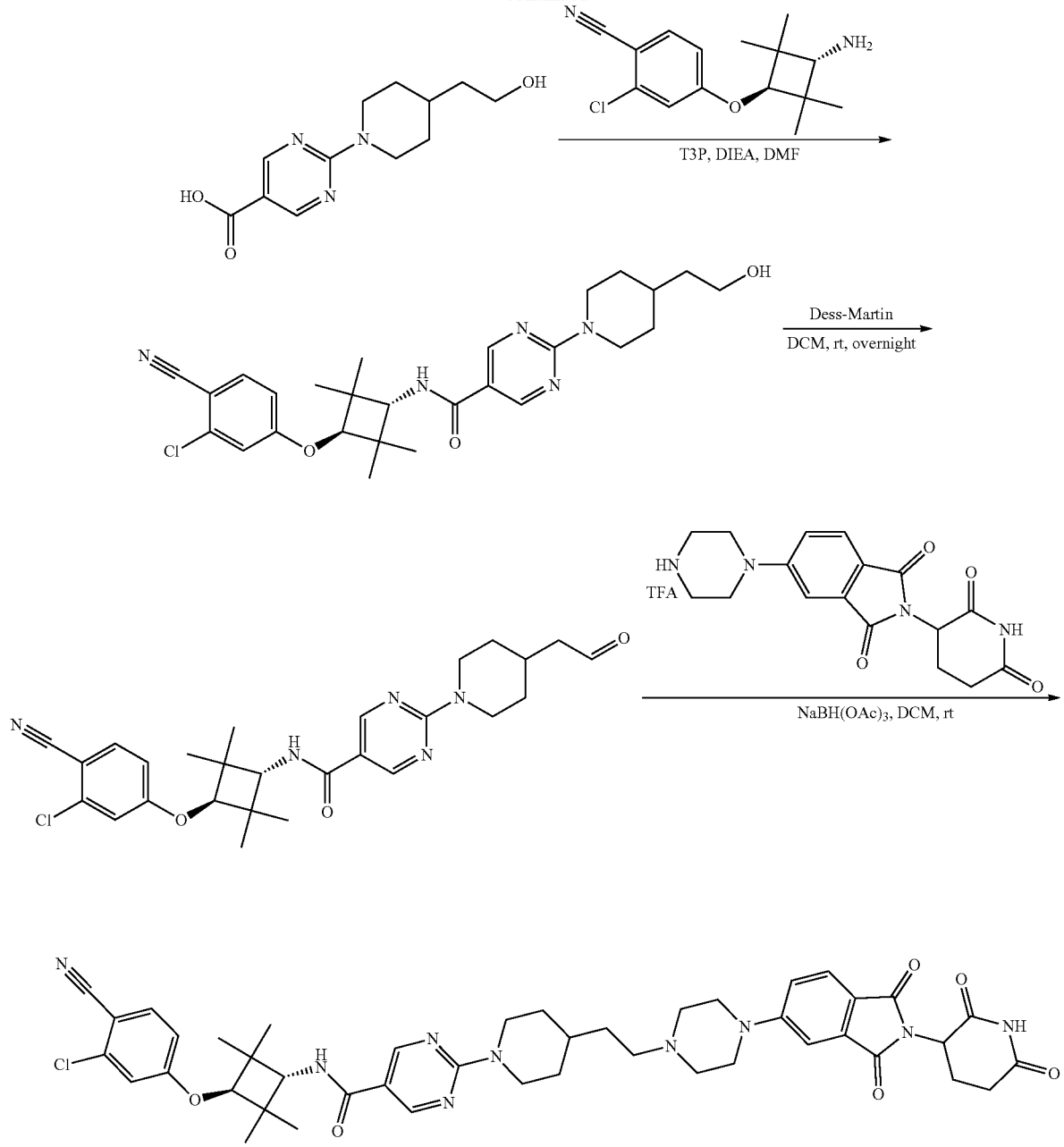
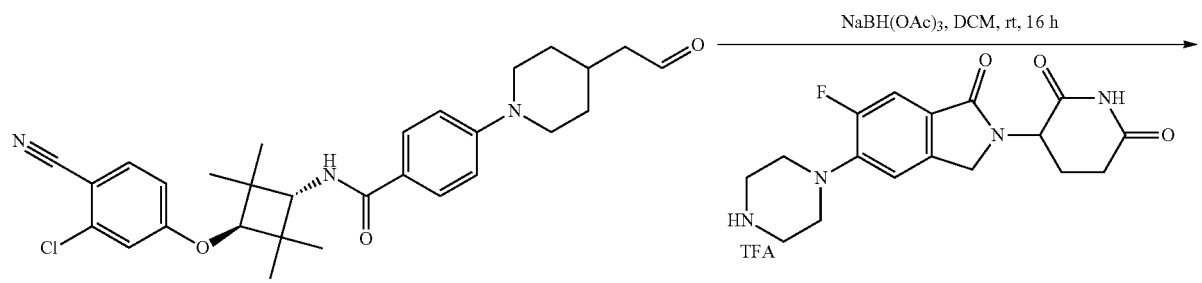
General Scheme 33

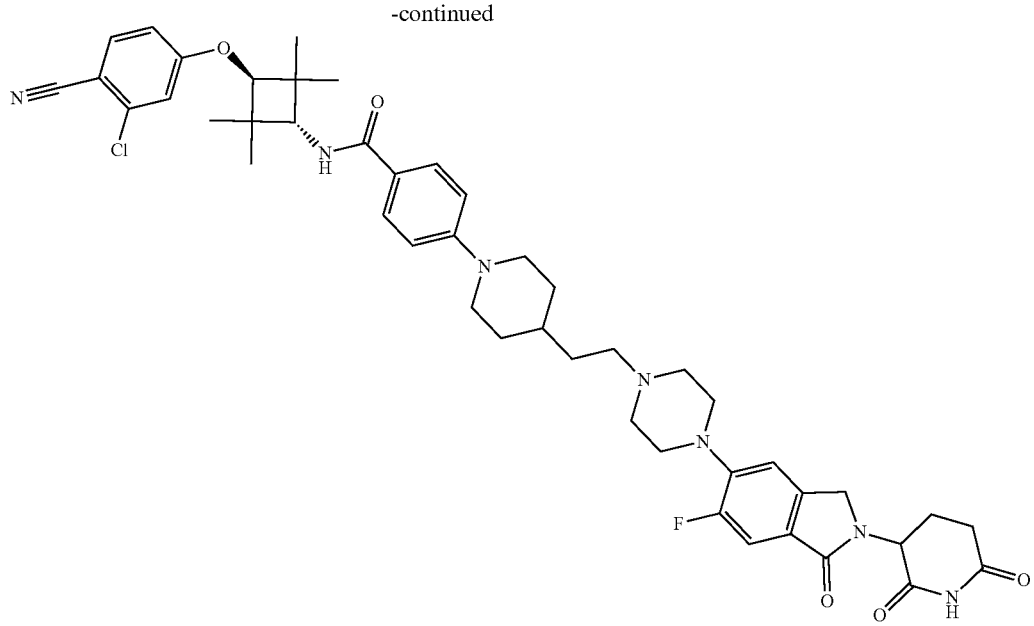
General Scheme 34
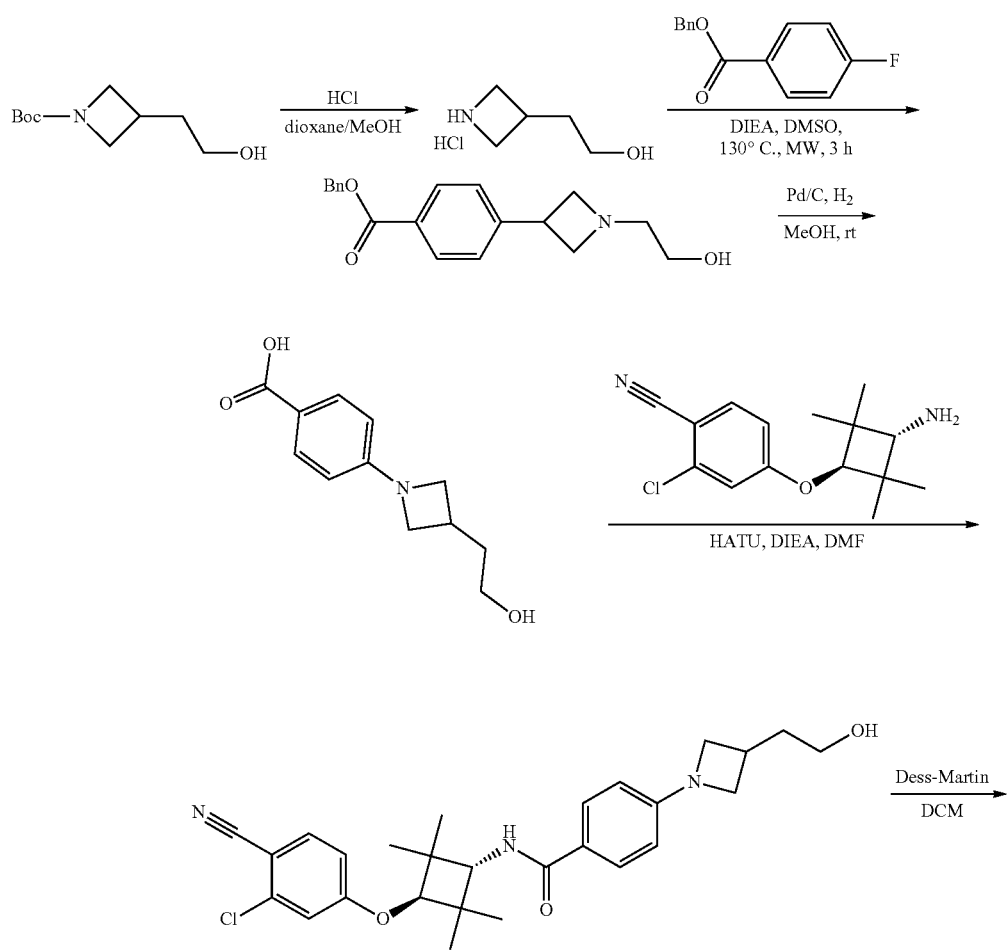

195 196
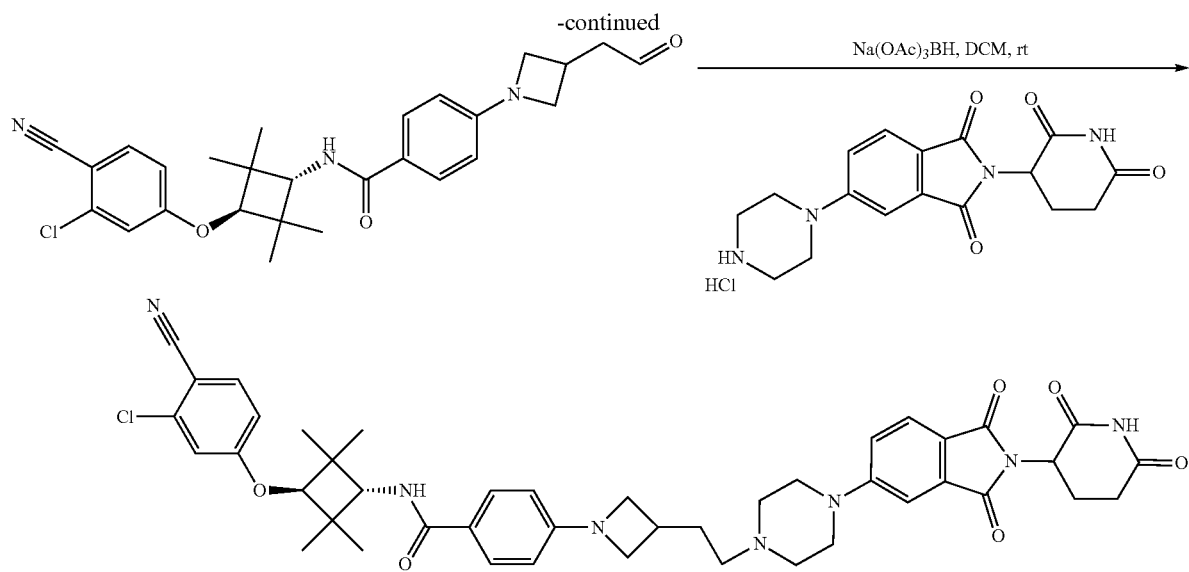
General Scheme 35
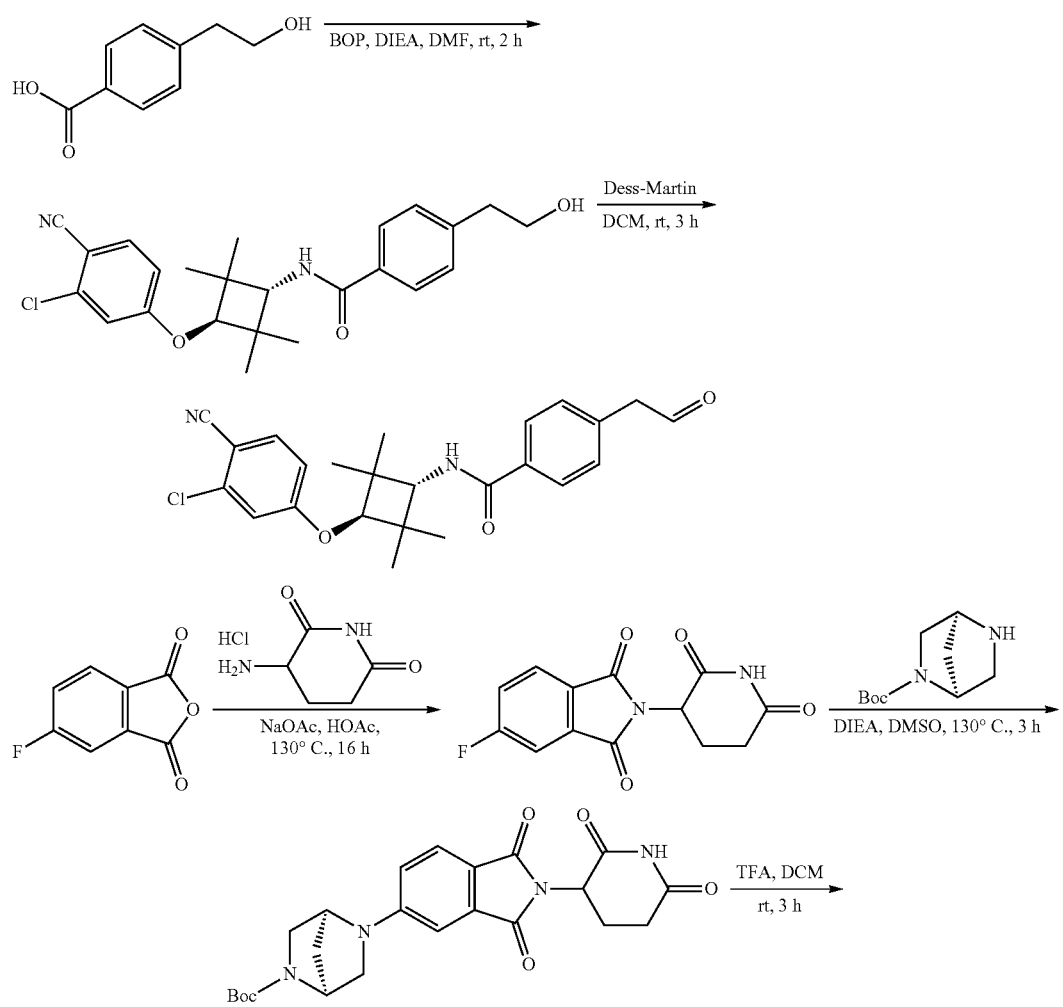

-continued
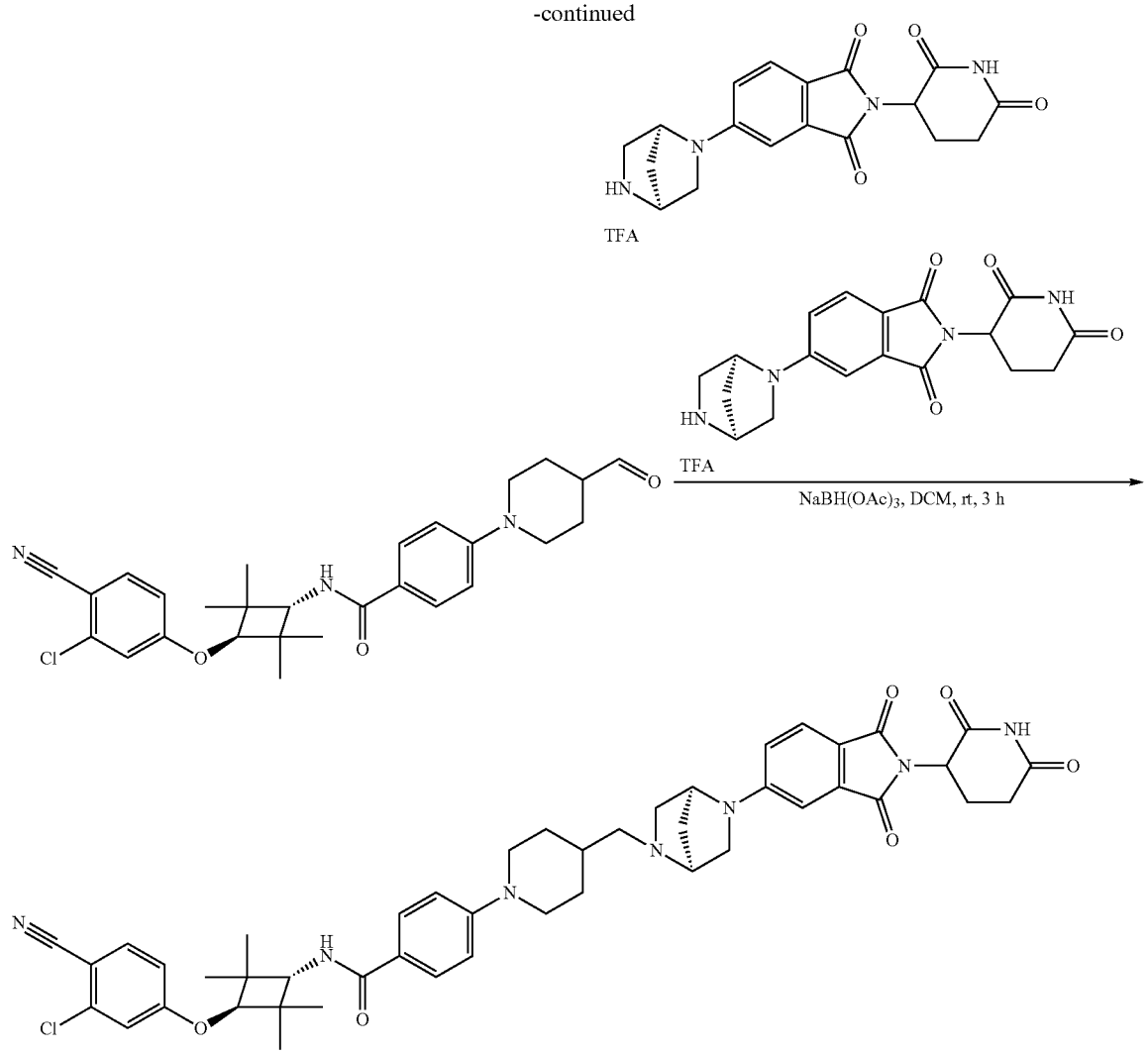
General Scheme 36
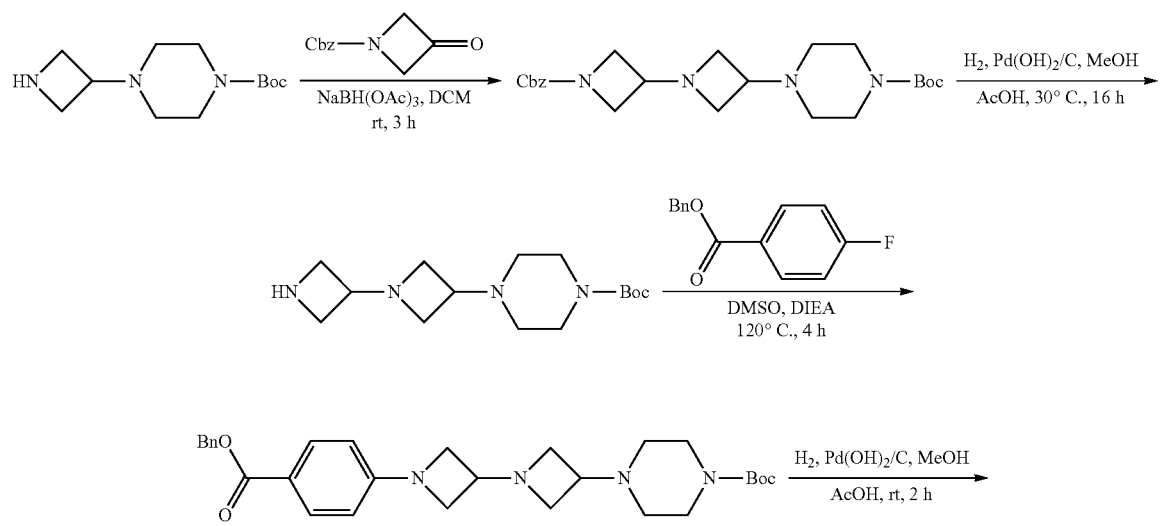

199 200
-continued
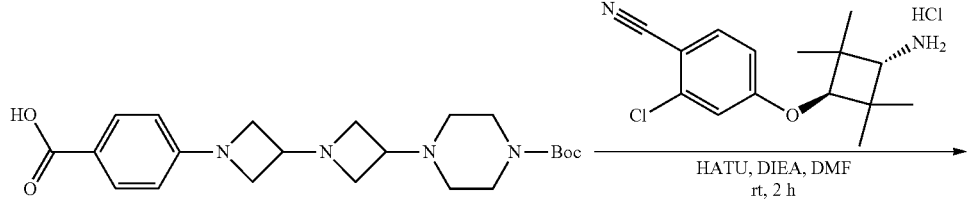
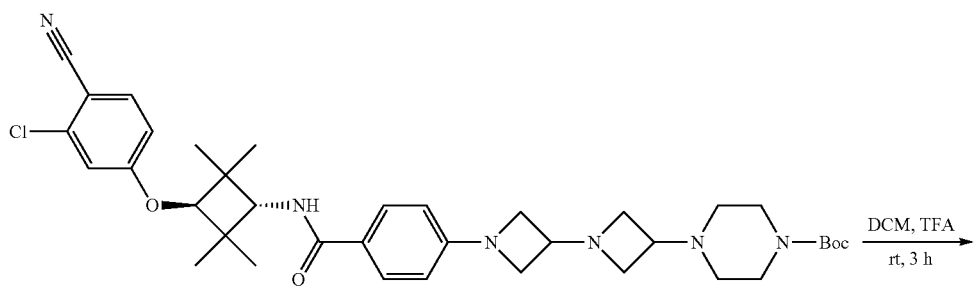
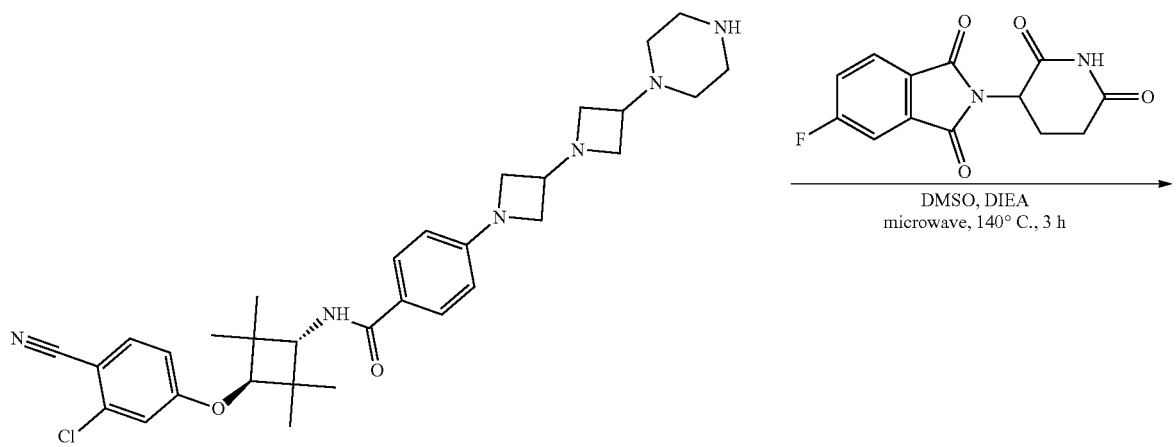
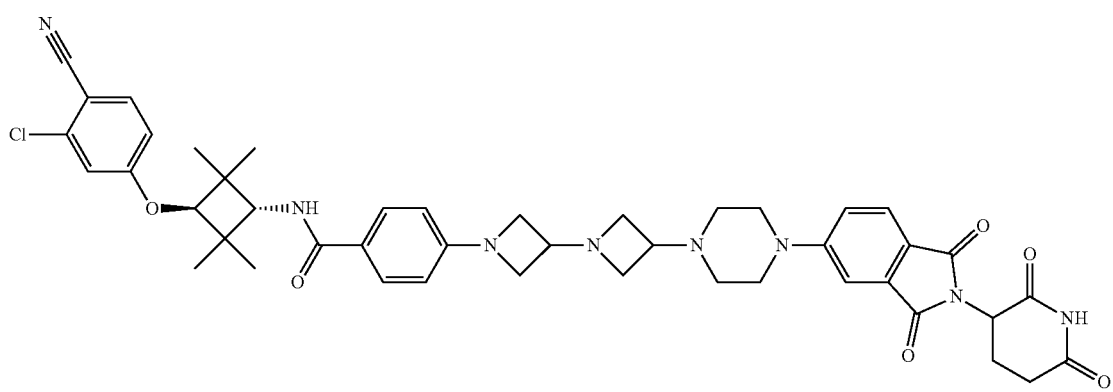

201 202
General Scheme 37
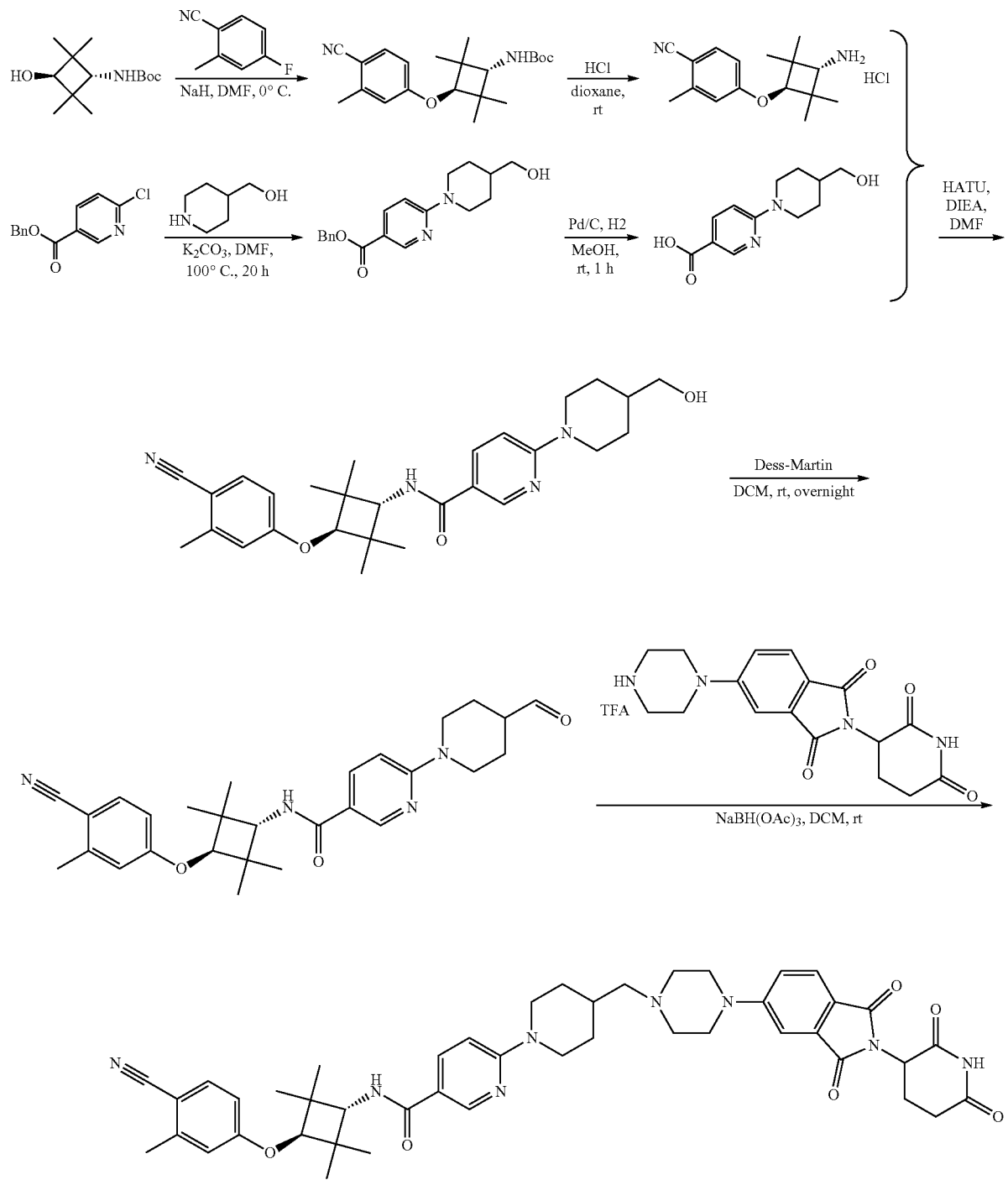
General Scheme 38
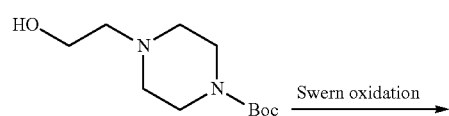

203
204
-continued
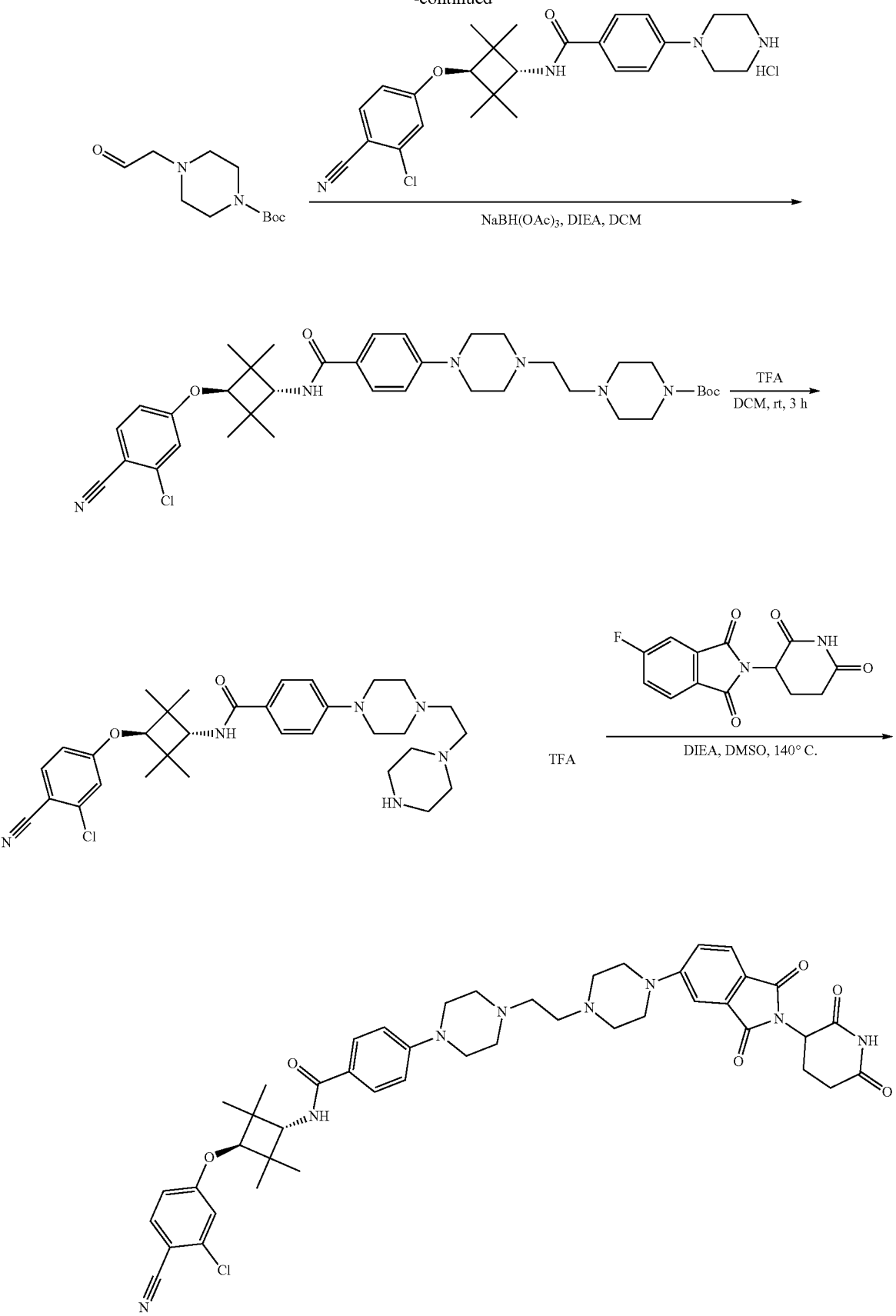

General Scheme 39
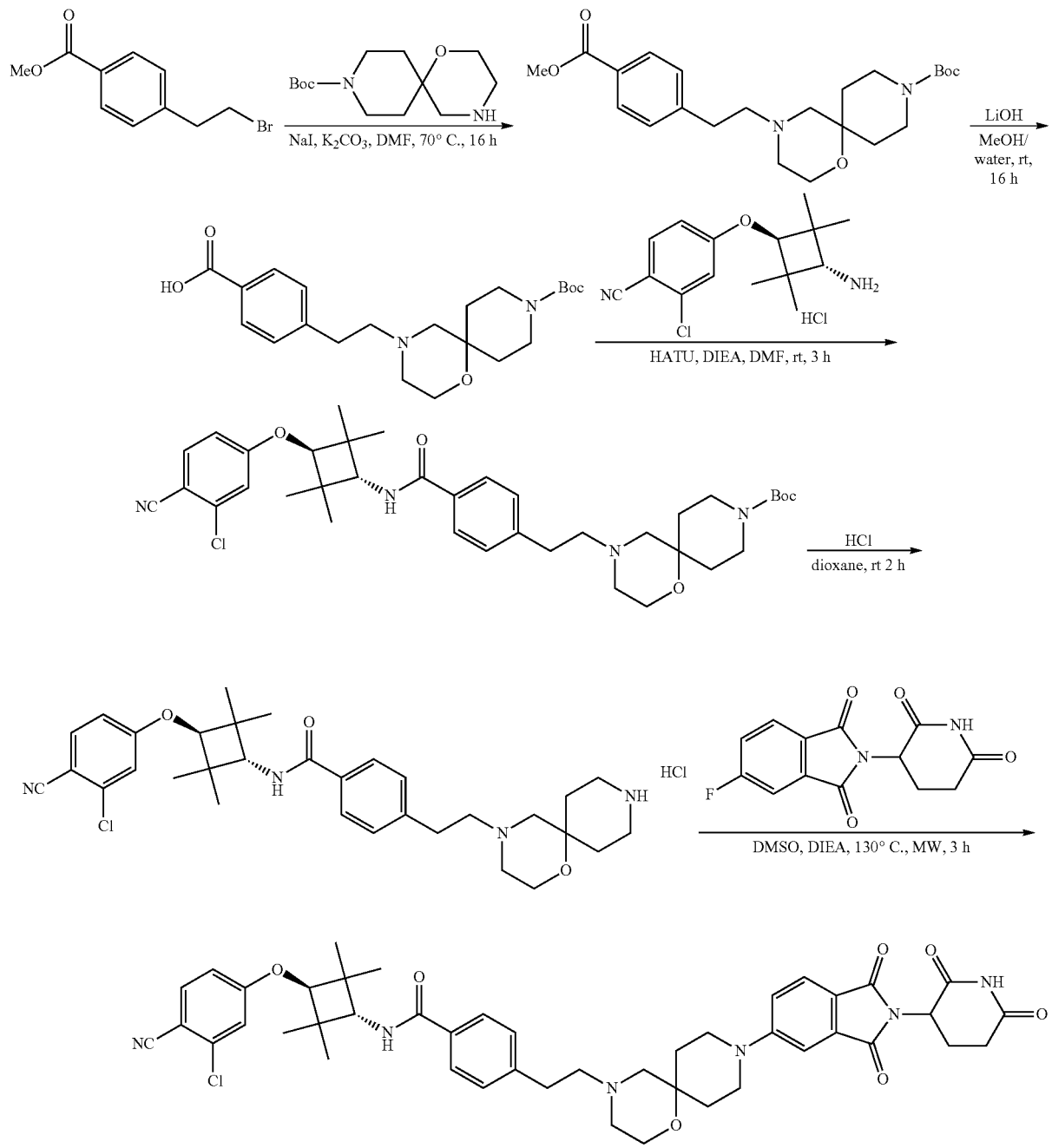
General Scheme 40
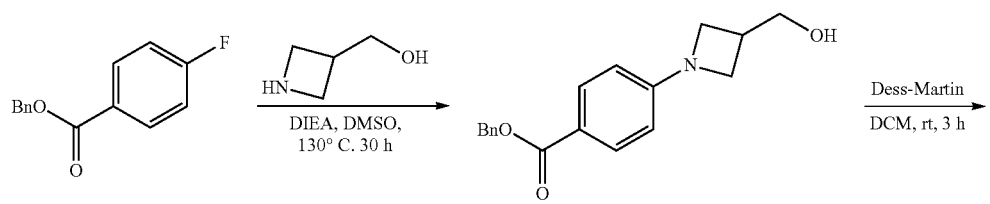

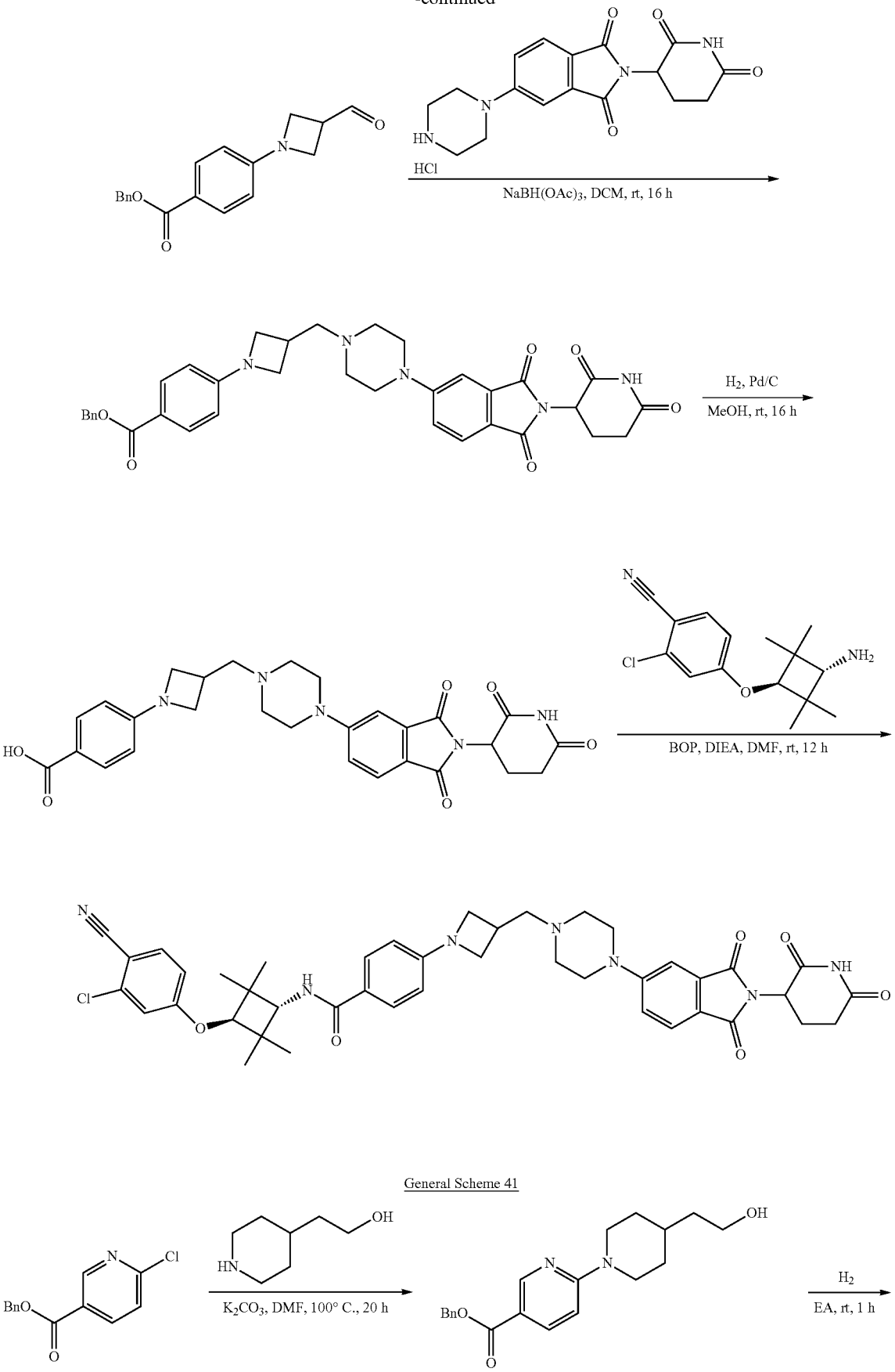

209
210
-continued
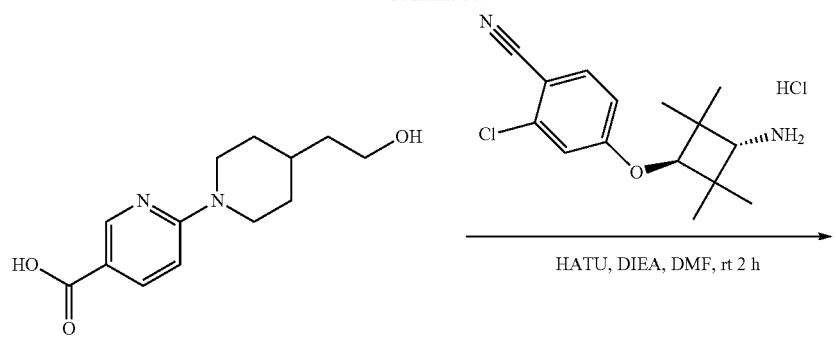
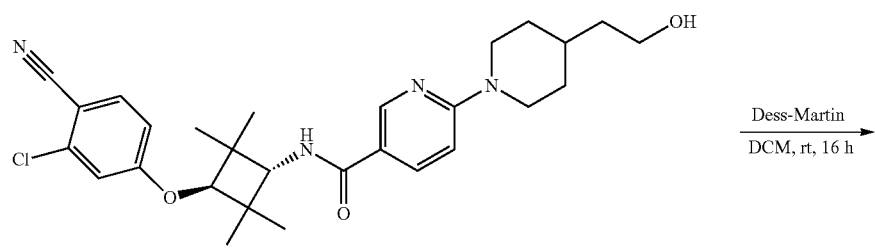
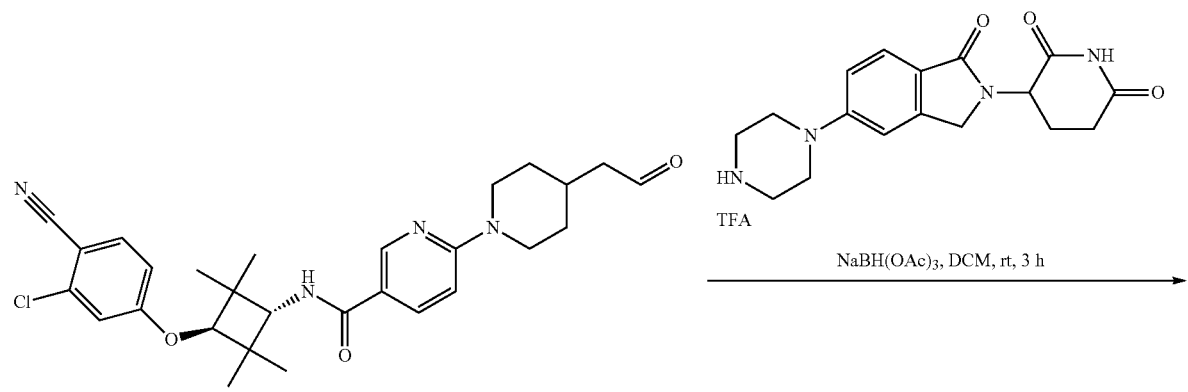
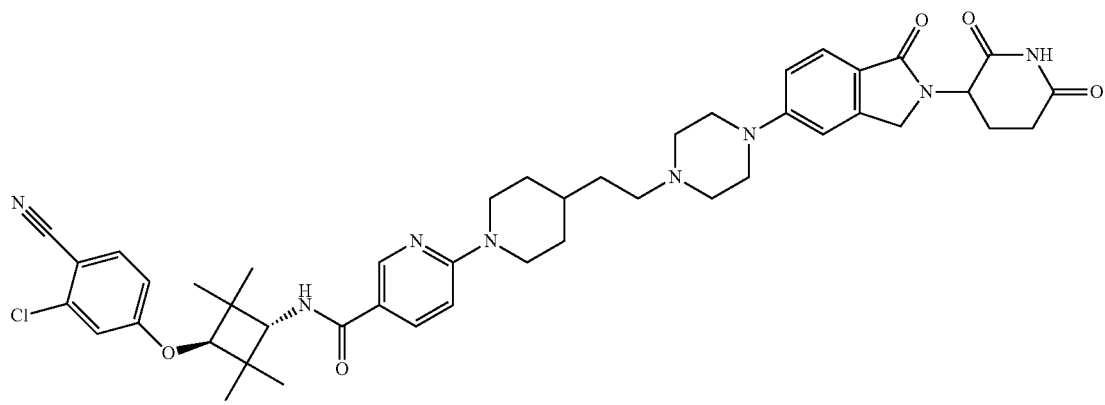 [SMILES: CC1(C)[C@H](NC(=O)c2ccc(N3CCC(CCN4CCN(c5ccc6c(c5)CN(C5CCC(=O)NC5=O)C6=O)CC4)CC3)nc2)C(C)(C)[C@H]1Oc1ccc(C#N)c(Cl)c1]

General Scheme 42
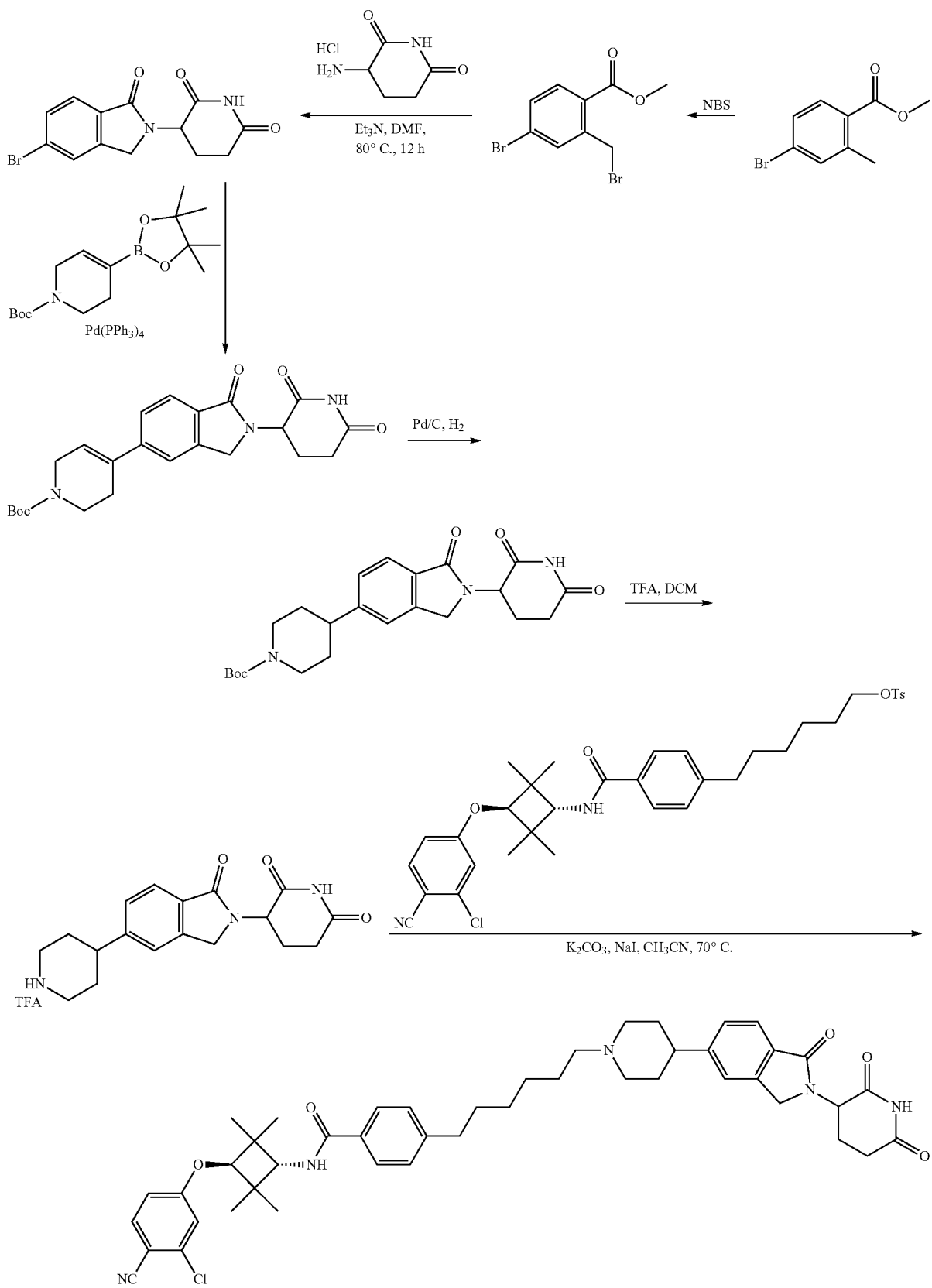

General Scheme 43
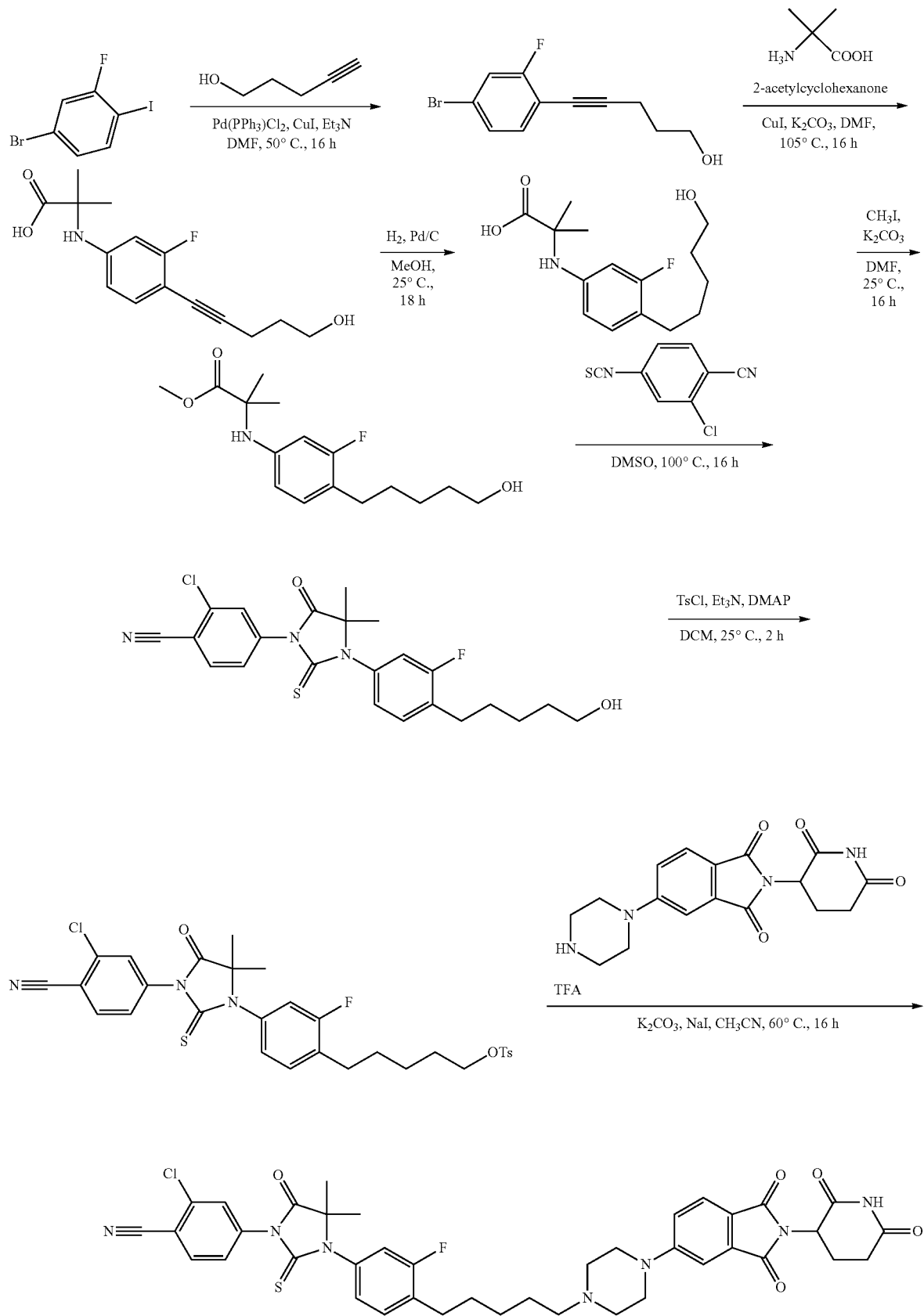

General Scheme 44
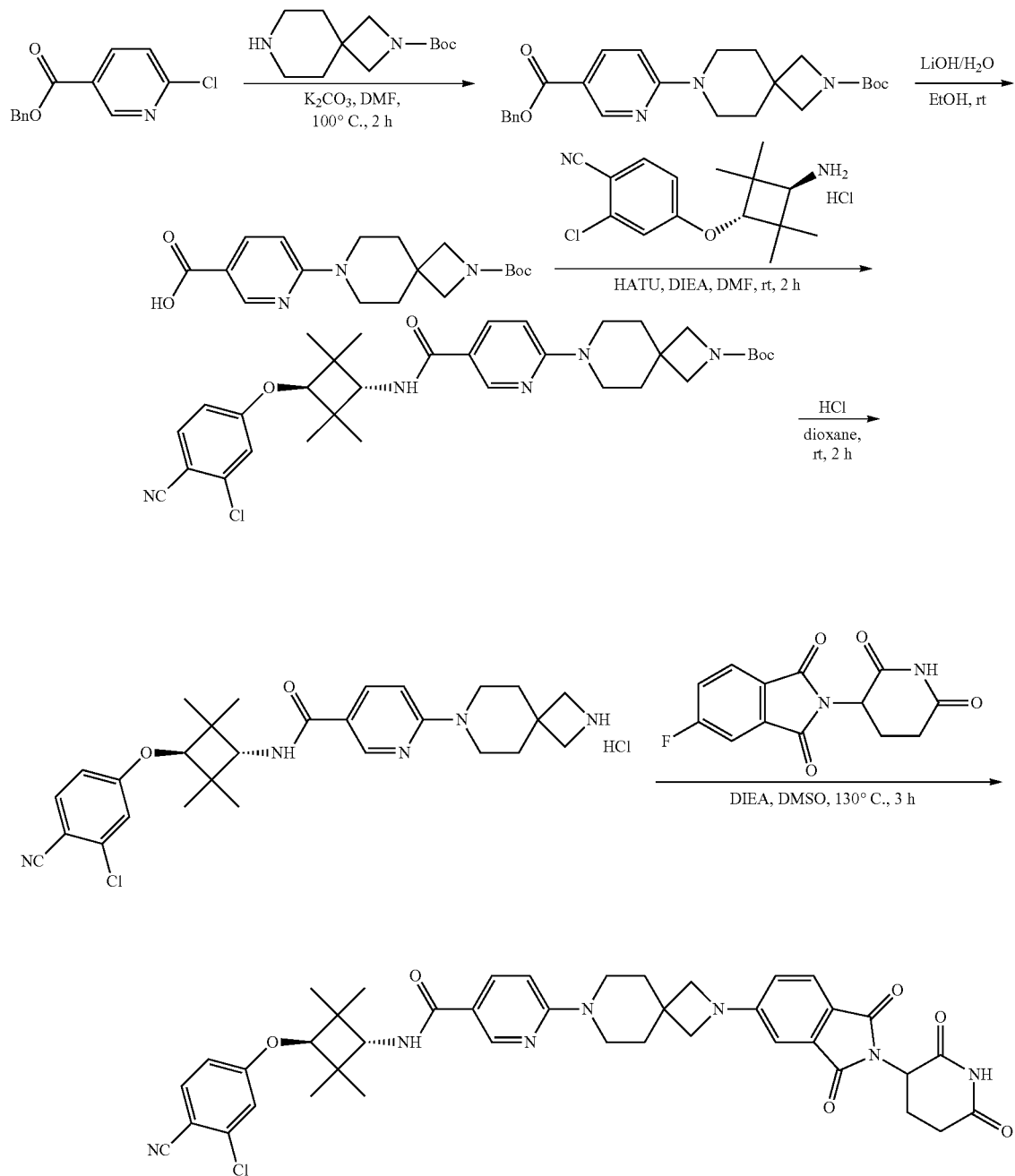
General Scheme 45
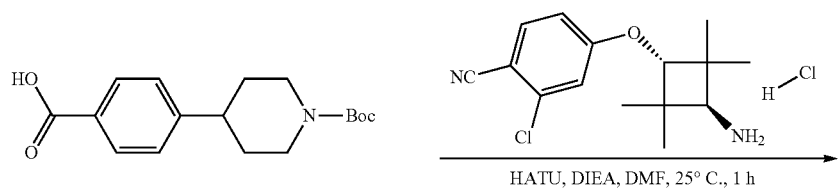

217 218
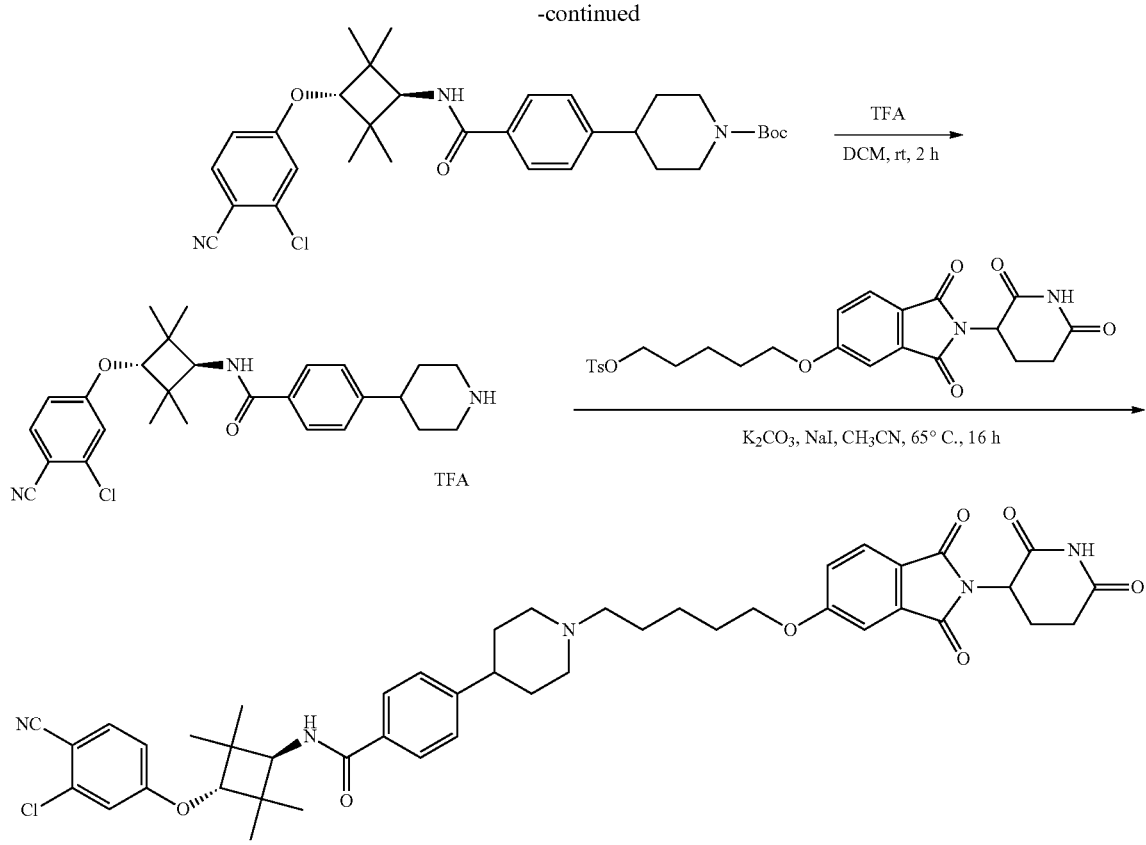
General Scheme 46
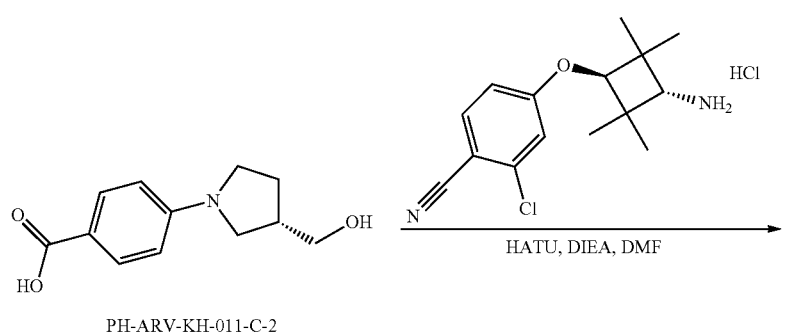
PH-ARV-KH-011-C-2
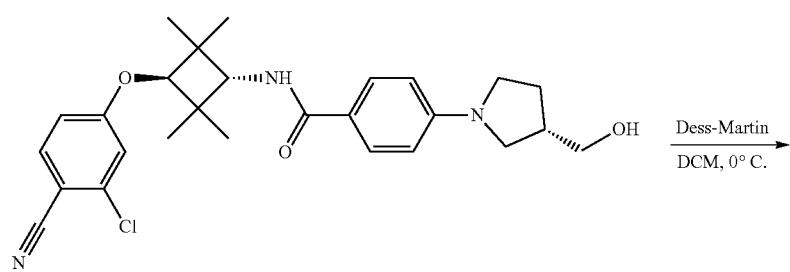
Dess-Martin
DCM, 0° C.

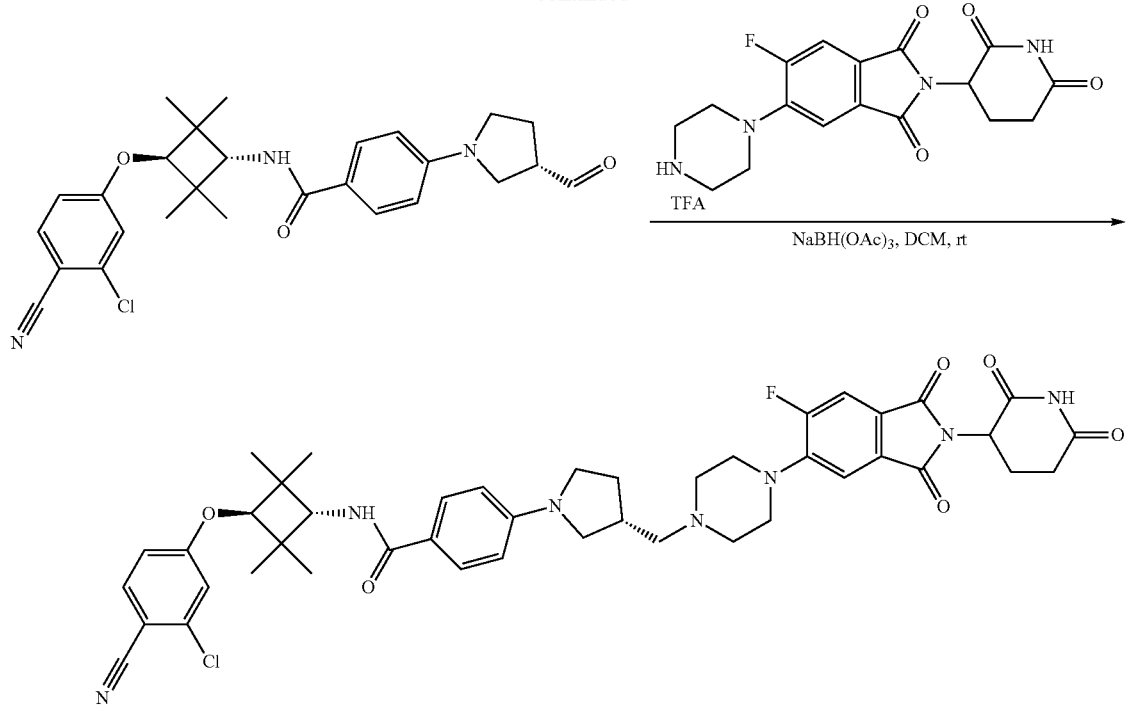
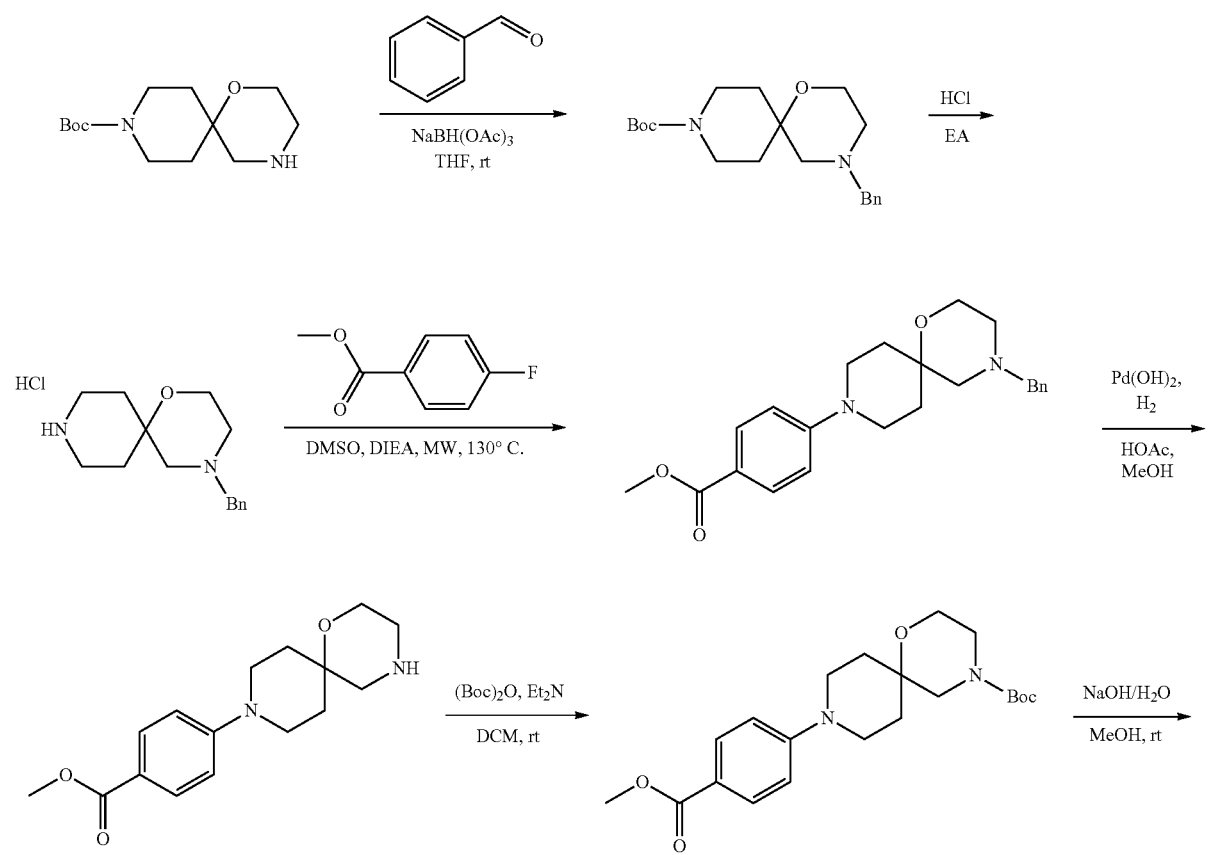
General Scheme 47

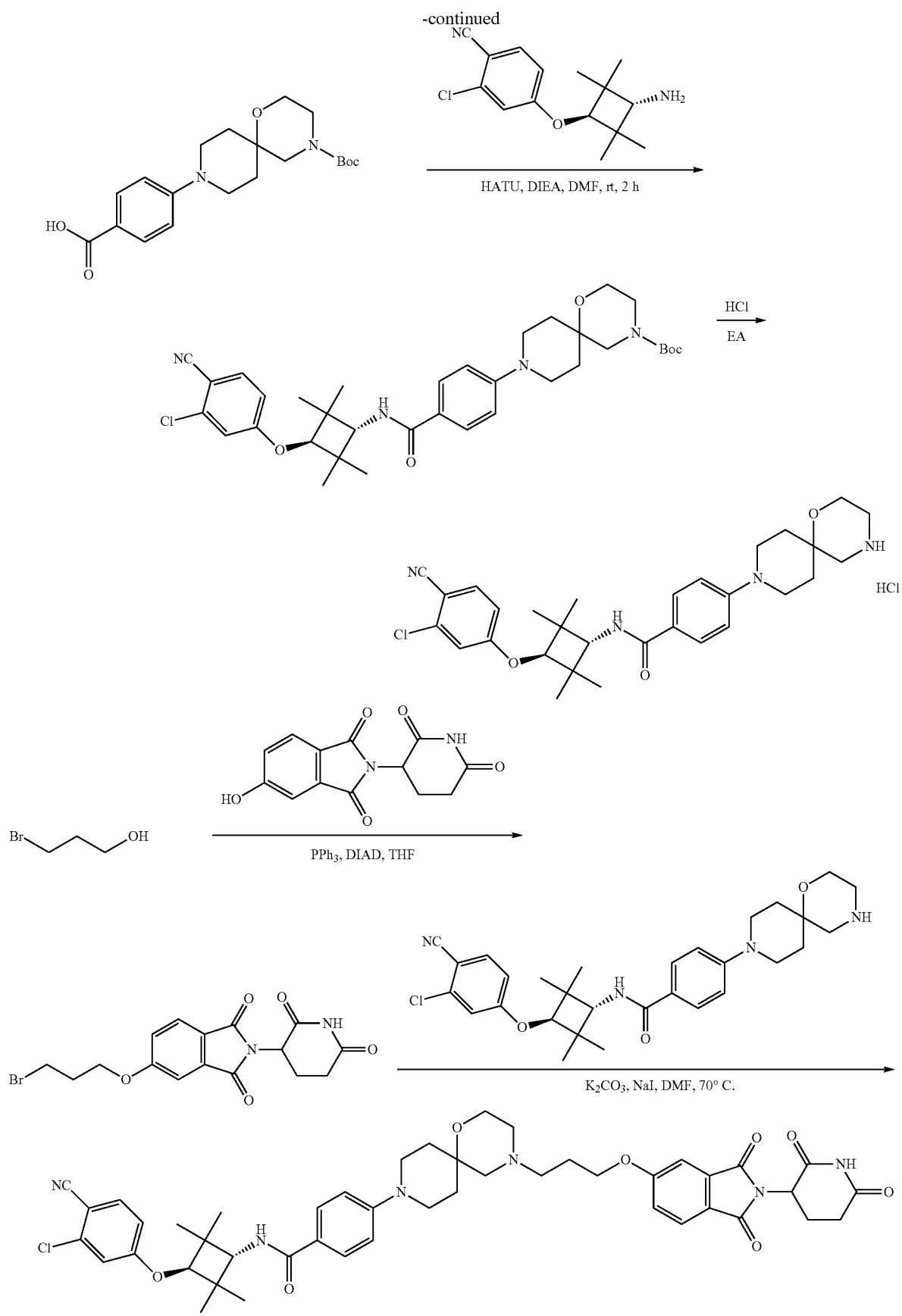

General Scheme 48
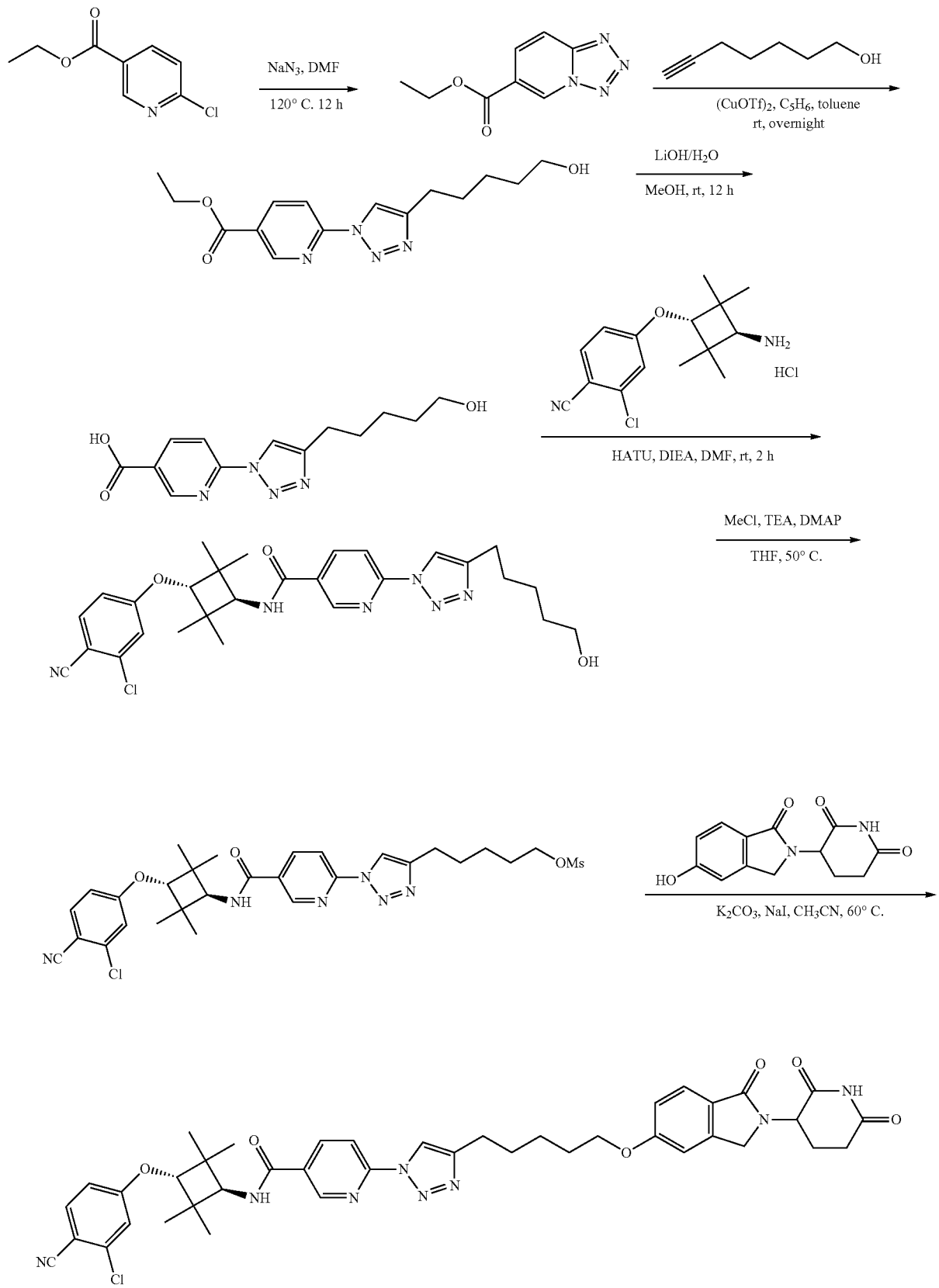

General Scheme 49
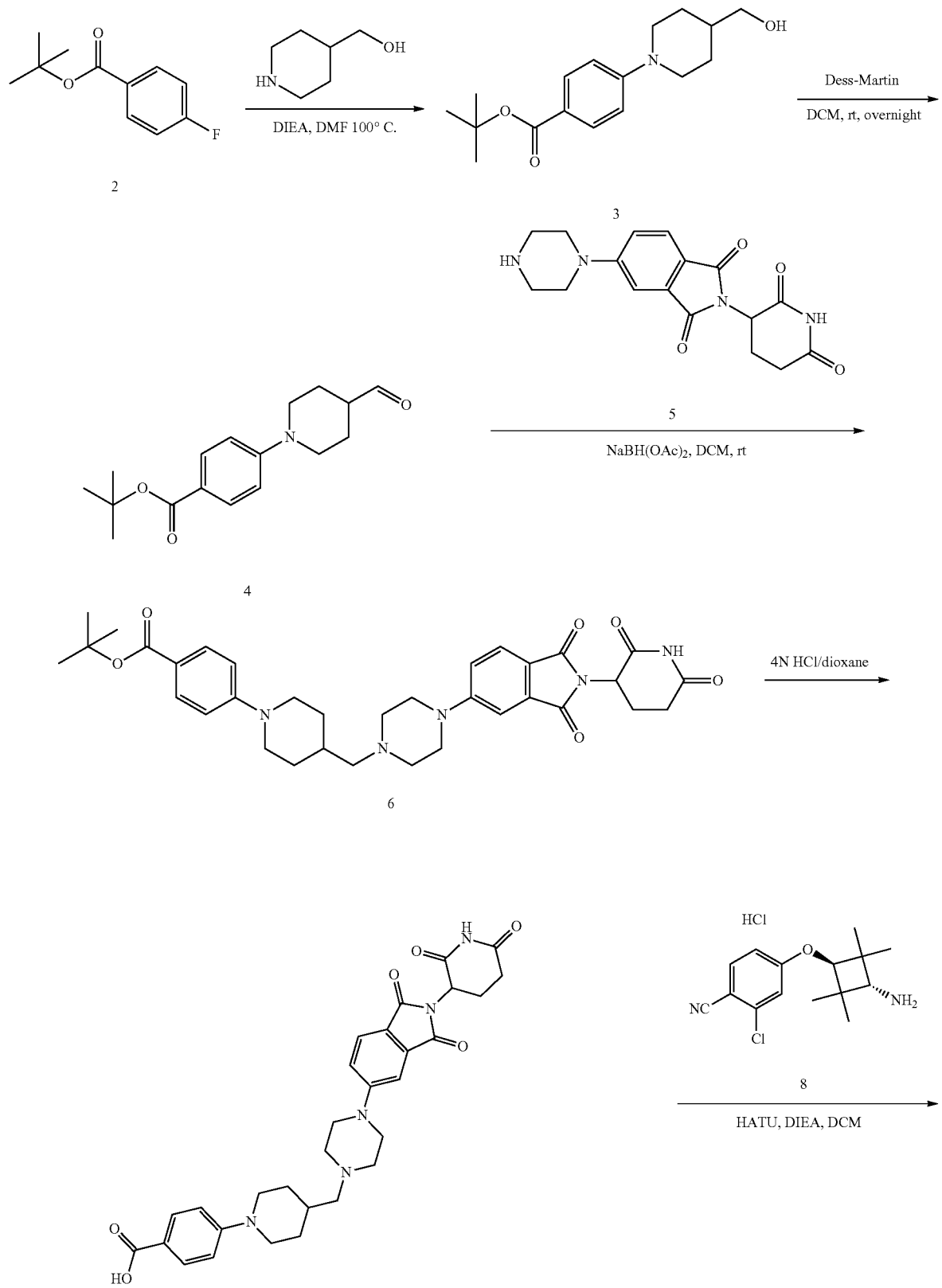

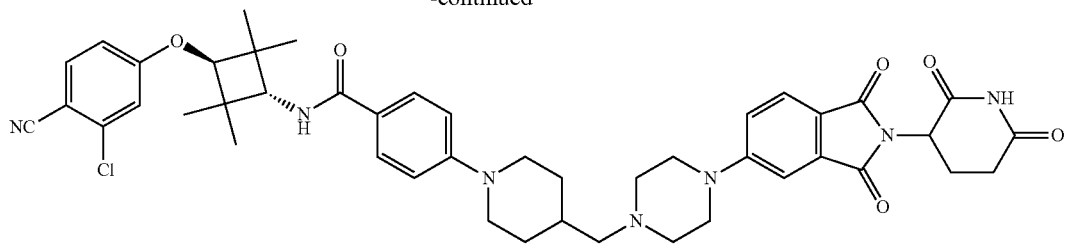

9

To a solution of tert-butyl 4-(4-(hydroxymethyl)piperidin-1-yl)benzoate 3 (15 g, 51.4 mmol) in DCM (100 mL) was added Dess-Martin periodinane (26.1 g, 61.6 mmol) in ice-water bath and the clear solution was stirred at room temperature for 2 hours. The solvent was evaporated and EtOAc was added. The mixture was passed through a pad of silica gel, washed with EtOAc, and the solvent was evaporated to give crude. (It was combined with another batch of crude which started from 10 g starting material for purification.) The crude was dry loaded to ISCO (0-10% MeOH/DCM) for separation. Light yellow solid 16.11 g 4 (yield 65%) was obtained as product.

To a mixture of tert-butyl 4-(4-formylpiperidin-1-yl)benzoate 4 (15.79 g, 54.2 mmol) and 2-(2,6-dioxopiperidin-3-yl)-5-(piperazin-1-yl)isoindoline-1,3-dione dihydrochloride 5 (22.5 g, 54.2 mmol) in DCM (500 mL) was added sodium acetate (4.44 g, 54.2 mmol). The reaction mixture was allowed to stir for 3 mins and lowered into ice-water bath. NaBH(OAc)₃ (20.0 g, 94.8 mmol) was added over 10 mins and the bath was removed after an additional 10 mins. After 21 h, water (500 mL) and DCM (150 mL) were added, the organic layer was removed and the aqueous layer was extracted with DCM (150 ml), the combined organics were dried with Na₂SO₄, and evaporated the to give crude 6 which was dry-loaded with silica gel to ISCO (0-10% MeOH/DCM, 750 g column) for separation. The fractions were collected and dried, exchanged with DCM twice, and dried under high vacuum for 26 hours to provide 18.15 g 6 (yield 60%) as a yellow solid.

4N HCl in dioxane (40 mL, 29.3 mmol) was added to tert-butyl 4-(4-((4-(2-(2,6-dioxopiperidin-3-yl)-1,3-dioxoisoindolin-5-yl)piperazin-1-yl)methyl)piperidin-1-yl)benzoate 6 (18.15 g, 29.3 mmol) and the reaction mixture was heated to 50° C. for 7 hours. The solvent was evaporated and DCM exchanged twice, dried under high vacuum for overnight. It was exchanged with DCM again twice, dried under high vacuum for 8 hours to provide 18.77 g (yield 101%) 7 as a light brown solid.

To a solution of 4-((1r,3r)-3-amino-2,2,4,4-tetramethylcyclobutoxy)-2-chlorobenzonitrile hydrochloride 8 (8.9 g, 28.2 mmol) and 4-(4-((4-(2-(2,6-dioxopiperidin-3-yl)-1,3-dioxoisoindolin-5-yl)piperazin-1-yl)methyl)piperidin-1-yl)benzoic acid dihydrochloride 7 (18.7 g, 29.6 mmol) in DCM (300 mL) was added Hunig's base (24.2 mL, 140 mmol), and HATU (11.0 g, 29.0 mmol) was added. The reaction mixture was allowed to stir at ambient temperature for 17 h at which time it was washed with sat. NaHCO₃ (250 mL) twice, dried with Na₂SO₄, and evaporated to dryness. The crude was dry-loaded with silica gel to column. ISCO (0% 3CV, 0-10% MeOH/DCM 30 CV, 750 g column) separated the mixture. The product was dried in heated vacuum oven at 40° C. for 16 hours to give 9 19.6 g (yield 85%, 99.55% pure by 18 mins analytical method) as a yellow solid.

General Scheme 50

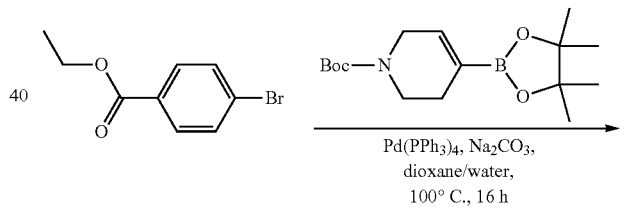

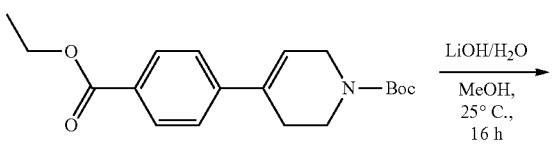

General Scheme 52
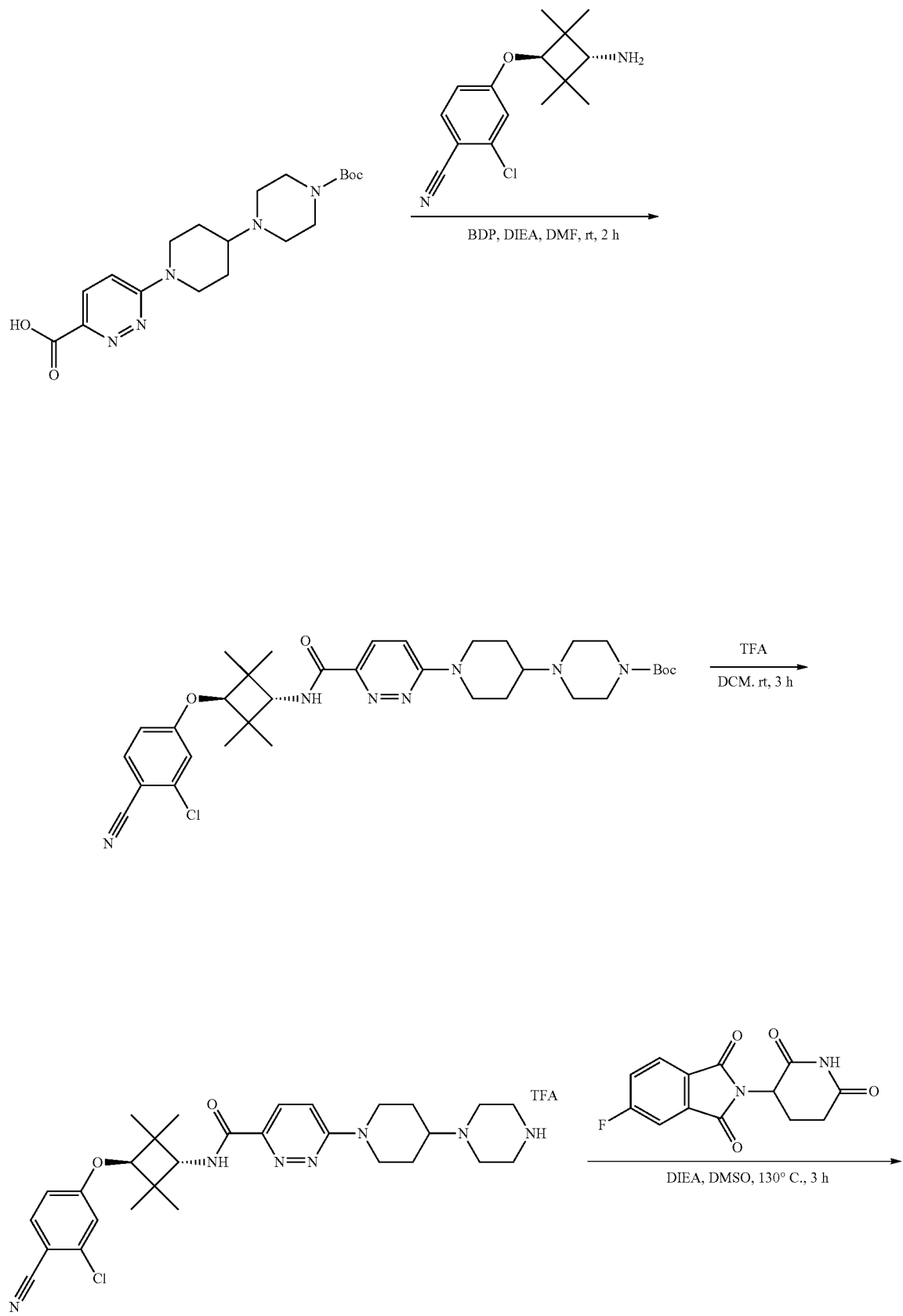

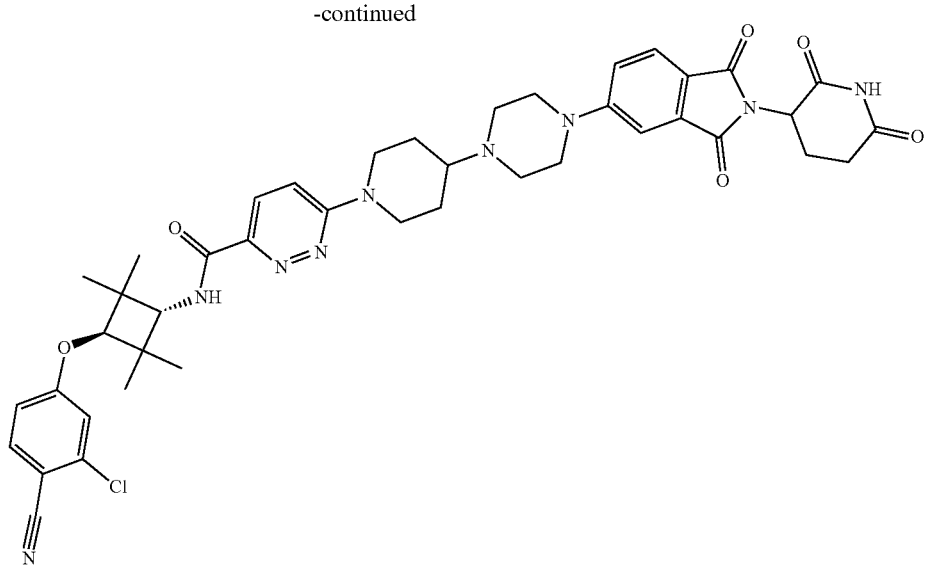
-continued
General Scheme 53
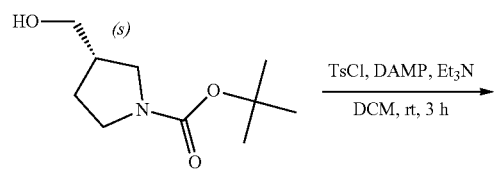
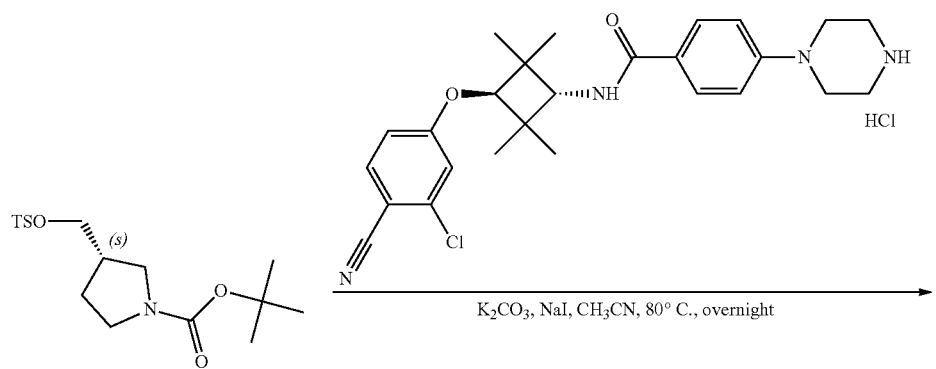
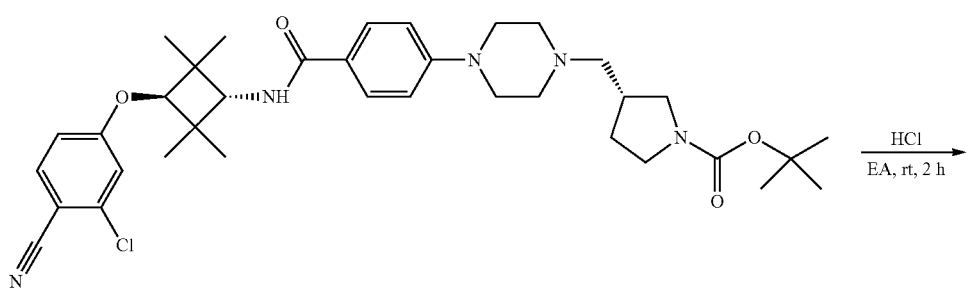

233
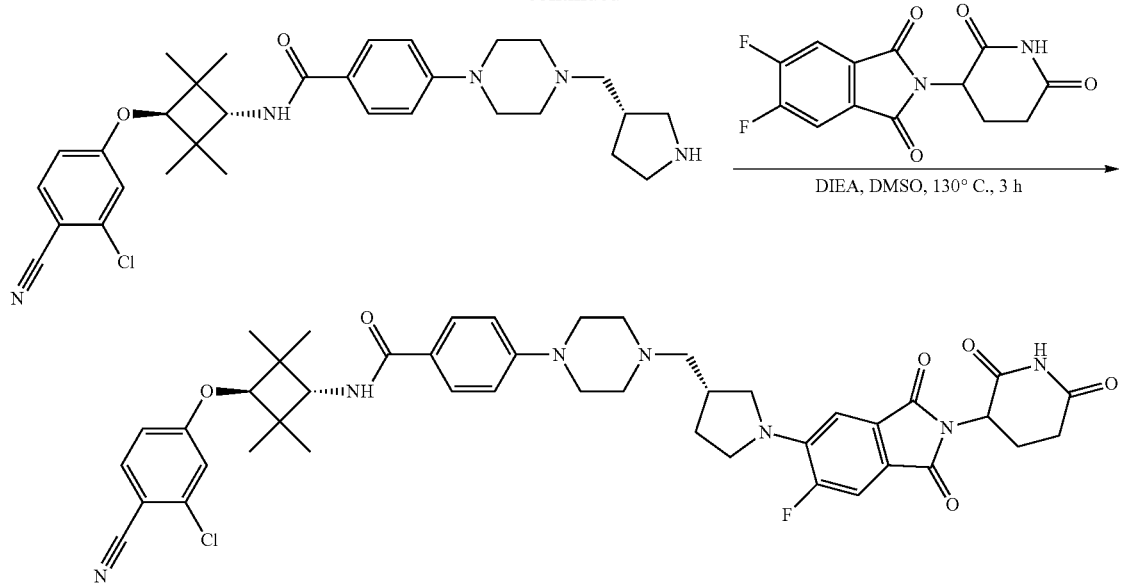
General Scheme 54
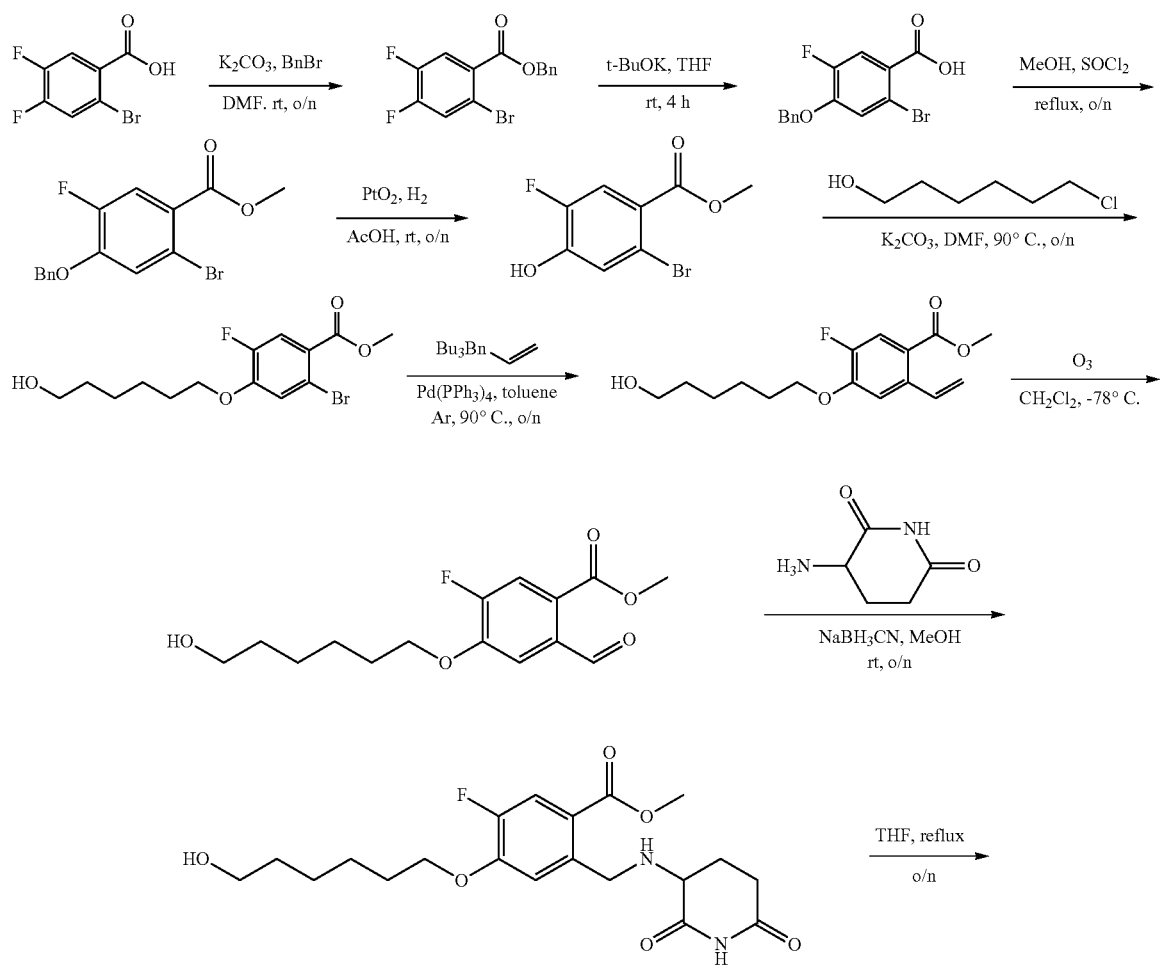

-continued
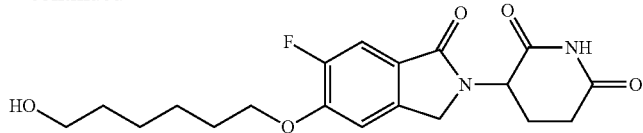
General Scheme 55
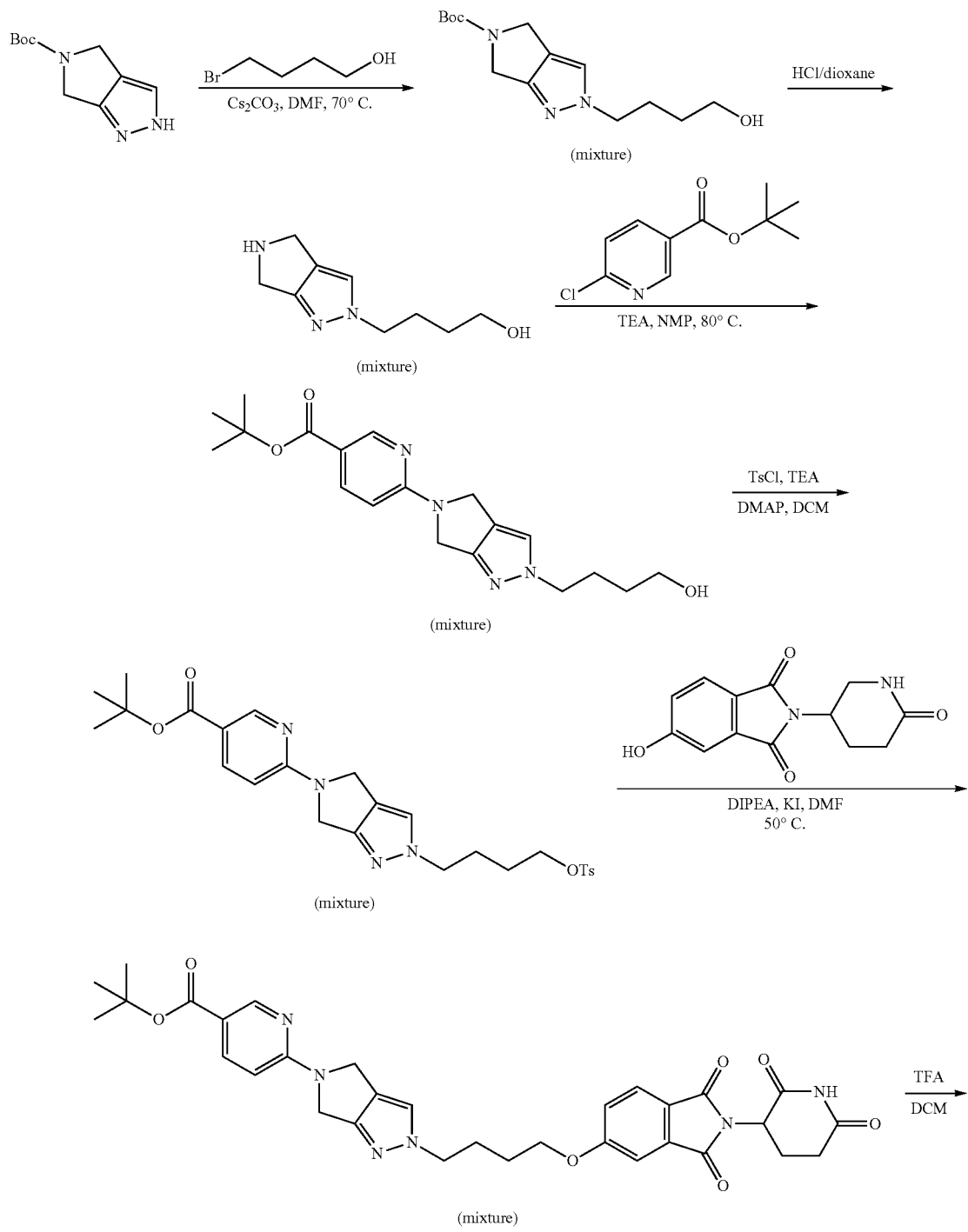

237
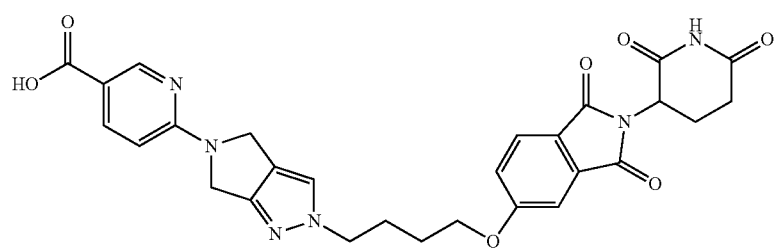
238
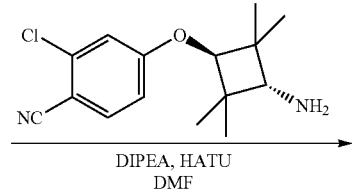
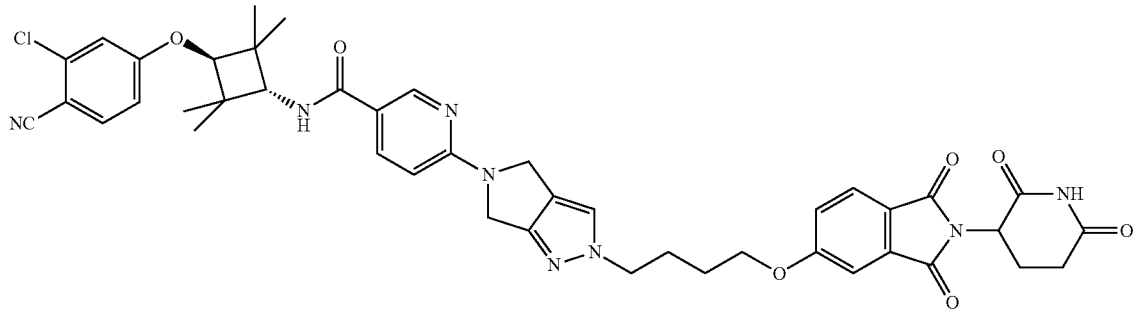
General Scheme 56
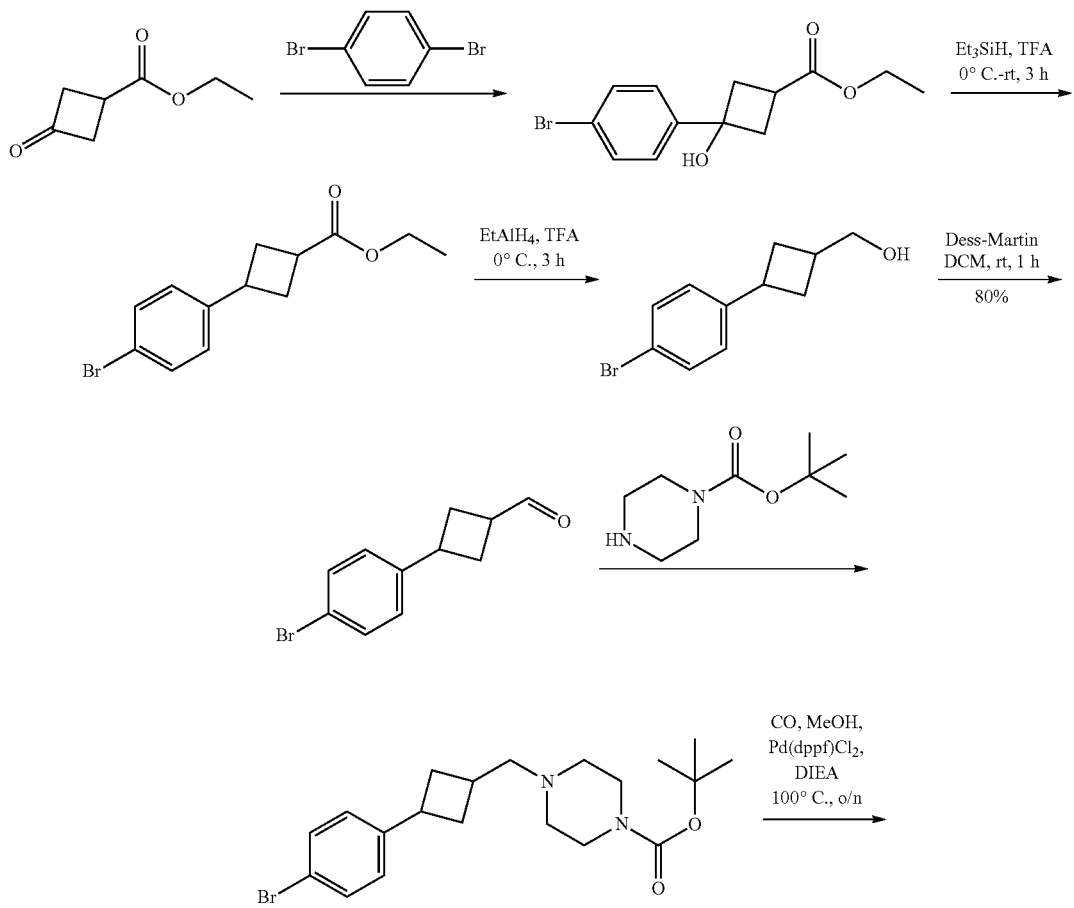

239
240
-continued
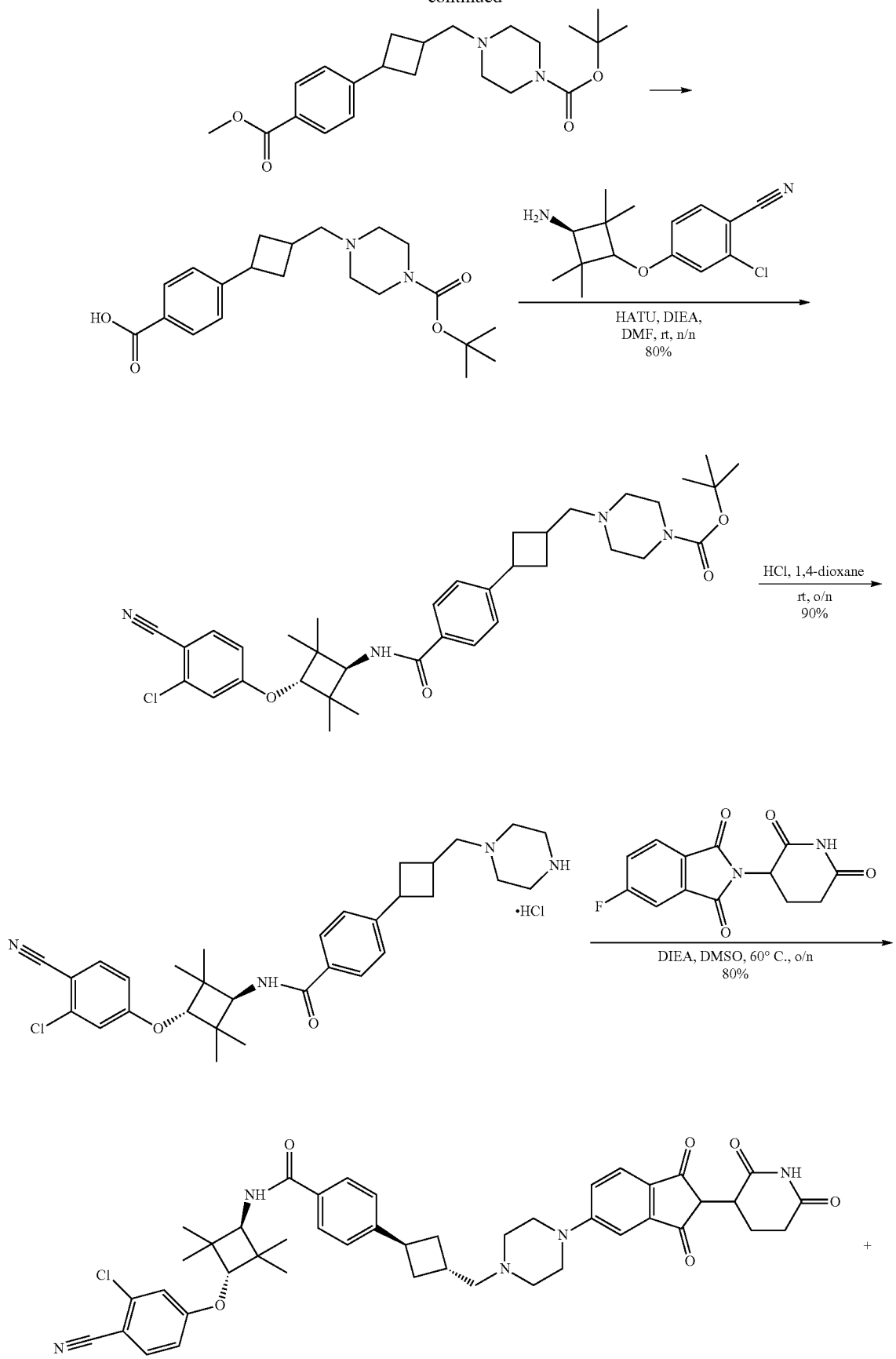

-continued
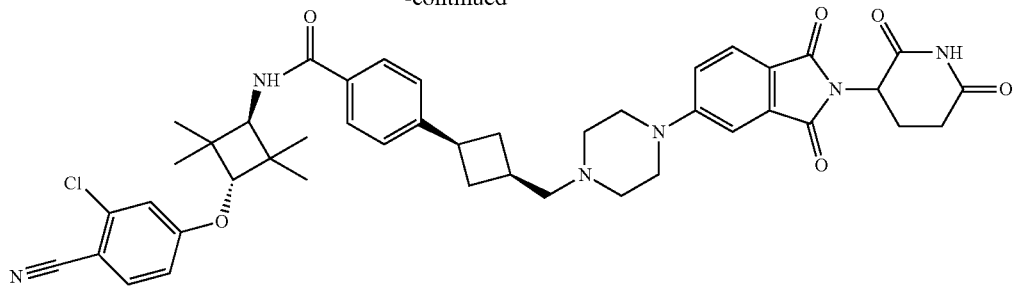
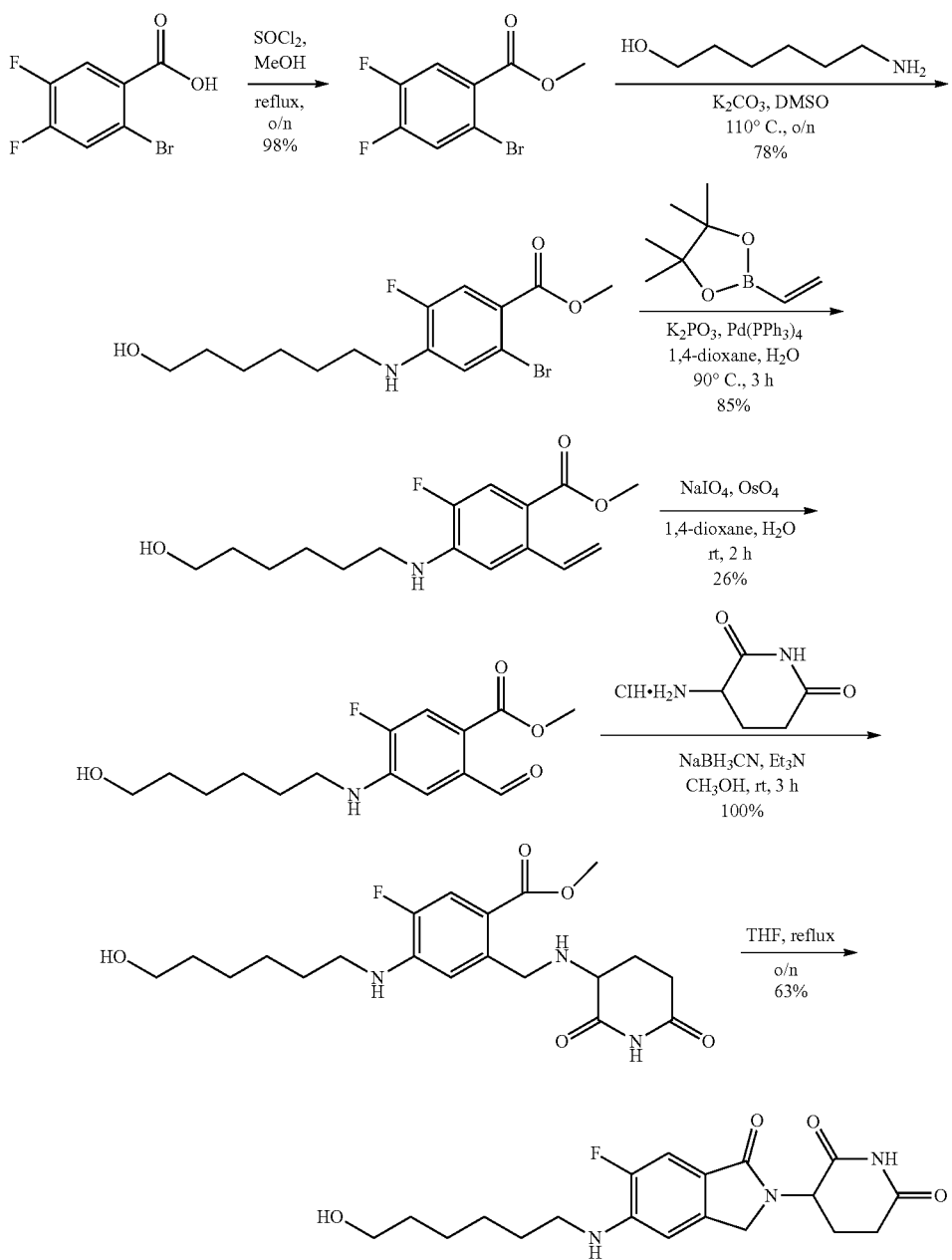

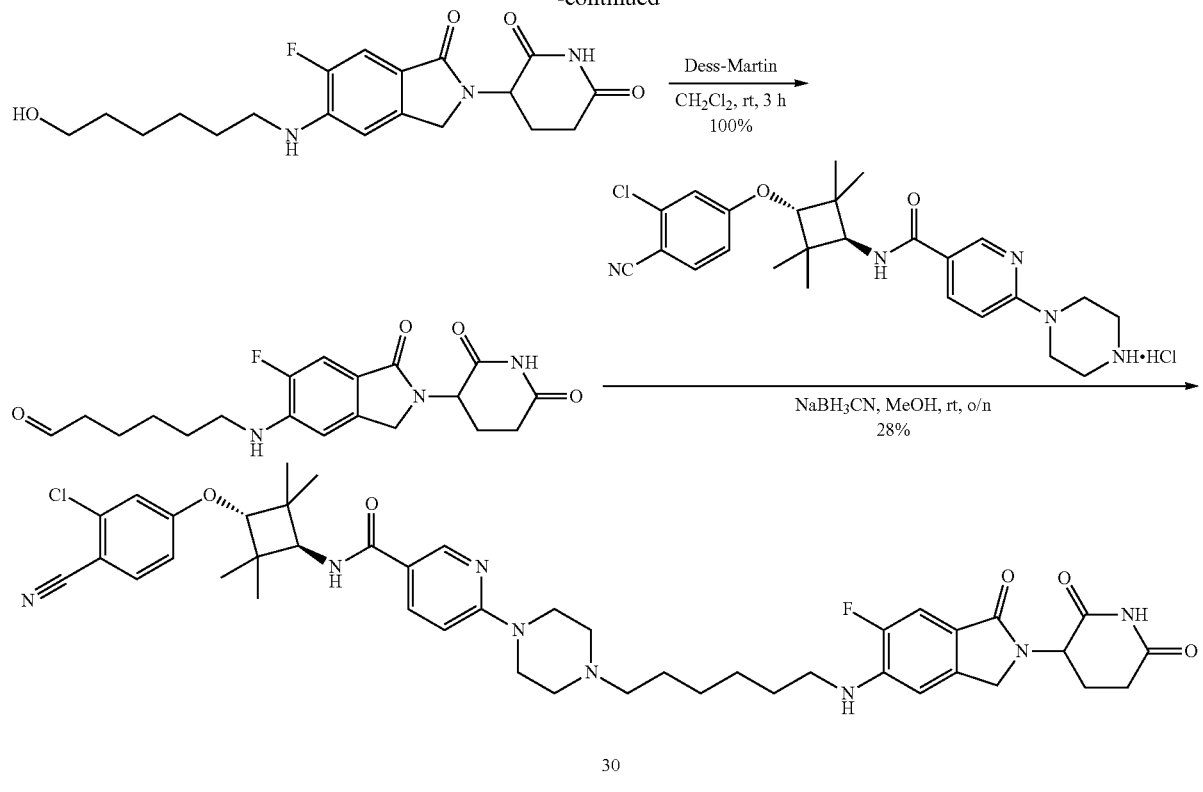
General Scheme 58
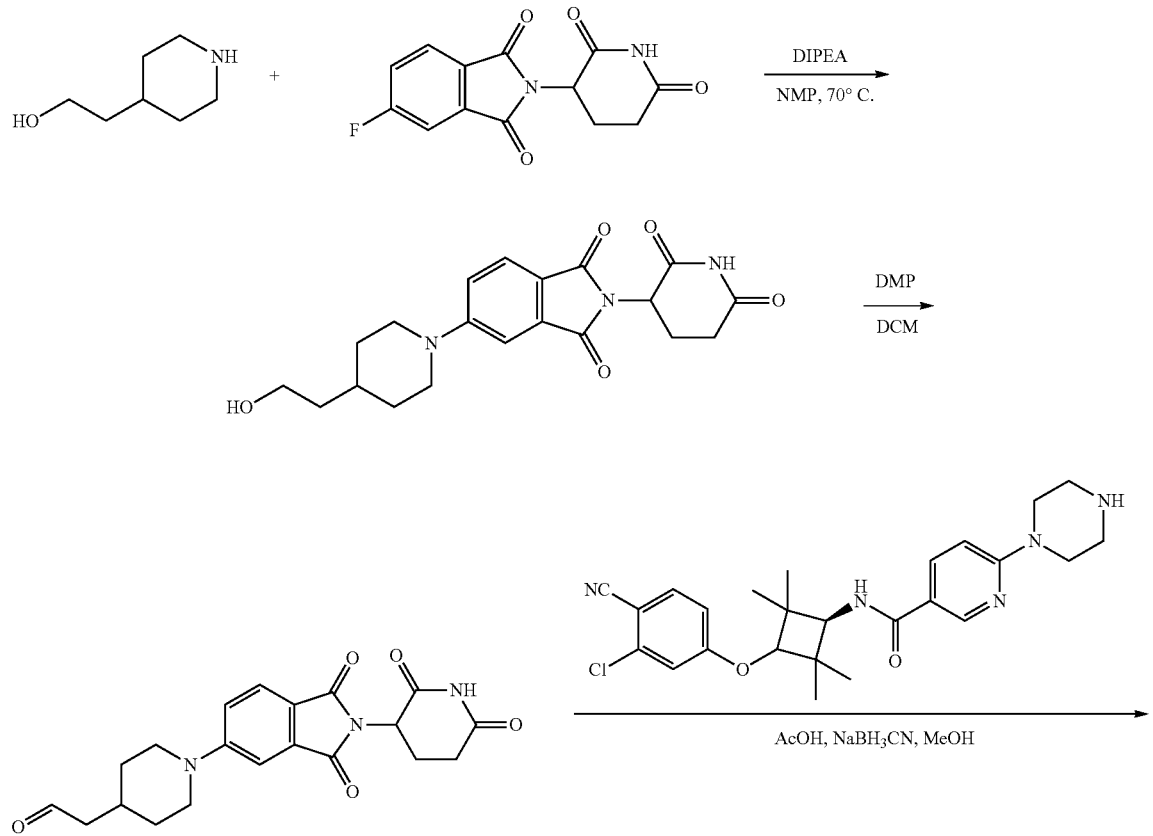

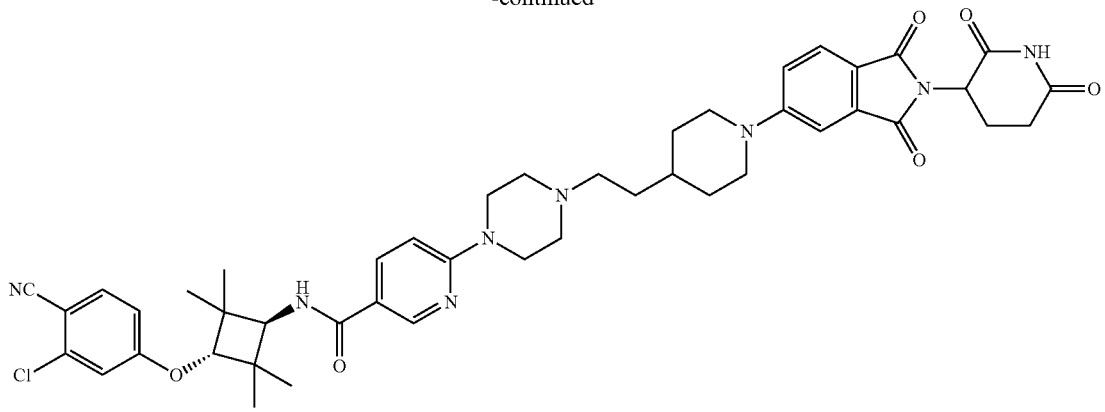
General Scheme 59
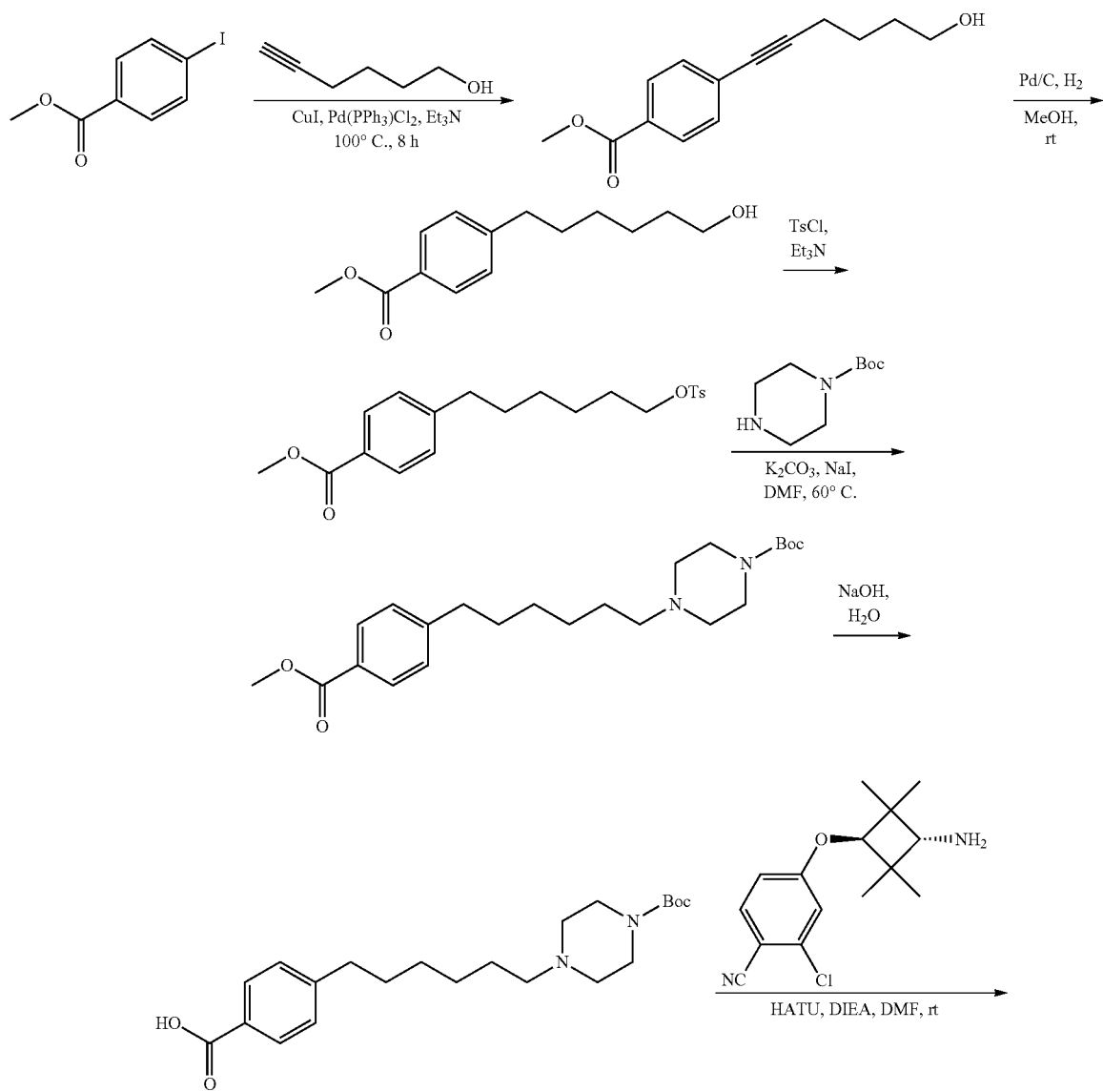

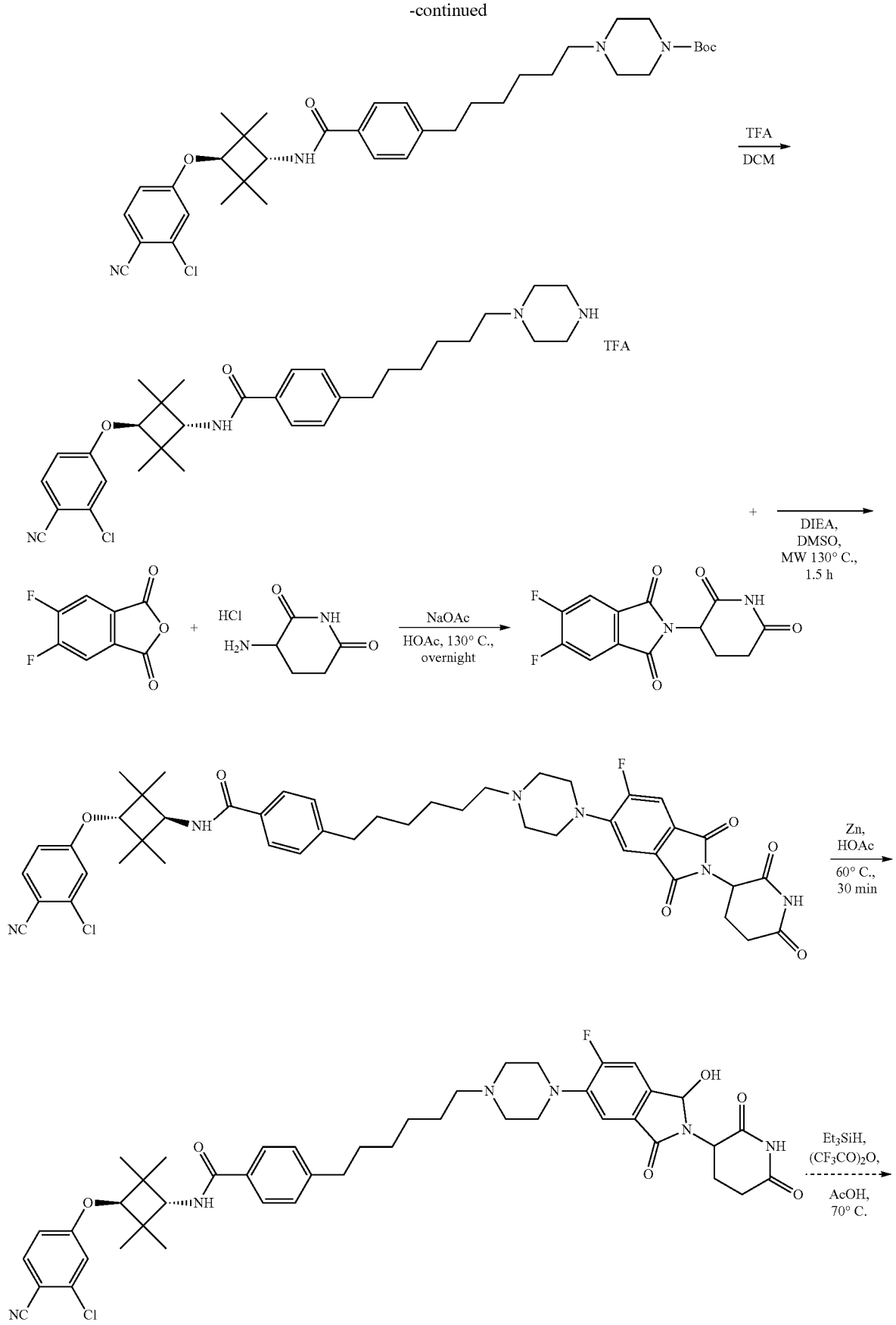

249 250
-continued
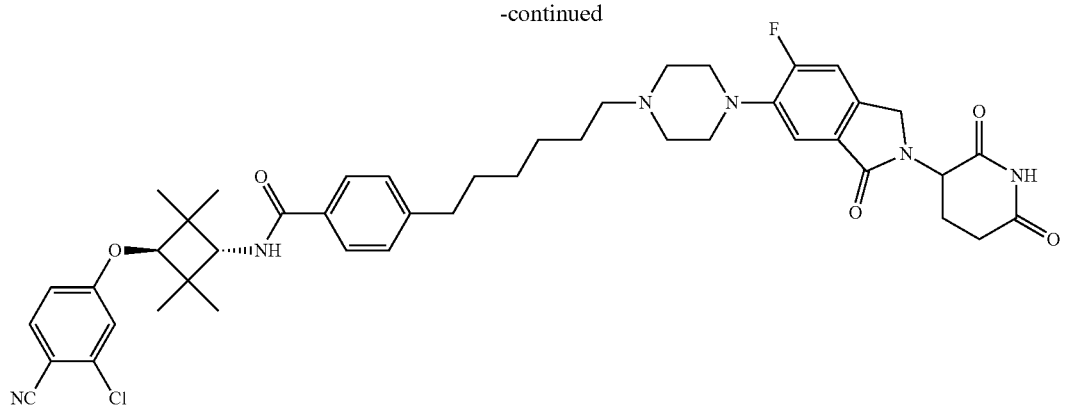
+
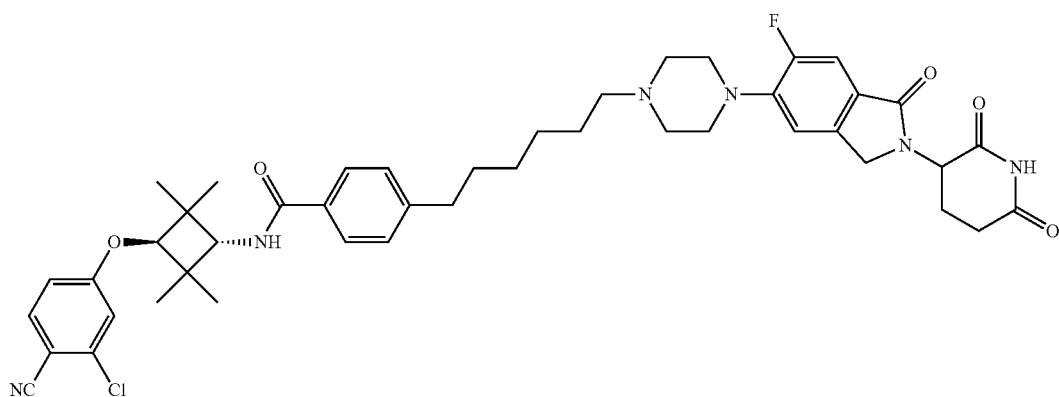 [SMILES: CC1(C)[C@H](NC(=O)c2ccc(CCCCCCN3CCN(c4cc5c(cc4F)C(=O)N(C4CCC(=O)NC4=O)C5)CC3)cc2)C(C)(C)[C@H]1Oc1ccc(C#N)c(Cl)c1]
General Scheme 60
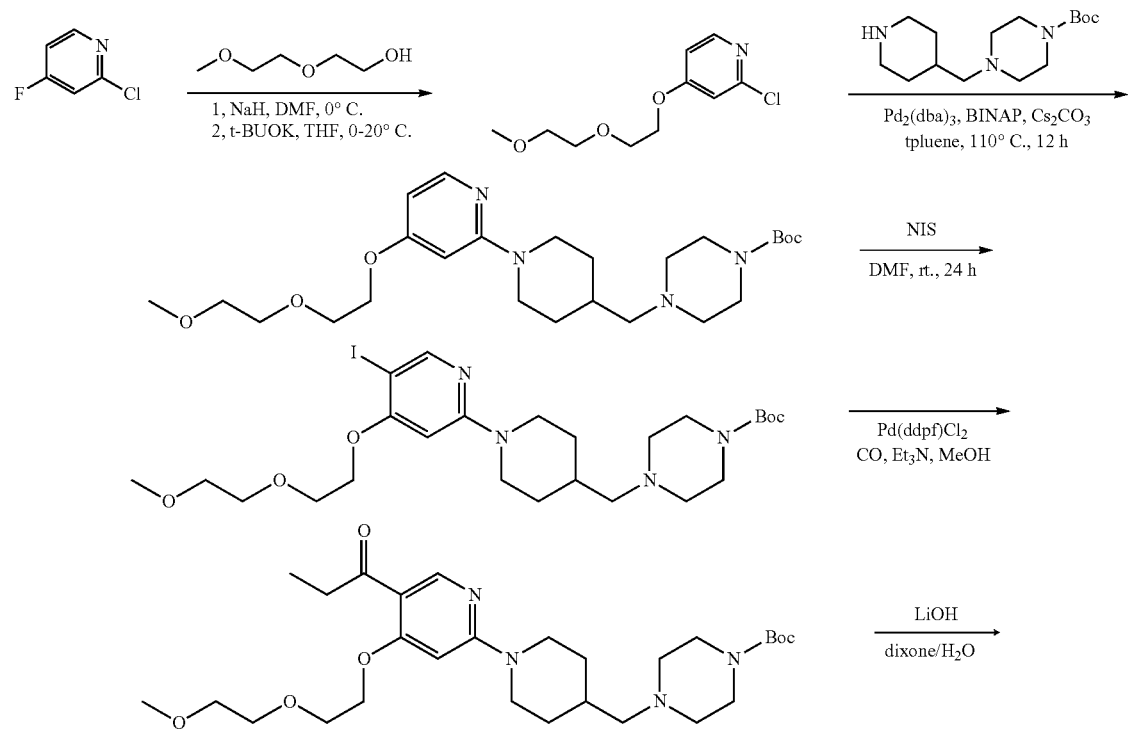

-continued
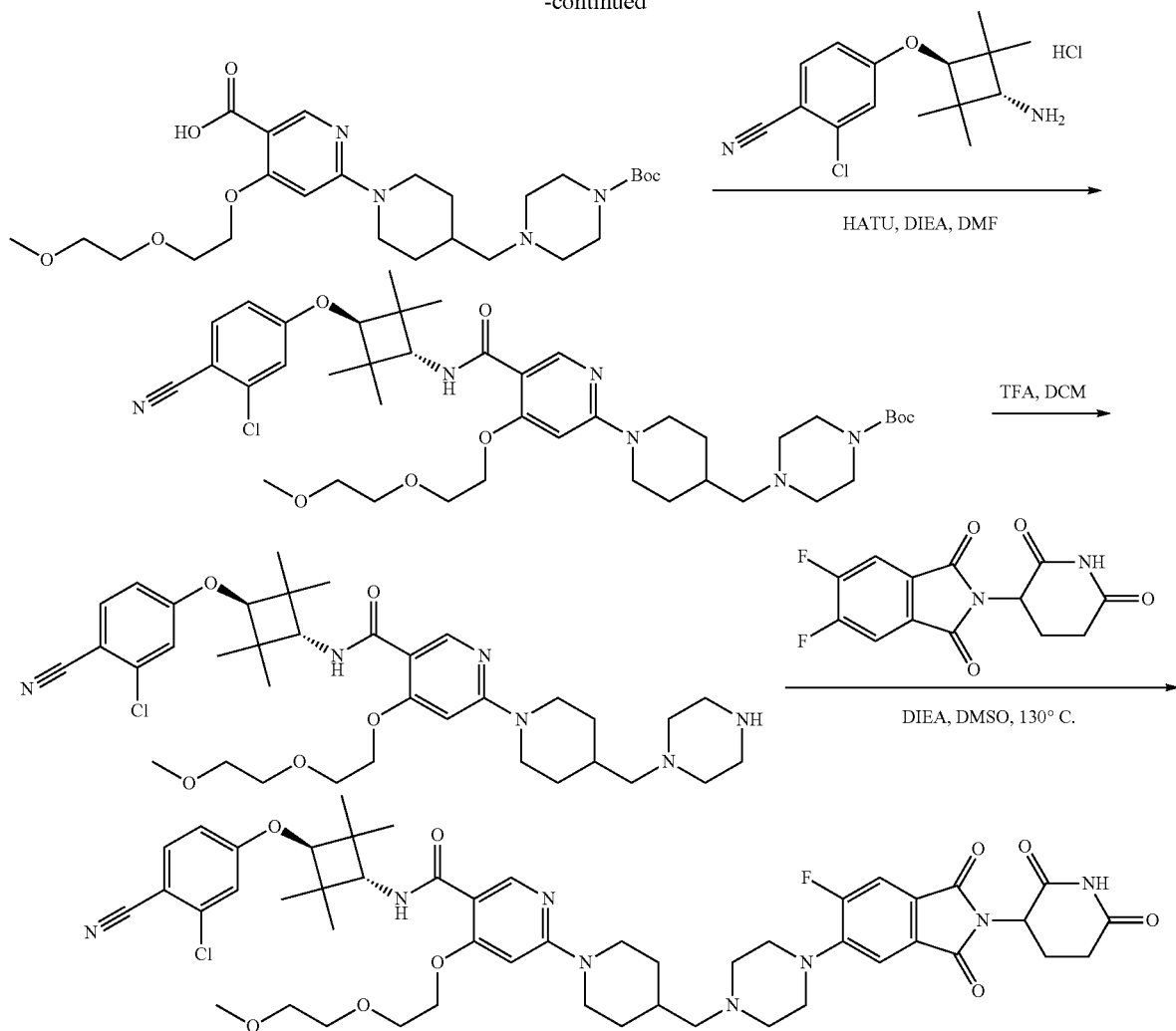
General Scheme 61
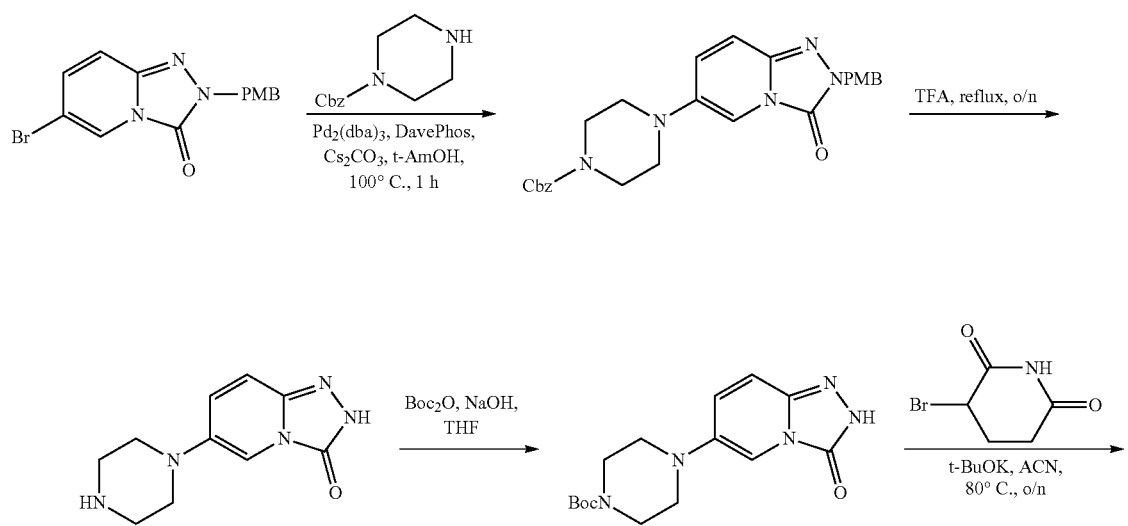

253 254
-continued
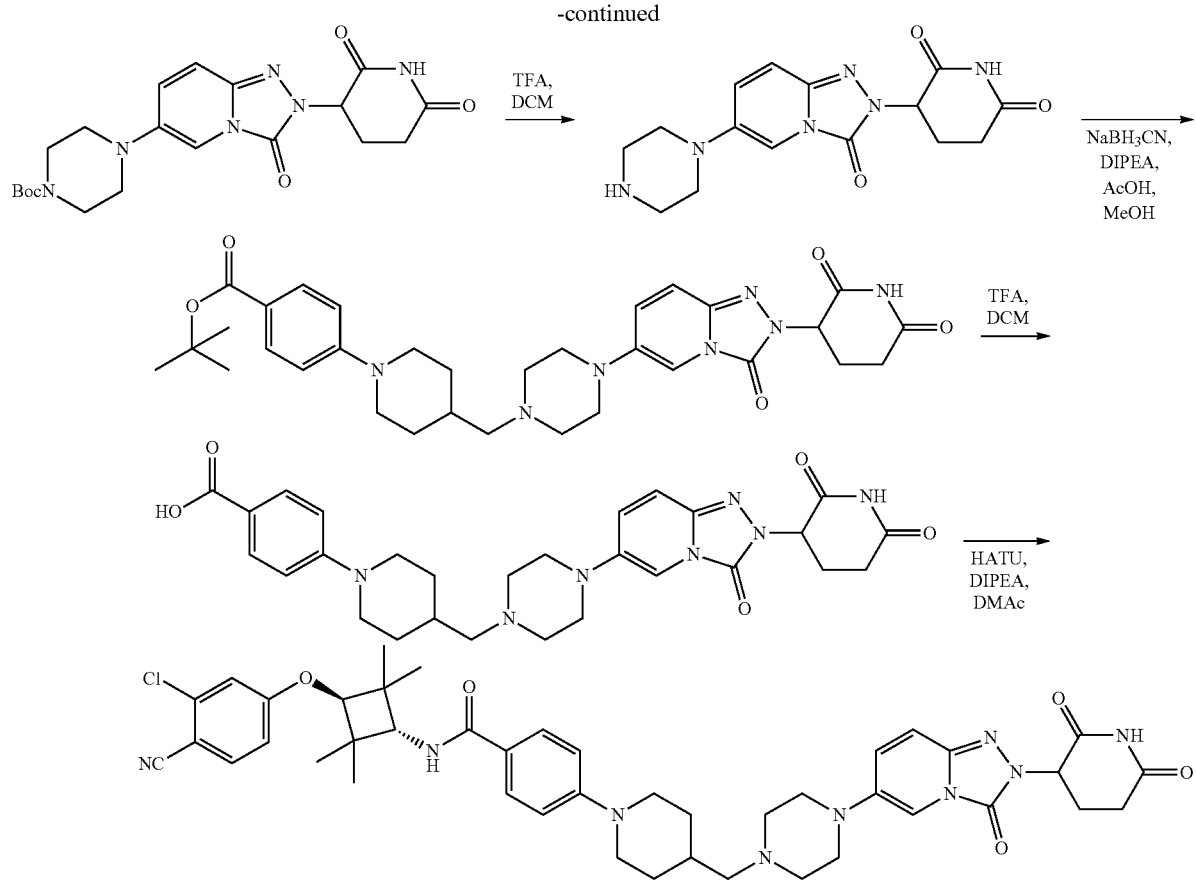
General Scheme 62
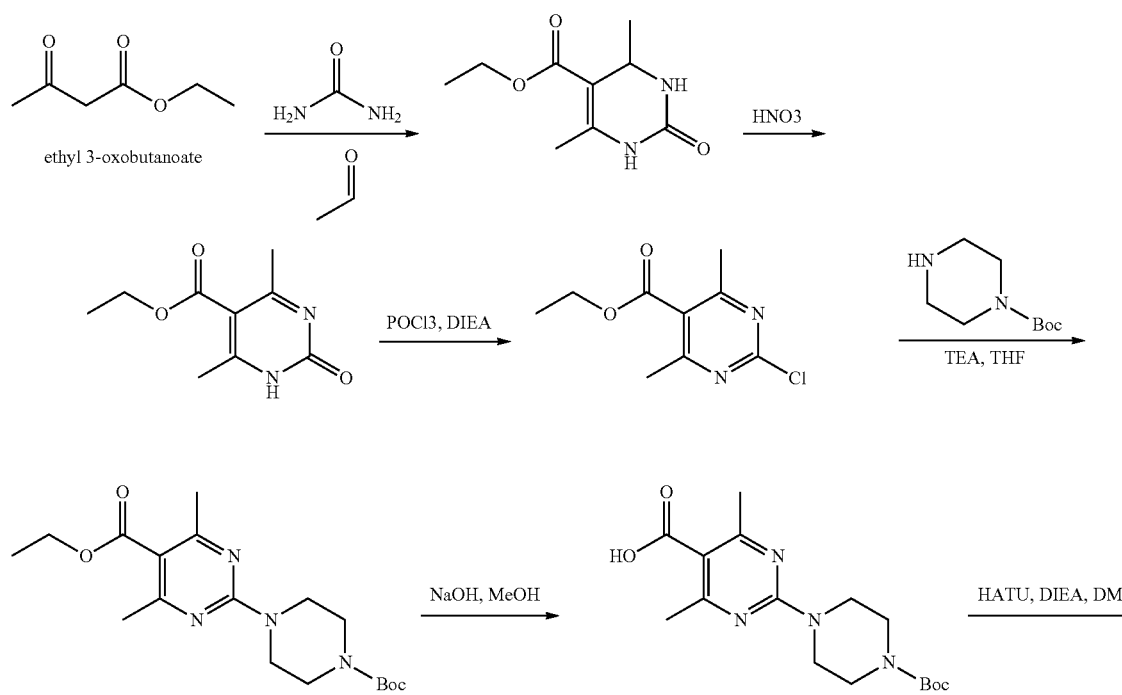

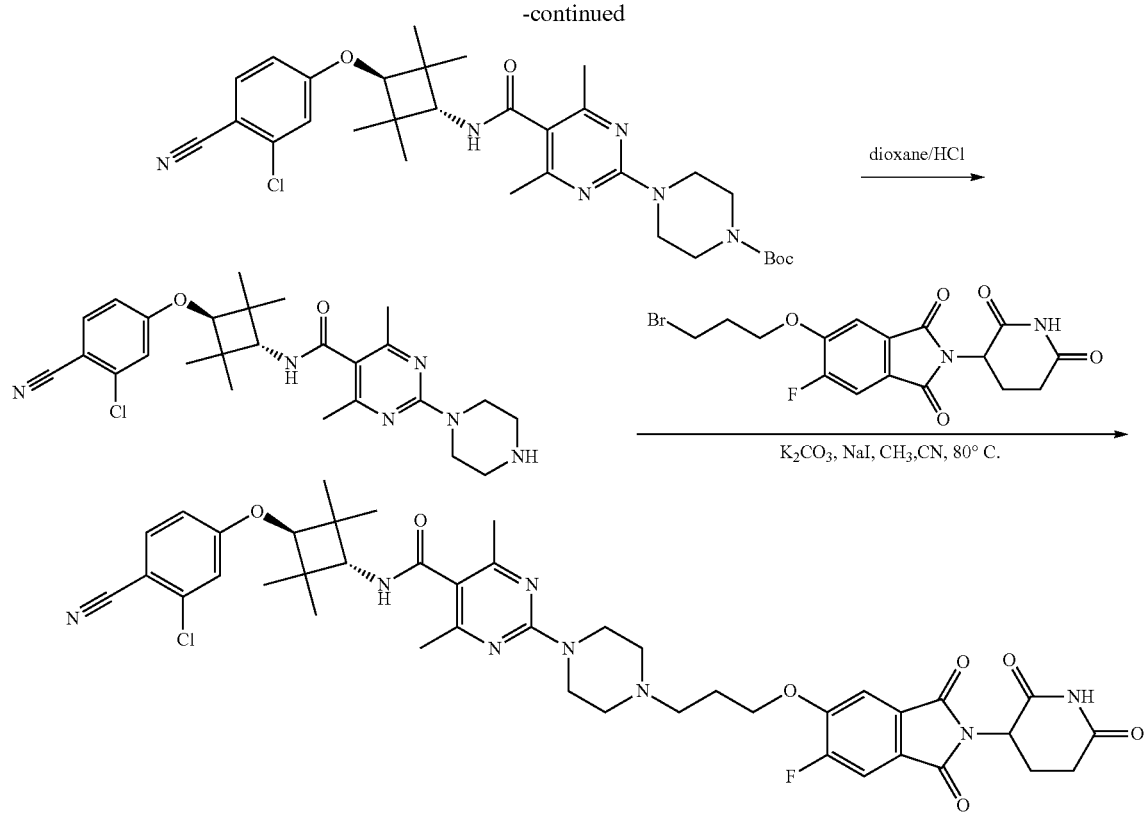
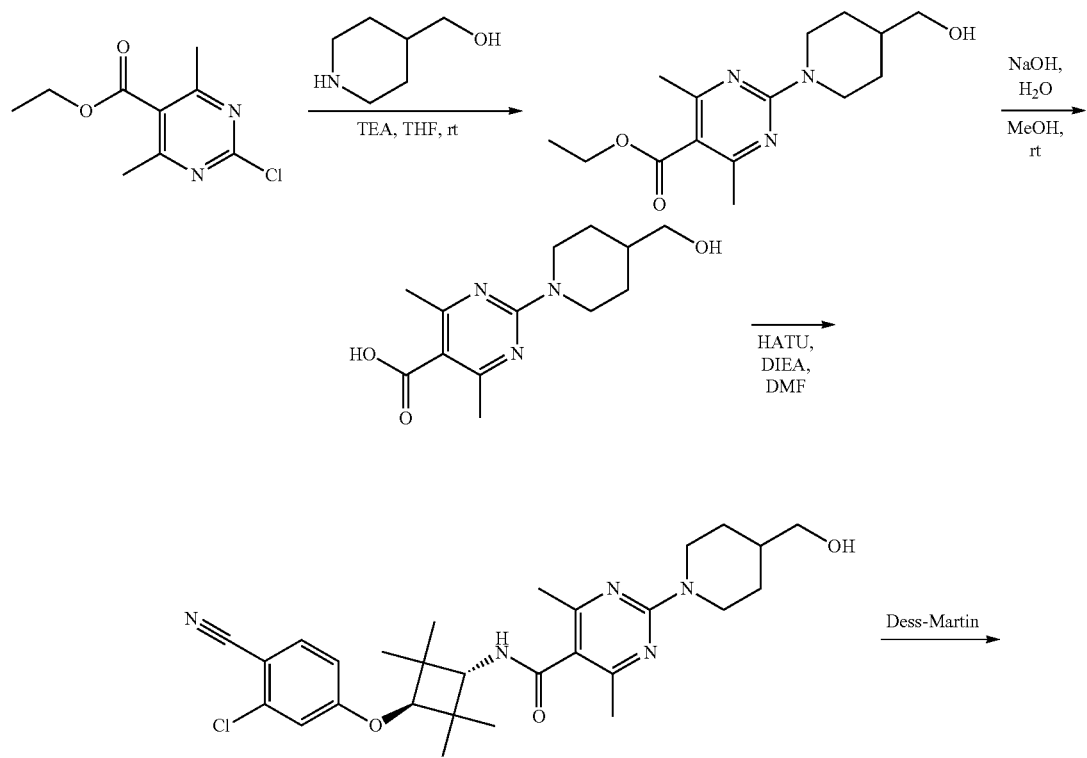
General Scheme 63

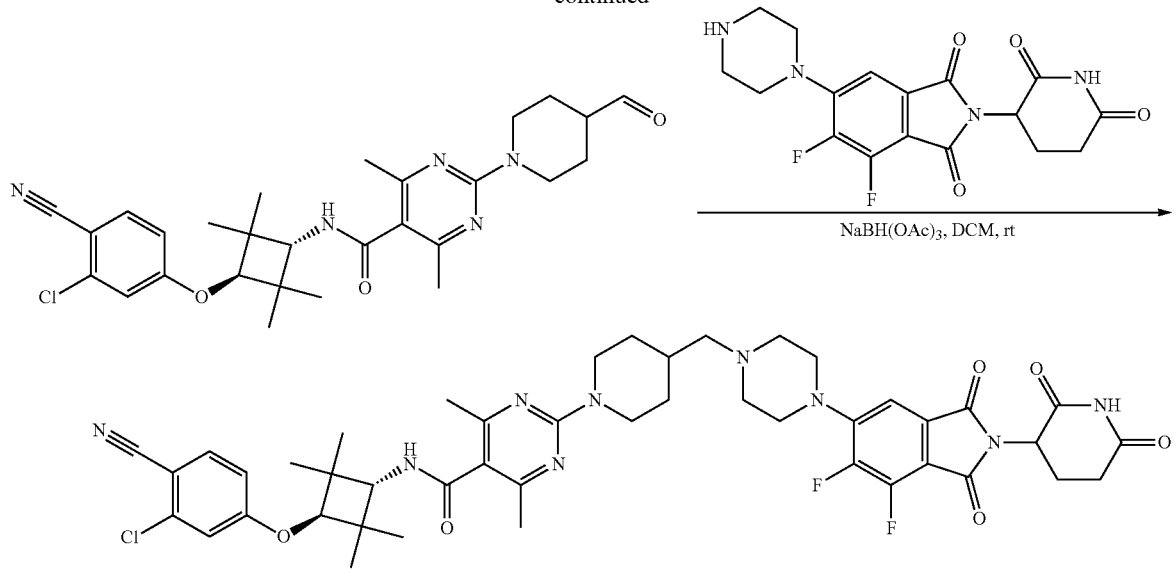
General Scheme 64
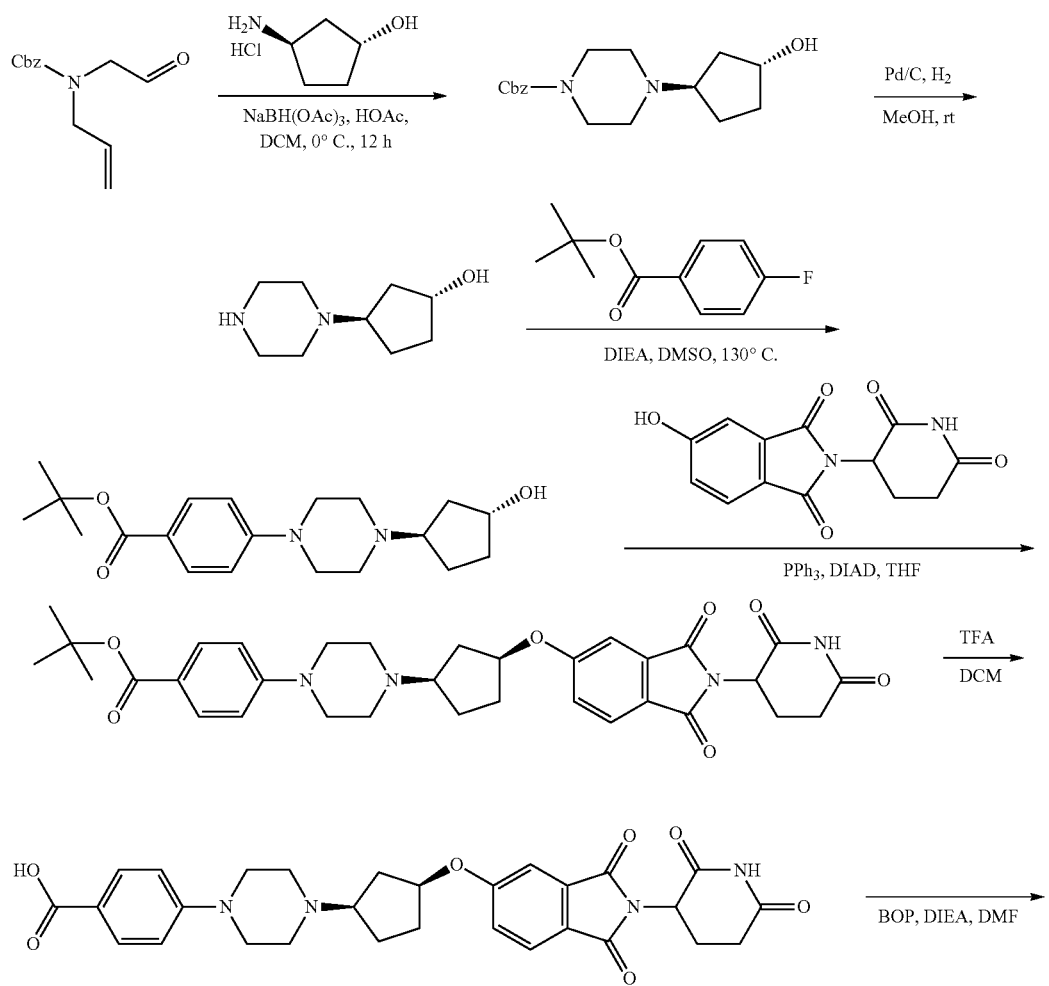

-continued
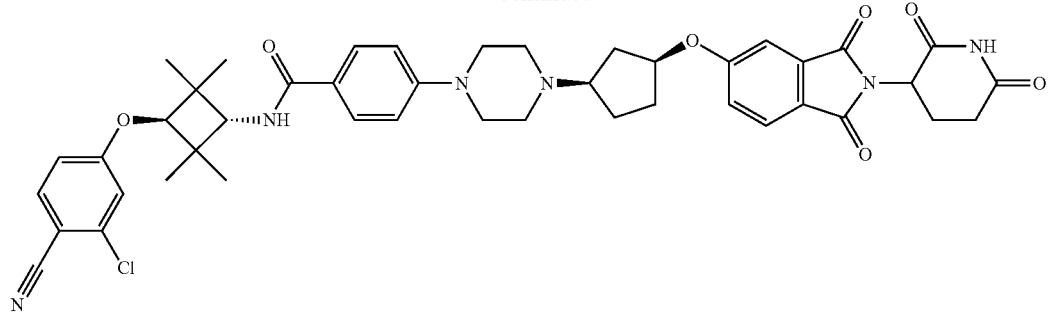
General Scheme 65
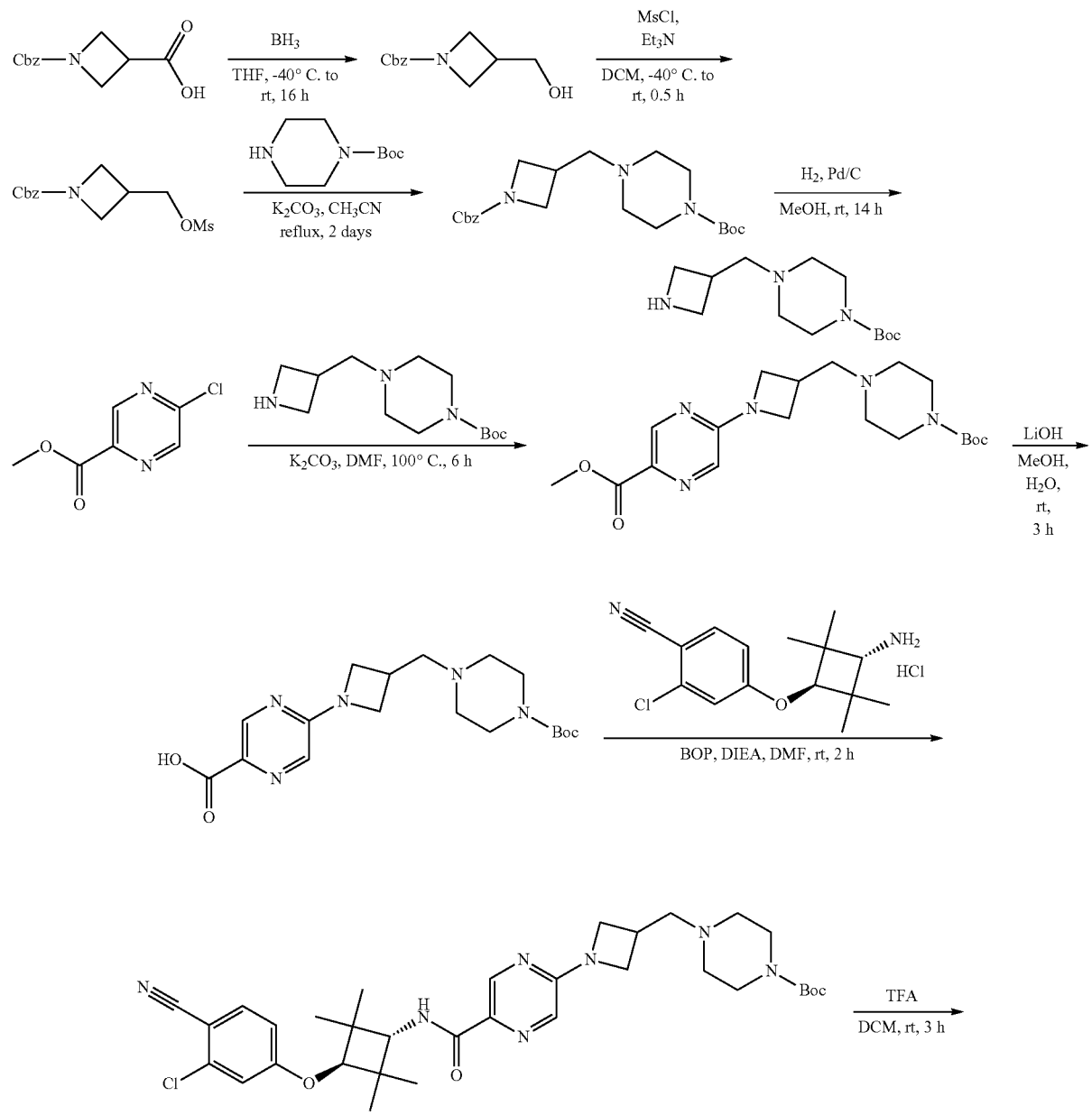

261
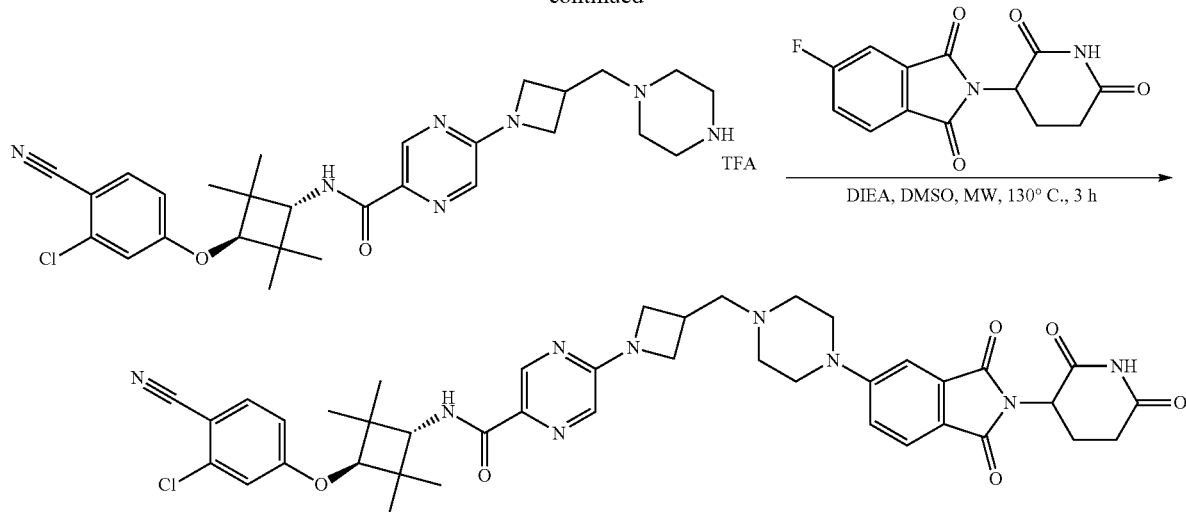
-continued
262
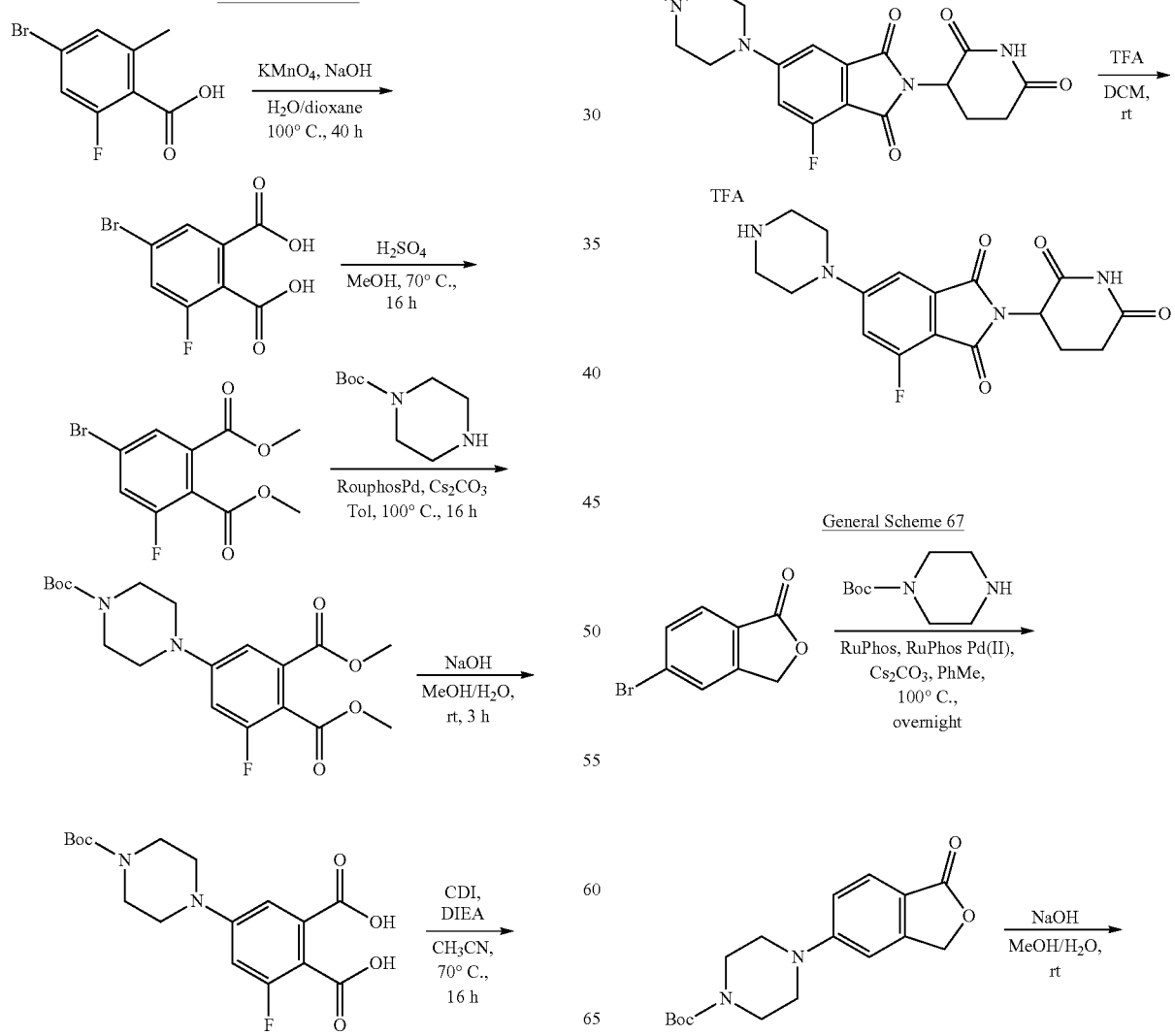

263
-continued
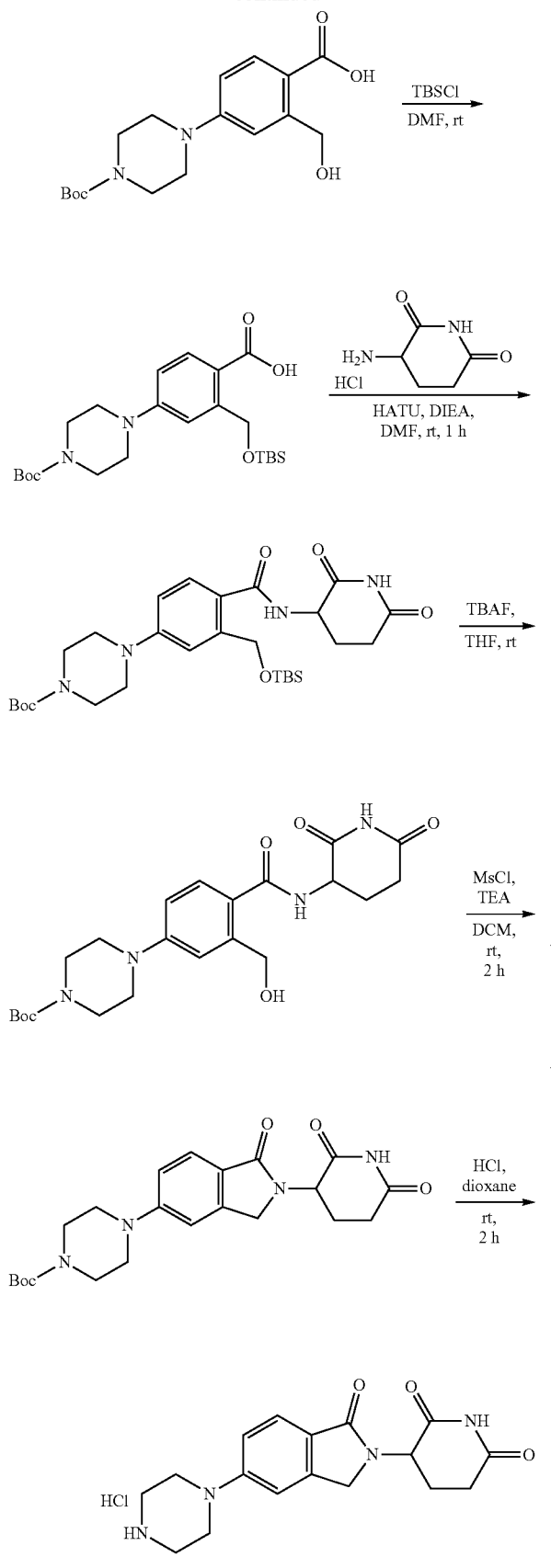
264
General Scheme 68
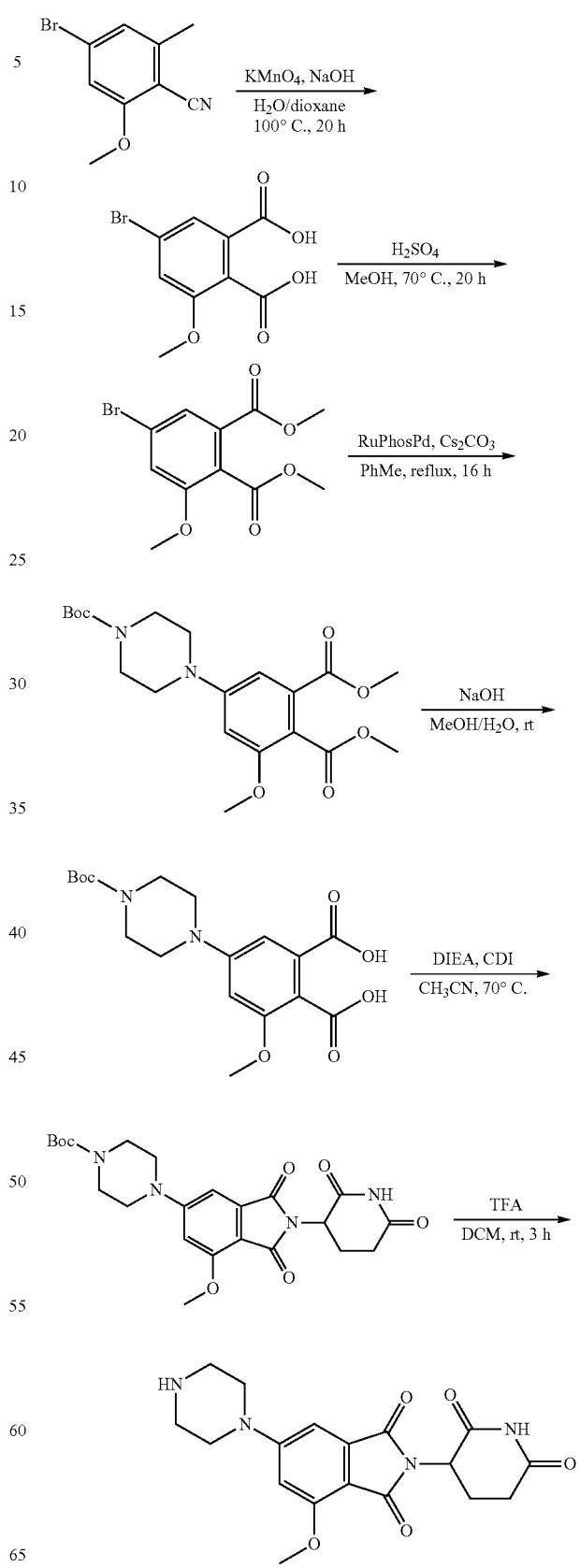

General Scheme 69
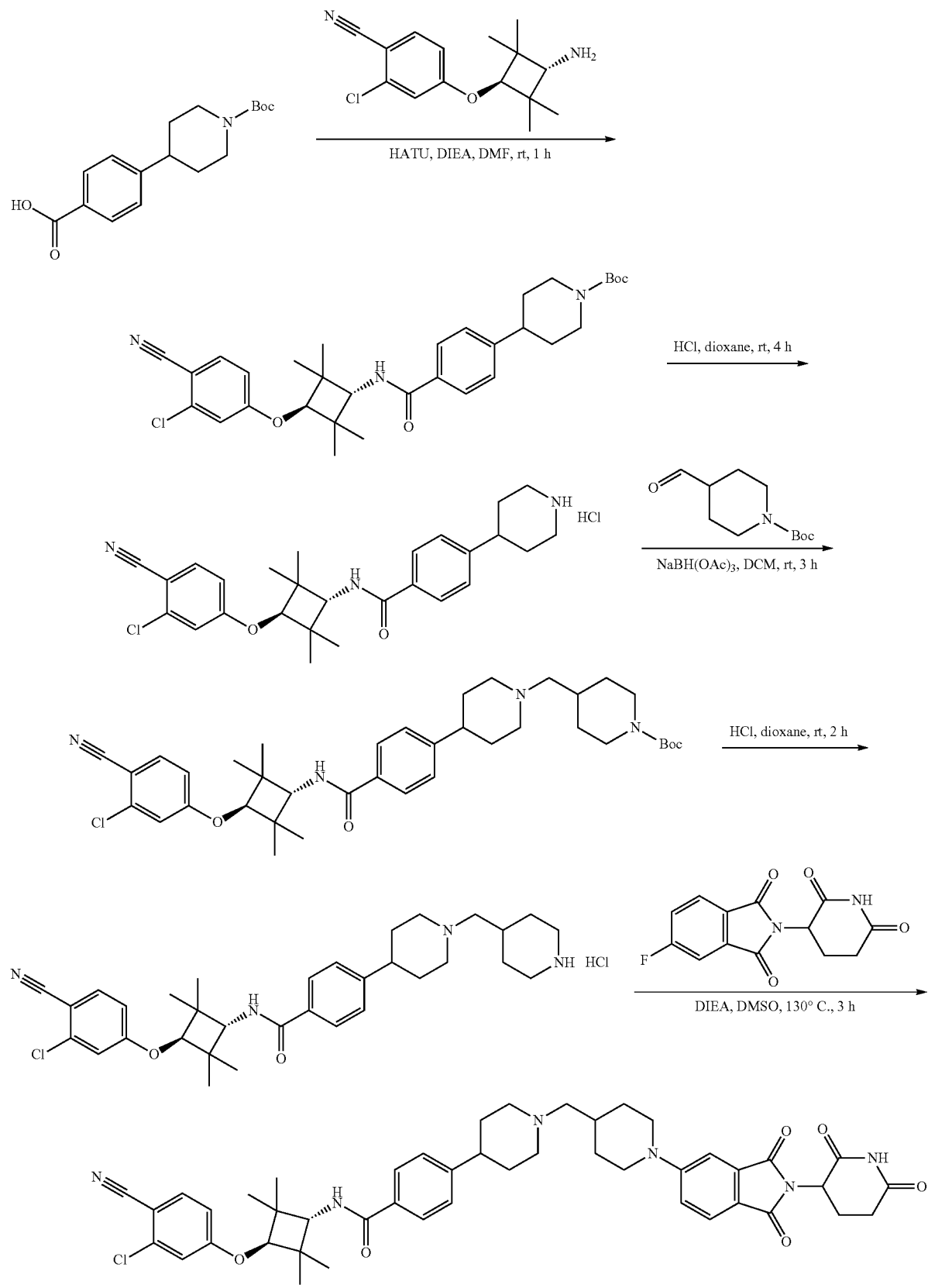

General Scheme 70
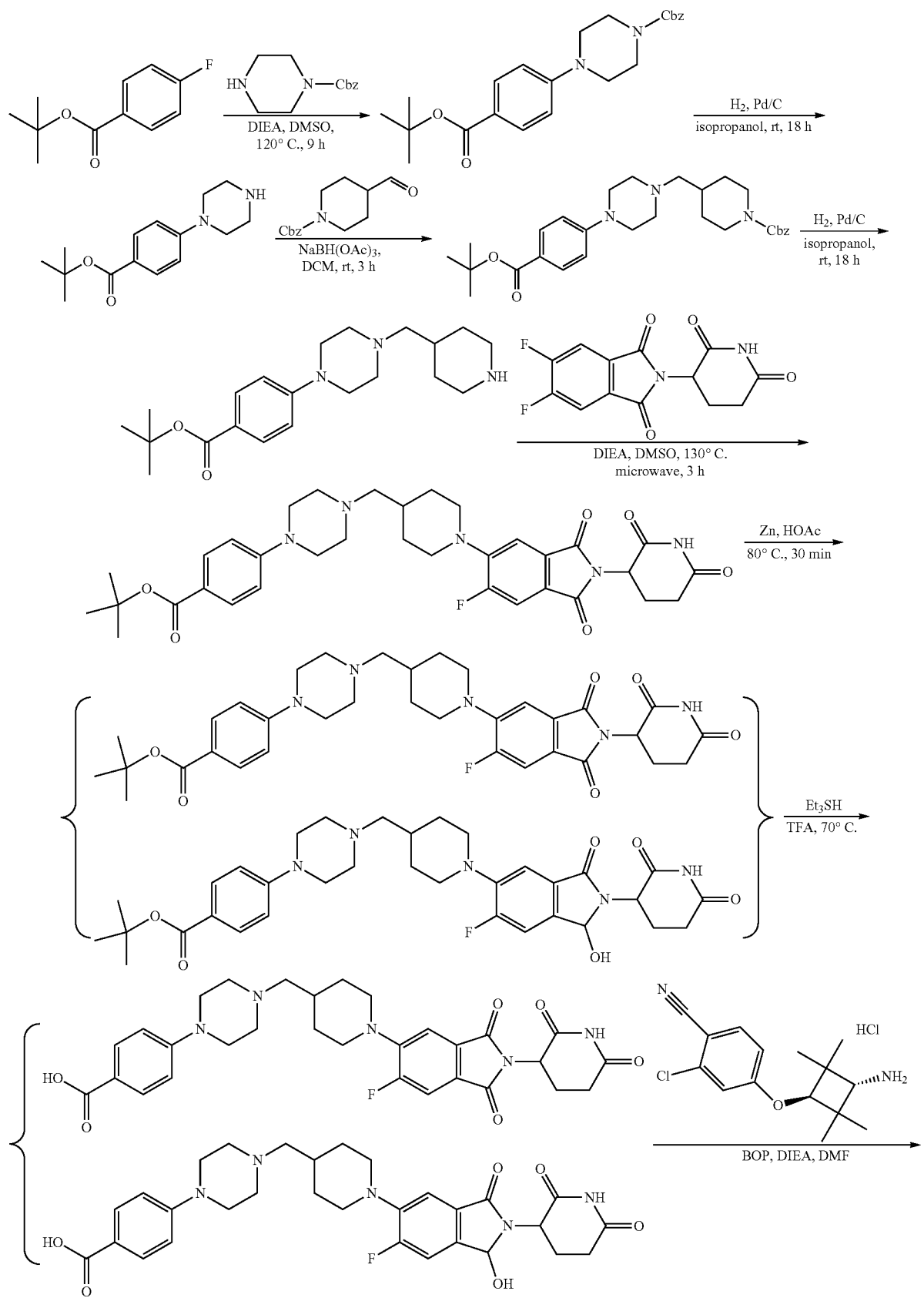

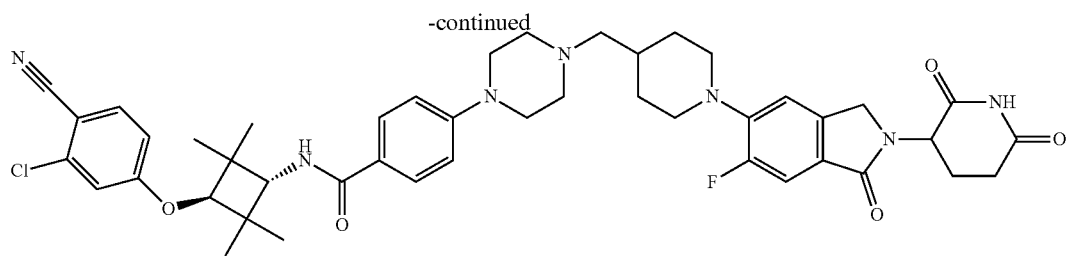
General Scheme 71
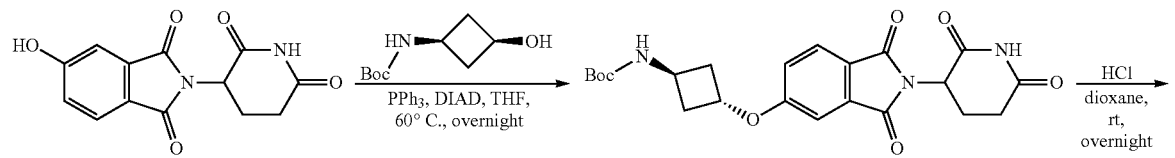
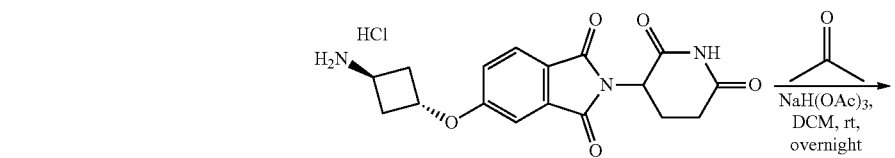
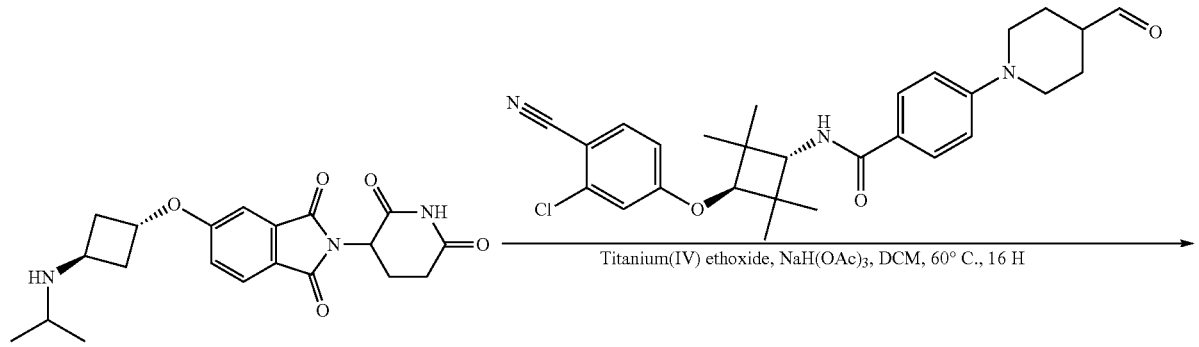
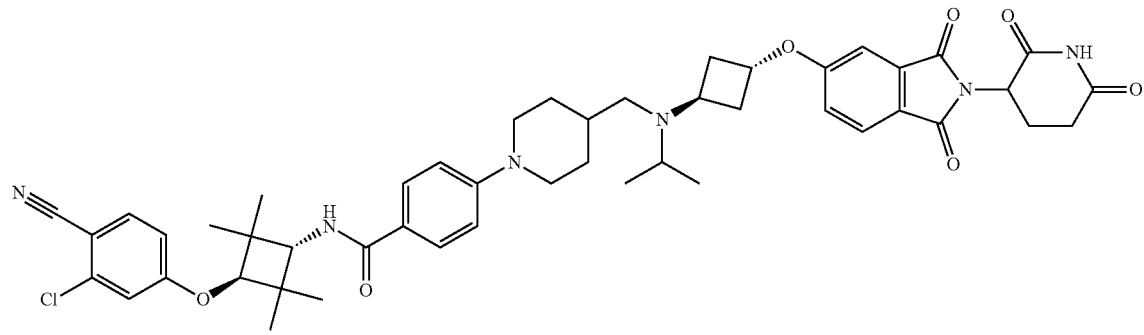

General Scheme 72
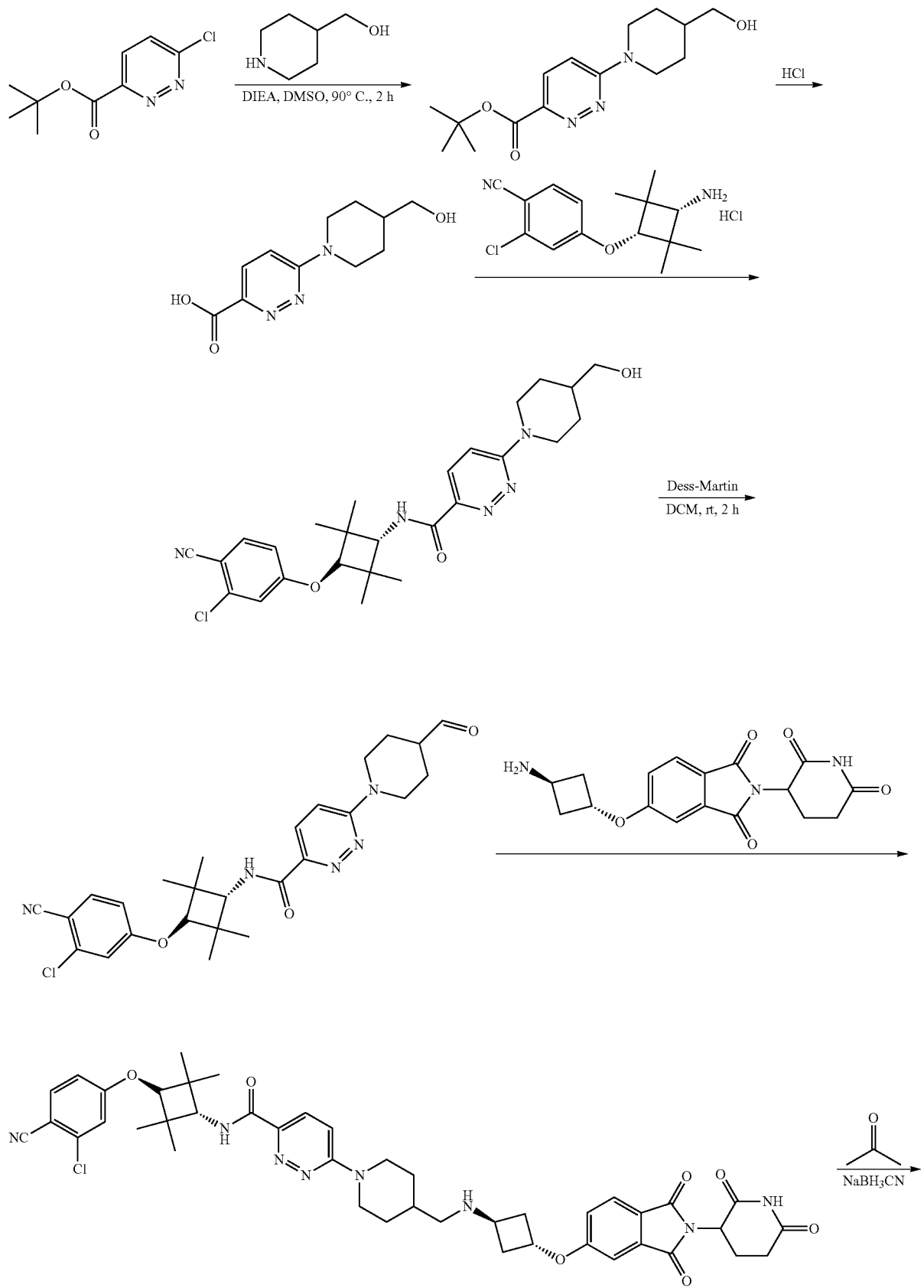

-continued
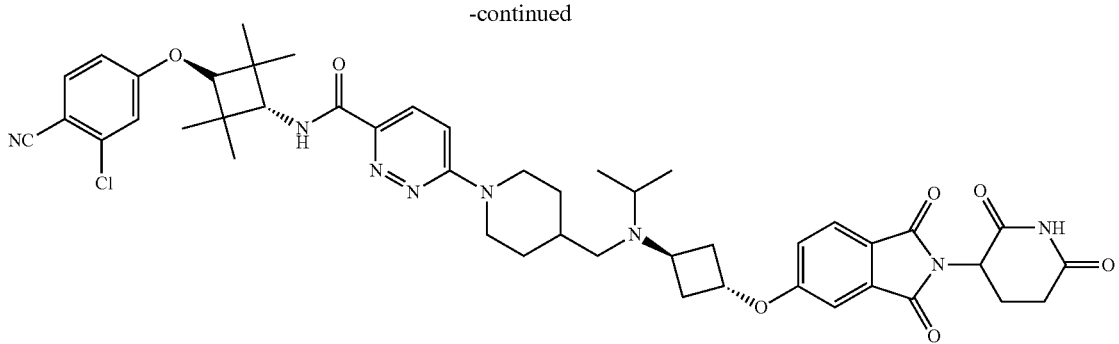
General Scheme 73
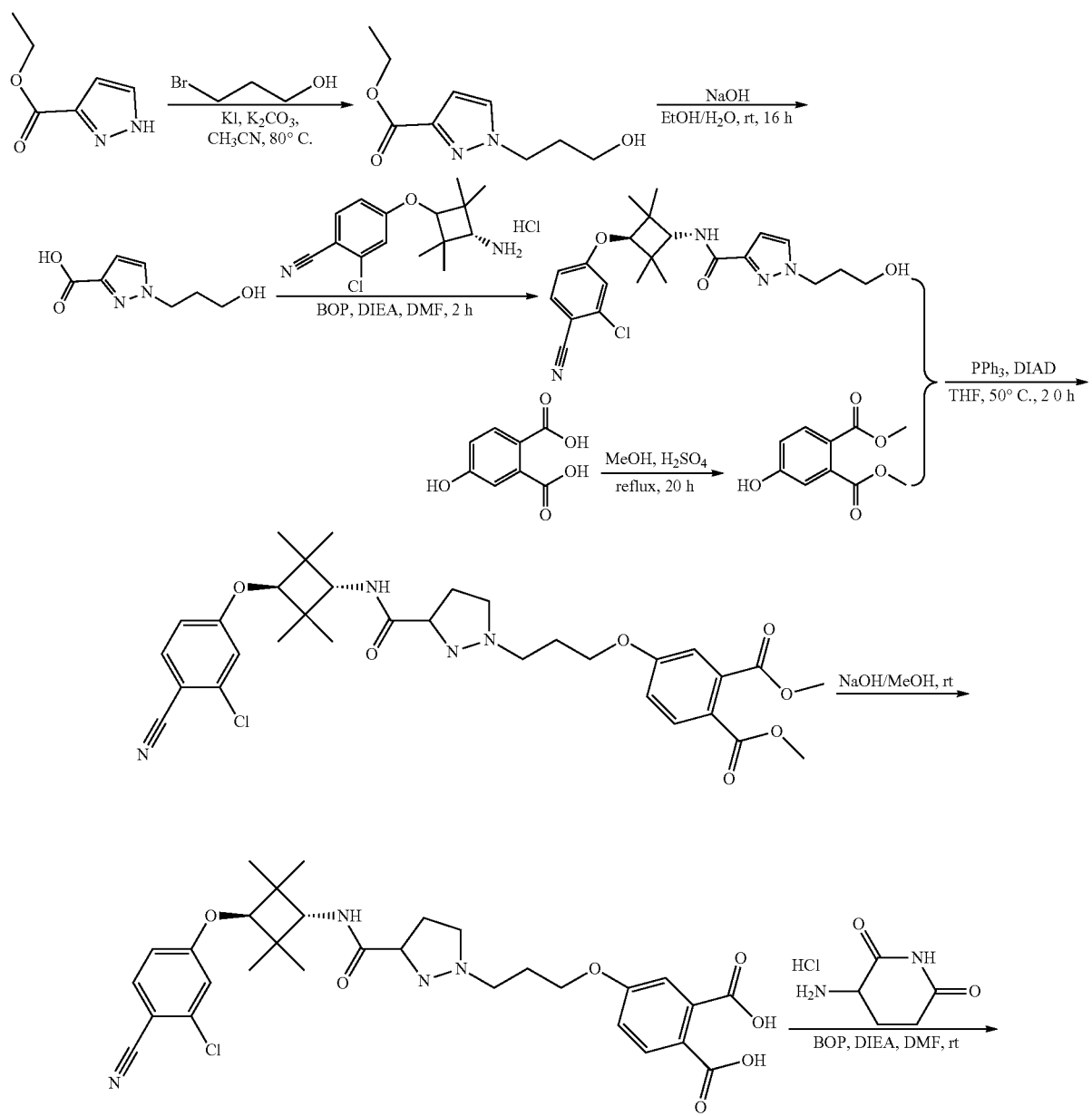

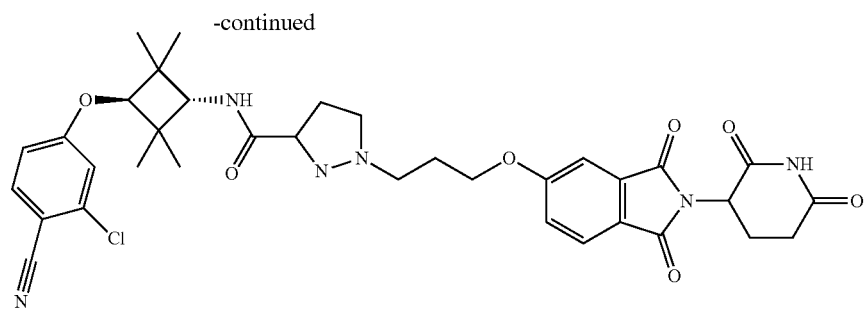
-continued
General Scheme 74
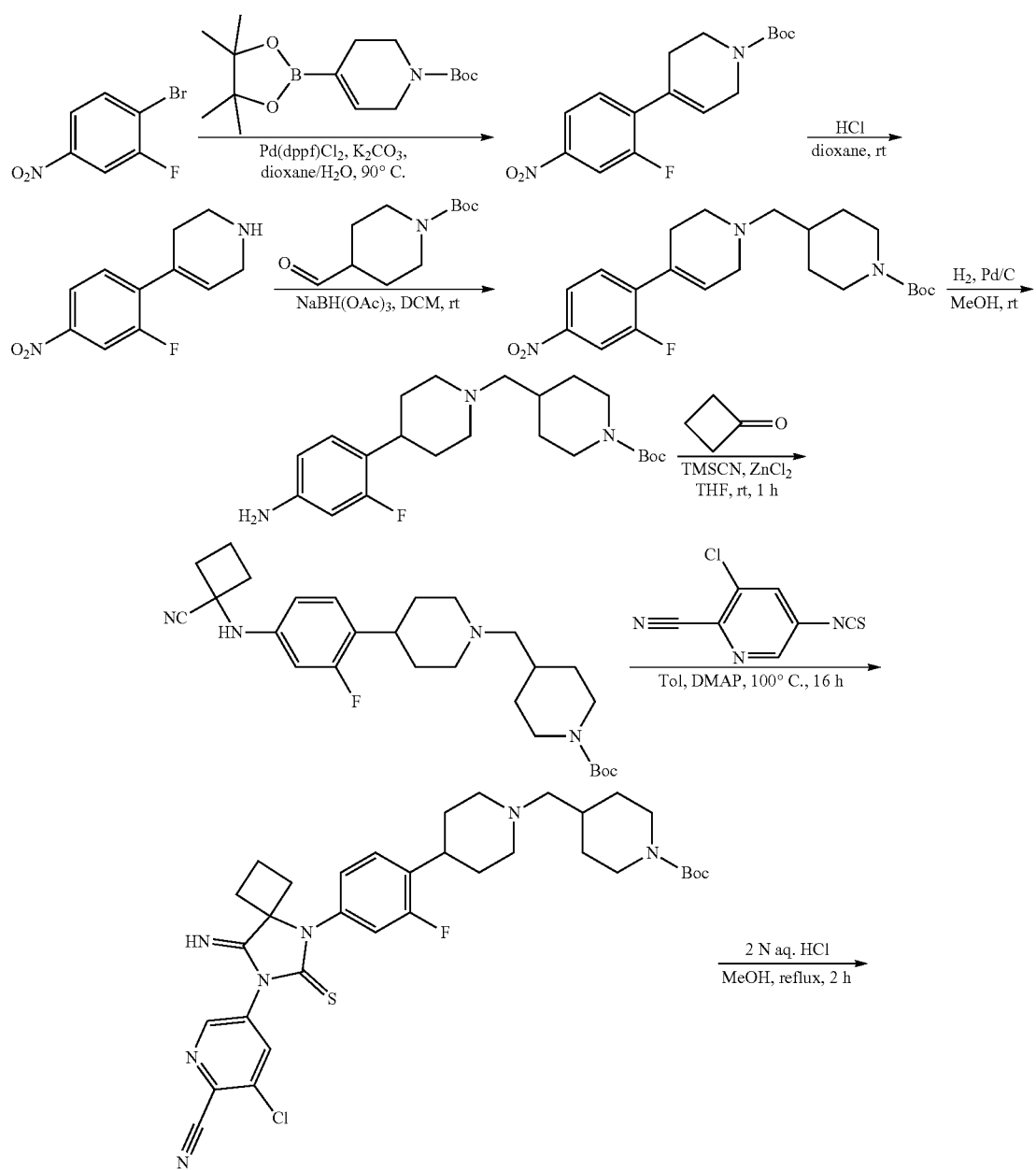

277 278
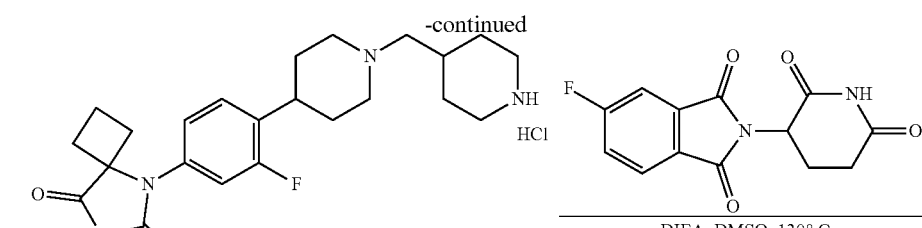
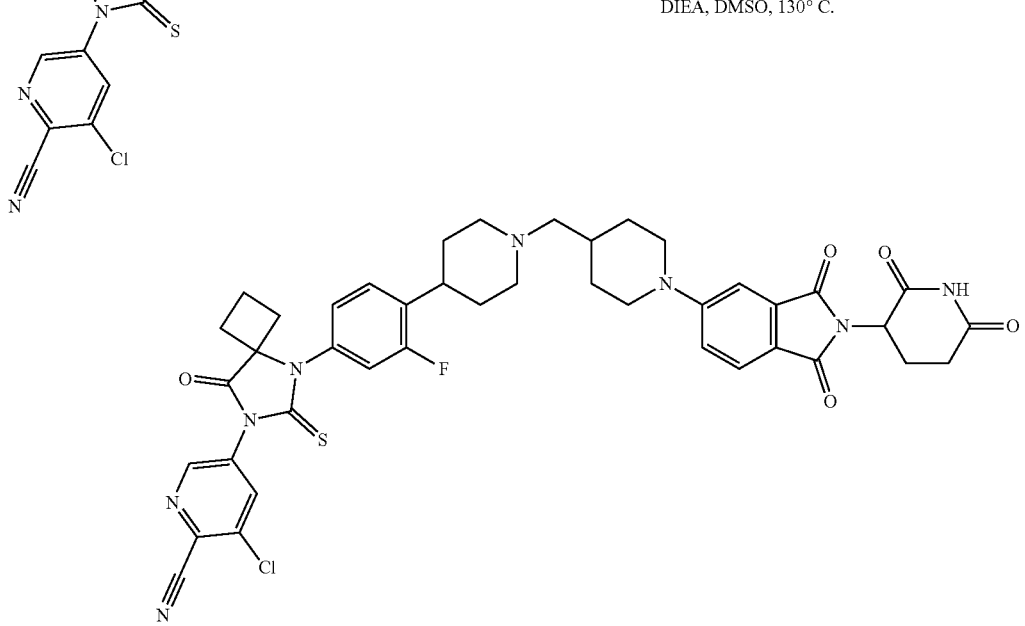
General Scheme 75
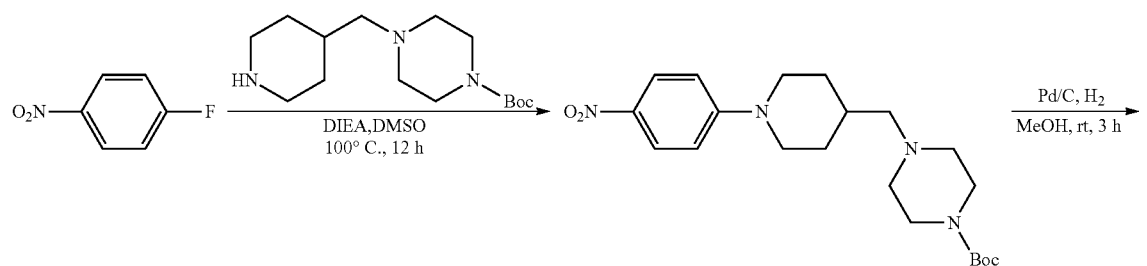
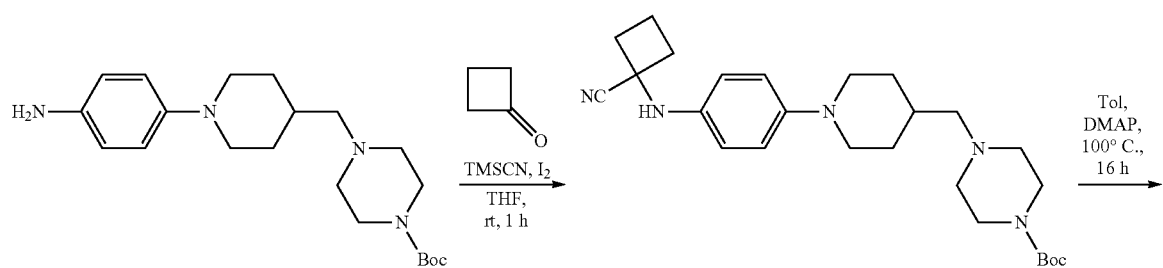

-continued
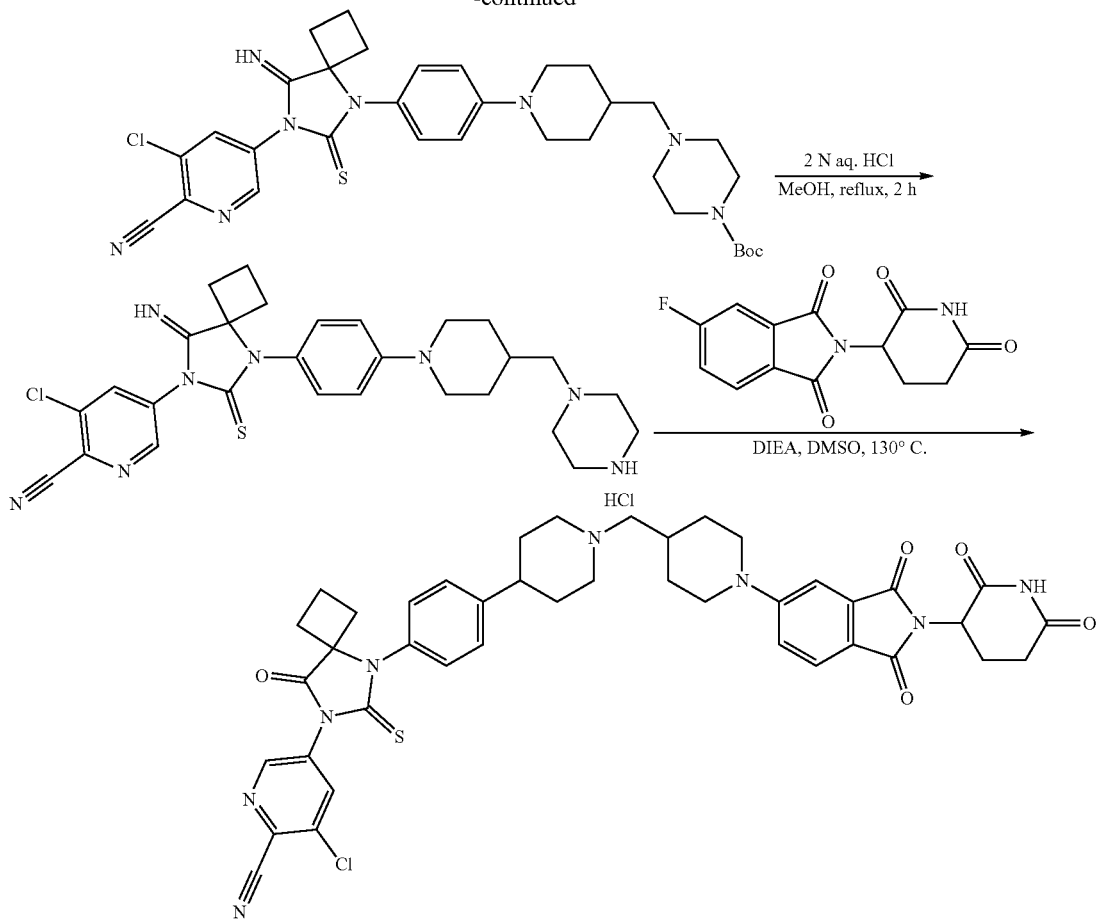
General Scheme 76
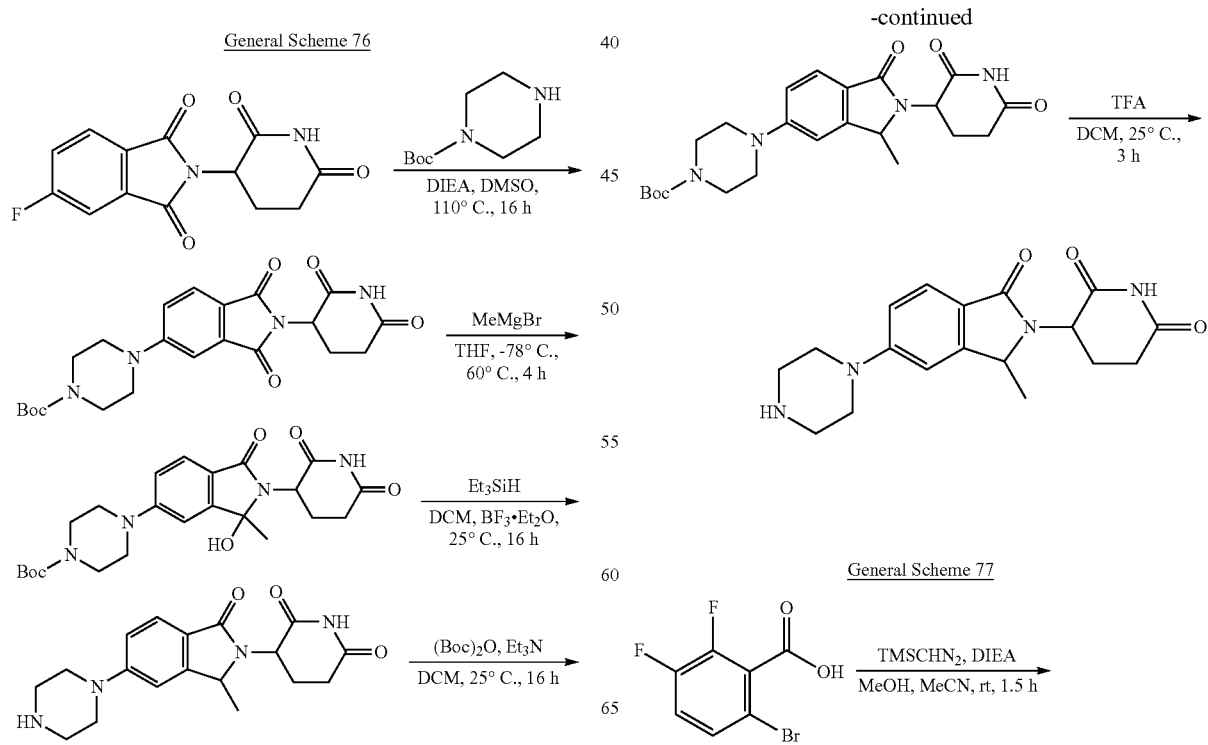
General Scheme 77

281
-continued
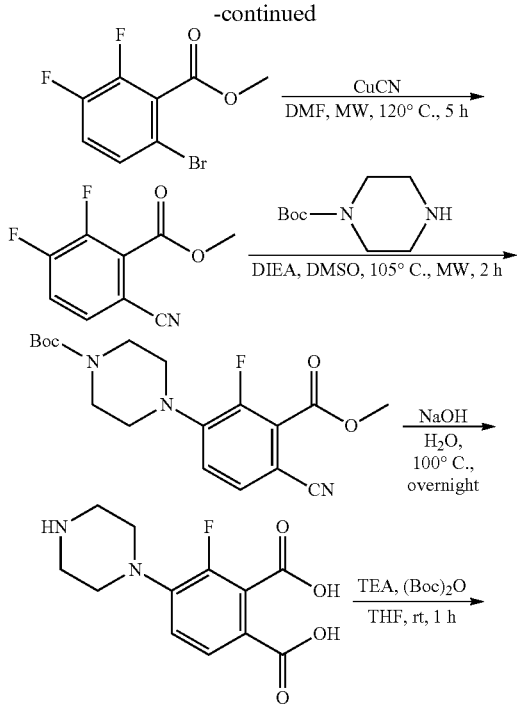
282
-continued
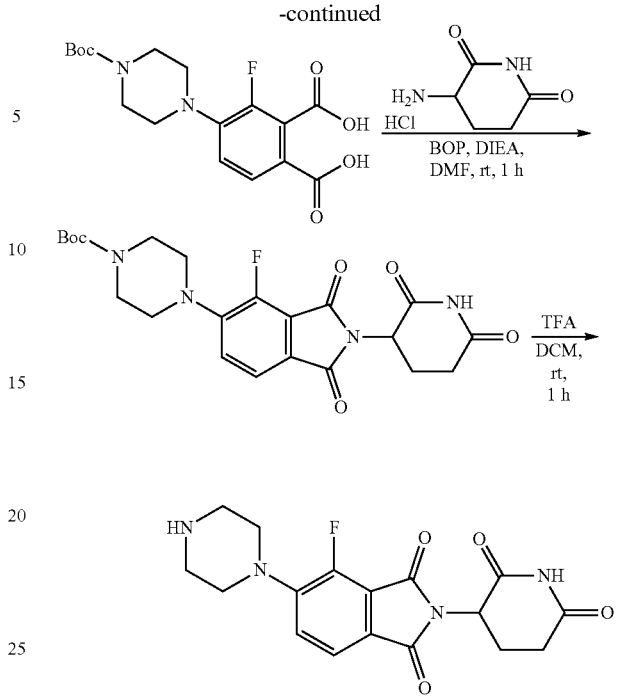
General Scheme 78
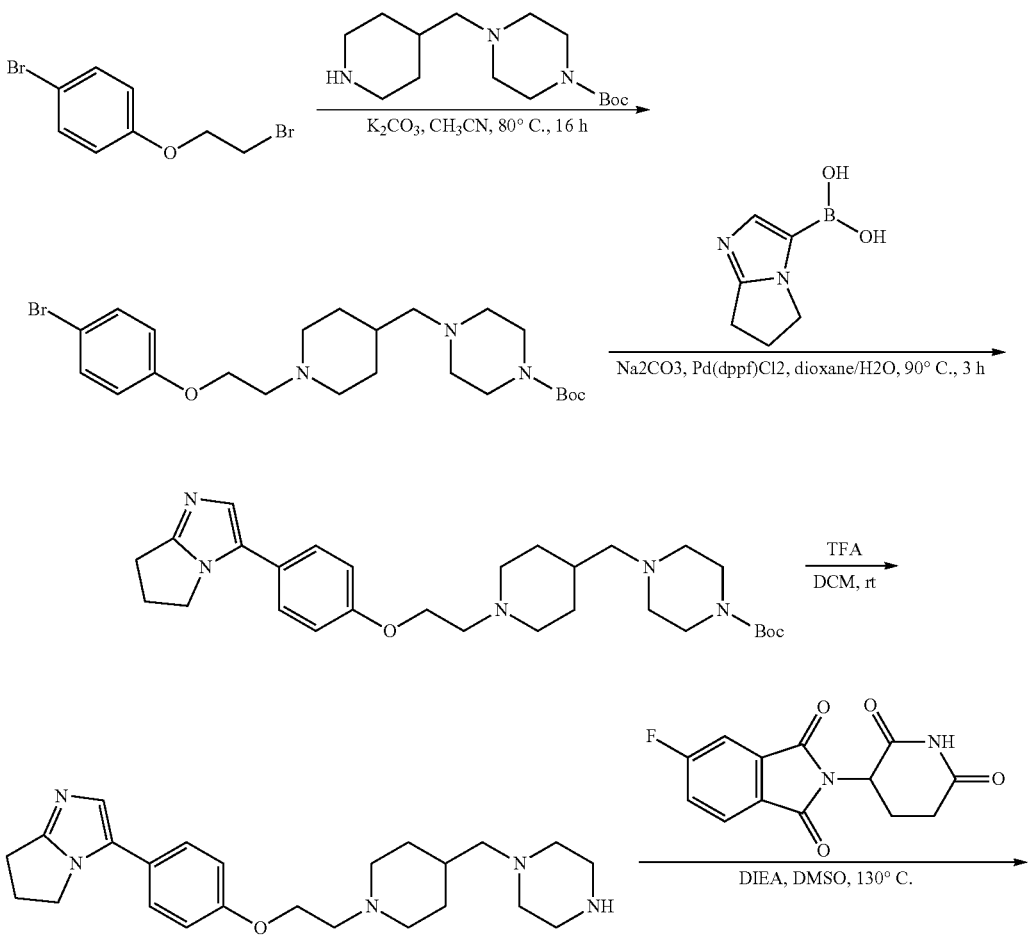

-continued
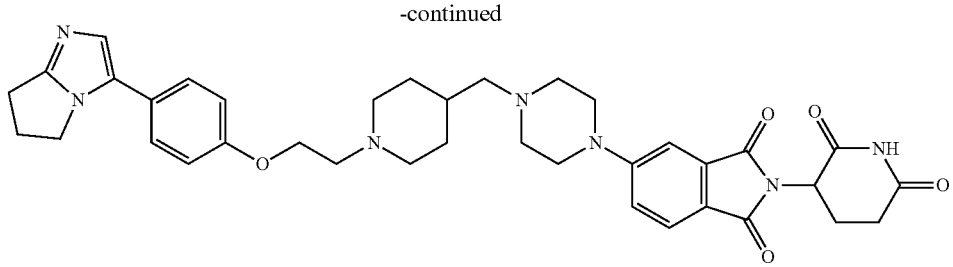
General Scheme 79
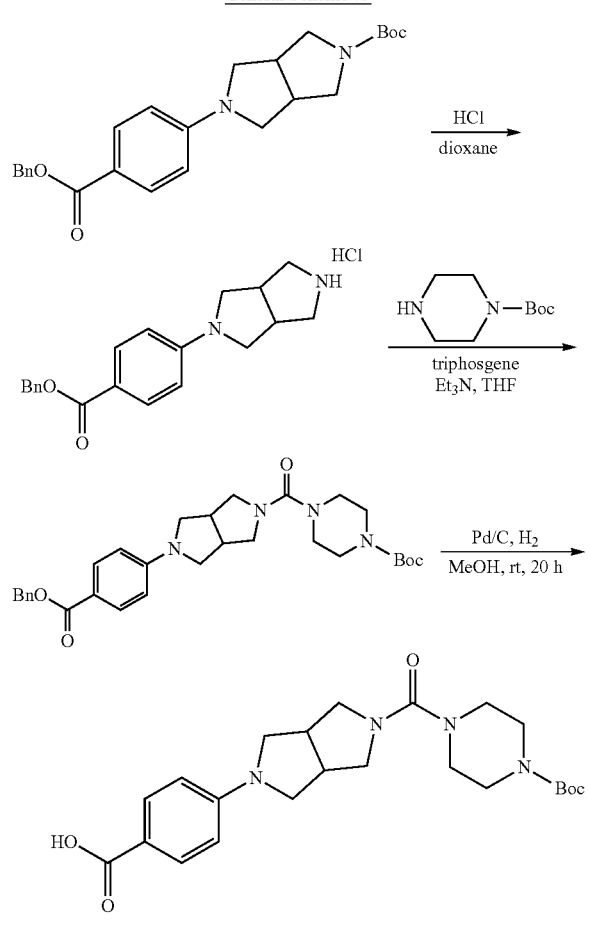
General Scheme 80
-continued
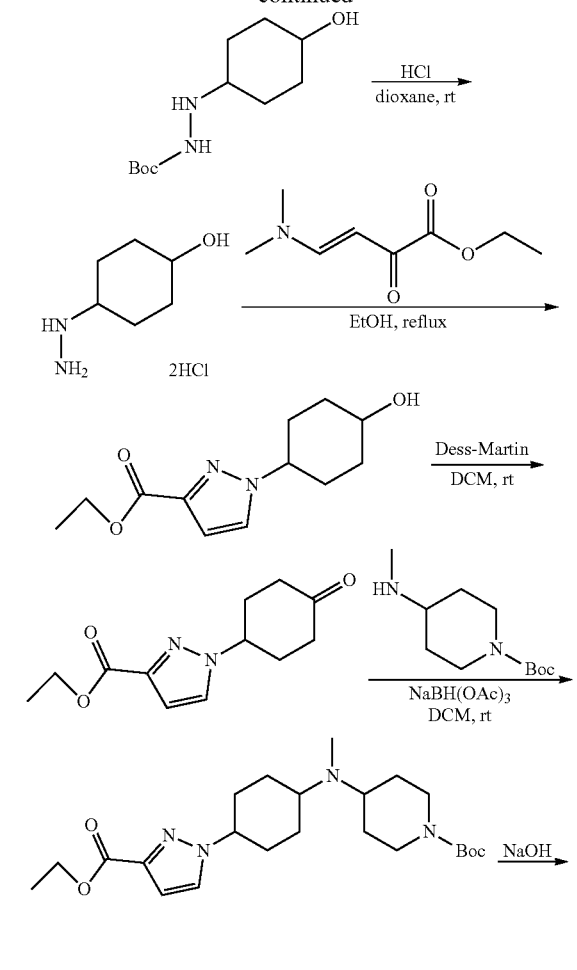
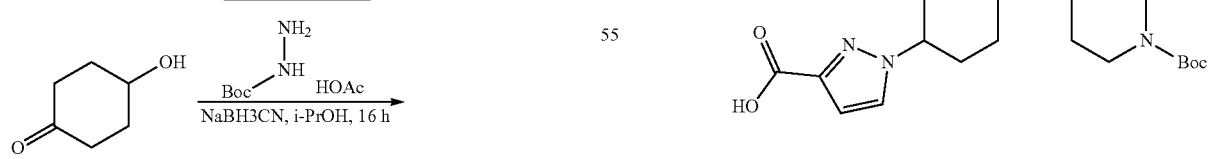

General Scheme 81
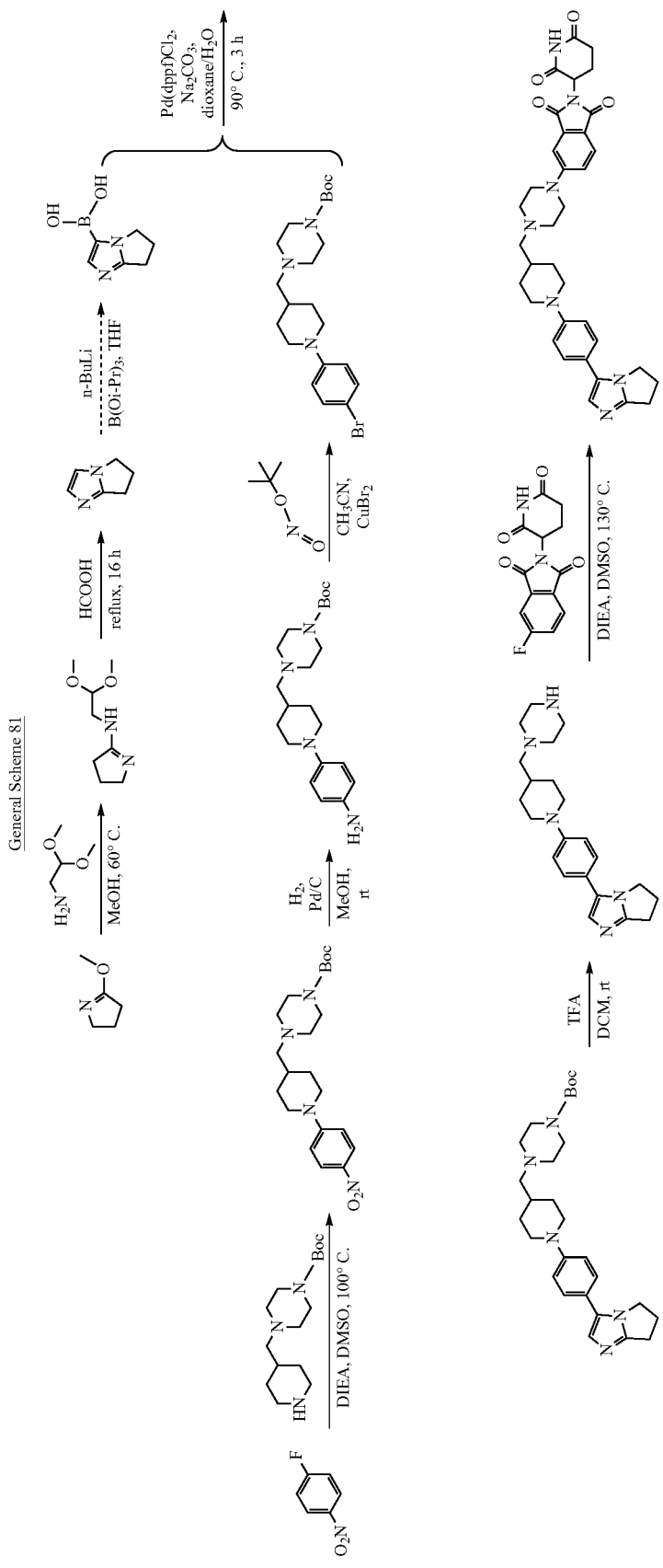

General Scheme 82
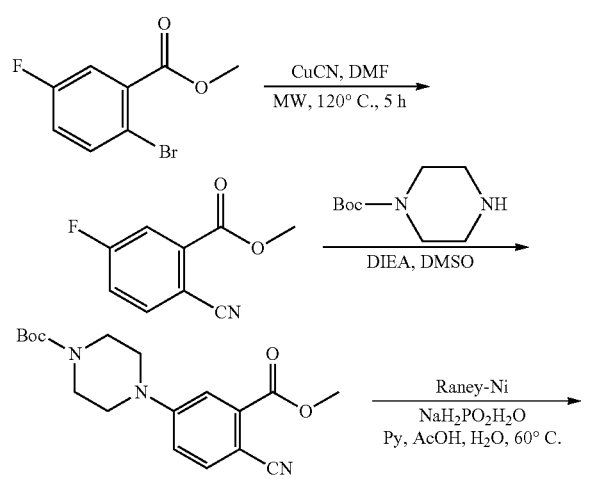
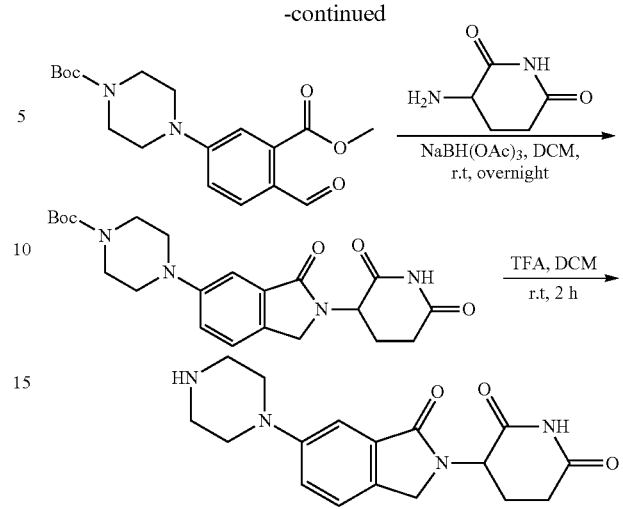
General Scheme 83
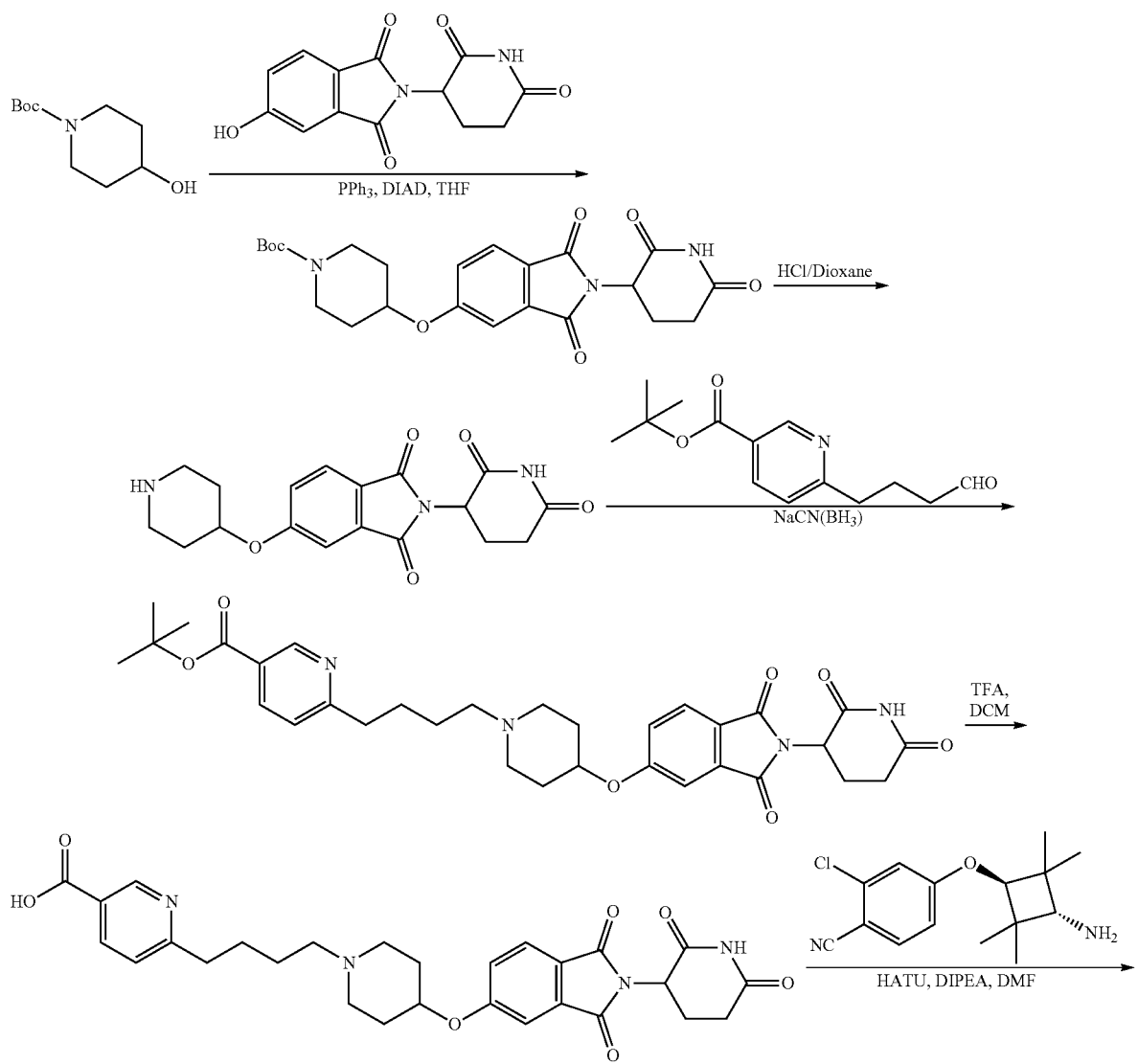

289　　　　　　　　　　　　　　　　290
-continued
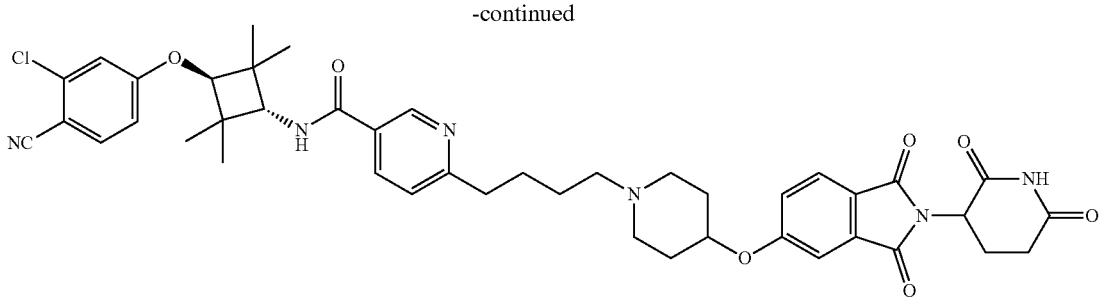
General Scheme 84
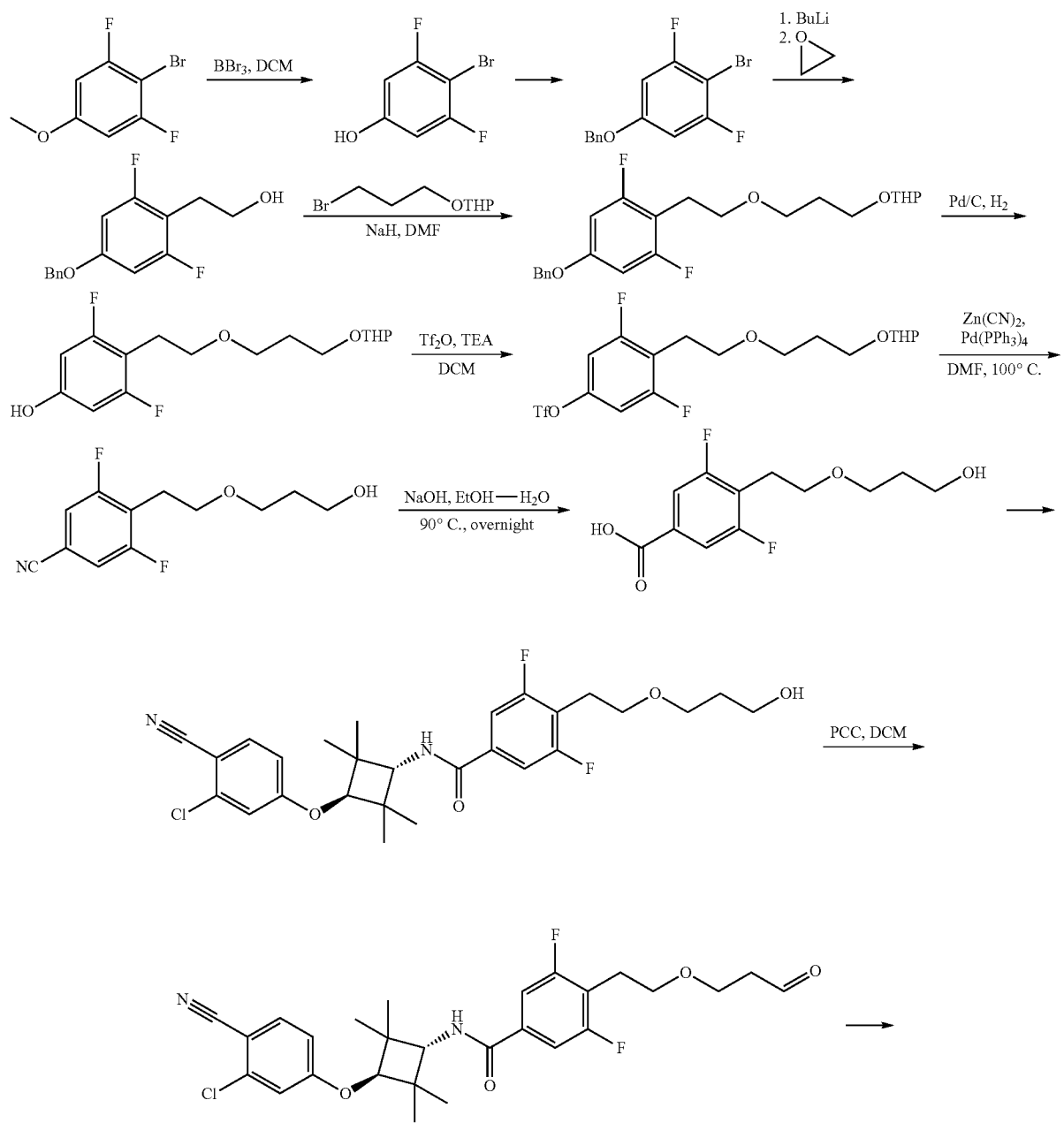

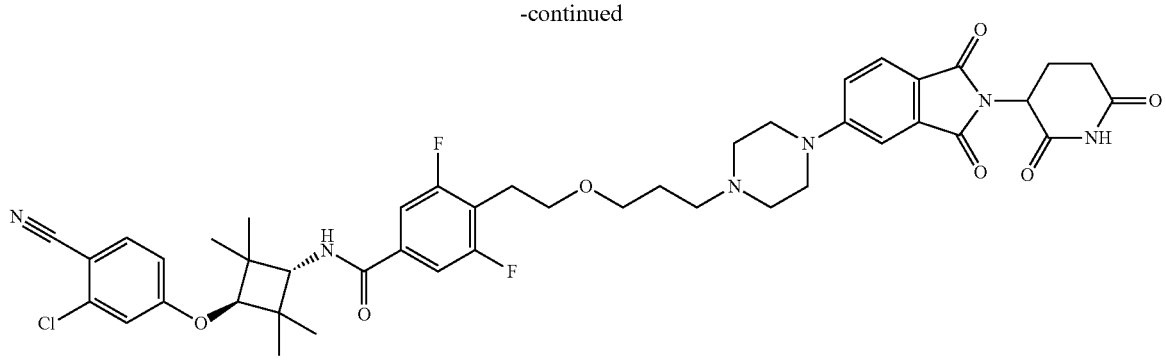
General Scheme 85
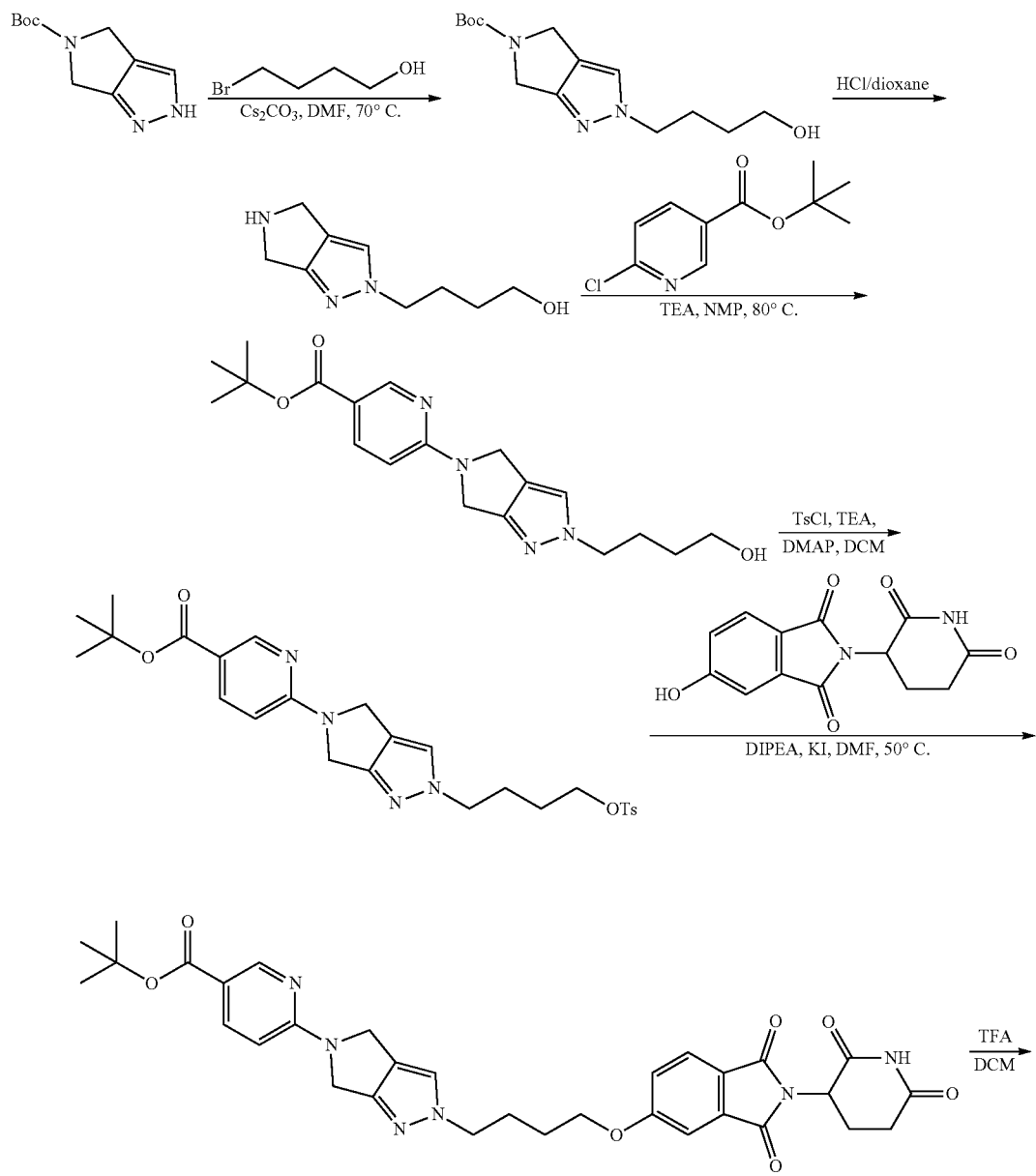

-continued
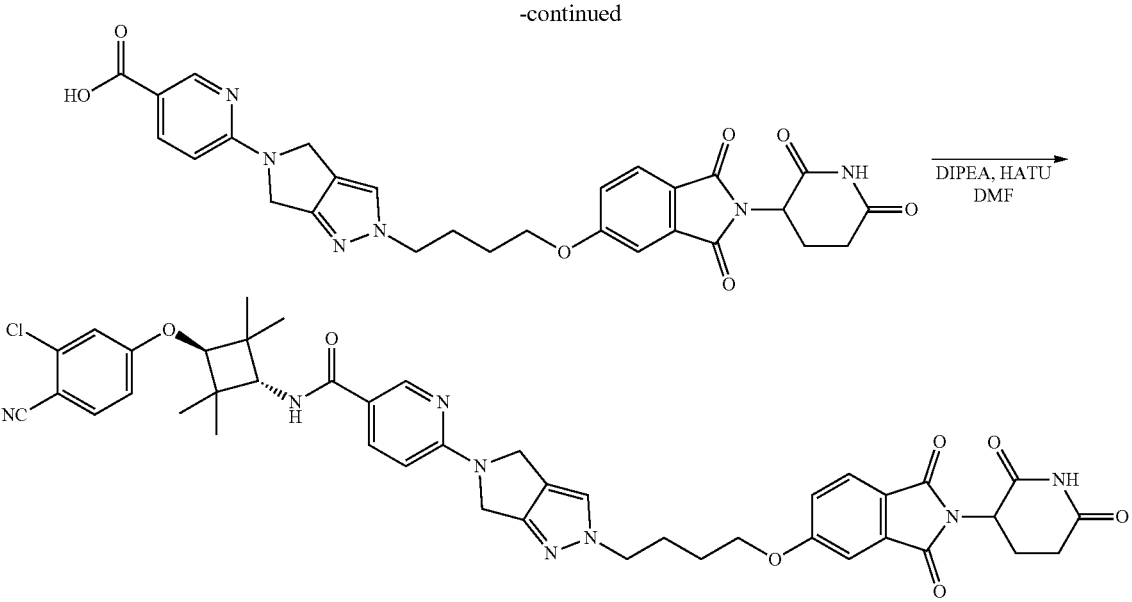
25
General Scheme 86
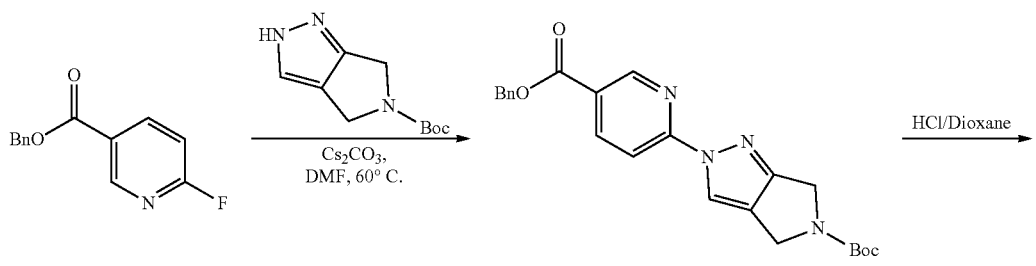
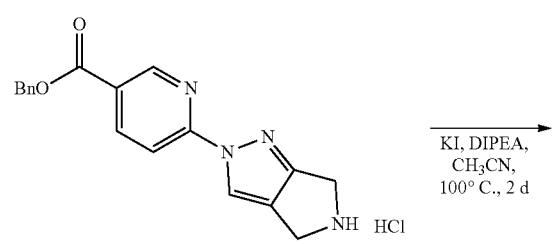
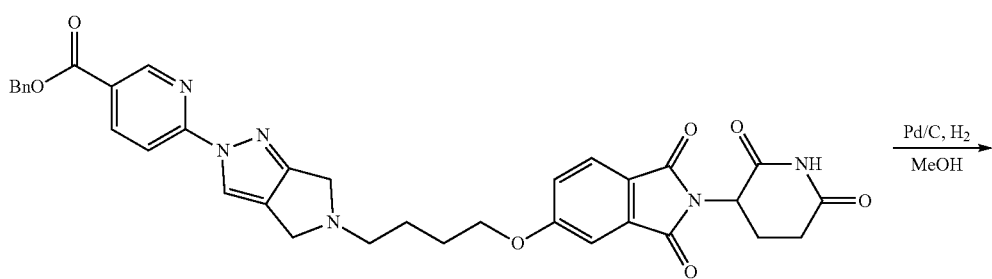

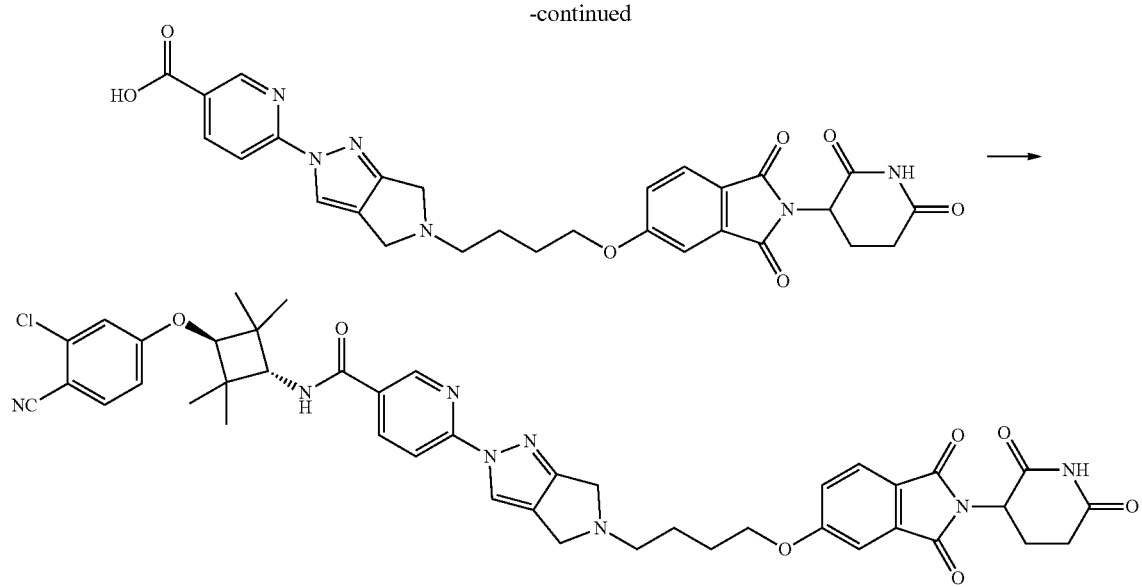
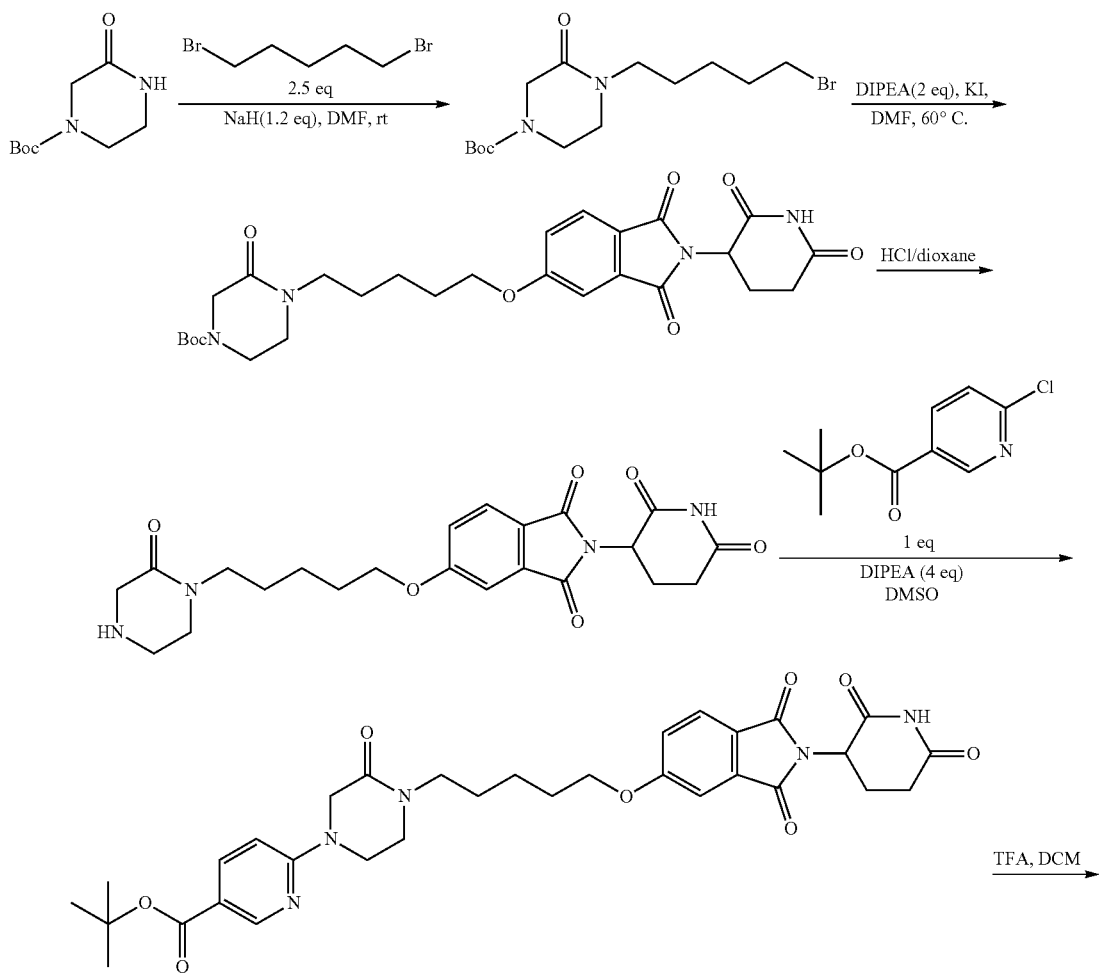
General Scheme 87

297 298
-continued
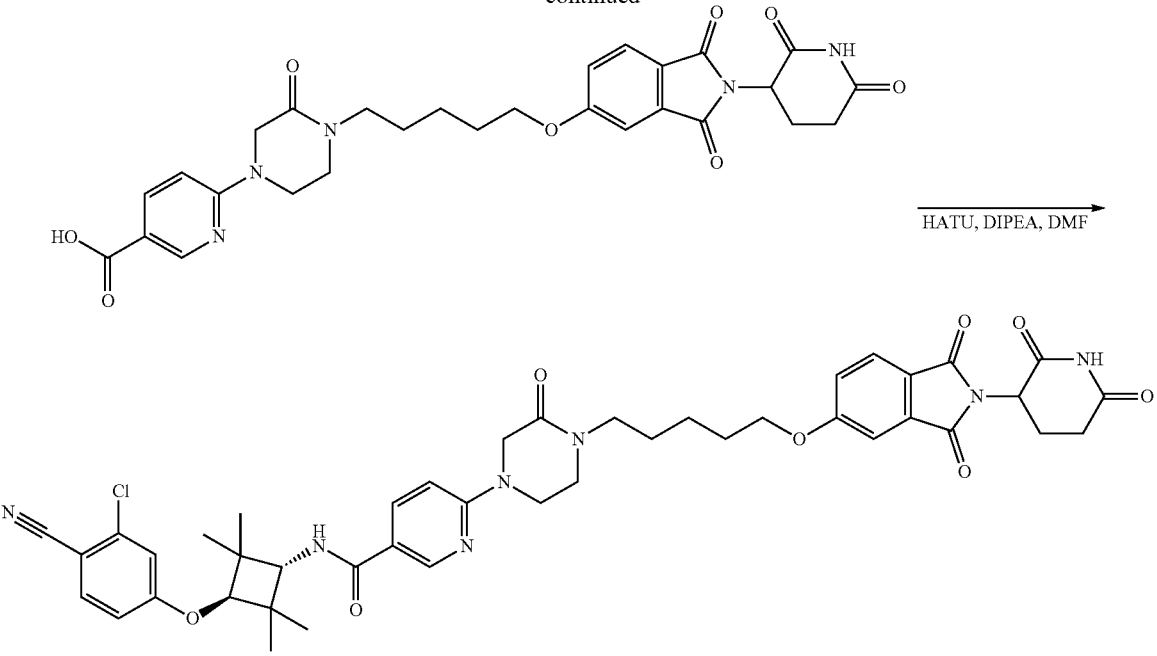
General Scheme 88
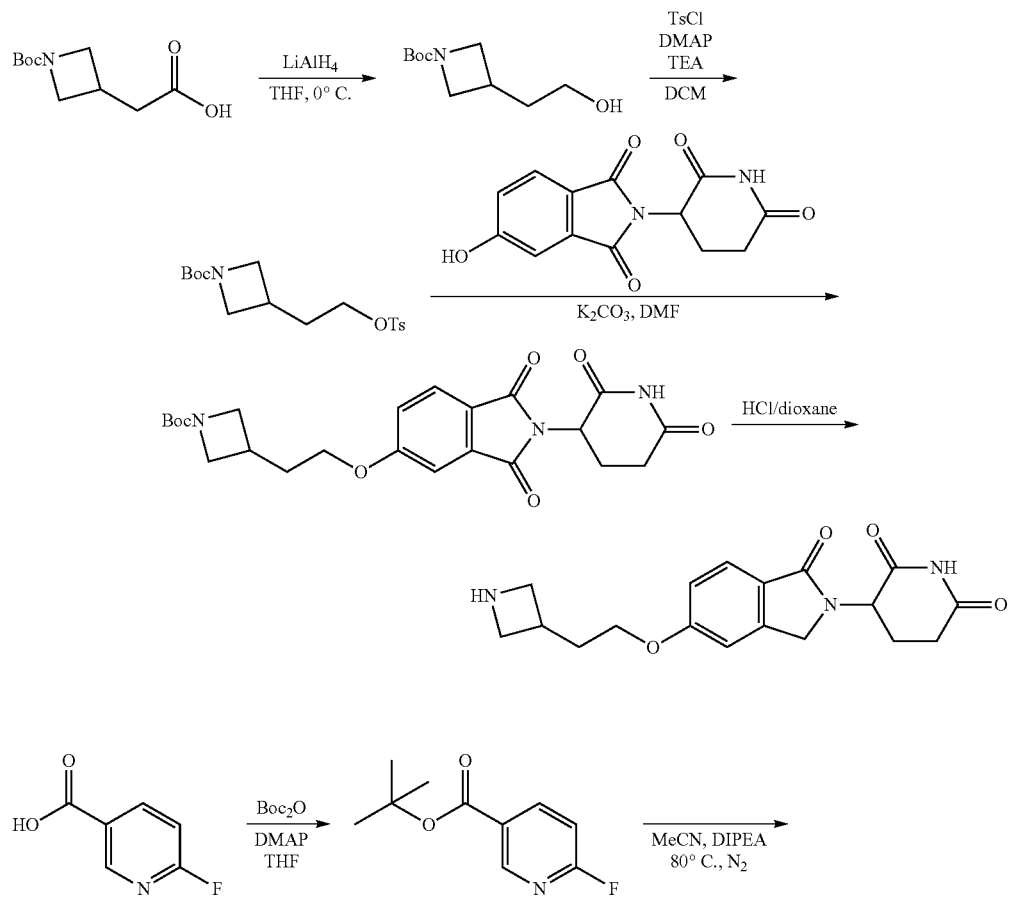

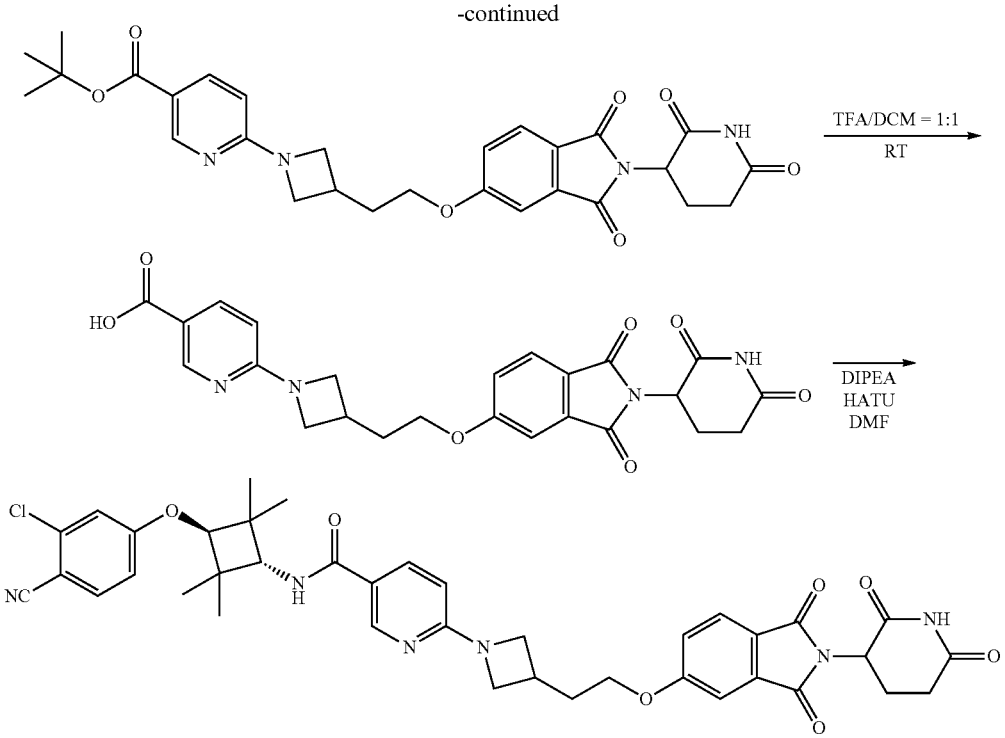
General Scheme 89
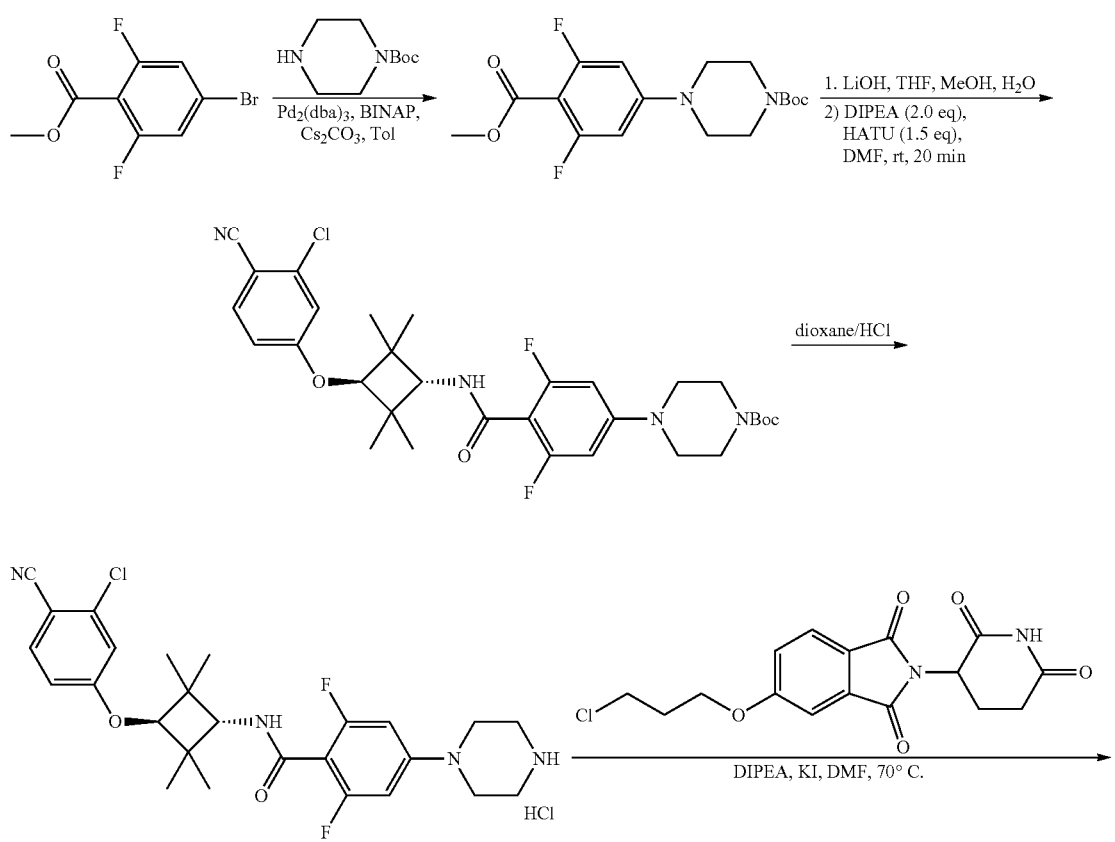

-continued
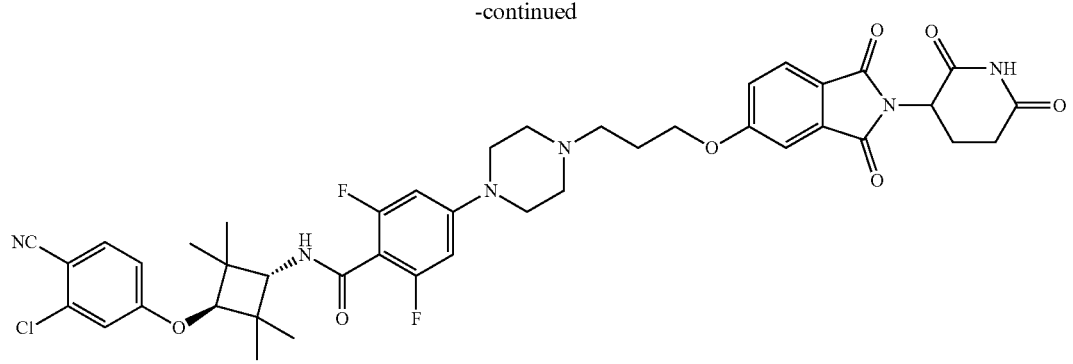
General Scheme 90
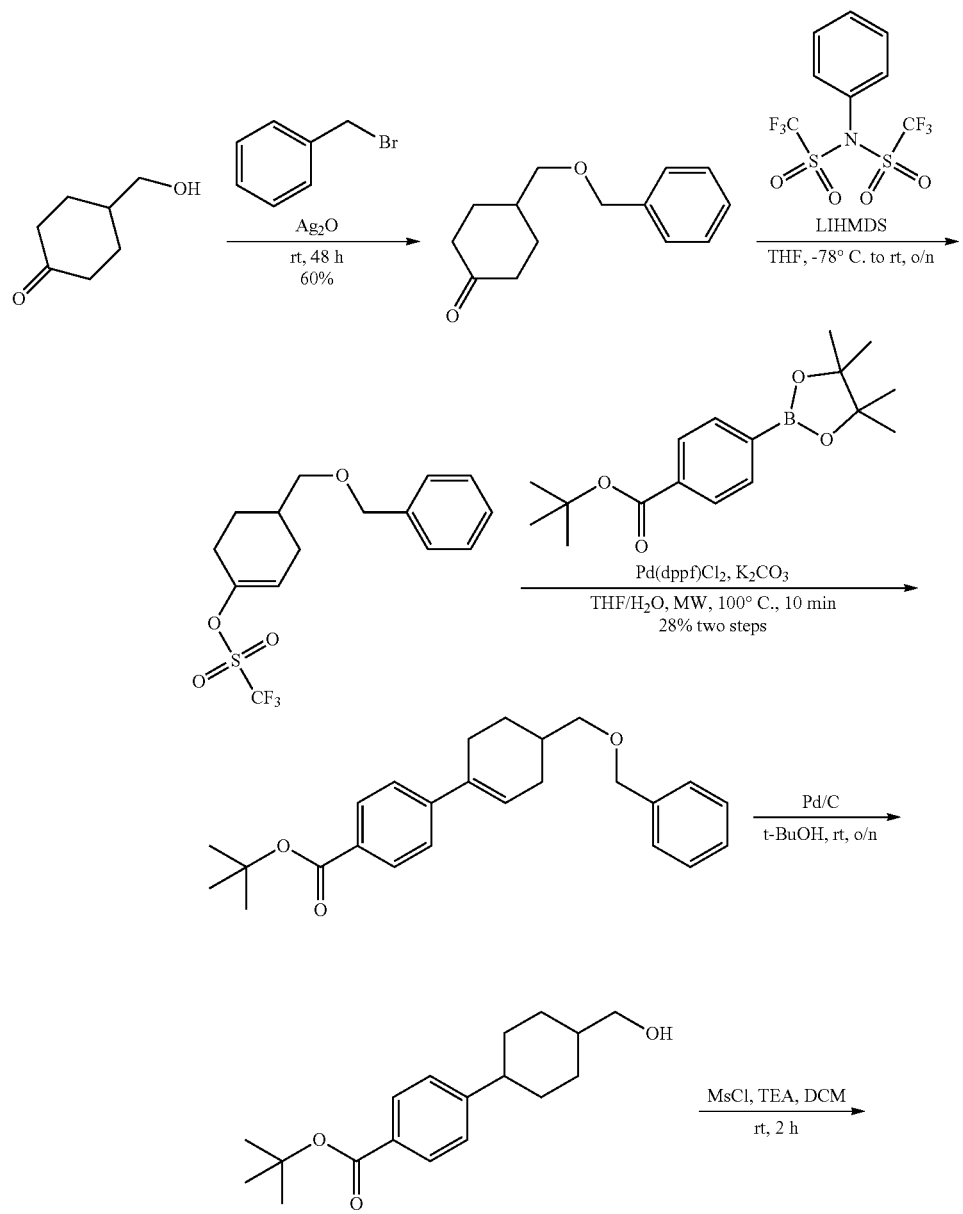

303    304
-continued
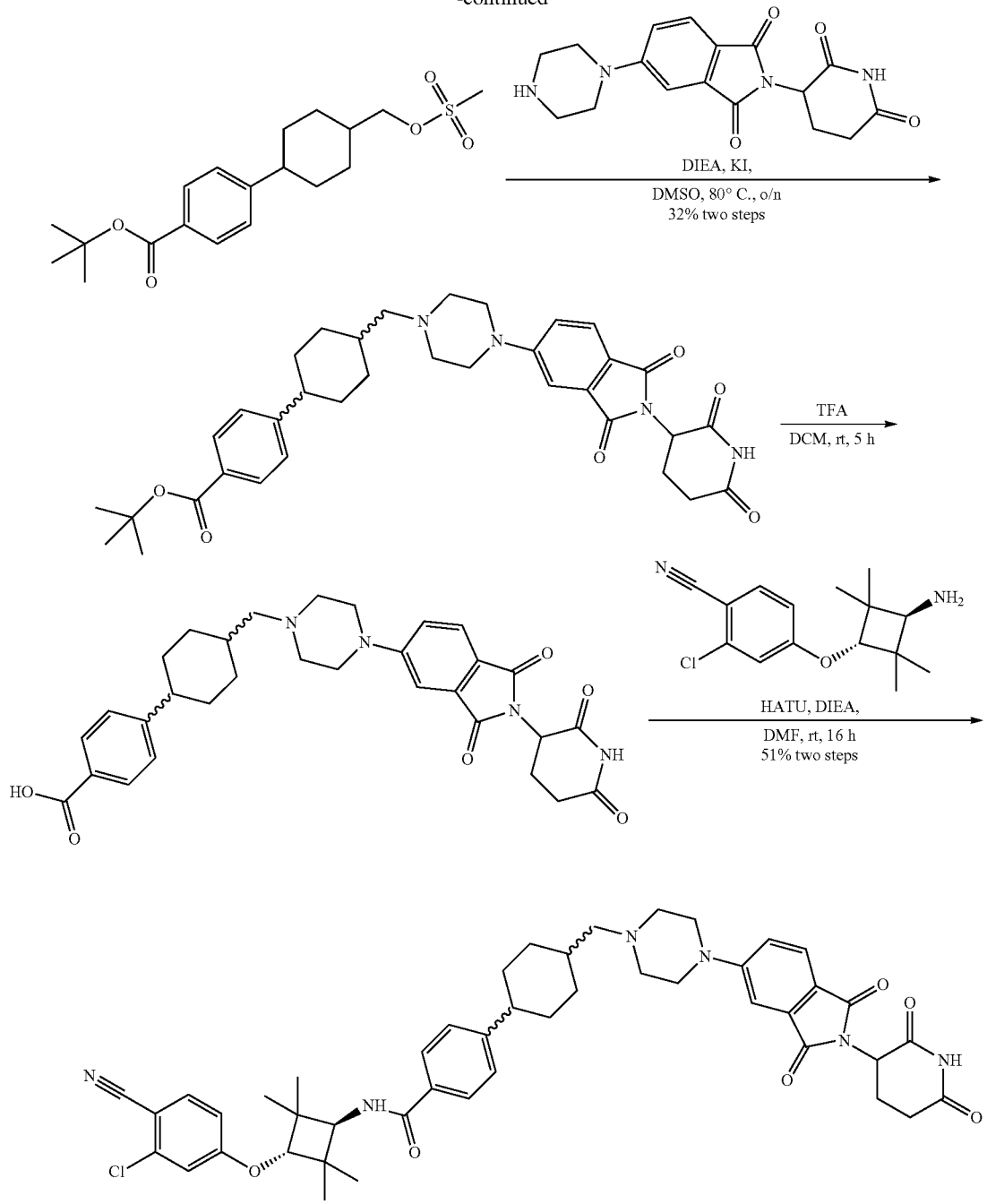
General Scheme 91
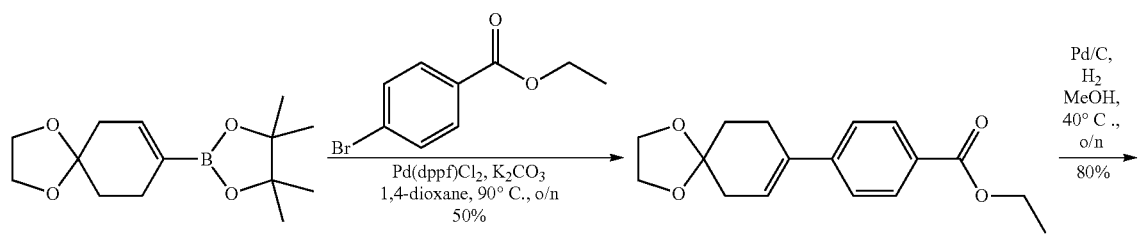

-continued
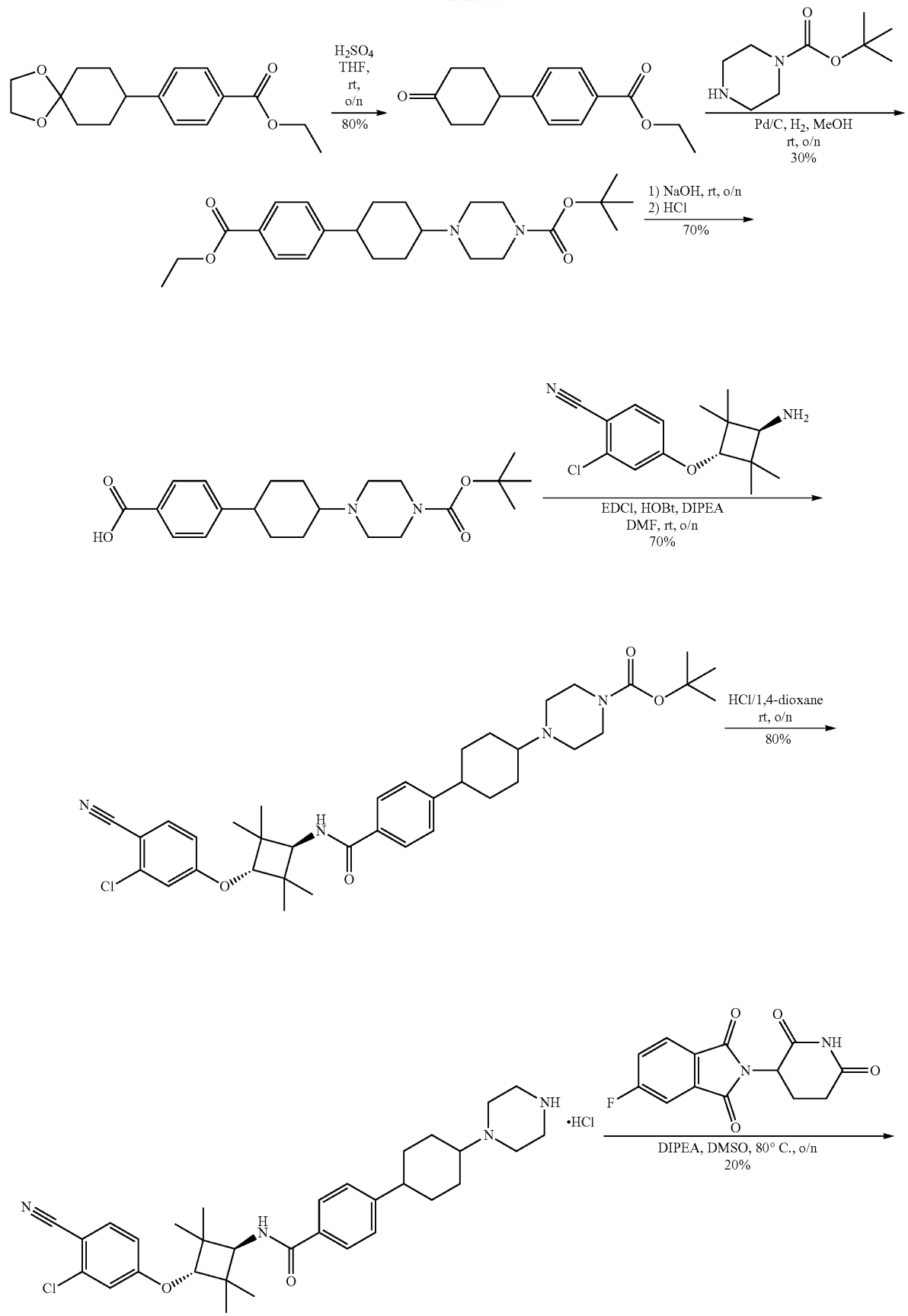

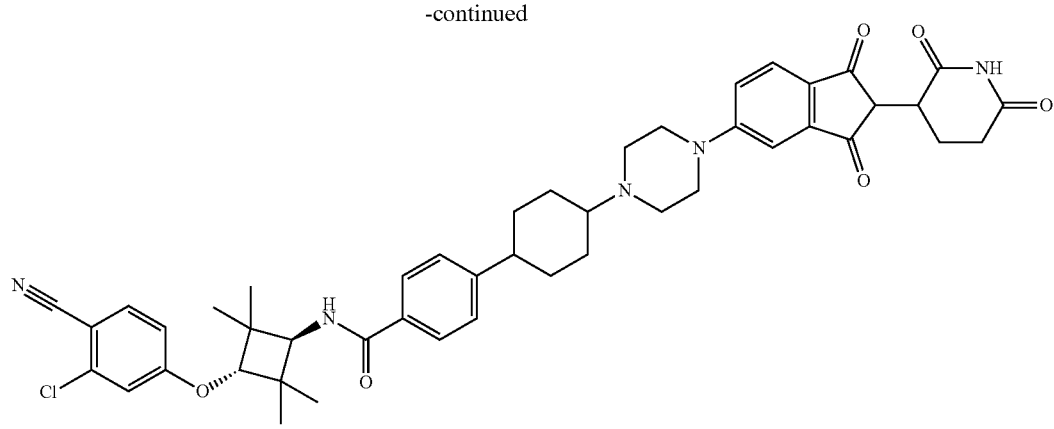
General Scheme 92
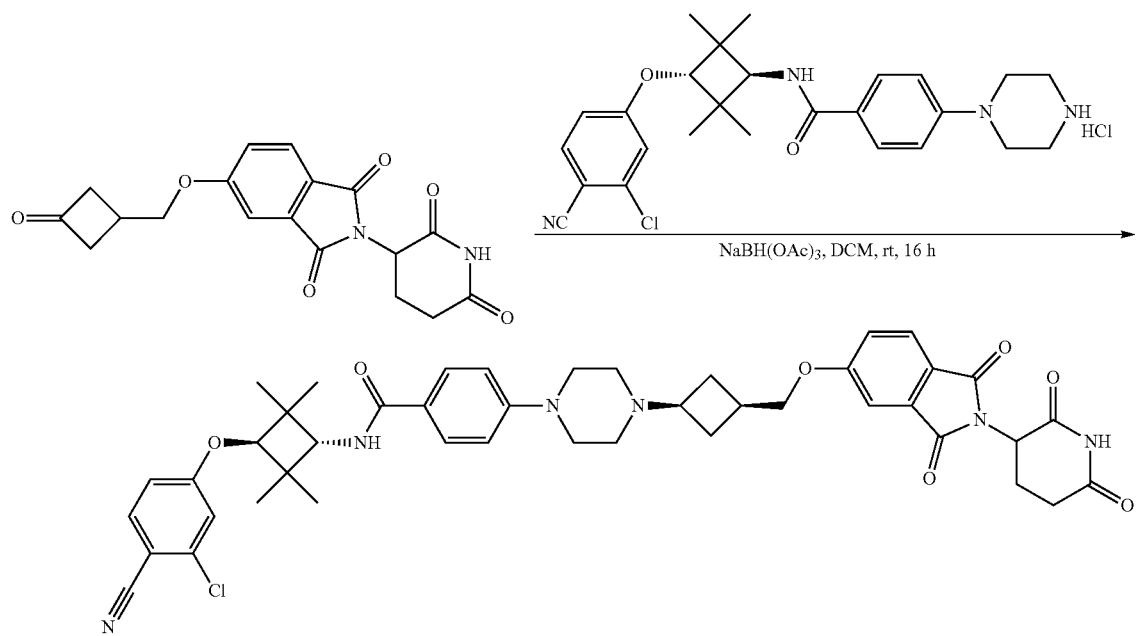
General Scheme 93
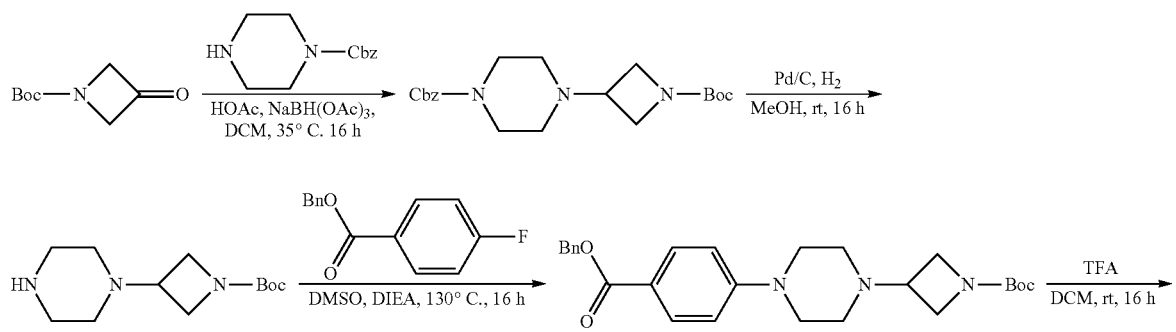

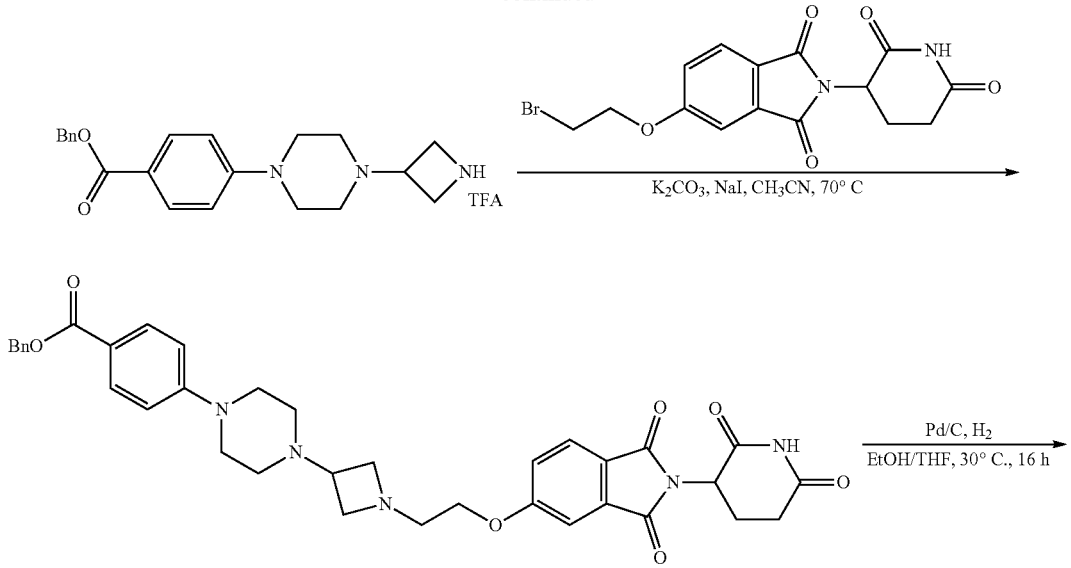
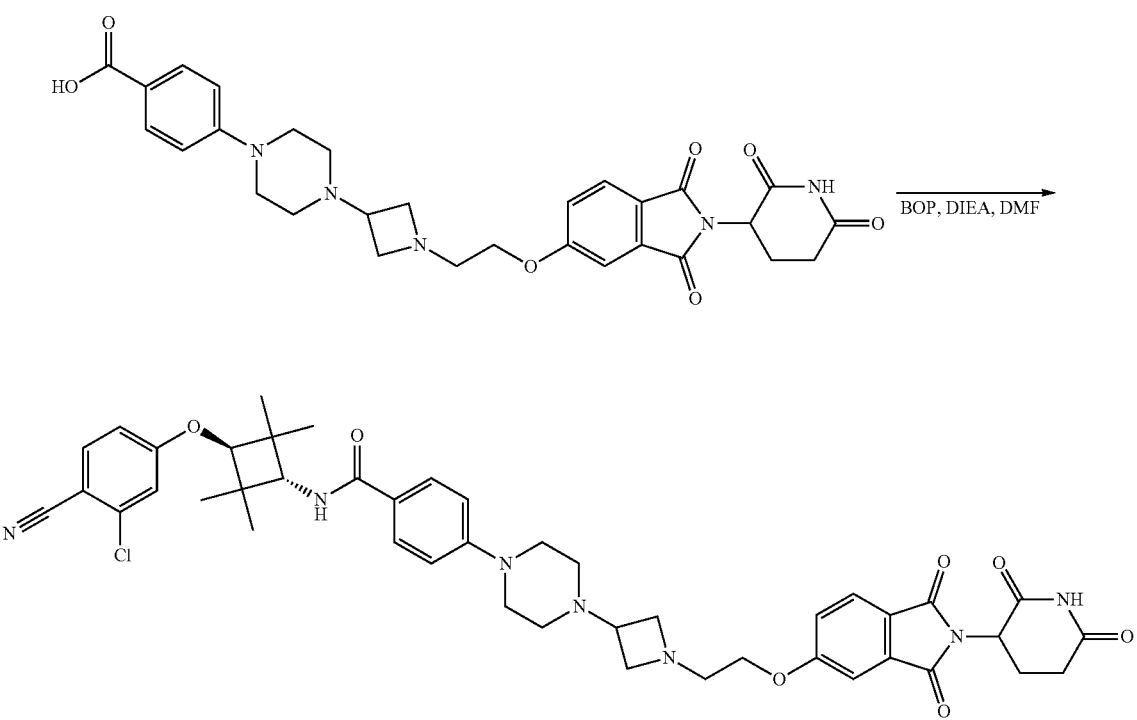
General Scheme 94
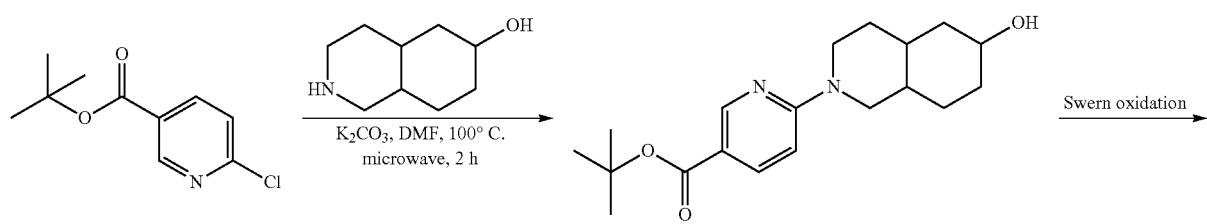

311 312
-continued
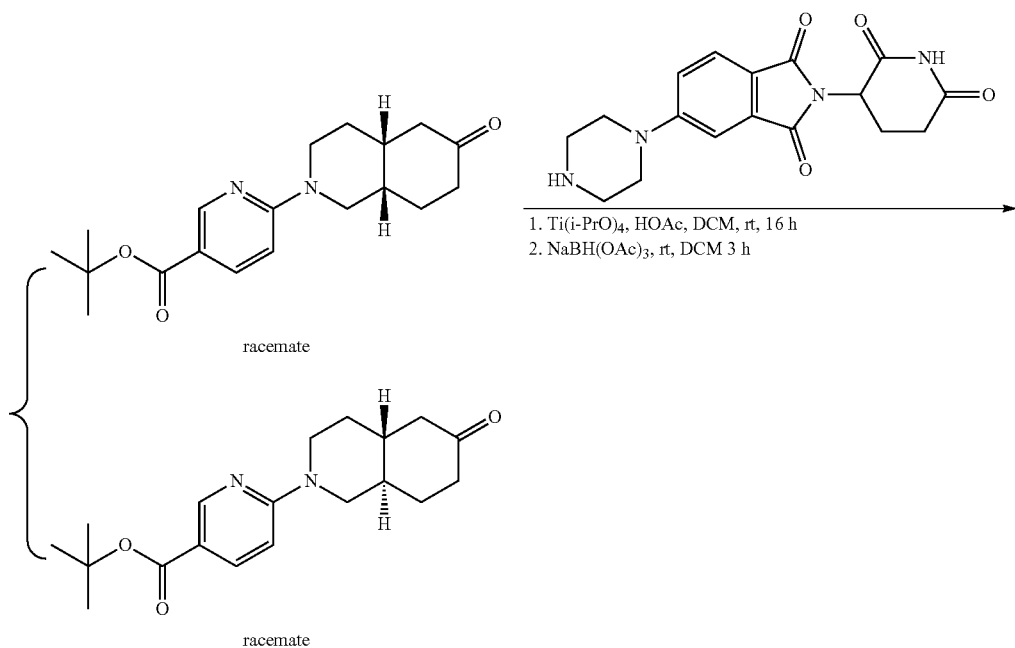
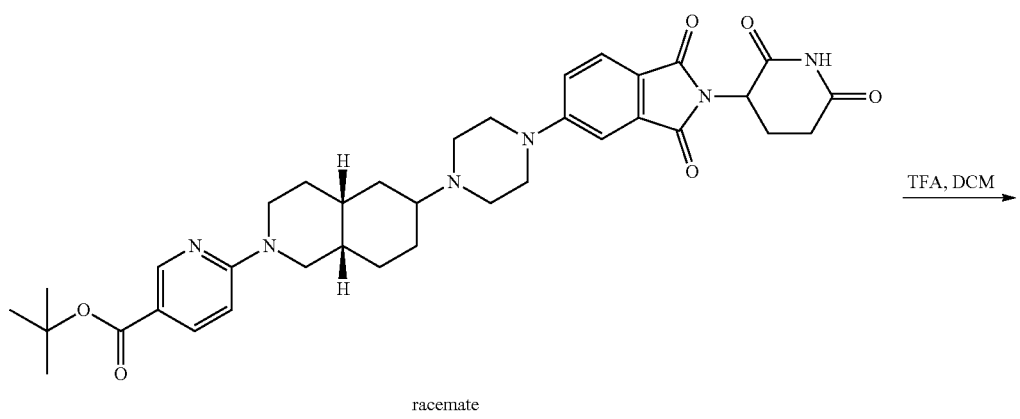
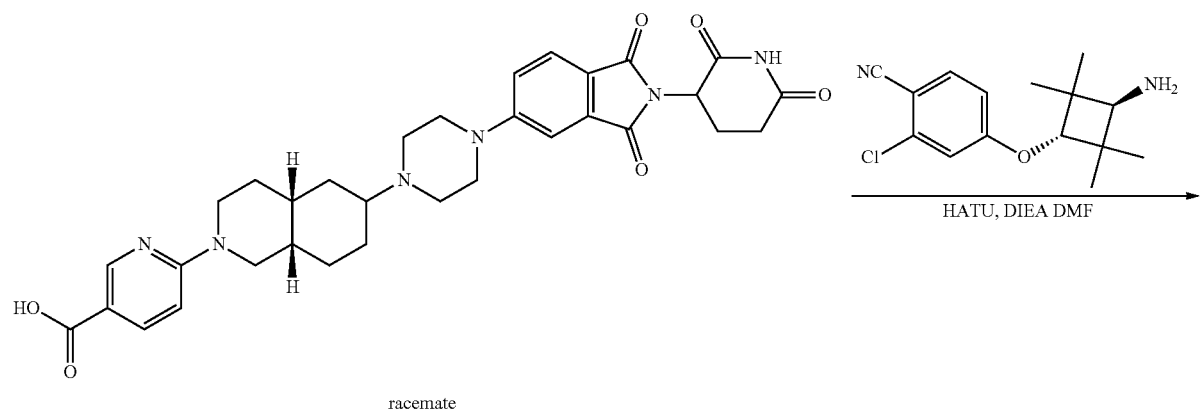

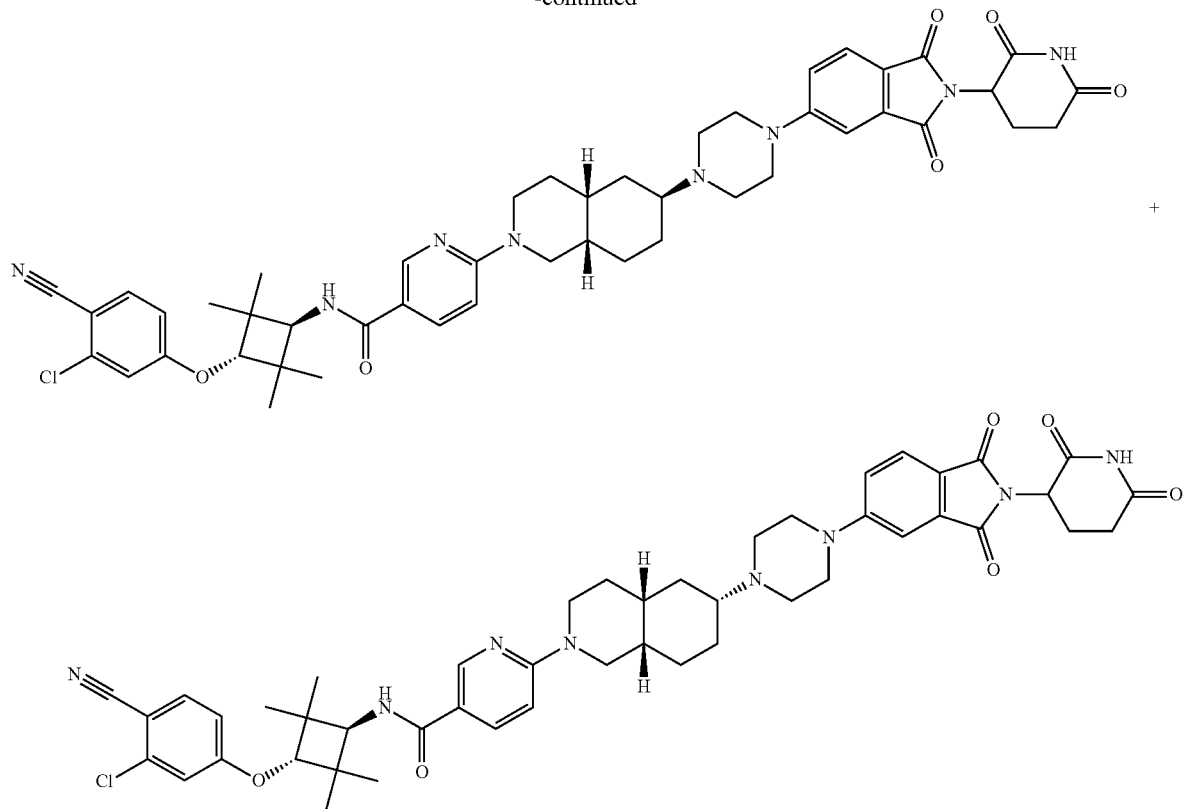
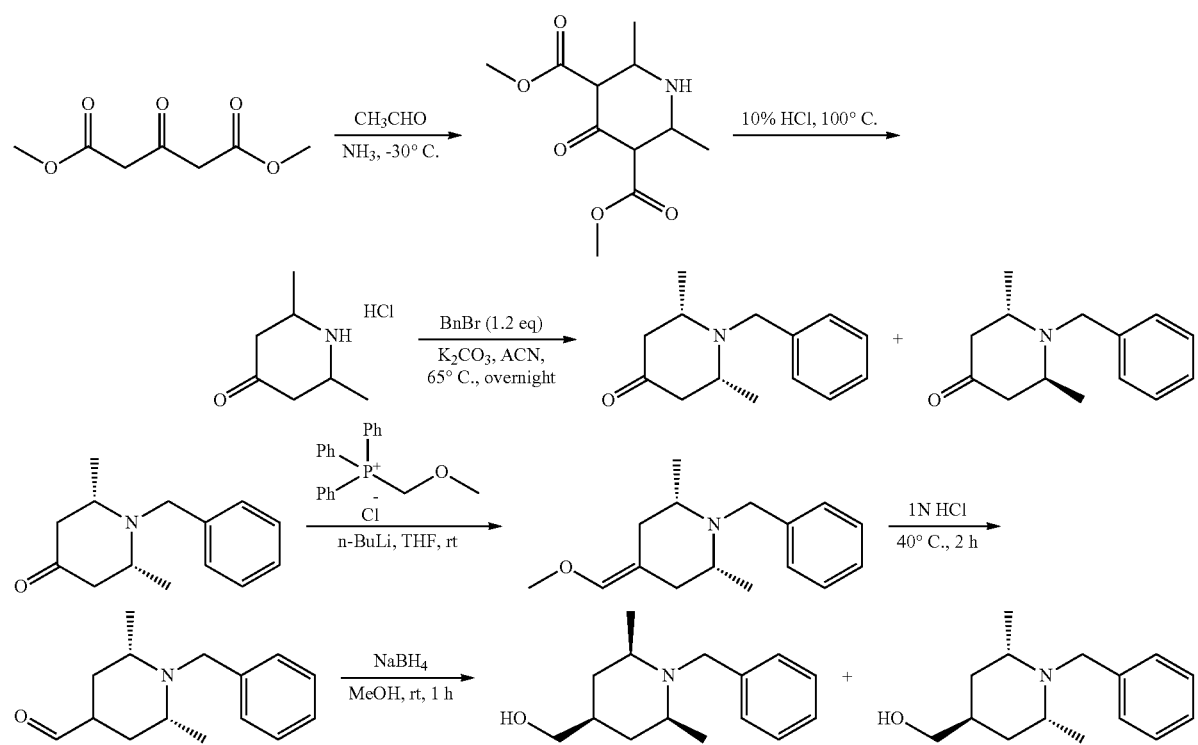
General Scheme 95

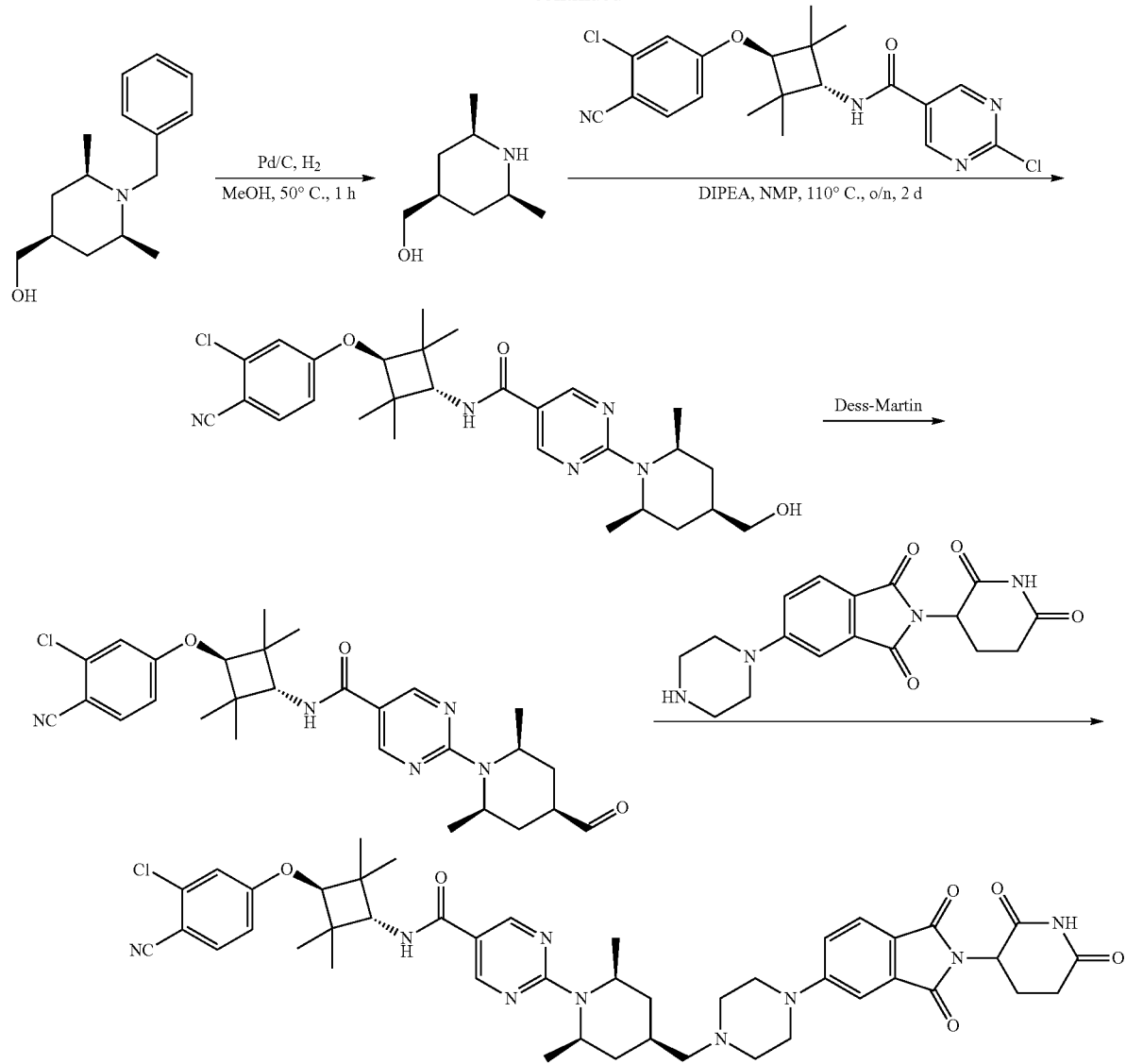
General Scheme 96
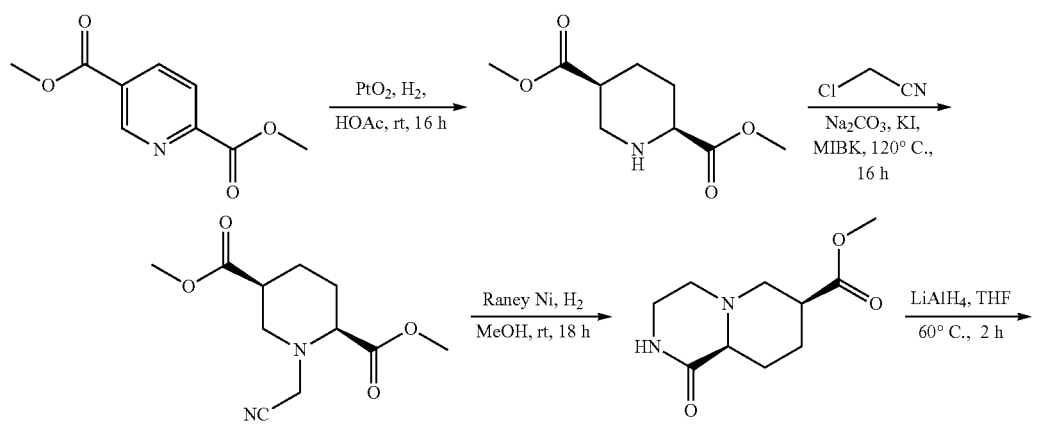

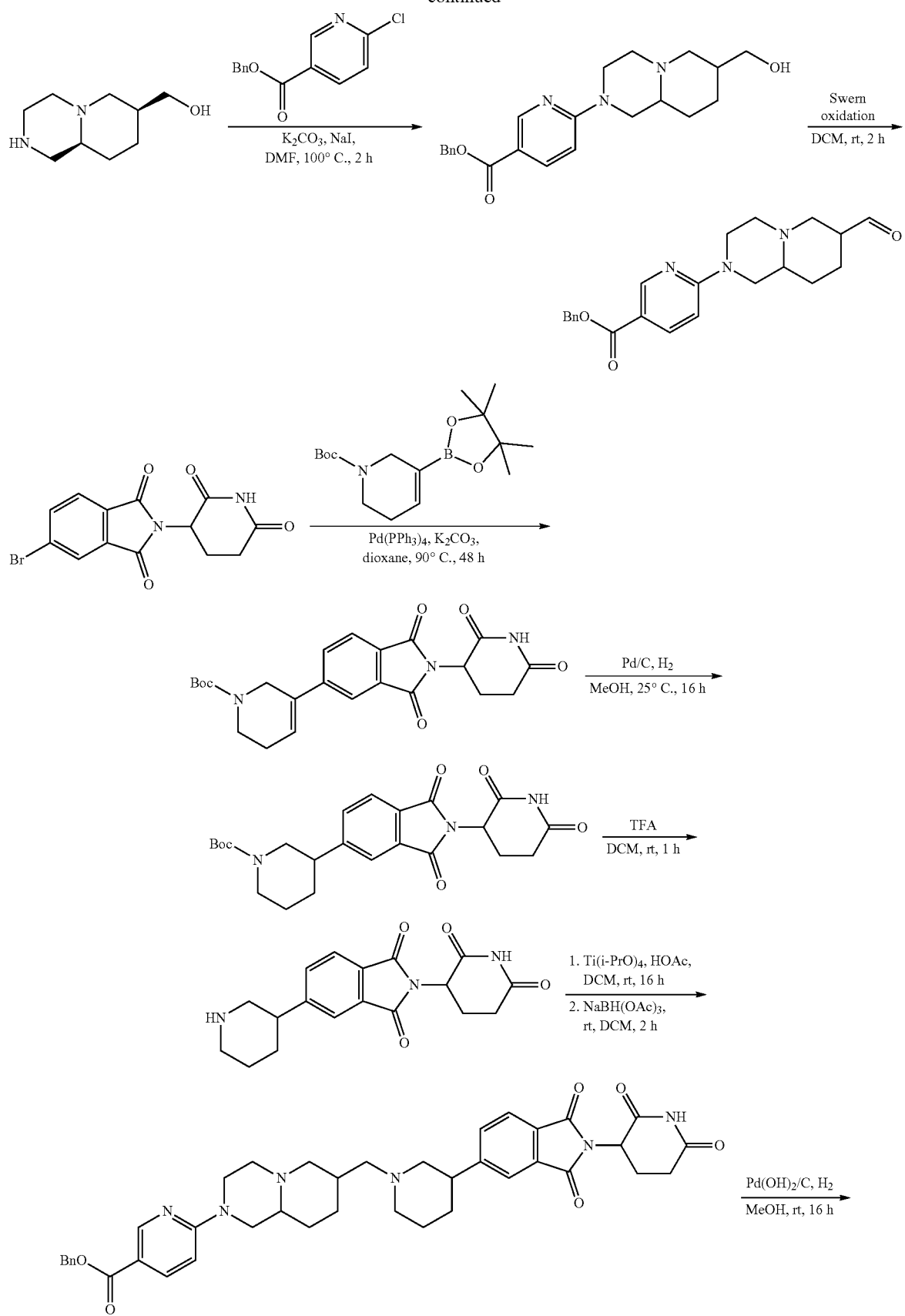
-continued

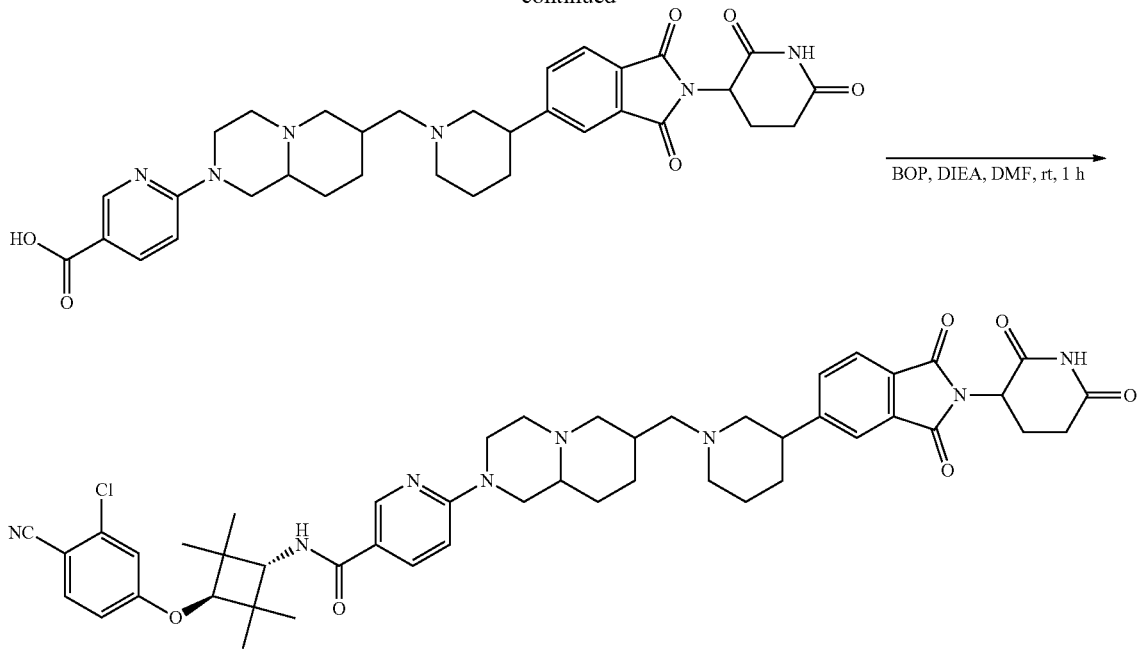
-continued
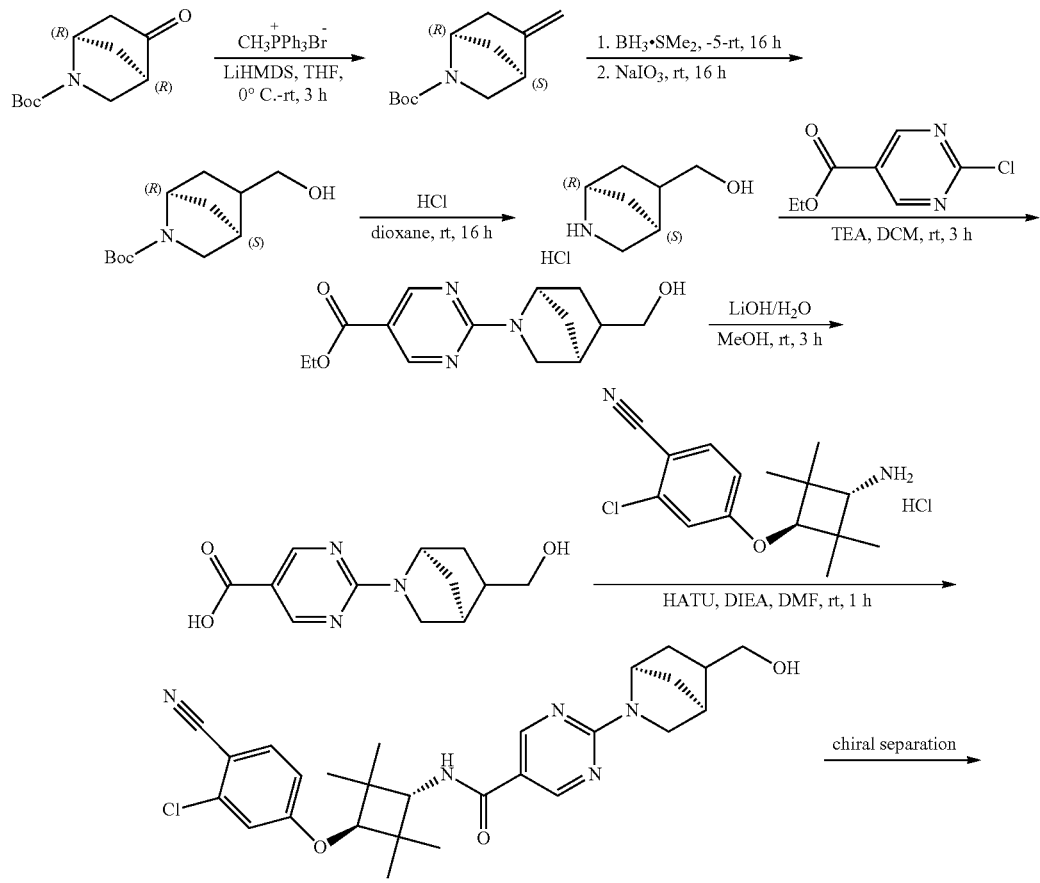
General Scheme 97

321
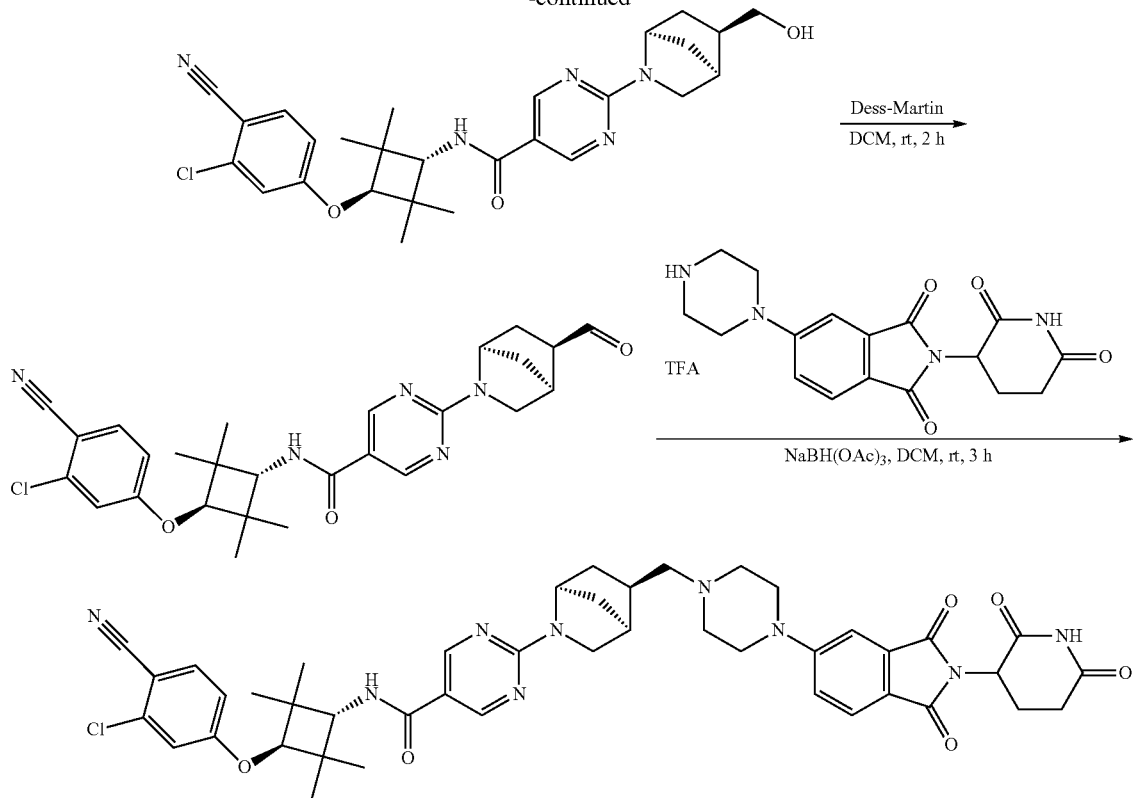
322
General Scheme 98
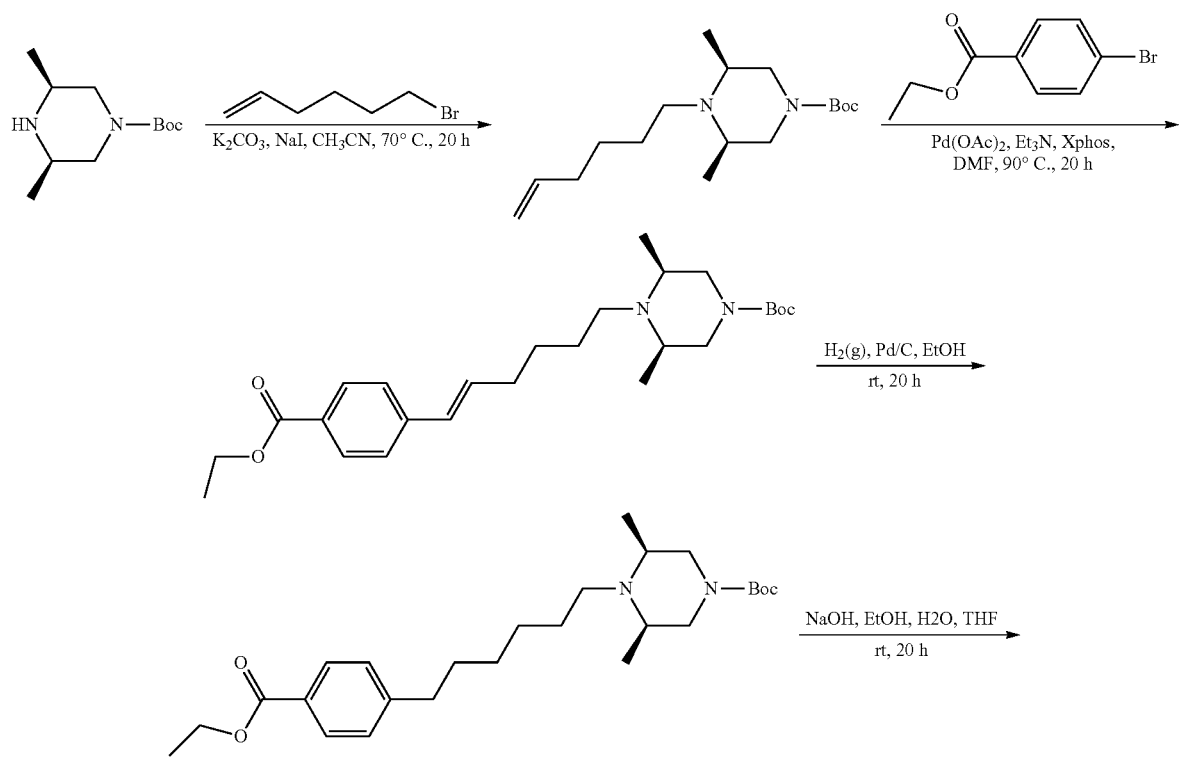

323
324
-continued
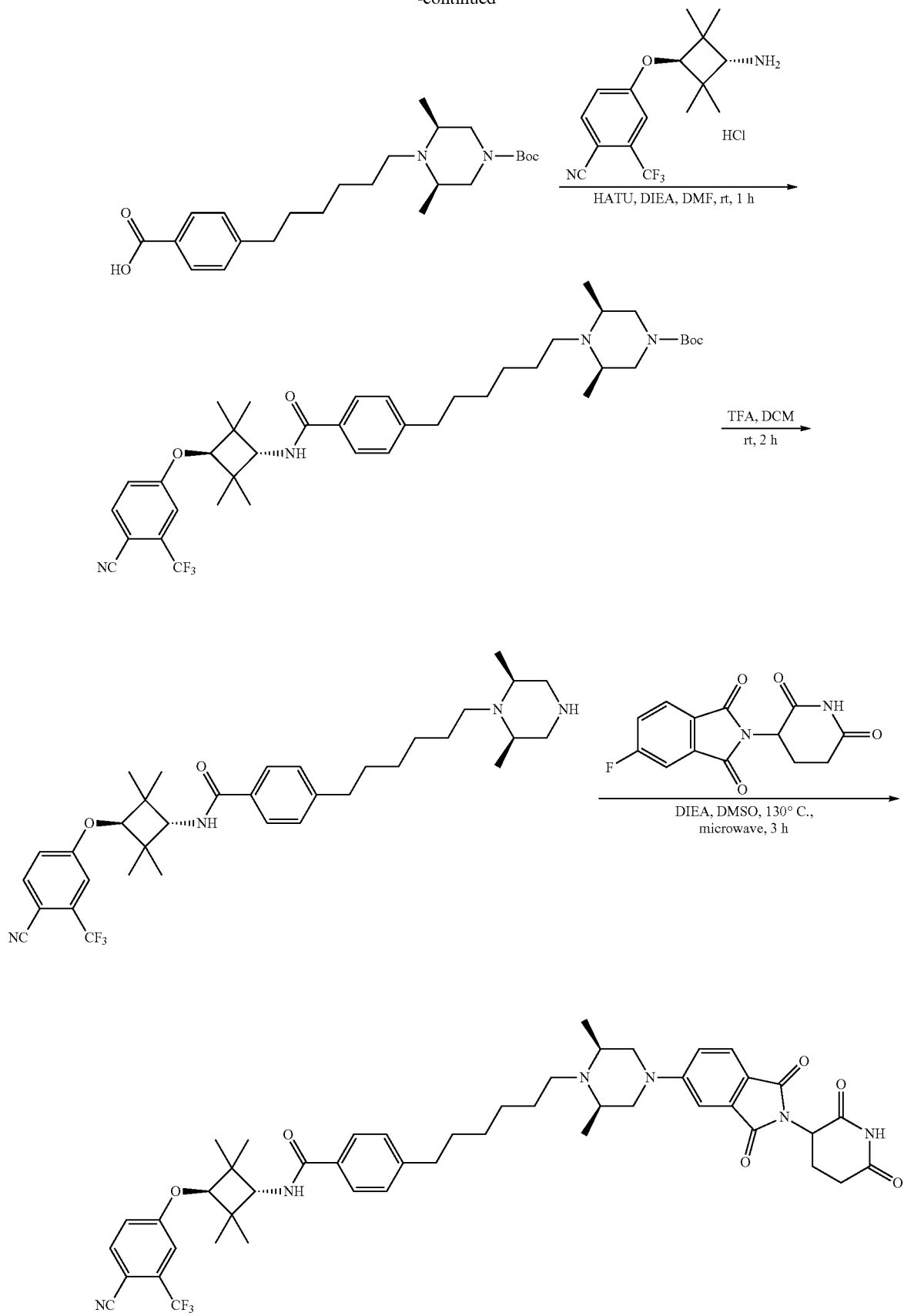

General Scheme 99
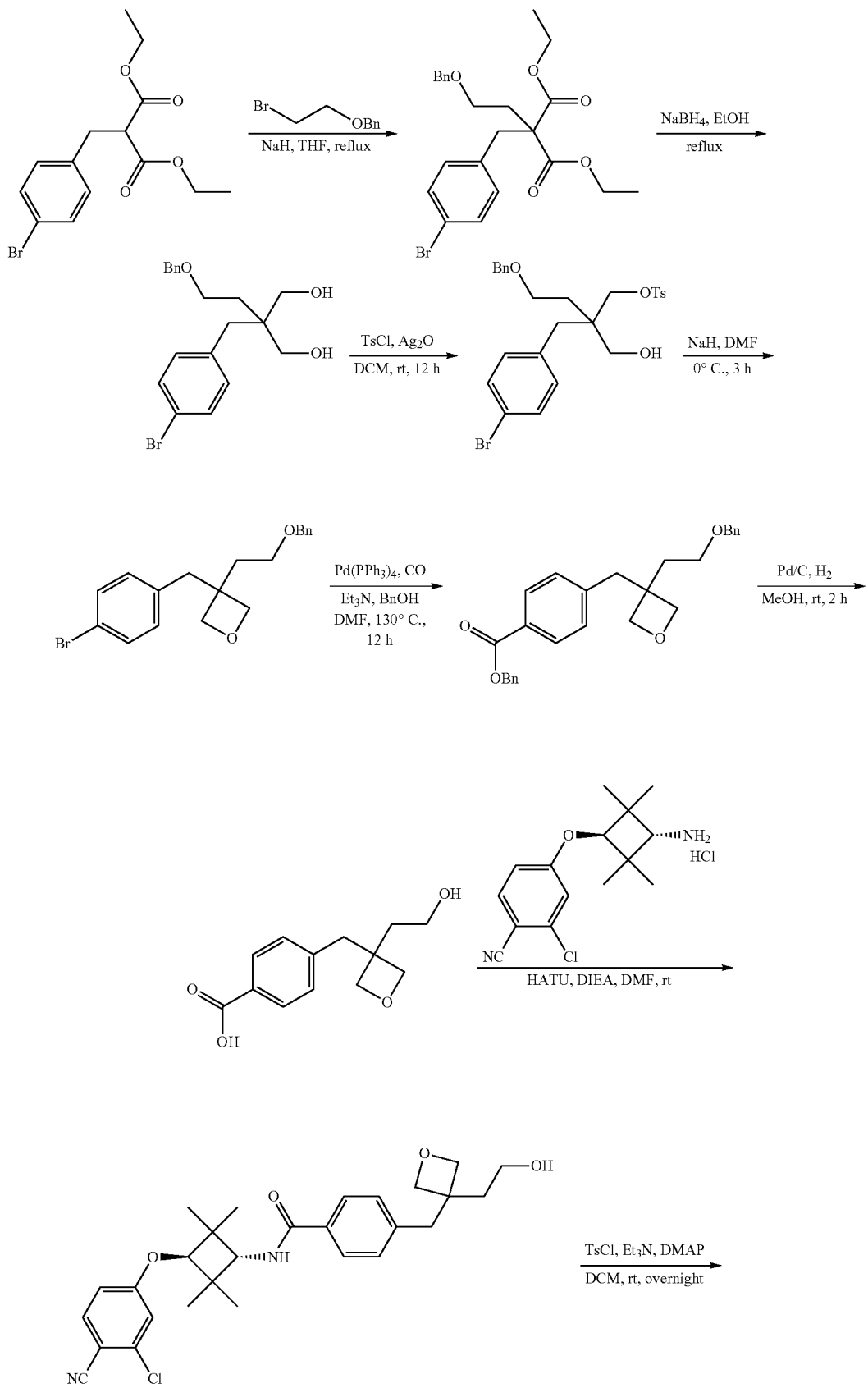

327 328
-continued
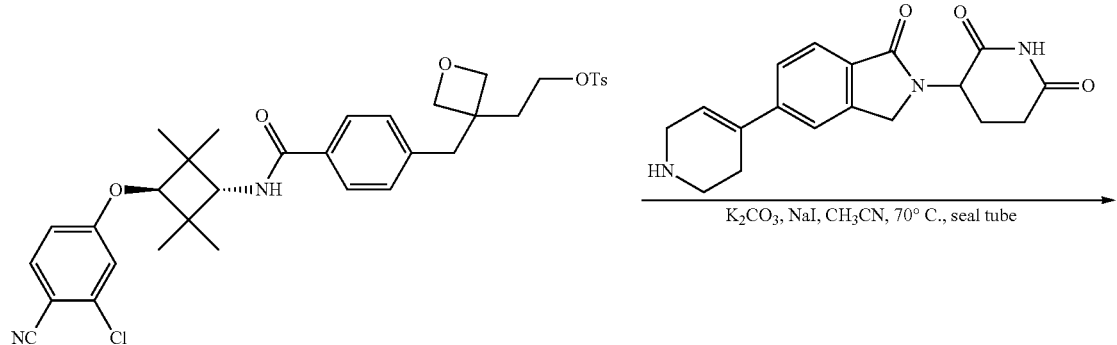
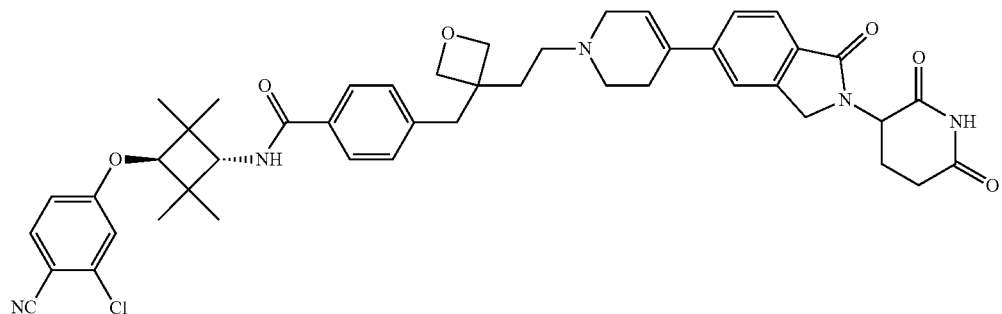
General Scheme 100
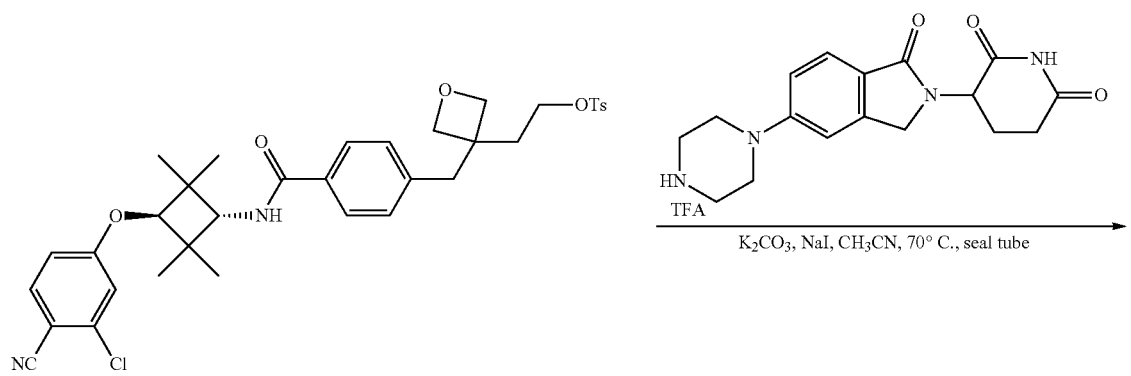
Scheme 99
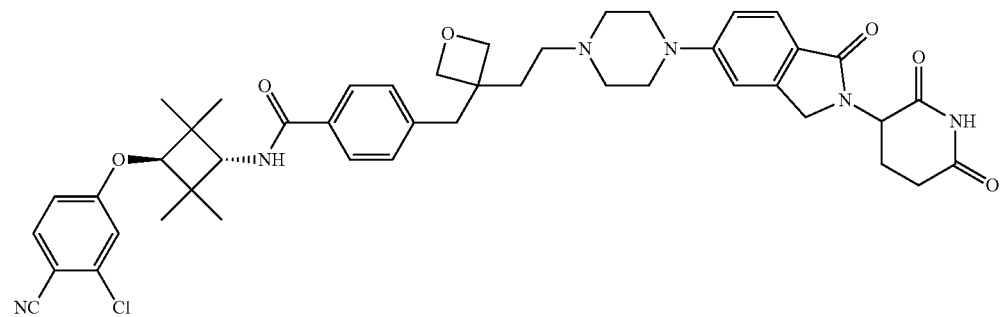

General Scheme 101
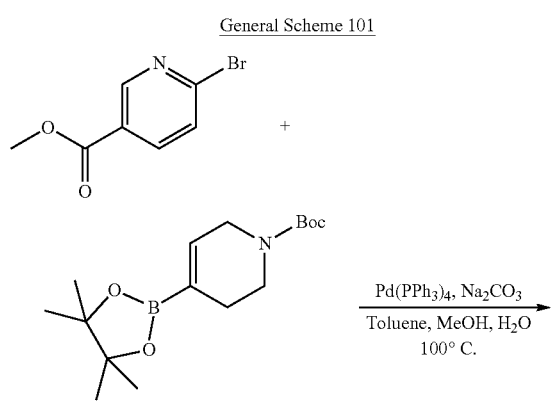
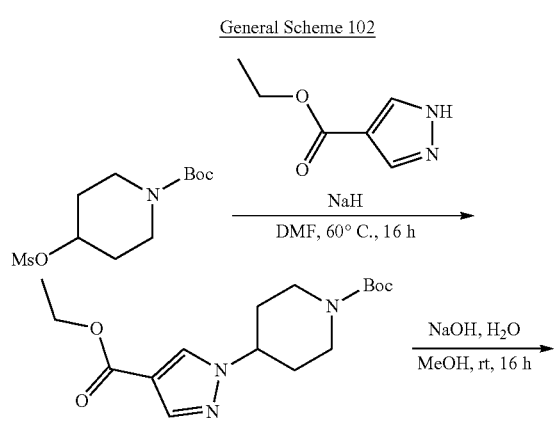
General Scheme 102
General Scheme 103
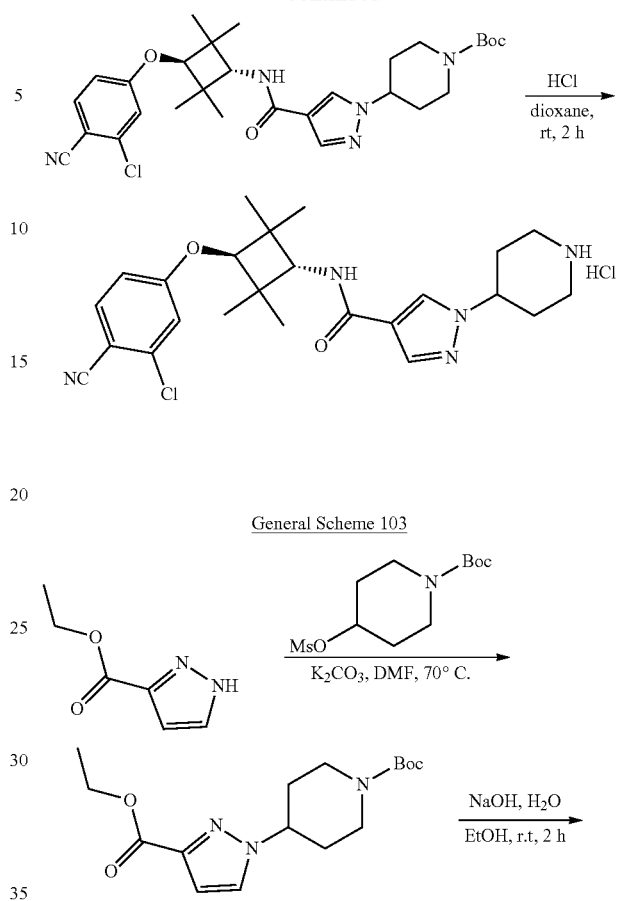
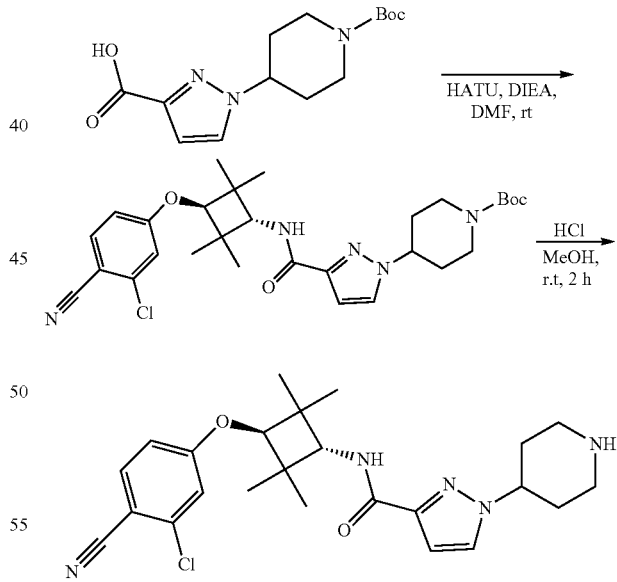
General Scheme 104
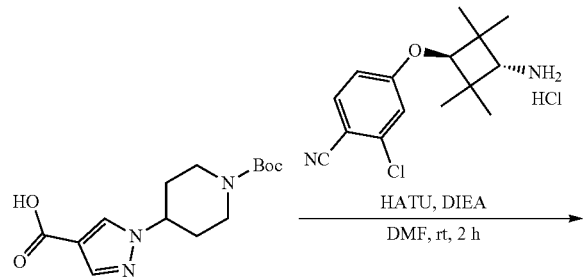

331
-continued
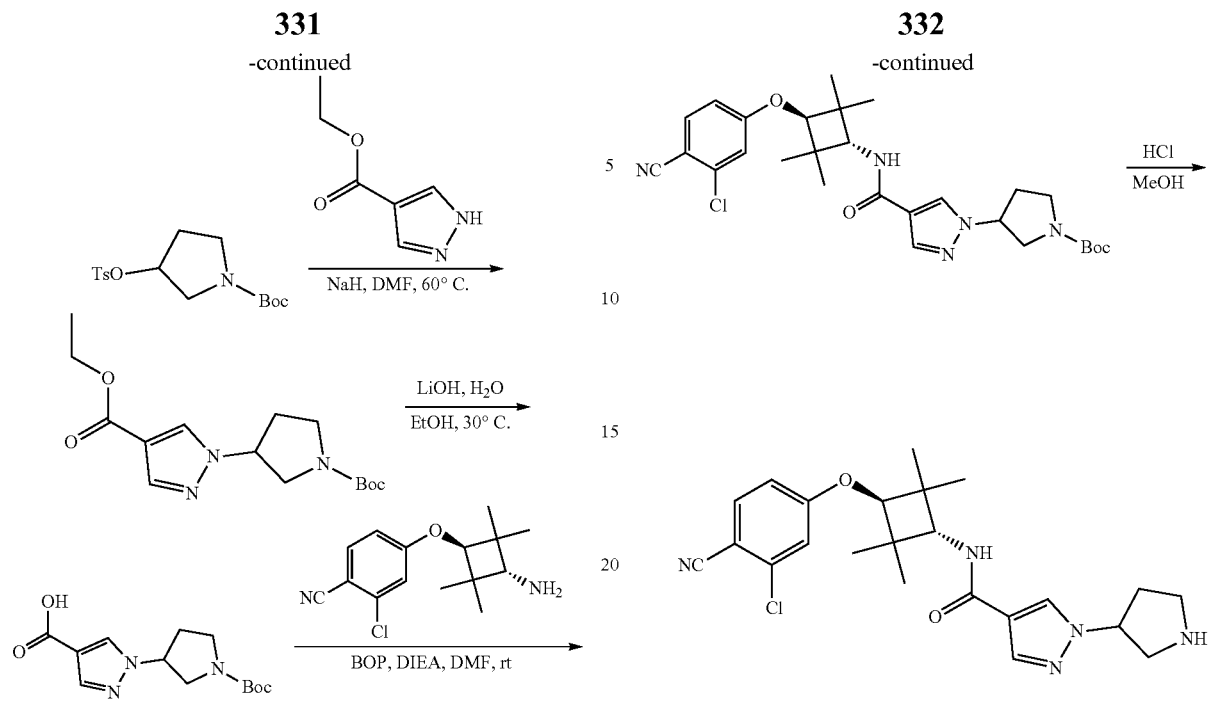
332
-continued
General Scheme 105
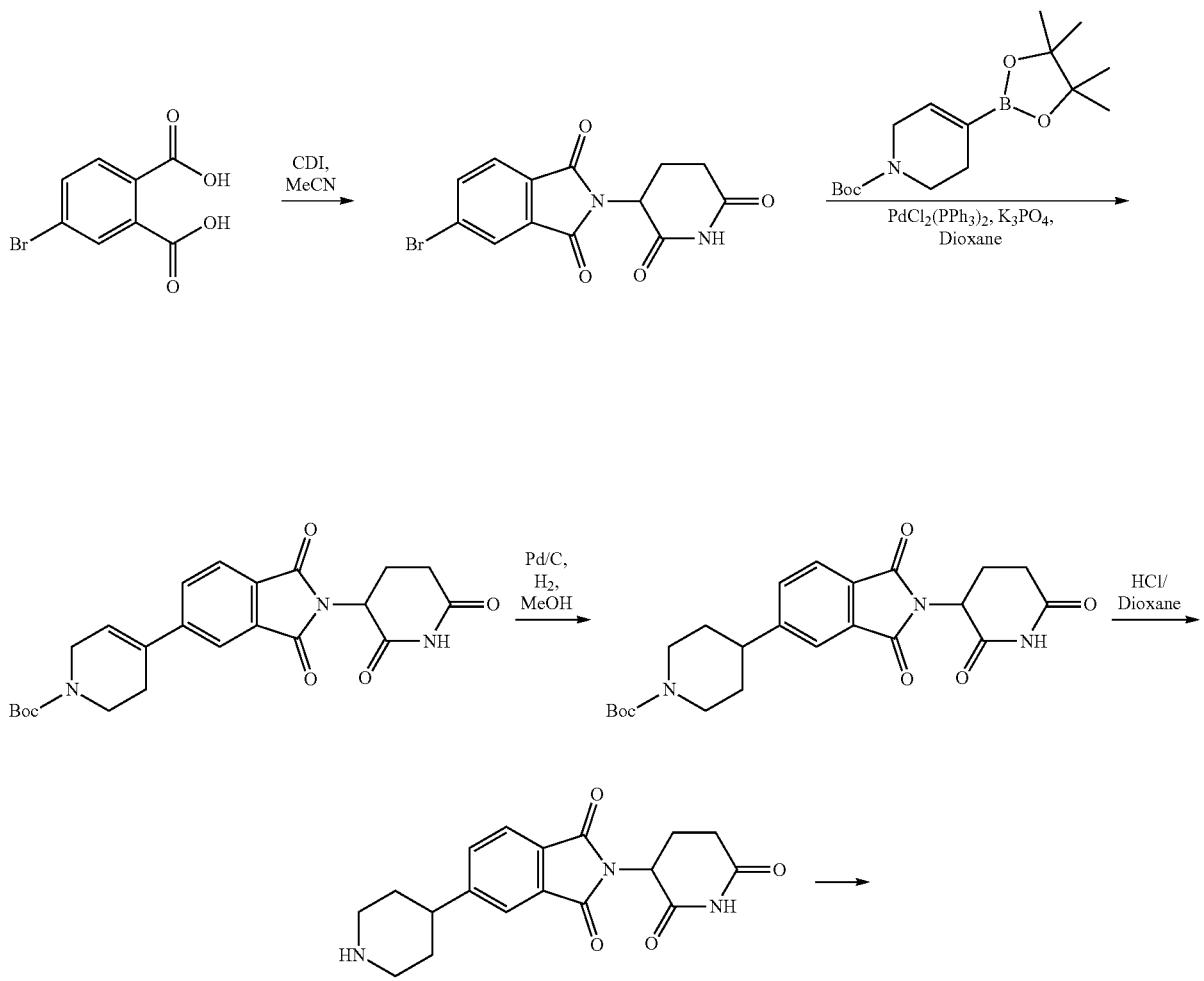

-continued
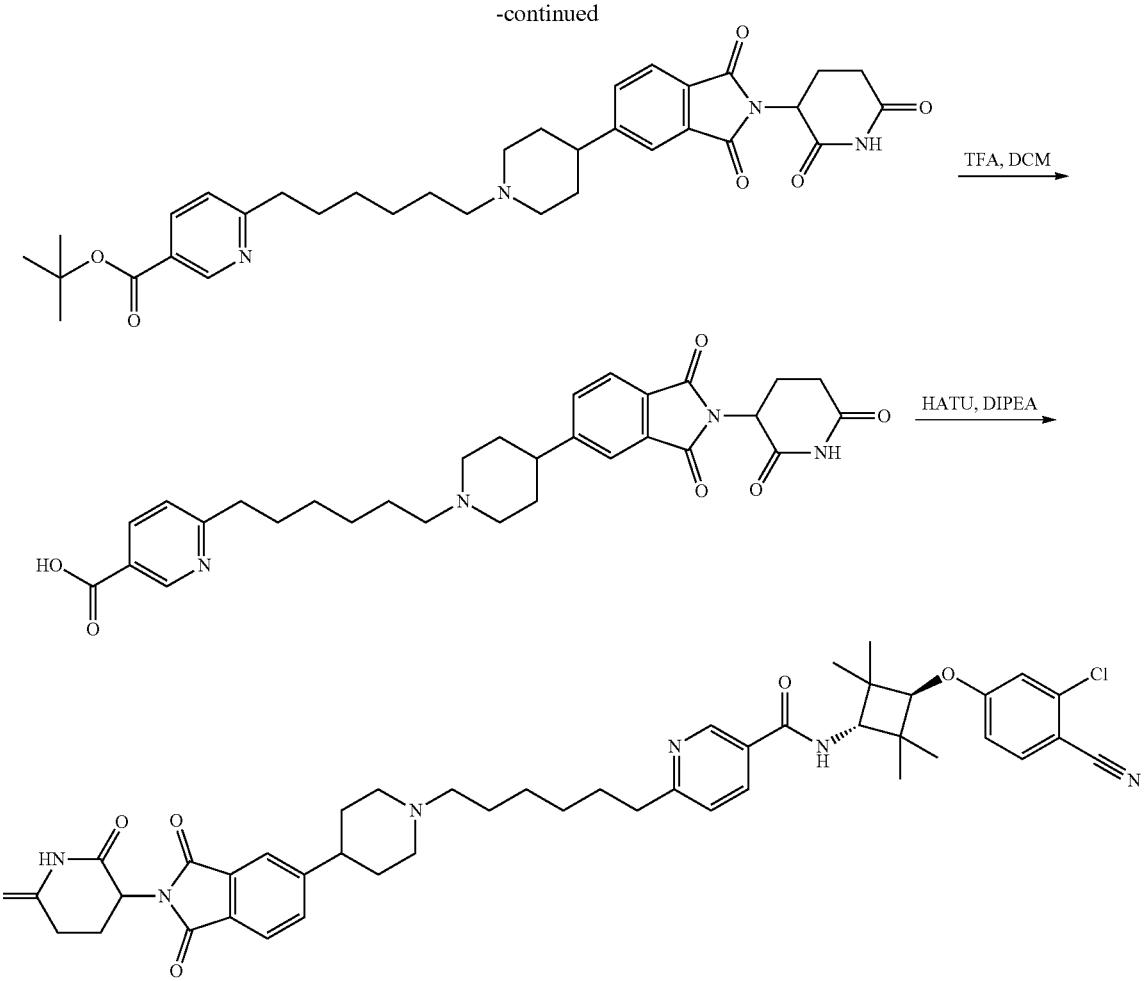
General Scheme 106
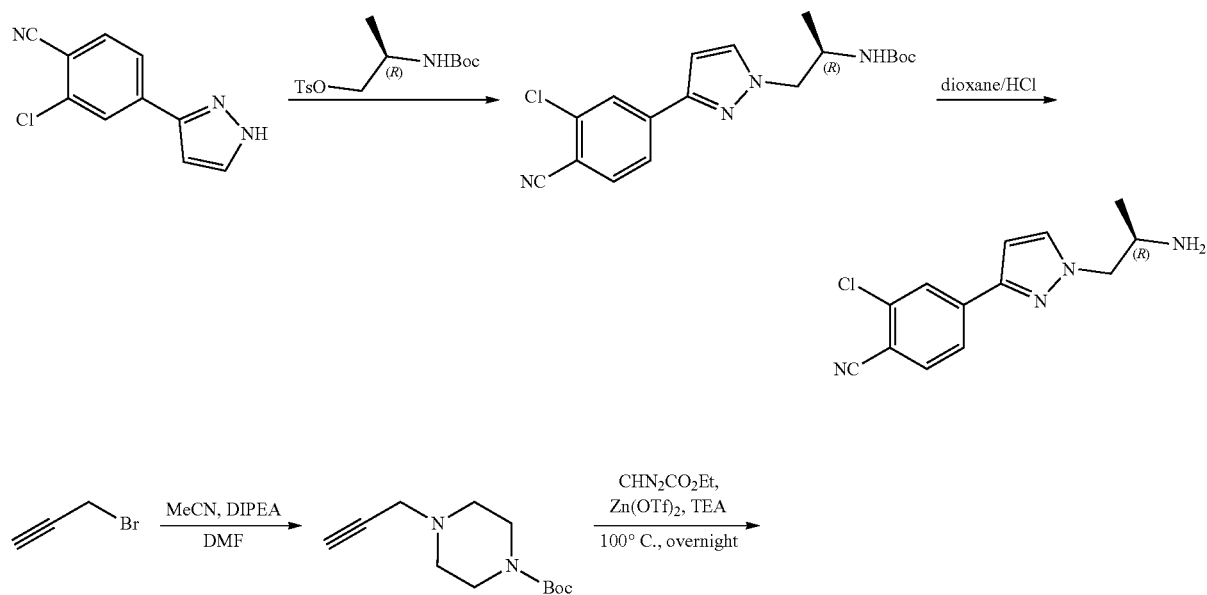

335 336
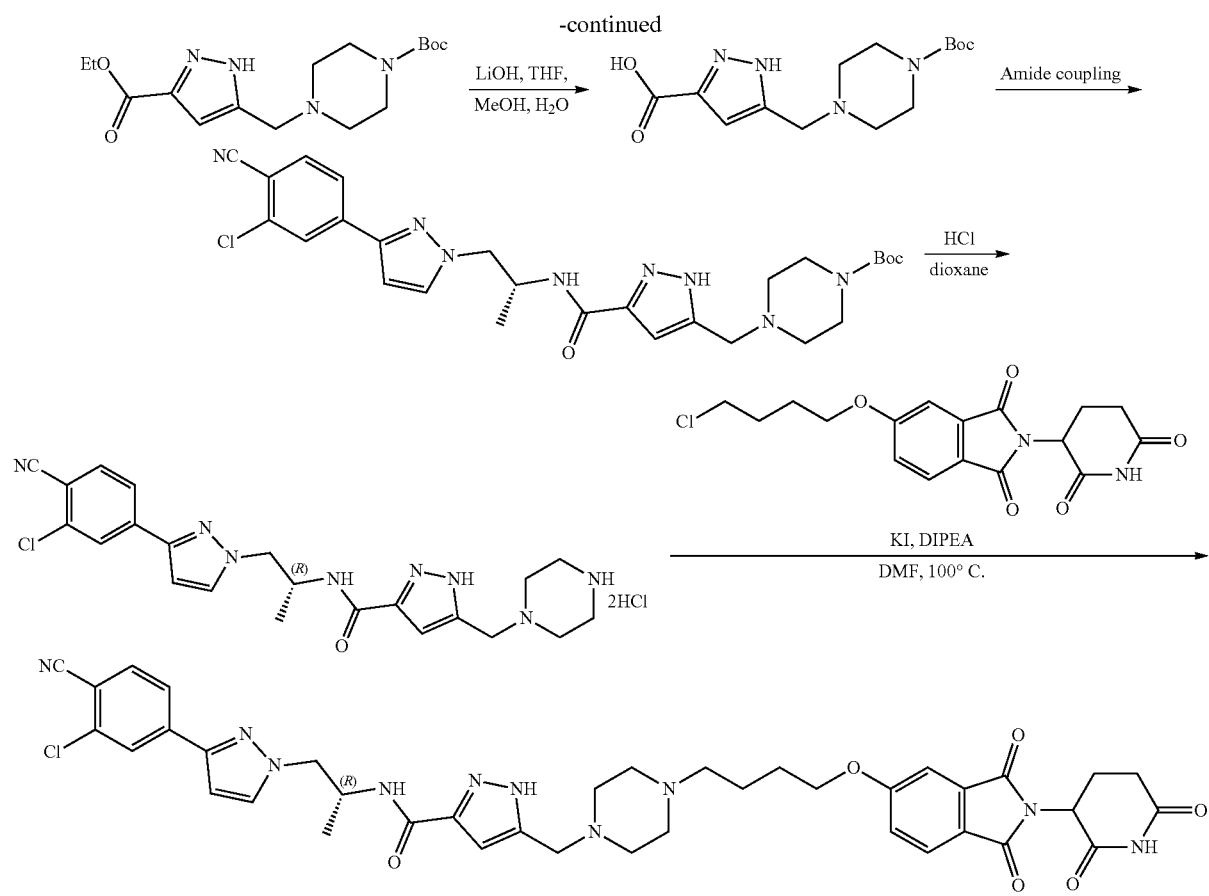
General Scheme 107
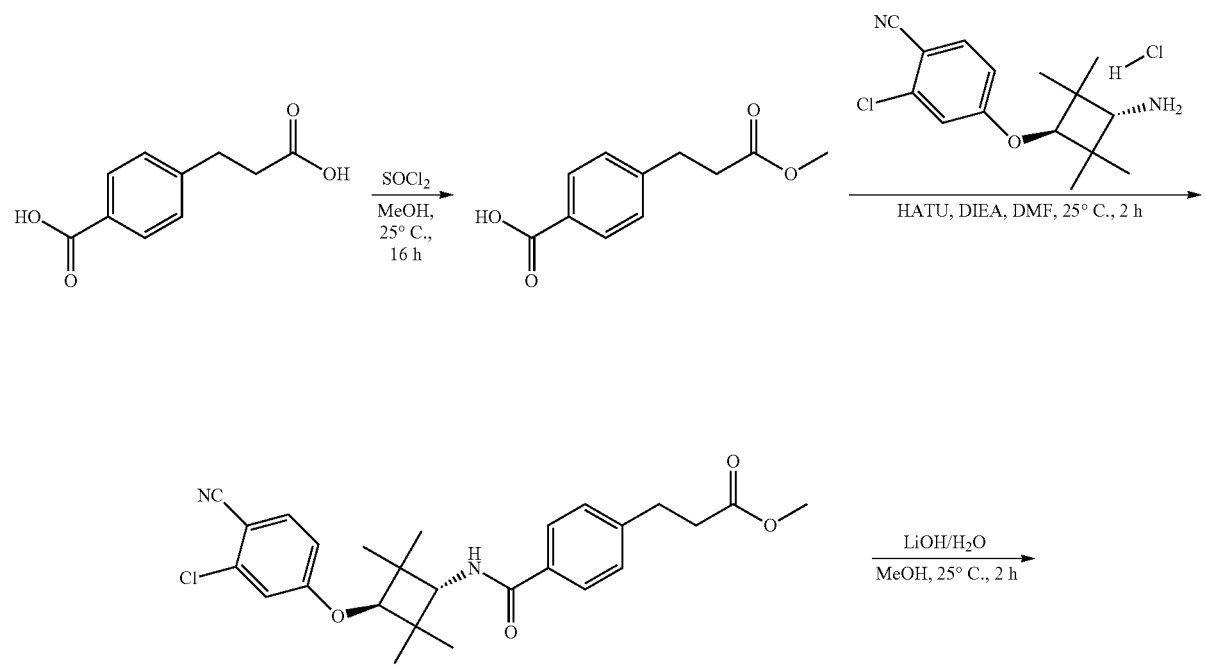

337 338
-continued
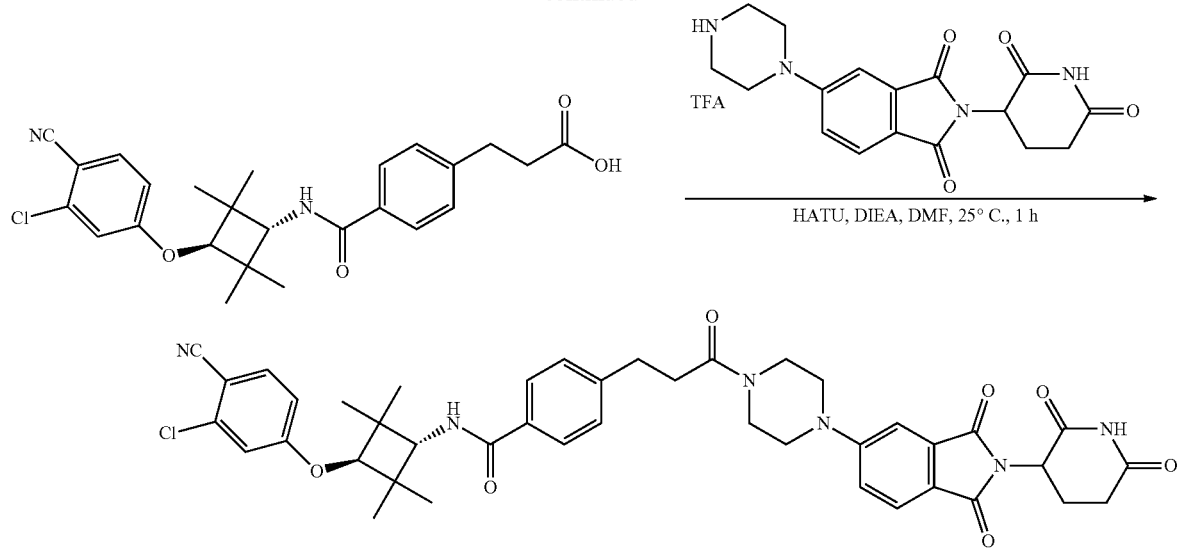
General Scheme 108
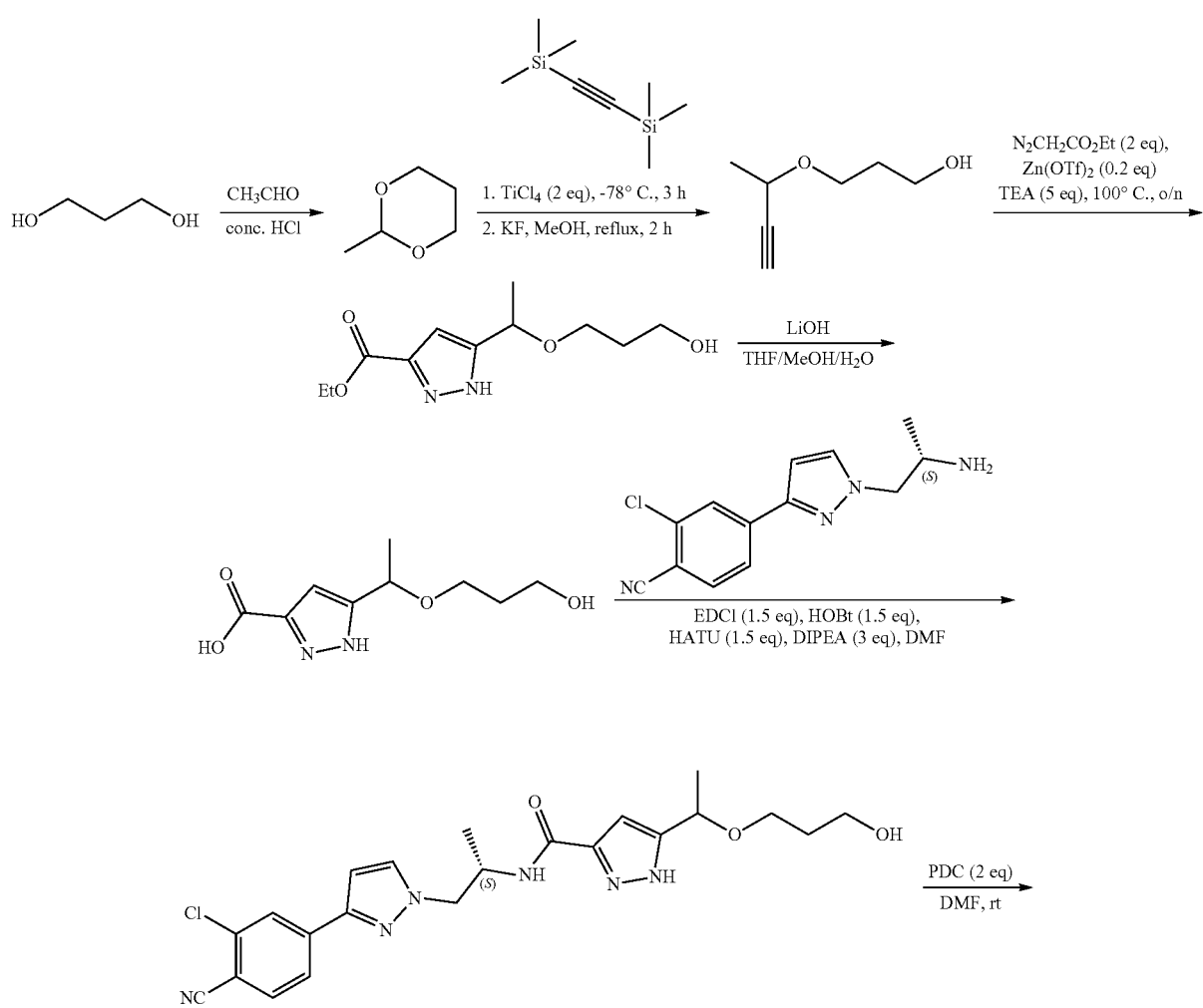

-continued
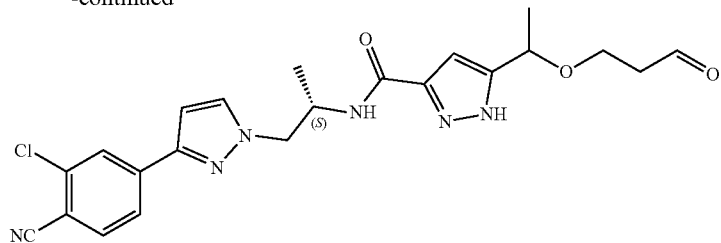
General Scheme 109
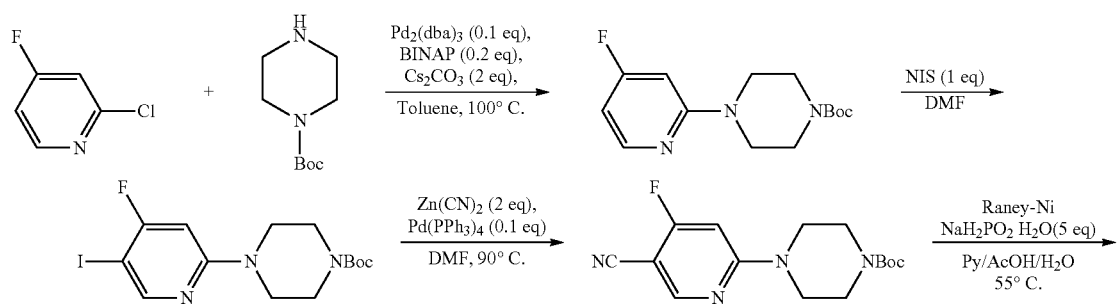
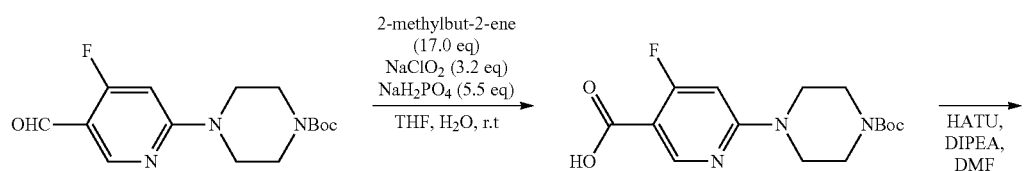
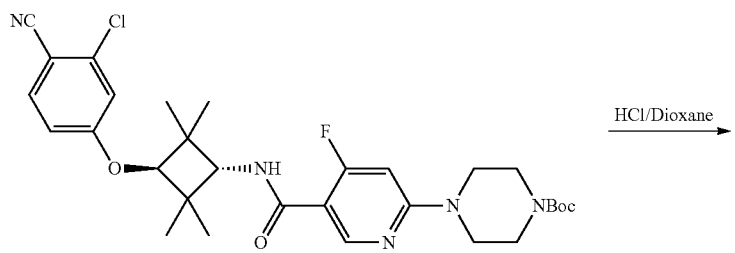
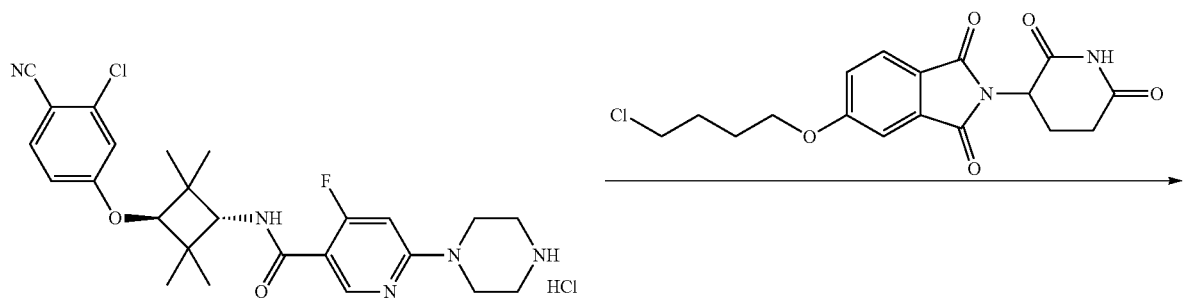

US 11,964,945 B2
341 342
-continued
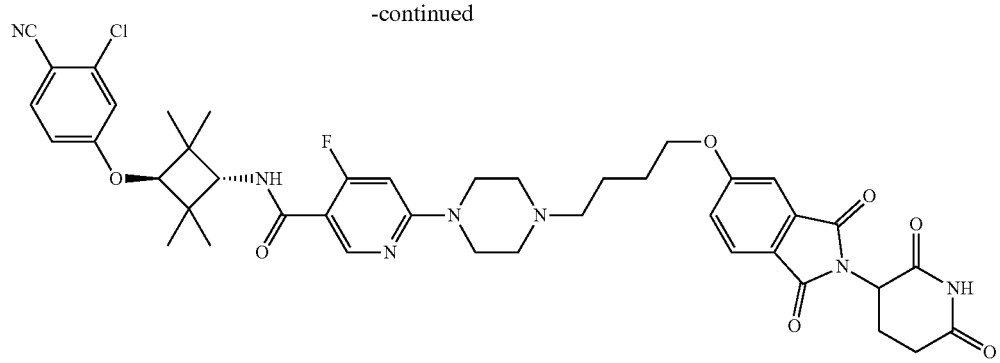
General Scheme 110
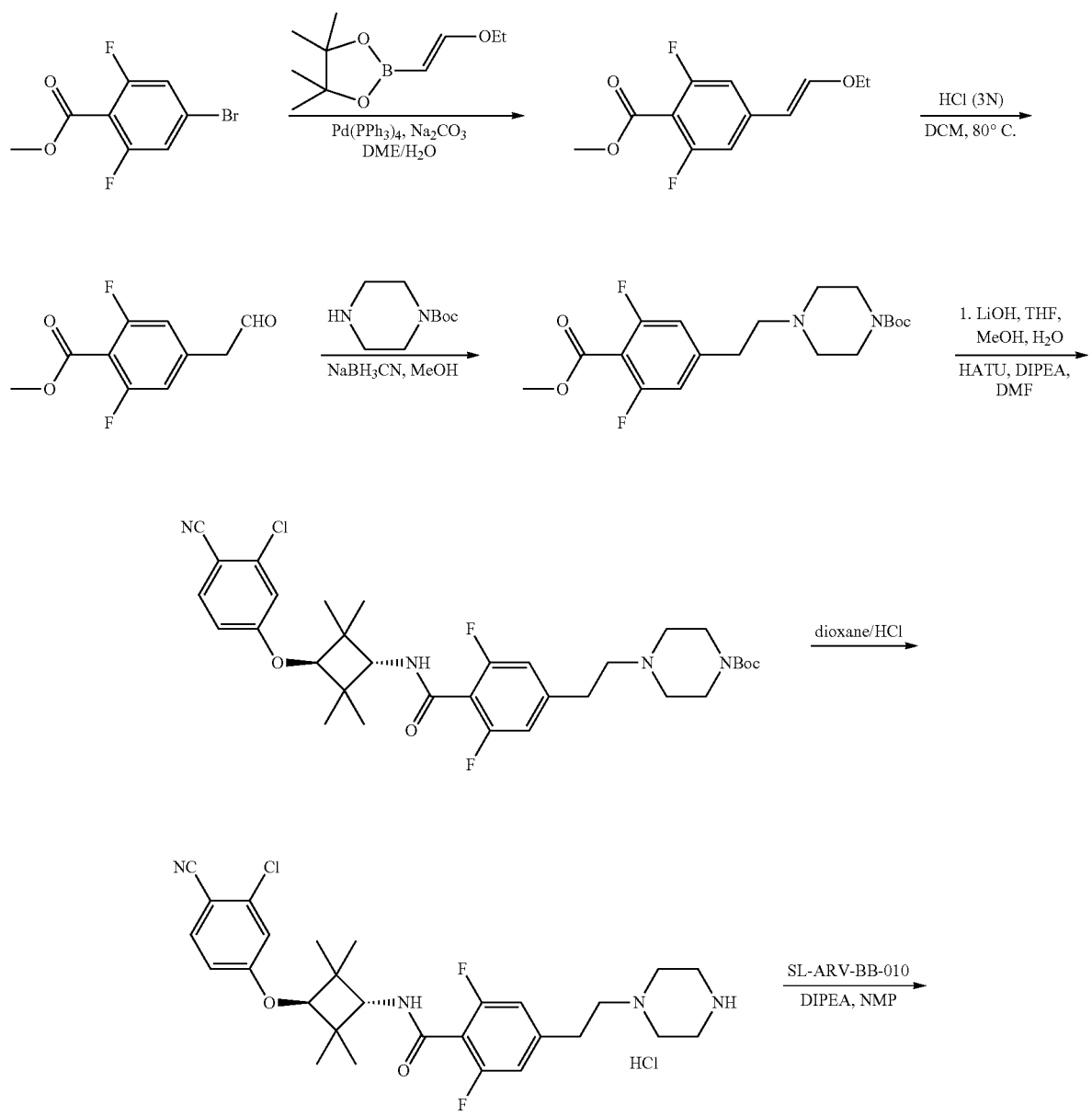

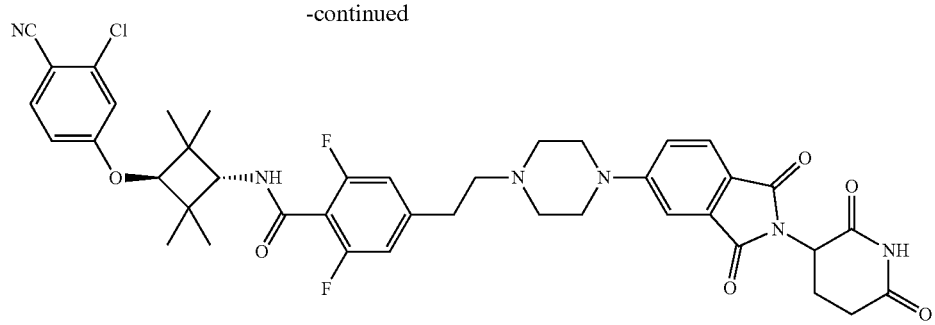
-continued
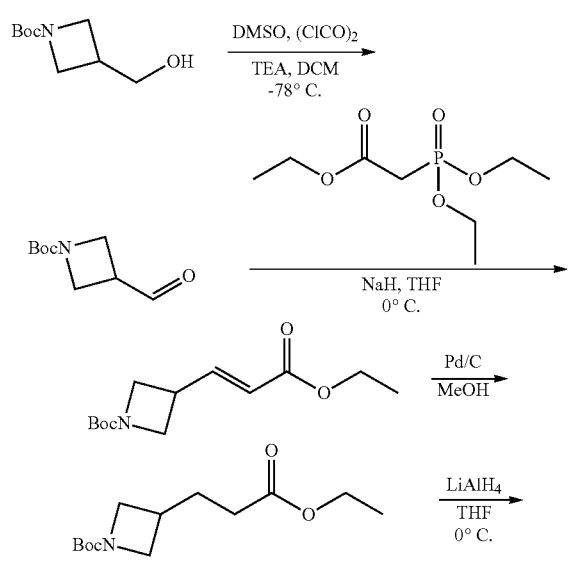
General Scheme 111
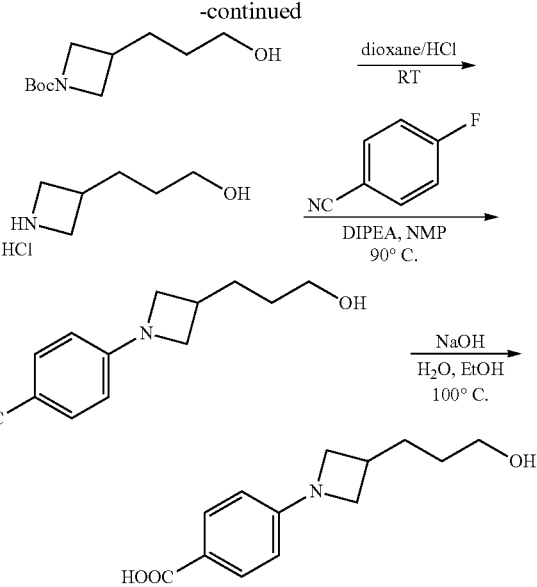
-continued
General Scheme 112
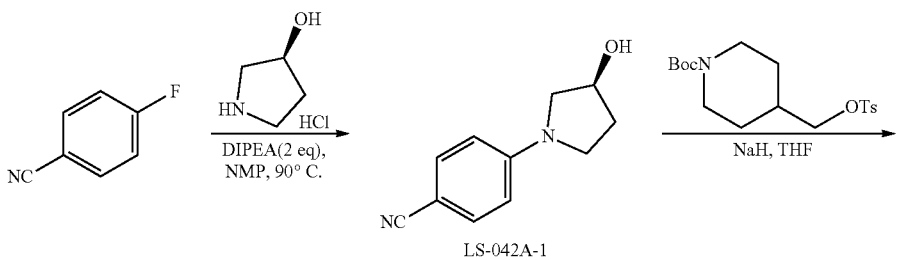
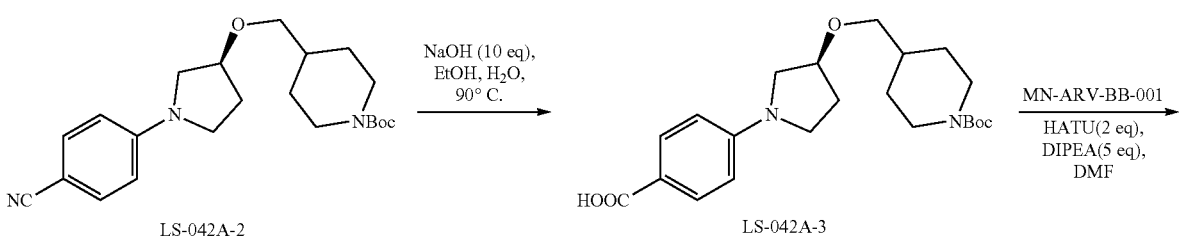

-continued
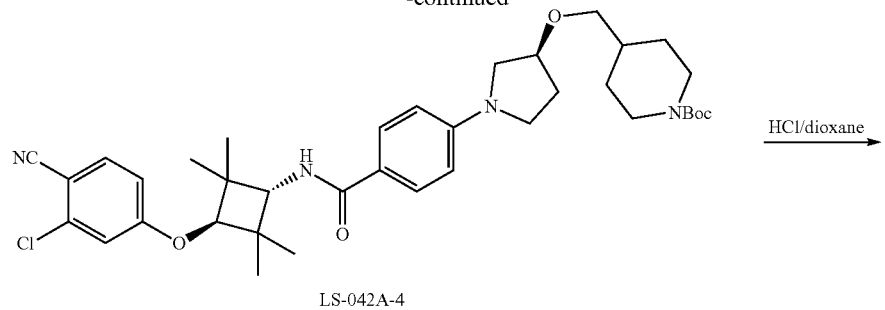
LS-042A-4
HCl/dioxane →
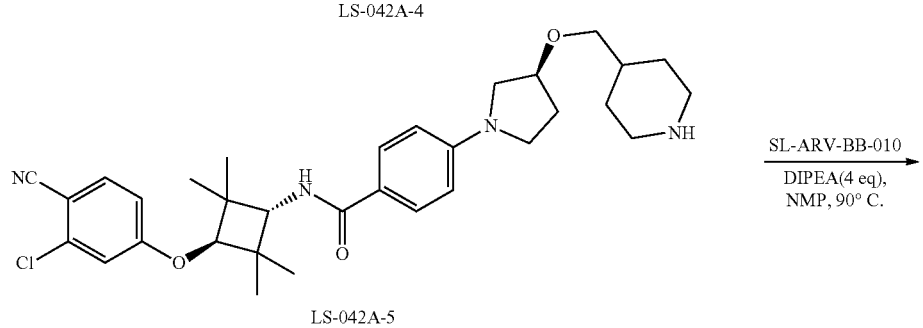
LS-042A-5
SL-ARV-BB-010
DIPEA(4 eq),
NMP, 90° C. →
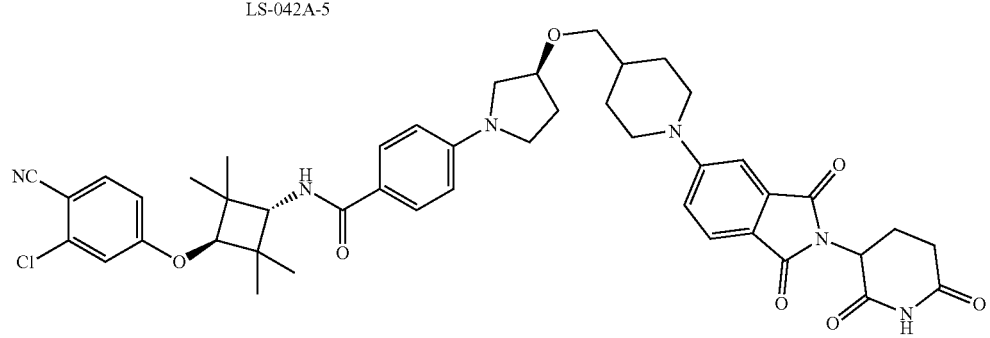
MN-ARV-LS-042A
General Scheme 113
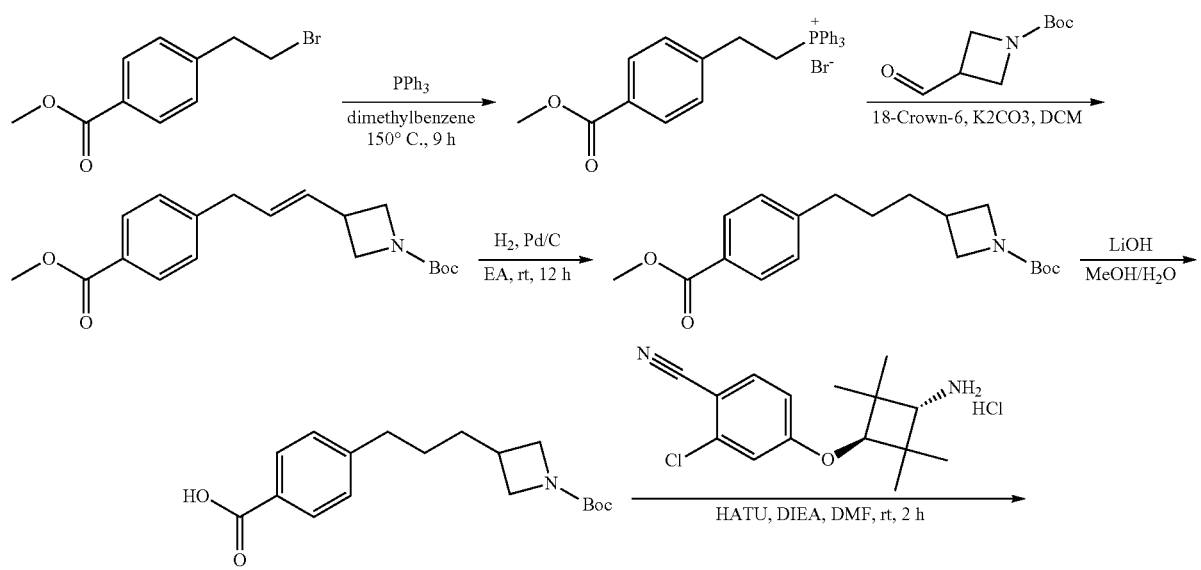

347 348
-continued
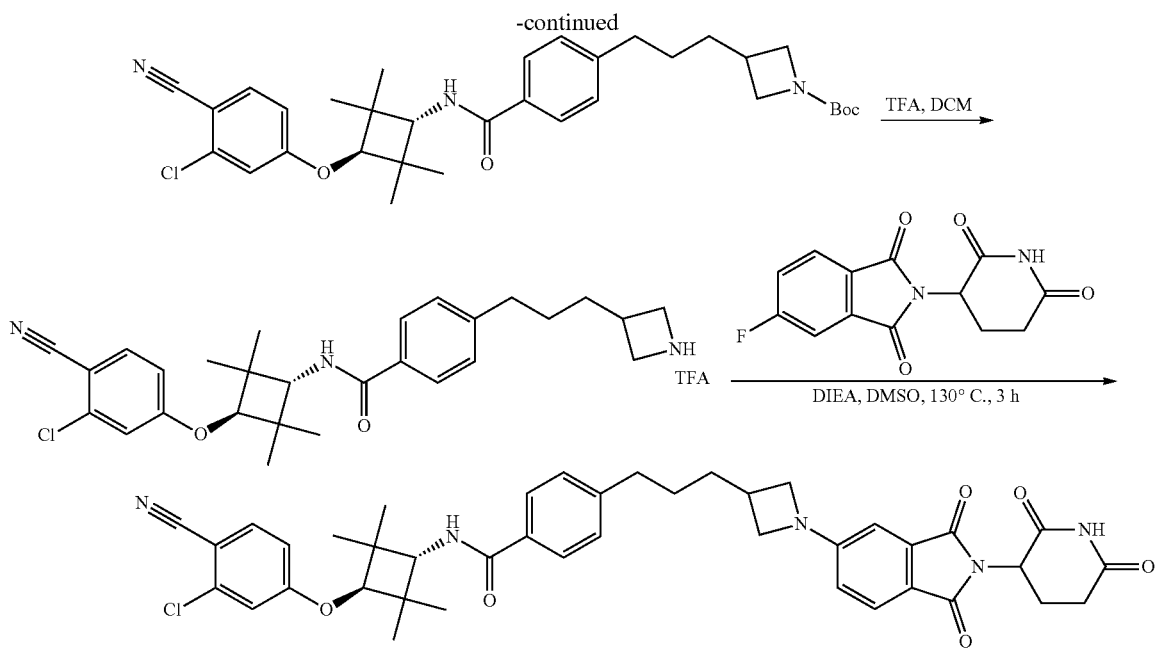
General Scheme 114
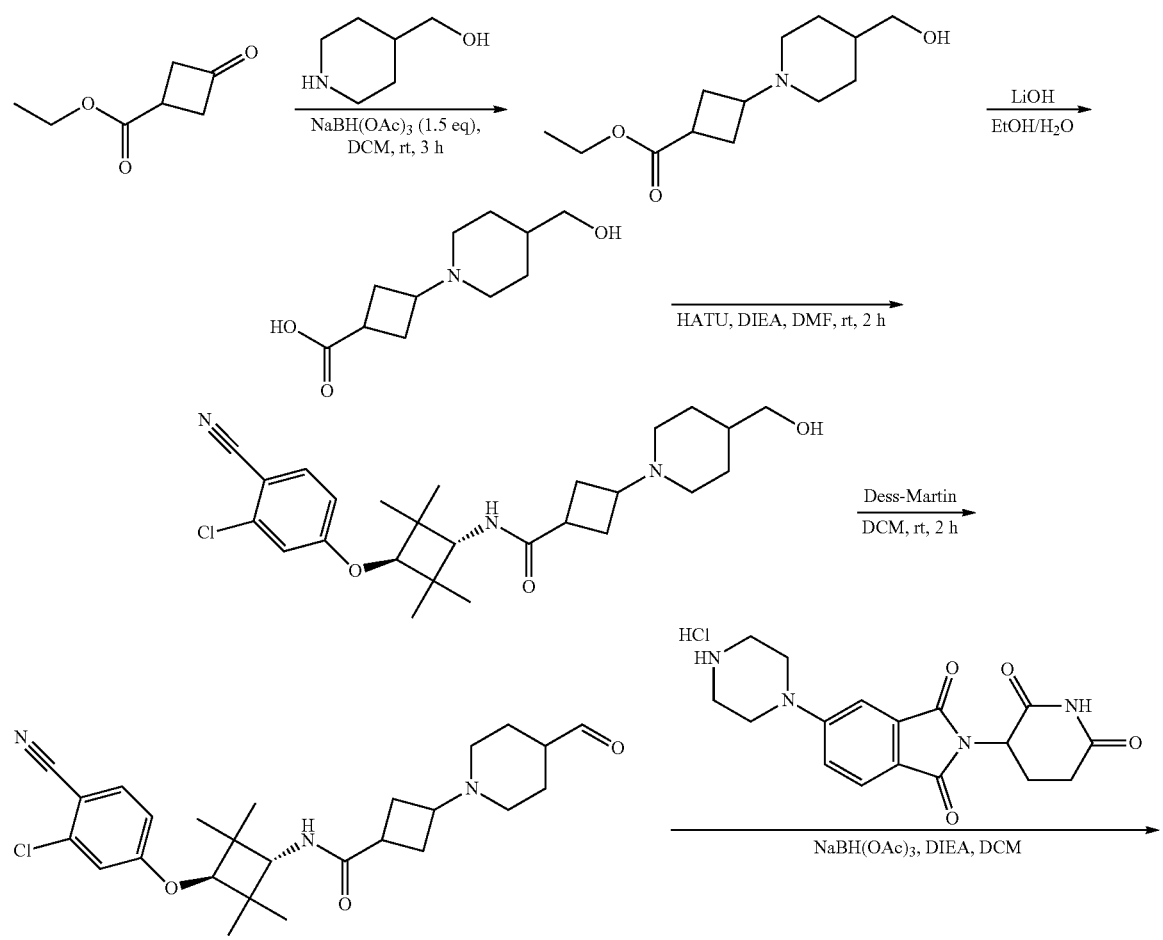

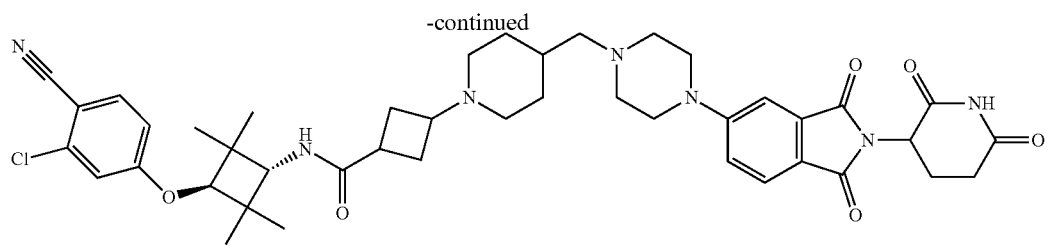
General Scheme 115
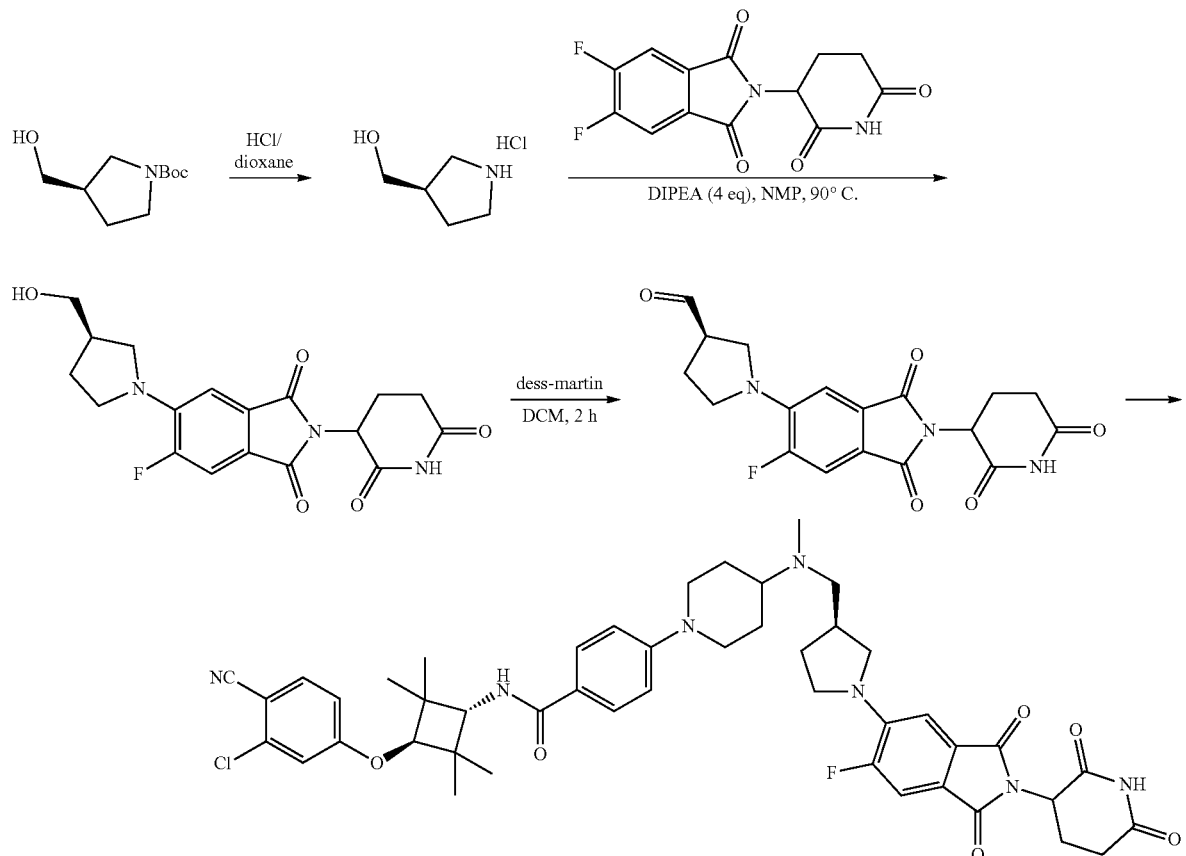
General Scheme 116
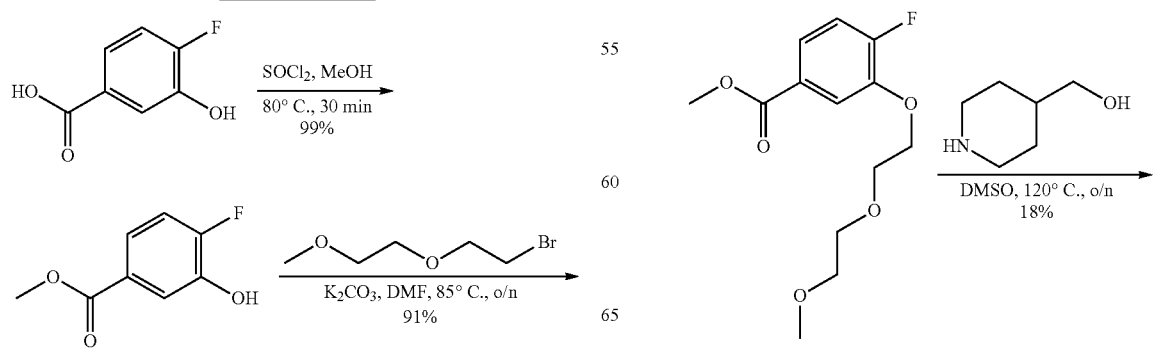

351 352
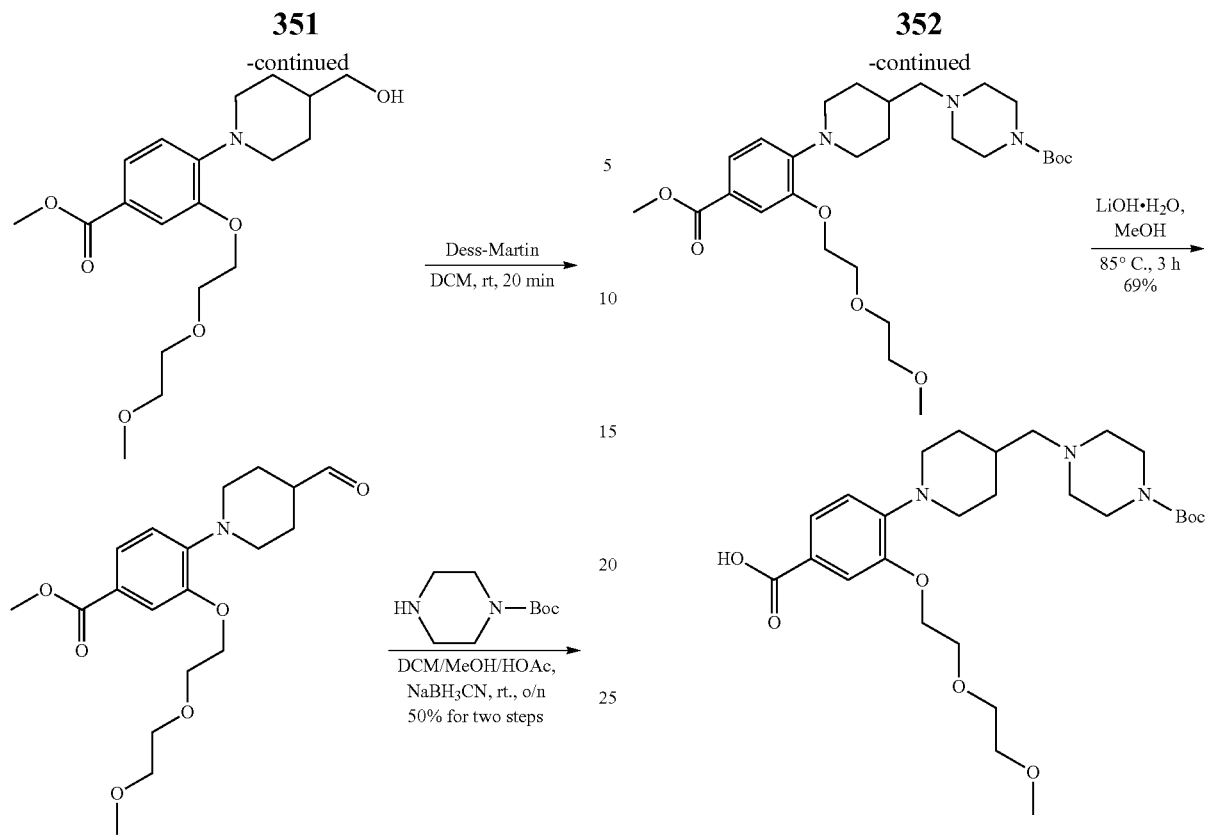
General Scheme 117
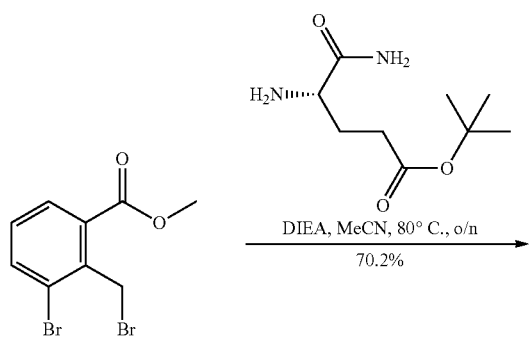
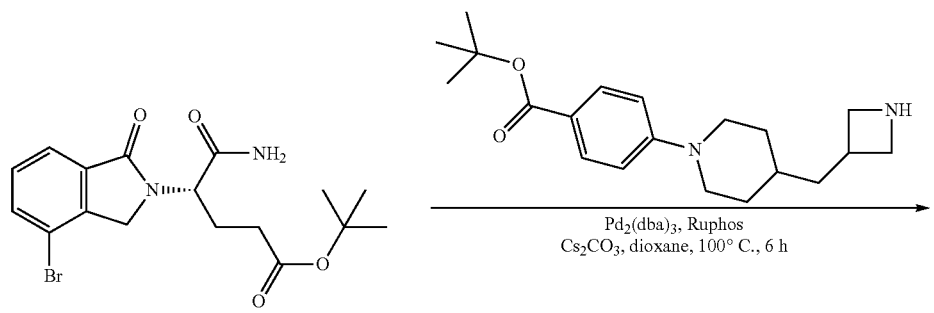

-continued
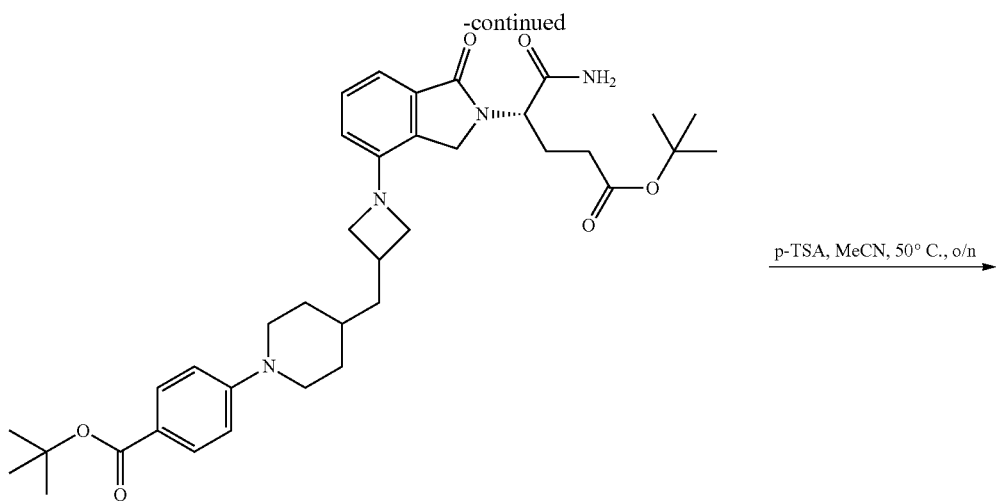
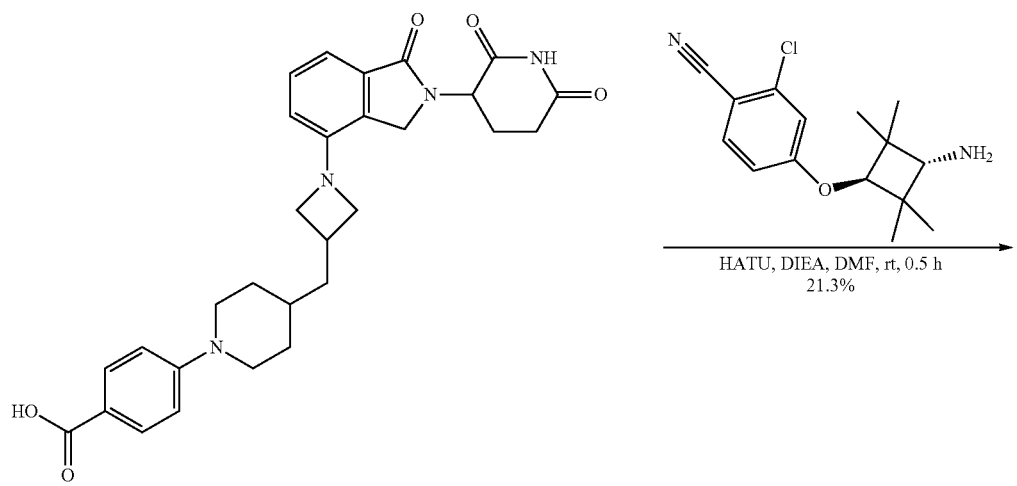
CP-ARV-LS-004H-3
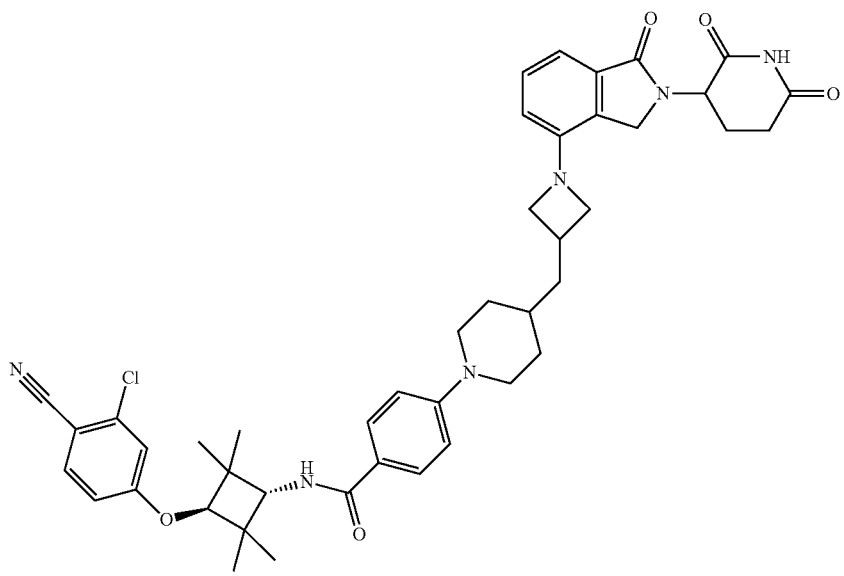 [SMILES: CC1(C)[C@H](NC(=O)c2ccc(N3CCC(CC4CN(c5cccc6c5CN(C5CCC(=O)NC5=O)C6=O)C4)CC3)cc2)C(C)(C)[C@H]1Oc1ccc(C#N)c(Cl)c1]

General Scheme 118
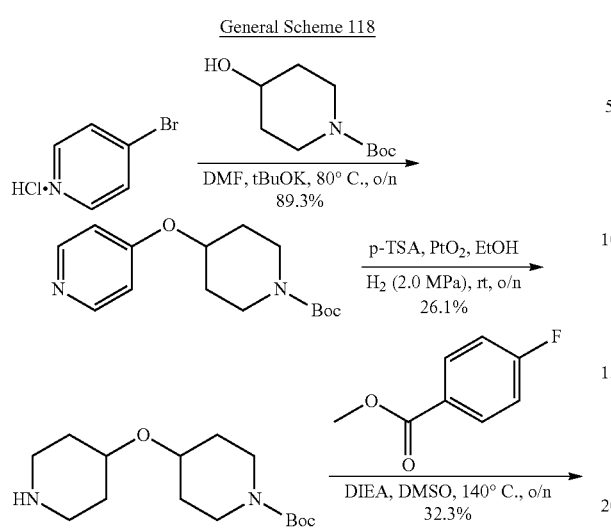
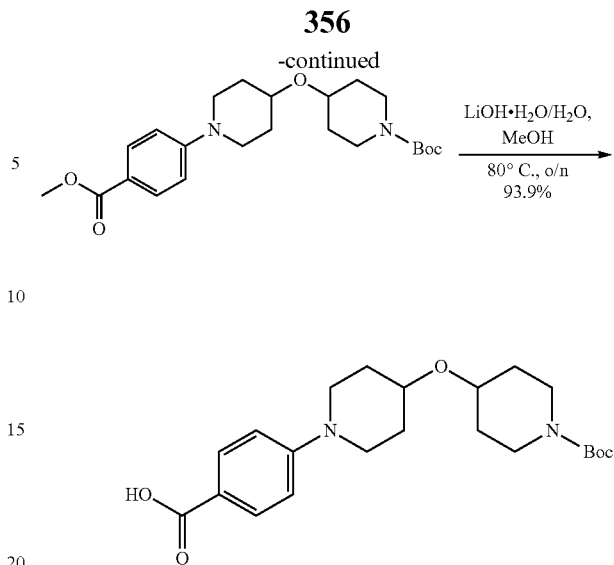
General Scheme 119
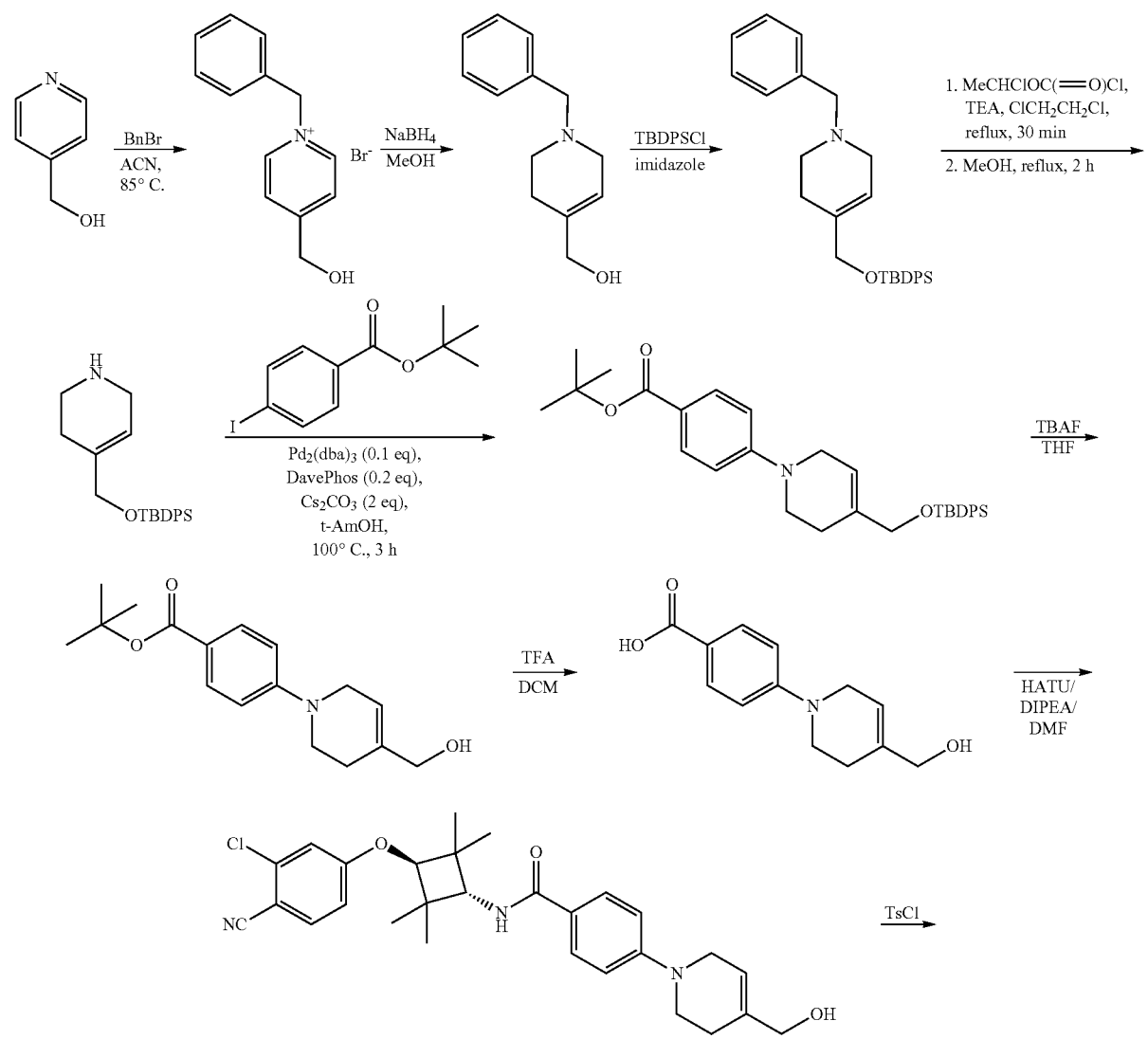

-continued
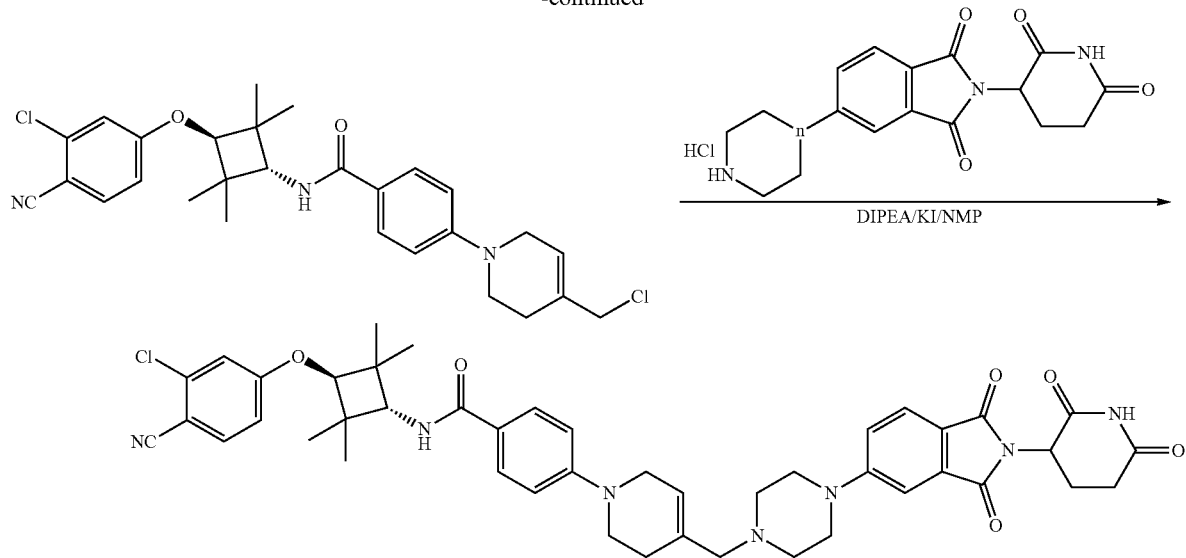
General Scheme 120
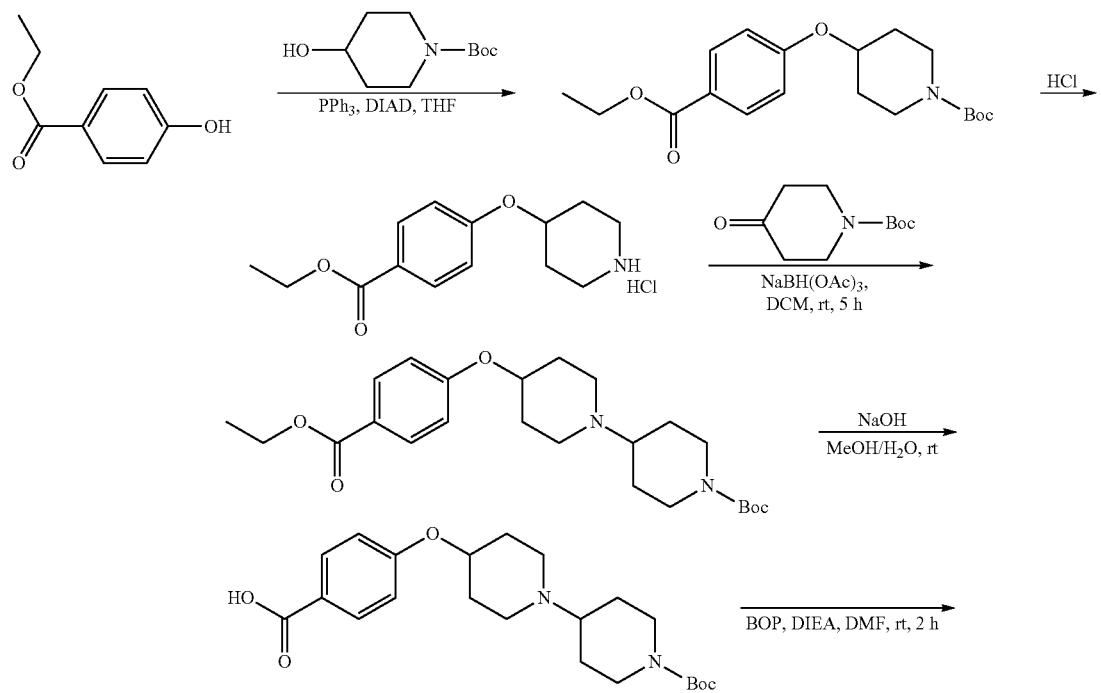
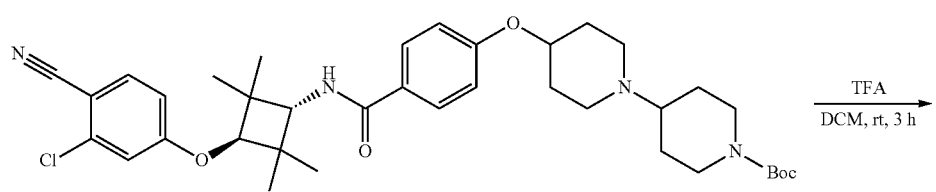

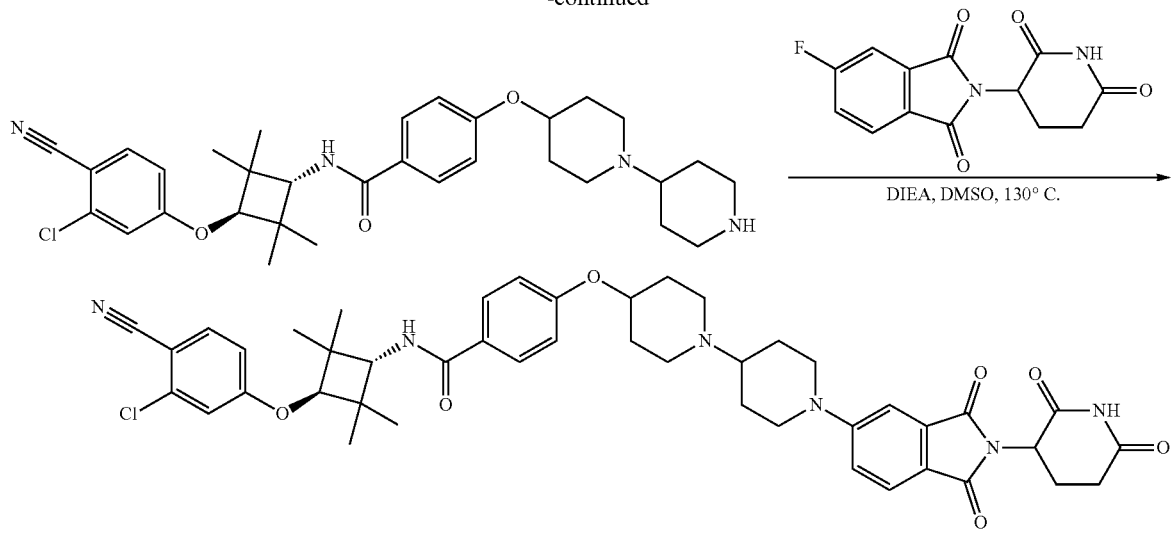
General Scheme 121
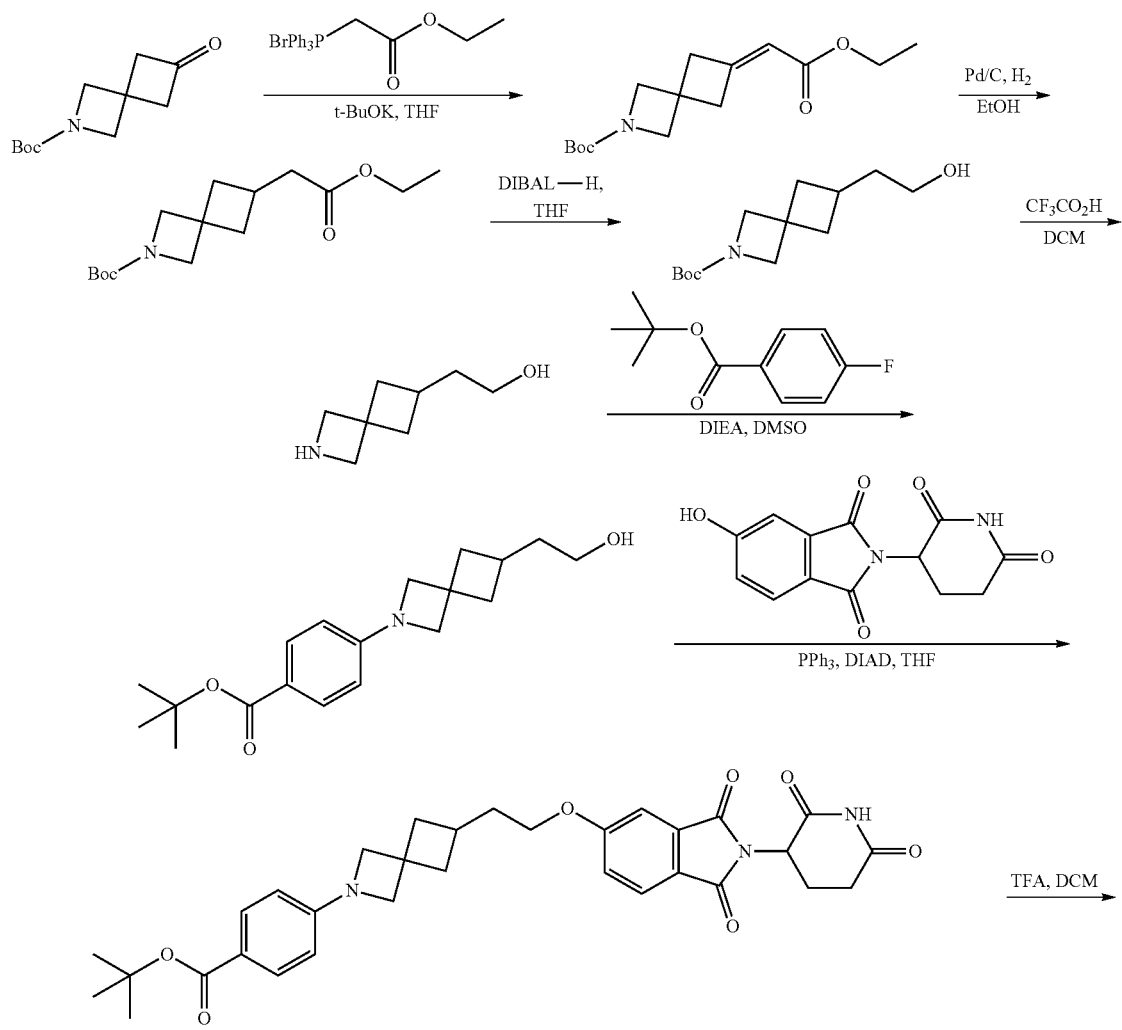

361
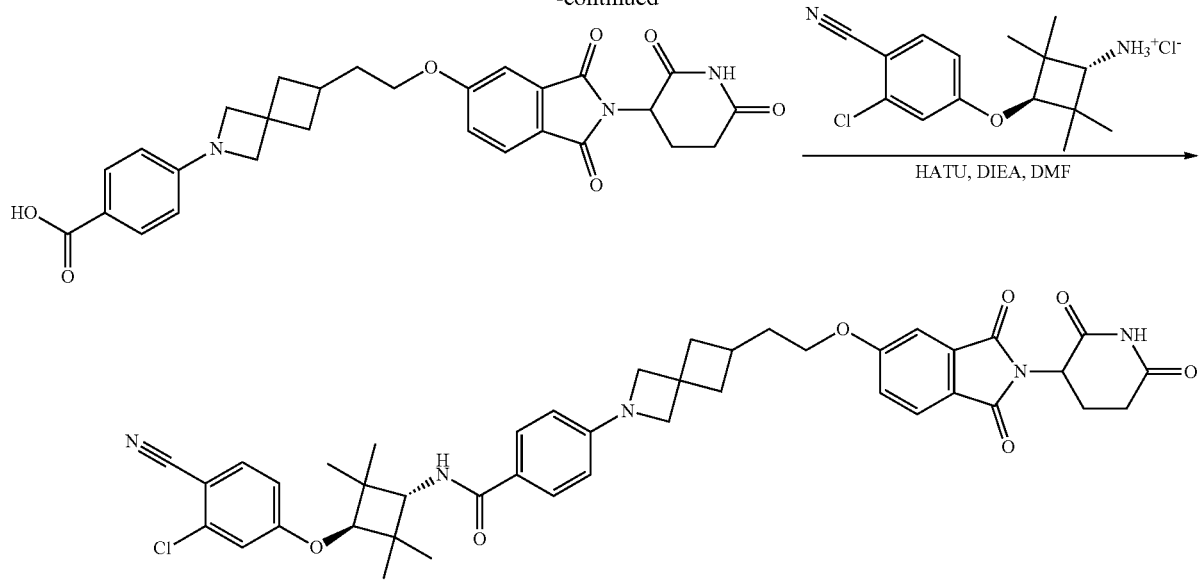
-continued
362
General Scheme 122
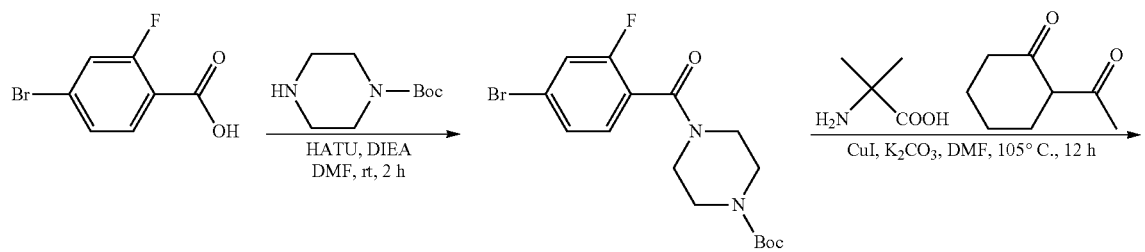
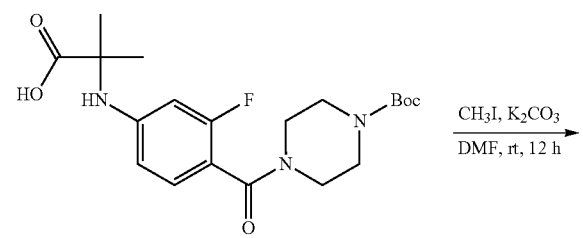
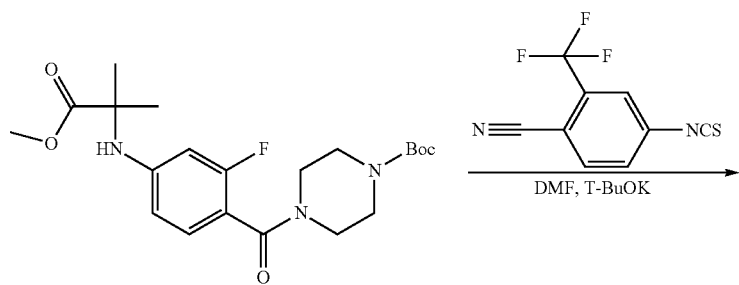

-continued
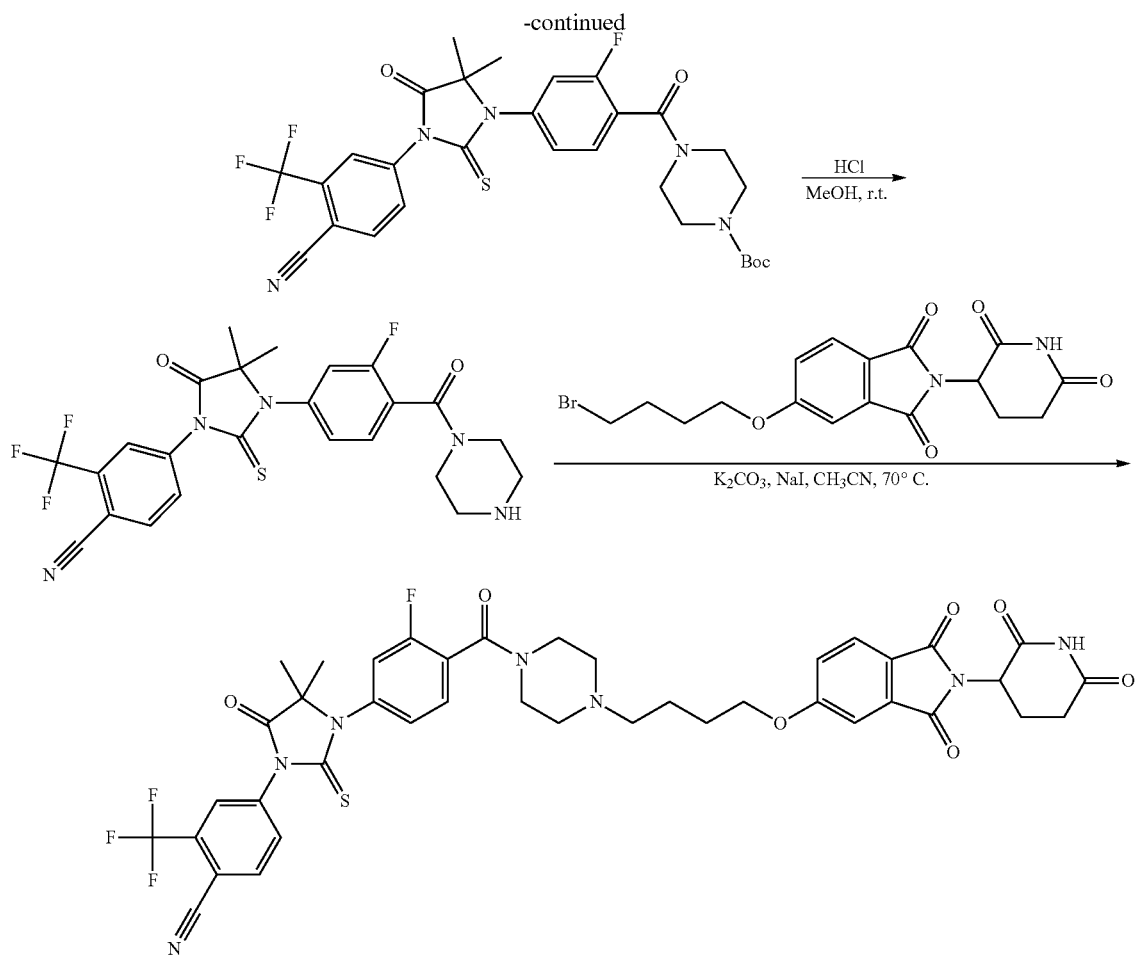
General Scheme 1A
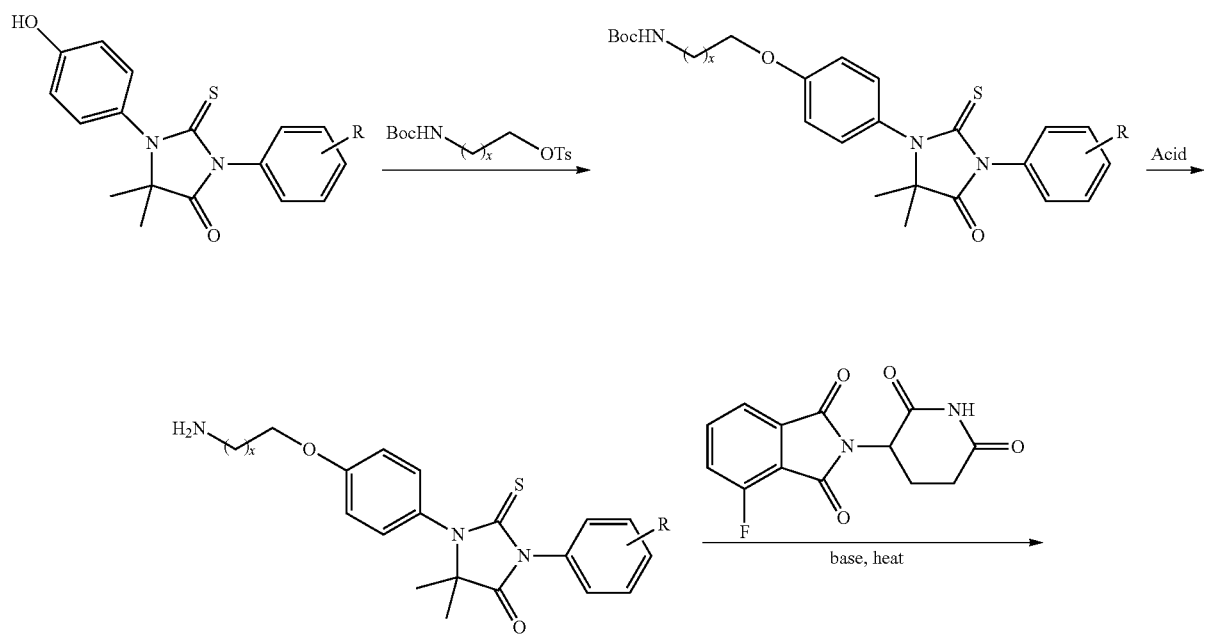

-continued
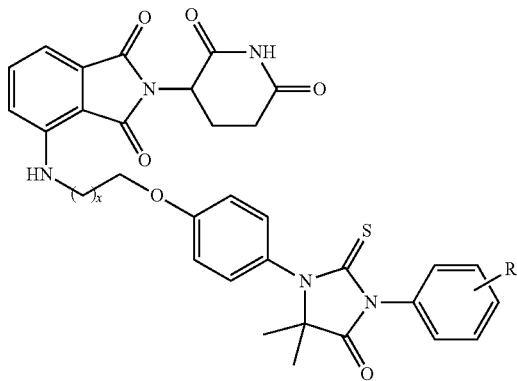
General Scheme 2A
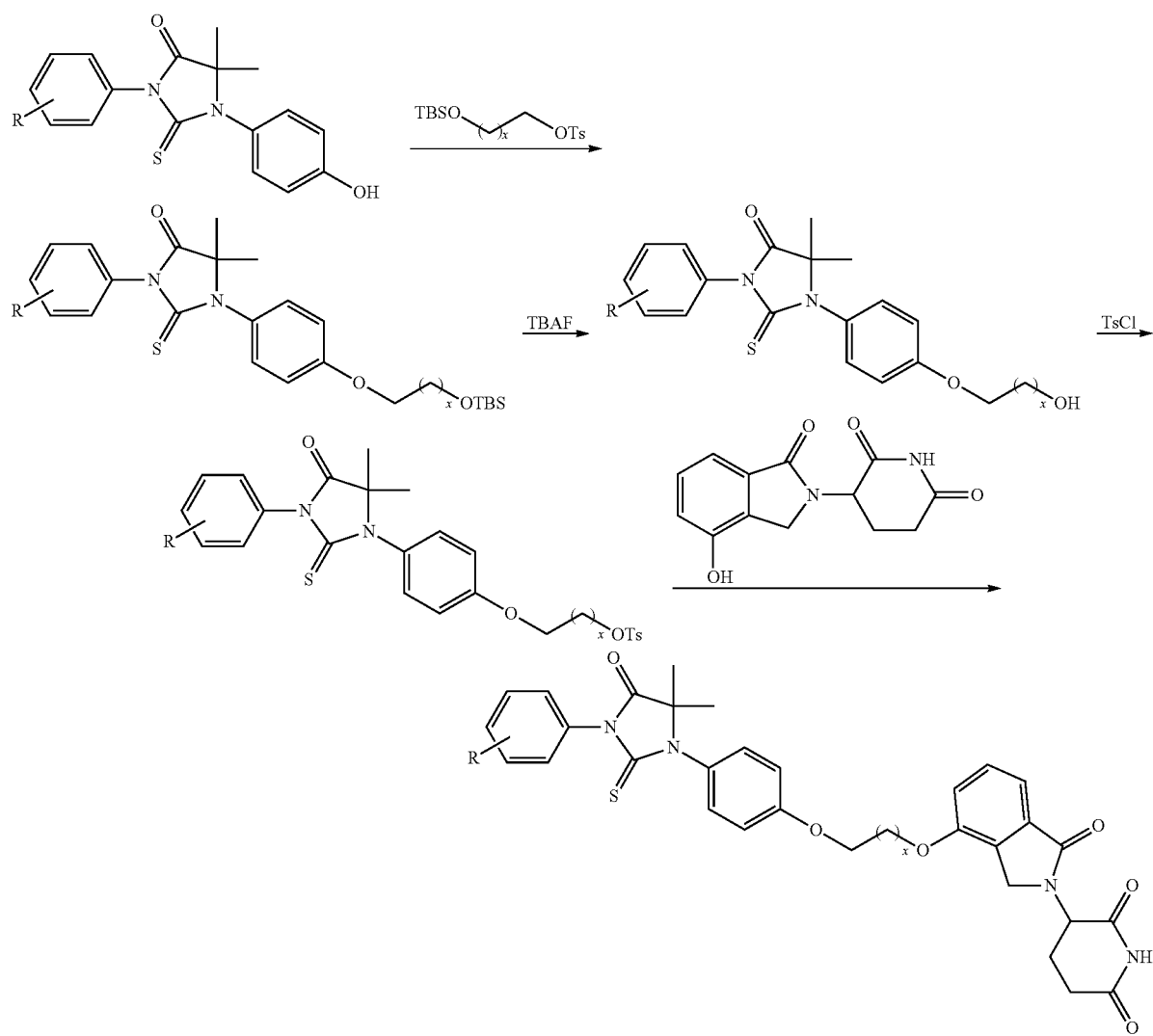

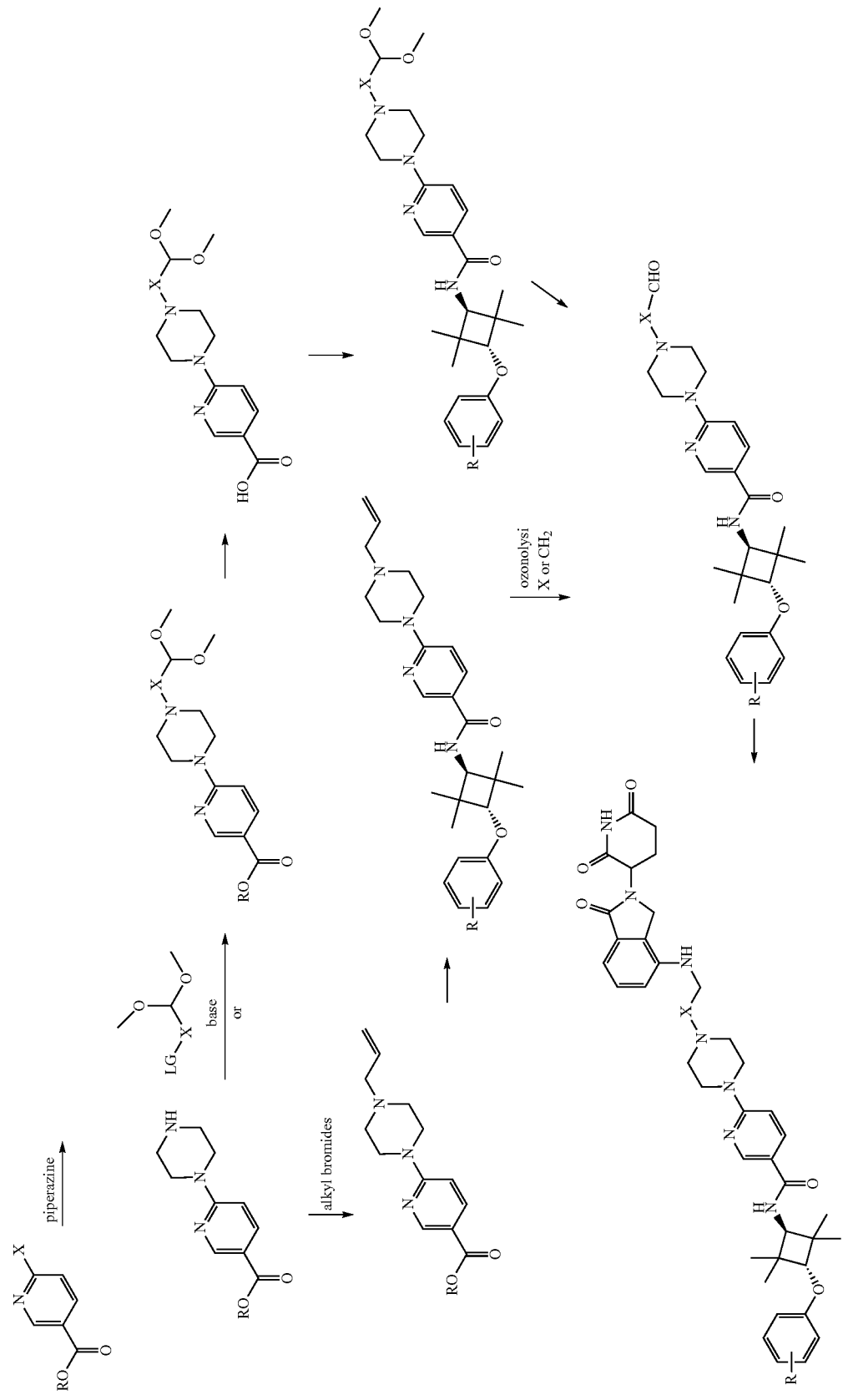

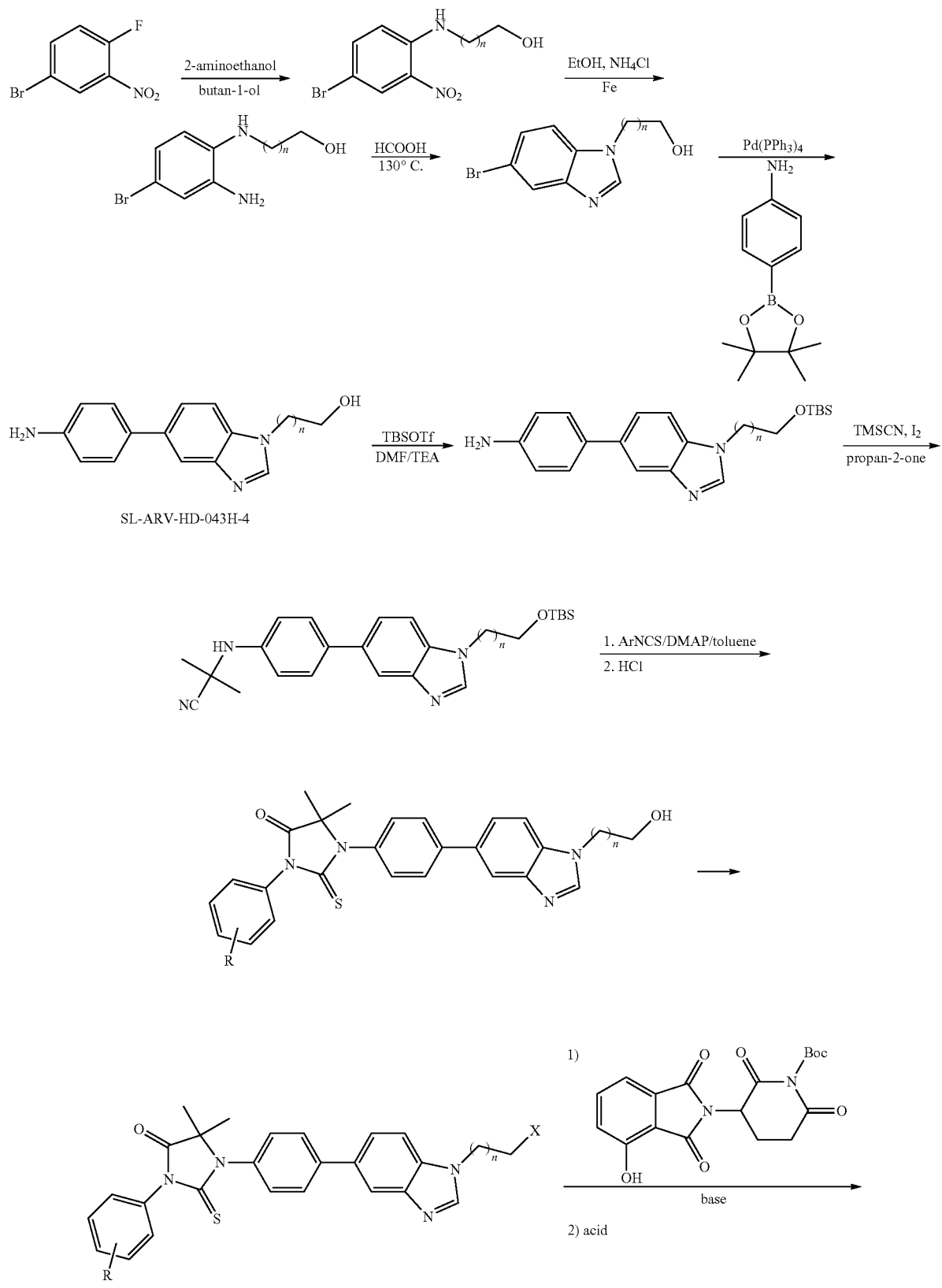
General Scheme 4A

-continued
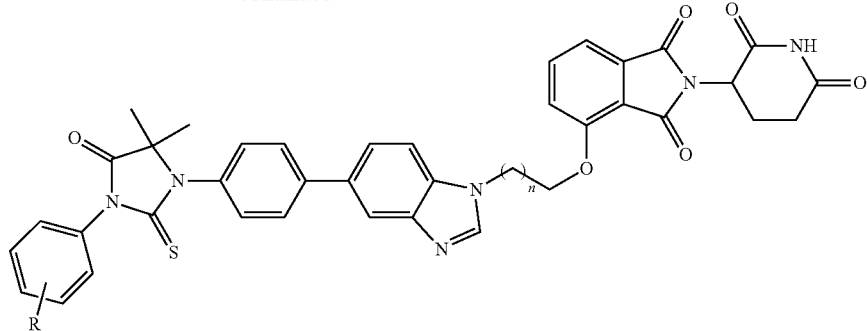
General Scheme 5A
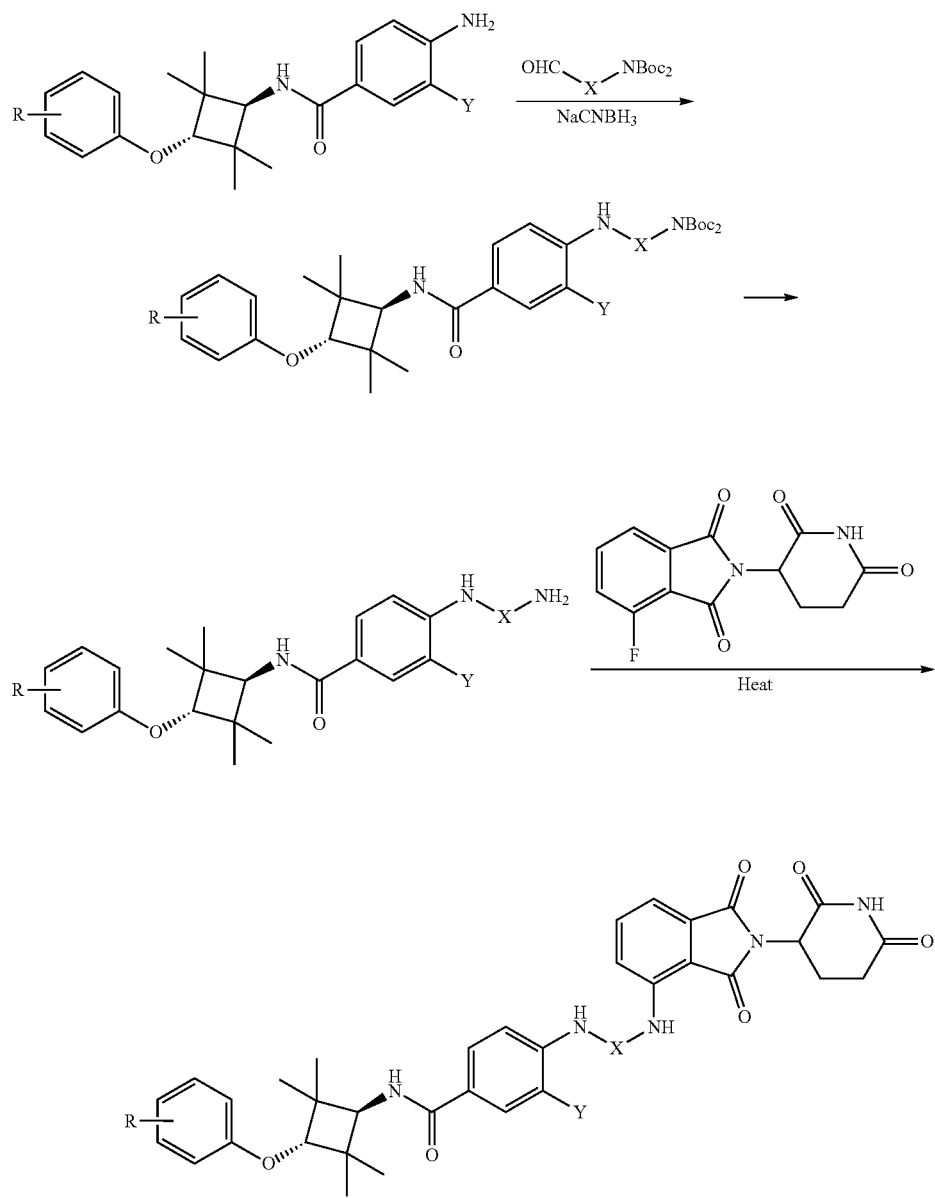

General Scheme 6A
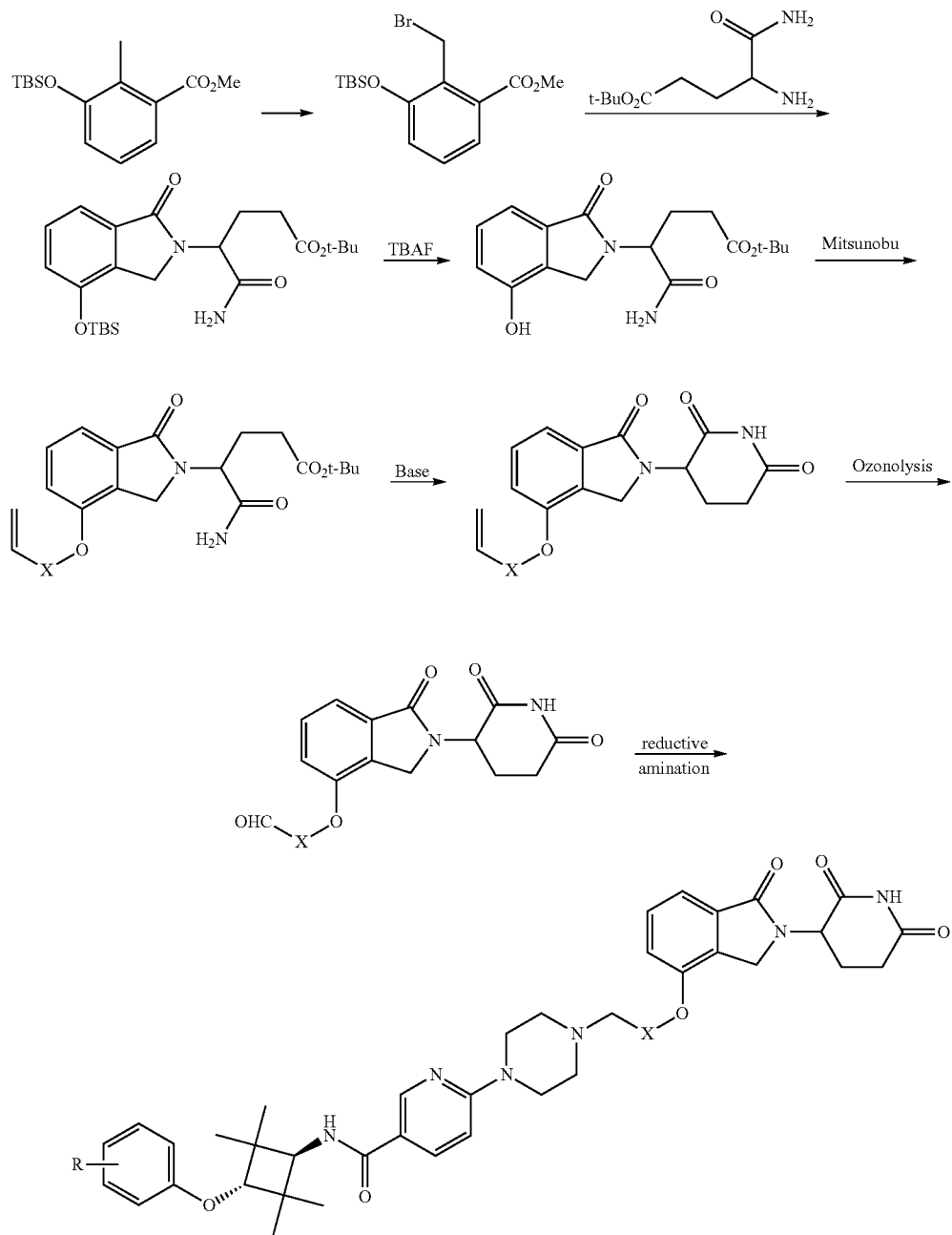
General Scheme 7A
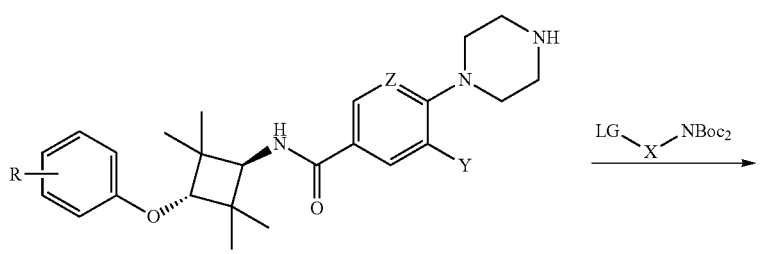

-continued
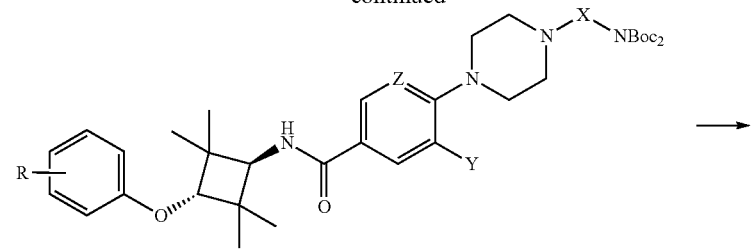
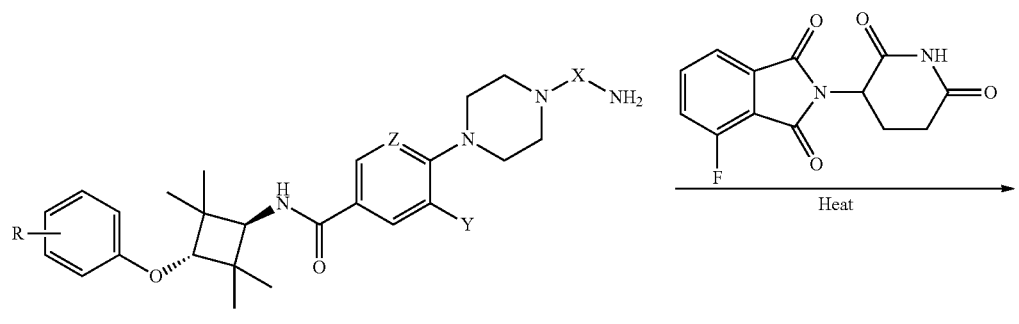
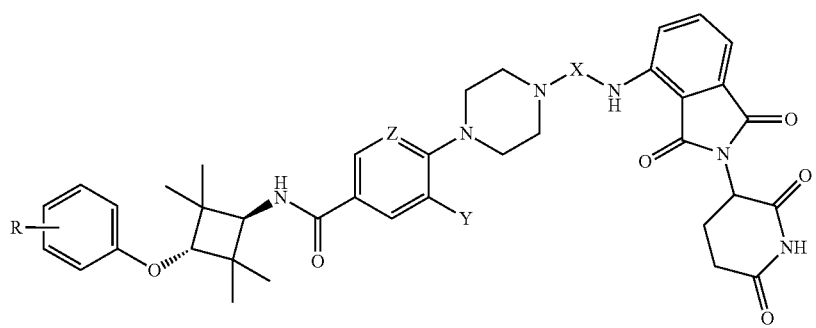
General Scheme 8A
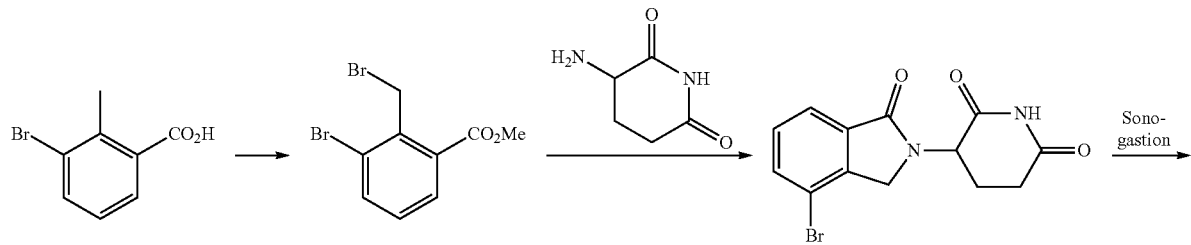

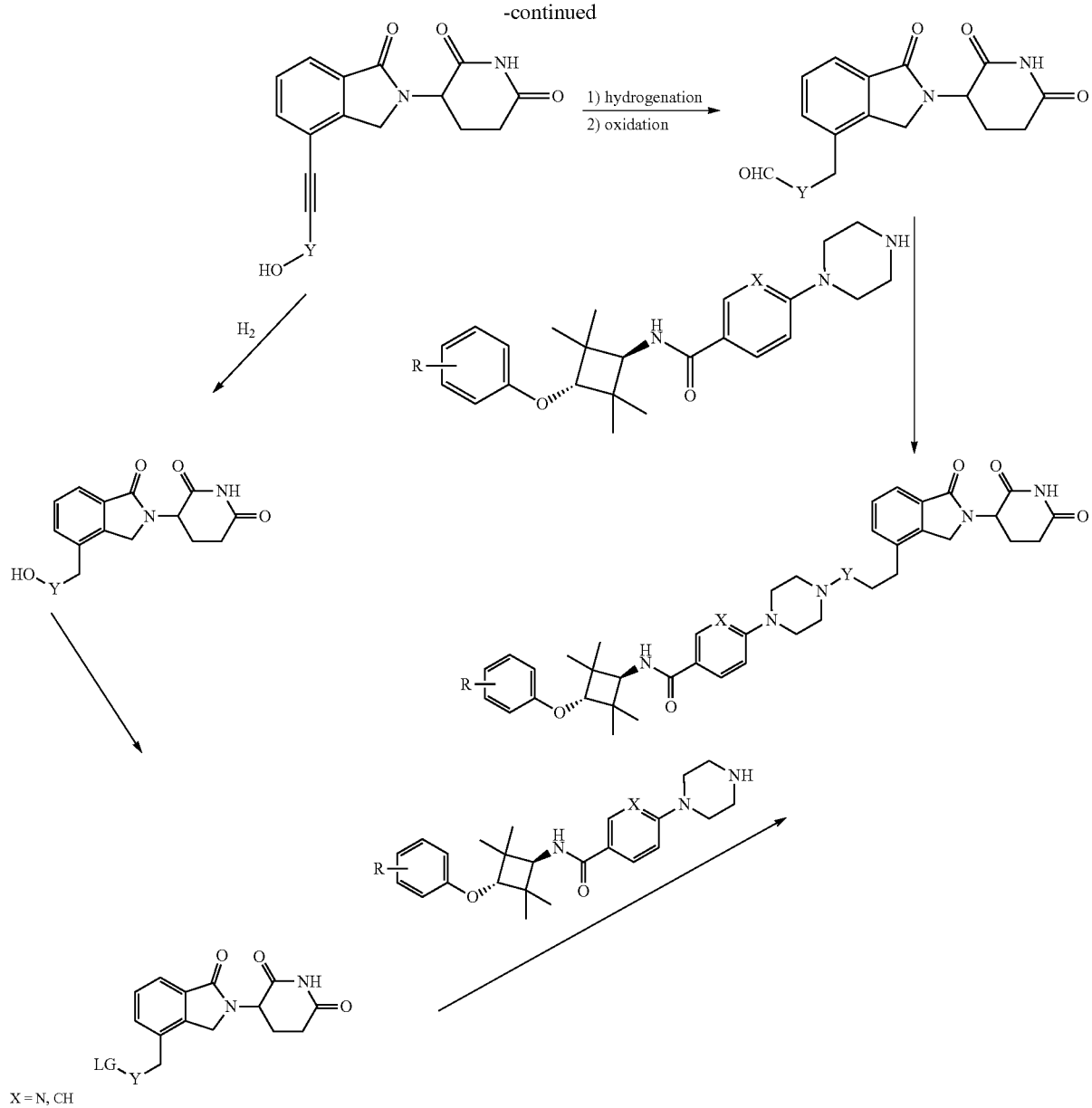
General Scheme 9A
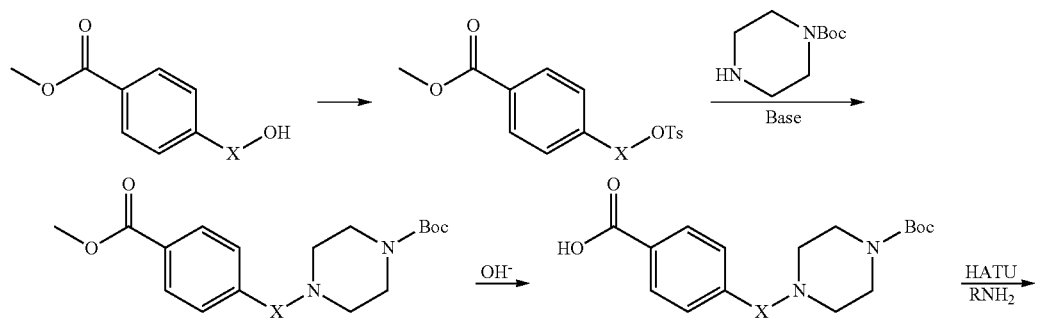

-continued
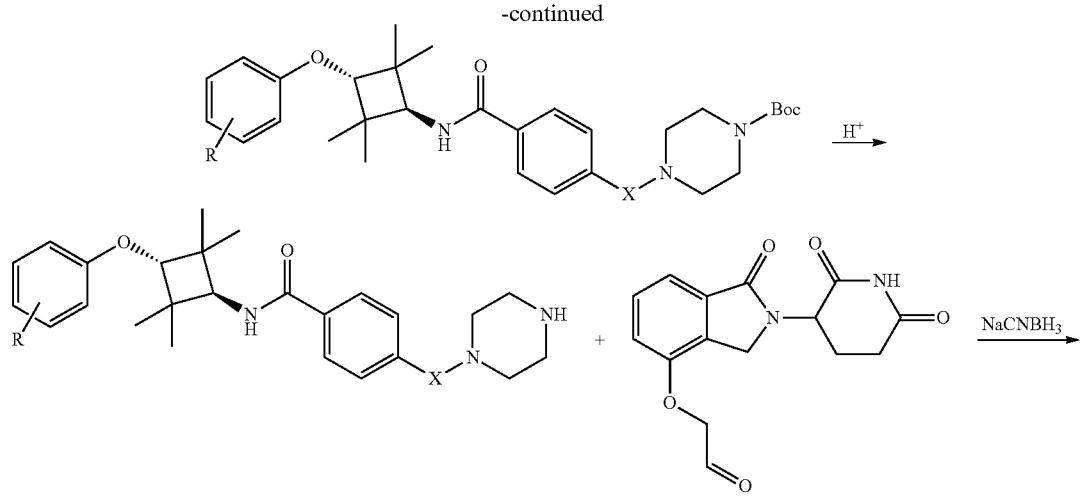
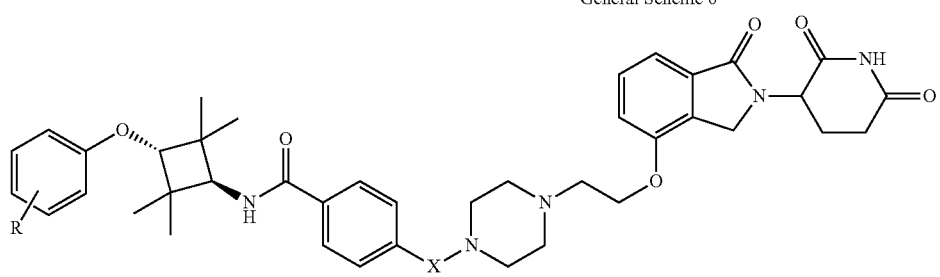
General Scheme 6
General Scheme 10A
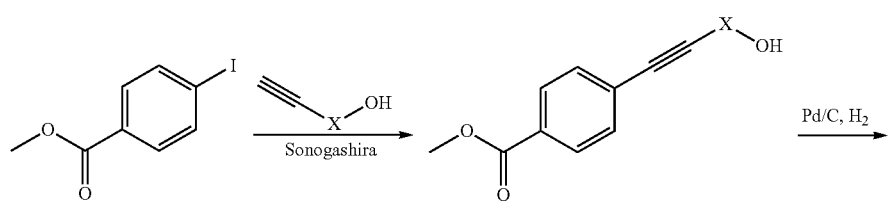
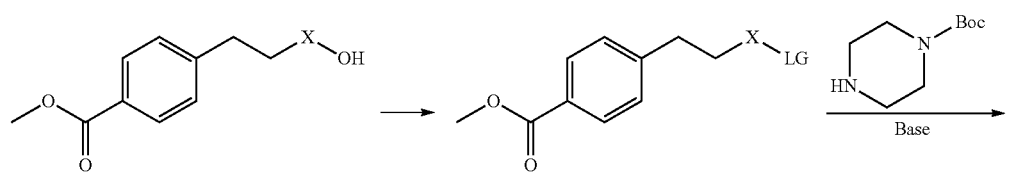
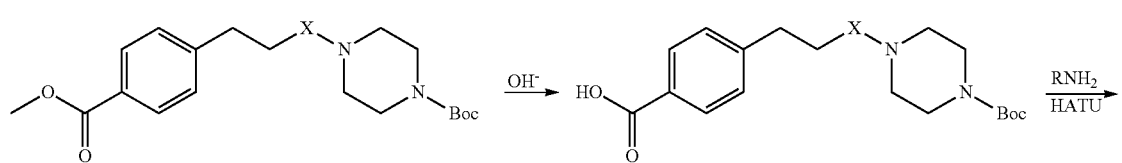

-continued
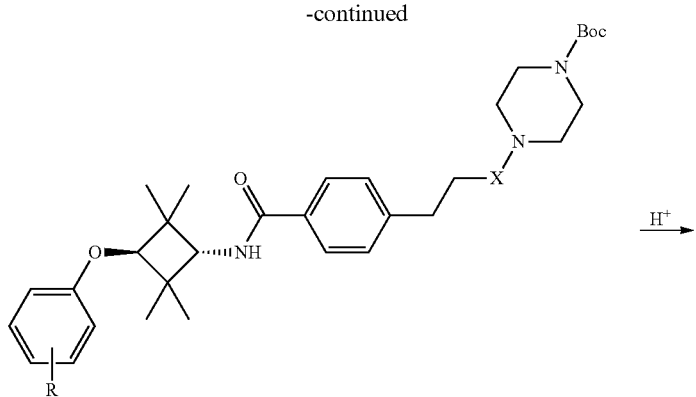
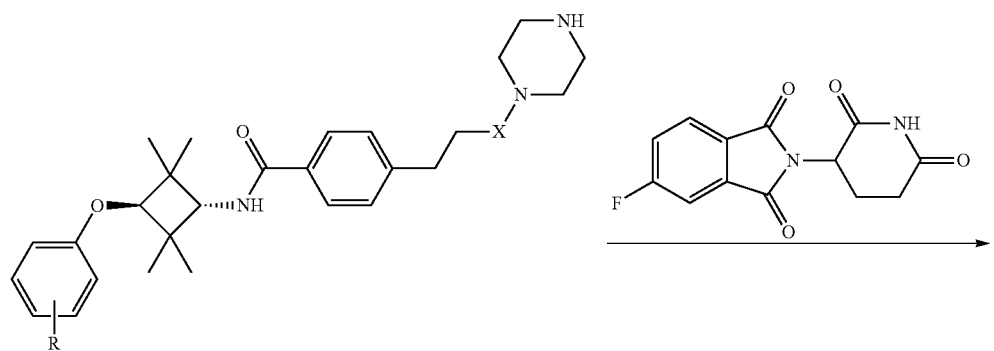
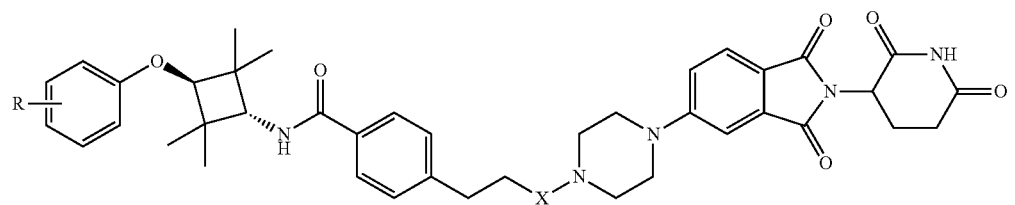
General Scheme 11A
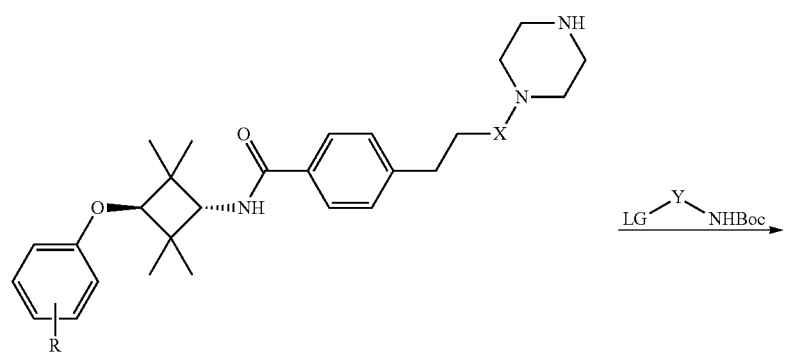

383
384
-continued
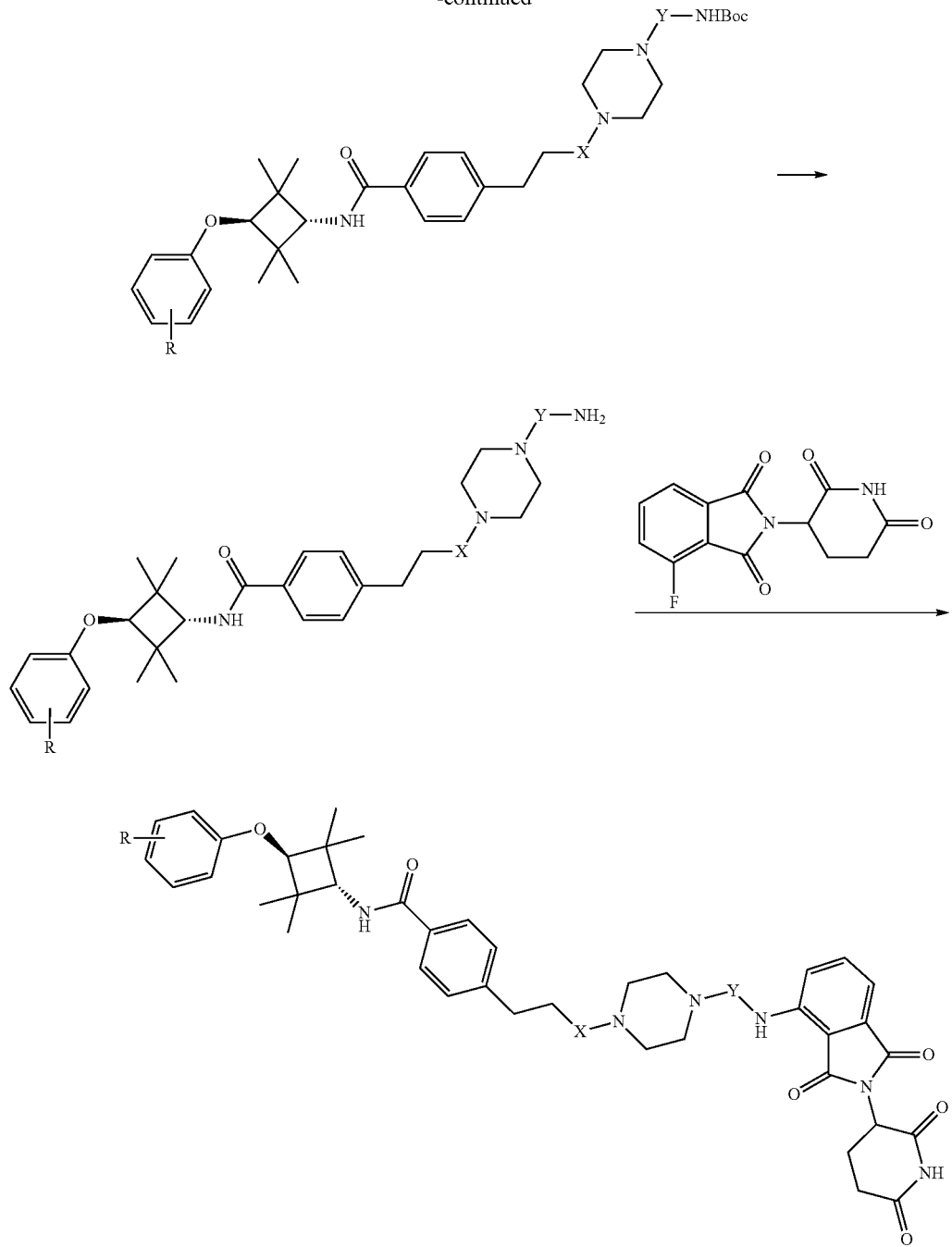
General Scheme 12A
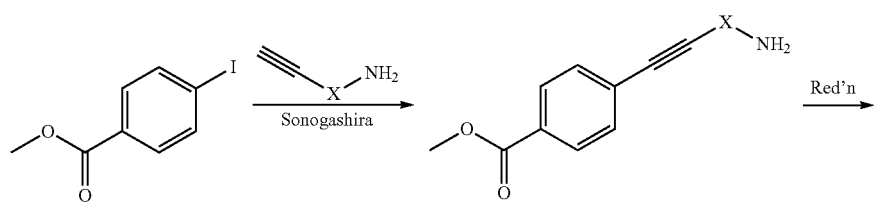

385 386
-continued
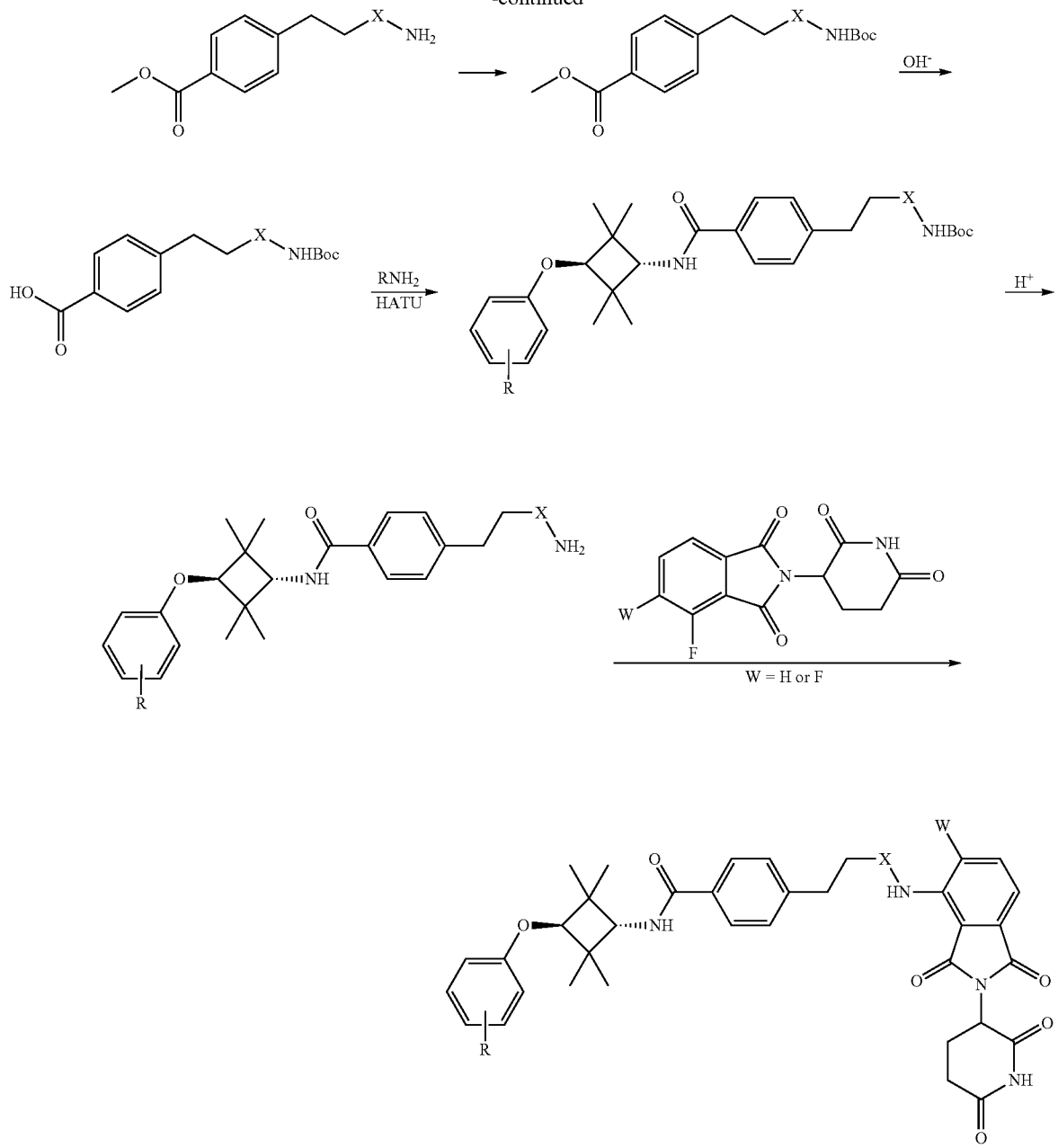
General Scheme 13A
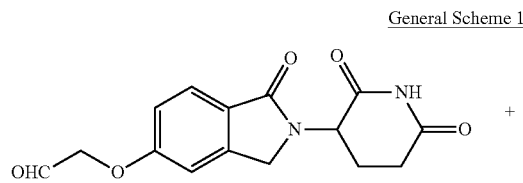
prepared as described
in General Scheme 6
starting with the
appropriately
substituted benzoic
acid derivative 387
-continued
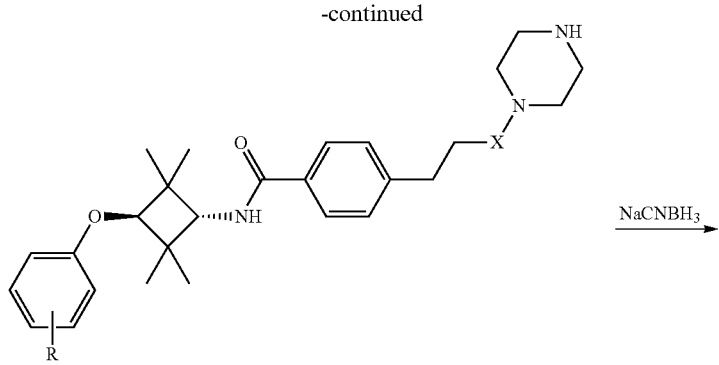
General Scheme 10
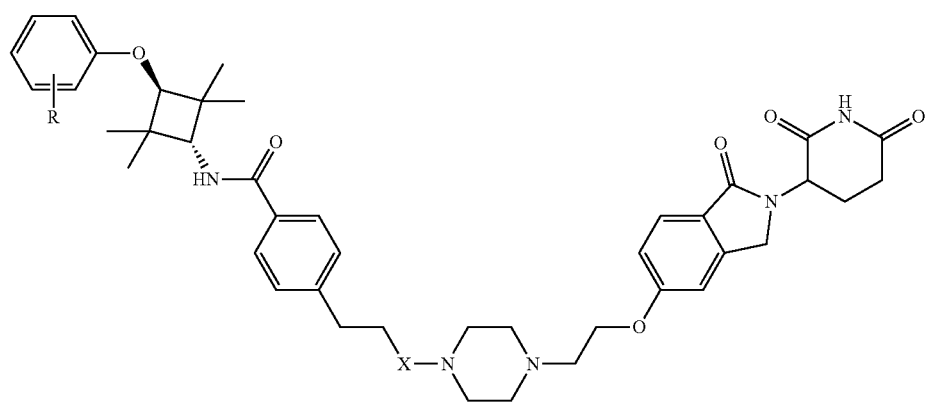
General Scheme 14A
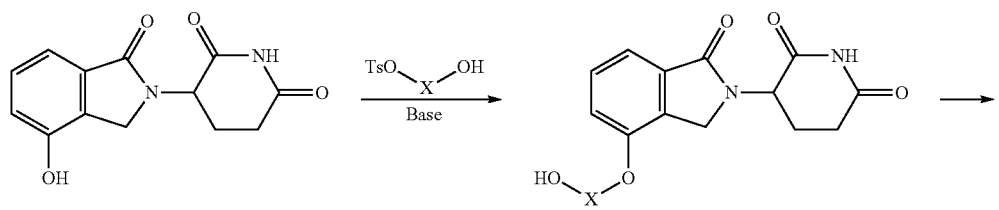
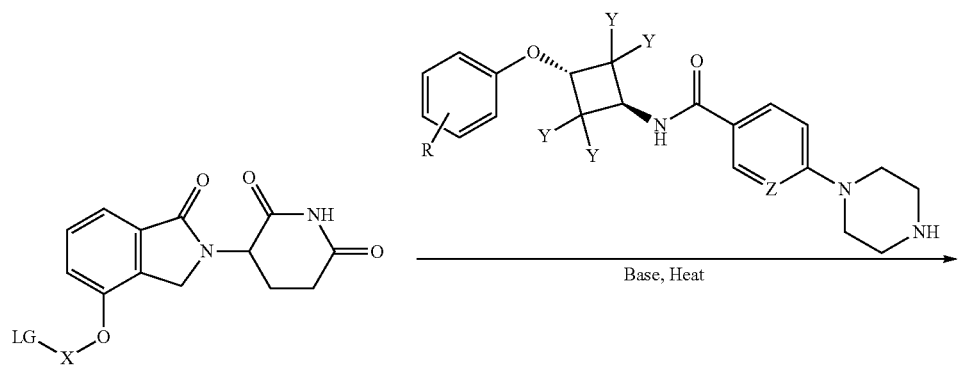

-continued
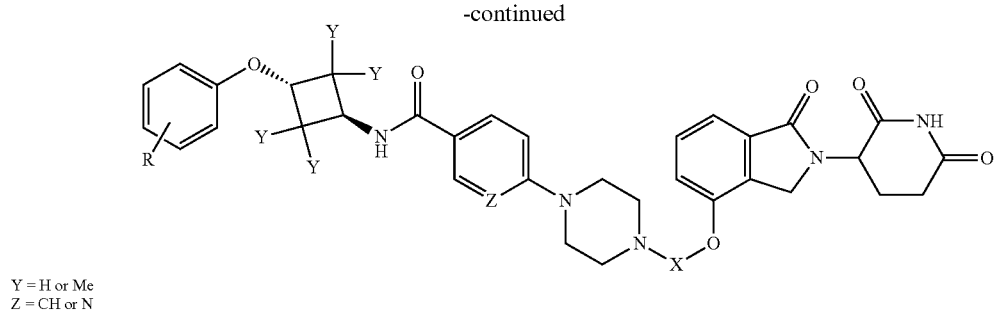
Y = H or Me
Z = CH or N
General Scheme 15A
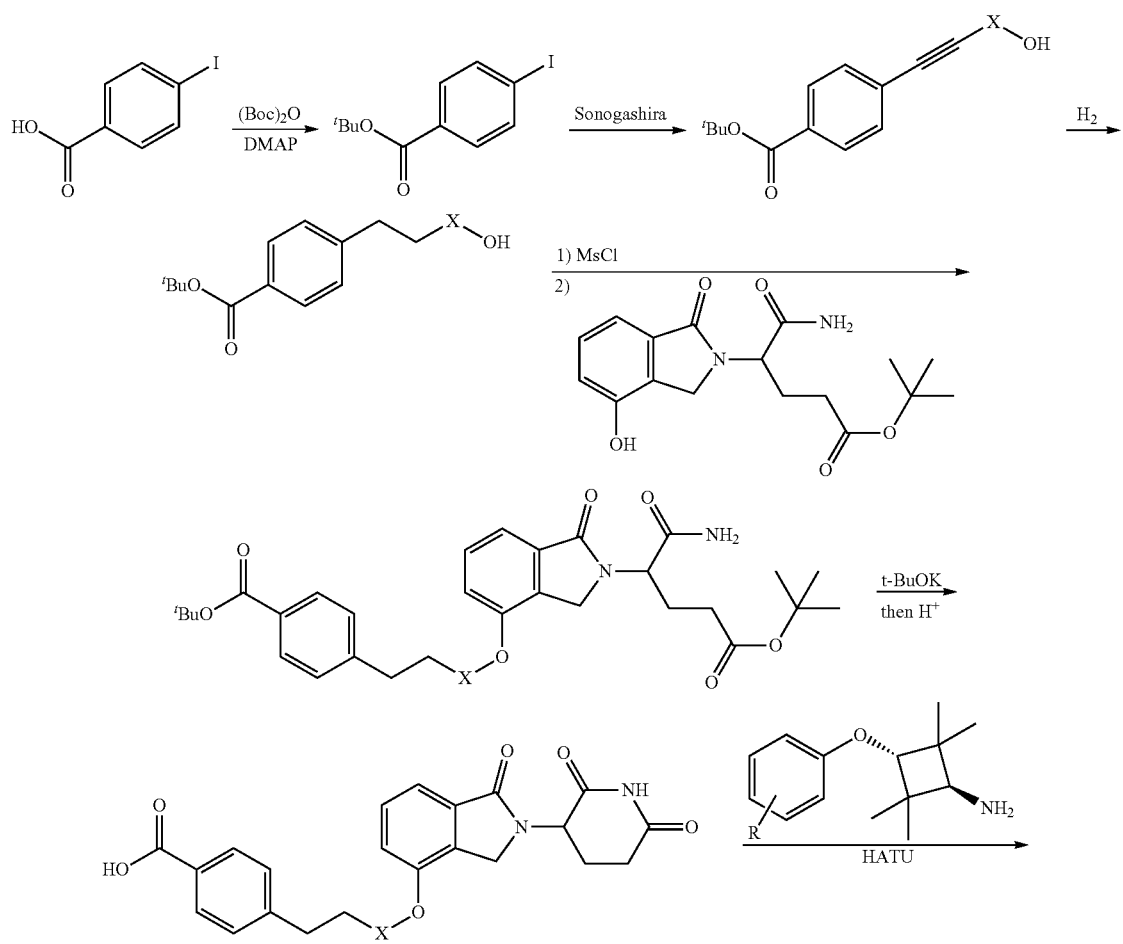
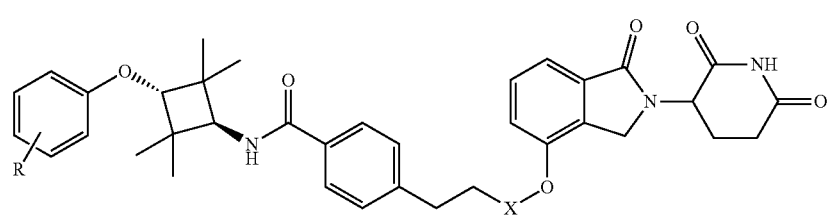

391 392
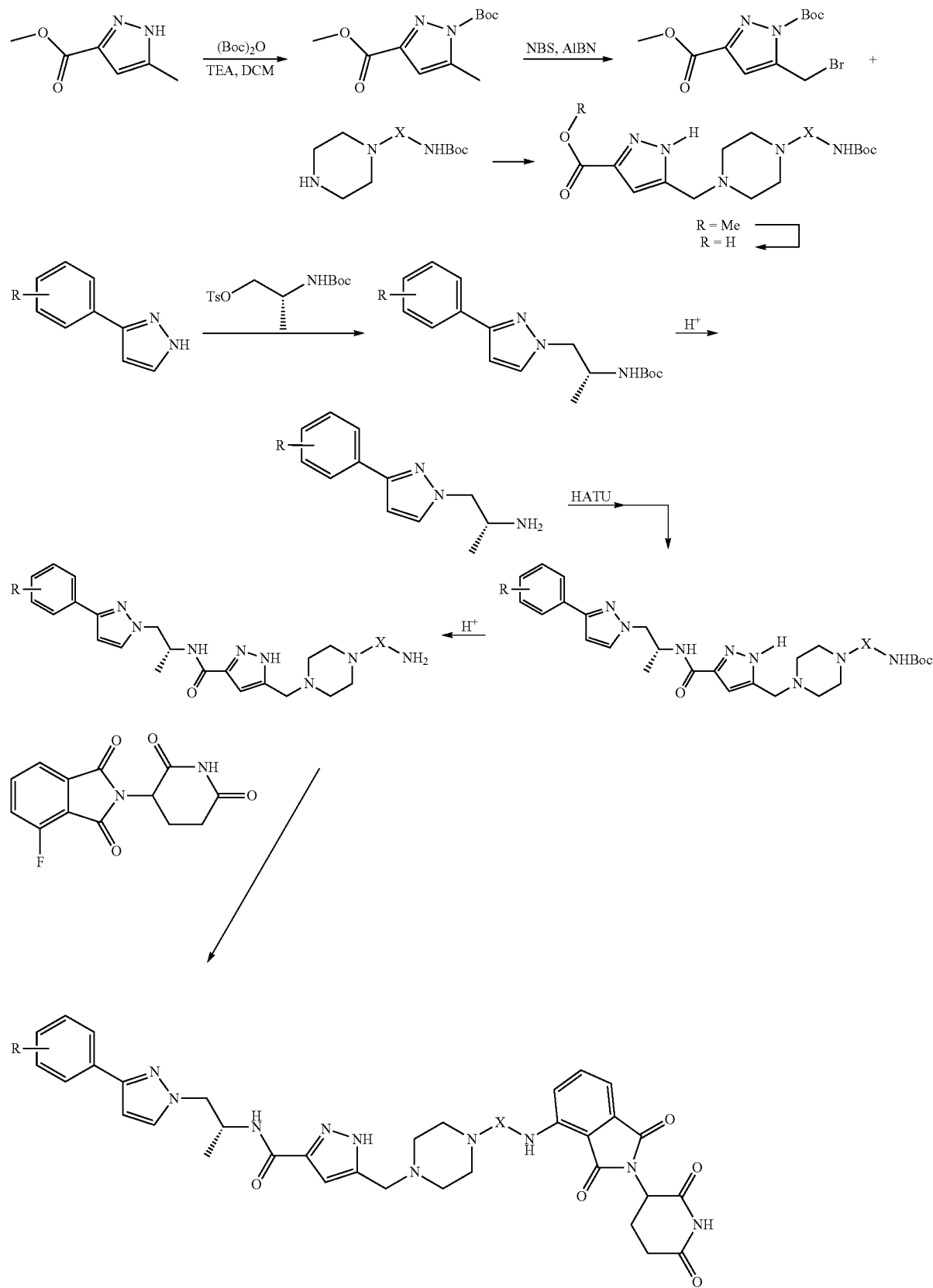
General Scheme 16A

General Scheme 17A
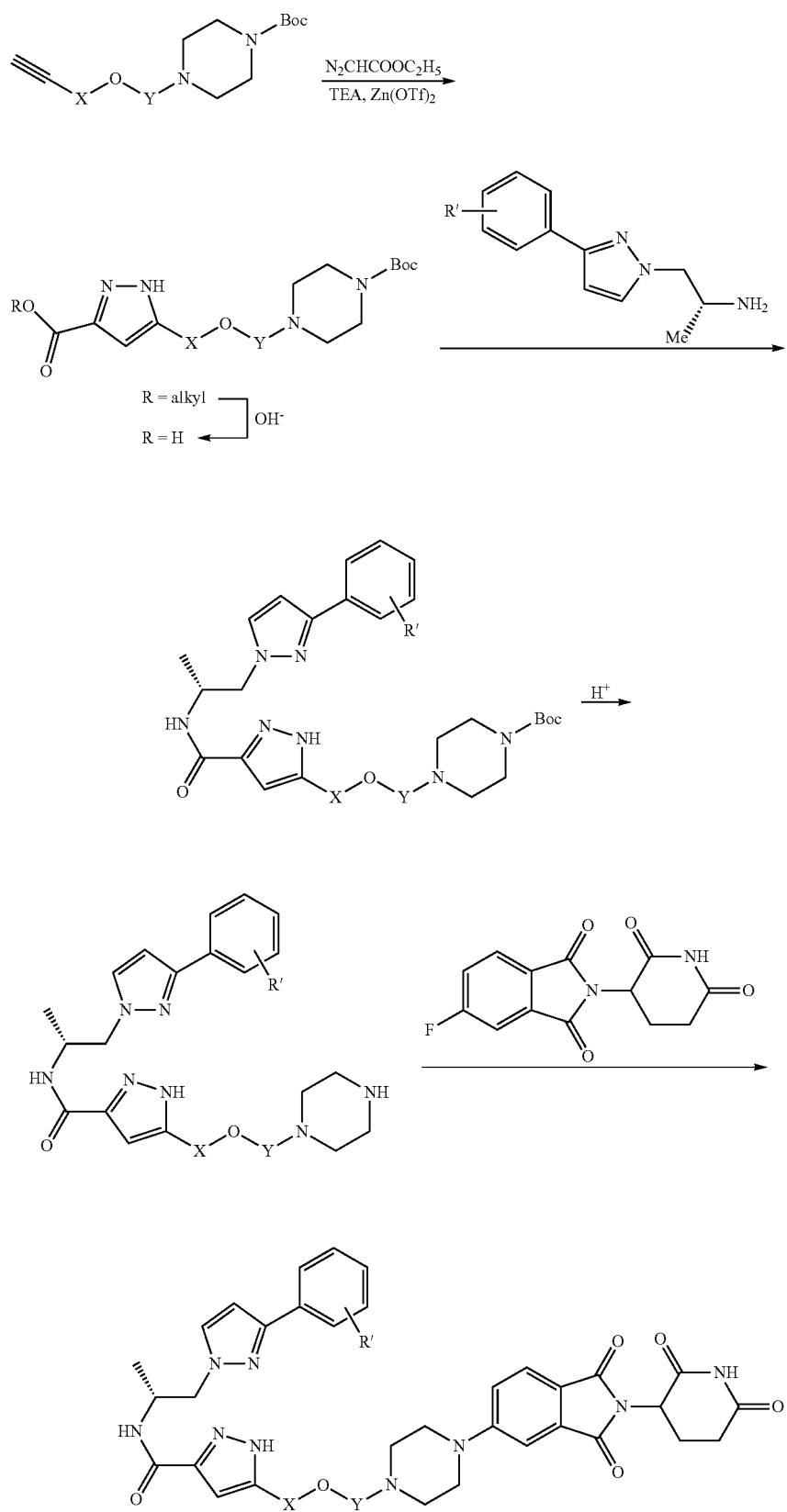

General Scheme 18A
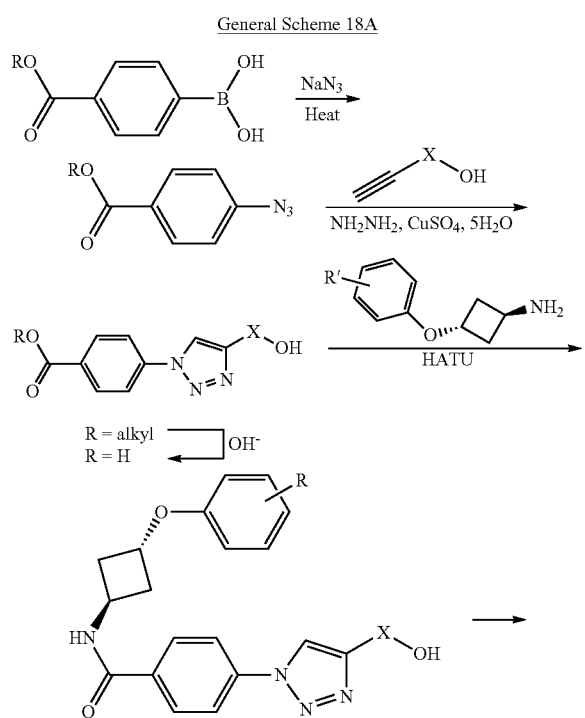
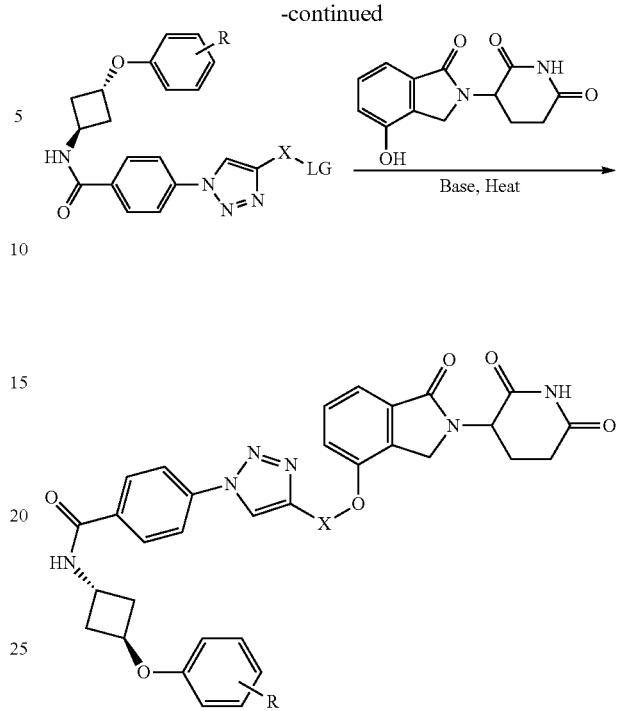
General Scheme 19A
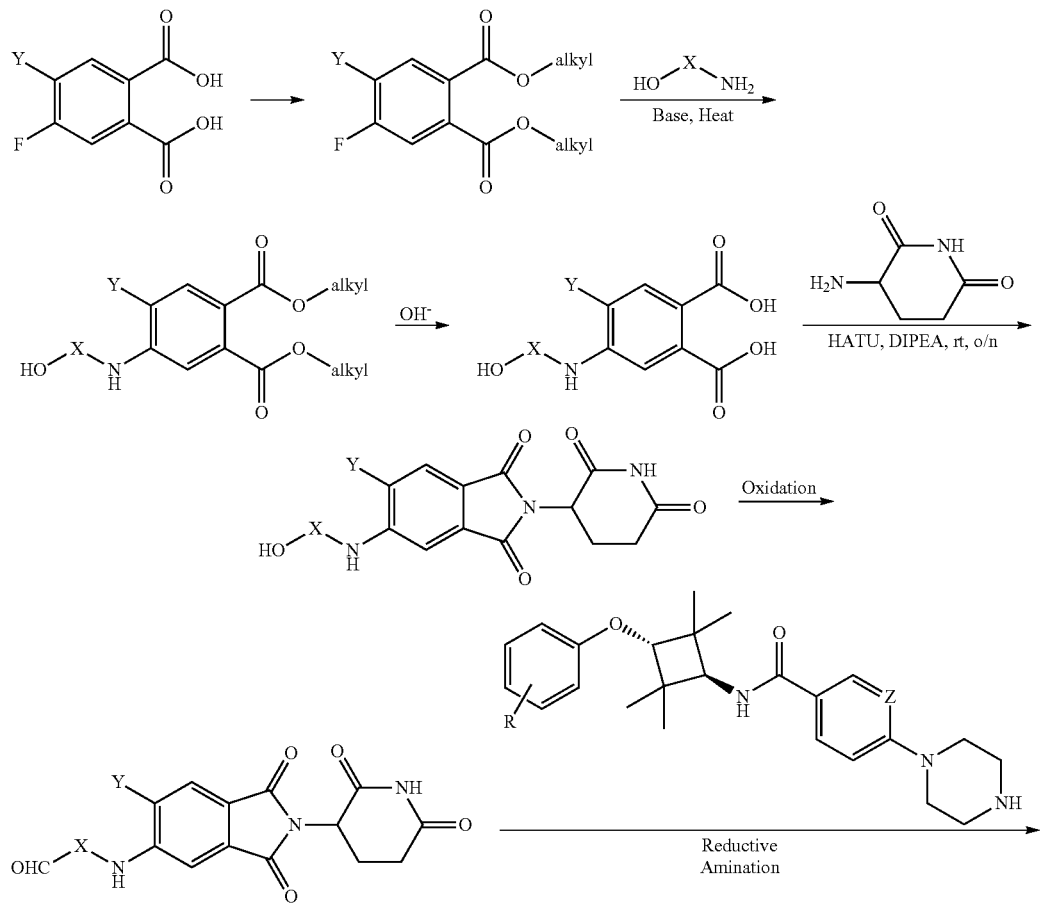

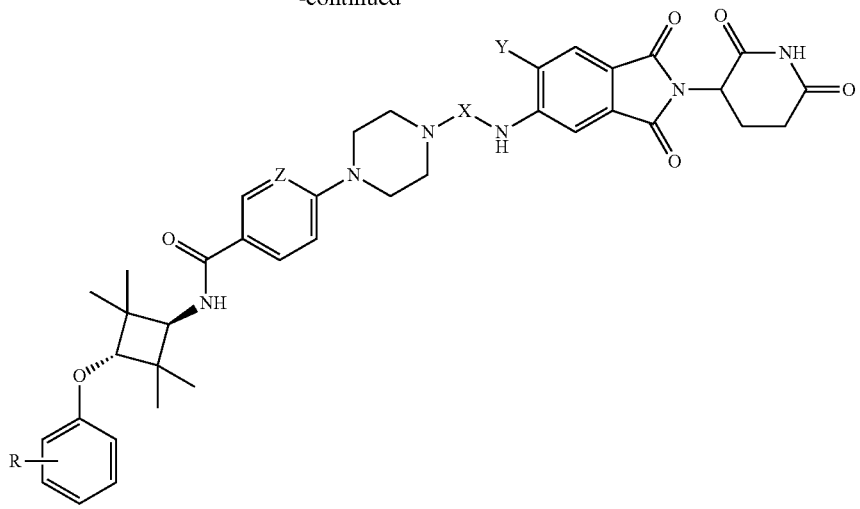
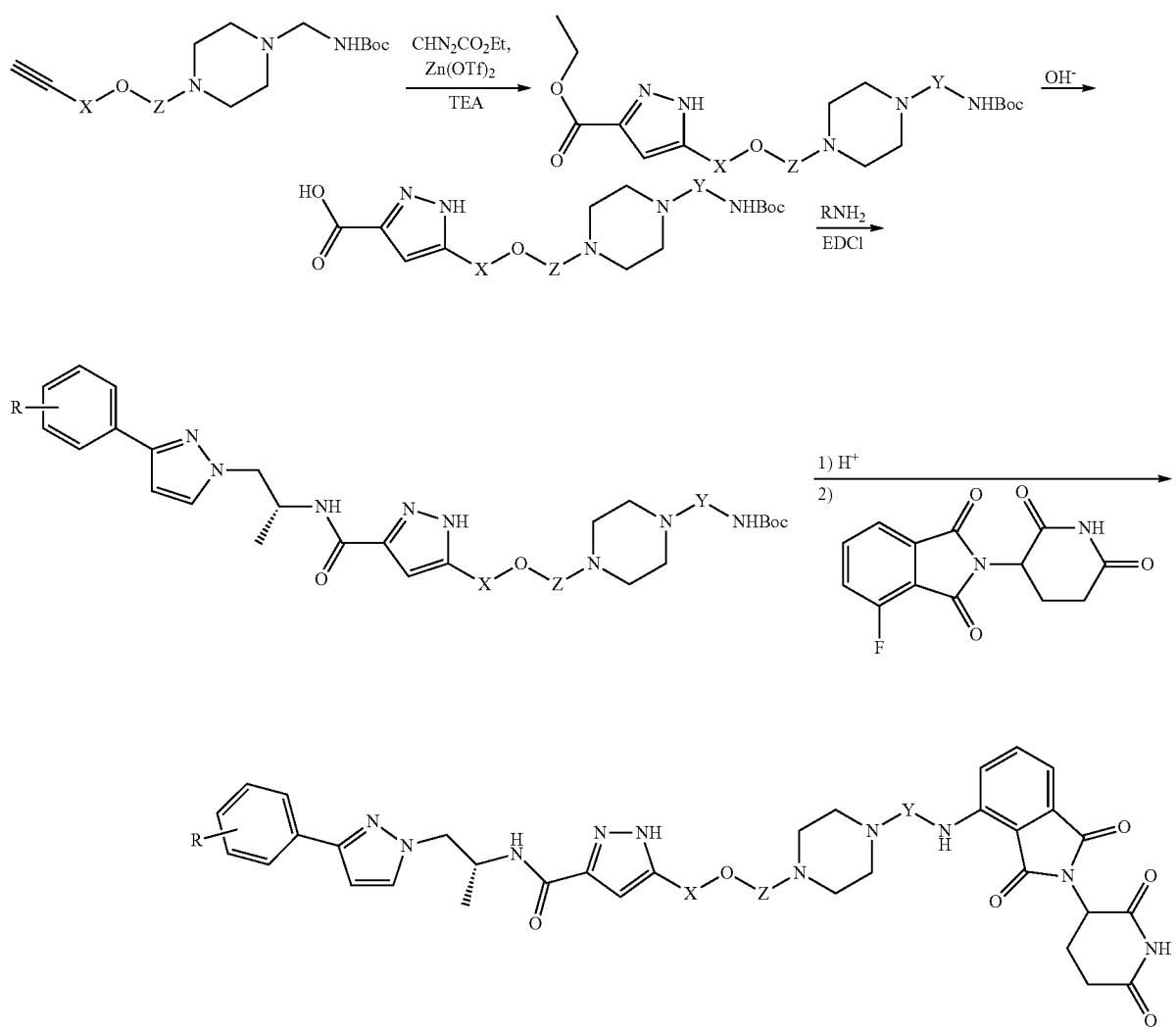

General Scheme 21A
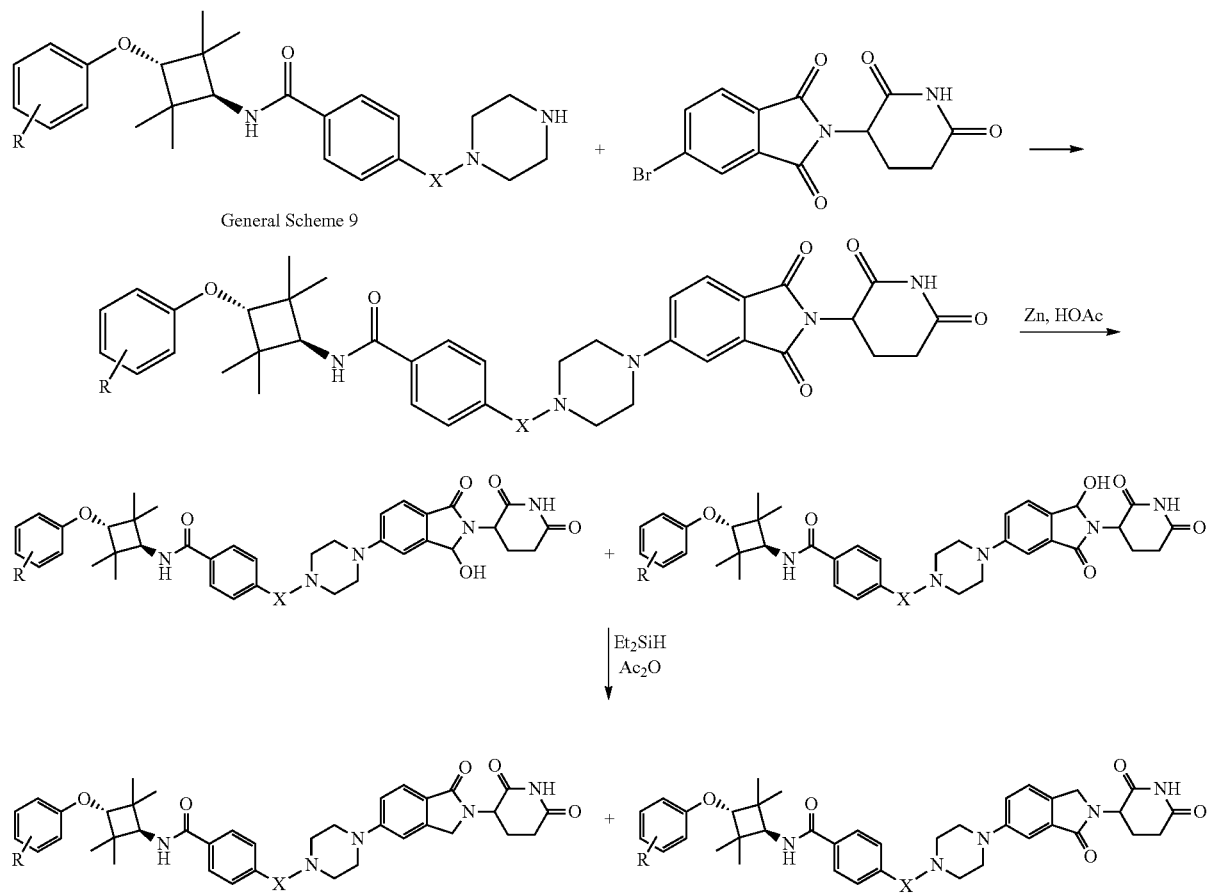
General Scheme 22A
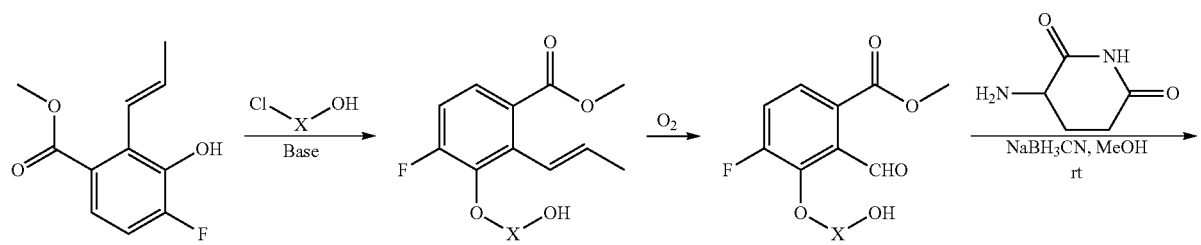
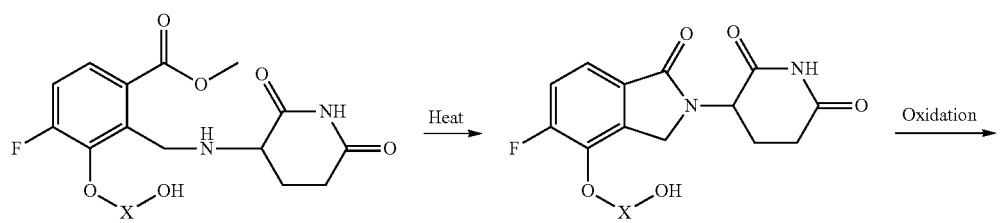

401
402
-continued
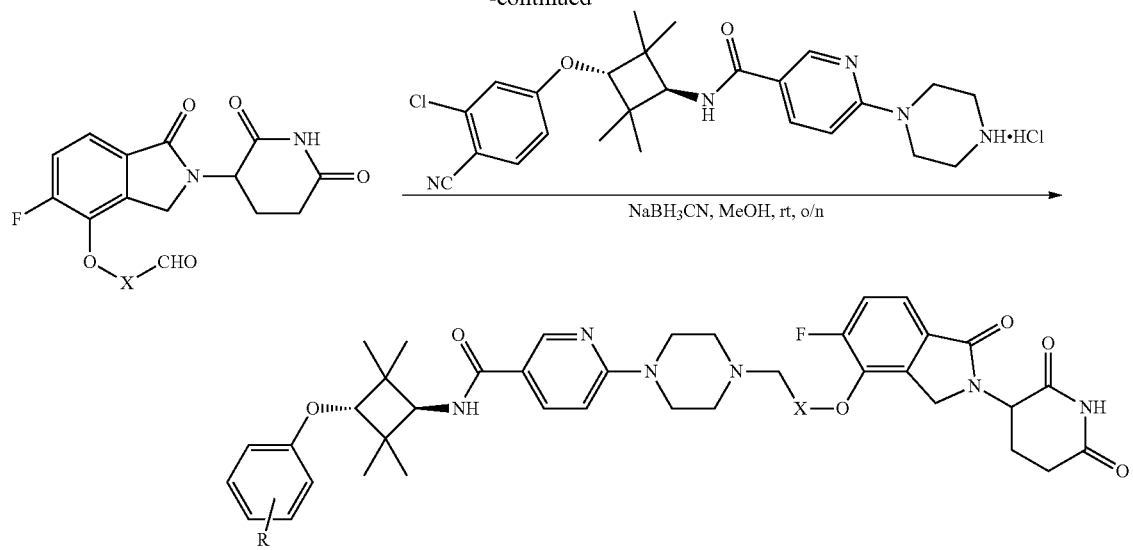
General Scheme 1B
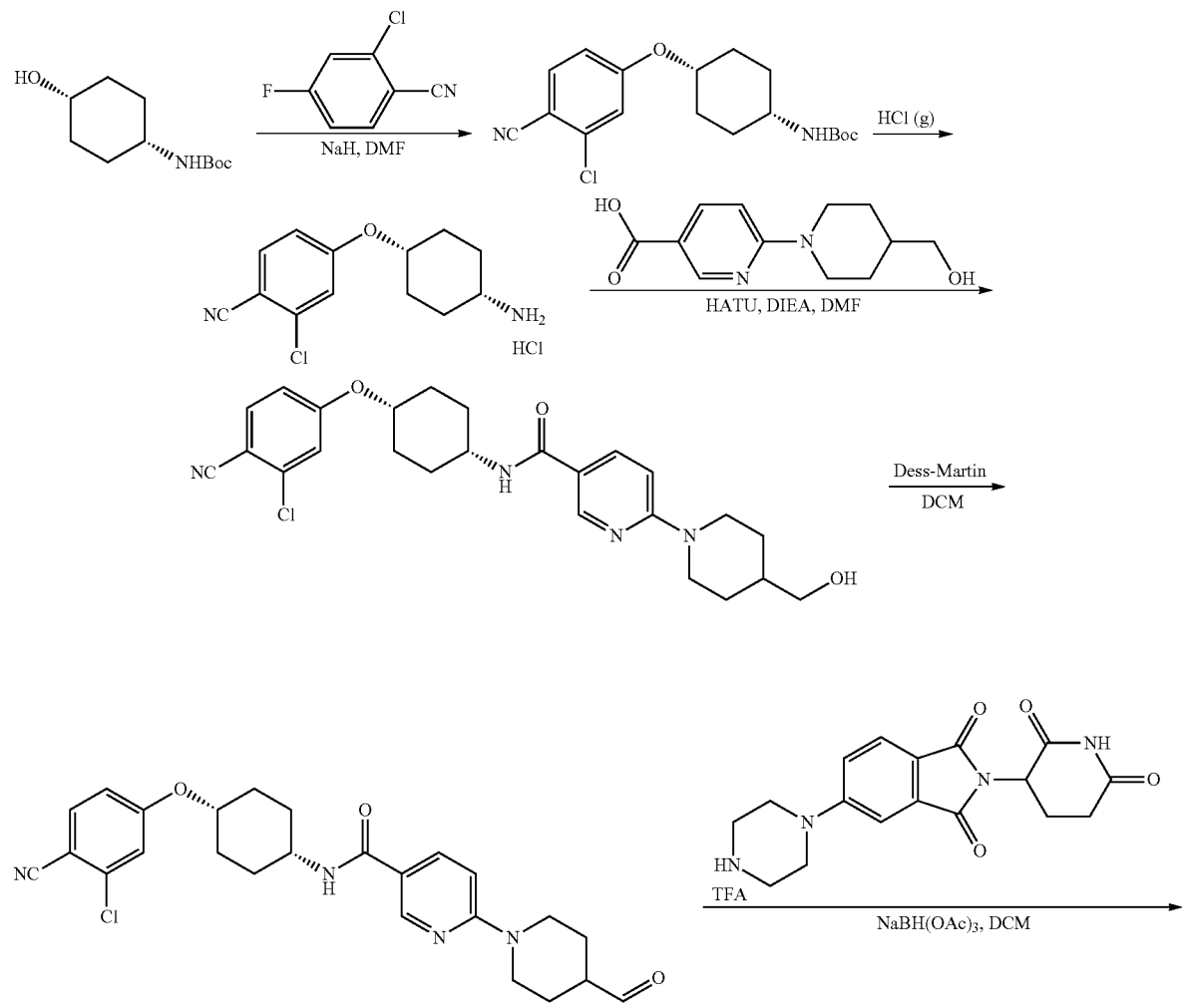

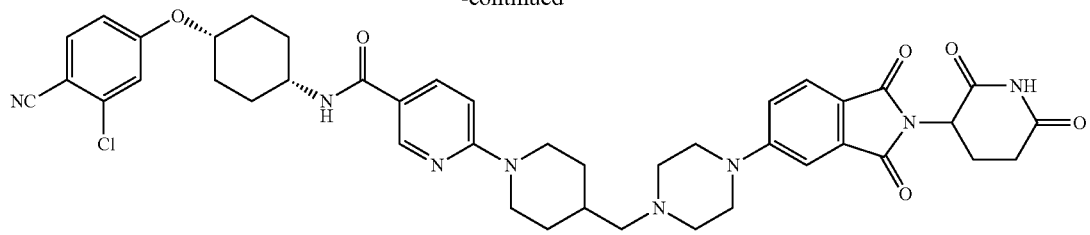
General Scheme 2B
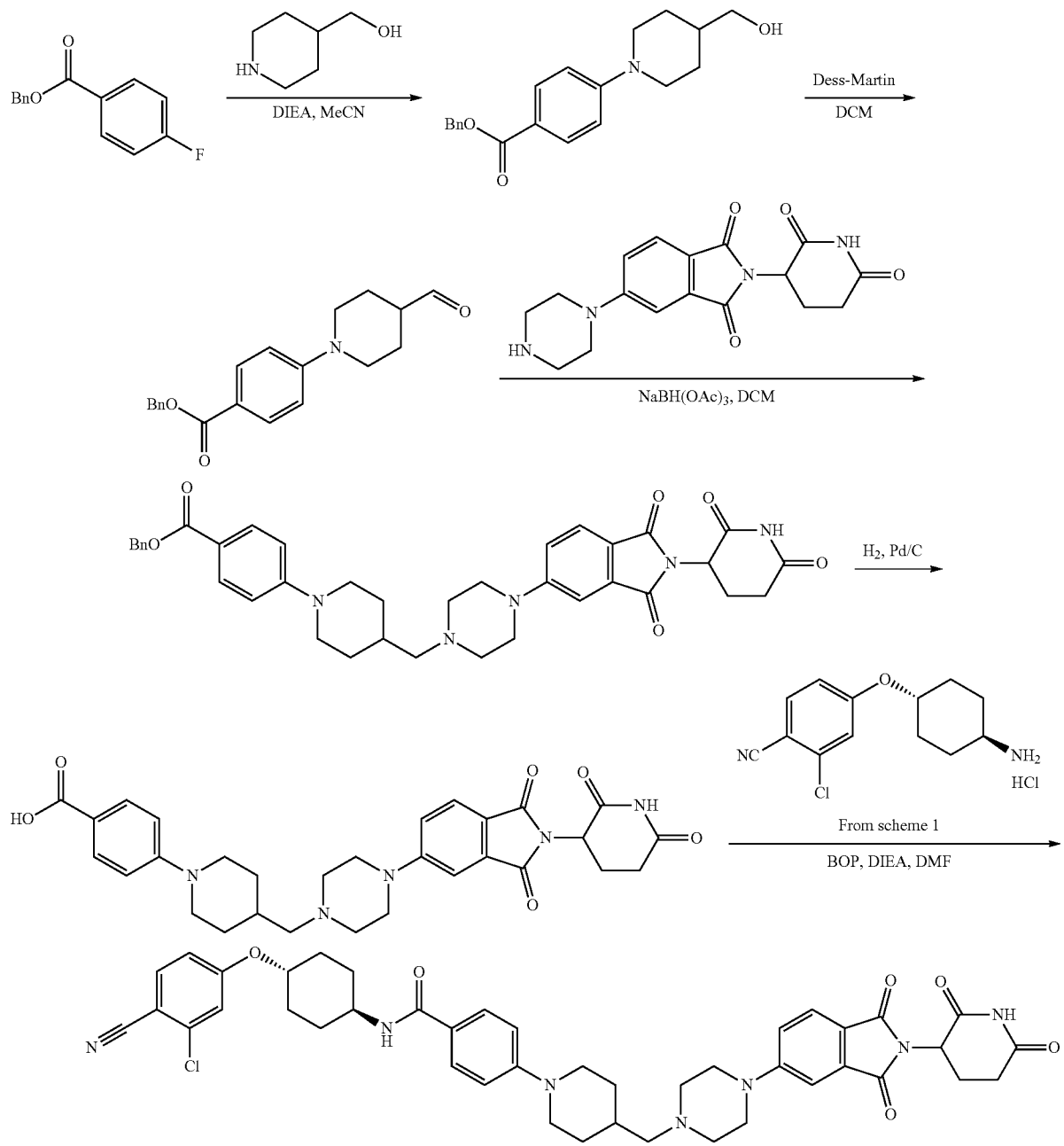

General Scheme 3B
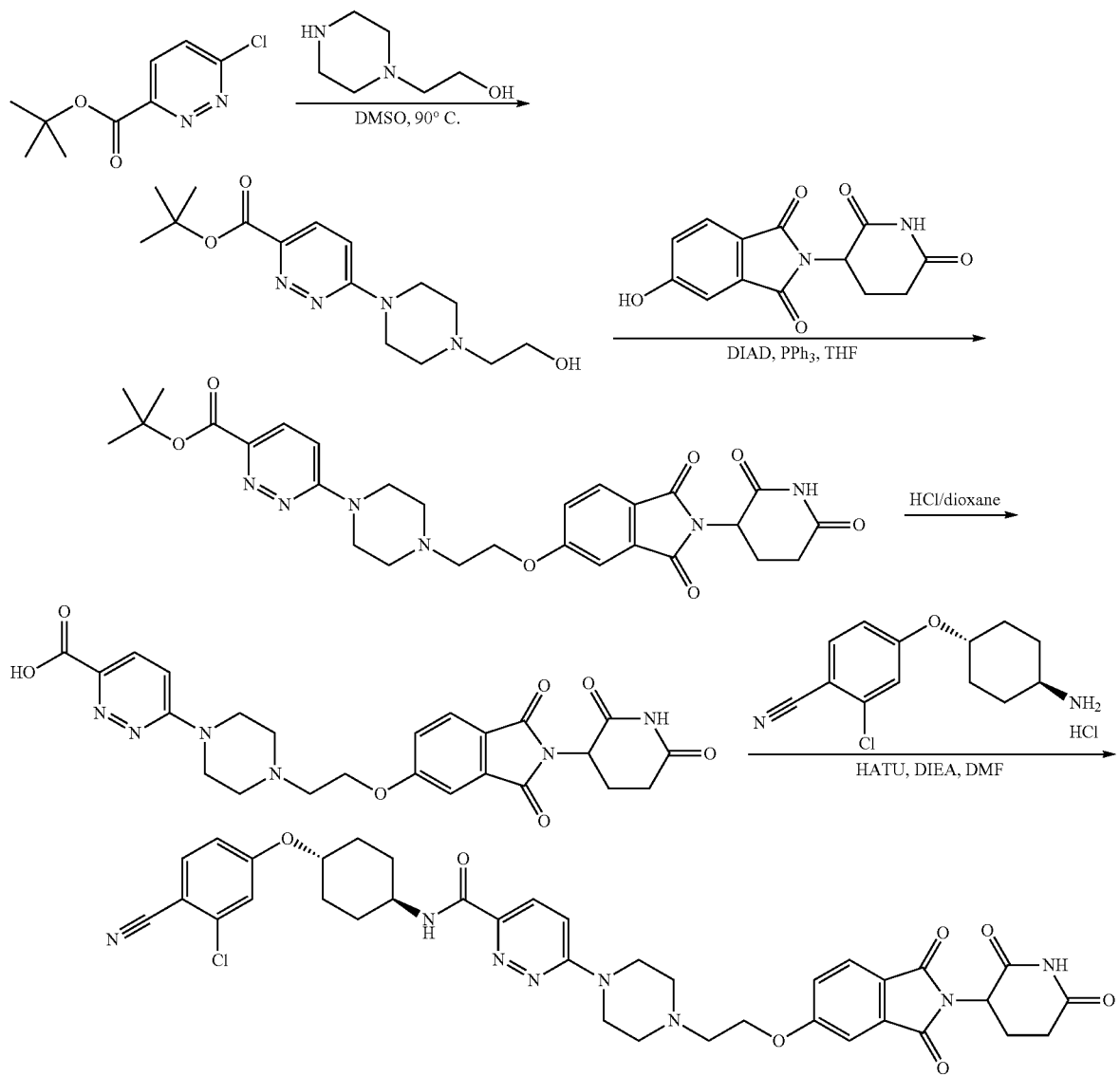
General Scheme 4B
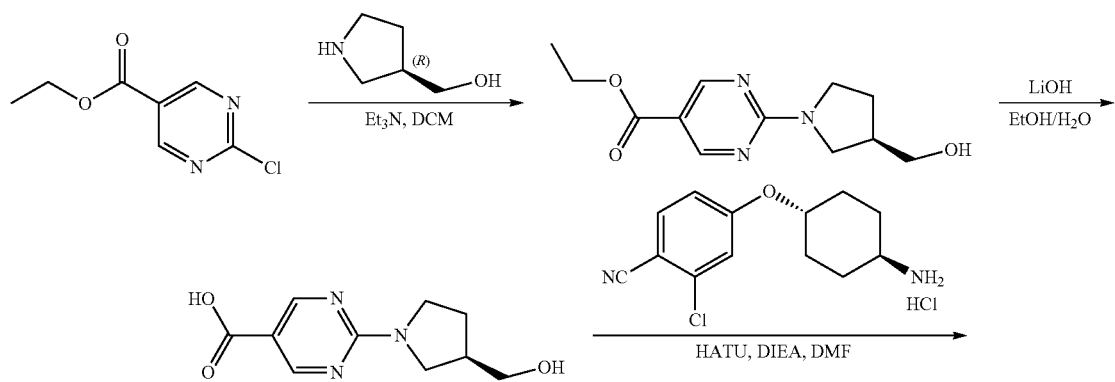

407 408
-continued
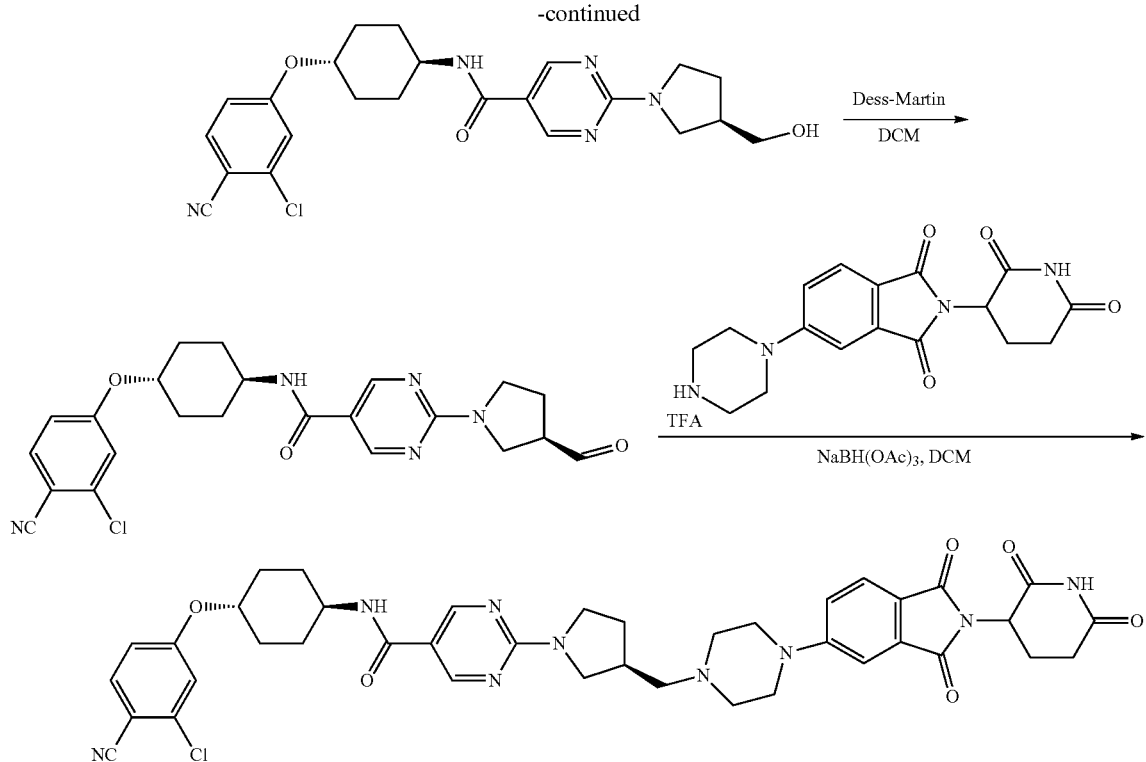
General Scheme 5B
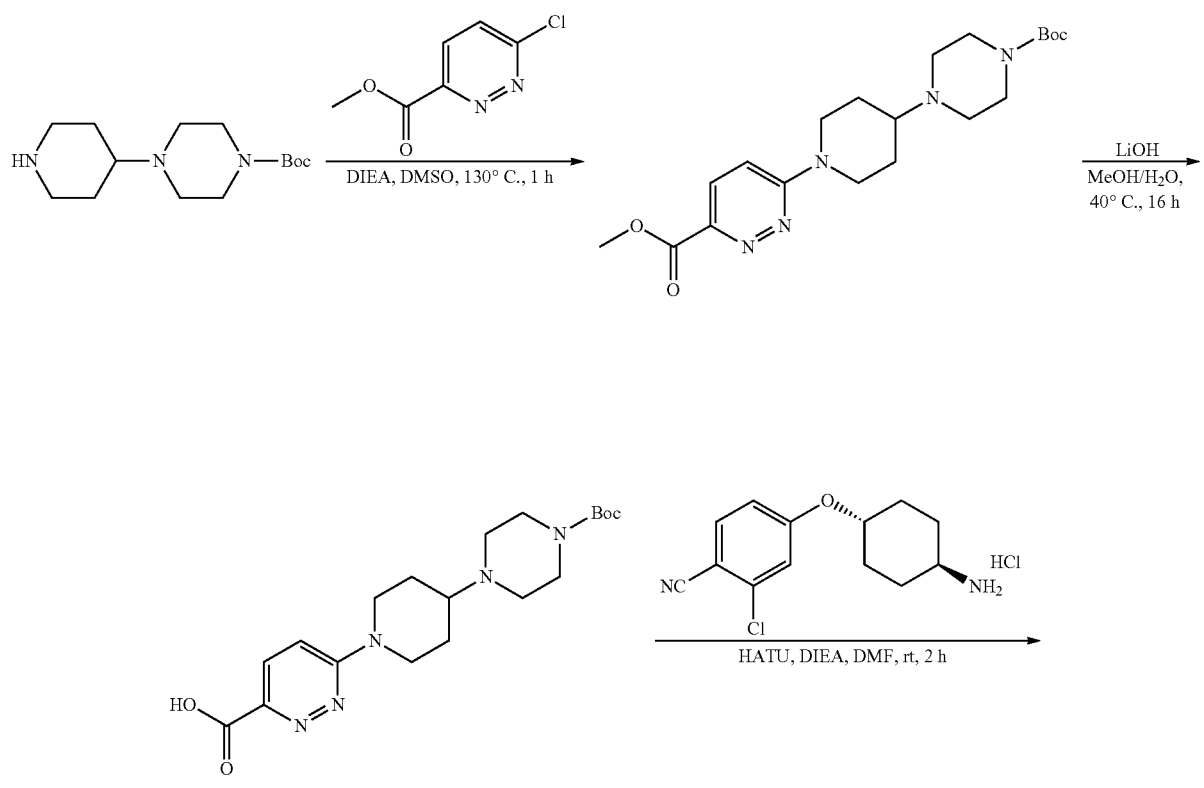
PH-ARV-LS-049-H-2

409
-continued
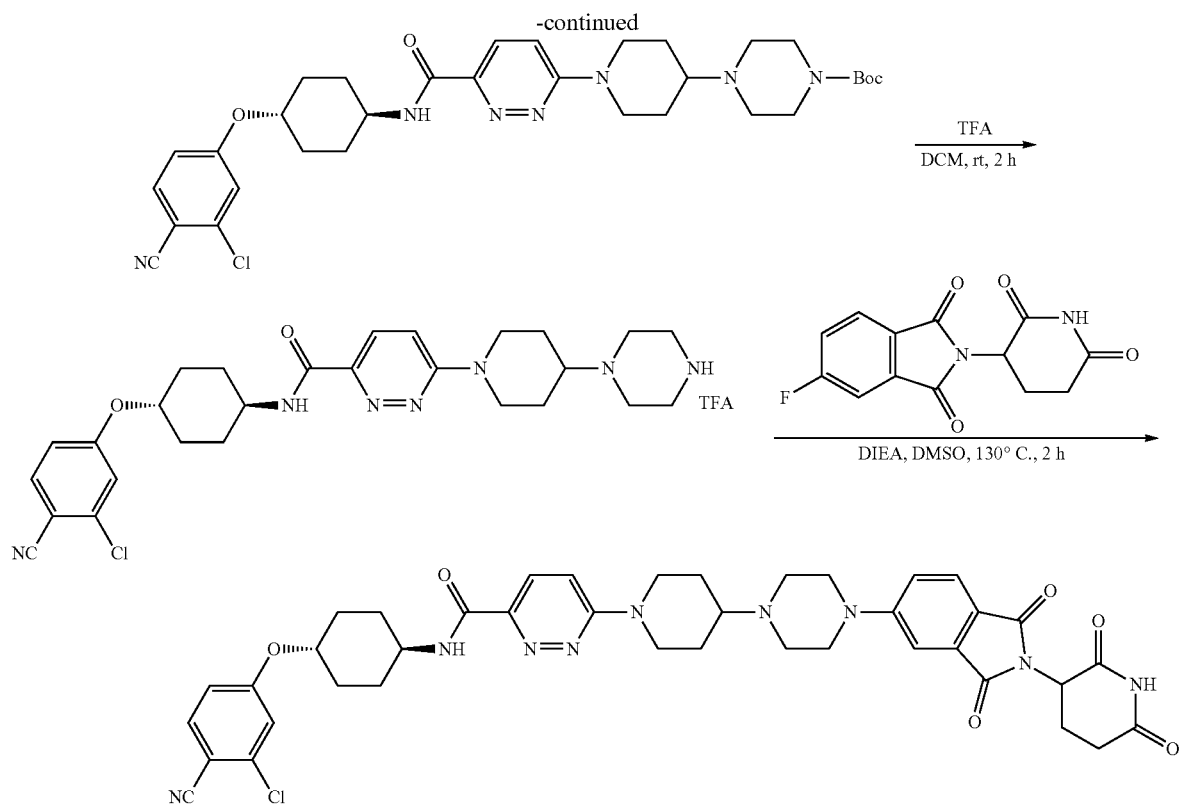
General Scheme 6B
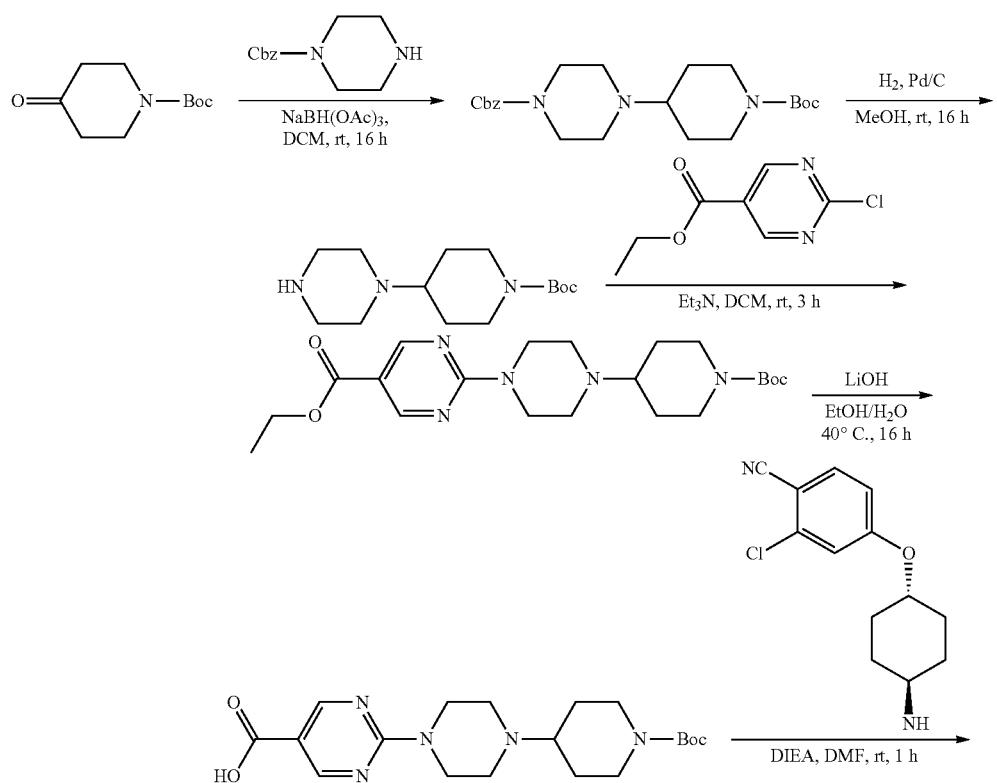

411
412
-continued
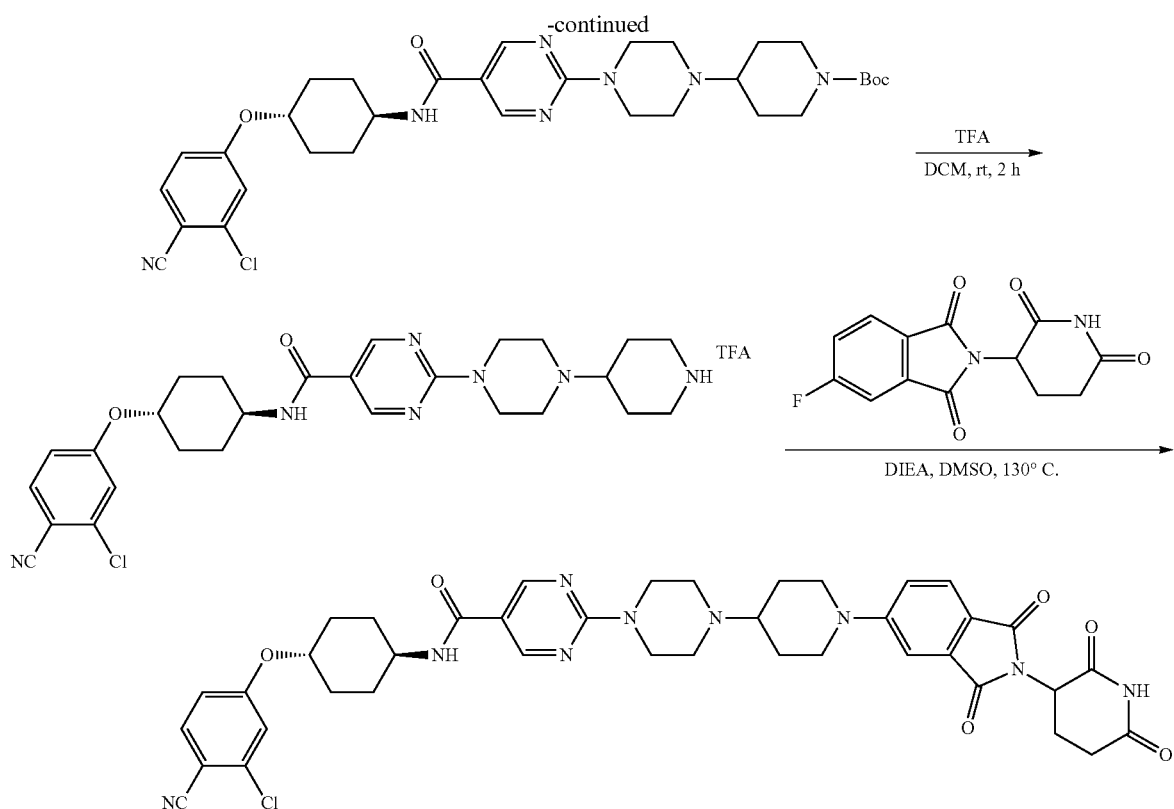
General Scheme 7B
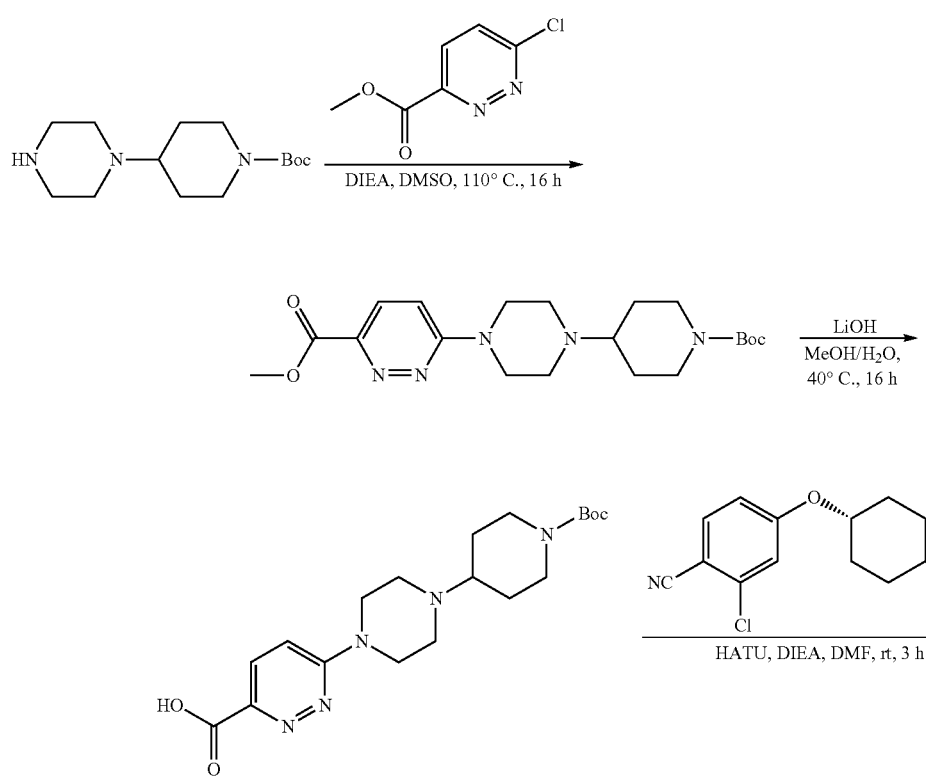

413 414
-continued
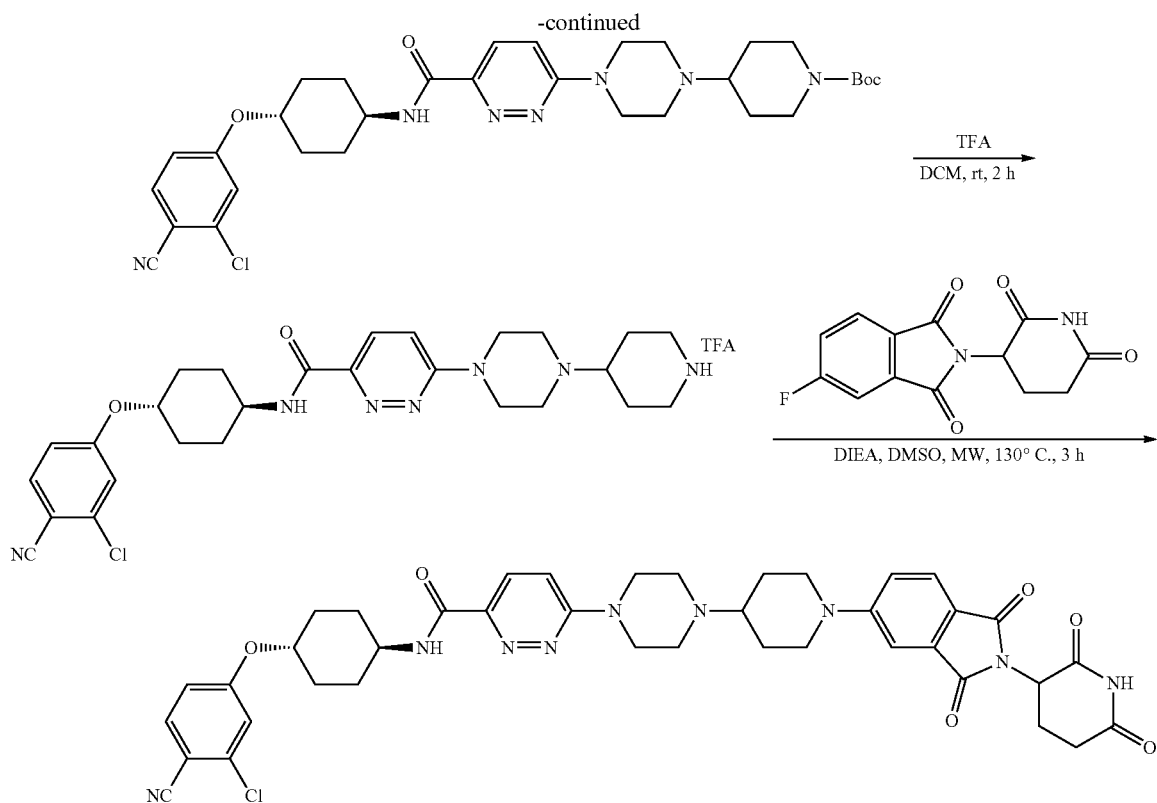
General Scheme 8B
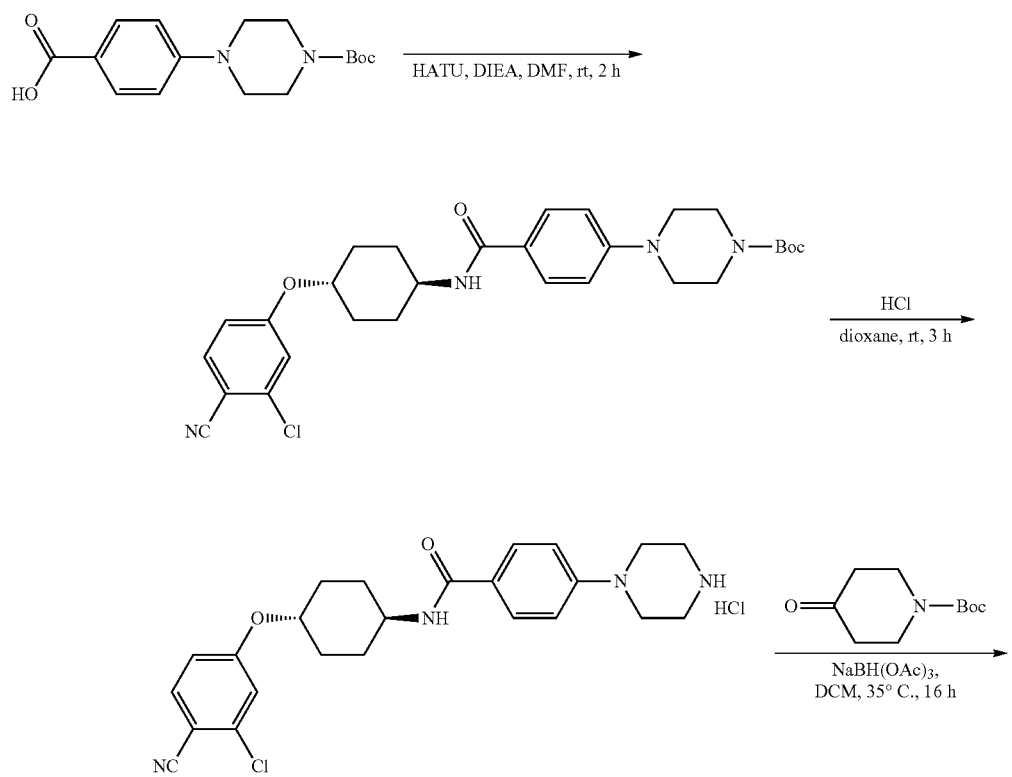

415 416
-continued
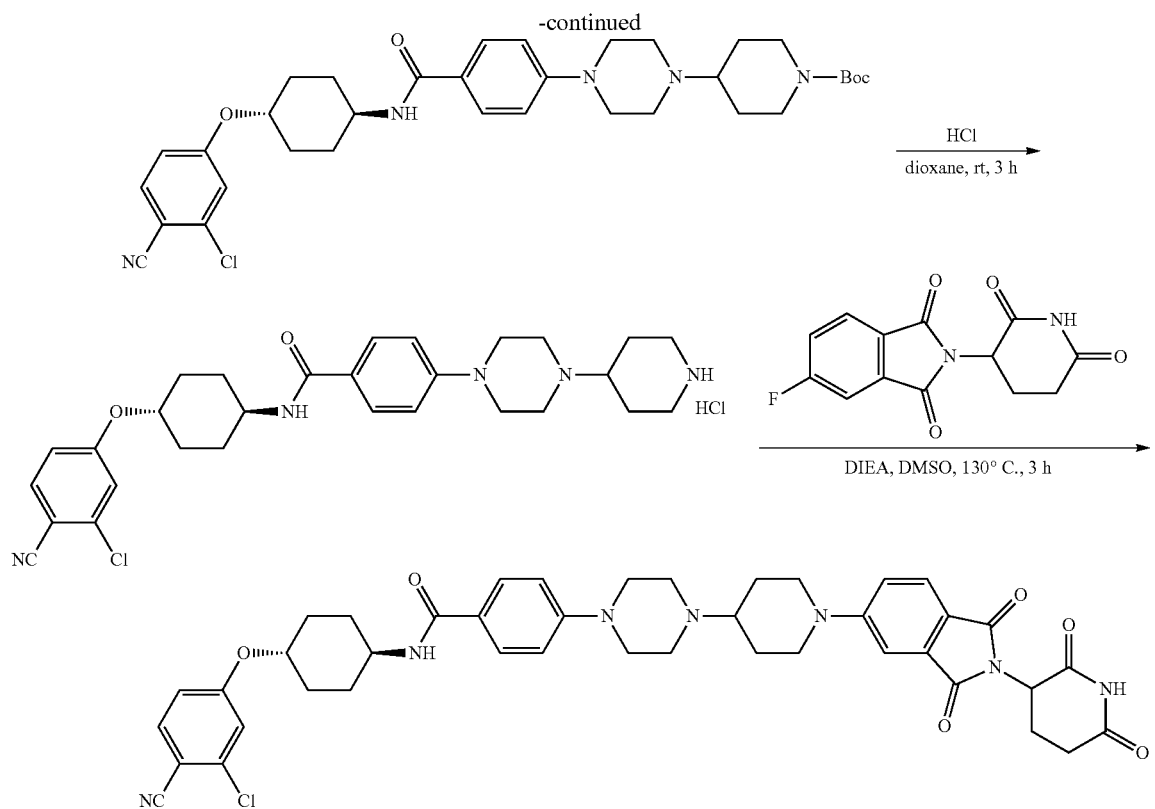
General Scheme 9B
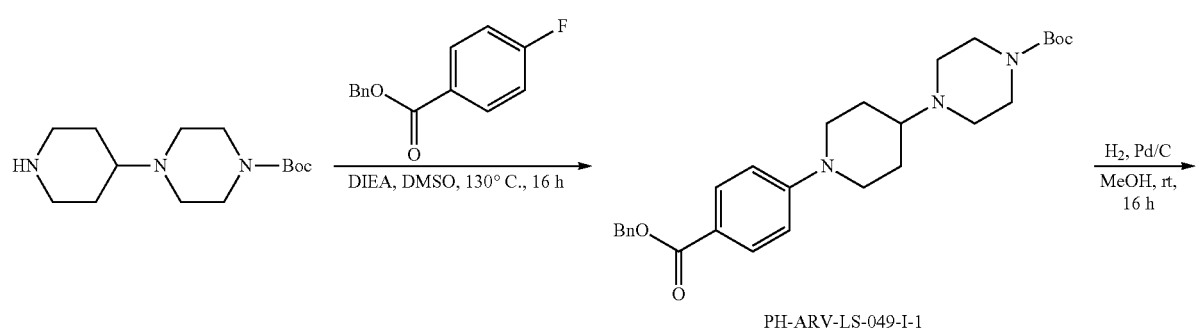
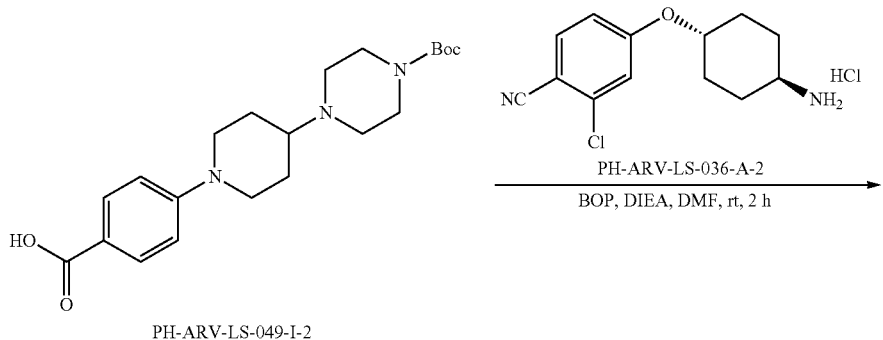

417 418
-continued
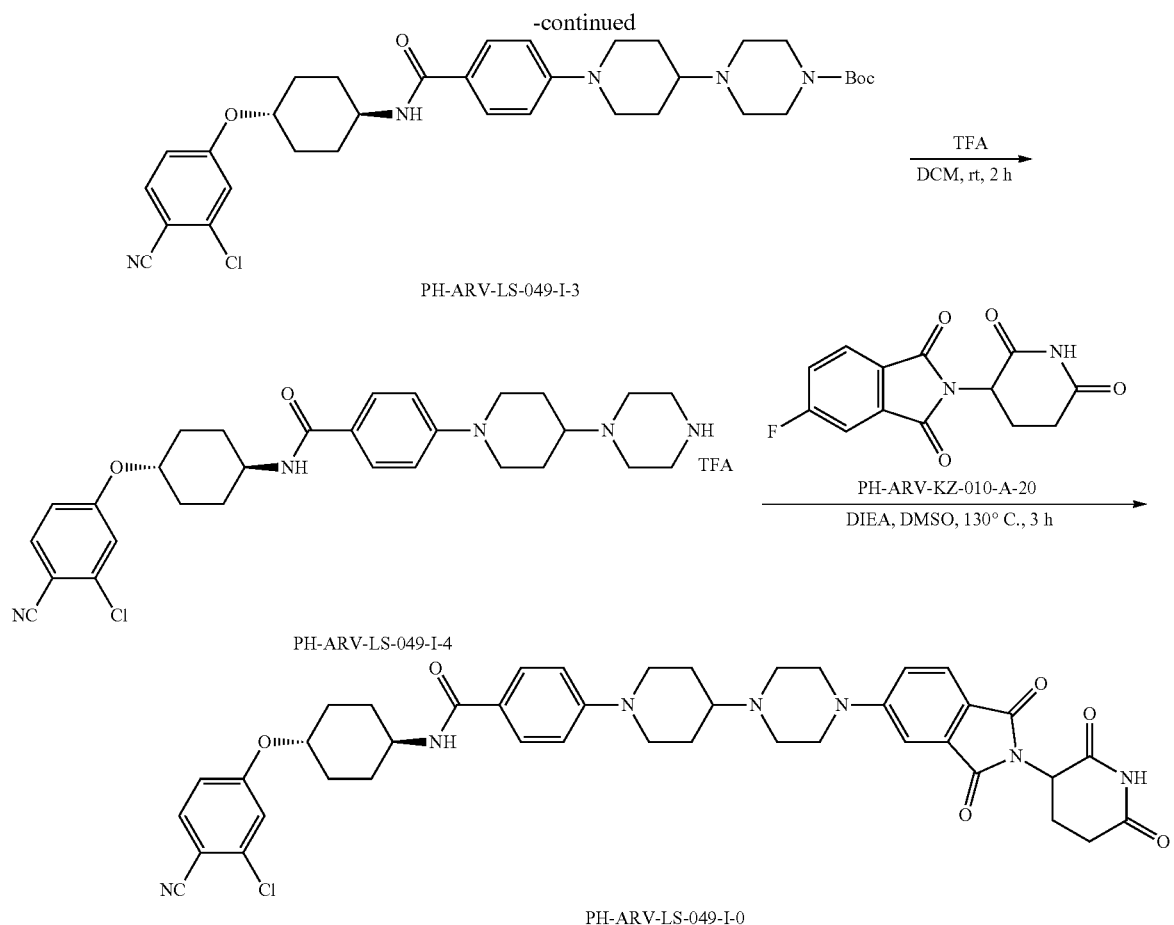
General Scheme 10B
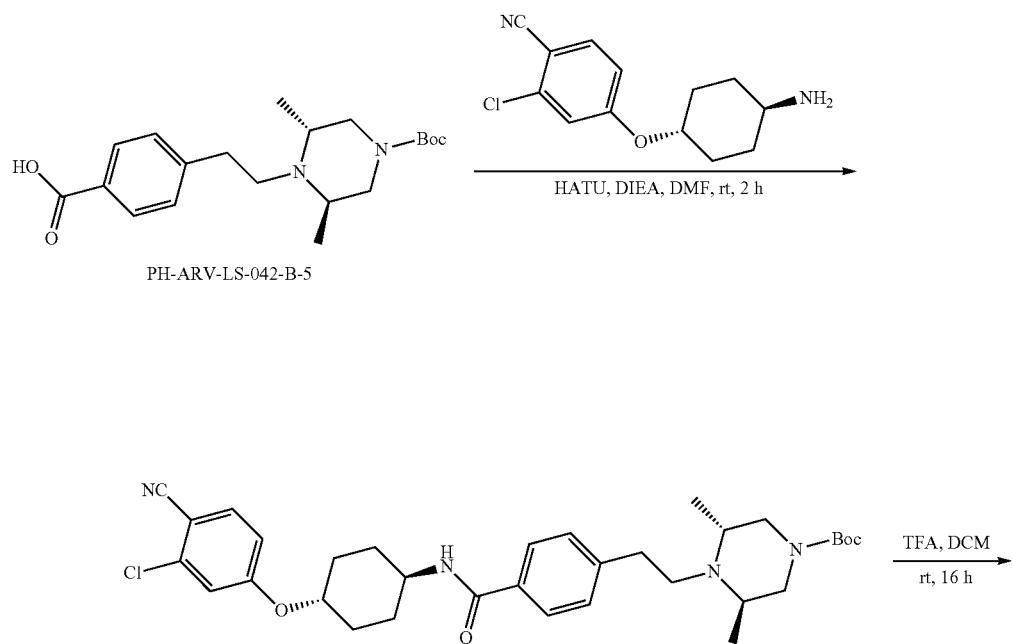

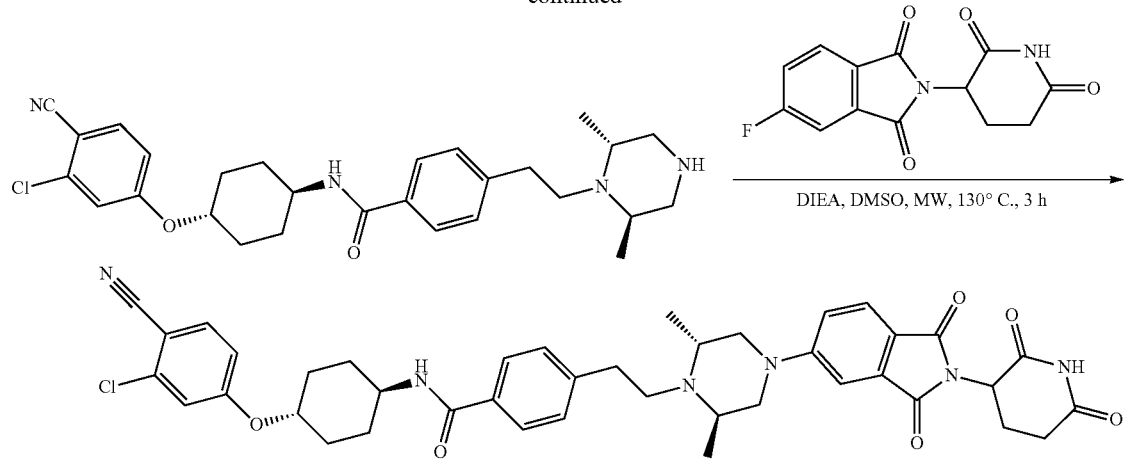
General Scheme 11B
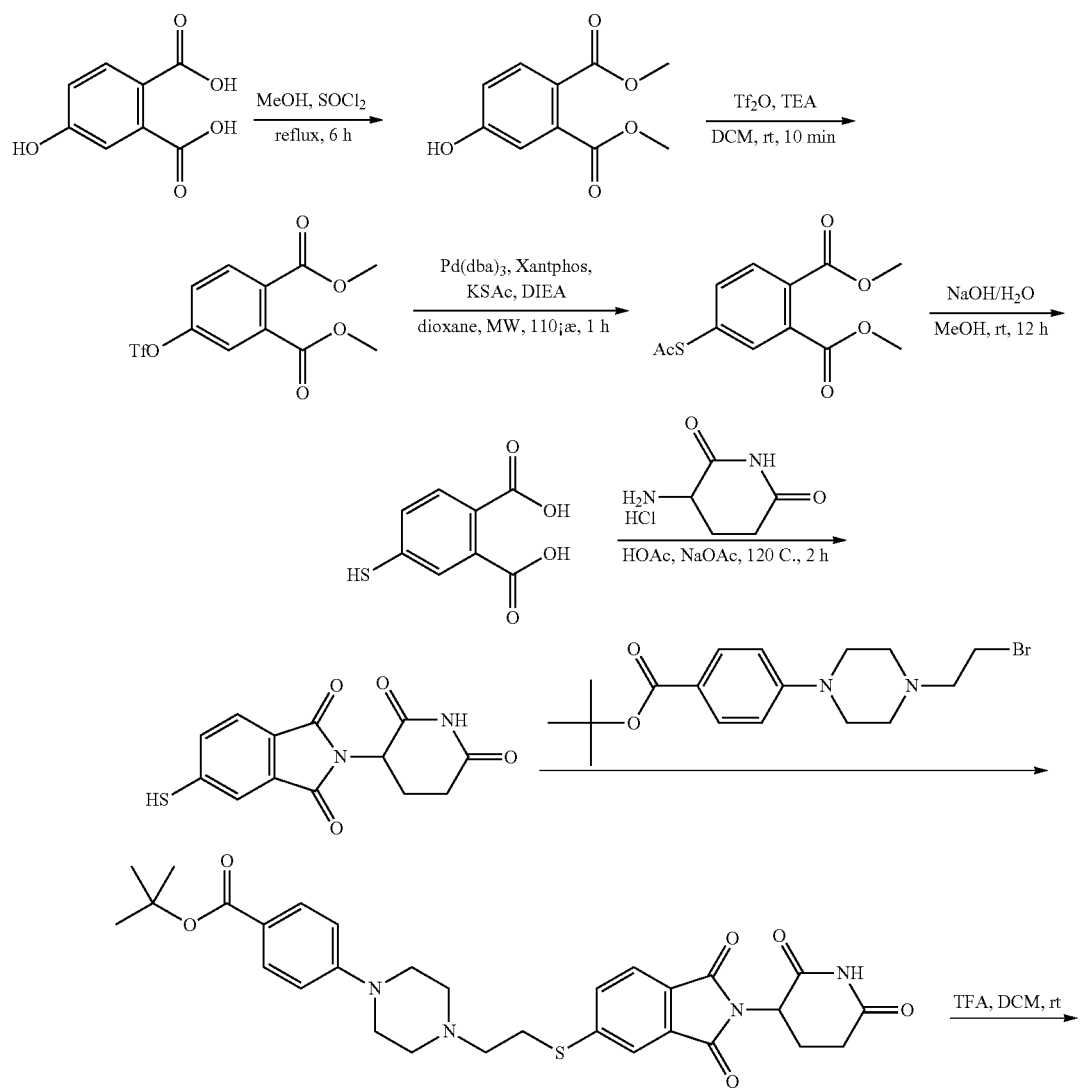

421
422
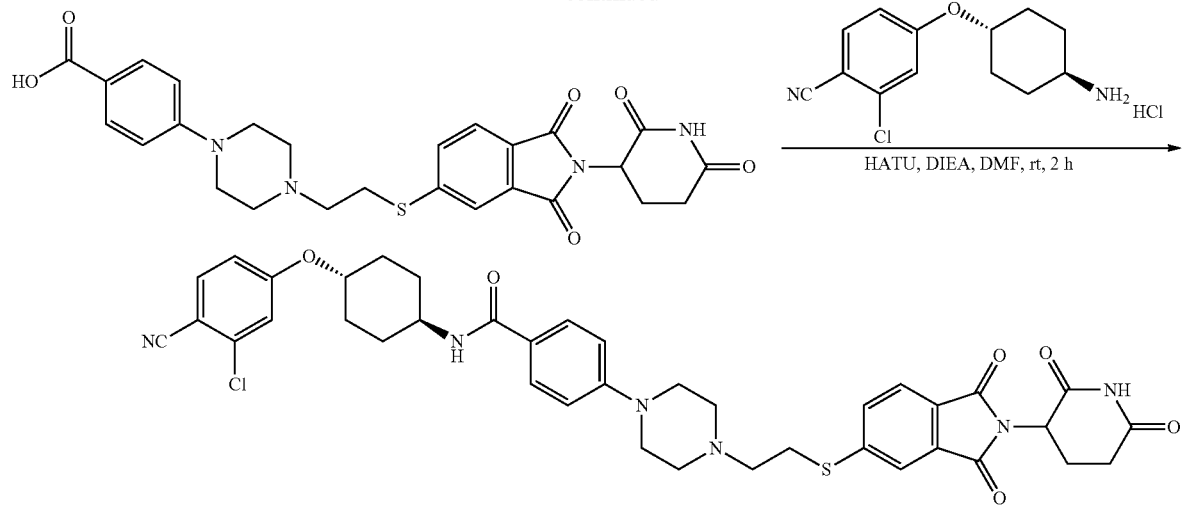
HATU, DIEA, DMF, rt, 2 h

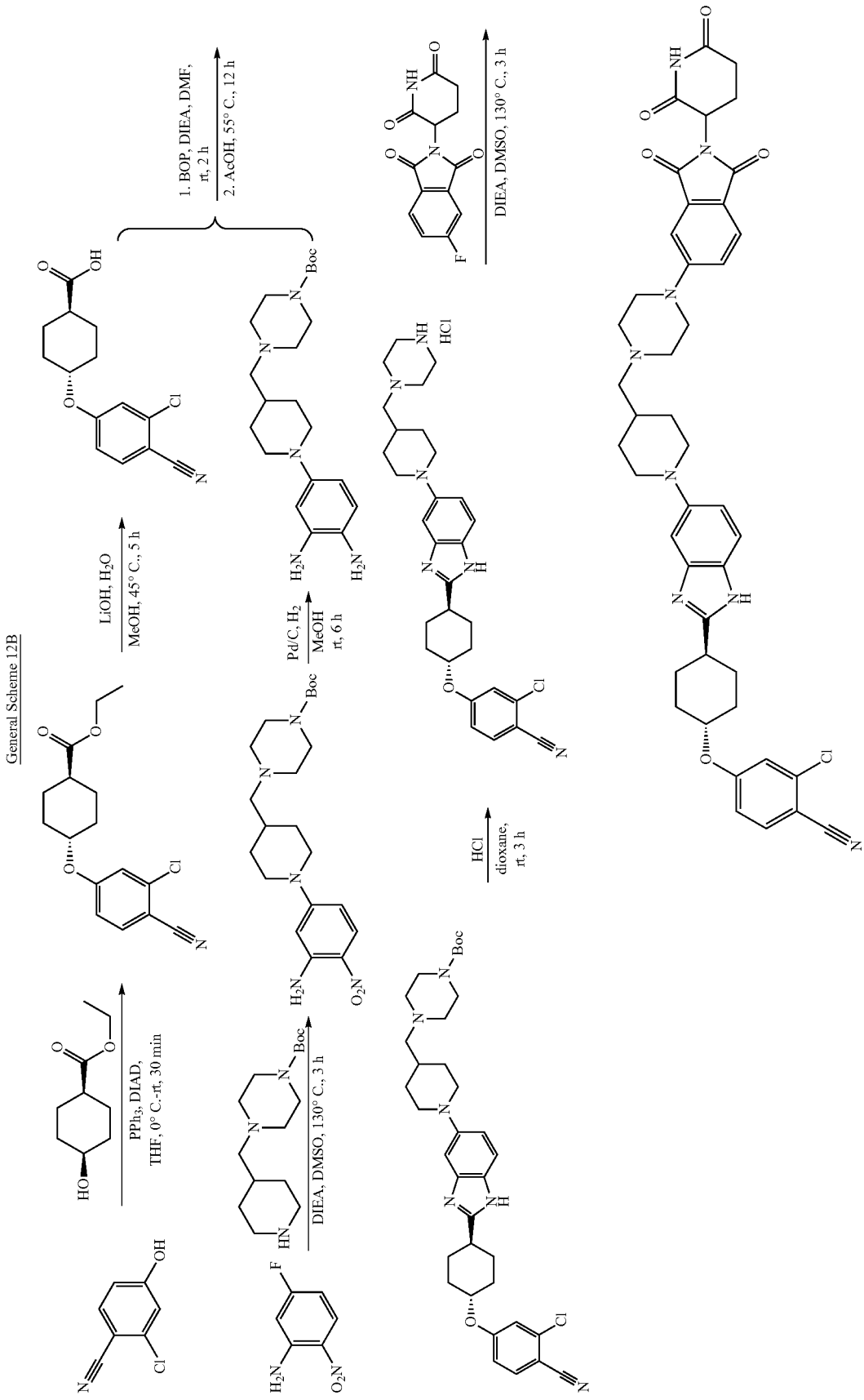

General Scheme 13B
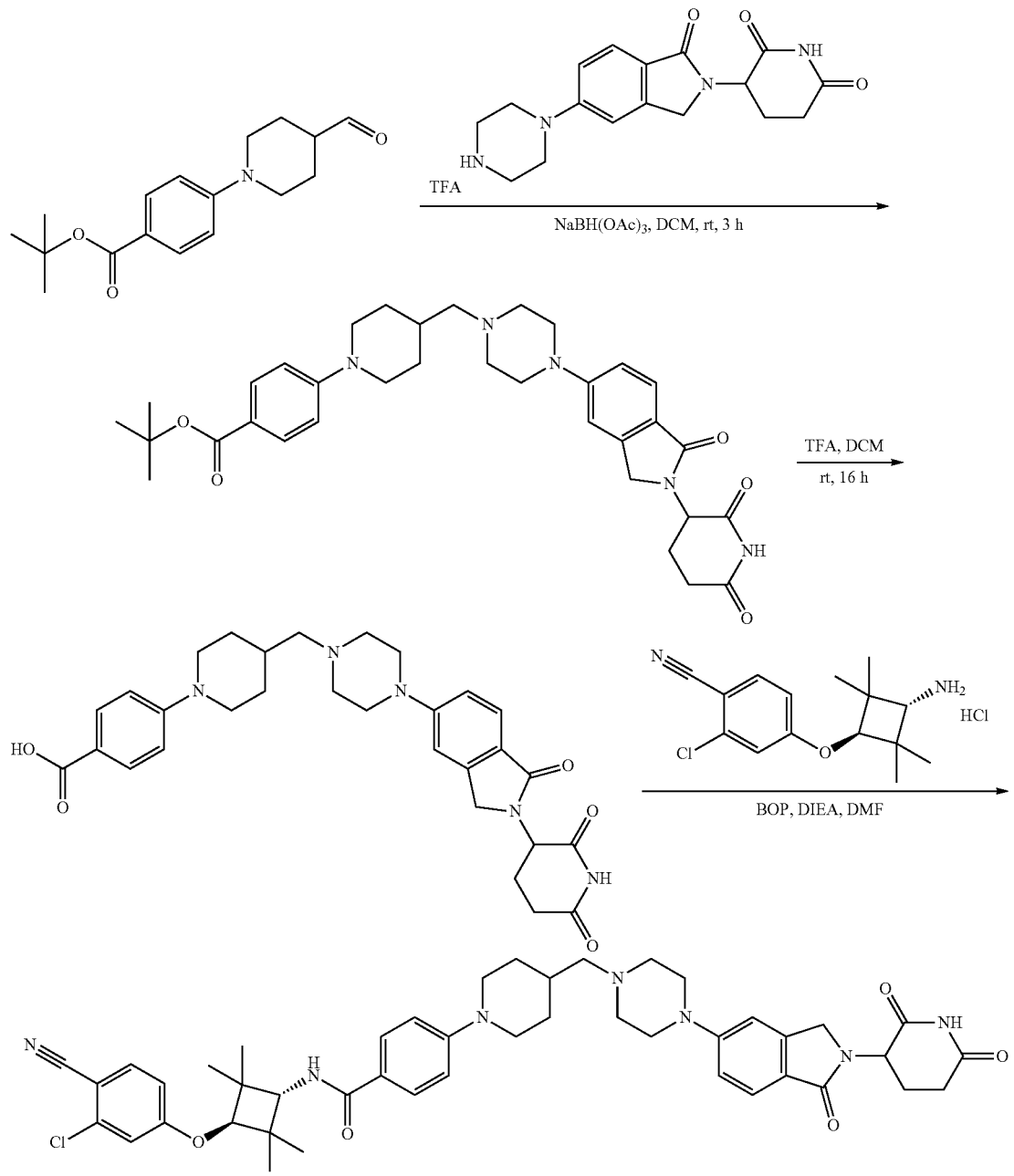
General Scheme 14B
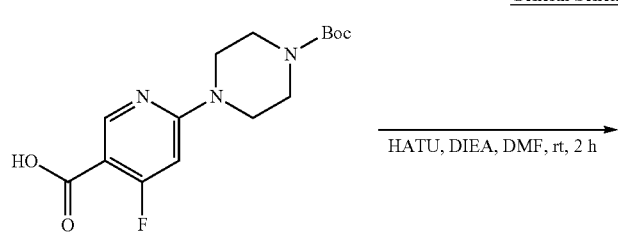

427 428
-continued
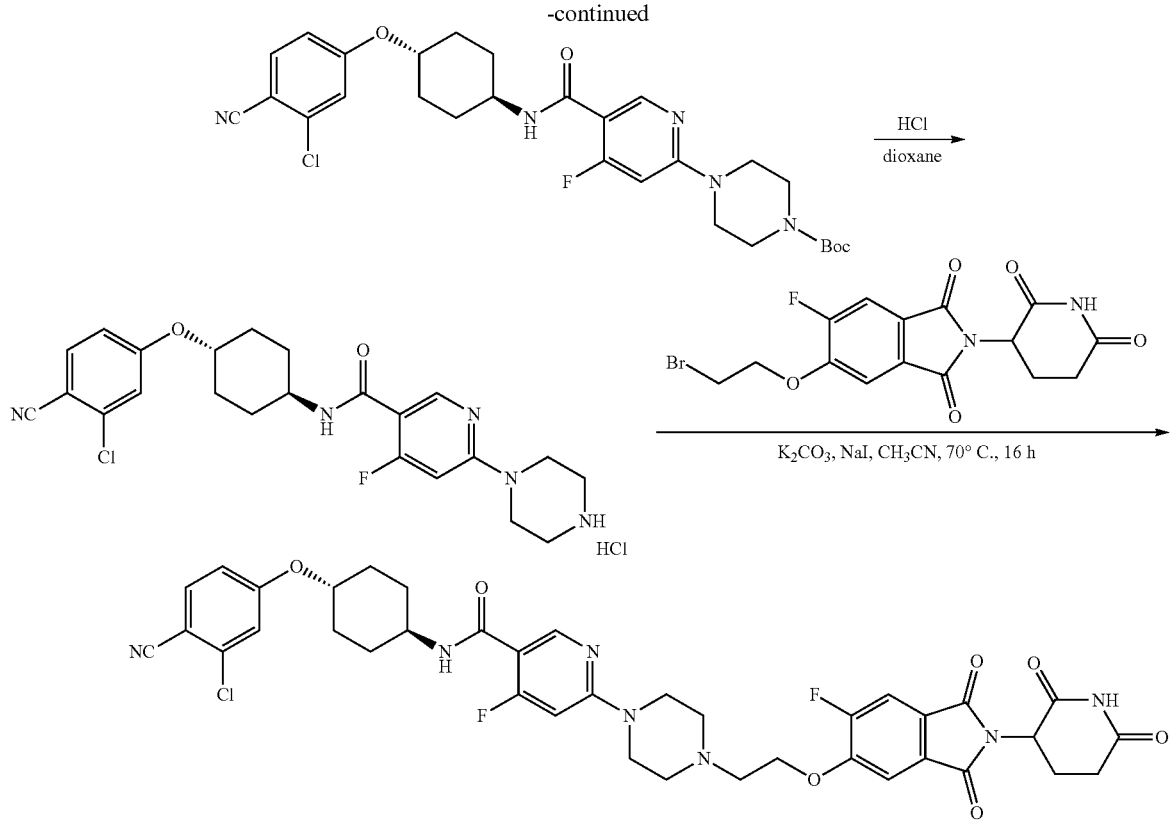
General Scheme 15B
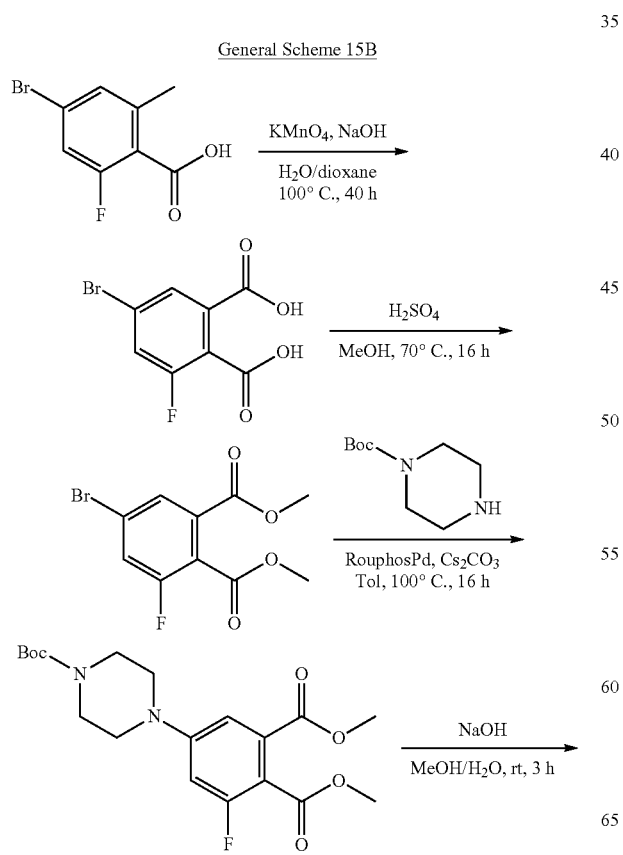
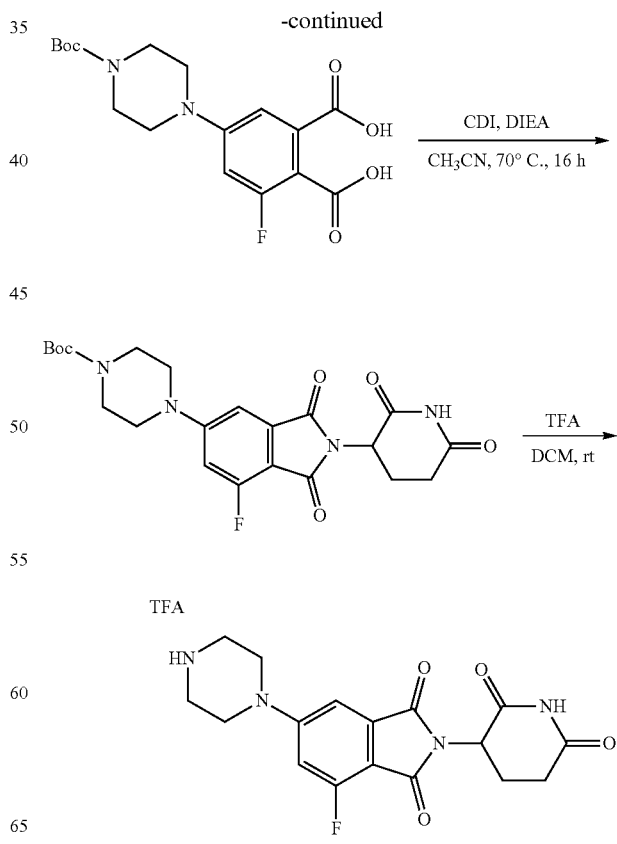

General Scheme 16B
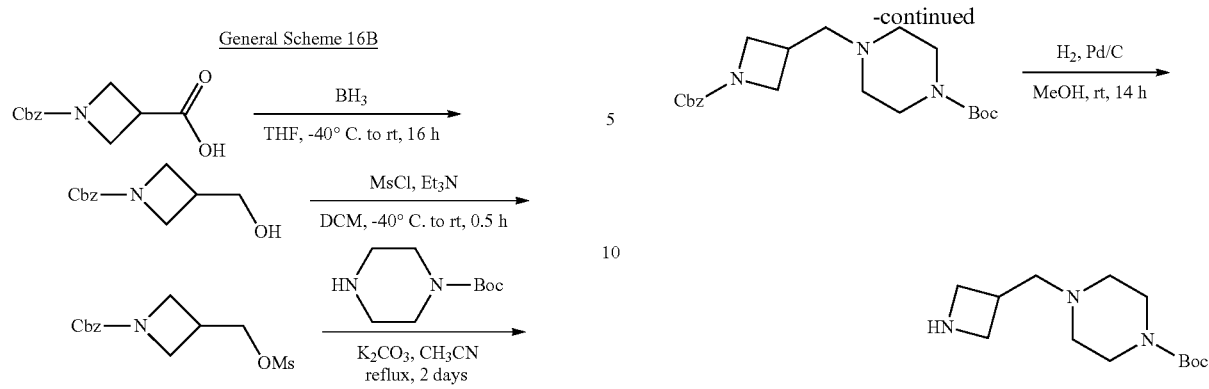
General Scheme 17B
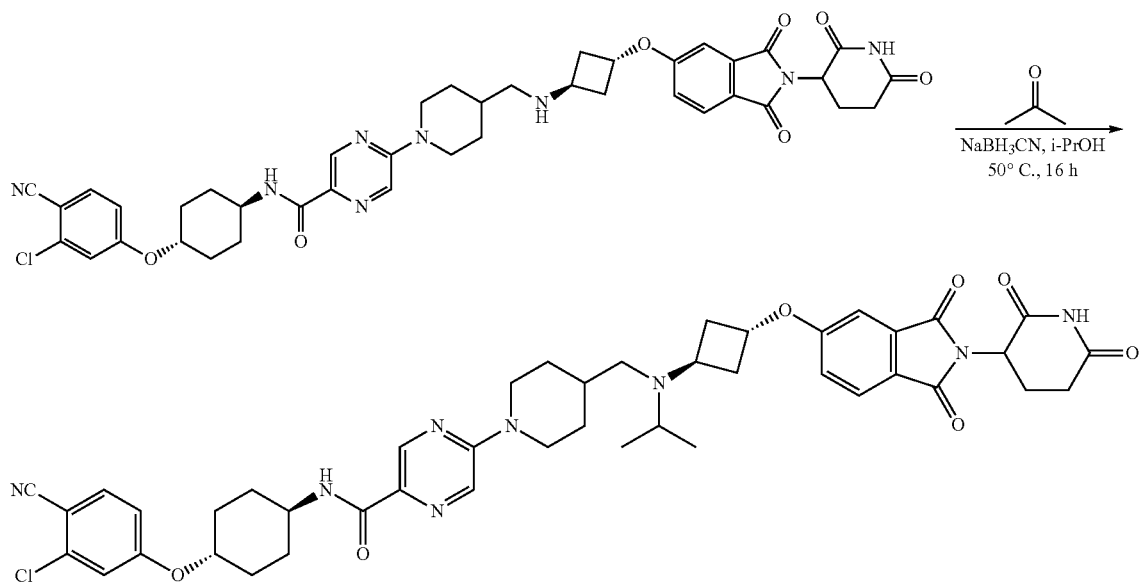
General Scheme 18B
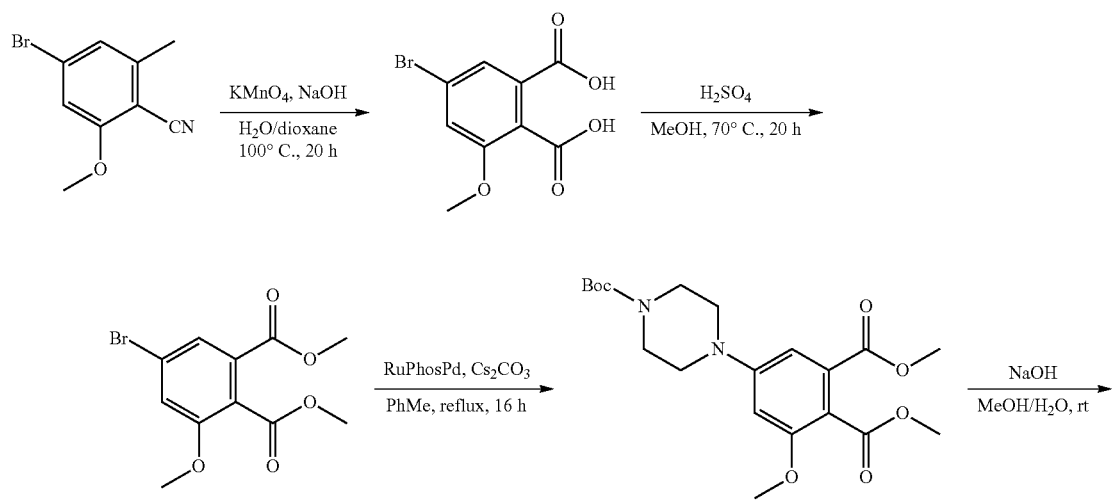

431
432
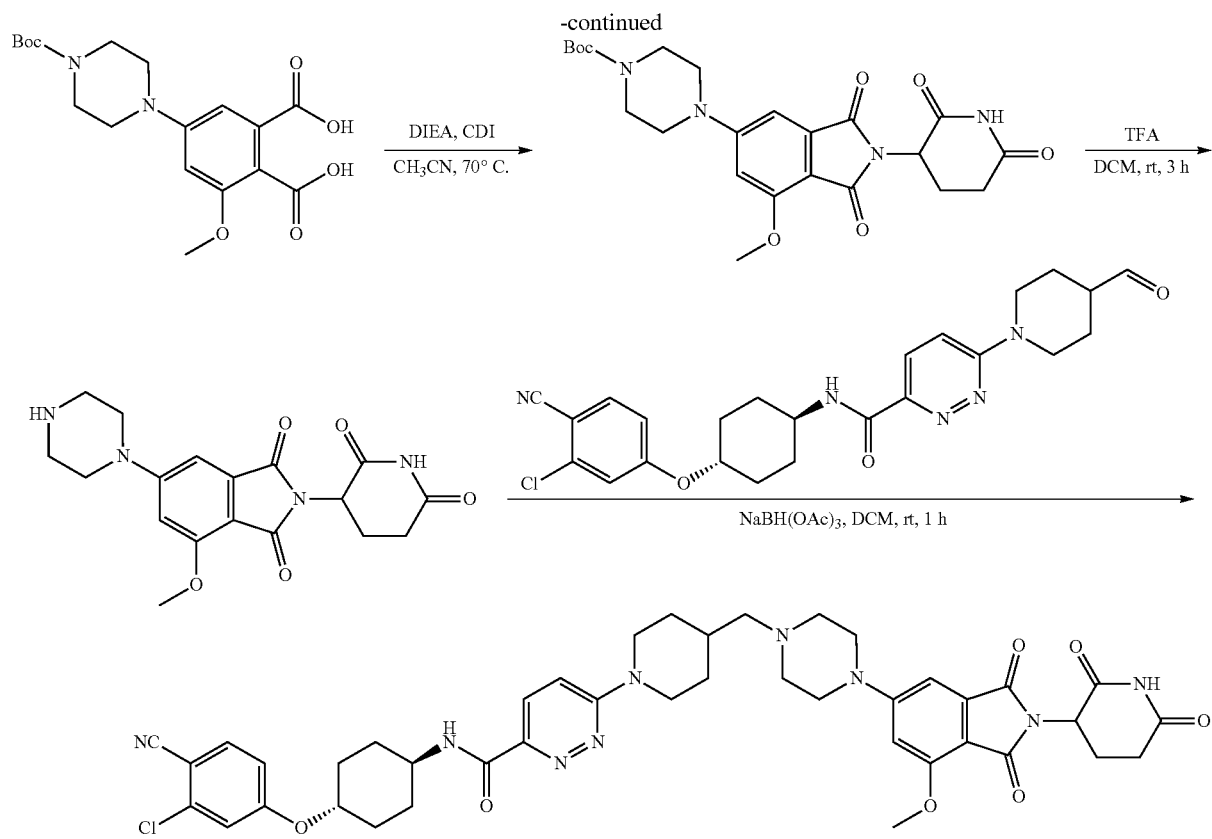
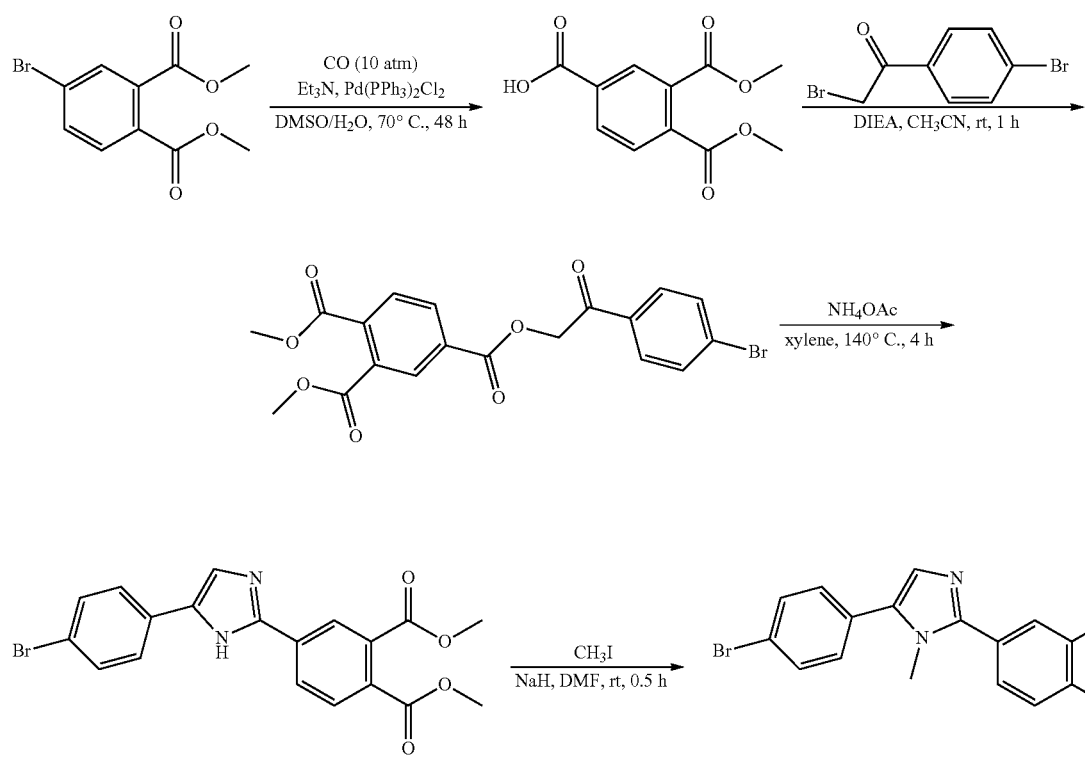

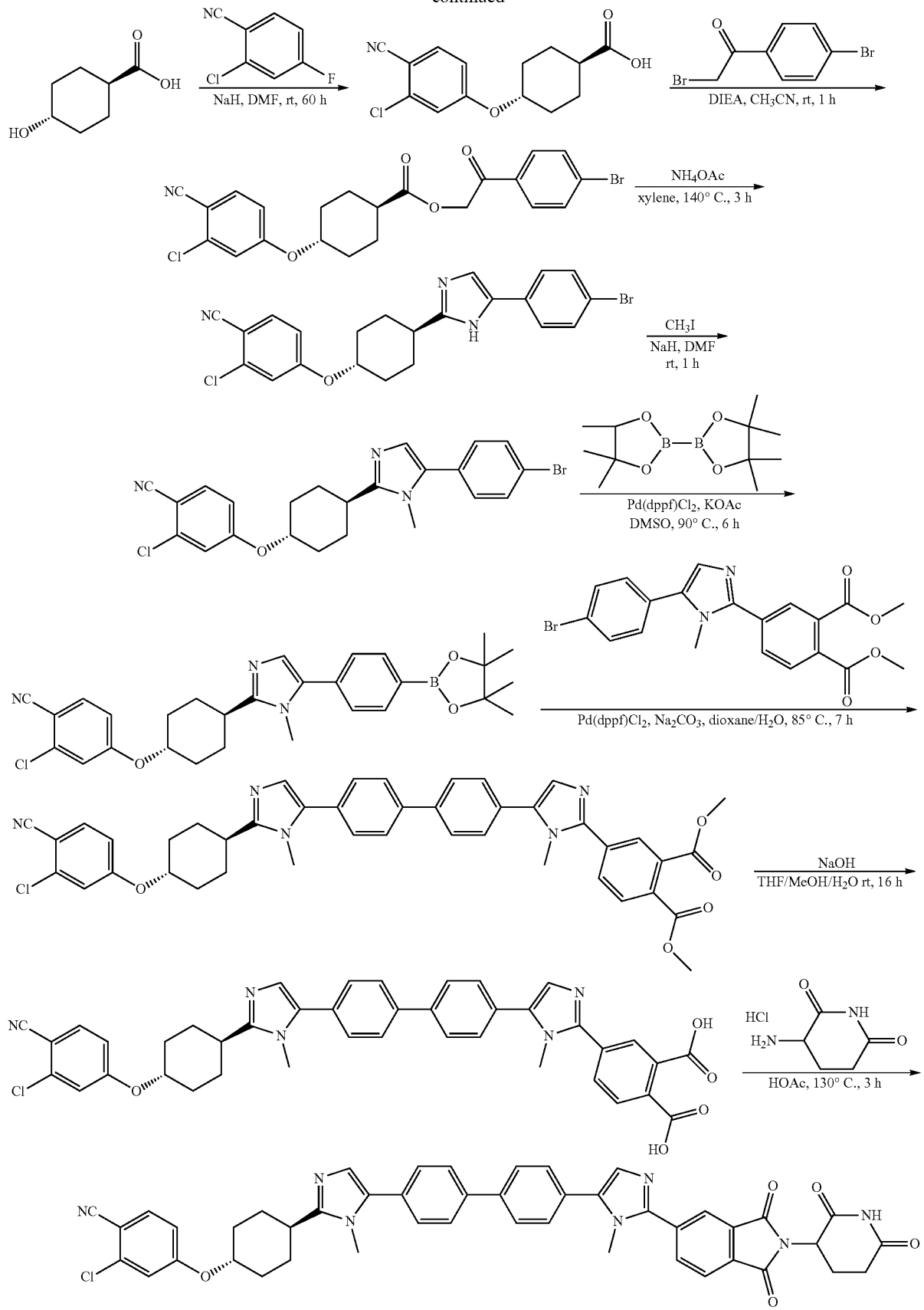

General Scheme 20B
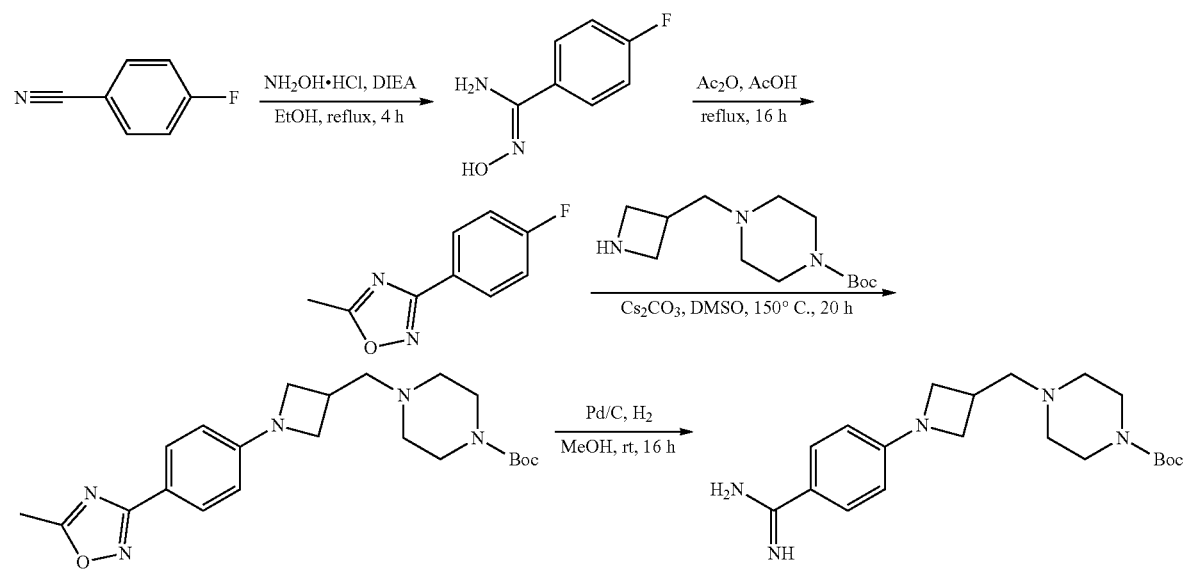
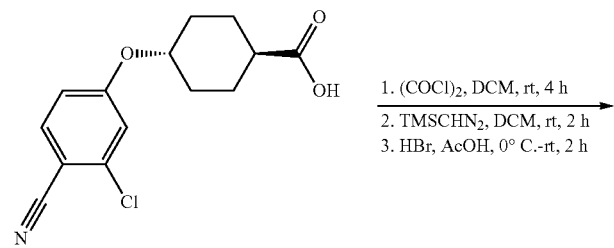
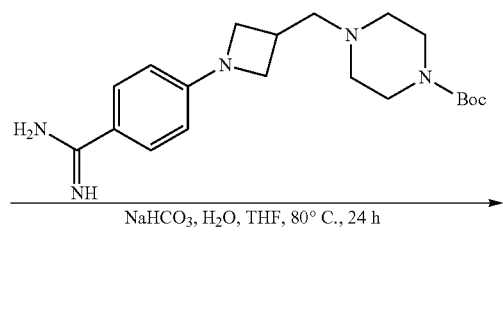
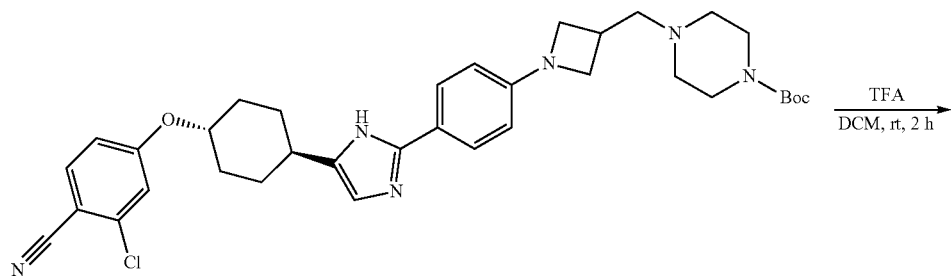

437 438
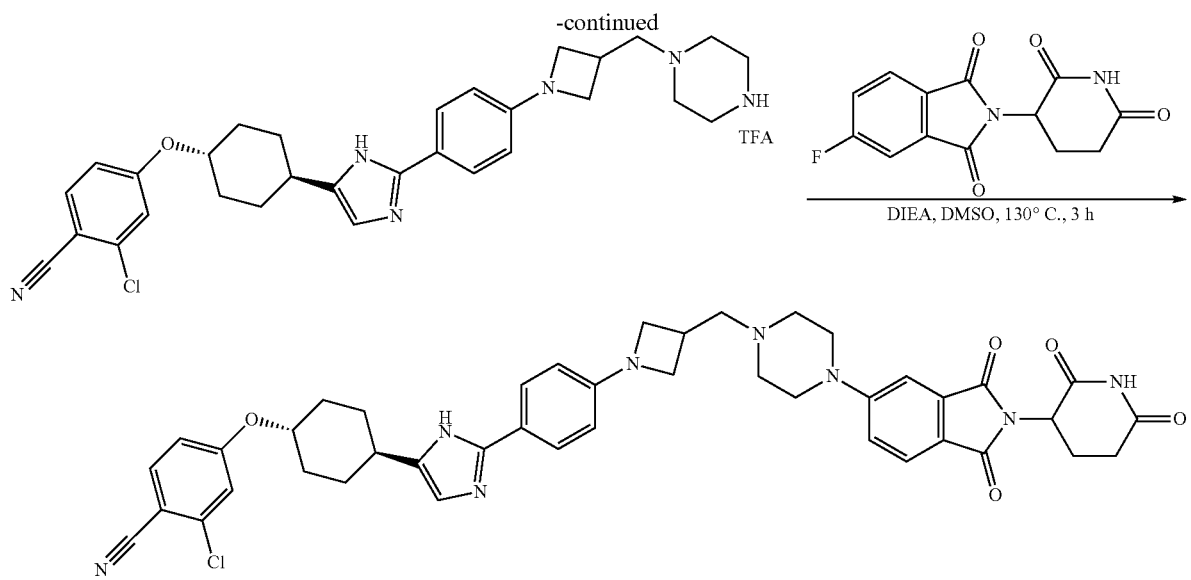
General Scheme 21B
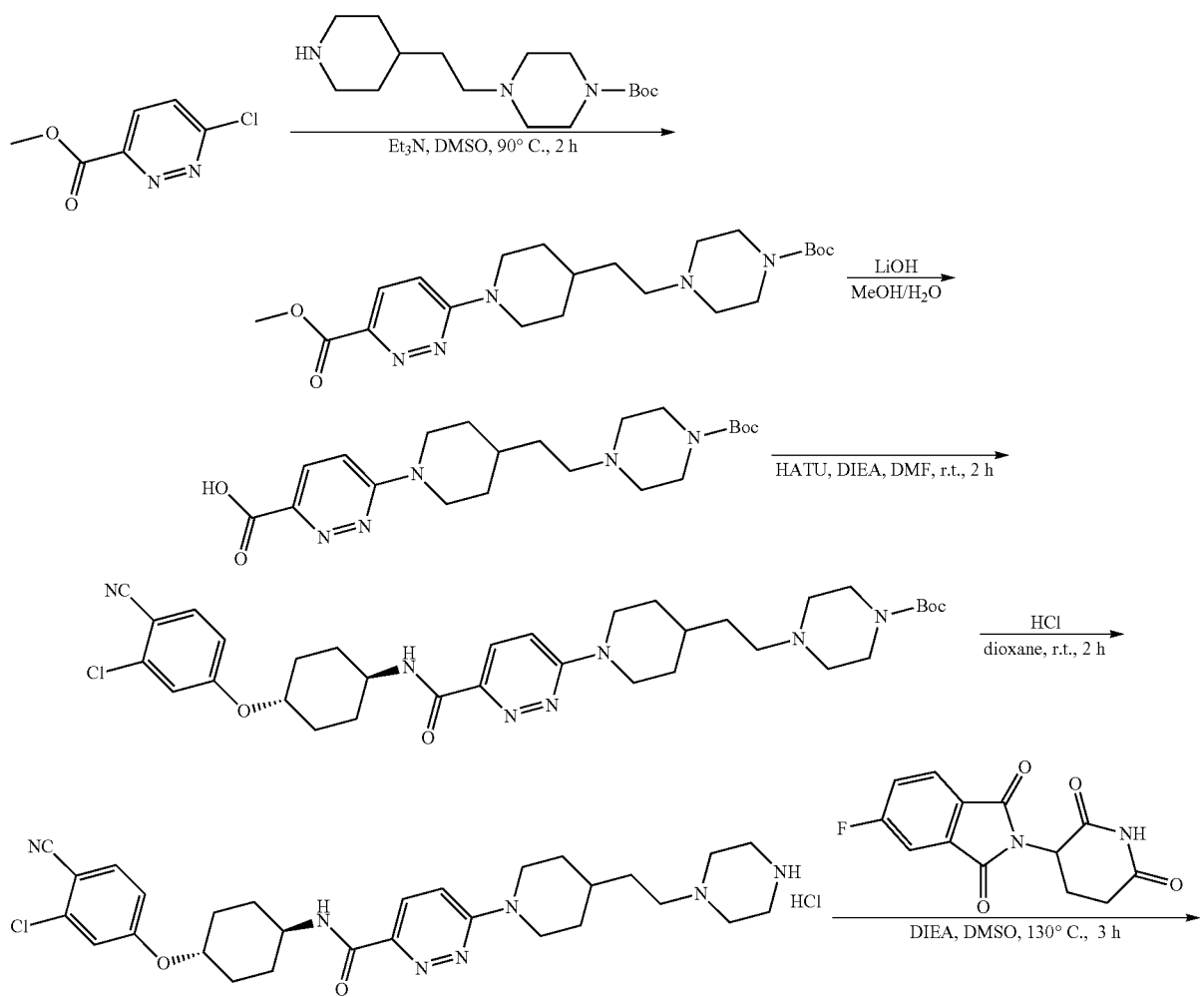

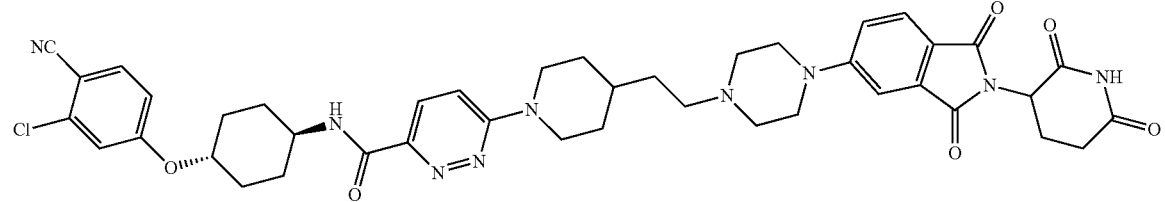
-continued
General Scheme 22B
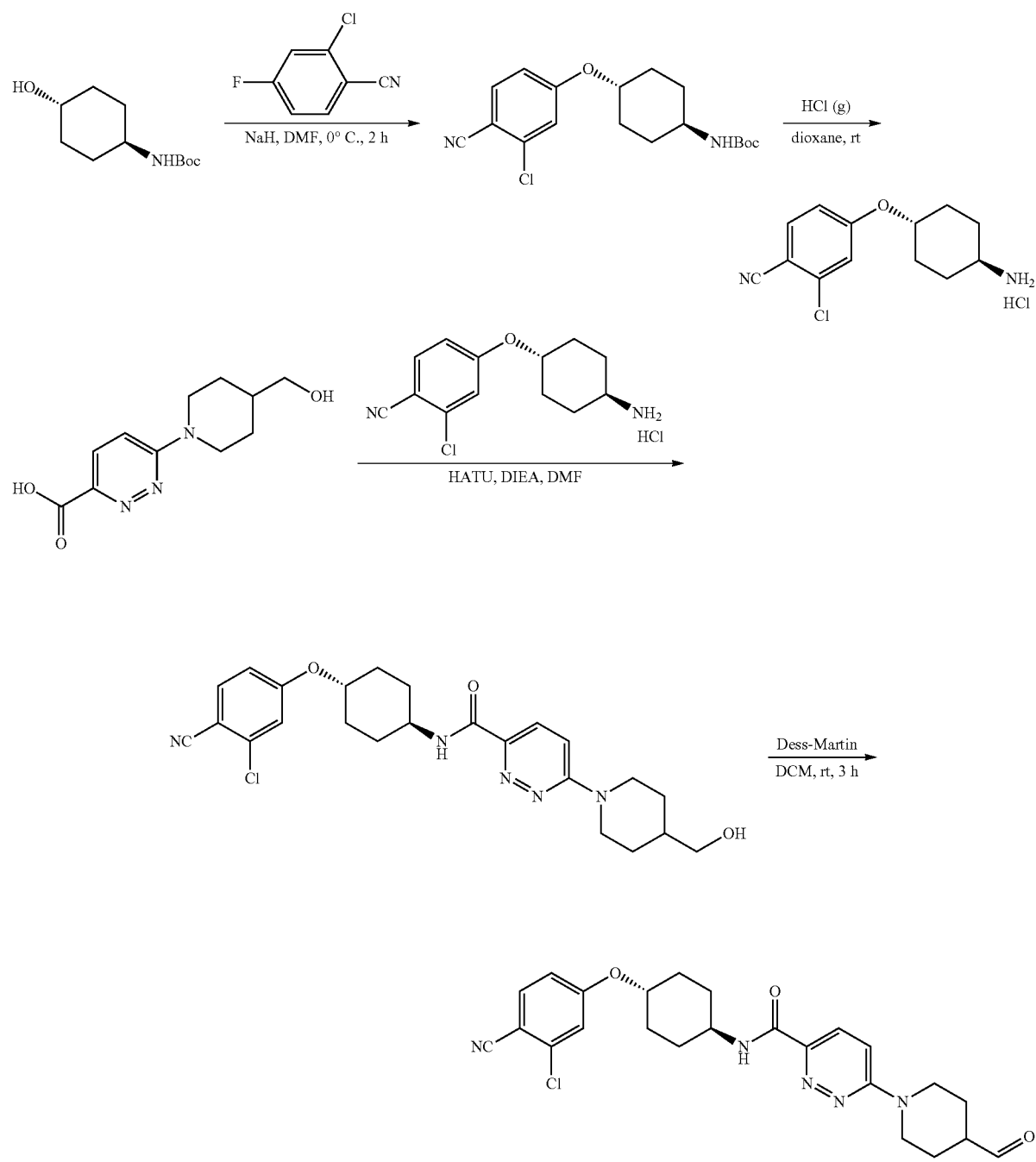

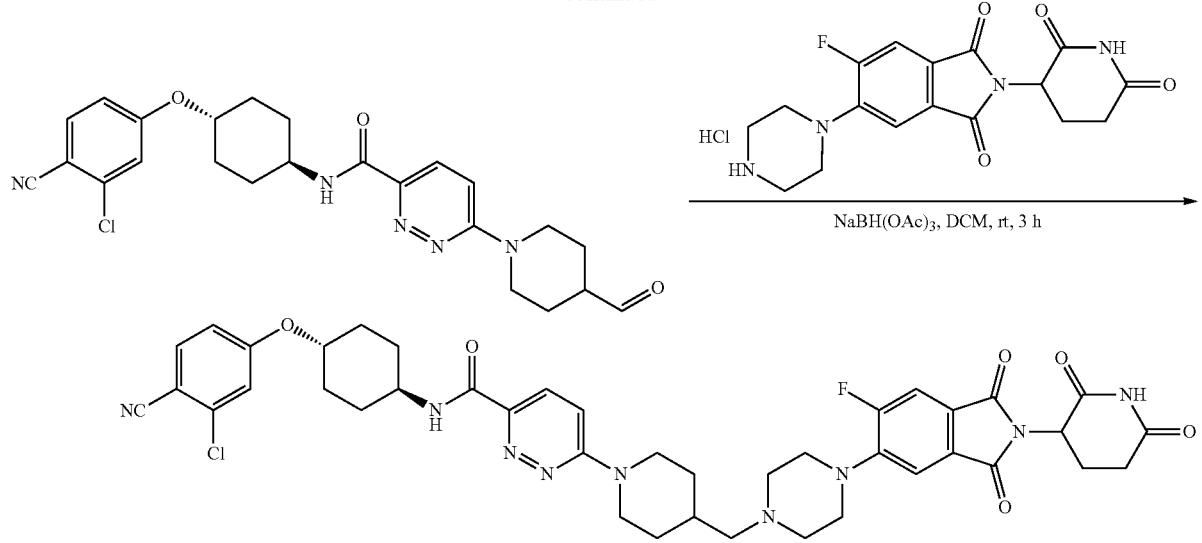
General Scheme 23B
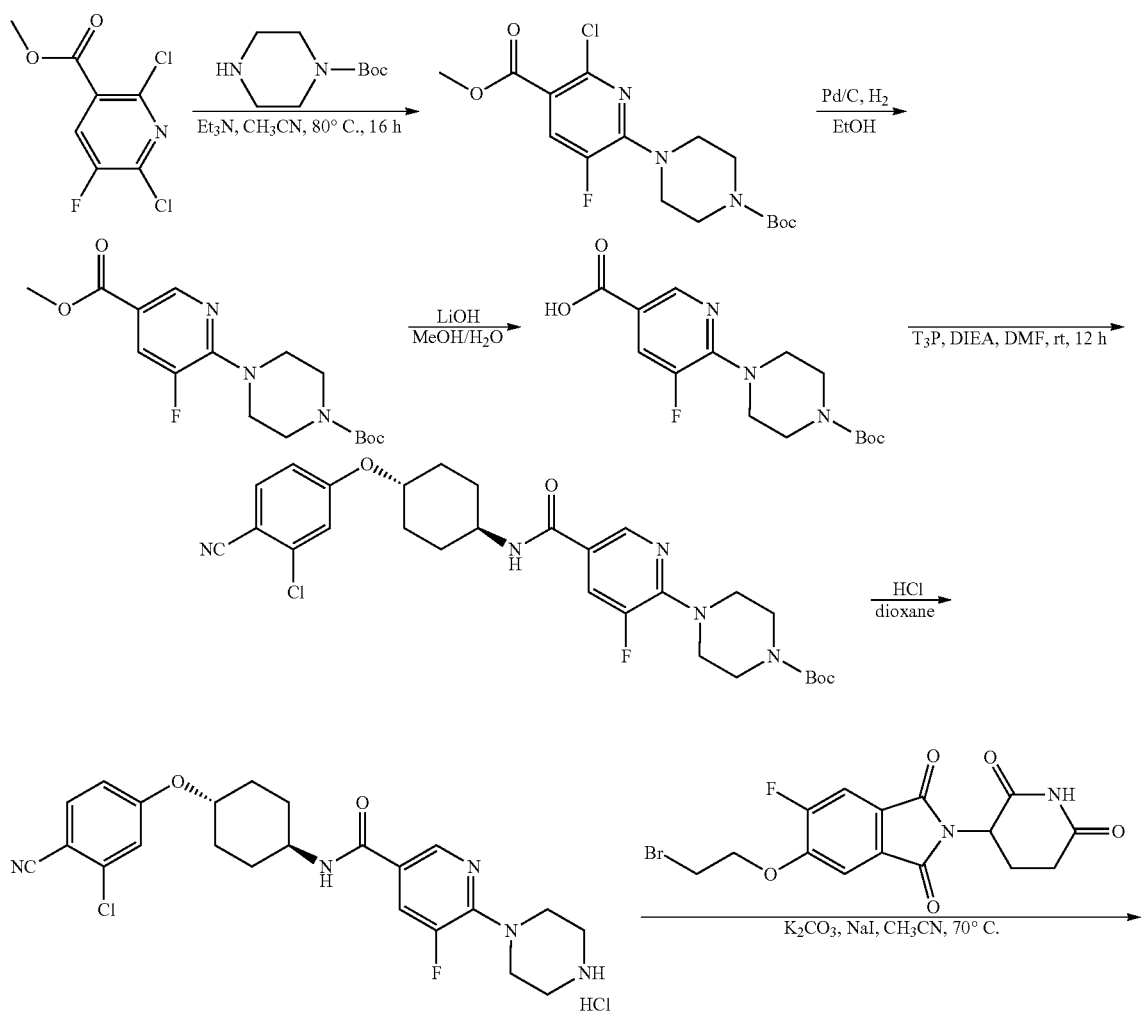

-continued
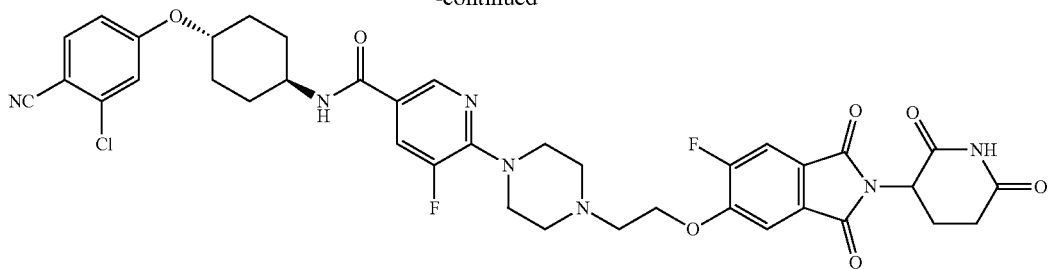
General Scheme 24B
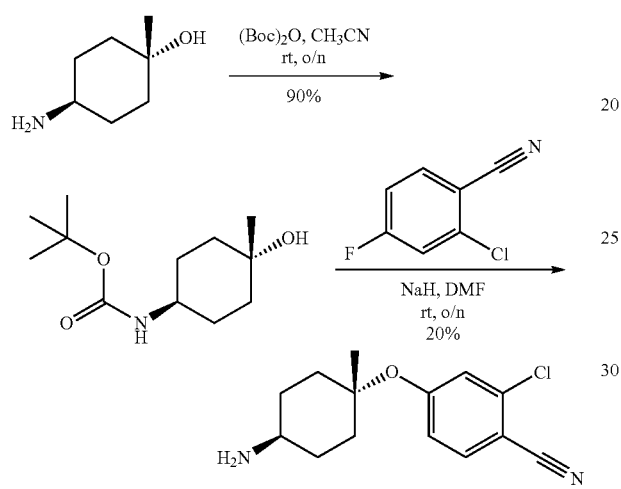
General Scheme 25B
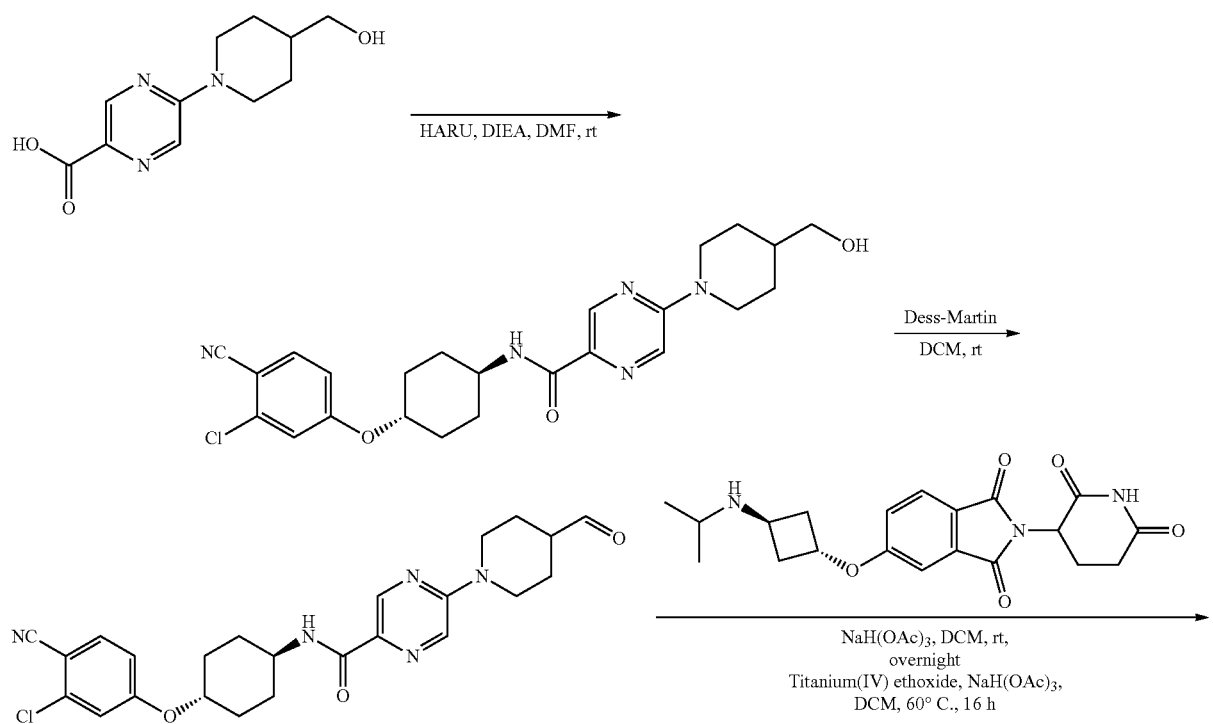

-continued

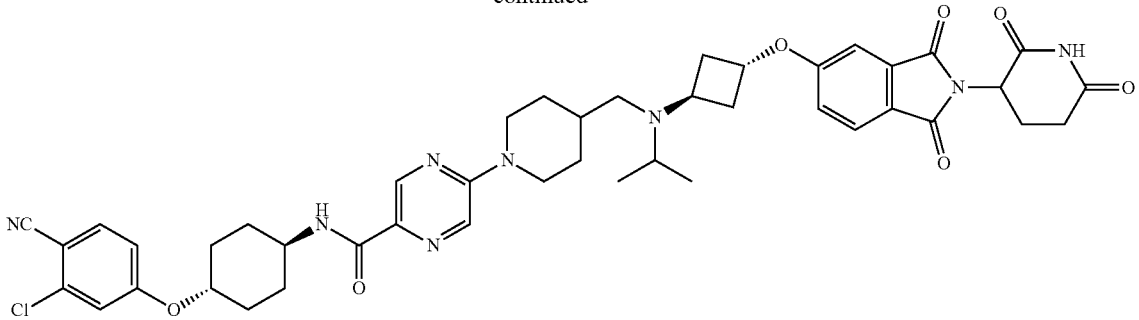

Synthetic Procedure for Compound 406

Synthesis of tert-butyl N-[(1r,4r)-4-(3-chloro-4-cyanophenoxy)cyclohexyl]carbamate Into a 50.0-mL round-bottom flask, was placed tert-butyl N-[(1r,4r)-4-hydroxycyclohexyl]carbamate (500.0 mg, 2.32 mmol, 1.00 equiv), N,N-dimethylformamide (10.0 mL), sodium hydride (82.8 mg, 3.45 mmol, 1.50 equiv), 2-chloro-4-fluorobenzonitrile (432.6 mg, 2.78 mmol, 1.20 equiv). The resulting solution was stirred for 2 hours at 0° C. in a water/ice bath. The reaction was then quenched by the addition of 20.0 mL of water. The resulting solution was extracted with ethyl acetate (40.0 mL) and the organic layers combined. The resulting mixture was washed with sodium chloride (40.0 mL). The mixture was dried over anhydrous sodium sulfate. The residue was applied onto a silica gel column with ethyl acetate/petroleum ether (1/2). The collected fractions were combined and concentrated under vacuum. This resulted in 470.0 mg (58%) of tert-butyl N-[(1r,4r)-4-(3-chloro-4-cyanophenoxy)cyclohexyl]carbamate as yellow oil.

LC-MS (ES$^+$): m/z 295.0 [MH$^+$], $t_R$=1.199 min, (1.90 minute run).

Chemical formula: $C_{18}H_{23}ClN_2O_3$ [350.14].

Synthesis of 4-(((1r,4r)-4-aminocyclohexyl)oxy)-2-chlorobenzonitrile

Into a 50.0-mL round-bottom flask, was placed tert-butyl N-[(1r,4r)-4-(3-chloro-4-cyanophenoxy)cyclohexyl]carbamate (470.0 mg, 1.34 mmol, 1.00 equiv), methanol (5.0 mL), hydrogen chloride. The resulting solution was stirred for 2 hours at room temperature. The resulting mixture was concentrated under vacuum. This resulted in 340.0 mg (88%) of 2-chloro-4-[[(1r,4r)-4-aminocyclohexyl]oxy]benzonitrile hydrochloride as a yellow solid.

LC-MS (ES$^+$): m/z 250.90 [MH$^+$], $t_R$=0.537 min, (1.90 minute run).

Chemical formula: $C_{13}H_{15}ClN_2O$ [250.09].

Synthesis of 6-[4-(hydroxymethyl)piperidin-1-yl]-N-[(1r,4r)-4-(3-chloro-4-cyanophenoxy) cyclohexyl] pyridazine-3-carboxamide)

Into a 100-mL round-bottom flask, was placed 6-[4-(hydroxymethyl)piperidin-1-yl]pyridazine-3-carboxylic acid (1.0 g, 4.21 mmol, 1.00 equiv), 2-chloro-4-[(1r,4r)-4-aminocyclohexyl]oxybenzonitrile hydrochloride (1.2 g, 4.18 mmol, 1.00 equiv), N,N-dimethylformamide (30 mL), N,N,N',N'-Tetramethyl-O-(7-azabenzotriazol-1-yl)uronium hexafluorophospate (2.4 g, 6.31 mmol, 1.50 equiv), N,N-diisopropylethylamine (1.6 g, 12.38 mmol, 3.00 equiv). The resulting solution was stirred for 1 hour at room temperature. The reaction was then quenched by the addition of water (50 mL) and extracted with ethyl acetate (50 mL×3). The combined organic layers was washed with brine (50 mL), dried over anhydrous sodium sulfate and concentrated under vacuum. The residue was applied onto a silica gel column with dichloromethane/methanol (v:v=12:1). This resulted in 1.1 g (56%) of 6-[4-(hydroxymethyl)piperidin-1-yl]-N-[(1r,4r)-4-(3-chloro-4-cyanophenoxy)cyclohexyl]pyridazine-3-carboxamide as yellow oil.

LC-MS (ES$^+$): m/z 470.0 [MH$^+$], $t_R$=0.90 min (1.8 minute run).

Synthesis of 6-(4-formylpiperidin-1-yl)-N-[(1r,4r)-4-(3-chloro-4-cyanophenoxy)cyclohexyl] pyridazine-3-carboxamide Into a 100-mL round-bottom flask, was placed 6-[4-(hydroxymethyl)piperidin-1-yl]-N-[(1r,4r)-4-(3-chloro-4-cyanophenoxy)cyclohexyl]pyridazine-3-carboxamide (700.0 mg, 1.49 mmol, 1.00 equiv), dichloromethane (20 mL), (1,1,1-Triacetoxy)-1,1-dihydro-1,2-benziodoxol-3 (1H)-one (947.2 mg, 2.23 mmol, 1.50 equiv). The resulting solution was stirred for 3 hours at room temperature. The resulting mixture was concentrated under vacuum. The residue was applied onto a silica gel column with ethyl acetate/petroleum ether (v:v=1:3). This resulted in 390.0 mg (56%) of 6-(4-formylpiperidin-1-yl)-N-[(1r,4r)-4-(3-chloro-4-cyanophenoxy)cyclohexyl]pyridazine-3-carboxamide as a yellow solid.

LC-MS (ES$^+$): m/z 468.2 [MH$^+$], $t_R$=1.06 min (2.0 minute run).

Synthesis of 6-[4-([4-[2-(2,6-dioxopiperidin-3-yl)-6-fluoro-1,3-dioxo-2,3-dihydro-1H-isoindol-5-yl]piperazin-1-yl]methyl)piperidin-1-yl]-N-[(1r,4r)-4-(3-chloro-4-cyanophenoxy)cyclohexyl]pyridazine-3-carboxamide Into a 100-mL round-bottom flask, was placed 6-(4-formylpiperidin-1-yl)-N-[(1r,4r)-4-(3-chloro-4-cyanophenoxy)cyclohexyl]pyridazine-3-carboxamide (180.0 mg, 0.38 mmol, 1.00 equiv), dichloromethane (10 mL), 2-(2,6-dioxopiperidin-3-yl)-5-fluoro-6-(piperazin-1-yl)-2,3-dihydro-1H-isoindole-1,3-dione hydrochloride (152.7 mg, 0.38 mmol, 1.00 equiv), sodium triacetoxyborohydride (244.6 mg, 3.00 equiv). The resulting solution was stirred for 3 hours at room temperature. The reaction was then quenched by water (30 mL), extracted with ethyl acetate (30 mL×3), washed with brine (30 mL) and concentrated under reduced pressure. The solid was filtered out. The crude product was purified by Prep-HPLC with the following conditions: Column, XBridge Prep C18 OBD Column, 19*150 mm 5 um; mobile phase, water (10 mmol/L ammonium bicarbonate) and acetonitrile (48.0% acetonitrile up to 73.0% in 8 min); Detector, UV 254 nm. This resulted in 146.1 mg (47%) of 6-[4-([4-[2-(2,6-dioxopiperidin-3-yl)-6-fluoro-1,3-dioxo-2,3-dihydro-1H-isoindol-5-yl]piperazin-1-yl]methyl)piperidin-1-yl]-N-[(1r,4r)-4-(3-chloro-4-cyanophenoxy)cyclohexyl]pyridazine-3-carboxamide as a yellow solid.

$^1$H NMR (400 MHz, DMSO): δ 11.11 (s, 1H), 8.58 (d, J=8.2 Hz, 1H), 7.86 (d, J=8.8 Hz, 1H), 7.81 (d, J=9.5 Hz, 1H), 7.73 (d, J=11.4 Hz, 1H), 7.46 (d, J=7.4 Hz, 1H), 7.39 (d, J=2.4 Hz, 1H), 7.34 (d, J=9.7 Hz, 1H), 7.15-7.12 (m, 1H), 5.13-5.08 (m, 1H), 4.59-4.45 (m, 3H), 3.90-3.83 (m, 1H), 3.27 (s, 4H), 3.03 (m, 2H), 2.97-2.82 (m, 1H), 2.64-2.53 (m, 5H), 2.46 (m, 1H), 2.23 (m, 2H), 2.14-2.09 (m, 2H), 2.07-2.02 (m, 1H), 1.96-1.79 (m, 5H), 1.65 (m, 2H), 1.52 (m, 2H), 1.19-10.09 (m, 2H); LC-MS (ES$^+$): m/z 812.25 [MH$^+$], t$_R$=1.57 min (3.0 minute run).

Chemical Formula: $C_{41}H_{43}ClFN_9O_6$ [811.30].
Total H count from HNMR data: 43.

Synthetic Procedure for Compound 109

1. Synthesis of benzyl 6-(6-hydroxyhex-1-yn-1-yl)pyridine-3-carboxylate)

Into a 250-mL round-bottom flask, was placed a solution of benzyl 6-chloropyridine-3-carboxylate (2.8 g, 11.31 mmol, 1.00 equiv) in triethylamine (50 mL), Cuprous iodide (1.2 g, 6.30 mmol, 1.50 equiv), four (triphenylphosphine) palladium (2.5 g, 0.50 equiv), hex-5-yn-1-ol (1.3 g, 13.25 mmol, 1.00 equiv). The resulting solution was stirred for 3 hours at 90° C. in an oil bath. The resulting solution was extracted with ethyl acetate and the organic layers combined. The resulting mixture was washed with brine. The mixture was dried over anhydrous sodium sulfate. The residue was applied onto a silica gel column with ethyl acetate/petroleum ether (1:1). The collected fractions were combined and concentrated under vacuum. This resulted in 1.1 g (31%) of benzyl 6-(6-hydroxyhex-1-yn-1-yl)pyridine-3-carboxylate as yellow oil. LC-MS (ES$^+$): m/z 309.95 [MH$^+$], t$_R$=0.873 min (1.90 minute run).

2. Synthesis of 6-(6-hydroxyhexyl)pyridine-3-carboxylic

Into a 250-mL round-bottom flask, was placed a solution of benzyl 6-(6-hydroxyhex-1-yn-1-yl)pyridine-3-carboxylate (1.1 g, 3.56 mmol, 1.00 equiv) in methanol (40 mL), Palladium carbon (2 g, 10.00 equiv), hydrogen (g). The resulting solution was stirred for 48 hours at room temperature. The resulting solution was diluted with 200 mL of methanol. The resulting mixture was concentrated under vacuum. This resulted in 700 mg (88%) of 6-(6-hydroxyhexyl)pyridine-3-carboxylic acid as yellow oil.

LC-MS (ES$^+$): m/z 223.95 [MH$^+$], t$_R$=0.377 min (1.90 minute run).

3. Synthesis of 6-(6-hydroxyhexyl)-N-[(1r,3r)-3-(3-chloro-4-cyanophenoxy)-2,2,4,4-tetramethylcyclobutyl]pyridine-3-carboxamide Into a 100-mL round-bottom flask, was placed a solution of 6-(6-hydroxyhexyl)pyridine-3-carboxylic acid (430 mg, 1.93 mmol, 1.00 equiv) in N,N-dimethylformamide (20 mL), N,N,N',N'-Tetramethyl-O-(7-azabenzotriazol-1-yl)uronium hexafluorophospate (1.5 g, 3.94 mmol, 2.00 equiv), N,N-diisopropylethylamine (1 mL, 0.30 equiv), 2-chloro-4-[(1r,3r)-3-amino-2,2,4,4-tetramethylcyclobutoxy]benzonitrile (690 mg, 2.48 mmol, 1.30 equiv). The resulting solution was stirred for 2 hours at room temperature. The reaction was then quenched by the addition of 50 mL of water. The resulting solution was extracted with ethyl acetate and the organic layers combined. The resulting mixture was washed with brine. The mixture was dried over anhydrous sodium sulfate and concentrated under vacuum. The residue was applied onto a silica gel column with ethyl acetate/hexane (1/3). The collected fractions were combined and concentrated under vacuum. This resulted in 580 mg (62%) of 6-(6-hydroxyhexyl)-N-[(1r,3r)-3-(3-chloro-4-cyanophenoxy)-2,2,4,4-tetramethylcyclobutyl]pyridine-3-carboxamide as a yellow solid.

LC-MS (ES$^+$): m/z 484.10/486.10 [MH$^+$], t$_R$=0.927 min (1.90 minute run).

4. Synthesis of 6-(5-[[(1r,3r)-3-(3-chloro-4-cyanophenoxy)-2,2,4,4-tetramethylcyclobutyl]carbamoyl]pyridin-2-yl)hexyl 4-methylbenzene-1-sulfonate Into a 100-mL round-bottom flask, was placed a solution of 6-(6-hydroxyhexyl)-N-[(1r,3r)-3-(3-chloro-4-cyanophenoxy)-2,2,4,4-tetramethylcyclobutyl]pyridine-3-carboxamide (580 mg, 1.20 mmol, 1.00 equiv) in dichloromethane (20 mL), 4-toluene sulfonyl chloride (750 mg, 3.93 mmol, 1.50 equiv), triethylamine (690 mg, 6.82 mmol, 3.00 equiv), 4-dimethylaminopyridine (35 mg, 0.29 mmol, 0.10 equiv). The resulting solution was stirred for 20 hours at room temperature. The reaction was then quenched by the addition of water. The resulting solution was extracted with ethyl acetate and the organic layers combined. The resulting mixture was washed with brine. The solid was dried in an oven under reduced pressure. The residue was applied onto a silica gel column with ethyl acetate/petroleum ether (1:1). This resulted in 430 mg (56%) of 6-(5-[[(1r,3r)-3-(3-chloro-4-cyanophenoxy)-2,2,4,4-tetramethylcyclobutyl]carbamoyl]pyridin-2-yl)hexyl 4-methylbenzene-1-sulfonate as a yellow solid.

LC-MS (ES$^+$): m/z 638.40/640.40[MH$^+$], t$_R$=1.336 min (2.00 minute run).

5. Synthesis of 6-(6-[4-[2-(2,6-dioxopiperidin-3-yl)-1,3-dioxo-2,3-dihydro-1H-isoindol-5-yl]piperazin-1-yl]hexyl)-N-[(1r,3r)-3-(3-chloro-4-cyanophenoxy)-2,2,4,4-tetramethylcyclobutyl]pyridine-3-carboxamide Into a 25-mL round-bottom flask, was placed a solution of 6-(5-[(1r,3r)-3-(3-chloro-4-cyanophenoxy)-2,2,4,4-tetramethylcyclobutyl]carbamoylpyridin-2-yl)hexyl 4-methylbenzene-1-sulfonate (220 mg, 0.34 mmol, 1.00 equiv) in acetonitrile (5 mL), 2-(2,6-dioxopiperidin-3-yl)-5-(piperazin-1-yl)-2,3-dihydro-1H-isoindole-1,3-dione; trifluoroacetic acid (162 mg, 0.35 mmol, 1.50 equiv), potassium carbonate (25 mg, 0.18 mmol, 3.00 equiv), sodium iodide (25 mg, 0.50 equiv). The resulting solution was stirred for 12 hours at 70° C. in an oil bath. The resulting mixture was concentrated under vacuum. The crude product (3 mL) was purified by Prep-HPLC with the following conditions: Column, XBridge Shield RP18 OBD Column, Sum, 19*150 mm; mobile phase, water (10 mmol/L ammonium bicarbonate) and acetonitrile (56.0% acetonitrile up to 65.0% in 8 min); Detector, UV 254 nm. 41.3 mg product was obtained.

This resulted in 41.3 mg (15%) of 6-(6-[4-[2-(2,6-dioxopiperidin-3-yl)-1,3-dioxo-2,3-dihydro-1H-isoindol-5-yl]piperazin-1-yl]hexyl)-N-[(1r,3r)-3-(3-chloro-4-cyanophenoxy)-2,2,4,4-tetramethylcyclobutyl]pyridine-3-carboxamide as a yellow solid.

$^{1}$HNMR (300 MHz, CD$_3$OD): δ 8.86 (s, 1H), 8.16-8.09 (m, 1H), 7.72-7.64 (m, 2H), 7.47-7.33 (m, 2H), 7.24-7.17 (m, 1H), 7.12 (s, 1H), 6.98-6.89 (m, 1H), 5.09-5.02 (m, 1H), 4.26 (s, 1H), 4.15 (s, 1H), 3.48-3.42 (m, 4H), 2.92-2.49 (m, 9H), 2.46-2.35 (m, 2H), 2.16-2.01 (m, 1H), 1.81-1.71 (m, 2H), 1.59-1.47 (m, 2H), 1.42-1.36 (m, 4H), 1.27-1.18 (m, 12H); LC-MS (ES$^+$): m/z 808.85/810.85 [MH$^+$], t$_R$=4.79 min (8.0 minute run).

Chemical formula: C$_{44}$H$_{50}$ClN$_7$O$_6$ [807.35/809.35].

Total H count from HNMR data: 48.

Synthetic Procedure for Compound 158

1. Synthesis of benzyl 4-fluorobenzoate

Into a 500-mL round-bottom flask, was placed 4-fluorobenzoic acid (14 g, 99.9 mmol, 1.0 equiv), N,N-dimethylformamide (150.0 mL), (bromomethyl)benzene (18.7 g, 109.3 mmol, 1.1 equiv), dicesium carbonate (27.6 g, 84.7 mmol, 2.0 equiv). The resulting solution was stirred for 4 hours at room temperature. The reaction was then quenched by the addition of 150 mL of water. The resulting solution was extracted with ethyl acetate (100 mL×3) and the organic layers combined and concentrated under vacuum. The residue was applied onto a silica gel column with ethyl acetate/petroleum ether (1/6). This resulted in 18.0 g (78%) of benzyl 4-fluorobenzoate as a solid.

2. Synthesis of benzyl 4-[4-(hydroxymethyl)piperidin-1-yl]benzoate

Into a 100-mL round-bottom flask, was placed benzyl 4-fluorobenzoate (5.0 g, 21.7 mmol, 1.1 equiv), N,N-Dimethylformamide (30.0 mL), piperidin-4-ylmethanol (2.3 g, 19.9 mmol, 1.0 equiv), N,N-Diisopropylethylamine (7.6 g, 59.1 mmol, 3.0 equiv). The resulting solution was stirred for 2 hours at 100° C. The reaction was then quenched by the addition of 60.0 mL of water. The resulting solution was extracted with ethyl acetate (60 mL×3) and the organic layers combined and concentrated under vacuum. The residue was applied onto a silica gel column with ethyl acetate/petroleum ether (1/1). This resulted in 3.6 g (55%) of benzyl 4-[4-(hydroxymethyl)piperidin-1-yl]benzoate as white oil.

LC-MS (ES$^+$): 326.30 m/z [MH$^+$], t$_R$=1.18 min, (1.90 minute run).

3. Synthesis of benzyl 4-(4-formylpiperidin-1-yl)benzoate

Into a 100-mL round-bottom flask, was placed benzyl 4-[4-(hydroxymethyl)piperidin-1-yl]benzoate (500 mg, 1.54 mmol, 1.00 equiv), dichloromethane (15.0 mL), (1,1,1-Triacetoxy)-1,1-dihydro-1,2-benziodoxol-3(1H)-one (978 mg, 2.31 mmol, 1.5 equiv). The resulting solution was stirred for 4 hours at room temperature. The resulting mixture was concentrated under vacuum. The residue was applied onto a silica gel column with ethyl acetate/petroleum ether (1:4). This resulted in 420.0 mg (85%) of benzyl 4-(4-formylpiperidin-1-yl)benzoate as a yellow solid.

LC-MS (ES$^+$): 323.95 m/z [MH$^+$], t$_R$=1.04 min, (1.80 minute run).

4. Synthesis of benzyl 4-[4-([4-[2-(2,6-dioxopiperidin-3-yl)-1,3-dioxo-2,3-dihydro-1H-isoindol-5-yl] piperazin-1-yl]methyl)piperidin-1-yl]benzoate Into a 150-mL round-bottom flask, was placed benzyl 4-(4-formylpiperidin-1-yl)benzoate (500.0 mg, 1.5 mmol, 1.0 equiv), dichloromethane (20.0 mL), 2-(2,6-dioxopiperidin-3-yl)-5-(piperazin-1-yl)-2,3-dihydro-1H-isoindole-1,3-dione, trifluoroacetyl (747 mg, 1.7 mmol, 1.1 equiv), Sodium triacetoxyborohydride (1.39 g, 6.5 mmol, 4.0 equiv). The resulting solution was stirred for 4 hours at room temperature. The reaction was then quenched by the addition of water (100.0 mL). The resulting solution was extracted with ethyl acetate (30 mL×3) and the organic layers combined and dried over anhydrous sodium sulfate and concentrated under vacuum. The residue was applied onto a silica gel column with ethyl acetate/petroleum ether (1:1). This resulted in 500.0 mg (50%) of benzyl 4-[4-([4-[2-(2,6-dioxopiperidin-3-yl)-1,3-dioxo-2,3-dihydro-1H-isoindol-5-yl]piperazin-1-yl]methyl)piperidin-1-yl]benzoate as a yellow solid.

LC-MS (ES$^+$): 650.45 m/z [MH$^+$], t$_R$=1.37 min, (1.90 minute run).

5. Synthesis of 4-[4-([4-[2-(2,6-dioxopiperidin-3-yl)-1,3-dioxo-2,3-dihydro-1H-isoindol-5-yl]piperazin-1-yl]methyl)piperidin-1-yl]benzoic acid To a solution of benzyl4-[4-([4-[2-(2,6-dioxopiperidin-3-yl)-1,3-dioxo-2,3-dihydro-1H-isoindol-5-yl]piperazin-1-yl]methyl)piperidin-1-yl]benzoate (500.0 mg, 0.8 mmol, 1.0 equiv) in 20.0 mL methyl alcohol (30.0 mL) was added Pd/C (10%, 300 mg) under nitrogen atmosphere in a 100.0 mL round bottom flask. The flask was then vacuumed and flushed with hydrogen. The reaction mixture was hydrogenated at room temperature for 12 hours under hydrogen atmosphere using a hydrogen balloon, then filtered through a Celite pad and concentrated under reduced pressure. This resulted in 300.0 mg (69.0%) of 4-[4-([4-[2-(2,6-dioxopiperidin-3-yl)-1,3-dioxo-2,3-dihydro-1H-isoindol-5-yl]piperazin-1-yl]methyl)piperidin-1-yl]benzoic acid as a yellow solid.

LC-MS (ES$^+$): 560.35 m/z [MH$^+$], t$_R$=0.74 min, (1.90 minute run).

6. Synthesis of 4-[4-([4-[2-(2,6-dioxopiperidin-3-yl)-1,3-dioxo-2,3-dihydro-1H-isoindol-5-yl]piperazin-1-yl]methyl)piperidin-1-yl]-N-[(1r,3r)-3-(3-chloro-4-cyanophenoxy)-2,2,4,4-tetramethylcyclobutyl] benzamide Into a 100-mL round-bottom flask, was placed 4-[4-([4-[2-(2,6-dioxopiperidin-3-yl)-1,3-dioxo-2,3-dihydro-1H-isoindol-5-yl]piperazin-1-yl]methyl)piperidin-1-yl]benzoic acid (300.0 mg, 0.5 mmol, 1.0 equiv), N,N-dimethylformamide (15.0 mL), N,N,N',N'-Tetramethyl-O-(7-azabenzotriazol-1-yl)uronium hexafluorophospate (307.0 mg, 0.8 mmol, 1.5 equiv), 2-chloro-4-[(1r,3r)-3-amino-2,2,4,4-tetramethylcyclobutoxy]benzonitrile hydrochloride (170.0 mg, 0.5 mmol, 1.0 equiv), N,N-Diisopropylethylamine (207.0 mg, 1.6 mmol, 3.0 equiv). The resulting solution was stirred for 1 hour at room temperature. The reaction was then quenched by the addition of water (80 mL). The resulting solution was extracted with ethyl acetate (30 mL×3) and the organic layers combined and concentrated under vacuum. The crude product (5 mL) was purified by Prep-HPLC with the following conditions: Column, XBridge Prep C18 OBD Column, 5 um, 19*150 mm; mobile phase, Water (10 MMOL/L ammonium bicarbonate) and acetonitrile (59.0% acetonitrile up to 80.0% in 8 min); Detector, UV 220 nm. 4 mL product was obtained. This resulted in 114 g (25921%) of 4-[4-([4-[2-(2,6-dioxopiperidin-3-yl)-1,3-dioxo-2,3-dihydro-1H-isoindol-5-yl]piperazin-1-yl]methyl)piperidin-1-yl]-N-[(1r,3r)-3-(3-chloro-4-cyanophenoxy)-2,2,4,4-tetramethylcyclobutyl]benzamide as a yellow solid.

1H NMR (300 MHz, DMSO-d6) δ 11.05 (s, 1H), 7.86 (d, J=8.7 Hz, 1H), 7.67 (dd, J=17.8, 8.4 Hz, 3H), 7.44 (d, J=9.2 Hz, 1H), 7.34-7.13 (m, 3H), 7.02-6.87 (m, 3H), 5.04 (dd, J=12.6, 5.3 Hz, 1H), 4.28 (s, 1H), 4.02 (d, J=9.0 Hz, 1H), 3.82 (d, J=12.5 Hz, 2H), 3.58-3.30 (m, 5H), 2.90-2.66 (m, 3H), 2.6-2.47 (m, 3H), 2.50-2.42 (m, 4H), 2.17 (d, J=6.5 Hz, 2H), 1.98 (dt, J=10.0, 4.5 Hz, 1H), 1.77 (d, J=11.9 Hz, 3H), 1.18 (s, 6H), 1.09 (s, 6H).

LC-MS (ES$^+$): 820.60 m/z [MH$^+$], $t_R$=2.99 min, (4.8 minute run).

Synthetic Procedure for Compound 357

1. Synthesis of tert-butyl 6-(2-ethoxy-2-oxoethylidene)-2-azaspiro[3.3]heptane-2-carboxylate)

A mixture of t-BuOK (3.98 g, 35.47 mmol, 2.498 equiv) and ethyl 2-(bromotriphenyl-$\$1^{\wedge}$[5]-phosphanyl)acetate (15.2 g, 35.41 mmol, 2.493 equiv) in THF (90 mL) in a 250-mL round-bottom flask was stirred for 1 hour at room temperature. Then tert-butyl 6-oxo-2-azaspiro[3.3]heptane-2-carboxylate (3 g, 14.20 mmol, 1 equiv) was added and the reaction mixture was stirred for an additional 6 hours at 35° C. Then filtered through Celite and filter cake was washed with THF. The crude was subjected to a silica gel column with ethyl acetate/petroleum ether (1:5). This resulted in 3.3 g (82.60%) of tert-butyl 6-(2-ethoxy-2-oxoethylidene)-2-azaspiro[3.3]heptane-2-carboxylate as a colorless oil.

LC-MS (ES$^+$): m/z 226.1 [M−(t-Bu)+H$^+$], $t_R$=1.267 min, (2.0 minute run).

2. Synthesis of tert-butyl 6-(2-ethoxy-2-oxoethyl)-2-azaspiro[3.3]heptane-2-carboxylate To a solution of tert-butyl 6-(2-ethoxy-2-oxoethylidene)-2-azaspiro[3.3]heptane-2-carboxylate (3.296 g, 11.72 mmol, 1 equiv) in ethanol (330 mL) in a 500-mL 3-necked round-bottom flask was added Pd/C (661.8 mg) under N$_2$ flow. The reaction flask was vacuumed and flushed with H$_2$ for three times. The resulting mixture was stirred for 3 hours at room temperature under H$_2$. Then the mixture was filtered through a celite pad. The collected filtrate was concentrated under reduced pressure and dried under vacuum. This resulted in 3.12 g (93.99%) of tert-butyl 6-(2-ethoxy-2-oxoethyl)-2-azaspiro[3.3]heptane-2-carboxylate as a colorless oil.

LC-MS (ES$^+$): m/z 228.1 [M−(t-Bu)+H$^+$], $t_R$=1.254 min, (2.0 minute run).

3. Synthesis of tert-butyl 6-(2-hydroxyethyl)-2-azaspiro[3.3]heptane-2-carboxylate Into a 250-mL round-bottom flask, was placed tert-butyl 6-(2-ethoxy-2-oxoethyl)-2-azaspiro[3.3]heptane-2-carboxylate (3.08 g, 10.87 mmol, 1 equiv), THF (120 mL), DIBAL-H in THF (1 M) (32.6 mL, 229.28 mmol, 3 equiv). The resulting solution was stirred for 3 hours at room temperature. The reaction was then quenched by the addition of water (60 mL×1). The resulting solution was extracted with ethyl acetate (120 mL×2). The resulting mixture was washed with brine (100 mL×1). The organic layer was dried over anhydrous sodium sulfate, concentrated and dried under vacuum. This resulted in 2.53 g (96.45%) of tert-butyl 6-(2-hydroxyethyl)-2-azaspiro[3.3]heptane-2-carboxylate as a white solid.

LC-MS (ES$^+$): m/z 186.1 [M−(t-Bu)+H$^+$], $t_R$=1.061 min, (2.0 minute run).

4. Synthesis of 2-[2-azaspiro[3.3]heptan-6-yl]ethan-1-ol; trifluoroacetic acid

Into a 500-mL round-bottom flask, was placed a solution of tert-butyl 6-(2-hydroxyethyl)-2-azaspiro[3.3]heptane-2-carboxylate (2.52 g, 10.44 mmol, 1 equiv) in DCM (120 mL), trifluoroacetic acid (7.7 mL). The resulting solution was stirred for 4 hours at room temperature. The resulting mixture was evaporated to dryness and dried under vacuum. This resulted in 2.66 g (99.80%) of 2-[2-azaspiro[3.3]heptan-6-yl]ethan-1-ol; trifluoroacetic acid as light yellow oil.

5. Synthesis of tert-butyl 4-[6-(2-hydroxyethyl)-2-azaspiro[3.3]heptan-2-yl]benzoate To a solution of tert-butyl 4-fluorobenzoate (10.25 g, 52.24 mmol, 5.012 equiv) in DMSO (50 mL) in a 250-mL round-bottom flask was added DIEA (14 mL, 84.71 mmol, 8.128 equiv). The mixture was stirred for 5 minutes, then 2-[2-azaspiro[3.3]heptan-6-yl]ethan-1-ol; trifluoroacetic acid (2.66 g, 10.42 mmol, 1 equiv) was added. The resulting solution was stirred for 16 hours at 130° C. After cooling to room temperature, the reaction was then quenched by addition of water (100 mL×1). The resulting solution was extracted with ethyl acetate (100 mL×3). The combined organic layers were washed with water (50 mL×2) and brine (50 mL×1). The organic layer was dried over anhydrous sodium sulfate. The crude was subjected to a silica gel column with ethyl acetate/petroleum ether (1:2). This resulted in 311.5 mg (9.42%) of tert-butyl 4-[6-(2-hydroxyethyl)-2-azaspiro[3.3]heptan-2-yl]benzoate as a light yellow solid.

LC-MS (ES$^+$): m/z 318.2 [MH$^+$], $t_R$=1.314 min, (2.0 minute run).

6. Synthesis of tert-butyl 4-[6-(2-[[2-(2,6-dioxopiperidin-3-yl)-1,3-dioxo-2,3-dihydro-1H-isoindol-5-yl]oxy]ethyl)-2-azaspiro[3.3]heptan-2-yl]benzoate To a solution of PPh3 (361.7 mg, 1.38 mmol, 1.506 equiv) in THF (15 mL) was added DIAD (280.2 mg, 1.39 mmol, 1.513 equiv) dropwise with stirring at room temperature under N$_2$. To this was added tert-butyl 4-[6-(2-hydroxyethyl)-2-azaspiro[3.3]heptan-2-yl]benzoate (290.7 mg, 0.92 mmol, 1 equiv), 2-(2,6-dioxopiperidin-3-yl)-5-hydroxy-2,3-dihydro-1H-isoindole-1,3-dione (377.4 mg, 1.38 mmol, 1.503 equiv). The resulting solution was stirred for 4 hours at room temperature. The reaction was then quenched by the addition of water (20 mL). The resulting solution was extracted with ethyl acetate (30 mL×3) and the combined organic layers were washed with brine (20 mL×1). The organic layer was dried over anhydrous sodium sulfate. The crude was subjected to a silica gel column with ethyl acetate/petroleum ether (1:1). This resulted in 90.8 mg (17.28%) of tert-butyl 4-[6-(2-[[2-(2,6-dioxopiperidin-3-yl)-1,3-dioxo-2,3-dihydro-1H-isoindol-5-yl]oxy]ethyl)-2-azaspiro[3.3]heptan-2-yl]benzoate as a light brown solid.

LC-MS (ES$^+$): m/z 574.05 [MH$^+$], t$_R$=1.443 min, (2.0 minute run).

7. Synthesis of 4-[6-(2-[[2-(2,6-dioxopiperidin-3-yl)-1,3-dioxo-2,3-dihydro-1H-isoindol-5-yl]oxy]ethyl)-2-azaspiro[3.3]heptan-2-yl]benzoic acid To a solution of tert-butyl 4-[6-(2-[[2-(2,6-dioxopiperidin-3-yl)-1,3-dioxo-2,3-dihydro-1H-isoindol-5-yl]oxy]ethyl)-2-azaspiro[3.3]heptan-2-yl]benzoate (70.2 mg, 0.12 mmol, 1 equiv) in DCM (2.0 mL) was added TFA (0.6 mL, 8.08 mmol, 66.008 equiv). The resulting solution was stirred for 2 hours at room temperature. The resulting mixture was evaporated to dryness and dried under vacuum. This resulted in 63.3 mg (99.95%) of 4-[6-(2-[[2-(2,6-dioxopiperidin-3-yl)-1,3-dioxo-2,3-dihydro-1H-isoindol-5-yl]oxy]ethyl)-2-azaspiro[3.3]heptan-2-yl]benzoic acid as a light brown solid.

LC-MS (ES$^+$): m/z 518.2 [MH$^+$], t$_R$=1.166 min, (2.0 minute run).

8. Synthesis of 4-[6-(2-[[2-(2,6-dioxopiperidin-3-yl)-1,3-dioxo-2,3-dihydro-1H-isoindol-5-yl]oxy]ethyl)-2-azaspiro[3.3]heptan-2-yl]-N-[(1r,3r)-3-(3-chloro-4-cyanophenoxy)-2,2,4,4-tetramethylcyclobutyl]benzamide To a solution of 4-[6-(2-[[2-(2,6-dioxopiperidin-3-yl)-1,3-dioxo-2,3-dihydro-1H-isoindol-5-yl]oxy]ethyl)-2-azaspiro[3.3]heptan-2-yl]benzoic acid (63.3 mg, 0.12 mmol, 1 equiv) in DMF (3.4 mL) was added DIEA (0.32 mL, 1.94 mmol, 15.830 equiv), then HATU (51.5 mg, 0.14 mmol, 1.107 equiv), finally 2-chloro-4-[(1r,3r)-3-amino-2,2,4,4-tetramethylcyclobutoxy]benzonitrile hydrochloride (43.4 mg, 0.14 mmol, 1.126 equiv). The resulting solution was stirred for 3 hours at room temperature. The reaction was then quenched by the addition of water (10 mL). The resulting solution was extracted with dichloromethane (20 mL×3); the combined organic layers were washed with water (10 mL×2) and brine (10 mL×1). The organic layer was dried over anhydrous sodium sulfate. The crude product was purified by Prep-HPLC with the following conditions: Column, XBridge Prep OBD C18 Column, 19*250 mm, 5 um; mobile phase, Water (10 mmol/L NH$_4$HCO$_3$) and acetonitrile (20% Phase B up to 60% in 8 min); Detector, UV254/220. This resulted in 57.4 mg (60.30%) of 4-[6-(2-[[2-(2,6-dioxopiperidin-3-yl)-1,3-dioxo-2,3-dihydro-1H-isoindol-5-yl]oxy]ethyl)-2-azaspiro[3.3]heptan-2-yl]-N-[(1r,3r)-3-(3-chloro-4-cyanophenoxy)-2,2,4,4-tetramethylcyclobutyl]benzamide as a white solid.

$^1$H NMR (300 MHz, d6-DMSO) δ 1.13 (s, 6H), 1.22 (s, 6H), 1.88-2.01 (m, 5H), 2.29 (d, J=5.7 Hz, 3H), 2.44-2.56 (m, 2H), 2.79-2.84 (m, 1H), 3.73 (s, 2H), 3.84 (s, 2H), 3.98 (d, J=9.0 Hz, 1H), 4.07 (t, J=6.2 Hz, 2H), 4.25 (s, 1H), 5.02-5.08 (m, 1H), 6.34 (d, J=8.4 Hz, 2H), 6.93 (dd, J1=2.1 Hz, J2=8.7 Hz, 1H), 7.13 (d, J=2.4 Hz, 1H), 7.26-7.29 (m, 1H), 7.35-7.39 (m, 2H), 7.63-7.66 (m, 2H), 7.75-7.85 (m, 2H), 11.05 (s, 1H); LC-MS (ES$^+$): m/z 778.30 [MH$^+$], t$_R$=3.222 min, (4.60 minute run); LC-MS (ES$^+$): m/z 778.30/780.30 [MH$^+$], t$_R$=3.222 min, (4.60 minute run).

Chemical formula: C$_{43}$H$_{44}$ClN$_5$O$_7$ [777.29/779.29].

Total H count from HNMR data: 44.

Synthetic Procedure for Compound 579

Synthesis of tert-butyl N-[(1r,4r)-4-(3-chloro-4-cyanophenoxy)cyclohexyl]carbamate Into a 50.0-mL round-bottom flask, was placed tert-butyl N-[(1r,4r)-4-hydroxycyclohexyl]carbamate (500.0 mg, 2.32 mmol, 1.00 equiv), N,N-dimethylformamide (10.0 mL), sodium hydride (82.8 mg, 3.45 mmol, 1.50 equiv), 2-chloro-4-fluorobenzonitrile (432.6 mg, 2.78 mmol, 1.20 equiv). The resulting solution was stirred for 2 hours at 0° C. in a water/ice bath. The reaction was then quenched by the addition of 20.0 mL of water. The resulting solution was extracted with ethyl acetate (40.0 mL) and the organic layers combined. The resulting mixture was washed with sodium chloride (40.0 mL). The mixture was dried over anhydrous sodium sulfate. The residue was applied onto a silica gel column with ethyl acetate/petroleum ether (1/2). The collected fractions were combined and concentrated under vacuum. This resulted in 470.0 mg (58%) of tert-butyl N-[(1r,4r)-4-(3-chloro-4-cyanophenoxy)cyclohexyl]carbamate as yellow oil.

LC-MS (ES$^+$): m/z 295.0 [MH$^+$], t$_R$=1.199 min, (1.90 minute run).

Chemical formula: C$_{18}$H$_{23}$ClN$_2$O$_3$ [350.14]

2. Synthesis of 4-(((1r,4r)-4-aminocyclohexyl)oxy)-2-chlorobenzonitrile hydrochloride Into a 50.0-mL round-bottom flask, was placed tert-butyl N-[(1r,4r)-4-(3-chloro-4-cyanophenoxy)cyclohexyl]carbamate (470.0 mg, 1.34 mmol, 1.00 equiv), methanol (5.0 mL), hydrogen chloride. The resulting solution was stirred for 2 hours at room temperature. The resulting mixture was concentrated under vacuum. This resulted in 340.0 mg (88%) of 4-(((1r,4r)-4-aminocyclohexyl)oxy)-2-chlorobenzonitrile hydrochloride as a yellow solid.

LC-MS (ES$^+$): m/z 250.90 [MH$^+$], t$_R$=0.537 min, (1.90 minute run).

Chemical formula: C$_{13}$H$_{15}$ClN$_2$O [250.09].

3. Synthesis of methyl 5-(4-(hydroxymethyl)piperidin-1-yl)pyrazine-2-carboxylate Into a 50-mL round-bottom flask, was placed methyl 5-chloropyrazine-2-carboxylate (2 g, 11.59 mmol, 1 equiv), DMSO (15 mL, 0.19 mmol, 0.017 equiv), DIEA (0.2 mL, 0.000 equiv), piperidin-4-ylmethanol (1.3 mg, 0.01 mmol, 1 equiv). The resulting solution was stirred for 16 hours at 120° C. in an oil bath. The resulting solution was extracted ethyl acetate (30 mL×3) and the organic layers combined. The resulting mixture was washed with brine (10 mL×1). The resulting mixture was concentrated under vacuum. The residue was applied onto a silica gel column with dichloromethane/methanol (1:1). This resulted in 2.21 g (65%) of methyl 5-[4-(hydroxymethyl)piperidin-1-yl]pyrazine-2-carboxylate as a white solid.

LC-MS (ES+): m/z 251.13 [MH+], t$_R$=0.61 min, (1.9 minute run).

4. Synthesis of 5-[4-(hydroxymethyl)piperidin-1-yl]pyrazine-2-carboxylic acid Into a 100-mL round-bottom flask, was placed methyl 5-[4-(hydroxymethyl)piperidin-1-yl]pyrazine-2-carboxylate (2.21 g, 8.79 mmol, 1 equiv), methanol (40 mL), lithiumol (0.633 mg, 0.03 mmol, 0.003 equiv), water (10 mL). The resulting solution was stirred for 16 hours at room temperature. The resulting mixture was concentrated. The PH was adjusted to 4 with 1M HCl. The resulting solution was extracted dichloromethane (30 mL×3) and the organic layers combined. The resulting mixture was washed with brine (10 mL×1). The resulting mixture was concentrated under vacuum. This resulted in 1.7042 g (81.67%) of 5-[4-(hydroxymethyl)piperidin-1-yl]pyrazine-2-carboxylic acid as a white solid.

LC-MS (ES+): m/z 237.11 [MH+], $t_R$=0.75 min, (2.0 minute run).

5. Synthesis of 5-[4-(hydroxymethyl)piperidin-1-yl]-N-[(1s,4s)-4-(3-chloro-4-cyanophenoxy)cyclohexyl]pyrazine-2-carboxamide Into a 100-mL round-bottom flask, was placed 5-[4-(hydroxymethyl)piperidin-1-yl]pyrazine-2-carboxylic acid (310 mg), DMF (15 mL), DIEA (563.69 mg), 2-chloro-4-[[(1s,4s)-4-aminocyclohexyl]oxy]benzonitrile (250 mg), BOP (386.28 mg). The resulting solution was stirred for 2 hours at room temperature. The resulting mixture was extracted with ethyl acetate (50 mL×3) and the organic layer was washed with brine (30 mL×1). The organic was dried over anhydrous sodium sulfate and concentrated under vacuum. The residue was applied onto a silica gel column with dichloromethane/methanol (10:1). The collected fractions were combined and concentrated under vacuum. This resulted in 243.5 mg of 5-[4-(hydroxymethyl)piperidin-1-yl]-N-[(1s,4s)-4-(3-chloro-4-cyanophenoxy)cyclohexyl]pyrazine-2-carboxamide as a white solid.

LC-MS (ES+): m/z 469.19 [MH+], $t_R$=0.99 min, (1.9 minute run).

6. Synthesis of 5-(4-formylpiperidin-1-yl)-N-[(1r,4r)-4-(3-chloro-4-cyanophenoxy)cyclohexyl]pyrazine-2-carboxamide Into a 100-mL round-bottom flask, was placed 5-[4-(hydroxymethyl)piperidin-1-yl]-N-[(1r,4r)-4-(3-chloro-4-cyanophenoxy)cyclohexyl]pyrazine-2-carboxamide (150.1 mg, 0.32 mmol, 1 equiv), dichloromethane (15 mL, 0.18 mmol, 0.553 equiv), Dess-martin (271.37 mg). The resulting mixture was extracted with dichloromethane (50 mL×3) and the organic layer was washed with brine (30 mL×1). The organic was dried over anhydrous sodium sulfate and concentrated under vacuum. This resulted in 200 mg (crude) of 5-(4-formylpiperidin-1-yl)-N-[(1r,4r)-4-(3-chloro-4-cyanophenoxy)cyclohexyl]pyrazine-2-carboxamide as a white solid.

LC-MS (ES+): m/z 467.17 [MH+], $t_R$=1.03 min, (1.9 minute run).

7. Synthesis of 5-(4-[[(propan-2-yl)[(1r,3r)-3-[[2-(2,6-dioxopiperidin-3-yl)-1,3-dioxo-2,3-dihydro-1H-isoindol-5-yl]oxy]cyclobutyl]amino]methyl]piperidin-1-yl)-N-[(1r,4r)-4-(3-chloro-4-cyanophenoxy)cyclohexyl]pyrazin Into a 100-mL round-bottom flask, was placed 5-(4-formylpiperidin-1-yl)-N-[(1r,4r)-4-(3-chloro-4-cyanophenoxy)cyclohexyl]pyrazine-2-carboxamide (220 mg, 0.47 mmol, 1 equiv), dichloromethane (20 mL, 0.24 mmol, 0.501 equiv), Titanium(IV)isopropoxide (2 mL, 0.01 mmol, 0.015 equiv), 2-(2,6-dioxopiperidin-3-yl)-5-[(1r,3r)-3-[(propan-2-yl)amino]cyclobutoxy]-2,3-dihydro-1H-isoindole-1,3-dione (420 mg, 1.09 mmol, 2.318 equiv), NaH(OAc)$_3$ (340 mg). The resulting solution was stirred for 16 hours at 60° C. in an oil bath. The resulting mixture was extracted with dichloromethane (50 mL×3) and the organic layer was washed with brine (30 mL×1). The crude product was purified by Prep-HPLC with the following conditions: Column, XSelect CSH Prep C18 OBD Column, Sum, 19×150 mm; mobile phase, water (10 mmol/L NH$_4$HCO$_3$) and acetonitrile (30% Phase B up to 55% in 8.5 min); Detector: UV254/220. This resulted in 26 mg (6.60%) of 5-(4-[[(propan-2-yl)[(1r,3r)-3-[[2-(2,6-dioxopiperidin-3-yl)-1,3-dioxo-2,3-dihydro-1H-isoindol-5-yl]oxy]cyclobutyl]amino]methyl]piperidin-1-yl)-N-[(1r,4r)-4-(3-chloro-4-cyanophenoxy)cyclohexyl]pyrazin as a light yellow solid.

$^1$H NMR (300 MHz, DMSO-d6) 11.09 (s, 1H), 8.56 (s, 1H), 8.23 (s, 1H), 8.12-8.05 (m, 1H), 7.92-7.82 (m, 2H), 7.40-7.36 (s, 1H), 7.26-7.20 (m, 2H), 7.12-7.09 (m, 1H), 5.12-5.10 (m, 1H), 4.90-4.81 (s, 1H), 4.51-4.48 (m, 3H), 3.91-3.80 (s, 1H), 3.72-3.62 (m, 1H), 3.00-2.81 (m, 4H), 2.79-2.68 (m, 1H), 2.50-2.42 (m, 3H), 2.30-2.00 (m, 7H), 1.99-1.81 (m, 4H), 1.80-1.36 (m, 5H), 1.21-1.01 (m, 2H), 0.91-0.71 (m, 6H); LC-MS (ES$^+$): m/z 837.30/839.30 [MH$^+$], $t_R$=2.934 min, (4.80 minute run).

Chemical formula: C$_{44}$H$_{49}$ClN$_6$O$_7$ [836.34/838.34].

Total H count from HNMR data: 49.

Synthetic Procedure for Compound 278

Step 1: [(R)-tert-butyl (1-(3-(3-chloro-4-cyanophenyl)-1H-pyrazol-1-yl)propan-2-yl)carbamate]

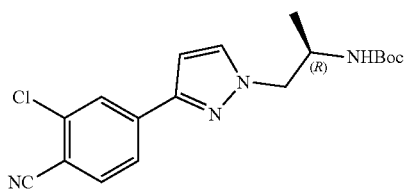

A mixture of (R)-2-((tert-butoxycarbonyl)amino)propyl 4-methylbenzenesulfonate (12.6 g, crude), 2-chloro-4-(1H-pyrazol-3-yl)benzonitrile (7.1 g, 34.9 mmol) and cesium carbonate (5.8 g, 48.8 mmol) in acetonitrile (100 ml) was stirred at 70° C. for 2 hours. TLC showed the reaction was complete. The reaction mixture was partitioned between water (50 ml) and ethyl acetate (100 ml). The organic layer was collected and the aqueous layer was extracted with ethyl acetate (50 ml×2). The combined organic layers were washed with brine (100 ml), dried over magnesium sulfate and evaporated under reduced pressure to give a crude residue, which was purified by silica gel flash column chromatography (eluted with 50%-100% ethyl acetate in hexane) to afford tert-butyl 4-(prop-2-yn-1-yl)piperazine-1-carboxylate (7.0 g, yield 58%) as white solid.

$^1$H NMR (400 MHz, CDCl$_3$): δ 1.16 (d, J=6.8 Hz, 3H), 1.42 (s, 9H), 4.02-4.11 (m, 1H), 4.16-4.30 (m, 2H), 6.61 (d, J=2.4 Hz, 1H), 7.46 (d, J=2.4 Hz, 1H), 7.67 (d, J=8.0 Hz, 1H), 7.74-7.80 (m, 1H), 7.96 (s, 1H).

Chemical Formula: C$_{18}$H$_{21}$ClN$_4$O$_2$; Molecular Weight: 360.84.

Total H count from HNMR data: 20.

Step 2: [(R)-4-(1-(2-aminopropyl)-1H-pyrazol-3-yl)-2-chlorobenzonitrile hydrochloride]

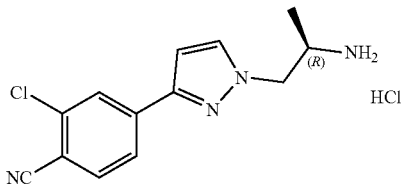

A solution of (R)-tert-butyl (1-(3-(3-chloro-4-cyanophenyl)-1H-pyrazol-1-yl)propan-2-yl)carbamate (7.0 g, 19.4 mmol) in hydrogen chloride in dioxane (4M, 15 ml) was stirred at room temperature for 2 hours. The volatiles were removed under reduced pressure to give a crude residue, which was triturated with dichloromethane (25 ml). The resulting solid was collected by filtration and dried under vacuum to afford (R)-4-(1-(2-aminopropyl)-1H-pyrazol-3-yl)-2-chlorobenzonitrile hydrochloride (4.3 g, yield 85%) as white solid which was used in next step without further purification.

Step 3: [tert-butyl 4-(prop-2-yn-1-yl)piperazine-1-carboxylate]

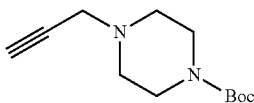

A mixture of tert-butyl piperazine-1-carboxylate (10 g, 53.7 mmol), N-ethyl-N-isopropylpropan-2-amine (12.6 g, 97.6 mmol) and 3-bromoprop-1-yne (5.8 g, 48.8 mmol) in acetonitrile (50 ml) was stirred for 2 hours. TLC showed the reaction was complete. The reaction mixture was partitioned between ethyl acetate (80 ml) and water (80 ml). The organic layer was collected, and the aqueous layer was extracted with ethyl acetate (45 ml×2). The combined organic layers were washed with brine (100 ml), dried over anhydrous sodium sulfate, and concentrated under reduced pressure to give a crude residue which was purified by silica gel flash column chromatography (eluted with 50% ethyl acetate in hexane) to afford tert-butyl 4-(prop-2-yn-1-yl)piperazine-1-carboxylate (10.5 g, yield 96%) as pale yellow oil.

$^1$H NMR (400 MHz, CDCl$_3$): δ 1.46 (s, 9H), 2.26 (t, J=2.4 Hz, 1H), 2.51 (t, J=4.8 Hz, 4H), 3.32 (d, J=2.4 Hz, 2H), 3.47 (t, J=4.8 Hz, 4H).

Chemical Formula: C$_{12}$H$_{20}$N$_2$O$_2$; Molecular Weight: 224.30.

Total H count from HNMR data: 20.

Step 2: [tert-butyl 4-((3-(ethoxycarbonyl)-1H-pyrazol-5-yl)methyl)piperazine-1-carboxylate]

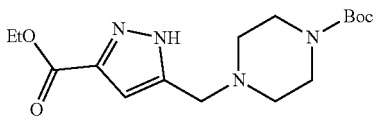 [SMILES: CC(C)(C)OC(=O)N1CCN(Cc2cc(C(=O)O)n[nH]2)CC1]

A mixture of tert-butyl 4-(prop-2-yn-1-yl)piperazine-1-carboxylate (3.0 g, 13.4 mmol), ethyl diazoacetate (2.3 g, 20.1 mmol) and zinc trifluoromethanesulfonate (974 mg, 2.68 mmol) in triethylamine (9.3 ml, 67 mmol) was stirred at 100° C. overnight. TLC showed the reaction was complete. The reaction mixture was allowed to cool to room temperature and partitioned between ethyl acetate (50 ml) and water (20 ml). The organic layer was collected, and the aqueous layer was extracted with ethyl acetate (30 ml×2). The combined organic layers were washed with brine (30 ml), dried over anhydrous sodium sulfate, and concentrated under reduced pressure to afford a crude residue, which was purified by silica gel flash chromatography (eluted with 100%-200% ethyl acetate in hexane) to afford tert-butyl 4-((3-(ethoxycarbonyl)-1H-pyrazol-5-yl)methyl)piperazine-1-carboxylate (2.1 g, yield 47%) as yellow oil.

LC_MS: (ES$^+$): m/z 339.5 [M+H]$^+$. t$_R$=1.772 min.

Step 3: [5-((4-(tert-butoxycarbonyl)piperazin-1-yl)methyl)-1H-pyrazole-3-carboxylic acid]

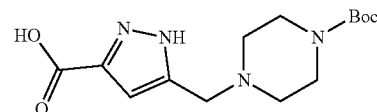

A mixture of tert-butyl 4-((3-(ethoxycarbonyl)-1H-pyrazol-5-yl)methyl)piperazine-1-carboxylate (500 mg, 1.48 mmol) and lithium hydroxide monohydrate (250 mg, 5.91 mmol) in tetrahydrofuran (10 ml)-water (2.5 ml)-methanol (2.5 ml) was stirred at 45° C. overnight. TLC showed the reaction was complete. The reaction mixture was acidified with diluted hydrochloride acid (1N) till pH 6-7, the resulting mixture was concentrated under reduced pressure to afford 5-((4-(tert-butoxycarbonyl)piperazin-1-yl)methyl)-1H-pyrazole-3-carboxylic acid (1.1 g, crude) as yellow solid.

LC_MS: (ES$^+$): m/z 311.3 [M+H]$^+$. t$_R$=1.378 min.

Step 4: [(R)-tert-butyl 4-((3-((1-(3-(3-chloro-4-cyanophenyl)-1H-pyrazol-1-yl)propan-2-yl)carbamoyl)-1H-pyrazol-5-yl)methyl)piperazine-1-carboxylate]

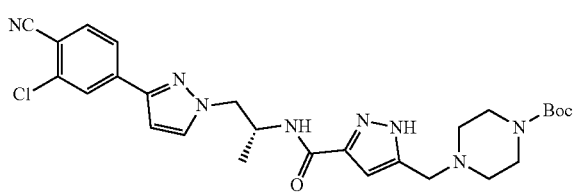 [SMILES: C[C@H](Cn1ccc(-c2ccc(C#N)c(Cl)c2)n1)NC(=O)c1cc(CN2CCN(C(=O)OC(C)(C)C)CC2)[nH]n1]

A mixture of 5-((4-(tert-butoxycarbonyl)piperazin-1-yl)methyl)-1H-pyrazole-3-carboxylic acid (1.1 g, crude), (R)-4-(1-(2-aminopropyl)-1H-pyrazol-3-yl)-2-chlorobenzonitrile hydrochloride (336 mg, 1.29 mmol), N-(3-dimethylaminopropyl)-N'-ethylcarbodiimide hydrochloride (371 mg, 1.94 mmol), 1-hydroxybenzotriazole (262 mg, 1.94 mmol) and N-ethyl-N-isopropylpropan-2-amine (835 mg, 6.5 mmol) in anhydrous N,N-dimethylformamide (8 ml) was stirred at room temperature for 2 hours, and then 2-(7-Aza-1H-benzotriazole-1-yl)-1,1,3,3-tetramethyluronium hexafluorophosphate (980 mg, 2.58 mmol) was added.

The resulting mixture was stirred at room temperature for 1 hour. TLC showed the reaction was complete. The mixture was partitioned between ethyl acetate (20 ml) and water (10 ml). The organic layer was collected, washed with brine (20 ml), dried over anhydrous sodium sulfate, and concentrated under reduced pressure to give a crude residue which was purified by silica gel flash chromatography (eluted with 100%-200% ethyl acetate in hexane) to afford (R)-tert-butyl 4-((3-((1-(3-(3-chloro-4-cyanophenyl)-1H-pyrazol-1-yl)propan-2-yl)carbamoyl)-1H-pyrazol-5-yl)methyl)piperazine-1-carboxylate (300 mg, yield 37% over 2 steps) as white solid.

$^1$H NMR (400 MHz, CDCl$_3$): δ 1.21 (d, J=6.8 Hz, 3H), 1.46 (s, 9H), 2.42 (t, J=4.8 Hz, 4H), 3.44 (t, J=4.8 Hz, 4H), 3.62 (s, 2H), 4.24-4.29 (m, 1H), 4.40-4.46 (m, 1H), 6.63 (d, J=2.4 Hz, 1H), 6.68 (s, 1H), 7.50 (d, J=2.0 Hz, 1H), 7.68 (d, J=8.0 Hz, 1H), 7.74-7.78 (m, 1H), 7.97 (d, J=8.0 Hz, 1H), 8.27 (d, J=1.2 Hz, 1H).

Chemical Formula: C$_{27}$H$_{33}$ClN$_8$O$_3$; Molecular Weight: 553.06.

Total H count from HNMR data: 31.

LC_MS: (ES$^+$): m/z 553.3 [M+H]$^+$. t$_R$=2.181 min.

Step 5: [(R)—N-(1-(3-(3-chloro-4-cyanophenyl)-1H-pyrazol-1-yl)propan-2-yl)-5-(piperazin-1-ylmethyl)-1H-pyrazole-3-carboxamide dihydrochloride]

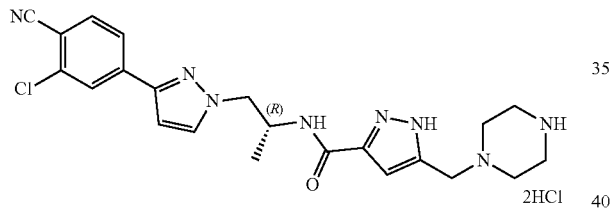

A solution of tert-butyl 4-(2-(2-(4-(5-(((1r,3r)-3-(3-chloro-4-cyanophenoxy)-2,2,4,4-tetramethylcyclobutyl)carbamoyl)pyridin-2-yl)piperazin-1-yl)ethoxy)ethyl)piperazine-1-carboxylate (160 mg, 0.29 mmol) in hydrogen chloride in dioxane (4M, 5 ml) was stirred at room temperature for 2 hours. The volatiles were removed under reduced pressure to give a crude residue which was triturated with dichloromethane (25 ml). The resulting solid was collected by filtration and dried under vacuum to afford (R)—N-(1-(3-(3-chloro-4-cyanophenyl)-1H-pyrazol-1-yl)propan-2-yl)-5-(piperazin-1-ylmethyl)-1H-pyrazole-3-carboxamide dihydrochloride (130 mg, yield 86%) as white solid.

$^1$H NMR (400 MHz, CD$_3$OD): δ 1.31 (d, J=6.8 Hz, 3H), 3.50-3.62 (m, 8H), 4.30-4.48 (m, 4H), 4.58-4.64 (m, 1H), 6.78 (d, J=2.0 Hz, 1H), 7.00-7.03 (m, 1H), 7.73 (d, J=2.0 Hz, 1H), 7.81 (d, J=8.0 Hz, 1H), 7.90 (d, J=8.0 Hz, 1H), 8.03 (s, 1H).

Chemical Formula: C$_{22}$H$_{27}$Cl$_3$N$_8$O; Molecular Weight: 525.86.

Total H count from HNMR data: 23.

LC_MS: (ES$^+$): m/z 453.3 [M+H]$^+$. t$_R$=1.916 min.

Step 6: [4-chlorobutyl 4-methylbenzenesulfonate]

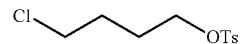 [SMILES: Cc1ccc(S(=O)(=O)OCCCCCl)cc1]

A mixture of 4-chlorobutan-1-ol (5 g, 46.05 mmol), triethylamine (9.3 g, 92.1 mmol), N,N-dimethylpyridin-4-amine (562 mg, 4.61 mmol) and 4-methylbenzene-1-sulfonyl chloride (9.63 g, 50.66 mmol) in dichloromethane (40 ml) was stirred at room temperature for 1.5 hours. TLC showed the reaction was complete. The reaction mixture was partitioned between water (50 ml) and ethyl acetate (100 ml). The organic layer was collected, and the aqueous layer was extracted with ethyl acetate (100 ml). The combined organic layers were washed with brine (100 ml), dried over sodium sulfate, and concentrated under reduced pressure to give a crude residue which was purified by silica gel flash column chromatography (eluted with 20% ethyl acetate in hexane) to afford 4-chlorobutyl 4-methylbenzenesulfonate (12.0 g, yield 99%) as colorless oil.

$^1$H NMR (400 MHz, CDCl$_3$): δ 1.80-1.84 (m, 4H), 2.46 (s, 3H), 3.49-3.53 (m, 2H), 4.04-4.08 (m, 2H), 7.35 (d, J=8.0 Hz, 2H), 7.79 (d, J=8.0 Hz, 2H).

Chemical Formula: C$_{11}$H$_{15}$ClO$_3$S; Molecular Weight: 262.75.

Total H count from HNMR data: 15.

LC_MS: (ES$^+$): m/z 263.1 [M+H]$^+$. t$_R$=2.888 min.

Step 7: [5-(4-chlorobutoxy)-2-(2,6-dioxopiperidin-3-yl)isoindoline-1,3-dione]

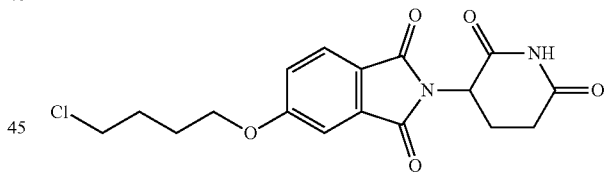

A mixture of 4-chlorobutyl 4-methylbenzenesulfonate (0.96 g, 3.65 mmol), 2-(2,6-dioxopiperidin-3-yl)-5-hydroxyisoindoline-1,3-dione (1 g, 3.65 mmol) and potassium carbonate (0.76 g, 5.47 mmol) in N,N-dimethylformamide (10 ml) was stirred at 70° C. overnight. TLC showed the reaction was complete. The reaction mixture was partitioned between ethyl acetate (30 ml) and water (20 ml). The organic layer was collected, and the aqueous layer was extracted with ethyl acetate (30 ml×2). The combined organic layers were washed with brine (30 ml), dried over anhydrous sodium sulfate, and concentrated under reduced pressure to afford a crude residue which was purified by silica gel flash chromatography (eluted with 33%-50% ethyl acetate in hexane) to afford 5-(4-chlorobutoxy)-2-(2,6-dioxopiperidin-3-yl)isoindoline-1,3-dione (220 mg, yield 18%) as white solid.

LC_MS: (ES$^+$): m/z 365.1 [M+H]$^+$. t$_R$=2.547 min.

Step 8: [N—((R)-1-(3-(3-chloro-4-cyanophenyl)-1H-pyrazol-1-yl)propan-2-yl)-5-((4-(4-((2-(2,6-dioxopiperidin-3-yl)-1,3-dioxoisoindolin-5-yl)oxy)butyl)piperazin-1-yl)methyl)-1H-pyrazole-3-carboxamide]

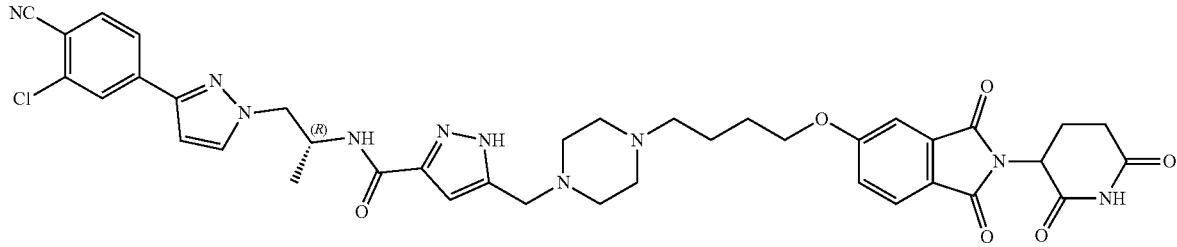

A mixture of (R)—N-(1-(3-(3-chloro-4-cyanophenyl)-1H-pyrazol-1-yl)propan-2-yl)-5-(piperazin-1-ylmethyl)-1H-pyrazole-3-carboxamide dihydrochloride (130 mg, 0.25 mmol), 5-(4-chlorobutoxy)-2-(2,6-dioxopiperidin-3-yl)isoindoline-1,3-dione (90 mg, 0.25 mmol), and N-ethyl-N-isopropylpropan-2-amine (162 mg, 1.25 mmol) and potassium iodide (124 mg, 0.75 mmol) in acetonitrile (3 ml) was stirred at 100° C. in sealed tube overnight. TLC showed the reaction was complete. The mixture was partitioned between ethyl acetate (30 ml) and water (20 ml). The organic layer was collected, washed with brine (30 ml), dried over anhydrous sodium sulfate, and concentrated under reduced pressure to give a crude residue which was purified by preparative TLC (eluted with 8% methanol in dichloromethane) to afford N—((R)-1-(3-(3-chloro-4-cyanophenyl)-1H-pyrazol-1-yl)propan-2-yl)-5-((4-(4-((2-(2,6-dioxopiperidin-3-yl)-1,3-dioxoisoindolin-5-yl)oxy)butyl)piperazin-1-yl)methyl)-1H-pyrazole-3-carboxamide (45 mg, yield 24%) as white solid.

$^1$H NMR (400 MHz, DMSO-d6): δ 1.11 (d, J=5.6 Hz, 3H), 1.23 (s, 1H), 1.57 (s, 1H), 1.70-1.80 (m, 2H), 1.98-2.08 (m, 2H), 2.22-2.40 (m, 8H), 2.52-2.68 (m, 2H), 2.84-2.94 (m, 1H), 3.30 (s, 1H), 3.51 (s, 2H), 4.18 (t, J=6.4 Hz, 2H), 4.42-4.48 (m, 3H), 5.08-5.15 (m, 1H), 6.43 (s, 1H), 6.94 (d, J=2.4 Hz, 1H), 7.32-7.6 (m, 1H), 7.42 (d, J=2.0 Hz, 1H), 7.80-7.85 (m, 2H), 7.99 (s, 2H), 8.08 (s, 1H), 8.23 (d, J=8.0 Hz, 1H), 11.1 (s, 1H), 13.1 (s, 1H).

Chemical Formula: $C_{39}H_{41}ClN_{10}O_6$; Molecular Weight: 781.26.

Total H count from HNMR data: 41.

LC_MS: (ES$^+$): m/z 781.4 [M+H]$^+$. $t_R$=2.113 min.

Synthetic Procedure for Compound 612

Synthesis of tert-butyl 4-[[1-(2-fluoro-4-nitrophenyl)piperidin-4-yl]methyl]piperazine-1-carboxylate Into a 20-30 mL sealed tube, was placed a solution of 1,2-difluoro-4-nitrobenzene (977.5 mg, 6.1 mmol, 1.0 equiv) in dimethylsulfoxide (10 mL), tert-butyl 4-(piperidin-4-ylmethyl)piperazine-1-carboxylate (1.5 g, 5.1 mmol, 0.8 equiv), N,N-Diisopropylethylamine (2.0 g, 15.3 mmol, 2.5 equiv). The resulting solution was stirred overnight at 100° C. in an oil bath. The reaction was then quenched by the addition of 10 mL of water/ice. The resulting solution was extracted with ethyl acetate (20 mL×2) and the organic layers combined and dried over anhydrous sodium sulfate and concentrated under reduced pressure. The residue was applied onto a silica gel column with ethyl acetate/petroleum ether (1:0). This resulted in 1.5 g (58%) of tert-butyl 4-[[1-(2-fluoro-4-nitrophenyl) piperidin-4-yl] methyl]piperazine-1-carboxylate as a yellow solid.

LC-MS (ES$^+$): m/z 423.30 [MH$^+$], $t_R$=1.58 min (1.9 minute run).

Synthesis of tert-butyl 4-[[1-(4-amino-2-fluorophenyl)piperidin-4-yl]methyl]piperazine-1-carboxylate To a solution of tert-butyl 4-[[1-(2-fluoro-4-nitrophenyl) piperidin-4-yl] methyl] piperazine-1-carboxylate (1.5 g, 3.6 mmol, 1.0 equiv) in 15 mL i-PrOH was added Pd/C (10%, 40.0 mg) under nitrogen atmosphere in a 100 ml round bottom flask. The flask was then vacuumed and flushed with hydrogen. The reaction mixture was hydrogenated at room temperature for 4 hours under hydrogen atmosphere using a hydrogen balloon, then filtered through a Celite pad and concentrated under reduced pressure. The resulting mixture was concentrated under reduced pressure. This resulted in 1.2 g (86%) of tert-butyl 4-[[1-(4-amino-2-fluorophenyl) piperidin-4-yl] methyl] piperazine-1-carboxylate as a pink solid.

LC-MS (ES$^+$): m/z 393.10 [MH$^+$], $t_R$=0.74 min (1.9 minute run).

3. Synthesis of tert-butyl 4-[(1-[4-[(1-cyanocyclobutyl)amino]-2-fluorophenyl]piperidin-4-yl)methyl]piperazine-1-carboxylate Into a 100 mL round-bottom flask, was placed a solution of tert-butyl 4-[[1-(4-amino-2-fluorophenyl) piperidin-4-yl] methyl]piperazine-1-carboxylate (1.2 g, 3.1 mmol, 1.0 equiv) in tetrahydrofuran (10 mL), cyclobutanone (428.6 mg, 6.1 mmol, 2.0 equiv), ZnCl$_2$ (2.1 g, 15.4 mmol, 5.0 equiv), TMSCN (606.1 mg). The resulting solution was stirred overnight at room temperature. The reaction was then quenched by the addition of 10 mL of 1 mmol/L FeSO$_4$ solvent. The resulting solution was extracted with ethyl acetate (20 mL×2) and the organic layers combined and dried over anhydrous sodium sulfate and concentrated under reduced pressure. The residue was applied onto a silica gel column with dichloromethane/methanol (5:1). This resulted in 990.0 mg (69%) of tert-butyl 4-[(1-[4-[(1-cyanocyclobutyl) amino]-2-fluorophenyl] piperidin-4-yl) methyl] piperazine-1-carboxylate as a black solid.

LC-MS (ES$^+$): m/z 472.35 [MH$^+$], $t_R$=1.50 min (1.9 minute run).

Synthesis of tert-butyl 4-[(1-[4-[7-(5-chloro-6-cyanopyridin-3-yl)-8-imino-6-sulfanylidene-5,7-diazaspiro[3.4]octan-5-yl]-2-fluorophenyl]piperidin-4-yl)methyl]piperazine-1-carboxylate Into a 100-mL round-bottom flask, was placed a solution of tert-butyl 4-[(1-[4-[(1-cyanocyclobutyl)amino]-2-fluorophenyl]piperidin-4-yl)methyl]piperazine-1-carboxylate (402.6 mg, 1.3 mmol, 1.0 equiv) in toluene (10 mL), 3-chloro-5-isothiocyanatopyridine-2-carbonitrile (200.0 mg, 1.5 mmol, 1.2 equiv), 4-dimethylaminopyridine (156.4 mg, 1.9 mmol, 1.5 equiv). The resulting solution was stirred overnight at 100° C. in an oil bath. The reaction was then quenched by the addition of 5 mL of ice water. The resulting solution was extracted with ethyl acetate (20 mL×2) and the organic layers combined and dried over anhydrous sodium sulfate and concentrated under reduced pressure. The residue was applied onto a silica gel column with ethyl acetate/petroleum ether (1:0). This resulted in 230.0 mg (30.4%) of tert-butyl 4-[(1-[4-[7-(5-chloro-6-cyanopyridin-3-yl)-8-imino-6-sulfanylidene-5, 7-diazaspiro [3.4] octan-5-yl]-2-fluorophenyl] piperidin-4-yl) methyl]piperazine-1-carboxylate as a yellow solid.

LC-MS (ES$^+$): m/z 667.30 [MH$^+$], t$_R$=1.52 min (1.9 minute run).

Synthesis 3-chloro-5-(5-[3-fluoro-4-[4-(piperazin-1-ylmethyl)piperidin-1-yl]phenyl]-8-oxo-6-sulfanylidene-5,7-diazaspiro[3.4]octan-7-yl)pyridine-2-carbonitrile hydrochloride Into a 100 mL round-bottom flask, was placed a solution of tert-butyl 4-[(1-[4-[7-(5-chloro-6-cyanopyridin-3-yl)-8-imino-6-sulfanylidene-5,7-diazaspiro[3.4]octan-5-yl]-2-fluorophenyl] piperidin-4-yl)methyl]piperazine-1-carboxylate (230.0 mg, 0.3 mmol, 1.0 equiv) in methanol (10 mL), hydrogen chloride (8 ml). The resulting solution was stirred for 2 hours at 80° C. in an oil bath. The reaction was then quenched by the addition of 5 mL of ice water. The resulting solution was extracted with ethyl acetate (20 mL×2) and the organic layers combined and dried over anhydrous sodium sulfate and concentrated under reduced pressure. This resulted in 200.1 mg (96%) of 3-chloro-5-(5-[3-fluoro-4-[4-(piperazin-1-ylmethyl) piperidin-1-yl]phenyl]-8-oxo-6-sulfanylidene-5, 7-diazaspiro [3.4] octan-7-yl) pyridine-2-carbonitrile hydrochloride as a yellow solid.

LC-MS (ES$^+$): m/z 568.25 [MH$^+$], t$_R$=1.26 min (1.9 minute run).

6. Synthesis 3-chloro-5-(5-[4-[4-([4-[2-(2, 6-dioxopiperidin-3-yl)-1,3-dioxo-2, 3-dihydro-1H-isoindol-5-yl] piperazin-1-yl] methyl) piperidin-1-yl]-3-fluorophenyl]-8-oxo-6-sulfanylidene-5, 7-diazaspiro [3.4]octan-7-yl)pyridine-2-carbonitrile Into a 20-30 mL sealed tube, was placed a solution of 3-chloro-5-(5-[3-fluoro-4-[4-(piperazin-1-ylmethyl)piperidin-1-yl]phenyl]-8-oxo-6-sulfanylidene-5,7-diazaspiro[3.4] octan-7-yl)pyridine-2-carbonitrile hydrochloride (100.0 mg, 0.2 mmol, 1.0 equiv) in dimethylsulfoxide (10 mL), 2-(2, 6-dioxopiperidin-3-yl)-5-fluoro-2,3-dihydro-1H-isoindole-1,3-dione (40.6 mg, 0.2 mmol, 0.9 equiv), N,N-Diisopropylethylamine (56.9 mg, 0.44 mmol, 2.66 equiv). The resulting solution was stirred for 2 hours at 130° C. in an oil bath. The reaction was then quenched by the addition of 5 mL of water/ice. The resulting solution was extracted with of ethyl acetate (20 mL×2) and the organic layers combined and dried over anhydrous sodium sulfate and concentrated under reduced pressure. The crude product was purified by Prep-HPLC with the following conditions: Mobile Phase A: Water (10 MMOL/L ammonium bicarbonate), Mobile Phase B: acetonitrile; Flow rate: 20 mL/min; Gradient: 56% B to 76% B in 8 min; 254 nm; Rt: 7.6 min; 5 mL product was obtained. This resulted in 72.7 mg (60%) of 3-chloro-5-(5-[4-[4-([4-[2-(2,6-dioxopiperidin-3-yl)-1,3-dioxo-2,3-dihydro-1H-isoindol-5-yl]piperazin-1-yl]methyl)piperidin-1-yl]-3-fluorophenyl]-8-oxo-6-sulfanylidene-5,7-diazaspiro [3.4]octan-7-yl)pyridine-2-carbonitrile as a yellow solid.

$^1$H NMR (300 MHz, DMSO-d$_6$) δ 11.10 (s, 1H), 8.90 (d, J=2.0 Hz, 1H), 8.54 (d, J=1.9 Hz, 1H), 7.70 (d, J=8.5 Hz, 1H), 7.37 (s, 1H), 7.33-7.13 (m, 4H), 5.09 (dd, J=12.6, 5.4 Hz, 1H), 3.50-3.45 (m, 6H), 2.90-2.81 (m, 4H), 2.71-2.2.60 (m, 3H), 2.61-2.45 (m, 5H), 2.38-2.36 (m, 1H), 2.30-2.28 (m, 2H), 2.05-1.99 (m, 2H), 1.89-1.80 (m, 2H), 1.76-1.72 (m, 1H), 1.61-1.55 (m, 1H), 1.39-1.22 (m, 2H); LC-MS (ES$^+$): m/z 824.35[MH$^+$], t$_R$=1.27 min (2.9 minute run).

Chemical formula: $C_{41}H_{39}ClFN_9O_5S$ [823.25].

Total H count from HNMR data: 39.

Synthetic Procedure for Compound 603

1. Synthesis of 4-fluoro-N-hydroxybenzene-1-carboximidamide

Into a 250-mL round-bottom flask, was placed 4-fluorobenzonitrile (5.00 g, 41.28 mmol, 1 equiv), hydroxylamine hydrochloride (14.0 g, 201.47 mmol, 4.880 equiv), ethanol (150 mL) and N-ethyl-N-isopropylpropan-2-amine (27.0 g, 208.90 mmol, 5.060 equiv). The resulting mixture was stirred for 4 hours at 85° C. in an oil bath. The resulting mixture was concentrated under reduced pressure. The residue was applied onto a silica gel column with methanol:ethyl acetate (1:10). This resulted in 5.70 g (89.57%) of 4-fluoro-N-hydroxybenzene-1-carboximidamide as a white solid.

LC-MS (ES$^+$): m/z 155.30 [MH]$^+$, t$_R$=0.60 min (2.00 minute run).

2. Synthesis of 3-(4-fluorophenyl)-5-methyl-1,2,4-oxadiazole

Into a 100-mL round-bottom flask, was placed 4-fluoro-N-hydroxybenzene-1-carboximidamide (5.70 g, 36.98 mmol, 1.0 equiv), acetyl acetate (54.1 g, 529.93 mmol, 14.3 equiv) and acetic acid (5 mL). The resulting solution was stirred for 16 hours at 120° C. in an oil bath. The reaction was then quenched by the addition of 150 mL of water. The pH value of the solution was adjusted to 7 with NaHCO$_3$ solution. The resulting solution was extracted with ethyl acetate (30 mL×2) and the organic layers combined. The resulting mixture was washed with brine (30 mL×2). The mixture was dried over with anhydrous sodium sulfate and the solid was filtered out. The resulting mixture was concentrated under reduced pressure. The residue was applied onto a silica gel column with ethyl acetate/petroleum ether (1:1). This resulted in 6.10 g (92.59%) of 3-(4-fluorophenyl)-5-methyl-1,2,4-oxadiazole as a white solid.

LC-MS (ES$^+$): m/z 178.95 [MH]$^+$, t$_R$=1.18 min (2.00 minute run).

3. Synthesis of tert-butyl 4-([1-[4-(5-methyl-1,2,4-oxadiazol-3-yl)phenyl]azetidin-3-yl]methyl)piperazine-1-carboxylate Into a 30-mL sealed tube, was placed 3-(4-fluorophenyl)-5-methyl-1,2,4-oxadiazole (523.0 mg, 2.94 mmol, 1.5 equiv), tert-butyl 4-(azetidin-3-ylmethyl)piperazine-1-carboxylate (500.0 mg, 1.96 mmol, 1 equiv), dimethyl sulphoxide (15 mL, 211.18 mmol, 107.852 equiv) and $Cs_2CO_3$ (1.91 g, 5.86 mmol, 3.0 equiv). The resulting suspension was stirred for 20 hours at 150° C. in an oil bath. The reaction was then quenched by the addition of 150 mL of water. The resulting solution was extracted with ethyl acetate (30 mL×2) and the organic layers combined. The resulting mixture was washed with brine (30 mL×2). The mixture was dried over anhydrous sodium sulfate. The solids were filtered out. The resulting mixture was concentrated under reduced pressure. The residue was applied onto a silica gel column with ethyl acetate/petroleum ether (1:1). This resulted in 380.0 mg (46.93%) of tert-butyl 4-([1-[4-(5-methyl-1,2,4-oxadiazol-3-yl)phenyl]azetidin-3-yl]methyl) piperazine-1-carboxylate as a light yellow solid.

LC-MS (ES$^+$): m/z 414.40 [MH]$^+$, $t_R$=0.90 min (2.00 minute run).

4. Synthesis of tert-butyl 4-[[1-(4-carbamimidoylphenyl)azetidin-3-yl]methyl]piperazine-1-carboxylate Into a 100-mL round-bottom flask purged and maintained with an inert atmosphere of nitrogen, was placed tert-butyl 4-([1-[4-(5-methyl-1,2,4-oxadiazol-3-yl)phenyl]azetidin-3-yl]methyl)piperazine-1-carboxylate (380.0 mg, 0.92 mmol, 1 equiv), methanol (50 mL), AcOH (2 mL, 34.90 mmol, 37.981 equiv) and 10% Pd/C (300 mg). The flask was rapidly evacuated and then recharged with hydrogen gas for three times, and finally connected with a tyre containing $H_2$ (10 L). The resulting suspension was stirred for 16 hours at room temperature. The solids were filtered out and further washed successively with 200 mL methanol and 200 ml of acetonitrile. The combined filtrate was concentrated under reduced pressure. This resulted in 100.0 mg (29.14%) of tert-butyl 4-[[1-(4-carbamimidoylphenyl)azetidin-3-yl] methyl]piperazine-1-carboxylate as a white solid.

LC-MS (ES$^+$): m/z 374.05 [MH]$^+$, $t_R$=0.75 min (2.00 minute run).

5. Synthesis of 2-chloro-4-[[(1r,4r)-4-(2-bromoacetyl)cyclohexyl]oxy]benzonitrile Into a 100-mL three-necked round-bottom flask purged and maintained with an inert atmosphere of nitrogen, was placed (1r,4r)-4-(3-chloro-4-cyanophenoxy)cyclohexane-1-carboxylic acid (400.0 mg, 1.43 mmol, 1.0 equiv), dichloromethane (30 mL), oxalyl chloride (220.0 mg, 1.73 mmol, 1.2 equiv) and a drop of N,N-dimethylacetamide (30.0 mg, 0.41 mmol, 0.29 equiv). The resulting solution was stirred for 4 hours at room temperature. The reaction mixture was concentrated under reduced pressure, and the residue was dissolved in acetonitrile (20 mL). Into the solution was added (Trimethylsilyl)diazomethane (2.2 mL, 4.4 mmol, 3.0 equiv, 2M in hexane). The resulting solution was stirred for 2 hours at room temperature, and then was cooled with an ice/water bath. Into the cooled mixture was added a solution of HBr in AcOH (40%) (1.05 g, 5.17 mmol, 3.613 equiv), and then the cool bath was removed. The resulting solution was allowed to react with stirring for an additional 2 hours at room temperature. The reaction was then quenched by the addition of 100 mL of water. The resulting solution was extracted with ethyl acetate (30 mL×2) and the organic layers combined. The resulting mixture was washed with brine (30 mL×2). The mixture was dried over anhydrous sodium sulfate and the solid was filtered out. The resulting mixture was concentrated under reduced pressure. The residue was applied onto a silica gel column with ethyl acetate/petroleum ether (1:5). This resulted in 380 mg (74.51%) of 2-chloro-4-[[(1r,4r)-4-(2-bromoacetyl)cyclohexyl]oxy]benzonitrile as a white solid.

LC-MS (ES$^+$): m/z 355.85 [MH]$^+$, $t_R$=1.05 min (1.90 minute run).

6. Synthesis of tert-butyl 4-[[1-(4-[5-[(1r,4r)-4-(3-chloro-4-cyanophenoxy)cyclohexyl]-1H-imidazol-2-yl]phenyl)azetidin-3-yl]methyl]piperazine-1-carboxylate Into a 50-mL 3-necked round-bottom flask, was placed tert-butyl 4-[[1-(4-carbamimidoylphenyl)azetidin-3-yl] methyl]piperazine-1-carboxylate (100.0 mg, 0.27 mmol, 1.0 equiv), tetrahydrofuran (15 mL) and a solution of $NaHCO_3$ (113.0 mg, 1.35 mmol, 5.0 equiv) in water (3 mL). After stirring the mixture at room temperature for 5 minutes, into the flask, was added a solution of 2-chloro-4-[[(1r,4r)-4-(2-bromoacetyl)cyclohexyl]oxy]benzonitrile (96.0 mg, 0.27 mmol, 1 equiv) in THF (5 mL). The resulting solution was stirred for 24 hours at 50° C. in an oil bath. The reaction was then quenched by the addition of 150 mL of water. The resulting solution was extracted with ethyl acetate (30 mL×2) and the organic layers combined. The resulting mixture was washed with brine (50 mL×2). The mixture was dried over anhydrous sodium sulfate and the solid was filtered out. The resulting mixture was concentrated under reduced pressure. The residue was applied onto a silica gel column with methanol:ethyl acetate (1:10). This resulted in 50.0 mg (29.43%) of tert-butyl 4-[[1-(4-[5-[(1r,4r)-4-(3-chloro-4-cyanophenoxy)cyclohexyl]-1H-imidazol-2-yl] phenyl)azetidin-3-yl]methyl]piperazine-1-carboxylate as an off-white solid.

LC-MS (ES$^+$): m/z 631.15 [MH]$^+$, $t_R$=0.94 min (2.00 minute run).

7. Synthesis of 4-[[1-(4-[5-[(1r,4r)-4-(3-chloro-4-cyanophenoxy)cyclohexyl]-1H-imidazol-2-yl]phenyl)azetidin-3-yl]methyl]piperazin-1-ium trifluoroacetate Into a 100-mL round-bottom flask, was placed tert-butyl 4-[[1-(4-[5-[(1r,4r)-4-(3-chloro-4-cyanophenoxy)cyclohexyl]-1H-imidazol-2-yl]phenyl)azetidin-3-yl]methyl]piperazine-1-carboxylate (50.0 mg, 0.08 mmol, 1 equiv), dichloromethane (20 mL, 314.60 mmol, 3971.566 equiv) and 2,2,2-trifluoroacetaldehyde (5 mL). The resulting solution was stirred for 2 hours at room temperature. The resulting mixture was concentrated under vacuum. This resulted in 50.0 mg (97.84%) of 4-[[1-(4-[5-[(1r,4r)-4-(3-chloro-4-cyanophenoxy)cyclohexyl]-1H-imidazol-2-yl] phenyl)azetidin-3-yl]methyl]piperazin-1-ium trifluoroacetate as an off-white solid.

8. Synthesis of 2-chloro-4-[[(1r,4r)-4-(2-[4-[3-([4-[2-(2,6-dioxopiperidin-3-yl)-1,3-dioxo-2,3-dihydro-1H-isoindol-5-yl]piperazin-1-yl]methyl)azetidin-1-yl]phenyl]-1H-imidazol-5-yl)cyclohexyl]oxy] benzonitrile Into a 8-mL sealed tube, was placed 4-[[1-(4-[5-[(1r,4r)-4-(3-chloro-4-cyanophenoxy)cyclohexyl]-1H-imidazol-2-yl]phenyl)azetidin-3-yl]methyl]piperazin-1-ium trifluoroacetate (50.0 mg, 0.08 mmol, 1 equiv), 2-(2,6-dioxopiperidin-3-yl)-5-fluoro-2,3-dihydro-1H-isoindole-1,3-dione (54.0 mg, 0.20 mmol, 2.522 equiv), dimethyl sulphoxide (4 mL, 56.31 mmol, 726.583 equiv) and N-ethyl-N-isopropylpropan-2-amine (2 mL, 12.10 mmol, 156.134 equiv). The resulting solution was stirred for 3 hours at 130° C. in an oil bath. The reaction was then quenched by the addition of 150 mL of water. The resulting solution was extracted with ethyl acetate (30 mL×2) and the organic layers combined. The resulting mixture was washed with brine (50 mL×2). The mixture was dried over anhydrous sodium sulfate and the solid was filtered out. The resulting mixture was concentrated under reduced pressure. The residue was applied onto a silica gel column with methanol:ethyl acetate (1:10). The crude product was further purified by Prep-HPLC (Column: XBridge Prep C18 OBD Column, Sum, 19*150 mm; Mobile Phase A: Water (10 mmoL/L $NH_4HCO_3$), Mobile Phase B: ACN; Flow rate: 20 mL/min; Gradient: 45% B to 63% B in 8 min; 254 nm; Rt: 7.8 min). This resulted in 31.5 mg (51.62%) of 2-chloro-4-[[(1r,4r)-4-(2-[4-[3-([4-[2-(2,6-dioxopiperidin-3-yl)-1,3-dioxo-2,3-dihydro-1H-isoindol-5-yl]piperazin-1-yl]methyl)azetidin-1-yl]phenyl]-1H-imidazol-5-yl)cyclohexyl]oxy]benzonitrile as a yellow solid.

$^1$H NMR (300 MHz, Me$_2$SO-d$_6$): δ 11.08 (s, 1H), 7.86 (d, J=8.8 Hz, 1H), 7.71-7.67 (m, 3H), 7.39-7.25 (m, 3H), 7.13 (dd, J=8.8, 2.3 Hz, 1H), 6.74 (s, 1H), 6.45 (d, J=8.4 Hz, 2H), 5.07 (dd, J=12.7, 5.5 Hz, 1H), 4.60 (brs, 1H), 3.98 (t, J=7.6 Hz, 2H), 3.54-3.30 (m, 7H), 3.29-3.120 (m, 5H), 3.11-2.79 (m, 3H), 2.67-2.55 (m, 3H), 2.18-2.01 (m, 5H), 1.75-1.35 (m, 4H); LC-MS (ES$^+$): m/z 787.50 [MH$^+$], HPLC: t$_R$=5.13 min (10.00 minute run).

Chemical Formula: $C_{43}H_{43}ClN_8O_5$ [787.31].
Total H count from HNMR data: 43.

Synthetic Procedure for Compound 609

1. Synthesis of tert-butyl N-[(1r,3r)-3-(3-chloro-4-cyanophenoxy)-2,2,4,4-tetramethylcyclobutyl]carbamate

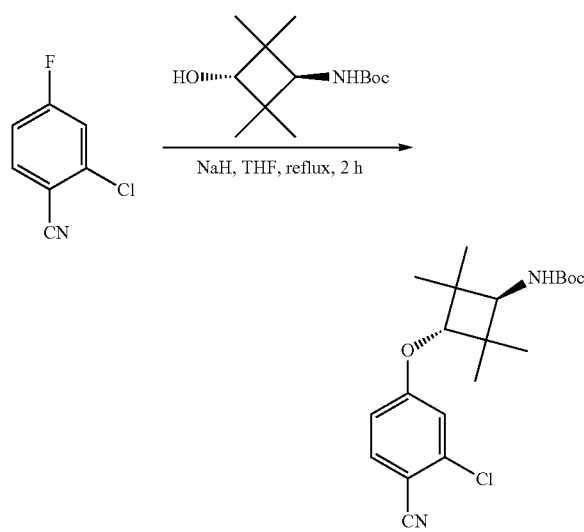

Into a 100-mL 3-necked round-bottom flask purged and maintained with an inert atmosphere of nitrogen, was placed a solution of tert-butyl N-[(1r,3r)-3-hydroxy-2,2,4,4-tetramethylcyclobutyl]carbamate (600.0 mg, 2.47 mmol, 1.00 equiv) in N,N-dimethylformamide (10.0 mL). This was followed by the addition of sodium hydride (198.0 mg, 8.25 mmol, 2.00 equiv), in portions at 0° C. After 30 minutes, to this was added 2-chloro-4-fluorobenzonitrile (459.0 mg, 2.95 mmol, 1.20 equiv). The resulting solution was stirred for 1 hour at 70° C. The reaction mixture was cooled to room temperature with a water bath. The reaction was then quenched by the addition of water (20 mL). The resulting solution was extracted with ethyl acetate (20 mL×3) and the organic layers combined. The residue was applied onto a silica gel column with ethyl acetate/petroleum ether (1/5). This resulted in 100.0 mg (11%) of tert-butyl N-[(1r,3r)-3-(3-chloro-4-cyanophenoxy)-2,2,4,4-tetramethylcyclobutyl] carbamate as colorless oil.

LC-MS (ES$^+$): m/z 279.10 [MH-100]$^+$, t$_R$=1.20 min (2.5 minute run).

2. Synthesis of 2-chloro-4-[(1r,3r)-3-amino-2,2,4,4-tetramethylcyclobutoxy]benzonitrile

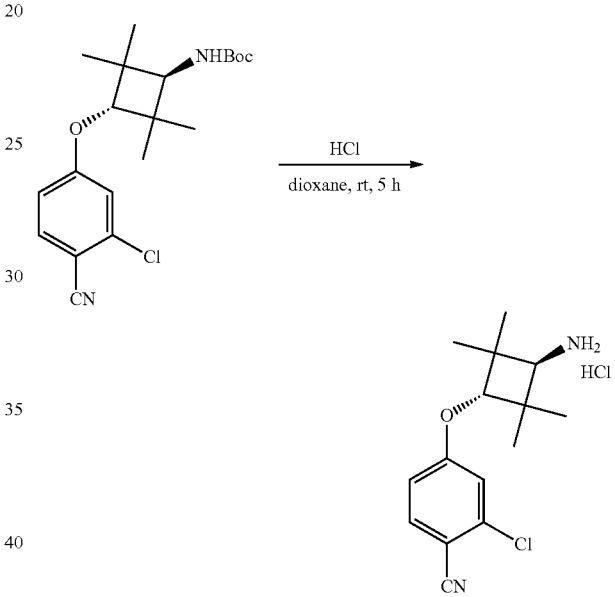

Into a 100-mL round-bottom flask purged and maintained with an inert atmosphere of nitrogen, was placed tert-butyl N-[(1r,3r)-3-(3-chloro-4-cyanophenoxy)-2,2,4,4-tetramethylcyclobutyl]carbamate (500.0 mg, 1.32 mmol, 1.00 equiv), hydrogen chloride/dioxane (3 mL, 4M), 1,4-dioxane (3 mL). The resulting solution was stirred for 1 hour at room temperature. The resulting mixture was concentrated under vacuum. This resulted in 447.0 mg (87%) of 2-chloro-4-[(1r,3r)-3-amino-2,2,4,4-tetramethylcyclobutoxy]benzonitrile as a white solid.

3. Synthesis of tert-butyl 4-[2-(2,6-dioxopiperidin-3-yl)-1,3-dioxo-2,3-dihydro-1H-isoindol-5-yl]piperazine-1-carboxylate Into a 100-mL a flask, was placed a solution of 2-(2,6-dioxopiperidin-3-yl)-5-fluoro-2,3-dihydro-1H-isoindole-1,3-dione (5 g, 18.10 mmol, 1.00 equiv) in methyl sulfoxide (30 mL), methyl sulfoxide (30 mL), N,N-diisopropylethylamine (12.5 mL, 2.00 equiv), tert-butyl piperazine-1-carboxylate (3.75 g, 20.13 mmol, 1.10 equiv). The resulting solution was stirred for 16 hours at 110° C. in an oil bath. The reaction was then quenched by the addition of water (100 mL). The resulting solution was extracted with ethyl acetate (100 mL×3) and the organic layers combined. The resulting mixture was washed with brine (200 mL). The mixture was dried over anhydrous sodium sulfate and concentrated under vacuum. This resulted in 6.5 g (81%) of tert-butyl 4-[2-(2,6-dioxopiperidin-3-yl)-1,3-dioxo-2,3-dihydro-1H-isoindol-5-yl]piperazine-1-carboxylate as a yellow solid.

LC-MS (ES$^+$): m/z 443.00 [MH$^+$], $t_R$=1.156 min, (2.0 minute run).

4. Synthesis of tert-butyl 4-[2-(2,6-dioxopiperidin-3-yl)-3-hydroxy-3-methyl-1-oxo-2,3-dihydro-1H-isoindol-5-yl]piperazine-1-carboxylate Into a 50-mL sealed tube purged and maintained with an inert atmosphere of nitrogen, was placed tert-butyl 4-[2-(2,6-dioxopiperidin-3-yl)-1,3-dioxo-2,3-dihydro-1H-isoindol-5-yl]piperazine-1-carboxylate (2 g, 4.52 mmol, 1.00 equiv), tetrahydrofuran (30 mL). This was followed by the addition of Methylmagnesium bromide (6 mL) dropwise with stirring at −75° C. in 20 minutes. The resulting solution was stirred for 4 hours at 60° C. The reaction was then quenched by the addition of water (50 mL). The resulting solution was extracted with ethyl acetate (30 mL×3) and the organic layers combined. The resulting mixture was washed with saturated sodium chloride aqueous solution (50 mL). The mixture was dried over anhydrous sodium sulfate and concentrated under vacuum. The residue was applied onto a silica gel column with ethyl acetate/petroleum ether (1:0). This resulted in 1.5 g (72%) of tert-butyl 4-[2-(2,6-dioxopiperidin-3-yl)-3-hydroxy-3-methyl-1-oxo-2,3-dihydro-1H-isoindol-5-yl]piperazine-1-carboxylate as yellow crude oil.

5. Synthesis of 3-[3-methyl-1-oxo-5-(piperazin-1-yl)-2,3-dihydro-1H-isoindol-2-yl]piperidine-2,6-dione Into a 100-mL round-bottom flask, was placed tert-butyl 4-[2-(2,6-dioxopiperidin-3-yl)-3-hydroxy-3-methyl-1-oxo-2,3-dihydro-1H-isoindol-5-yl]piperazine-1-carboxylate (1.5 g, 3.27 mmol, 1.00 equiv), dichloromethane (20 mL), triethylsilane (15 mL). This was followed by the addition of Boron trifluoride etherate (15 mL) dropwise with stirring. The resulting solution was stirred for 16 hours at 25° C. The resulting solution was diluted with water (35 mL). The resulting solution was extracted with ethyl acetate (15 mL×3) and the aqueous layers combined and concentrated under vacuum. This resulted in 1.12 g (100%) of 3-[3-methyl-1-oxo-5-(piperazin-1-yl)-2,3-dihydro-1H-isoindol-2-yl]piperidine-2,6-dione as yellow crude oil.

LC-MS (ES$^+$): m/z 343.00 [MH$^+$], $t_R$=0.658 min, (2.0 minute run).

6. Synthesis of tert-butyl 4-[2-(2,6-dioxopiperidin-3-yl)-3-methyl-1-oxo-2,3-dihydro-1H-isoindol-5-yl]piperazine-1-carboxylate Into a 100-mL round-bottom flask, was placed 3-[3-methyl-1-oxo-5-(piperazin-1-yl)-2,3-dihydro-1H-isoindol-2-yl]piperidine-2,6-dione (1.12 g, 3.27 mmol, 1.00 equiv), dichloromethane (50 mL), (Boc)$_2$O (1.5 g, 6.87 mmol, 2.10 equiv). This was followed by the addition of triethylamine (4 mL) dropwise with stirring. The resulting solution was stirred for 16 hours at 25° C. The resulting solution was diluted with water (50 mL). The resulting solution was extracted with dichloromethane (20 mL×3) and the organic layers combined. The resulting mixture was washed with saturated sodium chloride aqueous solution (15 mL×2). The mixture was dried over anhydrous sodium sulfate and concentrated under vacuum. The residue was applied onto a silica gel column with ethyl acetate/petroleum ether (8:2). The crude product was purified by Prep-HPLC with the following conditions: Column, XBridge Prep C18 OBD Column, 5 um, 19*150 mm; mobile phase, Water (10 MMOL/L NH$_4$HCO$_3$) and ACN (32.0% ACN up to 41.0% in 9 min); Detector, UV 254 nm. This resulted in 435 mg (30%) of tert-butyl 4-[2-(2,6-dioxopiperidin-3-yl)-3-methyl-1-oxo-2,3-dihydro-1H-isoindol-5-yl]piperazine-1-carboxylate as yellow oil.

LCMS42-PH-ARV-LS-046-E-20-3(60861-135Q)1T.

LC-MS (ES$^+$): m/z 443.40 [MH$^+$], $t_R$=2.034 min, (4.6 minute run).

7. Synthesis of 3-[3-methyl-1-oxo-5-(piperazin-1-yl)-2,3-dihydro-1H-isoindol-2-yl]piperidine-2,6-dione; trifluoroacetic acid Into a 50-mL round-bottom flask, was placed tert-butyl 4-[2-(2,6-dioxopiperidin-3-yl)-3-methyl-1-oxo-2,3-dihydro-1H-isoindol-5-yl]piperazine-1-carboxylate (435 mg, 0.98 mmol, 1.00 equiv), dichloromethane (30 mL), trifluoroacetic acid (1 mL). The resulting solution was stirred for 3 hours at 25° C. The resulting mixture was concentrated under vacuum. This resulted in 500 mg (1.11%) of 3-[3-methyl-1-oxo-5-(piperazin-1-yl)-2,3-dihydro-1H-isoindol-2-yl]piperidine-2,6-dione; trifluoroacetic acid as yellow crude oil.

8. Synthesis of 4-[4-(hydroxymethyl)piperidin-1-yl]-N-[(1r,3r)-3-(3-chloro-4-cyanophenoxy)-2,2,4,4-tetramethylcyclobutyl]benzamide Into a 25-mL round-bottom flask, was placed 4-[4-(hydroxymethyl)piperidin-1-yl]benzoic acid (250 mg, 1.06 mmol, 1.00 equiv), N,N-dimethylformamide (6 mL), HATU (485 mg, 1.28 mmol, 1.20 equiv). This was followed by the addition of N,N-diisopropylethylamine (550 mg, 4.26 mmol, 4.01 equiv) in 5 minutes. To this was added 2-chloro-4-[(1r,3r)-3-amino-2,2,4,4-tetramethylcyclobutoxy]benzonitrile hydrochloride (335 mg, 1.06 mmol, 1.00 equiv). The resulting solution was stirred for 2 hours at 25° C. The resulting solution was diluted with water (25 mL). The resulting solution was extracted with ethyl acetate (15 mL×3) and the organic layers combined. The resulting mixture was washed with saturated sodium chloride aqueous solution (20 mL). The mixture was dried over anhydrous sodium sulfate and concentrated under vacuum. The residue was applied onto a silica gel column with dichloromethane/methanol (10:1). This resulted in 514 mg (98%) of 4-[4-(hydroxymethyl)piperidin-1-yl]-N-[(1r,3r)-3-(3-chloro-4-cyanophenoxy)-2,2,4,4-tetramethylcyclobutyl]benzamide as a off-white solid.

LC-MS (ES$^+$): m/z 496.05 [MH$^+$], $t_R$=1.133 min, (2.0 minute run).

9. Synthesis of 4-(4-formylpiperidin-1-yl)-N-[(1r,3r)-3-(3-chloro-4-cyanophenoxy)-2,2,4,4-tetramethylcyclobutyl]benzamide Into a 50-mL round-bottom flask, was placed 4-[4-(hydroxymethyl)piperidin-1-yl]-N-[(1r,3r)-3-(3-chloro-4-cyanophenoxy)-2,2,4,4-tetramethylcyclobutyl]benzamide (600 mg, 1.21 mmol, 1.00 equiv), dichloromethane (20 mL). This was followed by the addition of Dess-Martin (1.02 g), in portions at 0° C. The resulting solution was stirred for 2 hours at 25° C. The reaction was then quenched by the addition of saturated sodium bicarbonate solution (50 mL) and sodium thiosulfate solution (50 mL). The resulting solution was extracted with dichloromethane (30 mL×3) and the organic layers combined. The resulting mixture was washed with saturated sodium chloride aqueous solution (50 mL). The mixture was dried over anhydrous sodium sulfate and concentrated under vacuum. The residue was applied onto a silica gel column with ethyl acetate/petroleum ether (1:1). This resulted in 450 mg (75%) of 4-(4-formylpiperidin-1-yl)-N-[(1r,3r)-3-(3-chloro-4-cyanophenoxy)-2,2,4,4-tetramethylcyclobutyl]benzamide as a off-white solid.

LC-MS (ES+): m/z 494.10 [MH+], $t_R$=1.074 min, (1.9 minute run).

10. Synthesis of 4-[4-([4-[2-(2,6-dioxopiperidin-3-yl)-3-methyl-1-oxo-2,3-dihydro-1H-isoindol-5-yl]piperazin-1-yl]methyl)piperidin-1-yl]-N-[(1r,3r)-3-(3-chloro-4-cyanophenoxy)-2,2,4,4-tetramethylcyclobutyl]benzamide Into a 50-mL round-bottom flask, was placed 4-(4-formylpiperidin-1-yl)-N-[(1r,3r)-3-(3-chloro-4-cyanophenoxy)-2,2,4,4-tetramethylcyclobutyl]benzamide (130 mg, 0.26 mmol, 1.00 equiv), 3-[3-methyl-1-oxo-5-(piperazin-1-yl)-2,3-dihydro-1H-isoindol-2-yl]piperidine-2,6-dione; trifluoroacetic acid (110 mg, 0.24 mmol, 0.92 equiv), dichloromethane (20 mL). This was followed by the addition of DIEA (0.3 mL) dropwise with stirring in 16 hours. To this was added sodium triacetoxyborohydride (550 mg), in portions. The resulting solution was stirred for 16 hours at 25° C. The reaction was then quenched by the addition of water (20 mL). The resulting solution was extracted with dichloromethane (15 mL×3) and the organic layers combined. The resulting mixture was washed with saturated sodium chloride aqueous solution (20 mL). The mixture was dried over anhydrous sodium sulfate and concentrated under vacuum. The crude product was purified by Prep-HPLC with the following conditions: Column, XBridge Prep C18 OBD Column, 5 um, 19*150 mm; mobile phase, Water (10 MMOL/L NH4HCO3) and ACN (53.0% ACN up to 72.0% in 8 min); Detector, UV 254 nm. This resulted in 53.4 mg (25%) of 4-[4-([4-[2-(2,6-dioxopiperidin-3-yl)-3-methyl-1-oxo-2,3-dihydro-1H-isoindol-5-yl]piperazin-1-yl]methyl)piperidin-1-yl]-N-[(1r,3r)-3-(3-chloro-4-cyanophenoxy)-2,2,4,4-tetramethylcyclobutyl]benzamide as a white solid.

H-NMR-PH-ARV-LS-046-E-0: (300 MHz, DMSO, ppm) δ 10.90-10.88 (br, 1H), 7.92-7.89 (d, J=9 Hz, 1H), 7.75-7.72 (d, J=9 Hz, 2H), 7.51-7.44 (m, 2H), 7.21 (br, 1H), 7.10-6.94 (m, 5H), 4.65-4.64 (m, 1H), 4.54-4.52 (m, 1H), 4.32 (s, 1H), 4.06-4.03 (d, J=9 Hz, 1H), 3.88-3.84 (m, 2H), 3.31-3.28 (m, 4H), 2.83-2.75 (m, 3H), 2.63-2.58 (m, 6H), 2.22-2.20 (m, 2H), 1.96-1.94 (m, 1H), 1.83-1.79 (m, 3H), 1.43-1.38 (m, 3H), 1.21 (s, 6H), 1.18-1.17 (m, 2H), 1.12 (s, 6H); LC-MS (ES+): m/z 820.30/822.30 [MH+], $t_R$=2.042 min, (3.0 minute run).

Chemical Formula: $C_{46}H_{54}ClN_7O_5$ [819.39/821.39].
Total H count from HNMR data: 54.

Synthetic Procedure for Compound 88

Synthesis of 4-(6-[4-[2-(2,6-dioxopiperidin-3-yl)-6-fluoro-3-hydroxy-1-oxo-2,3-dihydro-1H-isoindol-5-yl]piperazin-1-yl]hexyl)-N-[(1r,3r)-3-(3-chloro-4-cyanophenoxy)-2,2,4,4-tetramethylcyclobutyl]benzamide Into a 100-mL round-bottom flask, was placed a solution of 4-(6-[4-[2-(2,6-dioxopiperidin-3-yl)-6-fluoro-1,3-dioxo-2,3-dihydro-1H-isoindol-5-yl]piperazin-1-yl]hexyl)-N-[(1r,3r)-3-(3-chloro-4-cyanophenoxy)-2,2,4,4-tetramethylcyclobutyl]benzamide (330 mg, 0.40 mmol, 1.00 equiv) in acetic acid (20 mL), Zn (100 mg, 3.00 equiv). The resulting solution was stirred for 30 minutes at room temperature. The resulting solution was diluted with 100 of methyl alcohol. The resulting mixture was concentrated under vacuum. This resulted in 320 mg (97%) of 4-(6-[4-[2-(2,6-dioxopiperidin-3-yl)-6-fluoro-3-hydroxy-1-oxo-2,3-dihydro-1H-isoindol-5-yl]piperazin-1-yl]hexyl)-N-[(1r,3r)-3-(3-chloro-4-cyanophenoxy)-2,2,4,4-tetramethylcyclobutyl]benzamide as white oil. m/z 827.40 [MH+], $t_R$=0.799 min (1.90 minute run).

2. Synthesis of-(6-[4-[2-(2,6-dioxopiperidin-3-yl)-6-fluoro-1-oxo-2,3-dihydro-1H-isoindol-5-yl]piperazin-1-yl]hexyl)-N-[(1r,3r)-3-(3-chloro-4-cyanophenoxy)-2,2,4,4-tetramethylcyclobutyl]benzamide Into a 100-mL round-bottom flask, was placed a solution of 4-(6-[4-[2-(2,6-dioxopiperidin-3-yl)-6-fluoro-3-hydroxy-1-oxo-2,3-dihydro-1H-isoindol-5-yl]piperazin-1-yl]hexyl)-N-[(1r,3r)-3-(3-chloro-4-cyanophenoxy)-2,2,4,4-tetramethylcyclobutyl]benzamide (320 g, 386.76 mmol, 1.00 equiv) in trifluoroacetic acid (10 mL), triethylsilane (3 mL, 0.30 equiv). The resulting solution was stirred for 30 minutes at room temperature. The resulting mixture was concentrated under vacuum. The crude product (100 mg) was purified by Column: XBridge Prep OBD C18 Column 19*250 mm, 5 um; Mobile Phase A: Water (0.1% FA), Mobile Phase B: ACN; Flow rate: 20 mL/min; Gradient: 55% B to 75% B in 8 min; 220 nm; Rt: 6.05 min. This resulted in 49.2 mg of 4-(6-[4-[2-(2,6-dioxopiperidin-3-yl)-6-fluoro-1-oxo-2,3-dihydro-1H-isoindol-5-yl]piperazin-1-yl]hexyl)-N-[(1r,3r)-3-(3-chloro-4-cyanophenoxy)-2,2,4,4-tetramethylcyclobutyl] benzamide as a white solid. [(1r,3r)-3-[4-cyano-3-(trifluoromethyl)phenoxy]-2,2,4,4-tetramethylcyclobutyl] benzamide as a white solid.

$^1$H NMR (300 MHz, CD3OD): δ7.81-7.69 (m, 3H), 7.53-7.46 (m, 1H), 7.35-7.27 (m, 3H), 7.15 (s, 1H), 6.97-6.94 (m, 1H), 5.17-5.04 (m, 1H), 4.52-4.39 (m, 2H), 4.27 (s, 1H), 4.16 (s, 1H), 3.84-3.55 (m, 4H), 3.36 (s, 2H), 3.27-3.11 (m, 4H), 3.01-2.61 (m, 4H), 2.22-2.07 (m, 1H), 1.87-1.63 (m, 4H), 1.52-1.38 (m, 4H), 1.33-1.16 (m, 12), m/z 811.45 [MH+], $t_R$=2.415 min (3.20 minute run).

Chemical formula: C45H52ClFN6O5 [810.37].
Total H count from HNMR data: 52.

Synthetic Procedure for Compound 571

1. Synthesis of 5-bromo-3-fluorobenzene-1,2-dicarboxylic acid

Into a 100-mL round-bottom flask, was placed 4-bromo-2-fluoro-6-methylbenzoic acid (2.5 g, 10.73 mmol, 1.00 equiv), sodium hydroxide (1.72 g, 43.00 mmol, 4.00 equiv), water (20 mL), KMnO4 (3.41 g, 2.00 equiv). The resulting solution was stirred for 16 hours at 100° C. in an oil bath. The solids were filtered out. The pH value of the solution was adjusted to 3 with hydrogen chloride (2 mol/L). The resulting solution was extracted with dichloromethane (10 mL×1) and the organic layers combined. The resulting solution was extracted with ethyl acetate:methanol=10:3 (10 mL×3) and the organic layers combined and dried over anhydrous sodium sulfate and concentrated under vacuum.

This resulted in 518 mg (18%) of 5-bromo-3-fluorobenzene-1,2-dicarboxylic acid as a white solid and 1.365 g material as a white solid.

LC-MS (ES$^+$): m/z 264.75 [MH$^+$], $t_R$=0.675 min (2.0 minute run).

2. Synthesis of 1,2-dimethyl 5-bromo-3-fluorobenzene-1,2-dicarboxylate

Into a 100-mL round-bottom flask, was placed 5-bromo-3-fluorobenzene-1,2-dicarboxylic acid (1.4 g, 5.32 mmol, 1.00 equiv), methanol (40 mL), sulfuric acid (2 mL). The resulting solution was stirred for 16 hours at 70° C. The reaction was then quenched by the addition of water (10 mL). The pH value of the solution was adjusted to 7 with sodium carbonate. The resulting solution was extracted with ethyl acetate (20 mL×3) and the organic layers combined and dried over anhydrous sodium sulfate and concentrated under vacuum. The residue was applied onto a silica gel column with ethyl acetate/hexane (1:10). This resulted in 1.15 g (74%) of 1,2-dimethyl 5-bromo-3-fluorobenzene-1,2-dicarboxylate as colorless oil.

LC-MS (ES$^+$): m/z 292.80 [MH$^+$], $t_R$=0.939 min (2.0 minute run).

3. Synthesis of 1,2-dimethyl 5-[4-[(tert-butoxy)carbonyl]piperazin-1-yl]-3-fluorobenzene-1,2-dicarboxylate Into a 50-mL round-bottom flask, was placed 1,2-dimethyl 5-bromo-3-fluorobenzene-1,2-dicarboxylate (500 mg, 1.72 mmol, 1.00 equiv), tert-butyl piperazine-1-carboxylate (481 mg, 2.58 mmol, 1.50 equiv), Rouphos Pd (66 mg, 0.09 mmol, 0.05 equiv), Cs$_2$CO$_3$ (1.66 g, 5.09 mmol, 3.00 equiv), Toluene (20 mL). The resulting solution was stirred for 12 hours at 100° C. in an oil bath. The resulting solution was diluted with water (40 mL). The resulting solution was extracted with ethyl acetate (30 mL×3) and the organic layers combined and dried over anhydrous sodium sulfate and concentrated under vacuum. The residue was applied onto a silica gel column with ethyl acetate/petroleum ether (1:1). This resulted in 600 mg (88%) of 1,2-dimethyl 5-[4-[(tert-butoxy)carbonyl]piperazin-1-yl]-3-fluorobenzene-1,2-dicarboxylate as a solid.

LC-MS (ES$^+$): m/z 397.25 [MH$^+$], $t_R$=1.238 min (2.0 minute run).

4. Synthesis of 5-[4-[(tert-butoxy)carbonyl]piperazin-1-yl]-3-fluorobenzene-1,2-dicarboxylic acid Into a 100-mL round-bottom flask, was placed 1,2-dimethyl 5-[4-[(tert-butoxy)carbonyl]piperazin-1-yl]-3-fluorobenzene-1,2-dicarboxylate (800 mg, 2.02 mmol, 1.00 equiv), methanol/water/THF (16 mL), sodiumol (242.4 mg, 6.06 mmol, 3.00 equiv). The resulting solution was stirred for 16 hours at 25° C. The resulting solution was diluted with 16 mL of water (30 mL). The pH value of the solution was adjusted to 8 with hydrogen chloride (2 mol/L). Citric acid monohydrate was employed to adjust the pH to 3. The resulting solution was extracted with ethyl acetate/methanol=10:1 (30 mL×3) and the organic layers combined and dried over anhydrous sodium sulfate and concentrated under vacuum. This resulted in 740 mg (100%) of 5-[4-[(tert-butoxy)carbonyl]piperazin-1-yl]-3-fluorobenzene-1,2-dicarboxylic acid as a yellow solid.

LC-MS (ES$^+$): m/z 369.00 [MH$^+$], $t_R$=0.804 min (2.0 minute run).

5. Synthesis of tert-butyl 4-[2-(2,6-dioxopiperidin-3-yl)-7-fluoro-1,3-dioxo-2,3-dihydro-1H-isoindol-5-yl]piperazine-1-carboxylate Into a 100-mL round-bottom flask, was placed 5-[4-[(tert-butoxy)carbonyl]piperazin-1-yl]-3-fluorobenzene-1,2-dicarboxylic acid (560 mg, 1.52 mmol, 1.00 equiv) in acetonitrile (25 mL), CDI (986.6 mg, 6.08 mmol, 4.00 equiv), DIEA (785.6 mg, 6.08 mmol, 4.00 equiv), 3-aminopiperidine-2,6-dione (375.5 mg, 2.93 mmol, 1.50 equiv). The resulting solution was stirred for 5 hours at 70° C. in an oil bath. The resulting solution was diluted with water (40 mL). The resulting solution was extracted with ethyl acetate (30 mL×3) and the organic layers combined and dried over anhydrous sodium sulfate and concentrated under vacuum. The residue was applied onto a silica gel column with ethyl acetate/hexane (1:1). This resulted in 700 mg (100%) of tert-butyl 4-[2-(2,6-dioxopiperidin-3-yl)-7-fluoro-1,3-dioxo-2,3-dihydro-1H-isoindol-5-yl]piperazine-1-carboxylate as a yellow solid.

LC-MS (ES$^+$): m/z 483.05 [MNa$^+$], $t_R$=0.884 min (2.0 minute run).

6. Synthesis of 2,2,2-trifluoroacetaldehyde-2-(2,6-dioxopiperidin-3-yl)-4-fluoro-6-(piperazin-1-yl)-2,3-dihydro-1H-isoindole-1,3-dione Into a 100-mL round-bottom flask, was placed tert-butyl 4-[2-(2,6-dioxopiperidin-3-yl)-7-fluoro-1,3-dioxo-2,3-dihydro-1H-isoindol-5-yl]piperazine-1-carboxylate (710 mg, 1.54 mmol, 1.00 equiv), dichloromethane (10 mL), trifluoroacetic acid (3 mL). The resulting solution was stirred for 2 hours at 25° C. The resulting mixture was concentrated under vacuum. The crude product was purified by re-crystallization from ethanol. This resulted in 320 mg (45%) of 2,2,2-trifluoroacetaldehyde-2-(2,6-dioxopiperidin-3-yl)-4-fluoro-6-(piperazin-1-yl)-2,3-dihydro-1H-isoindole-1,3-dione as a yellow solid.

LC-MS (ES$^+$): m/z 361.2 [MH$^+$], $t_R$=0.210 min (2.0 minute run).

7. Synthesis of 2-[4-([4-[2-(2,6-dioxopiperidin-3-yl)-7-fluoro-1,3-dioxo-2,3-dihydro-1H-isoindol-5-yl]piperazin-1-yl]methyl)piperidin-1-yl]-N-[(1r,3r)-3-(3-chloro-4-cyanophenoxy)-2,2,4,4-tetramethylcyclobutyl]pyrimidine-5-carboxamide Into a 100-mL round-bottom flask, was placed 2-(4-formylpiperidin-1-yl)-N-[(1r,3r)-3-(3-chloro-4-cyanophenoxy)-2,2,4,4-tetramethylcyclobutyl]pyrimidine-5-carboxamide (110 mg, 0.22 mmol, 1.00 equiv), 2,2,2-trifluoroacetaldehyde; 2-(2,6-dioxopiperidin-3-yl)-4-fluoro-6-(piperazin-1-yl)-2,3-dihydro-1H-isoindole-1,3-dione (104 mg, 0.23 mmol, 1.30 equiv), dichloromethane (10 mL), acetyl ethaneperoxoate sodioboranyl acetate (70.67 mg, 0.33 mmol, 1.50 equiv). The resulting solution was stirred for 15 minutes at 25° C. The resulting solution was allowed to react, with stirring, for an additional 1 hour at 25° C. The resulting solution was allowed to react, with stirring, for an additional 2 hours at 25° C. The resulting solution was diluted with dichloromethane (30 mL). The resulting mixture was washed with water (30 mL×1. The mixture was dried over anhydrous sodium sulfate and concentrated under vacuum. The residue was applied onto a silica gel column with dichloromethane/ethyl acetate (3:1). The crude product was purified by Prep-HPLC with the following conditions: Column, XBridge Prep C18 OBD Column, 5 um, 19*150 mm; mobile phase, water (10 mmol/L NH$_4$HCO$_3$) and acetonitrile (32.0% acetonitrile up to 75.0% in 8 min); Detector, UV 254/220 nm. This resulted in 145 mg (78%) of 2-[4-([4-[2-(2,6-dioxopiperidin-3-yl)-7-fluoro-1,3-dioxo-2,3-dihydro-1H-isoindol-5-yl]piperazin-1-yl]methyl)piperidin-1-yl]-N-[(1r,3r)-3-(3-chloro-4-cyanophenoxy)-2,2,4,4-tetramethylcyclobutyl]pyrimidine-5-carboxamide as a yellow solid.

$^1$H NMR (300 MHz, DMSO-d6) δ 11.10 (s, 1H), 8.75 (s, 2H), 7.90 (d, J=8.7 Hz, 1H), 7.71 (d, J=9.0 Hz, 1H), 7.24-7.21 (m, 2H), 7.07-6.99 (m, 2H), 5.10 (m, 1H), 4.74 (d, J=13.2 Hz, 2H), 4.29 (s, 1H), 4.04 (d, J=9.0 Hz, 1H), 3.50 (s, 4H), 3.00-2.95 (m, 3H), 2.53-2.50 (m, 5H), 2.21-2.19 (m, 2H), 2.08-1.81 (m, 5H), 1.21-1.04 (m, 14H); LC-MS (ES$^+$): m/z 840.30/842.30 [MH$^+$], t$_R$=3.099 min (5.0 minute run).

Chemical Formula: C$_{43}$H$_{47}$ClFN$_9$O$_6$[839.33/841.33].

Total H count from HNMR data: 47.

Synthetic Procedure for Compound 358

1. Synthesis of ethyl 4,6-dimethyl-2-oxo-1,2,3,4-tetrahydropyrimidine-5-carboxylate Into a 500-mL round-bottom flask, was placed a solution of ethyl 3-oxobutanoate (10 g, 76.84 mmol, 1.00 equiv) in ethanol (200 mL), urea (6.9 g, 114.89 mmol, 1.50 equiv), acetaldehyde (5 g, 113.50 mmol, 1.50 equiv), hydrogen chloride (2 mL, 0.30 equiv). The resulting solution was stirred for 5 hours at 85° C. in an oil bath. The resulting mixture was concentrated under vacuum. This resulted in 12 g (79%) of ethyl 4,6-dimethyl-2-oxo-1,2,3,4-tetrahydropyrimidine-5-carboxylate as a white solid. m/z: 199.13[MH$^+$], t$_R$=0.865 min (2.00 minute run).

2. Synthesis of ethyl 4,6-dimethyl-2-oxo-1,2-dihydropyrimidine-5-carboxylate

Into a 100-mL round-bottom flask, was placed Nitric acid (20 mL, 5.00 equiv) over a period of 5 minutes. This was followed by the addition of ethyl 4,6-dimethyl-2-oxo-1,2,3,4-tetrahydropyrimidine-5-carboxylate (2 g, 10.09 mmol, 1.00 equiv) dropwise with stirring. The resulting solution was stirred for 3 hours at 0° C. in a water/ice bath. The resulting mixture was concentrated under vacuum. The residue was applied onto a silica gel column with dichloromethane/methanol (1:7). The collected fractions were combined and concentrated under vacuum. This resulted in 1.1 g (56%) of ethyl 4,6-dimethyl-2-oxo-1,2-dihydropyrimidine-5-carboxylate as yellow oil. m/z: 197.14[MH$^+$], t$_R$=0.477 min (1.80 minute run).

3. Synthesis of ethyl 2-chloro-4,6-dimethylpyrimidine-5-carboxylate

Into a 100-mL round-bottom flask, was placed a solution of ethyl 4,6-dimethyl-2-oxo-1,2-dihydropyrimidine-5-carboxylate (300 mg, 1.53 mmol, 1.00 equiv) in phosphoroyl trichloride (10 mL), N,N-Diethylaniline (0.1 mL, 0.10 equiv). The resulting solution was stirred for 3 hours at 105° C. in an oil bath. The reaction was then quenched by the addition of water. The resulting solution was extracted with ethyl acetate and the organic layers combined and concentrated under vacuum. This resulted in 100 mg (30%) of ethyl 2-chloro-4,6-dimethylpyrimidine-5-carboxylate as a yellow solid. m/z: 214.85[MH$^+$], t$_R$=0.842 min (1.90 minute run).

4. Synthesis of ethyl 2-[4-[(tert-butoxy)carbonyl]piperazin-1-yl]-4,6-dimethylpyrimidine-5-carboxylate Into a 100-mL round-bottom flask, was placed a solution of ethyl 2-chloro-4,6-dimethylpyrimidine-5-carboxylate (100 mg, 0.47 mmol, 1.00 equiv) in tetrahydrofuran (20 mL), triethylamine (0.3 mL, 0.30 equiv), tert-butyl piperazine-1-carboxylate (104 mg, 0.56 mmol, 1.20 equiv). The resulting solution was stirred for 2 hours at room temperature. The resulting mixture was concentrated under vacuum. The residue was applied onto a silica gel column with ethyl acetate/petroleum ether (1:4). The collected fractions were combined and concentrated under vacuum. This resulted in 180 mg (94%) of ethyl 2-[4-[(tert-butoxy)carbonyl]piperazin-1-yl]-4,6-dimethylpyrimidine-5-carboxylate as a yellow solid. m/z: 365.13[MH$^+$], t$_R$=1.418 min (2.00 minute run).

5. Synthesis of 2-[4-[(tert-butoxy)carbonyl]piperazin-1-yl]-4,6-dimethylpyrimidine-5-carboxylic acid Into a 100-mL round-bottom flask, was placed a solution of ethyl 2-[4-[(tert-butoxy)carbonyl]piperazin-1-yl]-4,6-dimethylpyrimidine-5-carboxylate (170 mg, 0.47 mmol, 1.00 equiv) in methanol/water (50/10 mL), sodium hydroxide (93 mg, 2.33 mmol, 5.00 equiv). The resulting solution was stirred for 12 hours at 50° C. in an oil bath. The resulting mixture was concentrated under vacuum. The pH value of the solution was adjusted to 5-6 with hydrogen chloride (1 mol/L). The resulting solution was extracted with ethyl acetate and the organic layers combined. The residue was applied onto a silica gel column with dichloromethane/methanol (4:1). The collected fractions were combined and concentrated under vacuum. This resulted in 150 mg (89%) of 2-[4-[(tert-butoxy)carbonyl]piperazin-1-yl]-4,6-dimethylpyrimidine-5-carboxylic acid as a white solid. m/z 337.24 [MH$^+$], t$_R$=1.106 min (2.00 minute run).

6. Synthesis of tert-butyl 4-(4,6-dimethyl-5-[[(1r,3r)-3-(3-chloro-4-cyanophenoxy)-2,2,4,4-tetramethylcyclobutyl]carbamoyl]pyrimidin-2-yl)piperazine-1-carboxylate Into a 100-mL round-bottom flask, was placed a solution of 2-[4-[(tert-butoxy)carbonyl]piperazin-1-yl]-4,6-dimethylpyrimidine-5-carboxylic acid (130 mg, 0.39 mmol, 1.00 equiv) in N,N-dimethylformamide (30 mL), N,N,N',N'-Tetramethyl-O-(7-azabenzotriazol-1-yl)uronium hexafluorophosphate (220 mg, 1.50 equiv), N,N-Diisopropylethylamine (0.3 mL, 0.30 equiv), 2-chloro-4-[(1r,3r)-3-amino-2,2,4,4-tetramethylcyclobutoxy]benzonitrile hydrochloride (129 mg, 0.41 mmol, 1.20 equiv). The resulting solution was stirred for 30 minutes at room temperature. The resulting solution was extracted with ethyl acetate and the organic layers combined. The resulting mixture was washed with of brine. The mixture was dried over anhydrous sodium sulfate and concentrated under vacuum. The residue was applied onto a silica gel column with ethyl acetate (100%). The collected fractions were combined and concentrated under vacuum. This resulted in 150 mg (63%) of tert-butyl 4-(4,6-dimethyl-5-[[(1r,3r)-3-(3-chloro-4-cyanophenoxy)-2,2,4,4-tetramethylcyclobutyl]carbamoyl]pyrimidin-2-yl)piperazine-1-carboxylate as a yellow solid. m/z 597.13[MH⁺], $t_R$=1.428 min (2.00 minute run).

7. Synthesis of 4,6-dimethyl-2-(piperazin-1-yl)-N-[(1r,3r)-3-(3-chloro-4-cyanophenoxy)-2,2,4,4-tetramethylcyclobutyl]pyrimidine-5-carboxamide hydrochloride Into a 100-mL round-bottom flask, was placed tert-butyl 4-(4,6-dimethyl-5-[[(1r,3r)-3-(3-chloro-4-cyanophenoxy)-2,2,4,4-tetramethylcyclobutyl]carbamoyl]pyrimidin-2-yl)piperazine-1-carboxylate (140 mg, 0.23 mmol, 1.00 equiv), dioxane/HCl (20 mL, 3.00 equiv). The resulting solution was stirred for 2 hours at room temperature. The resulting mixture was concentrated under vacuum. This resulted in 160 mg (122%) of 4,6-dimethyl-2-(piperazin-1-yl)-N-[(1r,3r)-3-(3-chloro-4-cyanophenoxy)-2,2,4,4-tetramethylcyclobutyl]pyrimidine-5-carboxamide hydrochloride as a yellow solid. m/z: 497.22[MH⁺], $t_R$=1.046 min (2.00 minute run).

8. Synthesis of 2-[4-(3-[[2-(2,6-dioxopiperidin-3-yl)-1,3-dioxo-2,3-dihydro-1H-isoindol-5-yl]oxy]propyl)piperazin-1-yl]-4,6-dimethyl-N-[(1r,3r)-3-(3-chloro-4-cyanophenoxy)-2,2,4,4-tetramethylcyclobutyl]pyrimidine-5-carboxamide Into a 25-mL sealed tube, was placed a solution of 4,6-dimethyl-2-(piperazin-1-yl)-N-[(1r,3r)-3-(3-chloro-4-cyanophenoxy)-2,2,4,4-tetramethylcyclobutyl]pyrimidine-5-carboxamide hydrochloride (140 mg, 0.26 mmol, 1.00 equiv) in acetonitrile (10 mL), potassium carbonate (181 mg, 1.31 mmol, 5.00 equiv), Sodium iodide (51 mg, 1.50 equiv), 5-(3-bromopropoxy)-2-(2,6-dioxopiperidin-3-yl)-2,3-dihydro-1H-isoindole-1,3-dione (125 mg, 0.32 mmol, 1.20 equiv). The resulting solution was stirred for 12 hours at 70° C. in an oil bath. The resulting solution was diluted with 20 mL of acetonitrile. The resulting mixture was concentrated under vacuum. The crude product (50 mL) was purified by Prep-HPLC with the following conditions: Mobile Phase A: Water (0.1% Formic acid), Mobile Phase B: acetonitrile; Flow rate: 20 mL/min; Gradient: 30% B to 48% B in 8 min; 254 nm; Rt: 7.83 min. This resulted in 51 mg (28%) of 2-[4-(3-[[2-(2,6-dioxopiperidin-3-yl)-1,3-dioxo-2,3-dihydro-1H-isoindol-5-yl]oxy]propyl)piperazin-1-yl]-4,6-dimethyl-N-[(1r,3r)-3-(3-chloro-4-cyanophenoxy)-2,2,4,4-tetramethylcyclobutyl]pyrimidine-5-carboxamide as a off-white solid.

1H NMR (300 MHz, CDCL3) δ 8.29 (s, 1H), 7.81 (d, J=8.3 Hz, 1H), 7.60 (d, J=8.6 Hz, 1H), 7.36 (d, J=2.2 Hz, 1H), 7.22 (dd, J=8.3, 2.3 Hz, 1H), 6.99 (d, J=2.4 Hz, 1H), 6.83 (dd, J=8.8, 2.4 Hz, 1H), 5.96 (d, J=8.6 Hz, 1H), 4.99 (dd, J=11.9, 5.5 Hz, 1H), 4.24 (dt, J=11.9, 7.0 Hz, 7H), 4.08 (s, 1H), 3.09 (s, 9H), 2.98-2.77 (m, 5H), 2.40 (s, 2H), 2.21-2.14 (m, 1H), 1.27 (d, J=3.9 Hz, 12H); LC-MS (ES⁺): m/z: 811.32 [MH⁺], $t_R$=6.278 min (10.00 minute run).

Chemical formula: $C_{42}H_{47}ClN_8O_7$[810.33].

Total H count from HNMR data: 46.

Synthetic Procedure for Compound 584

1. Synthesis of 5-bromo-3-methoxybenzene-1,2-dicarboxylic acid

Into a 100-mL round-bottom flask, was placed 4-bromo-2-methoxy-6-methylbenzonitrile (800 mg, 3.54 mmol, 1.00 equiv), water (10 mL), sodium hydroxide (708 mg, 17.70 mmol, 5.00 equiv), KMnO₄ (1.12 g, 7.09 mmol, 2.00 equiv). The resulting solution was stirred for 16 hours at 100° C. in an oil bath. The solids were filtered out. The pH value of the solution was adjusted to 3 with hydrogen chloride (2 mol/L). The resulting solution was extracted with dichloromethane (15 mL×3) and the aqueous layers combined. The resulting solution was extracted with ethyl acetate/methanol=10:1 (15 mL×3) and the organic layers combined and dried in an oven under reduced pressure, concentrated under vacuum. This resulted in 330 mg (34%) of 5-bromo-3-methoxybenzene-1,2-dicarboxylic acid as a white solid.

2. Synthesis of 1,2-dimethyl 5-bromo-3-methoxybenzene-1,2-dicarboxylate

Into a 100-mL round-bottom flask, was placed 5-bromo-3-methoxybenzene-1,2-dicarboxylic acid (330 mg, 1.20 mmol, 1.00 equiv), methanol (20 mL), sulfuric acid (5 mL). The resulting solution was stirred for 16 hours at 70° C. in an oil bath. The resulting solution was diluted with water (40 mL). The pH value of the solution was adjusted to 8 with sodium carbonate. The resulting solution was extracted with ethyl acetate (30 mL×3) and the organic layers combined and dried over anhydrous sodium sulfate and concentrated under vacuum. The residue was applied onto a silica gel column with ethyl acetate/petroleum ether (1:10). This resulted in 340 mg (93%) of 1,2-dimethyl 5-bromo-3-methoxybenzene-1,2-dicarboxylate as a white solid.

LC-MS (ES+): m/z 302.85 [MH+], $t_R$=0.906 min (2.0 minute run).

3. Synthesis of 1,2-dimethyl 5-[4-[(tert-butoxy)carbonyl]piperazin-1-yl]-3-methoxybenzene-1,2-dicarboxylate Into a 100-mL round-bottom flask, was placed 1,2-dimethyl 5-bromo-3-methoxybenzene-1,2-dicarboxylate (300 mg, 0.99 mmol, 1.00 equiv), tert-butyl piperazine-1-carboxylate (277 mg, 1.49 mmol, 1.50 equiv), RouphosPd (39 mg, 0.05 mmol, 0.05 equiv), Cs₂CO₃ (978 mg, 3.00 mmol, 3.00 equiv), toluene (15 mL). The resulting solution was stirred for 12 hours at 100° C. in an oil bath. The resulting solution was diluted with water (30 mL). The resulting solution was extracted with ethyl acetate (30 mL×3) and the organic layers combined and dried over anhydrous sodium sulfate and concentrated under vacuum. The residue was applied onto a silica gel column with dichloromethane/ethyl acetate (10:1). This resulted in 340 mg (84%) of 1,2-dimethyl 5-[4-[(tert-butoxy)carbonyl]piperazin-1-yl]-3-methoxybenzene-1,2-dicarboxylate as light yellow oil.

LC-MS (ES+): m/z 409.05 [MH+], $t_R$=0.963 min (2.0 minute run).

4. Synthesis of 5-[4-[(tert-butoxy)carbonyl]piperazin-1-yl]-3-methoxybenzene-1,2-dicarboxylic acid Into a 100-mL round-bottom flask, was placed 1,2-dimethyl 5-[4-[(tert-butoxy)carbonyl]piperazin-1-yl]-3-methoxybenzene-1,2-dicarboxylate (340 mg, 0.83 mmol, 1.00 equiv), methanol/H₂O/THF (8 mL), sodiumol (100 mg, 2.50 mmol, 3.00 equiv). The resulting solution was stirred for 12 hours at 25° C. The resulting solution was diluted with water (30 mL). The pH value of the solution was adjusted to 8 with hydrogen chloride (2 mol/L). citric acid monohydrate was employed to adjust the pH to 3. The resulting solution was extracted with ethyl acetate (30 mL×3) and the organic layers combined and dried over anhydrous sodium sulfate and concentrated under vacuum. This resulted in 300 mg (95%) of 5-[4-[(tert-butoxy)carbonyl]piperazin-1-yl]-3-methoxybenzene-1,2-dicarboxylic acid as colorless oil.

LC-MS (ES+): m/z 306.95 [MH+], $t_R$=0.853 min (2.0 minute run).

5. Synthesis of tert-butyl 4-[2-(2,6-dioxopiperidin-3-yl)-7-methoxy-1,3-dioxo-2,3-dihydro-1H-isoindol-5-yl]piperazine-1-carboxylate Into a 100-mL round-bottom flask, was placed tert-butyl 4-(7-methoxy-1,3-dioxo-1,3-dihydro-2-benzofuran-5-yl)piperazine-1-carboxylate (260 mg, 0.72 mmol, 1.00 equiv), 3-aminopiperidine-2,6-dione hydrochloride (153.6 mg, 0.93 mmol, 1.30 equiv), pyridine (10 mL). The resulting solution was stirred for 4 hours at 120° C. in an oil bath. The resulting solution was diluted with water (30 mL). The resulting solution was extracted with ethyl acetate (30 mL×3) and the organic layers combined and dried over anhydrous sodium sulfate and concentrated under vacuum. The residue was applied onto a silica gel column with dichloromethane/methanol (100:1). This resulted in 280 mg (83%) of tert-butyl 4-[2-(2,6-dioxopiperidin-3-yl)-7-methoxy-1,3-dioxo-2,3-dihydro-1H-isoindol-5-yl]piperazine-1-carboxylate as a yellow solid.

LC-MS (ES+): m/z 417.05 [MH+], $t_R$=0.852 min (2.0 minute run).

6. Synthesis of 2-(2,6-dioxopiperidin-3-yl)-4-methoxy-6-(piperazin-1-yl)isoindoline-1,3-dione Into a 50-mL round-bottom flask, was placed tert-butyl 4-[2-(2,6-dioxopiperidin-3-yl)-7-methoxy-1,3-dioxo-2,3-dihydro-1H-isoindol-5-yl]piperazine-1-carboxylate (270 mg, 0.57 mmol, 1 equiv), dichloromethane (6 mL, 0.07 mmol, 0.124 equiv), TFA (2 mL, 0.02 mmol, 0.031 equiv). The resulting solution was stirred for 2 hours at 25° C. The resulting mixture was concentrated to give 2-(2,6-dioxopiperidin-3-yl)-4-methoxy-6-(piperazin-1-yl)isoindoline-1,3-dione as a brown oil.

LC-MS (ES+): m/z 373.05 [MH+], $t_R$=0.155 min (2.0 minute run).

7. Synthesis of 6-[4-([4-[2-(2,6-dioxopiperidin-3-yl)-7-methoxy-1,3-dioxo-2,3-dihydro-1H-isoindol-5-yl]piperazin-1-yl]methyl)piperidin-1-yl]-N-[(1r,4r)-4-(3-chloro-4-cyanophenoxy)cyclohexyl]pyridazine-3-carboxamide Into a 100-mL round-bottom flask, was placed 2,2,2-trifluoroacetaldehyde; 2-(2,6-dioxopiperidin-3-yl)-4-methoxy-6-(piperazin-1-yl)-2,3-dihydro-1H-isoindole-1,3-dione (130 mg, 0.28 mmol, 1.078 equiv), dichloromethane (10 mL, 0.12 mmol), 6-(4-formylpiperidin-1-yl)-N-[(1r,4r)-4-(3-chloro-4-cyanophenoxy)cyclohexyl]pyridazine-3-carboxamide (120 mg, 0.26 mmol, 1 equiv), NaBH(OAc)$_3$ (163.4 mg, 0.77 mmol, 3.006 equiv). The resulting solution was stirred for 2 hours at 25° C. The resulting solution was diluted with dichloromethane (30 mL). The resulting mixture was washed with H$_2$O (30 mL×3). The mixture was dried over anhydrous sodium sulfate and concentrated under vacuum. The resulting mixture was concentrated under vacuum. The residue was applied onto a silica gel column with dichloromethane/ethyl acetate (3:1). The crude product was purified by Prep-HPLC with the following conditions: Column, XBridge Prep C18 OBD Column, 5 um, 19*150 mm; mobile phase, Water (10 mmol/L NH$_4$HCO$_3$) and acetonitrile (43% Phase B up to 65% in 8 min); Detector, uv. This resulted in 70 mg (33.11%) of 6-[4-([4-[2-(2,6-dioxopiperidin-3-yl)-7-methoxy-1,3-dioxo-2,3-dihydro-1H-isoindol-5-yl]piperazin-1-yl]methyl)piperidin-1-yl]-N-[(1r,4r)-4-(3-chloro-4-cyanophenoxy)cyclohexyl]pyridazine-3-carboxamide as a yellow solid.

$^1$H NMR (400 MHz, DMSO-d6) δ 11.04 (s, 1H), 8.57 (d, J=8.4 Hz, 1H), 7.87-7.79 (m, 2H), 7.39-7.32 (m, 2H), 7.15-7.12 (m, 1H), 6.96 (s, 1H), 6.68 (s, 1H), 5.04-4.98 (m, 1H), 4.50-4.47 (m, 3H), 4.93-3.85 (m, 4H), 3.35-3.33 (m, 5H), 3.07-2.81 (m, 3H), 2.51 (s, 3H), 2.27-22.1 (m, 2H), 2.09-2.01 (m, 2H), 2.00-1.49 (m, 11H), 1.23-1.11 (m, 3H); LC-MS (ES+): m/z 824.25/826.25 [MH+], $t_R$=182 min (3.0 minute run).

Chemical Formula: $C_{42}H_{46}ClN_9O_7$[823.32/825.32].

Total H count from HNMR data: 46.

Synthetic Procedure for Compound 618

1. Synthesis of N-(2,2-dimethoxyethyl)-3,4-dihydro-2H-pyrrol-5-amine

Into a 250-mL round-bottom flask, was placed 5-methoxy-3,4-dihydro-2H-pyrrole (4.4 g, 1 equiv), MeOH (50 mL), 2,2-dimethoxyethan-1-amine (4.6 g). The resulting solution was stirred for 12 hours at 60° C. in an oil bath. The resulting mixture was concentrated under vacuum. This resulted in 5.7 g of N-(2,2-dimethoxyethyl)-3,4-dihydro-2H-pyrrol-5-amine as brown oil.

LC-MS (ES$^+$): m/z 173.00[MH$^+$], $t_R$=0.17 min (1.9 minute run).

2. Synthesis of 5H,6H,7H-pyrrolo[1,2-a]imidazole

Into a 250-mL round-bottom flask, was placed N-(2,2-dimethoxyethyl)-3,4-dihydro-2H-pyrrol-5-amine (5.72 g, 33.21 mmol, 1 equiv), formic acid (100 mL). The resulting solution was stirred for 16 hours at 100° C. in an oil bath. The resulting mixture was concentrated under vacuum. This resulted in 3.1 g (86.31%) of 5H,6H,7H-pyrrolo[1,2-a]imidazole as a brown solid.

LC-MS (ES$^+$): m/z 108.95[MH$^+$], $t_R$=0.15 min (1.9 minute run).

3. Synthesis of [5H,6H,7H-pyrrolo[1,2-a]imidazol-3-yl]boronic acid

Into a 100-mL round-bottom flask purged and maintained with an inert atmosphere of nitrogen, was placed 5H,6H,7H-pyrrolo[1,2-a]imidazole (1.0 g, 9.25 mmol, 1 equiv). This was followed by the addition of THF (20 mL, 246.86 mmol, 26.696 equiv). The resulting solution was turned to −78° C. To this was added n-BuLi (10 mL, 106.16 mmol, 11.480 equiv). The resulting solution was stirred for 10 minutes at −78° C. To the mixture was added B(Oi-Pr)$_3$ (5.0 g, 26.59 mmol, 2.875 equiv). The resulting solution was stirred for 6 hours at room temperature. The PH was adjusted to 2 with 2 M HCL. The resulting mixture was concentrated under vacuum. This resulted in 2.1 g (crude) of [5H,6H,7H-pyrrolo[1,2-a]imidazol-3-yl]boronic acid as a brown solid.

LC-MS (ES$^+$): m/z 512.4 [MH$^+$], $t_R$=1.27 min (1.9 minute run).

4. Synthesis of tert-butyl 4-[[1-(4-nitrophenyl)piperidin-4-yl]methyl]piperazine-1-carboxylate Into a 250-mL round-bottom flask, was placed a solution of 1-fluoro-4-nitrobenzene (3 g, 21.26 mmol, 1.00 equiv) in DMSO (80 mL). This was followed by the addition of DIEA (2.7 g, 20.89 mmol, 1.00 equiv) in several batches in 2 minutes. To this was added tert-butyl 4-(piperidin-4-ylmethyl)piperazine-1-carboxylate (6 g, 21.17 mmol, 1.00 equiv). The resulting solution was stirred for 6 hours at 100° C. in an oil bath. The reaction was then quenched by the addition of water (100 mL). The resulting solution was extracted with ethyl acetate (100 mL×2) and the organic layers combined. The resulting mixture was washed with brine (30 mL×2). The resulting solution was concentrated under vacuum. The residue was applied onto a silica gel column with ethyl acetate/petroleum ether (1:1). This resulted in 8.0 g (93%) of tert-butyl 4-[[1-(4-nitrophenyl)piperidin-4-yl]methyl]piperazine-1-carboxylate as a light yellow solid.

LC-MS (ES$^+$): m/z 405.10 [MH$^+$], $t_R$=0.65 min (1.9 minute run).

5. Synthesis of tert-butyl 4-[[1-(4-aminophenyl)piperidin-4-yl]methyl]piperazine-1-carboxylate Into a 250-mL round-bottom flask, was placed a solution of tert-butyl 4-[[1-(4-nitrophenyl)piperidin-4-yl]methyl]piperazine-1-carboxylate (4.8 g, 11.87 mmol, 1.00 equiv) in methanol (60 mL) under nitrogen atmosphere. This was followed by the addition of Pd/C (0.96 g, 0.20 equiv). The flask was then vacuumed and flushed with hydrogen. The reaction mixture was hydrogenated at room temperature for 3 hours under hydrogen atmosphere using a hydrogen balloon, then filtered through a Celite pad and concentrated under reduced pressure. This resulted in 2.7 g (61%) of tert-butyl 4-[[1-(4-aminophenyl)piperidin-4-yl]methyl]piperazine-1-carboxylate as a light yellow solid.

LC-MS (ES$^+$): m/z 375.10 [MH$^+$], $t_R$=0.73 min (2.0 minute run).

6. Synthesis of tert-butyl 4-[[1-(4-bromophenyl)piperidin-4-yl]methyl]piperazine-1-carboxylate Into a 250-mL round-bottom flask purged and maintained with an inert atmosphere of nitrogen, was placed tert-butyl 4-[[1-(4-aminophenyl)piperidin-4-yl]methyl]piperazine-1-carboxylate (2.0 g), acetonitrile (100 mg). This was followed by the addition of tert-butyl nitrite (770 mg). It was stirred for 30 minutes. To this was added dibromocopper (1.4 g). The resulting solution was stirred for 3 hours at 0° C. in a water/ice bath. The residue was applied onto a silica gel column with ethyl acetate/petroleum ether (0:100-1:2). This resulted in 320 mg of tert-butyl 4-[[1-(4-bromophenyl)piperidin-4-yl]methyl]piperazine-1-carboxylate as a white solid.

LC-MS (ES$^+$): m/z 438.15 [MH$^+$], $t_R$=0.69 min (1.9 minute run).

7. Synthesis of tert-butyl 4-([1-[4-(1,2-dimethyl-1H-imidazol-5-yl)phenyl]piperidin-4-yl]methyl)piperazine-1-carboxylate Into a 25-mL sealed tube purged and maintained with an inert atmosphere of nitrogen, was placed tert-butyl 4-[[1-(4-bromophenyl)piperidin-4-yl]methyl]piperazine-1-carboxylate (230 mg), [5H,6H,7H-pyrrolo[1,2-a]imidazol-3-yl]boronic acid (1.0 g), dioxane/H$_2$O (8 mL/2 mL), Na$_2$CO$_3$ (170 mg), Pd(dppf)Cl$_2$ (50 mg). The resulting solution was stirred for 3 hours at 90° C. in an oil bath. The residue was applied onto a silica gel column with dichloromethane/methanol (10:1). This resulted in 150 mg of tert-butyl 4-([1-[4-(1,2-dimethyl-1H-imidazol-5-yl)phenyl]piperidin-4-yl]methyl)piperazine-1-carboxylate as brown oil.

LC-MS (ES$^+$): m/z 466.30 [MH$^+$], $t_R$=0.61 min (1.9 minute run).

8. Synthesis of 1-[[1-(4-[5H,6H,7H-pyrrolo[1,2-a]imidazol-3-yl]phenyl)piperidin-4-yl]methyl]piperazine Into a 100-mL round-bottom flask, was placed tert-butyl 4-[[1-(4-[5H,6H,7H-pyrrolo[1,2-a]imidazol-3-yl]phenyl)piperidin-4-yl]methyl]piperazine-1-carboxylate (100 mg, 0.21 mmol, 1 equiv), trifluoroacetyl (4 mL), dichloromethane (20 mL). The resulting solution was stirred for 4 hours at room temperature. The resulting mixture was concentrated under reduced pressure. This resulted in 80 mg (90.91%) of 1-[[1-(4-[5H,6H,7H-pyrrolo[1,2-a]imidazol-3-yl]phenyl)piperidin-4-yl]methyl]piperazine as brown oil.

LC-MS (ES$^+$): m/z 366.00 [MH$^+$], $t_R$=0.63 min (2.0 minute run).

9. Synthesis of 2-(2,6-dioxopiperidin-3-yl)-5-(4-[[1-(4-[5H,6H,7H-pyrrolo[1,2-a]imidazol-3-yl]phenyl)piperidin-4-yl]methyl]piperazin-1-yl)-2,3-dihydro-1H-isoindole-1,3-dione Into a 25-mL sealed tube purged and maintained with an inert atmosphere of nitrogen, was placed 1-[[1-(4-[5H,6H,7H-pyrrolo[1,2-a]imidazol-3-yl]phenyl)piperidin-4-yl]methyl]piperazine (100 mg, 0.27 mmol, 1 equiv), DMSO (5 mL), DIEA (1.5 m), 2-(2,6-dioxopiperidin-3-yl)-5-fluoro-2,3-dihydro-1H-isoindole-1,3-dione (80 mg, 0.29 mmol, 1.059 equiv). The resulting solution was stirred for 3 hours at 130° C. in an oil bath. The resulting solution was extracted with ethyl acetate (30 mL×3). The resulting mixture was washed with brine (30 mL×1). The resulting mixture was concentrated under reduced pressure. The crude product was purified by Prep-HPLC with the following conditions: Column, XB ridge Prep C18 OBD Column, 5 um, 19*150 mm; mobile phase, Water (10 mmol/L NH$_4$HCO$_3$) and acetonitrile (38% Phase B up to 55% in 8 min); Detector, UV. This resulted in 30.6 mg (17.99%) of 2-(2,6-dioxopiperidin-3-yl)-5-(4-[[1-(4-[5H,6H,7H-pyrrolo[1,2-a]imidazol-3-yl]phenyl)piperidin-4-yl]methyl]piperazin-1-yl)-2,3-dihydro-1H-isoindole-1,3-dione as a yellow solid.

$^1$H NMR (300 MHz, DMSO-d$_6$) δ 11.07 (s, 1H), 7.67 (d, J=8.5 Hz, 1H), 7.37-7.25 (m, 4H), 7.04-6.89 (m, 3H), 5.06 (dd, J=12.7, 5.4 Hz, 1H), 4.09 (t, J=7.0 Hz, 2H), 3.70 (d, J=12.2 Hz, 2H), 3.43-3.41 (m, 5H), 2.90-2.49 (m, 12H), 2.20-2.10 (m, 2H), 2.00-1.90 (m, 1H), 1.80-1.73 (m, 3H), 1.21-1.17 (m, 2H); LC-MS (ES$^+$): m/z 622.35 [M+H$^+$], $t_R$=0.68 min, (2.90 minute run).

Chemical Formula: C$_{35}$H$_{39}$N$_7$O$_4$ [621.31].

Total H count from HNMR data: 39.

Synthetic Procedure for Compound 77

Step 1: [6-(4-(tert-butoxycarbonyl)piperazin-1-yl)nicotinic acid]

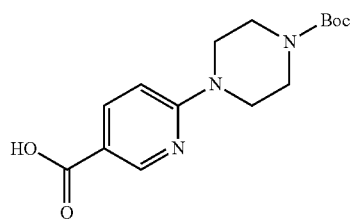 [SMILES: CC(C)(C)OC(=O)N1CCN(c2ccc(C(=O)O)cn2)CC1]

A mixture of tert-butyl 4-(5-((benzyloxy)carbonyl)pyridin-2-yl)piperazine-1-carboxylate (2.0 g, 5.03 mmol) and palladium on carbon (10%, 200 mg) in ethanol (20 ml) was stirred at 30° C. overnight under hydrogen atmosphere (hydrogen balloon). TLC showed the reaction was complete. Palladium on carbon was removed through filtration and washed with ethanol (20 ml×2). The combined filtrates were concentrated under reduced pressure to give 6-(4-(tert-butoxycarbonyl)piperazin-1-yl)nicotinic acid (1.6 g, crude) as colorless oil which was used in next step without purification.

Step 2: [tert-butyl 4-(5-(((1r,3r)-3-(3-chloro-4-cyanophenoxy)-2,2,4,4-tetramethylcyclobutyl)carbamoyl)pyridin-2-yl)piperazine-1-carboxylate]

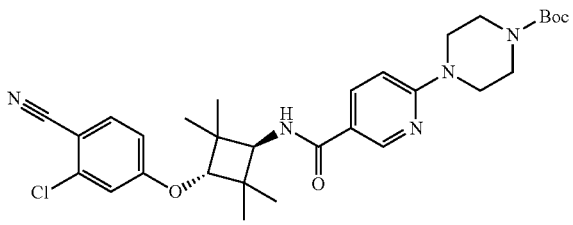 [SMILES: CC(C)(C)OC(=O)N1CCN(c2ccc(C(=O)N[C@H]3C(C)(C)[C@H](Oc4ccc(C#N)c(Cl)c4)C3(C)C)cn2)CC1]

To a stirred solution of 6-(4-(tert-butoxycarbonyl)piperazin-1-yl)nicotinic acid (300 mg, 0.97 mmol), 4-((1r,3r)-3-amino-2,2,4,4-tetramethylcyclobutoxy)-2-chlorobenzonitrile hydrochloride (306 mg, 0.97 mmol), and N-ethyl-N-isopropylpropan-2-amine (309 mg, 2.4 mmol) in anhydrous N,N-dimethylformamide (8 ml) was added HATU (2-(7-Aza-1H-benzotriazole-1-yl)-1,1,3,3-tetramethyluronium hexafluorophosphate) (684 mg, 1.8 mmol) at 0° C., the resulting mixture was allowed to warm to room temperature and stirred for 20 minutes. TLC showed the reaction was complete. The mixture was partitioned between ethyl acetate (50 ml) and water (80 ml). The organic layer was collected, washed with brine (10 ml), dried over anhydrous sodium sulfate, and concentrated under reduced pressure to give a crude residue which was purified by silica gel flash chromatography (eluted with 10% methanol in dichloromethane) to afford tert-butyl 4-(5-(((1r,3r)-3-(3-chloro-4-cyanophenoxy)-2,2,4,4-tetramethylcyclobutyl)carbamoyl)pyridin-2-yl)piperazine-1-carboxylate (400 mg, yield 72%) as white solid.

Step 3 [N-((1r,3r)-3-(3-chloro-4-cyanophenoxy)-2,2,4,4-tetramethylcyclobutyl)-6-(piperazin-1-yl)nicotinamide]

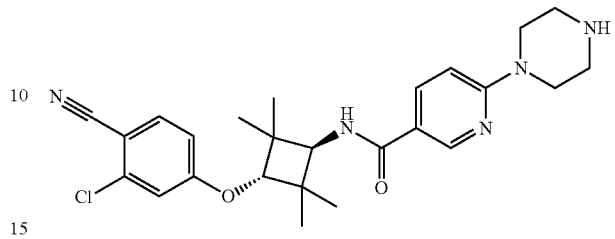

A mixture of tert-butyl 4-(5-(((1r,3r)-3-(3-chloro-4-cyanophenoxy)-2,2,4,4-tetramethylcyclobutyl)carbamoyl)pyridin-2-yl)piperazine-1-carboxylate (80 mg, 0.14 mmol) in hydrogen chloride in dioxane solution (4M, 2 ml) was stirred at room temperature for 2 hours. TLC showed the reaction was complete. The volatiles were evaporated under reduced pressure. The residue was taken up in dichloromethane (20 ml) and washed with aqueous sodium bicarbonate solution (1N, 5 ml), dried over anhydrous sodium sulfate, and concentrated under reduced pressure to give a crude residue which was purified by pre-TLC (eluted with 10% methanol in dichloromethane) to afford [N-((1r,3r)-3-(3-chloro-4-cyanophenoxy)-2,2,4,4-tetramethylcyclobutyl)-6-(piperazin-1-yl)nicotinamide (32 mg, yield 50%) as white solid.

LC_MS: (ES$^+$): m/z 468.6 [M+H]$^+$. $t_R$=2.285 min.
$^1$HNMR (400 MHz, CD$_3$OD): δ 1.07-1.38 (m, 12H), 3.12-3.40 (m, 4H), 3.51-3.86 (m, 1H), 3.94 (br, 3H), 4.17-4.30 (m, 2H), 6.99-7.15 (m, 2H), 7.74 (s, 1H), 8.05 (s, 1H), 8.48-8.68 (m, 2H).
Chemical Formula: C$_{25}$H$_{30}$ClN$_5$O$_2$; Molecular Weight: 467.99.
Total H count from HNMR data: 28.

Step 4: [2-(2,6-dioxopiperidin-3-yl)-5-(4-(2-hydroxyethyl)piperazin-1-yl)isoindoline-1,3-dione]

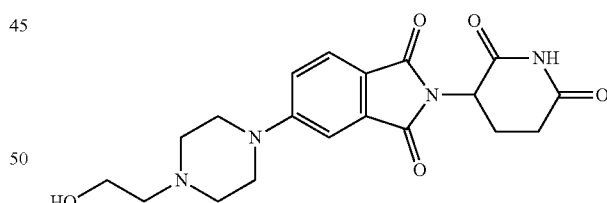

A mixture of 2-(piperazin-1-yl)ethanol (235.6 mg, 1.8 mmol), 2-(2,6-dioxopiperidin-3-yl)-5-fluoroisoindoline-1,3-dione (500 mg, 1.8 mmol) and N-ethyl-N-isopropylpropan-2-amine (468 mg, 3.6 mmol) in 1-methylpyrrolidin-2-one (5 ml) was stirred at 90° C. for 12 hours. TLC showed the reaction was complete. The reaction mixture was partitioned between ethyl acetate (30 ml) and water (50 ml). The organic layer was collected, washed with brine (20 ml), dried over anhydrous sodium sulfate, and concentrated under reduced pressure to give a crude residue which was purified by silica gel flash chromatography (eluted with 2-3% methanol in dichloromethane) to afford 2-(2,6-dioxopiperidin-3-yl)-5-(4-(2-hydroxyethyl)piperazin-1-yl)isoindoline-1,3-dione (370 mg, 62%) as yellow oil.

Step 2: [2-(4-(2-(2,6-dioxopiperidin-3-yl)-1,3-di-oxoisoindolin-5-yl)piperazin-1-yl)ethyl 4-methyl-benzenesulfonate]

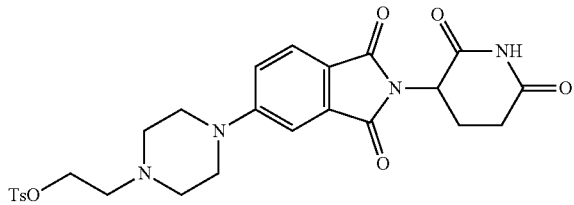 [SMILES: Cc1ccc(S(=O)(=O)OCCN2CCN(c3ccc4c(c3)C(=O)N(C3CCC(=O)NC3=O)C4=O)CC2)cc1]

To a solution of 2-(2,6-dioxopiperidin-3-yl)-5-(4-(2-hydroxyethyl)piperazin-1-yl)isoindoline-1,3-dione (370 mg, 0.96 mmol), N,N-dimethylpyridin-4-amine (12 mg, 0.1 mmol) and triethylamine (291 mg, 2.87 mmol) in dichloromethane (10 ml) was added 4-toluenesulfonyl chloride (201 mg, 1.05 mmol) at 0° C. The reaction mixture was allowed to warm up to room temperature and stirred at room temperature overnight. TLC showed the reaction was complete. The reaction mixture was diluted with dichloromethane (10 ml), washed with water (10 ml×2) then brine (10 ml), dried over anhydrous sodium sulfate and concentrated under reduced pressure to give 2-(4-(2-(2,6-dioxopiperidin-3-yl)-1,3-dioxoisoindolin-5-yl)piperazin-1-yl)ethyl 4-methylbenzenesulfonate (200 mg, 38%) as yellow solid which was used in next step without further purification.

LC_MS: (ES$^+$): m/z 541.20 [M+H]$^+$. $t_R$=1.965 min.

Step 3: [N-((1r,3r)-3-(3-chloro-4-cyanophenoxy)-2,2,4,4-tetramethylcyclobutyl)-6-(4-(2-(4-(2-(2,6-di-oxopiperidin-3-yl)-1,3-dioxoisoindolin-5-yl)piper-azin-1-yl)ethyl)piperazin-1-yl)nicotinamide]

A mixture of 2-(4-(2-(2,6-dioxopiperidin-3-yl)-1,3-di-oxoisoindolin-5-yl)piperazin-1-yl)ethyl 4-methylbenzenesulfonate (139 mg, 0.25 mmol), N-ethyl-N-isopropylpropan-2-amine (55.3 mg, 0.43 mmol) and N-((1r,3r)-3-(3-chloro-4-cyanophenoxy)-2,2,4,4-tetramethylcyclobutyl)-6-(piperazin-1-yl)nicotinamide (100 mg, 0.21 mmol) in dry N,N-dimethylformamide (2 ml) was stirred at 50° C. for 16 hours. TLC showed the reaction was complete. The mixture was partitioned between ethyl acetate (20 ml) and water (20 ml). The organic layer was collected, washed with brine (10 ml), dried over anhydrous sodium sulfate, and concentrated under reduced pressure to give a crude residue which was purified by pre-TLC (eluted with 10% methanol in dichloromethane) to afford N-((1r,3r)-3-(3-chloro-4-cyanophenoxy)-2,2,4,4-tetramethylcyclobutyl)-6-(4-(2-(4-(2-(2,6-di-oxopiperidin-3-yl)-1,3-dioxoisoindolin-5-yl)piperazin-1-yl)ethyl)piperazin-1-yl)nicotinamide (40 mg, 18%) as yellow solid.

$^1$H NMR (400 MHz, 66-DMSO): δ 1.12 (s, 6H), 1.22 (s, 6H), 1.99-2.05 (m, 1H), 2.54-2.73 (m, 12H), 2.84-2.92 (m, 1H), 3.41-3.70 (m, 10H), 4.06 (d, J=9.2 Hz, 1H), 4.30 (s, 1H), 5.05-5.10 (m, 1H), 6.89 (d, J=9.2 Hz, 1H), 6.99-7.02 (m, 1H), 7.21 (d, J=2.4 Hz, 1H), 7.25-7.30 (m, 1H), 7.37 (br, 1H), 7.63 (d, J=9.2 Hz, 1H), 7.69 (d, J=8.4 Hz, 1H), 7.90 (d, J=8.4 Hz, 1H), 7.96-7.99 (m, 1H), 8.63 (d, J=2.0 Hz, 1H), 11.08 (s, 1H).

Chemical Formula: $C_{44}H_{50}ClN_9O_6$; Molecular Weight: 836.38.

Total H count from HNMR data: 50.

LC_MS: (ES$^+$): m/z 836.40 [M+H]$^+$. $t_R$=2.408 min.

Synthetic Procedure for Compound 383

Synthesis of tert-butyl 4-[(4-bromo-2-fluorophenyl)carbonyl]piperazine-1-carboxylate Into a 100.0-mL round-bottom flask, was placed 4-bromo-2-fluorobenzoic acid (5.0 g, 22.83 mmol, 1.00 equiv), N,N-dimethylformamide (20.0 mL), HATU (10.5 g, 27.61 mmol, 1.20 equiv), DIEA (11.9 g, 92.08 mmol, 4.00 equiv), tert-butyl piperazine-1-carboxylate (4.3 g, 23.09 mmol, 1.00 equiv). The resulting solution was stirred overnight at room temperature. The reaction was then quenched by the addition of 20.0 mL of water. The resulting solution was extracted with ethyl acetate (40.0 mL) and the organic layers combined. The resulting mixture was washed with sodium chloride (40.0 mL). The mixture was dried over anhydrous sodium sulfate. The residue was applied onto a silica gel column with ethyl acetate/petroleum ether (1/4). The collected fractions were combined and concentrated under vacuum. This resulted in 8.82 g (100%) of tert-butyl 4-[(4-bromo-2-fluorophenyl)carbonyl]piperazine-1-carboxylate as a yellow solid.

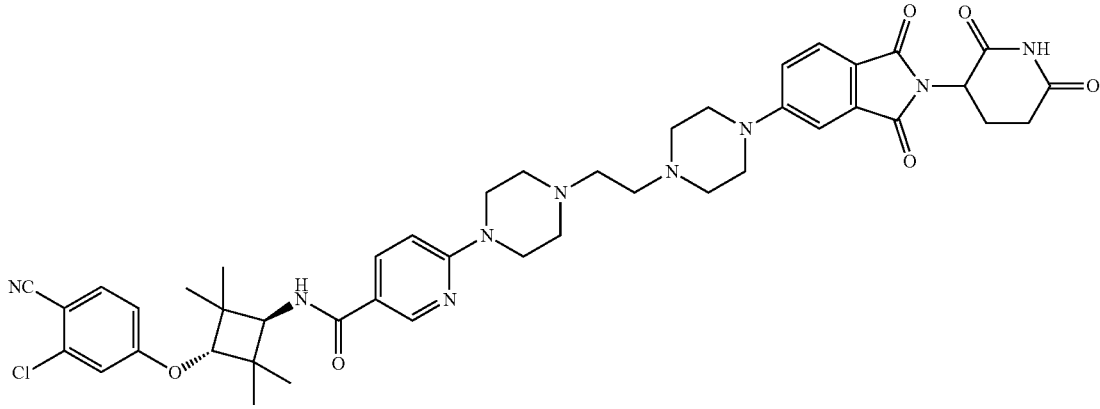 [SMILES: CC1(C)[C@H](NC(=O)c2ccc(N3CCN(CCN4CCN(c5ccc6c(c5)C(=O)N(C5CCC(=O)NC5=O)C6=O)CC4)CC3)nc2)C(C)(C)[C@H]1Oc1ccc(C#N)c(Cl)c1]

2. Synthesis of 2-[[4-([4-[(tert-butoxy)carbonyl]piperazin-1-yl]carbonyl)-3-fluorophenyl]amino]-2-methylpropanoic acid Into a 100.0-mL round-bottom flask, was placed tert-butyl 4-[(4-bromo-2-fluorophenyl)carbonyl]piperazine-1-carboxylate (4.0 g, 10.33 mmol, 1.00 equiv), N,N-dimethylformamide (10.0 mL), potassium carbonate (3.58 g, 25.90 mmol, 2.50 equiv), CuI (393.8 mg, 2.07 mmol, 0.20 equiv), 2-acetylcyclohexan-1-one (261.0 mg, 1.86 mmol, 0.20 equiv), 2-amino-2-methylpropanoic acid (1.6 g, 15.52 mmol, 1.50 equiv). The resulting solution was stirred overnight at 105.0° C. in an oil bath. The reaction was then quenched by the addition of 20.0 mL of water. The resulting solution was extracted with ethyl acetate (40.0 mL) and the organic layers combined. The pH value of the solution was adjusted to 8 with hydrogen chloride (1.0 mol/L). The resulting solution was extracted with ethyl acetate (40.0 mL) and the organic layers combined and dried over anhydrous sodium sulfate and concentrated under vacuum. This resulted in 3.9 g (92%) of 2-[[4-([4-[(tert-butoxy)carbonyl]piperazin-1-yl]carbonyl)-3-fluorophenyl]amino]-2-methylpropanoic acid as a yellow solid.

LC-MS (ES$^+$): m/z 410.2 [MH$^+$], t$_R$=1.049 min, (2.0 minute run).

Chemical formula: $C_{20}H_{28}FN_3O_5$ [409.20].

3. Synthesis of tert-butyl 4-([2-fluoro-4-[(1-methoxy-2-methyl-1-oxopropan-2-yl)amino]phenyl]carbonyl)piperazine-1-carboxylate Into a 250.0-mL round-bottom flask, was placed 2-[[4-([4-[(tert-butoxy)carbonyl]piperazin-1-yl]carbonyl)-3-fluorophenyl]amino]-2-methylpropanoic acid (2.7 g, 6.59 mmol, 1.00 equiv), N,N-dimethylformamide (20.0 mL), potassium carbonate (2.7 g, 19.54 mmol, 3.00 equiv), CH$_3$I (2.8 g, 19.73 mmol, 3.00 equiv). The resulting solution was stirred overnight at room temperature. The reaction was then quenched by the addition of 20.0 mL of water. The resulting solution was extracted with ethyl acetate (40.0 mL) and the organic layers combined. The resulting mixture was washed with sodium chloride (40.0 mL). The mixture was dried over anhydrous sodium sulfate. The residue was applied onto a silica gel column with ethyl acetate/petroleum ether (1/1). The collected fractions were combined and concentrated under vacuum. This resulted in 2.2 g (79%) of tert-butyl 4-([2-fluoro-4-[(1-methoxy-2-methyl-1-oxopropan-2-yl)amino]phenyl]carbonyl)piperazine-1-carboxylate as a yellow solid.

LC-MS (ES$^+$): m/z 424.05 [MH$^+$], t$_R$=0.920 min, (1.90 minute run).

Chemical formula: $C_{21}H_{30}FN_3O_5$ [423.22].

4. Synthesis of tert-butyl 4-[(4-[3-[4-cyano-3-(trifluoromethyl)phenyl]-5,5-dimethyl-4-oxo-2-sulfanylideneimidazolidin-1-yl]-2-fluorophenyl)carbonyl]piperazine-1-carboxylate Into a 100.0-mL round-bottom flask, was placed tert-butyl 4-([2-fluoro-4-[(1-methoxy-2-methyl-1-oxopropan-2-yl)amino]phenyl]carbonyl)piperazine-1-carboxylate (500.0 mg, 1.18 mmol, 1.00 equiv), N,N-dimethylformamide (5.0 mL), 4-isothiocyanato-2-(trifluoromethyl)benzonitrile (404.3 mg, 1.77 mmol, 1.50 equiv), t-BuOK (198.24 mg, 1.77 mmol, 1.50 equiv). The resulting solution was stirred overnight at 100.0° C. in an oil bath. The reaction was then quenched by the addition of 20.0 mL of water. The resulting solution was extracted with ethyl acetate (40.0 mL) and the organic layers combined. The resulting mixture was washed with sodium chloride (40.0 mL). The mixture was dried over anhydrous sodium sulfate. The residue was applied onto a silica gel column with ethyl acetate/petroleum ether (1/1). The collected fractions were combined and concentrated under vacuum. This resulted in 500.0 mg (68%) of tert-butyl 4-[(4-[3-[4-cyano-3-(trifluoromethyl)phenyl]-5,5-dimethyl-4-oxo-2-sulfanylideneimidazolidin-1-yl]-2-fluorophenyl)carbonyl]piperazine-1-carboxylate as a yellow solid.

5. Synthesis of 4-(3-[3-fluoro-4-[(piperazin-1-yl)carbonyl]phenyl]-4,4-dimethyl-5-oxo-2-sulfanylideneimidazolidin-1-yl)-2-(trifluoromethyl)benzonitrile hydrochloride Into a 50.0-mL round-bottom flask, was placed tert-butyl 4-[(4-[3-[4-cyano-3-(trifluoromethyl)phenyl]-5,5-dimethyl-4-oxo-2-sulfanylideneimidazolidin-1-yl]-2-fluorophenyl)carbonyl]piperazine-1-carboxylate (120.0 mg, 0.19 mmol, 1.00 equiv), methanol (3.0 mL), hydrogen chloride (0 mg). The resulting solution was stirred for 2 hours at room temperature. The crude product (mL) was purified by Prep-HPLC with the following conditions (2 #-Analyse HPLC-SHIMADZU (HPLC-10)): Column, XBridge Prep C18 OBD Column, 5 um, 19*150 mm; mobile phase, Water (0.1% FA) and acetonitrile (25.0% acetonitrile up to 62.0% in 8 min); This resulted in 89.9 mg (83%) of 4-(3-[3-fluoro-4-[(piperazin-1-yl)carbonyl]phenyl]-4,4-dimethyl-5-oxo-2-sulfanylideneimidazolidin-1-yl)-2-(trifluoromethyl)benzonitrile hydrochloride as a yellow solid.

H-NMR (300 MHz, CD3OD) δ 8.17-8.15 (d, J=5.4 Hz, 2H), 8.01-7.98 (d, J=8.4 Hz, 1H), 7.64-7.58 (m, 1H), 7.41-7.37 (m, 2H), 5.49 (s, 1H), 3.83 (s, 2H), 3.46 (s, 2H), 3.01-2.92 (d, J=28.5 Hz, 4H), 1.60 (s, 6H), 1.38 (s, 1H).

LC-MS (ES$^+$): m/z 520.05 [MH$^+$], t$_R$=1.315 min, (3.0 minute run).

Chemical formula: $C_{24}H_{21}F_4N_5O_2S$ [519.14].

Total H count from HNMR data: 22.

6. Synthesis of 4-[3-(4-[[4-(4-[[2-(2,6-dioxopiperidin-3-yl)-1,3-dioxo-2,3-dihydro-1H-isoindol-5-yl]oxy]butyl)piperazin-1-yl]carbonyl]-3-fluorophenyl)-4,4-dimethyl-5-oxo-2-sulfanylideneimidazolidin-1-yl]-2-(trifluoromethyl)benzonitrile Into a 50.0-mL round-bottom flask, was placed 4-(3-[3-fluoro-4-[(piperazin-1-yl)carbonyl]phenyl]-4,4-dimethyl-5-oxo-2-sulfanylideneimidazolidin-1-yl)-2-(trifluoromethyl)benzonitrile hydrochloride (150.0 mg, 0.27 mmol, 1.00 equiv), CH$_3$CN (5.0 mL), potassium carbonate (149.1 mg, 1.08 mmol, 4.00 equiv), NaI (40.5 mg, 1.00 equiv), 5-(4-bromobutoxy)-2-(2,6-dioxopiperidin-3-yl)-2,3-dihydro-1H-isoindole-1,3-dione (220.0 mg, 0.54 mmol, 2.00 equiv). The resulting solution was stirred overnight at 70.0° C. in an oil bath. The crude product (mL) was purified by Prep-HPLC with the following conditions (2 #-AnalyseHPLC-SHI- MADZU (HPLC-10)): Column, XBridge Prep C18 OBD Column, 5 um, 19*150 mm; mobile phase, Water (0.1% FA) and acetonitrile (25.0% acetonitrile up to 62.0% in 8 min); Detector, UV 254 nm. mL product was obtained. This resulted in 27.2 mg (12%) of 4-[3-(4-[[4-(4-[[2-(2,6-dioxopiperidin-3-yl)-1,3-dioxo-2,3-dihydro-1H-isoindol-5-yl]oxy]butyl)piperazin-1-yl]carbonyl]-3-fluorophenyl)-4,4-dimethyl-5-oxo-2-sulfanylideneimidazolidin-1-yl]-2-(trifluoromethyl)benzonitrile as a white solid.

H-NMR (300 MHz, CDCl3) δ 8.04-7.95 (m, 3H), 7.84-7.77 (m, 2H), 7.60-7.55 (m, 1H), 7.34-7.33 (d, J=1.8 Hz, 1H), 7.21-7.09 (m, 3H), 4.98-4.93 (m, 1H), 4.14-4.10 (m, 2H), 3.91 (s, 2H), 3.49 (s, 2H), 2.94-2.72 (m, 3H), 2.67-2.56 (m, 5H), 2.25-2.13 (m, 2H), 1.92-1.88 (m, 2H), 1.76 (s, 2H), 1.68 (s, 6H).

LC-MS (ES$^+$): m/z 848.20 [MH$^+$], $t_R$=3.304 min, (5.0 minute run).

Chemical formula: $C_{41}H_{37}F_4N_7O_7S$ [847.24].

Total H count from HNMR data: 37.

Synthetic Scheme for Compound 450

Experiments

Step 1: [chloromethyl 2,5,8,11-tetraoxatridecan-13-yl carbonate]

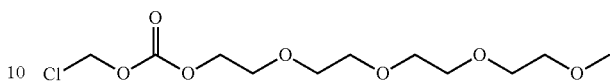

To a stirred solution of chloromethyl carbonochloridate (2.6 g, 20 mmol) in dichloromethane (40 mL) was added a mixture of 2,5,8,11-tetraoxatridecan-13-ol (4.16 g, 20 mmol) and triethylamine (2 g, 20 mmol) in dichloromethane (5 ml) dropwise at 0° C. The resulting reaction mixture was stirred at 0° C. for 0.5 hour. TLC showed the reaction was completed. The reaction mixture was partitioned between tert-Butyl methyl ether (100 ml) and water (60 ml). The organic layer were collected, washed with brine (50 ml), dried over anhydrous sodium sulfate, and concentrated under reduced pressure to give a crude residue which was

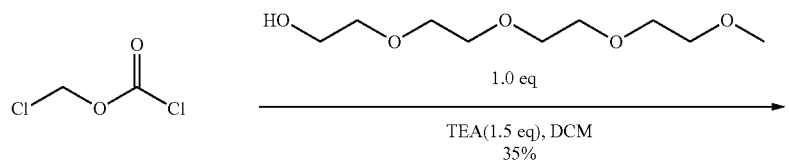

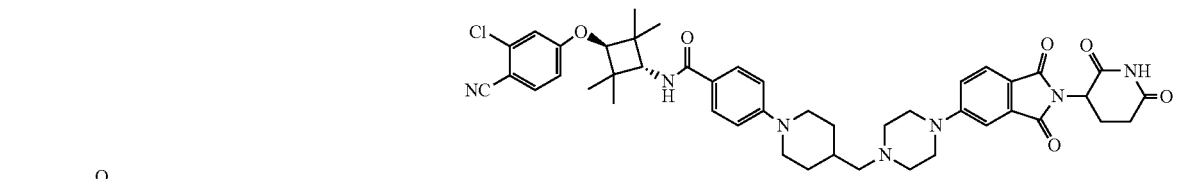

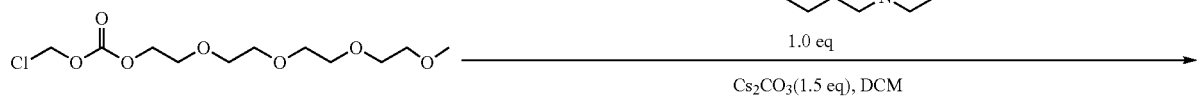

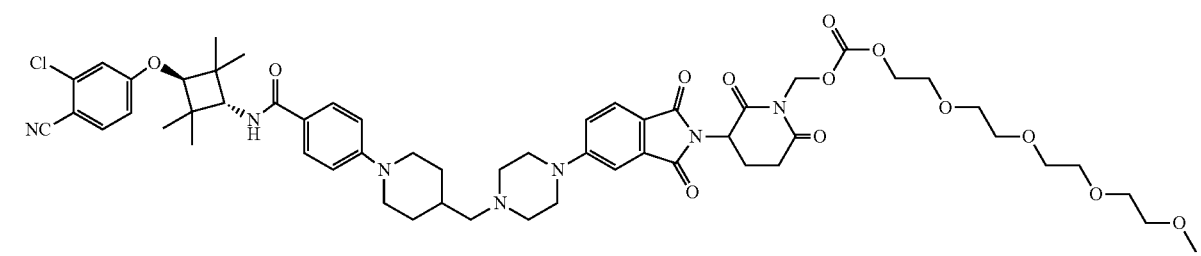

purified by silica gel flash chromatography (eluted with 30% ethyl acetate in hexane) to afford chloromethyl 2,5,8,11-tetraoxatridecan-13-yl carbonate (2.2 g, yield 35.2%) as colorless oil.

1H NMR (400 MHz, CDCl$_3$): δ 3.38 (s, 3H), 3.54-3.56 (m, 2H), 3.64-3.66 (m, 10H), 3.74-3.76 (m, 2H), 4.36-4.38 (m, 2H), 5.74 (s, 2H).

Chemical Formula: $C_{11}H_{21}ClO_7$; Molecular Weight: 300.73;

Total H count from HNMR data: 21.

Step 2: [(3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl) methyl 2,5,8,11-tetraoxatridecan-13-yl carbonate]

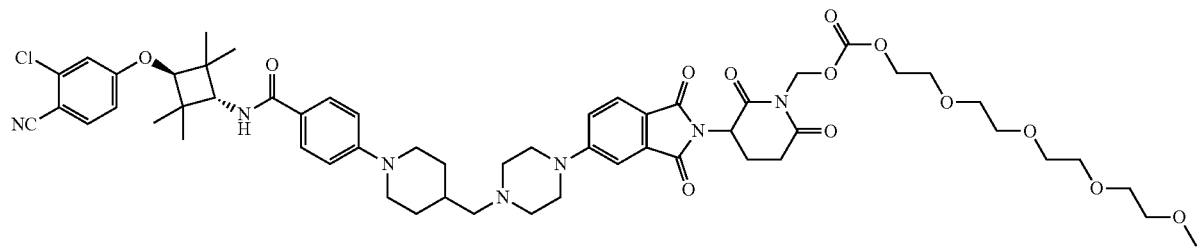 [SMILES: COCCOCCOCCOCCOC(=O)OCN1C(=O)CCC(N2C(=O)c3ccc(N4CCN(CC5CCN(c6ccc(C(=O)N[C@H]7C(C)(C)[C@H](Oc8ccc(C#N)c(Cl)c8)C7(C)C)cc6)CC5)CC4)cc3C2=O)C1=O]

A mixture of N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl) piperidin-1-yl)benzamide (320 mg, 0.39 mmol), cesium carbonate (190 mg, 0.58 mmol) and chloromethyl 2,5,8,11-tetraoxatridecan-13-yl carbonate (140 mg, 0.47 mmol) in N,N-dimethylformamide (6 mL) was stirred at room temperature for 2 hours. TLC showed the reaction was completed. The mixture was partitioned between ethyl acetate (50 ml) and water (40 ml). The organic layer were collected, washed with brine (30 ml), dried over anhydrous sodium sulfate, and concentrated under reduced pressure to give a crude residue which was purified by silica gel flash chromatography (eluting with 2.5% methanol in dichloromethane) to afford (3-(5-(4-((1-(4-(((1r,3r)-3-(3-chloro-4-cyanophenoxy)-2,2,4,4-tetramethylcyclobutyl)carbamoyl)phenyl) piperidin-4-yl)methyl)piperazin-1-yl)-1,3-dioxoisoindolin-2-yl)-2,6-dioxopiperidin-1-yl)methyl 2,5,8,11-tetraoxatridecan-13-yl carbonate (160 mg, yield 38%) as yellow solid.

LC_MS: (ES$^+$): m/z 1084.7 [M+H]$^+$. $t_R$=2.550 min.

$^1$H NMR (400 MHz, DMSO-d6): δ 1.13 (s, 6H), 1.18-1.27 (m, 2H), 1.22 (s, 6H), 1.77-1.83 (m, 3H), 2.04-2.12 (m, 1H), 2.21-2.22 (m, 2H), 2.31-2.45 (m, 1H), 2.58-2.67 (m, 3H), 2.73-2.85 (m, 3H), 3.01-3.12 (m, 1H), 3.23 (s, 3H), 3.31-3.33 (m, 2H), 3.40-3.52 (m, 15H), 3.59-3.62 (m, 2H), 3.86 (d, J=12.4 Hz, 2H), 4.05 (d, J=9.2 Hz, 1H), 4.19-4.21 (m, 2H), 4.32 (s, 1H), 5.25-5.29 (m, 1H), 5.67-5.69 (m, 2H), 6.96 (d, J=8.8 Hz, 2H), 7.00 (dd, J=2.4, 8.8 Hz, 1H), 7.21 (d, J=2.4 Hz, 1H), 7.28 (d, J=8.8 Hz, 1H), 7.36 (s, 1H), 7.50 (d, J=9.2 Hz, 1H), 7.68 (d, J=8.4 Hz, 1H), 7.74 (d, J=8.4 Hz, 2H), 7.92 (d, J=8.8 Hz, 1H).

Chemical Formula: $C_{56}H_{70}ClN_7O_{13}$; Molecular Weight: 1084.65;

Total H count from HNMR data: 70.

Synthetic Scheme for Compound 448

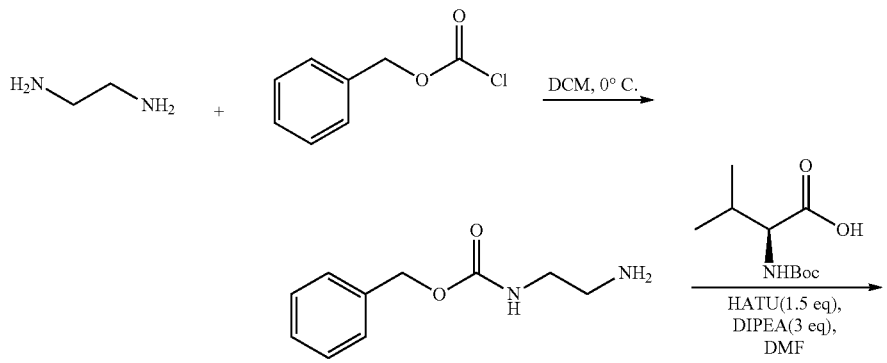

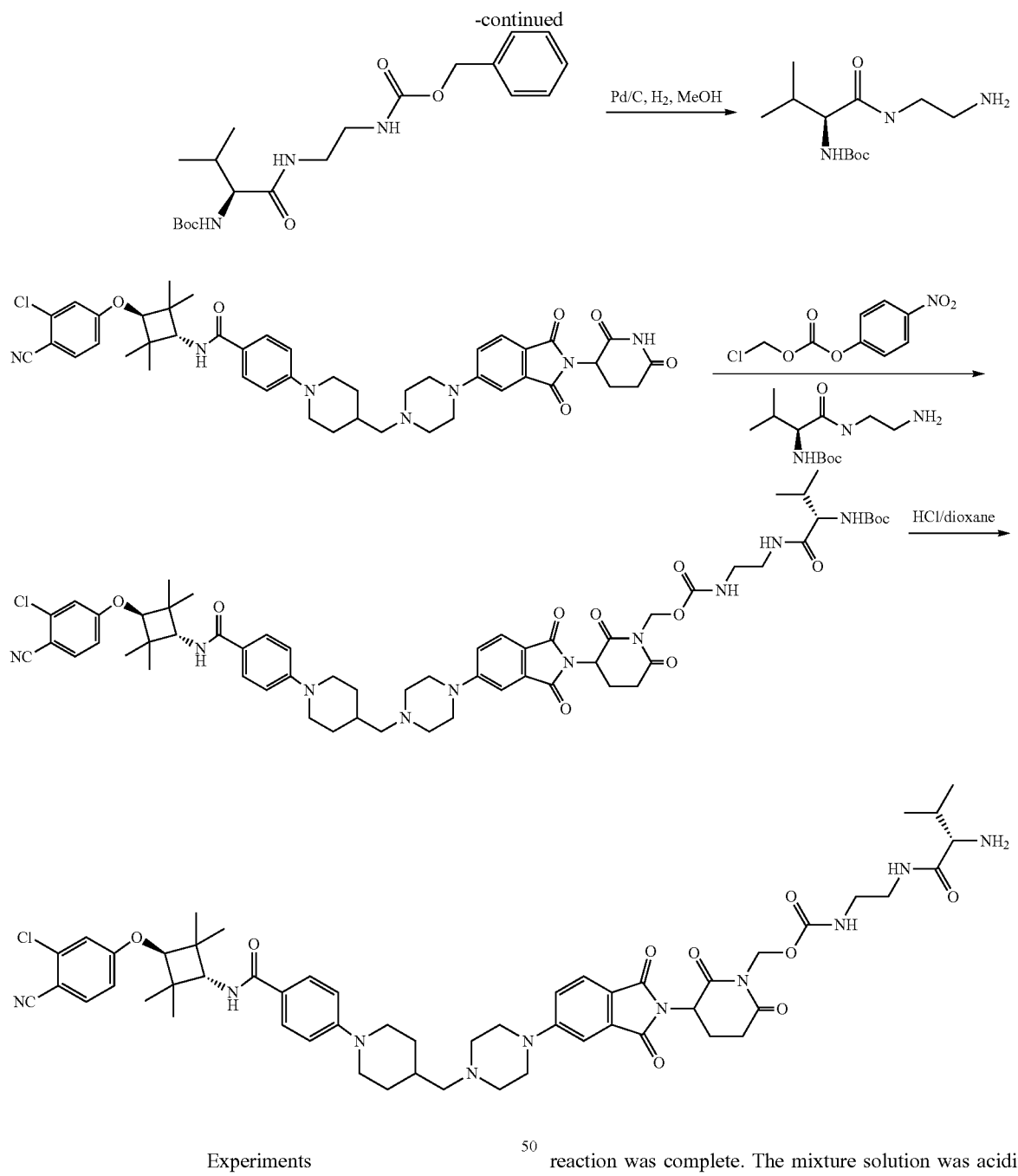

Experiments

Step 1: [benzyl (2-aminoethyl)carbamate]

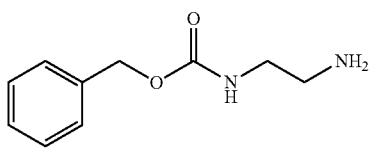 [SMILES: NCCNC(=O)OCc1ccccc1]

To a stirred solution of ethane-1,2-diamine (10 g, 166 mmol) in anhydrous dichloromethane (50 ml) was added benzyl chloroformate (2.83 g, 16.6 mmol) in dichloromethane (10 ml) dropwise at 0° C. over 30 min. The reaction mixture was stirred at 0° C. for 3 hours. TLC showed the reaction was complete. The mixture solution was acidified with diluted hydrochloride acid (1N) till pH 4-5, and extracted with ethyl acetate (100 ml). The aqueous layer was collected, acidified with saturated sodium hydroxide solution till pH 9-10, and extracted with ethyl acetate (50 ml×2). The combined organic layers were collected, dried over anhydrous sodium sulfate, and concentrated under reduced pressure to give benzyl (2-aminoethyl)carbamate (1.31 g, yield 40%) as colorless oil which was used in next step without further purification.

LC_MS: (ES$^+$): m/z 195.2 [M+H]$^+$. t$_R$=1.198 min.

$^1$H NMR (400 MHz, CDCl$_3$): 2.787 (t, J=6.0 Hz, 2H), 3.14-3.28 (m, 2H), 5.07 (s, 2H), 7.27-7.35 (m, 5H).

Chemical Formula: C$_{10}$H$_{14}$N$_2$O$_2$; Molecular Weight: 194.23;

Total H count from HNMR data: 11.

Step 2

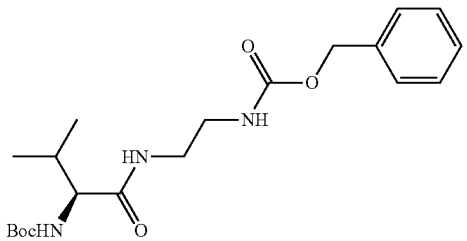 [SMILES: CC(C)[C@H](NC(=O)OC(C)(C)C)C(=O)NCCNC(=O)OCc1ccccc1]

Step 3: [(S)-tert-butyl (1-((2-aminoethyl)amino)-3-methyl-1-oxobutan-2-yl)carbamate]

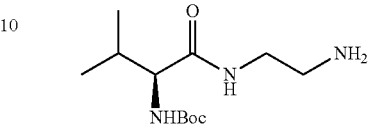

To a stirred solution of benzyl (2-aminoethyl)carbamate (400 mg, 2.06 mmol), (S)-2-((tert-butoxycarbonyl)amino)-3-methylbutanoic acid (447 mg, 2.06 mmol), and N-ethyl-N-isopropylpropan-2-amine (797 mg, 6.18 mmol) in anhydrous N,N-dimethylformamide (4 ml) was added HATU (2-(7-Aza-1H-benzotriazole-1-yl)-1,1,3,3-tetramethyluronium hexafluorophosphate) (1.56 g, 4.12 mmol) at room temperature and stirred for 20 min. TLC showed the reaction was complete. The mixture was partitioned between ethyl acetate (40 ml) and water (20 ml). The organic layer was collected, washed with brine (30 ml), dried over anhydrous sodium sulfate, and concentrated under reduced pressure to give a crude residue which was purified by silica gel flash chromatography (eluting with 5% methanol in dichloromethane) to afford Compound 448-2 (670 mg, yield 83%) as white solid.

$^1$H NMR (400 MHz, CDCl$_3$): 0.88 (d, J=6.8 Hz, 3H), 0.93 (d, J=6.8 Hz, 3H), 1.43 (s, 9H), 2.07-2.15 (m, 1H), 3.33-3.38 (m, 4H), 3.85 (t, J=1.2 Hz, 3H), 5.08 (s, 2H), 7.30-7.35 (m, 5H).

Chemical Formula: C$_{20}$H$_{31}$N$_3$O$_5$; Molecular Weight: 393.48;

Total H count from HNMR data: 28.

Palladium on carbon (10%, 200 mg) was added to a stirred solution of Compound 448-2 (670 mg, 1.70 mmol) in methanol (20 ml). The reaction mixture was stirred under hydrogen atmosphere (hydrogen balloon) at room temperature overnight. TLC showed the reaction was complete. Palladium on carbon was removed through filtration and washed with methanol (5 ml×2). The combined filtrates were concentrated under reduced pressure to afford (S)-tert-butyl (1-((2-aminoethyl)amino)-3-methyl-1-oxobutan-2-yl) carbamate (470 mg, crude) as colorless oil which was used in next step directly without purification.

$^1$H NMR (400 MHz, CDCl$_3$): 0.92 (d, J=6.8 Hz, 3H), 0.96 (d, J=6.8 Hz, 3H), 1.44 (s, 9H), 2.08-2.20 (m, 1H), 2.84 (t, J=5.6 Hz, 2H), 3.27-3.38 (m, 2H), 3.85-3.89 (m, 1H).

Chemical Formula: C$_{12}$H$_{25}$N$_3$O$_3$; Molecular Weight: 259.35;

Total H count from HNMR data: 21.

Step 4: (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl) methyl (2-((S)-2-((tert-butoxycarbonyl)amino)-3-methylbutanamido)ethyl)carbamate

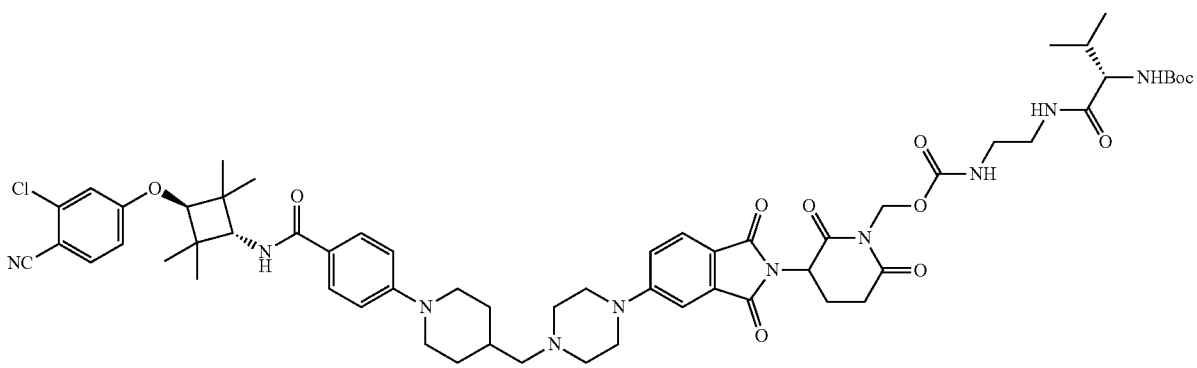 [SMILES: CC(C)[C@H](NC(=O)OC(C)(C)C)C(=O)NCCNC(=O)OCN1C(=O)CCC(N2C(=O)c3ccc(N4CCN(CC5CCN(c6ccc(C(=O)N[C@H]7C(C)(C)[C@H](Oc8ccc(C#N)c(Cl)c8)C7(C)C)cc6)CC5)CC4)cc3C2=O)C1=O]

To a stirred solution of N-((1r,3r)-3-(3-chloro-4-cyanophenoxy)-2,2,4,4-tetramethylcyclobutyl)-4-(4-((4-(2-(2,6-dioxopiperidin-3-yl)-1,3-dioxoisoindolin-5-yl)piperazin-1-yl)methyl)piperidin-1-yl)benzamide (300 mg, 0.36 mmol), and cesium carbonate (179 mg, 0.55 mmol) in dichloromethane (8 ml) and acetonitrile (1 ml) was added chloromethyl (4-nitrophenyl) carbonate (102 mg, 0.44 mmol) under nitrogen. The reaction mixture was stirred at room temperature under nitrogen for 3 hours. TLC showed the reaction was complete. To the reaction mixture was added (S)-tert-butyl (1-((2-aminoethyl)amino)-3-methyl-1-oxobutan-2-yl)carbamate (93 mg, 0.36 mmol), and the resulting mixture was continued stirring under nitrogen for 2 hours. TLC showed the reaction was complete. The mixture was partitioned between ethyl acetate (30 ml) and water (20 ml). The organic layer was collected, washed with brine (30 ml), dried over anhydrous sodium sulfate, and concentrated under reduced pressure to give a crude residue which was purified by silica gel flash chromatography (eluted with 2.5% methanol in dichloromethane) to afford desired product (240 mg, yield 59%) as yellow solid.

LC_MS: (ES$^+$): m/z 1135.7 [M+H]$^+$. $t_R$=2.578 min.

Step 5: [(3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl) methyl (2-((S)-2-amino-3-methylbutanamido)ethyl) carbamate]

A solution of (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-dioxopiperidin-1-yl)methyl (2-((S)-2-((tert-butoxycarbonyl)amino)-3-methylbutanamido)ethyl) carbamate (230 mg, 0.20 mmol) in dichloromethane (6 ml) in 4M hydrogen chloride in dioxane (2 ml) was stirred at room temperature for 2 hours. TLC showed the reaction was complete. The mixture solution was acidified with saturated sodium bicarbonate solution till pH 9-10, and extracted with dichloromethane (15 ml×2). The organic layers were combined, washed with brine (30 ml), dried over sodium sulfate and concentrated under reduced to give a crude residue which was purified by silica gel flash chromatography (eluted with 2.5% methanol in dichloromethane) to afford (3-(5-(4-((1-(4-(((1r,3r)-3-(3-chloro-4-cyanophenoxy)-2,2,4,4-tetramethylcyclobutyl)carbamoyl)phenyl)piperidin-4-yl)methyl)piperazin-1-yl)-1,3-dioxoisoindolin-2-yl)-2,6-di oxopiperidin-1-yl)methyl (2-((S)-2-amino-3-methylbutanamido)ethyl)carbamate (140 mg, yield 67%) as yellow solid.

LC_MS: (ES$^+$): m/z 1035.6 [M+H]$^+$. $t_R$=2.215 min.

$^1$H NMR (400 MHz, DMSO-d6): δ 0.76 (d, J=6.8 Hz, 3H), 0.84 (d, J=6.8 Hz, 3H), 1.12 (s, 6H), 1.18 (s, 2H), 1.22 (s, 6H), 1.80-1.87 (m, 4H), 2.07-2.09 (m, 2H), 2.21 (d, J=6.0 Hz, 2H), 2.50 (s, 4H), 2.58-2.62 (m, 2H), 2.76-2.85 (m, 3H), 2.90 (d, J=5.2 Hz, 1H), 3.00-3.06 (m, 3H), 3.11 (t, J=6.0 Hz, 2H), 3.45 (s, 4H), 3.86 (d, J=12.0 Hz, 2H), 4.05 (d, J=9.2 Hz, 1H), 4.32 (s, 1H), 5.20-5.24 (m, 1H), 5.55-5.61 (m, 2H), 6.95 (d, J=9.2 Hz, 2H), 6.99-7.02 (m, 1H), 7.20 (d, J=2.4 Hz, 1H), 7.27 (d, J=8.8 Hz, 1H), 7.32-7.35 (m, 2H), 7.48 (d, J=9.2 Hz, 1H), 7.69 (d, J=8.4 Hz, 1H), 7.73 (d, J=8.8 Hz, 2H), 7.90 (d, J=8.8 Hz, 2H).

Chemical Formula: $C_{54}H_{67}ClN_{10}O_9$; Molecular Weight: 1035.62;

Total H count from HNMR data: 67.

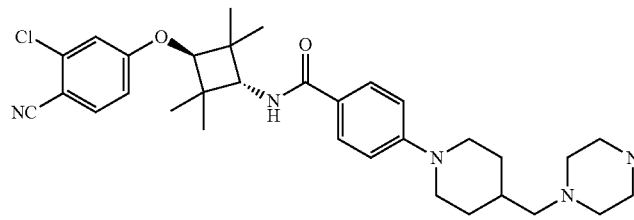
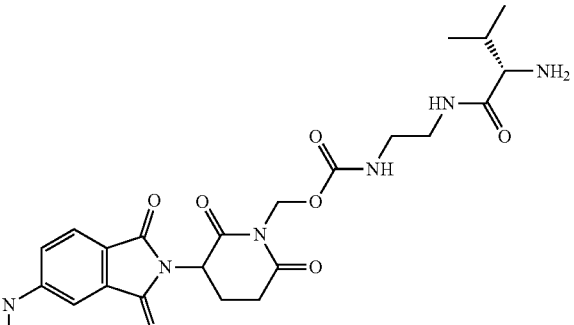

Synthesis of ABM Moieties

ABM-1: 2-chloro-4-(3-(4-hydroxyphenyl)-4,4-dimethyl-5-oxo-2-thioxoimidazolidin-1-yl)benzonitrile

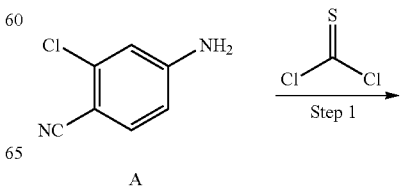

A

-continued

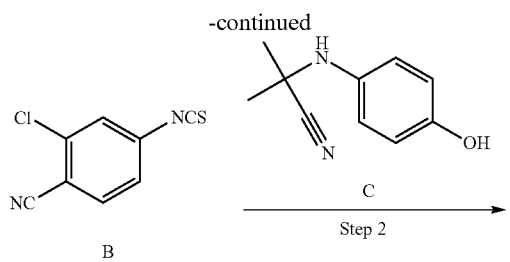

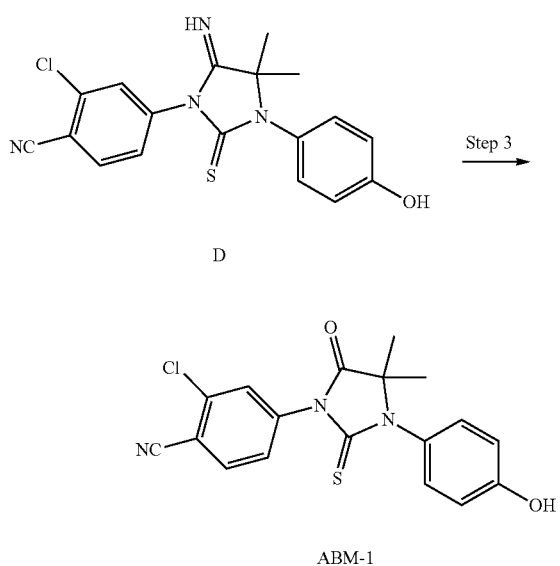

ABM-1

Step 1: Synthesis of 2-chloro-4-isothiocyanatobenzonitrile (B)

To a stirred solution of 4-amino-2-chlorobenzonitrile (A, 1 g, 6.55 mmol) in dichloromethane (9 mL) was added sodium bicarbonate (2.21 g, 26.31 mmol) and water (9 mL). The resulting mixture was cooled to 0° C., to which thiophosgene (817 mg, 7.11 mmol) was added in drop wise in 30 min at 0° C. The resulting mixture was then warmed up to room temperature and stirred at room temperature for 1 hour. The reaction mixture was diluted with dichloromethane (200 mL), washed with brine (50 mL×2), dried over anhydrous sodium sulfate and then concentrated under reduced pressure to give a crude residue. The residue was purified by flash silica gel chromatography (eluent: ethyl acetate/petroleum ether (v:v=1:30)) to give desired product (yield: 71%) $^1$HNMR (400 MHz, CDCl$_3$): δ 7.69 (d, J=8.0 Hz, 1H), 7.38 (s, 1H), 7.28 (m, 1H);

Step 2: Synthesis of 2-chloro-4-[3-(4-hydroxyphenyl)-5-imino-4, 4-dimethyl-2-sulfanylideneimidazolidin-1-yl]benzonitrile (D)

To a stirred solution of 2-chloro-4-isothiocyanatobenzonitrile (B, 399 mg, 2.05 mmol) in toluene (5 mL) was added 2-[(4-hydroxyphenyl)amino]-2-methylpropanenitrile (C, 300 mg, 1.70 mmol) and 4-dimethylaminopyridine (312 mg, 2.55 mmol). The resulting solution was then heated in an oil bath to 100° C. and stirred at the same temperature for 16 h. LC-MS indicated formation of the desired product. The reaction mixture was concentrated under vacuum to give a crude reside which was purified by flash silica gel chromatography (eluent: ethyl acetate/petroleum ether (v:v=1:1)) to give desired product (yield: 48%) as a brown solid. LC-MS (ES$^+$): m/z 370.95 [MH$^+$], $t_R$=0.74 min (2.0 minute run);

Step 3: Synthesis of 2-chloro-4-[3-(4-hydroxyphenyl)-4,4-dimethyl-5-oxo-2-sulfanylideneimidazolidin-1-yl]benzonitrile (ABM-1)

To a stirred solution of 2-chloro-4-[3-(4-hydroxyphenyl)-5-imino-4, 4-dimethyl-2-sulfanylideneimidazolidin-1-yl]benzonitrile (D, 300 mg, 0.81 mmol) in methanol (6 mL) was added aqueous hydrogen chloride (2N, 3.0 mL). The resulting solution was then heated in an oil bath to 100° C. and stirred at the same temperature for 2 h. The reaction mixture was diluted with water (30 mL), extracted with ethyl acetate (60 mL×3), washed with water (50 mL), dried over anhydrous sodium sulfate and concentrated under vacuum to give titled product (yield: 93%) as a yellow solid, which was used for the next step without any further purifications. LC-MS (ES$^+$): m/z 372.00 [MH$^+$], $t_R$=0.97 min (2.0 minute run).

Unless otherwise noted, the following intermediates and their analogs (for examples, but not limited to, analogs with substitutions such as halogens) were synthesized according to similar procedures described above for the synthesis of ABM-1, by utilizing corresponding starting materials and reagents.

ABM-2: 2-fluoro-4-(3-(4-hydroxyphenyl)-4,4-dimethyl-5-oxo-2-thioxoimidazolidin-1-yl)benzonitrile

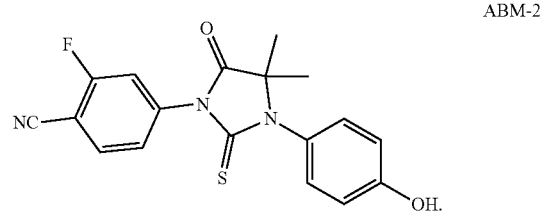 [SMILES: CC1(C)C(=O)N(c2ccc(C#N)c(F)c2)C(=S)N1c1ccc(O)cc1]

ABM-3: 4-(3-(4-hydroxyphenyl)-4,4-dimethyl-5-oxo-2-thioxoimidazolidin-1-yl)-2-(trifluoromethyl)benzonitrile

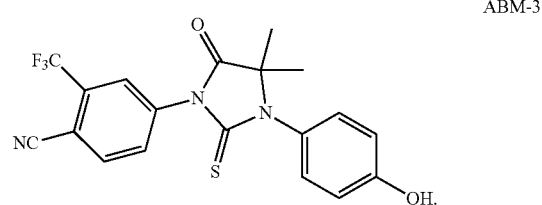 [SMILES: CC1(C)C(=O)N(c2ccc(C#N)c(C(F)(F)F)c2)C(=S)N1c1ccc(O)cc1]

ABM-4: 5-(3-(4-hydroxyphenyl)-4,4-dimethyl-5-oxo-2-thioxoimidazolidin-1-yl)-3-(trifluoromethyl)picolinonitrile

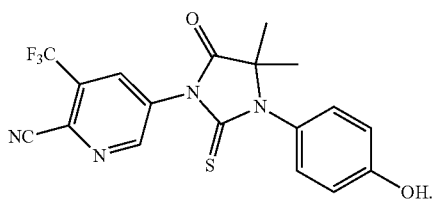
ABM-4

ABM-5: 4-(3-(4-hydroxyphenyl)-4,4-dimethyl-5-oxo-2-thioxoimidazolidin-1-yl)-2-methoxybenzonitrile:

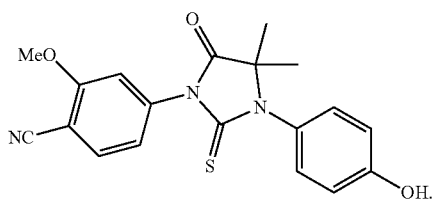
ABM-5

ABM-6: 4-(3-(4-hydroxyphenyl)-4,4-dimethyl-5-oxo-2-thioxoimidazolidin-1-yl)-2-methylbenzonitrile

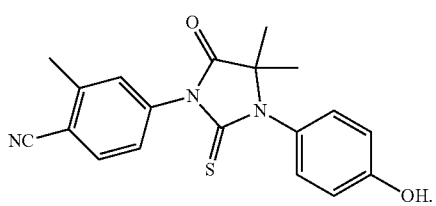
ABM-6

ABM-7: 3-chloro-5-(3-(4-hydroxyphenyl)-4,4-dimethyl-5-oxo-2-thioxoimidazolidin-1-yl)picolinonitrile

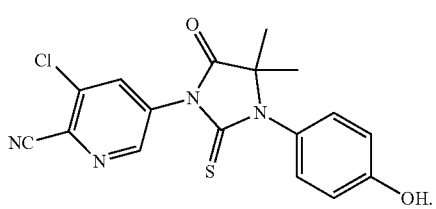
ABM-7

ABM-8: 4-(1-(4-hydroxyphenyl)-4-oxo-2-thioxo-8-oxa-1,3-diazaspiro[4.5]decan-3-yl)-2-(trifluoromethyl)benzonitrile

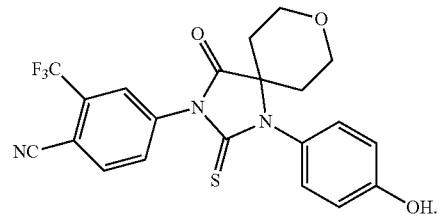
ABM-8

ABM-9: 4-(1-(4-hydroxyphenyl)-8-methyl-4-oxo-2-thioxo-1,3,8-triazaspiro[4.5]decan-3-yl)-2-(trifluoromethyl)benzonitrile

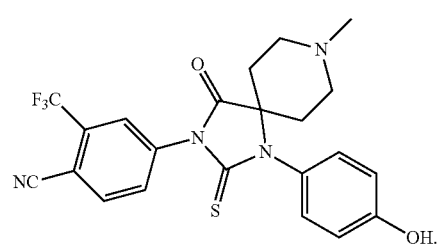
ABM-9

ABM-10: 4-(5-(4-hydroxyphenyl)-8-oxo-6-thioxo-5,7-diazaspiro[3.4]octan-7-yl)-2-(trifluoromethyl)benzonitrile

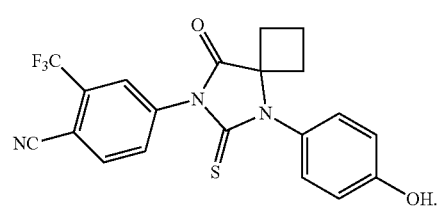
ABM-10

ABM-11: 5-(5-(4-hydroxyphenyl)-8-oxo-6-thioxo-5,7-diazaspiro[3.4]octan-7-yl)-3-(trifluoromethyl)picolinonitrile

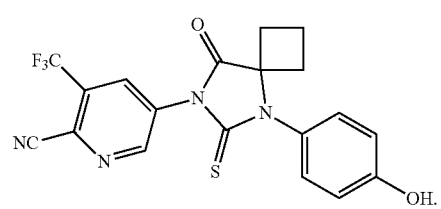
ABM-11

ABM-12: 4-(4-(3-(4-cyano-3-(trifluoromethyl)phenyl)-5,5-dimethyl-4-oxo-2-thioxoimidazolidin-1-yl)phenyl)butanoic acid

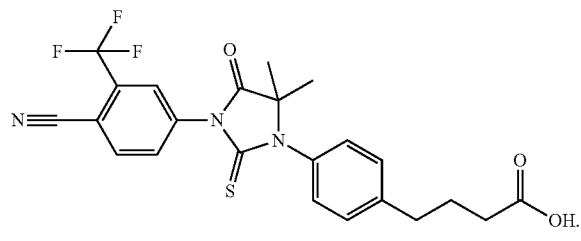

ABM-13: 2-chloro-4-(3-(4'-hydroxybiphenyl-4-yl)-4,4-dimethyl-5-oxo-2-thioxoimidazolidin-1-yl)benzonitrile

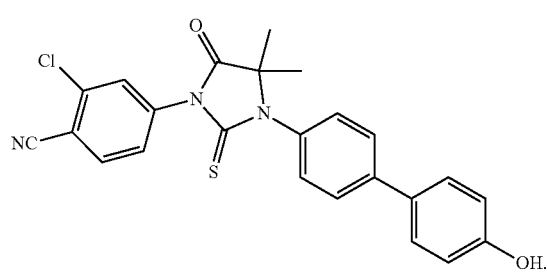

ABM-14: 4-(3-(4'-hydroxybiphenyl-4-yl)-4,4-dimethyl-5-oxo-2-thioxoimidazolidin-1-yl)-2-(trifluoromethyl)benzonitrile

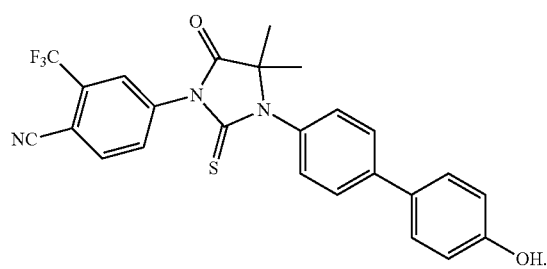

ABM-15: 5-(3-(4'-hydroxybiphenyl-4-yl)-4,4-dimethyl-5-oxo-2-thioxoimidazolidin-1-yl)-3-(trifluoromethyl)picolinonitrile

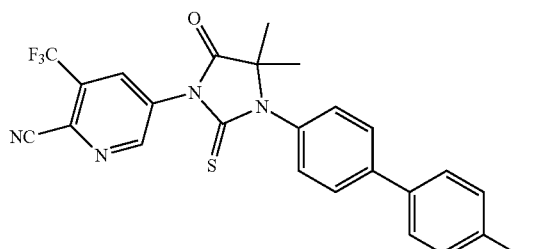

ABM-16: 4-(3-(3-fluoro-4-hydroxyphenyl)-4,4-dimethyl-5-oxo-2-thioxoimidazolidin-1-yl)-2-(trifluoromethyl)benzonitrile

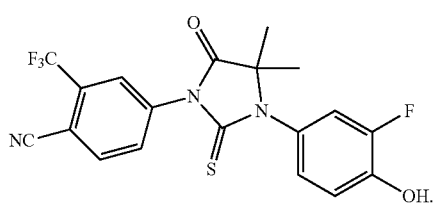

ABM-17: 1-(4-hydroxyphenyl)-5,5-dimethyl-3-(4-nitro-3-(trifluoromethyl)phenyl)-2-thioxoimidazolidin-4-one

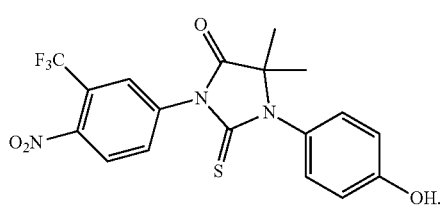

ABM-18: 4-(3-(3,5-difluoro-4-hydroxyphenyl)-4,4-dimethyl-5-oxo-2-thioxoimidazolidin-1-yl)-2-(trifluoromethyl)benzonitrile

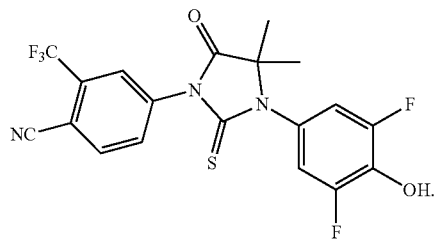

ABM-19: 4-(3-(4-hydroxyphenyl)-4,4-dimethyl-2,5-dioxoimidazolidin-1-yl)-2-(trifluoromethyl)benzonitrile

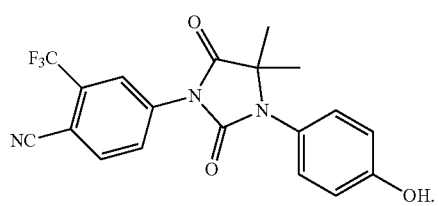

ABM-20: 4-(3-(6-hydroxypyridin-3-yl)-4,4-dimethyl-5-oxo-2-thioxoimidazolidin-1-yl)-2-(trifluoromethyl)benzonitrile

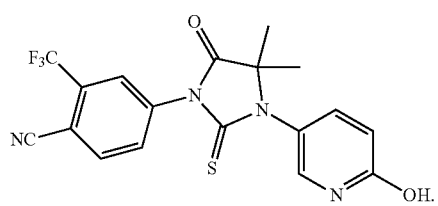

ABM-21: 2-chloro-4-(3-(3-fluoro-4-hydroxyphenyl)-4,4-dimethyl-5-oxo-2-thioxoimidazolidin-1-yl)benzonitrile

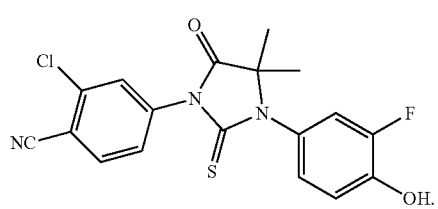

ABM-22: 4-(3-(3-fluoro-4-hydroxyphenyl)-4,4-dimethyl-5-oxo-2-thioxoimidazolidin-1-yl)-2-methoxybenzonitrile

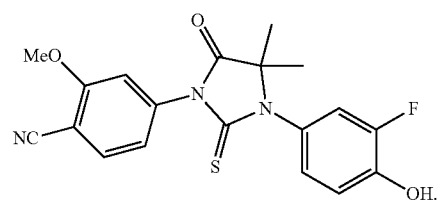

ABM-23: 5-(3-(3-fluoro-4-hydroxyphenyl)-4,4-dimethyl-5-oxo-2-thioxoimidazolidin-1-yl)-3-(trifluoromethyl)picolinonitrile

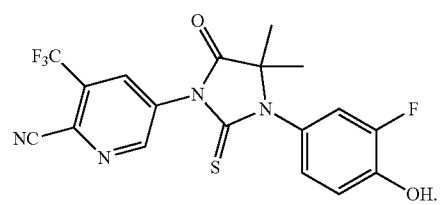

ABM-24: 5-(3-(2-fluoro-4'-hydroxybiphenyl-4-yl)-4,4-dimethyl-5-oxo-2-thioxoimidazolidin-1-yl)-3-(trifluoromethyl)picolinonitrile

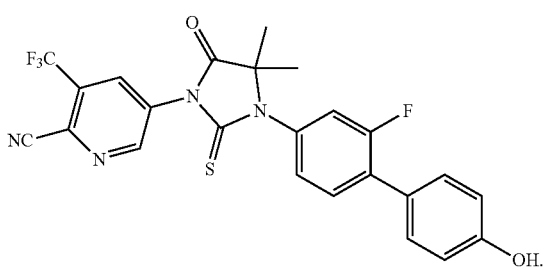

ABM-25: 4-(4,4-dimethyl-5-oxo-3-(4-(piperidin-4-yl)phenyl)-2-thioxoimidazolidin-1-yl)-2-(trifluoromethyl)benzonitrile

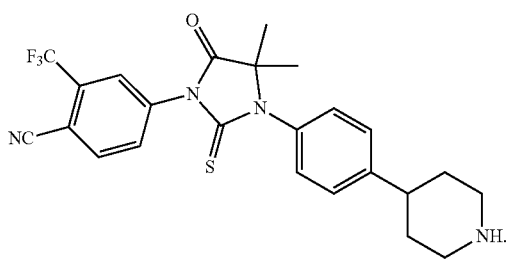

ABM-26: trans-2-Chloro-4-[3-amino-2,2,4,4-tetramethylcyclobutoxy]benzonitrile

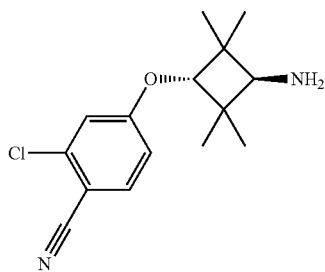 [SMILES: CC1(C)[C@H](N)C(C)(C)[C@H]1Oc1ccc(C#N)c(Cl)c1]

ABM-27: cis-2-Chloro-4-[3-amino-2,2,4,4-tetramethylcyclobutoxy]benzonitrile

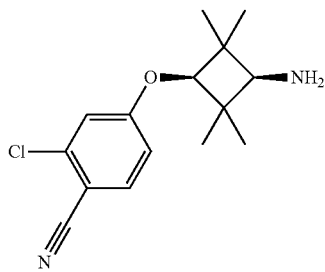 [SMILES: CC1(C)[C@H](N)C(C)(C)[C@@H]1Oc1ccc(C#N)c(Cl)c1]

ABM-28: trans 6-Amino-N-[3-(3-chloro-4-cyanophenoxy)-2,2,4,4-tetramethylcyclobutyl]pyridazine-3-carboxamide

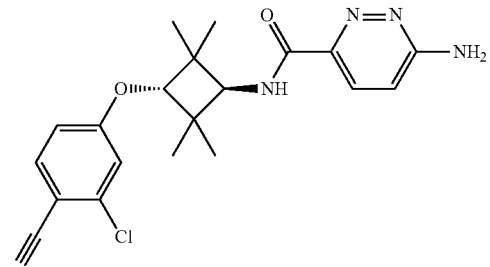

ABM-29: trans tert-Butyl N-[3-(3-chloro-4-cyanophenoxy)-2,2,4,4-tetramethylcyclobutyl]carbamate

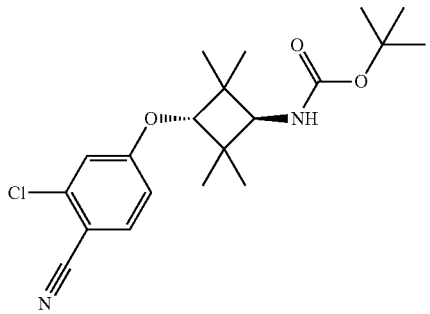 [SMILES: CC(C)(C)OC(=O)N[C@H]1C(C)(C)[C@H](Oc2ccc(C#N)c(Cl)c2)C1(C)C]

ABM-30: trans 4-Amino-N-[3-(3-chloro-4-cyanophenoxy)-2,2,4,4-tetramethylcyclobutyl]benzamide

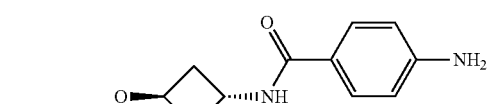

Step 1: Synthesis of tert-butyl (4-((trans-3-(3-chloro-4-cyanophenoxy)-2,2,4,4-tetramethylcyclobutyl)carbamoyl)phenyl)carbamate A suspension of 4-((tert-butoxycarbonyl)amino)benzoic acid (1.50 g, 6.34 mmol) in methylene dichloride (40 mL) was charged with N,N-diisopropylethylamine (3.30 mL, 19.0 mmol), followed by 4-(trans-3-amino-2,2,4,4-tetramethylcyclobutoxy)-2-chlorobenzonitrile hydrochloride (2.0 g, 6.34 mmol). The mixture was stirred for several minutes and then charged with HATU (2.41 g, 6.34 mmol). The reaction mixture was allowed to stir at room temperature for 2 hours. The mixture was diluted with methylene dichloride (40 mL), washed with aqueous 1N HCl (2×), saturated aqueous sodium bicarbonate (2×), brine, and dried over anhydrous Na₂SO₄. The crude product was used in next step;

Step 2: synthesis of trans 4-Amino-N-[3-(3-chloro-4-cyanophenoxy)-2,2,4,4-tetramethylcyclobutyl]benzamide 4M HCl in Dioxane (1.38 mL, 40.0 mmol) was added to a pre-mixed solution of tert-butyl (4-((trans-3-(3-chloro-4-cyanophenoxy)-2,2,4,4-tetramethylcyclobutyl)carbamoyl)phenyl)carbamate (2.00 g, 4.01 mmol) in MeOH (2 mL) and left to stir at room temperature for 1 hour till completion. The reaction mixture was concentrated in vacuo to a solid, which was dissolved with 5% MeOH in DCM. The organic layer was washed with sodium bicarbonate (2×), filtered through a Biotage Universal Phase Separator and then concentrated in vacuo to a solid. The crude product was recrystallized from EtOH/Heptanes to afford the desired product as a white solid, 1.2 g, 75% yield. ¹H NMR (400 MHz, METHANOL-d4) δ 7.72 (d, J=8.80 Hz, 1H), 7.61 (d, J=8.61 Hz, 2H), 7.13 (d, J=2.35 Hz, 1H), 6.98 (dd, J=2.45, 8.71 Hz, 1H), 6.69 (d, J=8.61 Hz, 2H), 4.28 (s, 1H), 4.12 (s, 1H), 1.27 (s, 6H), 1.22 (s, 6H). LC-MS (ES+): m/z 398.16/400.15 [MH⁺].

Unless otherwise noted, the following intermediates and their analogs (for examples, but not limited to, analogs with substitutions such as halogens) were synthesized according to similar procedures described above for the synthesis of ABM-30, by utilizing corresponding starting materials and reagents.

ABM-31: trans 5-Amino-N-[3-(3-chloro-4-cyanophenoxy)-2,2,4,4-tetramethylcyclobutyl]pyrazine-2-carboxamide

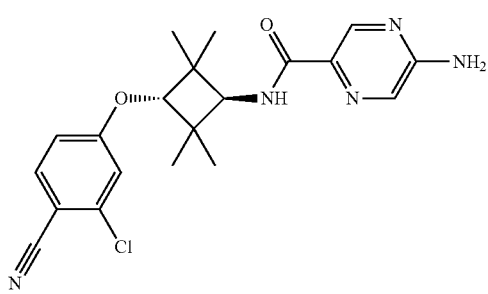 [SMILES: CC1(C)[C@H](NC(=O)c2cnc(N)cn2)C(C)(C)[C@H]1Oc1ccc(C#N)c(Cl)c1]

ABM-32: trans 2-Amino-N-[3-(3-chloro-4-cyanophenoxy)-2,2,4,4-tetramethylcyclobutyl]pyrimidine-5-carboxamid

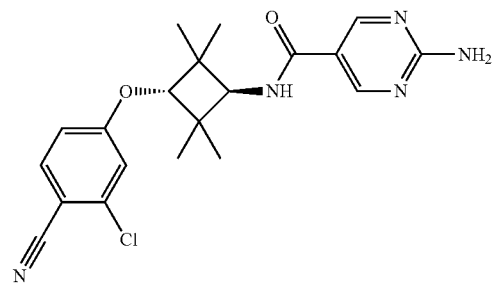 [SMILES: CC1(C)[C@H](NC(=O)c2cnc(N)nc2)C(C)(C)[C@H]1Oc1ccc(C#N)c(Cl)c1]

ABM-33: 4-Methoxy-N-[(1r,3r)-3-(3-chloro-4-cyanophenoxy)-2,2,4,4-tetramethylcyclobutyl]benzamide

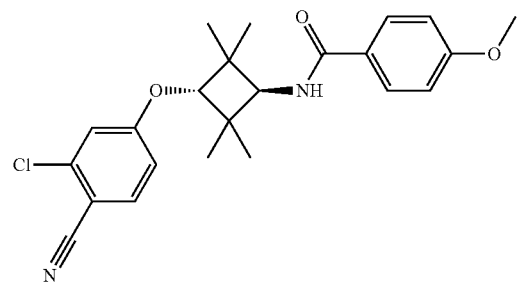 [SMILES: COc1ccc(C(=O)N[C@H]2C(C)(C)[C@H](Oc3ccc(C#N)c(Cl)c3)C2(C)C)cc1]

ABM-34: trans 1-(2-Hydroxyethyl)-N-[3-(3-chloro-4-cyanophenoxy)-2,2,4,4-tetramethylcyclobutyl]-1H-pyrazole-4-carboxamide

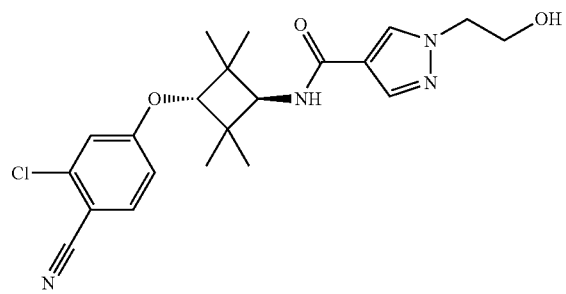 [SMILES: CC1(C)[C@H](NC(=O)c2cnn(CCO)c2)C(C)(C)[C@H]1Oc1ccc(C#N)c(Cl)c1]

ABM-35: trans 6-Amino-N-[3-(3-chloro-4-cyanophenoxy)-2,2,4,4-tetramethylcyclobutyl]pyridine-3-carboxamide

ABM-36: trans 4-[(5-Hydroxypentyl)amino]-N-[3-(3-chloro-4-cyanophenoxy)-2,2,4,4-tetramethylcyclobutyl]benzamide

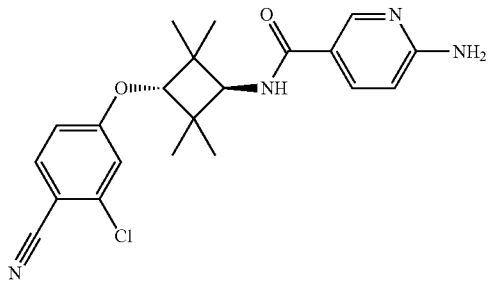 [SMILES: CC1(C)[C@H](NC(=O)c2ccc(N)nc2)C(C)(C)[C@H]1Oc1ccc(C#N)c(Cl)c1]

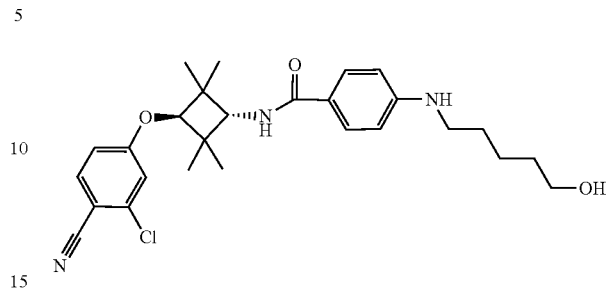

ABM-37: trans tert-Butyl 2-({5-[(4-{[3-(3-chloro-4-cyanophenoxy)-2,2,4,4-tetramethylcyclobutyl]carbamoyl}phenyl)aminopentyl}oxy)acetate

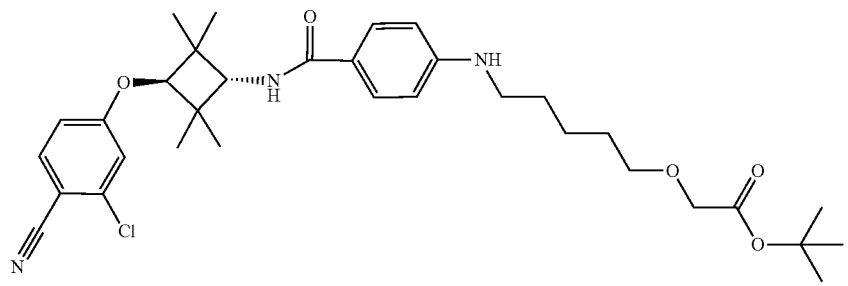 [SMILES: CC(C)(C)OC(=O)COCCCCCNc1ccc(C(=O)N[C@H]2C(C)(C)[C@H](Oc3ccc(C#N)c(Cl)c3)C2(C)C)cc1]

ABM-38: N-((1r,3r)-3-(4-cyanophenoxy)-2,2,4,4-tetramethylcyclobutyl)-4-methylbenzamide

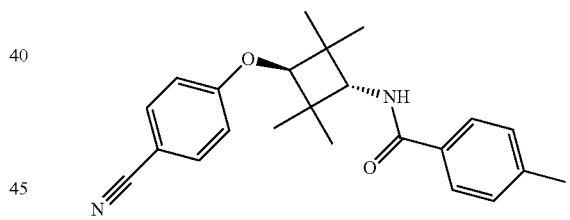

ABM-39: N-((1r,4r)-4-(3-chloro-4-cyanophenoxy)cyclohexyl)-6-methylpyridazine-3-carboxamide

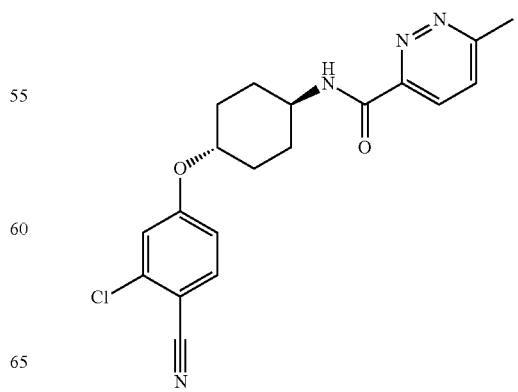

513
ABM-40: N-((1r,4r)-4-(3-chloro-4-cyanophenoxy)cyclohexyl)-6-methylpyridazine-3-carboxamide
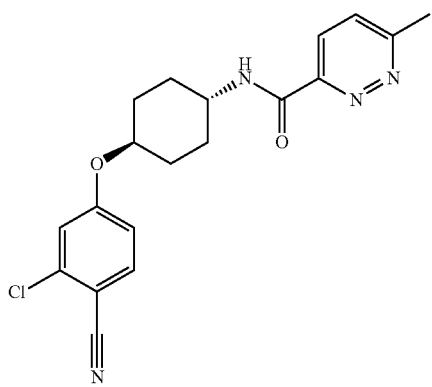 [SMILES: Cc1ccc(C(=O)N[C@H]2CC[C@H](Oc3ccc(C#N)c(Cl)c3)CC2)nn1]
Synthesis of CLM Moieties
Some non-limiting exemplary methods to generate the CLMs as described herein are summarized as shown below.
1
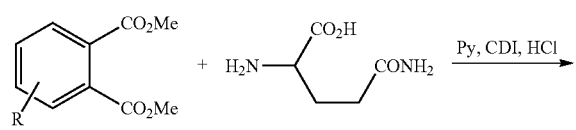
2
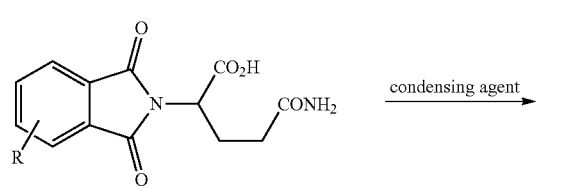
3
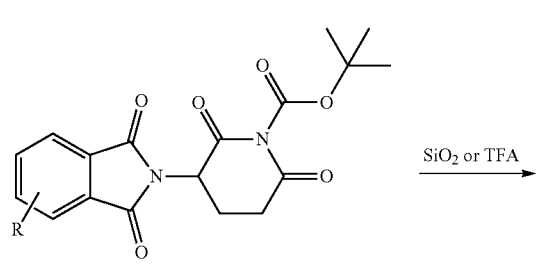
514
-continued
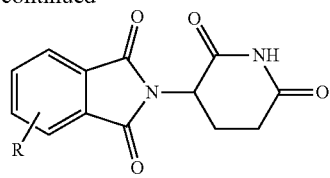
4
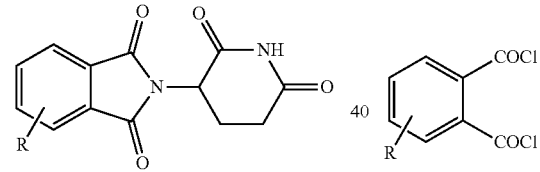
5
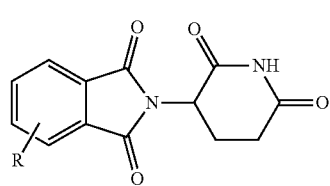
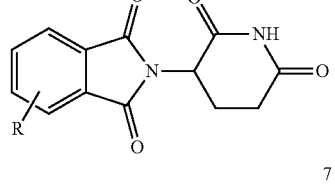
6
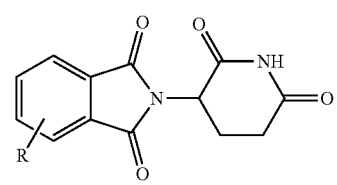
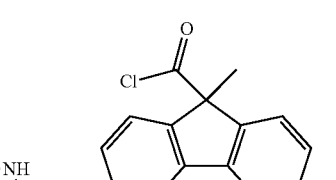
7
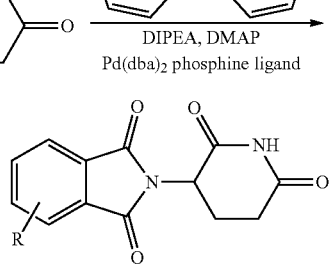

515
-continued
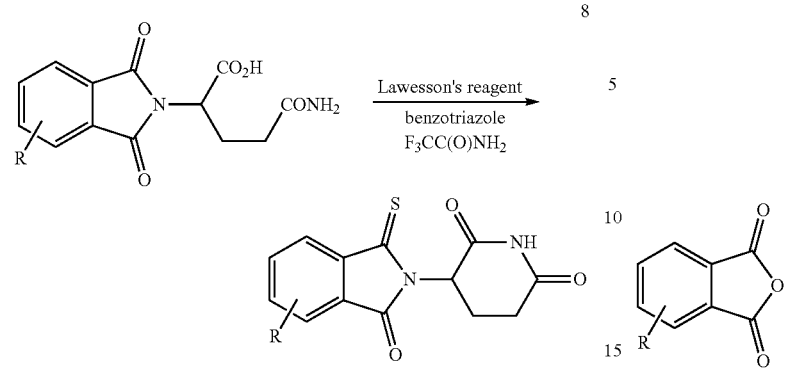
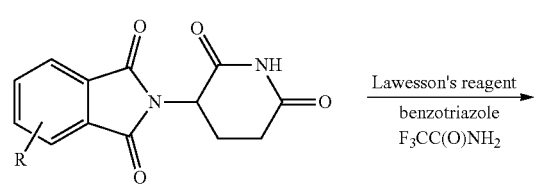
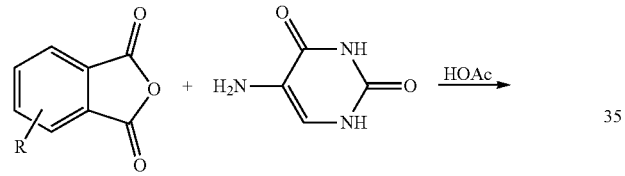
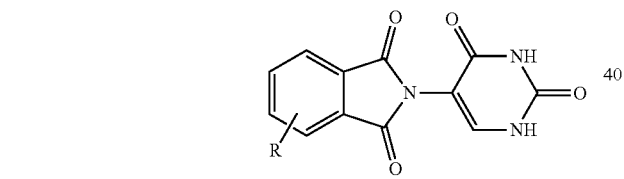
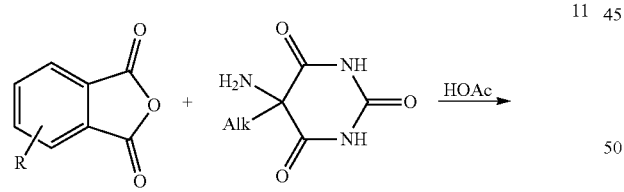
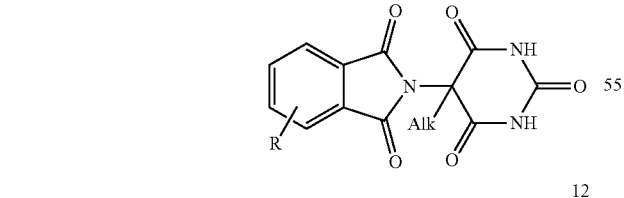
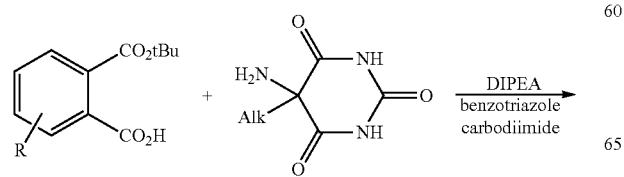
516
-continued
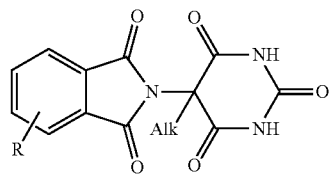
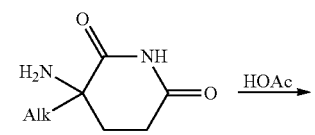
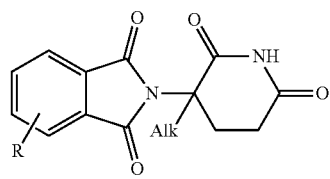
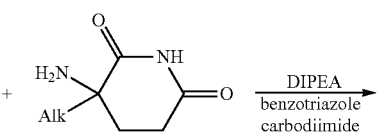
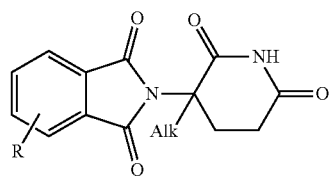
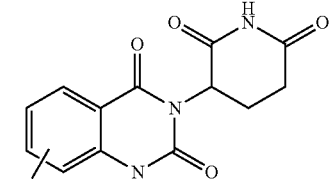
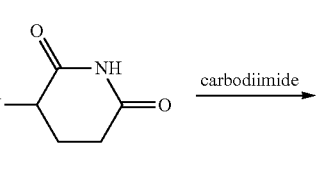
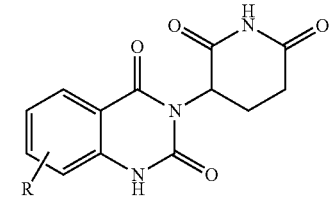

517
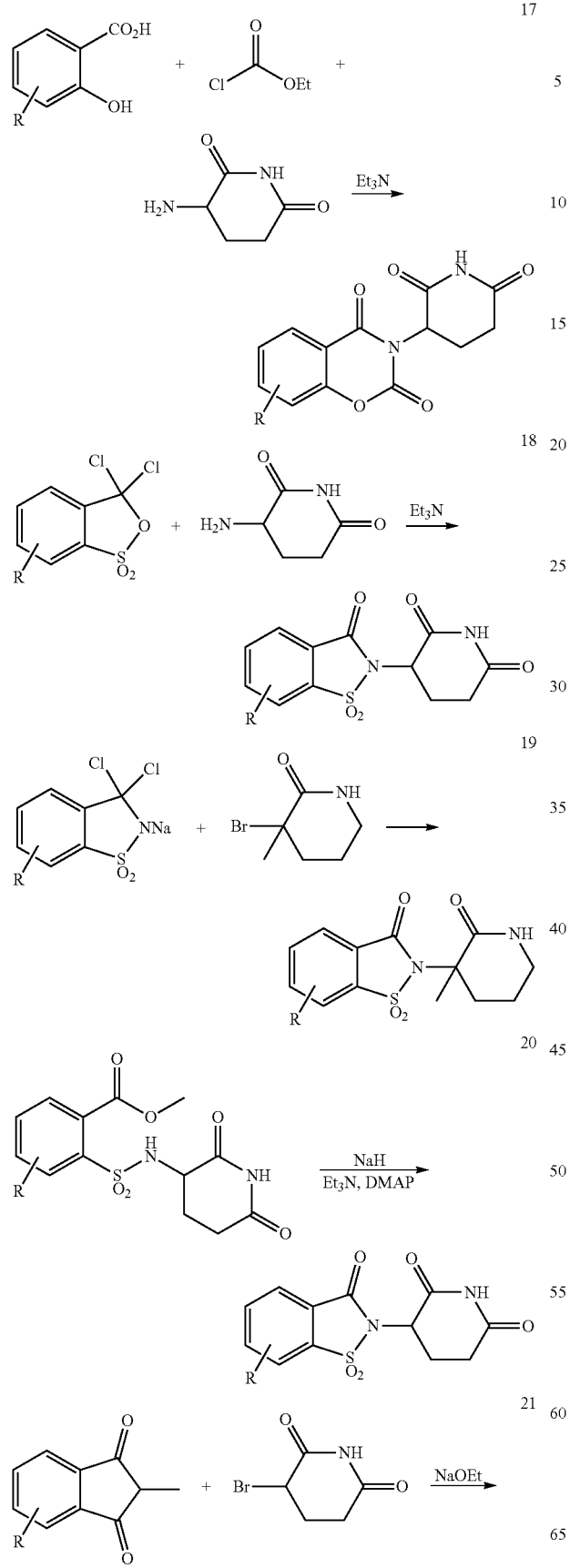
518
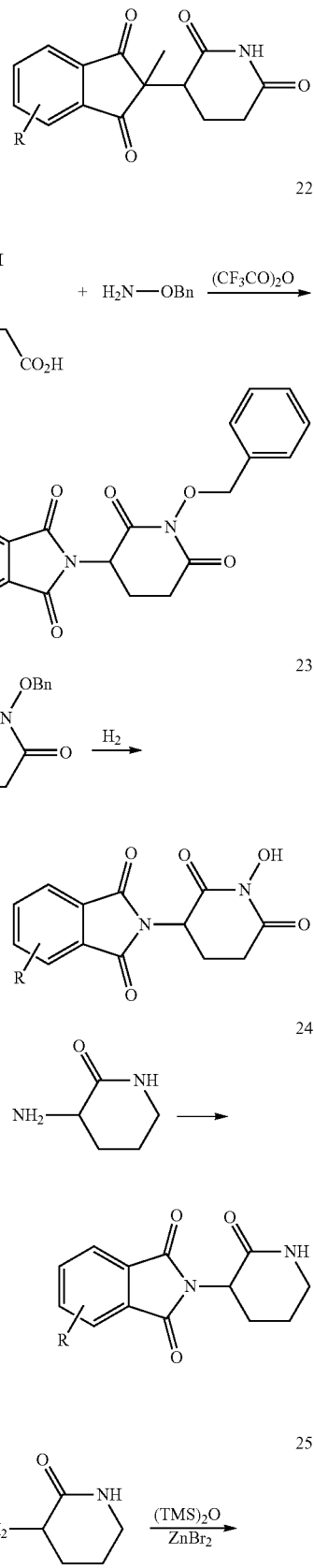

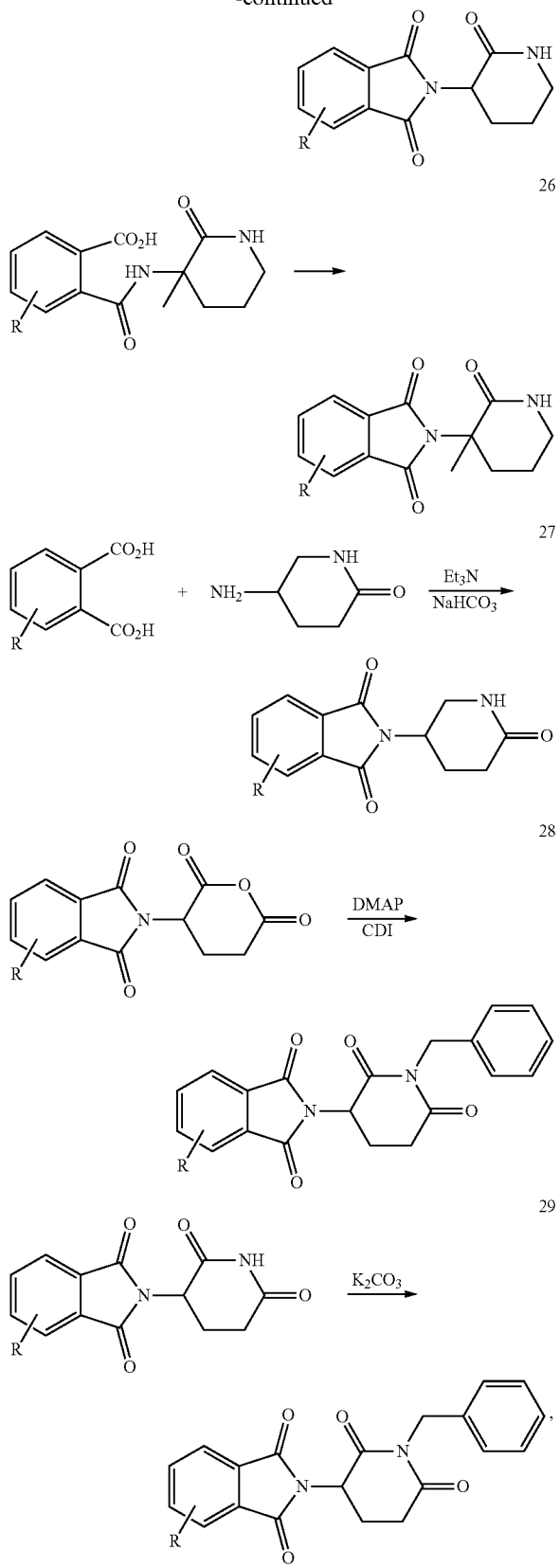

wherein R comprises 1-4 independently selected functional groups or atoms, and optionally, one of which is modified to be covalently joined to a ABM, a chemical linker group (L), a ULM, CLM (or CLM') or combination thereof.

As shown in representative reaction 1, dimethyl phthalate derivatives can be condensed with glutamine (racemate or enantiomer) or glutamine analogs then further reacted with agents such as carbonyl diimidazole to form 2-(2,6-dioxopiperidin-3-yl)-2,3-dihydro-1H-isoindole-1,3-dione derivatives.

Alternatively as shown in representative reaction 2, the intermediate phthalimide produced in the initial condensation described above may be separately prepared and/or isolated and then reacted with dehydrating agents such as trifluoroacetamide, POCl₃ or acetic anhydride to form the desired 2-(2,6-dioxopiperidin-3-yl)-2,3-dihydro-1H-isoindole-1,3-dione derivatives. The same type of intermediate phthalimide can also be reacted with Lawesson's reagent prior to the dehydration step to provide thio analogs such as that shown in representative reactions 8 and 9.

Protected examples of 2-(2,6-dioxopiperidin-3-yl)-2,3-dihydro-1H-isoindole-1,3-dione derivatives such as the $N^1$-BOC species shown in representative example 3 can be deprotected to reveal the target 2-(2,6-dioxopiperidin-3-yl)-2,3-dihydro-1H-isoindole-1,3-dione derivatives by using, in this case, reagents such as TFA or silica.

Phthalic anhydrides such as that shown in representative example 4 can be ring-opened by reaction with amines such as 3-aminopiperidine-2,6-dione to form an intermediate carboxylate species, that on treatment with carbonyldiimidazole and benzotriazole will form the target 2-(2,6-dioxopiperidin-3-yl)-2,3-dihydro-1H-isoindole-1,3-dione derivatives. Alternatively, the two components may be combined in the presence of acetic acid to provide desired product as shown in representative reaction 13.

In an analogous reaction, anhydride derivatives like those shown in representative reaction 5 may be reacted with amines (ammonia in the example shown) then carbonyldiimidazole to form the desired 2-(2,6-dioxopiperidin-3-yl)-2,3-dihydro-1H-isoindole-1,3-dione derivatives.

Where phthaloyl chlorides are available, direct condensation with glutamine (racemate or enantiomer) or glutamine analogs is possible, followed by further reaction with agents such as carbonyl diimidazole to form 2-(2,6-dioxopiperidin-3-yl)-2,3-dihydro-1H-isoindole-1,3-dione derivatives as shown in representative reaction 6.

o-Bromobenzamides can be reacted with a source of CO such as the acid chloride shown in representative reaction 7 in the presence of a palladium catalyst and associated phosphine ligand to produce the desired 2-(2,6-dioxopiperidin-3-yl)-2,3-dihydro-1H-isoindole-1,3-dione derivatives. Alternatively CO gas itself may be used in conjunction with rhodium (II) catalysts and silver carbonate to provide the desired products.

2-(2,4-dioxo-1,2,3,4-tetrahydropyrimidin-5-yl)-2,3-dihydro-1H-isoindole-1,3-dione, and 5-(1,3-dioxo-2,3-dihydro-1H-isoindol-2-yl)-1,3-diazinane-2,4,6-trione derivatives can be prepared by analogous means to some of the methods described above for 2-(2,6-dioxopiperidin-3-yl)-2,3-dihydro-1H-isoindole-1,3-dione derivatives. In representative reactions 20 and 21, a phthalic anhydride can be reacted with 5-amino-1,2,3,4-tetrahydropyrimidine-2,4-dione or 5-amino-1,3-diazinane-2,4,6-trione derivatives, respectively, in the presence of acetic acid to form the desired products.

Alternatively, 5-(1,3-dioxo-2,3-dihydro-1H-isoindol-2-yl)-1,3-diazinane-2,4,6-trione derivatives can be prepared by reaction of 5-amino-1,3-diazinane-2,4,6-trione derivatives with phthalic acid mono tert-butyl esters in the presence of Hunig's base, a carbodiimide and benzotriazole as shown in representative reaction 12. Similar conditions can be employed for the preparation of 2-(2,6-dioxopiperidin-3-yl)-2,3-dihydro-1H-isoindole-1,3-dione derivatives from phthalic acid mono tert-butyl esters as shown in representative reaction 14.

Compounds such as 3-(2,6-dioxopiperidin-3-yl)-1,2,3,4-tetrahydroquinazoline-2,4-dione can be prepared from anthranilic acid derivatives by reaction of 3-aminopiperidine-2,6-diones with a carbodiimide as in representative reaction 16. The intermediate benzamide product may be isolated (or separately produced) and further reacted with a carbodiimide to produce 3-(2,6-dioxopiperidin-3-yl)-1,2,3,4-tetrahydroquinazoline-2,4-dione derivatives as shown in representative reaction 15.

3-(2,6-Dioxopiperidin-3-yl)-3,4-dihydro-2H-1,3-benzoxazine-2,4-dione analogs can be prepared by activation of salicylic acids with chloroformates then condensation with 3-aminopiperidine-2,6-diones as shown in representative reaction 17.

3,3-Dichloro-2,1$\lambda^6$-benzoxathiole-1,1-diones as shown in representative reaction 18 can be prepared by reaction of 2-sulfobenzoic acids with $POCl_3$ and $PCl_5$. These compounds can be reacted with amino derivatives to produce, for example, desired 2-(2,6-dioxopiperidin-3-yl)-2,3-dihydro-1$\lambda^6$,2-benzothiazole-1,1,3-trione derivatives.

As shown in representative reaction 19, anions of saccharin derivatives can be alkylated with electrophiles such as the 3-bromo-3-methylpiperidin-2-one to produce targeted 2-(3-methyl-2-oxopiperidin-3-yl)-2,3-dihydro-1$\lambda^6$,2-benzothiazole-1,1,3-trione derivatives.

Analogs of 2-(2,6-dioxopiperidin-3-yl)-2,3-dihydro-1$\lambda^6$,2-benzothiazole-1,1,3-trione may also be prepared by reaction of methyl 2-[(2,6-dioxopiperidin-3-yl)sulfamoyl]benzoate with strong bases such as sodium hydride (see representative reaction 20).

Deprotonation of 2-methyl-2,3-dihydro-1H-indene-1,3-dione derivatives with sodium ethoxide then reaction with electrophiles such as 3-bromopiperidin-2,6-dione affords 3-(2-methyl-1,3-dioxo-1H-inden-2-yl)piperidine-2,6-dione as shown in representative reaction 21.

Preparation of Ni-substituted compounds such as 2-[1-(benzyloxy)-2,6-dioxopiperidin-3-yl]-2,3-dihydro-1H-isoindole-1,4-dione (representative reaction 22) can be achieved by reaction of 2-(1,3-dioxo-2,3-dihydro-1H-isoindol-2-yl)pentanedioic acid with N-benzylhydroxylamine and with trifluoroacetic anhydride.

In turn, molecules such as 2-[1-(benzyloxy)-2,6-dioxopiperidin-3-yl]-2,3-dihydro-1H-isoindole-1,4-dione (representative reaction 23) may be subject to benzyl removal under hydrogenation conditions to yield $N^1$-hydroxy analogs such as 2-(1-hydroxy-2,6-dioxopiperidin-3-yl)-2,3-dihydro-1H-isoindole-1,3-dione.

In representative reaction 24, methyl 1,3-dioxo-2,3-dihydro-1H-isoindole-2-carboxylate (and analogs) is reacted with 3-aminopiperidin-2-one to provide 2-(2-oxopiperidin-3-yl)-2,3-dihydro-1H-isoindole-1,3-diones.

The same amine can also be reacted with phthalic anhydride derivatives in the presence of a Lewis acid such as zinc bromide and trimethylsilyl ether to yield the same type of product as shown in representative reaction 25. Intermediate products from this reaction if isolated or otherwise prepared (representative reaction 26) can be pushed to full cyclization through use of a dehydrating agent.

The isomeric derivatives such as 2-(6-oxopiperidin-3-yl)-2,3-dihydro-1H-isoindole-1,3-dione shown in representative reaction 27 are attainable through reaction of phthalic acid with 5-aminopiperidin-2-one.

Preparation of $N^1$-substituted compounds such as 2-(1-benzyl-2,6-dioxopiperidin-3-yl)-2,3-dihydro-1H-isoindole-1,4-dione (representative reactions 28 and 29) can be achieved through multiple routes. For example the anhydride (2-(2,6-dioxooxan-3-yl)-2,3-dihydro-1H-isoindole-1,3-dione) can be condensed with 3-aminopiperidine-2,6-dione in the presence of DMAP and carbonyldiimidazole (representative reaction 28), or 2-(2,6-dioxopiperidin-3-yl)-2,3-dihydro-1H-isoindole-1,3-dione derivatives can be alkylated with electrophiles such as benzyl bromide in the presence of base as shown in representative reaction 29.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Synthesis of Linker Chemistry, L

L-1: 2-(3-(5-(tosyloxy)pentyloxy)propoxy)acetic acid

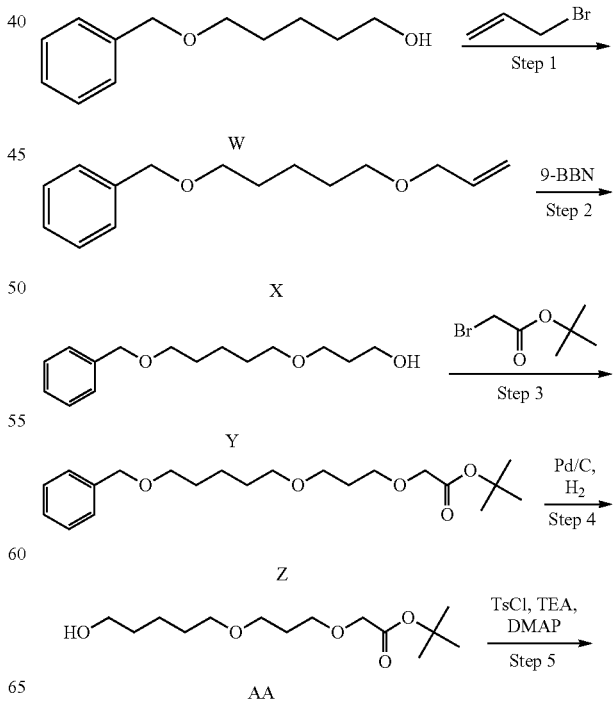

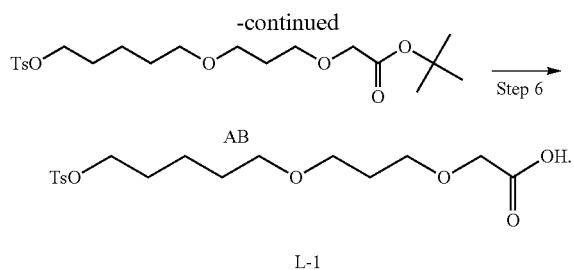

Step 1: Synthesis of ({[5-(prop-2-en-1-yloxy)pentyl]oxy}methyl)benzene

To a stirred solution of 5-(benzyloxy)pentan-1-ol (W, 4.0 g, 20.59 mmol) in N,N-dimethylformamide (50 mL) was added sodium hydride (1.24 g, 51.67 mmol) in portions at 0° C. under an atmosphere of nitrogen. The resulting mixture was then stirred at room temperature for 1 hour. To this mixture was added 3-bromoprop-1-ene (3.71 g, 30.67 mmol), the reaction mixture was stirred overnight at 60° C. in an oil bath. LC-MS indicated formation of the desired product. The reaction mixture was cooled to 0° C. and then quenched by water (100 mL), the resulting mixture was extracted with ethyl acetate (200 mL×2). The organic layers were combined, washed with saturated aqueous solution of sodium chloride (60 mL), dried over anhydrous sodium sulfate and then concentrated under reduced pressure to give a crude residue. The residue was purified by a flash silica gel chromatography (eluent: ethyl acetate/petroleum ether (v:v=1:40)) to give 4.57 g of X. $^1$H NMR (300 MHz, CDCl$_3$): δ 7.36 (s, 4H), 7.32 (m, 1H), 5.98 (m, 1H), 5.33 (m, 1H), 5.21 (m, 1H), 4.53 (s, 2H), 3.99 (m, 2H), 3.53 (m, 4H), 1.72 (m, 4H), 1.52 (m, 2H). LC-MS (ES$^+$): m/z 235.00 [MH$^+$], $t_R$=1.18 min (2.0 minute run).

Step 2: Synthesis of 3-{[5-(benzyloxy)pentyl]oxy}propan-1-ol (Y)

To a 250-mL round-bottom flask with 9-BBN (0.5 M in THF, 77 mL) was added a solution of ({[5-(prop-2-en-1-yloxy)pentyl]oxy}methyl)benzene (X, 3.0 g, 12.80 mmol) in anhydrous tetrahydrofuran (20 mL) with stirring at 0° C. under an atmosphere of nitrogen. The resulting solution was stirred overnight at room temperature. LC-MS indicated formation of the desired product. Methanol (15 mL, with 30% sodium hydroxide and 30% H$_2$O$_2$) was added to the reaction and the resulting mixture was stirred at room temperature for 2 hours. This mixture was then extracted with ethyl acetate (20 mL×3). The organic layers were combined, washed with saturated aqueous solution of sodium chloride (100 mL), dried over anhydrous sodium sulfate and then concentrated under reduced pressure to give a crude residue. The residue was purified by a flash silica gel chromatography (eluent: ethyl acetate/petroleum ether (v:v=1:1)) to provide 1.96 g of Y as light yellow oil. $^1$H NMR (300 MHz, CDCl$_3$): δ 7.34 (m, 5H), 4.49 (s, 2H), 3.75 (m, 2H), 3.59 (m, 2H), 3.49 (m, 4H), 2.65 (bs, 1H), 1.84 (m, 2H), 1.68 (m, 4H), 1.50 (m, 2H). LC-MS (ES$^+$): m/z 253.17 [MH$^+$], $t_R$=1.44 min (2.6 minute run).

Step 3: Synthesis of tert-butyl 2-(3-{[5-(benzyloxy)pentyl]oxy}propoxy)acetate (Z)

To a stirred solution of 3-{[5-(benzyloxy)pentyl]oxy}propan-1-ol (Y, 3.7 g, 14.66 mmol) in dichloromethane (30 mL) was added a solution of NaOH in water (37%, 30 mL) followed by tert-butyl 2-bromoacetate (11.39 g, 58.39 mmol) and TBACl (4.17 g). The resulting mixture was stirred at room temperature overnight. LC-MS indicated formation of the desired product. The reaction mixture was then extracted with ethyl acetate (50 mL×3). The organic layers were combined, washed with saturated aqueous solution of sodium chloride (60 mL), dried over anhydrous sodium sulfate and then concentrated under reduced pressure to give a crude residue. The residue was purified by a flash silica gel chromatography (eluent: ethyl acetate/petroleum ether (v:v=1:2) to give 3.2 g of Z as a yellow oil. $^1$H NMR (400 MHz, CDCl$_3$): δ 7.34 (s, 4H), 7.29 (m, 1H), 4.50 (s, 4H), 4.3 (m, 2H), 3.51 (m, 4H), 3.42 (m, 2H), 1.98 (m, 2H), 1.67 (m, 4H), 1.48 (s, 9H), 1.46 (m, 2H). LC-MS (ES$^+$): m/z 367.25 [MH$^+$], $t_R$=1.28 min (2.0 minute run).

Step 4: Synthesis of tert-butyl 2-[3-[(5-hydroxypentyl)oxy]propoxy]acetate (AA)

To a stirred solution of tert-butyl 2-(3-{[5-(benzyloxy)pentyl]oxy}propoxy)acetate (Z, 3.2 g, 8.73 mmol) in methanol (30 mL) was added AcOH (1.5 mL), palladium on carbon (1.5 g) under an atmosphere of nitrogen. Hydrogen was then introduced to the reaction mixture via a hydrogen balloon, and the reaction was stirred at room temperature for 3 hours. The solid material was removed by filtration, the solution was concentrated under vacuum to provide 2.3 g of AA as light yellow oil, which was used for the next step without any further purifications. LC-MS (ES$^+$): m/z 277.10 [MH$^+$], $t_R$=0.86 min (2.0 minute run).

Step 5: Synthesis of tert-butyl 2-[3-({5-[(4-methylbenzenesulfonyl)oxy]pentyl}oxy)propoxy]acetate (AB)

To a stirred solution of tert-butyl 2-[3-[(5-hydroxypentyl)oxy]propoxy]acetate (AA, 2.3 g, 8.32 mmol) in dichloromethane (30 mL) was added 4-methylbenzene-1-sulfonyl chloride (3.17 g, 16.63 mmol), triethylamine (2.52 g, 24.90 mmol) and 4-dimethylaminopyridine (203 mg, 1.66 mmol) at room temperature. The resulting mixture was stirred overnight at room temperature. The resulting mixture was concentrated under reduced pressure to give a crude residue, which was purified by a flash silica gel chromatography (eluent: ethyl acetate/petroleum ether (v:v=1:2) to give 2.6 g of AB as a yellow oil. $^1$H NMR (300 MHz, CDCl$_3$): δ 7.77 (d, J=8.1 Hz, 2H), 7.36 (d, J=8.1 Hz, 2H), 4.51 (s, 2H), 4.31 (m, 2H), 4.13 (m, 2H), 3.52 (m, 4H), 2.05 (s, 3H), 1.97 (m, 2H), 1.69 (m, 4H), 1.48 (s, 9H), 1.46 (m, 2H). LC-MS (ES$^+$): m/z 431.20 [MH$^+$], $t_R$=1.21 min (2.0 minute run).

Step 1: Synthesis of 2-[3-({5-[(4-methylbenzenesulfonyl)oxy]pentyl}oxy)propoxy]acetic acid (L-1)

To a stirred solution of tert-butyl 2-[3-({5-[(4-methylbenzenesulfonyl)oxy]pentyl}oxy)propoxy]acetate (AB, 1.3 g, 3.02 mmol) in dichloromethane (10 mL) was added trifluoroacetic acid (10 mL) at room temperature. The resulting solution was stirred at room temperature for 3 hours. The reaction mixture was then concentrated under vacuum to give 1.5 g (crude) of L-1, which was used for next step without any further purification. LC-MS (ES$^+$): m/z 375.34 [MH$^+$], $t_R$=1.39 min (2.6 minute run).

The following Linkers (L) were prepared in a similar manner as for the preparation of L-1.

525

L-2: 2-(3-(3,3-dimethyl-5-(tosyloxy)pentyloxy)propoxy)acetic acid

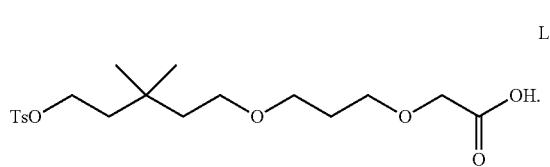

L-2

L-3: 2-(3-(3-hydroxy-5-(tosyloxy)pentyloxy)propoxy)acetic acid

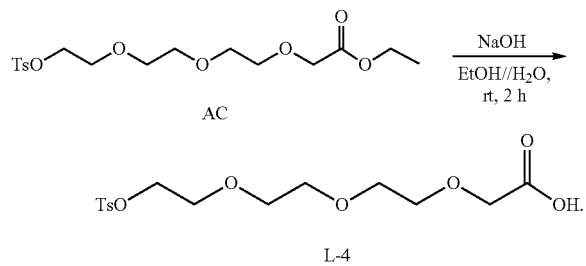

L-3

L-4: 2-(2-(2-(2-(tosyloxy)ethoxy)ethoxy)ethoxy)acetic acid

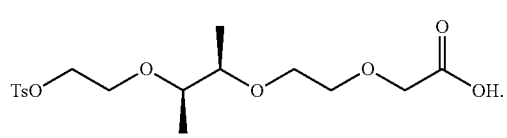

L-4

To a stirred solution of ethyl 2-[2-(2-{2-[(4-methylbenzenesulfonyl)oxy]ethoxy}ethoxy)ethoxy]acetate (AC, 2 g, 5.12 mmol, 1.00 equiv) in methanol (20 mL) was added a solution of NaOH (500 mg, 12.50 mmol) in water (4 mL), and the resulting mixture was stirred at room temperature for 2 hours. Aqueous hydrogen chloride (1 M) was then added to the reaction mixture to adjust pH to ~5. Solids precipitated were collected by filtration to give L-4 (yield: 98%). Mass (ES+): m/z 363, [MH+].

The following Linkers (L) were prepared in a similar manner as for the preparation of L-4.

L-5: 2-(2-((2R,3R)-3-(2-(tosyloxy)ethoxy)butan-2-yloxy)ethoxy)acetic acid

L-5

526

L-6: 2-(2-((2S,3S)-3-(2-(tosyloxy)ethoxy)butan-2-yloxy)ethoxy)acetic acid

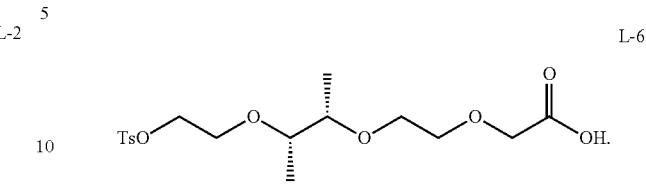

L-6

L-7: 2-(4-(4-(tosyloxy)butoxy)butoxy)acetic acid

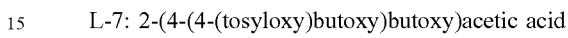

Step 1: Synthesis of 4-{4-[(4-methylbenzenesulfonyl)oxy]butoxy}butan-1-ol (AE)

To a stirred solution of 4-(4-hydroxybutoxy)butan-1-ol (AD, 2 g, 12.33 mmol) in dichloromethane (20 mL) was added Ag$_2$O (4.25 g, 18.49 mmol), KI (409 mg, 2.46 mmol) and TsCl (2.345 g, 12.30 mmol). The resulting mixture was stirred at room temperature for 12 hours. The inorganic salt formed was removed by filtration and the organic solution was concentrated under reduced pressure to give a crude residue. The residue was purified by flash silica gel chromatography (eluent: ethyl acetate/petroleum ether (v:v=1:1)) to give AE (yield: 28%) as a colorless oil.

Step 2: Synthesis of ethyl 2-(4-{4-[(4-methylbenzenesulfonyl)oxy]butoxy}butoxy)acetate (AF)

To a stirred solution of 4-{4-[(4-methylbenzenesulfonyl)oxy]butoxy}butan-1-ol (AE, 1.1 g, 3.48 mmol) in dichloromethane (10 mL) was slowly added BF$_3$·Et$_2$O (49.4 mg, 0.35 mmol) followed by ethyl 2-diazoacetate (794 mg, 6.96 mmol) at 0° C. The resulting mixture was stirred overnight at room temperature. The reaction was then quenched by water (2.0 mL). The resulting mixture was extracted with dichloromethane (50 mL×3), the organic layers were combined, dried over anhydrous sodium sulfate and then concentrated under reduced pressure to give a crude residue. The residue was purified by flash silica gel chromatography (eluent: ethyl acetate/petroleum ether (v:v=1:4) to give AF (yield: 93 as light yellow oil. Mass (ES+): m/z 403.10 [MH+].

Step 3: Synthesis of 2-(4-{4-[(4-methylbenzene-sulfonyl)oxy]butoxy}butoxy)acetic acid (L-7)

To a stirred solution of ethyl 2-(4-{4-[(4-methylbenzene-sulfonyl)oxy]butoxy}butoxy)acetate (AF, 1.3 g, 3.23 mmol) in methanol (25 mL) was added a solution of NaOH (388 mg, 9.70 mmol) in water (6 mL) at room temperature. The resulting solution was stirred at room temperature for 4 hours. The bulk of organic solvent was removed under reduced pressure, to the resulting mixture was added aqueous hydrogen chloride (1.0 M) to adjust the pH=~5. The solution was then extracted with ethyl acetate (250 mL×3), the organic layers were combined and dried over anhydrous sodium sulfate, concentrated under reduced pressure to give I-7 (yield: 93%) as light yellow oil. Mass (ES+): m/z 375.05 [MH+].

L-8: tert-butyl 2-(3-(4-(tosyloxy)butoxy)propoxy)acetate

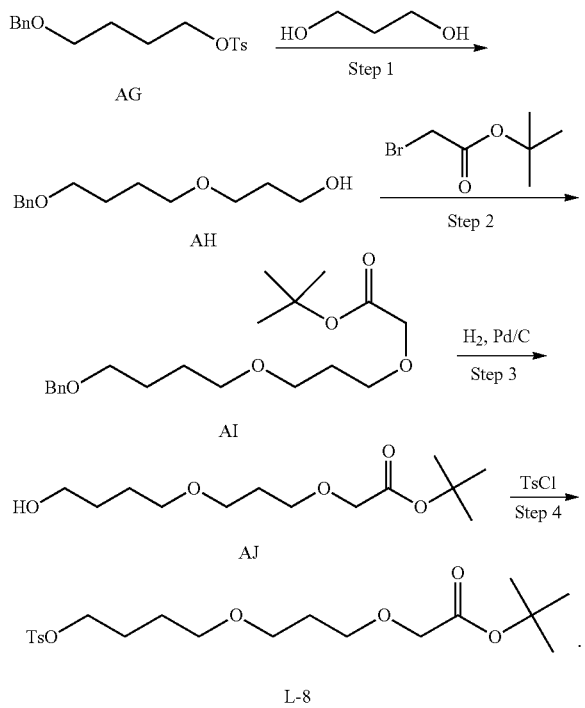

L-8

Step 1. Synthesis of 3-[4-(benzyloxy)butoxy]propan-1-ol (AH)

To a stirred solution of propane-1, 3-diol (1.52 g, 19.98 mmol) in N, N-dimethylformamide (20 mL) was added sodium hydride (840 mg, 35.00 mmol) at room temperature, the resulting mixture was stirred at room temperature for 30 minutes. Then to the mixture was added 4-(benzyloxy) butyl 4-methylbenzene-1-sulfonate (AG, 6.68 g, 19.97 mmol) and the reaction was stirred overnight at 50° C. TLC indicated formation of the desired product, at this time the reaction was allowed to cool down to room temperature. Water (10 mL) was added slowly to quench the reaction; the resulting mixture was then extracted with ethyl acetate (80 mL×2). The organic layers were combined, washed with saturated aqueous solution of sodium chloride (20 mL), dried over anhydrous sodium sulfate and then concentrated under reduced pressure to give a crude residue, which was purified by flash silica gel chromatography (eluent: ethyl acetate/petroleum ether (v:v=1:2)) to give AH (yield: 67%) as a light yellow oil. $^1$H NMR (300 MHz, CDCl$_3$) δ 7.38-7.29 (m, 5H), 4.52 (m, 2H), 3.80 (m, 2H), 3.61 (m, 2H), 3.49-3.46 (m, 4H), 2.04 (m, 2H), 1.82 (m, 2H), 1.68 (m, 2H); Mass (ES+): m/z 239.05 [MH+].

Step 2. Synthesis of tert-butyl 2-[3-[4-(benzyloxy)butoxy]propoxy]acetate (AI)

To a stirred solution of 3-[4-(benzyloxy)butoxy]propan-1-ol (AH, 2.38 g, 9.99 mmol) in dichloromethane (15 mL) was added tert-butyl 2-bromoacetate (7.76 g, 39.78 mmol), TBAC (2.78 g, 10.00 mmol) followed by aqueous sodium hydroxide (37%, 15 mL). The resulting mixture was stirred overnight at room temperature. The reaction mixture was then extracted with dichloromethane (100 mL×3), the organic layers were combined, washed with saturated aqueous solution of sodium chloride (20 mL), dried over anhydrous sodium sulfate and then concentrated under reduced pressure to give a crude residue. The residue was purified by flash silica gel chromatography (eluent: ethyl acetate/petroleum ether (v:v=1:5)) to give AI (yield 57%) as a yellow oil. Mass (ES+): m/z 353.10 [MH+].

Step 3. Synthesis of tert-butyl 2-[3-(4-hydroxybutoxy)propoxy]acetate (AJ)

To a stirred mixture of tert-butyl 2-[3-[4-(benzyloxy)butoxy]propoxy]acetate (AI, 1 g, 2.84 mmol), palladium on carbon (10%, 200 mg) in methanol (20 mL) was added acetic acid (0.05 mL) under a nitrogen atmosphere. Hydrogen was then introduced to the reaction mixture via a balloon, the reaction was then stirred overnight at room temperature. The insoluble solids were removed by filtration and the solution phase was concentrated under reduced pressure to give the desired product (yield: 94%) as a yellow oil. Mass (ES+): m/z 263.05 [MH+].

Step 4. Synthesis of tert-butyl 2-(3-{4-[(4-methyl-benzenesulfonyl)oxy]butoxy}propoxy)acetate (L-8)

To a stirred solution of tert-butyl 2-[3-(4-hydroxybutoxy)propoxy]acetate (AJ, 700 mg, 2.67 mmol) in dichloromethane (10 mL) was added 4-methylbenzene-1-sulfonyl chloride (558.4 mg, 2.93 mmol), TEA (539.5 mg, 5.33 mmol) and 4-dimethylaminopyridine (32.6 mg, 0.27 mmol). The resulting mixture was stirred overnight at room temperature. The bulk of solvent was removed under reduced pressure to give a crude residue, which was purified by flash silica gel chromatography (eluent: ethyl acetate/petroleum ether (v:v=1:2)) to give titled product (yield: 52%) as a yellow oil. $^1$H NMR (300 MHz, CDCl$_3$) δ7.79 (d, J=8.4 Hz, 2H), 7.35 (d, J=8.0 Hz, 2H), 4.05 (m, 2H), 3.95 (s, 2H), 3.59 (m, 2H), 3.48 (m, 2H), 3.38 (m, 2H), 2.46 (s, 3H), 1.82 (m, 2H), 1.70 (m, 2H), 1.57 (m, 2H), 1.50 (s, 9H); Mass (ES+): m/z 417.05 [MH+].

529
L-9: tert-butyl 2-(4-(3-(tosyloxy)propoxy)butoxy)acetate

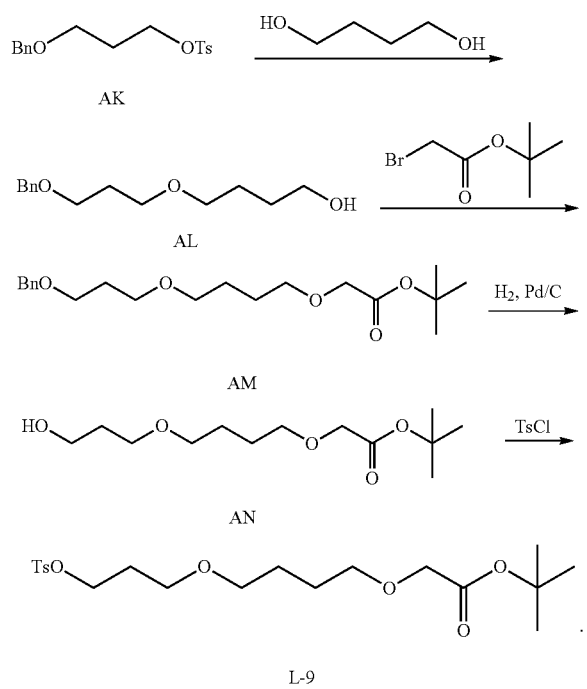

L-9 was prepared in a similar manner as that used to prepare L-8, except that AK was used in place of AG. Mass (ES$^+$): m/z 439.15 [MNa$^+$]

L-10: tert-butyl 2-(6-(tosyloxy)hexa-2,4-diynyloxy)acetate

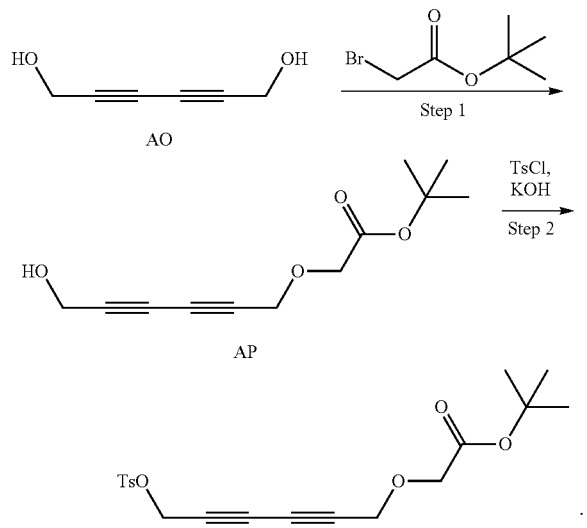

530
Step 1: Synthesis of tert-butyl 2-[(6-hydroxyhexa-2,4-diyn-1-yl)oxy]acetate (AP)

To a stirred solution of hexa-2, 4-diyne-1, 6-diol (AO, 100 mg, 0.91 mmol) in N, N-dimethylformamide (5 mL) was added sodium hydride (32 mg, 1.33 mmol) at 0° C. The resulting mixture was then warmed up to room temperature and stirred at room temperature for 30 minutes. The reaction mixture was cooled to 0° C. followed by addition of tert-butyl 2-bromoacetate (176 mg, 0.90 mmol), and the resulting mixture was stirred at 0° C. for 2 h. LC-MS indicated formation of the desired product. The reaction was then quenched by water (10 mL, added slowly) at 0° C., and was extracted with ethyl acetate (20×2 mL). The organic layers were combined, dried over anhydrous sodium sulfate and then concentrated under reduced pressure to give a crude residue, which was purified by flash silica gel chromatography (eluent: ethyl acetate/petroleum ether (v:v=1:2)) to give AP (yield: 49%) as a yellow oil.

Step 2. Synthesis of tert-butyl 2-({6-[(4-methylbenzenesulfonyl)oxy]hexa-2,4-diyn-1-yl}oxy)acetate (L-10)

To a stirred solution of tert-butyl 2-[(6-hydroxyhexa-2,4-diyn-1-yl) oxy] acetate (AP, 50 mg, 0.22 mmol) in ether (2 mL) was added 4-toluenesulfonyl chloride (51 mg, 0.27 mmol) at 0° C., followed by potassium hydroxide (125 mg, 2.23 mmol) in several batches at 0° C. The resulting mixture was stirred at 0° C. for 4 hours. LC-MS indicated formation of the desired product. Water (10 mL) was added to the reaction, and the resulting mixture was extracted with ethyl acetate (20 mL×2). The organic layers were combined, dried over anhydrous sodium sulfate and then concentrated under reduced pressure to give a crude residue, which was purified by flash silica gel chromatography (eluent: ethyl acetate/petroleum ether (v:v=1:2)) to give L-10 (yield: 71%) as a yellow oil. $^1$H NMR (300 MHz, CDCl$_3$): δ 7.83 (d, J=6.0 Hz, 2H), 7.39 (d, J=6.0 Hz, 2H), 4.79 (s, 2H), 4.37 (s, 2H), 4.05 (s, 2H), 2.48 (s, 3H), 1.51 (s, 9H); LC-MS (ES$^+$): m/z 401.05 [MNa$^+$], t$_R$=1.71 min (2.6 minute run).

The following Linkers (L) were prepared in a similar manner as for the preparation of L-10.

L-11: tert-butyl 3-(6-(tosyloxy)hexa-2,4-diynyloxy)propanoate

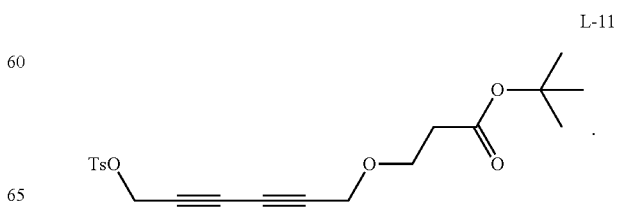

L-12: tert-butyl 4-(6-(tosyloxy)hexa-2,4-diynyloxy)butanoate

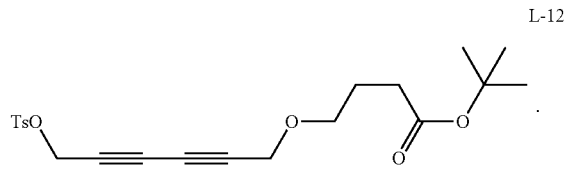

L-13: ethyl 2-(2-(2-aminoethoxy)ethoxy)acetate hydrochloride

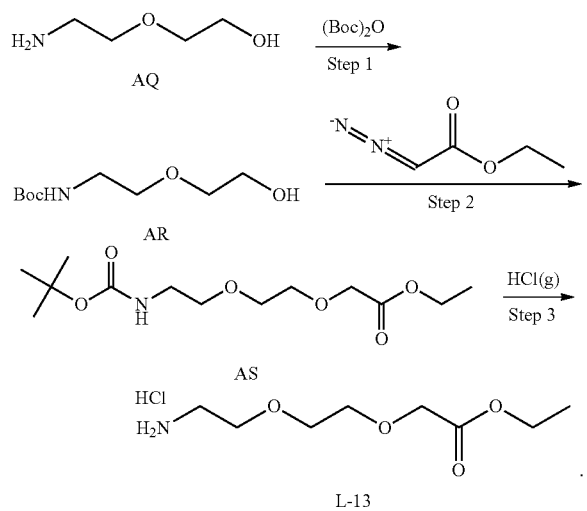

Step 1: Synthesis of tert-butyl N-[2-(2-hydroxyethoxy)ethyl]carbamate (AR)

To a stirred solution of 2-(2-aminoethoxy)ethan-1-ol (AQ, 5.25 g, 49.94 mmol) in tetrahydrofuran (100 mL) was added aqueous solution of sodium bicarbonate (20% (w/w), 40 ml) and (Boc)$_2$O (11.4 g, 52.23 mmol, added in several batches) at 0° C. The resulting mixture was then warmed up slowly to room temperature and stirred at room temperature for 5 hours. The bulk of organic solvent was removed under reduced pressure and the resulting residue was diluted with water (300 mL), extracted with of ethyl acetate (100 mL×3). The organic layers were combined, washed with saturated aqueous solution of sodium chloride (20 mL×2), dried over anhydrous sodium sulfate and then concentrated under reduced pressure to give AR (yield: 98%) as colorless oil.

Step 2: Synthesis of ethyl 2-[2-(2-{[(tert-butoxy)carbonyl]amino}ethoxy)ethoxy]acetate (AS)

To a stirred solution of tert-butyl N-[2-(2-hydroxyethoxy)ethyl]carbamate (AR, 4.0 g, 19.49 mmol) in dichloromethane (30 mL) was added 1-diazo-3-methoxypropan-2-one (3.34 g, 29.27 mmol) and BF$_3$·Et$_2$O (0.2 mL) at room temperature. The resulting solution was stirred at room temperature for 2 hours. Water (20 mL) was added to the reaction mixture, organic layer was separated and washed with brine (20 mL), dried over anhydrous sodium sulfate and concentrated under reduced pressure to give a crude residue. The residue was purified by flash silica gel chromatography (eluent: ethyl acetate/petroleum ether (v:v=1:2)) to give AS (yield: 18%) as yellow solid. $^1$H NMR (400 MHz, CDCl$_3$): δ 4.25-4.22 (q, J=7.2 Hz, 2H), 4.14 (s, 2H), 3.74 (b, 2H), 3.72 (b, 1H), 3.67-3.32 (m, 4H), 1.414 (s, 9H), 1.31 (t, J=7.2 Hz, 3H).

Step 3: Synthesis of ethyl 2-[2-(2-aminoethoxy)ethoxy]acetate hydrochloride (L-13)

To a stirred solution of ethyl 2-[2-(2-{[(tert-butoxy)carbonyl]amino}ethoxy)ethoxy]acetate (AS, 500 mg, 1.72 mmol) in 1,4-dioxane (10 mL) was introduced hydrogen chloride (gas) via bubbling at room temperature for 2 hours. The solvent was then removed under vacuum to give L-13 (yield: 99%). LC-MS (ES$^+$): m/z 192.00 [MH$^+$], t$_R$=0.41 min (2.0 minute run).

L-14: ethyl 2-(5-aminopentyloxy)acetate

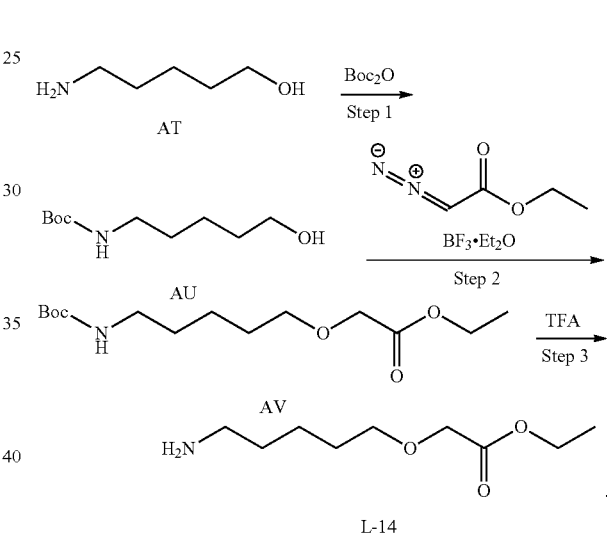

Step 1: Synthesis of tert-butyl 5-hydroxypentylcarbamate (AU)

To a stirred solution of 5-aminopentan-1-ol (AT, 3.1 g, 30.05 mmol) in dichloromethane (30 mL) was added di-tert-butyl dicarbonate (6.56 g, 30.06 mmol) at 0° C. The resulting mixture was then stirred at room temperature for 4 hours. The solvent was removed under reduced pressure to give a crude residue which was purified by flash silica gel chromatography (eluent: ethyl acetate/petroleum ether (v:v=1:2)) to give AU (yield: 98%) as a colorless oil. LC-MS (ES$^+$): m/z 204.00 [MH$^+$], t$_R$=1.29 min (2.6 minute run).

Step 2: Synthesis of ethyl 2-[(5-{[(tert-butoxy)carbonyl]amino}pentyl)oxy]acetate (AV)

To a stirred solution of tert-butyl N-(5-hydroxypentyl)carbamate (AU, 1.5 g, 7.38 mmol) in dichloromethane (10 mL) was added BF$_3$·Et$_2$O (0.1 mL) at 0° C. To this mixture was then added a solution of ethyl 2-diazoacetate (850 mg, 7.45 mmol) in dichloromethane (2 mL) at 0° C. The resulting mixture was allowed to warm up to room temperature and stirred at room temperature for 2 hours. Saturated aqueous sodium bicarbonate (30 mL) was added to the reaction, the resulting mixture was extracted with ethyl acetate (150 mL×3). The organic layers were combined, dried over anhydrous sodium sulfate and then concentrated under reduced pressure to give a crude residue, which was purified by flash silica gel chromatography (eluent: ethyl acetate/petroleum ether (v:v=1:7)) to give AV (yield: 15%) as a colorless oil. LC-MS (ES$^+$): m/z 290.05 [MH$^+$], $t_R$=1.55 min (2.6 minute run).

Step 3: Synthesis of ethyl 2-(5-aminopentyloxy)acetate (L-14)

To a stirred solution of ethyl ethyl 2-[(5-{[(tert-butoxy)carbonyl]amino}pentyl)oxy]acetate (AV, 400 mg, 1.38 mmol) in dichloromethane (5 mL) was added trifluoroacetic acid (5 mL) at room temperature. The resulting solution was stirred at room temperature for 2 hours. The reaction mixture was then concentrated under vacuum to give L-14 (yield: 84%) as a yellow oil. LC-MS (ES$^+$): m/z 190.00 [MH$^+$], $t_R$=1.01 min (2.6 minute run).

L-15: methyl 2-(2-(2-(methylamino)ethoxy)ethoxy)acetate

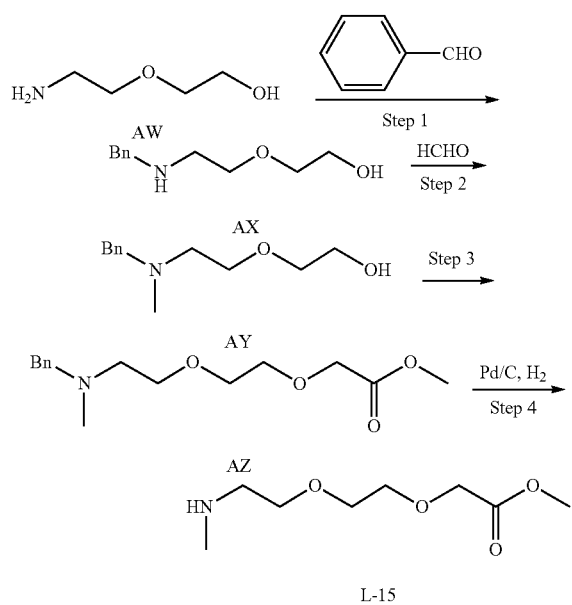

Step 1: Synthesis of 2-[2-(benzylamino)ethoxy]ethan-1-ol (AX)

To a stirred solution of 2-(2-aminoethoxy)ethan-1-ol (AW, 5.0 g) and benzaldehyde (5.0 g) in THF (50 mL) was added sodium triacetoxyborohydride (15.8 g, 74.5 mmol) at 0° C. The resulting solution was then stirred at room temperature for 4 hours. Water (50 mL) was added to the reaction and the resulting mixture was extracted with ethyl acetate (50 mL×2). The organic layers were combined, dried over anhydrous sodium sulfate and then concentrated under reduced pressure to give a crude residue, which was purified by flash silica gel chromatography (eluent: dichlorometh-ane/methanol (v:v=3:1) to give AX (yield: 85%) as a white solid. LC-MS (ES$^+$): m/z 195.95[MH$^+$], $t_R$=0.22 min (2.0 minute run).

Step 2: Synthesis of 2-{2-[benzyl(methyl)amino]ethoxy}ethan-1-ol (AY)

To a stirred solution of 2-[2-(benzylamino)ethoxy]ethan-1-ol (AX, 10.0 g) in methanol (200 mL) was added formaldehyde (38% in water) (4.9 mL) and triacetoxyborohydride (17.0 g) at room temperature. The resulting solution was stirred at room temperature for 2 hours. Saturated aq. sodium bicarbonate (100 mL) was added to the reaction, and bulk of organic solvent was then removed under reduced pressure. The resulting mixture was extracted with ethyl acetate (200 mL×3). The organic layers were combined, dried over anhydrous sodium sulfate and then concentrated under reduced pressure followed by high vacuum pump to give AY (yield: 33%) as a yellow oil. LC-MS (ES$^+$): m/z 210.00 [MH$^+$], $t_R$=0.43 min (2.0 minute run).

Step 3: Synthesis of methyl 2-(2-{2-[benzyl(methyl)amino]ethoxy}ethoxy)acetate (AZ)

To a stirred solution of 2-{2-[benzyl(methyl)amino]ethoxy}ethan-1-ol (AY, 2 g) in dichloromethane (20 mL) was added a solution of sodium hydroxide (37%) in water (20 mL) followed by tert-butyl 2-bromoacetate (7.76 g) and TBAC (2.78 g) at room temperature. The resulting mixture was stirred at room temperature for 15 hours. The aqueous layer was separated, and to which aq. hydrogen chloride (4N) was added to adjust the pH to ~3 before it was concentrated under reduced pressure to give a crude residue. Methanol (20 mL) was then added to this residue and insoluble salts were filtered out. The solution was concentrated under vacuum to give 2-(2-[2-[benzyl(methyl)amino]ethoxy]ethoxy)acetic acid (yield: 78%) as a yellow oil. To a stirred solution of 2-(2-{2-[benzyl(methyl)amino]ethoxy}ethoxy)acetic acid (2 g, 7.48 mmol, 1.00 equiv) prepare above in methanol (50 mL) was slowly added sulfuric acid (2 mL) at room temperature. The resulting solution was stirred at 70° C. in an oil bath for 3 hours. The bulk of solvent was removed under reduced pressure to give a residue, which was diluted with H$_2$O (30 mL). Sodium carbonate was then added to the mixture to adjust the pH to ~8. The mixture was then extracted with ethyl acetate (50 mL×2), the organic layers were combined, dried over anhydrous sodium sulfate and then concentrated under reduced pressure followed by high vacuum pump to give AZ (yield: 29%) as a yellow oil. LC-MS (ES$^+$): m/z 281.95 [MH$^+$], $t_R$=0.30 min (2.0 minute run).

Step 4: Synthesis of methyl 2-{2-[2-(methylamino)ethoxy]ethoxy}acetate (L-15)

To a stirred mixture of methyl 2-(2-{2-[benzyl(methyl)amino]ethoxy}ethoxy)acetate (AZ, 600 mg, 2.13 mmol) and palladium on carbon (300 mg) in methanol (30 mL) under a nitrogen atmosphere was charged with hydrogen gas via a balloon. The resulting mixture was stirred at room temperature for 15 hours. The solid material was removed by filtration and the solution was concentrated under vacuum to give L-15 (400 mg) as yellow oil, which was used for next step without any further purifications. LC-MS (ES$^+$): m/z 191.95 [MH$^+$], $t_R$=0.31 min (2.0 minute run).

535

L-16: ethyl 2-(5-(methylamino)pentyloxy)acetate

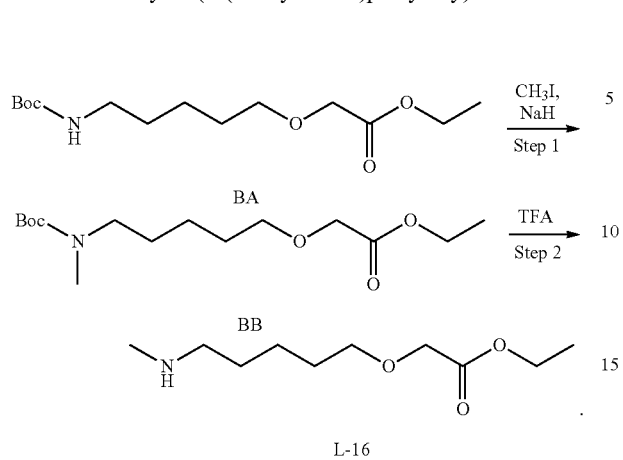

Step 1: Synthesis of ethyl 2-[(5-{[(tert-butoxy)carbonyl](methyl)amino}pentyl)oxy]acetate (BB)

To a stirred solution of ethyl 2-[(5-{[(tert-butoxy)carbonyl]amino}pentyl)oxy]acetate (BA, 1.1 g, 3.8 mmol) in N,N-dimethylformamide (10 mL) was added CH₃I (0.71 mL, 11.4 mmol) at 0° C., followed by sodium hydride (304 mg, 7.60 mmol, 60% in mineral oil) in several portions at 0° C. The resulting mixture was stirred at room temperature for 16 hours. Water (1.0 mL) was added and the resulting mixture was extracted with ethyl acetate (50 mL×2). The organic layers were combined, washed with saturated aqueous solution of sodium chloride (100 mL), dried over anhydrous sodium sulfate and then concentrated under reduced pressure to give a crude residue which was purified by a flash silica gel chromatography (eluent: ethyl acetate/petroleum ether (v:v=1:10)) to give BB (yield: 21%) as a yellow oil. LC-MS (ES⁺): m/z 326.20 [MNa⁺], $t_R$=1.55 min (2.6 minute run).

Step 2: Synthesis of ethyl 2-{[5-(methylamino)pentyl]oxy}acetate (L-16)

To a stirred solution of ethyl 2-[(5-{[(tert-butoxy)carbonyl](methyl)amino}pentyl)oxy]acetate (BB, 240 mg, 0.79 mmol) in dichloromethane (5 mL) was added trifluoroacetic acid (0.5 mL). The resulting solution was stirred at room temperature for 16 hours. The solvents were removed under recued pressure followed by high vacuum pump to give L-16 (yield: 99%) as a yellow oil. LC-MS (ES⁺): m/z 204.20 [MH⁺], $t_R$=0.56 min (2.0 minute run).

L-17: 2-(3-(2-(tosyloxy)ethoxy)propoxy)acetic acid

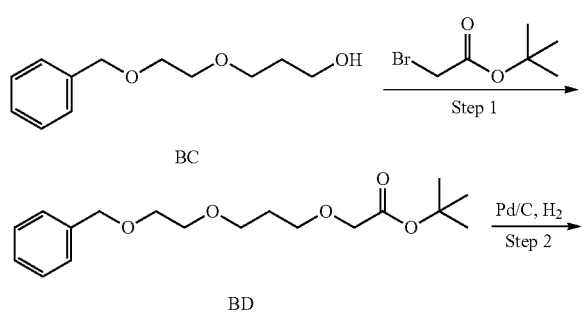

536

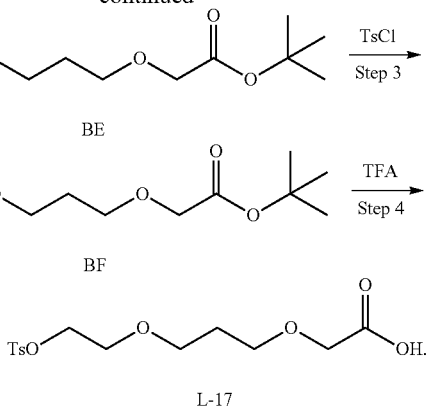

Step 1: Synthesis of tert-butyl 2-{3-[2-(benzyloxy)ethoxy]propoxy}acetate (BD)

To a stirred solution of 3-[2-(benzyloxy)ethoxy]propan-1-ol (BC, 1.8 g, 8.56 mmol) and tert-butyl 2-bromoacetate (6.6 g, 33.84 mmol, 4.00 equiv) in dichloromethane (40 mL) was added TBAC (2.4 g) and aq. Solution of sodium hydroxide (37%, 40 mL). The resulting mixture was stirred at room temperature overnight. LC-MS indicated formation of the desired product. The reaction mixture was then extracted with ethyl acetate (150×3 mL), the organic layers combined, dried over anhydrous sodium sulfate and concentrated under reduced pressure to give a crude residue, which was purified by a flash silica gel chromatography (eluent: ethyl acetate/petroleum ether (v:v=1:2) to give BD (yield: 90%) as a colorless oil. ¹H NMR (300 MHz, CDCl₃): δ 7.35-7.27 (m, 5H), 4.57 (s, 2H), 3.94 (s, 2H), 3.63-3.57 (m, 8H), 1.96-1.87 (m, 2H), 1.47 (s, 9H); LC-MS (ES⁺): m/z 347.10 [MNa⁺], $t_R$=1.72 min (2.6 minute run).

Step 2: Synthesis of tert-butyl 2-[3-(2-hydroxyethoxy)propoxy]acetate (BE)

To a stirred mixture of tert-butyl 2-{3-[2-(benzyloxy)ethoxy]propoxy}acetate (BD, 2.5 g, 7.71 mmol) and palladium on carbon (2.0 g) in methanol (20 mL) under a nitrogen atmosphere was introduced hydrogen gas via a balloon. The resulting mixture was stirred overnight at room temperature under hydrogen gas atmosphere. LC-MS indicated completion of the reaction. The solids were removed by filtration, the solution was concentrated under vacuum to give BE (yield: 99%) as a colorless oil. LC-MS (ES⁺): m/z 257.10 [MNa⁺], $t_R$=1.21 min (2.6 minute run).

Step 3: Synthesis of tert-butyl 2-(3-{2-[(4-methylbenzenesulfonyl)oxy]ethoxy}propoxy)acetate (BF)

To a stirred solution of tert-butyl 2-[3-(2-hydroxyethoxy)propoxy]acetate (BE, 1.8 g, 7.68 mmol) in dichloromethane (50 mL) was added 4-toluenesulfonyl chloride (2.2 g, 11.54 mmol), triethylamine (2.33 g, 23.03 mmol) and 4-dimethylaminopyridine (95 mg, 0.78 mmol). The resulting mixture was stirred overnight at room temperature. LC-MS indicated formation of the desired product. The reaction mixture was concentrated under reduced pressure to give a crude residue, which was purified by a flash silica gel chromatography (eluent: ethyl acetate/petroleum ether (v:v=1:2) to give BF (yield: 80%) as a yellow oil. ¹H NMR (400 MHz, CDCl₃):

δ 7.80 (d, J=8.0 Hz, 2H), 7.34 (d, J=8.4 Hz, 2H), 4.15 (t, J=3.6 Hz, 2H), 3.93 (s, 2H), 3.61 (t, J=3.6 Hz, 2H), 3.55-3.49 (m, 4H), 2.45 (s, 3H), 1.85-1.78 (m, 2H), 1.48 (s, 9H); LC-MS (ES$^+$): m/z 411.00 [MNa$^+$], $t_R$=1.12 min (2.0 minute run).

Step 4: Synthesis of 2-(3-{2-[(4-methylbenzenesulfonyl)oxy]ethoxy}propoxy)acetic acid (L-17)

To a stirred solution of tert-butyl 2-(3-{2-[(4-methylbenzenesulfonyl)oxy]ethoxy}propoxy)acetate (BF, 400 mg, 1.03 mmol) in dichloromethane (3 mL) was added trifluoroacetic acid (1 mL) at room temperature. The resulting solution was stirred at room temperature for 1 hour. LC-MS indicated completion of the reaction. The reaction mixture was concentrated under reduced pressure to give L-17 (350 mg) as a yellow oil, which was used for next step without further purifications. LC-MS (ES$^+$): m/z 332.90 [MH$^+$], $t_R$=0.81 min (2.0 minute run).

Unless otherwise noted, the following intermediates and their analogs (for examples, but not limited to, analogs with substitutions such as halogens) were synthesized according to similar procedures described above for the synthesis of L-17, by utilizing corresponding starting materials and reagents.

L-18: 2-(2-hydroxyethoxy)ethyl 4-methylbenzenesulfonate

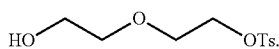

L-19: ethyl 2-(2-(2-(tosyloxy)ethoxy)ethoxy)acetate

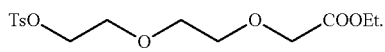 [SMILES: CCOC(=O)COCCOCCOS(=O)(=O)c1ccc(C)cc1]

L-20: ethyl 3-(2-(2-(tosyloxy)ethoxy)ethoxy)propanoate

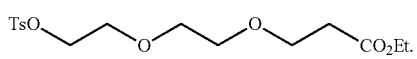

L-21: ethyl 5-(tosyloxy)pentanoat

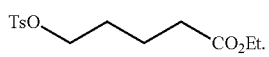

L-22: ethyl 3-(2-(tosyloxy)ethoxy)propanoate

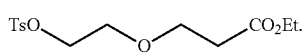

L-23: ethyl 2-(5-(tosyloxy)pentyloxy)acetate

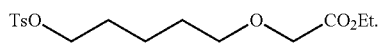

L-24: ethyl 3-(5-(tosyloxy)pentyloxy)propanoate

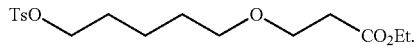

L-25: 5-hydroxypentyl 4-methylbenzenesulfonate

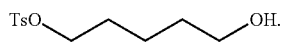 [SMILES: Cc1ccc(S(=O)(=O)OCCCCCO)cc1]

L-26: ethyl 2-(5-(tosyloxy)pentyloxy)acetate

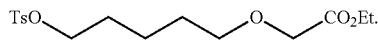

L-27: ethyl 2-(3-(tosyloxy)propoxy)acetate

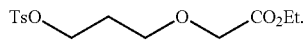

L-28: ethyl 2-(2-(tosyloxy)ethoxy)acetate

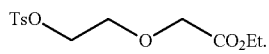

L-29: ethyl 2-(4-(2-(tosyloxy)ethoxy)butoxy)acetate

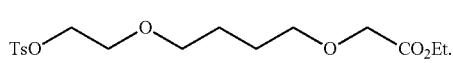

L-30: 2-(2-(2-hydroxyethoxy)ethoxy)ethyl 4-methylbenzenesulfonate

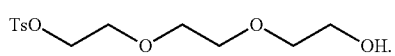 [SMILES: Cc1ccc(S(=O)(=O)OCCOCCOCCO)cc1]

L-31: 2-((2R,3R)-3-(2-hydroxyethoxy)butan-2-yloxy)ethyl 4-methylbenzenesulfonate

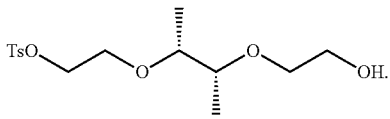 [SMILES: Cc1ccc(S(=O)(=O)OCCO[C@H](C)[C@@H](C)OCCO)cc1]

L-32: 1-methyl-4-((1-methylpiperidin-4-yl)methyl)piperazine

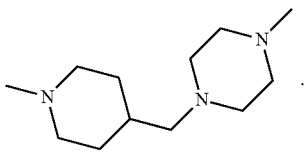

When referring to the specific exemplary compounds presented herein, the specification uses the terms "example #." For example, compound 1 (Table 2 of FIG. 2) is also referred to as Example 1. DC50 (μM) categories (degradation of AR ELISA in LNCaP and/or VCaP cells) of Table 2-7 are as follows: A<1 nM; B: 1-10 nM; C: 10-100 nM; D: >100 nM. Dmax categories (degradation of AR-maximum inhibition (%) AR ELISA in LNCaP and/or VCaP cells): A>50%; B<50%.

Androgen Receptor ELISA Assay.

Compounds have been evaluated in this assay in LNCaP and/or VCaP cells utilizing similar protocols. The protocols used with VCaP cells are described below. The androgen receptor ELISA assay was performed using PathScan AR Sandwich ELISA (Cell Signaling Catalog #12850) according to the following assay steps:

VCaP cells are seeded at 40,000 cells/well at a volume of 100 μL/well in VCaP assay medium [Phenol red free RPMI (Gibco Cat #11835-030); 5% Charcoal Stripped (Dextran treated) FBS (Omega Scientific, Cat #FB-04); 1% penstrep (Life Technologies, Gibco Cat #: 10378-016)] in Corning 3904 plates. The cells are grown for a minimum of 3 days.

First, cells are dosed with compounds diluted in 0.01% DMSO—use a polypropylene plate avoiding the use of outer columns according to the following protocol: (1)(i) make 1000× stock plate in DMSO; (ii) 20 mM stock diluted 1/6.7 with DMSO (5 μL+28.3 μL DMSO)=3 mM into row H; (iii) perform serial dilutions in ½ log doses (10 μL of PROTAC+20 μL DMSO) from row H towards row B. Reserve row A for DMSO; (iv) 7 doses total (final concentration in this 1000× plate will be 3 mM, 1 mM, 333 μM, 111 μM, etc). (2)(i) Make 10× stock plate in media; (ii) transfer 2.5 μL of the 1000× stock to a new 10× stock plate (use 12 channel pipet, start at A (DMSO control) work thru H. When 247.5 μL of media is added to this plate, it will serve as a 10× stock; (iii) make media+1 nM R1881 for making 10× stock plate; (iv) add 247.5 μL of media with 1 nM R1881 to each well of the 10× stock plate, mix.

Then 22 μL of 10× stock is added to cells and incubated for 5 hours. 1× Cell Signaling Cell lysis buffer is made (Catalogue #9803; comes with the kit)—prepare for 50 μL/well. Keep on ice. Media is aspirated, and 100 μL 1× cell lysis buffer/well is added. The cells are placed on a shaker located in a cold room for 10 minutes and shaken at speek of 7. The lysate mixture is mix and 20 μL transferred to 100 μl of Diluent in ELISA plate (0.15 μg/ml-0.075 μg/ml). The lysate-diluent mixture is store at 4° C. overnight on a shaker located in a cold room at speed 5 (gentle swirl).

The lysate-diluent mixture is shaken for 30 minutes at 37° C. Allow mouse AR antibody, anti-mouse antibody, TMB, and STOP solution to come to room temperature. Make 1×ELISA buffer included in kit, load in reservoir. Run primer program on plate washer. Media from the plates is discarded, the ELISA plate tapped hard on paper towel, and washed 4×200 μl ELISA wash buffer using a plate washer for the first three washes and an eight channel aspirator for the fourth wash to more thoroughly aspirate the solution.

Add 100 μL/well mouse AR detection Ab; cover and shake, 37° C. for 1 hour; media is discarded from the places, tap the plates on a paper towel, wash 4×200 μL ELISA wash buffer with a plate washer for the first three washed and an eight channel aspirator for the fourth wash; add 100 μL/well anti-mouse-HRP conjugated Ab (comes with the kit); cover and shake, 37° C. for 30 minutes; allow TMB reagent to come to room temperature; discard media from the plate, tap plates on paper towel, wash 4×200 μL ELISA wash buffer with a plate washer for the first three washed and an eight channel aspirator for the fourth wash; tap the plates on paper towel; add 100 μL TMB and shake for 2 minutes—while watching color. Add 100 μL Stop solution when light blue color develops. Shake plates and read at 450 nM.

Progression of prostate cancer in patients treated with anti-androgen therapy usually involves one of several mechanisms of enhanced Androgen Receptor (AR) signaling, including increased intratumoral androgen synthesis, increased AR expression and AR mutations. PROTACs (PROteolysis TArgeting Chimera), which uses bi-functional molecules that simultaneously bind a target of choice and an E3 ligase, cause ubiquitination via induced proximity and degradation of the targeted, pathological protein. As opposed to traditional target inhibition, which is a competitive process, degradation is a progressive process. As such, it is less susceptible to increases in endogenous ligand, target expression, or mutations in the target. Thus this technology seems ideal for addressing the mechanisms of AR resistance in patients with prostate cancer.

Data is analyzed and plotted using GraphPad Prism software. Compounds described in this application were assayed and c-myc suppression potency is listed in the Table 2-7.

Apoptosis in VCaP Cells.

VCaP cells may be cultured in Charcoal Stripped Serum containing media supplemented with 0.1 nM R1881 for 48 hours. The degree of apoptosis can then be ascertained with CaspaseGlo assay (Promega).

Anti-Proliferation in LNCaP F876L.

LNCaP cells transduced with an AR construct were cultured in Charcoal Stripped Serum containing media. Indicated doses of enzalutamide or Exemplary Compounds can be added for 7 days. CellTiterGlo reagent (Promega) can be employed to assess proliferation.

PSA suppression in LNCaP F876L. LNCaP F876L cells transduced with an AR construct were cultured in Charcoal Stripped Serum containing media supplemented with 0.1 nM R1881 for 7 days. Secreted PSA in the media was detected by PSA ELISA (Sigma).

Prostate Involution in C57B6 Mouse Model.

12-week old male C57BL/6 mice are treated with an AR PROTAC and its inactive epimer analog which is unable to bind to cereblon E3 ligase. Compounds are administered for 10 days, upon which the prostates were isolated and weighed.

Tumor Growth Inhibition in VCaP Xenograft Model.

VcaP Xenograft and Drug Treatment. Three million VCaP cells 75% MatriGel/25% RPMI suspension are implanted into CB17 scid mice subcutaneously. Once the tumors reach about 200-300 mm$^3$, the mice are surgically castrated, leading to temporary tumor stasis. Allow the mice to recover for at least one week. The mice are then dosed with enzalutamide (PO, QD, 30 mpk) or AR PROTAC (IP, QD, at 30, 10 and 3 mpk) as indicated by oral gavage. Sixteen hours after the last does, the mice are sacrificed and the tumors excised.

Tissue Lysis Buffer.

Final concentrations: 25 mM HEPES (pH 7.4), 50 mM NaCl, 1% NP-40, 0.1% SDS, protease inhibitor tablets/EDTA free mini (A32955) 1/10 ml (if DNA is a problem, protease inhibitor tablets with EDTA is used); if phosphoproteins are observed at end point—a phosphatase inhibitor is added. One 1 per mg of tissue is utilized. Protease Inhibitor Cocktail mini is added fresh to the lysis buffer prior to homogenization.

Tissue Lysis.

Five mm stainless steel bead in 2 ml tube or 2.5 mm bead for 1.5 ml tubes is added to frozen tumor chunk on dry ice. Bead and tumor is transferred to wet ice. Add 1 µl of tissue lysis buffer per mg of tissue to the tumor and beads mixture. Bead milling of the tissue was performed for 4 minutes, 25 Hz, 4° C. The beads are removed with a magnet. The lysates are spun for 15 minutes 14,000×g, 4° C. The total lysate volume is transferred to block plate. The tumor lysate is normalized, usually ~50 µg/µl.

Western Blotting.

10 µg/lane are used for LnCAP lysates and 5 ug/lane for VCaP lysates. Samples are run at 150 V for 85 minutes. Transfer to nitrocellulose membrane. Block the nitrocellulose membrane for 1 hour at room temperature with 3% BSA. Primary antibody: Cell Signaling antibody AR #5153 1/2000 o.n., mitoC abcam #ab92824 1:1000, ERG antibody Abcam #ab92513 1:1000. Secondary antibody: Cell signaling antibody #7074/7076 1/20000 for 1 hour (Anti-mouse/rabbit HRP). Detect with Femto (THERMO FISHER) or Clarity (BIO-RAD).

Xenograft data is shown below in Table 8.

TABLE 8

Xenograft data for select compounds of the present disclosure

| Ex. # | PD_AR_castrated_VCaP % AR degraded @10 mg_kg @ 16 hr (%) |
|---|---|
| 382 | C |
| 378 | C |
| 265 | C |
| 177 | C |
| 124 | C |
| 263 | C |
| 400 | B |
| 134 | B |
| 133 | B |
| 183 | B |
| 293 | B |
| 316 | B |
| 193 | B |
| 377 | B |
| 289 | B |

TABLE 8-continued

Xenograft data for select compounds of the present disclosure

| Ex. # | PD_AR_castrated_VCaP % AR degraded @10 mg_kg @ 16 hr (%) |
|---|---|
| 185 | B |
| 41 | A |
| 91 | A |
| 127 | A |
| 178 | A |
| 180 | A |
| 315 | A |
| 359 | A |
| 288 | A |
| 131 | A |
| 179 | A |
| 440 | A |
| 126 | A |
| 310 | A |
| 182 | A |
| 346 | A |
| 132 | A |
| 181 | A |
| 420 | A |
| 270 | A |
| 240 | A |
| 343 | A |
| 426 | A |
| 145 | A |
| 215 | A |
| 114 | A |
| 158 | A |
| 210 | A |
| 234 | A |
| 122 | A |
| 129 | A |
| 247 | A |
| 406 | A |

AR Degradation of PROTAC is E3 Ligase Dependent.

An AR PROTAC is added to LNCaP cells at indicated concentrations for 24 hours in the presence or absence of 10 uM cereblon E3 ligase ligand. (A) AR decradation activity of the AR PROTAC is examined to determine if there is diminished degradation as a result of competition from the cereblon E3 ligase ligand with AR PROTAC in cereblon E3 ligase binding. (B) LNCaP cells are treated with an AR PROTAC and its inactive epimer analog which is unable to bind to cereblon E3 ligase.

PROTAC Prodrug Oral Pharmacokinetics and PROTAC Subcutaneous Phamacokinetics.

Representative Pharmacokinetic Procedure

Male CD-1 mice (6-8 weeks old, weighing 20-30 g, 3 per study) with free access to food and water are administered with the test article at 10 mg/kg either by oral gavage or sub-cutaneous injection in the formulation specified in tables 20 and 21, at 10 mL/kg.

Approximately 0.04 mL blood samples are collected from the dorsal metatarsal vein serially at 0.25, 0.5, 1, 2, 4, 8 and 24 hours timepoints; heparin is used as the anticoagulant. The samples are centrifuged at 4000 g for 5 minutes at 4° C. then stored at −75° C. prior to analysis.

The plasma samples are analysed via an LC/MS/MS method quantitating for unchanged, administered test article, and/or a derivative species as appropriate. WinNonlin (Phoenix™) is used for the pharmacokinetic calculations and modeling, to generate parameters such as Cmax and AUC.

Specific Embodiments

In certain embodiments, the description provides a compound having a structure selected from the group consisting of Examples 1-452 and 528-625 (see Tables 2-7), a salt, a polymorph, and prodrug thereof. In certain additional embodiments, the description provides a composition comprising at least one of the compounds of Examples 1-452 and 528-625 including a salt, polymorph, and prodrug thereof. In still additional embodiments, the description provides a therapeutic composition comprising at least one of the compounds of Examples 1-452 and 528-625 including a salt, a polymorph, and a prodrug thereof, and a pharmaceutically acceptable carrier.

An aspect or the present disclosure provides a compound having the structure:

ABM-L-CLM, wherein ABM is an androgen receptor (AR) binding moiety, L is a chemical linker moiety, CLM is a cereblon E3 ubiquitin ligase binding moiety, wherein the ABM comprises a structure selected from the group consisting of:

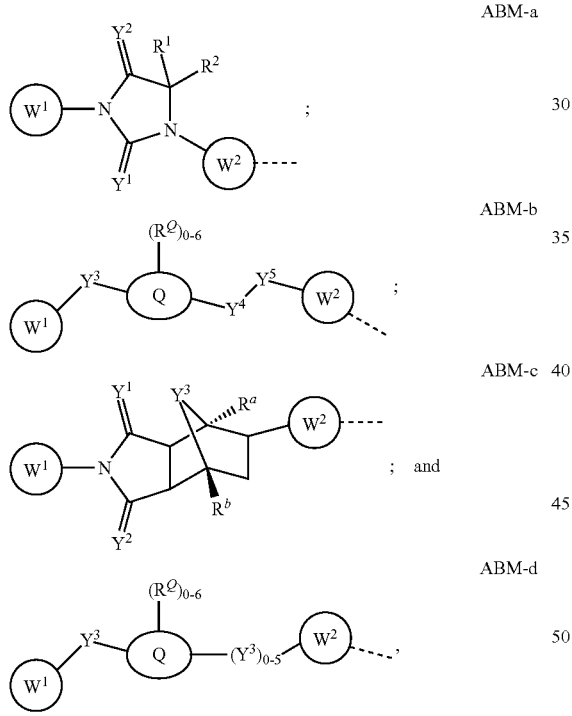

wherein:
$W^1$ is aryl, heteroaryl, bicyclic, or biheterocyclic, each independently substituted by 1 or more H, halo, hydroxyl, nitro, CN, C≡CH, $C_{1-6}$ alkyl (linear, branched, optionally substituted; for example, optionally substituted by 1 or more halo, $C_{1-6}$ alkoxyl), $C_{1-6}$ alkoxyl (linear, branched, optionally substituted; for example, optionally substituted by 1 or more halo), $C_{2-6}$ alkenyl, $C_{2-6}$ alkynyl, or $CF_3$;
$Y^1$, $Y^2$ are each independently $NR^{Y1}$, O, S, $SO_2$, heteroaryl, or aryl;
$Y^3$, $Y^4$, $Y^5$ are each independently a bond, O, $NR^{Y2}$, $CR^{Y1}R^{Y2}$, C=O, C=S, SO, $SO_2$, heteroaryl, or aryl;

Q is a 3-6 membered ring with 0-4 heteroatoms, optionally substituted with 0-6 $R^Q$, each $R^Q$ is independently H, $C_{1-6}$ alkyl (linear, branched, optionally substituted; for example, optionally substituted by 1 or more halo, $C_{1-6}$ alkoxyl), halogen, $C_{1-6}$ alkoxy, or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted; for example, optionally substituted by 1 or more halo, $C_{1-6}$ alkoxyl), halogen, $C_{1-6}$ alkoxy, cyclic, heterocyclic, or $R^1$, $R^2$ together with the atom they are attached to, form a 3-8 membered ring system containing 0-2 heteroatoms);

$W^2$ is a bond, $C_{1-6}$ alkyl, $C_{1-6}$ heteroalkyl, O, aryl, heteroaryl, alicyclic, heterocyclic, biheterocyclic, biaryl, or biheteroaryl, each optionally substituted by 1-10 $R^{W2}$;

each $R^{W2}$ is independently H, halo, $C_{1-6}$ alkyl (linear or branched optionally substituted; for example, optionally substituted by 1 or more F), —$OR^{W2A}$, $C_{3-6}$ cycloalkyl, $C_{4-6}$ cycloheteroalkyl, $C_{1-6}$ alicyclic (optionally substituted), heterocyclic (optionally substituted), aryl (optionally substituted), or heteroaryl (optionally substituted), bicyclic heretoaryl or aryl, $OC_{1-3}$alkyl (optionally substituted; for example, optionally substituted by 1 or more —F), OH, $NH_2$, $NR^{Y1}R^{Y2}$, CN; and $R^{W2A}$ is H, $C_{1-6}$ alkyl (linear, branched), or $C_{1-6}$ heteroalkyl (linear, branched), each optionally substituted by a cycloalkyl, cycloheteroalkyl, aryl, heterocyclic, heteroaryl, halo, or $OC_{1-3}$alkyl.

In any aspect or embodiment described herein, $W^1$ is selected from the group consisting of:

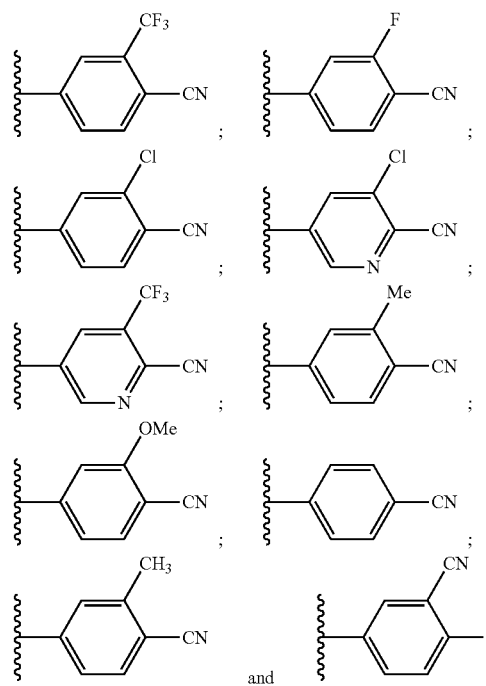

In any aspect or embodiment described herein, $W^2$ is selected from the group consisting of:

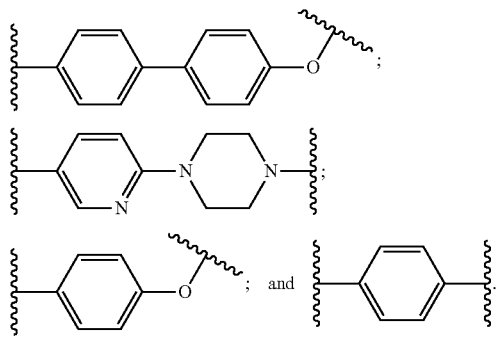

In any aspect or embodiment described herein, the CLM comprises a chemical group derived from an imide, a thioimide, an amide, or a thioamide that binds to the cereblon E3 ubiquitin ligase.

In any aspect or embodiment described herein, the chemical group is a phthalimido group, or an analog or derivative thereof.

In any aspect or embodiment described herein, the CLM is thalidomide, lenalidomide, pomalidomide, analogs thereof, isosteres thereof, or derivatives thereof.

In any aspect or embodiment described herein, the CLM has a chemical structure represented by:

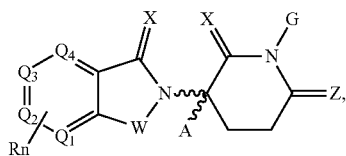 (a)

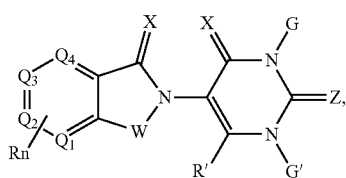 (b)

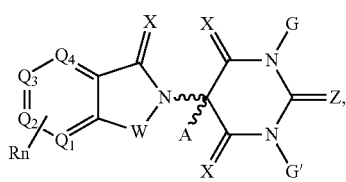 (c)

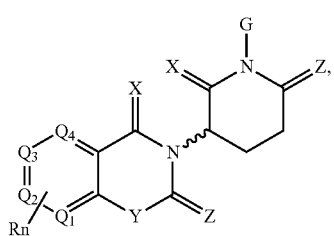 (d)

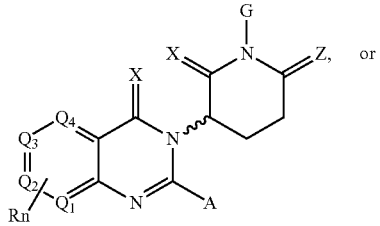 (e) or

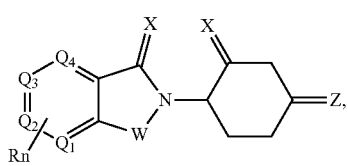 (f)

wherein
W is selected from the group consisting of $CH_2$, CHR, C=O, $SO_2$, NH, and N-alkyl;
each X is independently selected from the group consisting of O, S, and $H_2$;
Y is selected from the group consisting of NH, N-alkyl, N-aryl, N-hetaryl, N-cycloalkyl, N-heterocyclyl, O, and S;
Z is selected from the group consisting of O, S, and $H_2$;
G and G' are each independently selected from the group consisting of H, alkyl (linear, branched, optionally substituted), OH, R'OCOOR, R'OCONRR", $CH_2$-heterocyclyl optionally substituted with R', and benzyl optionally substituted with R';
$Q_1$, $Q_2$, $Q_3$, and $Q_4$ represent a carbon C optionally substituted with a group independently selected from R', N or N-oxide;
A is selected from the group consisting of H, alkyl, cycloalkyl, $C_1$ and F;
R is selected from the group consisting of —CONR'R", —OR', —NR'R", —SR', —$SO_2$R', —$SO_2$NR'R", —CR'R"—, —CR'NR'R"—, -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$, —R'NR'R", (—R'O)$_n$R", or and —$OCF_3$;
R' and R" are each independently selected from the group consisting of a bond, H, alkyl (linear, branched), cycloalkyl, aryl, hetaryl, heterocyclyl, or —C(=O)R, each of which is optionally substituted;
∿∿∿ represents a bond that may be stereospecific ((R) or (S)) or non-stereospecific; and
$R_n$ is a functional group or an atom,
wherein n is an integer from 1-10 (e.g., 1-4, 1, 2, 3, 4, 5, 6, 7, 8, 9, or 10), and wherein
when n is 1, $R_n$ is modified to be covalently joined to the linker group (L), and
when n is 2, 3, or 4, then one $R_n$ is modified to be covalently joined to the linker group (L), and any other $R_n$ is optionally modified to be covalently joined to a ABM, a CLM, a second CLM having the same chemical structure as the CLM, a CLM', a second linker, or any multiple or combination thereof.

In any aspect or embodiment described herein, the CLM or ULM has a chemical structure represented by:

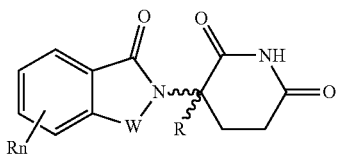

wherein:
- W is independently selected from the group CH2, C=O, NH, and N-alkyl;
- R is independently selected from a H, methyl, alkyl;
- ⁓ represents a bond that may be stereospecific ((R) or (S)) or non-stereospecific; and
- Rn comprises 1-4 independently selected functional groups or atoms, and optionally, one of which is modified to be covalently joined to a ABM, a chemical linker group (L), a ULM, CLM (or CLM') or combination thereof.

Another aspect of the present disclosure provides a bifunctional compound comprising the chemical structure: ABM-L-CLM, wherein ABM is an androgen receptor (AR) binding moiety, L is absent (a bond) or a chemical linker, and CLM is a cereblon E3 ubiquitin ligase binding moiety is a chemical group derived from an imide, a thioimide, an amide, or a thioamide, wherein the ABM comprises a structure selected from the group consisting of:

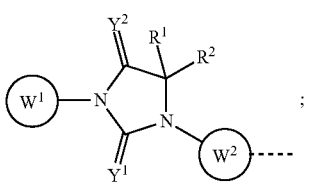
ABM-a

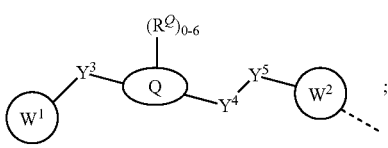
ABM-b

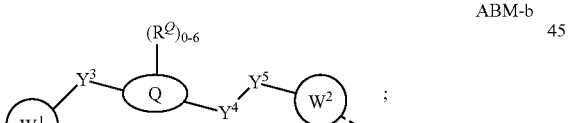
ABM-c and

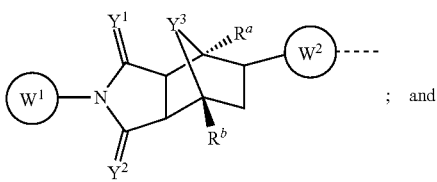
ABM-d wherein:
- $W^1$ is aryl, heteroaryl, bicyclic, or biheterocyclic, each independently substituted by 1 or more H, halo, hydroxyl, nitro, CN, C≡CH, $C_{1-6}$ alkyl (linear, branched, optionally substituted; for example, optionally substituted by 1 or more halo, $C_{1-6}$ alkoxyl), $C_{1-6}$ alkoxyl (linear, branched, optionally substituted; for example, optionally substituted by 1 or more halo), $C_{2-6}$ alkenyl, $C_{2-6}$ alkynyl, or $CF_3$;
- $Y^1$, $Y^2$ are each independently $NR^{Y1}$, O, S;
- $Y^3$, $Y^4$, $Y^5$ are each independently a bond, O, $NR^{Y2}$, $CR^{Y1}R^{Y2}$, C=O, C=S, SO, $SO_2$, heteroaryl, or aryl;
- Q is a 3-6 membered ring with 0-4 heteroatoms, optionally substituted with 0-6 $R^Q$, each $R^Q$, is independently H, $C_{1-6}$ alkyl (linear, branched, optionally substituted; for example, optionally substituted by 1 or more halo, $C_{1-6}$ alkoxyl), halogen, $C_{1-6}$ alkoxy, or 2 $R^Q$ groups taken together with the atom they are attached to, form a 3-8 membered ring system containing 0-2 heteroatoms);
- $R^1$, $R^2$, $R^a$, $R^b$, $R^{Y1}$, $R^{Y2}$ are each independently H, $C_{1-6}$ alkyl (linear, branched, optionally substituted; for example, optionally substituted by 1 or more halo, $C_{1-6}$ alkoxyl), halogen, $C_{1-6}$ alkoxy, cyclic, heterocyclic, or $R^1$, $R^2$ together with the atom they are attached to, form a 3-8 membered ring system containing 0-2 heteroatoms);
- $W^2$ is a bond, $C_{1-6}$ alkyl, $C_{1-6}$ heteroalkyl, O, aryl, heteroaryl, alicyclic, heterocyclic, biheterocyclic, biaryl, or biheteroaryl, each optionally substituted by 1-10 $R^{W2}$;
- each $R^{W2}$ is independently H, halo, $C_{1-6}$ alkyl (linear or branched optionally substituted; for example, optionally substituted by 1 or more F), $-OR^{W2A}$, $C_{3-6}$ cycloalkyl, $C_{4-6}$ cycloheteroalkyl, $C_{1-6}$ alkyl (optionally substituted), $C_{1-6}$ alicyclic (optionally substituted), heterocyclic (optionally substituted), aryl (optionally substituted), or heteroaryl (optionally substituted), bicyclic heretoaryl or aryl, $OC_{1-3}$alkyl (optionally substituted; for example, optionally substituted by 1 or more —F), OH, $NH_2$, $NR^{Y1}R^{Y2}$, CN; and
- RW2A is H, C1-6 alkyl (linear, branched), or C1-6 heteroalkyl (linear, branched), each optionally substituted by a cycloalkyl, cycloheteroalkyl, aryl, heterocyclic, heteroaryl, halo, or OC1-3alkyl.

In any aspect or embodiment described herein, $W^1$ is selected from the group consisting of:

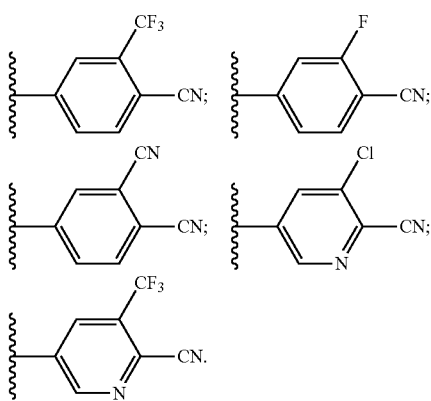

In any aspect or embodiment described herein, W² is selected from the group consisting of:

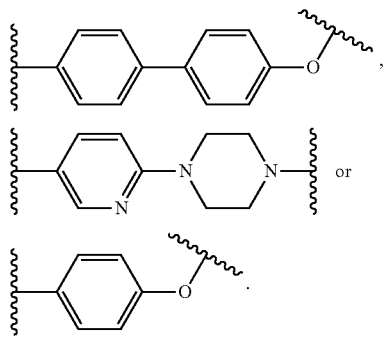

In any aspect or embodiment described herein, CLM comprises a chemical group derived from an imide, a thioimide, an amide, or a thioamide that binds cereblon E3 ubiquitin ligase.

In any aspect or embodiment described herein, the chemical group is a phthalimido group, or an analog or derivative thereof.

In any aspect or embodiment described herein, the CLM is thalidomide, lenalidomide, pomalidomide, analogs thereof, isosteres thereof, or derivatives thereof.

In any aspect or embodiment described herein, the CLM has a chemical structure represented by:

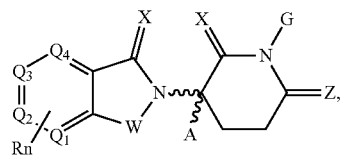 (a)

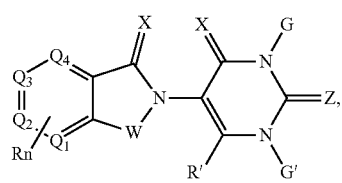 (b)

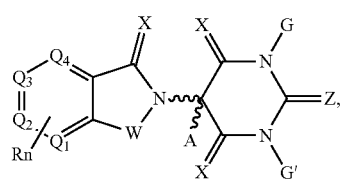 (c)

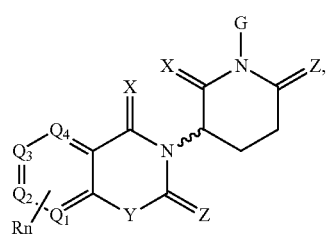 (d)

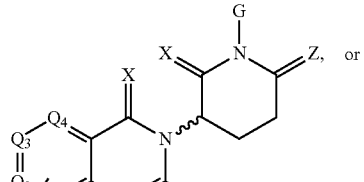 (e)

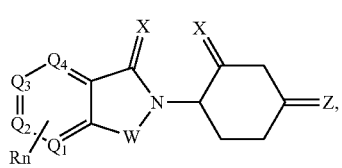 (f)

wherein
  W is selected from the group consisting of $CH_2$, CHR, C=O, $SO_2$, NH, and N-alkyl; each X is independently selected from the group consisting of O, S, and $H_2$;
  Y is selected from the group consisting of $CH_2$, —C=CR', NH, N-alkyl, N-aryl, N-hetaryl, N-cycloalkyl, N-heterocyclyl, O, and S;
  Z is selected from the group consisting of O, S, and $H_2$;
  G and G' are independently selected from the group consisting of H, alkyl (linear or branched optionally substituted; for example optionally substituted with R'), OH, R'OCOOR,
  R'OCONRR", $CH_2$-heterocyclyl optionally substituted with R', and benzyl optionally substituted with R';
  $Q_1$, $Q_2$, $Q_3$, and $Q_4$ are independently a carbon C optionally substituted with a group independently selected from R', N or N-oxide;
  A is independently selected from the group H, alkyl, cycloalkyl, $C_1$ and F;
  R comprises —CONR'R", —OR', —NR'R", —SR', —$SO_2$R', —$SO_2$NR'R", —CR'R"—, —CR'NR'R"—, (—CR'O)$_n$R", -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ or —$OCF_3$;
  R' and R" are independently selected from the group consisting of a bond, H, alkyl, cycloalkyl, aryl, hetaryl, heterocyclyl, —C(=O)R, each of which is optionally substituted;
  ∿∿ represents a bond that may be stereospecific ((R) or (S)) or non-stereospecific; and
  $R_n$ comprises a functional group or an atom,
  wherein n is an integer from 1-10 (e.g., 1-4, 1, 2, 3, 4, 5, 6, 7, 8, 9, or 10), and wherein
    when n is 1, $R_n$ is modified to be covalently joined to the linker group (L), and
    when n is 2, 3, or 4, then one $R_n$ is modified to be covalently joined to the linker group (L), and any other $R_n$ is optionally modified to be covalently joined to a ABM, a CLM, a second CLM having the same chemical structure as the CLM, a CLM', a second linker, or any multiple or combination thereof.

In any aspect or embodiment described herein, the CLM or ULM has a chemical structure represented by:

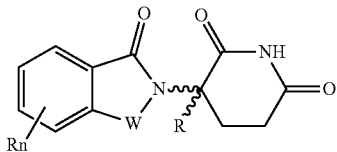

wherein:
W is independently selected from the group CH$_2$, C=O, NH, and N-alkyl;
R is independently selected from a H, methyl, alkyl;
∿ represents a bond that may be stereospecific ((R) or (S)) or non-stereospecific; and
Rn comprises 1-4 independently selected functional groups or atoms, and optionally, one of which is modified to be covalently joined to a ABM, a chemical linker group (L), a ULM, CLM (or CLM') or combination thereof.

In any aspect or embodiment described herein, the linker group L is a group comprises a chemical structural unit represented by the formula:

-A$_q$- wherein A$_q$ is a group coupled to at least one of CLM, ABM, or both; and
q is an integer greater than or equal to 1,
wherein Aq is selected from the group consisting of, a bond, CR$^{L1}$R$^{L2}$, S, SO, O$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 0-6 RL1 and/or RL2 groups, C$_{5-13}$ spirocycloalkyl optionally substituted with 0-9 R$^{L1}$ and/or R$^{L2}$ groups, C$_{3-11}$ heterocyclyl optionally substituted with 0-6 R$^{L1}$ and/or R$^{L2}$ groups, C$_{5-13}$ spiroheterocycloalkyl optionally substituted with 0-8 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups;
R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In any aspect or embodiment described herein, the linker (L) comprises a group represented by a general structure selected from the group consisting of:
—N(R)—(CH2)$_m$-O(CH2)$_n$-O(CH2)$_o$-O(CH2)$_p$-O(CH2)$_q$-O(CH2)$_r$-OCH2-, —O—(CH2)$_m$-O(CH2)$_n$-O(CH2)$_o$-O(CH2)$_p$-O(CH2)$_q$-O(CH2)$_r$-OCH2-,
—O—(CH2)$_m$-O(CH2)$_n$-O(CH2)$_o$-O(CH2)$_p$-O(CH2)$_q$-O(CH2)$_r$-O—; —N(R)—(CH2)$_m$-O(CH2)$_n$-O(CH2)$_o$-O(CH2)$_p$-O(CH2)$_q$-O(CH2)$_r$-O—;
—(CH2)$_m$-O(CH2)$_n$-O(CH2)$_o$-O(CH2)$_p$-O(CH2)$_q$-O(CH2)$_r$-O—; —(CH2)$_m$-O(CH2)$_n$-O(CH2)$_o$-O(CH2)$_p$-O(CH2)$_q$-O(CH2)$_r$-OCH2-;

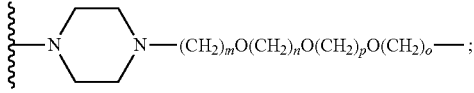

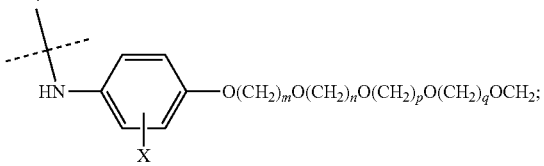

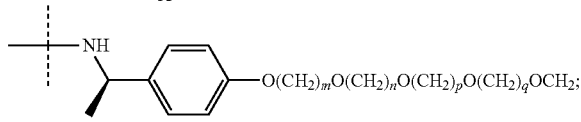

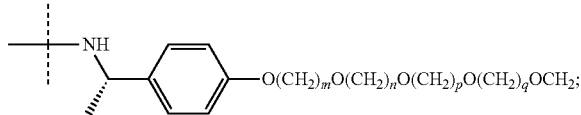

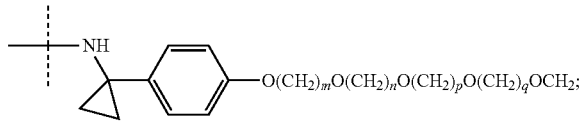

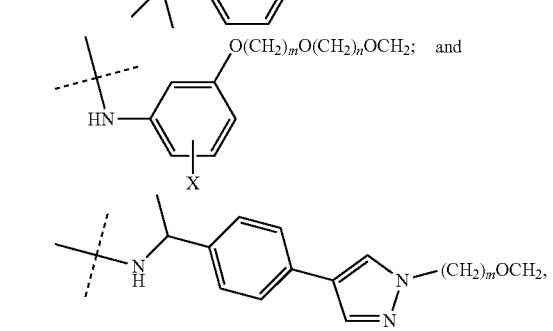

wherein m, n, o, p, q, and r are each independently 0, 1, 2, 3, 4, 5, 6, with the provision that when the number is zero, there is no N—O or O—O bond, R is selected from the group H, methyl or ethyl, and X is selected from the group H or F.

In any aspect or embodiment described herein, the linker (L) comprises a group represented by a general structure:
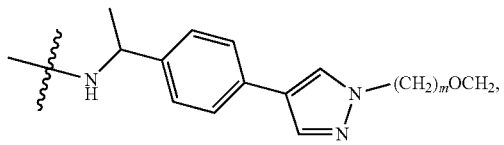
wherein m can be 2, 3, 4, 5.
In any aspect or embodiment described herein, the linker (L) comprises a group represented by a general structure selected from the group consisting of:
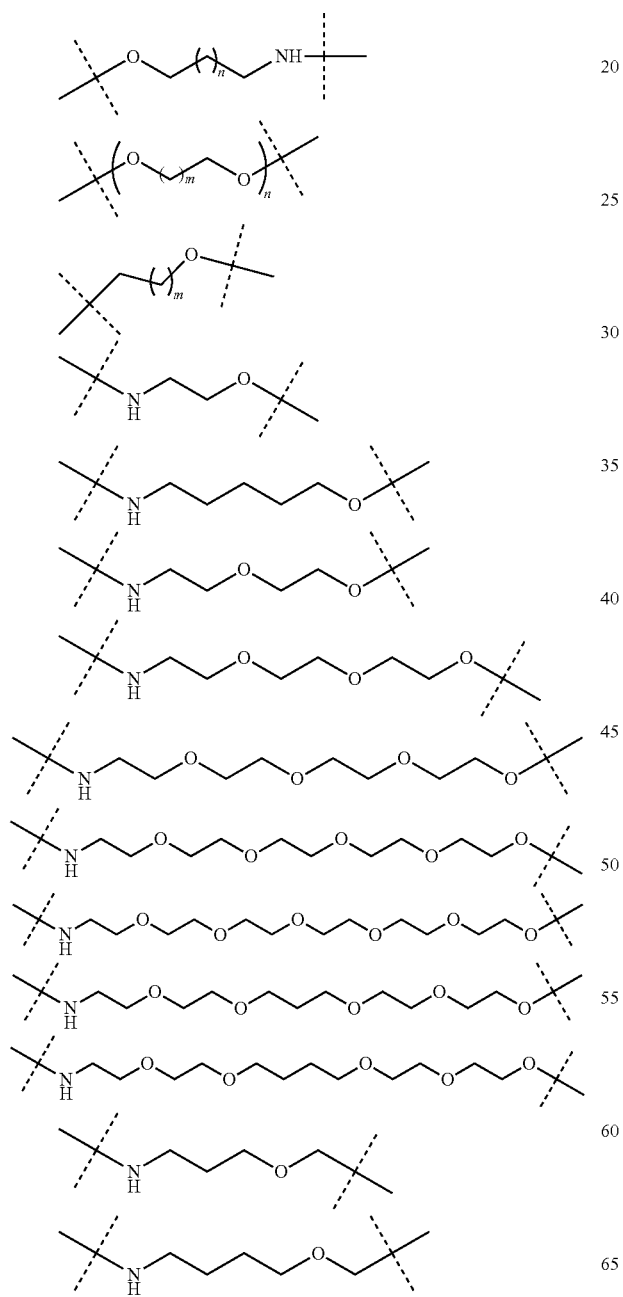
-continued
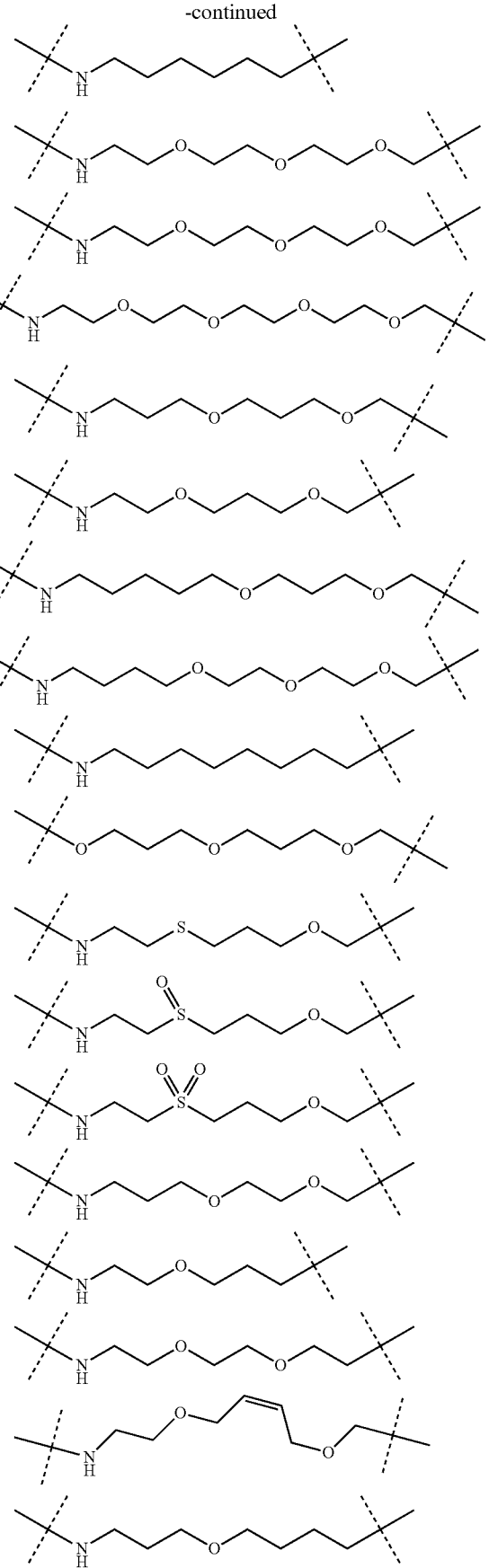

555
-continued
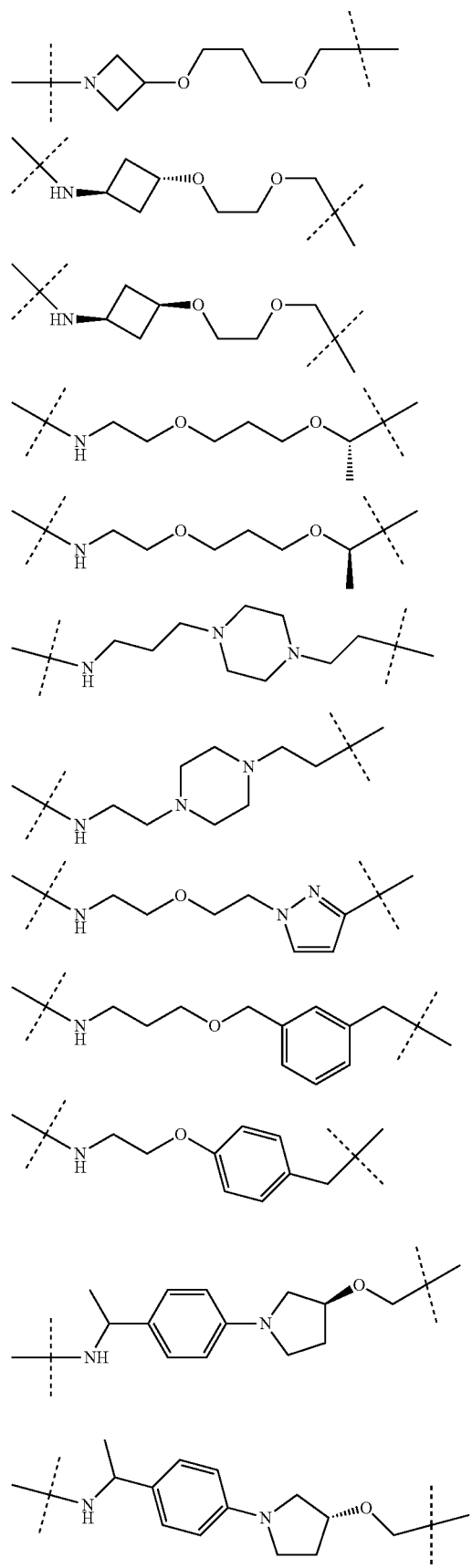
556
-continued
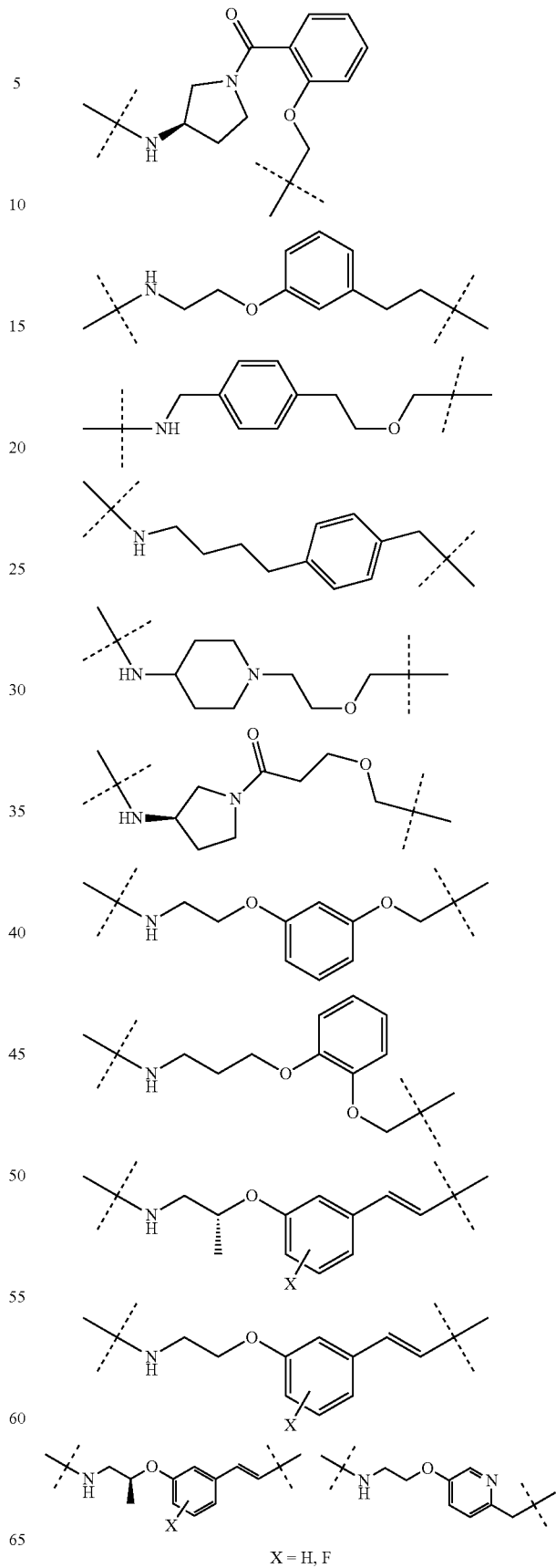
X = H, F

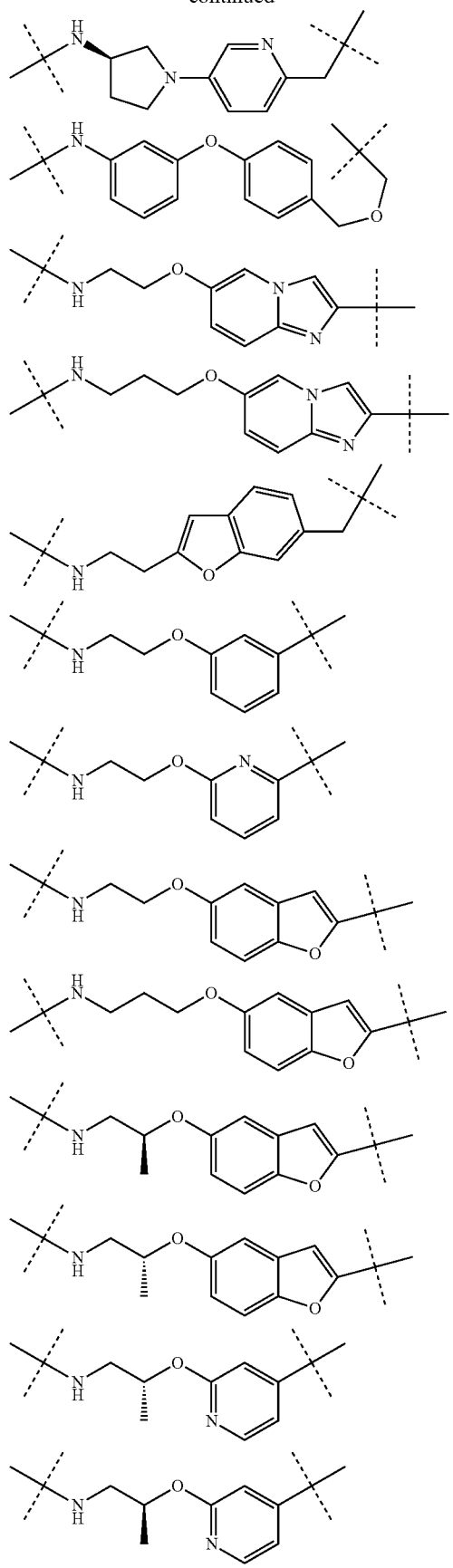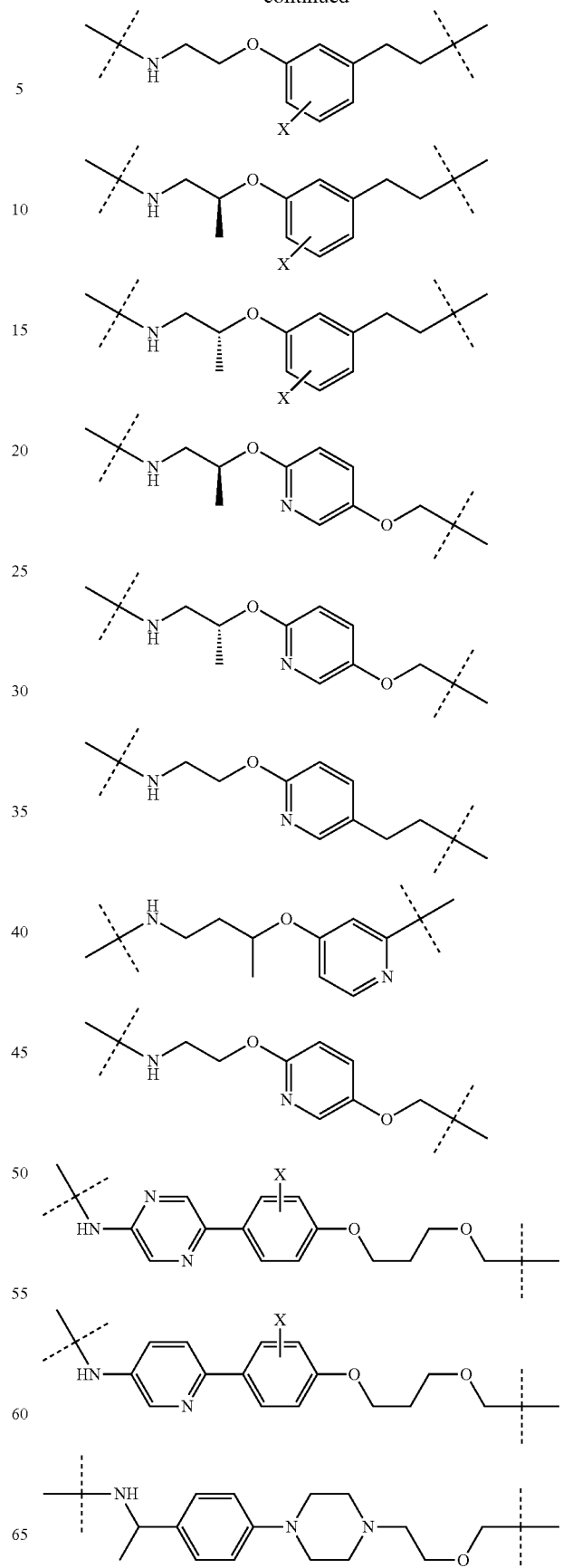

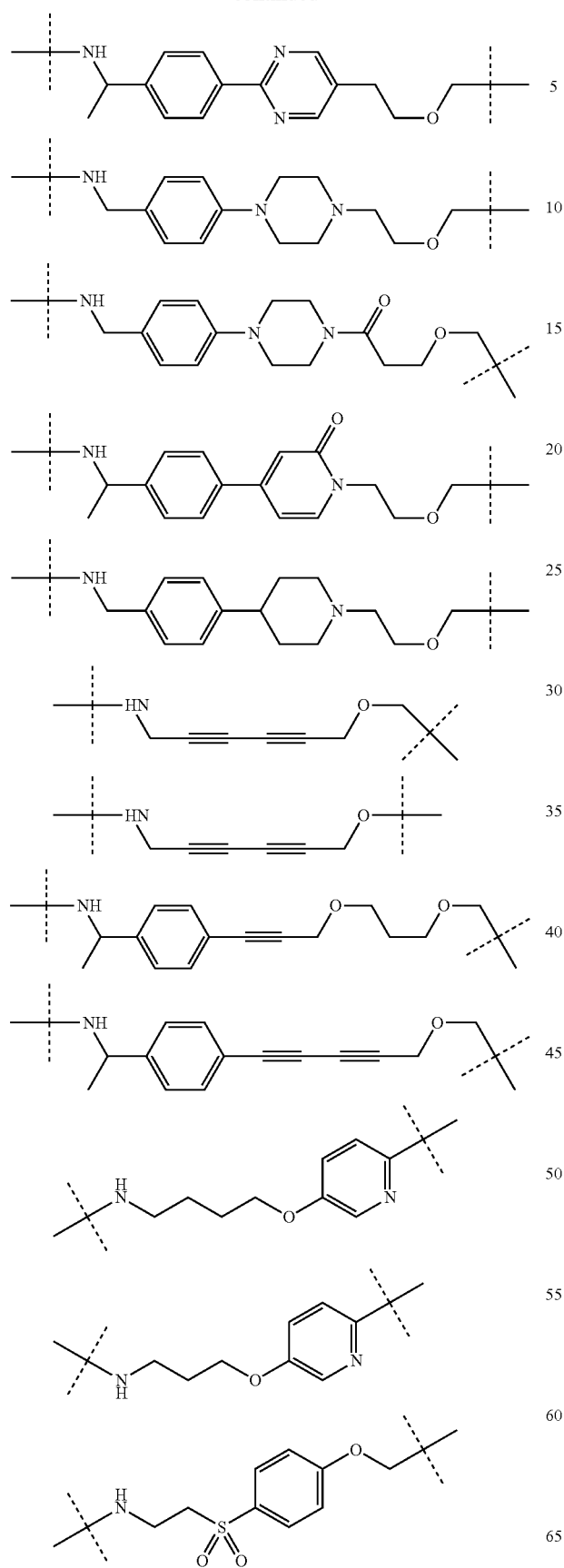
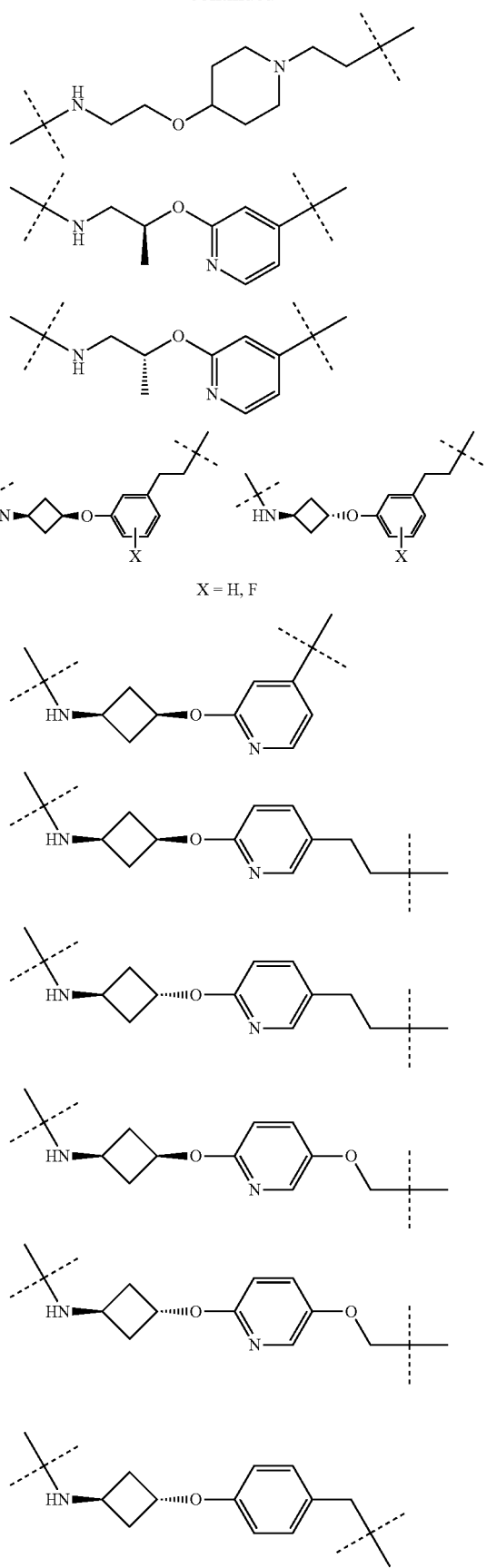
X = H, F

561
-continued
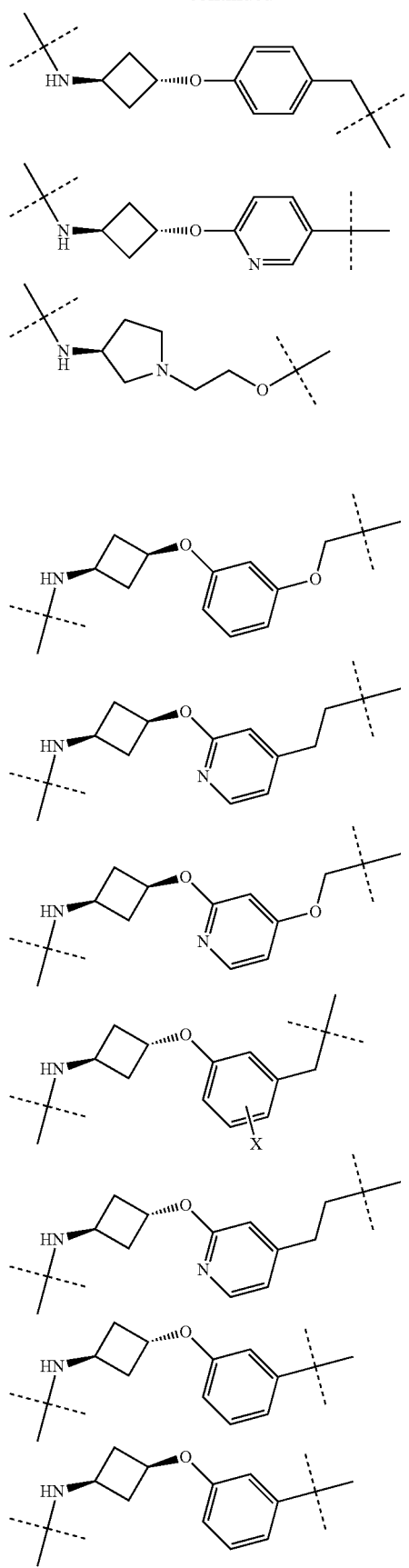
562
-continued
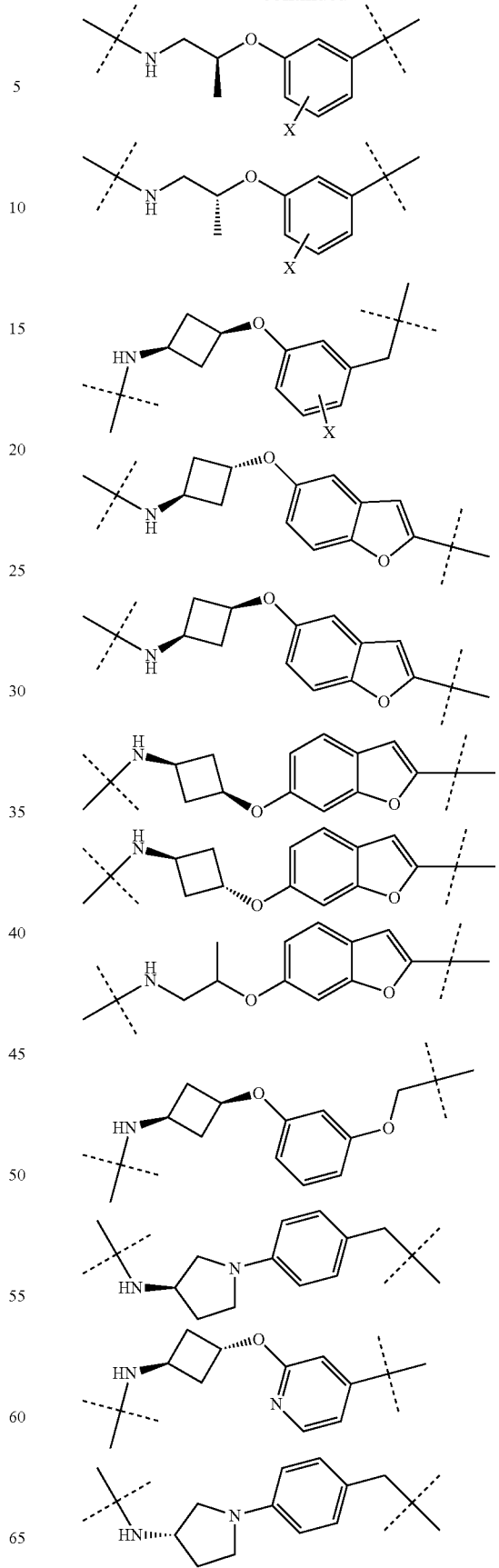

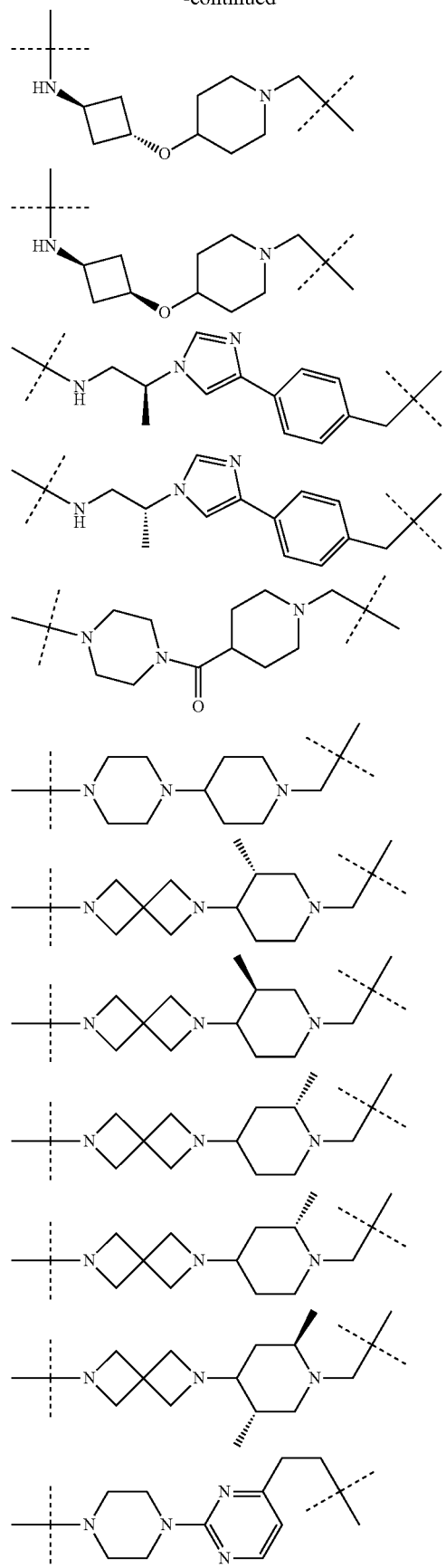
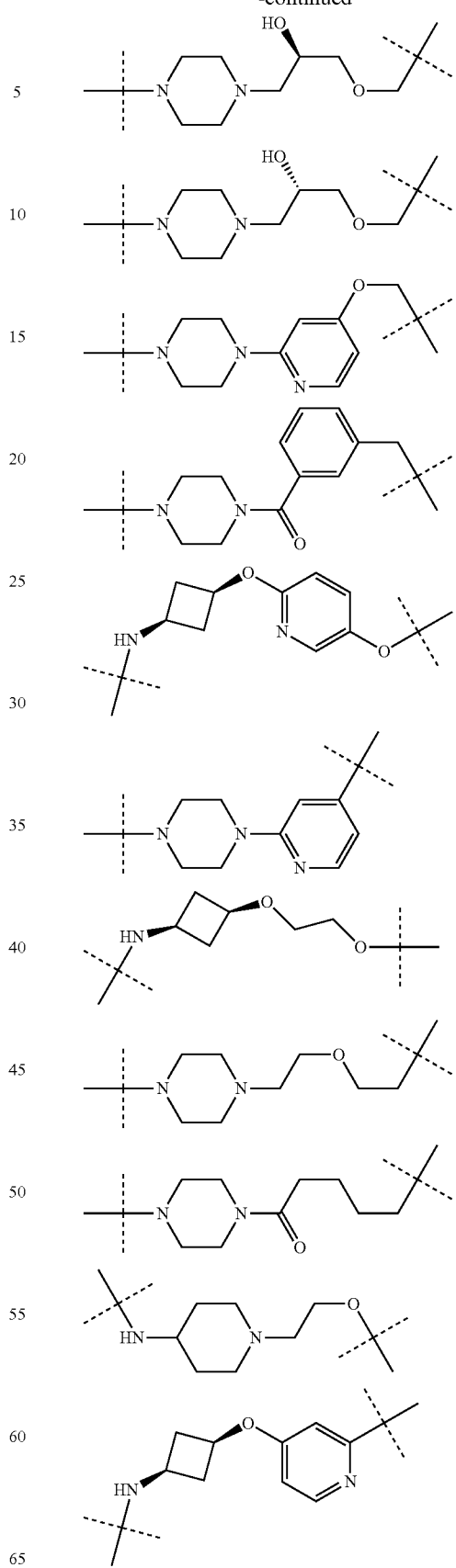

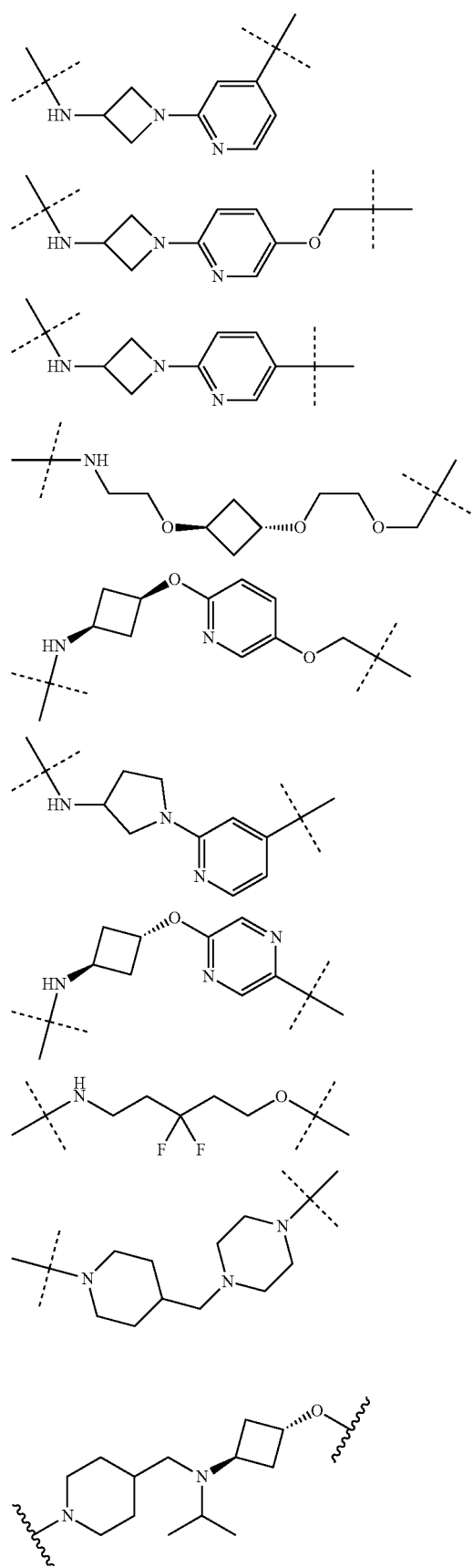
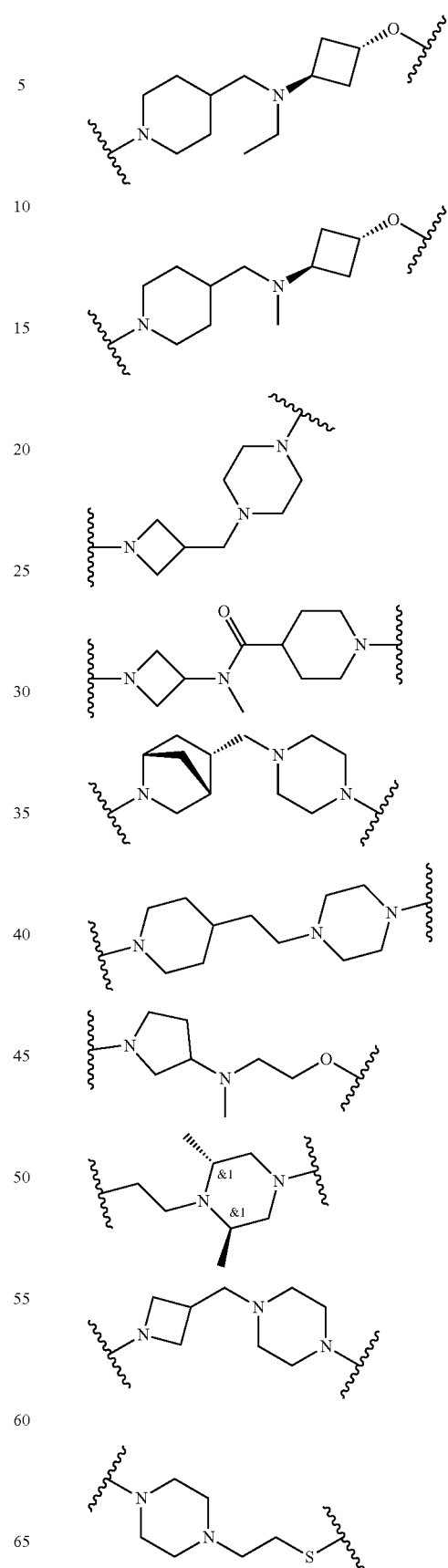

567
-continued
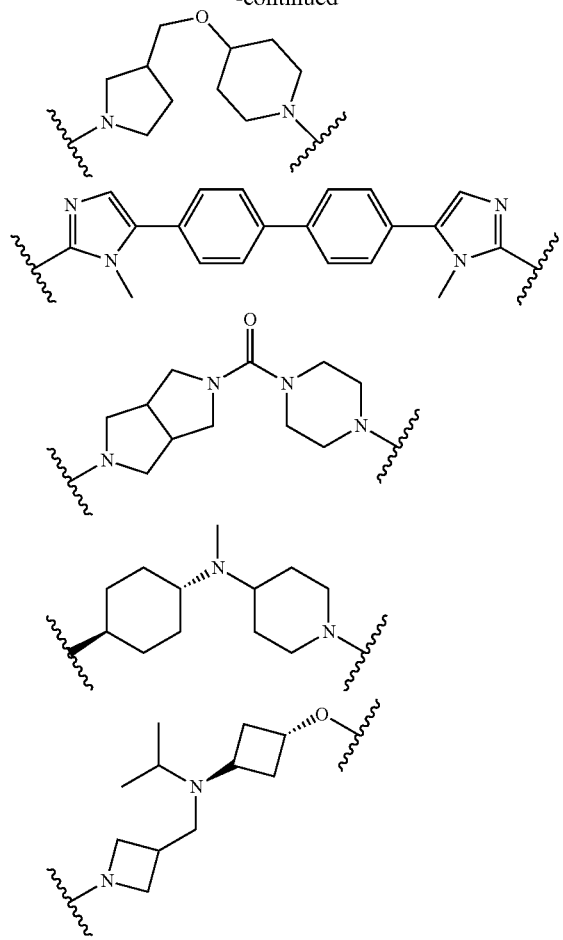
568
-continued
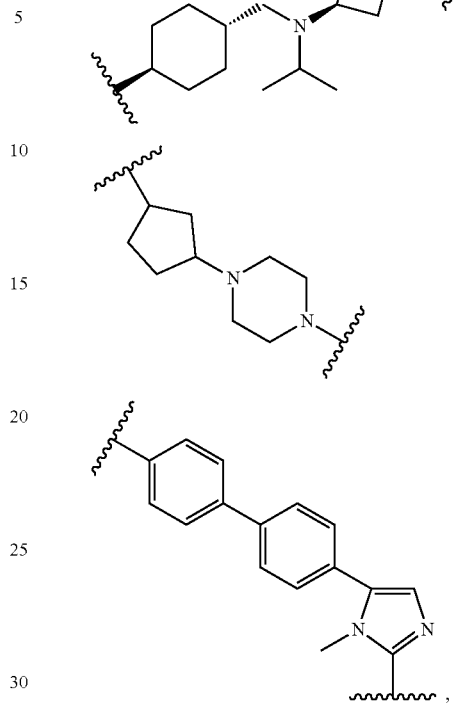
wherein n and m are each independently 0, 1, 2, 3, 4, 5, 6, and X is H, or F.
In any aspect or embodiment described herein, linker (L) is selected from the group consisting of:
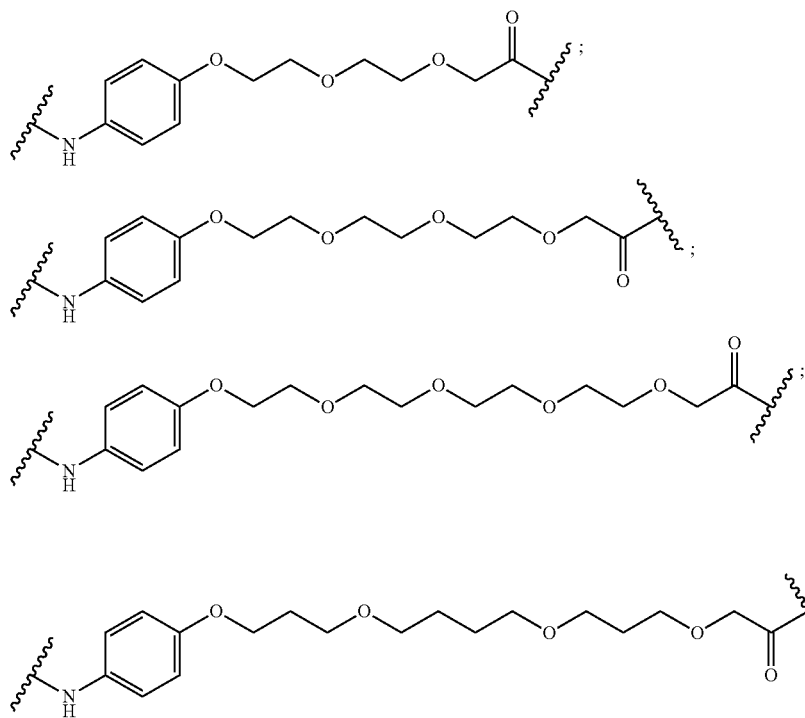

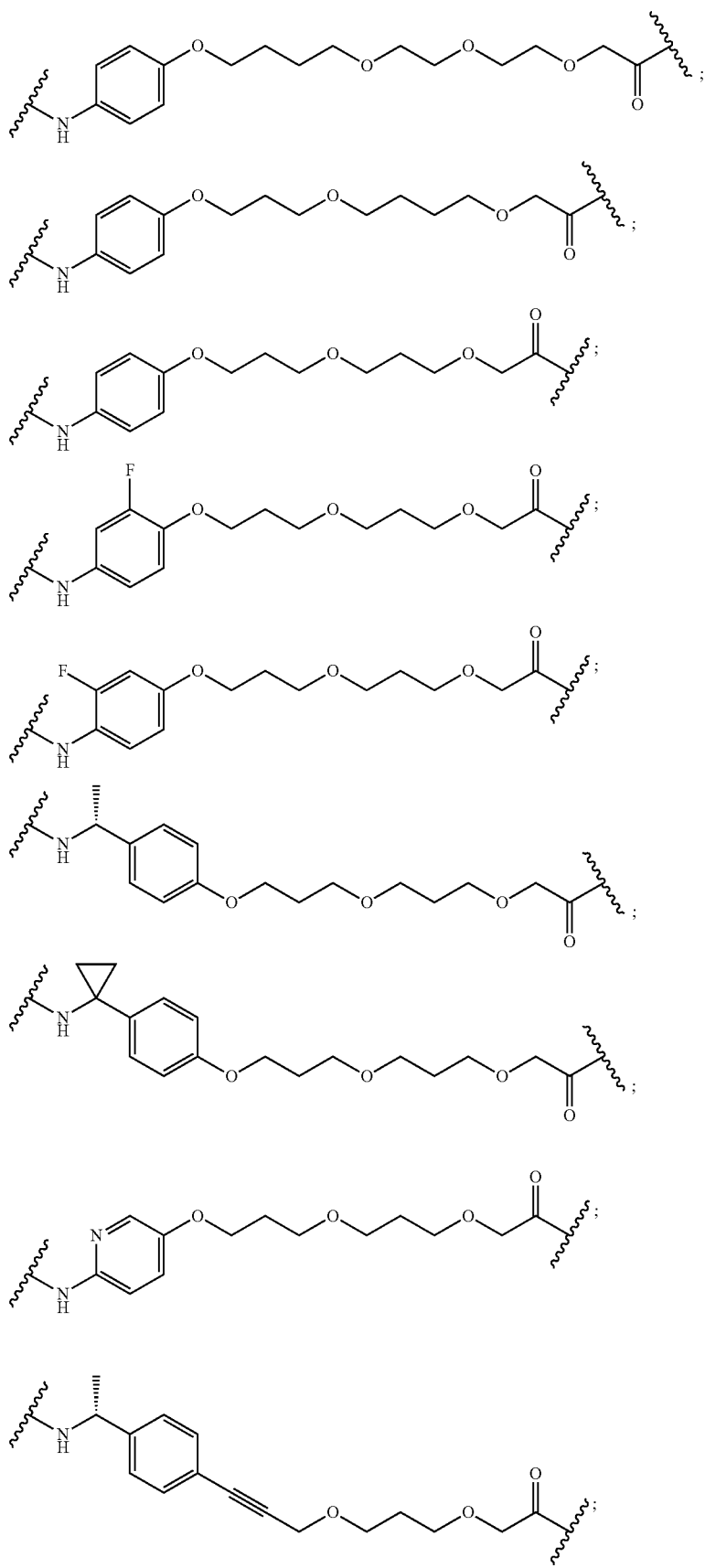

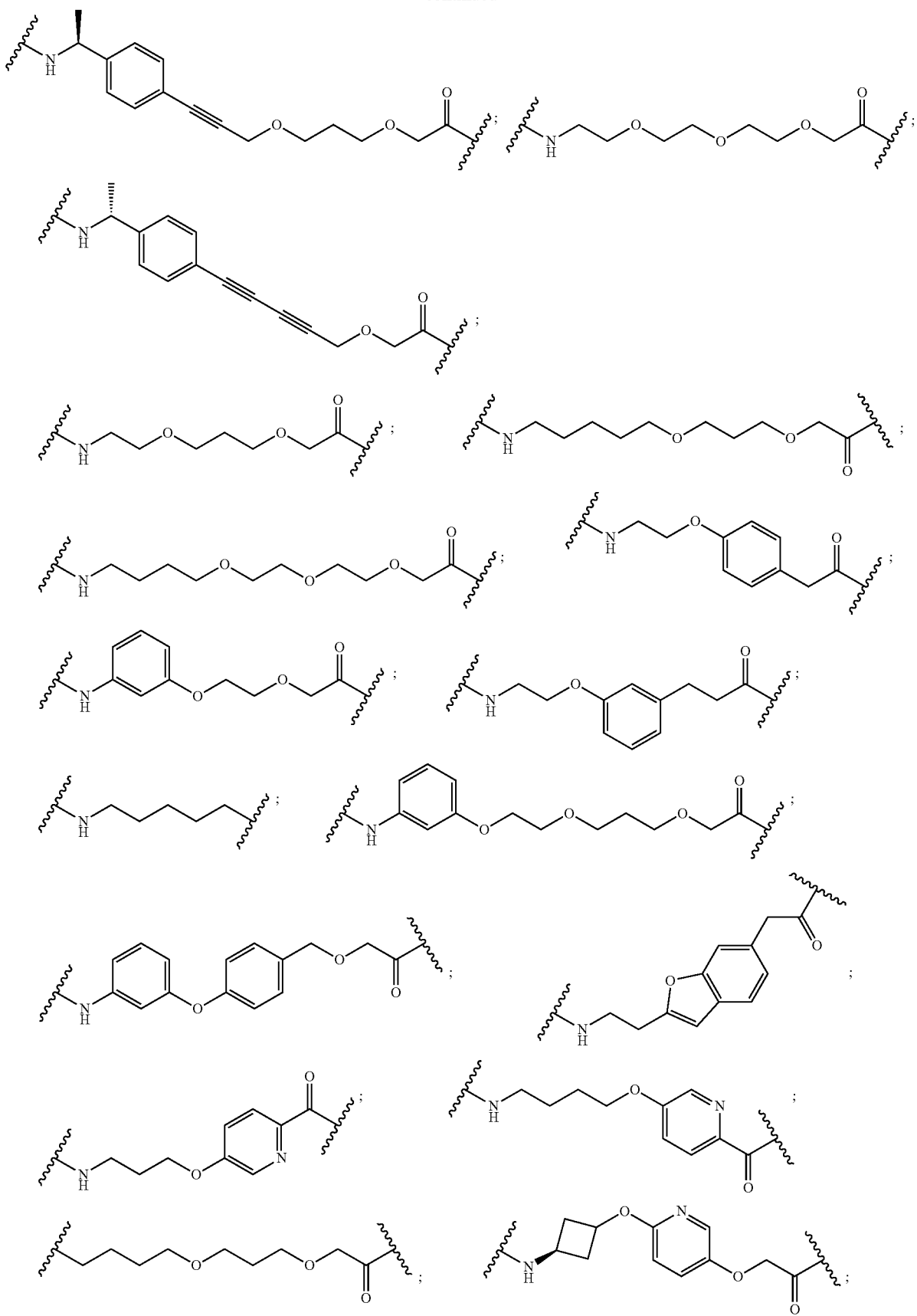

573 574
-continued
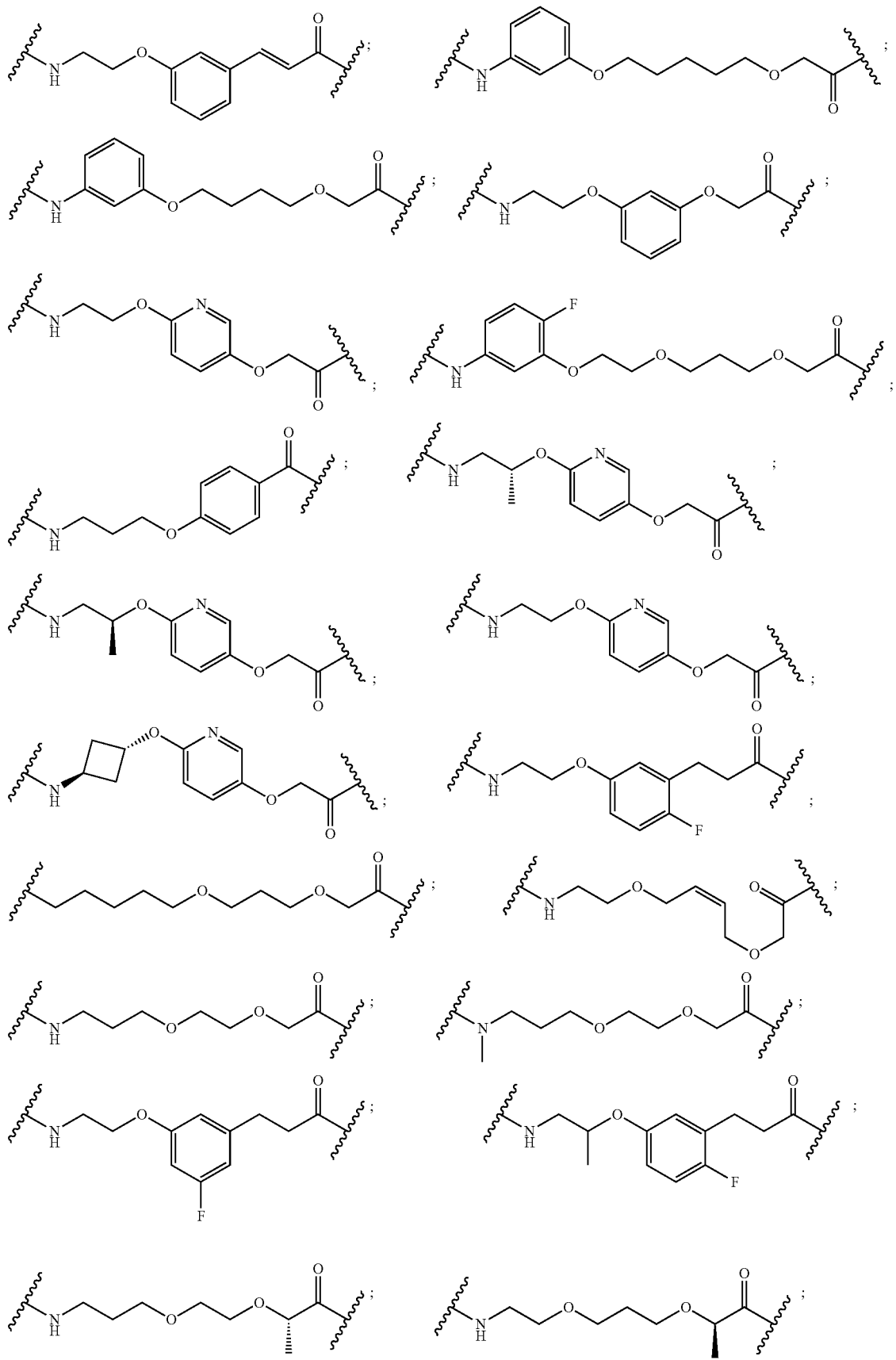

575
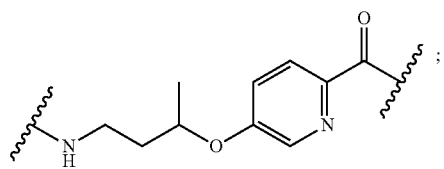
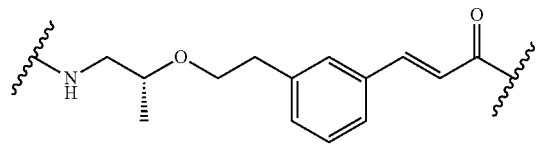
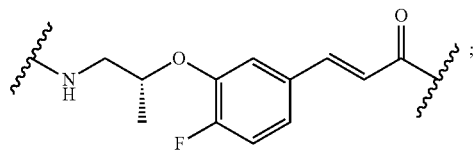
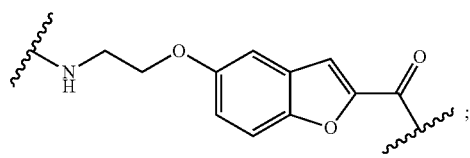
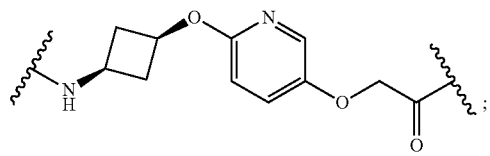
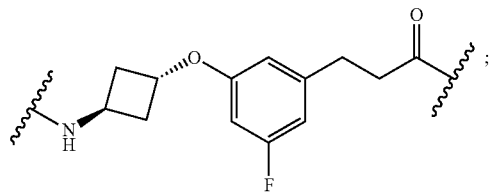
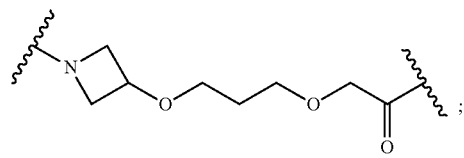
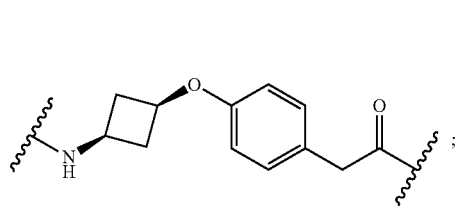
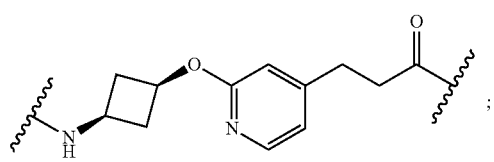
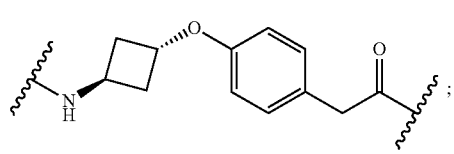
576
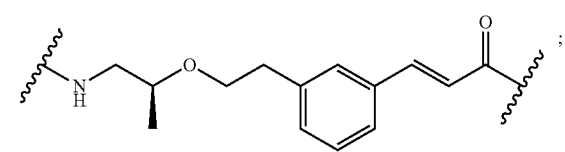
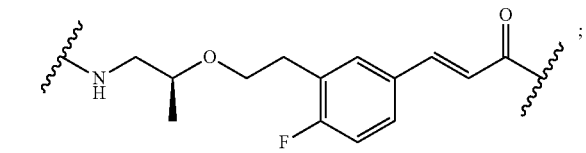
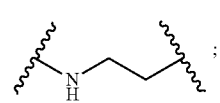
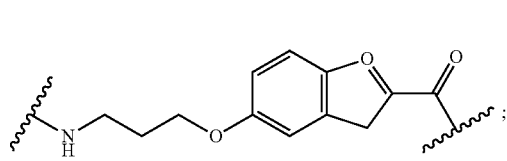
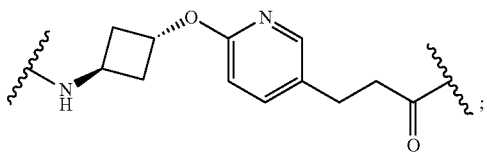
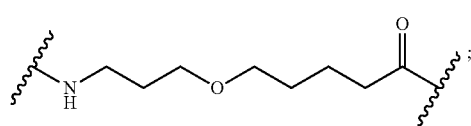
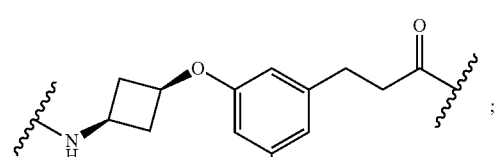
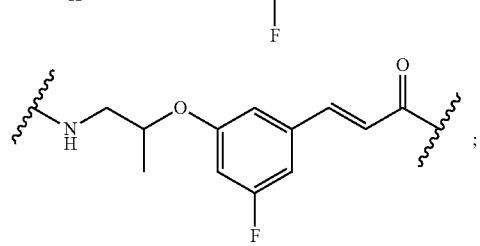
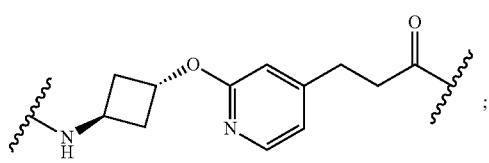
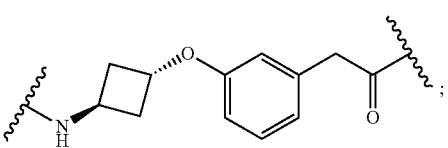

577 578
-continued
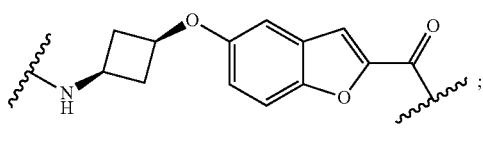
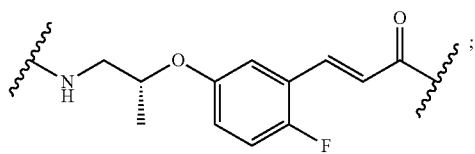
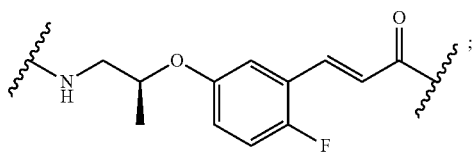
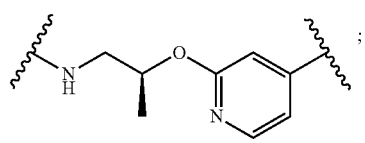
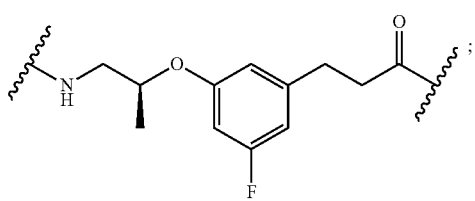
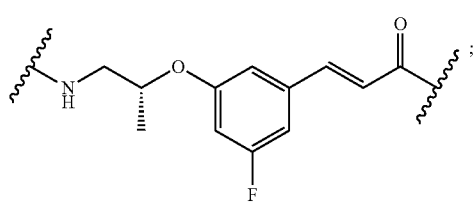
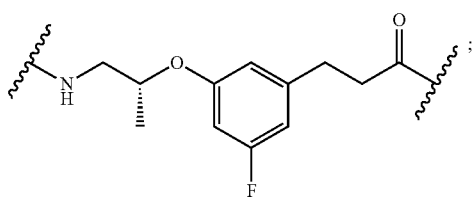
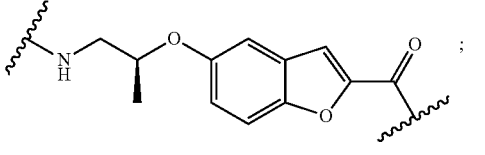
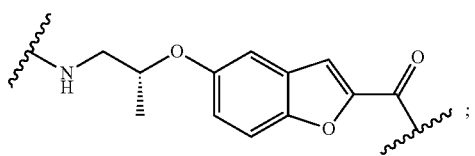
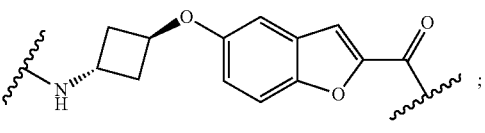
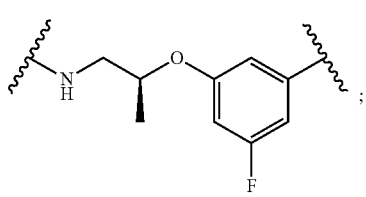
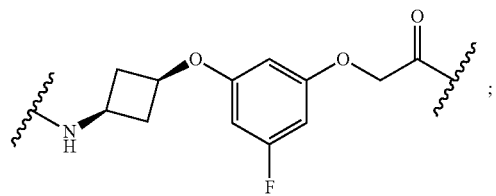
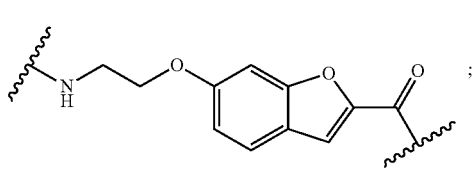
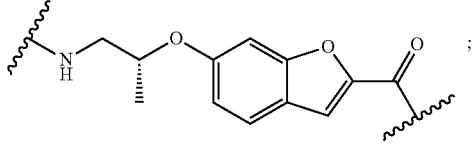
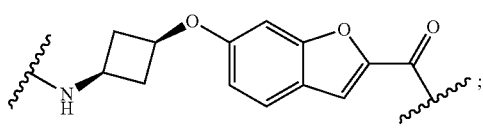
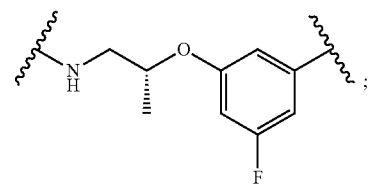
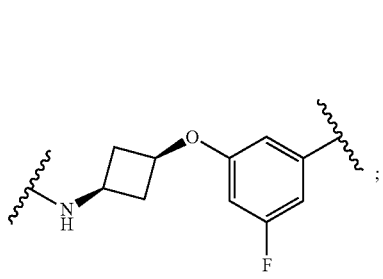
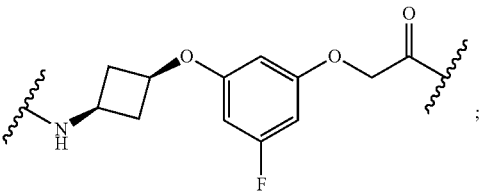

-continued

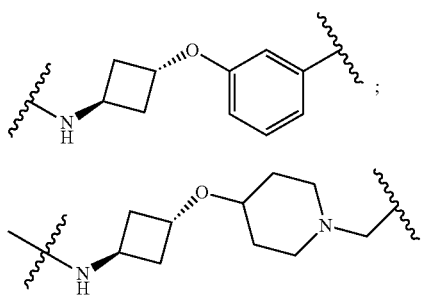

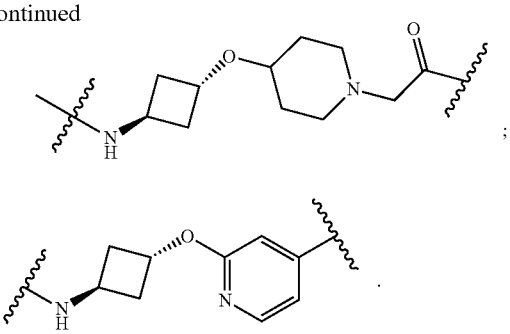 and

In any aspect or embodiment described herein, L is a polyethylene group optionally substituted with aryl or phenyl comprising from 1 to 10 ethylene glycol units.

In any aspect or embodiment described herein, the compound comprises multiple LCMs, multiple ABMs, multiple linkers or any combinations thereof.

In any aspect or embodiment described herein, the compound is a member selected from the group consisting of Examples 1-452 and 528-625 (e.g., a compound from Tables 2-7), a salt, a polymorph, isotopic derivative, and a prodrug thereof.

In any aspect or embodiment described herein, the compound is selected from Tables 2-7 (i.e., Exemplary Compounds 1-452 and 528-625).

In any aspect or embodiment described herein, the ABM is selected from the group consisting of:

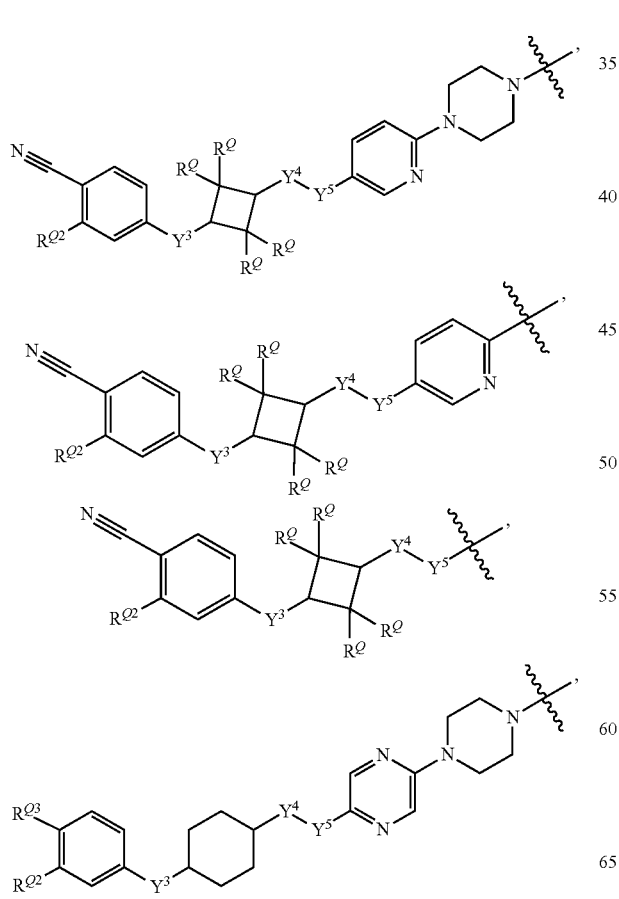

-continued

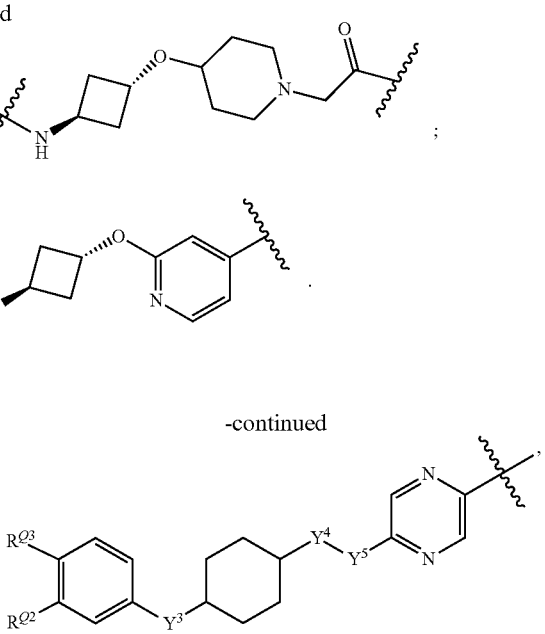

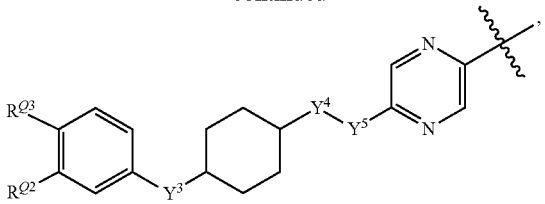

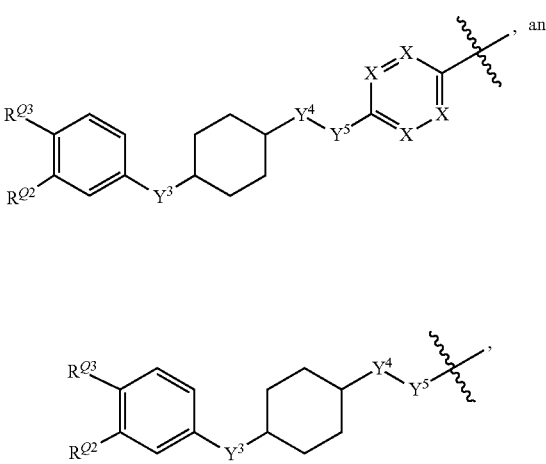

wherein:
R$^{Q2}$ is a H, halogen, CH$_3$ or CF$_3$;
RQ3 is a H, halo, hydroxyl, nitro, CN, C≡CH, C$_{1-6}$ alkyl (linear, branched, optionally substituted by 1 or more halo, C$_{1-6}$ alkoxyl), C$_{1-6}$ alkoxyl (linear, branched, optionally substituted by 1 or more halo), C$_{2-6}$ alkenyl, C$_{2-6}$ alkynyl, or CF$_3$;
Y$^3$, Y$^4$, Y$^5$ are each independently a bond, O, NR$^{Y2}$, CR$^{Y1}$R$^{Y2}$, C=O, heteroaryl, or aryl;
R$^{Y1}$, R$^{Y2}$ are each independently H, or C$_{1-6}$ alkyl (linear, branched, optionally substituted by 1 or more halo, C$_{1-6}$ alkoxyl, cyclic, or heterocyclic);
R$^Q$ each independently is H, C$_1$-C$_6$ alkyl (linear, branched, optionally substituted by 1 or more halo, or C$_{1-6}$ alkoxyl), or two R$^Q$ together with the atom they are attached to, form a 3-8 membered ring system containing 0-2 heteroatoms; and
X is N or C.

In any aspect or embodiment described herein, each R$^Q$ is independently H or CH$_3$.

In any aspect or embodiment described herein, $R^{Q3}$ is CN;
In any aspect or embodiment described herein, the ABM is selected from the group consisting of:
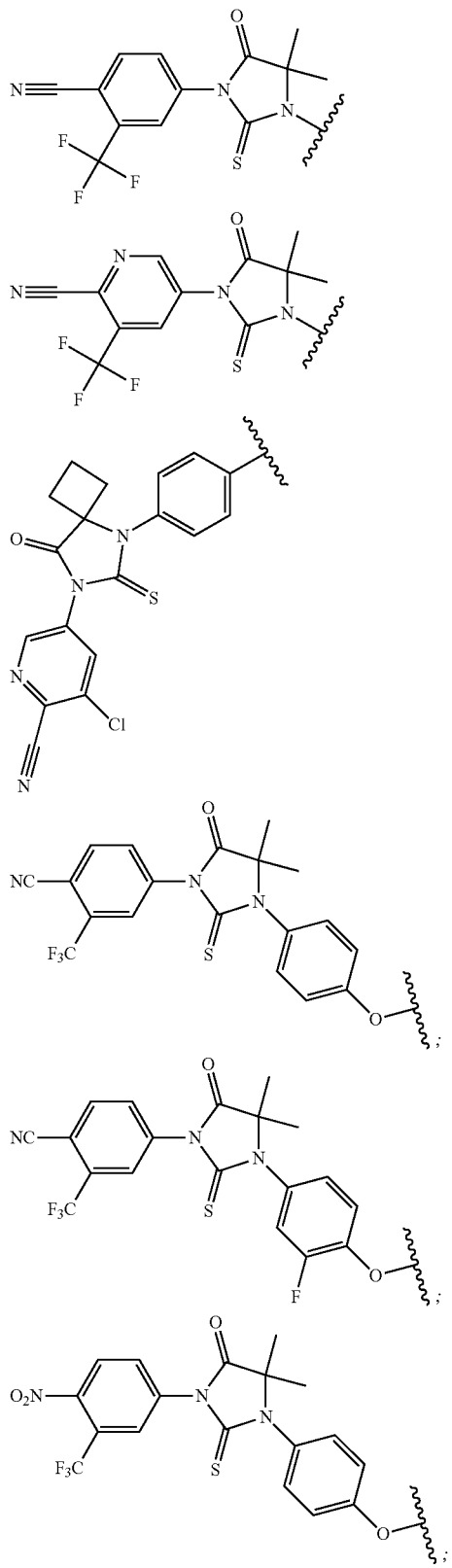
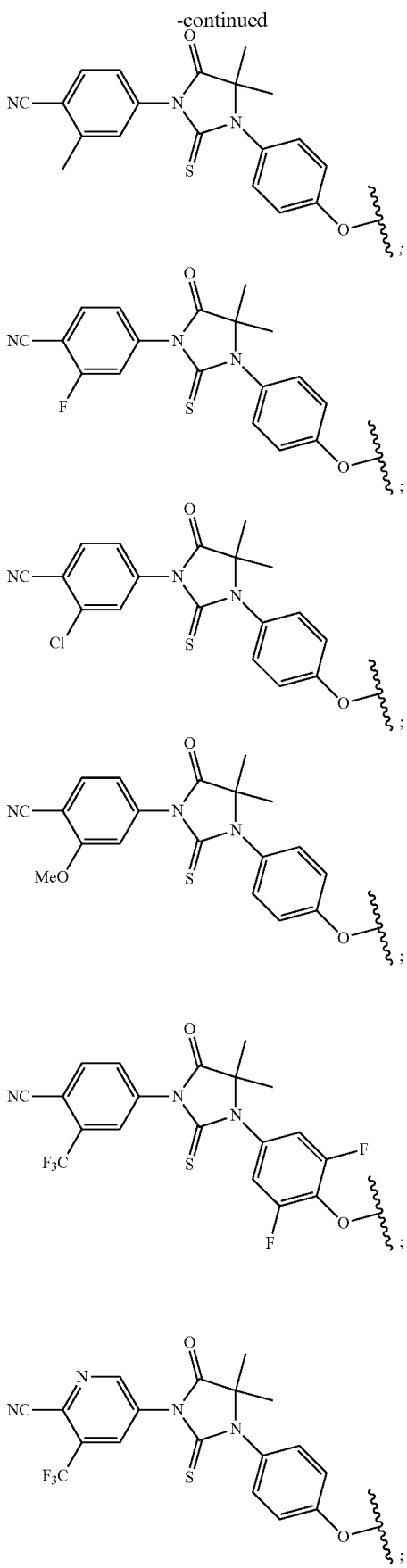

583
-continued
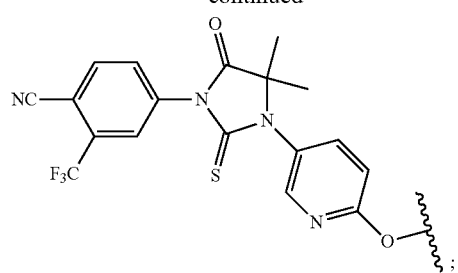
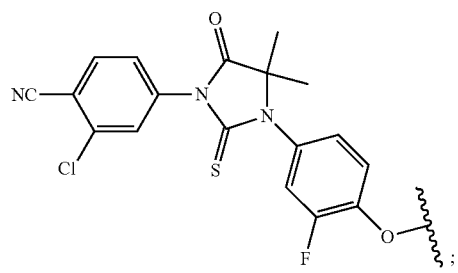
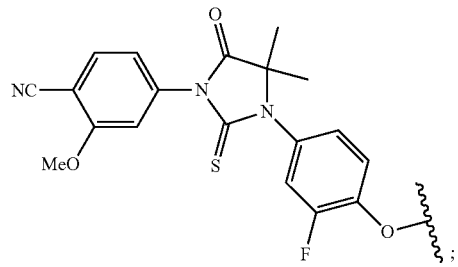
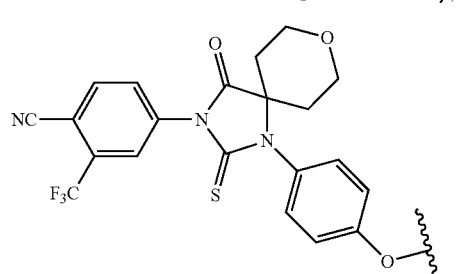
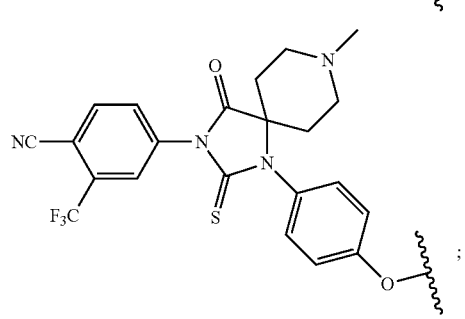
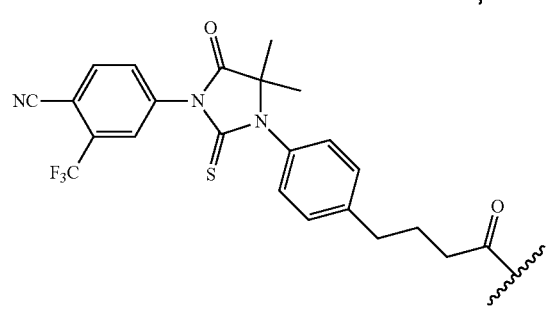
584
-continued
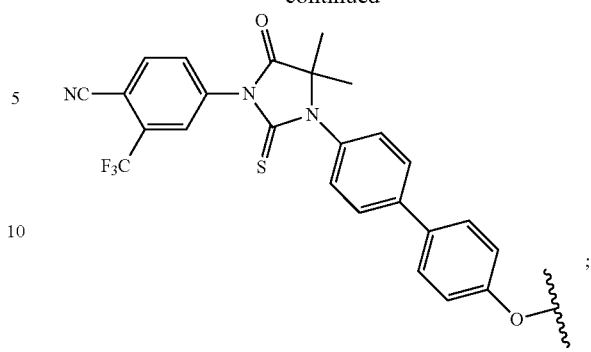
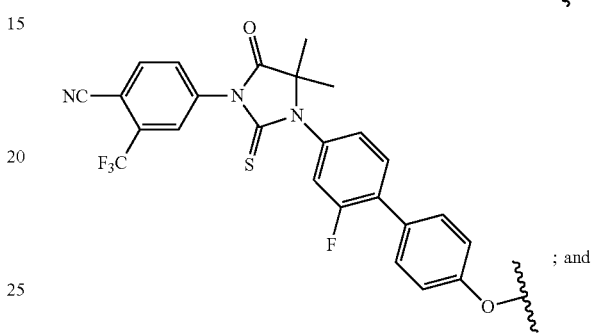
; and
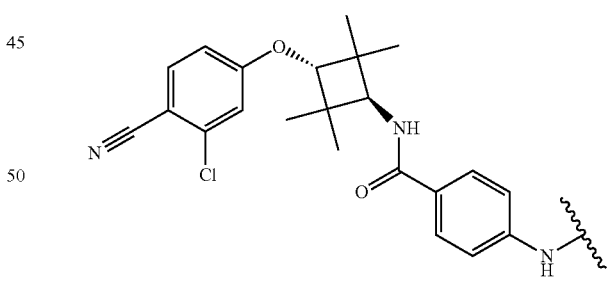
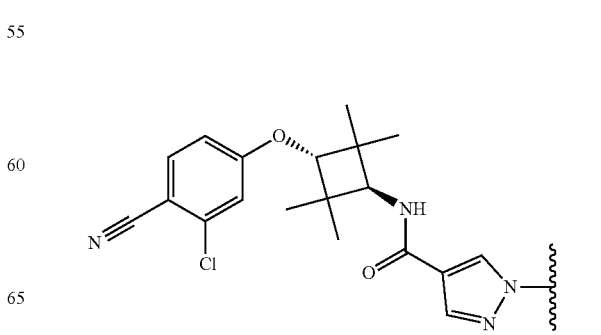

585
-continued
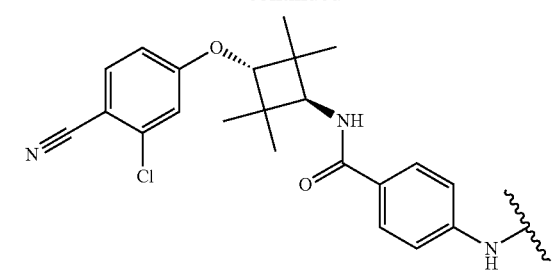
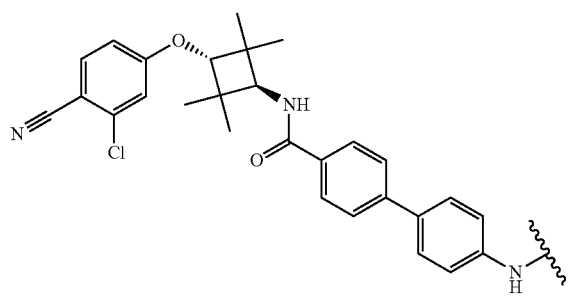
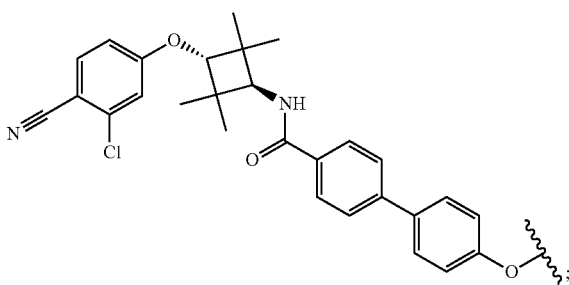
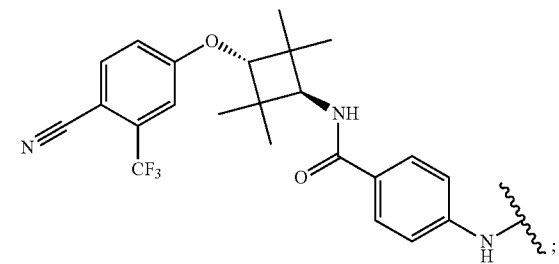
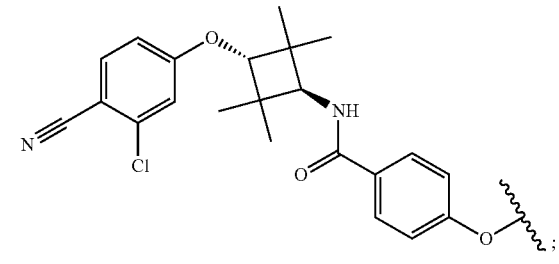
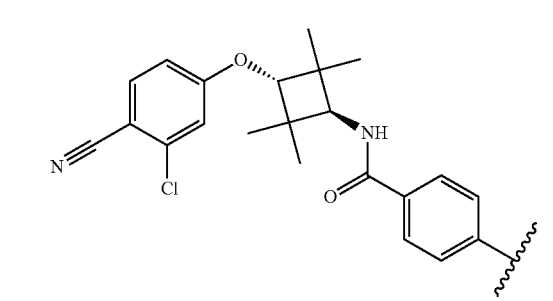
586
-continued
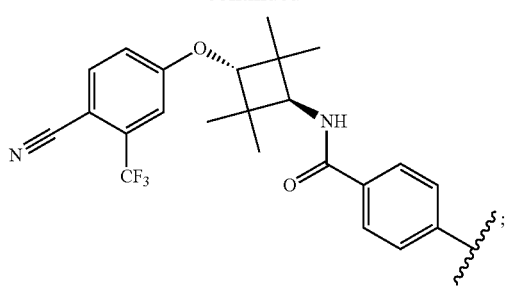
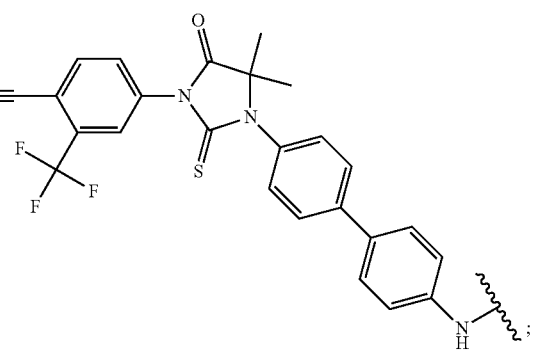
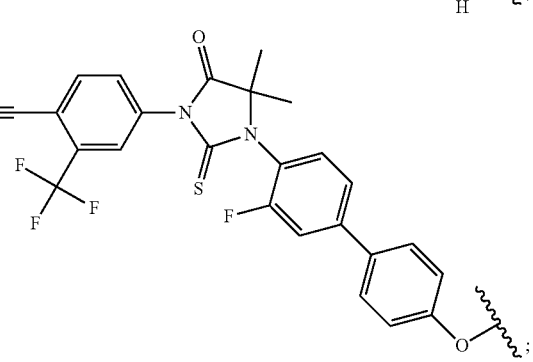
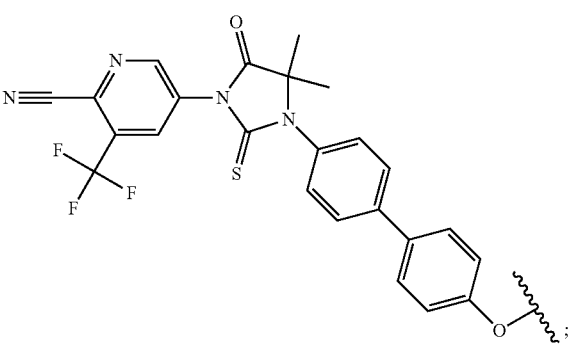
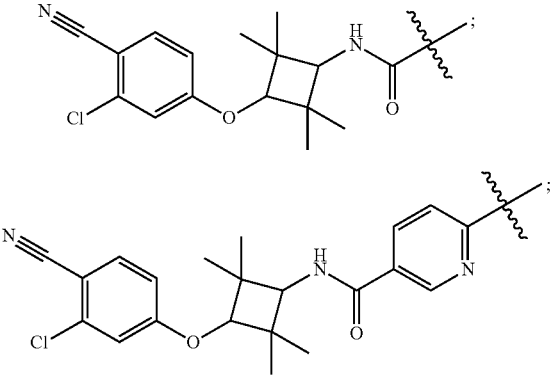

587
-continued
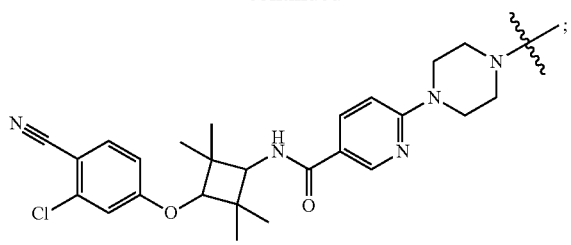
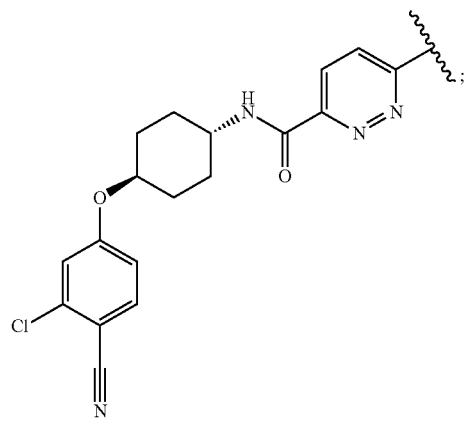
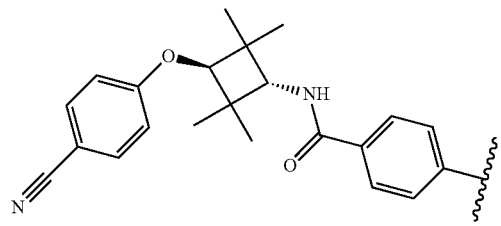
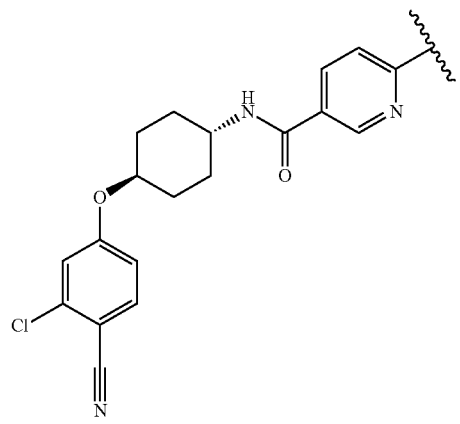
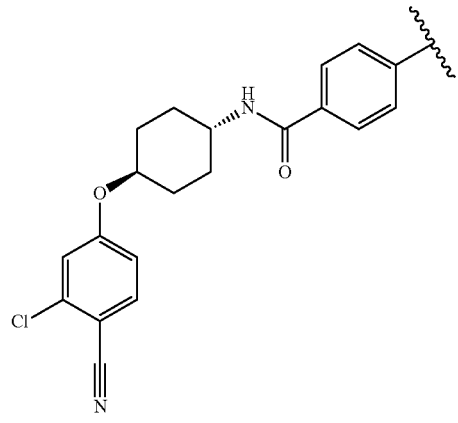
588
-continued
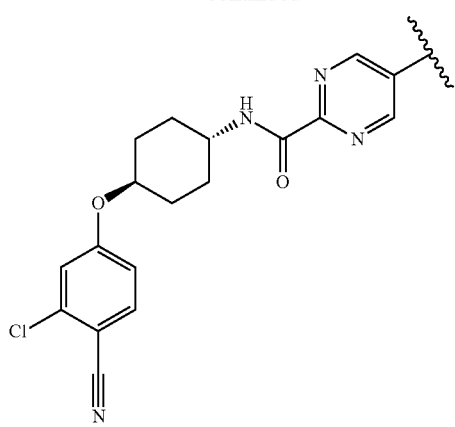
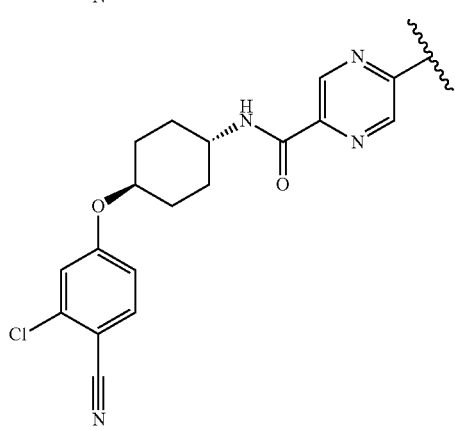
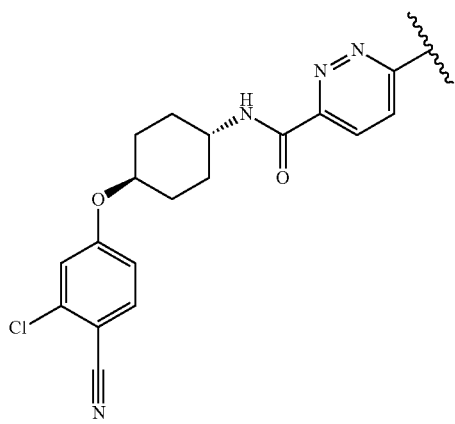
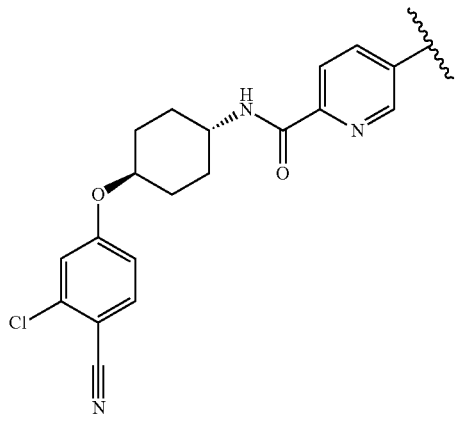

589
-continued
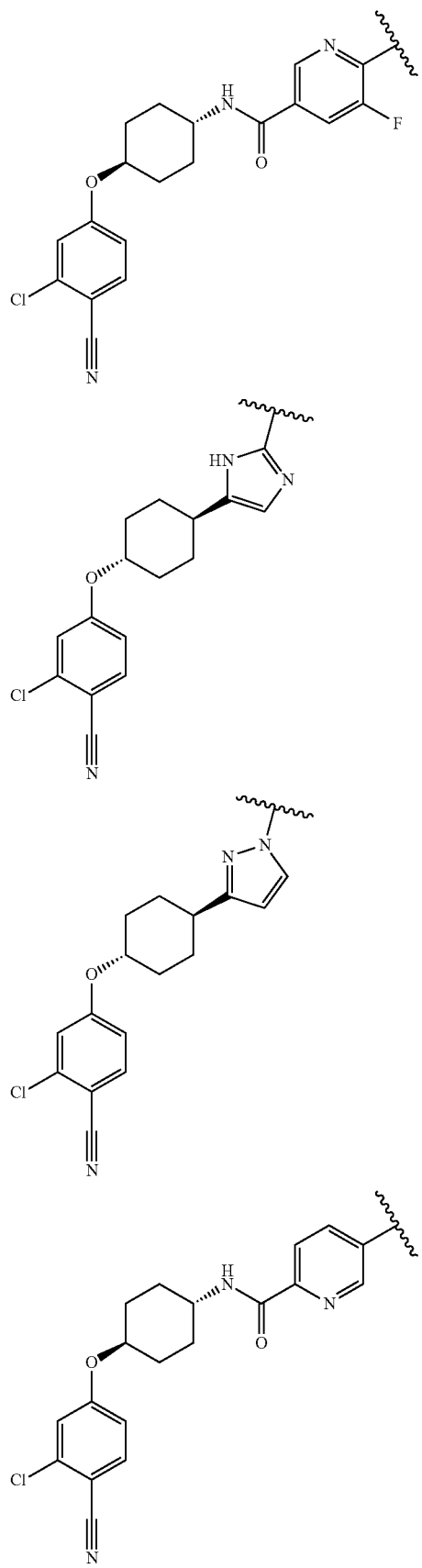 [SMILES: *c1ncc(C(=O)N[C@H]2CC[C@H](Oc3ccc(C#N)c(Cl)c3)CC2)cc1F ; *c1ncc([C@H]2CC[C@H](Oc3ccc(C#N)c(Cl)c3)CC2)[nH]1 ; *n1ccc([C@H]2CC[C@H](Oc3ccc(C#N)c(Cl)c3)CC2)n1 ; *c1ccc(C(=O)N[C@H]2CC[C@H](Oc3ccc(C#N)c(Cl)c3)CC2)nc1]
590
-continued
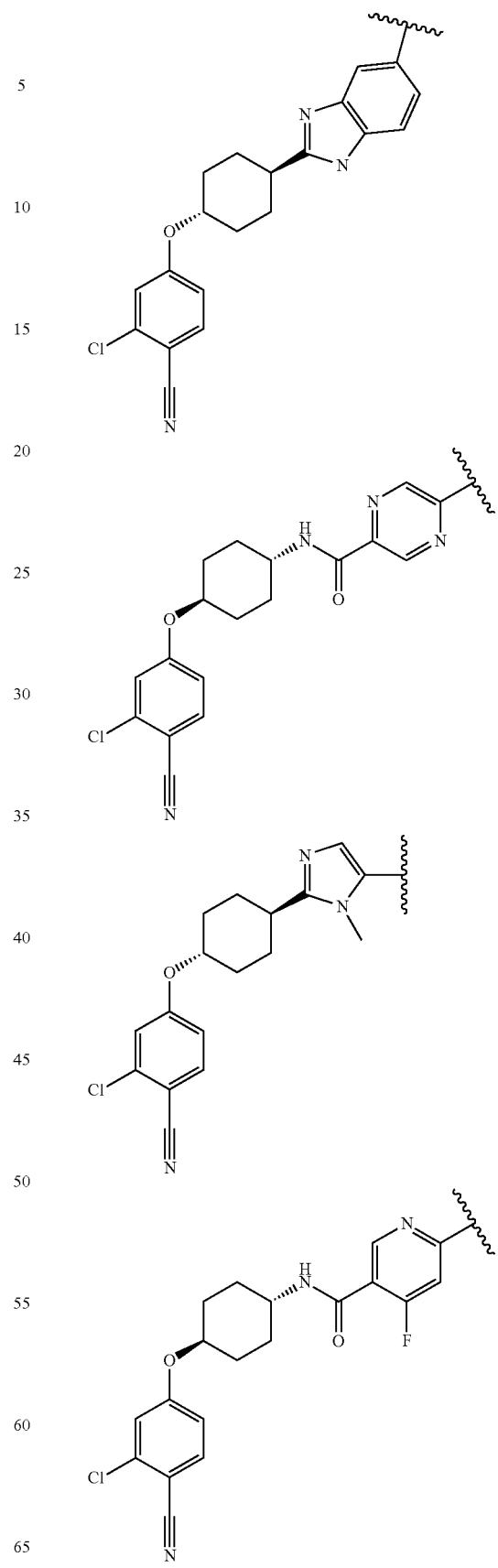

591
-continued
592
-continued
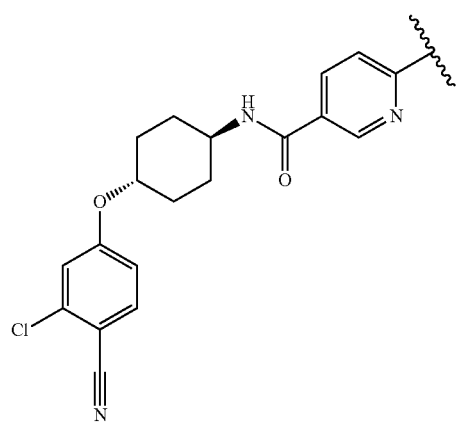
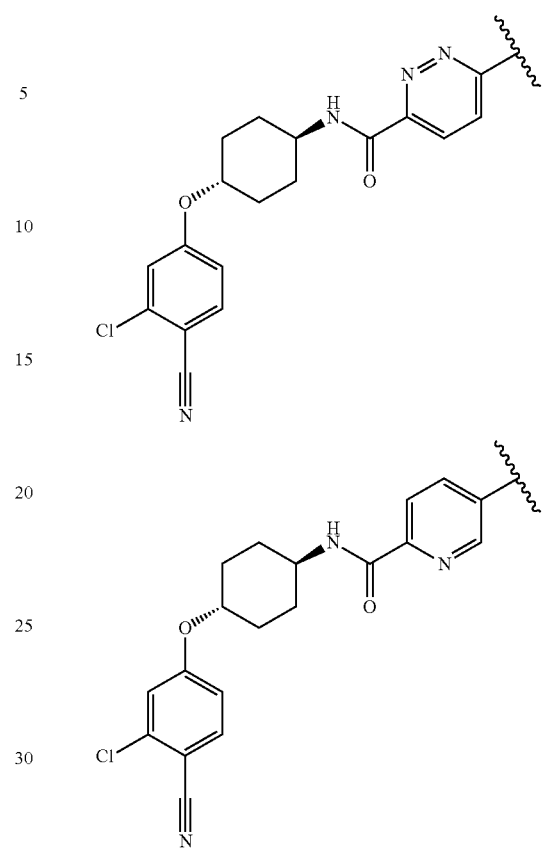
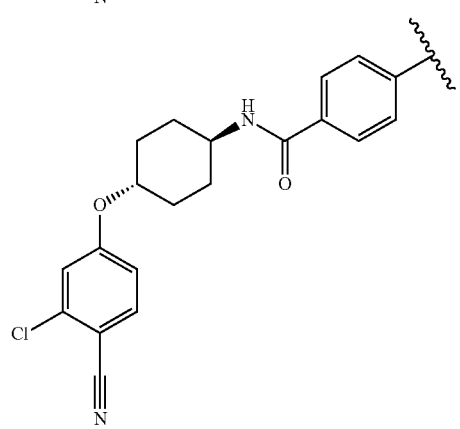
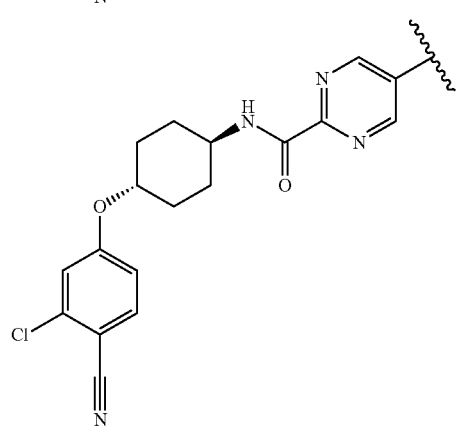
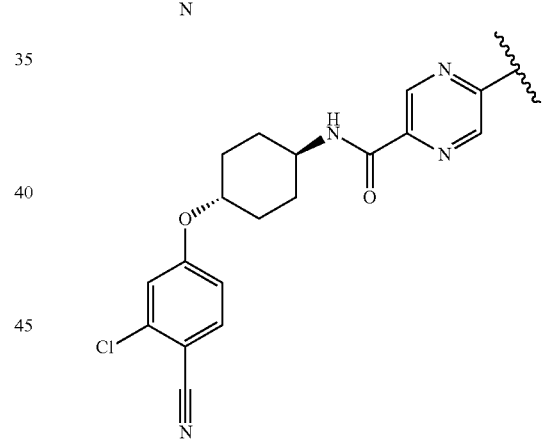
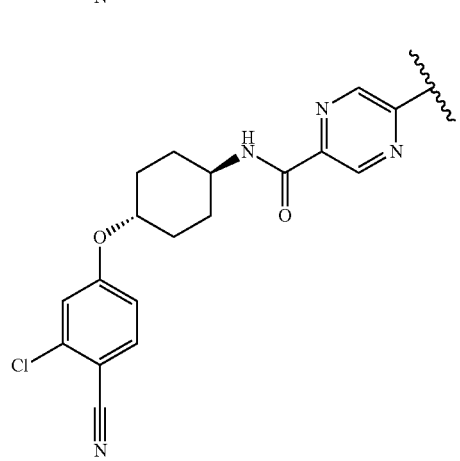
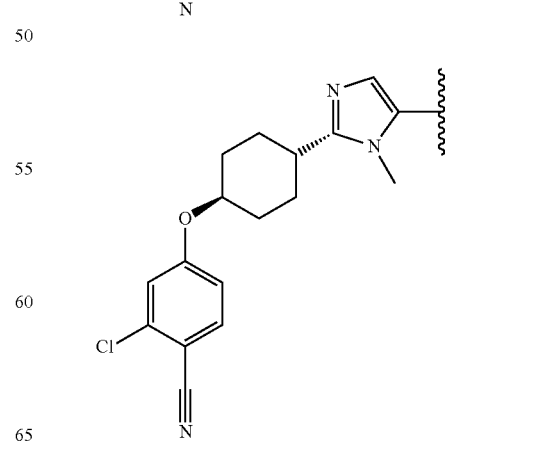

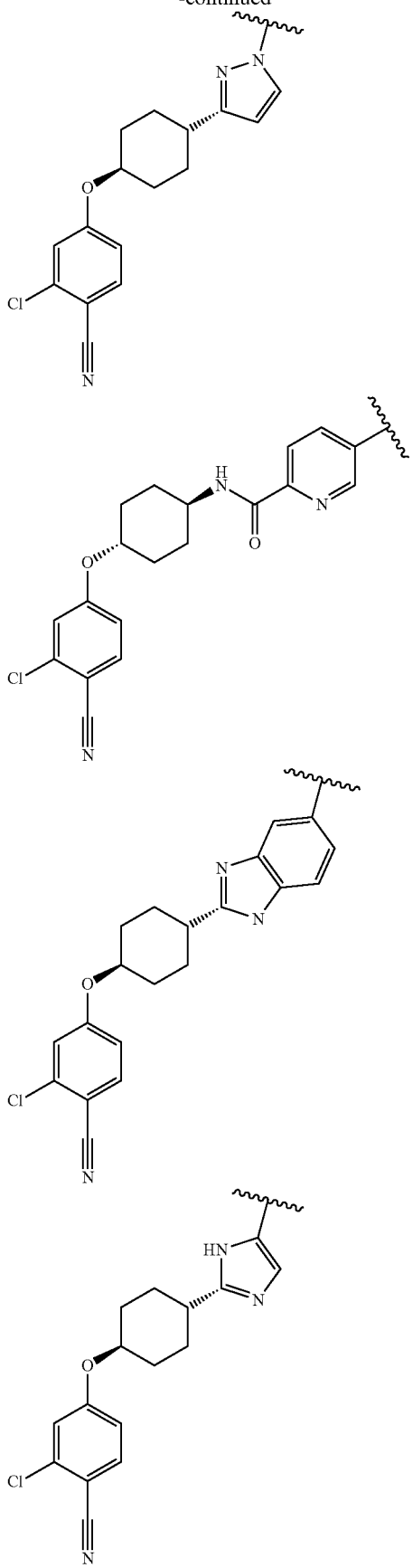

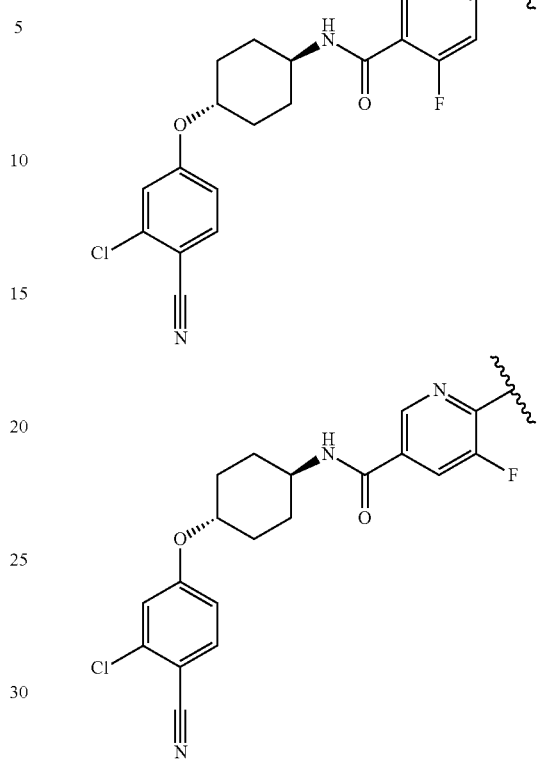

A further aspect of the present disclosure provides a composition comprising an effective amount of a compound or bifunctional compound of any of claims 1-25, and a pharmaceutically acceptable carrier.

In any aspect or embodiment described herein, the composition further comprises at least one additional bioactive agent.

In any aspect or embodiment described herein, the bioactive agent is an anti-cancer agent.

An additional aspect of the present disclosure provides a therapeutic composition comprising an effective amount of at least two different compounds as described in any of claims 1-25.

Another aspect of the present disclosure provides a method of treating a disease or disorder in a subject comprising the steps of administering a composition comprising a pharmaceutically acceptable carrier and an effective amount of a compound or bifunctional compound as described in any of claims 1-25 to a subject in need thereof, wherein the compound is effective in treating or ameliorating at least one symptom of the disease or disorder.

In any aspect or embodiment described herein, the disease or disorder is cancer or Kennedy's Disease or both.

In any aspect or embodiment described herein, the cancer is prostate cancer.

In any aspect or embodiment described herein, the composition further comprises an effective amount of at least one additional anti-cancer agent.

The contents of all references, patents, pending patent applications and published patents, cited throughout this application are hereby expressly incorporated by reference. Except in the Examples, or where otherwise explicitly indicated, all numerical quantities in this description specifying amounts of materials, and the like, are to be understood as modified by the word "about". It is to be understood that the upper and lower amount, range, and ratio limits set forth herein may be independently combined. Similarly, the ranges and amounts for each element of the disclosure can be used together with ranges or amounts for any of the other elements.

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:
1. A compound represented by the structure:

ABM-L-CLM, or a pharmaceutically acceptable salt thereof, wherein:

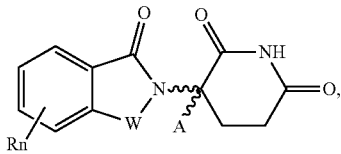

(a) CLM is
wherein:
W is $CH_2$ or $C=O$;
A is H;
n is an integer from 1 to 4;
wherein when n is 1, R is an aryl, heteroaryl, cycloalkyl, or heterocyclyl covalently joined to the linker group (L); and when n is 2, 3, or 4, one R is an aryl, heteroaryl, cycloalkyl, or heterocyclyl covalently joined to the linker group (L) and the remaining R are selected from OR', —NR'R", —SR', —$C_{1-6}$ alkyl, —Cl, —F, —Br, —I, —$CF_3$, —CN, and —$OCF_3$;
R' and R" are each independently selected from H, $C_{1-6}$ alkyl, cycloalkyl, aryl, heteroaryl, and heterocyclyl; and
⁓ represents a bond that may be stereospecific ((R) or (S)) or non-stereospecific;
(b) L is a chemical linker group that is covalently bound to the ABM and the CLM, and has the chemical structure -$(A^L)_q$-, wherein:

q is an integer greater than or equal to 1;
each $A^L$ is selected from $CR^{L1}R^{L2}$, O, S, $NR^{L3}$, CO, $CR^{L1}=CR^{L2}$, C≡C, $C_{3-11}$ cycloalkyl optionally substituted with 1-6 $R^{L1}$, $C_{5-13}$ spirocycloalkyl optionally substituted with 1-9 $R^{L1}$, $C_{3-11}$ heterocyclyl optionally substituted with 1-6 $R^{L1}$, $C_{5-13}$ spiroheterocycloalkyl optionally substituted with 1-8 $R^{L1}$, aryl optionally substituted with 1-4 $R^{L1}$, and heteroaryl optionally substituted with 1-4 $R^{L1}$; and
$R^{L1}$, $R^{L2}$, and $R^{L3}$ are each, independently, H, halogen, $C_{1-8}$alkyl, $OC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{3-8}$cycloalkyl, $NHC_{3-8}$cycloalkyl, $N(C_{3-8}cycloalkyl)_2$, $N(C_{3-8}cycloalkyl)(C_{1-8}alkyl)$, OH, $NH_2$, $COC_{1-8}$alkyl, $CO_2H$, CN, $CF_3$, $CHF_2$, $CH_2F$, $NO_2$, $CONHC_{1-8}$alkyl, or $CON(C_{1-8}alkyl)_2$, or $R^{L1}$ and $R^{L2}$ are linked to form a cycloalkyl or a heterocyclyl moiety; and
(c) ABM is:

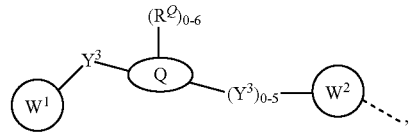

wherein:
$W^1$ is aryl optionally substituted by 1 or more halogen; hydroxyl; nitro; CN; $C_{1-6}$ alkyl optionally substituted by 1 or more halogen or $C_{1-6}$ alkoxyl; or $C_{1-6}$ alkoxyl optionally substituted by 1 or more halogen;
each $Y^3$ is independently a bond, O, $NR^{Y2}$, $CR^{Y1}R^{Y2}$, or C=O;
Q is a 6-membered alicyclic substituted with 0-6 $R^Q$;
each $R^Q$ is independently halogen; $C_{1-6}$ alkoxy; or $C_{1-6}$ alkyl optionally substituted by 1 or more halogen or $C_{1-6}$ alkoxyl;
$R^{Y1}$ and $R^{Y2}$ are each, independently, H, halogen, $C_{1-6}$ alkoxy, or $C_{1-6}$ alkyl optionally substituted by 1 or more halogen or $C_{1-6}$ alkoxyl;
$W^2$ is aryl optionally substituted by 1-4 $R^{W2}$ or heteroaryl optionally substituted by 1-4 $R^{W2}$;
each $R^{W2}$ is, independently, halogen; $C_{1-6}$ alkyl optionally substituted by 1 or more —F; OH; $NR^{Y1}R^{Y2}$; CN; or $OC_{1-3}$alkyl optionally substituted by 1 or more —F; and ⁓ is the point of attachment of the ABM to the chemical linker group (L).

2. The compound of claim 1, wherein the ABM is:

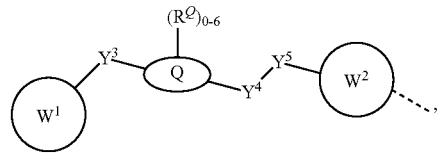

wherein:
$Y^4$ and $Y^5$ are each individually selected from: O, $NR^{Y2}$, $CR^{Y1}R^{Y2}$, and C=O; and is the point of attachment of the ABM to the chemical linker group (L).

3. The compound of claim 1, wherein $W^1$ is:

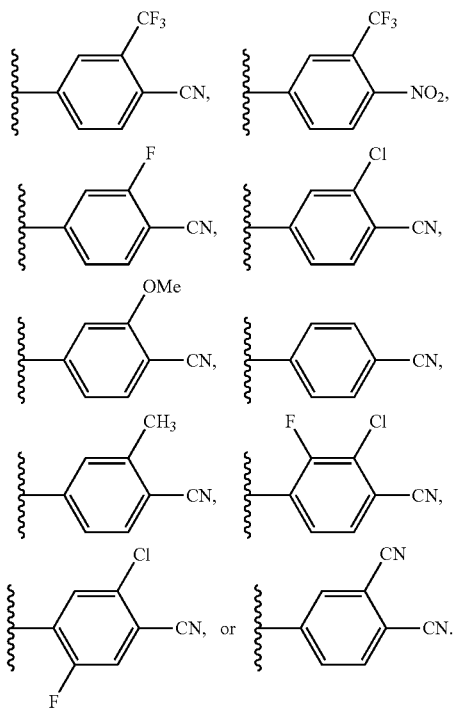

4. The compound of claim 2, wherein $W^2$ is:

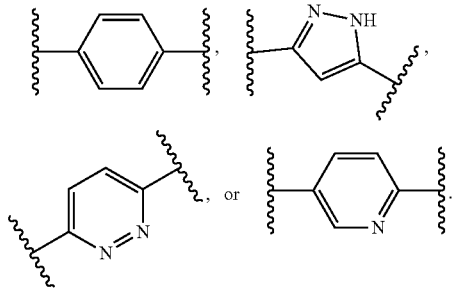

5. The compound of claim 1, wherein $W^2$ is:

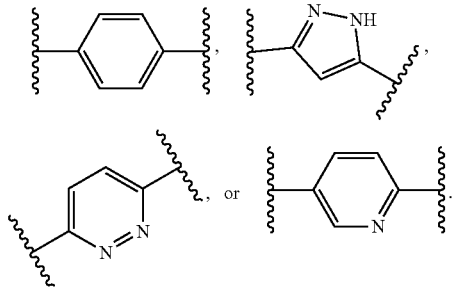

6. The compound of claim 1, wherein the ABM is:

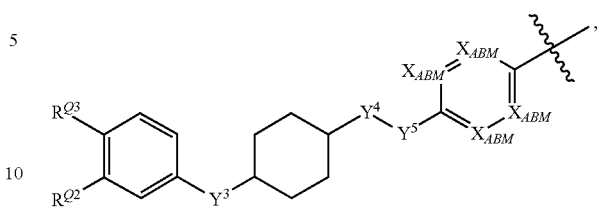

wherein:

$R^{Q2}$ is H, halogen, $CH_3$ or $CF_3$;

$R^{Q3}$ is H, halogen, hydroxyl, nitro, CN, $C_{1-6}$ alkyl optionally substituted by 1 or more halogen; or $C_{1-6}$ alkoxyl optionally substituted by 1 or more halogen;

$Y^3$, $Y^4$, and $Y^5$ are each, independently, O, $NR^{Y2}$, $CR^{Y1}R^{Y2}$, or C=O;

$R^{Y1}$ and $R^{Y2}$ are each, independently, H or $C_{1-6}$ alkyl optionally substituted by 1 or more halogen or $C_{1-6}$ alkoxyl; and $X_{ABM}$ is N or CH.

7. The compound of claim 1, wherein the ABM is:

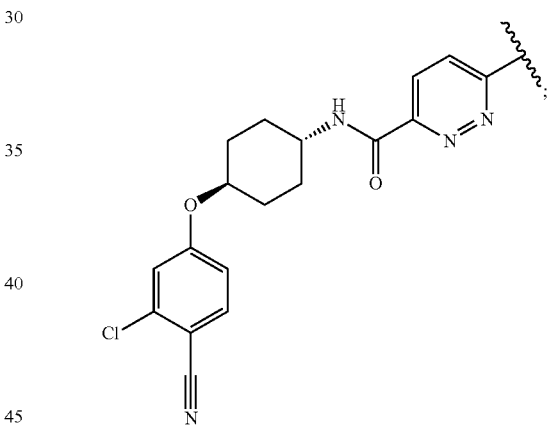

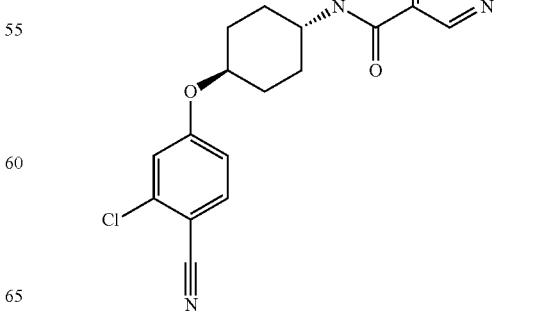

599
-continued
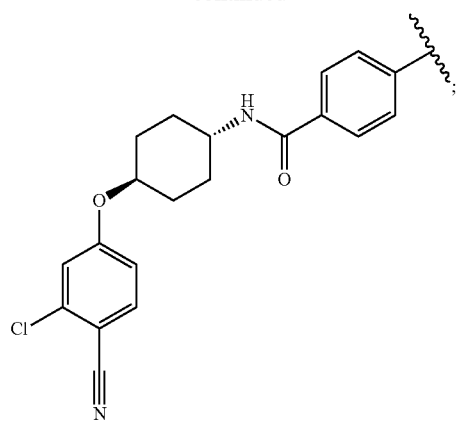
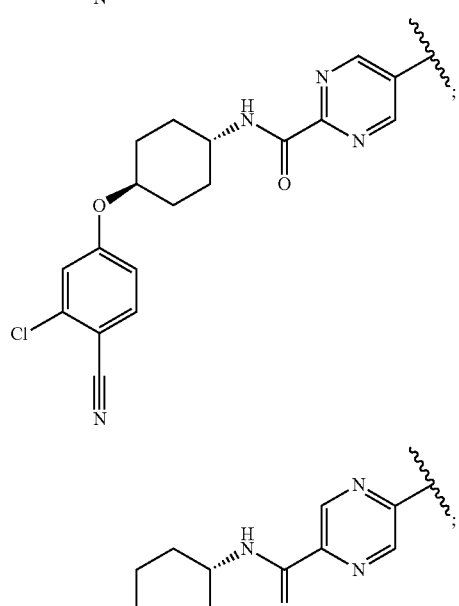
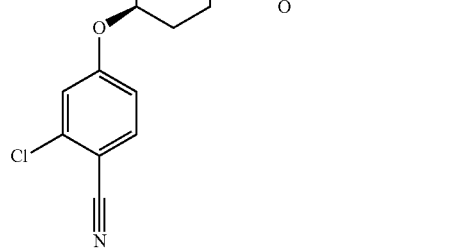
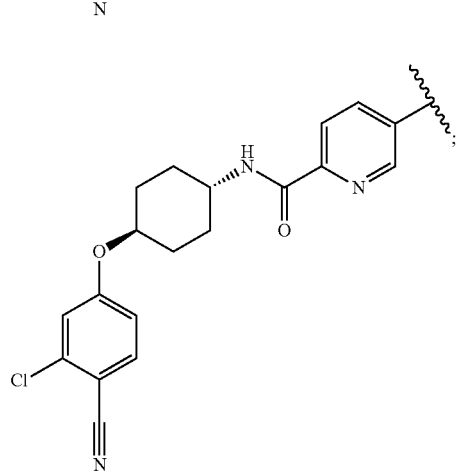
600
-continued
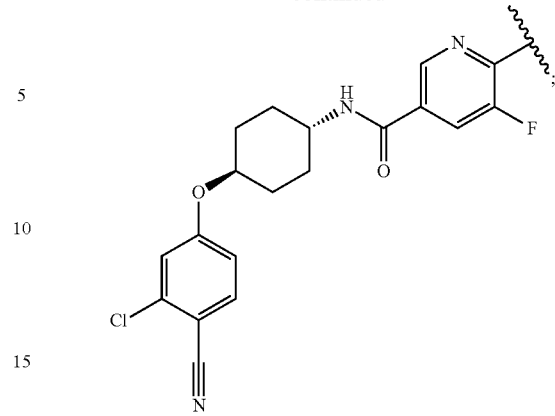
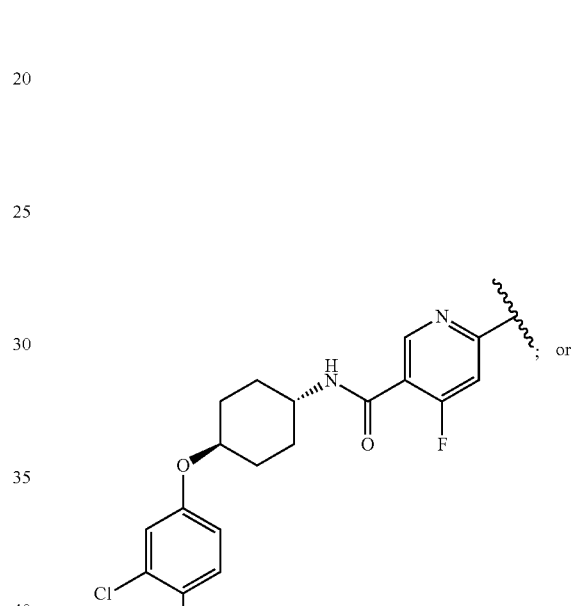
; or
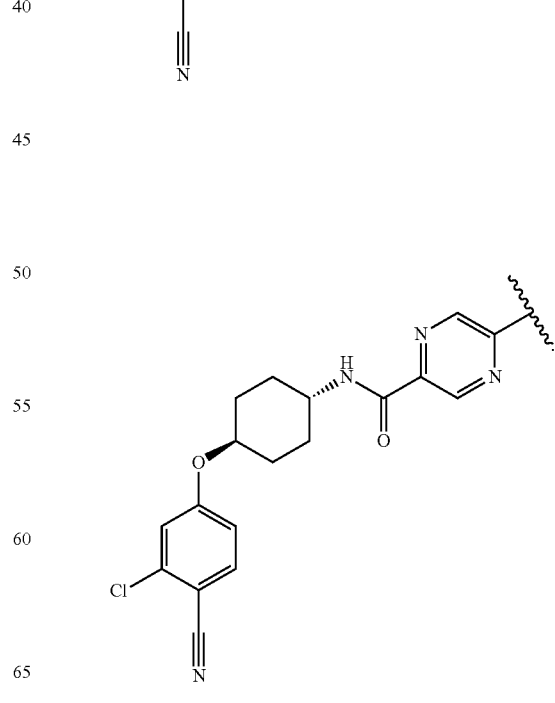

8. The compound of claim 1, wherein the chemical linker group (L) is:
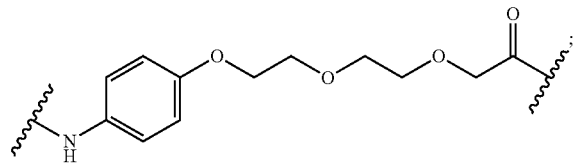 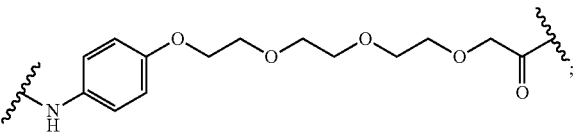
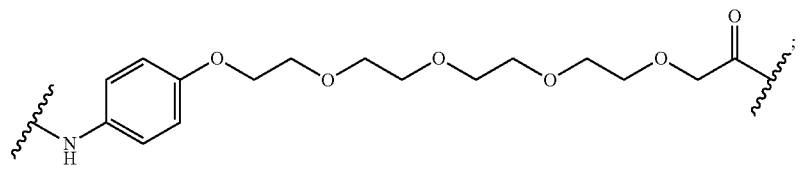
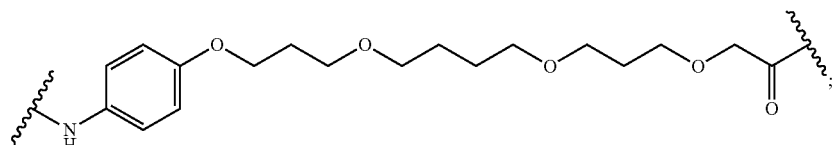
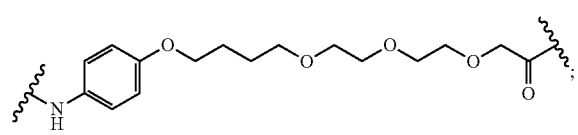 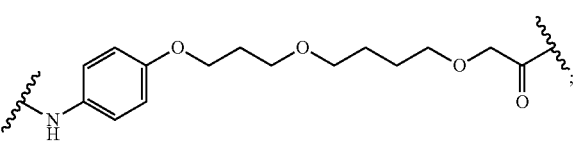
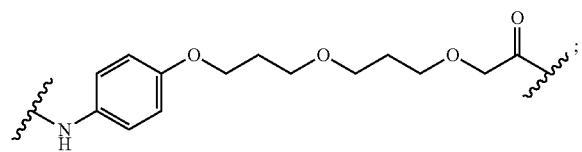 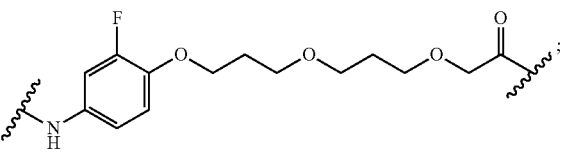
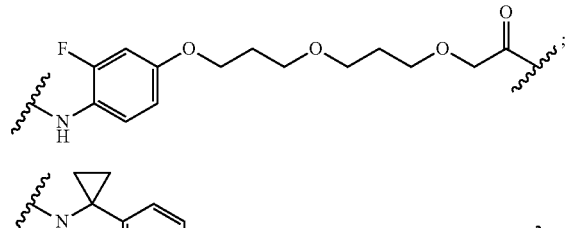 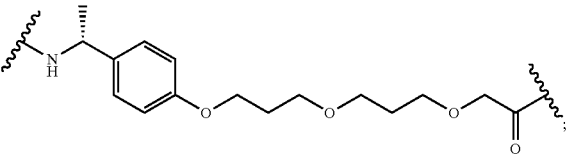
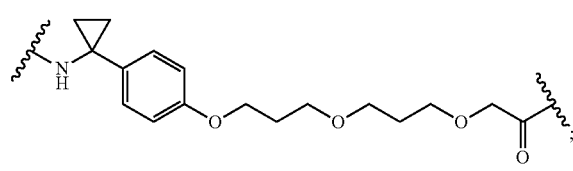 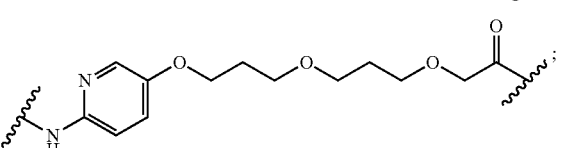
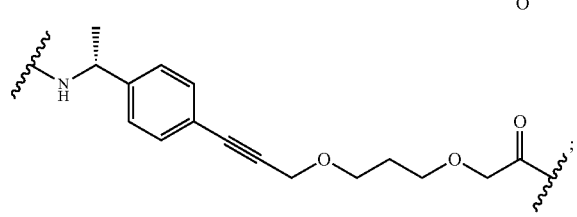 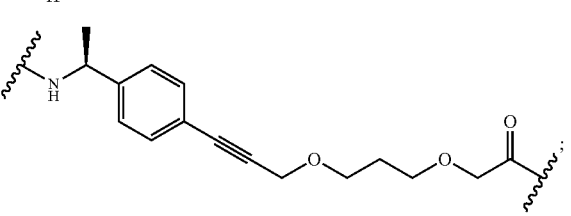
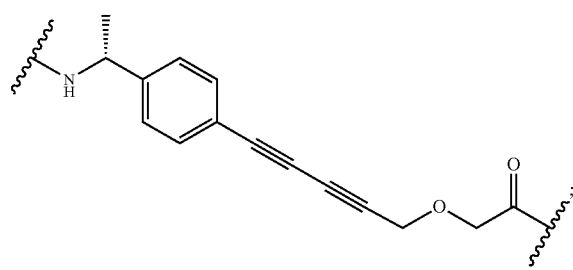 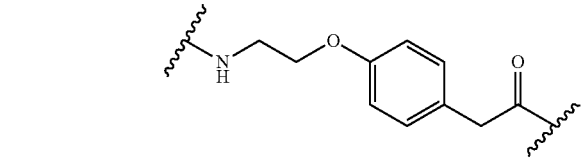

603 604
-continued
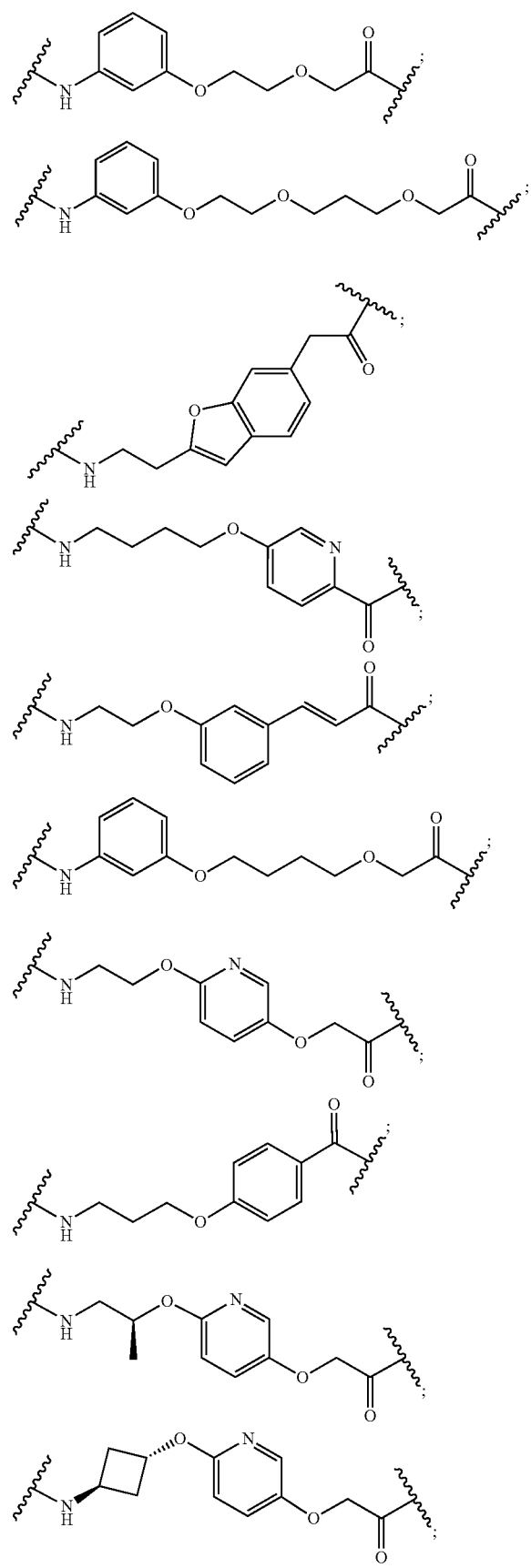
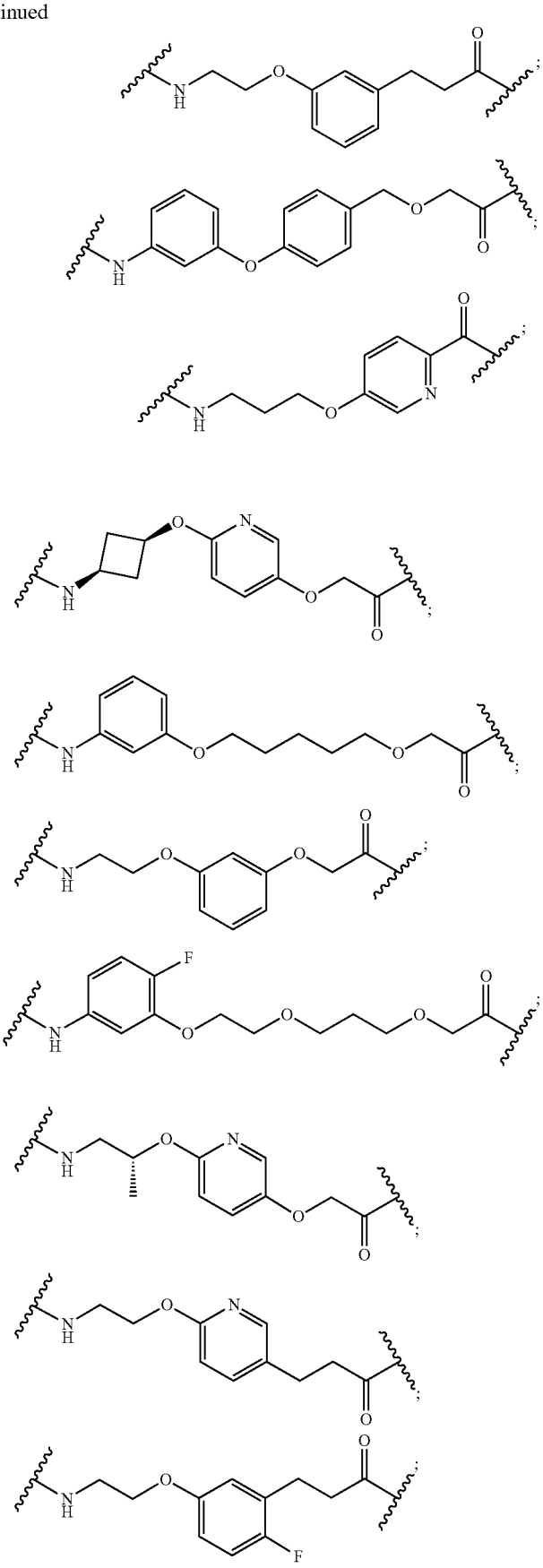

605 606
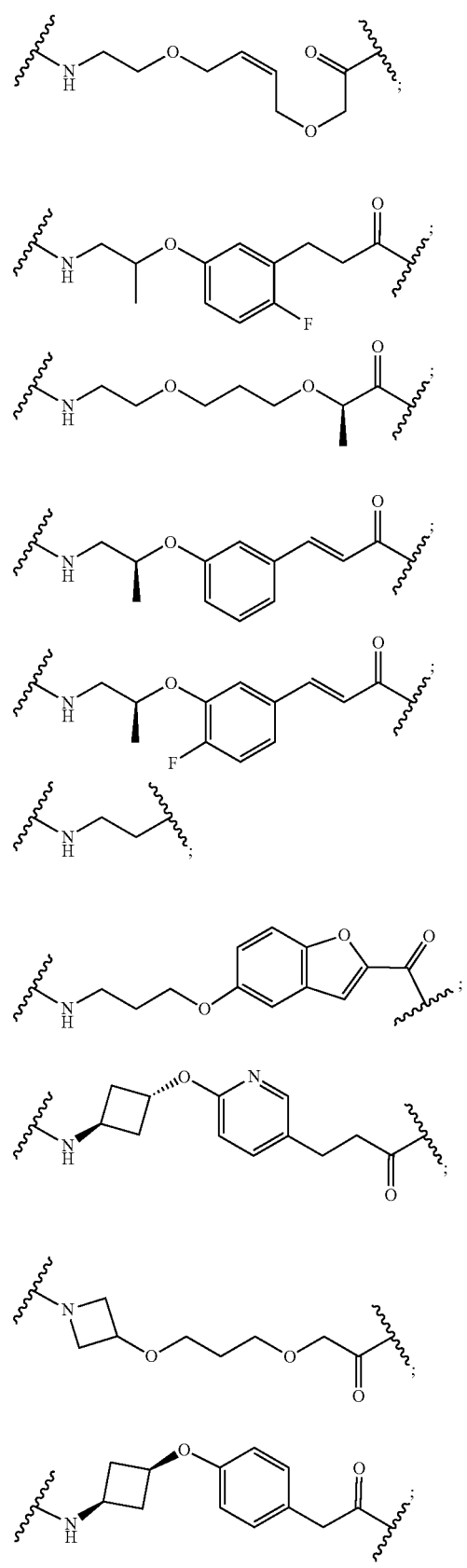
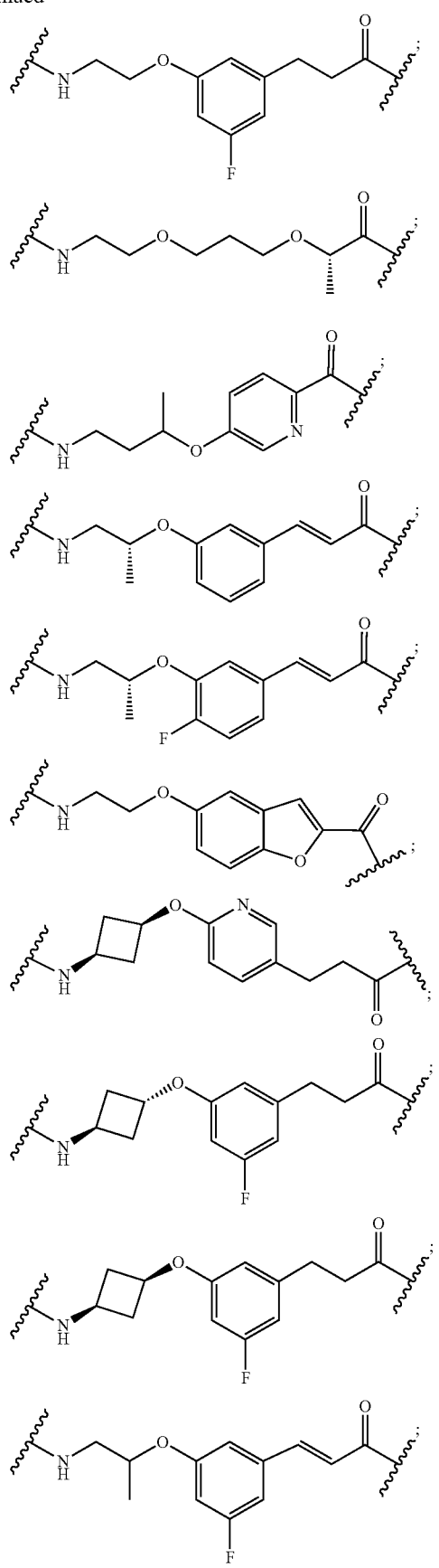

607
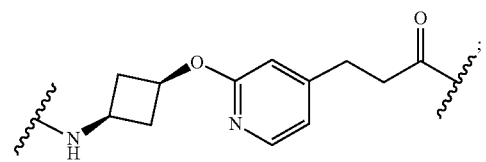
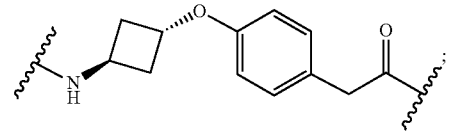
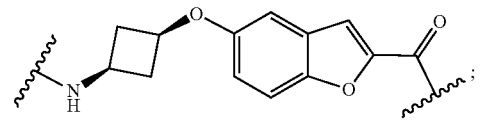
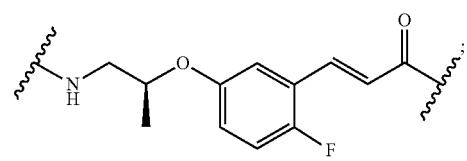
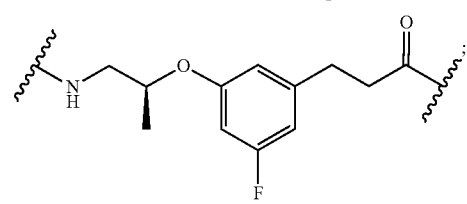
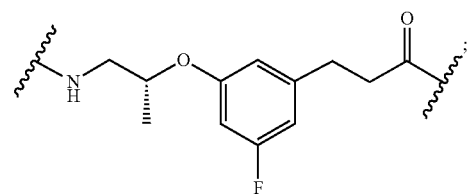
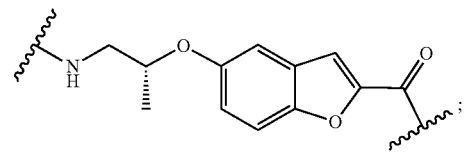
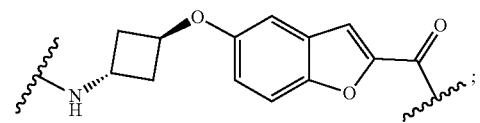
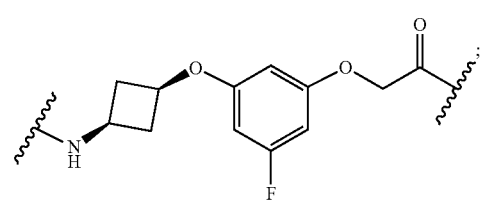
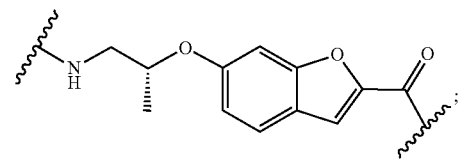
608
-continued
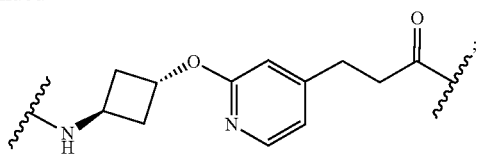
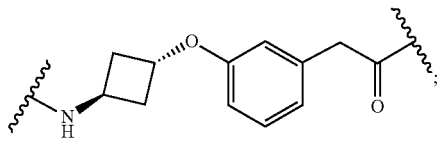
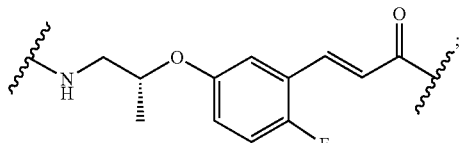
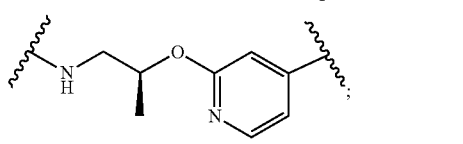
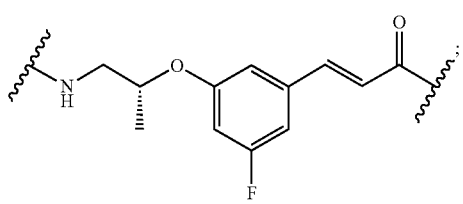
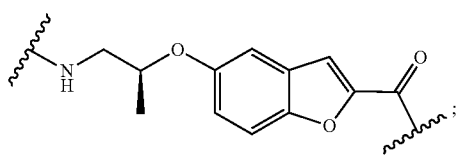
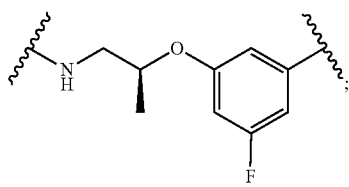
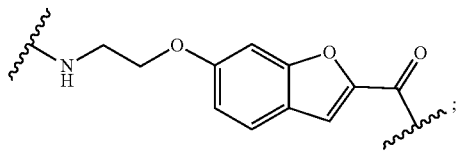
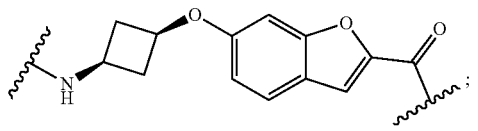

609
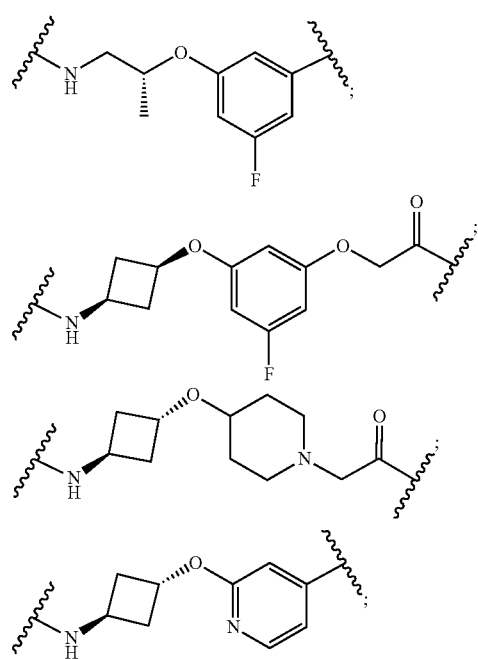
610
-continued
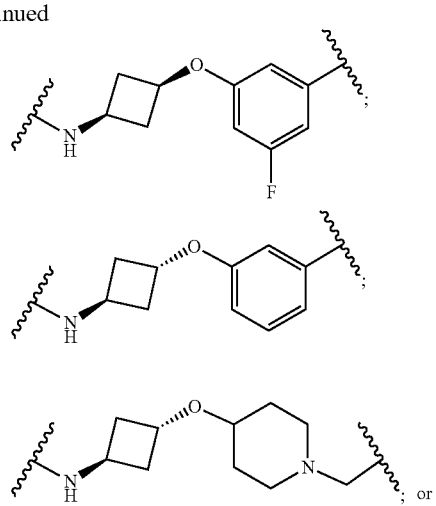
9. The compound of claim 1, wherein the compound is:
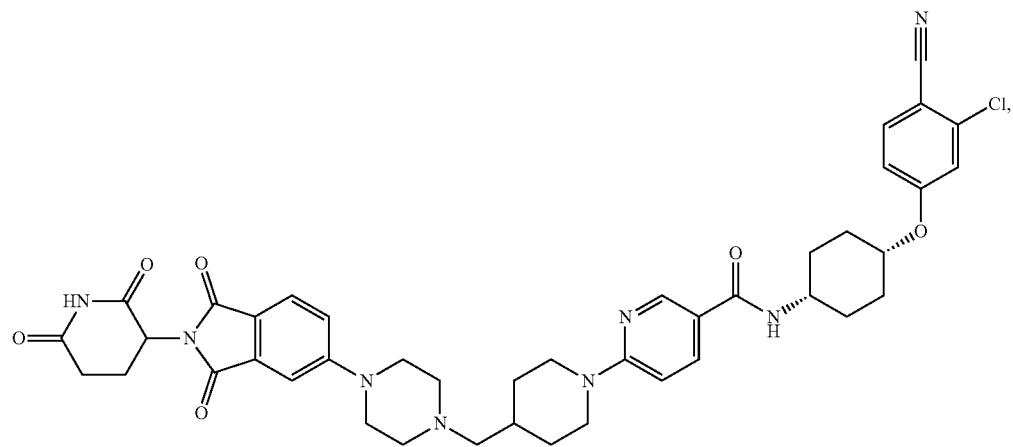
(399)
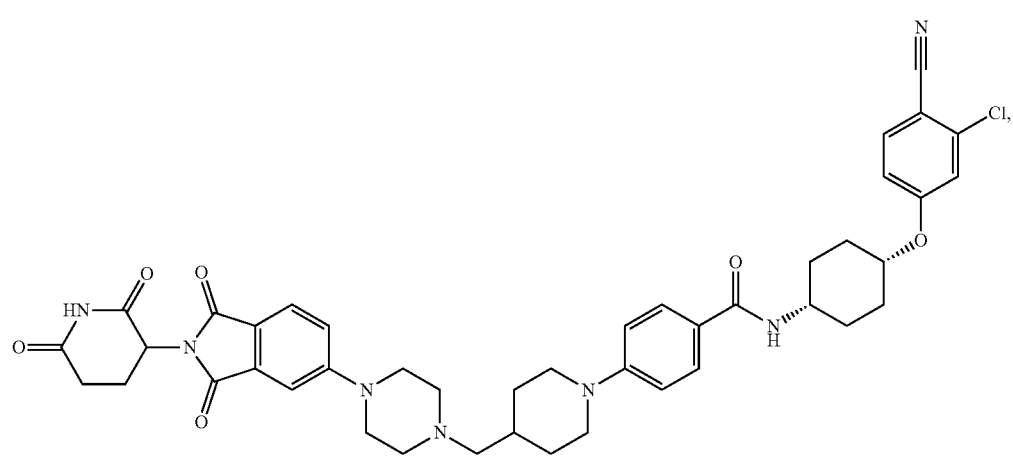
(402)

(409)
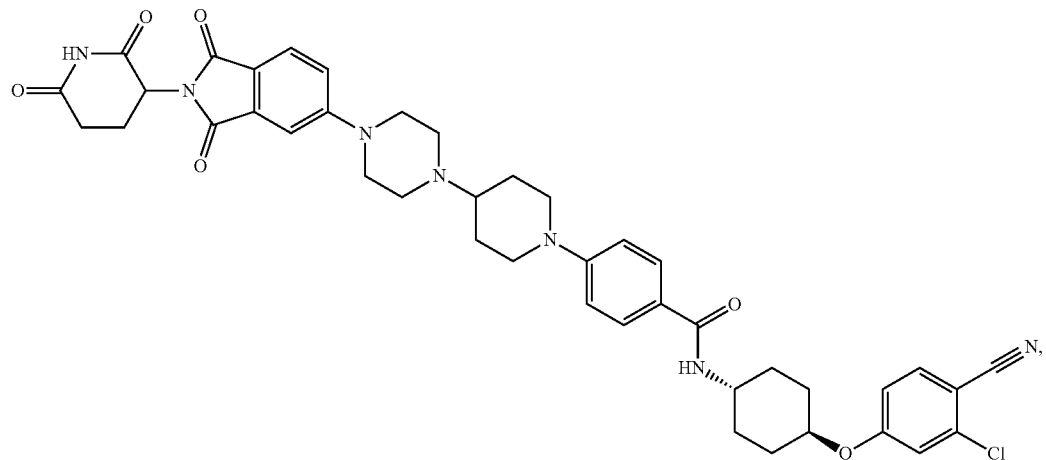
(410)
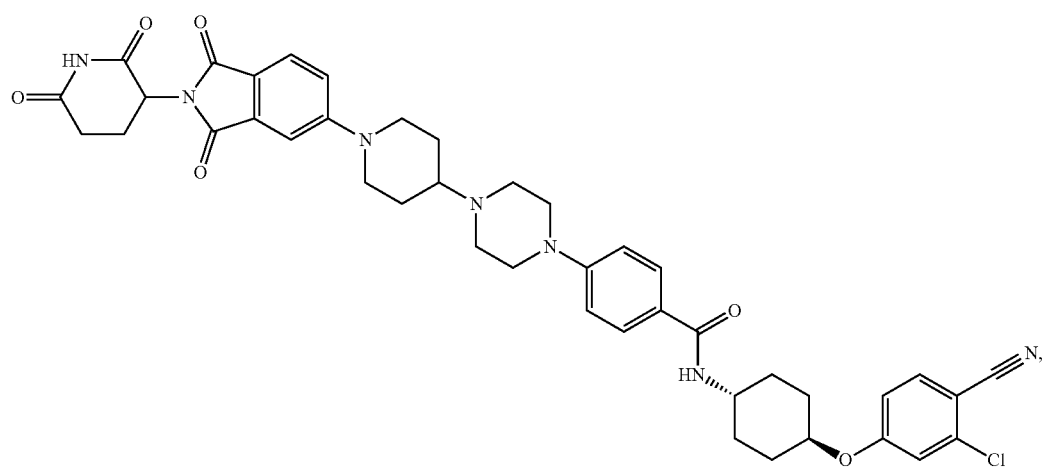
(411)
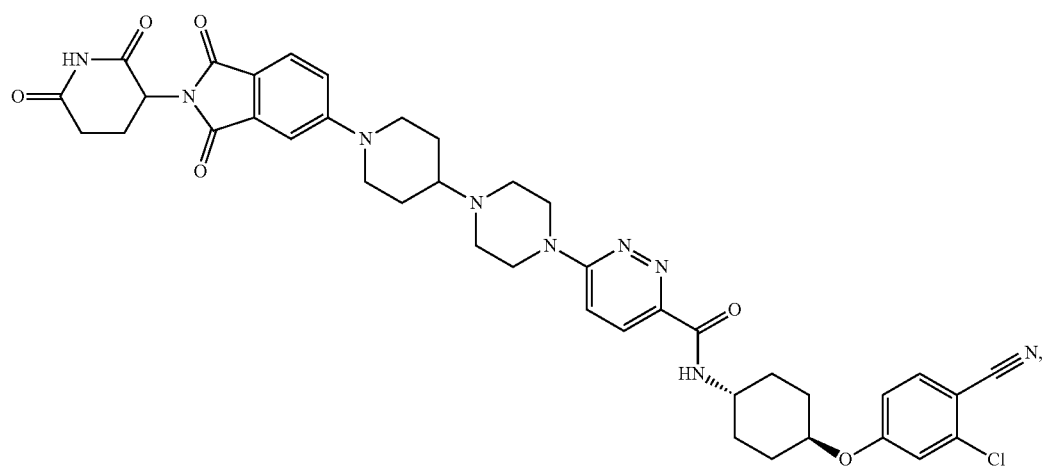

(412)
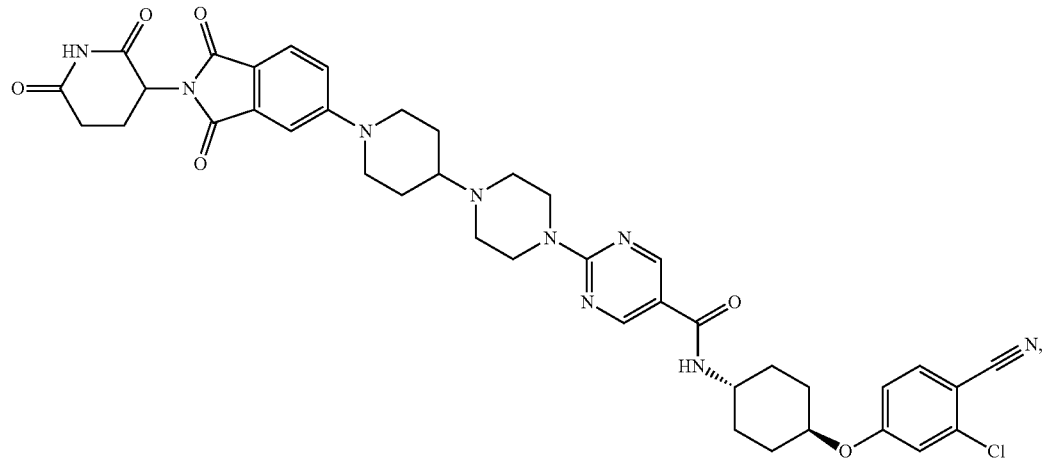
(413)
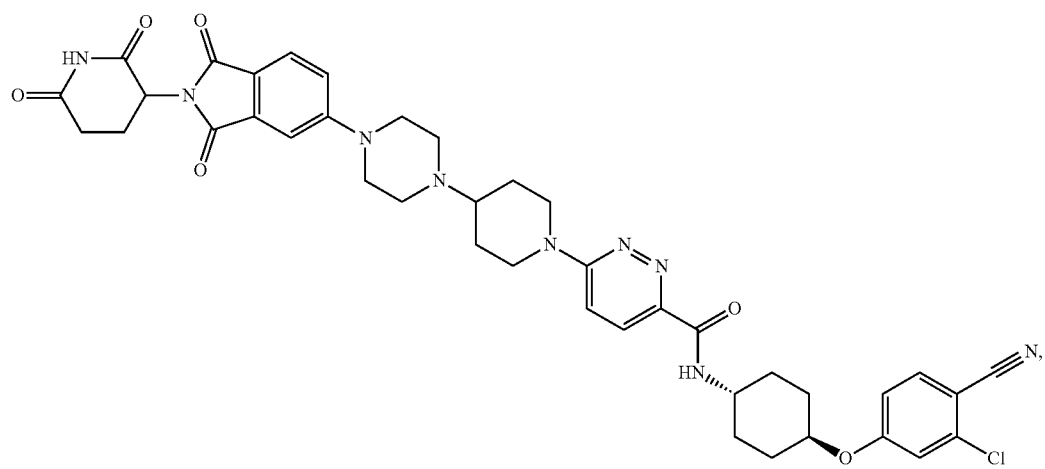
(419)
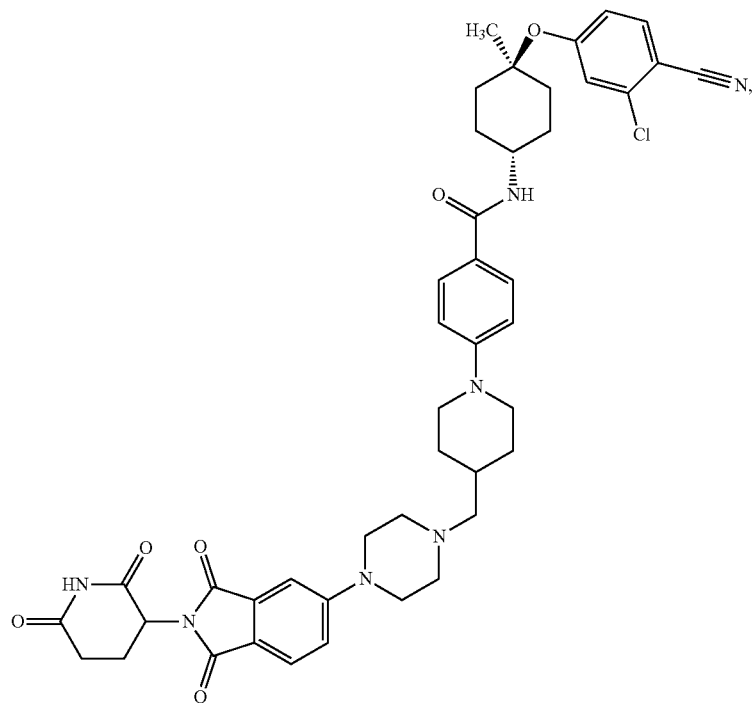

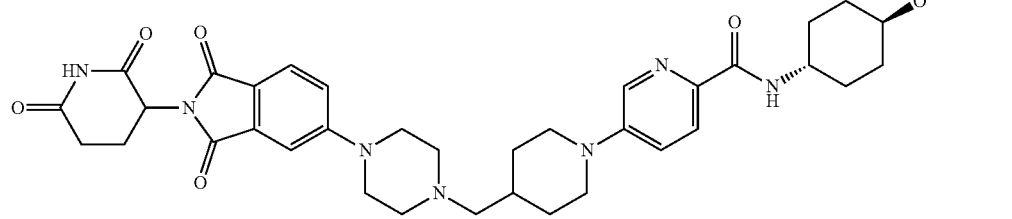
(421)
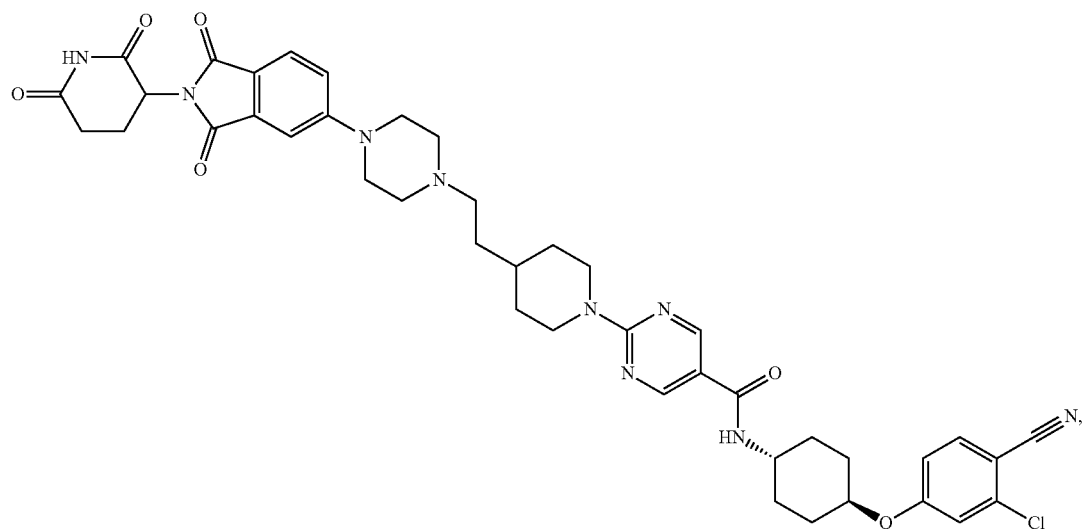
(424)
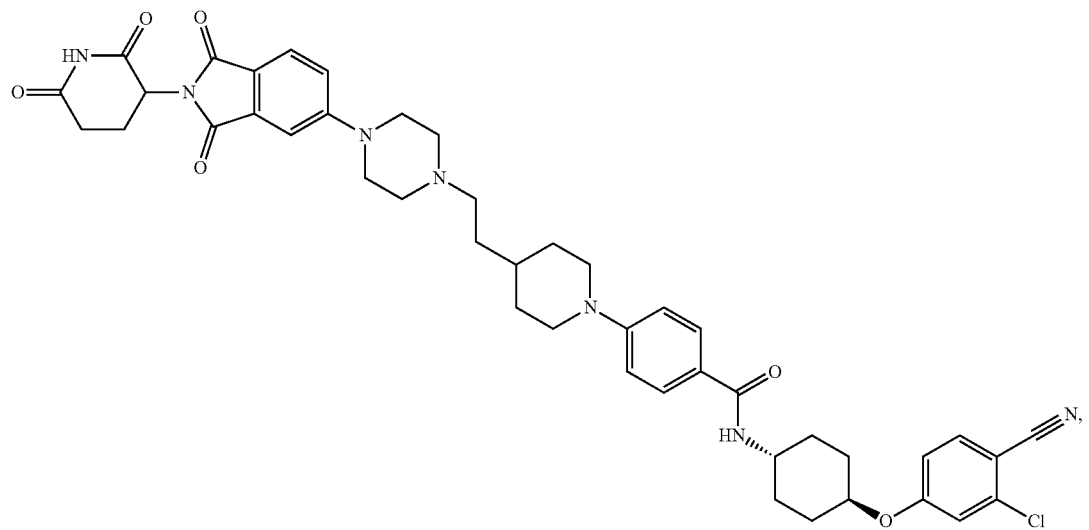
(425)

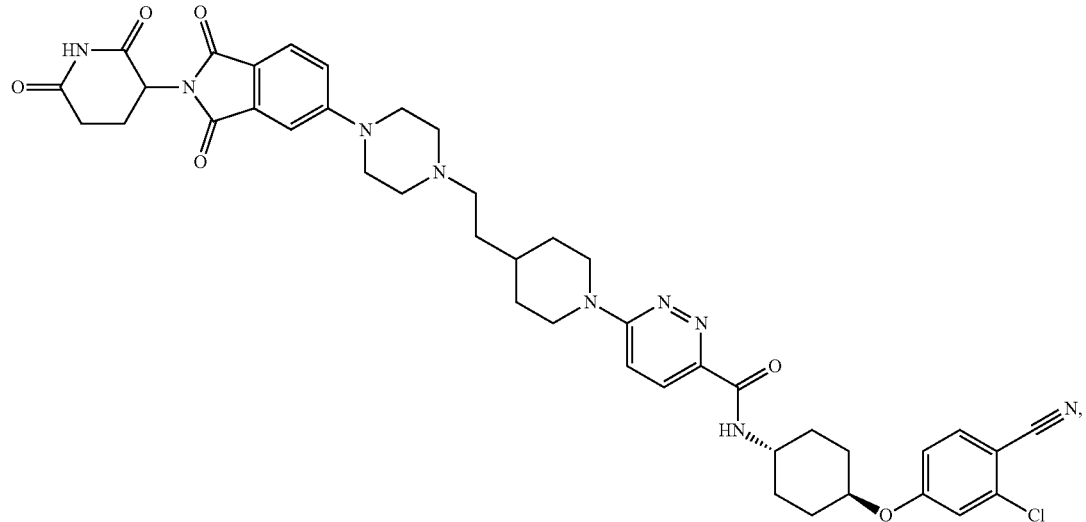
(427)
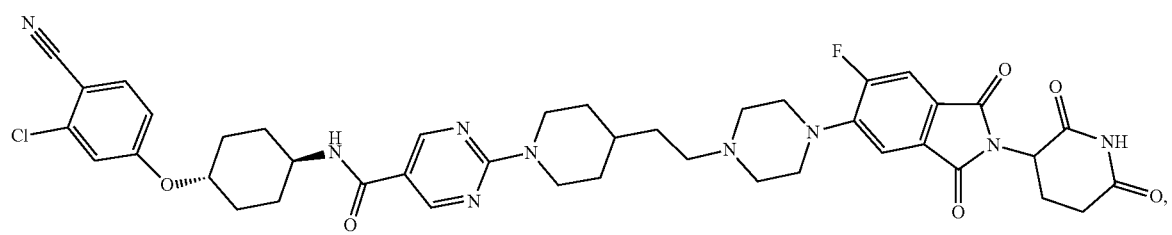
(534)
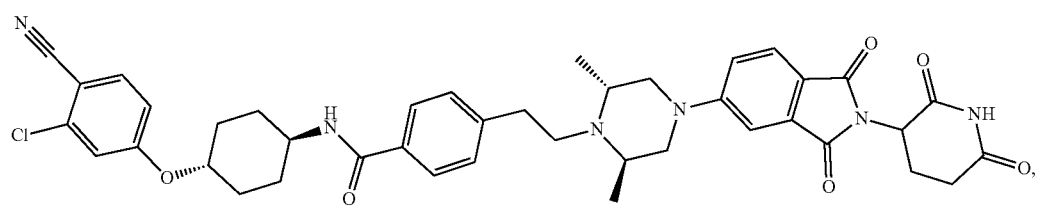
(536)
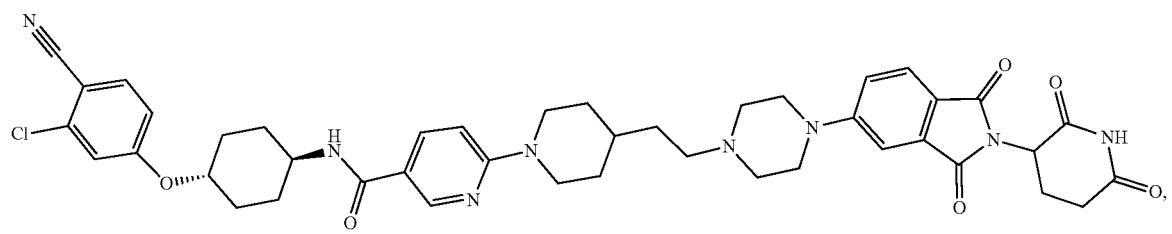
(547)
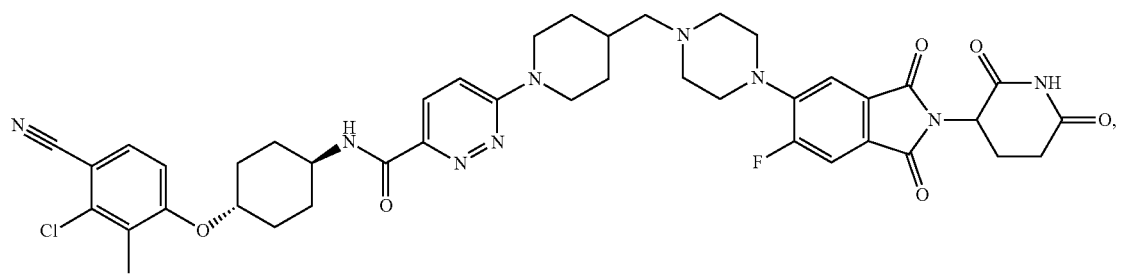
(548)

-continued
(549)
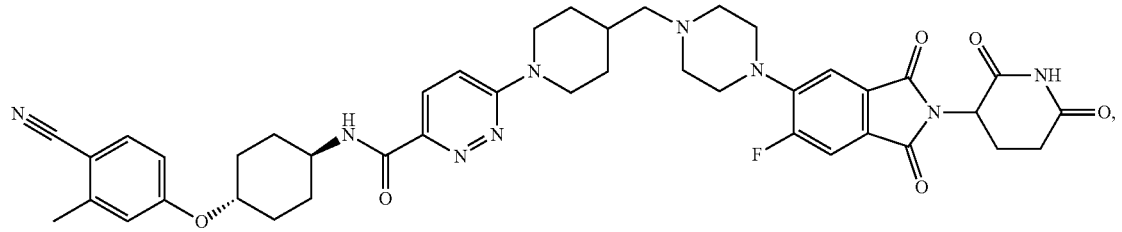
(559)
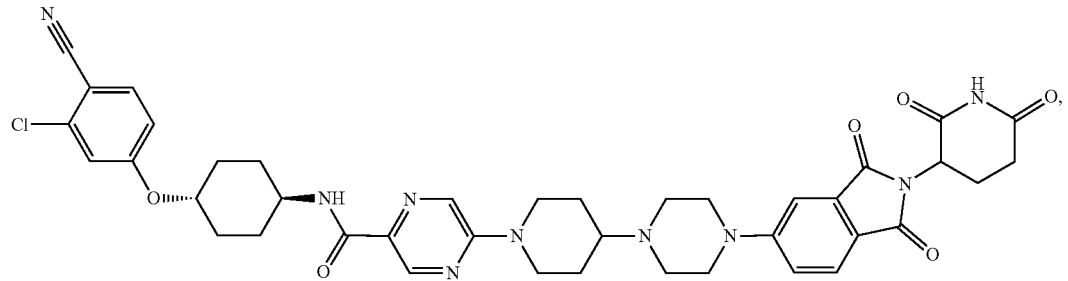
(560)
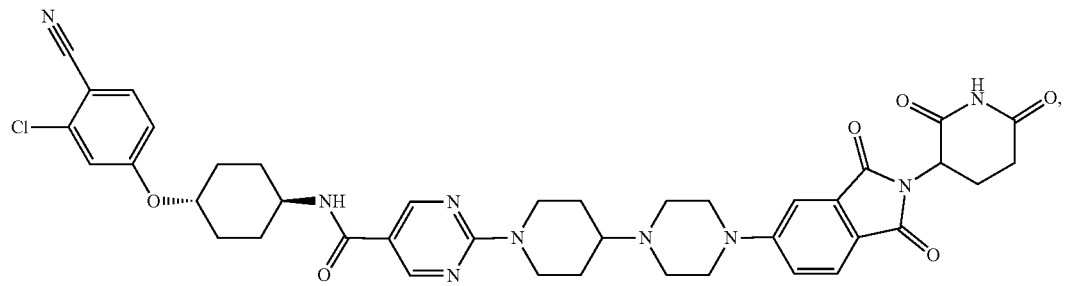
(567)
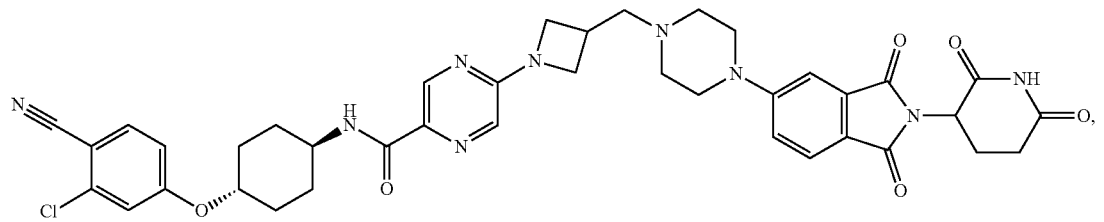
(570)
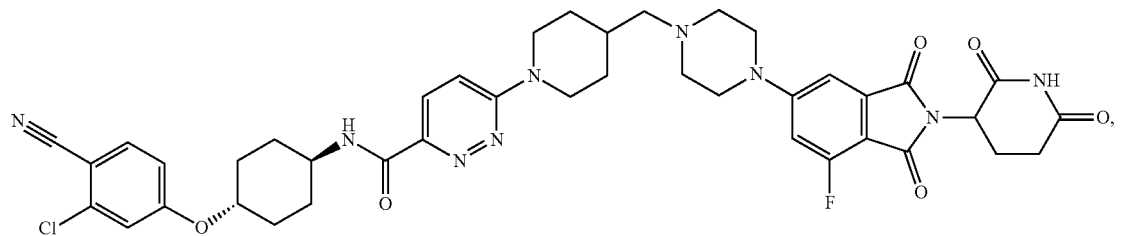
(574)
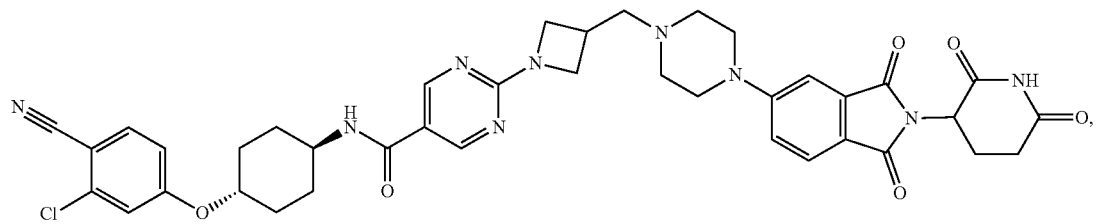

-continued

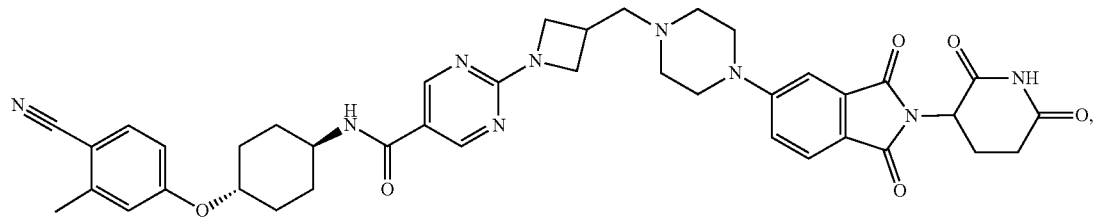
(575)

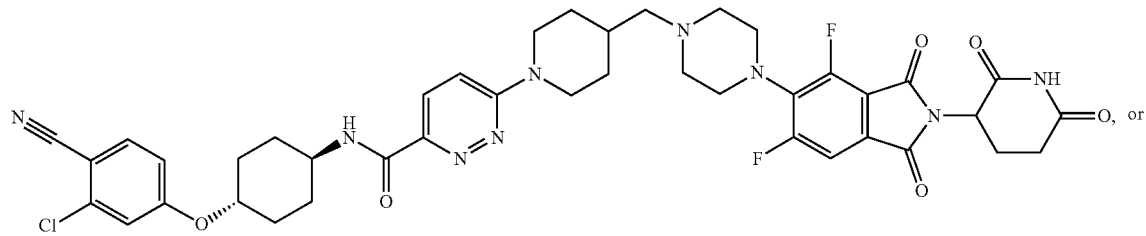
(594)

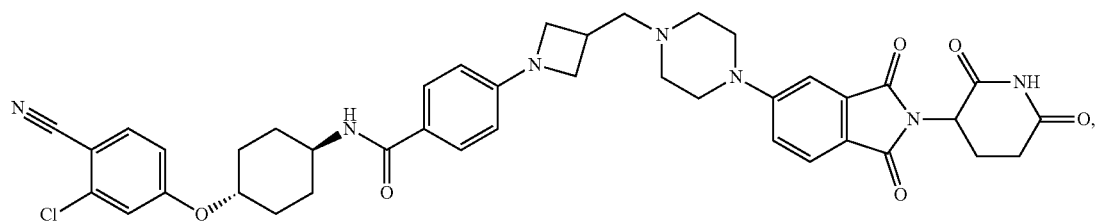
(596)

or a pharmaceutically acceptable salt thereof.

10. A pharmaceutical composition comprising an effective amount of the compound of claim 1, and a pharmaceutically acceptable carrier.

11. The pharmaceutical composition of claim 10, wherein the composition further comprises an anti-cancer agent.

12. The compound of claim 1, wherein the chemical linker group (L) is:

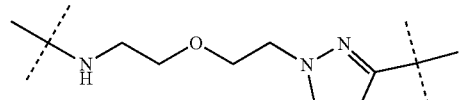

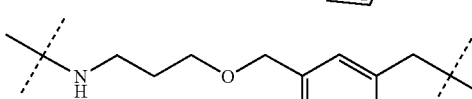

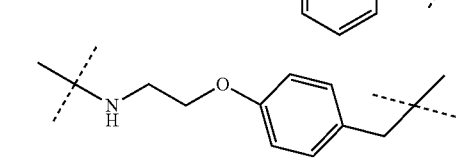

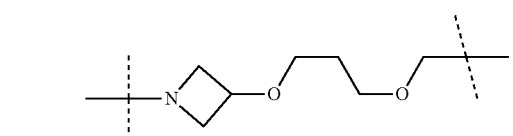

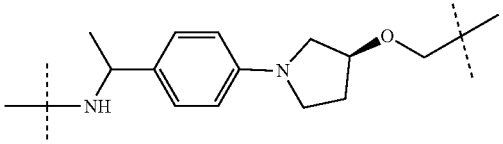

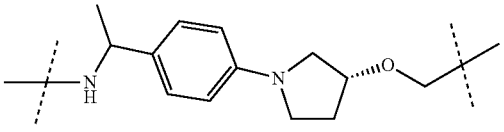

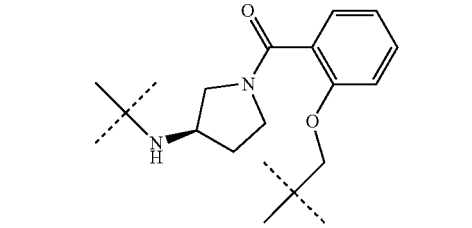

-continued

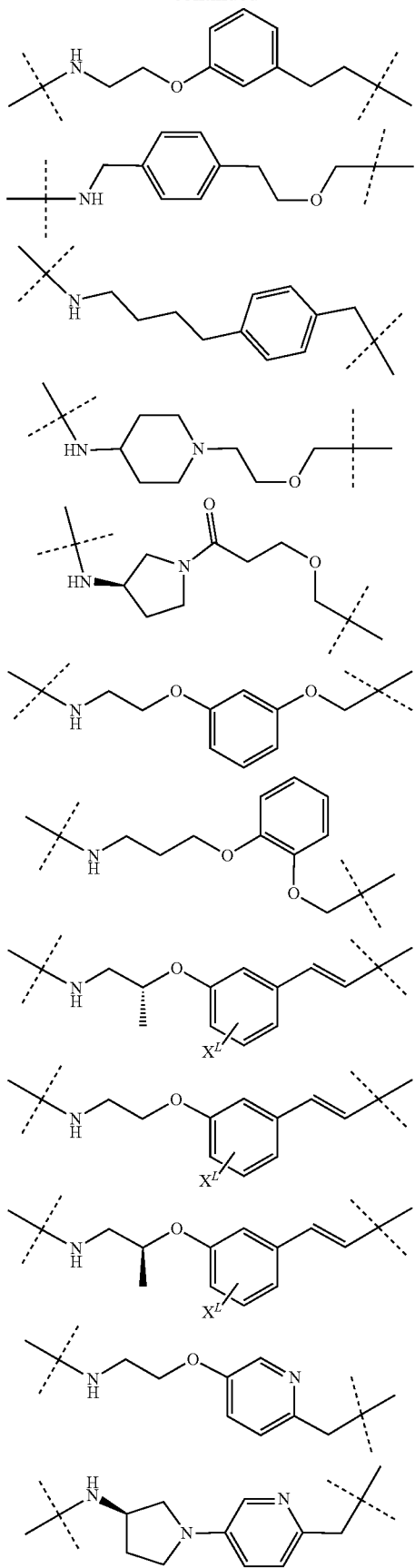
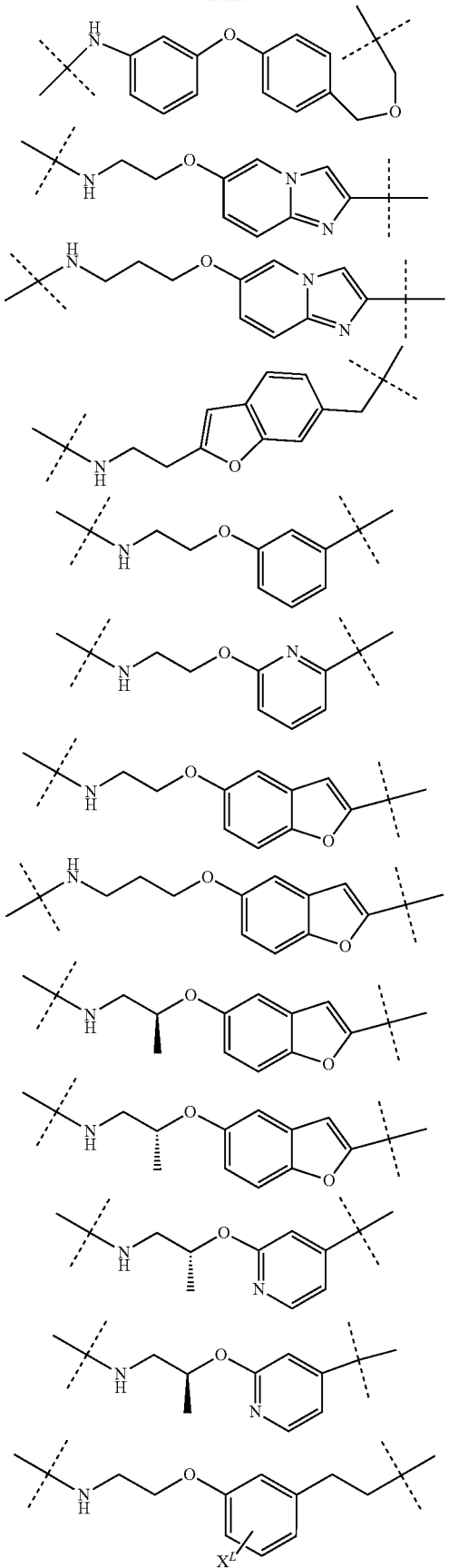

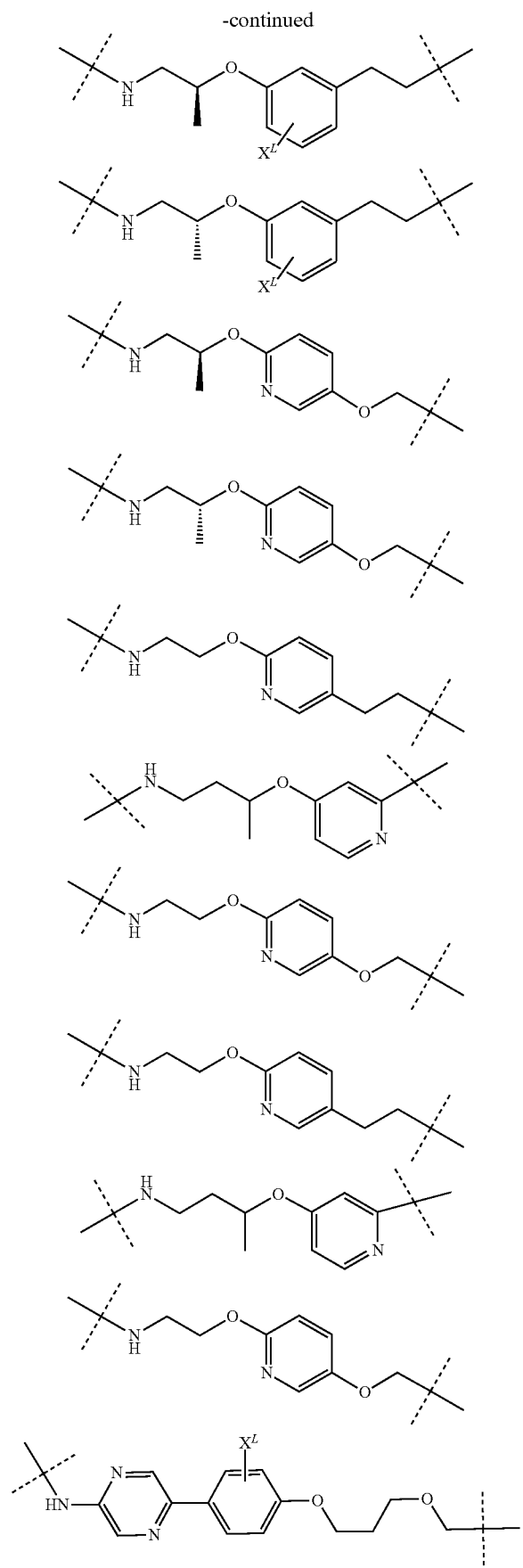

627
-continued
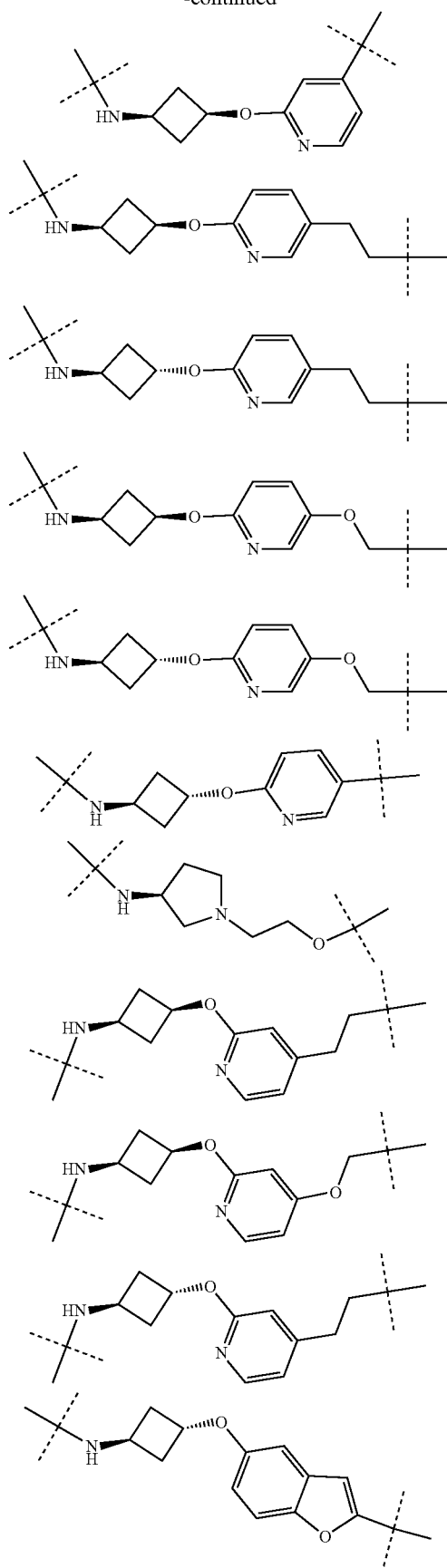
628
-continued
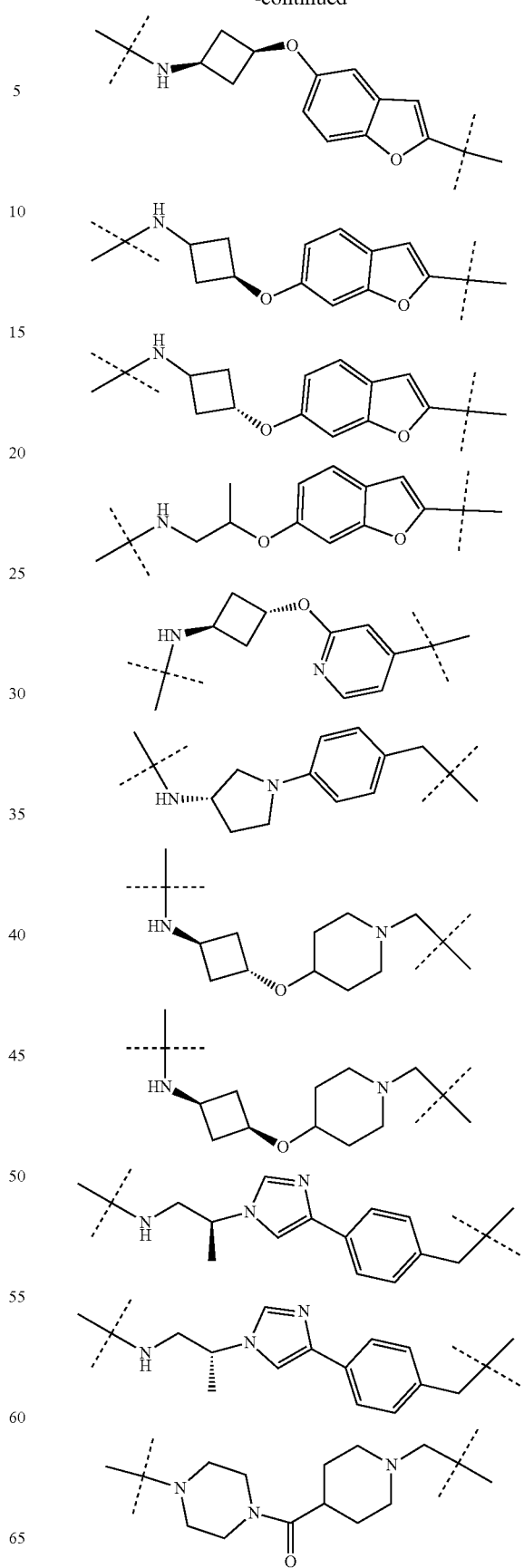

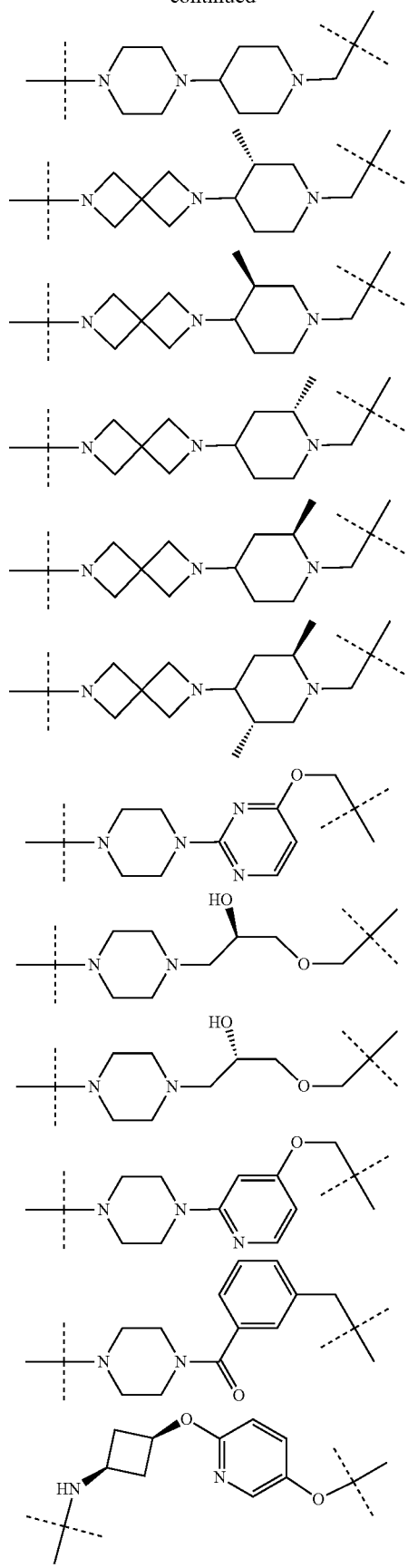
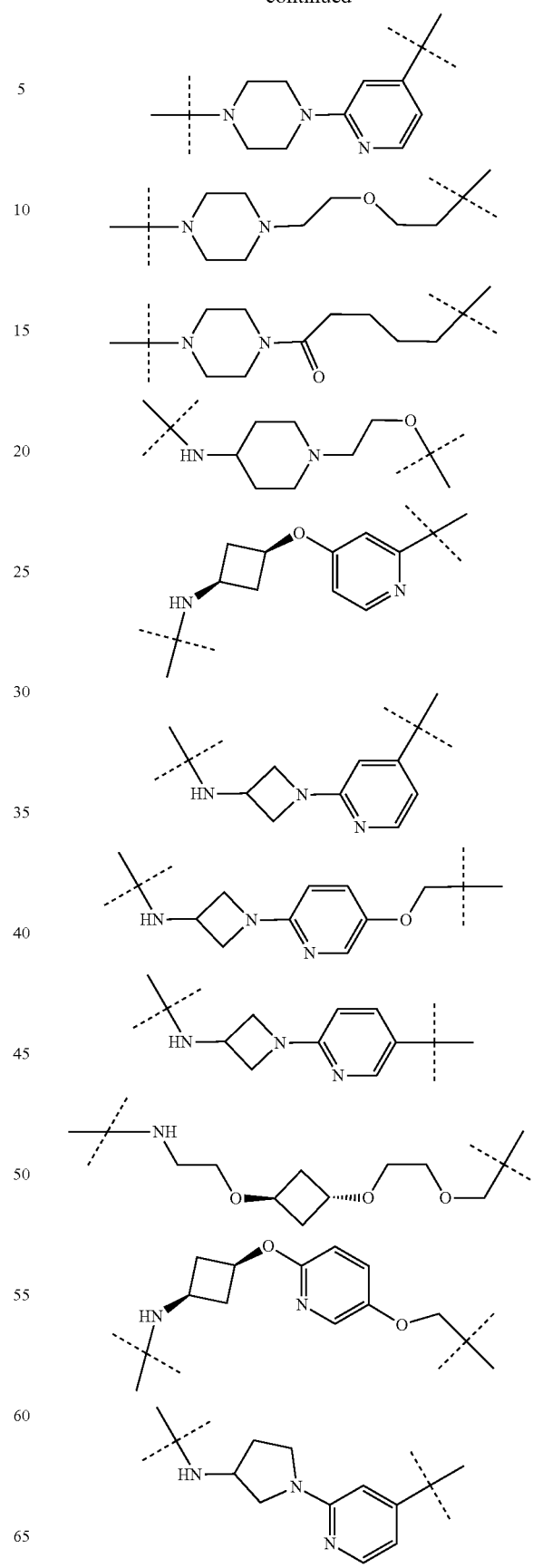

-continued
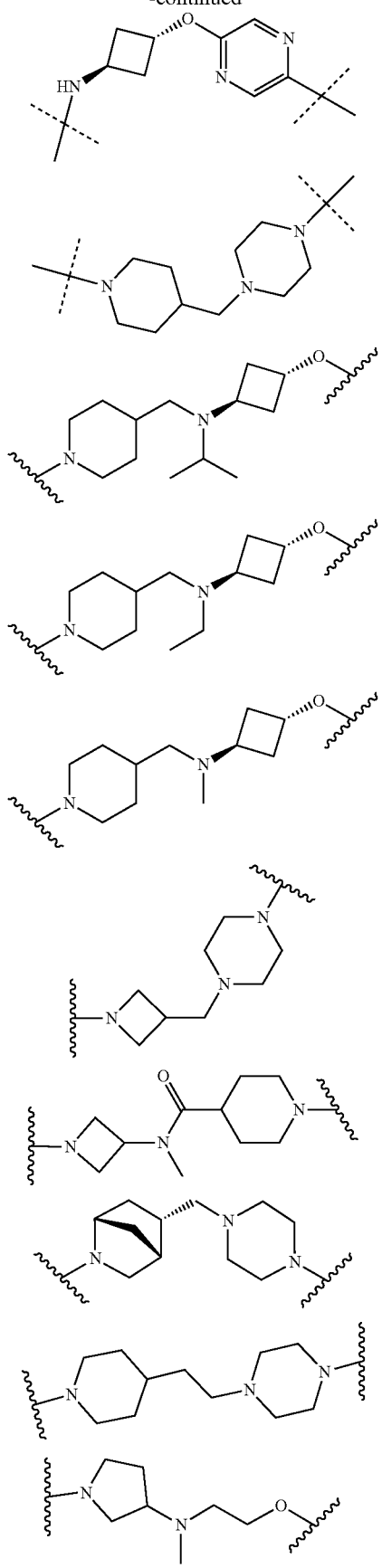
-continued
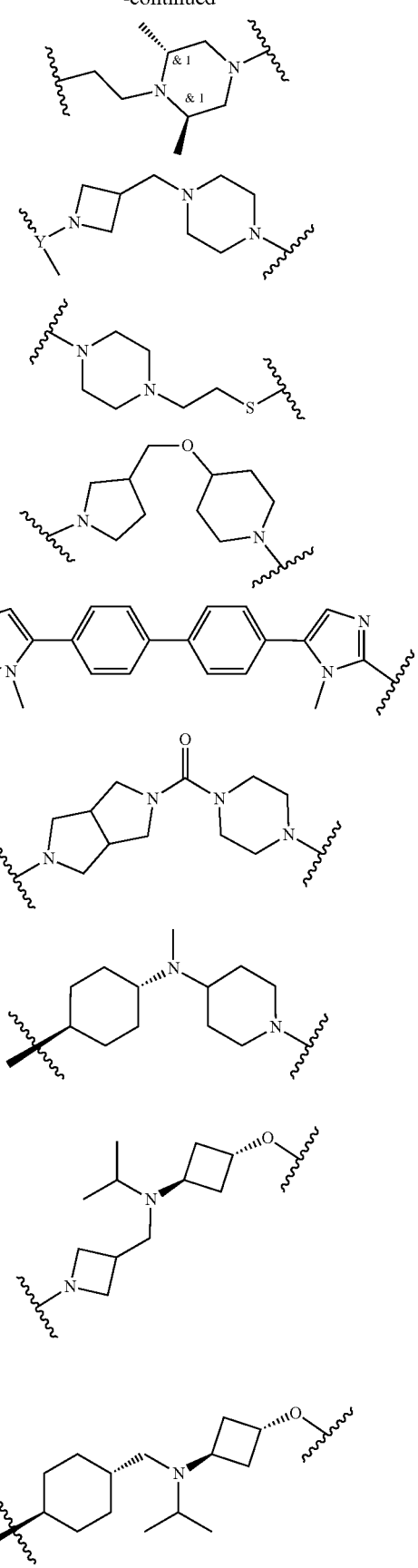

633

-continued

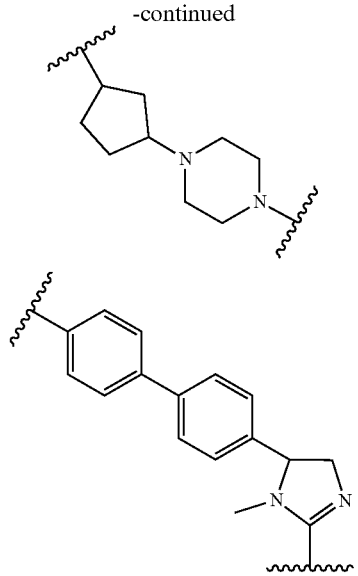

634

-continued $$-(CH_2)_mO(CH_2)_r-N\underset{\phantom{x}}{\overset{\phantom{x}}{N}}-(CH_2)_oO(CH_2)_p-;$$

$$\xi-N\underset{\phantom{x}}{\overset{\phantom{x}}{N}}-(CH_2)_mO(CH_2)_nO(CH_2)_pO(CH_2)_o-; \text{ and}$$

[structure with NH, phenyl, pyrazole, $-(CH_2)_mOCH_2$]

wherein each m, n, o, p, and r is independently 0, 1, 2, 3, 4, 5, or 6, provided that the chemical linker group does not contain a N—O or O—O bond; and wherein $X^L$ is H or F.

13. The compound of claim 1, wherein the compound is:

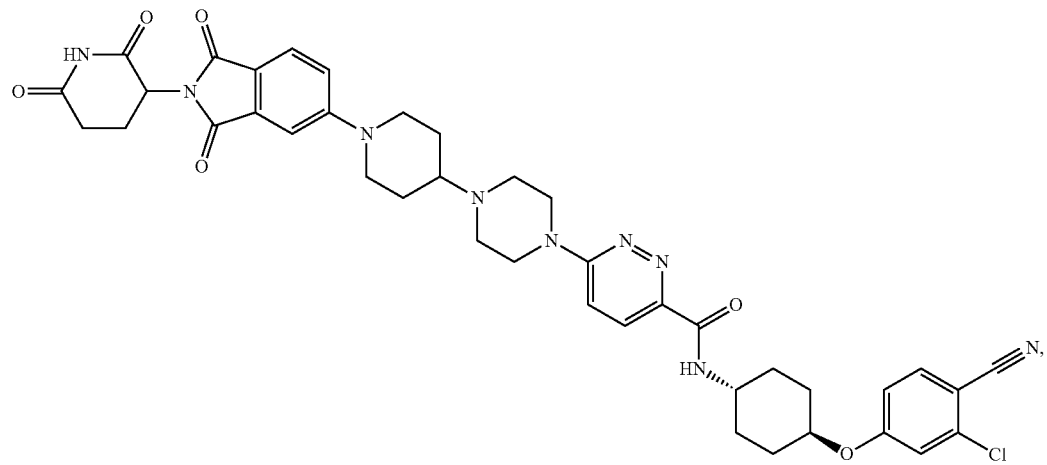

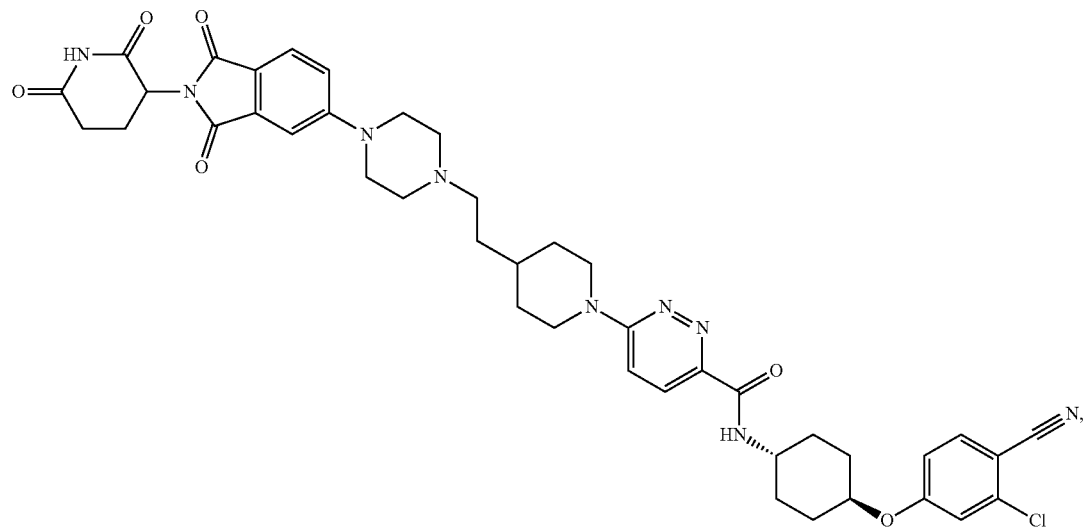

-continued
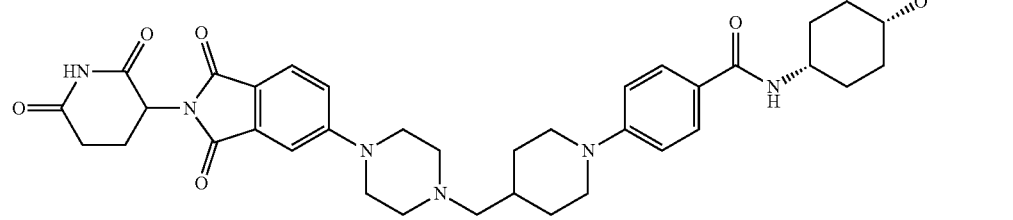
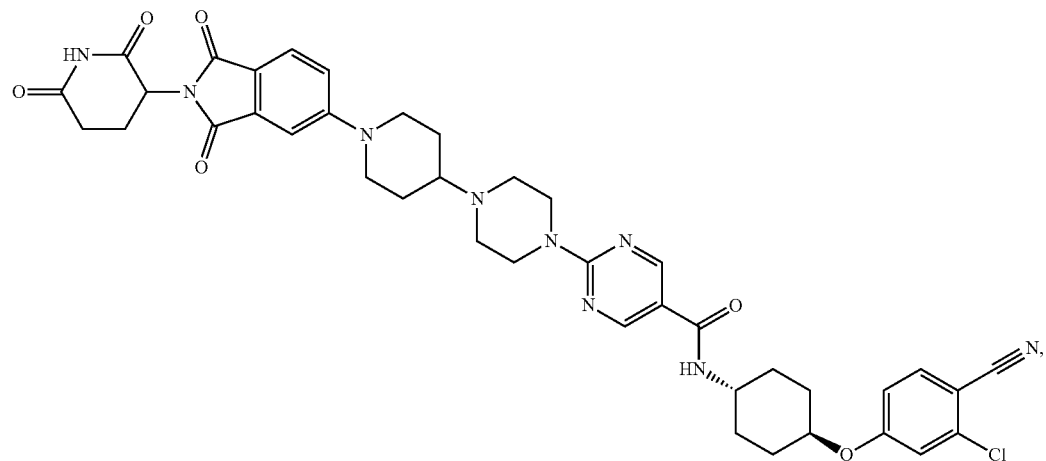
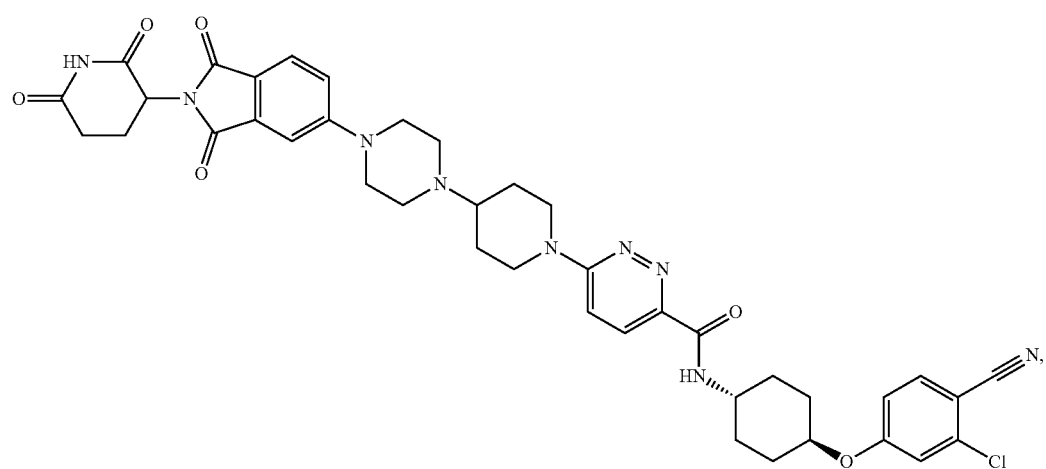

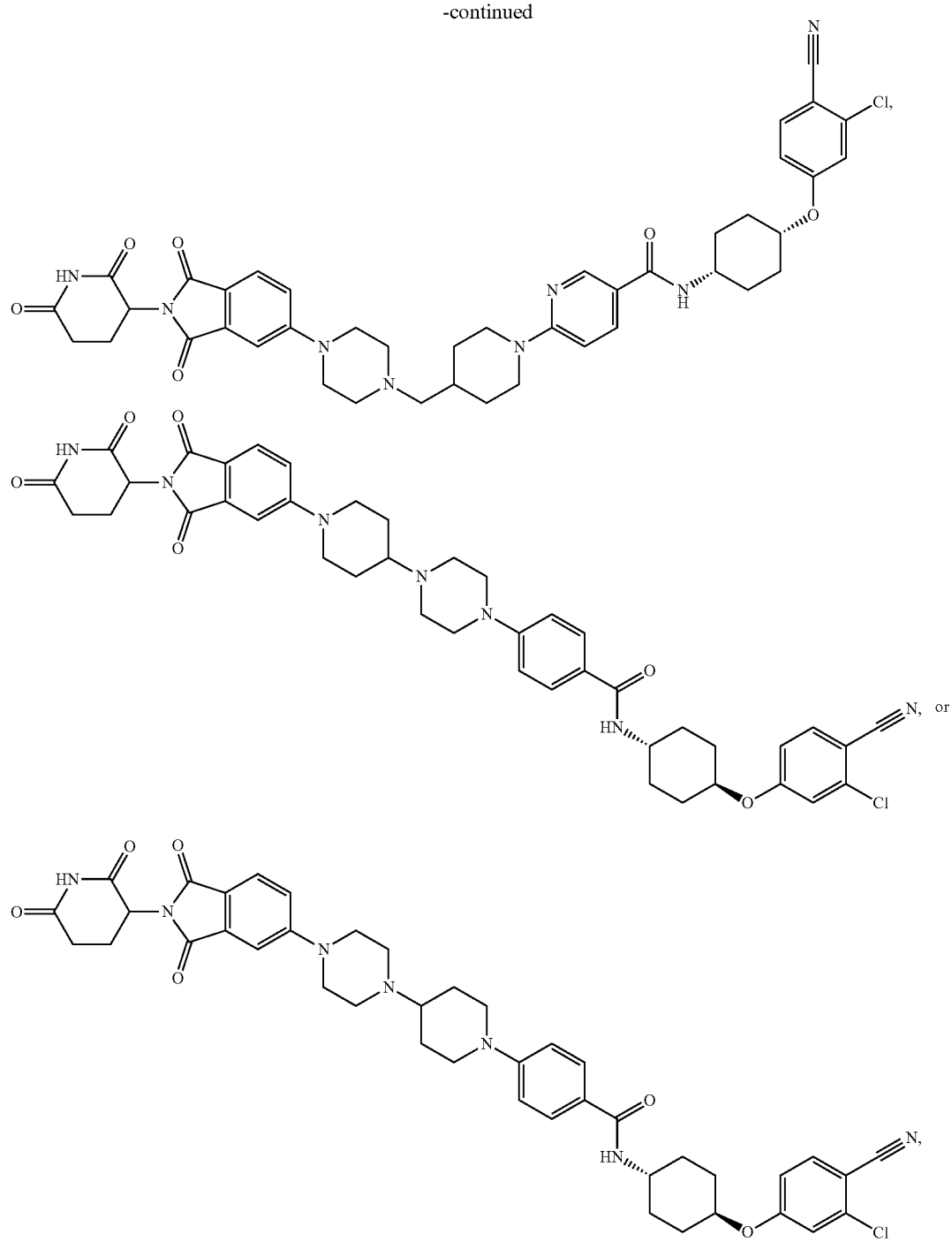
or a pharmaceutically acceptable salt thereof.
14. The compound of claim 3, wherein $W^1$ is:
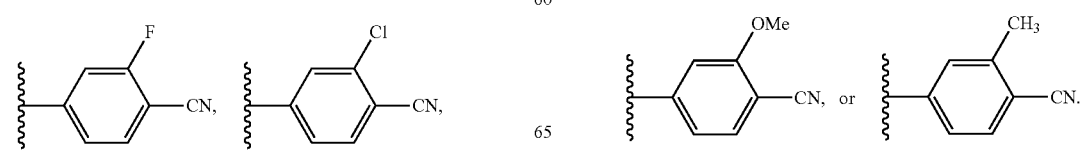
-continued 15. The compound of claim 14, wherein $W^1$ is

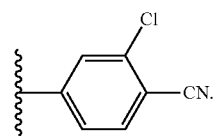 [SMILES: *c1ccc(C#N)c(Cl)c1]

16. The compound of claim 4, wherein $W^2$ is

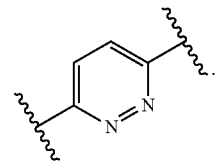 [SMILES: *c1ccc(*)nn1]

17. The compound of claim 5, wherein $W^2$ is

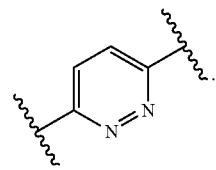 [SMILES: *c1ccc(*)nn1]

18. The compound according to claim 7, wherein the ABM is

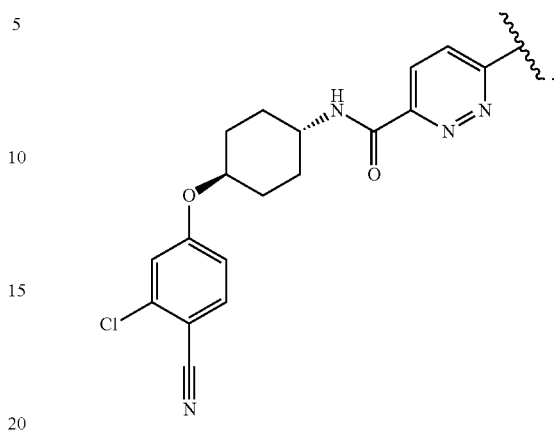

19. The compound of claim 1, wherein n is 1; and R is a heterocyclyl covalently joined to the linker group (L).

20. The compound of claim 1, wherein n is 1; and R is a piperazinyl or piperidinyl covalently joined to the linker group (L).

21. The compound of claim 1, wherein n is 2; one R is a heterocyclyl covalently joined to the linker group (L); and the other R is —F.

22. The compound of claim 1, wherein n is 2; one R is a piperazinyl covalently joined to the linker group (L); and the other R is —F.

23. The compound of claim 1, wherein n is 2; one R is a piperidinyl covalently joined to the linker group (L); and the other R is —F.

24. The compound of claim 1, wherein each $A^L$ is selected from $CR^{L1}R^{L2}$ and $C_{3-11}$ heterocyclyl optionally substituted with 1-6 $R^{L1}$.

25. The compound of claim 24, wherein each $A^L$ is selected from $CH_2$, piperazinyl, and piperidinyl.

26. The compound of claim 24, wherein each $A^L$ is selected from $CH_2$ and piperidinyl.

* * * * *

UNITED STATES PATENT AND TRADEMARK OFFICE
CERTIFICATE OF CORRECTION

PATENT NO. : 11,964,945 B2
APPLICATION NO. : 16/888484
DATED : April 23, 2024
INVENTOR(S) : Andrew P. Crew et al.

Page 1 of 2

It is certified that error appears in the above-identified patent and that said Letters Patent is hereby corrected as shown below:

In the Claims

At Column 628, in Claim number 12, Line numbers 10 – 15:

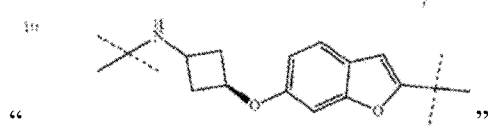

Should read:

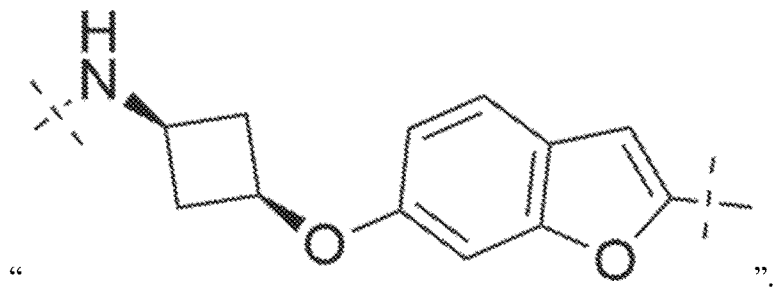

At Column 628, in Claim number 12, Line numbers 15 – 20:

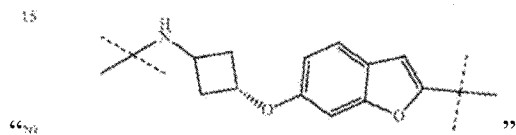

Signed and Sealed this
Twenty-second Day of October, 2024

Katherine Kelly Vidal
*Director of the United States Patent and Trademark Office*

CERTIFICATE OF CORRECTION (continued)
U.S. Pat. No. 11,964,945 B2

Should read:

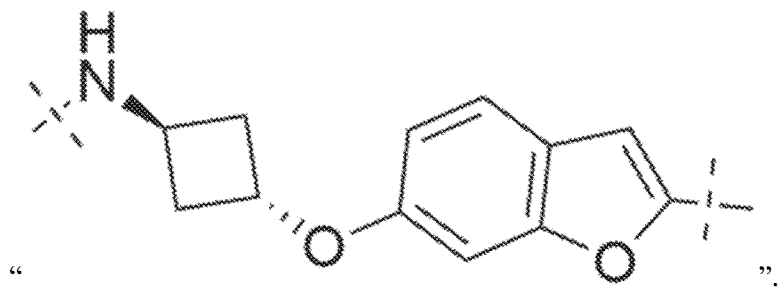

" ".